(12) United States Patent
Frederick et al.

(10) Patent No.: US 10,646,549 B2
(45) Date of Patent: May 12, 2020

(54) POLYNUCLEOTIDES ENCODING INTERLEUKIN-12 (IL12) AND USES THEREOF

(71) Applicant: ModernaTX, Inc., Cambridge, MA (US)

(72) Inventors: Joshua Frederick, Charlestown, MA (US); Susannah Hewitt, Jamaica Plain, MA (US); Ailin Bai, Newton, MA (US); Stephen Hoge, Brookline, MA (US); Vladimir Presnyak, Manchester, NH (US); Iain Mcfadyen, Arlington, MA (US); Kerry Benenato, Sudbury, MA (US); Ellalahewage Sathyajith Kumarasinghe, Harvard, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/192,274

(22) Filed: Nov. 15, 2018

(65) Prior Publication Data

US 2019/0125839 A1    May 2, 2019

Related U.S. Application Data

(63) Continuation of application No. PCT/US2017/033422, filed on May 18, 2017.

(60) Provisional application No. 62/443,693, filed on Jan. 7, 2017, provisional application No. 62/338,483, filed on May 18, 2016.

(51) Int. Cl.

| | |
|---|---|
| *A61K 48/00* | (2006.01) |
| *A61K 38/20* | (2006.01) |
| *A61K 9/51* | (2006.01) |
| *C07K 14/54* | (2006.01) |
| *A61P 35/00* | (2006.01) |
| *A61K 9/00* | (2006.01) |

(52) U.S. Cl.
CPC .......... *A61K 38/208* (2013.01); *A61K 9/0019* (2013.01); *A61K 9/5123* (2013.01); *A61P 35/00* (2018.01); *C07K 14/5434* (2013.01); *A61K 48/00* (2013.01)

(58) Field of Classification Search
None
See application file for complete search history.

(56) References Cited

U.S. PATENT DOCUMENTS

| | | |
|---|---|---|
| 5,891,680 A | 4/1999 | Lieschke et al. |
| 5,922,685 A | 7/1999 | Rakhmilevich et al. |
| 5,994,104 A | 11/1999 | Anderson et al. |
| 6,423,308 B1 | 7/2002 | Yarchoan et al. |
| 6,509,321 B1 | 1/2003 | Yarchoan et al. |
| 7,320,890 B2 | 1/2008 | Mahato et al. |
| 7,595,303 B1 | 9/2009 | Mohapatra et al. |
| 7,833,754 B2 | 11/2010 | Felber et al. |
| 7,872,107 B2 | 1/2011 | Webster et al. |
| 7,910,564 B2 | 3/2011 | Sung et al. |
| 8,026,223 B1 | 9/2011 | Heller et al. |
| 8,188,248 B2 | 5/2012 | Webster et al. |
| 8,253,151 B2 | 8/2012 | Kang |
| 8,556,882 B2 | 10/2013 | Morgan et al. |
| 8,603,458 B2 | 12/2013 | Mohapatra et al. |
| 8,715,964 B2 | 5/2014 | Felber et al. |
| 9,029,330 B2 | 5/2015 | Webster et al. |
| 9,272,024 B2 | 3/2016 | Weiner et al. |
| 9,636,388 B2 | 5/2017 | Lawman et al. |
| 9,868,691 B2 * | 1/2018 | Benenato ............. A61K 9/5123 |
| 9,981,036 B2 | 5/2018 | Weiner et al. |
| 2002/0018767 A1 | 2/2002 | Lee et al. |
| 2003/0118564 A1 | 6/2003 | Molling et al. |
| 2005/0032730 A1 | 2/2005 | Von Der Mulbe et al. |
| 2009/0053171 A1 | 2/2009 | Hwang et al. |
| 2014/0004154 A1 | 1/2014 | Pascolo |
| 2014/0056931 A1 | 2/2014 | Mohapatra et al. |
| 2014/0206758 A1 | 7/2014 | Felber et al. |
| 2015/0004188 A1 | 1/2015 | Weiner et al. |
| 2016/0311879 A1 * | 10/2016 | Sopczynski ........ A61K 31/7088 |
| 2017/0000870 A1 | 1/2017 | Hoerr et al. |

(Continued)

FOREIGN PATENT DOCUMENTS

| | | |
|---|---|---|
| EP | 1032428 B1 | 6/2003 |
| EP | 1640018 A1 | 3/2006 |

(Continued)

OTHER PUBLICATIONS

Bontkes, H. J., et al., "Dendritic cells transfected with interleukin-12 and tumor-associated antigen messenger RNA induce high avidity cytotoxic T cells," Gene Therapy, vol. 14: 366-375 (2007).
Kauffman, et at. "Materials for non-viral Intracellular Delivery of Messenger RNA Therapeutics," Journal of Controlled Release (2016), v. 240, pp. 227-234.
Reichmuth, et al., "mRNA Vaccine Delivery Using Lipid Nanoparticles," Therapeutic Delivery (2016), v. 7, No. 5, pp. 319-334.

(Continued)

*Primary Examiner* — J. E Angell
(74) *Attorney, Agent, or Firm* — Nelson Mullins Riley & Scarborough LLP; Amy E. Mandragouras, Esq.; Ariana D. Harris

(57) ABSTRACT

The present disclosure relates to polynucleotides comprising an open reading frame of linked nucleosides encoding human interleukin-12 (IL12), functional fragments thereof, and fusion proteins comprising IL12. In some embodiments, the open reading frame is sequence-optimized. In particular embodiments, the disclosure provides sequence-optimized polynucleotides comprising nucleotides encoding the polypeptide sequence of human IL12, or sequences having high sequence identity with those sequence optimized polynucleotides.

20 Claims, 69 Drawing Sheets
Specification includes a Sequence Listing.

(56) References Cited

U.S. PATENT DOCUMENTS

| | | | |
|---|---|---|---|
| 2017/0232090 A1 | 8/2017 | Lawman et al. | |
| 2017/0291934 A1 | 10/2017 | Reed et al. | |
| 2018/0207295 A1* | 7/2018 | Fotin-Mleczek | A61K 39/39558 |

FOREIGN PATENT DOCUMENTS

| | | |
|---|---|---|
| EP | 1268759 B1 | 9/2006 |
| EP | 1966238 B1 | 4/2012 |
| EP | 2623121 A1 | 8/2013 |
| EP | 2424887 B1 | 9/2015 |
| EP | 3053592 A1 | 8/2016 |
| EP | 3173092 A2 | 5/2017 |
| EP | 3250250 A1 | 12/2017 |
| EP | 3326641 A1 | 5/2018 |
| WO | 96/24676 A1 | 8/1996 |
| WO | 97/46263 A1 | 12/1997 |
| WO | 98/17814 A2 | 4/1998 |
| WO | 99/26663 A2 | 6/1999 |
| WO | 200152874 A2 | 7/2001 |
| WO | 01/62274 A1 | 8/2001 |
| WO | 02/098443 A2 | 12/2002 |
| WO | 2005/058349 A2 | 6/2005 |
| WO | 2006/024518 A1 | 3/2006 |
| WO | 2008052770 A2 | 5/2008 |
| WO | 2008134879 A1 | 11/2008 |
| WO | 2009034172 A1 | 3/2009 |
| WO | 2009/149539 A1 | 12/2009 |
| WO | 2010/126766 A1 | 11/2010 |
| WO | 2012116811 A1 | 9/2012 |
| WO | 2013/053775 A1 | 4/2013 |
| WO | 2013/090296 A1 | 6/2013 |
| WO | 2013/151671 A1 | 10/2013 |
| WO | 2013/151672 A2 | 10/2013 |
| WO | 2014089486 A1 | 6/2014 |
| WO | 2014/127917 A1 | 8/2014 |
| WO | 2015/058069 A1 | 4/2015 |
| WO | 2015/061491 A1 | 4/2015 |
| WO | 2015/095249 A1 | 6/2015 |
| WO | 2016/048903 A1 | 3/2016 |
| WO | 2016170176 A1 | 10/2016 |
| WO | 2017/137461 A1 | 8/2017 |
| WO | 2017/144602 A1 | 8/2017 |
| WO | 2017/201350 A1 | 11/2017 |
| WO | 2018/033254 A2 | 2/2018 |
| WO | 2018/068008 A1 | 4/2018 |

OTHER PUBLICATIONS

Communication pursuant to Rule 114(2) EPC, issued by the European Patent Office dated Feb. 10, 2020 (6 pgs).
Amos, S.M. et al., "Adoptive immunotherapy combined with intrautmoral TLR agonist delivery eradicates established melanoma in mice," Cancer Immunology and Immunotherapy, vol. 60(5):671-683 (2011).
Anwer, K. et al., "Phase-I clinical trial of IL-12 plasnnid/ lipopolynner complexes for the treatment of recurrent ovarian cancer," Gene Therapy, vol. 17:360-369 (2009).
Bontkes, H. J., et al., "Tumor associated antigen and interleukin-12 mRNA transfected dendritic cells enhance effector function of natural killer cells and antigen specific T-cells," Clinical Immunology, vol. 127(3): 375-384 (2008).
Charoensit, P. et al., "Enhanced growth inhibition of metastatic lung tumors by intravenous injection of ATRA-cationic liposome/IL-12 pDNA complexes in mice," Cancer Gene Therapy, vol. 17(7) 512-522 (2010).

Chen, J. et al., Production and clinical development of nanoparticles for gene delivery, Official journal of the American Society of Gene & Cell Therapy, vol. 3 (16023) 8 pages (2016).
Chowdhury, F.Z. et al., "IL-12 selectively programs effector pathways that are stably expressed in human CD8+ effector memory T cells in vivo," Blood, vol. 118 (14):3890-3900 (2011).
Colombo, M. et al., "Interleukin-12 in anti-tumor immunity and immunotherapy," Cytokine and Growth Factor Reviews, vol. 13 (2):155-168 (2002).
Fotin-Mleczek, M. et al, "Highly potent mRNA based cancer vaccines represent an attractive platform for combination therapies supporting an improved therapeutic effect," Journal of Gene Medicine, vol. 14 (6):428-439 (2012).
International Preliminary Report on Patentability, PCT/US2017/033422, dated Nov. 20, 2018, 10 pages.
International Search Report and Written Opinion, PCT/US2017/033422, dated Jul. 19, 2017, 15 pages.
Lasek, W. et al., "Interleukin 12: still a promising candidate for tumor immunotherapy?," Cancer Immunol Immunother., vol. 63:419-435 (2014).
Mahvi, DM, et al., "Intratumoral injection of IL-12 plasmid DNA—results of a phase; I/IB clinical trial," Cancer Gene Therapy, vol. 14: 717-723 (2007).
Meraz, I. et al., "Adjuvant Cationic Liposomes Presenting MPL and IL-12 Induce Cell Death, Suppress Tumor Growth, and Alter the Cellular Phenotype of Tumors in a Murine Model of Breast Cancer," Molecular Pharmaceutics, vol. 11(10):3484-3491(2014).
Putzer B. M. et al. "Interleukin 12 and B7-1 costimulatory molecule expressed by an adenovirus vector act synergistically to facilitate tumor regression," PNAS,vol. 94 (20):10889-10894 (1997).
Sahin, U. et al., "mRNA-based therapeutics—developing a new class of drugs," Nature Reviews Drug Discovery, vol. 13(10):759-780 (2014).
Sayour, E.J. et al., "Bridging infectious disease vaccines with cancer immunotherapy: a role for targeted RNA based immunotherapeutics," Journal for Imunotherapy of Cancer, vol. 3(1): 7 pages (2015).
Schirrmacher V., et al., "Intra-pinna anti-tumor vaccination with self-replicating infectious RNA or with DNA encoding a model tumor antigen and a cytokine," Gene Therapy, vol. 7(13):1137-1147 (2000).
Shim, G. et al., "Application of cationic liposomes for delivery of nucleic acids," Asian Journal of Pharmaceutical Sciences, vol. 8 (2):72-80 (2013).
Suzuki, R. et al., "Cancer gene therapy by IL-12 gene delivery using liposomal bubbles and tumoral ultrasound exposure" Journal of Controlled Release, vol. 142: 245-250(2009).
Third Party Observation, filed in PCT/US2017/033422, dated Sep. 17, 2018, 5 pages.
Tugues, S. et al., "New insights into IL-12-mediated tumor suppression," Cell Death and Differentiation, vol. 22 (2):237-246 (2014).
Van Der Jeught, K. et al., "Intratumoral administration of mRNA encoding a fusokine; consisting of IFN-? and the ectodomain of the TGF-? receptor II potentiates antitumor immunity," Oncotarget, vol. 5 (20):10100-10113 (2014).
Van Der Jeught, K. et al., "Intratumoral delivery of mRNA: Overcoming obstacles for effective immunotherapy," OncoImmunolog, vol. 4(5): e1005504-1-e1005504-3 (2015).
Van Der Jeught, K. et al., "Targeting the tumor microenvironment to enhance antitumor immune responses," Oncotarget, vol. 6(3): 1359-1381(2014).
Wilgenhof S., et al., "A phase IB study on intravenous synthetic mRNA electroporated dendritic cell immunotherapy in pretreated advanced melanoma patients," Annals of Oncology, vol. 24 (10): 2686-2693(2013).

* cited by examiner

FIG. 1.

(1) Wild Type IL12B without signal (IL12B) Amino Acids (SEQ ID NO: 1):
IWELKKDVYVVELDWYPDAPGEMVVLTCDTPEEDGITWTLDQSSEVLGSGKTLTIQVKEFGDAGQYTCHKGGEV
LSHSLLLLHKKEDGIWSTDILKDQKEPKNKTFLRCEAKNYSGRFTCWWLTTISTDLTFSVKSSRGSSDPQGVTC
GAATLSAERVRGDNKEYEYSVECQEDSACPAAEESLPIEVMVDAVHKLKYENYTSSFFIRDIIKPDPPKNLQLK
PLKNSRQVEVSWEYPDTWSTPHSYFSLTFCVQVQGKSKREKKDRVFTDKTSATVICRKNASISVRAQDRYYSSS
WSEWASVPCS (2) Wild Type IL12B without signal (IL12B) Nucleic Acids (SEQ ID NO: 2):
ATATGGGAACTGAAGAAAGATGTTTATGTCGTAGAATTGGATTGGTATCCGGATGCCCCTGGAGAAATGGTGGT
CCTCACCTGTGACACCCCTGAAGAAGATGGTATCACCTGGACCTTGGACCAGAGCAGTGAGGTCTTAGGCTCTG
GCAAAACCCTGACCATCCAAGTCAAAGAGTTTGGAGATGCTGGCCAGTACACCTGTCACAAAGGAGGCGAGGTT
CTAAGCCATTCGCTCCTGCTGCTTCACAAAAAGGAAGATGGAATTTGGTCCACTGATATTTTAAAGGACCAGAA
AGAACCCAAAAATAAGACCTTTCTAAGATGCGAGGCCAAGAATTATTCTGGACGTTTCACCTGCTGGTGGCTGA
CGACAATCAGTACTGATTTGACATTCAGTGTCAAAAGCAGCAGAGGCTCTTCTGACCCCCAAGGGGTGACGTGC
GGAGCTGCTACACTCTCTGCAGAGAGTCAGAGGGGACAACAAGGAGTATGAGTACTCAGTGGAGTGCCAGGA
GGACAGTGCCTGCCCAGCTGCTGAGGACAGTCTGCCCATTGAGGTCATGGTGGATGCCGTTCACAAGCTCAAGT
ATGAAAACTACACCAGCAGCTTCTTCATCAGGGACATCATCAAACCTGACCCACCCAAGAACTTGCAGCTGAAG
CCATTAAAGAATTCTCGGCAGGTGGAGGTCAGCTGGGAGTACCCTGACACCTGGAGTACTCCACATTCCTACTT
CTCCCTGACATTCTGCGTTCAGGTCCAGGGCAAGAGCAAGAGAGAAAAGAAAGATAGAGTCTTCACGGACAAGA
CCTCAGCCACGGTCATCTGCCGCAAAAATGCCAGCATTAGCGTGCGGGCCCAGGACCGCTACTATAGCTCATCT
TGGAGCGAATGGGCATCTGTGCCCTGCAGT (3) Wild Type IL12A without signal peptide Amino acids (SEQ ID NO: 3):
RNLPVATPDPGMFPCLHHSQNLLRAVSNMLQKARQTLEFYPCTSEEIDHEDITKDKTSTVEACLPLELTKNESC
LNSRETSFITNGSCLASRKTSFMMALCLSSIYEDLKMYQVEFKTMNAKLLMDPKRQIFLDQNMLAVIDELMQAL
NFNSETVPQKSSLEEPDFYKTKIKLCILLHAFRIRAVTIDRVMSYLNAS (4) Wild Type IL12A without signal peptide Nucleic acids (SEQ ID NO: 4):
AGAAACCTCCCCGTGGCCACTCCAGACCCAGGAATGTTCCCATGCCTTCACCACTCCCAAAACCTGCTGAGGGCC
GTCAGCAACATGCTCCAGAAGGCCAGACAAACTCTAGAATTTTACCCTTGCACTTCTGAAGAGATTGATCATGAA
GATATCACAAAAGATAAAACCAGCACAGTGGAGGCCTGTTTACCATTGGAATTAACCAAGAATGAGAGTTGCCTA
AATTCCAGAGAGACCTCTTTCATAACTAATGGGAGTTGCCTGGCCTCCAGAAAGACCTCTTTTATGATGGCCCTG
TGCCTTAGTAGTATTTATGAAGACTTGAAGATGTACCAGGTGGAGTTCAAGACCATGAATGCAAAGCTTCTGATG
GATCCTAAGAGGCAGATCTTTCTAGATCAAAACATGCTGGCAGTTATTGATGAGCTGATGCAGGCCCTGAATTTC
AACAGTGAGACTGTGCCACAAAAATCCTCCCTTGAAGAACCGGATTTTTATAAAACTAAAATCAAGCTCTGCATA
CTTCTTCATGCTTTCAGAATTCGGGCAGTGACTATTGATAGAGTGATGAGCTATCTGAATGCTTCC (5) Wild Type IL12B signal peptide Amino acids: (SEQ ID NO: 45)
MCHQQLVISWFSLVFLASPLVA (6) Wild Type IL12B signal peptide Nucleic acids: (SEQ ID NO: 46)
ATGTGTCACCAGCAGTTGGTCATCTCTTGGTTTTCCCTGGTTTTTCTGGCATCTCCCCTCGTGGCC

FIG. 2A. IL12 Levels
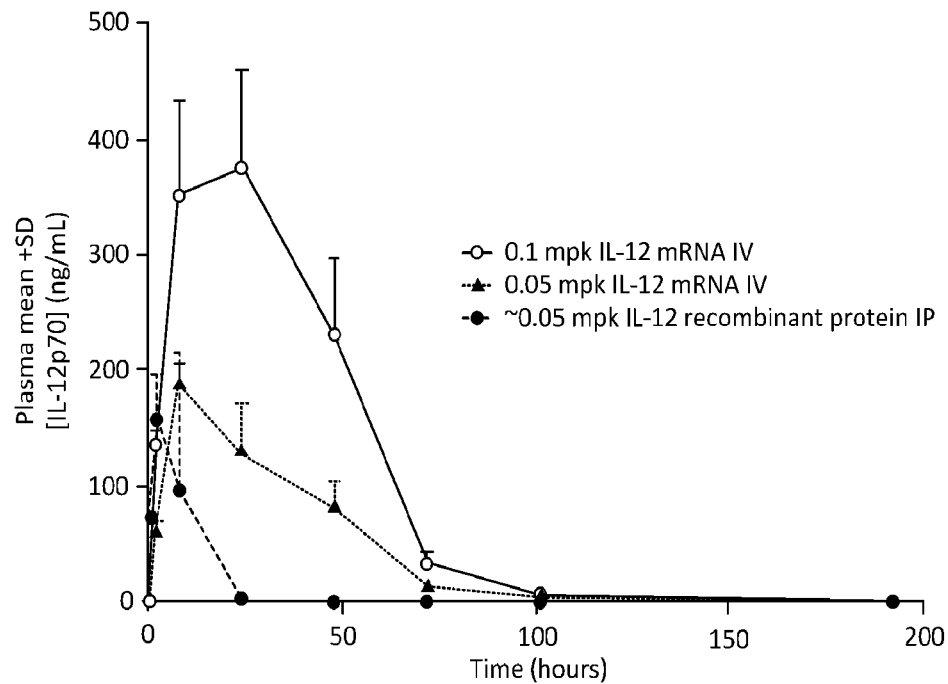
FIG. 2B. IFNγ Levels
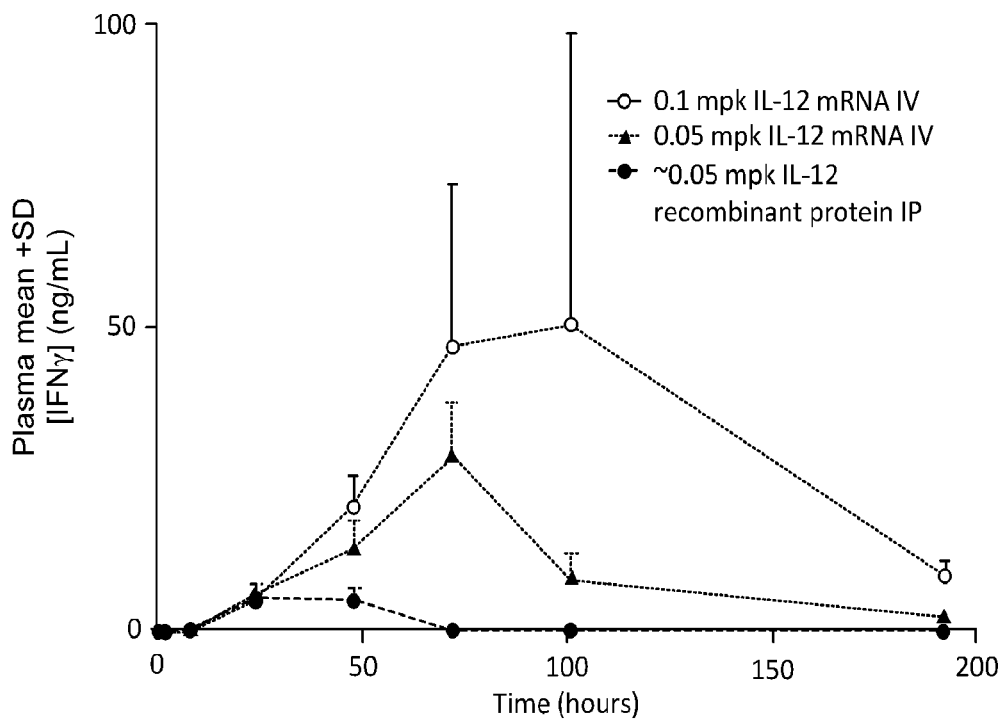

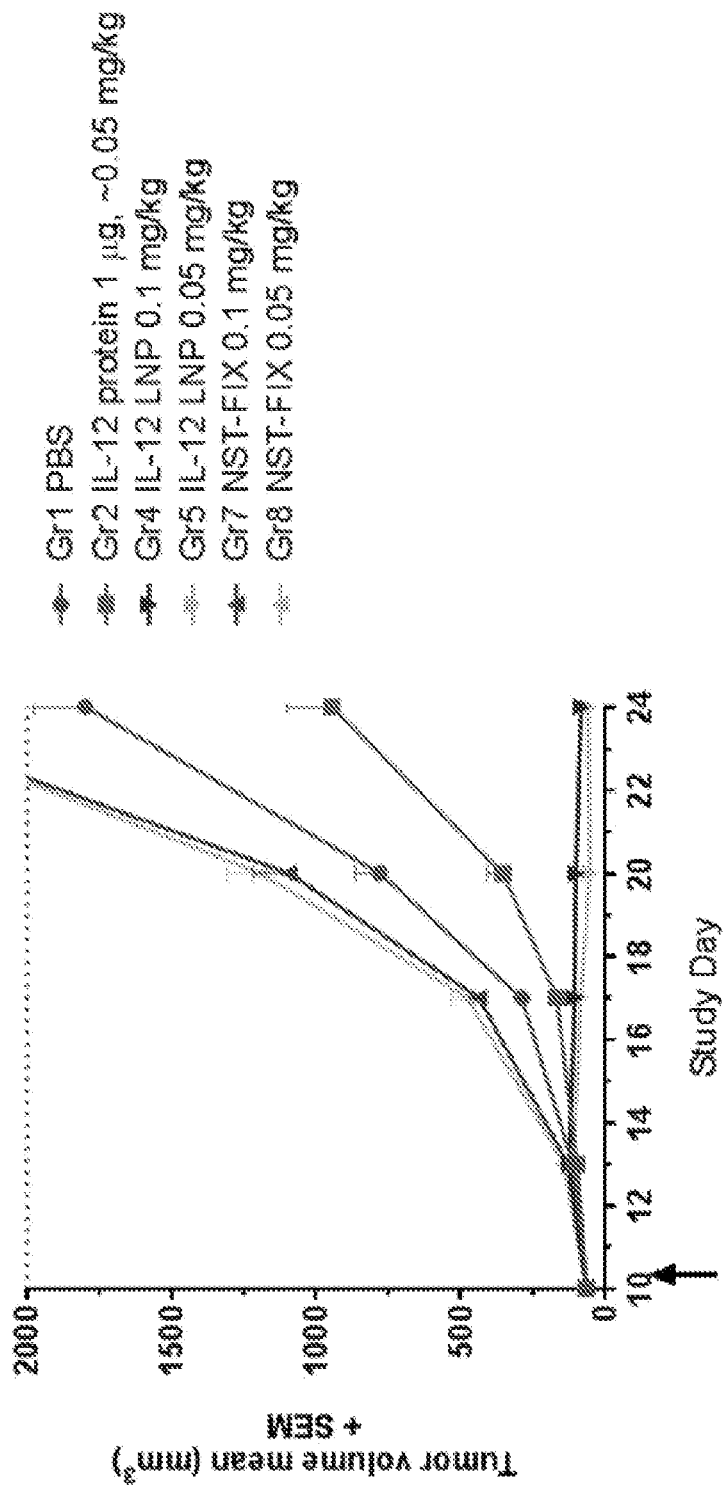
FIG. 3. A single IV dose of IL12 mRNA in LNP has robust efficacy

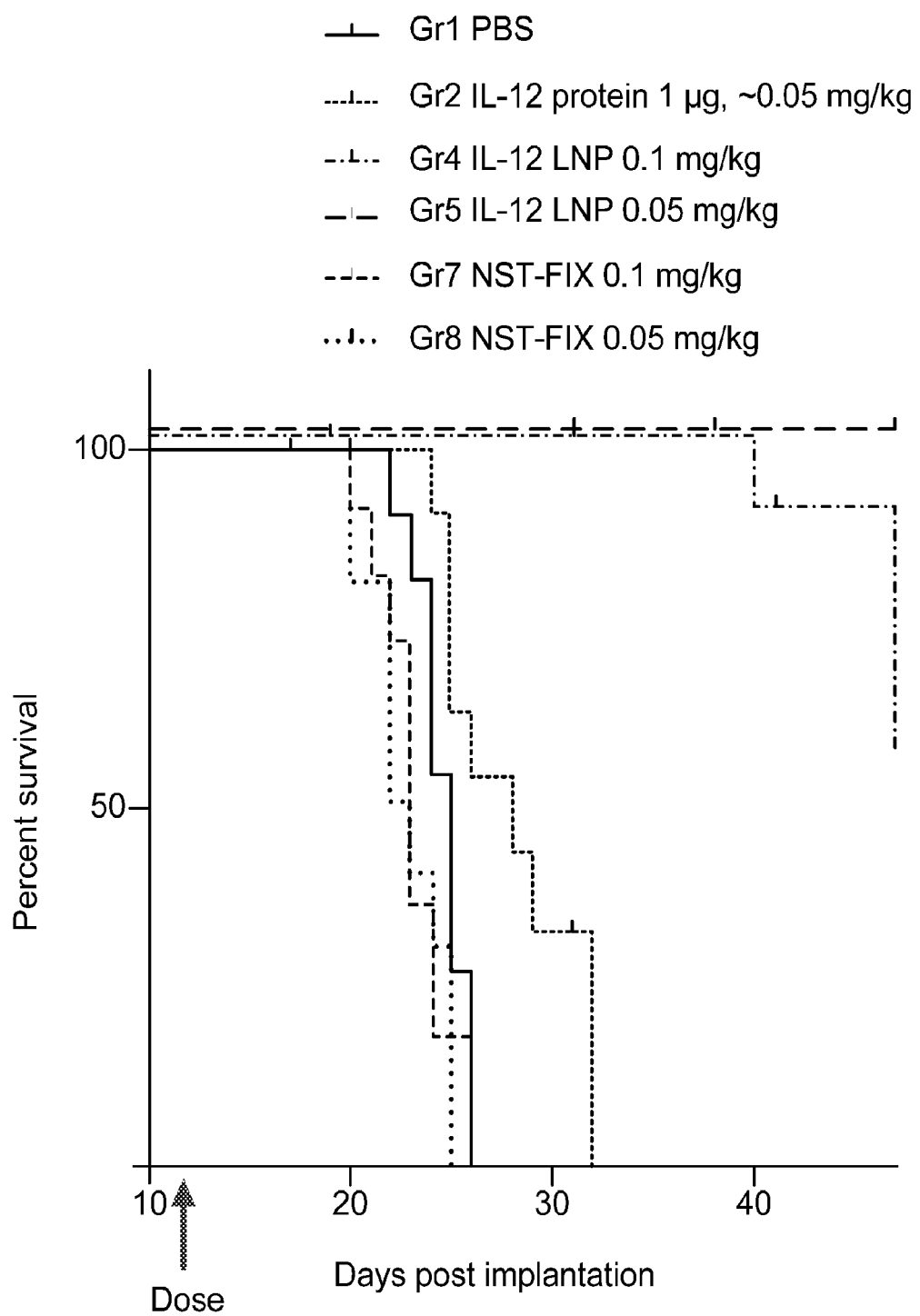

NST 5 μg

IL-12 miRless 5 μg

5 CRs

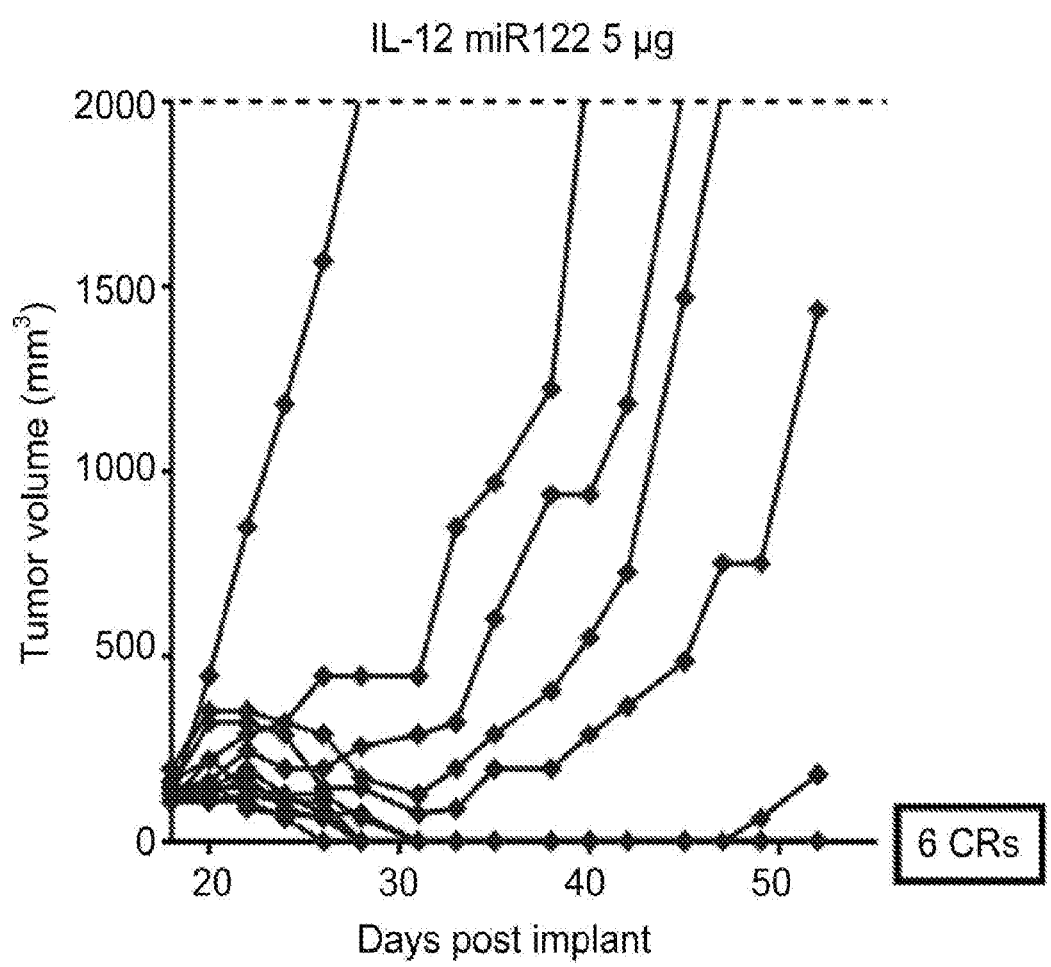

IL-12 miRless 0.5 µg

IL-12 miR122 0.5 µg

Plasma IFNγ

Tumor IFNγ

Plasma IP-10

Tumor IP-10

Plasma IL-6

Tumor IL-6

Plasma G-CSF

Tumor G-CSF

Plasma GROα

Tumor GROα

| Protein | Length | Theoretical Minimum U (%) | Theoretical Minimum U (abs) | | |
|---|---|---|---|---|---|
| IL12B WT | 306 | 10.78% | 99 | | |

| Nucleic Acid | Length | U Content (abs) | U Content (%) | U Content v WT (%) | U Content v Theoretical Minimum (%) |
|---|---|---|---|---|---|
| IL12B WT | 918 | 195 | 21.24% | 100.00% | 196.97% |
| MAX | | 275 | 29.96% | 141.03% | 277.78% |
| MIN | | 109 | 11.87% | 55.90% | 110.10% |
| MEAN | | 173.25 | 18.87% | 88.85% | 175.00% |
| MEDIAN | | 176 | 19.17% | 90.26% | 177.78% |
| STD DEV | | 44.19 | 4.81% | 22.66% | 44.63% |

FIG. 12A

| Protein | Length | Theoretical Maximum G (%) | Theoretical Maximum G (abs) | | |
|---|---|---|---|---|---|
| IL12B WT | 306 | 40.74% | 374 | | |

| Nucleic Acid | Length | G Content(abs) | G Content(%) | G Content v WT(%) | G Content v Theoretical Maximum (%) |
|---|---|---|---|---|---|
| IL12B WT | 918 | 243 | 26.47% | 100.00% | 64.97% |
| MAX | | 374 | 40.74% | 153.91% | 100.00% |
| MIN | | 219 | 23.86% | 90.12% | 58.56% |
| MEAN | | 260.55 | 28.38% | 107.22% | 69.67% |
| MEDIAN | | 249.5 | 27.18% | 102.67% | 66.71% |
| STD DEV | | 35.31 | 3.85% | 14.53% | 9.44% |

FIG. 12B

| Protein | Length | Theoretical Maximum C (%) | Theoretical Maximum C (abs) | | | |
|---|---|---|---|---|---|---|
| IL12B WT | 306 | 41.61% | 382 | | | |

| Nucleic Acid | Length | C Content (abs) | C Content (%) | C Content v WT (%) | C Content v Theoretical Maximum (%) |
|---|---|---|---|---|---|
| IL12B WT | 918 | 223 | 24.29% | 100.00% | 58.38% |
| MAX | | 279 | 30.39% | 125.11% | 73.04% |
| MIN | | 213 | 23.20% | 95.52% | 55.76% |
| MEAN | | 238.05 | 25.93% | 106.75% | 62.32% |
| MEDIAN | | 238.5 | 25.98% | 106.96% | 62.43% |
| STD DEV | | 18.41 | 2.01% | 8.26% | 4.82% |

FIG. 12C

| Protein | Length | Theoretical Maximum GC (%) | Theoretical Maximum GC (abs) | | | |
|---|---|---|---|---|---|---|
| IL12B WT | 306 | 65.25% | 599 | | | |

| Nucleic Acid | Length | GC Content (abs) | GC Content (%) | GC Content v WT (%) | GC Content v Theoretical Minimum (%) |
|---|---|---|---|---|---|
| IL12B WT | 918 | 466 | 50.76% | 100.00% | 77.80% |
| MAX | | 587 | 63.94% | 125.97% | 98.00% |
| MIN | | 449 | 48.91% | 96.35% | 74.96% |
| MEAN | | 498.6 | 54.31% | 107.00% | 83.24% |
| MEDIAN | | 489.5 | 53.32% | 105.04% | 81.72% |
| STD DEV | | 43.23 | 4.71% | 9.28% | 7.22% |

FIG. 12D

| Protein | Length | Theoretical Minimum U (%) | | | |
|---|---|---|---|---|---|
| IL12B WT | 306 | 10.78% | | | |
| Nucleic Acid | Length | Theoretical Minimum U (abs) | U Content (%) | U Content v WT (%) | U Content v Theoretical Minimum (%) |
| | | 99 | | | |
| IL12B WT | 918 | U Content (abs) | | | |
| MAX | | 195 | 21.24% | 100.00% | 196.97% |
| MIN | | 149 | 16.23% | 76.41% | 150.51% |
| MEAN | | 131 | 14.27% | 67.18% | 132.32% |
| MEDIAN | | 141.1 | 15.37% | 72.36% | 142.53% |
| STD DEV | | 141 | 15.36% | 72.31% | 142.42% |
| | | 5.37 | 0.58% | 2.75% | 5.42% |

FIG. 13A

| Protein | Length | Theoretical Maximum G (%) | | | |
|---|---|---|---|---|---|
| IL12B WT | 306 | 40.74% | | | |
| Nucleic Acid | Length | Theoretical Maximum G (abs) | G Content (%) | G Content v WT (%) | G Content v Theoretical Minimum (%) |
| | | 374 | | | |
| IL12B WT | 918 | G Content (abs) | | | |
| MAX | | 243 | 26.47% | 100.00% | 64.97% |
| MIN | | 294 | 32.03% | 120.99% | 78.61% |
| MEAN | | 279 | 30.39% | 114.81% | 74.60% |
| MEDIAN | | 287.35 | 31.30% | 118.25% | 76.83% |
| STD DEV | | 288 | 31.37% | 118.52% | 77.01% |
| | | 4.63 | 0.50% | 1.90% | 1.24% |

| Protein | Length | Theoretical Maximum C (%) | Theoretical Maximum C (abs) | | |
|---|---|---|---|---|---|
| IL12B WT | 306 | 41.61% | 382 | | |

| Nucleic Acid | Length | C Content (abs) | C Content (%) | C Content v WT (%) | C Content v Theoretical Maximum (%) |
|---|---|---|---|---|---|
| IL12B WT | 918 | 223 | 24.29% | 100.00% | 58.38% |
| MAX | | 279 | 30.39% | 125.11% | 73.04% |
| MIN | | 262 | 28.54% | 117.49% | 68.59% |
| MEAN | | 270.15 | 29.43% | 121.14% | 70.72% |
| MEDIAN | | 270 | 29.41% | 121.08% | 70.68% |
| STD DEV | | 4.76 | 0.52% | 2.13% | 1.25% |

FIG. 13D

| Protein | Length | Theoretical Maximum GC (%) | Theoretical Maximum GC (abs) | | |
|---|---|---|---|---|---|
| IL12B WT | 306 | 65.25% | 599 | | |

| Nucleic Acid | Length | GC Content (abs) | GC Content (%) | GC Content v WT (%) | GC Content v Theoretical Maximum (%) |
|---|---|---|---|---|---|
| IL12B WT | 918 | 466 | 50.76% | 100.00% | 77.80% |
| MAX | | 565 | 61.55% | 121.24% | 94.32% |
| MIN | | 547 | 59.59% | 117.38% | 91.32% |
| MEAN | | 557.5 | 60.73% | 119.64% | 93.07% |
| MEDIAN | | 557 | 60.68% | 119.53% | 92.99% |
| STD DEV | | 4.67 | 0.51% | 1.00% | 0.78% |

FIG. 14A

| Protein | Length | Theoretical Minimum U (%) | |
|---|---|---|---|
| IL12A WT | 197 | 12.86% | |

| Nucleic Acid | Length | U Content (abs) | Theoretical Minimum U (abs) | U Content (%) | U Content v WT (%) | U Content v Theoretical Minimum (%) |
|---|---|---|---|---|---|---|
| IL12A WT | 591 | 151 | 76 | 25.55% | 100.00% | 198.68% |
| MAX | | 189 | | 31.98% | 125.17% | 248.68% |
| MIN | | 83 | | 14.04% | 54.97% | 109.21% |
| MEAN | | 126.3 | | 21.37% | 83.64% | 166.18% |
| MEDIAN | | 125 | | 21.15% | 82.78% | 164.47% |
| STD DEV | | 28.03 | | 4.74% | 18.56% | 36.88% |

FIG. 14B

| Protein | Length | Theoretical Maximum G (%) | |
|---|---|---|---|
| IL12A WT | 197 | 34.69% | |

| Nucleic Acid | Length | G Content (abs) | Theoretical Maximum G (abs) | G Content (%) | G Content v WT (%) | G Content v Theoretical Maximum (%) |
|---|---|---|---|---|---|---|
| IL12A WT | 591 | 123 | 205 | 20.81% | 100.00% | 60.00% |
| MAX | | 205 | | 34.69% | 166.67% | 100.00% |
| MIN | | 108 | | 18.27% | 87.80% | 52.68% |
| MEAN | | 134.7 | | 22.79% | 109.51% | 65.71% |
| MEDIAN | | 131 | | 22.17% | 106.50% | 63.90% |
| STD DEV | | 22.88 | | 3.87% | 18.60% | 11.16% |

| Protein | Length | Theoretical Maximum C (%) | Theoretical Maximum C (abs) | | |
|---|---|---|---|---|---|
| IL12A WT | 197 | 43.82% | 259 | | |

| Nucleic Acid | Length | C Content (abs) | C Content (%) | C Content v WT (%) | C Content v Theoretical Maximum (%) |
|---|---|---|---|---|---|
| IL12A WT | 591 | 138 | 23.35% | 100.00% | 53.28% |
| | MAX | 191 | 32.32% | 138.41% | 73.75% |
| | MIN | 140 | 23.69% | 101.45% | 54.05% |
| | MEAN | 164.8 | 27.88% | 119.42% | 63.63% |
| | MEDIAN | 164 | 27.75% | 118.84% | 63.32% |
| | STD DEV | 12.22 | 2.07% | 8.85% | 4.72% |

FIG. 14C

| Protein | Length | Theoretical Maximum GC (%) | Theoretical Maximum GC (abs) | | |
|---|---|---|---|---|---|
| IL12A WT | 197 | 62.27% | 368 | | |

| Nucleic Acid | Length | GC Content (abs) | GC Content (%) | GC Content v WT (%) | GC Content v Theoretical Maximum (%) |
|---|---|---|---|---|---|
| IL12A WT | 591 | 261 | 44.16% | 100.00% | 70.92% |
| | MAX | 359 | 60.74% | 137.55% | 97.55% |
| | MIN | 265 | 44.84% | 101.53% | 72.01% |
| | MEAN | 299.5 | 50.68% | 114.75% | 81.39% |
| | MEDIAN | 293 | 49.58% | 112.26% | 79.62% |
| | STD DEV | 29.23 | 4.95% | 11.20% | 7.94% |

FIG. 14D

| Protein | Length | Theoretical Minimum U (%) | | |
|---|---|---|---|---|
| IL12A WT | 197 | 12.86% | | |

| Nucleic Acid | Length | Theoretical Minimum U (abs) | U Content (abs) | U Content (%) | U Content v WT (%) | U Content v Theoretical Maximum (%) |
|---|---|---|---|---|---|---|
| IL12A WT | 591 | 76 | 151 | 25.55% | 100.00% | 198.68% |
| | MAX | | 109 | 18.44% | 72.19% | 143.42% |
| | MIN | | 95 | 16.07% | 62.91% | 125.00% |
| | MEAN | | 101.9 | 17.24% | 67.48% | 134.08% |
| | MEDIAN | | 102 | 17.26% | 67.55% | 134.21% |
| | STD DEV | | 4.27 | 0.72% | 2.83% | 5.61% |

FIG. 15A

| Protein | Length | Theoretical Maximum G (%) | | |
|---|---|---|---|---|
| IL12A WT | 197 | 34.69% | | |

| Nucleic Acid | Length | Theoretical Maximum G (abs) | G Content (abs) | G Content (%) | G Content v WT (%) | G Content v Theoretical Maximum (%) |
|---|---|---|---|---|---|---|
| IL12A WT | 591 | 205 | 123 | 20.81% | 100.00% | 60.00% |
| | MAX | | 160 | 27.07% | 130.08% | 78.05% |
| | MIN | | 147 | 24.87% | 119.51% | 71.71% |
| | MEAN | | 153.45 | 25.96% | 124.76% | 74.85% |
| | MEDIAN | | 153.5 | 25.97% | 124.80% | 74.88% |
| | STD DEV | | 3.38 | 0.57% | 2.75% | 1.65% |

FIG. 15B

| Protein | Length | Theoretical Maximum C (%) | Theoretical Maximum C (abs) | | |
|---|---|---|---|---|---|
| IL12A WT | 197 | 43.82% | 259 | | |
| Nucleic Acid | Length | C Content (abs) | C Content (%) | C Content v WT (%) | C Content v Theoretical Maximum (%) |
| IL12A WT | 591 | | | | |
| MAX | | 138 | 23.35% | 100.00% | 53.28% |
| MIN | | 195 | 32.99% | 141.30% | 75.29% |
| MEAN | | 179 | 30.29% | 129.71% | 69.11% |
| MEDIAN | | 187.8 | 31.78% | 136.09% | 72.51% |
| STD DEV | | 187.5 | 31.73% | 135.87% | 72.39% |
| | | 4.05 | 0.68% | 2.93% | 1.56% |

FIG. 15C

| Protein | Length | Theoretical Maximum GC (%) | Theoretical Maximum GC (abs) | | |
|---|---|---|---|---|---|
| IL12A WT | 197 | 62.27% | 368 | | |
| Nucleic Acid | Length | GC Content (abs) | GC Content (%) | GC Content v WT (%) | GC Content v Theoretical Maximum (%) |
| IL12A WT | 591 | | | | |
| MAX | | 261 | 44.16% | 100.00% | 70.92% |
| MIN | | 350 | 59.22% | 134.10% | 95.11% |
| MEAN | | 337 | 57.02% | 129.12% | 91.58% |
| MEDIAN | | 341.25 | 57.74% | 130.75% | 92.73% |
| STD DEV | | 340 | 57.53% | 130.27% | 92.39% |
| | | 4.08 | 0.69% | 1.56% | 1.11% |

FIG. 15D

IL12B (w/o SP) G5 SEQUENCES

| Sequence | GC | GC 1st | GC 2nd | GC 3rd |
|---|---|---|---|---|
| IL12B_WT | 50.76 | 48.04 | 43.14 | 61.11 |
| MAX | 63.94 | 50.65 | 43.14 | 100 |
| MIN | 48.91 | 48.04 | 43.14 | 54.25 |
| MEAN | 54.31 | 49.46 | 43.14 | 70.34 |
| MEDIAN | 53.325 | 49.35 | 43.14 | 66.34 |
| STD DEV | 4.71 | 0.80 | 0.00 | 14.42 |

FIG. 16A

IL12B (w/o SP) G6 SEQUENCES

| Sequence | GC | GC 1st | GC 2nd | GC 3rd |
|---|---|---|---|---|
| IL12B_WT | 50.76 | 48.04 | 43.14 | 61.11 |
| MAX | 61.55 | 51.63 | 43.14 | 91.83 |
| MIN | 59.59 | 49.35 | 43.14 | 85.29 |
| MEAN | 60.73 | 50.33 | 43.14 | 88.73 |
| MEDIAN | 60.68 | 50.33 | 43.14 | 88.725 |
| STD DEV | 0.51 | 0.61 | 0.00 | 1.60 |

FIG. 16B

IL12A (w/o SP) G5 SEQUENCES

| Sequence | GC | GC 1st | GC 2nd | GC 3rd |
|---|---|---|---|---|
| IL12A_WT | 44.16 | 45.18 | 35.53 | 51.78 |
| MAX | 60.74 | 48.73 | 35.53 | 100 |
| MIN | 44.84 | 43.65 | 35.53 | 52.28 |
| MEAN | 50.68 | 46.35 | 35.53 | 70.15 |
| MEDIAN | 49.58 | 46.7 | 35.53 | 67.765 |
| STD DEV | 4.94 | 1.44 | 0.00 | 14.35 |

FIG. 16C

IL12B (w/o SP) G6 SEQUENCES

| Sequence | GC | GC 1st | GC 2nd | GC 3rd |
|---|---|---|---|---|
| IL12A_WT | 44.16 | 45.18 | 35.53 | 51.78 |
| MAX | 59.22 | 51.27 | 35.53 | 93.91 |
| MIN | 57.02 | 46.7 | 35.53 | 85.79 |
| MEAN | 57.74 | 48.45 | 35.53 | 89.24 |
| MEDIAN | 57.53 | 48.22 | 35.53 | 88.83 |
| STD DEV | 0.69 | 1.02 | 0.00 | 1.80 |

Negative controls:

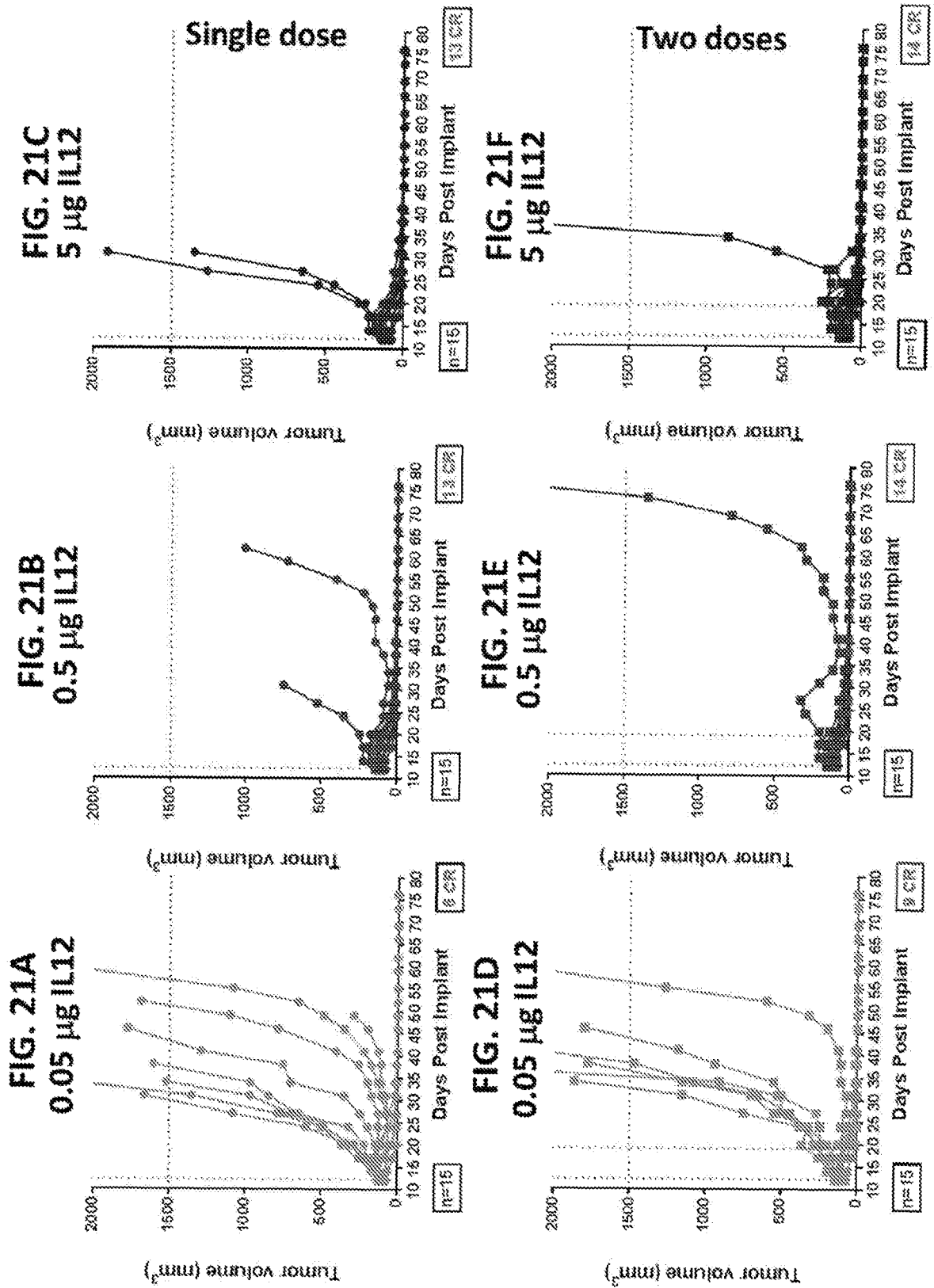

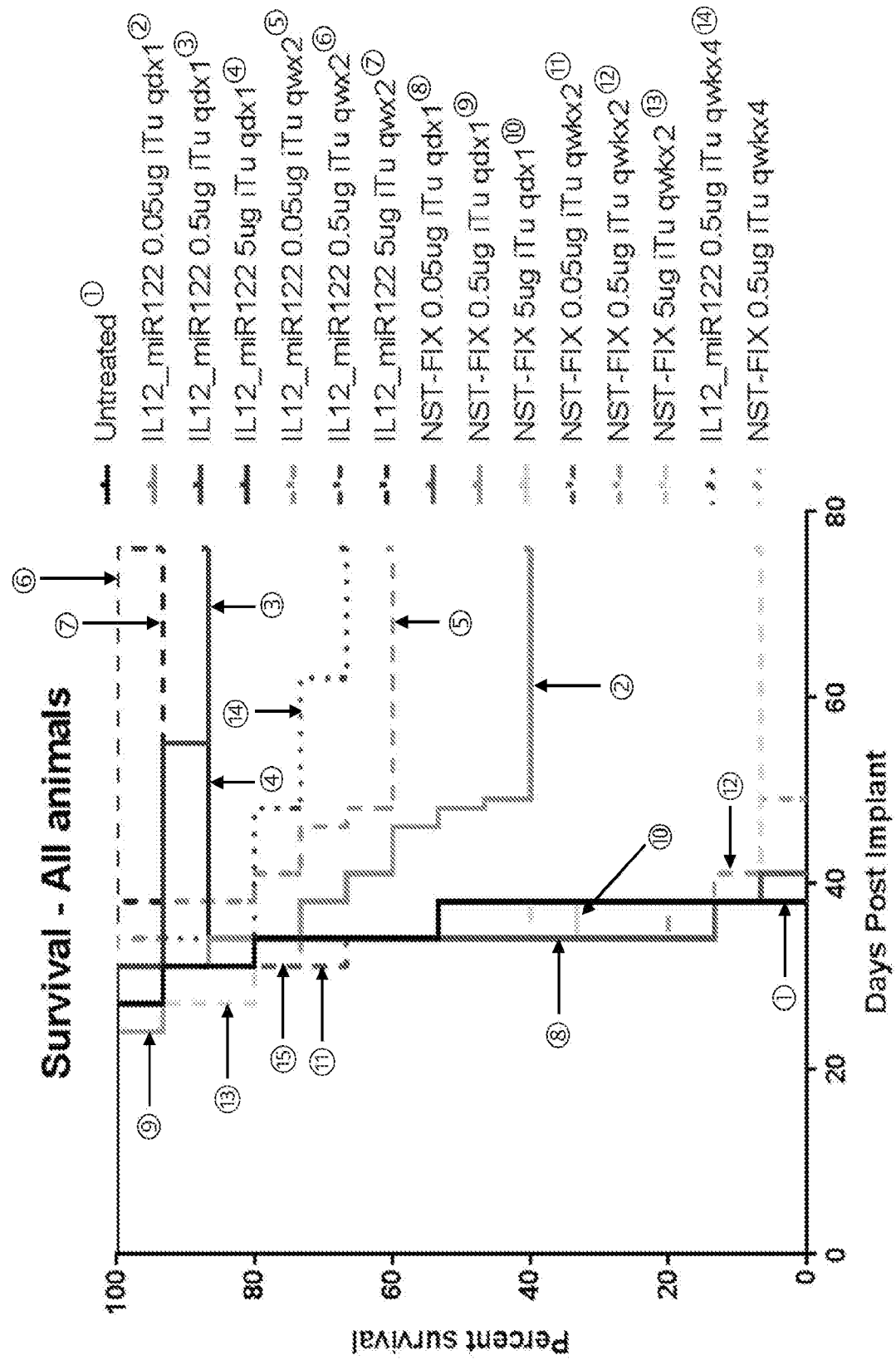

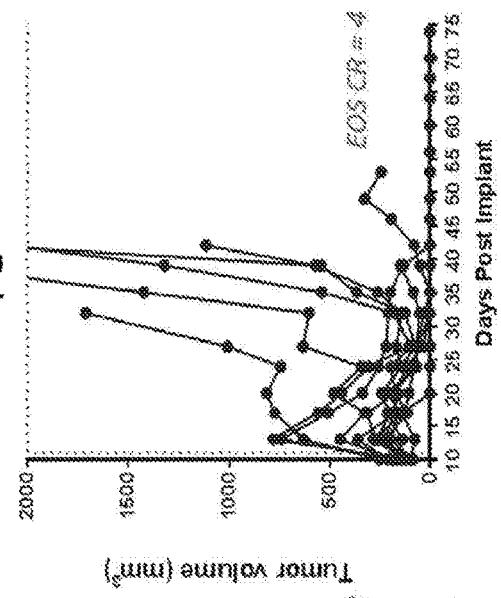
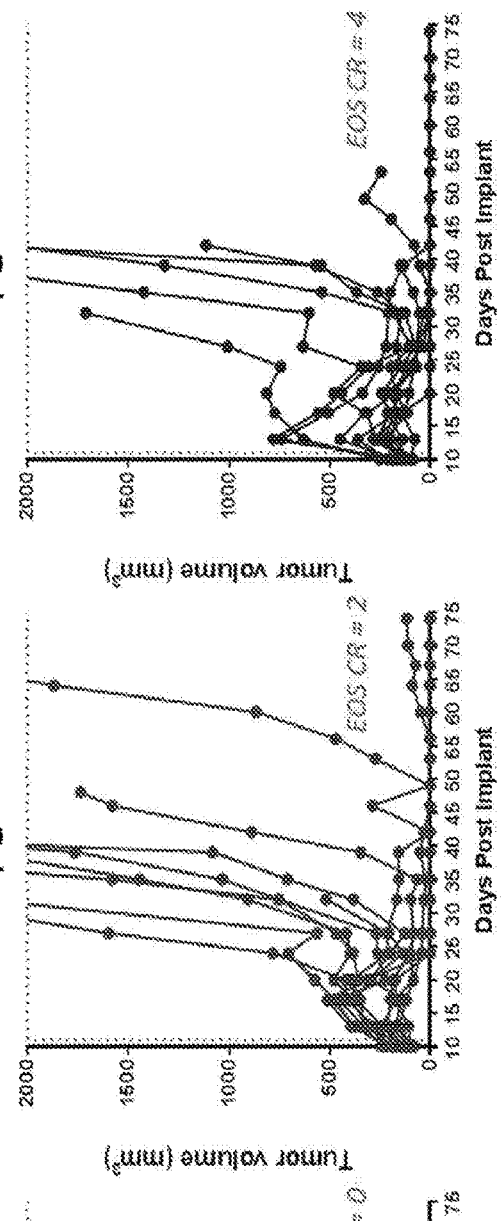
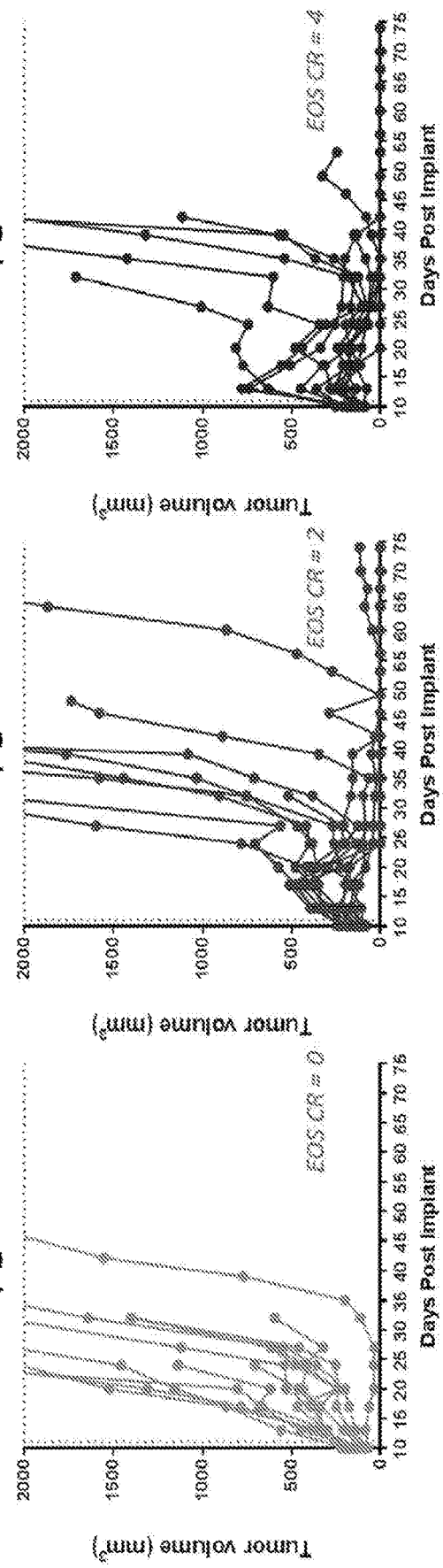
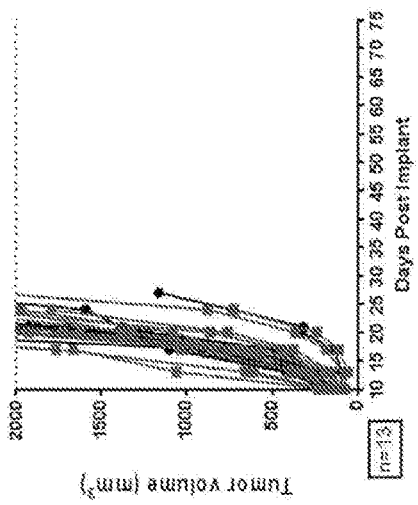

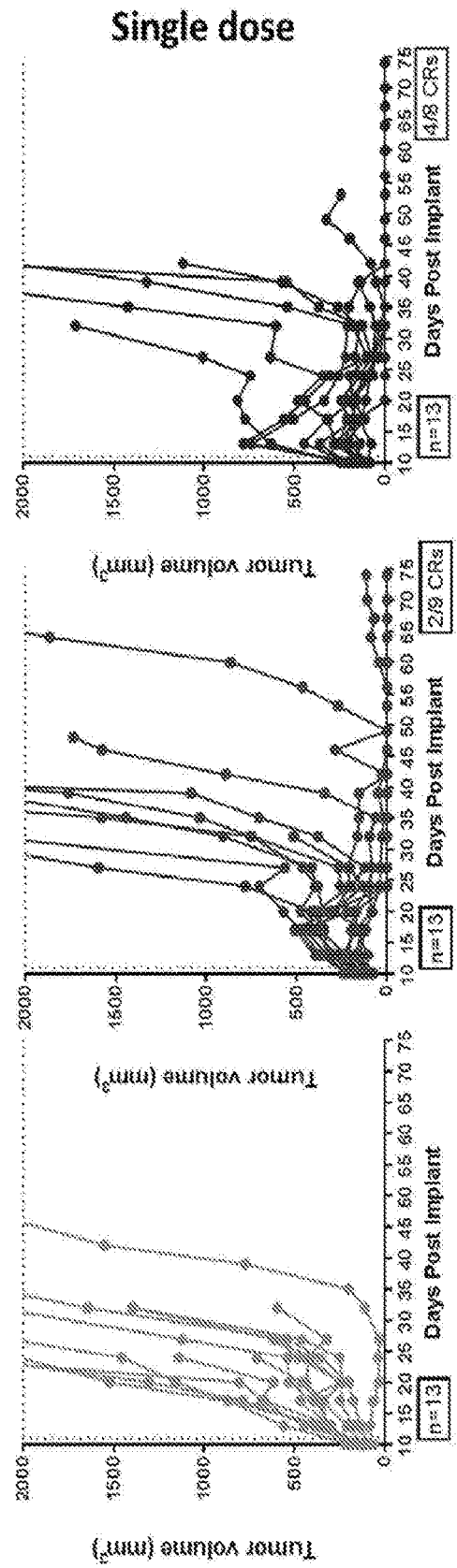
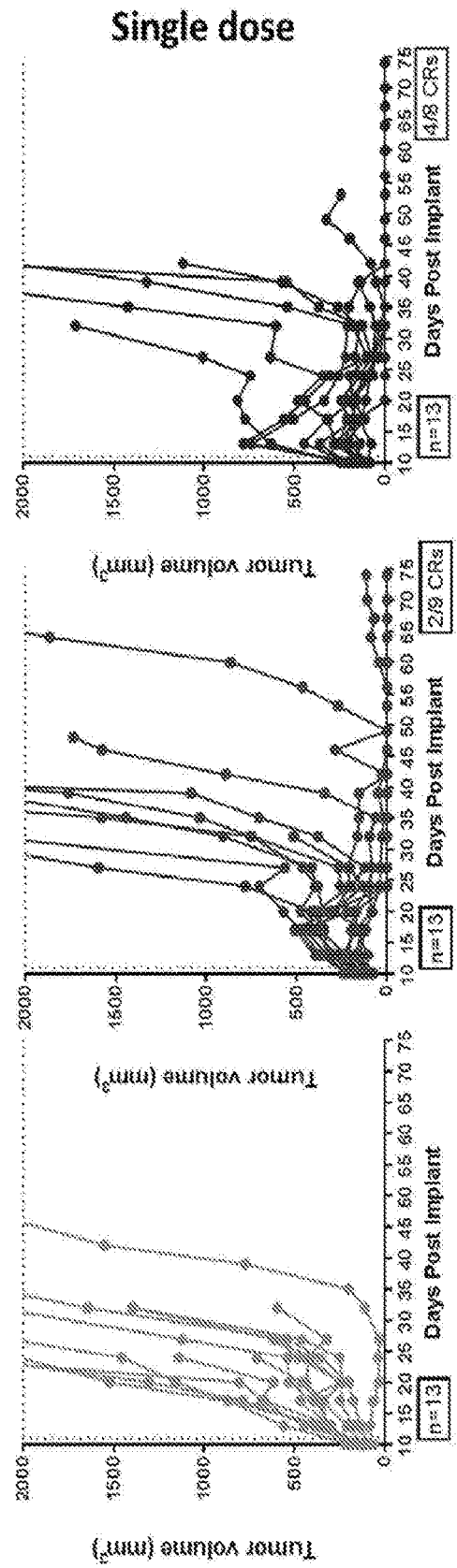
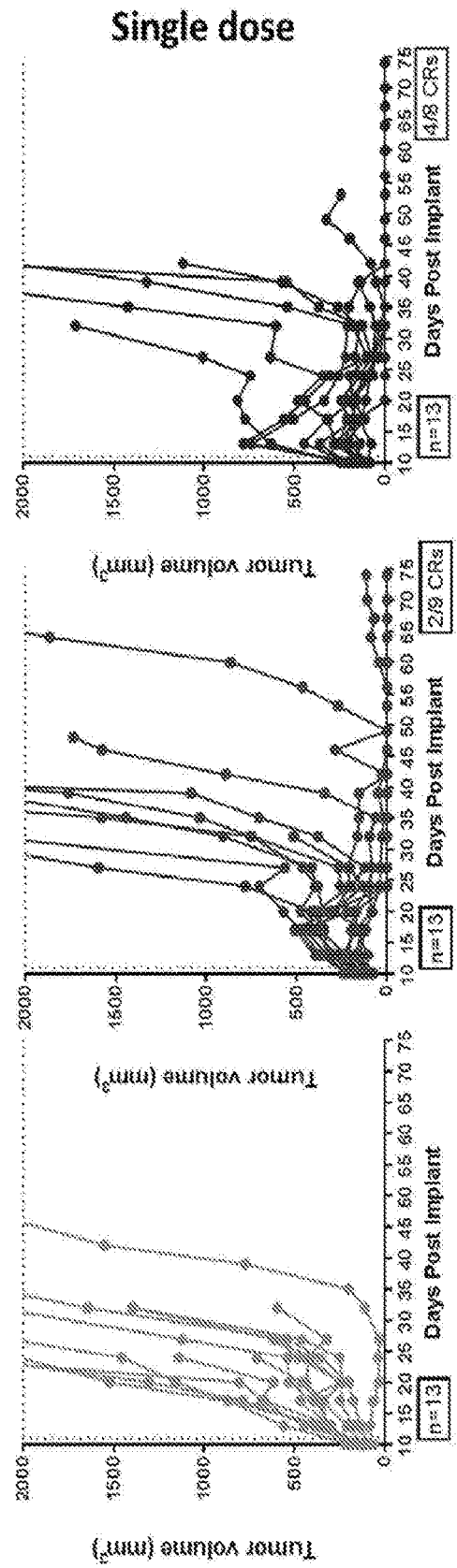
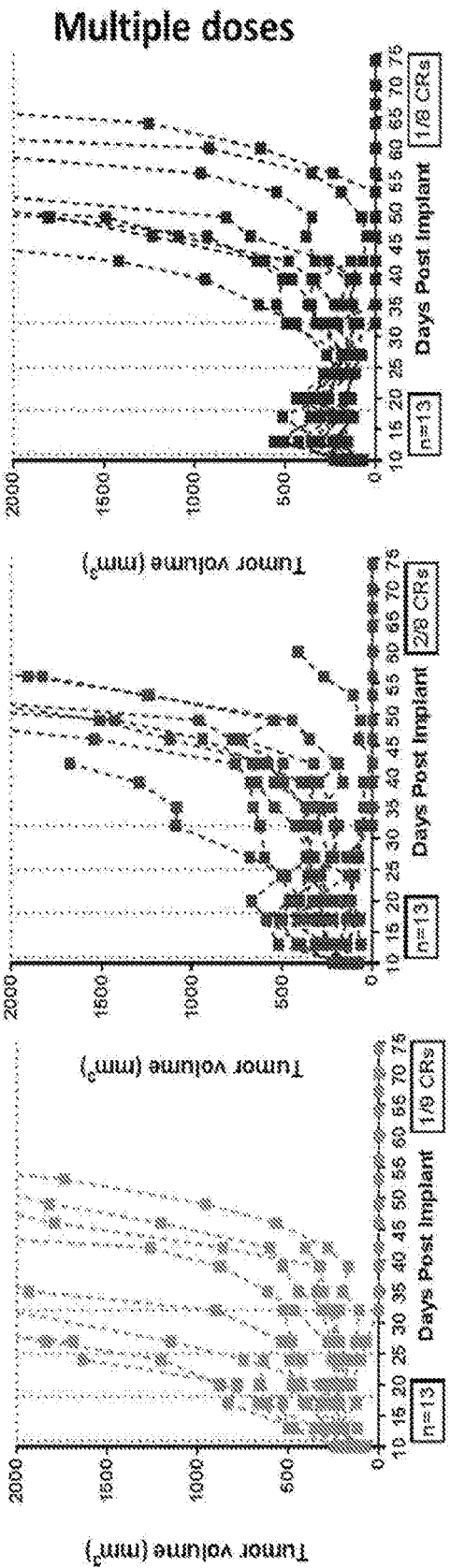
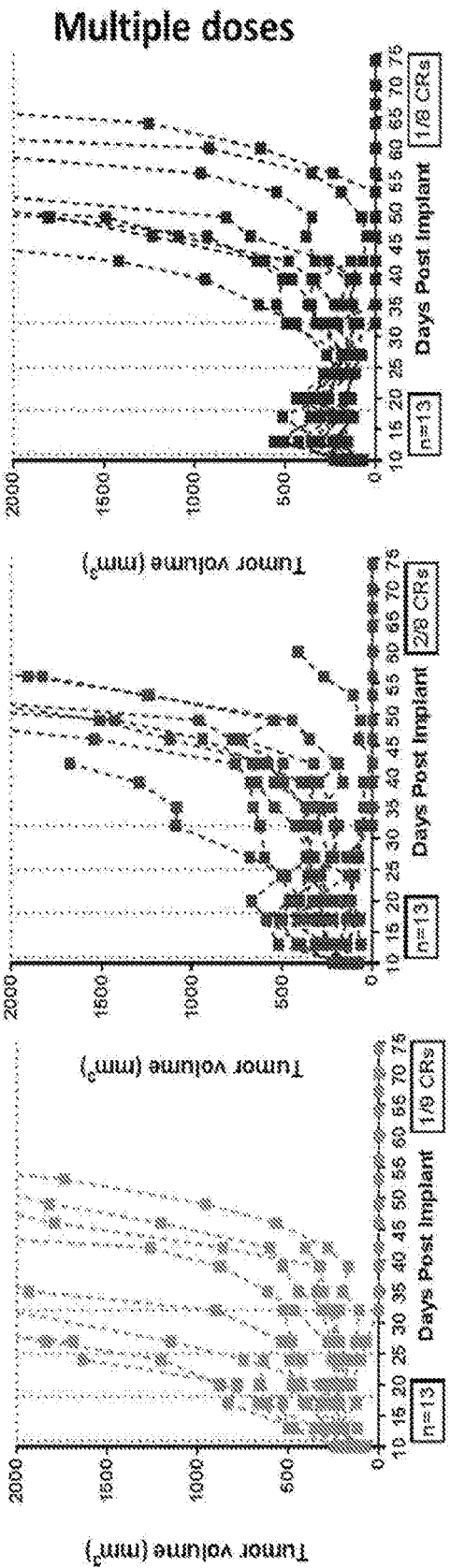
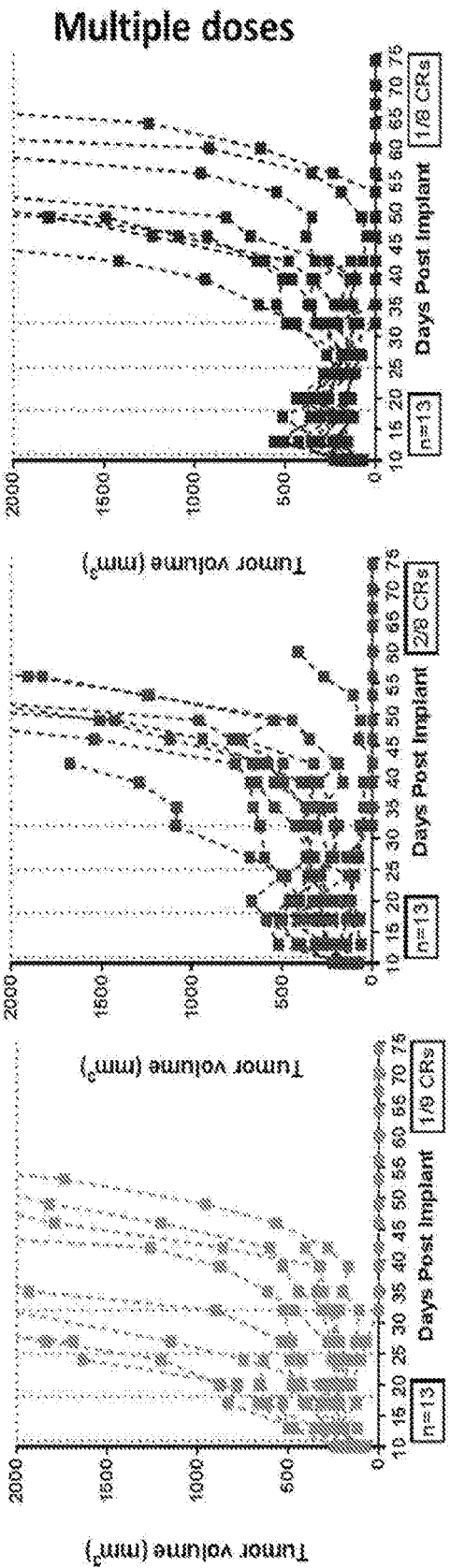

FIG. 25
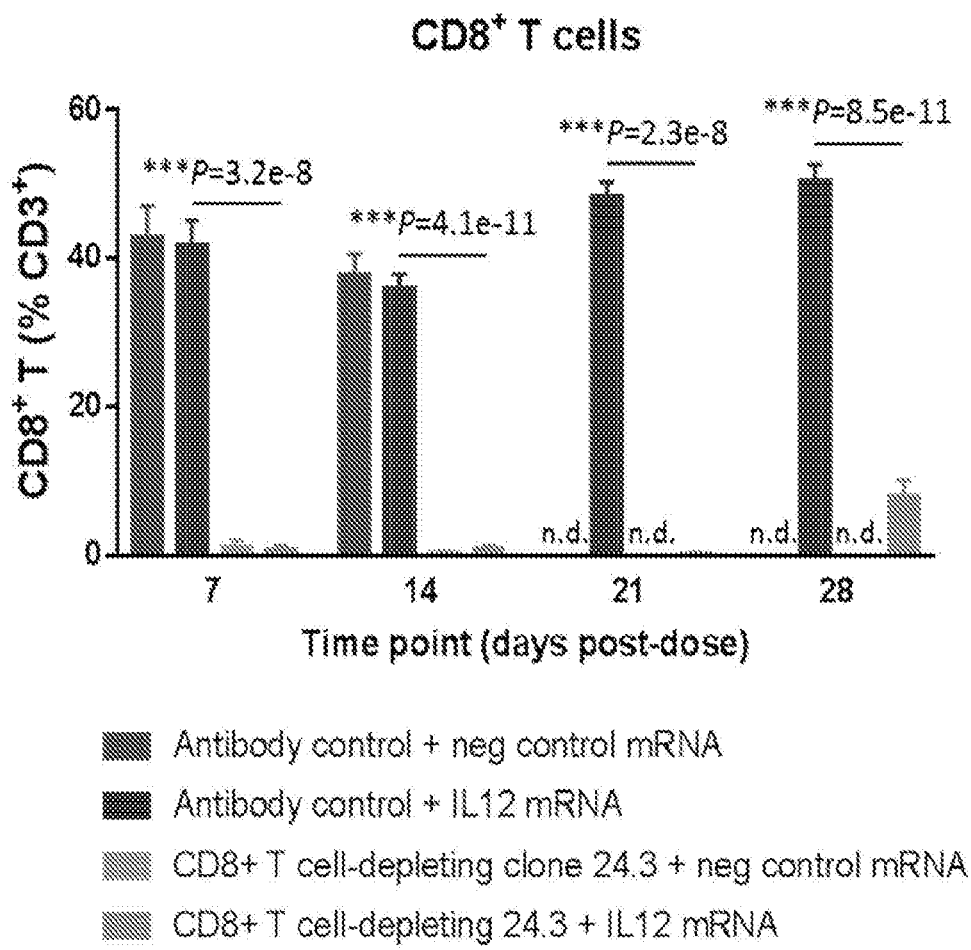
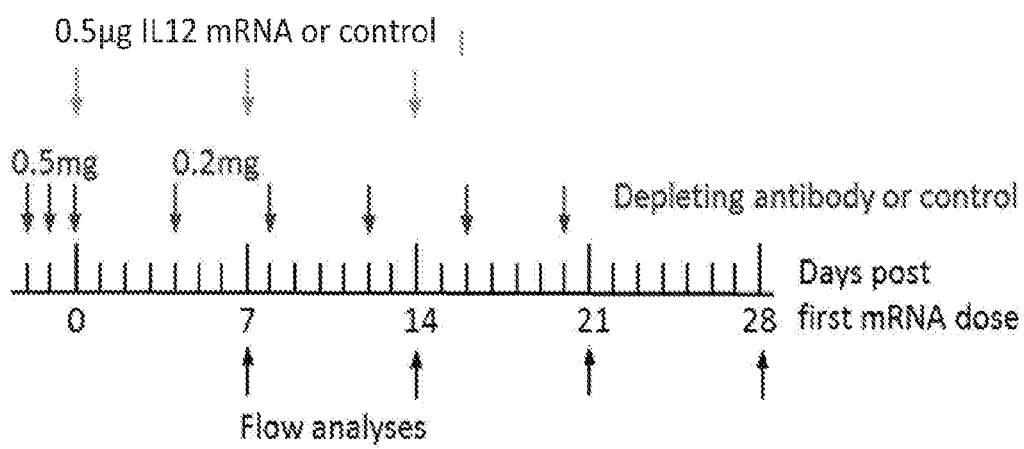

MC38-R

B16F10-AP3

CD69 early activation marker expression on CD8+ T cells

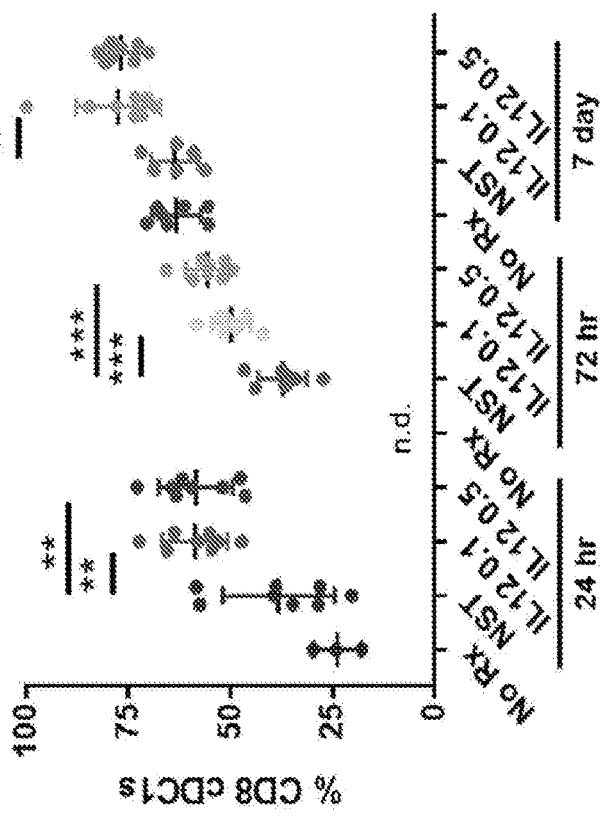
FIG. 32A
FIG. 32B
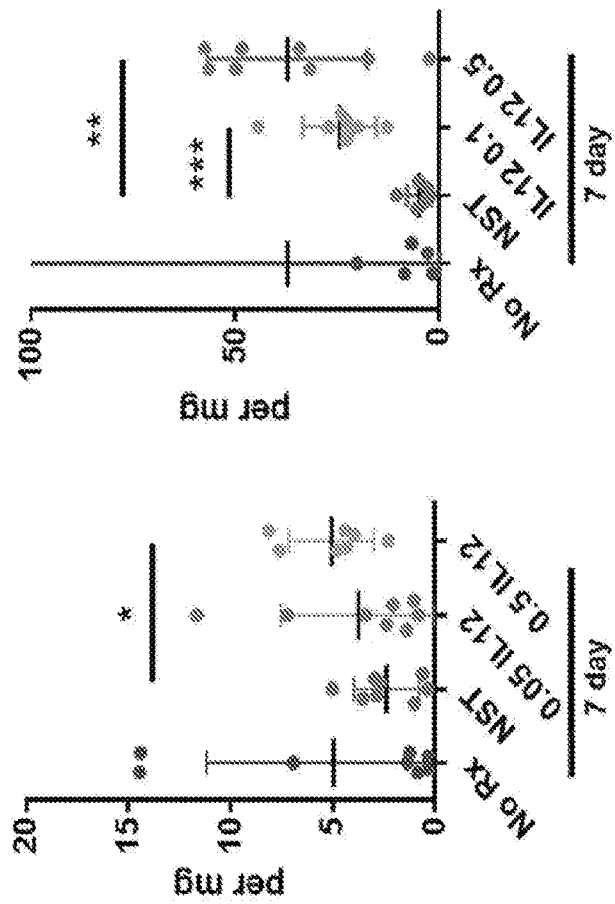
FIG. 32C

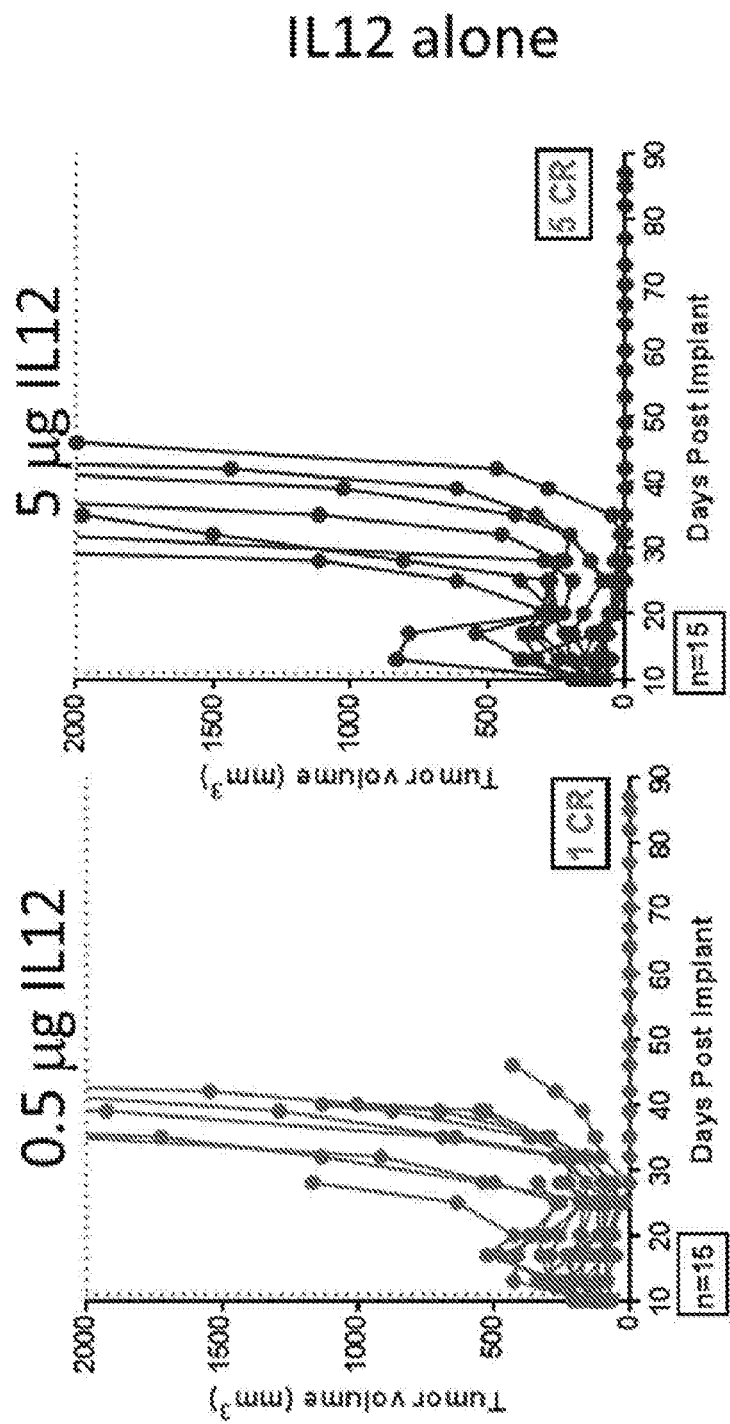

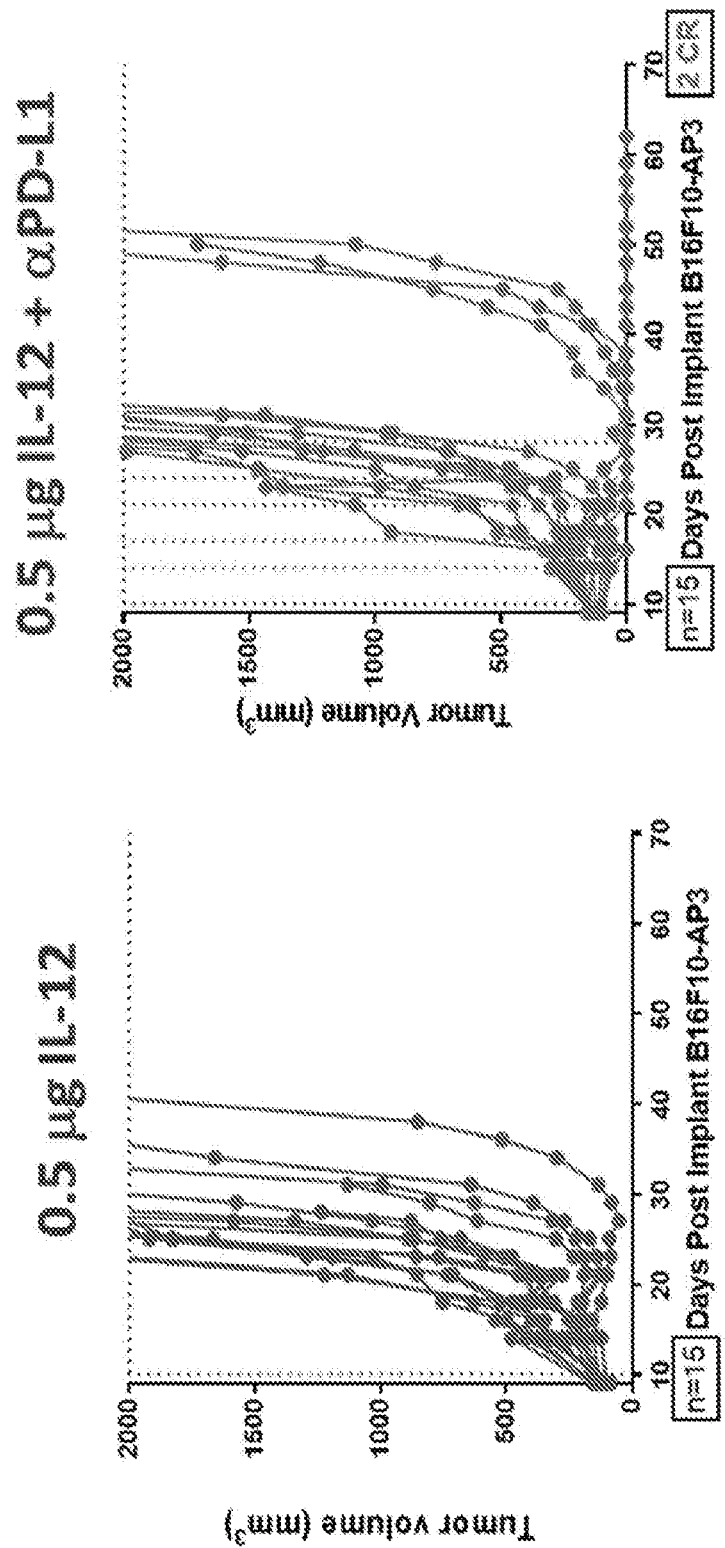

FIG. 36A
FIG. 36B
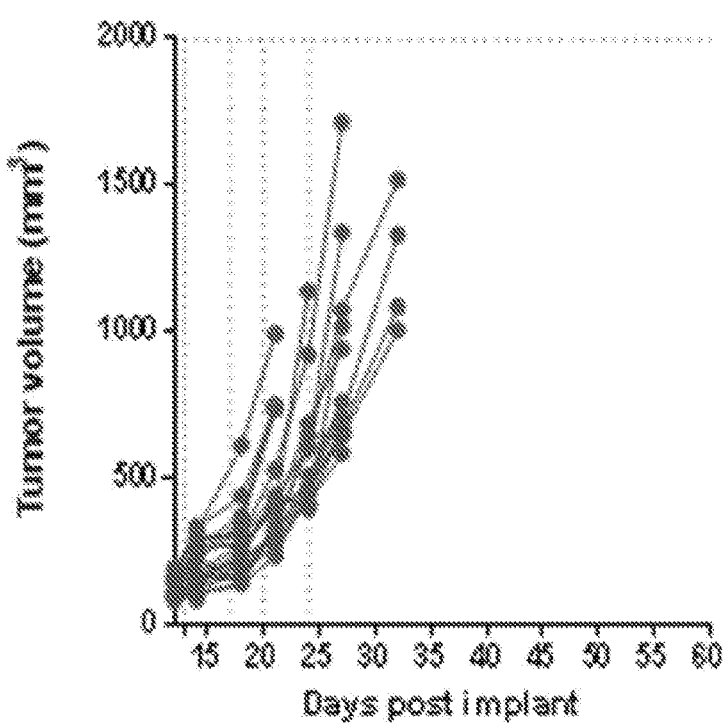
FIG. 36C
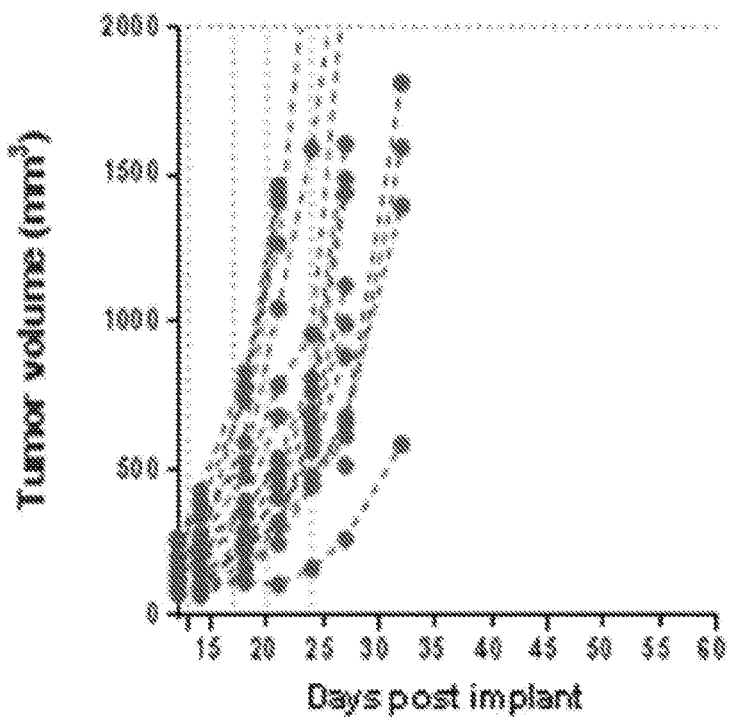

~3/20 CRs

~16/20 CRs

POLYNUCLEOTIDES ENCODING INTERLEUKIN-12 (IL12) AND USES THEREOF

CROSS-REFERENCE TO RELATED APPLICATIONS

This application is a continuation of International Application No. PCT/US2017/033422, filed May 18, 2017, which claims the benefit of U.S. Provisional Patent Application Ser. No. 62/338,483, filed May 18, 2016, and U.S. Provisional Patent Application Ser. No. 62/443,693, filed Jan. 7, 2017. The entire contents of the above-referenced patent applications are incorporated herein by this reference.

REFERENCE TO SEQUENCE LISTING SUBMITTED ELECTRONICALLY

The instant application contains a Sequence Listing which has been submitted in ASCII format via EFS-Web and is hereby incorporated by reference in its entirety. The name of the text file containing the Sequence Listing is Said ASCII copy, created on Nov. 15, 2018, is named MDN_714PCCN_Sequence_Listing and is 390121 bytes in size.

BACKGROUND

Interleukin-12 (IL12) is a pro-inflammatory cytokine that plays an important role in innate and adaptive immunity. Gately, M K et al., *Annu Rev Immunol.* 16: 495-521 (1998). IL12 functions primarily as a 70 kDa heterodimeric protein consisting of two disulfide-linked p35 and p40 subunits. IL12 p40 homodimers do exist, but other than functioning as an antagonist that binds the IL12 receptor, they do not appear to mediate a biologic response. Id. The precursor form of the IL12 p40 subunit (NM_002187; P29460; also referred to as IL12B, natural killer cell stimulatory factor 2, cytotoxic lymphocyte maturation factor 2) is 328 amino acids in length, while its mature form is 306 amino acids long. The precursor form of the IL12 p35 subunit (NM_000882; P29459; also referred to as IL12A, natural killer cell stimulatory factor 1, cytotoxic lymphocyte maturation factor 1) is 219 amino acids in length and the mature form is 197 amino acids long. Id. The genes for the IL12 p35 and p40 subunits reside on different chromosomes and are regulated independently of each other. Gately, M K et al., *Annu Rev Immunol.* 16: 495-521 (1998). Many different immune cells (e.g., dendritic cells, macrophages, monocytes, neutrophils, and B cells) produce IL12 upon antigenic stimuli. The active IL12 heterodimer is formed following protein synthesis. Id.

Due to its ability to activate both NK cells and cytotoxic T cells, IL12 protein has been studied as a promising anti-cancer therapeutic since 1994. See Nastala, C. L. et al., *J Immunol* 153: 1697-1706 (1994). But despite high expectations, early clinical studies did not yield satisfactory results. Lasek W. et al., *Cancer Immunol Immunother* 63: 419-435, 424 (2014). Repeated administration of IL12, in most patients, led to adaptive response and a progressive decline of IL12-induced interferon gamma (IFN-γ) levels in blood. Id. Moreover, while it was recognized that IL12-induced anti-cancer activity is largely mediated by the secondary secretion of IFNγ, the concomitant induction of IFN-γ along with other cytokines (e.g., TNF-α) or chemokines (IP-10 or MIG) by IL12 caused severe toxicity. Id.

In addition to the negative feedback and toxicity, the marginal efficacy of the IL12 therapy in clinical settings may be caused by the strong immunosuppressive environment in humans. Id. To minimize IFN-γ toxicity and improve IL12 efficacy, scientists tried different approaches, such as different dose and time protocols for IL12 therapy. See Sacco, S. et al., *Blood* 90: 4473-4479 (1997); Leonard, J. P. et al., *Blood* 90: 2541-2548 (1997); Coughlin, C. M. et al., *Cancer Res.* 57: 2460-2467 (1997); Asselin-Paturel, C. et al., *Cancer* 91: 113-122 (2001); and Saudemont, A. et al., *Leukemia* 16: 1637-1644 (2002). Nonetheless, these approaches have not significantly impacted patient survival. Kang, W. K., et al., *Human Gene Therapy* 12: 671-684 (2001).

Currently, a number of IL12 clinical trials are on-going. Though these multiple clinical trials have been on-going for nearly 20 years since the first human clinical trial of IL12 in 1996, an FDA-approved IL12 product is still not available. Thus, there is a need in the art for an improved therapeutic approach for using IL12 to treat tumors.

BRIEF SUMMARY

The present disclosure provides mRNA therapeutics for the treatment of cancer. The mRNA therapeutics of the disclosure are particularly well-suited for the treatment of cancer as the technology provides for the intracellular delivery of mRNA encoding immune modulating polypeptides (for example, immune stimulating polypeptides, such as IL-12, and the like, useful in immuno-oncology ("IO")), followed by de novo synthesis of functional proteins within target cells, e.g., within target cells in tumors. The disclosure features therapeutic mRNAs having modified nucleotides to (1) minimize unwanted immune activation (e.g., the innate immune response associated with in vivo introduction of foreign nucleic acids) and (2) optimize the translation efficiency of mRNA to protein. Exemplary aspects of the disclosure feature therapeutic mRNAs having a combination of nucleotide modifications to reduce the innate immune response and sequence optimization, in particular, within the open reading frame (ORF) of therapeutic mRNAs encoding immune modulating polypeptides (e.g., immune stimulating polypeptides such as IL-12) to enhance protein expression.

In other aspects, the mRNA therapeutic technology of the disclosure features delivery of mRNA(s) encoding immune modulating (e.g., immune stimulating) polypeptides via a lipid nanoparticle (LNP) delivery system. In exemplary embodiments, the mRNA therapeutic technology of the disclosure features delivery of mRNA(s) encoding immune modulating polypeptides into tumors via a lipid nanoparticle (LNP) delivery system. The disclosure also features novel ionizable lipid-based LNPs which have improved properties when combined with mRNA(s) encoding immune modulating (e.g., immune stimulating) polypeptides and administered in vivo, for example, cellular uptake, intracellular transport and/or endosomal release or endosomal escape. The LNP formulations of the disclosure also demonstrate reduced immunogenicity associated with the in vivo administration of LNPs.

Certain aspects of the present disclosure are directed to a method of reducing the size of a tumor or inhibiting growth of a tumor in a subject in need thereof comprising administering to the subject an effective amount of a composition comprising one or more polynucleotides encoding an IL-12 polypeptide, wherein the polynucleotide comprises an open reading frame ("ORF") encoding an interleukin 12 p40 subunit ("IL12B") polypeptide and an interleukin 12 p35 subunit ("IL12A") polypeptide. In some embodiments, the method further comprises administering to the subject an effective amount of a composition comprising a polynucleotide comprising an ORF encoding a checkpoint inhibitor polypeptide or an effective amount of a composition comprising a checkpoint inhibitor polypeptide. In some embodiments, the checkpoint inhibitor polypeptide inhibits PD1, PD-L1, CTLA-4, or a combination thereof. In certain embodiments, the checkpoint inhibitor polypeptide comprises an antibody. In some embodiments, administering the composition activates T cells in the subject.

Another aspect of the present disclosure is directed to a method of activating T cells in a subject in need thereof comprising administering to the subject an effective amount of a composition comprising one or more polynucleotides encoding an IL-12 polypeptide, wherein the polynucleotide comprises an ORF encoding an IL12B polypeptide and an IL12A polypeptide. In some embodiments, the T cell activation comprises inducing T cell proliferation. In some embodiments, the T cell activation comprises inducing T cell infiltration in the tumor or increasing the number of tumor-infiltrating T cells. In some embodiments, the T cell activation comprises inducing a memory T cell response. In some embodiments, the activated T cells comprise CD4$^+$ T cells, CD8$^+$ T cells, or both. In certain embodiments, administering the composition alone or in combination with a composition comprising a polynucleotide comprising an ORF encoding a checkpoint inhibitor polypeptide or a composition comprising a checkpoint inhibitor polypeptide increases an effector to suppressor T cell ratio in the tumor. In some embodiments, administering the composition further increases the number of activated NK cells in the subject. In some embodiments, administering the composition increases cross-presenting dendritic cells in the tumor of the subject. In some embodiments, administering the composition reduces the size of a distal tumor or inhibits growth of a distal tumor in the subject.

Another aspect of the present disclosure is directed to a method of increasing an effector to suppressor T cell ratio in a tumor of a subject in need thereof comprising administering to the subject an effective amount of a composition comprising one or more polynucleotides encoding an IL-12 polypeptide, wherein the polynucleotide comprises an ORF encoding an IL12B polypeptide and an IL12A polypeptide. In some embodiments, the effector to suppressor T cell ratio is a CD8$^+$ T cells:T regulatory (Treg) cells ratio.

Another aspect of the present disclosure is directed to a method of increasing the number of activated Natural Killer (NK) cells in a subject in need thereof comprising administering to the subject an effective amount of a composition comprising one or more polynucleotides encoding an IL-12 polypeptide, wherein the polynucleotide comprises an ORF encoding an IL12B polypeptide and an IL12A polypeptide.

Another aspect of the present disclosure is directed to a method of increasing cross-presenting dendritic cells in a tumor of a subject in need thereof comprising administering to the subject an effective amount of a composition comprising one or more polynucleotides encoding an IL-12 polypeptide, wherein the polynucleotide comprises an ORF encoding an IL12B polypeptide and an IL12A polypeptide. In some embodiments, the cross-presenting dendritic cells are CD103$^+$ cells.

Another aspect of the present disclosure is directed to a lipid nanoparticle comprising a polynucleotide encoding a human IL12 polypeptide, wherein the polynucleotide comprises an ORF encoding a human IL12B polypeptide operably linked to a human IL12A polypeptide.

In some embodiments, the IL12B polypeptide and the IL12A polypeptide are fused directly or by a nucleic acid encoding a linker. In some embodiments, the IL12B polypeptide comprises an amino acid sequence at least 80%, at least 90%, at least 95%, or at least 98% identical to amino acids 23 to 328 of SEQ ID NO: 48, wherein the amino acid sequence has IL12B activity. In some embodiments, the IL12A polypeptide comprises an amino acid sequence at least 80%, at least 90%, at least 95%, or at least 98% identical to amino acids 336 to 532 of SEQ ID NO: 48, wherein the amino acid sequence has IL12A activity. In some embodiments, the polynucleotide comprises a nucleotide sequence encoding a signal peptide. In some embodiments, the signal peptide is an IL12B signal peptide.

In some embodiments, the composition comprises a polynucleotide comprising an ORF encoding an IL12B polypeptide operably linked via a linker to an IL12A polypeptide. In some embodiments, the composition comprises a polynucleotide comprising an ORF encoding an IL12B signal peptide, an IL12B polypeptide, a linker and an IL12A polypeptide. In some embodiments, the linker comprises a Gly/Ser linker.

In some embodiments, the IL12 polypeptide comprises an amino acid sequence at least 80%, at least 90%, at least 95%, or at least 98% identical to SEQ ID NO: 48. the polynucleotide comprises a nucleotide sequence at least 60%, at least 70%, at least 80%, at least 90%, at least 95%, at least 98%, or at least 99% identical to a nucleotide sequence selected from the group consisting of SEQ ID NOs: 5 to 44, 236, and 237. In some embodiments, the polynucleotide comprises a nucleotide sequence at least 60%, at least 70%, at least 80%, at least 90%, at least 95%, at least 98%, or at least 99% identical to SEQ ID NO: 236 or 237.

In some embodiments, the polynucleotide comprises an ORF comprising at least one chemically modified nucleoside. In some embodiments, the at least one chemically modified nucleoside is selected from the group consisting of pseudouridine, N1-methylpseudouridine, 5-methylcytosine, 5-methoxyuridine, and a combination thereof. In some embodiments, the chemically modified nucleosides in the ORF are selected from the group consisting of uridine, adenine, cytosine, guanine, and any combination thereof.

In some embodiments, the polynucleotide comprises a miRNA binding site. In some embodiments, the miRNA binding site is a miR-122 binding site. In some embodiments, the miRNA binding site is a miR-122-3p or miR-122-5p binding site. In certain embodiments, the miRNA binding site comprises a nucleotide sequence at least about 80%, at least about 85%, at least about 90%, at least about 95%, or about 100% identical to aacgccauua ucacacuaaa ua (SEQ ID NO: 51), wherein the miRNA binding site binds to miR-122. In certain embodiments, the miRNA binding site comprises a nucleotide sequence at least about 80%, at least about 85%, at least about 90%, at least about 95%, or about 100% identical to uggaguguga caugguguu ug (SEQ ID NO: 53), wherein the miRNA binding site binds to miR-122. In certain embodiments, the miRNA binding site comprises a nucleotide sequence at least about 80%, at least about 85%, at least about 90%, at least about 95%, or about 100% identical to caaacaccau ugucacacuc ca (SEQ ID NO: 54), wherein the miRNA binding site binds to miR-122.

In some embodiments, the polynucleotide comprises a 5' untranslated region (UTR). In certain embodiments, the 5' UTR comprises a nucleic acid sequence at least about 90%, 95%, 96%, 97%, 98%, 99%, or 100% identical to a sequence listed in Table 3. In some embodiments, the polynucleotide comprises a 3' untranslated region (UTR). In certain embodiments, the 3' UTR comprises a nucleic acid sequence at least 90%, 95%, 96%, 97%, 98%, 99%, or 100% identical to a sequence listed in Table 4A or 4B. In some embodiments, the polynucleotide comprises a miRNA binding site within the 3' UTR. In some embodiments, the polynucleotide comprises a nucleotide spacer sequence fused to the miRNA binding site. In some embodiments, the polynucleotide comprises a 5' terminal cap structure. In some embodiments, the polynucleotide comprises a 3' polyA tail. In some embodiments, the polynucleotide comprises a codon optimized ORF. In certain embodiments, the polynucleotide is in vitro transcribed (IVT) polynucleotide. In certain embodiments, the polynucleotide is circular.

In certain aspects, the polynucleotide is formulated with a delivery agent. In some embodiments, the delivery agent comprises a lipidoid, a liposome, a lipoplex, a lipid nanoparticle, a polymeric compound, a peptide, a protein, a cell, a nanoparticle mimic, a nanotube, or a conjugate. In some embodiments, the delivery agent is a lipid nanoparticle. In some embodiments, the delivery agent comprises a compound having formula (I)

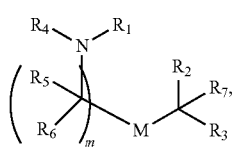
(I)

or a salt or stereoisomer thereof, wherein $R_1$ is selected from the group consisting of $C_{5-20}$ alkyl, $C_{5-20}$ alkenyl, —R*YR", —YR", and —R"M'R'; $R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle; $R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5; each $R_5$ is independently selected from the group consisting of $C_{1-3}$ alkyl, $C_{2-3}$ alkenyl, and H; each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$— an aryl group, and a heteroaryl group; $R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H; each R' is independently selected from the group consisting of $C_{1-18}$ alkyl, $C_{2-18}$ alkenyl, —R*YR", —YR", and H; each R" is independently selected from the group consisting of $C_{3-14}$ alkyl and $C_{3-14}$ alkenyl; each R* is independently selected from the group consisting of $C_{1-12}$ alkyl and $C_{2-12}$ alkenyl; each Y is independently a $C_{3-6}$ carbocycle; each X is independently selected from the group consisting of F, Cl, Br, and I; and m is selected from 5, 6, 7, 8, 9, 10, 11, 12, and 13; and provided when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, the compound is of Formula (IA):

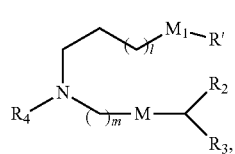
(IA)

or a salt or stereoisomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —(CH$_2$)$_n$Q, in which n is 1, 2, 3, 4, or 5 and Q is OH, —NHC(S)N(R)$_2$, or —NHC(O)N(R)$_2$; M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, the compound is of Formula (II):

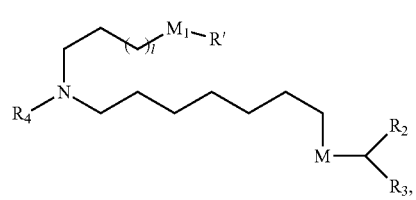
(II)

or a salt or stereoisomer thereof, wherein l is selected from 1, 2, 3, 4, and 5;

$M_1$ is a bond or M'; $R_4$ is unsubstituted $C_{1-3}$ alkyl, or —(CH$_2$)$_n$Q, in which n is 2, 3, or 4 and Q is OH, —NHC(S)N(R)$_2$, or —NHC(O)N(R)$_2$; M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, the compound is selected from Compound 1 to Compound 147, and salts and stereoisomers thereof. In some embodiments, the delivery agent comprises a compound having the formula (I)

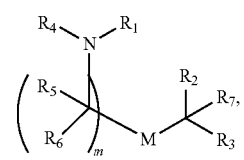
(I)

or a salt or stereoisomer thereof, wherein $R_1$ is selected from the group consisting of $C_{530}$ alkyl, $C_{520}$ alkenyl, —R*YR", —R", and R"M'R'; $R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle; $R_4$ is selected from the group consisting of a $C_{36}$ carbocycle, (CH$_2$)$_n$Q, —(CH$_2$)$_n$CHQR, CHQR, CQ(R)$_2$, and unsubstituted $C_{16}$ alkyl, where Q is selected from a carbocycle, heterocycle, —OR, —(CH$_2$)$_n$N(R)$_2$, —(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)

N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5; each R$_5$ is independently selected from the group consisting of C$_{13}$ alkyl, C$_{23}$ alkenyl, and H; each R$_6$ is independently selected from the group consisting of C$_{13}$ alkyl, C$_{23}$ alkenyl, and H; M and M' are independently selected from —C(O)O—, —OC(O)—, —C(O)N(R')—, —N(R')C(O)—, —(O)—, —C(S)—, —C(S)S—, —SC(S)—, —(OH)—, —P(O)(OR')O—, —S(O)$_2$—, —S—S—, an aryl group, and a heteroaryl group; R$_7$ is selected from the group consisting of C$_{13}$ alkyl, C$_{23}$ alkenyl, and H; R$_8$ is selected from the group consisting of C$_{3-6}$ carbocycle and heterocycle; R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle; each R is independently selected from the group consisting of C$_{13}$ alkyl, C$_{23}$ alkenyl, and H; each R' is independently selected from the group consisting of C$_{118}$ alkyl, C$_{218}$ alkenyl, R*YR", YR", and H; each R" is independently selected from the group consisting of C$_{314}$ alkyl and C$_{314}$ alkenyl; each R* is independently selected from the group consisting of C$_{112}$ alkyl and C$_{212}$ alkenyl; each Y is independently a C$_{36}$ carbocycle; each X is independently selected from the group consisting of F, Cl, Br, and I; and m is selected from 5, 6, 7, 8, 9, 10, 11, 12, and 13; and provided that when R$_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, the delivery agent further comprises a phospholipid. In some embodiments, the phospholipid is selected from the group consisting of 1,2 dilinoleoyl sn glycero 3 phosphocholine (DLPC), 1,2 dimyristoyl sn glycero phosphocholine (DMPC), 1,2 dioleoyl sn glycero 3 phosphocholine (DOPC), 1,2 dipalmitoyl sn glycero 3 phosphocholine (DPPC), 1,2 distearoyl sn glycero 3 phosphocholine (DSPC), 1,2 diundecanoyl sn glycero phosphocholine (DUPC), 1 palmitoyl 2 oleoyl sn glycero 3 phosphocholine (POPC), 1,2 di O octadecenyl sn glycero 3 phosphocholine (18:0 Diether PC), 1 oleoyl 2 cholesterylhemisuccinoyl sn glycero 3 phosphocholine (OChemsPC), 1 hexadecyl sn glycero 3 phosphocholine (C16 Lyso PC), 1,2 dilinolenoyl sn glycero 3 phosphocholine, 1,2 diarachidonoyl sn glycero 3 phosphocholine, 1,2 didocosahexaenoyl sn glycero 3 phosphocholine, 1,2 dioleoyl sn glycero 3 phosphoethanolamine (DOPE), 1,2 diphytanoyl sn glycero 3 phosphoethanolamine (ME 16:0 PE), 1,2 distearoyl sn glycero 3 phosphoethanolamine, 1,2 dilinoleoyl sn glycero 3 phosphoethanolamine, 1,2 dilinolenoyl sn glycero 3 phosphoethanolamine, 1,2 diarachidonoyl sn glycero 3 phosphoethanolamine, 1,2 didocosahexaenoyl sn glycero 3 phosphoethanolamine, 1,2 dioleoyl sn glycero 3 phospho rac (1 glycerol) sodium salt (DOPG), sphingomyelin, and mixtures thereof. In some embodiments, the phospholipid is selected from the group consisting of 1 myristoyl 2 palmitoyl sn glycero 3 phosphocholine (14:0-16:0 PC, MPPC), 1 myristoyl 2 stearoyl sn glycero 3 phosphocholine (14:0-18:0 PC, MSPC), 1 palmitoyl 2 acetyl sn glycero 3 phosphocholine (16:0-02:0 PC), 1 palmitoyl 2 myristoyl sn glycero 3 phosphocholine (16:0-14:0 PC, PMPC), 1 palmitoyl 2 stearoyl sn glycero 3 phosphocholine (16:0-18:0 PC, PSPC), 1 palmitoyl 2 oleoyl sn glycero 3 phosphocholine (16:0-18:1 PC, POPC), 1 palmitoyl 2 linoleoyl sn glycero 3 phosphocholine (16:0-18:2 PC, PLPC), 1 palmitoyl 2 arachidonoyl sn glycero 3 phosphocholine (16:0-20:4 PC), 1 palmitoyl 2 docosahexaenoyl sn glycero 3 phosphocholine (14:0-22:6 PC), 1 stearoyl 2 myristoyl sn glycero 3 phosphocholine (18:0-14:0 PC, SMPC), 1 stearoyl 2 palmitoyl sn glycero 3 phosphocholine (18:0-16:0 PC, SPPC), 1 stearoyl 2 oleoyl sn glycero 3 phosphocholine (18:0-18:1 PC, SOPC), 1 stearoyl 2 linoleoyl sn glycero 3 phosphocholine (18:0-18:2 PC), 1 stearoyl 2 arachidonoyl sn glycero 3 phosphocholine (18:0-20:4 PC), 1 stearoyl 2 docosahexaenoyl sn glycero 3 phosphocholine (18:0-22:6 PC), 1 oleoyl 2 myristoyl sn glycero 3 phosphocholine (18:1-14:0 PC, OMPC), 1 oleoyl 2 palmitoyl sn glycero 3 phosphocholine (18:1-16:0 PC, OPPC), 1 oleoyl 2 stearoyl sn glycero 3 phosphocholine (18:1-18:0 PC, OSPC), 1 palmitoyl 2 oleoyl sn glycero 3 phosphoethanolamine (16:0-18:1 PE, POPE), 1 palmitoyl 2 linoleoyl sn glycero 3 phosphoethanolamine (16:0-18:2 PE), 1 palmitoyl 2 arachidonoyl sn glycero 3 phosphoethanolamine (16:0-20:4 PE), 1 palmitoyl 2 docosahexaenoyl sn glycero 3 phosphoethanolamine (16:0-22:6 PE), 1 stearoyl 2 oleoyl sn glycero 3 phosphoethanolamine (18:0-18:1 PE), 1 stearoyl 2 linoleoyl sn glycero 3 phosphoethanolamine (18:0-18:2 PE), 1 stearoyl 2 arachidonoyl sn glycero 3 phosphoethanolamine (18:0-20:4 PE), 1 stearoyl 2 docosahexaenoyl sn glycero 3 phosphoethanolamine (18:0-22:6 PE), 1 oleoyl 2 cholesterylhemisuccinoyl sn glycero 3 phosphocholine (OChemsPC), and any combination thereof.

In some embodiments, the delivery agent further comprises a structural lipid. In some embodiments, the delivery agent further comprises a PEG lipid. In some embodiments, the delivery agent further comprises an ionizable lipid selected from the group consisting of 3 (didodecylamino) N1,N1,4 tridodecyl 1 piperazineethanamine (KL10), N1 [2 (didodecylamino)ethyl] N1,N4,N4 tridodecyl 1,4 piperazinediethanamine (KL22), 14,25 ditridecyl 15,18,21,24-tetraaza-octatriacontane (KL25), 1,2 dilinoleyloxy N,N dimethylaminopropane (DLin-DMA), 2,2 dilinoleyl 4 dimethylaminomethyl [1,3]dioxolane (DLin-K-DMA), heptatriaconta 6,9,28,31 tetraen 19 yl 4 (dimethylamino)butanoate (DLin-MC3-DMA), 2,2 dilinoleyl 4 (2 dimethylaminoethyl) [1,3] dioxolane (DLin-KC2-DMA), 1,2 dioleyloxy N,N dimethylaminopropane (DODMA), 2 ({8 [(3β) cholest 5 en 3 yloxy]octyl}oxy) N,N dimethyl 3 [(9Z,12Z) octadeca 9,12 dien 1 yloxy]propan 1 amine (Octyl-CLinDMA), (2R) 2 ({8 [(3β) cholest 5 en 3 yloxy]octyl}oxy) N,N dimethyl 3 [(9Z,12Z) octadeca 9,12 dien 1 yloxy]propan 1 amine (Octyl-CLinDMA (2R)), and (2S) 2 ({8 [(3β) cholest 5 en 3 yloxy]octyl}oxy) N,N dimethyl 3 [(9Z,12Z) octadeca 9,12 dien 1 yloxy]propan 1 amine (Octyl-CLinDMA (2S)).

In some embodiments, the delivery agent further comprises a quaternary amine compound. In certain embodiments, the quaternary amine compound is selected from the group consisting of 1,2-dioleoyl-3-trimethylammonium-propane (DOTAP), N-[1-(2,3-dioleoyloxy)propyl]-N,N,N-trimethyl ammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), N,N-distearyl-N,N-dimethylammonium bromide (DDAB), N-(1,2-dimyristyloxyprop-3-yl)-N,N-dimethyl-N-hydroxyethyl ammonium bromide (DMRIE), N-(1,2-dioleoyl oxyprop-3-yl)-N,N-dimethyl-N-hydroxyethyl ammonium bromide (DORIE), N,N-dioleyl-N,N-dimethylammonium chloride (DODAC), 1,2-dilauroyl-sn-glycero-3-ethylphosphocholine (DLePC), 1,2-distearoyl-3-trimethylammonium-propane (DSTAP), 1,2-dipalmitoyl-3-trimethylammonium-propane (DPTAP), 1,2-dilinoleoyl-3-trimethylammonium-propane (DLTAP), 1,2-dimyristoyl-3-trimethylammonium-propane (DMTAP), 1,2-distearoyl-sn-glycero-3-ethylphosphocholine (DSePC), 1,2-dipalmitoyl-sn-glycero-3-ethylphosphocholine (DPePC), 1,2-dimyristoyl-sn-glycero-3-ethylphosphocholine (DMePC), 1,2-dioleoyl-sn-glycero-3-ethylphosphocholine (DOePC), 1,2-di-(9Z-tetradecenoyl)-sn-glycero-3-ethylphosphocholine (14:1 EPC), 1-palmitoyl-2-oleoyl-sn-glycero-3-ethylphosphocholine (16:0-18:1 EPC), and any combination thereof.

In certain aspects, the composition is formulated for in vivo delivery. In some aspects, the composition is formulated for intramuscular, subcutaneous, intratumoral, or intradermal delivery.

In certain aspects, the administration treats a cancer. In some embodiments, the cancer is selected from the group consisting of adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, hepatocellular carcinoma (HCC), non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and any combination thereof.

In certain aspects, the composition is administered by a device comprising a pump, patch, drug reservoir, short needle device, single needle device, multiple needle device, micro-needle device, jet injection device, ballistic powder/particle delivery device, catheter, lumen, cryoprobe, cannula, microcanular, or devices utilizing heat, RF energy, electric current, or any combination thereof. In some aspects, the effective amount is between about 0.10 mg/kg to about 1,000 mg/kg.

BRIEF DESCRIPTION OF THE DRAWINGS/FIGURES

FIG. 1 shows (1) the wild-type IL12B amino acid sequence, (2) the wild-type nucleic acid encoding the wtIL12B, (3) the wild-type IL12A amino acid sequence, (4) the wild-type nucleic acid encoding the wtIL12A, (5) the wild-type IL12B signal peptide amino acid sequence, and (6) the wild-type nucleic acid encoding the wtIL12B signal peptide.

FIGS. 2A-2B. FIG. 2A is a graph depicting the higher AUC and $C_{max}$ for IL12 plasma levels observed following intravenous administration of IL12 mRNA in lipid nanoparticle (LNP) compared to the corresponding IL12 recombinant protein. FIG. 2B is a graph depicting the higher AUC and $C_{max}$ for IFNγ plasma levels observed following intravenous administration of IL12 mRNA administered in lipid nanoparticle (LNP) compared to IL12 recombinant protein.

FIG. 3 is a graph depicting the robust efficacy of a single intravenous (IV) dose of IL12 mRNA in lipid nanoparticle (LNP), at doses of 0.1 mg/kg (Group 4) and 0.05 mg/kg (Group 5) (as indicated by lines with the inverted triangles), compared to Groups 1 (PBS), 2 (IL12 protein), 7 and 8 (controls NST-FIX, 0.1 mg/kg and 0.05 mg/kg, respectively).

FIGS. 4A-4F are graphs depicting the mean tumor volume and the number of complete responses (CR) seen following administration of a single intravenous (IV) dose of: IL12 mRNA in lipid nanoparticle (LNP), at doses of 0.1 mg/kg (Group 4) (FIG. 4F) and 0.05 mg/kg (Group 5) (FIG. 4E), PBS (Group 1) (FIG. 4A), IL12 protein (Group 2) (FIG. 4D), controls NST-FIX, 0.1 mg/kg and 0.05 mg/kg (Groups 7 and 8, respectively) (FIG. 4C and FIG. 4B, respectively). Complete responses (CRs) are shown in FIGS. 4E and 4F only. FIG. 4E shows that 6 of 8 CRs were seen in Group 5 (IL12 mRNA in lipid nanoparticle (LNP), at a dose of 0.05 mg/kg). FIG. 4F shows that 5 of 9 CRs were seen in Group 4 (IL12 mRNA in lipid nanoparticle (LNP), at a dose of 0.1 mg/kg). Aside from the IL12 mRNA groups, all other groups did not observe any CRs.

FIG. 5 is a graph depicting the survival benefit at day 47 post tumor-implantation from a single intravenous (IV) dose of IL12 mRNA in lipid nanoparticle (LNP) at a dose of 0.05 mg/kg (Group 5) and a dose of 0.1 mg/kg (Group 4) compared to a single IV dose of IL12 protein at 1 μg (~0.05 mg/kg) (Group 2), NST-FIX at 0.1 mg/kg (Group 7) or 0.05 mg/kg (Group 8), or PBS (Group 1).

FIGS. 6A-6B are graphs showing the in vivo anti-tumor efficacy of a single intratumoral dose of IL12 mRNA (4 μg) in a lipid nanoparticle (LNP) administered to mice bearing adenocarcinoma (MC38) tumors. FIG. 6A shows the tumor volume means (mm³), up to day 24, starting at day 10 post implantation. Group 1 (circles) represents mice (n=7) administered 4 μg IL12 mRNA LNP at day 10 post-implantation; Group 2 (squares) represents mice (n=7) administered 4 μg of control mRNA encoding non-translated factor IX (NST-FIX LNP); and Group 3 (triangles) represents another control group of mice (n=7) administered PBS. FIG. 6B shows the individual tumor volumes (mm³) for each group of mice, up to day 47, starting at day 10 post implantation. Complete responses (CR) were achieved in 3 of 7 (44%) animals administered 4 μg IL12 mRNA LNP (circles).

FIGS. 7A-7B are graphs showing the in vivo anti-tumor efficacy of an intratumoral dose of IL12 mRNA (5 μg) in MC3-based lipid nanoparticle (LNP) administered to mice bearing A20 B-cell lymphoma tumors. FIG. 7A shows the individual tumor volume (mm³) for mice (n=12) administered 5 μg non-translated control mRNA (NST). FIG. 7B shows the individual tumor volumes for mice (n=12) administered 5 μg of IL12 (miRless) mRNA. Complete responses (CR) were achieved in 5 of 12 animals that received IL12 mRNA.

FIG. 7C is a graph showing comparable in vivo anti-tumor efficacy of IL12 mRNA (5 μg) containing a miR122 binding site (FIG. 7C) in a B-cell lymphoma tumor model (A20). Both IL12 mRNAs (with miR122 binding site and without (i.e., miRless)) were formulated in an MC3-based lipid nanoparticle (LNP). The IL12 mRNAs were administered to mice bearing A20 B-cell lymphoma tumors. Complete responses (CR) were achieved in 6 out of 12 mice in the IL12 miR122 group (FIG. 7C).

Figure 8A:
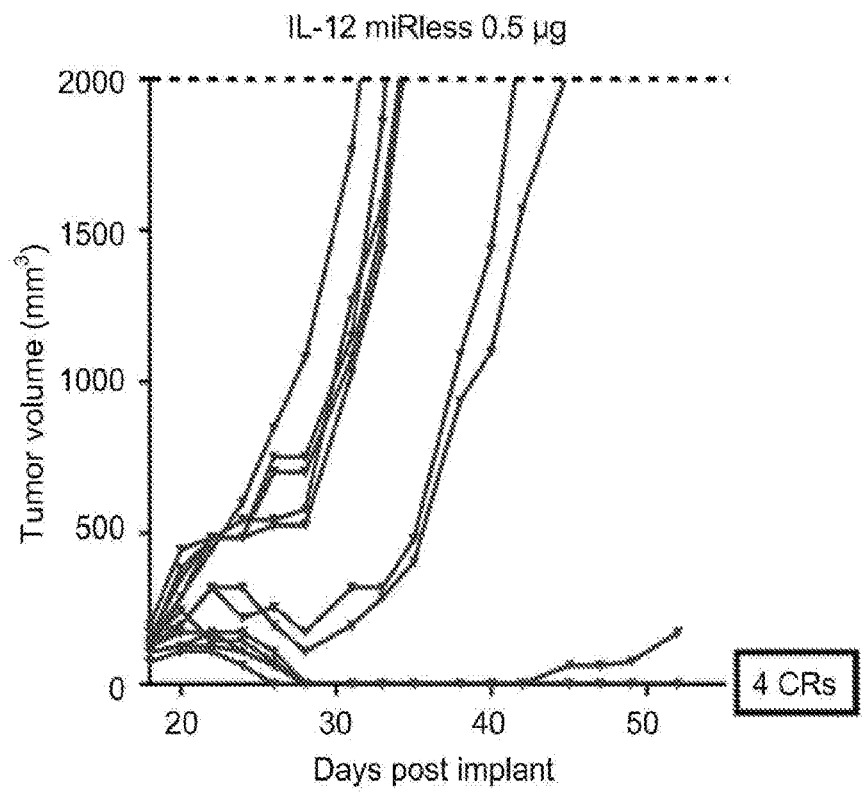
FIGS. 8A-8B are graphs showing in vivo anti-tumor efficacy of a single dose of 0.5 µg IL12 mRNA in MC3-based lipid nanoparticle (LNP) administered to mice bearing A20 B-cell lymphoma tumors. Complete responses (CR) were achieved in 4 of 12 mice in the IL12 miRless (0.5 µg) group (FIG. 8A) and 3 of 12 mice in the IL12 miR122 (0.5 µg) group (FIG. 8B).
Figure 8B:
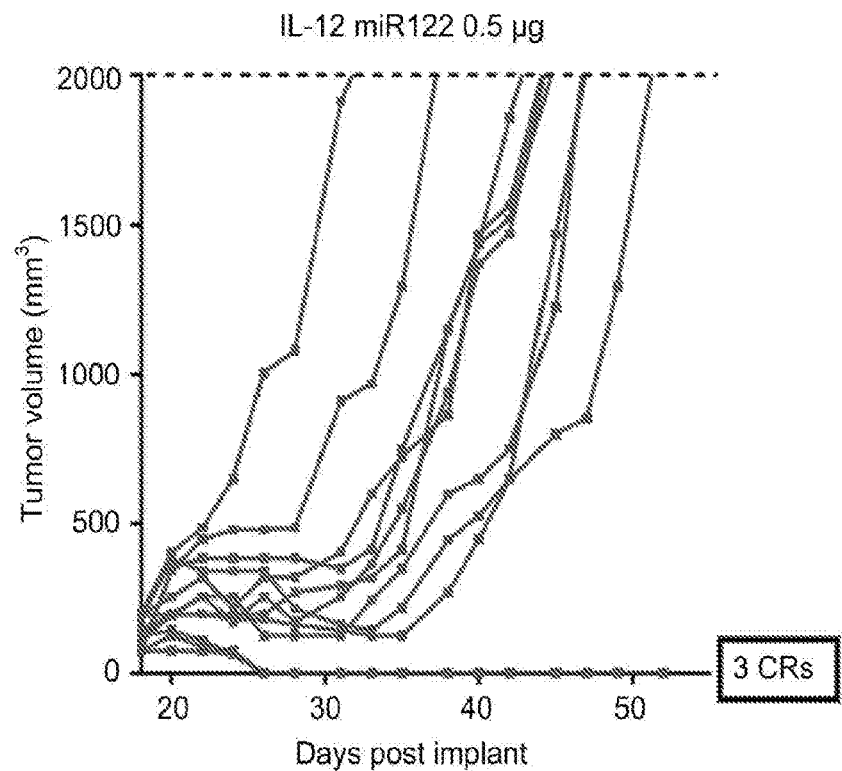
Figure 8C:
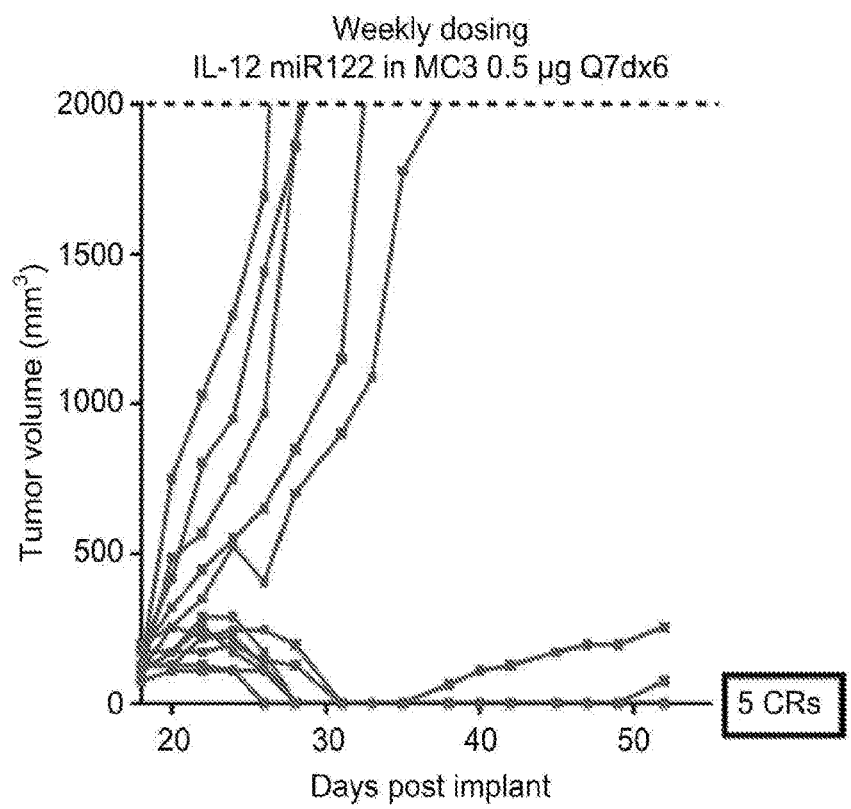
FIG. 8C is a graph showing enhanced in vivo anti-tumor efficacy in a B-cell lymphoma tumor model (A20) by administering multiple doses of 0.5 µg IL12 mRNA in MC3-based lipid nanoparticle (LNP) to mice bearing A20 tumors. Complete responses (CR) were achieved in 5 out of 12 mice administered weekly dosing of 0.5 µg IL12 miR122 for seven (7) days×6.
Figure 8D:
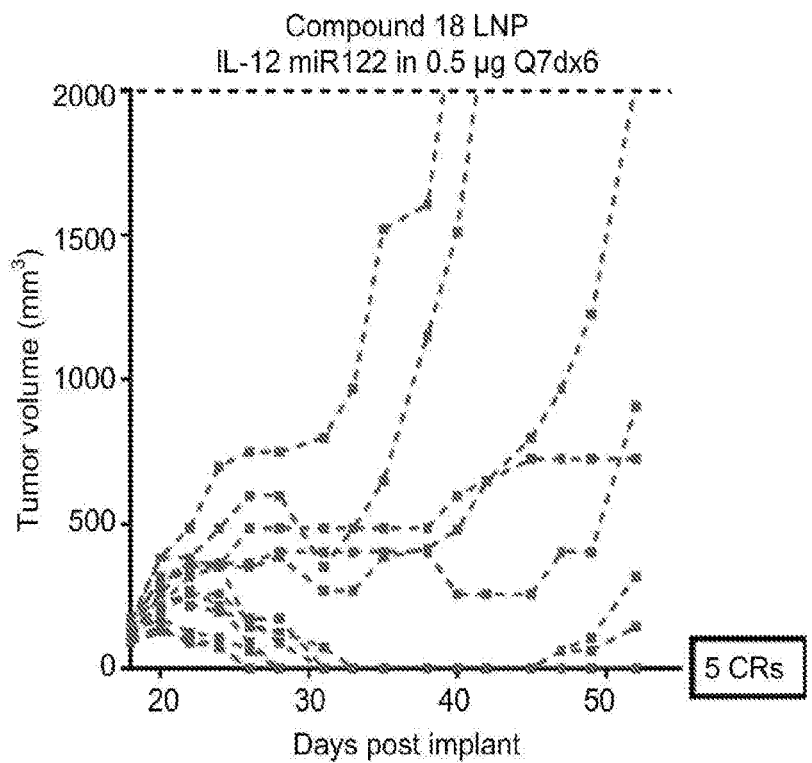

FIG. 8D is a graph showing that the in vivo anti-tumor efficacy of weekly intratumoral doses of 0.5 µg IL12 mRNA in lipid nanoparticle (LNP) (i.e., Compound 18) administered to mice bearing A20 B-cell lymphoma tumors is similar to the in vivo anti-tumor efficacy of 0.5 µg IL12 mRNA in MC3-based LNP. FIG. 14 shows the individual tumor volumes for 12 mice administered 0.5 µg of IL12 mRNA in Compound 18-based LNP for 7 days×6. Complete responses (CR) were also achieved in 5 out of 12 animals.

Figure 8E:
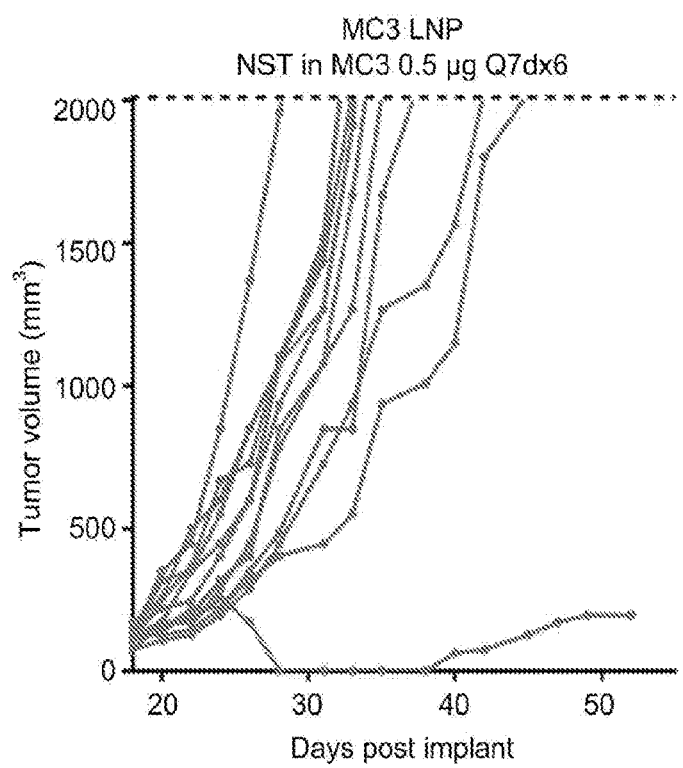
Figure 8F:
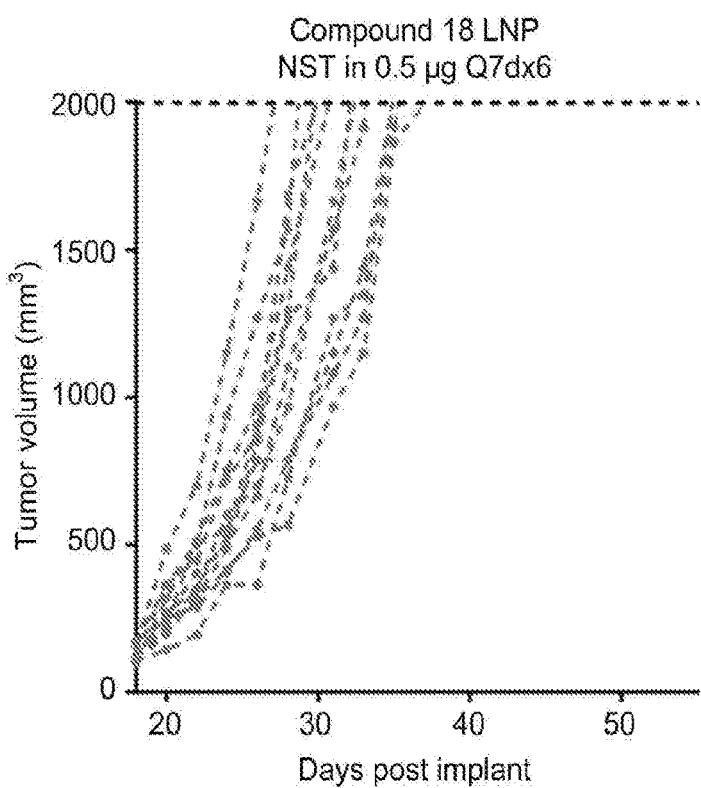

FIGS. 8E-8F are graphs showing tumor growth in mice bearing A20 tumors administered weekly dosing (7 days×6) of 0.5 µg non-translated negative control mRNA (NST) in MC3-based lipid nanoparticle (LNP) (FIG. 8E) and 0.5 µg non-translated negative control mRNA (NST) in Compound 18-based LNP (FIG. 8F).

Figure 9A:
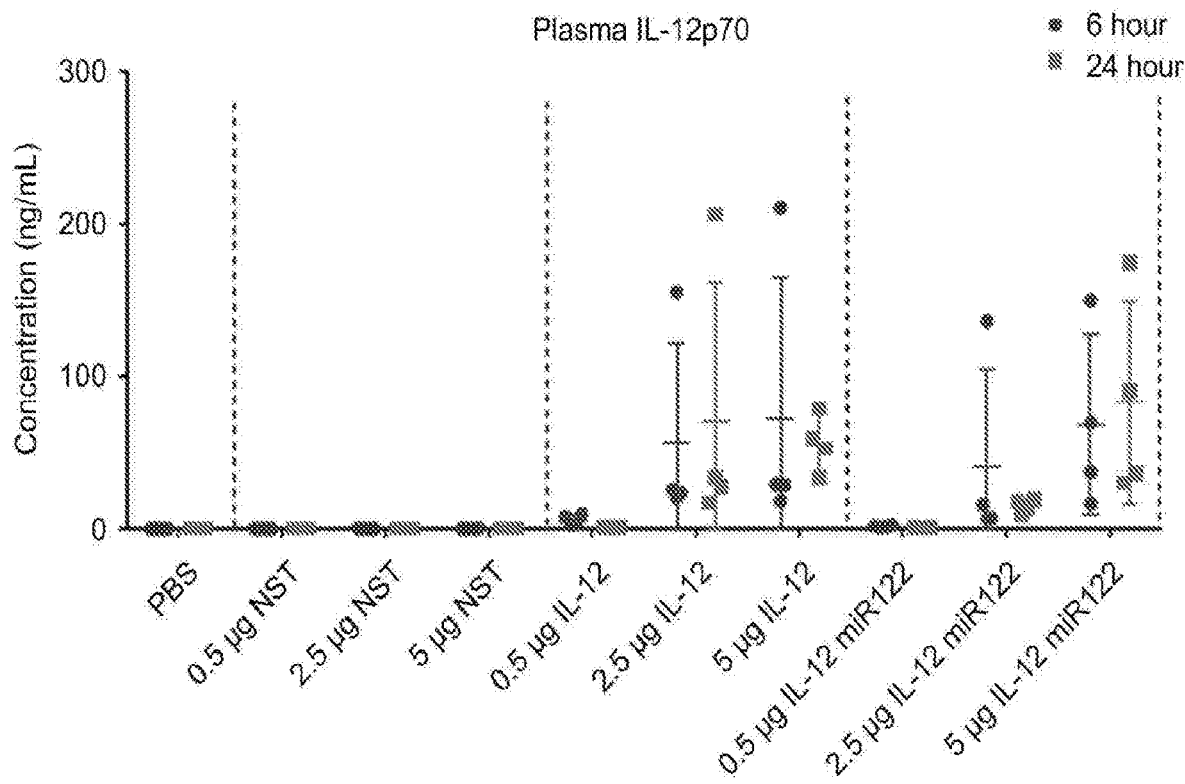
Figure 9B:
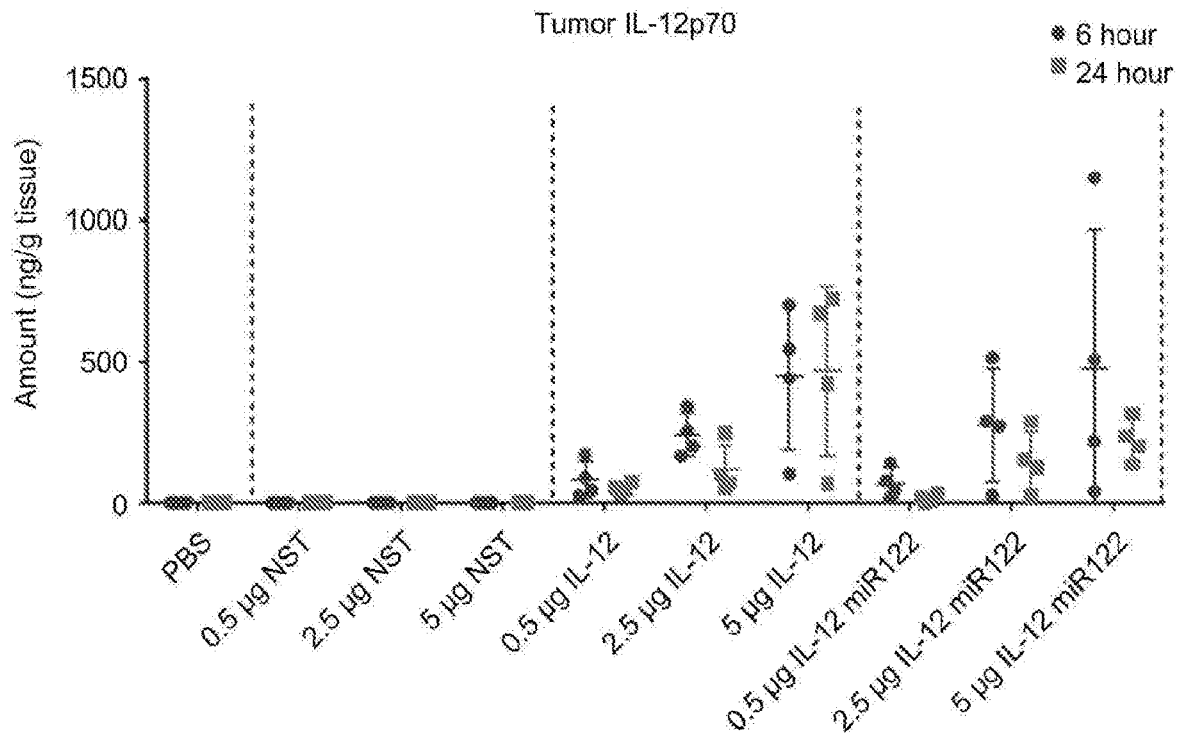

FIGS. 9A-9B are graphs showing dose-dependent levels of IL12 in plasma (FIG. 9A) and tumor (FIG. 9B) at 6 hours and 24 hours following intratumoral administration of the indicated doses of IL12 mRNA in MC3-based LNPs to mice bearing A20 tumors. From left to right, the mice were given (i) PBS, (ii) 0.5 µg NST, (iii) 2.5 µg NST, (iv) 5 g NST, (v) 0.5 µg IL12, (vi) 2.5 µg IL12, (vii) 5 µg IL12, (viii) 0.5 µg IL12 miR122, (ix) 2.5 µg IL12 miR122, and (x) 5 µg IL12 miR122.

Figure 9C:
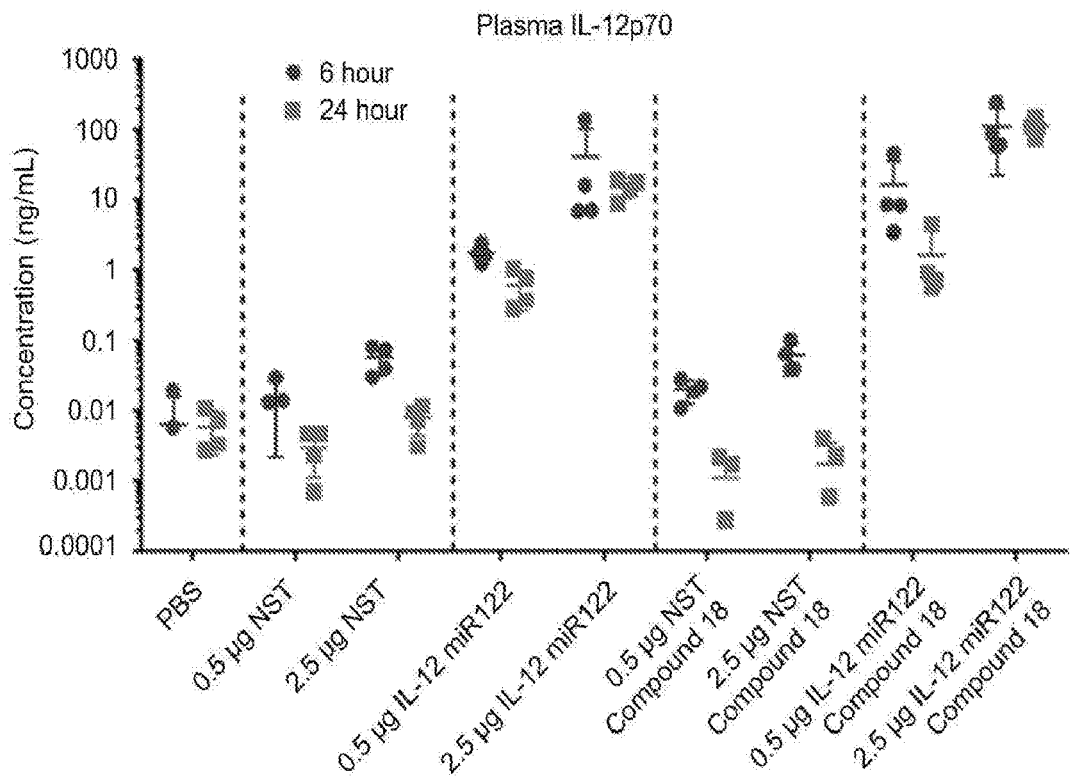
Figure 9D:
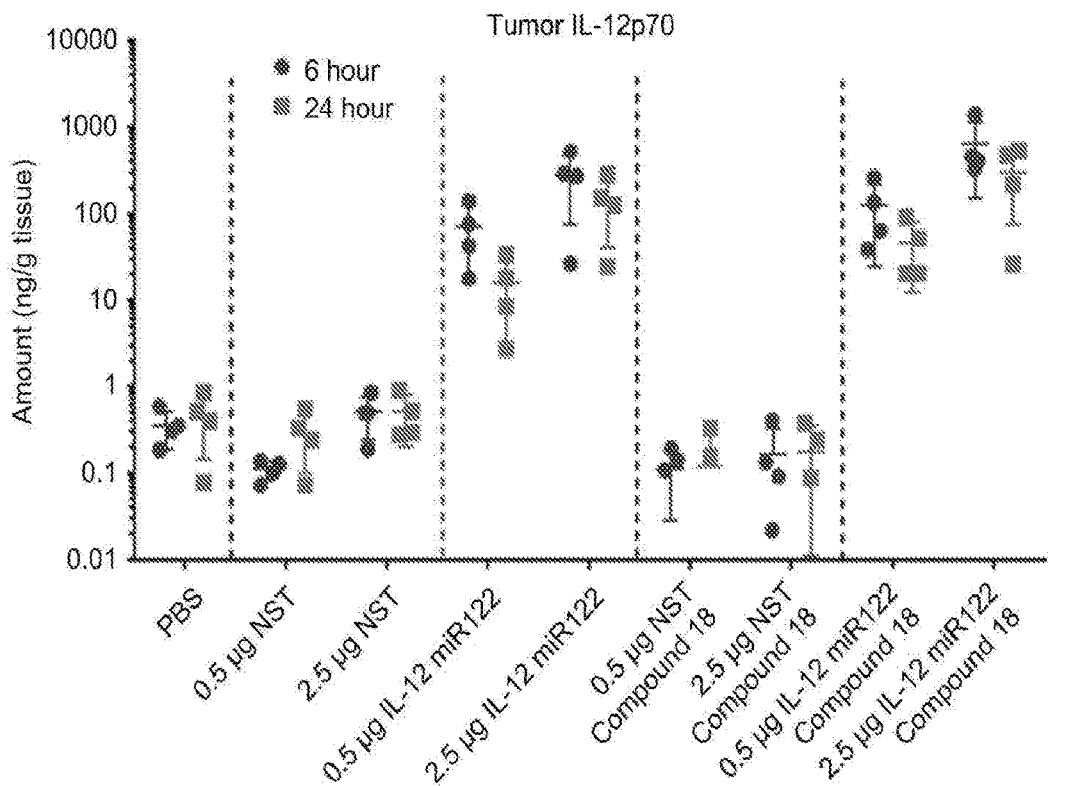

FIGS. 9C-9D are graphs showing elevated levels of IL12 in plasma and tumor following administration of indicated doses of IL12 mRNA in Compound 18-based LNPs compared to IL12 mRNA in MC3-based LNPs. FIG. 9C shows plasma IL12 levels at 6 hours and 24 hours; FIG. 9D shows tumor IL12 levels at 6 hours and 24 hours. From left to right, the mice were given (i) PBS, (ii) 0.5 µg NST in MC3, (iii) 2.5 µg NST in MC3, (iv) 0.5 µg IL12 miR122 in MC3, (v) 2.5 µg IL12 miR122 in MC3, (vi) 0.5 µg NST in Compound 18, (vii) 2.5 µg NST in Compound 18, (viii) 5 µg IL12 miR122, (ix) 0.5 µg IL12 miR122 in Compound 18, and (x) 2.5 µg IL12 miR122 in Compound 18.

Figure 9E:
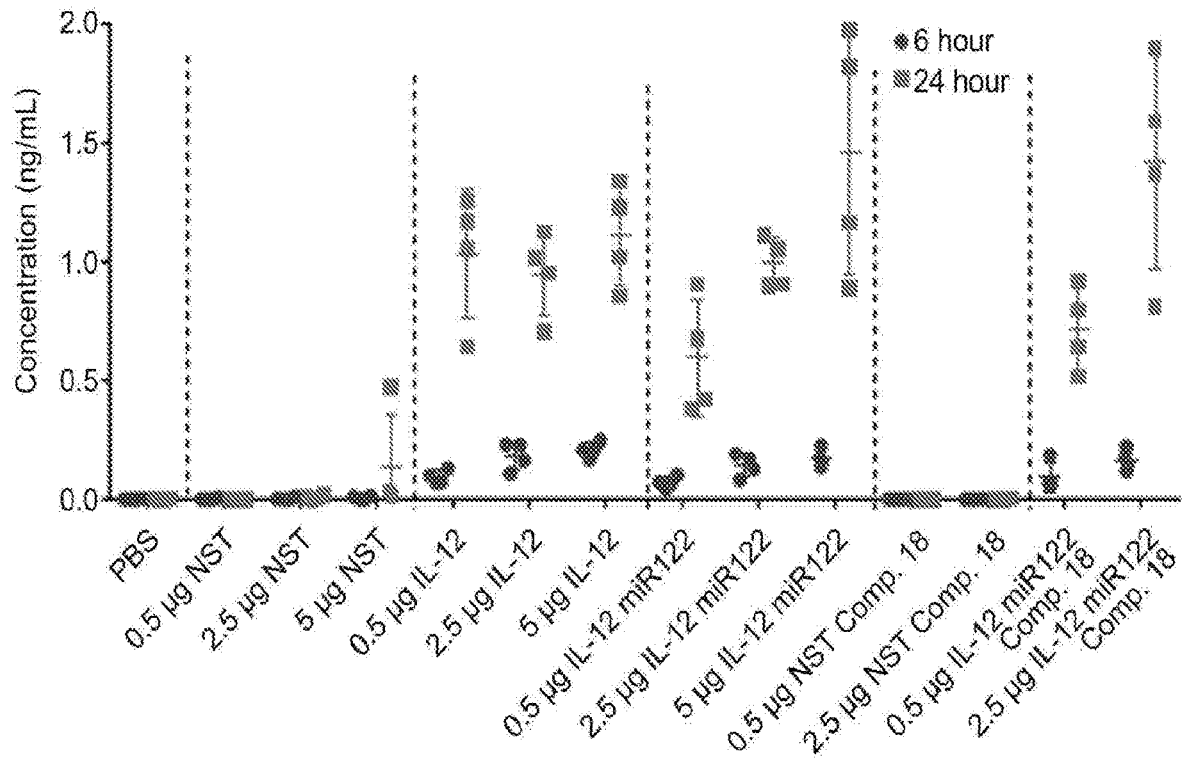
Figure 9F:
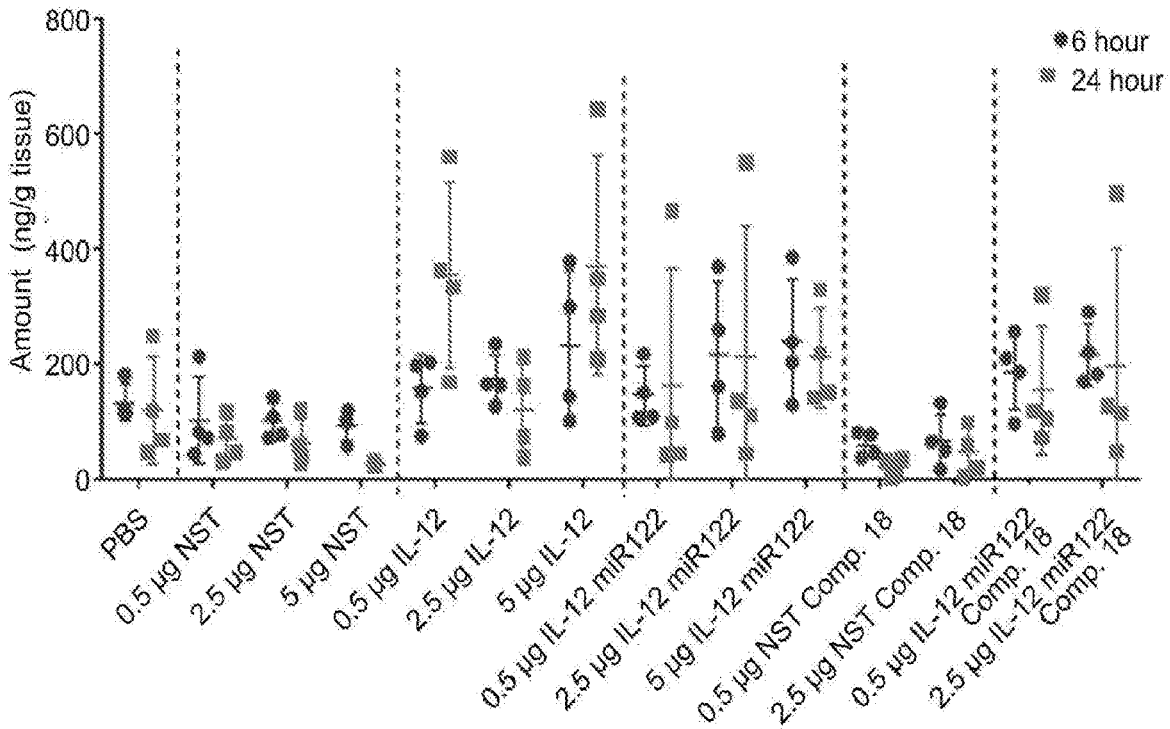

FIGS. 9E-9F are graphs showing increased levels of IFNγ at 6 hours and 24 hours in plasma (FIG. 9E) and in tumor (FIG. 9F) following administration of IL12 mRNA to mice bearing A20 tumors. From left to right, the mice were given (i) PBS, (ii) 0.5 µg NST in MC3, (iii) 2.5 µg NST in MC3, (iv) 5 µg NST in MC3, (v) 0.5 µg IL12 in MC3, (vi) 2.5 µg IL12 in MC3, (vii) 5 µg IL12 in MC3, (viii) 0.5 µg IL12 miR122 in MC3, (ix) 2.5 g IL12 miR122 in MC3, (x) 5 µg IL12 miR122 in MC3, (xi) 0.5 µg NST in Compound 18, (xii) 2.5 µg NST in Compound 18, (xiii) 0.5 µg IL12 miR122 in Compound 18, and (xiv) 2.5 µg IL12 miR122 in Compound 18.

Figure 9G:
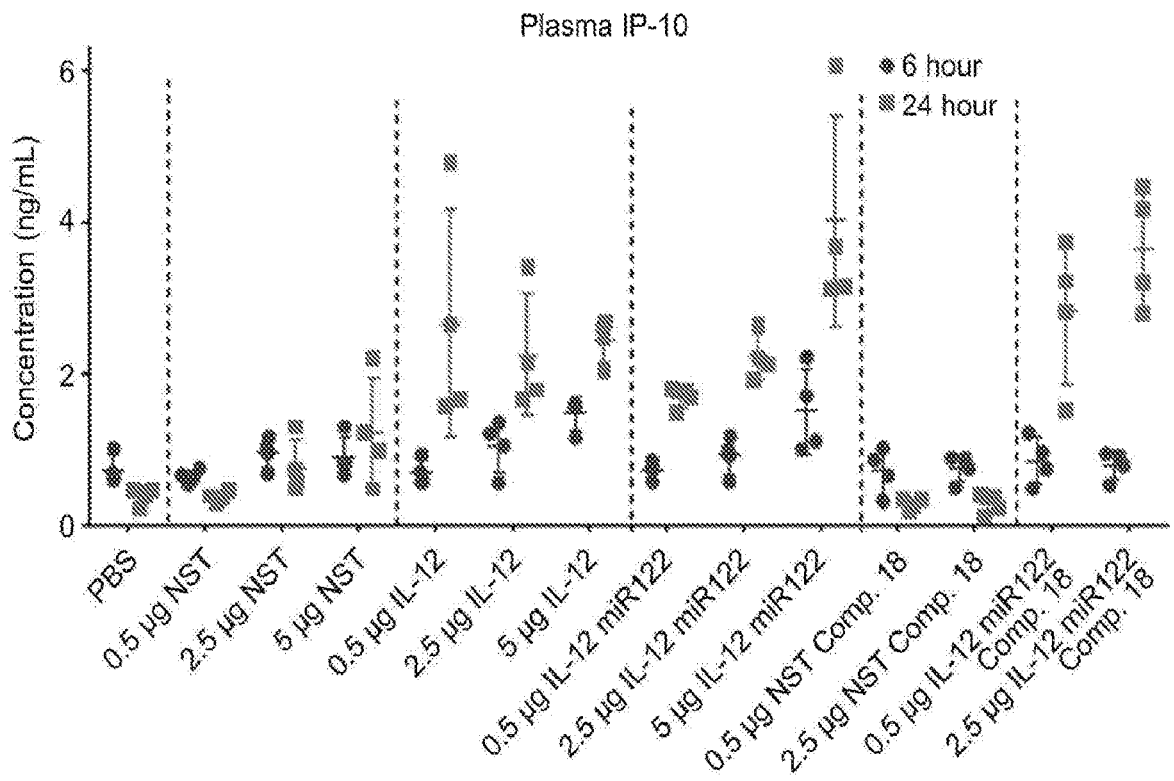
Figure 9H:
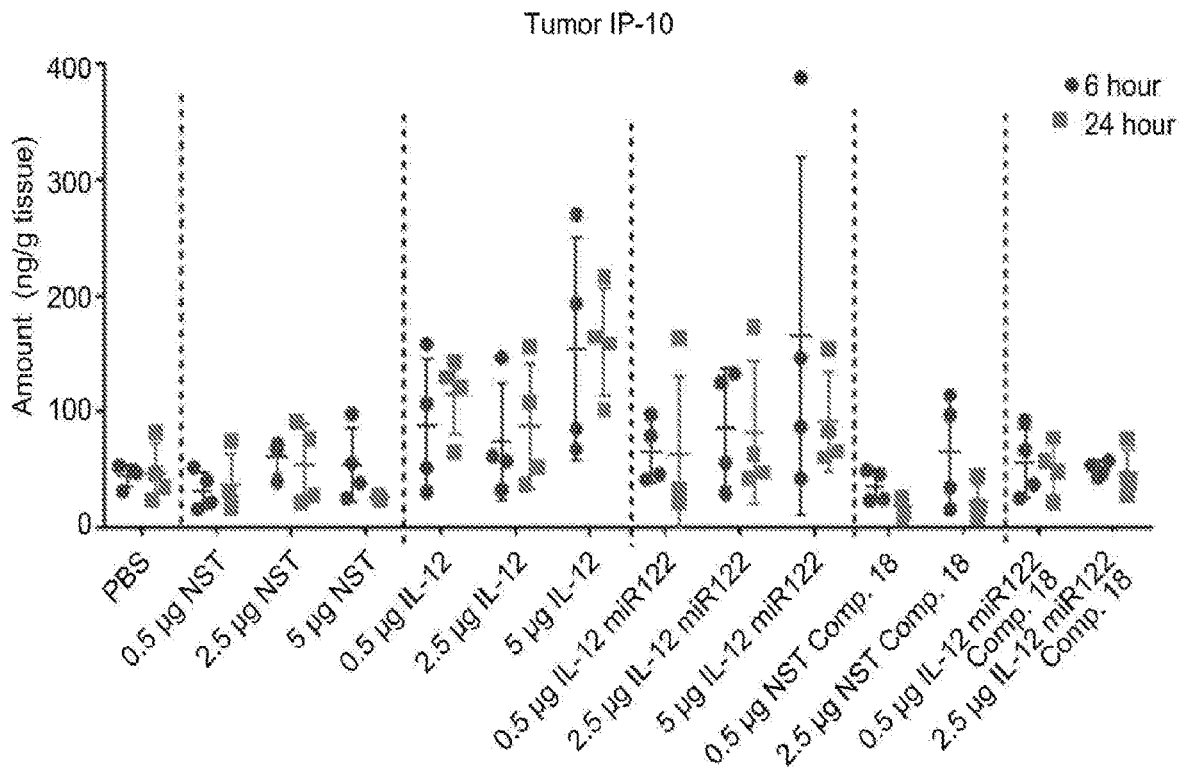

FIGS. 9G-9H are graphs showing increased levels of IP10 at 6 hours and 24 hours in plasma (FIG. 9G) and in tumor (FIG. 9H) following administration of IL12 mRNA to mice bearing A20 tumors. From left to right, the mice were given (i) PBS, (ii) 0.5 µg NST in MC3, (iii) 2.5 µg NST in MC3, (iv) 5 µg NST in MC3, (v) 0.5 µg IL12 in MC3, (vi) 2.5 µg IL12 in MC3, (vii) 5 µg IL12 in MC3, (viii) 0.5 µg IL12 miR122 in MC3, (ix) 2.5 g IL12 miR122 in MC3, (x) 5 µg IL12 miR122 in MC3, (xi) 0.5 µg NST in Compound 18, (xii) 2.5 µg NST in Compound 18, (xiii) 0.5 µg IL12 miR122 in Compound 18, and (xiv) 2.5 µg IL12 miR122 in Compound 18.

Figure 9I:
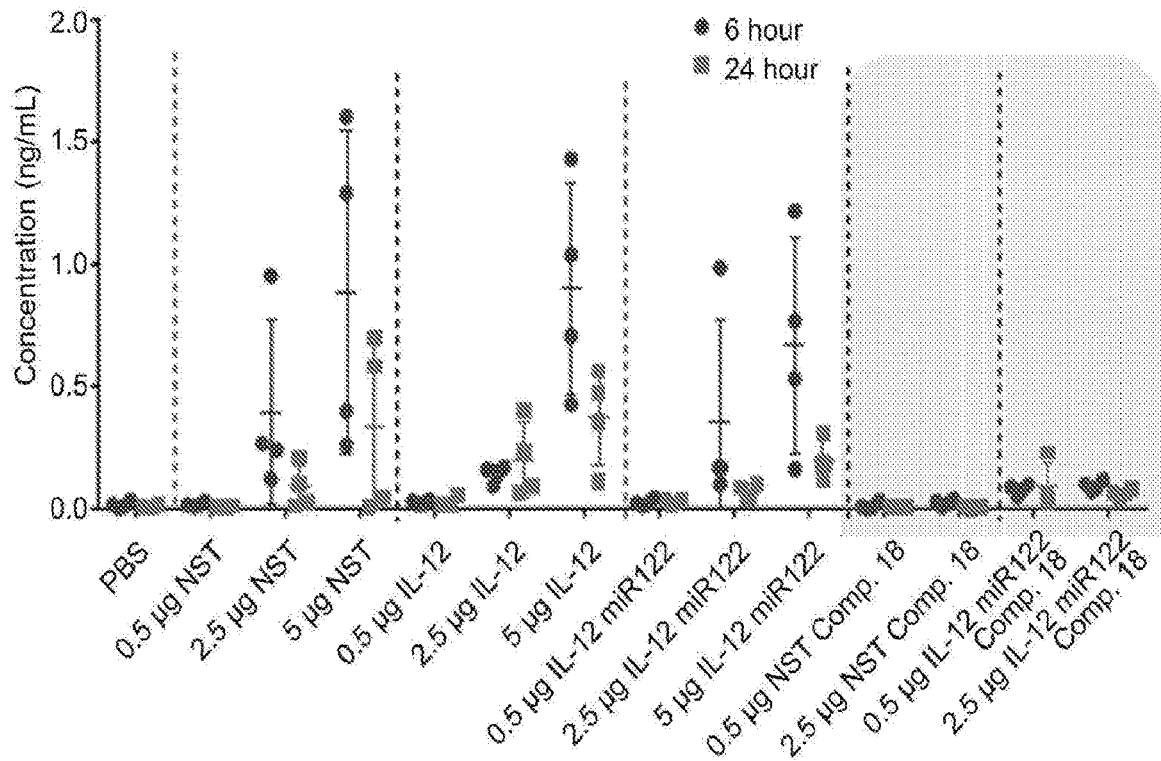
Figure 9J:
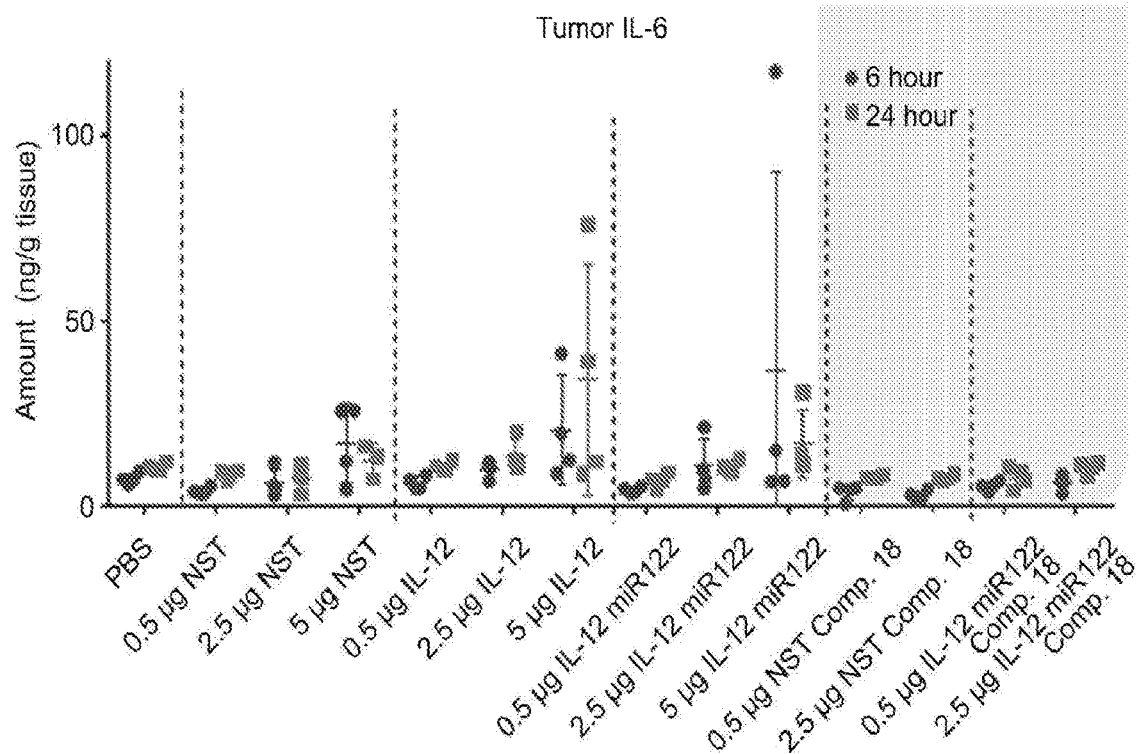

FIGS. 9I-9J are graphs showing decreased levels of IL6 at 6 hours and 24 hours in plasma (FIG. 9I) and in tumor (FIG. 9J) following administration of IL12 mRNA. From left to right, the mice were given (i) PBS, (ii) 0.5 µg NST in MC3, (iii) 2.5 µg NST in MC3, (iv) 5 µg NST in MC3, (v) 0.5 µg IL12 in MC3, (vi) 2.5 µg IL12 in MC3, (vii) 5 g IL12 in MC3, (viii) 0.5 µg IL12 miR122 in MC3, (ix) 2.5 µg IL12 miR122 in MC3, (x) 5 µg IL12 miR122 in MC3, (xi) 0.5 µg NST in Compound 18, (xii) 2.5 µg NST in Compound 18, (xiii) 0.5 µg IL12 miR122 in Compound 18, and (xiv) 2.5 µg IL12 miR122 in Compound 18.

Figure 9K:
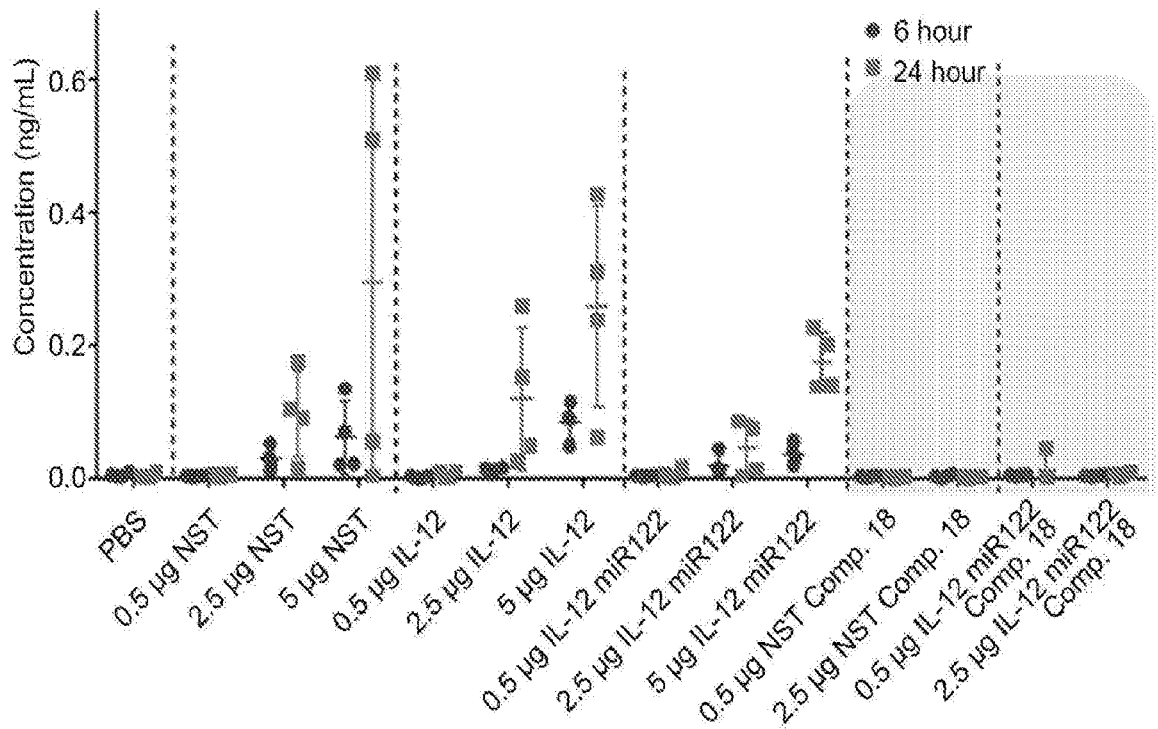
Figure 9L:
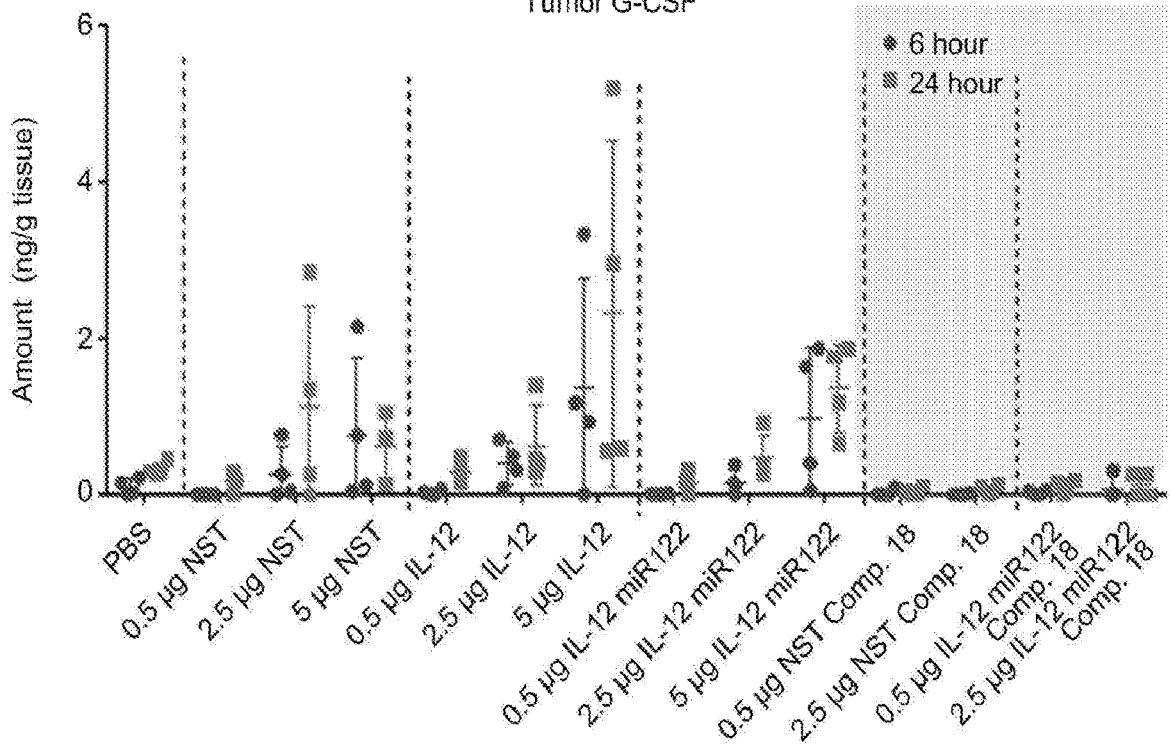

FIGS. 9K-9L are graphs showing decreased levels of G-CSF at 6 hours and 24 hours in plasma (FIG. 9K) and in tumor (FIG. 9L) following administration of IL12 mRNA. From left to right, the mice were given (i) PBS, (ii) 0.5 µg NST in MC3, (iii) 2.5 g NST in MC3, (iv) 5 µg NST in MC3, (v) 0.5 µg IL12 in MC3, (vi) 2.5 µg IL12 in MC3, (vii) 5 µg IL12 in MC3, (viii) 0.5 µg IL12 miR122 in MC3, (ix) 2.5 µg IL12 miR122 in MC3, (x) 5 µg IL12 miR122 in MC3, (xi) 0.5 µg NST in Compound 18, (xii) 2.5 µg NST in Compound 18, (xiii) 0.5 µg IL12 miR122 in Compound 18, and (xiv) 2.5 g IL12 miR122 in Compound 18.

Figure 9M:
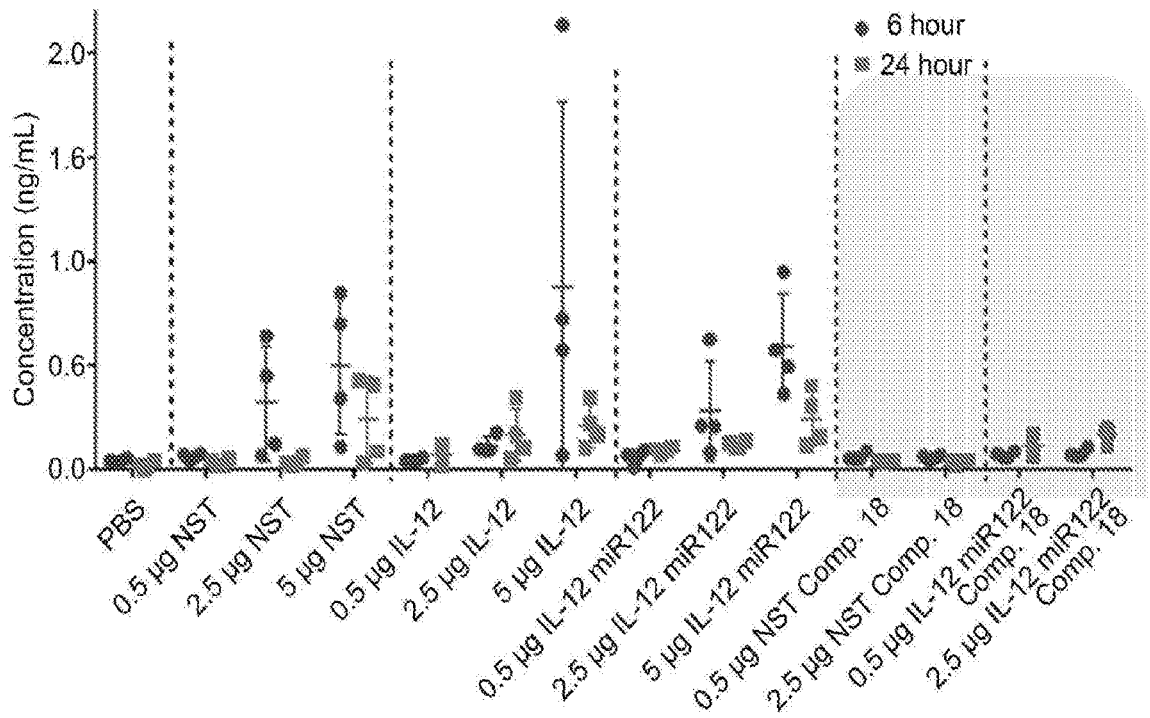
Figure 9N:
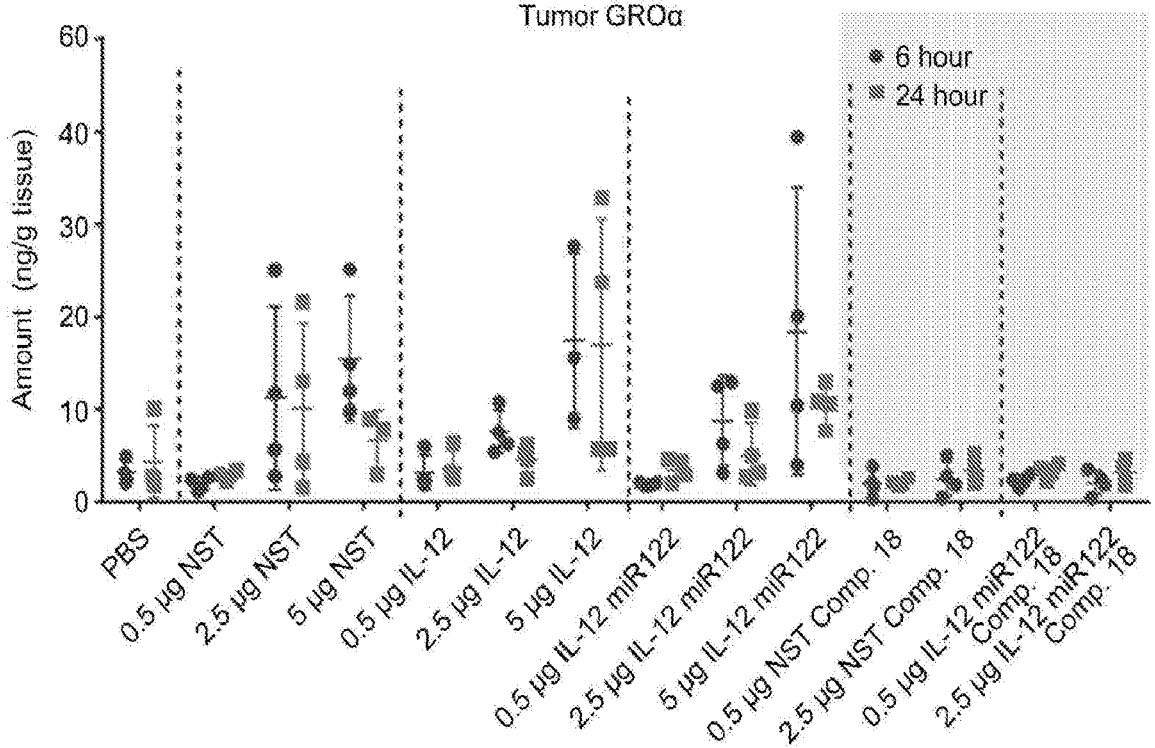

FIGS. 9M-9N are graphs showing decreased levels of GROα at 6 hours and at 24 hours in plasma (FIG. 9M) and tumor (FIG. 9N) following administration of IL12 mRNA. From left to right, the mice were given (i) PBS, (ii) 0.5 µg NST in MC3, (iii) 2.5 g NST in MC3, (iv) 5 µg NST in MC3, (v) 0.5 µg IL12 in MC3, (vi) 2.5 µg IL12 in MC3, (vii) 5 µg IL12 in MC3, (viii) 0.5 µg IL12 miR122 in MC3, (ix) 2.5 µg IL12 miR122 in MC3, (x) 5 µg IL12 miR122 in MC3, (xi) 0.5 µg NST in Compound 18, (xii) 2.5 µg NST in Compound 18, (xiii) 0.5 µg IL12 miR122 in Compound 18, and (xiv) 2.5 g IL12 miR122 in Compound 18.

Figure 10A:
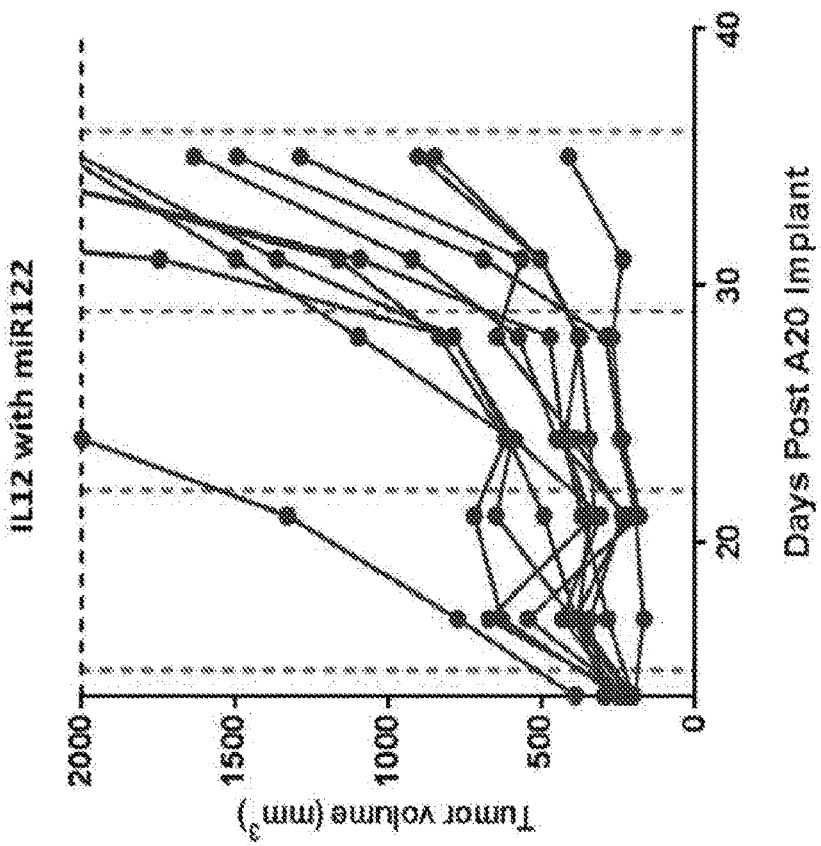
Figure 10B:
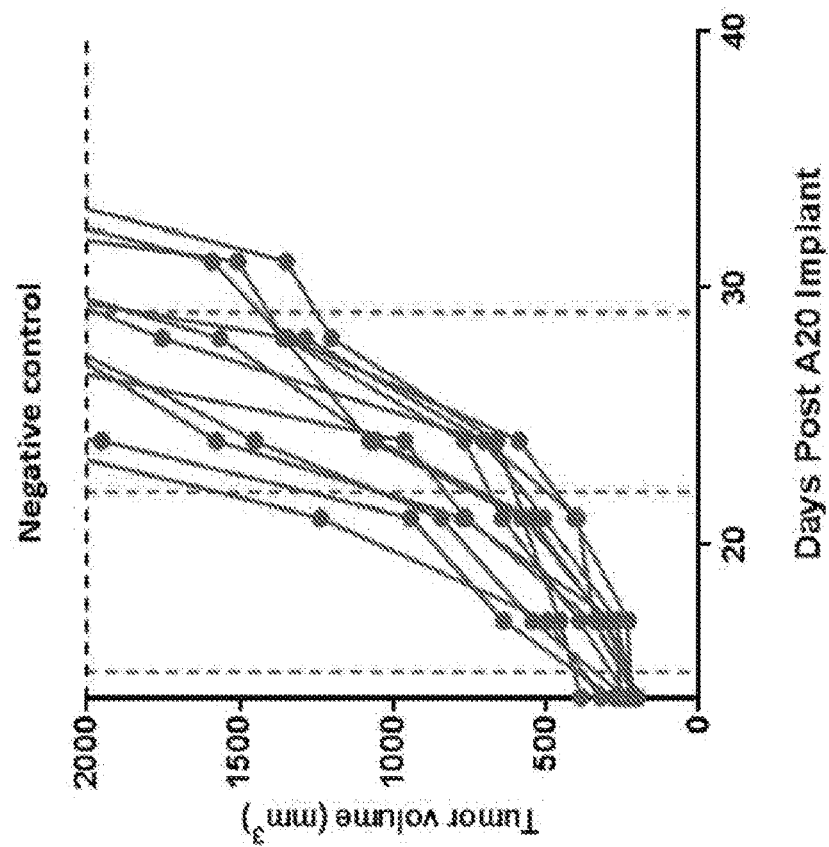

FIGS. 10A-10B are graphs showing individual tumor volumes through day 35 post disease induction with A20 tumor following treatment with IL12_miR122 mRNA (FIG. 10B) compared to negative control mRNA (FIG. 10A).

Figure 10D:
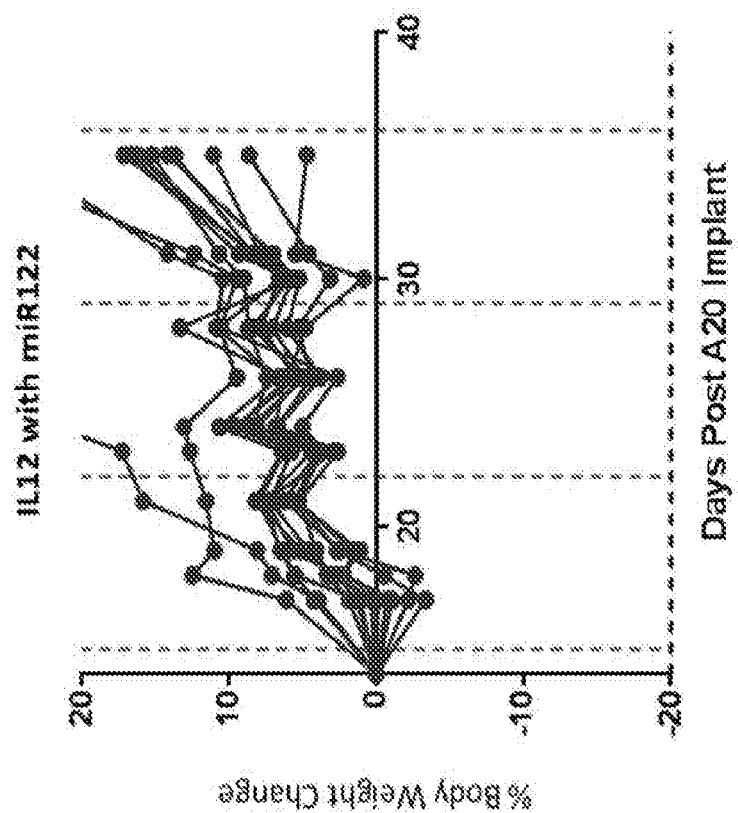
Figure 10C:
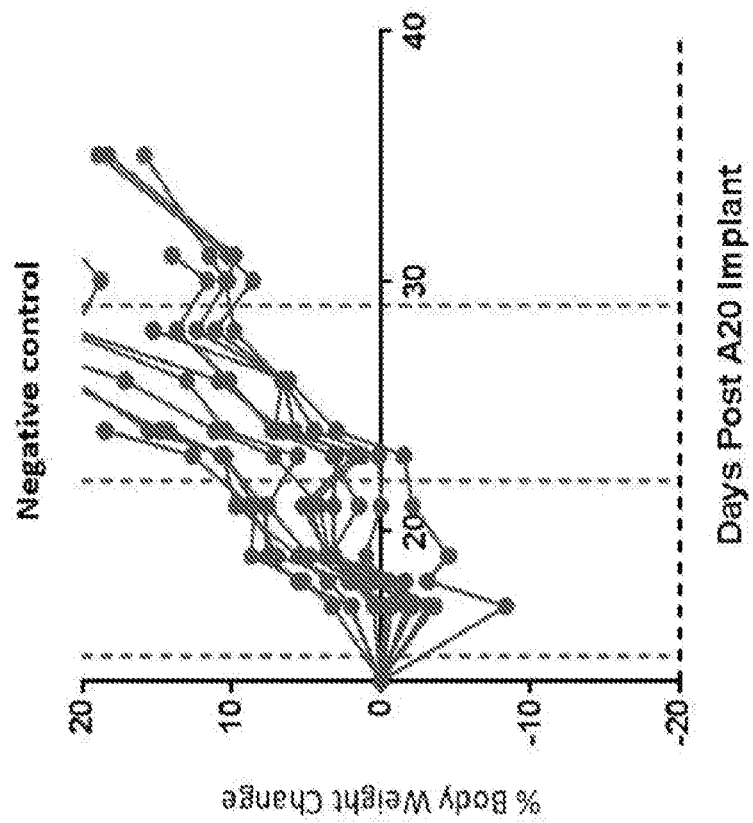

FIGS. 10C-10D are graphs showing body weight measurements of mice through day 35 post disease induction with A20 tumor following treatment with IL12_miR122 mRNA (FIG. 10D) compared to negative control mRNA (FIG. 10C).

Figure 11A:
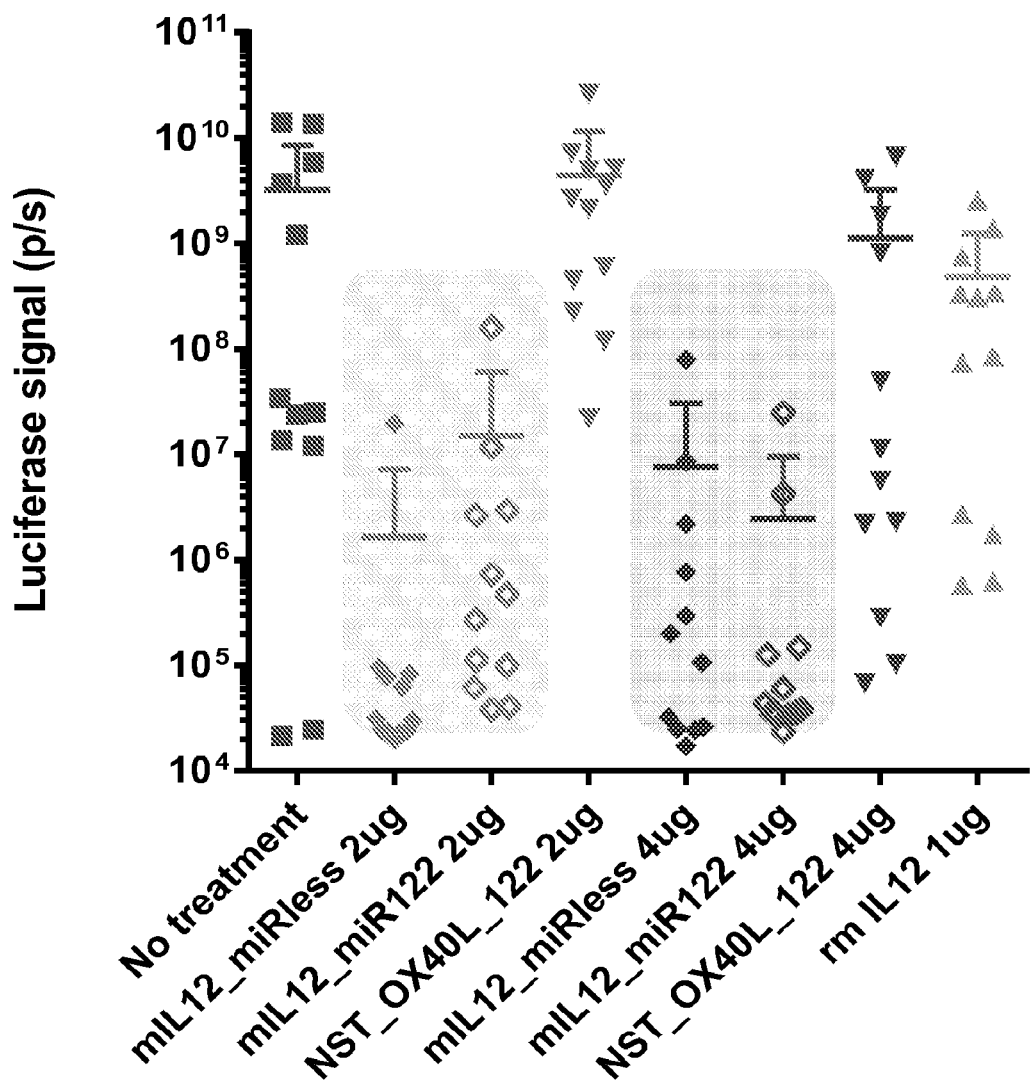

FIG. 11A is a graph depicting bioluminescence (BL) as a surrogate for tumor burden at day 22 post disease induction with a luciferase-enabled MC38 colon cancer cell line in mice. From left to right, mice were administered no treatment, 2 µg mIL12_miRless, 2 µg mIL12_miR122, 2 µg NST_OX40L_122, 4 µg mIL12_miRless, 4 g mIL12_miR122, 4 g NST_OX40L_122, and 1 µg rm IL12.

Figure 11B:
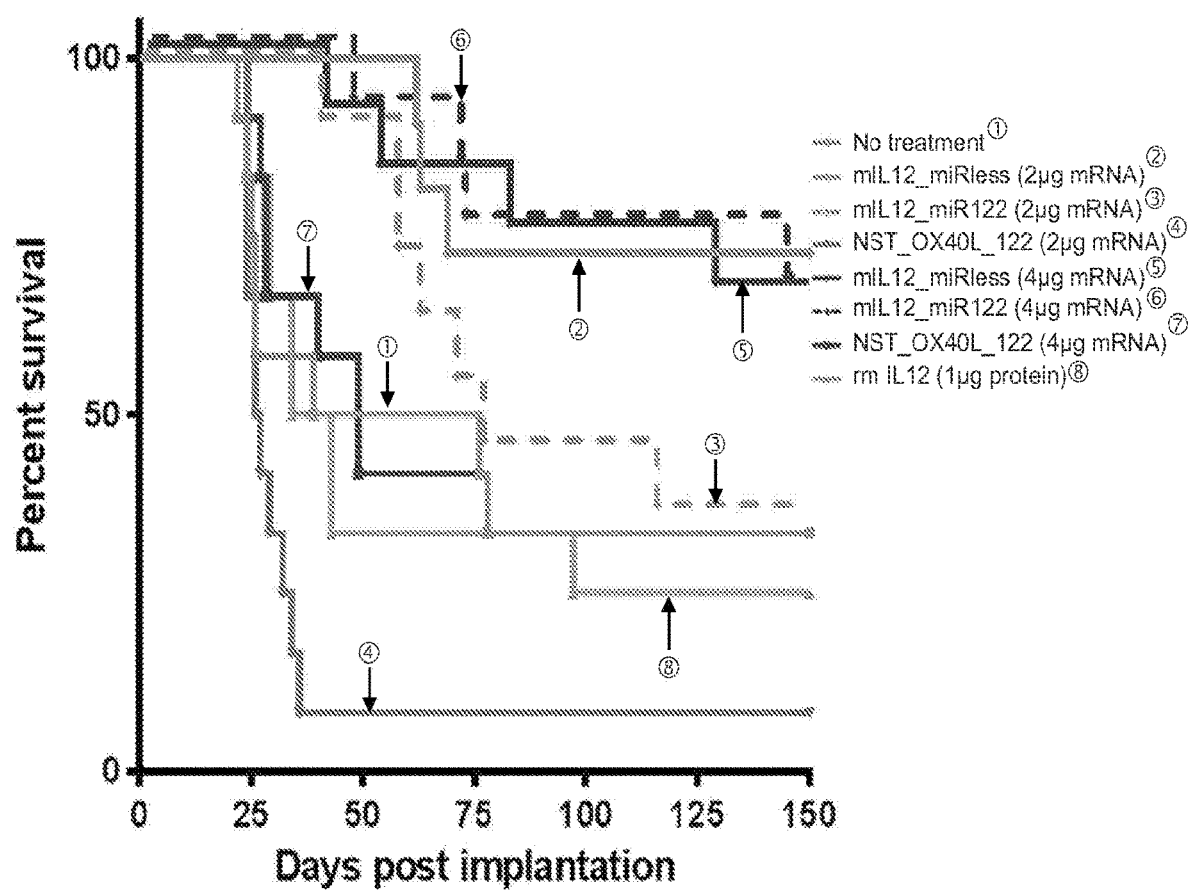

FIG. 11B is a Kaplan-Meier curve showing the percent survival of mice treated with LNPs carrying IL12 mRNA compared to NST-OX40L negative controls. The graph shows survival to day 150 post implantation with A20 tumor.

FIG. 12A shows uracil (U) metrics corresponding to wild type IL12B and 20 sequence optimized IL12B polynucleotides (hIL12AB_001 to hIL12AB_020). FIG. 12B shows guanine (G) metrics corresponding to wild type IL12B and 20 sequence optimized IL12B polynucleotides (hIL12AB_001 to hIL12AB_020). FIG. 12C shows cytosine (C) metrics corresponding to wild type IL12B and 20 sequence optimized IL12B polynucleotides (hIL12AB_001 to hIL12AB_020). FIG. 12D shows guanine plus cytosine (G/C) metrics corresponding to wild type IL12B and 20 sequence optimized IL12B polynucleotides (hIL12AB_001 to hIL12AB_020).

FIG. 13A shows uracil (U) metrics corresponding to wild type IL12B and 20 sequence optimized IL12B polynucleotides (hIL12AB_021 to hIL12AB_040). FIG. 13B shows guanine (G) metrics corresponding to wild type L12B and 20 sequence optimized IL12B polynucleotides (hIL12AB_021 to hIL12AB_040). FIG. 13C shows cytosine (C) metrics corresponding to wild type IL12B and 20 sequence optimized IL12B polynucleotides (hIL12AB_021 to hIL12AB_040). FIG. 13D shows guanine plus cytosine (G/C) metrics corresponding to wild type IL12B and 20 sequence optimized IL12B polynucleotides (hIL12AB_021 to hIL12AB_040).

FIG. 14A shows uracil (U) metrics corresponding to wild type IL12A and 20 sequence optimized IL12A polynucleotides (hIL12AB_001 to hIL12AB_020). FIG. 14B shows guanine (G) metrics corresponding to wild type L12A and 20 sequence optimized IL12A polynucleotides (hIL12AB_001 to hIL12AB_020). FIG. 14C shows cytosine (C) metrics corresponding to wild type IL12A and 20 sequence optimized IL12A polynucleotides (hIL12AB_001 to hIL12AB_020). FIG. 14D shows guanine plus cytosine (G/C) metrics corresponding to wild type IL12A and 20 sequence optimized IL12A polynucleotides (hIL12AB_001 to hIL12AB_020).

FIG. 15A shows uracil (U) metrics corresponding to wild type IL12A and 20 sequence optimized IL12A polynucleotides (hIL12AB_021 to hIL12AB_040). FIG. 15B shows guanine (G) metrics corresponding to wild type L12A and 20 sequence optimized IL12A polynucleotides (hIL12AB_021 to hIL12AB_040). FIG. 15C shows cytosine (C) metrics corresponding to wild type IL12A and 20 sequence optimized IL12A polynucleotides (hIL12AB_021 to hIL12AB_040). FIG. 15D shows guanine plus cytosine (G/C) metrics corresponding to wild type IL12A and 20 sequence optimized IL12A polynucleotides (hIL12AB_021 to hIL12AB_040). The column labeled "G/C Content (%)" corresponds to % G/Cm.

FIG. 16A shows a comparison between the G/C compositional bias for codon positions 1, 2, 3 corresponding to the wild type IL12B and 20 sequence optimized IL12B polynucleotides (hIL12AB_001 to hIL12AB_020). FIG. 16B shows a comparison between the G/C compositional bias for codon positions 1, 2, 3 corresponding to the wild type IL12B and 20 sequence optimized IL12B polynucleotides (hIL12AB_021 to hIL12AB_040). FIG. 16C shows a comparison between the G/C compositional bias for codon positions 1, 2, 3 corresponding to the wild type IL12A and 20 sequence optimized IL12A polynucleotides (hIL12AB_0-1 to hIL12AB_020). FIG. 16D shows a comparison between the G/C compositional bias for codon positions 1, 2, 3 corresponding to the wild type IL12A and 20 sequence optimized IL12A polynucleotides (hIL12AB_021 to hIL12AB_040).

Figure 17A:
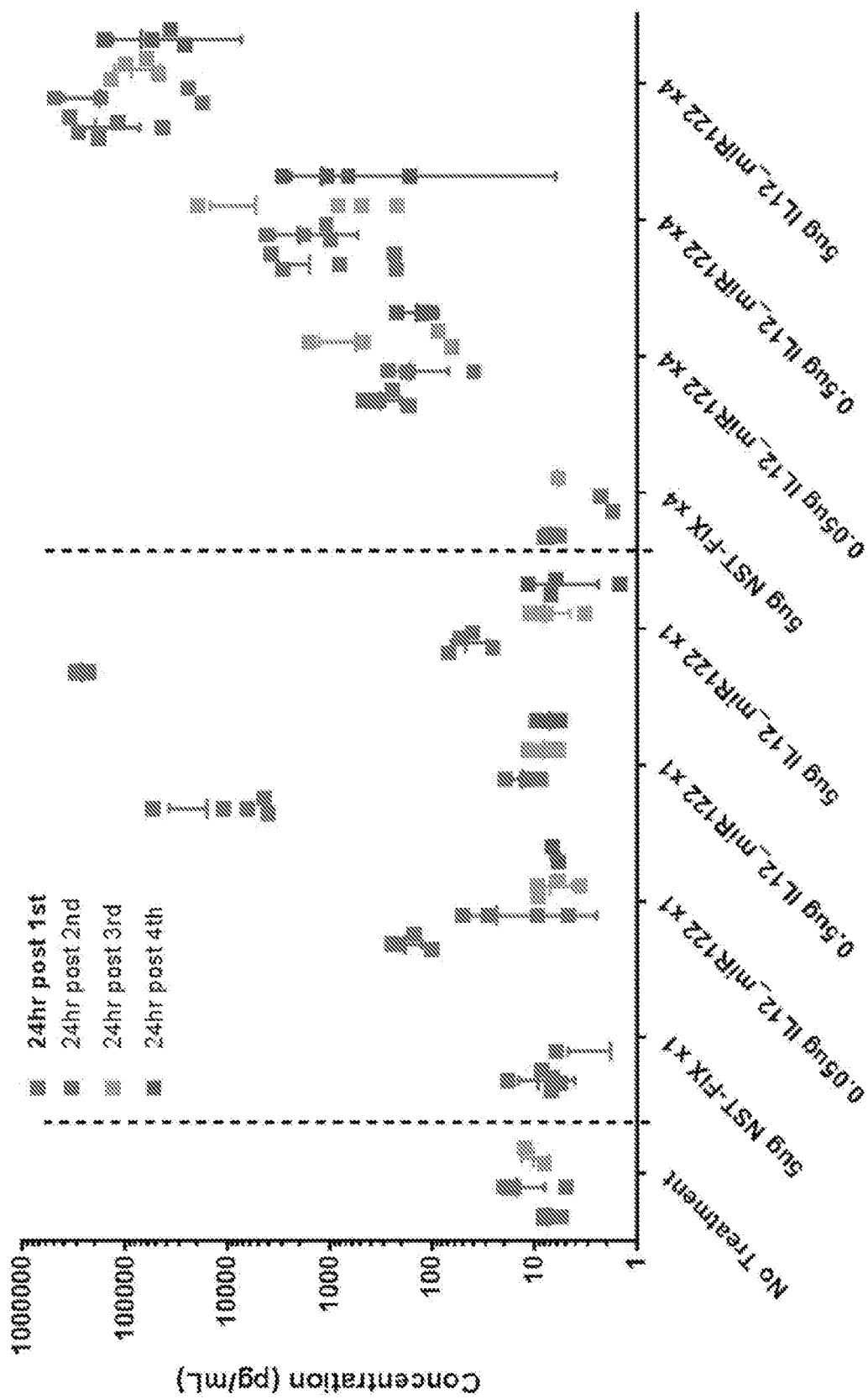

FIG. 17A is a graph showing dose-dependent levels of IL12 in plasma at 24 hours following intratumoral administration of the indicated doses of IL12 mRNA to mice bearing tumors. From left to right, the mice were given (i) no treatment, (ii) 5 μg NST, (iii) 0.05 μg IL12 miR122, (iv) 0.5 μg IL12 miR122, (v) 5 μg IL12 miR122, (vi) 5 μg NST, (vii) 0.5 μg IL12 miR122 (4 doses), (viii) 2.5 μg IL12 miR122 (4 doses), and (ix) 5 g IL12 miR122 (4 doses).

Figure 17B:
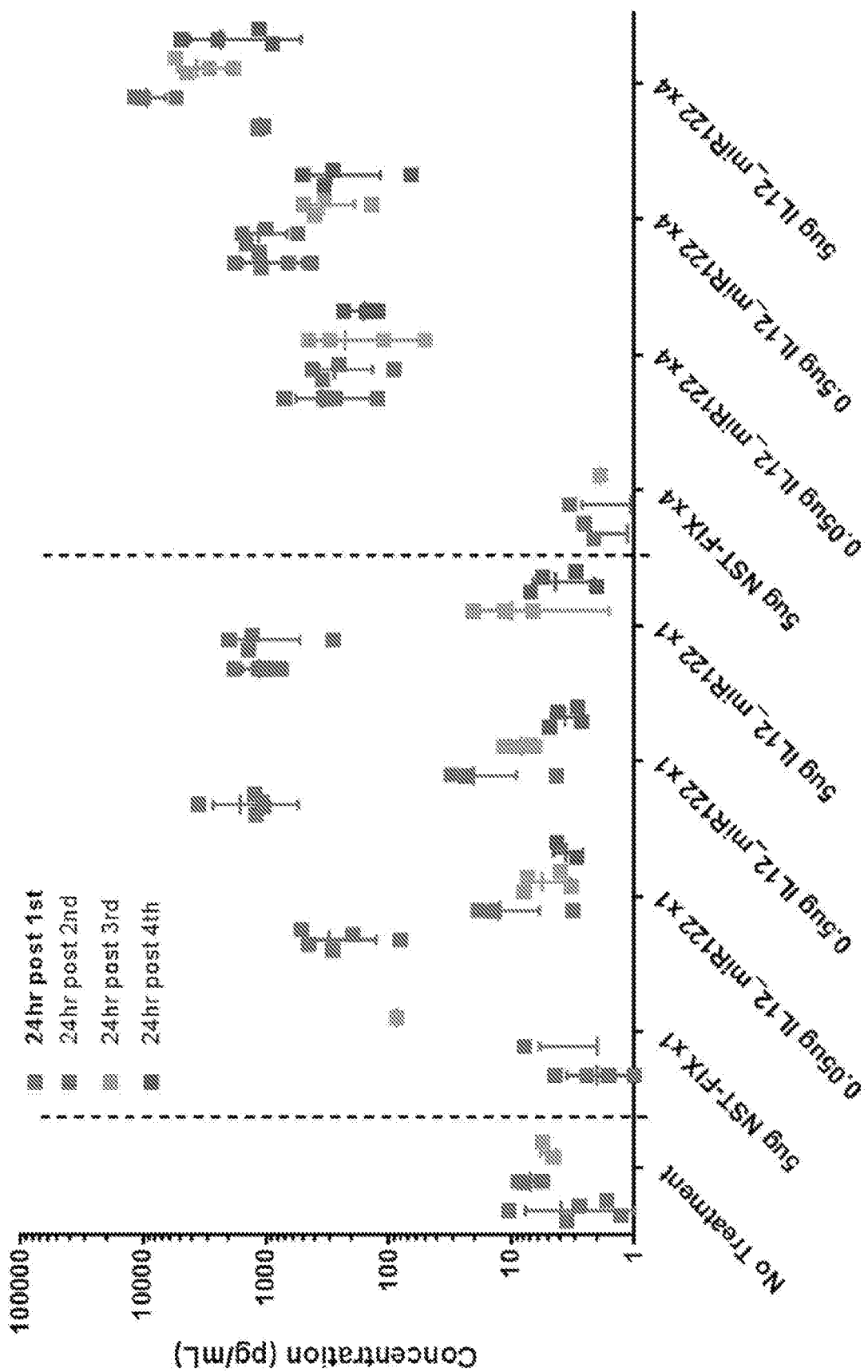

FIG. 17B is a graph showing increased levels of IFNγ in plasma at 24 hours following intratumoral administration of IL12 mRNA to mice bearing tumors. From left to right, the mice were given (i) no treatment, (ii) 5 μg NST, (iii) 0.05 μg IL12 miR122, (iv) 0.5 μg IL12 miR122, (v) 5 μg IL12 miR122, (vi) 5 μg NST, (vii) 0.5 μg IL12 miR122 (4 doses), (viii) 2.5 μg IL12 miR122 (4 doses), and (ix) 5 μg IL12 miR122 (4 doses).

Figure 18A:
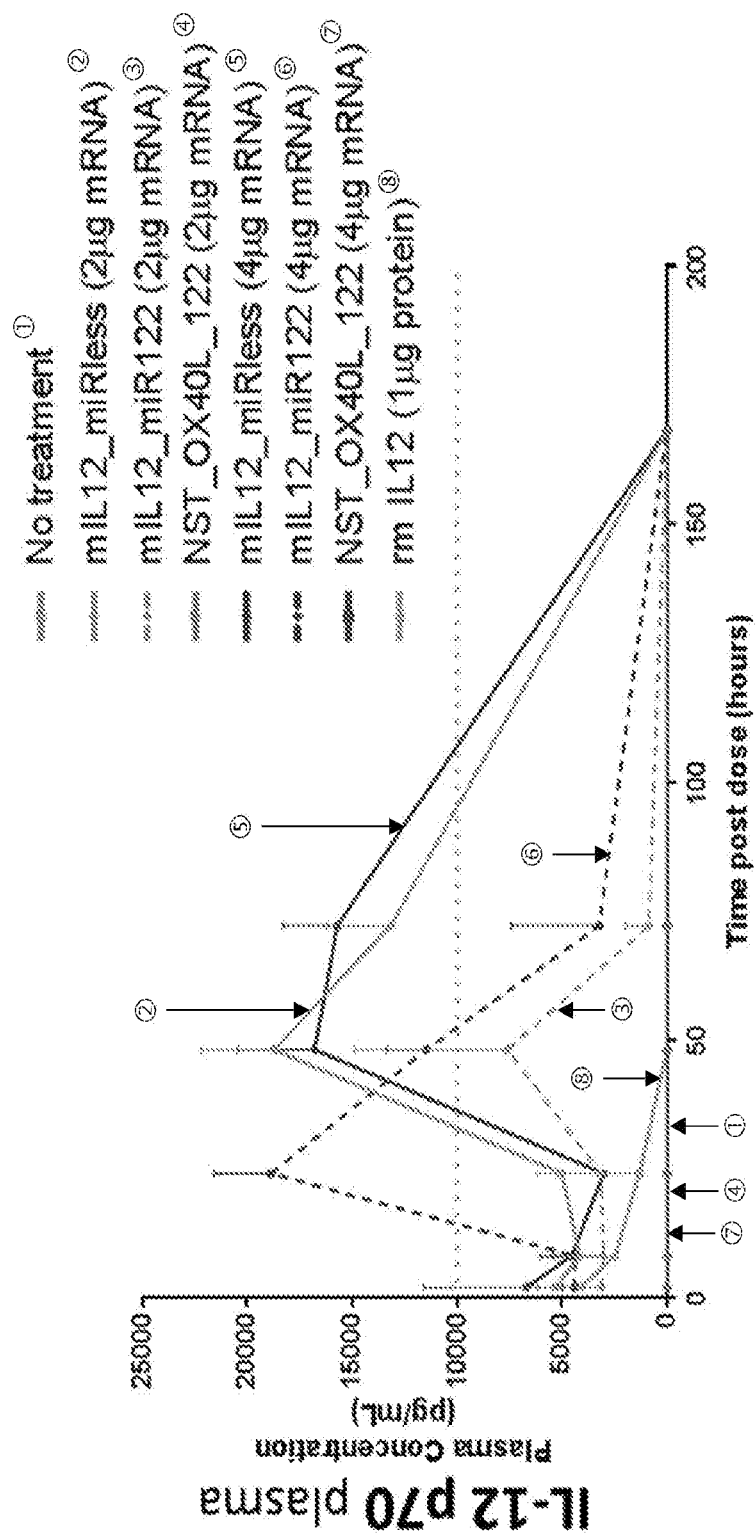
Figure 18B:
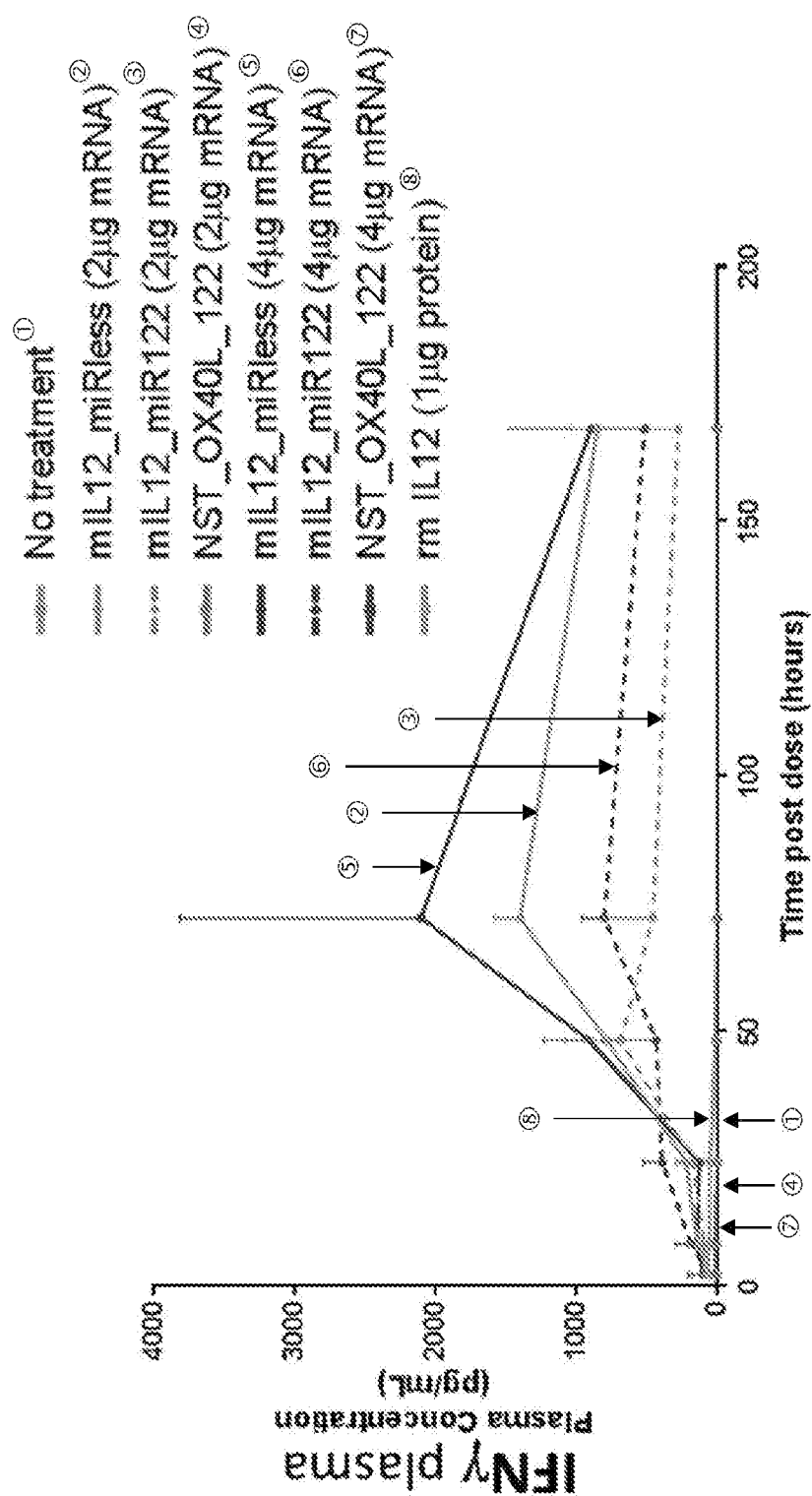

FIGS. 18A-18B are graphs showing increased levels of IL12 in plasma (FIG. 18A) and IFNγ in plasma (FIG. 18B) over the course of 200 hours following intraperitoneal administration of IL12 mRNA to mice bearing MC38 tumors. Mice were given (i) no treatment, (ii) 2 μg IL12 miRless, (iii) 2 μg IL12 miR122, (iv) 4 μg IL12 miRless, (v) 4 μg miR122, (vi) 1 μg IL12 protein, (vii) 2 μg NST_OX40L_122, or (viii) 4 μg NST_OX40L_122.

Figure 19A:
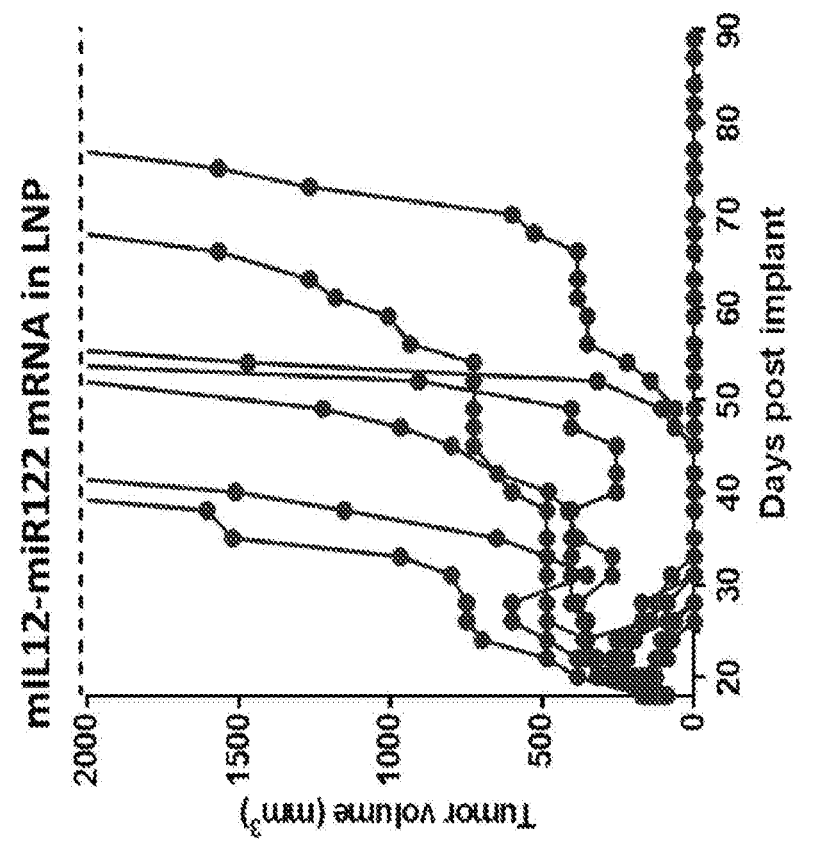
Figure 19B:
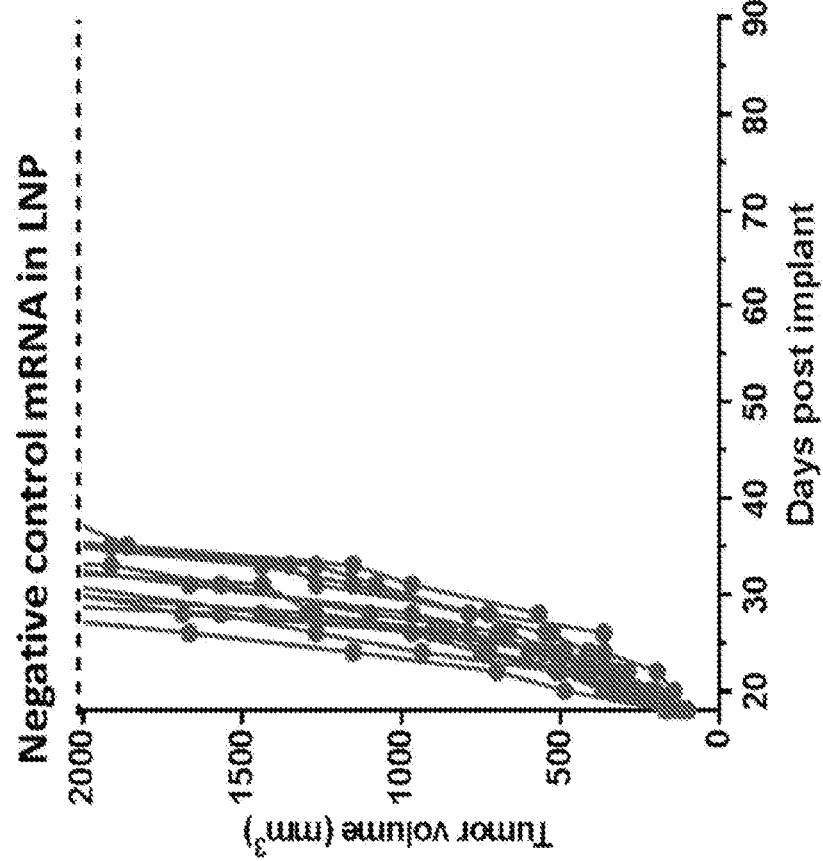

FIGS. 19A-19B are graphs showing individual tumor volumes through day 90 post disease induction with A20 tumor following treatment with 0.5 μg IL12_miR122 mRNA in a Compound 18-based lipid nanoparticle (LNP) (FIG. 19B) compared to negative control mRNA (FIG. 19A).

Figure 19D:
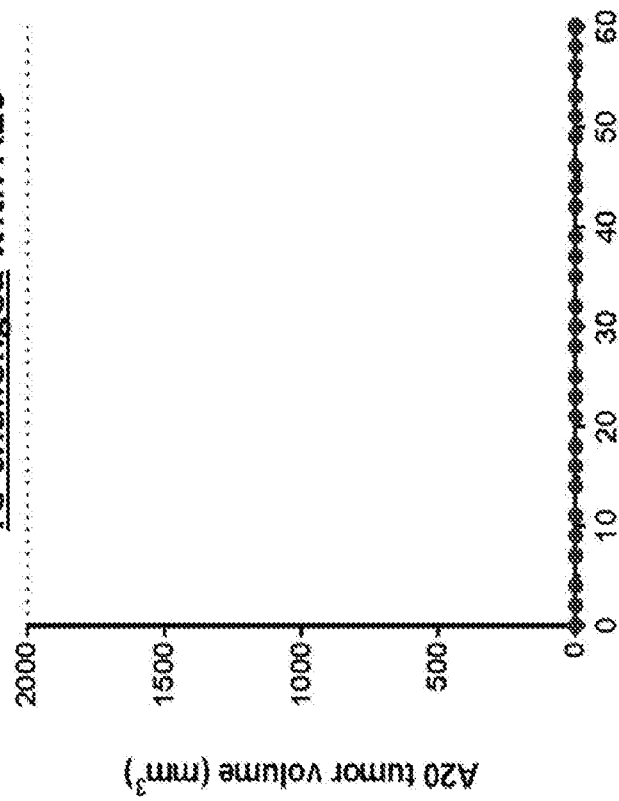
Figure 19C:
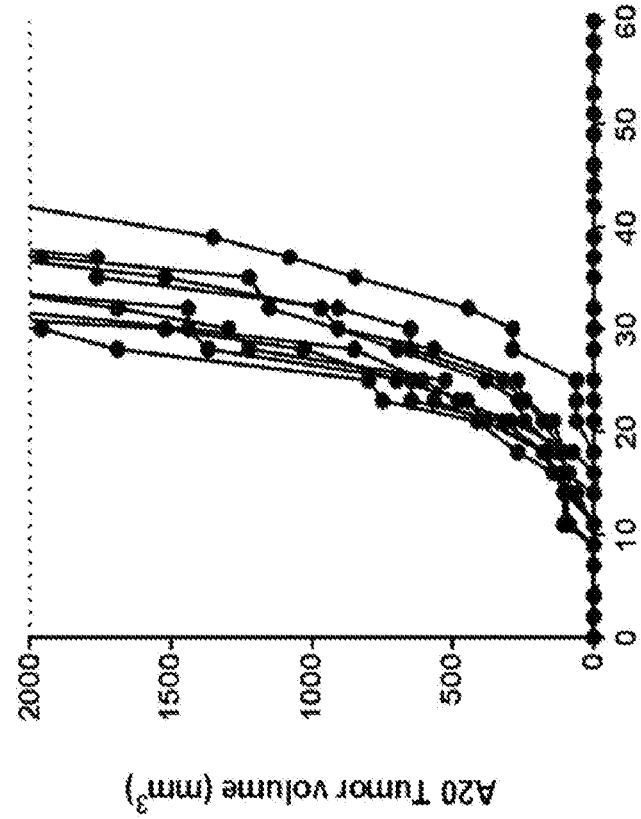

FIGS. 19C-19D are graphs showing individual tumor volumes through day 60 post disease induction with A20 tumor in naïve mice (FIG. 19C) or in complete responder mice previously treated with IL12_miR122 mRNA and rechallenged (FIG. 19D).

Figure 20A:
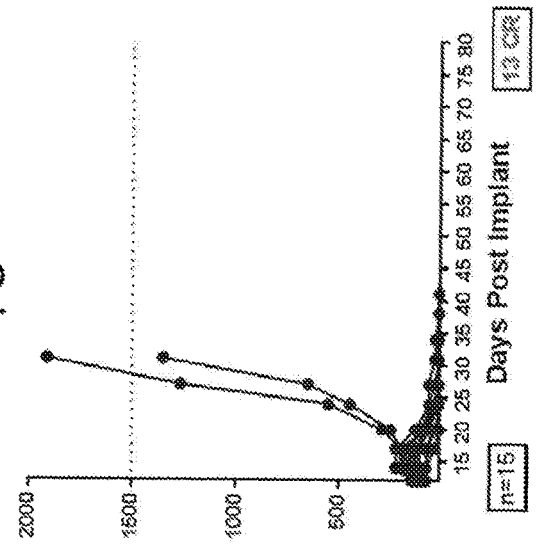
Figure 20B:
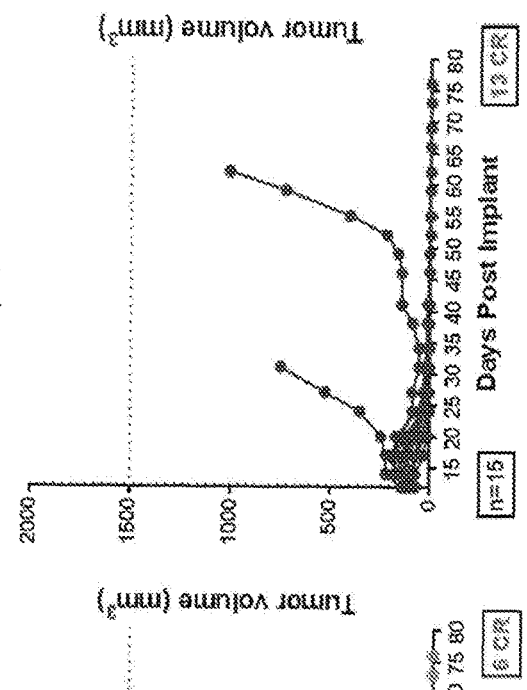
Figure 20C:
Figure 20D:
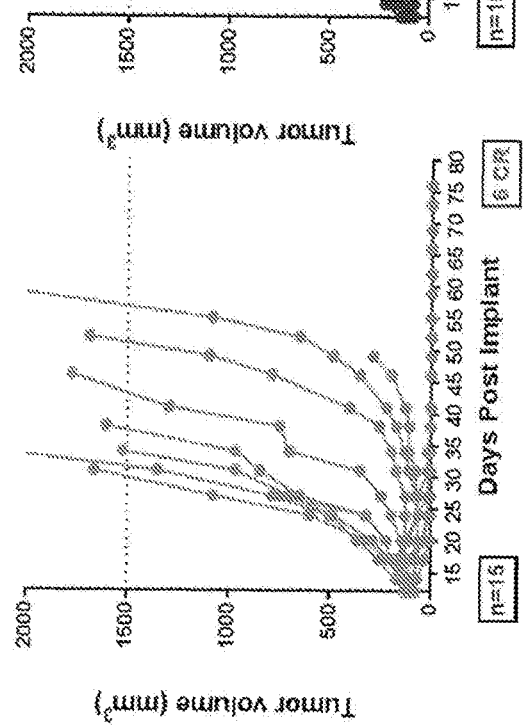

FIGS. 20A-20D are graphs showing individual tumor volumes through 80 days following a single intratumoral dose of IL12 mRNA to mice bearing MC38-S tumors. Mice were given 0.05 μg IL12 mRNA (FIG. 20A), 0.5 μg IL12 mRNA (FIG. 20B), 5 μg IL12 mRNA (FIG. 20C), or NST (FIG. 20D).

FIGS. 21A-21F are graphs showing individual tumor volumes through 80 days following a single dose or multiple doses of IL12 mRNA to mice bearing MC38-S tumors. Mice were given a single dose of 0.05 μg IL12 mRNA (FIG. 21A), a single dose of 0.5 μg IL12 mRNA (FIG. 21B), a single dose of 5 μg IL12 mRNA (FIG. 21C), two doses of 0.05 μg IL12 mRNA (FIG. 21D), two doses of 0.5 μg IL12 mRNA (FIG. 21E), two doses of 5 μg IL12 mRNA (FIG. 21F).

FIG. 22 is a Kaplan-Meier curve showing the percent survival of mice treated with LNPs carrying IL12 mRNA compared to NST-FIX negative controls. The graph shows survival to day 80 post implantation with MC38-S tumor.

FIG. 23A-23D are graphs showing individual tumor volumes through 75 days following a single dose of IL12 mRNA to mice bearing MC38-R tumors. Mice were given 0.05 μg IL12 mRNA (FIG. 23A), 0.5 μg IL12 mRNA (FIG. 23B), 5 μg IL12 mRNA (FIG. 23C), or NST (FIG. 23D).

FIG. 23E-23J are graphs showing individual tumor volumes through 75 days following a single dose or multiple doses of IL12 mRNA to mice bearing MC38-R tumors. Mice were given a single dose of 0.05 μg IL12 mRNA (FIG. 23E), a single dose of 0.5 μg IL12 mRNA (FIG. 23F), a single dose of 5 μg IL12 mRNA (FIG. 23G), multiple doses of 0.05 μg IL12 mRNA (FIG. 23H), multiple doses of 0.5 μg IL12 mRNA (FIG. 23I), or multiple doses of 5 μg IL12 mRNA (FIG. 23J).

Figure 24:
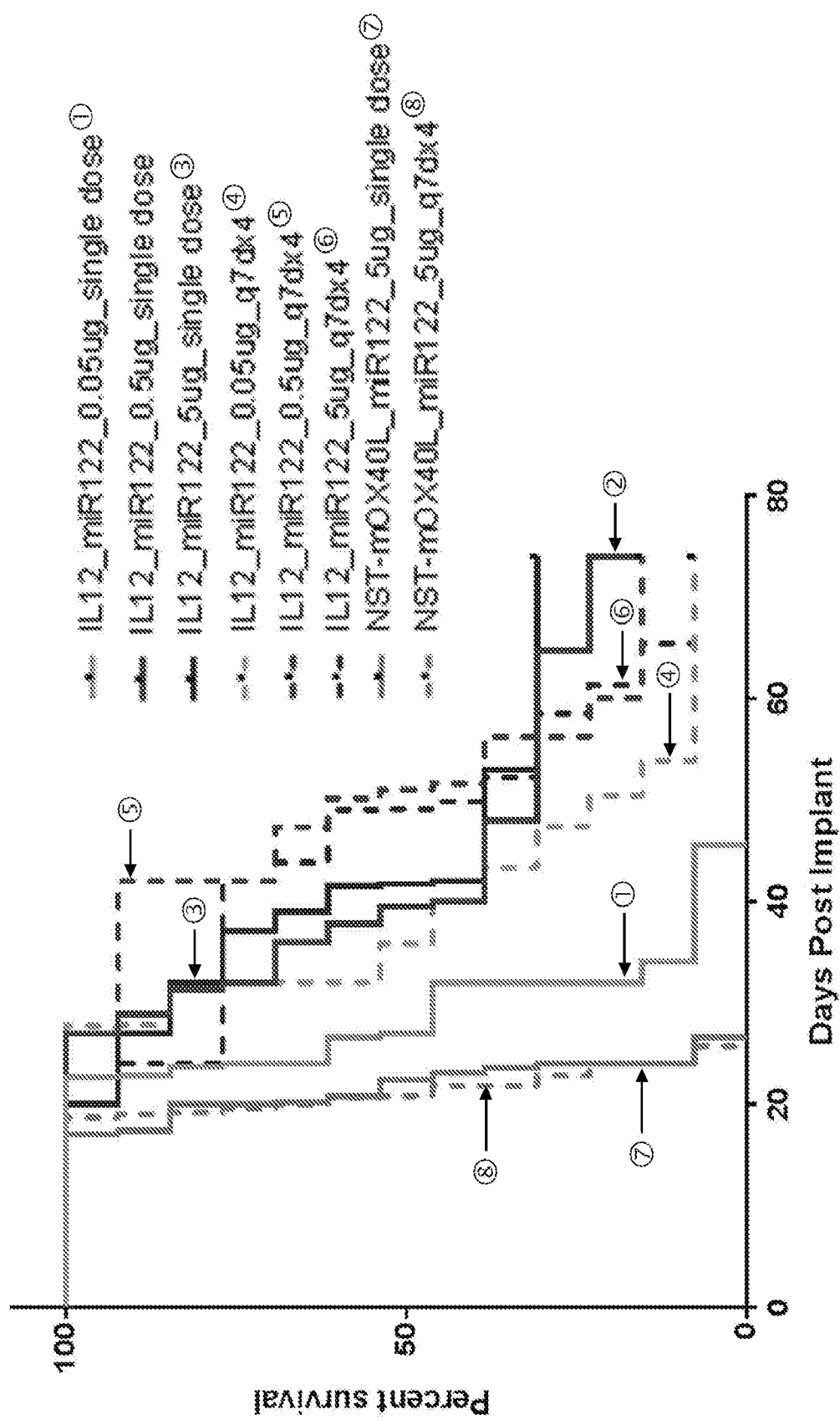

FIG. 24 is a Kaplan-Meier curve showing the percent survival of mice treated with LNPs carrying IL12 mRNA compared to NST-OX40L negative controls. The graph shows survival to day 80 post implantation with MC38-R tumor.

FIG. 25 is a graph showing depletion of CD8+ T cells over the course of 28 days.

Figure 26A:
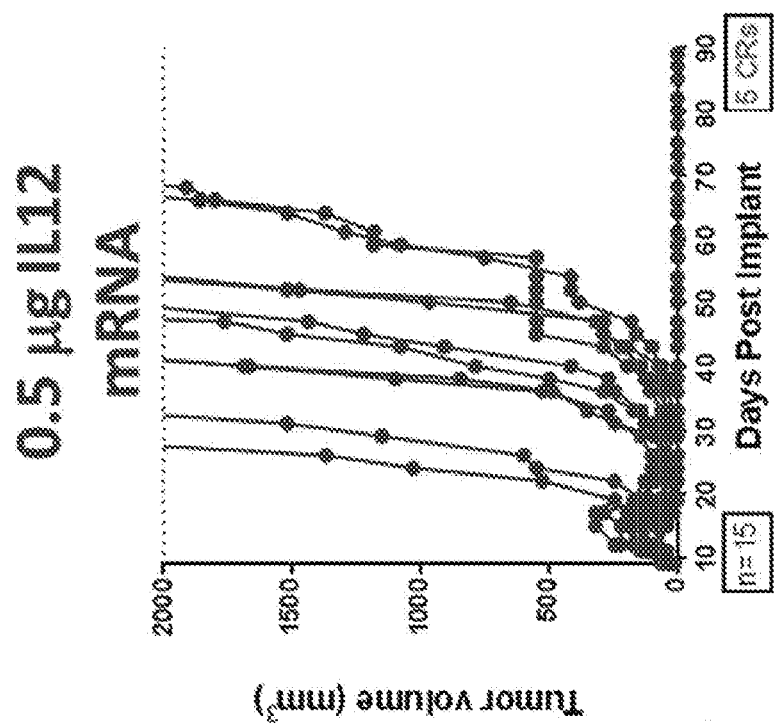
Figure 26B:
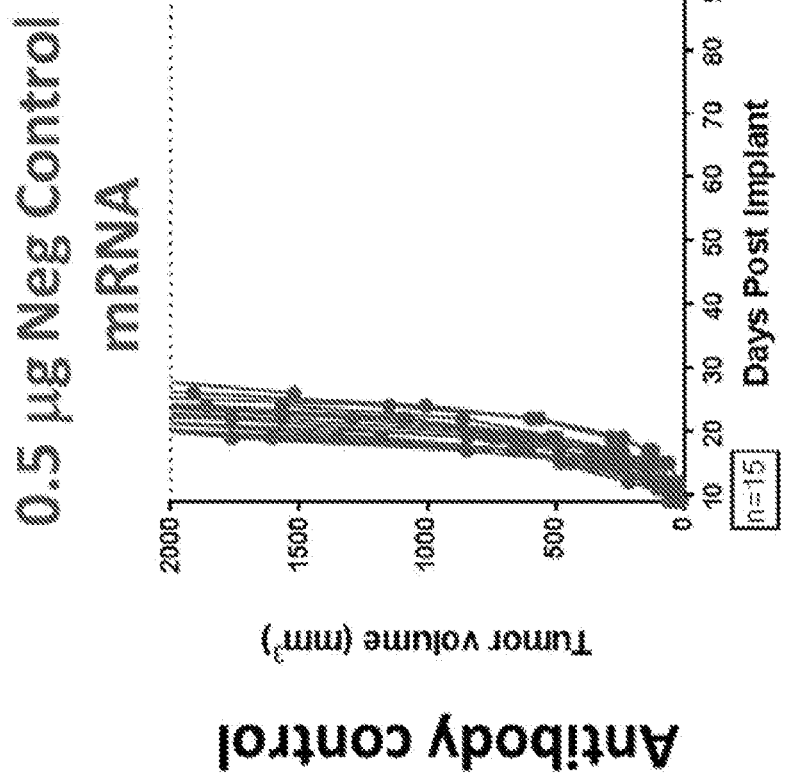
Figure 26C:
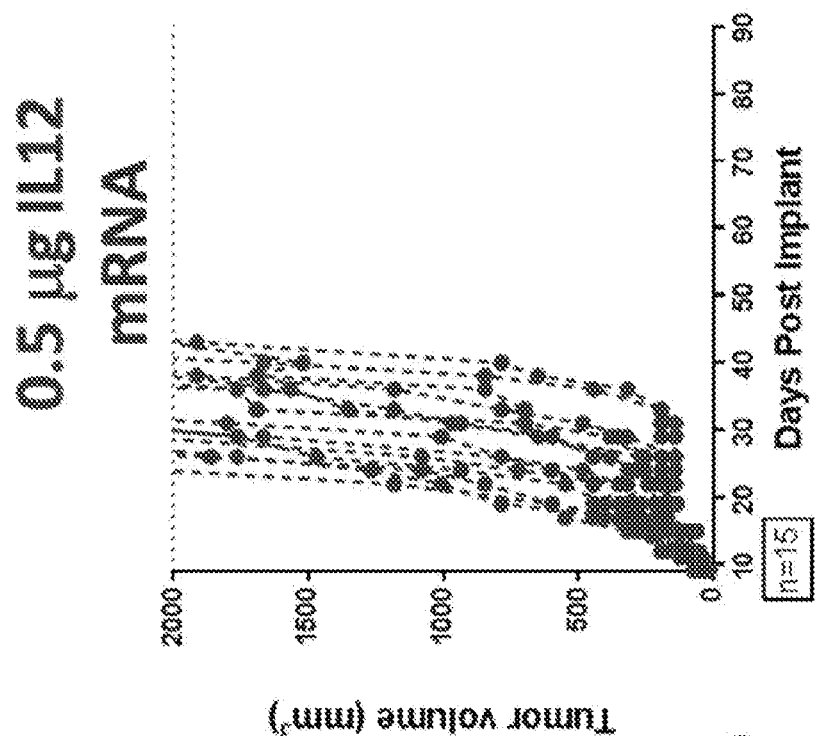
Figure 26D:
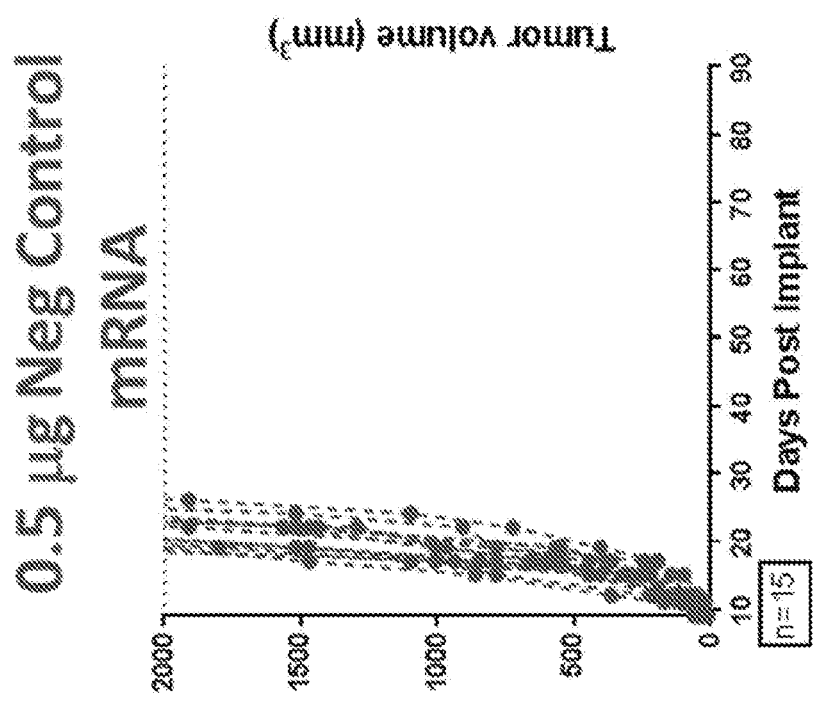

FIGS. 26A-26E are graphs showing individual tumor volumes following CD8+ T cell depletion and subsequent administration of a single dose of IL12 mRNA to mice bearing MC38-R tumors. Mice were given an antibody control for CD8+ T cell depletion and then 0.5 µg negative control mRNA (FIG. 26A), an antibody control for CD8+ T cell depletion and then 0.5 µg IL12 mRNA (FIG. 26B), CD8+ T cell-depleting antibody clone 24.3 and then 0.5 µg negative control mRNA (FIG. 26C), or CD8+ T cell-depleting antibody clone 24.3 and then 0.5 µg IL12 mRNA (FIG. 26D).

Figure 26E:
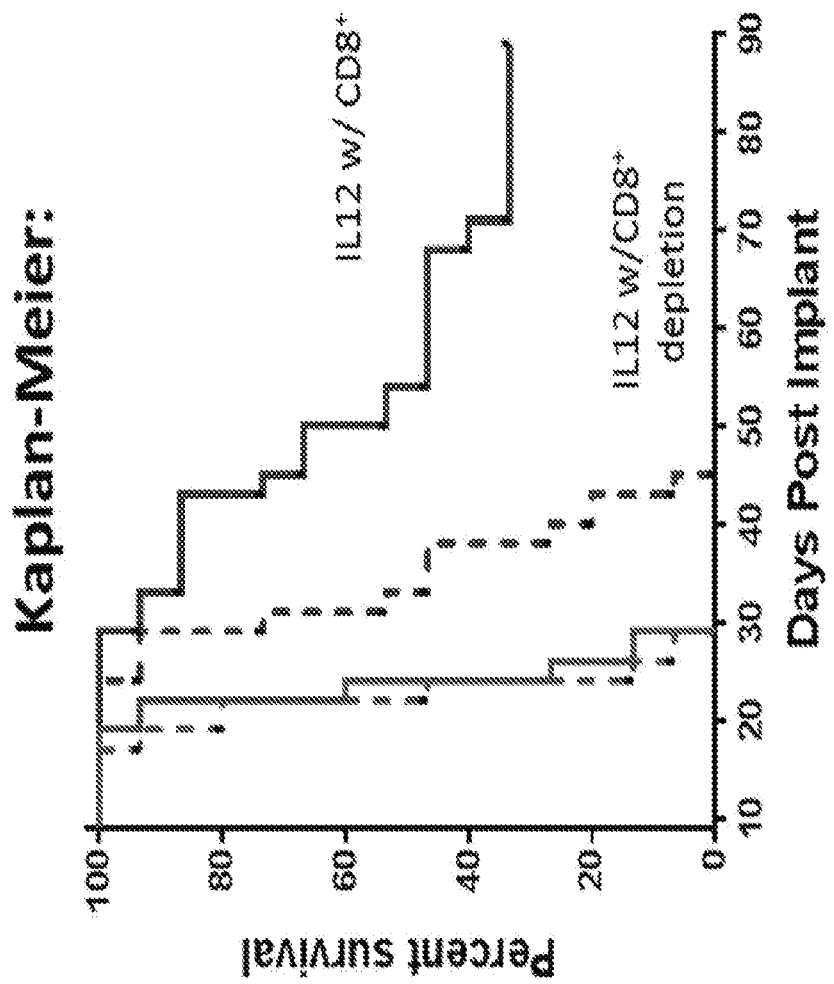

FIG. 26E is a Kaplan-Meier curve showing the percent survival of mice treated with IL12 mRNA absent CD8+ T cell depletion compared to mice treated with IL12 mRNA after CD8+ T cell depletion. The graph shows survival to day 90 post implantation with MC38-R tumor.

Figure 27A:
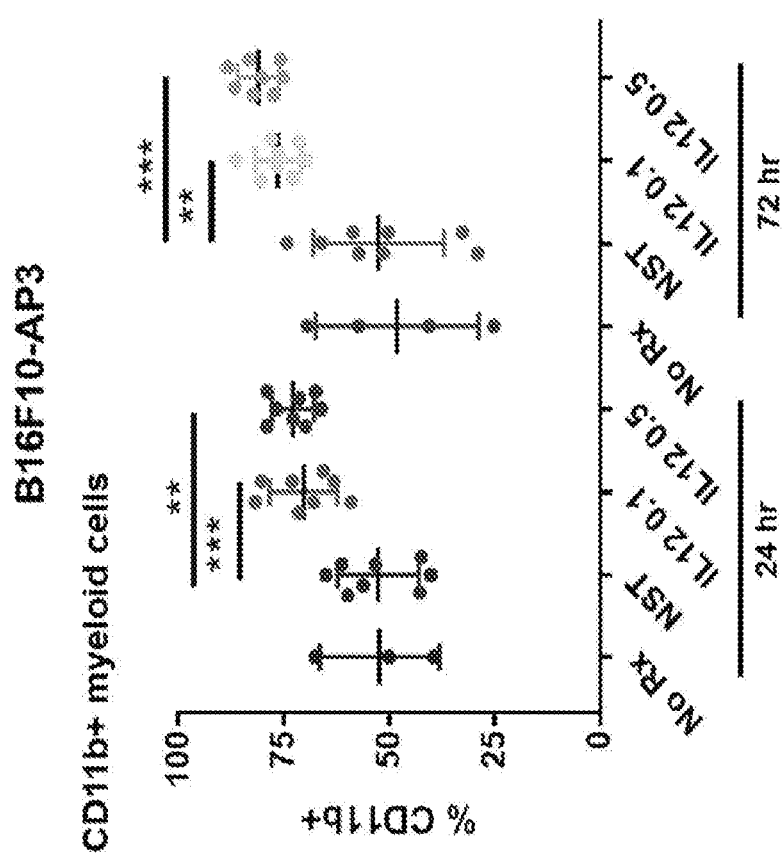
Figure 27B:
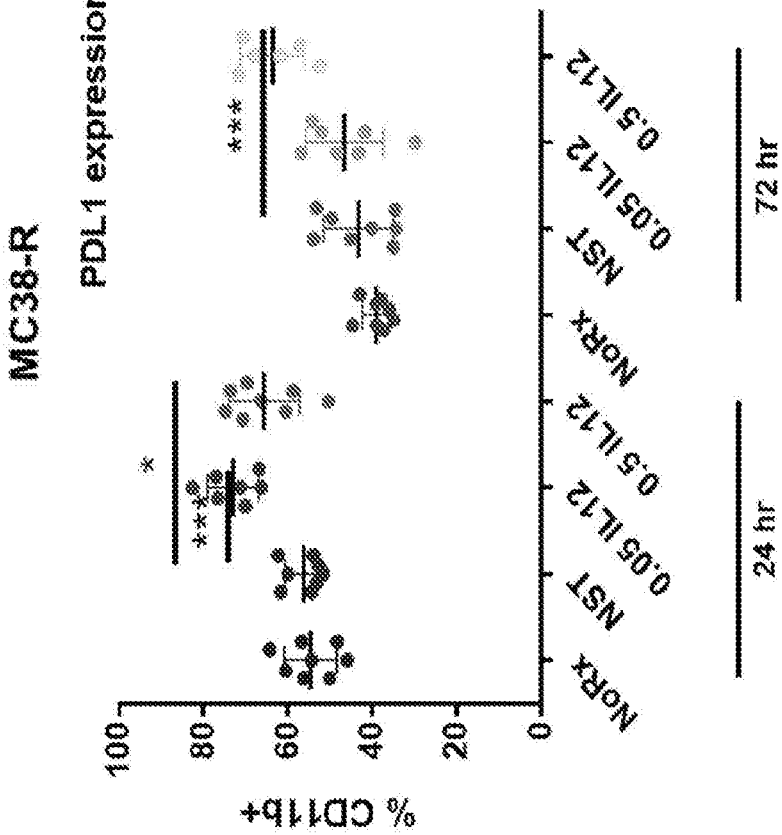

FIGS. 27A-27B are graphs showing the percent of CD1 lb+ myeloid cells staining positive for PDL1 expression in MC38-R (FIG. 27A) and B16F10-AP3 (FIG. 27B) tumors 24 hours or 72 hours after no treatment, treatment with an NST negative control or two different intratumoral doses of IL12 mRNA. Statistical significance is indicated by asterisks.

Figure 28A:
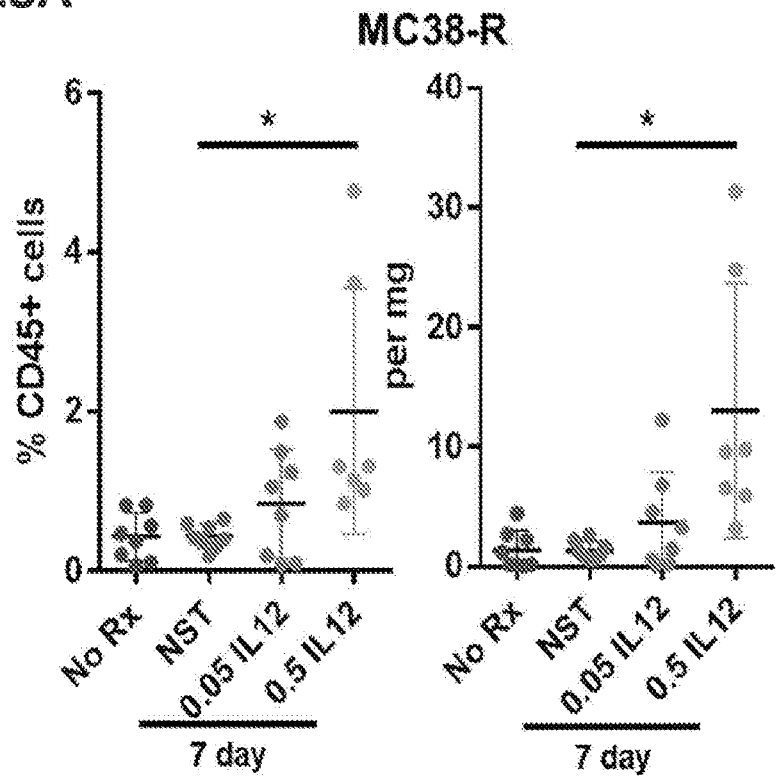
Figure 28B:
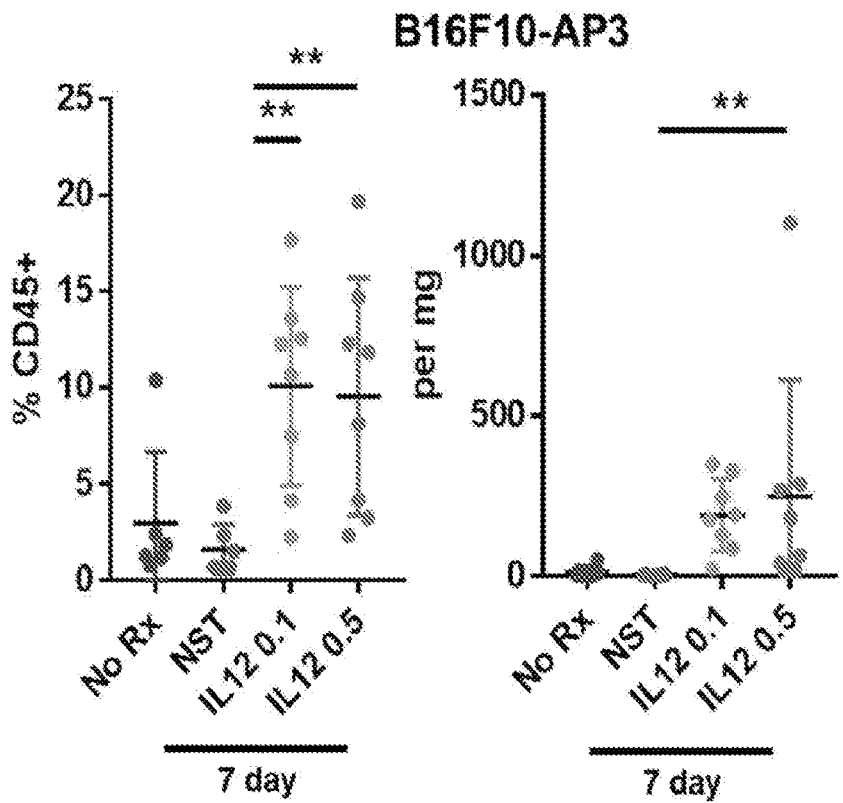

FIGS. 28A-28B are graphs showing CD8+ T cells in tumors as a proportion of the immune infiltrate (CD45+ cells) (left panels) and per mg of tumor (right panels) in MC38-R (FIG. 28A) and B16F10-AP3 (FIG. 28B) tumors 7 days after no treatment, treatment with an NST negative control or two different doses of IL12 mRNA. Statistical significance is indicated by asterisks.

Figure 29A:
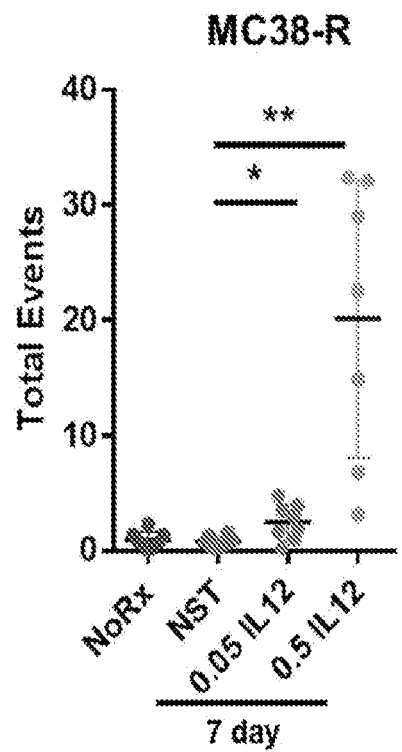
Figure 29B:
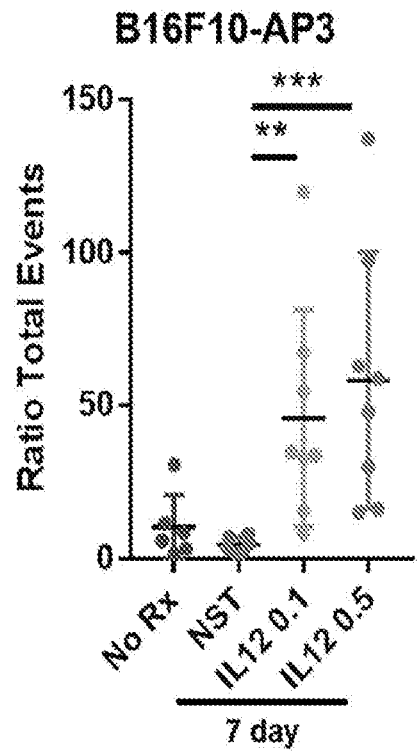

FIGS. 29A-29B are graphs showing ratio of CD8+ T cells to Treg cells in MC38-R (FIG. 29A) and B16F10-AP3 (FIG. 29B) tumors 7 days after no treatment, treatment with an NST negative control or two different doses of IL12 mRNA. Statistical significance is indicated by asterisks.

Figure 30A:
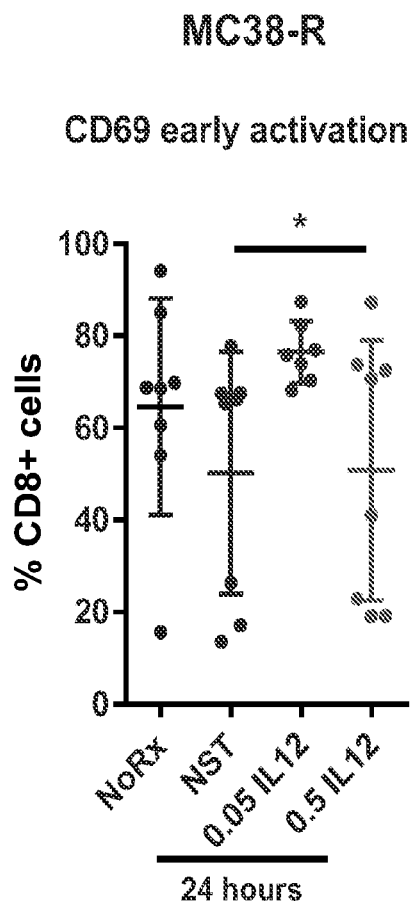
Figure 30B:
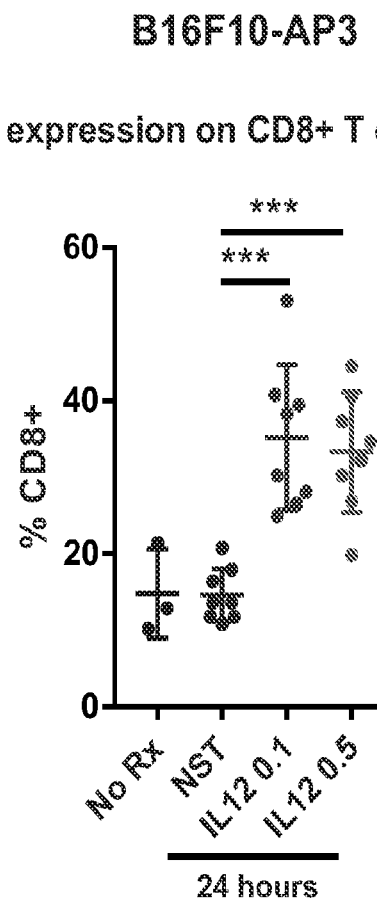

FIGS. 30A-30B are graphs showing the percent of cells CD8+ T cells staining positive for the early activation marker CD69 in MC38-R (FIG. 30A) and B16F10-AP3 (FIG. 30B) tumors 24 hours after no treatment, treatment with an NST negative control or two different doses of IL12 mRNA. Statistical significance is indicated by asterisks.

Figure 31A:
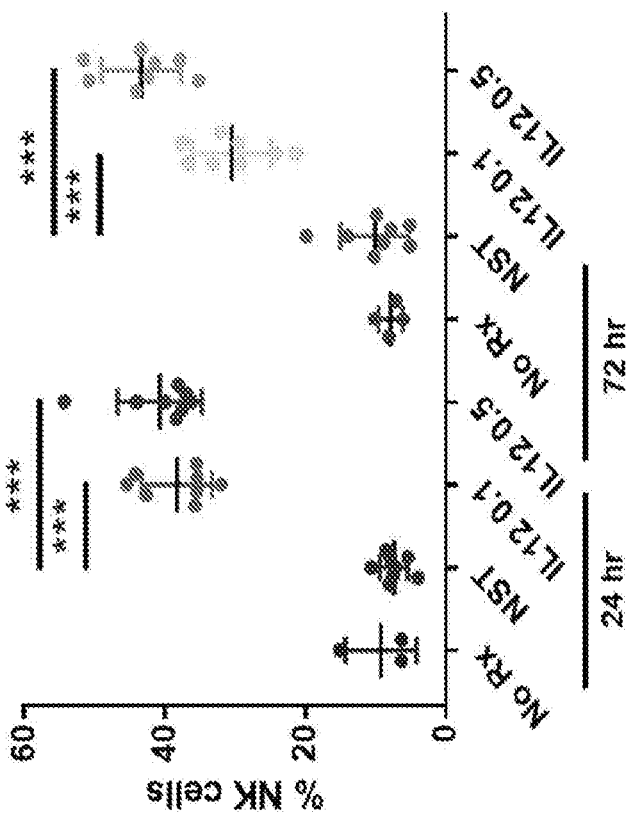
Figure 31B:
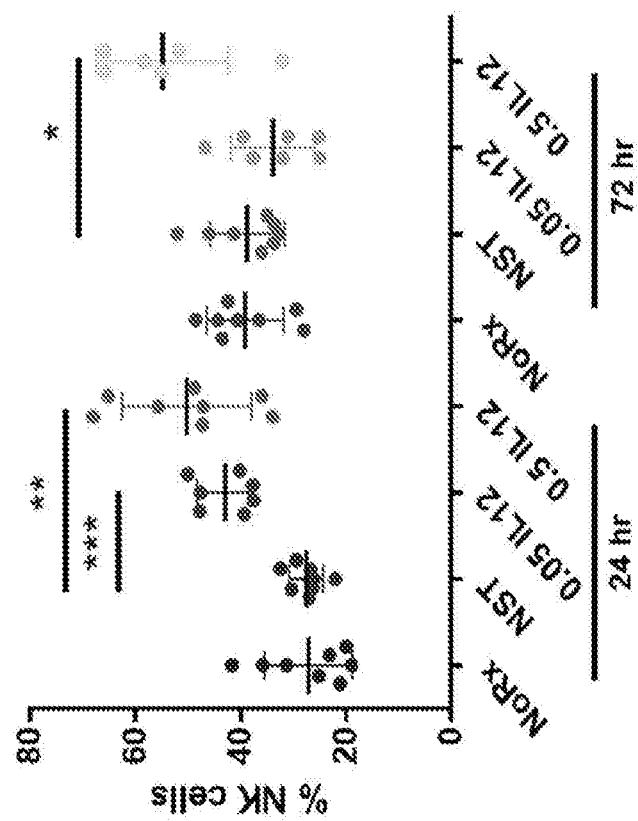

FIGS. 31A-31B are graphs showing the percent of NK cells staining positive for the early activation marker CD69 in MC38-R (FIG. 31A) and B16F10-AP3 (FIG. 31B) tumors 24 hours or 72 hours after no treatment, treatment with an NST negative control or two different doses of IL12 mRNA. Statistical significance is indicated by asterisks.

FIGS. 32A-32B are graphs showing the number of CD103+ classical dendritic cells per mg of MC38-R (FIG. 32A) and B16F10-AP3 (FIG. 32B) tumors 7 days after no treatment, treatment with an NST negative control or two different doses of IL12 mRNA.

FIG. 32C is a graph showing the percent of CD8+ classical dendritic cells staining positive for CD86 in the tumor draining lymph node (LN) of a B16F10-AP3 tumor 24 hours, 72 hours, or 7 days after no treatment, treatment with an NST negative control or two different dose of IL12 mRNA. Statistical significance is indicated by asterisks.

Figure 33A:
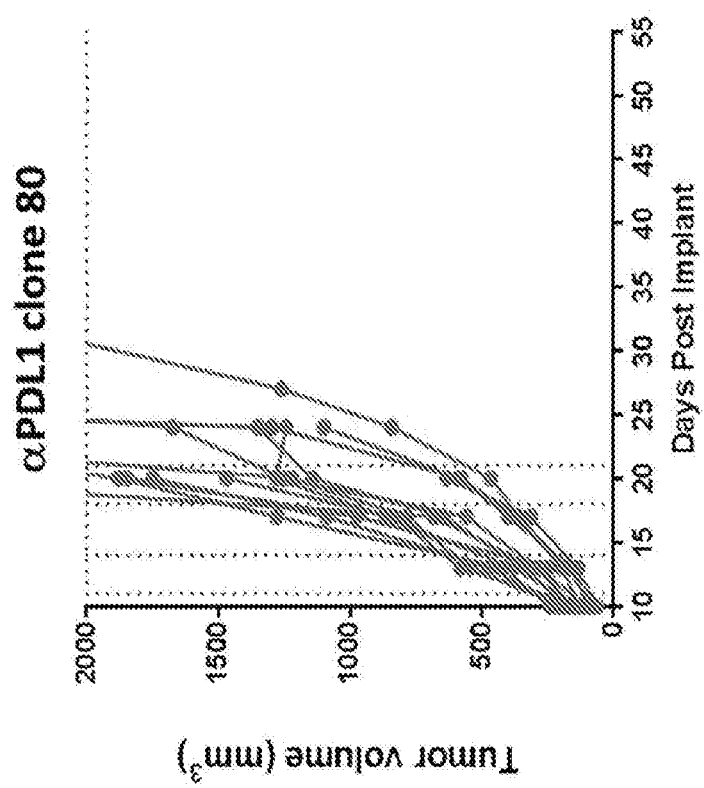
Figure 33B:
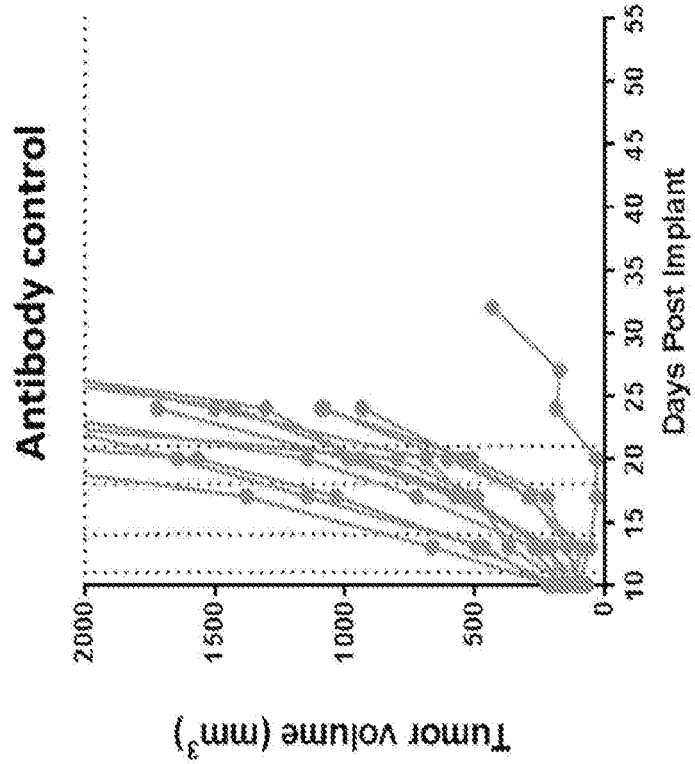

FIGS. 33A-33B are graphs showing individual tumor volumes through 55 days following administration of anti-PD-L1 antibody to mice bearing MC38-R tumors. Mice were given an antibody control (FIG. 33A) or an anti-PD-L1 antibody (clone 80) (FIG. 33B). FIGS. 33C-33G are graphs showing individual tumor volumes in mice bearing MC38-R tumors through 90 days following administration of IL12 mRNA alone or in combination with an anti-PD-L1 antibody. Mice were given (i) a single iTu dose of 0.5 g IL12 mRNA as a monotherapy (FIG. 33C), (ii) a single iTu dose of 5.0 µg IL12 miR122 as a monotherapy (FIG. 33D), (iii) a single iTu dose of 0.5 µg IL12 miR122 in combination with multiple intraperitoneal doses of anti-PD-L1 antibody (FIG. 33E), (iv) a single iTu dose of 5.0 µg IL12 mRNA in combination with multiple intraperitoneal doses of anti-PD-L1 antibody (FIG. 33F); or (v) multiple intraperitoneal doses of anti-PD-L1 antibody (FIG. 33G).

Figure 34A:
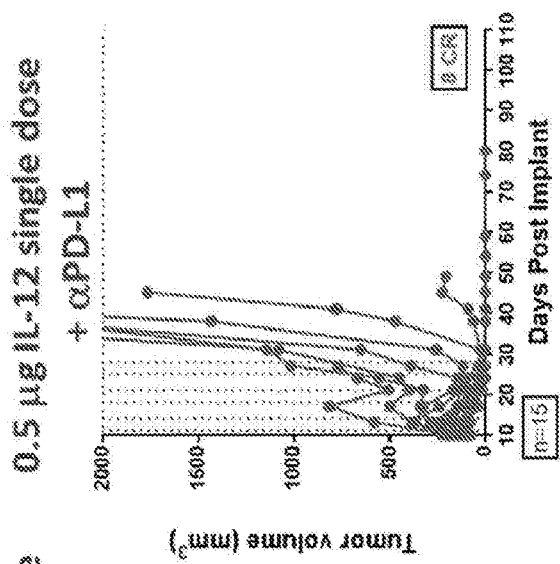
Figure 34B:
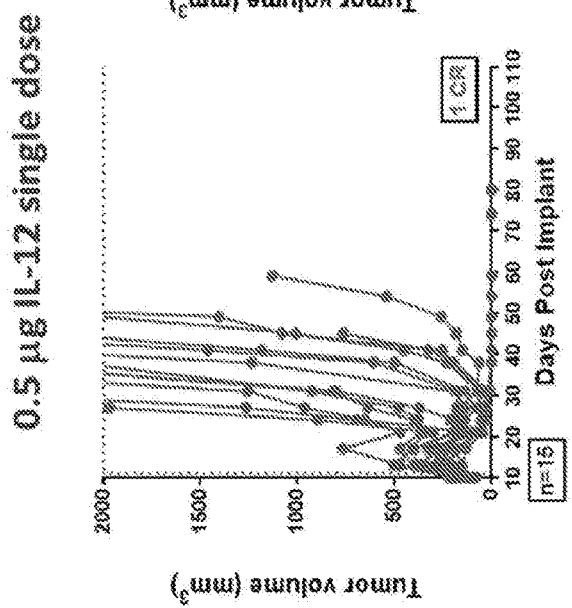
Figure 34C:
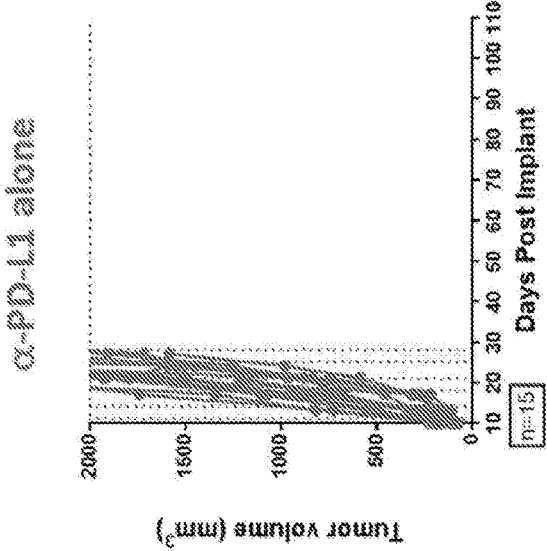

FIGS. 34A-34C are graphs showing individual tumor volumes through 75 days. Mice bearing MC38-R tumors were treated 10 days post implant with an anti-PD-L1 antibody alone (FIG. 34A), 0.5 µg IL12 mRNA alone (FIG. 34B), or both an anti-PD-L1 antibody and 0.5 µg IL12 mRNA (FIG. 34C). The anti-PD-L1 antibody was administered over 6 doses. Vertical dashed lines indicate dose days.

Figure 35A:
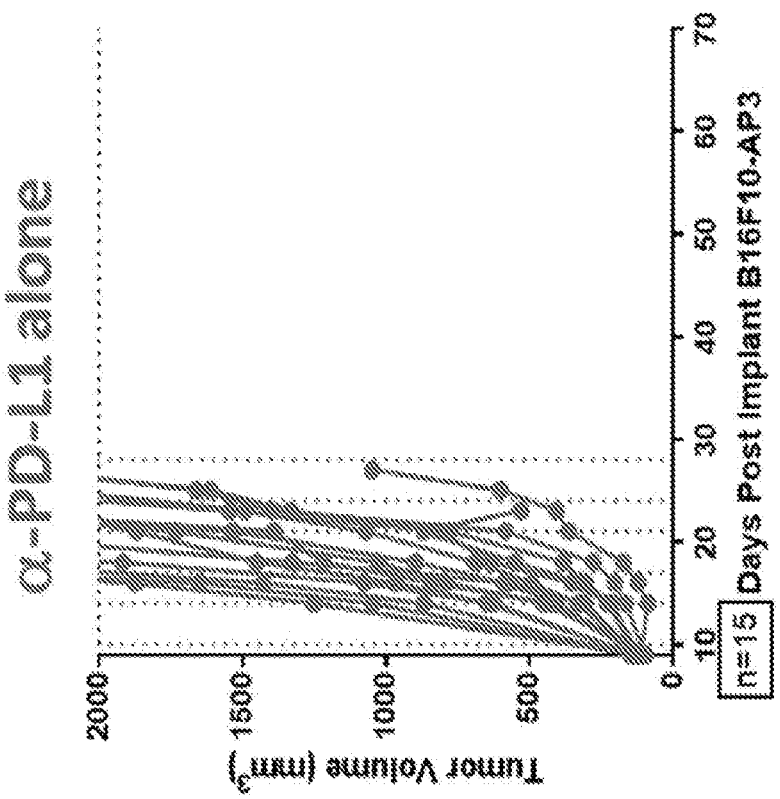
Figure 35B:
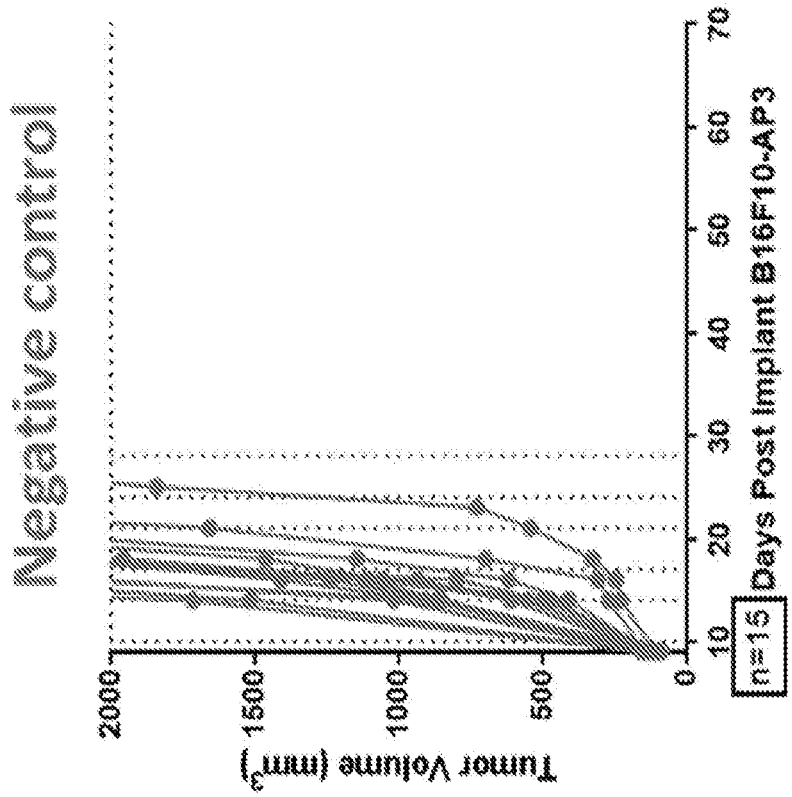

FIGS. 35A-35D are graphs showing individual tumor volumes through 70 days. Mice bearing B16F10-AP3 tumors were treated 10 days post implant with a negative control (FIG. 35A), an anti-PD-L1 antibody alone (FIG. 35B), a single dose of 0.5 µg IL12 mRNA alone (FIG. 35C), or with both an anti-PD-L1 antibody and 0.5 µg IL12 mRNA (FIG. 35D). The anti-PD-L1 antibody was administered over 6 doses. Vertical dashed lines indicate dose days.

Figure 36D:
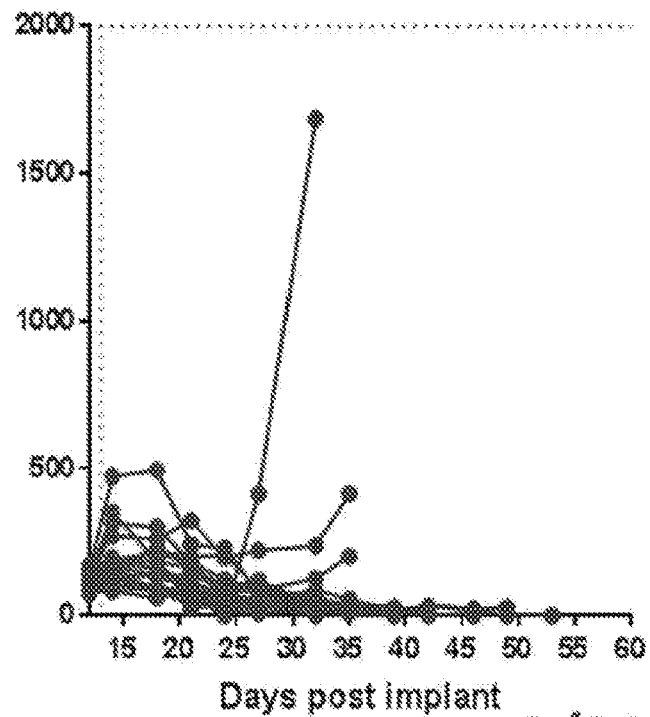
Figure 36E:
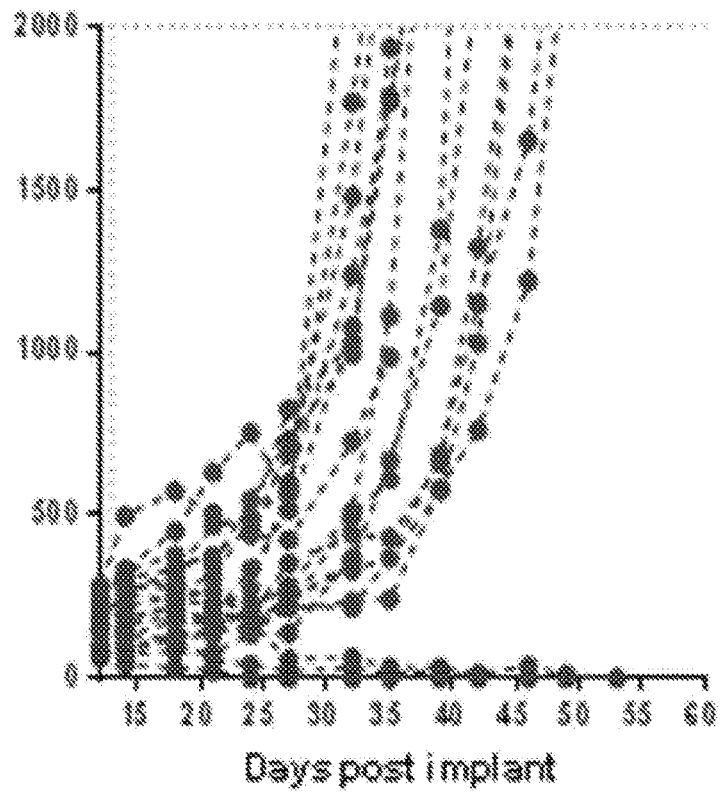
Figure 36F:
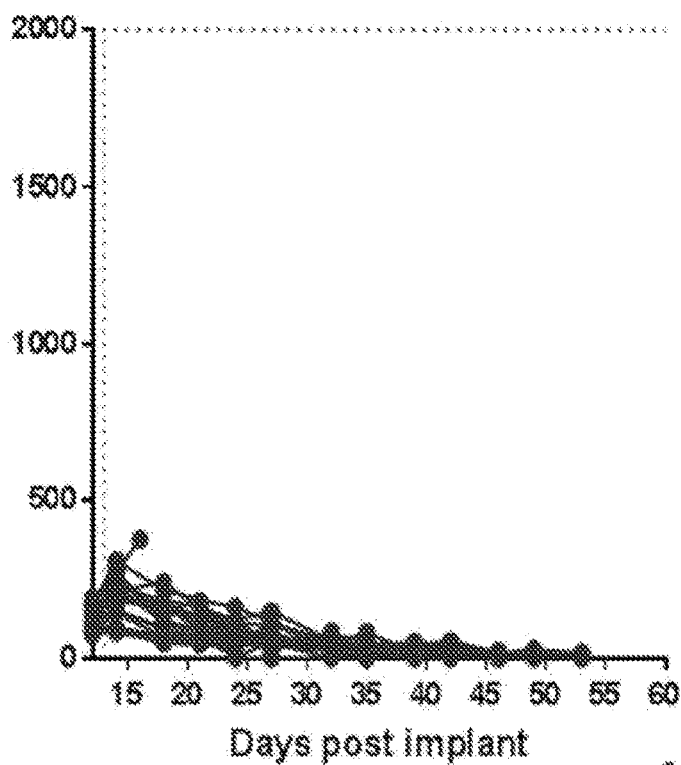
Figure 36G:
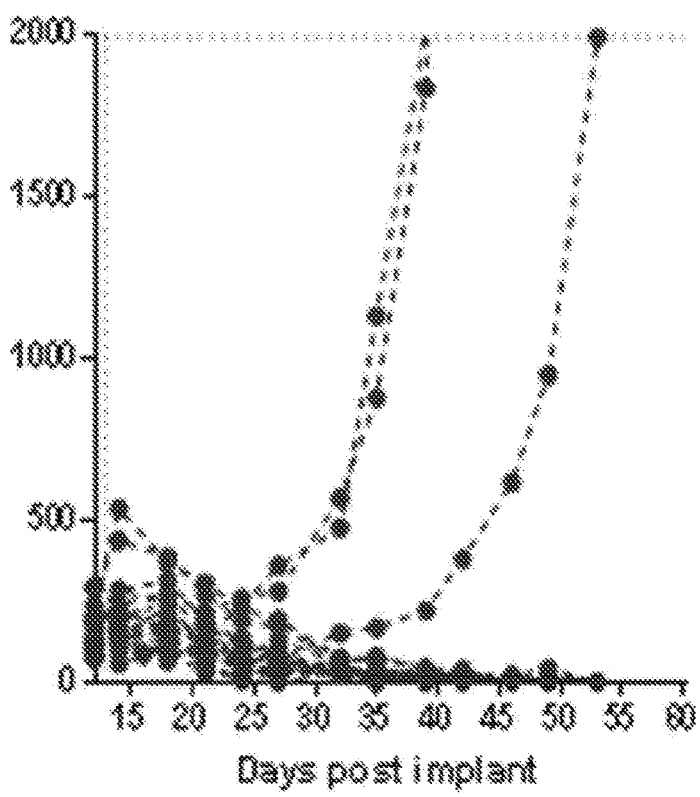

FIG. 36A is a drawing of a mouse implanted bilaterally with tumor cells. FIGS. 36B-36G are graphs showing individual tumor volumes in bilaterally implanted MC38-S mice through 60 days in treated (FIGS. 36B, 36D, and 36F) and distal (FIGS. 36C, 36E, and 36G) tumors following treatment with a negative control (NST mRNA plus isotype antibody control) (FIGS. 36B-36C), 0.5 µg IL12 mRNA (FIG. 36D-36E), or 5 µg IL12 mRNA (FIGS. 36F-36G). Vertical dashed lines indicate dose days.

Figure 37A:
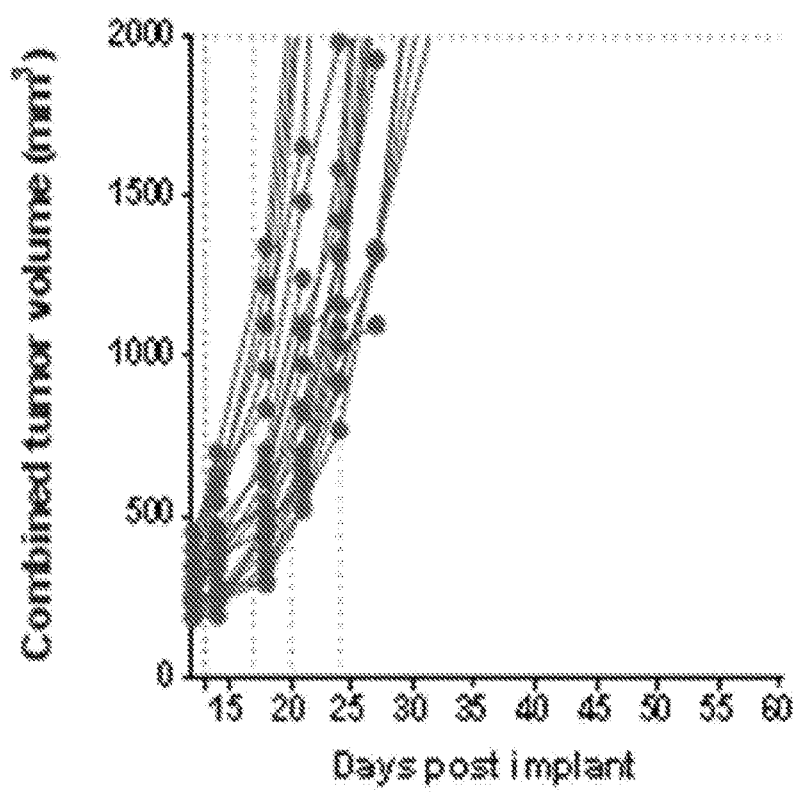
Figure 37B:
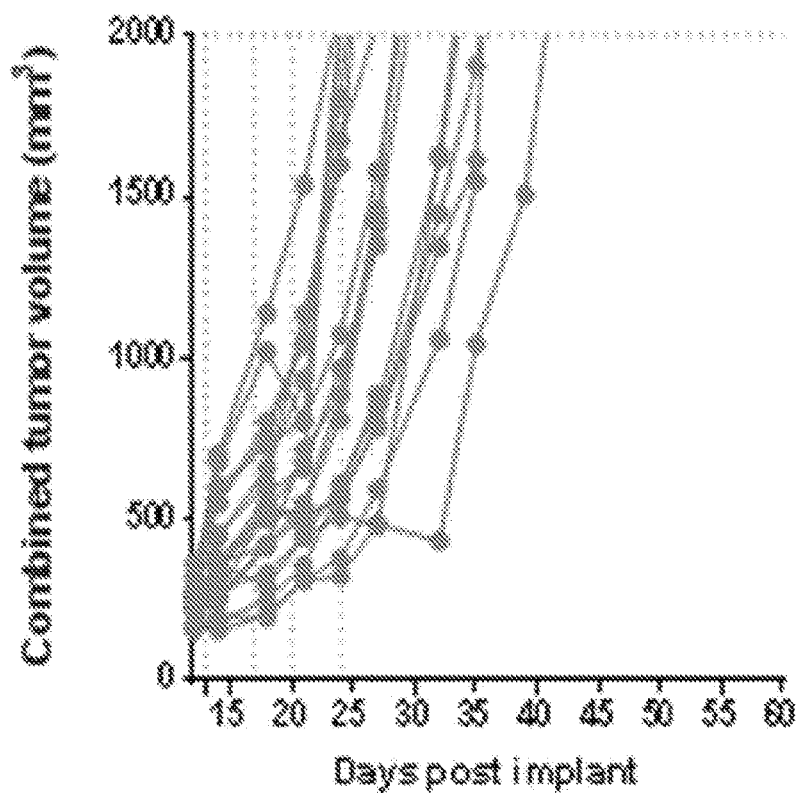
Figure 37C:
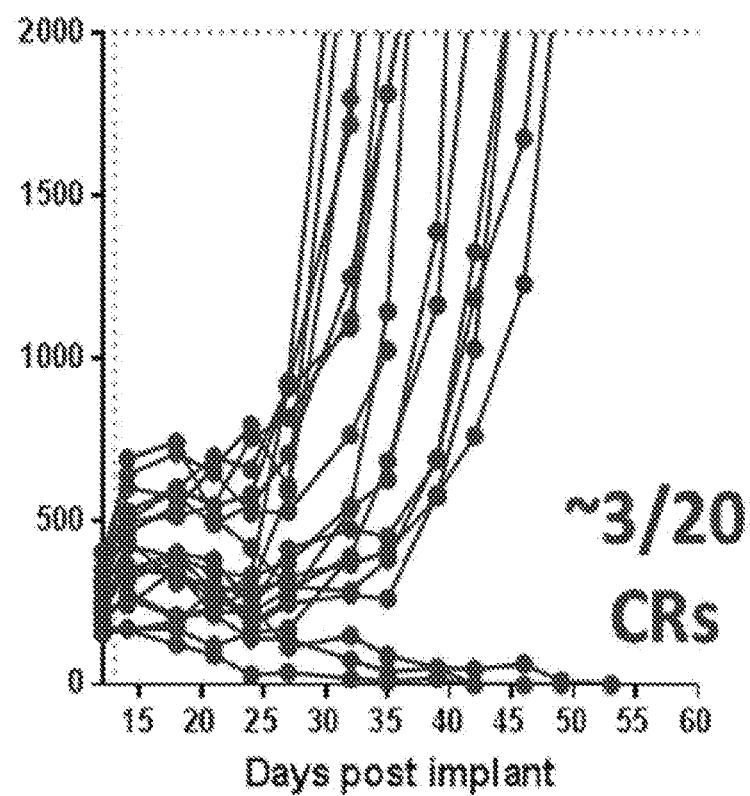
Figure 37D:
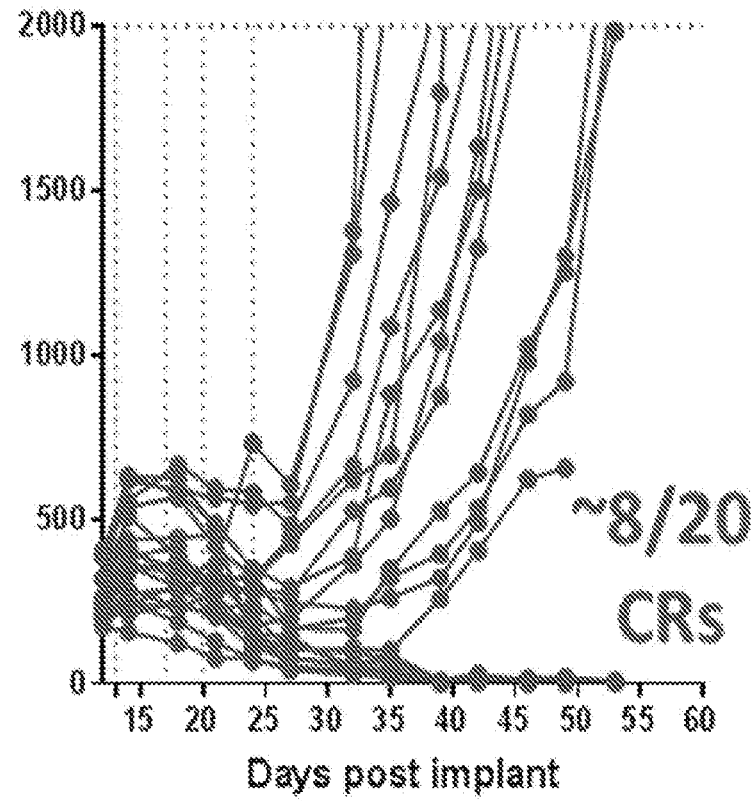
Figure 37E:
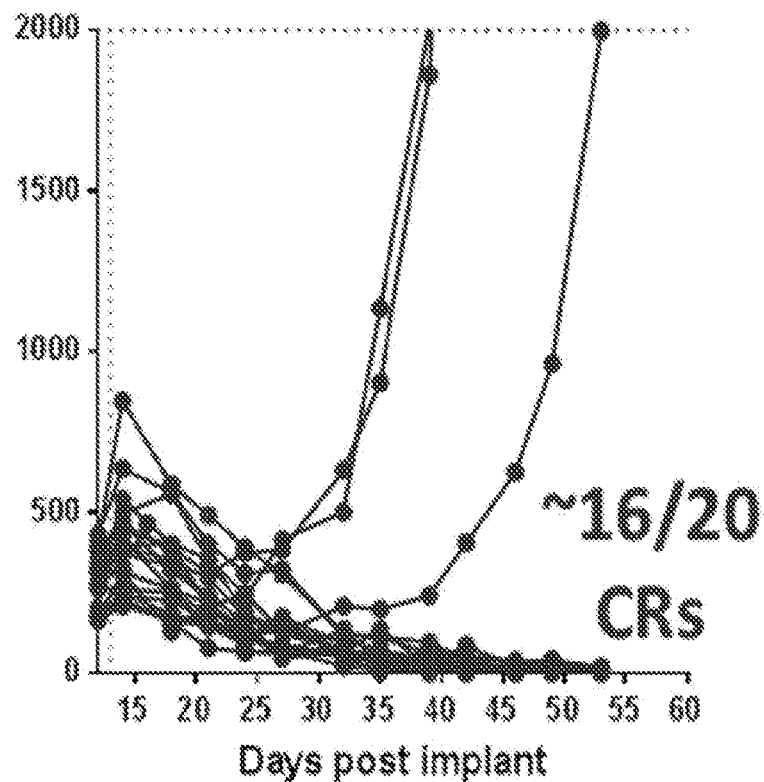
Figure 37F:
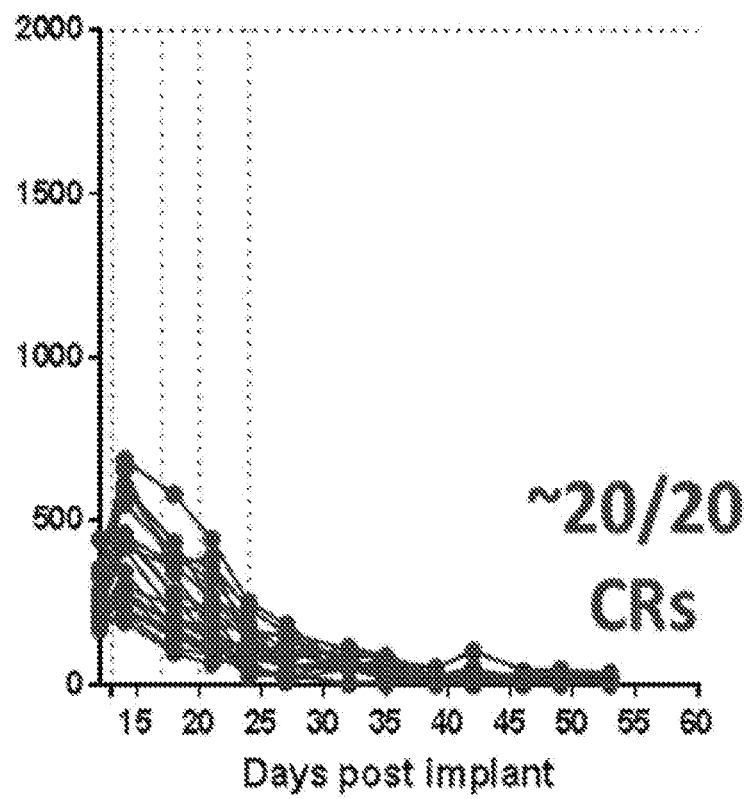

FIGS. 37A-37F are graphs showing individual tumor volumes in bilaterally implanted MC38-S mice through 60 days following treatment with no active mRNA (NST mRNA) (FIGS. 37A-37B), 0.5 µg IL12 mRNA (FIG. 37C-37D), or 5 µg IL12 mRNA (FIGS. 37E-37F), combined with either an isotype control antibody (FIG. 37A, 37C, or 37E) or an anti-PD-L1 antibody (FIG. 37B, 37D, or 37F). Vertical dashed lines indicate dose days.

Figure 38:
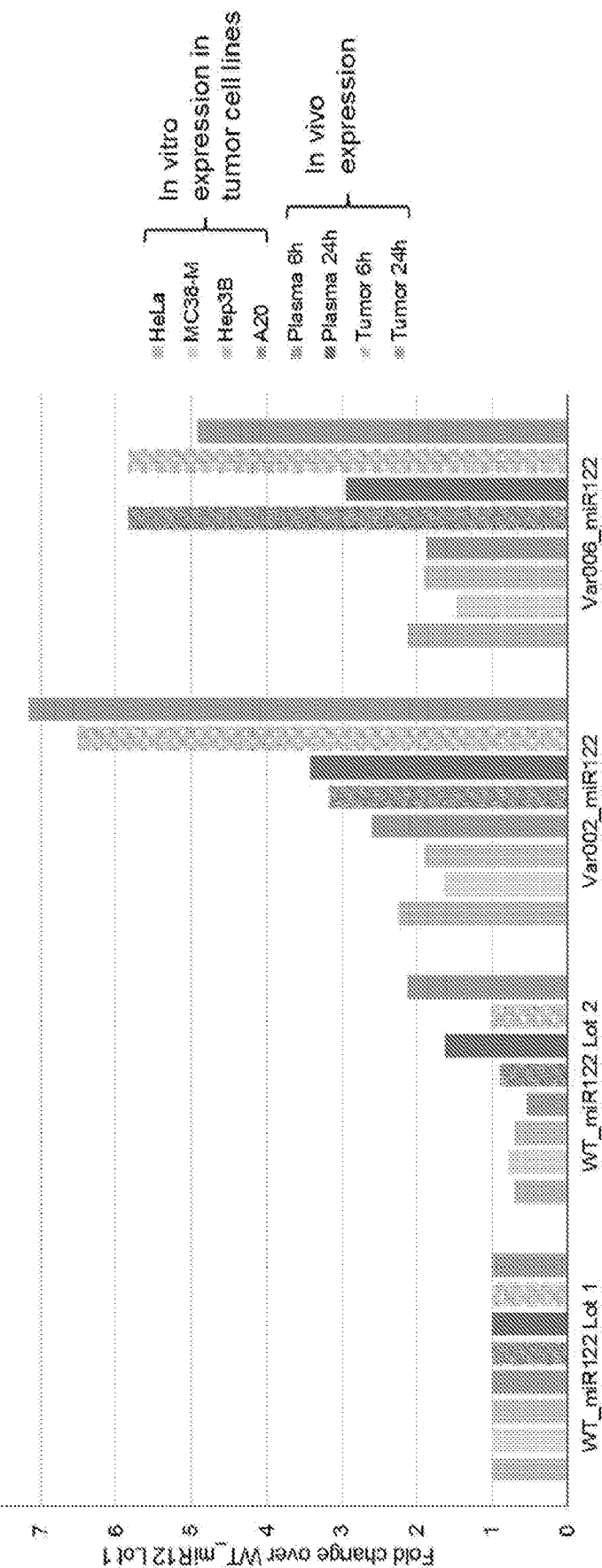

FIG. 38 is a graph showing human IL-12 expression in vitro and in vivo by wild-type and codon optimized IL-12 mRNA constructs.

DETAILED DESCRIPTION

The present disclosure provides a new approach to treat cancer involving the prevention or treatment of disease with substances (e.g., mRNAs encoding IL12) that stimulate the immune response, i.e., immunotherapy.

In one aspect, the disclosure relates to methods of treating cancer using a polynucleotide encoding IL12. An IL12 polypeptide as disclosed herein comprises IL12A, IL12B, or both IL12A and IL12B. In another aspect, the disclosure provides methods of treating cancer using a combination approach that features mRNAs encoding IL12 and an anti-cancer agent, e.g., an immune-checkpoint inhibitor, e.g., anti-PD-1 antibody, anti-PD-L1 antibody, and/or anti-CTLA-4 antibody. Without being bound by any theory, it is believed that priming of an anti-cancer immune response is possible by administering, e.g., intratumorally, mRNAs encoding IL12 in the stimulation of, for example, T-cells and/or natural killer cells. Therefore, an mRNA encoding IL12 is believed to provide a first stimulation signal to the immune system, for example, within the tumor environment, e.g., via intratumoral injection of the mRNA. IL12 can also stimulate the production of interferon-gamma (IFN-γ) and tumor necrosis factor-alpha (TNF-α) from T cells and natural killer (NK) cells. As disclosed herein, IL12, either directly or indirectly through IFN-γ, can also increase expression of PD-L1 in tumor cells, which can impair local tumor immunity. Therefore, in some aspects, the disclosure provides a method of treating tumor comprising administering a polynucleotide (e.g., mRNA) encoding IL12 in combination with an anti-PD-1 antibody or anti-PD-L1 antibody to block the interaction between PD-L1 and its receptor, i.e., PD-1. In other aspects, the disclosure includes a method of treating tumor comprising administering a polynucleotide (e.g., mRNA) encoding IL2 in combination with an anti-CTLA-4 antibody. In further aspects, the disclosure provides a method of treating tumor comprising administering a polynucleotide (e.g., mRNA) encoding IL2 in combination with an anti-PD-1 antibody or anti-PD-L1 antibody and an anti-CTLA-4 antibody. Some aspects of the disclosure also include additional agents, e.g., OX40L, a polynucleotide encoding OX40L, or mRNA encoding an OX40L. In other aspects, the anti-PD-1 antibody or anti-PD-L1 antibody can be administered in the form of a polynucleotide. Similarly, the anti-CTLA-4 antibody can be administered in the form of a polynucleotide. Exemplary aspects feature treatment with lipid nanoparticle-(LNP-) encapsulated mRNAs. Exemplary aspects feature intratumoral administration of mRNAs in cationic lipid-based LNPs.

1. Methods of Treating Cancer

Certain aspects of the present disclosure are directed to methods of reducing or decreasing size, mass, and/or volume of a tumor or preventing the growth of a tumor in a subject in need thereof comprising administering a polynucleotide, e.g., mRNA, encoding an IL12B and/or IL12A polypeptide disclosed herein, or a vector or a host cell comprising the polynucleotide, or an IL12B and/or IL12A polypeptide encoded by the polynucleotide. In certain embodiments, the polynucleotide encodes an IL-12 polypeptide, wherein the polynucleotide comprises an ORF encoding an IL12B and an IL12A polypeptides. In some embodiments, the methods of reducing the size (including mass and/or volume) of a tumor or inhibiting growth of a tumor in a subject in need thereof comprise administering to the subject an effective amount of a composition comprising one or more polynucleotides. In some embodiments, the one or more polynucleotides encode an IL-12 polypeptide. In some embodiments, the one or more polynucleotides comprise an ORF encoding an IL12B polypeptide. In some embodiments, the one or more polynucleotides comprise an ORF encoding an IL12A polypeptide. In certain embodiments, the one or more polynucleotides comprise an ORF encoding an IL12B polypeptide and an IL12A polypeptide.

In some embodiments, the methods further comprise administering a second agent. In some embodiments, the second agent comprises an effective amount of a composition comprising a polynucleotide comprising an ORF encoding a checkpoint inhibitor polypeptide. In some embodiments, the second agent comprises an effective amount of a composition comprising a checkpoint inhibitor polypeptide. In some embodiments, the checkpoint inhibitor is any checkpoint inhibitor known in the art or described herein. In some embodiments, the checkpoint inhibitor is an anti-PD-1 antibody. In other embodiments, the checkpoint inhibitor is an anti-PD-L1 antibody. In other embodiments, the checkpoint inhibitor is an anti-CTLA-4 antibody. In some embodiments, the second agent comprises an effective amount of a composition comprising a polynucleotide comprising an ORF encoding OX40L. In some embodiments, the checkpoint inhibitor is selected from an anti-PD-1 antibody, an anti-PD-L1 antibody, and/or an anti-CTLA-4 antibody, or a polynucleotide encoding OX40L or any other agents disclosed herein. In certain embodiments, the composition comprising a checkpoint inhibitor comprises more than one checkpoint inhibitor. In one particular embodiment, the method comprises administering (i) an mRNA, encoding an IL12B and/or IL12A polypeptide disclosed herein, and (ii) an anti-PD-L1 antibody, an anti-PD-1 antibody, an anti-CTLA-4 antibody, a polynucleotide encoding OX40L, or any combination thereof.

In some embodiments, the methods reduce the size of a tumor in a subject as compared to the size of the tumor before the administration. In certain embodiments, the size of the tumor is reduced by at least about 5%, at least about 10%, at least about 15%, at least about 20%, at least about 25%, at least about 30%, at least about 35%, at least about 40%, at least about 45%, at least about 50%, least about 60%, at least about 70%, at least about 80%, at least about 90%, or about 100%. In certain embodiments, the subject exhibits a partial response. In certain embodiments, the subject exhibits a complete response.

In some embodiments, the methods of the present disclosure inhibit, stop or delay tumor growth in a subject in need thereof. In certain embodiments, the tumor growth is inhibited, stopped or delayed for at least about 1 week, at least about 2 weeks, at least about 3 weeks, at least about 1 month, at least about 2 months, at least about 3 months, at least about 4 months, at least about 5 months, at least about 6 months, at least about 9 months, at least about 12 months, at least about 15 months, at least about 18 months, at least about 24 months, or at least about 36 months. In other embodiments, the tumor growth is inhibited indefinitely.

In other embodiments, the present disclosure provides methods of promoting an anti-tumor effect (e.g., induce T cell proliferation, induce T cell infiltration in a tumor, induce a memory T cell response, increasing the number of NK cells, etc.) by administering the polynucleotide (e.g., mRNA) encoding IL12 alone or the polynucleotide in combination with any agents disclosed herein.

In one embodiment, the present disclosure provides a method of activating T cells in a subject in need thereof, inducing T cell proliferation in a subject in need thereof, inducing T cell infiltration in a tumor of a subject in need thereof, and/or inducing a memory T cell response in a subject in need thereof, comprising administering to the subject a composition disclosed herein, e.g., a polynucleotide (e.g., mRNA) encoding IL12, alone or in combination with composition comprising a second agent, e.g., a checkpoint inhibitor polypeptide or a polynucleotide comprising an ORF encoding a checkpoint inhibitor polypeptide, e.g., an anti-PD-1 antibody, an anti-PD-L1 antibody, and/or an anti-CTLA-4 antibody, or a polynucleotide encoding OX40L or any other agents disclosed herein. In certain embodiments, the intratumoral administration of the polynucleotide (e.g., mRNA) encoding IL12 alone or in combination with a second agent can increase the efficacy of the anti-tumor effect (e.g., T cell infiltration in a tumor) compared to other routes of administration.

In some embodiments, the administering of the compositions described herein, e.g., a polynucleotide encoding an IL12, alone or in combination with a composition comprising a polynucleotide comprising an ORF encoding a checkpoint inhibitor polypeptide or a composition comprising a checkpoint inhibitor polypeptide, activates T cells in the subject. T cell activation can be characterized in any way known in the art. In some embodiments, the activated T cells express CD4. In some embodiments, the activated T cells express CD8. In certain embodiments the activated T cells express CD4 and CD8. In certain embodiments, the activated T cells comprise CD4$^+$ T cells, CD8$^+$ T cells, or both CD4$^+$ T cells and CD8$^+$ T cells.

In one embodiment, activated T cells in the subject reduce the size of a tumor or inhibit the growth of a tumor in the subject. Activation of T cells can be measured using applications in the art such as measuring T cell proliferation; measuring cytokine production with enzyme-linked immunosorbant assays (ELISA) or enzyme-linked immunospot assays (ELISPOT); or detection of cell-surface markers associated with T cell activation (e.g., CD69, CD40L, CD137, CD25, CD71, CD26, CD27, CD28, CD30, CD154, and CD134) with techniques such as flow cytometry.

In some embodiments, T cell activation comprises inducing T cell proliferation. In some embodiments, T cell proliferation is increased by at least about 1.5 fold, at least about 2 fold, at least about 3 fold, at least about 4 fold, at least about 5 fold, at least about 6 fold, at least about 7 fold, at least about 8 fold, at least about 9 fold, at least about 10 fold, at least about 20 fold, at least about 30 fold, at least about 50 fold, or at least about 100 fold, as compared to the level of T cell proliferation prior to the administration of the IL12 encoding polynucleotide (e.g., mRNA).

In one embodiment, T cell proliferation in the subject is directed to an anti-tumor immune response in the subject. In another aspect, the T cell proliferation in the subject reduces or decreases the size of a tumor or inhibits the growth of a tumor in the subject. T cell proliferation can be measured using applications in the art such as cell counting, viability staining, optical density assays, or detection of cell-surface markers associated with T cell activation (e.g., CD69, CD40L, CD137, CD25, CD71, CD26, CD27, CD28, CD30, CD154, and CD134) with techniques such as flow cytometry.

In some embodiments, T cell activation comprises induction of T cell infiltration of the tumor. In some embodiments, T cell infiltration in the tumor is increased by at least about 2 fold, at least about 3 fold, at least about 4 fold, at least about 5 fold, at least about 6 fold, at least about 7 fold, at least about 8 fold, at least about 9 fold, at least about 10 fold, at least about 20 fold, at least about 30 fold, at least about 50 fold, or at least about 100 fold, as compared to the level of T cell infiltration of the tumor prior to the administration of the IL12 encoding polynucleotide (e.g., mRNA).

In some embodiments, T cell activation comprises increasing the number of tumor-infiltrating T cells. In certain embodiments, the number of tumor-infiltrating T cells in the tumor is increased by at least about 2 fold, at least about 3 fold, at least about 4 fold, at least about 5 fold, at least about 6 fold, at least about 7 fold, at least about 8 fold, at least about 9 fold, at least about 10 fold, at least about 20 fold, at least about 30 fold, at least about 50 fold, or at least about 100 fold, as compared to the number of tumor infiltrating T cells in the tumor prior to the administration of the IL12 encoding polynucleotide (e.g., mRNA)

In one embodiment, T cell infiltration in a tumor of the subject is directed to an anti-tumor immune response in the subject. In another aspect, the T cell infiltration in a tumor of the subject reduces or decreases the size of a tumor or inhibits the growth of a tumor in the subject. T cell infiltration in a tumor can be measured using applications in the art such as tissue sectioning and staining for cell markers, measuring local cytokine production at the tumor site, or detection of T cell-surface markers with techniques such as flow cytometry.

In some embodiments, T cell activation comprises inducing a memory T cell response in a subject in need thereof. In certain embodiments, the memory T cell response is increased by at least about 2 fold, at least about 3 fold, at least about 4 fold, at least about 5 fold, at least about 6 fold, at least about 7 fold, at least about 8 fold, at least about 9 fold, at least about 10 fold, at least about 20 fold, at least about 30 fold, at least about 50 fold, or at least about 100 fold, as compared to the memory T cell response prior to the administration of the IL12 encoding polynucleotide (e.g., mRNA).

In one embodiment, the memory T cell response in the subject is directed to an anti-tumor immune response in the subject. In another aspect, the memory T cell response in the subject reduces or decreases the size of a tumor or inhibits the growth of a tumor in the subject. A memory T cell response can be measured using applications in the art such as measuring T cell markers associated with memory T cells, measuring local cytokine production related to memory immune response, or detecting memory T cell-surface markers with techniques such as flow cytometry.

In some embodiments, the administering of the compositions described herein, e.g., a polynucleotide encoding an IL12, alone or in combination with a composition comprising a polynucleotide comprising an ORF encoding a checkpoint inhibitor polypeptide or a composition comprising a checkpoint inhibitor polypeptide, increases an effector to suppressor T cell ratio in the tumor. In certain embodiments, the effector to suppressor T cell ratio is characterized by the ratio of (i) CD8+, CD4+, or CD8+/CD4+ T cells to (ii) Treg cells in a subject. In certain embodiments, the increase in the effector to suppressor T cell ratio correlates with an increase in the number of CD8+ T cells. In some embodiments, the increase in the effector to suppressor T cell ratio correlates with an increase in the number of CD4+ T cells. In some embodiments, the increase in the effector to suppressor T cell ratio correlates with an increase in the number of CD8+/CD4+ T cells. In some embodiments, the increase in the effector to suppressor T cell ratio correlates with a decrease in the number of Treg cells.

In some embodiments, the effector to suppressor T cell ratio, e.g., the CD8$^+$ T cell to Treg cell ratio, following administration of the IL12 encoding polynucleotide (e.g., mRNA) (alone or in combination with an anti-PD-L1 antibody, an anti-PD-1 antibody, an anti-CTLA-4 antibody, or a polynucleotide encoding OX40L) is at least about 1.5:1, at least about 2:1, at least about 2.5:1, at least about 3:1, at least about 3.5:1, at least about 3.5:1, at least about 4:1, at least about 4.5:1, at least about 5:1, at least about 6:1, at least about 7:1, at least about 8:1, at least about 9:1, at least about 10:1, at least about 15:1, at least about 20:1, at least about 25:1, at least about 30:1, at least about 35:1, at least about 40:1, at least about 45:1, at least about 50:1, at least about 60:1, at least about 70:1, at least about 80:1, at least about 90:1, at least about 100:1, at least about 110:1, at least about 120:1, at least about 130:1, at least about 140:1, at least about 150:1, at least about 200:1, at least about 250:1, or at least about 500:1.

In some embodiments, the effector to suppressor T cell ratio, e.g., the CD8$^+$ T cell to Treg cell ratio, following administration of the IL12 encoding polynucleotide (e.g., mRNA) (alone or in combination with an anti-PD-L1 antibody, an anti-PD-1 antibody, an anti-CTLA-4 antibody, or a polynucleotide encoding OX40L) is at least about 1.5, at least about 2, at least about 2.5, at least about 3, at least about 3.5, at least about 3.5, at least about 4, at least about 4.5, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, at least about 100, at least about 110, at least about 120, at least about 130, at least about 140, at least about 150, at least about 200, at least about 250, or at least about 500.

In one embodiment, the increase in the effector to suppressor T cell ratio in the tumor is directed to an anti-tumor immune response in the subject. In another aspect, the increase in the effector to suppressor T cell ratio in the tumor reduces or decreases the size of a tumor or inhibits the growth of a tumor in the subject. The effector to suppressor T cell ratio in the tumor can be measured using applications in the art such as measuring the ratio of CD8+, CD4+, or CD8+/CD4+ T cells to Treg cells, using any methods known in the art including IHC and/or flow cytometry.

In certain embodiments, the activated T cells by the present methods are CD4$^+$ cells, CD8$^+$ cells, CD62$^+$ (L-selectin$^+$) cells, CD69$^+$ cells, CD40L$^+$ cells, CD137$^+$ cells, CD25$^+$ cells, CD71$^+$ cells, CD26$^+$ cells, CD27$^+$ cells, CD28$^+$ cells, CD30$^+$ cells, CD45$^+$ cells, CD45RA$^+$ cells, CD45RO$^+$ cells, CD11b$^+$ cells, CD154$^+$ cells, CD134$^+$ cells, CXCR3$^+$ cells, CCR4$^+$ cells, CCR6$^+$ cells, CCR7$^+$ cells, CXCR5$^+$ cells, Crth2$^+$ cells, gamma delta T cells, or any combination thereof. In some embodiments, the activated T cells by the present methods are Th$_1$ cells. In other embodiments, the T cells activated by the present methods are Th$_2$ cells. In other embodiments, the T cells activated by the present disclosure are cytotoxic T cells.

In some embodiments, the infiltrating T cells by the present methods are CD4$^+$ cells, CD8$^+$ cells, CD62$^+$ (L-selectin$^+$) cells, CD69$^+$ cells, CD40L$^+$ cells, CD137$^+$ cells, CD25$^+$ cells, CD71$^+$ cells, CD26$^+$ cells, CD27$^+$ cells, CD28$^+$ cells, CD30$^+$ cells, CD45$^+$ cells, CD45RA$^+$ cells, CD45RO$^+$ cells, CD11b$^+$ cells, CD154$^+$ cells, CD134$^+$ cells, CXCR3$^+$ cells, CCR4$^+$ cells, CCR6$^+$ cells, CCR7$^+$ cells, CXCR5$^+$ cells, Crth2$^+$ cells, gamma delta T cells, or any combination thereof. In some embodiments, the infiltrating T cells by the present methods are Th$_1$ cells. In other embodiments, the infiltrating T cells by the present methods are Th$_2$ cells. In other embodiments, the infiltrating T cells by the present disclosure are cytotoxic T cells.

In some embodiments, the memory T cells induced by the present methods are CD4$^+$ cells, CD8$^+$ cells, CD62$^+$ (L-selectin$^+$) cells, CD69$^+$ cells, CD40L$^+$ cells, CD137$^+$ cells, CD25$^+$ cells, CD71$^+$ cells, CD26$^+$ cells, CD27$^+$ cells, CD28$^+$ cells, CD30$^+$ cells, CD45$^+$ cells, CD45RA$^+$ cells, CD45RO$^+$ cells, CD11b$^+$ cells, CD154$^+$ cells, CD134$^+$ cells, CXCR3$^+$ cells, CCR4$^+$ cells, CCR6$^+$ cells, CCR7$^+$ cells, CXCR5$^+$ cells, Crth2$^+$ cells, gamma delta T cells, or any combination thereof. In some embodiments, the memory T cells by the present methods are Th$_1$ cells. In other embodiments, the memory T cells by the present methods are Th$_2$ cells. In other embodiments, the memory T cells by the present disclosure are cytotoxic T cells.

In certain embodiments, the disclosure includes a method of inducing an adaptive immune response, an innate immune response, or both adaptive and innate immune response against tumor comprising administering a polynucleotide, e.g., mRNA, encoding IL12 alone or in combination with a second agent, e.g., a checkpoint inhibitor, e.g., an anti-PD-1 antibody, an anti-PD-L1 antibody, and/or an anti-CTLA-4 antibody, a polynucleotide encoding OX40L, and/or any other agents disclosed herein.

The present disclosure further provides a method of increasing the number of Natural Killer (NK) cells in a subject in need thereof comprising administering a polynucleotide comprising an mRNA encoding IL12 alone or in combination with a second agent, e.g., a checkpoint inhibitor, e.g., an anti-PD-1 antibody, an anti-PD-L1 antibody, and/or an anti-CTLA-4 antibody, a polynucleotide encoding OX40L, and/or any other agents disclosed herein. In one aspect, the increase in the number of NK cells in the subject is directed to an anti-tumor immune response in the subject. In another aspect, the increase in the number of NK cells in the subject reduces or decreases the size of a tumor or inhibits the growth of a tumor in the subject. Increases in the number of NK cells in a subject can be measured using applications in the art such as detection of NK cell-surface markers (e.g., CD335/NKp46; CD336/NKp44; CD337/NPp30) or intracellular NK cell markers (e.g., perforin; granzymes; granulysin).

In some embodiments, the administering of the compositions described herein, e.g., a polynucleotide (e.g., mRNA) encoding an IL12, alone or in combination with a composition comprising a polynucleotide comprising an ORF encoding a checkpoint inhibitor polypeptide or a composition comprising a checkpoint inhibitor polypeptide, increases the number of activated NK cells in the subject as compared to the number of activated NK cells prior to the administration. In some embodiments, the number of activated NK cells is increased by at least about 1.5 fold, at least about 2 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 35 fold, at least about 40 fold, at least about 45 fold, at least about 50 fold, at least about 60 fold, at least about 70 fold, at least about 80 fold, at least about 90 fold, or at least about 100 fold. In some embodiments, the increase in activated NK cells is maintained for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, or at least about 28 days.

In some embodiments, the administering of the compositions described herein, e.g., a polynucleotide (e.g., mRNA) encoding an IL12, alone or in combination with a composition comprising a polynucleotide comprising an ORF encoding a checkpoint inhibitor polypeptide or a composition comprising a checkpoint inhibitor polypeptide, increases the number of cross-presenting dendritic cells in the tumor of the subject as compared to the number of cross-presenting dendritic cells in the tumor prior to the administration. In some embodiments, the number of cross-presenting dendritic cells in the tumor is increased by at least about 1.5 fold, at least about 2 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 35 fold, at least about 40 fold, at least about 45 fold, at least about 50 fold, at least about 60 fold, at least about 70 fold, at least about 80 fold, at least about 90 fold, or at least about 100 fold. In some embodiments, the increase in cross-presenting dendritic cells in the tumor is maintained for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, or at least about 28 days.

In certain embodiments, the present disclosure is also directed to a method of increasing IFNγ expression in a subject having tumor comprising administering a polynucleotide, e.g., mRNA, encoding IL12 alone or in combination with a second agent, e.g., a checkpoint inhibitor, e.g., an anti-PD-1 antibody, an anti-PD-L1 antibody, and/or an anti-CTLA-4 antibody, a polynucleotide encoding OX40L, and/ or any other agents disclosed herein.

Other embodiments also include a method of increasing expression of IFNγ, TNFα, IL-10, IL-13, IL-15/15R, IL-27, MIP-1β, MIP-1α, MCP-1, MCP-3, M-CSF, IL-4, IL-5, or any combination thereof in a subject having tumor comprising administering a polynucleotide, e.g., mRNA, encoding IL12 alone or in combination with another agent disclosed herein. In yet other embodiments, the methods of the present disclosure can include methods of inducing expression of GM-CSF, IL-18, IL-3, RANTES, IL-6, or any combination thereof.

The polynucleotide encoding IL12 can be formulated as a pharmaceutical composition that is suitable for administration either directly or indirectly to tumors. The term "tumor" is used herein in a broad sense and refers to any abnormal new growth of tissue that possesses no physiological function and arises from uncontrolled usually rapid cellular proliferation. The term "tumor" as used herein relates to both benign tumors and to malignant tumors.

Certain aspects of the disclosure provide methods of intratumorally administering a single administration dose of a polynucleotide, e.g., mRNA, encoding IL12 alone or in combination with any agents disclosed herein. In such embodiments, an mRNA encoding IL12 can be administered only once while the other agent can be administered regularly, following its regular dosing schedule. In certain embodiments, a checkpoint inhibitor, e.g., an anti-PD-1 antibody, an anti-PD-L1 antibody, and/or an anti-CTLA-4 antibody, is administered prior to administration of a polynucleotide, e.g., mRNA, encoding 1L12. In some embodiments, the polynucleotide is formulated in a lipid nanoparticle, e.g., Compound 18, disclosed herein. Not being bound by any theory, in some aspects, the intratumoral delivery of a polynucleotide encoding IL12 and/or the lipid nanoparticle formulation disclosed herein allow single dose administration that is sufficient for the dose to trigger anti-tumor efficacy and treat tumor. Given the potential toxicity of IFNγ induced by IL-12, this single dosing regimen of the disclosed polynucleotide can be beneficial to the subjects in need of the treatment.

In certain embodiments, the method comprises administering a single dose of a polynucleotide encoding IL12 in combination with a second agent, e.g., an anti-PD-1 antibody, an anti-PD-L1 antibody, and/or an anti-CTLA-4 antibody, which can be given also in single administration or multiple administrations following its regular (e.g., approved) schedule. In other embodiments, the method comprises not more than two administrations of a polynucleotide encoding IL2, not more than three administrations of a polynucleotide encoding IL12, not more than four administrations of a polynucleotide encoding IL12, or not more than five administrations of a polynucleotide encoding IL12, optionally in combination with a checkpoint inhibitor, e.g., an anti-PD-1 antibody, an anti-PD-L1 antibody, and/or an anti-CTLA-4 antibody, or a polynucleotide encoding an OX40L polypeptide.

In other embodiments, the present methods can result in abscopal effects, e.g., a treatment of tumor where localized treatment of a tumor, e.g., intratumoral delivery, by a polynucleotide, e.g., mRNA, encoding IL2 causes not only a shrinking of the treated tumor, but also a shrinking of tumors outside the scope of the localized treatment ("distal tumor").

In some embodiments, the administering of the compositions described herein, e.g., a polynucleotide encoding an IL12 polypeptide, alone or in combination with a composition comprising a polynucleotide comprising an ORF encoding a checkpoint inhibitor polypeptide or a composition comprising a checkpoint inhibitor polypeptide, reduces the size of a distal tumor. In certain embodiments, the administering is intratumoral to a first tumor, and the administering reduces the size of a second, distal tumor. In some embodiments, the size of the distal tumor is reduced by at least about 10%, at least about 20% at least about 30%, at least about 40%, at least about 50%, at least about 60%, at least about 70%, at least about 80%, at least about 90%, at least about 95%, or about 100%.

In certain embodiments, the administering of the compositions described herein, e.g., a polynucleotide encoding an IL12 polypeptide, alone or in combination with a composition comprising a polynucleotide comprising an ORF encoding a checkpoint inhibitor polypeptide or a composition comprising a checkpoint inhibitor polypeptide, inhibits the growth of a distal tumor. In certain embodiments, the administering is intratumoral to a first tumor, and the administering inhibits the growth of a second, distal tumor. In some embodiments, the growth of the distal tumor is inhibited for at least about 7 days, at least about 14 days, at least about 21 days, at least about 28 days, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 18 months, at least about 24 months, at least about 30 months, at least about 36 months, at least about 4 years, or at least about 5 years.

The delivery of the polynucleotide encoding IL12 to a tumor using a pharmaceutical compositions for intratumoral administration disclosed herein can:

(i) increase the retention of the polynucleotide in the tumor;
(ii) increase the levels of expressed polypeptide in the tumor compared to the levels of expressed polypeptide in peritumoral tissue;
(iii) decrease leakage of the polynucleotide or expressed product to off-target tissue (e.g., peritumoral tissue, or to distant locations, e.g., liver tissue); or,
(iv) any combination thereof, wherein the increase or decrease observed for a certain property is relative to a corresponding reference composition (e.g., composition in which compounds of formula (I) are not present or have been substituted by another ionizable amino lipid, e.g., MC3).

In one embodiment, a decrease in leakage can be quantified as decrease in the ratio of polypeptide expression in the tumor to polypeptide expression in non-tumor tissues, such as peritumoral tissue or to another tissue or organ, e.g., liver tissue.

Delivery of a polynucleotide encoding IL12 to a tumor involves administering a pharmaceutical composition disclosed herein, e.g., in nanoparticle form, including the polynucleotide encoding IL12 to a subject, where administration of the pharmaceutical composition involves contacting the tumor with the composition.

In the instance that the polynucleotide encoding IL12 is an mRNA, upon contacting a cell in the tumor with the pharmaceutical composition, a translatable mRNA may be translated in the cell to produce a polypeptide of interest. However, mRNAs that are substantially not translatable may also be delivered to tumors. Substantially non-translatable mRNAs may be useful as vaccines and/or may sequester translational components of a cell to reduce expression of other species in the cell.

The pharmaceutical compositions disclosed herein can increase specific delivery. As used herein, the term "specific delivery," means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide encoding an IL12B polypeptide, IL12A polypeptide, or both IL12B and IL12A polypeptides by pharmaceutical composition disclosed herein (e.g., in nanoparticle form) to a target tissue of interest (e.g., a tumor) compared to an off-target tissue (e.g., mammalian liver).

The level of delivery of a nanoparticle to a particular tissue may be measured, for example, by comparing
(i) the amount of protein expressed from a polynucleotide encoding IL12 in a tissue to the weight of the tissue;
(ii) comparing the amount of the polynucleotide in a tissue to the weight of the tissue; or
(iii) comparing the amount of protein expressed from a polynucleotide encoding IL12 in a tissue to the amount of total protein in the tissue.

Specific delivery to a tumor or a particular class of cells in the tumor implies that a higher proportion of pharmaceutical composition including a polynucleotide encoding an IL12B polypeptide, IL12A polypeptide, or both IL12B and IL12A polypeptides is delivered to the target destination (e.g., target tissue) relative to other off-target destinations upon administration of a pharmaceutical composition to a subject.

The present disclosure also provides methods to deliver intratumorally a polynucleotide encoding an IL12B polypeptide, IL12A polypeptide, or both IL12B and IL12A polypeptides when a pharmaceutical composition comprising the polynucleotides disclosed herein (e.g., in nanoparticle form) are administered to a tumor. The intratumoral administration can show one or more properties selected from the group consisting of:
(i) increased retention of the polynucleotide encoding an IL12B polypeptide, IL12A polypeptide, or both IL12B and IL12A polypeptides in the tumor;
(ii) increased levels of expressed polypeptide in the tumor compared to the levels of expressed polypeptide in peritumoral tissue;
(iii) decreased leakage of the polynucleotide or expressed product to off-target tissue (e.g., peritumoral tissue, or to distant locations, e.g., liver tissue); and,
(iv) any combination thereof,
wherein the increase or decrease observed for a certain property is relative to a corresponding reference composition (e.g., composition in which compounds of formula (I) are not present or have been substituted by another ionizable amino lipid, e.g., MC3).

In one embodiment, a decrease in leakage can be quantified as decrease in the ratio of polypeptide expression in the tumor to polypeptide expression in non-tumor tissues, such as peritumoral tissue or to another tissue or organ, e.g., liver tissue.

In some embodiments, another property in delivery caused as a result of using the pharmaceutical compositions disclosed herein is a reduction in immune response with respect to the immune response observed when other lipid components are used to deliver the same a therapeutic agent or polynucleotide encoding a therapeutic agent.

Accordingly, the present disclosure provides a method of increasing retention of a therapeutic agent (e.g., a polynucleotide or a polypeptide administered as part of the pharmaceutical composition or a polypeptide expressed as a result of the administration) in a tumor tissue in a subject, comprising administering intratumorally to the tumor tissue a pharmaceutical composition disclosed herein, wherein the retention of the therapeutic agent in the tumor tissue is increased compared to the retention of the therapeutic agent in the tumor tissue after administering a corresponding reference composition (e.g., MC3).

Also provided is a method of increasing retention of a polynucleotide in a tumor tissue in a subject, comprising administering intratumorally to the tumor tissue a pharmaceutical composition disclosed herein, wherein the retention of the polynucleotide in the tumor tissue is increased compared to the retention of the polynucleotide in the tumor tissue after administering a corresponding reference composition (e.g., MC3).

Also provided is a method of increasing retention of an expressed polypeptide in a tumor tissue in a subject, comprising administering to the tumor tissue a pharmaceutical composition disclosed herein, wherein the pharmaceutical composition comprises a polynucleotide encoding the expressed polypeptide, and wherein the retention of the expressed polypeptide in the tumor tissue is increased compared to the retention of the polypeptide in the tumor tissue after administering a corresponding reference composition (e.g., MC3).

The present disclosure also provides a method of decreasing expression leakage of a polynucleotide administered intratumorally to a subject in need thereof, comprising administering said polynucleotide intratumorally to the tumor tissue as a pharmaceutical composition disclosed herein, wherein the expression level of the polypeptide in non-tumor tissue is decreased compared to the expression level of the polypeptide in non-tumor tissue after administering a corresponding reference composition (e.g., MC3).

Also provided is a method of decreasing expression leakage of a therapeutic agent (e.g., a polypeptide administered as part of the pharmaceutical composition) administered intratumorally to a subject in need thereof, comprising administering the therapeutic agent intratumorally to the tumor tissue as a pharmaceutical composition disclosed herein, wherein the amount of therapeutic agent in non-tumor tissue is decreased compared to the amount of therapeutic in non-tumor tissue after administering a corresponding reference composition (e.g., MC3).

Also provided is a method of decreasing expression leakage of an expressed polypeptide in a tumor in a subject, comprising administering to the tumor tissue a pharmaceutical composition disclosed herein, wherein the pharmaceutical composition comprises a polynucleotide encoding the expressed polypeptide, and wherein the amount of expressed polypeptide in non-tumor tissue is decreased compared to the amount of expressed polypeptide in non-tumor tissue after administering a corresponding reference composition (e.g., MC3).

In some embodiments, the non-tumoral tissue is peritumoral tissue. In other embodiments, the non-tumoral tissue is liver tissue.

The present disclosure also provides a method to reduce or prevent the immune response caused by the intratumoral administration of a pharmaceutical composition, e.g., a pharmaceutical composition comprising lipids known in the art, by replacing one or all the lipids in such composition with a compound of Formula (I). For example, the immune response caused by the administration of a polynucleotide encoding an IL12B polypeptide, IL12A polypeptide, or both IL12B and IL12A polypeptides in a pharmaceutical composition comprising MC3 (or other lipids known in the art) can be prevented (avoided) or ameliorated by replacing MC3 with a compound of Formula (I), e.g., Compound 18.

In some embodiments, the immune response observed after a polynucleotide encoding an IL12B polypeptide, IL12A polypeptide, or both IL12B and IL12A polypeptides is administered in a pharmaceutical composition disclosed herein is not elevated compared to the immune response observed when the therapeutic agent or a polynucleotide encoding an IL12B polypeptide, IL12A polypeptide, or both IL12B and IL12A polypeptides is administered in phosphate buffered saline (PBS) or another physiological buffer solution (e.g., Ringer's solution, Tyrode's solution, Hank's balanced salt solution, etc.).

In some embodiments, the immune response observed after a therapeutic agent or a polynucleotide encoding an IL12B polypeptide, IL12A polypeptide, or both IL12B and IL12A polypeptides is administered in a pharmaceutical composition disclosed herein is not elevated compared to the immune response observed when PBS or another physiological buffer solution is administered alone.

In some embodiments, no immune response is observed when a pharmaceutical composition disclosed herein is administered intratumorally to a subject.

Accordingly, the present disclosure also provides a method of delivering a therapeutic agent or a polynucleotide encoding an IL12B polypeptide, IL12A polypeptide, or both IL12B and IL12A polypeptides to a subject in need thereof, comprising administering intratumorally to the subject a pharmaceutical composition disclosed herein, wherein the immune response caused by the administration of the pharmaceutical composition is not elevated compared to the immune response caused by the intratumoral administration of
(i) PBS alone, or another physiological buffer solution (e.g., Ringer's solution, Tyrode's solution, Hank's balanced salt solution, etc.);
(ii) the therapeutic agent or polynucleotide encoding an IL12B polypeptide, IL12A polypeptide, or both IL12B and IL12A polypeptides in PBS or another physiological buffer solution; or,
(iii) a corresponding reference composition, i.e., the same pharmaceutical composition in which the compound of Formula (I) is substituted by another ionizable amino lipid, e.g., MC3.

In certain embodiments, the administration treats a cancer.

The polynucleotide (e.g., mRNA) of the present disclosure can be administered in any route available, including, but not limited to, intratumoral, enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraperitoneal (into the peritoneum), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In other embodiments, the mRNA of the present disclosure is administered parenterally (e.g., includes subcutaneous, intravenous, intraperitoneal, intratumoral, intramuscular, intra-articular, intra-synovial, intrasternal, intrathecal, intrahepatic, intralesional and intracranial injection or infusion techniques), intraventricularly, orally, by inhalation spray, topically, rectally, nasally, buccally, vaginally or via an implanted reservoir. In particular embodiments, the polynucleotide, composition, or polypeptide is administered subcutaneously, intravenously, intraperitoneally, intratumorally, intramuscularly, intra-articularly, intra-synovially, intrasternally, intrathecally, intrahepatically, intradermally, intralesionally, intracranially, intraventricularly, orally, by inhalation spray, topically, rectally, nasally, buccally, vaginally or via an implanted reservoir. In one particular embodiment, the polynucleotide (e.g., mRNA) of the present disclosure is administered intratumorally.

In some embodiments, the polynucleotide is delivered by a device comprising a pump, patch, drug reservoir, short needle device, single needle device, multiple needle device, micro-needle device, jet injection device, ballistic powder/particle delivery device, catheter, lumen, cryoprobe, cannula, microcanular, or devices utilizing heat, RF energy, electric current, or any combination thereof.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

In some embodiments, the polynucleotide, e.g., mRNA, is administered at an amount between about 0.10 µg/kg and about 1000 mg/kg.

In some embodiments, the administration of the polynucleotide, pharmaceutical composition or formulation of the disclosure results in expression of IL12 in cells of the subject. In some embodiments, administering the polynucleotide, pharmaceutical composition or formulation of the disclosure results in an increase of IL12 activity in the subject. For example, in some embodiments, the polynucleotides of the present disclosure are used in methods of administering a composition or formulation comprising an mRNA encoding an IL12B polypeptide, IL12A polypeptide, and both IL12B and IL12A polypeptides to a subject, wherein the method results in an increase of IL12 activity in at least some cells of a subject.

In some embodiments, the administration of a composition or formulation comprising an mRNA encoding an IL12B polypeptide, IL12A polypeptide, and both IL12B and IL12A polypeptides to a subject results in an increase of IL12 activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the activity level expected in a normal subject.

Other embodiments of the disclosure also provide a method of treating a cancer in a subject in need thereof comprising administering (e.g., intratumorally, intraperitoneally, or intravenously) a polynucleotide comprising an mRNA encoding an IL12B polypeptide, IL12A polypeptide, and both IL12B and IL12A polypeptides with one or more anti-cancer agents to the subject.

In some embodiments, the polynucleotides (e.g., mRNA) encoding an IL12B polypeptide, IL12A polypeptide, and both IL12B and IL12A polypeptides of the present disclosure can be used to reduce the size of a tumor or inhibit tumor growth in a subject in need thereof.

In some embodiments, the tumor is associated with a disease, disorder, and/or condition. In a particular embodiment, the disease, disorder, and/or condition is a cancer. Thus, in one aspect, the administration of the polynucleotide (e.g., mRNA) encoding an IL12B polypeptide, IL12A polypeptide, and both IL12B and IL12A polypeptides treats a cancer.

A "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. A "cancer" or "cancer tissue" can include a tumor at various stages. In certain embodiments, the cancer or tumor is stage 0, such that, e.g., the cancer or tumor is very early in development and has not metastasized. In some embodiments, the cancer or tumor is stage I, such that, e.g., the cancer or tumor is relatively small in size, has not spread into nearby tissue, and has not metastasized. In other embodiments, the cancer or tumor is stage II or stage III, such that, e.g., the cancer or tumor is larger than in stage 0 or stage I, and it has grown into neighboring tissues but it has not metastasized, except potentially to the lymph nodes. In other embodiments, the cancer or tumor is stage IV, such that, e.g., the cancer or tumor has metastasized. Stage IV can also be referred to as advanced or metastatic cancer.

In some aspects, the cancer can include, but is not limited to, adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, hepatocellular carcinoma (HCC), non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and any combination thereof.

In some aspects, the tumor is a solid tumor. A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" refers to a tumor arising from the melanocytic system of the skin and other organs. Melanomas include, for example, acra-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas include, e.g., acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma viflosum.

Additional cancers that can be treated include, e.g., Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Müllerian cancer, ovarian cancer, peritoneal cancer, fallopian tube cancer, or uterine papillary serous carcinoma.

2. Combination Therapy

The disclosure further includes a polynucleotide comprising an ORF (e.g., mRNA) encoding an IL12B polypeptide, IL12A polypeptide, or both IL12B and IL12A polypeptide or uses thereof as a combination therapy, i.e., with any other anti-cancer agent in combination. In certain embodiments, the polynucleotide encodes an IL-12 polypeptide, wherein the polynucleotide comprises an ORF encoding an IL12B polypeptide and an IL12A polypeptide or uses thereof as a combination therapy, i.e., with any other anti-cancer agent in combination.

In certain embodiments, the disclosure is directed to a polynucleotide comprising an mRNA encoding an IL12B polypeptide, IL12A polypeptide, or both IL12B and IL12A polypeptide in combination with one or more anti-cancer agents or uses of the polynucleotide in combination with one or more anti-cancer agents to the subject. In one embodiment, the combination therapy can be a combination of the polynucleotide encoding IL12 and one or more standard therapy. In another embodiment, the methods of the disclosure include two additional anti-cancer agents, three additional agents, four additional agents, etc. The additional anti-cancer agents can be a protein, e.g., an antibody, or a polynucleotide, e.g., mRNA. In some embodiments, the one or more anti-cancer agents are an mRNA. In certain embodiments, the one or more anti-cancer agents are an mRNA encoding a tumor antigen. In other embodiments, the one or more anti-cancer agents are not a tumor antigen or an mRNA encoding a tumor antigen. In other embodiments, the one or more anti-cancer agents are a protein, e.g., an antibody.

In some embodiments, the one or more anti-cancer agents are an approved agent by the United States Food and Drug Administration. In other embodiments, the one or more anti-cancer agents are a pre-approved agent by the United States Food and Drug Administration.

One skilled in the art would also appreciate that alternative embodiments of the present disclosure include a combination therapy of IL12 and any other agents, e.g., an anti-PD-1 antibody, an anti-PD-L1 antibody, and/or an anti-CTLA-4 antibody, or OX40L as polynucleotides and/or proteins. For example, the present disclosure encompasses combination therapy of (i) a polynucleotide (e.g., mRNA) encoding IL2 and a protein comprising an anti-PD-1 antibody or an anti-PD-L1 antibody; (iii) a polynucleotide (e.g., mRNA) encoding IL12 and a second protein comprising an anti-CTLA-4 antibody, or (iv) a polynucleotide (e.g., mRNA) encoding IL12 and a second protein comprising OX40L. In other embodiments, the IL12 can also be administered as a protein.

In other embodiments, the additional agents can be formulated together with the polynucleotide encoding IL12, e.g., mRNA, or separately. Moreover, even when formulated separately, the additional agents can be administered concurrently with the polynucleotide encoding IL12 or sequentially. In one embodiment, the polynucleotide encoding IL12 is administered prior to the second agent. In another embodiment, the polynucleotide encoding IL12 is administered after the second agent.

In certain embodiments, the additional agents, e.g., any antibody disclosed herein or a polynucleotide encoding OX40L, are also administered intratumorally. In other embodiments, the second agents, e.g., any antibody disclosed herein or a polynucleotide encoding OX40L, are administered via different routes, e.g., intravenously, subcutaneously, intraperitoneally, etc.

In some aspects, the subject for the present methods or compositions has been treated with one or more standard of care therapies. In other aspects, the subject for the present methods or compositions has not been responsive to one or more standard of care therapies or anti-cancer therapies. In one aspect, the subject has been previously treated with an IL2 protein or an IL2 DNA gene therapy. In another aspect, the subject is treated with an anti-PD-1 antagonist or an anti-CTLA-4 antagonist prior to the polynucleotide of the present disclosure. In another aspect, the subject has been treated with a monoclonal antibody that binds to PD-1 prior to the polynucleotide of the present disclosure and/or a monoclonal antibody that binds to CTLA-4 prior to the polynucleotide of the present disclosure. In another aspect, the subject has been treated with an anti-PD-1 monoclonal antibody and/or anti-CTLA-4 monoclonal antibody therapy prior to the polynucleotide of the present methods or compositions.

In recent years, the introduction of immune checkpoint inhibitors for therapeutic purposes has revolutionized cancer treatment. Of interest are therapies featuring combinations of checkpoint inhibitors with other costimulatory or inhibitory molecules.

T cell regulation, i.e., activation or inhibition is mediated via co-stimulatory or co-inhibitory signals. This interaction is exerted via ligand/receptor interaction. T cells harbor a myriad of both activating receptors, such as OX40, and inhibitory receptors (i.e., immune checkpoints) such as programmed death receptor 1 (PD-1) or cytotoxic T lymphocyte-associated protein 4 (CTLA-4) (Mellman et al. 2011 Nature; 480:480-489). Activation of this immune checkpoints results in T cell deactivation and commandeering these pathways by tumor cells contributes to their successful immune escape.

In some embodiments, the methods of reducing the size of a tumor or inhibiting growth of a tumor in a subject in need thereof comprise administering to the subject an effective amount of a composition comprising one or more polynucleotides. In some embodiments, the one or more polynucleotides encode an IL-12 polypeptide. In some embodiments, the one or more polynucleotides comprise an open reading frame ("ORF") encoding an IL12B polypeptide. In some embodiments, the one or more polynucleotides comprise an ORF encoding an IL12A polypeptide. In certain embodiments, the one or more polynucleotides comprise an ORF encoding an IL12B polypeptide and an IL12A polypeptide.

In some embodiments, the methods further comprise administering a second agent. In some embodiments, the second agent comprises an effective amount of a composition comprising a polynucleotide comprising an ORF encoding a checkpoint inhibitor polypeptide. In some embodiments, the second agent comprises an effective amount of a composition comprising a checkpoint inhibitor polypeptide. In some embodiments, the checkpoint inhibitor is any checkpoint inhibitor known in the art or described herein. In some embodiments, the checkpoint inhibitor is an anti-PD-1 antibody. In other embodiments, the checkpoint inhibitor is an anti-PD-L1 antibody. In other embodiments, the checkpoint inhibitor is an anti-CTLA-4 antibody. In some embodiments, the second agent comprises an effective amount of a composition comprising a polynucleotide comprising an ORF encoding OX40L. In some embodiments, the checkpoint inhibitor is selected from the group consisting of an anti-PD-1 antibody, an anti-PD-L1 antibody, an anti-CTLA-4 antibody, a polynucleotide encoding OX40L any other agents disclosed herein, and any combination thereof. In certain embodiments, the composition comprising a checkpoint inhibitor comprises more than one checkpoint inhibitor. In one particular embodiment, the method comprises administering (i) an mRNA, encoding an IL12B and/or IL12A polypeptide disclosed herein, and (ii) an anti-PD-L1 antibody, an anti-PD-1 antibody, anti-CTLA-4 antibody, a polynucleotide encoding OX40L, or any combination thereof.

In some embodiments, the checkpoint inhibitor comprises an antigen binding fragment of an antibody. In some embodiments, the antibody is an anti-CTLA-4 antibody or antigen-binding fragment thereof that specifically binds CTLA-4, an anti-PD-1 antibody or antigen-binding fragment thereof that specifically binds PD-1, an anti-PD-L1 antibody or antigen-binding fragment thereof that specifically binds PD-L1, or a combination thereof. In one embodiment, the antibody is an anti-CTLA4 antibody or antigen-binding fragment thereof that specifically binds CTLA4. In another embodiment, the antibody is an anti-PD-1 antibody or antigen-binding fragment thereof that specifically binds PD-1. In another embodiment, the antibody is an anti-PD-L1 antibody or antigen-binding fragment thereof that specifically binds PD-L1.

Immune checkpoint inhibitors such as pembrolizumab or nivolumab, which target the interaction between programmed death receptor i/programmed death ligand 1 (PD-1/PDL-1) and PDL-2, have been recently approved for the treatment of various malignancies and are currently being investigated in clinical trials for cancers including melanoma, head and neck squamous cell carcinoma (HNSCC). Data available from these trials indicate substantial activity accompanied by a favorable safety and toxicity profile in these patient populations.

For example, checkpoint inhibitors have been tested in clinical trials for the treatment of melanoma. In particular, phase III clinical trials have revealed that therapies such as ipilimumab and pembrolizumab, which target the CTLA-4 and PD-1 immune checkpoints, respectively, have raised the three-year survival of patients with melanoma to ~70%, and overall survival (>5 years) to ~30%.

Likewise, checkpoint inhibitors have been tested in clinical trials for the treatment of head and neck cancer. In preclinical studies, it had been shown that that 45-80% of HNSCC tumors express programmed death ligand 1 (PD-L1) (Zandberg et al. (2014) Oral Oncol. 50:627-632). Currently there are dozens of clinical trials evaluating the efficacy and safety of immune checkpoint inhibitors as monotherapy or in combination regimens in HNSCC. For example, clinical trials with PD 1, PD-L1, and CTLA-4 inhibitors are being tested in HNSCC. Data that the PD-1 antibody pembrolizumab might be effective in metastatic/recurrent (R/M) HNSCC patients were generated in the phase 1b Keynote-012 phase I/II trial (Cheng. ASCO 2015, oral presentation). More recently the data of the randomized CheckMate-141 phase III clinical trial were presented (Gillison. AACR 2016, oral presentation). This study investigated the efficacy of the monoclonal PD-1 antibody nivolumab given every 2 weeks in platinum-refractory R/M HNSCC patients. The study was stopped early due to superiority of the nivolumab arm of the study.

In one aspect, the subject has been previously treated with a PD-1 antagonist prior to the polynucleotide of the present disclosure. In another aspect, the subject has been treated with a monoclonal antibody that binds to PD-1 prior to the polynucleotide of the present disclosure. In another aspect, the subject has been treated with an anti-PD-1 monoclonal antibody therapy prior to the polynucleotide of the present methods or compositions. In other aspects, the anti-PD-1 monoclonal antibody therapy comprises nivolumab, pembrolizumab, pidilizumab, or any combination thereof. In another aspect, the subject has been treated with a monoclonal antibody that binds to PD-L1 prior to the polynucleotide of the present disclosure. In another aspect, the subject has been treated with an anti-PD-L1 monoclonal antibody therapy prior to the polynucleotide of the present methods or compositions. In other aspects, the anti-PD-L1 monoclonal antibody therapy comprises durvalumab, avelumab, MEDI473, BMS-936559, aezolizumab, or any combination thereof.

In some aspects, the subject has been treated with a CTLA-4 antagonist prior to treatment with the compositions of present disclosure. In another aspect, the subject has been previously treated with a monoclonal antibody that binds to CTLA-4 prior to the compositions of the present disclosure. In another aspect, the subject has been treated with an anti-CTLA-4 monoclonal antibody prior to the polynucleotide of the present disclosure. In other aspects, the anti-CTLA-4 antibody therapy comprises ipilimumab or tremelimumab.

In some aspects, the disclosure is directed to a method of treating cancer and/or a method of immunotherapy in a subject in need thereof comprising administering to the subject (e.g., intratumorally, intraperitoneally, or intravenously) the polynucleotide (e.g., RNA, e.g., mRNA) encoding an IL12 polypeptide in combination with a PD-L1 antagonist, e.g., an antibody or antigen-binding portion thereof that specifically binds to PD-L1, e.g., an anti-PD-L1 monoclonal antibody, e.g., an anti-PD-L1 monoclonal antibody comprises Durvalumab, Avelumab, MEDI473, BMS-936559, Atezolizumab, or any combination thereof.

In certain embodiments, the anti-PD-L1 antibody useful for the disclosure is MSB0010718C (also called Avelumab; See US 2014/0341917) or BMS-936559 (formerly 12A4 or MDX-1105) (see, e.g., U.S. Pat. No. 7,943,743; WO 2013/173223). In other embodiments, the anti-PD-L1 antibody is atezolizumab (also known as TECENTRIQ®). In other embodiments, the anti-PD-L1 antibody is MPDL3280A (also known as atezolizumab, TECENTRIQ®, and RG7446) (see, e.g., Herbst et al. (2013) J Clin Oncol 3 (suppl):3000. Abstract; U.S. Pat. No. 8,217,149), MEDI4736 (also called Durvalumab; Khleif (2013) In: Proceedings from the European Cancer Congress 2013; Sep. 27-Oct. 1, 2013; Amsterdam, The Netherlands.

In some aspects, the disclosure is directed to a method of treating cancer and/or a method of immunotherapy in a subject in need thereof comprising administering to the subject (e.g., intratumorally, intraperitoneally, or intravenously) the polynucleotide (e.g., RNA, e.g., mRNA) encoding an IL12 polypeptide, in combination with a PD-1 antagonist, e.g., an antibody or antigen-binding portion thereof that specifically binds to PD-1, e.g., an anti-PD-1 monoclonal antibody.

In one embodiment, the anti-PD-1 antibody (or an antigen-binding portion thereof) useful for the disclosure is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also http://www-.cancer.gov/drugdictionary?cdrid=695789 (last accessed: Dec. 14, 2014). Pembrolizumab has been approved by the FDA for the treatment of relapsed or refractory melanoma and advanced NSCLC.

In another embodiment, the anti-PD-1 antibody useful for the disclosure is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223.

In other embodiments, the anti-PD-1 antibody is MEDI0680 (formerly AMP-514), which is a monoclonal antibody against the PD-1 receptor. MEDI0680 is described, for example, in U.S. Pat. No. 8,609,089B2 or in http://www.cancer.gov/drugdictionary?cdrid=756047 (last accessed Dec. 14, 2014).

In certain embodiments, the anti-PD-1 antibody is BGB-A317, which is a humanized monoclonal antibody. BGB-A317 is described in U.S. Publ. No. 2015/0079109.

In certain embodiments, a PD-1 antagonist is AMP-224, which is a B7-DC Fc fusion protein. AMP-224 is discussed in U.S. Publ. No. 2013/0017199 or in http://www.cancer-.gov/publications/dictionaries/cancer-drug?cdrid=700595 (last accessed Jul. 8, 2015).

In other embodiments, the disclosure includes a method of treating cancer and/or a method of immunotherapy in a subject in need thereof comprising administering to the subject (e.g., intratumorally, intraperitoneally, or intravenously) the polynucleotide (e.g., RNA, e.g., mRNA) encoding an IL12 polypeptide together with an antibody or an antigen binding portion thereof that specifically binds to PD-1, e.g., an anti-PD-1 monoclonal antibody, e.g., an anti-PD-1 monoclonal antibody comprises Nivolumab, Pembrolizumab, Pidilizumab, or any combination thereof.

In other aspects, the disclosure is directed to a method of treating cancer and/or a method of immunotherapy in a subject in need thereof comprising administering to the subject (e.g., intratumorally, intraperitoneally, or intravenously) the polynucleotide (e.g., RNA, e.g., mRNA) encoding an IL12 polypeptide in combination with a CTLA-4 antagonist, e.g., an antibody or antigen-binding portion thereof that specifically binds to CTLA-4, e.g., an anti-CTLA-4 monoclonal antibody, e.g., an anti-CTLA-4 monoclonal antibody comprises Ipilimumab or Tremelimumab, or any combination thereof.

An exemplary clinical anti-CTLA-4 antibody is the human mAb 10D1 (now known as ipilimumab and marketed as YERVOY®) as disclosed in U.S. Pat. No. 6,984,720. Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

In one embodiment, a first polynucleotide (e.g. a first mRNA) encoding IL12 and a second polynucleotide (e.g., a second mRNA) encoding an OX40L polypeptide are administered in combination. In another embodiment, the first polynucleotide (e.g. a first mRNA) encoding IL12 and the second polynucleotide (e.g. a second mRNA) encoding an OX40L polypeptide are administered in combination with an antibody or an antigen-binding portion thereof which specifically binds to CTLA-4, an antibody or antigen-binding portion thereof which specifically binds to a PD-1 receptor, or an antibody or antigen-binding portion thereof which specifically binds to a PD-L1 receptor.

In one embodiment, a first polynucleotide (e.g. a first mRNA) encoding an IL12 polypeptide and a second polynucleotide (e.g. a second mRNA) encoding an OX40L polypeptide are administered in combination with an antibody or an antigen-binding portion thereof that specifically binds to a PD-1 or PD-L1 receptor or a polynucleotide encoding the same.

In another embodiment, a first polynucleotide (e.g. a first mRNA) encoding an IL12 polypeptide and a second polynucleotide (e.g. a second mRNA) encoding an OX40L polypeptide are administered in combination with an antibody or an antigen-binding portion thereof that specifically binds to a CTLA-4 or a polynucleotide encoding the same.

In yet another embodiment, a first polynucleotide (e.g. a first mRNA) encoding an IL12 polypeptide and a second polynucleotide (e.g. a second mRNA) encoding an OX40L polypeptide are administered in combination with an antibody or an antigen-binding portion thereof that specifically binds to a PD-1 or PD-L1 receptor and an antibody or an antigen-binding portion thereof that specifically binds to a CTLA-4 (or polynucleotides of the same).

In some embodiments, the compositions disclosed herein comprise (i) a first polynucleotide (e.g. a first mRNA) encoding IL12 and (ii) a second polynucleotide (e.g. a second mRNA) encoding an antibody or an antigen binding portion thereof which specifically binds to CTLA-4 in a single formulation.

In some embodiments, the compositions disclosed herein comprise a polynucleotide encoding IL12 and a polynucleotide encoding an OX40L protein in a single formulation.

Human OX40L was first identified on the surface of human lymphocytes infected with human T-cell leukemia virus type-I (HTLV-I) by Tanaka et al. (Tanaka et al., International Journal of Cancer (1985), 36(5):549-55). OX40L is the ligand for OX40 (CD134). OX40L has also been designated CD252 (cluster of differentiation 252), tumor necrosis factor (ligand) superfamily, member 4, tax-transcriptionally activated glycoprotein 1, TXGP1, or gp34. Human OX40L is 183 amino acids in length and contains three domains: a cytoplasmic domain of amino acids 1-23; a transmembrane domain of amino acids 24-50, and an extracellular domain of amino acids 51-183.

In some embodiments, a polynucleotide encoding OX40L that can be combined with the polynucleotide encoding IL12 comprises an mRNA encoding a mammalian OX40L polypeptide. In some embodiments, the mammalian OX40L polypeptide is a murine OX40L polypeptide. In some embodiments, the mammalian OX40L polypeptide is a human OX40L polypeptide. In some embodiments, the OX40L polypeptide comprises an amino acid sequence set forth in Table 1.

In some embodiments, each polynucleotide of the disclosure comprises an mRNA, i.e., an mRNA encoding an IL12 polypeptide and an mRNA encoding an OX40L polypeptide. In some embodiments, the mRNA encoding an IL12 polypeptide encodes a mammalian IL12 polypeptide. In some embodiments, the mRNA encoding an OX40L polypeptide encodes a mammalian OX40L polypeptide. In some embodiments, the mRNA encoding an IL12 polypeptide encodes a murine IL12 polypeptide. In some embodiments, the mRNA encoding an OX40L polypeptide encodes a murine OX40L polypeptide. In some embodiments, the mRNA encoding an IL12 polypeptide encodes a human IL12 polypeptide. In some embodiments, the mRNA encoding an OX40L polypeptide encodes a human OX40L polypeptide.

In some embodiments, the IL12 polypeptide comprises a human amino acid sequence set forth in Table 4. In other embodiments, the OX40L polypeptide comprises a human amino acid sequence set forth in Table 1.

In some embodiments, the OX40L polypeptide comprises an amino acid sequence at least 50%, at least 60%, at least 70%, at least 80%, at least 85%, at least 90%, at least 95%, at least 99%, or 100% identical to an amino acid sequence listed in Table 1 or an amino acid sequence encoded by a nucleotide sequence listed in Table 1, wherein the amino acid sequence is capable of binding to an OX40 receptor.

In certain embodiments, the OX40L polypeptide encoded by a polynucleotide of the disclosure comprises an amino acid sequence listed in Table 1 with one or more conservative substitutions, wherein the conservative substitutions do not significantly affect the binding activity of the OX40L polypeptide to its receptor, i.e., the OX40L polypeptide binds to the OX40 receptor after the substitutions.

In other embodiments, a nucleotide sequence (i.e., mRNA) encoding an OX40L polypeptide comprises a sequence at least 50%, at least 60%, at least 70%, at least 80%, at least 85%, at least 90%, at least 95%, at least 99%, or 100% identical to a nucleic acid sequence listed in Table 1. One skilled in the art would know that if a sequence is written in DNA form (containing thymidine) in the present application, the corresponding RNA sequence would contain uridine instead of thymidine.

In some embodiments, the polynucleotide (e.g., mRNA) useful for the methods and compositions comprises an open reading frame encoding an extracellular domain of OX40L. In other embodiments, the polynucleotide (e.g., mRNA) comprises an open reading frame encoding a cytoplasmic domain of OX40L. In some embodiments, the polynucleotide (e.g., mRNA) comprises an open reading frame encoding a transmembrane domain of OX40L. In certain embodiments, the polynucleotide (e.g., mRNA) comprises an open reading frame encoding an extracellular domain of OX40L and a transmembrane of OX40L. In other embodiments, the polynucleotide (e.g., mRNA) comprises an open reading frame encoding an extracellular domain of OX40L and a cytoplasmic domain of OX40L. In yet other embodiments, the polynucleotide (e.g., mRNA) comprises an open reading frame encoding an extracellular domain of OX40L, a transmembrane of OX40L, and a cytoplasmic domain of OX40L.

Table 1 presents, e.g., precursor and mature sequences for OX40L as well as constructs comprising the OX40L sequences. Furthermore, a construct comprising a polynucleotide encoding OX40L and further comprising components such 3' UTR and 5' UTR would be considered an OX40L encoding polynucleotide. A person of skill in the art would understand that in addition to the native signal sequences and propeptide sequences disclosed in Table 1 (sequences present in the precursor for and absent in the mature corresponding form) and the non-native signal peptide disclosed in Table 1, other signal sequences can be used. Accordingly, references to an OX40L polypeptide or polynucleotide according to Table 1 encompass variants in which an alternative signal peptide (or encoding sequence) known in the art has been attached to the OX40L polypeptide (or polynucleotide). It is also understood that references to the sequences disclosed in Table 1 through the application are equally applicable and encompass orthologs and functional variants (for example polymorphic variants) and isoforms of those sequences known in the art at the time the application was filed.

TABLE 1

OX40L Polypeptide and Polynucleotide sequences

| Encoded Polypeptide | Description | Sequence | SEQ ID NO: |
|---|---|---|---|
| OX40L (TNFSF4) | Tumor necrosis factor ligand superfamily member 4 isoform 1 [Homo sapiens] NP_003317 | MERVQPLEENVGNAARPRFERNKLLLVASVIQGLGLLLCFTYICLHFSA LQVSHRYPRIQSIKVQFTEYKKEKGFILTSQKEDEIMKVQNNSVIINCD GFYLISLKGYFSQEVNISLHYQKDEEPLFQLKKVRSVNSLMVASLTYKD KVYLNVTTDNTSLDDFHVNGGELILIHQNPGEFCVL | SEQ ID NO: 178 183 aa |
| OX40L (TNFSF4) | TNFSF4 isoform 2 [Homo sapiens] NP_001284491 | MVSHRYPRIQSIKVQFTEYKKEKGFILTSQKEDEIMKVQNNSVIINCDG FYLISLKGYFSQEVNISLHYQKDEEPLFQLKKVRSVNSLMVASLTYKDK VYLNVTTDNTSLDDFHVNGGELILIHQNPGEFCVL | SEQ ID NO: 179 133 aa |

TABLE 1-continued

OX40L Polypeptide and Polynucleotide sequences

| Encoded Polypeptide | Description | Sequence | SEQ ID NO: |
|---|---|---|---|
| OX40L (TNFSF4) | TNFSF4 [Mus musculus] NP_033478 | MEGEGVQPLDENLENGSRPRFKWKKTLRLVVSGIKGAGMLLCFIYVCLQ LSSSPAKDPPIQRLRGAVTRCEDGQLFISSYKNEYQTMEVQNNSVVIKC DGLYIIYLKGSFFQEVKIDLHFREDHNPISIPMLNDGRRIVFTVVASLA FKDKVYLTVNAPDTLCEHLQINDGELIVVQLTPGYCAPEGSYHSTVNQV PL | SEQ ID NO: 180 198 aa |
| OX40L (TNFSF4) | TNFSF4, ORF [Homo sapiens] | AUGGAAAGGGUCCAACCCCUGGAAGAGAAUGUG GGAAAUGCAGCCAGGCCAAGAUUCGAGAGGAAC AAGCUAUUGCUGGUGGCCUCUGUAAUUCAGGGA CUGGGGCUGCUCCUGUGCUUCACCUACAUCUGC CUGCACUUCUCUGCUCUUCAGGUAUCACAUCGG UAUCCUCGAAUUCAAAGUAUCAAAGUACAAUUU ACCGAAUAUAAGAAGGAGAAAGGUUUCAUCCUC ACUUCCCAAAAGGAGGAUGAAAUCAUGAAGGUG CAGAACAACUCAGUCAUCAUCAACUGUGAUGGG UUUUAUCUCAUCUCCCUGAAGGGCUACUUCUCC CAGGAAGUCAACAUUAGCCUUCAUUACCAGAAG GAUGAGGAGCCCCUCUUCCAACUGAAGAAGGUC AGGUCUGUCAACUCCUUGAUGGUGGCCUCUCUG ACUUACAAAGACAAAGUCUACUUGAAUGUGACC ACUGACAAUACCUCCCUGGAUGACUUCCAUGUG AAUGGCGGAGAACUGAUUCUUAUCCAUCAAAAU CCUGGUGAAUUCUGUGUCCUU | SEQ ID NO: 181 552nts |
| OX40L (TNFSF4) | TNFSF4, transcript variant 1, mRNA NM_003326 | GGCCCUGGGACCUUUGCCUAUUUUCUGAUUGAU AGGCUUUGUUUUGUCUUUACCUCCUUCUUUCUG GGGAAAACUUCAGUUUUAUCGCACGUUCCCCUU UUCCAUAUCUUCAUCUUCCCUCUACCCAGAUUG UGAAGAUGGAAAGGGUCCAACCCCUGGAAGAGA AUGUGGGAAAUGCAGCCAGGCCAAGAUUCGAGA GGAACAAGCUAUUGCUGGUGGCCUCUGUAAUUC AGGGACUGGGGCUGCUCCUGUGCUUCACCUACA UCUGCCUGCACUUCUCUGCUCUUCAGGUAUCAC AUCGGUAUCCUCGAAUUCAAAGUAUCAAAGUAC AAUUUACCGAAUAUAAGAAGGAGAAAGGUUUCA UCCUCACUUCCCAAAAGGAGGAUGAAAUCAUGA AGGUGCAGAACAACUCAGUCAUCAUCAACUGUG AUGGGUUUUAUCUCAUCUCCCUGAAGGGCUACU UCUCCCAGGAAGUCAACAUUAGCCUUCAUUACC AGAAGGAUGAGGAGCCCCUCUUCCAACUGAAG AAGGUCAGGUCUGUCAACUCCUUGAUGGUGGC CUCUCUGACUUACAAAGACAAAGUCUACUUGA AUGUGACCACUGACAAUACCUCCCUGGAUGAC UUCCAUGUGAAUGGCGGAGAACUGAUUCUUAU CCAUCAAAAUCCUGGUGAAUUCUGUGUCCUUU GAGGGGCUGAUGGCAAUAUCUAAAACCAGGCA CCAGCAUGAACACCAAGCUGGGGGUGGACAGG GCAUGGAUUCUUCAUUGCAAGUGAAGGAGCCU CCCAGCUCAGCCACGUGGGAUGUGACAAGAAG CAGAUCCUGGCCCUCCCGCCCCCACCCCUCAG GGAUAUUUAAAACUUAUUUUAUAUACCAGUUA AUCUUAUUUAUCCUUAUAUUUUCUAAAUUGCC UAGCCGUCACACCCCAAGAUUGCCUUGAGCCU ACUAGGCACCUUUGUGAGAAAGAAAAAAUAGA UGCCUCUUCUUCAAGAUGCAUUGUUUCUAUUG GUCAGGCAAUUGCAUAAUAAACUUAUGUCAU UGAAAACGGUACCUGACUACCAUUUGCUGGAA AUUUGACAUGUGUGUGGCAUUAUCAAAAUGAA GAGGAGCAAGGAGUGAAGGAGUGGGGUUAUGA AUCUGCCAAAGGUGGUAUGAACCAACCCCUGG AAGCCAAAGCGGCCUCUCCAAGGUUAAAUUGA UUGCAGUUUGCAUAUUGCCUAAAUUUAAACUU UCUCAUUUGGUGGGGUUCAAAAGAAGAAUCA GCUUGUGAAAAUCAGGACUUGAAGAGAGCCG UCUAAGAAAUACCACGUGCUUUUUUCUUUAC CAUUUUGCUUUCCCAGCCUCCAAACAUAGUUA AUAGAAAUUUCCCUUCAAAGAACUGUCUGGGG AUGUGAUGCUUUGAAAAAUCUAAUCAGUGACU UAAGAGAGAUUUCUUGUAUACAGGGAGAGUG AGAUAACAUUGUGAAGGGUUAGCUUUUACUG UACAGGAUAGCAGGGAACUGGACAUCUCAGGG UAAAAGUCAGUACGGAUUUUAAUAGCCUGGGG AGGAAAACACAUUCUUUGCCACAGACAGGCAA AGCAACACAUGCUCAUCCUCCUGCCUAUGCUG AGAUACGCACUCAGCUCCAUGUCUUGUACACA | SEQ ID NO: 182 3484 nts |

TABLE 1-continued

OX40L Polypeptide and Polynucleotide sequences

| Encoded Polypeptide Description | | Sequence | SEQ ID NO: |
|---|---|---|---|
| | | CAGAAACAUUGCUGGUUUCAAGAAAUGAGGUG<br>AUCCUAUUAUCAAAUUCAAUCUGAUGUCAAAU<br>AGCACUAAGAAGUUAUUGUGCCUUAUGAAAAA<br>UAAUGAUCUCUGUCUAGAAAUACCAUAGACCA<br>UAUAUAGUCUCACAUUGAUAAUUGAAACUAGA<br>AGGGUCUAUAAUCAGCCUAUGCCAGGGCUUCA<br>AUGGAAUAGUAUCCCCUUAUGUUUAGUUGAAA<br>UGUCCCCUUAACUUGAUAUAAUGUGUUAUGCU<br>UAUGGCGCUGUGGACAAUCUGAUUUUUCAUGU<br>CAACUUUCCAGAUGAUUUGUAACUUCUCUGUG<br>CCAAACCUUUUAUAAACAUAAAUUUUUGAGAU<br>AUGUAUUUUAAAAUUGUAGCACAUGUUUCCCU<br>GACAUUUUCAAUAGAGGAUACAACAUCACAGA<br>AUCUUUCUGGAUGAUUCUGUGUUAUCAAGGAA<br>UUGUACUGUGCUACAAUUAUCUCUAGAAUCUC<br>CAGAAAGGUGGAGGGCUGUUCGCCCUUACACU<br>AAAUGGUCUCAGUUGGAUUUUUUUUUCCUGUU<br>UUCUAUUUCCUCUUAAGUACACCUUCAACUAU<br>AUUCCCAUCCCUCUAUUUUAAUCUGUUAUGAA<br>GGAAGGUAAAUAAAAAUGCUAAAUGAAGAAA<br>UUGUAGGUAAGGUAAGAGGAAUCAAGUUCUGA<br>GUGGCUGCCAAGGCACUCACAGAAUCAUAAUC<br>AUGGCUAAAUAUUUAUGGAGGGCCUACUGUGG<br>ACCAGGCACUGGGCUAAAUACUUACAUUUACA<br>AGAAUCAUUCUGAGACAGAUAUUCAAUGAUAU<br>CUGGCUUCACUACUCAGAAGAUUGUGUGUGUG<br>UUUGUGUGUGUGUGUGUGUGUAUUUCACUU<br>UUUGUUAUUGACCAUGUUCUGCAAAAUUGCAG<br>UUACUCAGUGAGUGAUAUCCGAAAAAGUAAAC<br>GUUUAUGACUAUAGGUAAUAUUUAAGAAAAUG<br>CAUGGUUCAUUUUAAGUUUGGAAUUUUUAUC<br>UAUAUUUCUCACAGAUGUGCAGUGCACAUGCA<br>GGCCUAAGUAUAUGUUGUGUGUGUUGUUUGUC<br>UUUGAUGUCAUGGUCCCCUCUCUUAGGUGCUC<br>ACUCGCUUUGGGUGCACCUGGCCUGCUCUUCC<br>CAUGUUGGCCUCUGCAACCACACAGGGAUAUU<br>UCUGCUAUGCACCAGCCUCACUCCACCUUCCU<br>UCCAUCAAAAAUAUGUGUGUGUGUCUCAGUCC<br>CUGUAAGUCAUGUCCUUCACAGGGAGAAUUAA<br>CCCUUCGAUAUACAUGGCAGAGUUUUGUGGGA<br>AAAGAAUUGAAUGAAAAGUCAGGAGAUCAGAA<br>UUUUAAAUUUGACUUAGCCACUAACUAGCCAU<br>GUAACCUUGGGAAAGUCAUUUCCAUUUCUGG<br>GUCUUGCUUUUCUUUCUGUUAAAUGAGAGGAA<br>UGUUAAAUAUCUAACAGUUUAGAAUCUUAUGC<br>UUACAGUGUUAUCUGUGAAUGCACAUAUUAAA<br>UGUCUAUGUUCUUGUUGCUAUGAGUCAAGGAG<br>UGUAACCUUCUCCUUUACUAUGUUGAAUGUAU<br>UUUUUUCUGGACAAGCUUACAUCUUCCUCAGC<br>CAUCUUUGUGAGUCCUUCAAGAGCAGUUAUCA<br>AUUGUUAGUUAGAUAUUUCUAUUUAGAGAAU<br>GCUUAAGGGAUUCCAAUCCCGAUCCAAAUCAU<br>AAUUUGUUCUUAAGUAUACUGGGCAGGUCCCC<br>UAUUUUAAGUCAUAAUUUUGUAUUUAGUGCUU<br>UCCUGGCUCUCAGAGAGUAUUAAUAUUGAUAU<br>UAAUAAUAUAGUUAAUAGUAAUAUUGCUAUUU<br>ACAUGGAAACAAAUAAAAGAUCUCAGAAUUCA<br>CUAAAAAAAAAAA | |
| OX40L<br>(TNFSF4) | Mus musculus<br>Tnfsf4, mRNA<br>NM_009452 | AUUGCUUUUGUCUCCUGUUCUGGGACCUUUA<br>UCUUCUGACCCGCAGGCUUGACUUUGCCCUUA<br>UUGGCUCCUUUGUGGUGAAGAGCACGCUUCCC<br>CCAGGUUCCCGCCACAGCUGUAUCUCCUCUG<br>CACCCCGACUGCAGAGAUGUGAAGGGGAAGGGG<br>UUCAACCCCUGGAUGAGAAUCUGGAAAACGGA<br>UCAAGGCCAAGAUUCAAGUGGAAGAAGACGCU<br>AAGGCUGGUGGUCUCUGGGAUCAAGGGAGCAG<br>GGAUGCUUCUGUGCUUCAUCUAUGUCUGCCUG<br>CAACUCUCUUCCUCUCCGGCAAAGGACCCUCC<br>AAUCCAAAGACUCAGAGGAGCAGUUACCAGAU<br>GUGAGGAUGGGCAACUAUUCAUCAGCUCAUAC<br>AAGAAUGAGUAUCAAACUAUGGAGGUGCAGAA<br>CAAUUCGGUUGUCAUCAAGUGCGAUGGGCUUU<br>AUAUCAUCUACCUGAAGGGCUCCUUUUUCCAG<br>GAGGUCAAGAUUGACCUUCAUUUCCGGGAGGA | SEQ ID<br>NO: 183<br>1609 nts |

TABLE 1-continued

OX40L Polypeptide and Polynucleotide sequences

| Encoded Polypeptide Description | | Sequence | SEQ ID NO: |
|---|---|---|---|
| | | UCAUAAUCCCAUCUCUAUUCCAAUGCUGAACG AUGGUCGAAGGAUUGUCUUCACUGUGGUGCC UCUUUGGCUUUCAAAGAUAAAGUUUACCUGAC UGUAAAUGCUCCUGAUACUCUCUGCGAACACC UCCAGAUAAAUGAUGGGGAGCUGAUUGUUGUC CAGCUAACGCCUGGAUACUGUGCUCCUGAAGG AUCUUACCACAGCACUGUGAACCAAGUACCAC UGUGAAUUCCACUCUGAGGGUGGACGGGACAC AGGUUCUUUCUCGAGAGAGAUGAGUGCAUCCU GCUCAUGAGAUGUGACUGAAUGCAGAGCCUAC CCUACUUCCUCACUCAGGGAUAUUUAAAUCAU GUCUUACAUAACAGUUGACCUCUCAUUCCCAG GAUUGCCUUGAGCCUGCUAAGAGCUGUUCUGG GAAUGAAAAAAAAAUAAAUGUCUCUUCAAGA CACAUUGCUUCUGUCGGUCAGAAGCUCAUCGU AAUAAACAUCUGCCACUGAAAAUGGCGCUUGA UUGCUAUCUUCUAGAAUUUUGAUGUUGUCAAA AGAAAGCAAACAUGGAAAGGGUGGUGUCCAC CGGCCAGUAGGAGCUGGAGUGCUCUCUUCAAG GUUAAGGUGAUAGAAGUUUACAUUGCUAA AACUGUCUCUCAUCUCAUGGGGGGCUUGGAAA GAAGAUUACCCCGUGGAAAGCAGGACUUGAAG AUGACUGUUUAAGCAACAAGGUGCACUCUUUU CCUGGCCCCUGAAUACACAUAAAAGACAACUU CCUUCAAAGAACUACCUAGGGACUAUGAUACC CACCAAAGAACCACGUCAGCGAUGCAAAGAAA ACCAGGAGAGCUUUGUUUAUUUUGCAGAGUAU ACGAGAGAUUUUACCCUGAGGGCUAUUUUUAU UAUACAGGAUGAGAGUGAACUGGAUGUCUCAG GAUAAAGGCCAAGAAGGAUUUUUCACAGUCUG AGCAAGACUGUUUUUGUAGGUUCUCUCUCCAA AACUUUUAGGUAAAUUUUUGAUAAUUUUAAAA UUUUUAGUUAUAUUUUUGGACCAUUUUCAAUA GAAGAUUGAAACAUUUCCAGAUGGUUUCAUAU CCCCACAAG | |
| Human OX40L | mRNA sequence: Human OX40L with 5'-UTR, 3'-UTR, and miR-122 binding site | GGGAAAUAAGAGAGAAAAGAAGAGUAAGAAGA AAUAUAAGAGCCACCAUGGAAAGGGUCCAACC CCUGGAAGAGAAUGUGGGAAAUGCAGCCAGGC CAAGAUUCGAGAGGAACAAGCUAUUGCUGGUG GCCUCUGUAAUUCAGGGACUGGGGCUGCUCCU GUGCUUCACCUACAUCUGCCUGCACUUCUCUG CUCUUCAGGUAUCACAUCGGUAUCCUCGAAUU CAAAGUAUCAAAGUACAAUUUACCGAAUAUAA GAAGGAGAAAGGUUUCAUCCUCACAUUCCCAAA AGGAGGAUGAAAUCAUGAAGGUGCAGAACAAC UCAGUCAUCAUCAACUGUGAUGGGUUUUAUCU CAUCUCCCUGAAGGGCUACUUCUCCCAGGAAG UCAACAUUAGCCUUCAUUACCAGAAGGAUGAG GAGCCCCUCUUCCAACUGAAGAAGGUCAGGUC UGUCAACUCCUUGAUGGUGGCCUCUCUGACUU ACAAAGACAAAGUCUACUUGAAUGUGACCACU GACAAUACCUCCCUGGAUGACUUCCAUGUGAA UGGCGGAGAACUGAUUCUUAUCCAUCAAAAUC CUGGUGAAUUCUGUGUCCUUUGAUAAUAGGCU GGAGCCUCGGUGGCCAUGCUUCUUGCCCCUUG GGCCUCCCCCCAGCCCCUCCUCCCCUUCCUGC ACCCGUACCCCCAAACACCAUUGUCACACUC CAGUGGUCUUUGAAUAAAGUCUGAGUGGGCGG C | SEQ ID NO: 184 |
| Murine OX40L | mRNA sequence: murine OX40L with 5'-UTR, 3'-UTR, and miR-122 binding site | GGGAAAUAAGAGAGAAAAGAAGAGUAAGAAGAA AUAUAAGAGCCACCAUGGAAGGGGAAGGGGUUC AACCCCUGGAUGAGAAUCUGGAAAACGGAUCAA GGCCAAGAUUCAAGUGGAAGAAGACGCUAAGGC UGGUGGUCUCUGGGAUCAAGGGAGCAGGGAUGC UUCUGUGCUUCAUCUAUGUCUGCCUGCAACUCU CUUCCUCUCCGGCAAAGGACCCUCCAAUCCAAA GACUCAGAGGAGCAGUUACCAGAUGUGAGGAUG GGCAACUAUUCAUCAGCUCAUACAAGAAUGAGU AUCAAACUAUGGAGGUGCAGAACAAUUCGGUUG UCAUCAAGUGCGAUGGGCUUUAUAUCAUCUACC UGAAGGGCUCCUUUUUCCAGGAGGUCAAGAUUG ACCUUCAUUUCCGGGAGGAUCAUAAUCCCAUCU CUAUUCCAAUGCUGAACGAUGGUCGAAGGAUUG TABLE 1-continued OX40L Polypeptide and Polynucleotide sequences

| Encoded Polypeptide | Description | Sequence | SEQ ID NO: |
|---|---|---|---|
| | | UCUUCACUGUGGUGGCCUCUUUGGCUUUCAAAG<br>AUAAAGUUUACCUGACUGUAAAUGCUCCUGAUA<br>CUCUCUGCGAACACCUCCAGAUAAAUGAUGGGG<br>AGCUGAUUGUUGUCCAGCUAACGCCUGGAUACU<br>GUGCUCCUGAAGGAUCUUACCACAGCACUGUGA<br>ACCAAGUACCACUGUGAUAAUAGGCUGGAGCCU<br>CGGUGGCCAUGCUUCUUGCCCCUUGGGCUCUC<br>CCCAGCCCCUCCUCCCCUUCCUGCACCCGUACC<br>CCCCAAACACCAUUGUCACACUCCAGUGGUCUU<br>UGAAUAAAGUCUGAGUGGGCGGC | |
| hOX40L miR-122 | Codon optimized human OX40L sequences | ATGGAAAGGGTCCAACCCCTGGAAGAGAATGTGGGAAATGCAGCCAGGC<br>CAAGATTCGAGAGGAACAAGCTATTGCTGGTGGCCTCTGTAATTCAGGG<br>ACTGGGGCTGCTCCTGTGCTTCACCTACATCTGCCTGCACTTCTCTGCT<br>CTTCAGGTATCACATCGGTATCCTCGAATTCAAAGTATCAAAGTACAAT<br>TTACCGAATATAAGAAGGAGAAAGGTTTCATCCTCACTTCCCAAAAGGA<br>GGATGAAATCATGAAGGTGCAGAACAACTCAGTCATCATCAACTGTGAT<br>GGGTTTTATCTCATCTCCCTGAAGGGCTACTTCTCCCAGGAAGTCAACA<br>TTAGCCTTCATTACCAGAAGGATGAGGAGCCCCTCTTCCAACTGAAGAA<br>GGTCAGGTCTGTCAACTCCTTGATGGTGGCCTCTCTGACTTACAAAGAC<br>AAAGTCTACTTGAATGTGACCACTGACAATACCTCCCTGGATGACTTCC<br>ATGTGAATGGCGGAGAACTGATTCTTATCCATCAAAATCCTGGTGAATT<br>CTGTGTCCTT | SEQ ID NO: 186 |
| mOX40L + miR-122 | Codon optimized mouse OX40L sequences | ATGGAAGGGGAAGGGGTTCAACCCCTGGATGAGAATCTGGAAAACGGAT<br>CAAGGCCAAGATTCAAGTGGAAGAAGACGCTAAGGCTGGTGGTCTCTGG<br>GATCAAGGGAGCAGGGATGCTTCTGTGCTTCATCTATGTCTGCCTGCAA<br>CTCTCTTCCTCTCCGGCAAAGGACCCTCCAATCCAAAGACTCAGAGGAG<br>CAGTTACCAGATGTGAGGATGGGCAACTATTCATCAGCTCATACAAGAA<br>TGAGTATCAAACTATGGAGGTGCAGAACAATTCGGTTGTCATCAAGTGC<br>GATGGGCTTTATATCATCTACCTGAAGGGCTCCTTTTTCCAGGAGGTCA<br>AGATTGACCTTCATTTCCGGGAGGATCATAATCCCATCTCTATTCCAAT<br>GCTGAACGATGGTCGAAGGATTGTCTTCACTGTGGTGGCCTCTTTGGCT<br>TTCAAAGATAAAGTTTACCTGACTGTAAATGCTCCTGATACTCTCTGCG<br>AACACCTCCAGATAAATGATGGGGAGCTGATTGTTGTCCAGCTAACGCC<br>TGGATACTGTGCTCCTGAAGGATCTTACCACAGCACTGTGAACCAAGTA<br>CCACTG | SEQ ID NO: 187 |
| OX40L (TNFSF4) | Codon-optimized sequence 1 for ENSP 281834 | AUGGAGAGAGUGCAGCCCCUGGAGGAGAACGUG<br>GGCAACGCCGCCAGACCCAGAUUCGAGAGAAAC<br>AAGCUGCUGCUGGUGGCCAGCGUGAUCCAGGGC<br>CUGGGCCUGCUGCUGUGCUUCACCUACAUCUGC<br>CUGCACUUCAGCGCCCUGCAGGUGAGCCACAGA<br>UACCCCAGAAUCCAGAGCAUCAAGGUGCAGUUC<br>ACCGAGUACAAGAAGGAGAAGGGCUUCAUCCUG<br>ACCAGCCAGAAGGAGGACGAGAUCAUGAAGGUG<br>CAGAACAACAGCGUGAUCAUCAACUGCGACGGC<br>UUCUACCUGAUCAGCCUGAAGGGCUACUUCAGC<br>CAGGAGGUGAACAUCAGCCUGCACUACCAGAAG<br>GACGAGGAGCCCCUGUUCCAGCUGAAGAAGGUG<br>AGAAGCGUGAACAGCCUGAUGGUGGCCAGCCUG<br>ACCUACAAGGACAAGGUGUACCUGAACGUGACC<br>ACCGACAACACCAGCCUGGACGACUUCCACGUG<br>AACGGCGGCGAGCUGAUCCUGAUCCACCAGAAC<br>CCCGGCGAGUUCUGCGUGCUG | SEQ ID NO: 188 |
| OX40L (TNFSF4) | Codon-optimized sequence 2 for ENSP 281834 | AUGGAGCGUGUGCAGCCUCUUGAGGAGAAUGUG<br>GGAAAUGCAGCCCGGCCUCGAUUCGAACGUAAU<br>AAACUCCUGCUCUGGCCUCCGUGAUCCAGGGU<br>CUCGGUUUAUUGCUGUGUUUUACCUAUAUAUGC<br>UUACACUUUAGUGCAUUACAGGUCUCACACCGG<br>UACCCUCGCAUUCAGUCUAUAAAAGUGCAGUUU<br>ACCGAGUAUAAGAAGGAGAAAGGUUUUAUACUG<br>ACUUCUCAGAAAGAGGACGAGAUCAUGAAGGUG<br>CAGAAUAAUAGCGUCAUUAUCAACUGCGAUGGA<br>UUCUAUCUAAUUUCCCUAAAGGGGUACUUCAGC<br>CAGGAGGUCAAUAUAUCACUGCACUAUCAAAAG<br>GACGAGGAGCCCCUGUUUCAACUGAAGAAAGUG<br>CGAUCAGUUAACUCUCUGAUGGUUGCCUCUCUG<br>ACCUAUAAGGACAAAGUCUACUUGAACGUGACA<br>ACUGACAACACCUCACUGGAUGACUUUCAUGUG<br>AAUGGGGGGAACUGAUUCUUAUCCAUCAGAAU<br>CCAGGAGAAUUCUGUGUGCUC | SEQ ID NO: 189 |

TABLE 1-continued

OX40L Polypeptide and Polynucleotide sequences

| Encoded Polypeptide | Description | Sequence | SEQ ID NO: |
|---|---|---|---|
| OX40L (TNFSF4) | Codon-optimized sequence 3 for ENSP 281834 | AUGGAGCGGGUGCAGCCCCUGGAGGAGAAUGUG GGCAAUGCUGCCCGCCCAGGUUUGAAAGAAAC AAGCUGCUGCUGGUGGCCAGCGUCAUCCAGGGC CUGGGCCUGCUGCUGUGCUUCACCUACAUCUGC CUGCACUUCAGCGCCCUGCAGGUGAGCCACCGC UACCCCCGCAUCCAGAGCAUCAAGGUGCAGUUC ACAGAGUACAAGAAGGAGAAGGGCUUCAUCCUG ACCAGCCAGAAGGAGGAUGAGAUCAUGAAGGUG CAGAACAACAGCGUCAUCAUCAACUGUGAUGGC UUCUACCUGAUCAGCCUGAAGGGCUACUUCAGC CAGGAGGUGAACAUCAGCCUGCACUACCAGAAG GAUGAGGAGCCCCUCUUCCAGCUGAAGAAGGUG CGCUCUGUGAACAGCCUGAUGGUGGCCAGCCUG ACCUACAAGGACAAGGUGUACCUGAAUGUGACC ACAGACAACACCAGCCUGGAUGACUUCCACGUG AAUGGAGGAGAGCUGAUCCUGAUCCACCAGAAC CCUGGAGAGUUCUGUGUGCUG | SEQ ID NO: 190 |
| OX40L (TNFSF4) | Codon-optimized sequence 4 for ENSP 281834 | AUGGAGCGGGUGCAGCCCCUGGAGGAGAACGUG GGCAACGCCGCCCGCCCGCGUUUUGAGCGAAAU AAGUUACUGCUUGUUGCAUCUGUGAUACAGGGG UUGGGUUUACUUCUUUGCUUUACAUAUAUUUGU CUCCACUUUAGUGCGCUUCAGGUAUCCCAUCGG UACCCGCAUCCAGUCAAUCAAGGUCCAGUUC ACUGAAUAUAAAAAGGAGAAAGGAUUCAUUCUG ACUUCACAAAAAGAGGACGAAAUCAUGAAAGUG CAGAACAACUCUGUAAUUAUAAACUGCGAUGGG UUCUAUCUGAUCAGUCUGAAGGGAUAUUUUAGC CAGGAAGUAAAUAUUUCACUACAUUAUCAGAAG GACGAAGAACCACUUUUUCAACUGAAGAAAGUC CGGUCCGUGAACUCCCUGAUGGUUGCUAGCCUU ACCUACAAGGAUAAAGUCUAUUUAAACGUCACA ACAGAUAACACUAGCCUCGACGAUUUCCAUGUG AACGGAGGUGAACUGAUAUUGAUCCAUCAAAAC CCCGGCGAGUUCUGCGUUUUA | SEQ ID NO: 191 |
| OX40L (TNFSF4) | Codon-optimized sequence 5 for ENSP 281834 | AUGGAGCGGGUCCAGCCCCUCGAGGAGAACGUU GGUAAUGCCGCACGUCCCAGGUUUGAACGCAAC AAGCUGCUGUUGGUGGCCAGCGUCAUUCAGGGG CUGGGUUUGUUGCUGUGCUUCACUUACAUCUGU CUGCAUUUUAGUGCACUCCAGGUGUCCCACCGC UACCCCCGUAUCCAAUCCAUUAAAGUCCAAUUU ACCGAAUACAAAAAAGAGAAGGGUUUCAUUCUU ACCUCCCAGAAGGAGGAUGAAAUUAUGAAGGUG CAGAACAAUUCUGUUAUCAUCAACUGUGACGGA UUCUAUCUGAUUUCACUGAAGGGAUACUUUUCC CAGGAGGUGAACAUCAGCCUGCAUUAUCAGAAG GACGAAGAACCGCUUUUUCAACUGAAGAAGGUU AGGAGUGUGAACUCCUUAAUGGUAGCCAGCCUG ACAUAUAAGGACAAGGUAUAUCUGAACGUCACC ACUGAUAACACCUCUUUAGACGAUUUUCAUGUA AAUGGGGGAGAAUUGAUACUCAUUCACCAGAA UCCGGGUGAGUUUUGUGUUCUG | SEQ ID NO: 192 |
| OX40L (TNFSF4) | Codon-optimized sequence 1 for ENSP 356691 | AUGGUGAGCCACAGAUACCCCAGAAUCCAGAGCA UCAAGGUGCAGUUCACCGAGUACAAGAAGGAGAA GGGCUUCAUCCUGACCAGCCAGAAGGAGGACGAG AUCAUGAAGGUGCAGAACAACAGCGUGAUCAUCA ACUGCGACGGCUUCUACCUGAUCAGCCUGAAGGG CUACUUCAGCCAGGAGGUGAACAUCAGCCUGCAC UACCAGAAGGACGAGGAGCCCCUGUUCCAGCUGA AGAAGGUGAGAAGCGUGAACAGCCUGAUGGUGGC CAGCCUGACCUACAAGGACAAGGUGUACCUGAAC GUGACCACCGACAACACCAGCCUGGACGACUUCC ACGUGAACGGCGGCGAGCUGAUCCUGAUCCACCA GAACCCCGGCGAGUUCUGCGUGCUG | SEQ ID NO: 193 |
| OX40L (TNFSF4) | Codon-optimized sequence 2 for ENSP 356691 | AUGGUUUCUCACCGUUACCCACGGAUCCAGUCUA UCAAGGUUCAGUUUACCGAGUACAAAAAGGAAAA AGGGUUCAUCCUCACCUCUCAGAAAGAGGACGAA AUCAUGAAGGUGCAGAAUAACUCUGUAAUCAUUA AUUGCGACGGUUUUUAUCUGAUUUCACUGAAGGG CUACUUUAGUCAGGAAGUUAAUAUUAGUUUGCAC UACCAAAAGGACGAGGAGCCUCUCUUCCAACUAA | SEQ ID NO: 194 |

TABLE 1-continued

OX40L Polypeptide and Polynucleotide sequences

| Encoded Polypeptide | Description | Sequence | SEQ ID NO: |
|---|---|---|---|
| | | AAAAGGUAAGAUCCGUUAAUUCCCUUAUGGUGGC<br>CUCCUUAACUUAUAAGGACAAGGUGUAUCUGAAU<br>GUGACCACAGAUAACACAUCCCUGGACGACUUUC<br>AUGUAAAUGGCGGCGAGUUAAUUCUGAUACACCA<br>GAACCCUGGCGAGUUCUGCGUGCUG | |
| OX40L (TNFSF4) | Codon-optimized sequence 3 for ENSP 356691 | AUGGUGAGCCACCGCUACCCCGCAUCCAGAGCA<br>UCAAGGUGCAGUUCACAGAGUACAAGAAGGAGAA<br>GGGCUUCAUCCUGACCAGCCAGAAGGAGGAUGAG<br>AUCAUGAAGGUGCAGAACAACAGCGUCAUCAUCA<br>ACUGUGAUGGCUUCUACCUGAUCAGCCUGAAGGG<br>CUACUUCAGCCAGGAGGUGAACAUCAGCCUGCAC<br>UACCAGAAGGAUGAGGAGCCCCUCUUCCAGCUGA<br>AGAAGGUGCGCUCUGUGAACAGCCUGAUGGUGGC<br>CAGCCUGACCUACAAGGACAAGGUGUACCUGAAU<br>GUGACCACAGACAACACCAGCCUGGAUGACUUCC<br>ACGUGAAUGGAGGAGAGCUGAUCCUGAUCCACCA<br>GAACCCUGGAGAGUUCUGUGUGCUG | SEQ ID NO: 195 |
| OX40L (TNFSF4) | Codon-optimized sequence 4 for ENSP 356691 | AUGGUGAGCCACCGGUACCCCGGAUCCAGAGCA<br>UCAAGGUGCAGUUCACCGAAUACAAGAAGGAGAA<br>GGGUUUUAUCCUGACGAGCCAGAAGGAAGACGAG<br>AUUAUGAAGGUCCAAAACAACUCAGUCAUCAUAA<br>ACUGCGAUGGAUUUUACCUGAUCUCUCUGAAAGG<br>GUACUUCUCCCAGGAAGUGAAUAUUAGCUUGCAC<br>UAUCAAAAAGAUGAGGAGCCUCUAUUCCAGCUCA<br>AGAAGGUCAGAAGCGUCAAUAGUCUGAUGGUCGC<br>AUCAUUAACCUAUAAAGACAAAGUAUAUCUAAAU<br>GUGACGACAGACAAUACAUCCCUCGAUGAUUUUC<br>ACGUCAACGGAGGCGAACUCAUUCUGAUCCACCA<br>GAAUCCAGGGGAAUUUUGCGUGCUG | SEQ ID NO: 196 |
| OX40L (TNFSF4) | Codon-optimized sequence 5 for ENSP 356691 | AUGGUCUCACACCGGUACCCCCGUAUCCAGAGUA<br>UUAAGGUGCAAUUCACGGAGUAUAAAAAAGAAAA<br>GGGAUUCAUUCUGACGUCUCAGAAGGAAGAUGAG<br>AUCAUGAAGGUCCAGAACAAUUCUGUGAUCAUUA<br>AUUGCGAUGGAUUUUAUCUGAUUUCACUUAAAGG<br>AUAUUUUUCCCAGGAGGUUAAUAUCAGUUUGCAC<br>UAUCAGAAAGACGAGGAGCCAUUAUUCCAGCUGA<br>AGAAGGUGAGAUCAGUGAAUAGCCUGAUGGUUGC<br>GUCACUGACGUAUAAAGACAAAGUUUAUCUAAAC<br>GUUACCACUGAUAAUUACAUCCCUUGAUGAUUUUC<br>AUGUGAACGGGGGUGAACUGAUCCUUAUACACCA<br>GAACCCCGGAGAGUUCUGUGUGUUG | SEQ ID NO: 197 |
| OX40L (TNFSF4) | Codon-optimized sequence 1 for ENSP 439704 | AUGGUGAGCCACAGAUACCCCAGAAUCCAGAGCAU<br>CAAGGUGCAGUUCACCGAGUACAAGAAGGAGAAG<br>GGCUUCAUCCUGACCAGCCAGAAGGAGGACGAGA<br>UCAUGAAGGUGCAGAACAACAGCGUGAUCAUCAA<br>CUGCGACGGCUUCUACCUGAUCAGCCUGAAGGGC<br>UACUUCAGCCAGGAGGUGAACAUCAGCCUGCACU<br>ACCAGAAGGACGAGGAGCCCCUGUUCCAGCUGAA<br>GAAGGUGAGAAGCGUGAACAGCCUGAUGGUGGCC<br>AGCCUGACCUACAAGGACAAGGUGUACCUGAACG<br>UGACCACCGACAACACCAGCCUGGACGACUUCCA<br>CGUGAACGGCGGCGAGCUGAUCCUGAUCCACCAG<br>AACCCCGGCGAGUUCUGCGUGCUG | SEQ ID NO: 198 |
| OX40L (TNFSF4) | Codon-optimized sequence 2 for ENSP 439704 | AUGGUGUCACACCGGUACCCUCGGAUCCAGUCUA<br>UUAAAGUUCAAUUUACGGAGUACAAGAAAGAAAA<br>AGGCUUUAUCCUUACAAGCCAAAAGGAAGACGAG<br>AUCAUGAAAGUGCAAAACAACAGUGUGAUUAUAA<br>AUUGUGAUGGCUUCUACCUUAUUAGUCUGAAGGG<br>CUACUUUAGUCAGGAAGUCAAUAUUAGCCUACAC<br>UACCAGAAAGACGAGGAGCCCCUCUUUCAACUGA<br>AAAAGGUGCGCUCCGUGAAUUCGUUGAUGGUCGC<br>CUCUCUGACCUACAAAGAUAAGGUGUAUCUUAAC<br>GUUACUACCGACAAUACUAGUCUGGACGACUUUC<br>ACGUCAACGGAGGCGAACUUAUUCUGAUCCACCA<br>GAACCCCGGCGAAUUCUGCGUGCUG | SEQ ID NO: 199 |
| OX40L (TNFSF4) | Codon-optimized sequence 3 for ENSP 439704 | AUGGUGAGCCACCGCUACCCCCGCAUCCAGAGCA<br>UCAAGGUGCAGUUCACAGAGUACAAGAAGGAGAA<br>GGGCUUCAUCCUGACCAGCCAGAAGGAGGAUGAG<br>AUCAUGAAGGUGCAGAACAACAGCGUCAUCAUCA | SEQ ID NO: 200 |

TABLE 1-continued

OX40L Polypeptide and Polynucleotide sequences

| Encoded Polypeptide | Description | Sequence | SEQ ID NO: |
|---|---|---|---|
| | | ACUGUGAUGGCUUCUACCUGAUCAGCCUGAAGGG CUACUUCAGCCAGGAGGUGAACAUCAGCCUGCAC UACCAGAAGGAUGAGGAGCCCCUCUUCCAGCUGA AGAAGGUGCGCUCUGUGAACAGCCUGAUGGUGGC CAGCCUGACCUACAAGGACAAGGUGUACCUGAAU GUGACCACAGACAACACCAGCCUGGAUGACUUCC ACGUGAAUGGAGGAGAGCUGAUCCUGAUCCACCA GAACCCUGGAGAGUUCUGUGUGCUG | |
| OX40L (TNFSF4) | Codon-optimized sequence 4 for ENSP 439704 | AUGGUGAGCCACCGGUACCCCCGGAUCCAGAGCA UCAAGGUGCAGUUCACAGAGUACAAGAAGGAGAA GGGAUUUAUUCUCACAAGUCAGAAAGAAGAUGAG AUCAUGAAGGUUCAGAACAACUCAGUCAUUAUUA AUUGCGACGGAUUCUAUCUCAUUAGCCUCAAAGG CUAUUUCAGCCAGGAGGUCAAUAUCAGCCUGCAC UACCAGAAGGAUGAGGAACCUCUCUUUCAGCUGA AAAAAGUCCGCUCUGUGAAUUCCCUCAUGGUCGC UUCCCUGACCUACAAGGAUAAAGUUUAUUUGAAC GUUACAACAGAUAAUACAUCGCUGGACGACUUCC AUGUGAAUGGUGGCGAACUAAUUCUAAUACACCA AAAUCCAGGCGAAUUUUGUGUCCUU | SEQ ID NO: 201 |
| OX40L (TNFSF4) | Codon-optimized sequence 5 for ENSP 439704 | AUGGUAUCCCAUAGAUACCCACGUAUUCAAAGCA UUAAGGUGCAGUUCACAGAGUACAAAAAGGAGAA GGGUUUCAUACUGACGUCACAGAAGGAGGACGAG AUAAUGAAGGUGCAGAAUAAUAGUGUGAUCAUCA AUUGUGAUGGAUUCUAUUUGAUCAGCCUCAAAGG UUAUUUCUCACAGGAAGUCAACAUUUCCCUGCAC UACCAGAAGGACGAAGAGCCUUUGUUUCAGCUGA AGAAGGUGCGCUCAGUGAACAGUUUGAUGGUAGC CUCCCUAACUUAUAAAGAUAAAGUUUAUCUGAAC GUGACAACCGAUAACACAUCCCUGGACGACUUUC ACGUCAAUGGAGGUGAGUUAAUCCUGAUCCAUCA GAAUCCCGGAGAAUUCUGCGUUCUU | SEQ ID NO: 202 |

3. Interleukin-12 (IL12)

IL12 (also shown as IL-12) is a pleiotropic cytokine, the actions of which create an interconnection between innate and adaptive immunity. IL12 functions primarily as a 70 kDa heterodimeric protein consisting of two disulfide-linked p35 and p40 subunits. The precursor form of the IL12 p40 subunit (NM_002187; P29460; also referred to as IL12B, natural killer cell stimulatory factor 2, cytotoxic lymphocyte maturation factor 2) is 328 amino acids in length, while its mature form is 306 amino acids long. The precursor form of the IL12 p35 subunit (NM_000882; P29459; also referred to as IL12A, natural killer cell stimulatory factor 1, cytotoxic lymphocyte maturation factor 1) is 219 amino acids in length and the mature form is 197 amino acids long. Id. The genes for the IL12 p35 and p40 subunits reside on different chromosomes and are regulated independently of each other. Gately, M K et al., *Annu Rev Immunol.* 16: 495-521 (1998). Many different immune cells (e.g., dendritic cells, macrophages, monocytes, neutrophils, and B cells) produce IL12 upon antigenic stimuli. The active IL12 heterodimer is formed following protein synthesis. Id.

IL12 is composed of a bundle of four alpha helices. It is a heterodimeric cytokine encoded by two separate genes, IL12A (p35) and IL12B (p40). The active heterodimer (referred to as 'p70'), and a homodimer of p40 are formed following protein synthesis.

Therefore, in some embodiments, the IL12 polypeptide of the present disclosure comprises a single polypeptide chain comprising the IL12B and IL12A fused directly or by a linker. In other embodiments, the IL12 polypeptide of the present disclosure comprises two polypeptides, the first polypeptide comprising IL12B and the second polypeptide comprising IL12A. In certain aspects, the disclosure provides an IL12A polypeptide and an IL12B polypeptide, wherein the IL12A and IL12B polypeptides are on the same chain or different chains. In some embodiments, the IL12A or IL12B polypeptide of the disclosure is a variant, a peptide or a polypeptide containing a substitution, and insertion and/or an addition, a deletion and/or a covalent modification with respect to a wild-type IL12A or IL12B sequence. In some embodiments, sequence tags (such as epitope tags, e.g., a V5 tag) or amino acids, can be added to the sequences encoded by the polynucleotides of the disclosure (e.g., at the N-terminal or C-terminal ends), e.g., for localization. In some embodiments, amino acid residues located at the carboxy, amino terminal, or internal regions of a polypeptide of the disclosure can optionally be deleted providing for fragments.

In some embodiments, the IL12A and/or IL12B polypeptide encoded by a polynucleotide of the disclosure (e.g., a RNA, e.g., an mRNA) comprises a substitutional variant of an IL12A and/or IL12B sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

In other embodiments, the IL12A and/or IL12B polypeptide encoded the polynucleotide (e.g., a RNA, e.g., an mRNA) comprises a linker fusing the IL12A and IL12B polypeptides. Non-limiting examples of linkers are disclosed elsewhere herein.

Some aspects of the present disclosure are directed to a lipid nanoparticle comprising a polynucleotide (e.g., mRNA) encoding a human IL12 polypeptide, wherein the polynucleotide comprises an ORF encoding a human IL12B polypeptide operably linked to a human IL12A polypeptide. In some embodiments, the IL12B polypeptide is operably linked to the IL12A polypeptide by a peptide linker. In some embodiments, the IL12B polypeptide is located at the 5' terminus of the IL12A polypeptide or the peptide linker. In other embodiments, the IL12A polypeptide is located at the 5' terminus of the IL12B polypeptide or the peptide linker.

As recognized by those skilled in the art, IL12 protein fragments, functional protein domains, variants, and homologous proteins (orthologs) are also considered to be within the scope of the IL12 polypeptides of the disclosure. Nonlimiting examples of polypeptides encoded by the polynucleotides of the disclosure are shown in FIGS. 1 to 2. For example, Table 2 shows the correlating amino acid numbering in SEQ ID NOs, nucleotide numbering in SEQ ID NOs, and the 5' UTR, IL12B signal peptide, mature IL12A and IL12B peptides, and linker.

TABLE 2

Domains of IL12.

| | Amino acids | Nucleotides |
|---|---|---|
| Signal Peptide IL12B | 1-22 of SEQ ID NO: 48 | 1-66 of SEQ ID NOs: 5-44 |
| Mature IL12B | 23-328 of SEQ ID NO: 48 | 67-984 of SEQ ID NOs: 5-44 |
| Linker | 329-335 of SEQ ID NO: 48 | 985-1005 of SEQ ID NOs: 5-44 |
| Mature IL12A | 336-532 of SEQ ID NO: 48 | 1006-1596 of SEQ ID NOs: 5-44 |

4. Polynucleotides and Open Reading Frames (ORFS)

In certain aspects, the disclosure provides polynucleotides (e.g., a RNA, e.g., an mRNA) that comprise a nucleotide sequence (e.g., an ORF, e.g., mRNA) encoding one or more IL12 polypeptides. In certain embodiments, the polynucleotides encode an IL-12 polypeptide, wherein the polynucleotides comprise a single ORF encoding an IL12B polypeptide and an IL12A polypeptide. In some embodiments, the polynucleotide (e.g., a RNA, e.g., an mRNA) of the disclosure encodes a single IL12 polypeptide chain comprising an IL12B polypeptide and an IL12A polypeptide, which are fused directly or by a linker, wherein the IL12B polypeptide is selected from the group consisting of:
(i) the full-length IL12B polypeptide (e.g., having the same or essentially the same length as wild-type IL12B);
(ii) a functional fragment of the full-length IL12B polypeptide (e.g., a truncated (e.g., deletion of carboxy, amino terminal, or internal regions) sequence shorter than an IL12B wild-type; but still retaining IL12B enzymatic activity);
(iii) a variant thereof (e.g., full length or truncated IL12B proteins in which one or more amino acids have been replaced, e.g., variants that retain all or most of the IL12B activity of the polypeptide with respect to the wild type IL12B polypeptide (such as, e.g., V33I, V298F, or any other natural or artificial variants known in the art); and
(iv) a fusion protein comprising (i) a full length IL12B wild-type, a functional fragment or a variant thereof, and (ii) a heterologous protein; and/or
wherein the IL12A polypeptide is selected from the group consisting of:
(v) the full-length IL12A polypeptide (e.g., having the same or essentially the same length as wild-type IL12A);
(vi) a functional fragment of the full-length IL12A polypeptide (e.g., a truncated (e.g., deletion of carboxy, amino terminal, or internal regions) sequence shorter than an IL12A wild-type; but still retaining IL12A enzymatic activity);
(vii) a variant thereof (e.g., full length or truncated IL12A proteins in which one or more amino acids have been replaced, e.g., variants that retain all or most of the IL12A activity of the polypeptide with respect to the wtIL12A polypeptide (such as natural or artificial variants known in the art); and
(viii) a fusion protein comprising (i) a full length IL12A wild-type, a functional fragment or a variant thereof, and (ii) a heterologous protein.

In other embodiments, the polynucleotide (e.g., a RNA, e.g., an mRNA) of the disclosure encodes two polypeptide chains, the first chain comprising an IL12B polypeptide and the second chain comprising an IL12A polypeptide, wherein the IL12B polypeptide is selected from the group consisting of:
(i) the mature IL12B polypeptide (e.g., having the same or essentially the same length as wild-type IL12B) with or without a signal peptide;
(ii) a functional fragment of any of the mature IL12B polypeptide (e.g., a truncated (e.g., deletion of carboxy, amino terminal, or internal regions) sequence shorter than an IL12B wild-type; but still retaining IL12B enzymatic activity);
(iii) a variant thereof (e.g., full length, mature, or truncated IL12B proteins in which one or more amino acids have been replaced, e.g., variants that retain all or most of the IL12B activity of the polypeptide with respect to the wild type IL12B polypeptide (such as, e.g., V33I, V298F, or any other natural or artificial variants known in the art); and
(iv) a fusion protein comprising (i) a mature IL12B wild-type, a functional fragment or a variant thereof, with or without a signal peptide and (ii) a heterologous protein; and/or
wherein the IL12A is selected from the group consisting of:
(v) the mature IL12A polypeptide (e.g., having the same or essentially the same length as wild-type IL12A) with or without a signal peptide;
(vi) a functional fragment of any of the wild-type IL12A polypeptide (e.g., a truncated (e.g., deletion of carboxy, amino terminal, or internal regions) sequence shorter than an IL12A wild-type; but still retaining IL12A enzymatic activity);
(vii) a variant thereof (e.g., full length, mature, or truncated IL12A proteins in which one or more amino acids have been replaced, e.g., variants that retain all or most of the IL12A activity of the polypeptide with respect to a reference isoform (such as natural or artificial variants known in the art); and (viii) a fusion protein comprising (i) a mature IL12A wild-type, a functional fragment or a variant thereof, with or without a signal peptide and (ii) a heterologous protein.

In certain embodiments, the polynucleotide (e.g., a RNA, e.g., an mRNA) of the disclosure encodes a mammalian IL12 polypeptide, such as a human IL12 polypeptide, a functional fragment or a variant thereof.

In some embodiments, the polynucleotide (e.g., a RNA, e.g., an mRNA) of the disclosure increases IL12B and/or IL12A protein expression levels and/or detectable IL12 enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to IL12B and/or IL12A protein expression levels and/or detectable IL12 enzymatic activity levels in the cells prior to the administration of the polynucleotide of the disclosure. IL12B and/or IL12A protein expression levels and/or IL12 enzymatic activity can be measured according to methods known in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the disclosure comprise a nucleotide sequence (e.g., an ORF) that encodes a wild-type human IL12B and/or IL12A, (see FIG. 1).

In some embodiments, the polynucleotide (e.g., a RNA, e.g., an mRNA) of the disclosure comprises a codon optimized nucleic acid sequence, wherein the open reading frame (ORF) of the codon optimized nucleic sequence is derived from a wild-type IL12A and/or IL12B sequence.

In some embodiments, the polynucleotides (e.g., a RNA, e.g., an mRNA) of the disclosure comprise a nucleotide sequence encoding IL12B and/or IL12A having the full length sequence of human IL12B and/or IL12A (i.e., including the initiator methionine and the signal peptides). In mature human IL12B and/or IL12A, the initiator methionine and/or signal peptides can be removed to yield a "mature IL12B" and/or "mature IL12A" comprising amino acid residues of SEQ ID NO: 1 and SEQ ID NO: 3, respectively. SEQ ID NO: 1 corresponds to amino acids 23 to 328 of SEQ ID NO: 48, and SEQ ID NO: 3 corresponds to amino acids 336 to 532 of SEQ ID NO: 48, respectively. The teachings of the present disclosure directed to the full sequence of human IL12B and/or IL12A are also applicable to the mature form of human IL12B and/or IL12A lacking the initiator methionine and/or the signal peptide. Thus, in some embodiments, the polynucleotides (e.g., a RNA, e.g., an mRNA) of the disclosure comprise a nucleotide sequence encoding IL12B and/or IL12A having the mature sequence of human IL12B and/or IL12A. In some embodiments, the polynucleotide (e.g., a RNA, e.g., an mRNA) of the disclosure comprising a nucleotide sequence encoding IL12B and/or IL12A is sequence optimized.

In some embodiments, the polynucleotides (e.g., a RNA, e.g., an mRNA) of the disclosure comprise a nucleotide sequence (e.g., an ORF) encoding a mutant IL12B and/or IL12A polypeptide. In some embodiments, the polynucleotides of the disclosure comprise an ORF encoding an IL12B and/or IL12A polypeptide that comprises at least one point mutation, at least two point mutations, at least three mutations, at least four mutations, at least five mutations, at least six mutations, at least seven mutations, at least eight mutations, at least nine mutations, or at least ten mutations in the IL12B and/or IL12A sequence and retains IL12B and/or IL12A enzymatic activity. In some embodiments, the mutant IL12B and/or IL12A polypeptide has an IL12B and/or IL12A activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the IL12B and/or IL12A activity of the corresponding wild-type IL12B and/or IL12A (i.e., the same IL12B and/or IL12A but without the mutation(s)). In some embodiments, the polynucleotide (e.g., a RNA, e.g., an mRNA) of the disclosure comprising an ORF encoding a mutant IL12B and/or IL12A polypeptide is sequence optimized.

In some embodiments, the polynucleotide (e.g., a RNA, e.g., an mRNA) of the disclosure comprises a nucleotide sequence (e.g., an ORF) that encodes an IL12B and/or IL12A polypeptide with mutations that do not alter IL12B and/or IL12A enzymatic activity. Such mutant IL12B and/or IL12A polypeptides can be referred to as function-neutral. In some embodiments, the polynucleotide comprises an ORF that encodes a mutant IL12B and/or IL12A polypeptide comprising one or more function-neutral point mutations.

In some embodiments, the mutant IL12B and/or IL12A polypeptide has higher IL12B and/or IL12A enzymatic activity than the corresponding wild-type IL12B and/or IL12A. In some embodiments, the mutant IL12B and/or IL12A polypeptide has an IL12B and/or IL12A activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type IL12B and/or IL12A (i.e., the same IL12B and/or IL12A but without the mutation(s)).

In some embodiments, the polynucleotides (e.g., a RNA, e.g., an mRNA) of the disclosure comprise a nucleotide sequence (e.g., an ORF) encoding a functional IL12B and/or IL12A fragment, e.g., where one or more fragments correspond to a polypeptide subsequence of a wild type IL12B and/or IL12A polypeptide and retain IL12B and/or IL12A enzymatic activity. In some embodiments, the IL12B and/or IL12A fragment has an IL12B and/or IL12A activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the IL12 activity of the corresponding full length IL12B and/or IL12A. In some embodiments, the polynucleotide (e.g., a RNA, e.g., an mRNA) of the disclosure comprising an ORF encoding a functional IL12B and/or IL12A fragment is sequence optimized.

In some embodiments, the polynucleotide (e.g., a RNA, e.g., an mRNA) of the disclosure comprises a nucleotide sequence (e.g., an ORF) encoding an IL12B and/or IL12A fragment that has higher IL12B and/or IL12A enzymatic activity than the corresponding full length IL12B and/or IL12A. Thus, in some embodiments the IL12B and/or IL12A fragment has an IL12B and/or IL12A activity which is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% higher than the IL12B and/or IL12A activity of the corresponding full length IL12B and/or IL12A.

In some embodiments, the polynucleotide (e.g., a RNA, e.g., an mRNA) of the disclosure comprises a nucleotide sequence (e.g., an ORF) encoding an IL12B and/or IL12A fragment that is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type IL12B and/or IL12A.

In other embodiments, the polynucleotide (e.g., a RNA, e.g., an mRNA) of the disclosure comprises a nucleotide sequence (e.g., an ORF) encoding an IL12B polypeptide, which has:

(i) at least about 83%, 84%, 85%, 86%, 87%, 88%, 89%, 90%, 91%, 92%, 93%, 94%, 95%, 96%, 97%, 98%, 99%, or 100% sequence identity to nucleotides 67-984 of hIL12AB_007, hIL12AB_010, or hIL12AB_012;
(ii) at least about 84%, 85%, 86%, 87%, 88%, 89%, 90%, 91%, 92%, 93%, 94%, 95%, 96%, 97%, 98%, 99%, or 100% sequence identity to nucleotides 67-984 of hIL12AB_018 or hIL12AB_019;
(iii) at least about 86%, 87%, 88%, 89%, 90%, 91%, 92%, 93%, 94%, 95%, 96%, 97%, 98%, 99%, or 100% sequence identity to nucleotides 67-984 of hIL12AB_008;
(iv) at least about 87%, 88%, 89%, 90%, 91%, 92%, 93%, 94%, 95%, 96%, 97%, 98%, 99%, or 100% sequence identity to nucleotides 67-984 of hIL12AB_005, hIL12AB_013, or hIL12AB_017 or nucleotides 70-987 of hIL12AB_004;
(v) at least about 88%, 89%, 90%, 91%, 92%, 93%, 94%, 95%, 96%, 97%, 98%, 99%, or 100% sequence identity to nucleotides 67-984 of hIL12AB_001 or hIL12AB_009;
(vi) at least about 85%, 86%, 87%, 88%, 89%, 90%, 91%, 92%, 93%, 94%, 95%, 96%, 97%, 98%, 99%, or 100% sequence identity to nucleotides 67-984 of hIL12AB_012 or hIL12AB_005;
(vii) at least about 89%, 90%, 91%, 92%, 93%, 94%, 95%, 96%, 97%, 98%, 99%, or 100% sequence identity to nucleotides 67-984 of hIL12AB_022 or hIL12AB_038;
(viii) at least about 90%, 91%, 92%, 93%, 94%, 95%, 96%, 97%, 98%, 99%, or 100% sequence identity to nucleotides 67-984 of hIL12AB_024, hIL12AB_031, hIL12AB_032, or hIL12AB_036;
(ix) at least about 91%, 92%, 93%, 94%, 95%, 96%, 97%, 98%, 99%, or 100% sequence identity to nucleotides 67-984 of hIL12AB_021, hIL12AB_023, hIL12AB_025, hIL12AB_026, hIL12AB_027, hIL12AB_029, hIL12AB_030, hIL12AB_034, hIL12AB_039, or hIL12AB_040;
(x) at least about 92%, 93%, 94%, 95%, 96%, 97%, 98%, 99%, or 100% sequence identity to nucleotides 67-984 of hIL12AB_016, hIL12AB_035, or hIL12AB_037;
(xi) at least about 93%, 94%, 95%, 96%, 97%, 98%, 99%, or 100% sequence identity to nucleotides 67-984 of hIL12AB_011, hIL12AB_028, or hIL12AB_033;
(xii) at least about 94%, 95%, 96%, 97%, 98%, 99%, or 100% sequence identity to nucleotides 67-984 of hIL12AB_015;
(xiii) at least about 95%, 96%, 97%, 98%, 99%, or 100% sequence identity to nucleotides 67-984 of hIL12AB_020; or
(xiv) 100% sequence identity to nucleotides 67-984 of hIL12AB_006.

In other embodiments, the polynucleotide (e.g., a RNA, e.g., an mRNA) of the disclosure comprises a nucleotide sequence (e.g., an ORF) encoding an IL12A polypeptide, which has:

(i) at least about 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_010;
(ii) at least about 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_019;
(iii) at least about 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_013;
(iv) at least about 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_007 or hIL12AB_014;
(v) at least about 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_002, hIL12AB_008;
(vi) at least about 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_012 or hIL12AB_005;
(vii) at least about 86%, 87%, 88%, 89%, 90%, 91%, 92%, 93%, 94%, 95%, 96%, 97%, 98%, 99%, or 100% sequence identity to nucleotides 1006-1596 of hIL12AB_001, or hIL12AB_009 or nucleotides 1009-1589 of hIL12AB_004;
(viii) at least about 88%, 89%, 90%, 91%, 92%, 93%, 94%, 95%, 96%, 97%, 98%, 99%, or 100% sequence identity to nucleotides 1006-1596 of hIL12AB_17;
(ix) at least about 89%, 90%, 91%, 92%, 93%, 94%, 95%, 96%, 97%, 98%, 99%, or 100% sequence identity to nucleotides 1006-1596 of hIL12AB_029 or hIL12AB_027;
(x) at least about 90%, 91%, 92%, 93%, 94%, 95%, 96%, 97%, 98%, 99%, or 100% sequence identity to nucleotides 1006-1596 of hIL12AB_039 or hIL12AB_040;
(xi) at least about 91%, 92%, 93%, 94%, 95%, 96%, 97%, 98%, 99%, or 100% sequence identity to nucleotides 1006-1596 of hIL12AB_036, hIL12AB_034, hIL12AB_016, hIL12AB_023, hIL12AB_030, hIL12AB_031, hIL12AB_025, or hIL12AB_035;
(xii) at least about 92%, 93%, 94%, 95%, 96%, 97%, 98%, 99%, or 100% sequence identity to nucleotides 1006-1596 of hIL12AB_021, hIL12AB_024, hIL12AB_032, hIL12AB_033, hIL12AB_037, or hIL12AB_022;
(xiii) at least about 93%, 94%, 95%, 96%, 97%, 98%, 99%, or 100% sequence identity to nucleotides 1006-1596 of hIL12AB_020, hIL12AB_026, or hIL12AB_038;
(xiv) at least about 94%, 95%, 96%, 97%, 98%, 99%, or 100% sequence identity to nucleotides 1006-1596 of hIL12AB_015, hIL12AB_011, or hIL12AB_028; or
(xv) about 100% sequence identity to nucleotides 1006-1596 of hIL12AB_003.

In certain embodiments, the polynucleotide (e.g., a RNA, e.g., an mRNA) of the disclosure comprises a single ORF encoding IL12B and IL12A, wherein the ORF comprises a sequence that has:

(i) at least about 83%, 84%, 85%, 86%, 87%, 88%, 89%, 90%, 91%, 92%, 93%, 94%, 95%, 96%, 97%, 98%, 99%, or 100% sequence identity to nucleotides 67-984 of hIL12AB_007, hIL12AB_010, or hIL12AB_012;
(ii) at least about 84%, 85%, 86%, 87%, 88%, 89%, 90%, 91%, 92%, 93%, 94%, 95%, 96%, 97%, 98%, 99%, or 100% sequence identity to nucleotides 67-984 of hIL12AB_018 or hIL12AB_019;
(iii) at least about 86%, 87%, 88%, 89%, 90%, 91%, 92%, 93%, 94%, 95%, 96%, 97%, 98%, 99%, or 100% sequence identity to nucleotides 67-984 of hIL12AB_008;
(iv) at least about 87%, 88%, 89%, 90%, 91%, 92%, 93%, 94%, 95%, 96%, 97%, 98%, 99%, or 100% sequence identity to nucleotides 67-984 of hIL12AB_005, hIL12AB_013, or hIL12AB_017 or nucleotides 70-987 of hIL12AB_004;
(v) at least about 88%, 89%, 90%, 91%, 92%, 93%, 94%, 95%, 96%, 97%, 98%, 99%, or 100% sequence identity to nucleotides 67-984 of hIL12AB_001 or hIL12AB_009;
(vi) at least about 85%, 86%, 87%, 88%, 89%, 90%, 91%, 92%, 93%, 94%, 95%, 96%, 97%, 98%, 99%, or 100% sequence identity to nucleotides 67-984 of hIL12AB_012 or hIL12AB_005;
(vii) at least about 89%, 90%, 91%, 92%, 93%, 94%, 95%, 96%, 97%, 98%, 99%, or 100% sequence identity to nucleotides 67-984 of hIL12AB_022 or hIL12AB_038;
(viii) at least about 90%, 91%, 92%, 93%, 94%, 95%, 96%, 97%, 98%, 99%, or 1009% sequence identity to nucleotides 67-984 of hIL12AB_024, hIL12AB_031, hIL12AB_032, or hIL12AB_036;
(ix) at least about 91%, 92%, 93%, 94%, 95%, 96%, 97%, 98%, 99%, or 100% sequence identity to nucleotides 67-984 of hIL12AB_021, hIL12AB_023, hIL12AB_025, hIL12AB_026, hIL12AB_027, hIL12AB_029, hIL12AB_030, hIL12AB_034, hIL12AB_039, or hIL12AB_040;
(x) at least about 92%, 93%, 94%, 95%, 96%, 97%, 98%, 99%, or 100% sequence identity to nucleotides 67-984 of hIL12AB_016, hIL12AB_035, or hIL12AB_037;
(xi) at least about 93%, 94%, 95%, 96%, 97%, 98%, 99%, or 100% sequence identity to nucleotides 67-984 of hIL12AB_011, hIL12AB_028, or hIL12AB_033;
(xii) at least about 94%, 95%, 96%, 97%, 98%, 99%, or 100% sequence identity to nucleotides 67-984 of hIL12AB_015;
(xiii) at least about 95%, 96%, 97%, 98%, 99%, or 100% sequence identity to nucleotides 67-984 of hIL12AB_020; or
(xiv) about 100% sequence identity to nucleotides 67-984 of hIL12AB_006; and
a sequence that has:
(i) at least about 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_010;
(ii) at least about 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_019;
(iii) at least about 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_013;
(iv) at least about 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_007 or hIL12AB_014;
(v) at least about 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_002, hIL12AB_008;
(vi) at least about 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_012 or hIL12AB_005;
(vii) at least about 86%, 87%, 88%, 89%, 90%, 91%, 92%, 93%, 94%, 95%, 96%, 97%, 98%, 99%, or 100% sequence identity to nucleotides 1006-1596 of hIL12AB_001, or hIL12AB_009 or nucleotides 1009-1599 of hIL12AB_004;
(viii) at least about 88%, 89%, 90%, 91%, 92%, 93%, 94%, 95%, 96%, 97%, 98%, 99%, or 100% sequence identity to nucleotides 1006-1596 of hIL12AB_17;
(ix) at least about 89%, 90%, 91%, 92%, 93%, 94%, 95%, 96%, 97%, 98%, 99%, or 100% sequence identity to nucleotides 1006-1596 of hIL12AB_029 or hIL12AB_027;
(x) at least about 90%, 91%, 92%, 93%, 94%, 95%, 96%, 97%, 98%, 99%, or 100% sequence identity to nucleotides 1006-1596 of hIL12AB_039 or hIL12AB_040;
(xi) at least about 91%, 92%, 93%, 94%, 95%, 96%, 97%, 98%, 99%, or 100% sequence identity to nucleotides 1006-1596 of hIL12AB_036, hIL12AB_034, hIL12AB_016, hIL12AB_023, hIL12AB_030, hIL12AB_031, hIL12AB_025, or hIL12AB_035;
(xii) at least about 92%, 93%, 94%, 95%, 96%, 97%, 98%, 99%, or 100% sequence identity to nucleotides 1006-1596 of hIL12AB_021, hIL12AB_024, hIL12AB_032, hIL12AB_033, hIL12AB_037, or hIL12AB_022;
(xiii) at least about 93%, 94%, 95%, 96%, 97%, 98%, 99%, or 100% sequence identity to nucleotides 1006-1596 of hIL12AB_020, hIL12AB_026, or hIL12AB_038;
(xiv) at least about 94%, 95%, 96%, 97%, 98%, 99%, or 100% sequence identity to nucleotides 1006-1596 of hIL12AB_015, hIL12AB_011, or hIL12AB_028; or
(xv) about 100% sequence identity to nucleotides 1006-1596 of hIL12AB_003.

In certain embodiments, the polynucleotide (e.g., a RNA, e.g., an mRNA) of the disclosure comprises a first ORF encoding IL12B and a second ORF encoding IL12A or, wherein the first ORF comprises a sequence that has:
(i) at least about 83%, 84%, 85%, 86%, 87%, 88%, 89%, 90%, 91%, 92%, 93%, 94%, 95%, 96%, 97%, 98%, 99%, or 100% sequence identity to nucleotides 67-984 of hIL12AB_007, hIL12AB_010, or hIL12AB_012;
(ii) at least about 84%, 85%, 86%, 87%, 88%, 89%, 90%, 91%, 92%, 93%, 94%, 95%, 96%, 97%, 98%, 99%, or 100% sequence identity to nucleotides 67-984 of hIL12AB_018 or hIL12AB_019;
(iii) at least about 86%, 87%, 88%, 89%, 90%, 91%, 92%, 93%, 94%, 95%, 96%, 97%, 98%, 99%, or 100% sequence identity to nucleotides 67-984 of hIL12AB_008;
(iv) at least about 87%, 88%, 89%, 90%, 91%, 92%, 93%, 94%, 95%, 96%, 97%, 98%, 99%, or 100% sequence identity to nucleotides 67-984 of hIL12AB_005, hIL12AB_013, or hIL12AB_017 or nucleotides 70-987 of hIL12AB_004;
(v) at least about 88%, 89%, 90%, 91%, 92%, 93%, 94%, 95%, 96%, 97%, 98%, 99%, or 100% sequence identity to nucleotides 67-984 of hIL12AB_001 or hIL12AB_009;
(vi) at least about 85%, 86%, 87%, 88%, 89%, 90%, 91%, 92%, 93%, 94%, 95%, 96%, 97%, 98%, 99%, or 100% sequence identity to nucleotides 67-984 of hIL12AB_012 or hIL12AB_005;
(vii) at least about 89%, 90%, 91%, 92%, 93%, 94%, 95%, 96%, 97%, 98%, 99%, or 100% sequence identity to nucleotides 67-984 of hIL12AB_022 or hIL12AB_038;

(viii) at least about 90%, 91%, 92%, 93%, 94%, 95%, 96%, 97%, 98%, 99%, or 100% sequence identity to nucleotides 67-984 of hIL12AB_024, hIL12AB_031, hIL12AB_032, or hIL12AB_036;

(ix) at least about 91%, 92%, 93%, 94%, 95%, 96%, 97%, 98%, 99%, or 100% sequence identity to nucleotides 67-984 of hIL12AB_021, hIL12AB_023, hIL12AB_025, hIL12AB_026, hIL12AB_027, hIL12AB_029, hIL12AB_030, hIL12AB_034, hIL12AB_039, or hIL12AB_040;

(x) at least about 92%, 93%, 94%, 95%, 96%, 97%, 98%, 99%, or 100% sequence identity to nucleotides 67-984 of hIL12AB_016, hIL12AB_035, or hIL12AB_037;

(xi) at least about 93%, 94%, 95%, 96%, 97%, 98%, 99%, or 100% sequence identity to nucleotides 67-984 of hIL12AB_011, hIL12AB_028, or hIL12AB_033;

(xii) at least about 94%, 95%, 96%, 97%, 98%, 99%, or 100% sequence identity to nucleotides 67-984 of hIL12AB_015;

(xiii) at least about 95%, 96%, 97%, 98%, 99%, or 100% sequence identity to nucleotides 67-984 of hIL12AB_020; or (xiv) about 100% sequence identity to nucleotides 67-984 of hIL12AB_006; and/or wherein the second ORF comprises a sequence that has:

(i) at least about 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_010;

(ii) at least about 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_019;

(iii) at least about 81%, 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_013;

(iv) at least about 82%, 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_007 or hIL12AB_014;

(v) at least about 83%, 84%, 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_002, hIL12AB_008;

(vi) at least about 85%, 86%, 87%, 88%, 89%, 90%, 91%, 92%, 93%, 94%, 95%, 96%, 97%, 98%, 99%, or 100% sequence identity to nucleotides 1006-1596 of hIL12AB_012 or hIL12AB_005;

(vii) at least about 86%, 87%, 88%, 89%, 90%, 91%, 92%, 93%, 94%, 95%, 96%, 97%, 98%, 99%, or 100% sequence identity to nucleotides 1006-1596 of hIL12AB_001, or hIL12AB_009 or nucleotides 1009-1599 of hIL12AB_004;

(viii) at least about 88%, 89%, 90%, 91%, 92%, 93%, 94%, 95%, 96%, 97%, 98%, 99%, or 100% sequence identity to nucleotides 1006-1596 of hIL12AB_17;

(ix) at least about 89%, 90%, 91%, 92%, 93%, 94%, 95%, 96%, 97%, 98%, 99%, or 100% sequence identity to nucleotides 1006-1596 of hIL12AB_029 or hIL12AB_027;

(x) at least about 90%, 91%, 92%, 93%, 94%, 95%, 96%, 97%, 98%, 99%, or 100% sequence identity to nucleotides 1006-1596 of hIL12AB_039 or hIL12AB_040;

(xi) at least about 91%, 92%, 93%, 94%, 95%, 96%, 97%, 98%, 99%, or 100% sequence identity to nucleotides 1006-1596 of hIL12AB_036, hIL12AB_034, hIL12AB_016, hIL12AB_023, hIL12AB_030, hIL12AB_031, hIL12AB_025, or hIL12AB_035;

(xii) at least about 92%, 93%, 94%, 95%, 96%, 97%, 98%, 99%, or 100% sequence identity to nucleotides 1006-1596 of hIL12AB_021, hIL12AB_024, hIL12AB_032, hIL12AB_033, hIL12AB_037, or hIL12AB_022;

(xiii) at least about 93%, 94%, 95%, 96%, 97%, 98%, 99%, or 100% sequence identity to nucleotides 1006-1596 of hIL12AB_020, hIL12AB_026, or hIL12AB_038;

(xiv) at least about 94%, 95%, 96%, 97%, 98%, 99%, or 100% sequence identity to nucleotides 1006-1596 of hIL12AB_015, hIL12AB_011, or hIL12AB_028; or (xv) about 100% sequence identity to nucleotides 1006-1596 of hIL12AB_003.

In some embodiments, the polynucleotide sequence comprises an ORF comprising the sequence set forth as hIL12AB_002 (SEQ ID NO: 6) or a nucleotide sequence at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to hIL12AB_002 (SEQ ID NO: 6).

In one embodiment, the first nucleotide sequence (e.g, first ORF) encoding the IL12B polypeptide and the second nucleotide sequence (e.g., second ORF) encoding the IL12A polypeptide are fused directly or by a linker. In another embodiment, the first nucleotide sequence (e.g, first ORF) encoding the IL12B polypeptide and the second nucleotide sequence (e.g., second ORF) encoding the IL12A polypeptide are not fused to each other.

In some embodiments, the polynucleotide (e.g., a RNA, e.g., an mRNA) of the disclosure comprises a nucleotide sequence (e.g., an ORF) encoding an IL12B-IL12A fusion polypeptide (e.g., the wild-type sequence, functional fragment, or variant thereof), wherein the nucleotide sequence has at least about 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from the group consisting of SEQ ID NOs: 5 to 44. See Table 4.

In some embodiments, the polynucleotide (e.g., a RNA, e.g., an mRNA) of the disclosure comprises a nucleotide sequence (e.g., an ORF) encoding an IL12B-IL12A fusion polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 5 to 44. See Table 4.

In some embodiments, the polynucleotide (e.g., a RNA, e.g., an mRNA) of the disclosure comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,083 to 1,200, from 1,083 to 1,400, from 1,083 to 1,600, from 1,083 to 1,800, from 1,083 to 2,000, from 1,083 to 3,000, from 1,083 to 5,000, from 1,083 to 7,000, from 1,083 to 10,000, from 1,083 to 25,000, from 1,083 to 50,000, from 1,083 to 70,000, or from 1,083 to 100,000).

In some embodiments, the polynucleotide of the disclosure (e.g., a RNA, e.g., an mRNA) comprises a nucleotide sequence (e.g., an ORF) encoding an IL12B-IL12A fusion polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,083, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the disclosure (e.g., a RNA, e.g., an mRNA) comprises a nucleotide sequence (e.g., an ORF) encoding an IL12B and/or IL12A polypeptide (e.g., the wild-type sequence, functional fragment, or variant thereof) further comprises at least one nucleic acid sequence that is noncoding, e.g., a miRNA binding site.

In some embodiments, the polynucleotide of the disclosure (e.g., a RNA, e.g., an mRNA) comprises a nucleotide sequence (e.g., an ORF) encoding an IL12B and/or IL12A polypeptide that is single stranded or double stranded.

In some embodiments, the polynucleotide of the disclosure comprising a nucleotide sequence (e.g., an ORF) encoding an IL12B and/or IL12A polypeptide (e.g., the wild-type sequence, functional fragment, or variant thereof) is DNA or RNA. In some embodiments, the polynucleotide of the disclosure is RNA. In some embodiments, the polynucleotide of the disclosure is, or functions as, a messenger RNA (mRNA). In some embodiments, the mRNA comprises a nucleotide sequence (e.g., an ORF) that encodes at least one IL12B and/or IL12A polypeptide, and is capable of being translated to produce the encoded IL12B and/or IL12A polypeptide in vitro, in vivo, in situ or ex vivo.

In some embodiments, the polynucleotide of the disclosure (e.g., a RNA, e.g., an mRNA) comprises a sequence-optimized nucleotide sequence (e.g., an ORF) encoding an IL12B and/or IL12A polypeptide (e.g., the wild-type sequence, functional fragment, or variant thereof), wherein the polynucleotide comprises at least one chemically modified nucleobase, e.g., 5-methoxyuracil. In some embodiments, the polynucleotide further comprises a miRNA binding site, e.g., a miRNA binding site that binds to miR-122. In some embodiments, the polynucleotide disclosed herein is formulated with a delivery agent, e.g., a compound having Formula (I), e.g., any of Compounds 1-147 or any of Compounds 1-232.

The polynucleotides (e.g., a RNA, e.g., an mRNA) of the disclosure can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked a nucleotide sequence that encodes an IL12B and/or IL12A polypeptide described herein.

In some embodiments, the "signal sequence" or "signal peptide" is a polynucleotide or polypeptide, respectively, which is from about 9 to 200 nucleotides (3-70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the disclosure comprises a nucleotide sequence encoding an IL12B and/or IL12A polypeptide, wherein the nucleotide sequence further comprises a 5' nucleic acid sequence encoding a native signal peptide. In another embodiment, the polynucleotide of the disclosure comprises a nucleotide sequence encoding an IL12B and/or IL12A polypeptide, wherein the nucleotide sequence lacks the nucleic acid sequence encoding a native signal peptide.

In some embodiments, the polynucleotide of the disclosure comprises a nucleotide sequence encoding an IL12B and/or IL12A polypeptide, wherein the nucleotide sequence further comprises a 5' nucleic acid sequence encoding a heterologous signal peptide.

In some embodiments, the polynucleotide further comprises a nucleic acid sequence encoding a signal peptide that is located at the 5' terminus of the first ORF.

In some embodiments, the first ORF comprises a nucleic acid sequence encoding a signal peptide.

In some embodiments, the signal peptide is a human IL12B signal peptide.

In some embodiments, the signal peptide comprises a sequence at least about 80%, at least about 90%, at least about 95%, at least 96%, at least 97%, at least 98%, at least 99%, or 100% identical to amino acids 1 to 22 of SEQ ID NO: 48.

Based on the RNA sequences provided, a person of ordinary skill in the art would understand the corresponding DNA sequence (e.g., conversion of uracil to thymine). Likewise, based on the DNA sequences provided, a person of ordinary skill in the art would understand the corresponding RNA sequence (e.g., conversion of thymine to uracil).

5. Chimeric Proteins

In some embodiments, the polynucleotide of the disclosure (e.g., a RNA, e.g., an mRNA) can comprise more than one nucleic acid sequence (e.g., more than one ORF) encoding one or more polypeptide of interest. In some embodiments, polynucleotides of the disclosure comprise a single ORF encoding an IL12B and/or IL12A polypeptide, a functional fragment, or a variant thereof. However, in some embodiments, the polynucleotide of the disclosure can comprise more than one nucleotide sequence, for example, a first nucleotide sequence encoding an IL12B polypeptide (a first polypeptide of interest), a functional fragment, or a variant thereof, a second nucleotide sequence encoding an IL12A polypeptide (a second polypeptide of interest), a functional fragment, or a variant thereof, and a third nucleotide sequence expressing a third polypeptide of interest (e.g., a polypeptide heterologous to IL12). In one embodiment, the third polypeptide of interest can be fused to the IL12B polypeptide directly or by a linker. In another embodiment, the third polypeptide of interest can be fused to the IL12A polypeptide directly or by a linker. In other embodiments, the third polypeptide of interest can be fused to both the IL12B polypeptide and the IL12A polypeptide directly or by a linker. In further embodiments, the polynucleotide of the disclosure can comprise more than three nucleotide sequences, for example, a first nucleotide sequence encoding an IL12B polypeptide (a first polypeptide of interest), a functional fragment, or a variant thereof, a second nucleotide sequence encoding an IL12A polypeptide (a second polypeptide of interest), a functional fragment, or a variant thereof, a third nucleotide sequence expressing a third polypeptide of interest, and a fourth nucleotide sequence expressing a fourth polypeptide of interest. In other embodiments, the third polypeptide of interest is fused to the IL12A polypeptide directly or by a linker, and the fourth polypeptide of interest is fused to the IL12B polypeptide directly or by a linker. In some embodiments, two or more polypeptides of interest can be genetically fused, i.e., two or more polypeptides can be encoded by the same nucleotide sequence. In some embodiments, the polynucleotide can comprise a nucleic acid sequence encoding a linker (e.g., a $G_4S$ peptide linker or another linker known in the art) between two or more polypeptides of interest.

In some embodiments, a polynucleotide of the disclosure (e.g., a RNA, e.g., an mRNA) can comprise two, three, four, or more nucleotide sequences, each expressing a polypeptide of interest.

In some embodiments, the polynucleotide of the disclosure (e.g., a RNA, e.g., an mRNA) can comprise a first nucleic acid sequence (e.g., a first ORF) encoding an IL12B polypeptide, IL12A polypeptide, or both IL12B and IL12A polypeptides and a second nucleic acid sequence (e.g., a second ORF) encoding a second polypeptide of interest.

6. Linker

In one aspect, the IL12B and/or IL12A can be fused directly or by a linker. In other embodiments, the IL12B and/or IL12A can be fused directly to by a linker to a heterologous polypeptide. The linkers suitable for fusing the IL12B to IL12A or the IL12B and/or IL12A to a heterologous polypeptide can be a polypeptide (or peptide) moiety or a non-polypeptide moiety.

Some aspects of the present disclosure are directed to a lipid nanoparticle comprising a polynucleotide encoding a human IL12 polypeptide, wherein the polynucleotide comprises an ORF encoding a human IL12B polypeptide operably linked to a human IL12A polypeptide. In some embodiments, the IL12B polypeptide is operably linked to the IL12A polypeptide by a peptide linker. In some embodiments, the IL12B polypeptide is located at the 5' terminus of the IL12A polypeptide or the peptide linker. In other embodiments, the IL12A polypeptide is located at the 5' terminus of the IL12B polypeptide or the peptide linker.

In some embodiments, the linker is a peptide linker, including from one amino acid to about 200 amino acids. In some embodiments, the linker comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 amino acids.

In some embodiments, the linker can be GS (Gly/Ser) linkers, for example, comprising $(G_nS)_m$, wherein n is an integer from 1 to 20 and m is an integer from 1 to 20. In some embodiments, the Gly/Ser linker comprises $(G_nS)_m$ (SEQ ID NO: 203), wherein n is 1, 2 3, 4, 5, 6, 7, 8, 9, 10, 15, or 20 and m is 1, 2, 3, 4, 5, 6, 7, 8, 9, 10, 15, or 20. In some embodiments, the GS linker can comprise (GGGGS)$_o$ (SEQ ID NO: 204), wherein o is an integer from 1 to 5. In some embodiments, the GS linker can comprise GGSGGGGSGG (SEQ ID NO: 205), GGSGGGGG (SEQ ID NO: 206), or GSGSGSGS (SEQ ID NO: 207). In certain embodiments, the Gly/Ser linker comprises $(G_nS)_m$, wherein n is 6 and m is 1.

In some embodiments, the linker suitable for the disclosure can be a Gly-rich linker, for example, comprising (Gly)$_p$ (SEQ ID NO: 208), wherein p is an integer from 1 to 40. In some embodiments, a Gly-rich linker can comprise GGGGG, GGGGGG, GGGGGGG or GGGGGGGG.

In some embodiments, the linker suitable for the disclosure can comprise (EAAAK)$_q$ (SEQ ID NO: 209), wherein q is an integer from 1 to 5. In one embodiment, the linker suitable for the disclosure can comprise (EAAAK)$_3$.

Further exemplary linkers include, but not limited to, GGGGSLVPRGSGGGGS (SEQ ID NO: 210), GSGSGS (SEQ ID NO: 211), GGGGSLVPRGSGGGG (SEQ ID NO: 212), GGSGGHMGSGG (SEQ ID NO: 213), GGSGGSGGSGG (SEQ ID NO: 214), GGSGG (SEQ ID NO: 215), GSGSGSGS (SEQ ID NO: 216), GGGSEGGGSEGGGSEGGG (SEQ ID NO: 217), AAGAATAA (SEQ ID NO: 218), GGSSG (SEQ ID NO: 219), GSGGGTGGGSG (SEQ ID NO: 220), GSGSGSGSGGSG (SEQ ID NO: 221), GSGGGSGSGGSGGSG (SEQ ID NO: 222), and GSGGGSGGSGSGGS (SEQ ID NO: 223).

The nucleotides encoding the linkers can be constructed to fuse the nucleotide sequences of the present disclosure. Based on the RNA sequences provided, a person of ordinary skill in the art would understand the corresponding DNA sequence (e.g., conversion of uracil to thymine). Likewise, based on the DNA sequences provided, a person of ordinary skill in the art would understand the corresponding RNA sequence (e.g., conversion of thymine to uracil).

7. Sequence Optimization of Nucleotide Sequence Encoding an IL12 Polypeptide

In some embodiments, the polynucleotide (e.g., a RNA, e.g., an mRNA) of the disclosure is sequence optimized. In some embodiments, the polynucleotide (e.g., a RNA, e.g., an mRNA) of the disclosure comprises a nucleotide sequence (e.g., an ORF) encoding an IL12B and/or IL12A polypeptide, a nucleotide sequence (e.g., an ORF) encoding another polypeptide of interest, a 5'-UTR, a 3'-UTR, a miRNA, a nucleotide sequence encoding a linker, or any combination thereof that is sequence optimized.

A sequence-optimized nucleotide sequence, e.g., an codon-optimized mRNA sequence encoding an IL12B and/or IL12A polypeptide, is a sequence comprising at least one synonymous nucleobase substitution with respect to a reference sequence (e.g., a wild type nucleotide sequence encoding an IL12B and/or IL12A polypeptide).

A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon, T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park Calif.) and/or proprietary methods.

Codon options for each amino acid are given in Table 3.

TABLE 3

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocysteine insertion element (SECTS) |
| Stop codons | Stop | TAA, TAG, TGA |

In some embodiments, a polynucleotide (e.g., a RNA, e.g., an mRNA) of the disclosure comprises a sequence-optimized nucleotide sequence (e.g., an ORF) encoding an IL12B and/or IL12A polypeptide, a functional fragment, or a variant thereof, wherein the IL12B and/or IL12A polypeptide, functional fragment, or a variant thereof encoded by the sequence-optimized nucleotide sequence has improved properties (e.g., compared to an IL12B and/or IL12A polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the disclosure comprise a nucleotide sequence (e.g., a nucleotide sequence (e.g., an ORF) encoding an IL12B and/or IL12A polypeptide, a nucleotide sequence (e.g., an ORF) encoding an additional polypeptide of interest, a 5'-UTR, a 3'-UTR, a microRNA, a nucleic acid sequence encoding a linker, or any combination thereof) that is sequence-optimized according to a method comprising:

(i) substituting at least one codon in a reference nucleotide sequence (e.g., an ORF encoding an IL12B and/or IL12A polypeptide) with an alternative codon to increase or decrease uridine content to generate a uridine-modified sequence;

(ii) substituting at least one codon in a reference nucleotide sequence (e.g., an ORF encoding an IL12B and/or IL12A polypeptide) with an alternative codon having a higher codon frequency in the synonymous codon set;

(iii) substituting at least one codon in a reference nucleotide sequence (e.g., an ORF encoding an IL12B and/or IL12A polypeptide) with an alternative codon to increase G/C content; or (iv) a combination thereof.

In some embodiments, the sequence-optimized nucleotide sequence (e.g., an ORF encoding an IL12B and/or IL12A polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the disclosure, can be encoded by or within regions of the polynucleotide and such regions can be upstream (5') to, downstream (3') to, or within the region that encodes the IL12B and/or IL12A polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that may have XbaI recognition.

In some embodiments, the polynucleotide of the disclosure comprises a 5' UTR, a 3' UTR and/or a miRNA binding site. In some embodiments, the polynucleotide comprises two or more 5' UTRs and/or 3' UTRs, which can be the same or different sequences. In some embodiments, the polynucleotide comprises two or more miRNA binding sites, which can be the same or different sequences. Any portion of the 5' UTR, 3' UTR, and/or miRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, neurospora, maize, drosophila, etc. where high copy plasmid-like or chromosome structures occur by methods described herein.

8. Sequence-Optimized Nucleotide Sequences Encoding IL12 Polypeptides

In some embodiments, the polynucleotide of the disclosure comprises a sequence-optimized nucleotide sequence encoding an IL12B and/or IL12A polypeptide disclosed herein. In some embodiments, the polynucleotide of the disclosure comprises an open reading frame (ORF) encoding an IL12B and/or IL12A polypeptide, wherein the ORF has been sequence optimized.

Exemplary sequence-optimized nucleotide sequences encoding human IL12B and/or IL12A are shown in Tables 4A-4D. In some embodiments, the sequence optimized IL12B and/or IL12A sequences in Table 4A-4D, fragments, and variants thereof are used to practice the methods disclosed herein. In some embodiments, the sequence optimized IL12B and/or IL12A sequences in Table 4A-4D, fragments and variants thereof are combined with or alternatives to the wild-type sequences disclosed in FIG. 1. Based on the RNA sequences provided, a person of ordinary skill in the art would understand the corresponding DNA sequence (e.g., conversion of uracil to thymine). Likewise, based on the DNA sequences provided, a person of ordinary skill in the art would understand the corresponding RNA sequence (e.g., conversion of thymine to uracil).

TABLE 4A

Sequence optimized Open Reading Frame sequences for human IL12

```
> hIL12AB_001 (SEQ ID NO: 5)
ATGTGTCACCAGCAGCTGGTCATTAGCTGGTTTAGCCTTGTGTTCCTGGCCTCCCCCCTTGTCGCTATTTGGGAGCTCAAGAAGGA
CGTGTACGTGGTGGAGCTGGACTGGTACCCAGACGCGCCCGGAGAGATGGTAGTTCTGACCTGTGATACCCCAGAGGAGGACGGCA
TCACCTGGACTCTGGACCAAAGCAGCGAGGTTTTGGGCTCAGGGAAAACGCTGACCATCCAGGTGAAGGAATTCGGCGACGCCGGA
CAGTACACCTGCCATAAGGGAGGAGAGGTGCTGAGCCATTCCTTTCTTCTGCTGCACAAGAAAGAGGACGGCATCTGGTCTACCGA
CATCCTGAAAGACCAGAAGGAGCCCAAGAACAAAACCTTCCTGAGGTGCGAGGCCAAGAACTACTCCGGCAGGTTCACTTGTTGGT
GGCTGACCACCATCAGTACAGACCTGACTTTTAGTGTAAAAAGCTCCAGAGGCTCGTCCGATCCCAAGGGGTGACCTGCGGCGCA
GCCACTCTGAGCGCTGAGCGCGTGCGCGGTGACAATAAAGAGTACGAGTACAGCGTTGAGTGTCAAGAAGACAGCGCTTGCCCTGC
CGCCGAGGAGAGCCTGCCTATCGAGGTGATGGTTGACGCAGTGCACAAGCTTAAGTACGAGAATTACACCAGCTCATTCTTCATTA
GAGATATAATCAAGCCTGACCCACCCAAGAACCTGCAGCTGAAGCCACTGAAAAACTCACGGCAGGTCGAAGTGAGCTGGGAGTAC
CCCGACACCTGGAGCACTCCTCATTCCTATTTCTCTCTTACATTCTGCGTCCAGGTGCAGGGCAAGAGCAAGCGGGAAAGAAGGA
TCGAGTCTTCACCGACAAAACAAGCGCGACCGTGATTTGCAGGAAGAACGCCAGCATCTCCGTCAGAGCCCAGGATAGATACTATA
GTAGCAGCTGGAGCGAGTGGGCAAGCGTGCCCTGTTCCGGCGGCGGGGGCGGGGGCAGCCGAAACTTGCCTGTCGCTACCCCGGAC
CCTGGAATGTTTCCGTGTCTGCACCACAGCCAGAACCTGCTGAGAGCCGTGTCGAATATGCTCCAGAAGGCCCGGCAGACCCTTGA
GTTCTACCCCTGTACCAGCGAAGAGATCGATCATGAGGACATCACGAAAGACAAGACTTCCACCGTCGAGGCTTGTCTCCCGCTGG
AGCTGACCAAGAACGAGAGCTGTCTGAATAGCCGGGAGACATCTTTCATCACGAATGGTAGCTGTCTGGCCAGCAGGAAAACTTCC
TTCATGATGGCTCTCTGCCTGAGCTCTATCTATGAAGATCTGAAGATGTATCAGGTGGAGTTTAAGACTATGAACGCCAAACTCCT
GATGGACCCAAAAAGGCAAATCTTTCTGGACCAGAATATGCTGGCCGTGATAGACGAGCTGATGCAGGCACTGAACTTCAACAGCG
AGACAGTGCCACAGAAATCCAGCCTGGAGGAGCCTGACTTTTACAAAACTAAGATCAAGCTGTGTATCCTGCTGCACGCCTTTAGA
ATCCGTGCCGTGACTATCGACAGGGTGATGTCATACCTCAACGCTTCA

> hIL12AB_002 (SEQ ID NO: 6)
ATGTGCCACCAGCAGCTGGTGATCAGCTGGTTCAGCCTGGTGTTCCTGGCCAGCCCCCTGGTGGCCATCTGGGAGCTGAAGAAGGA
CGTGTACGTGGTGGAGCTGGACTGGTACCCCGACGCCCCCGGCGAGATGGTGGTGCTGACCTGCGACACCCCCGAGGAGGACGGCA
TCACCTGGACCCTGGACCAGAGCAGCGAGGTGCTGGGCAGCGGCAAGACCCTGACCATCCAGGTGAAGGAGTTCGGCGACGCCGGC
CAGTACACCTGCCACAAGGGCGGCGAGGTGCTGAGCCACAGCCTGCTGCTGCTGCACAAGAAGGAGGACGGCATCTGGAGCACCGA
CATCCTGAAGGACCAGAAGGAGCCCAAGAACAAGACCTTCCTGAGATGCGAGGCCAAGAACTACAGCGGCAGATTCACCTGCTGGT
GGCTGACCACCATCAGCACCGACCTGACCTTCAGCGTGAAGAGCAGCAGAGGCAGCAGCGACCCCCAGGGCGTGACCTGCGGCGCC
GCCACCCTGAGCGCCGAGAGATGAGGGCGACAACAAGGAGTACGAGTACAGCGTGGAGTGCCAGGAGGACAGCGCCTGCCCCGC
CGCCGAGGAGAGCCTGCCCATCGAGGTGATGGTGGACGCCGTGCACAAGCTGAAGTACGAGAATACACCAGCCTTCTTCATCA
GAGACATCATCAAGCCCGACCCCCCCAAGAACCTGCAGCTGAAGCCCCTGAAGAACAGCAGACAGGTGGAGGTGAGCTGGGAGTAC
CCCGACACCTGGAGCACCCCCCACAGCTACTTCAGCCTGACCTTCTGCGTGCAGGTGCAGGGCAAGAGCAAGAGAGAAGAAGGA
CAGAGTGTTCACCGACAAGACCAGCGCCACCGTGATCTGCAGAAAGAACGCCAGCATCAGCGTGAGAGCCCAGGACAGATACTACA
GCAGCAGCTGGAGCGAGTGGGCCAGCGTGCCCTGCAGCGGCGGCGGCGGCGGCGGCAGCGAGAAACCTGCCCGTGGCCACCCCCGAC
CCCGGCATGTTCCCCTGCCTGCACCACAGCCAGAACCTGCTGAGAGCCGTGAGCAACATGCTGCAGAAGGCCAGACAGACCCTGGA
GTTCTACCCCTGCACCAGCGAGGAGATCGACCACGAGGACATCACCAAGGACAAGACCAGCACCGTGGAGGCCTGCCTGCCCCTGG
AGCTGACCAAGAACGAGAGCTGCCTGAACAGCAGAGAGACCAGCTTCATCACCAACGGCAGCTGCCTGGCCAGCAGAAAGACCAGC
TTCATGATGGCCCTGTGCCTGAGCAGCATCTACGAGGACCTGAAGATGTACCAGGTGGAGTTCAAGACCATGAACGCCAAGCTGCT
GATGGACCCCAAGAGACAGATCTTCCTGGACCAGAATATGCTGGCCGTGATCGACGAGCTGATGCAGGCCCTGAACTTCAACAGCG
AGACCGTGCCCCAGAAGAGCAGCCTGGAGGAGCCCGACTTCTACAAGACCAAGATCAAGCTGTGCATCCTGCTGCACGCCTTCAGA
ATCAGAGCCGTGACCATCGACAGAGTGATGAGCTACCTGAACGCCAGC

> hIL12AB_003 (SEQ ID NO: 7)
ATGTGTCACCAGCAGTTGGTCATCTCTTGGTTTTCCCTGGTTTTTCTGGCATCTCCCCTCGTGGCCATATGGGAACTGAAGAAAGA
TGTTTATGTCGTAGAATTGGATTGGTATCCGGATGCCCCTGGAGAAATGGTGGTCCTCACCTGTGACACCCCTGAAGAAGATGGTA
TCACCTGGACCTTGGACCAGAGCAGTGAGGTCTTAGGCTCTGGCAAAACCCTGACCATCCAAGTCAAAGAGTTTGGAGATGCTGGC
CAGTACACCTGTCACAAAGGAGGCGAGGTTCTAAGCCATTCGCTCCTGCTGCTTCACAAAAAGGAAGATGGAATTTGGTCCACTGA
```

TABLE 4A-continued

Sequence optimized Open Reading Frame sequences for human IL12

TATTTTAAAGGACCAGAAAGAACCCAAAAATAAGACCTTTCTAAGATGCGAGGCAAGAATTATTCTGGACGTTTCACCTGCTGGT
GGCTGACGACAATCAGTACTGATTTGACATTCAGTGTCAAAAGCAGCAGAGGCTCTTCTGACCCCCAAGGGGTGACGTGCGGAGCT
GCTACACTCTCTGCAGAGAGAGTCAGAGGGGACAACAAGGAGTATGAGTACTCAGTGGAGTGCCAGGAGGACAGTGCCTGCCCAGC
TGCTGAGGAGAGTCTGCCCATTGAGGTCATGGTGGATGCCGTTCACAAGCTCAAGTATGAAAACTACACCAGCAGCTTCTTCATCA
GGGACATCATCAAACCTGACCCACCCAAGAACTTGCAGCTGAAGCCATTAAAGAATTCTCGGCAGGTGGAGGTCAGCTGGGAGTAC
CCTGACACCTGGAGTACTCCACATTCCTACTTCTCCCTGACATTCTGCGTTCAGGTCCAGGGCAAGAGCAAGAGAGAAAGAAAGA
TAGAGTCTTCACGGACAAGACCTCAGCCACGGTCATCTGCCGCAAAAATGCCAGCATTAGCGTGCGGGCCCAGGACCGCTACTATA
GCTCATCTTGGAGCGAATGGGCATCTGTGCCCTGCAGTGGCGGAGGGGCGGAGGGAGCAGAAACCTCCCCGTGGCCACTCCAGAC
CCAGGAATGTTCCCATGCCTTCACCACTCCCAAAACCTGCTGAGGGCCGTCAGCAACATGCTCCAGAAGGCCAGACAAACTTTAGA
ATTTTACCCTTGCACTTCTGAAGAGATTGATCATGAAGATATCACAAAAGATAAAACCAGCACAGTGGAGGCCTGTTTACCATTGG
AATTAACCAAGAATGAGAGTTGCCTAAATTCCAGAGAGACCTCTTTCATAACTAATGGGAGTTGCCTGGCCTCCAGAAAGACCTCT
TTTATGATGGCCCTGTGCCTTAGTAGTATTTATGAAGACTTGAAGATGTACCAGGTGGAGTTCAAGACCATGAATGCAAAGCTTCT
GATGGATCCTAAGAGGCAGATCTTTTTAGATCAAACATGCTGGCAGTTATTGATGAGCTGATGCAGGCCCTGAATTTCAACAGTG
AGACTGTGCCACAAAAATCCTCCCTTGAAGAACCGGACTTCTACAAGACCAAGATCAAGCTCTGCATACTTCTTCATGCTTTCAGA
ATTCGGGCAGTGACTATTGATAGAGTGATGAGCTATCTGAATGCTTCC

> hIL12AB_004 (SEQ ID NO: 8)
ATGGGCTGCCACCAGCAGCTGGTCATCAGCTGGTTCTCCCTGGTCTTCCTGGCCAGCCCCCTGGTGGCCATCTGGGAGCTGAAGAA
AGATGTCTATGTTGTAGAGCTGGACTGGTACCCAGATGCTCCTGGAGAAATGGTGGTTCTCACCTGTGACACGCCAGAAGAAGATG
GCATCACCTGGACGCTGGACCAGAGCTCAGAAGTTCTTGGCAGTGGAAAAACGCTGACCATACAAGTAAAAGAATTTGGGGATGCT
GGCCAGTACACCTGCCACAAAGGAGGAGAAGTTCTCAGCCACAGCCTGCTGCTGCTGCACAAGAAAGAAGATGGCATCTGGAGCAC
AGACATTTTAAAAGACCAGAAGGAGCCCAAGAACAAAACCTTCCTTCGATGTGAGGCAAGAACTACAGTGGCCGCTTCACCTGCT
GGTGGCTCACCACCATCAGCACAGACCTCACCTTCTCGGTGAAGAGCAGCCGTGGCAGCTCAGACCCCCAAGGAGTCACCTGTGGG
GCGGCCACGCTGTCGGCAGAAAGAGTTCGAGGGGACAACAAGGAATATGAATACTCGGTGGAATGTCAAGAAGACTCGGCCTGCCC
GGCGGCAGAAGAAAGTCTTCCCATAGAAGTCATGGTGGATGCTGTTCACAAATTAAAATATGAAAACTACACCAGCAGCTTCTTCA
TCAGAGACATCATCAAGCCAGACCCGCCCAAGAACCTGCAGCTGAAGCCCCTGAAGAACAGCAGACAAGTGGAAGTTTCCTGGGAG
TACCCAGACACGTGGAGCACGCCGCACAGCTACTTCAGCCTCACCTTCTGTGTACAAGTACAAGGCAAGAGCAAGAGAGAAGAAGA
AGATCGTGTCTTCACAGACAAAACCTCGGCGACGGTCATCTGCAGGAAGAATGCCTCCATCGCGGTTCGAGCCCAGGACCGCTACT
ACAGCAGCAGCTGGAGTGAGTGGGCCTCGGTGCCCTGCAGTGGTGGCGGCGGCGGCGGCAGCAGAAACCTTCCTGTGGCCACGCCG
GACCCTGGCATGTTCCCGTGCCTGCACCACAGCCAAAATTTACTTCGAGCTGTTTCTAACATGCTGCAGAAAGCAAGACAAACTTT
AGAATTCTACCCCTGCACCTCAGAAGAAATAGAACCATGAAGACATCACCAAAGATAAAACCAGCACTGTAGAGGCCTGCCTGCCCC
TGGAGCTCACCAAGAATGAATCCTGCCTCAACAGCAGAGAGACCAGCTTCATCACCAATGGCAGCTGCCTGGCCAGCAGGAAAACC
AGCTTCATGATGGCGCTCTGCCTGAGCAGCATCTATGAAGATTTGAAGATGTACCAAGTAGAATTTAAAACCATGAATGCCAAGCT
GCTCATGGACCCCAAGAGACAAATATTTTTGGATCAAAACATGCTGGCTGTCATTGATGAGCTCATGCAAGCATTAAACTTCAACT
CAGAGACGGTGCCCCAGAAGAGCAGCCTGGAGGAGCCAGACTTCTACAAAACCAAGATCAAGCTCTGCATCTTATTACATGCCTTC
CGCATCCGGGCGGTCACCATTGACCGTGTCATGTCCTACTTAAATGCCAGC

> hIL12AB_005 (SEQ ID NO: 9)
ATGTGCCACCAGCAGCTGGTCATCAGCTGGTTCTCCCTGGTCTTCCTGGCCAGCCCCCTGGTGGCCATCTGGGAGCTGAAGAAAGA
TGTCTATGTTGTAGAGCTGGACTGGTACCCAGATGCTCCTGGAGAAATGGTGGTTCTCACCTGTGACACGCCAGAAGAAGATGGCA
TCACCTGGACGCTGGACCAGAGCTCAGAAGTTCTTGGCAGTGGAAAAACGCTGACCATACAAGTAAAAGAATTTGGGGATGCTGGC
CAGTACACCTGCCACAAAGGAGGAGAAGTTCTCAGCCACAGCCTGCTGCTGCTGCACAAGAAAGAAGATGGCATCTGGAGCACAGA
CATTTTAAAAGACCAGAAGGAGCCCAAGAACAAAACCTTCCTTCGATGTGAGGCAAGAACTACAGTGGCCGCTTCACCTGCTGGT
GGCTCACCACCATCAGCACAGACCTCACCTTCTCGGTGAAGAGCAGCCGTGGCAGCCCCCAAGGAGTCACCTGTGGGCG
GCCACGCTGTCGGCAGAAAGAGTTCGAGGGGACAACAAGGAATATGAATACTCGGTGGAATGTCAAGAAGACTCGGCCTGCCCGGC
GGCGAAGAAAGTCTTCCCATAGAAGTCATGGTGGATGCTGTTCACAAATTAAAATATGAAAACTACACCAGCAGCTTCTTCATCA
GAGACATCATCAAGCCAGACCCGCCCAAGAACCTGCAGCTGAAGCCCCTGAAGAACAGCAGACAAGTGGAAGTTTCCTGGGAGTAC
CCAGACACGTGGAGCACGCCGCACAGCTACTTCAGCCTCACCTTCTGTGTACAAGTACAAGGCAAGAGCAAGAGAAGAAGAAGA
TCGTGTCTTCACAGACAAAACCTCGGCGACGGTCATCTGCAGGAAGAATGCCTCCATCGCGGTTCGAGCCCAGGACCGCTACTACA
GCAGCAGCTGGAGTGAGTGGGCCTCGGTGCCCTGCAGTGGTGGCGGCGGCGGCGGCAGCAGAAACCTTCCTGTGGCCACGCCGGAC
CCTGGCATGTTCCCGTGCCTGCACCACAGCCAAAATTTACTTCGAGCTGTTTCTAACATGCTGCAGAAAGCAAGACAAACTTTAGA
ATTCTACCCCTGCACCTCAGAAGAAATAGAACCATGAAGACATCACCAAAGATAAAACCAGCACTGTAGAGGCCTGCCTGCCCCTG
GAGCTCACCAAGAATGAATCCTGCCTCAACAGCAGAGAGACCAGCTTCATCACCAATGGCAGCTGCCTGGCCAGCAGGAAAACCAGC
TTCATGATGGCGCTCTGCCTGAGCAGCATCTATGAAGATTTGAAGATGTACCAAGTAGAATTTAAAACCATGAATGCCAAGCTGCT
CATGGACCCCAAGAGACAAATATTTTTGGATCAAAACATGCTGGCTGTCATTGATGAGCTCATGCAAGCATTAAACTTCAACTCAG
AGACGGTGCCCCAGAAGAGCAGCCTGGAGGAGCCAGACTTCTACAAAACCAAGATCAAGCTCTGCATCTTATTACATGCCTTCCGC
ATCCGGGCGGTCACCATTGACCGTGTCATGTCCTACTTAAATGCCAGC

> hIL12AB_006 (SEQ ID NO: 10)
ATGTGCCACCAGCAGCTGGTGATCAGCTGGTTCAGCCTGGTGTTCCTGGCCAGCCCCCTGGTGGCCATCTGGGAGCTGAAGAAGGA
CGTGTACGTGGTGGAGCTGGACTGGTACCCCGACGCCCCCGGCGAGATGGTGGTGCTGACCTGTGACACCCCCGAGGAGGACGGCA
TCACCTGGACCCTGGACCAGAGCAGCGAGGTGCTGGGCAGCGGCAAGACCCTGACCATCCAGGTGAAGGAGTTCGGGGACGCCGGC
CAGTACACCTGCCACAAGGGCGGCGAGGTGCTGAGCCACAGCCTGCTGCTGCTGCACAAGAAGGAGGACGGCATCTGGAGCACAGA
TATCCTGAAGGACCAGAAGGAGCCCAAGAACAAGACCTTCCTGAGATGCGAGGCAAGAACTACAGCGGCAGATTCACCTGCTGGT
GGCTGACCACCATCAGCACAGACTTGACCTTCAGCGTGAAGAGCAGCAGAGGCAGCTCAGACCCCCAGGGAGTGACCTGCGGCGCC
GCCACCCTGAGCGCCGAGAGAGTGAGAGGGGACAACAAGGAGTACGAGTACAGCGTGGAGTGCCAGGAGGACAGCGCCTGCCCCGC
CGCCGAGGAGAGCCTGCCCATCGAGGTGATGGTGGACGCCGTGCACAAGCTGAAGTACGAGAACTACACCAGCAGCTTCTTCATCA
GAGACATCATCAAGCCCGACCCGCCGAAGAACCTGCAGCTGAAGCCCCTGAAGAACAGCAGACAGGTGGAGGTGAGCTGGGAGTAC
CCCGACACCTGGAGCACCCCCCACAGCTACTTCAGCCTGACCTTCTGCGTGCAGGTGCAGGGCAAGAGCAAGAGAGAGAAGAAGGA
CAGAGTGTTCACAGATAAGACCAGCGCCACCGTGATCTGCAGAAAGAACGCCAGCATCAGCGTGAGAGCCCAGGACAGATACTACA
GCAGCAGCTGGAGCGAGTGGGCCAGCGTGCCCTGCAGCGGCGGCGGCGGCGGCAGCAGAAACCTGCCCGTGGCCACCCCCGAC
CCCGGCATGTTCCCCTGCCTGCACCACAGCCAGAACCTGCTGAGAGCCGTGAGCAACATGCTGCAGAAGGCCAGACAGACCCTGGA
GTTCTACCCCTGCACCAGCGAGGAGATCGACCACGAGGACATCACCAAAGATAAGACCAGCACCGTGGAGGCCTGCCTGCCCCTGG
AGCTGACCAAGAATGAAAGTGCCTGAACAGCAGAGAGACCAGCTTCATCACCAACGGCAGCTGCCTGGCCAGCAGAAAGACCAGC
TTCATGATGGCCCTGTGCCTGAGCAGCATCTACGAGGACCTGAAGATGTACCAGGTGGAGTTCAAGACCATGAACGCCAAGCTGCT
GATGGACCCCAAGAGACAGATCTTCCTGGACCAGAACATGCTGGCCGTGATCGACGAGCTGATGCAGGCCCTGAACTTCAACAGCG
AGACCGTGCCCCAGAAGAGCAGCCTGGAGGAGCCCGACTTCTACAAGACCAAGATCAAGCTGTGCATCCTGCTGCACGCCTTCAGA
ATCAGAGCCGTGACCATCGACAGAGTGATGAGCTACCTGAACGCCAGC

TABLE 4A-continued

Sequence optimized Open Reading Frame sequences for human IL12

> hIL12AB_007 (SEQ ID NO: 11)
ATGTGCCACCAGCAGCTTGTCATCTCCTGGTTCTCTCTTGTCTTCCTTGCTTCTCCTCTTGTGGCCATCTGGGAGCTGAAGAAGGA
TGTTTATGTTGTGGAGTTGGACTGGTACCCTGATGCTCCTGGAGAAATGGTGGTTCTCACCTGTGACACTCCTGAGGAGGATGGCA
TCACCTGGACTTTGGACCAGTCTTCTGAGGTTCTTGGCAGTGGAAAAACTCTTACTATTCAGGTGAAGGAGTTTGGAGATGCTGGC
CAGTACACCTGCCACAAGGGTGGTGAAGTTCTCAGCCACAGTTTACTTCTTCTTCACAAGAAGGAGGATGGCATCTGGTCTACTGA
CATTTTAAAAGACCAGAAGGAGCCCAAGAACAAGACTTTCCTTCGTTGTGAAGCCAAGAACTACAGTGGTCGTTTCACCTGCTGGT
GGCTTACTACTATTTCTACTGACCTTACTTTCTCTGTGAAGTCTTCTCGTGGCTCTTCTGACCCTCAGGGTGTCACCTGTGGGGCT
GCTACTCTTTCTGCTGAGCGTGTGCGTGGGGACAACAAGGAGTATGAATACTCGGTGGAGTGCCAGGAGGACTCTGCCTGCCCTGC
TGCTGAGGAGTCTCTTCCTATTGAGGTGATGGTGGATGCTGTGCACAAGTTAAAATATGAAAACTACACTTCTTCTTTCTTCATTC
GTGACATTATAAAACCTGACCCTCCCAAGAACCTTCAGTTAAAACCTTTAAAAAACTCTCGTCAGGTGGAGGTGTCCTGGGAGTAC
CCTGACACGTGGTCTACTCCTCACTCCTACTTCTCTCTTACTTTCTGTGTCCAGGTGCAGGGCAAGTCCAAGCGTGAGAAGGAAGGA
CCGTGTCTTCACTGACAAGACTTCTGCTACTGTCATCTGCAGGAAGAATGCATCCATCTCTGTGCGTGCTCAGGACCGTTACTACA
GCTCTTCCTGGTCTGAGTGGGCTTCTGTGCCCTGCTCTGGCGGCGGCGGCGGCGGCAGCAGAAATCTTCCTGTGGCTACTCCTGAC
CCTGGCATGTTCCCCTGCCTTCACCACTCGCAGAACCTTCTTCGTGCTGTGAGCAACATGCTTCAGAAGGCTCGTCAGACTTTAGA
ATTCTACCCCTGCACTTCTGAGGAGATTGACCATGAAGACATCACCAAGGACAAGACTTCTACTGTGGAGGCCTGCCTTCCTTTAG
AGCTGACCAAGAATGAATCCTGCTTAAATTCTCGTGAGACTTCTTTCATCACCAATGGCAGCTGCCTTGCCTCGCGCAAGACTTCT
TTCATGATGGCTCTTTGCCTTTCTTCCATCTATGAAGACTTAAAAATGTACCAGGTGGAGTTCAAGACCATGAATGCAAAGCTTCT
CATGGACCCCAAGCGTCAGATATTTTTGGACCAGAACATGCTTGCTGTCATTGATGAGCTCATGCAGGCTTTAAACTTCAACTCTG
AGACTGTGCCTCAGAAGTCTTCTTTAGAAGAGCCTGACTTCTACAAGACCAAGATAAAACTTTGCATTCTTCTTCATGCTTTCCGC
ATCCGTGCTGTGACTATTGACCGTGTGATGTCCTACTTAAATGCTTCT

> hIL12AB_008 (SEQ ID NO: 12)
ATGTGTCATCAACAACTCGTGATTAGCTGGTTCAGTCTCGTGTTCCTGGCCTCTCCGCTGGTGGCCATCTGGGAGCTTAAGAAGGA
CGTGTACGTGGTGGAGCTCGATTGGTACCCCGATGCTCCTGGCGAGATGGTGGTGCTAACCTGCGATACCCCCGAGGAGGACGGGA
TCACTTGGACCCTGGATCAGAGTAGCGAAGTCCTGGGCTCTGGCAAGACACTCACAATCCAGGTGAAGGAATTCGGAGACGCTGGT
CAGTACACTTGCCACAAGGGGGGTGAAGTGCTGTCTCACAGCCGTCTGTTACTGCACAAGAAGGAGGATGGGATCTGGTCAACCGA
CATCCTGAAGGATCAGAAGGAGCCTAAGAACAAGACCTTTCTGAGGTGTGAAGCTAAGAACTATTCCGGAAGATTCACTTGCTGGT
GGTTGACCACAATCAGCACTGACCTGACCTTTTCCGTGAAGTCCAGCAGAGGAAGCAGCGATCCTCAGGGCGTAACGTGCGGCGCG
GCTACCCTGTCAGCTGAGCGGGTTAGAGGCGACAACAAGGAGTATGAGTACTCCGTGGAGTGTCAGGAGGACAGCGCCTGCCCCGC
AGCCGAGGAGAGTCTGCCCATCGAGGTGATGGTGGACGCTGTCCATAAGTTAAAATACGAAAATTACACAAGTTCCTTTTTCATCC
GCGATATTATCAAACCCGATCCCCCCAAGAACCTGCAGCTGAAGCCCCTGAAGAATAGCCGACAGGTGGAAGTCTCTTGGGAGTAT
CCTGACACCTGGTCCACGCCTCACAGCTACTTTAGTCTGACTTTCTGTGTCCAGGTCCAGGGCAAGAGCAAGAGAGAGAAAAAGGA
TAGAGTGTTTACTGACAAGACATCTGCTACAGTCATCTGCAGAAAGAACGCCAGTATCTCAGTGAGGGCGCAGGACAGATACTACA
GTAGTAGCTGGAGCGAATGGGCTAGCGTGCCCTGTTCAGGGGGCGGCGGAGGGGGCTCCAGGAATCTGCCCGTGGCCACCCCCGAC
CCTGGGATGTTCCCTTGCCTCCATCACTCACAGAACCTGCTCAGAGCAGTGAGCAACATGCTCCAAAAGGCCCGCCAGACCCTGGA
GTTTTACCCTTGTACTTCAGAAGAGATCGATCACGAAGACATAACAAAGGATAAAACCAGCACCGTGGAGGCCTGTCTGCCTCTAG
AACTCACAAAGAATGAAAGCTGTCTGAATTCCAGGGAAACCTCCTTCATTACTAACGGAAGCTGTCTCGCATCTCGCAAAACATCA
TTCATGATGGCCCTCTGCCTGTCTTCATCTATGAAGATCTCAAGATGTATCAGGTGGAGTTCAAAACAATGAACGCCAAGCTGCT
GATGGACCCCAAGAGACAGATCTTCCTGGACCAGAACATGCTGGCAGTGATCGATGAGCTGATGCAAGCCTTGAACTTCAACTCAG
AGACAGTGCCGCAAAAGTCCTCGTTGGAGGAACCAGATTTTTACAAAACCAAAATCAAGCTGTGTATCCTTCTTCACGCCTTTCGG
ATCAGAGCCGTGACTATCGACCGGGTGATGTCATACCTGAATGCTTCC

> hIL12AB_009 (SEQ ID NO: 13)
ATGTGCCACCAGCAGCTGGTCATCAGCTGGTTTAGCCTGGTCTTCCTGGCCAGCCCCCTGGTGGCCATCTGGGAGCTGAAGAAAGA
TGTCTATGTTGTAGAGCTGGACTGGTACCAGATGCTCCTGGAGAAATGGTGGTTCTCACCTGCGACACGCCAGAAGAAGATGGCA
TCACCTGGACGCTGGACCAGAGCAGCGAAGTACTGGGCAGTGGAAAAACGCTGACCATACAAGTAAAAGAATTTGGCGATGCTGGC
CAGTACACCTGCCACAAGGGAGGAAGTACTGAGCCACAGCCGTCTGCTGCACAAGAAGAAGGAGATGGCATCTGGTCCACCGA
CATTTTAAAAGACCAGAAGGAGCCCAAGAACAAAACCTTCCTTCGATGTGAGGCGAAGAACTACAGTGGCCGCTTCACCTGCTGGT
GGCTCACCACCATCAGCACCGACCTCACCTTCTCGGTGAAGAGCAGCCGTGGTAGCTCAGACCCCCAGGAGTCACCTGTGGGGCG
GCCACGCTGTCGGCAGAAAGAGTTCGAGGCGACAACAAGGAATATGAATACTCGGTGGAATGTCAAGAAGACTCGGCCTGCCCGGC
GGCAGAGAAAGTCTGCCCATAGAAGTCATGGTGGATGCTGTTCACAAATTAAAATATGAAAATTACACCAGCAGCTTCTTCATCA
GAGACATCATCAAGCCAGACCCCCCCAAGAACCTGCAGCTGAAGCCCCTGAAGAACAGCAGACAAGTGGAAGTTTCCTGGGAGTAC
CCAGACACGTGGAGCACGCCGCACAGCTACTTCAGCCTCACCTTCTGTGTACAAGTACAAGGCAAGAGCAAGAGAGAAGAAAAGA
TCGTGTCTTCACCGACAAAACCTCGGCGACGGTCATCTGCAGGAAGAATGCAAGCATCTCGGTTCGAGCCCAGGACCGCTACTACA
GCAGCAGCTGGAGTGAGTGGGCCTCGGTGCCTTGCAGTGGTGGCGGCGGCGGCGGCAGCAGAAACCTTCCTGTGGCCACGCCGGAC
CCTGGCATGTTCCGTGCCTGCACACAGCCAAAATTTATTACGAGCTGTTAGCAACATGCTCAGAAAGCAAGACAAACTTTAGA
ATTCTACCCCTGCACCTCAGAAGAAATAGACCATGAAGACATCACCAAAGATAAACCAGCACTGTAGAGGCCTGCCTGCCCCTGG
AGCTCACCAAGAACGAGAGCTGCCTCAATAGCAGAGAGACCAGCTTCATCACCAATGGCAGCTGCCTGGCCAGCAGGAAAACCAGC
TTCATGATGGCGCTCTGCCTGAGCAGCATCTATGAAGATCTGAAGATGTACCAAGTAGAATTTAAAACCATGAATGCCAAGCTGCT
CATGGACCCCAAGAGACAAATATTCCTCGACCAAAACATGCTGGCTGTCATTGATGAGCTCATGCAAGCATTAAACTTCAACTCAG
AGACGGTGCCCCAGAAGAGCAGCCTGGAGGAGCCAGACTTCTACAAAACCAAGATCAAGCTCTGCATCTTATTACATGCCTTCCGC
ATCCGGGCGGTCACCATTGACCGTGTCATGTCCTACTTAAATGCCAGC

> hIL12AB_010 (SEQ ID NO: 14)
ATGTGCCACCAGCAGCTTGTCATCTCCTGGTTTTCTCTTGTCTTCCTCGCTTCTCCTCTTGTGGCCATCTGGGAGCTGAAGAAAGA
TGTCTATGTTGTAGAGCTGGACTGGTACCCGGACGCTCCTGGAGAAATGGTGGTTCTCACCTGCGACACTCCTGAAGAAGATGGCA
TCACCTGGACGCTGGACCAAAGCAGCGAAGTTTTAGGCTCTGGAAAAACGCTGACCATACAAGTAAAAGAATTTGGCGACGCTGGC
CAGTACACGTGCCACAAAGGAGGAAGTTTAAGCCACAGTTTACTTCTTCTTCACAAGAAGAAGGATGGCATCTGGTCAGACGTACGGA
CATTTTAAAAGACCAGAAGGCCTAAGAACAAAACCTTCCTCCGCTGTGAAGCTAAGAACTACAGTGGTCGTTTCACCTGCTGGT
GGCTCACCACCATCTCCACTGACCTCACCTTCTCTGTAAAATCAAGCCGTGGTTCTTCTGACCCCCAAGGAGTCACCTGTGGGGCT
GCCACGCTCAGCGCTGAAAGAGTTCGAGGCGACAACAAGGAATATGAATATTCTGTGGAATGTCAAGAAGATTCTGCCTGCCCGGC
GGCAGAGAAAGTCTTCCCATAGAAGTCATGGTGGACGCTGTTCACAAATTAAAATATGAAAACTACACCAGCAGCTTCTTCATTC
GTGACATCATCAAACCAGACCCTCCTAAGAACCTTCAGTTAAAACGCTGAAGAACAGCAGACAAGTGGAAGTTTCCTGGGAGTAC
CCGGACACGTGGAGTACGCCGCACTCCTACTTCAGTTTAACCTTCTGTGTACAAGTACAAGGAAAATCAAAAGAGAAGAAAAGA
TCGTGTCTTCACTGACAAAACATCTGCCACGGTCATCTGCCGTAAGAACGCTTCCATCTCGGTTCGAGCCCAGGACCGCTACTACA
GCAGCAGCTGGAGTGAGTGGGCATCTGTTCCCTGCAGTGGTGGCGGCGGCGGCGGCAGCCGCAACCTTCCTGTGGCCACGCCGGAC
CCTGGCATGTTCCCGTGCCTTCACCACTCGCAAAATCTTCTTCGTGCTGTTTCTAACATGCTGCAGAAGGCGAGACAAACTTTAGA

TABLE 4A-continued

Sequence optimized Open Reading Frame sequences for human IL12

ATTCTACCCGTGCACTTCTGAAGAAATAGACCATGAAGACATCACCAAGGACAAAACCAGCACGGTGGAGGCCTGCCTTCCTTTAG
AACTTACTAAGAACGAAAGTTGCCTTAACAGCCGTGAGACCAGCTTCATCACCAATGGCAGCTGCCTTGCTAGCAGGAAGACCAGC
TTCATGATGGCGCTGTGCCTTTCTTCCATCTATGAAGATCTTAAGATGTACCAAGTAGAATTTAAAACCATGAATGCCAAATTATT
AATGGACCCCAAGAGACAAATATTCCTCGACCAAAACATGCTGGCTGTCATTGATGAGCTCATGCAAGCATTAAACTTCAACTCAG
AAACTGTTCCCCAGAAGTCATCTTTAGAAGAACCGGACTTCTACAAAACAAAAATAAAACTCTGCATTCTTCTTCATGCCTTCCGC
ATCCGTGCTGTCACCATTGACCGTGTCATGTCCTACTTAAATGCTTCT

> hIL12AB_011 (SEQ ID NO: 15)
ATGTGCCACCAGCAGCTGGTGATCAGCTGGTTCAGCCTGGTGTTCCTGGCCAGCCCCCTGGTGGCCATCTGGGAGCTGAAGAAGGA
CGTGTACGTGGTGGAGCTGGACTGGTACCCGGACGCGCCGGGGGAGATGGTGGTGCTGACGTGCGACACGCCGGAGGAGGACGGGA
TCACGTGGACGCTGGACCAGAGCAGCGAGGTGCTGGGGAGCGGGAAGACGCTGACGATCCAGGTGAAGGAGTTCGGGGACGCGGGG
CAGTACACGTGCCACAAGGGGGGGGAGGTGCTGAGCCACAGCCTGCTGCTGCTGCACAAGAAGGAGGACGGGATCTGGAGCACGGA
CATCCTGAAGGACCAGAAGGAGCCGAAGAACAAGACGTTCCTGAGGTGCGAGGCGAAGAACTACAGCGGGAGGTTCACGTGCTGGT
GGCTGACGACGATCAGCACGGACCTGACGTTCAGCGTGAAGAGCAGCAGGGGGAGCAGCGACCCGCAGGGGGTGACGTGCGGGGCG
GCGACGCTGAGCGCGGAGAGGGTGAGGGGGGACAACAAGGAGTACGAGTACAGCGTGGAGTGCCAGGAGGACAGCGCGTGCCCGGC
GGCGGAGGAGAGCCTGCCGATCGAGGTGATGGTGGACGCGGTGCACAAGCTGAAGTACGAGAACTACACGAGCAGCTTCTTCATCA
GGGACATCATCAAGCCGGACCCGCCGAAGAACCTGCAGCTGAAGCCGCTGAAGAACAGCAGGCAGGTGGAGGTGAGCTGGGAGTAC
CCGGACACGTGGAGCACGCCGCACAGCTACTTCAGCCTGACGTTCTGCGTGCAGGTGCAGGGGAAGAGCAAGAGGGAGAAGAAGGA
CAGGGTGTTCACGGACAAGACGAGCGCGACGGTGATCTGCAGGAAGAACGCGAGCATCAGCGTGAGGGCGCAGGACAGGTACTACA
GCAGCAGCTGGAGCGAGTGGGCGAGCGTGCCGTGCAGCGGGGGGGGGGGGGGGGGAGCAGGAACCTGCCGGTGGCGACGCCGGAC
CCGGGGATGTTCCCGTGCCTGCACCACAGCCAGAACCTGCTGAGGGCGGTGAGCAACATGCTGCAGAAGGCGAGGCAGACGCTGGA
GTTCTACCCGTGCACGAGCGAGGAGATCGACCACGAGGACATCACGAAGGACAAGACGAGCACGGTGGAGGCGTGCCTGCCGCTGG
AGCTGACGAAGAACGAGAGCTGCCTGAACAGCAGGGAGACGAGCTTCATCACGAACGGGAGCTGCCTGGCGAGCAGGAAGACGAGC
TTCATGATGGCGCTGTGCCTGAGCAGCATCTACGAGGACCTGAAGATGTACCAGGTGGAGTTCAAGACGATGAACGCGAAGCTGCT
GATGGACCCGAAGAGGCAGATCTTCCTGGACCAGAACATGCTGGCGGTGATCGACGAGCTGATGCAGGCGCTGAACTTCAACAGCG
AGACGGTGCCGCAGAAGAGCAGCCTGGAGGAGCCGGACTTCTACAAGACGAAGATCAAGCTGTGCATCCTGCTGCACGCGTTCAGG
ATCAGGGCGGTGACGATCGACAGGGTGATGAGCTACCTGAACGCGAGC

> hIL12AB_012 (SEQ ID NO: 16)
ATGTGCCATCAGCAGCTGGTGATCAGCTGGTTCAGCCTCGTGTTTCTGGCCAGCCCCCTGGTGGCCATTTGGGAACTCAAGAAGGA
CGTGTATGTAGTGGAACTCGACTGGTACCCTGACGCCCCAGGCGAAATGGTGGTCTTAACCTGCGACACCCCTGAGGAGGACGGAA
TCACCTGGACCTTGGACCAGAGCTCCGAGGTCCTCGGCAGTGGCAAGACCCTGACCATACAGGTGAAAGAATTTGGAGACGCAGGG
CAATACACATGTCACAAGGGCGGGGAGGTTCTTTCTCACTCCCTTCTGCTTCTACATAAAAAGGAAGACGGAATTTGGTCTACCGA
CATCCTCAAGGACCAAAAGGAGCCTAAGAATAAAACCTTCTTACGCTGTGAAGCTAAAAACTACAGCGGCAGATTCACTTGCTGGT
GGCTCACCACCATTTCTACCGACCTGACCTTCTCGGTGAAGTCTTCAAGGGGCTCTAGTGATCCACAGGGAGTGACATGCGGGGCC
GCCACACTGAGCGCTGAACGGGTGAGGGGCGATAACAAGGAGTATGAATACTCTGTCGAGTGTCAGGAGGATTCAGCTTGTCCCGC
AGCTGAAGAGTCACTCCCCATAGAGGTTATGGTCGATGCTGTGCATAAACTGAAGTACGAAAACTACACCAGCAGCTTCTTCATTC
GGGACATTATAAAACCTGACCCCCCCAAGAACCTGCAACTTAAACCCCTGAAAAACTCTCGGCAGGTCGAAGTTAGCTGGGAGTAC
CCTGATACTTGGTCCACCCCCCACTCGTACTTCTCACTGACTTTCTGTGTGCAGGTGCAGGGCAAGAGCAAGAGAGAGAAAAAAGA
TCGTGTATTCACAGACAAGACCTCTGCCACCGTGATCTGCAGAAAAAACGCTTCCATCAGTGTCAGAGCCCAAGACCGGTACTATA
GTAGTAGCTGGAGCGAGTGGGCAAGTGTCCCCTGCTCTGGCGGCGGAGGGGGCGGCTCTCGAAACCTCCCCGTCGCTACCCCTGAT
CCAGGAATGTTCCCTTGCCTGCATCACTCACAGAATCTGCTGAGAGCGGTCAGCAACATGCTGCAGAAAGCTAGGCAAACACTGGA
GTTTTATCCTTGTACCTCAGAGGAGATCGACCACGAGGATATTACCAAGGACAAGACCAGCACGGTGGAGGCCTGCTTGCCCCTGG
AACTGACAAAGAATGAATCCTGCCTTAATAGCCGTGAGACCTCTTTTATAACAAACGGATCCTGCCTGGCCAGCAGGAAGACCTCC
TTCATGATGGCCCTCTGCCTGTCCTCAATCTACGAAGACCTGAAGATGTACCAGGTGGAATTTAAAACTATGAACGCCAAGCTGTT
GATGGACCCCAAGCGGCAGATCTTTCTGGATCAAAATATGCTGGCTGTGATCGACGAACTGATGCAGGCCCTCAACTTTAACAGCG
AGACCGTGCCACAAAAGAGCAGTCTTGAGGAGCCCGACTTCTACAAGACCAAGATCAAGCTGTGCATCCTCCTTCATGCCTTCAGG
ATAAGAGCTGTCACCATCGACAGAGTCATGAGTTACCTGAATGCATCC

> hIL12AB_013 (SEQ ID NO: 17)
ATGTGCCACCAGCAGCTGGTCATCTCCTGGTTCAGTCTTGTCTTCCTGGCCTCGCCGCTGGTGGCCATCTGGGAGCTGAAGAAAGA
TGTTTATGTTGTAGAGCTGGACTGGTACCCAGATGCTCCTGGAGAAATGGTGGTCCTCACCTGTGACACGCCAGAAGAAGATGGCA
TCACCTGGACGCTGGACCAGAGCAGTGAAGTTCTTGGAAGTGGAAAAACGCTGACCATACAAGTAAAAGAATTTGGAGATGCTGGC
CAGTACACCTGCCACAAAGGAGGAGAAGTTCTCAGCCACAGTTTATTATTACTTCACAAGAAAGAAGATGGCATCTGGTCCACGGA
CATTTTAAAAGACCAGAAGGAGCCCAAAAATAAAACATTTCTTCGATGTGAGGCCAAGAACTACAGTGGTCGTTTCACCTGCTGGT
GGCTGACCACCATCTCCACAGACCTCACCTTCAGTGTAAAAAGCAGCCGTGGTTCTTCTGACCCCCAAGGAGTCACCTGTGGGGCT
GCCACGCTCTCTGCAGAAAGAGTTCGAGGGGACAACAAAGAATATGAGTACTCGGTGGAATGTCAAGAAGACTCGGCCTGCCCAGC
TGCTGAGGAGAGTCTTCCCATAGAAGTCATGGTGGATGCTGTTCACAAATTAAAATATGAAAACTACACCAGCAGCTTCTTCATCA
GAGACATCATCAAACCTGACCCGCCCAAGAACTTACAGCTGAAGCCGCTGAAAAACAGCAGACAAGTAGAAGTTTCCTGGGAGTAC
CCGGACACCTGGTCCACGCCGCACTCCTACTTCTCCCTCACCTTCTGTGTACAAGTACAAGGCAAGAGCAAGAGAGAGAAGAAAGA
TCGTGTCTTCACGGACAAAACATCAGCCACGGTCATCTGCAGGAAAAATGCCAGCATCTCGGTGCGGGCCCAGGACCGCTACTACA
GCAGCAGCTGGAGTGAGTGGGCATCTGTGCCCTGCAGTGGTGGTGGGGGTGGTGGCAGCAGAAACCTTCCTGTGGCCACTCCAGAC
CCTGGCATGTTCCCGTGCCTTCACCACTCCCAAAATTTACTTCGAGCTGTTTCTAACATGCTGCAGAAAGCAAGACAAACTTTAGA
ATTCTACCCGTGCACTTCTGAAGAAATTGACCATGAAGACATCACAAAAGATAAAACCAGCACAGTGGAGGCCTGTCTTCCTTTAG
AGCTGACCAAAAATGAATCCTGCCTCAACAGCAGAGAGACCAGCTTCATCACCAATGGCAGCTGCCTGGCCTCCAGGAAAACCAGC
TTCATGATGGCGCTCTGCCTCAGCTCCATCTATGAAGATTTGAAGATGTACCAAGTAGAATTTAAAACCATGAATGCCAAATTATT
AATGGACCCCAAGAGGCAGATATTTTTAGATCAAAACATGCTGGCAGTTATTGATGAGCTCATGCAAGCATTAAACTTCAACAGTG
AGACTGTACCTCAAAAAAGCAGCCTTGAAGAGCCGGACTTCTACAAAACCAAGATCAAACTCTGCATTTTACTTCATGCCTTCCGC
ATCCGGGCGGTCACCATTGACCGTGTCATGTCCTACTTAAATGCCTCG

> hIL12AB_014 (SEQ ID NO: 18)
ATGTGCCACCAGCAGCTTGTGATTTCTTGGTTCTCTCTTGTGTTCCTTGCTTCTCCTCTTGTGGCTATTTGGGAGTTAAAAAAGGA
CGTGTACGTGGTGGAGCTTGACTGGTACCCTGATGCTCCTGGCGAGATGGTGGTGCTTACTTGTGACACTCCTGAGGAGGACGGCA
TTACTTGGACTCTTGACCAGTCTTCTGAGGTGCTTGGCTCTGGCAAGACTCTTACTATTCAGGTGAAGGAGTTCGGGGATGCTGGC
CAGTACACTTGCCACAAGGGCGGCGAGGTGCTTTCTCACTCTCTTCTTCTTCTTCACAAGAAGGAGGACGGCATTTGGTCTACTGA
CATTTTAAAAGACCAGAAGGAGCCCAAGAACAAGACTTTCCTTCGTTGCGAGGCCAAGAACTACTCTGGCCGTTTCACTTGCTGGT
GGCTTACTACTATTTCTACTGACCTTACTTTCTCTGTGAAGTCTTCTCGTGGCTCTTCTGACCCTCAGGGCGTGACTTGTGGGGCT
GCTACTCTTTCTGCTGAGCGTGTGCGTGGGGACAACAAGGAGTACGAGTACTCTGTGGAGTGCCAGGAGGACTCTGCTTGCCCTGC

TABLE 4A-continued

Sequence optimized Open Reading Frame sequences for human IL12

TGCTGAGGAGTCTCTTCCTATTGAGGTGATGTGGATGCTGTGCACAAGTTAAAATACGAGAACTACACTTCTTCTTTCTTCATTC
GTGACATTATTAAGCCTGACCCTCCCAAGAACCTTCAGTTAAAACCTTTAAAAAACTCTCGTCAGGTGGAGGTGTCTTGGGAGTAC
CCTGACACTTGGTCTACTCCTCACTCTTACTTCTCTCTTACTTTCTGCGTGCAGGTGCAGGGCAAGTCTAAGCGTGAGAAGAAGGA
CCGTGTGTTCACTGACAAGACTTCTGCTACTGTGATTTGCAGGAAGAATGCATCTATTTCTGTGCGTGCTCAGGACCGTTACTACT
CTTCTTCTTGGTCTGAGTGGGCTTCTGTGCCTTGCTCTGGCGGCGGCGGCGGCTCTAGAAATCTTCCTGTGGCTACTCCTGAC
CCTGGCATGTTCCCTTGCCTTCACCACTCTCAGAACCTTCTTCGTGCTGTGAGCAACATGCTTCAGAAGGCTCGTCAGACTCTTGA
GTTCTACCCTTGCACTTCTGAGGAGATTGACCACGAGGACATCACCAAGGACAAGACTTCTACTGTGGAGGCTTGCCTTCCTCTTG
AGCTTACCAAGAATGAATCTTGCTTAAATTCTCGTGAGACTTCTTTCATCACCAACGGCTCTTGCCTTGCCTCGCGCAAGACTTCT
TTCATGATGGCTCTTTGCCTTTCTTCTATTTACGAGGACTTAAAAATGTACCAGGTGGAGTTCAAGACTATGAATGCAAAGCTTCT
TATGGACCCCAAGCGTCAGATTTTCCTTGACCAGAACATGCTTGCTGTGATTGACGAGCTTATGCAGGCTTTAAATTTCAACTCTG
AGACTGTGCCTCAGAAGTCTTCTCTTGAGGAGCCTGACTTCTACAAGACCAAGATTAAGCTTTGCATTCTTCTTCATGCTTTCCGT
ATTCGTGCTGTGACTATTGACCGTGTGATGTCTTACTTAAATGCTTCT

> hIL12AB_015 (SEQ ID NO: 19)
ATGTGTCACCAGCAGCTGGTGATCAGCTGGTTTAGCCTGGTGTTTCTGGCCAGCCCCCTGGTGGCCATATGGGAACTGAAGAAAGA
TGTGTATGTGGTAGAACTGGATTGGTATCCGGATGCCCCCGGCGAAATGGTGGTGCTGACCTGTGACACCCCCGAAGAAGATGGTA
TCACCTGGACCCTGGACCAGAGCAGCGAGGTGCTGGGCAGCGGCAAAACCCTGACCATCCAAGTGAAAGAGTTTGGCGATGCCGGC
CAGTACACCTGTCACAAAGGCGGCGAGGTGCTAAGCCATTCGCTGCTGCTGCTGCACAAAAAGGAAGATGGCATCTGGAGCACCGA
TATCCTGAAGGACCAGAAAGAACCCAAAAATAAGACCTTTCTAAGATGCGAGGCCAAGAATTATAGCGGCCGTTTCACCTGCTGGT
GGCTGACGACCATCAGCACCGATCTGACCTTCAGCGTGAAAAGCAGCAGAGGCAGCAGCGACCCCCAAGGCGTGACGTGCGGCGCC
GCCACCCTGAGCGCCGAGAGAGTGAGAGGCGACAACAAGGAGTATGAGTACAGCGTGGAGTGCCAGGAGGACAGCGCCTGCCCCGC
CGCCGAGGAGAGCCTGCCCATCGAGGTGATGGTGGATGCCGTGCACAAGCTGAAGTATGAAAACTACACCAGCAGCTTCTTCATCA
GAGACATCATCAAACCCGACCCCCCCAAGAACCTGCAGCTGAAGCCTCTGAAGAATAGCAGACAGGTGGAGGTGAGCTGGGAGTAC
CCCGACACCTGGAGCACCCCCCATAGCTACTTCAGCCTGACCTTCTGCGTGCAGGTGCAGGGCAAGAGCAAGAGAGAAAAGAAAGA
TAGAGTGTTCACGGACAAGACCAGCGCCACGGTGATCTGCAGAAAAAATGCCAGCATCAGCGTGAGAGCCCAGGACAGATACTATA
GCAGCAGCTGGAGCGAATGGGCCAGCGTGCCCTGCAGCGGCGGCGGCGGCGGCAGCAGAAACCTGCCCGTGGCCACCCCCGAC
CCCGGCATGTTCCCCTGCCTGCACCACAGCCAAAACCTGCTGAGAGCCGTGAGCAACATGCTGCAGAAGGCCAGACAAACCCTGGA
ATTTTACCCCTGCACCAGCGAAGAGATCGATCATGAAGATATCACCAAAGATAAAACCAGCACCGTGGAGGCCTGTCTGCCCCTGG
AACTGACCAAGAATGAGAGCTGCCTAAATAGCAGAGAGACCAGCTTCATAACCAATGGCAGCTGCCTGGCCAGCAGAAAGACCAGC
TTTATGATGGCCCTGTGCCTGAGCAGCATCTATGAAGACCTGAAGATGTACCAGGTGGAGTTCAAGACCATGAATGCCAAGCTGCT
GATGGATCCCAAGAGACAGATCTTTCTGGATCAAAACATGCTGGCCGTGATCGATGAGCTGATGCAGGCCCTGAATTTCAACAGCG
AGACCGTGCCCCAAAAAGCAGCCTGGAAGAACCGGATTTTATAAAACCAAAATCAAGCTGTGCATACTGCTGCATGCCTTCAGA
ATCAGAGCCGTGACCATCGATAGAGTGATGAGCTATCTGAATGCCAGC

> hIL12AB_016 (SEQ ID NO: 20)
ATGTGCCACCAGCAGCTGGTCATCAGCTGGTTCAGCCTGGTCTTCCTGGCCAGCCCCCTGGTGGCCATCTGGGAGCTGAAGAAGGA
TGTTTATGTTGTGGAGCTGGACTGGTACCCAGATGCCCCTGGGGAGATGGTGGTGCTGACCTGTGACACCCCAGAAGAGGATGGCA
TCACCTGGACCCTGGACCAGAGCTCAGAAGTGCTGGGCAGTGGAAAAACCCTGACCATCCAGGTGAAGGAGTTTGGAGATGCTGGC
CAGTACACCTGCCACAAGGGTGGTGAAGTGCTGAGCCACAGCCTGCTGCTGCTGCACAAGAAGGAGGATGGCATCTGGAGCACAGA
CATCCTGAAGGACCAGAAGGAGCCCAAGAACAAGACCTTCCTTCGCTGTGAAGCCAAGAACTACAGTGGCCGCTTCACCTGCTGGT
GGCTGACCACCATCAGCACAGACCTCACCTTCTCGGTGAAGAGCAGCAGAGGCAGCTCAGACCCCCAGGGTGTCACCTGTGGGGCG
GCCACGCTGTCGGCGGAGAGAGTTCGAGGGGACAACAAGGAGTATGAATACTCGGTGGAGTGCCAGGAGGACTCGGCGTGCCCGGC
GGCAGAGGAGAGCCTGCCCATAGAAGTGATGGTGGATGCTGTGCACAAGCTGAAGTATGAAAACTACACCAGCAGCTTCTTCATCA
GAGACATCATCAAGCCAGACCCGCCCAAGAACCTGCAGCTGAAGCCCCTGAAGAACAGCAGACAAGTGGAGGTTTCCTGGGAGTAC
CCAGACACGTGGAGCACCCCCCACAGCTACTTCAGCCTGACCTTCTGTGTCCAGGTGCAGGGCAAGAGCAAGAGAGAGAAGAAGGA
CAGAGTCTTCACAGACAAGACCTCGGCCACGGTCATCTGCAGAAAGAATGCCTCCATCTCGGTTCGAGCCCAGGACAGATACTACA
GCAGCAGCTGGTCAGAATGGGCCTCGGTGCCCTGCAGTGGTGGCGGCGGCGGCGGCAGCAGAAACCTGCCTGTTGCCACCCCAGAC
CCTGGGATGTTCCCCTGCCTGCACCACAGCCAGAACTTATTACGAGCTGTTTCTAACATGCTGCAGAAGGCCAGACAAACCCTGGA
GTTCTACCCCTGCACCTCAGAAGAGATTGACCATGAAGACATCACCAAGGACAAGACCAGCACTGTAGAGGCCTGCCTGCCCCTGG
AGCTGACCAAGAATGAAAGCTGCCTGAACAGCAGAGAGACCAGCTTCATCACCAATGGAAGCTGCCTGGCCAGCAGAAAGACCAGC
TTCATGATGGCCCTGTGCCTGAGCAGCATCTATGAAGACCTGAAGATGTACCAGGTGGAGTTCAAGACCATGAATGCAAAGCTGCT
GATGGACCCCAAGAGACAAATATTTTGGACCAGAACATGCTGGCTGTCATTGATGAGCTGATGCAGGCCCTGAACTTCAACTCAG
AAACTGTACCCCAGAAGAGCAGCCTGGAGGAGCCAGACTTCTACAAGACCAAGATCAAGCTGTGCATCCTGCTTCATGCTTTCAGA
ATCAGAGCTGTCACCATTGACCGCGTGATGAGCTACTTAAATGCCTCG

> hIL12AB_017 (SEQ ID NO: 21)
ATGTGCCACCAGCAGCTGGTAATCAGCTGGTTTTCCCTCGTCTTTCTGGCATCACCCCTGGTGGCTATCTGGGAGCTGAAGAAGGA
CGTGTACGTGGTGGAGCTGGATTGGTACCCTGACGCCCCGGGGGAAATGGTGGTGTTAACATGCGACACGCCTGAGGAGGACGGCA
TCACCTGGACACTGGACCAGAGCAGCGAGGTGCTTGGGTCTGGTAAAACTCTGACTATTCAGGTGAAGAGTTTCGGGGATGCCGGC
CAATATACTTGCCACAAGGGTGGCGAGGTGCTTTCTCATTCTCTGCTCCTGCTGCACAAGAAAGAAGATGGCATTTGGTCTACTGA
TATTCTGAAAGACCAGAAGGAGCCCAAGAACAAGACCTTTCTGAGATGCGAGGCTAAAAACTACAGCGGAAGATTTACCTGCTGGT
GGCTGACCACAATCTCAACCGACCTGACATTTTCAGTGAAGTCCAGCAGAGGGAGCTCCGACCCTCAGGGCGTGACCTGCGGAGCC
GCCACTCTGTCCGCAGAAAGAGTGAGAGGTGATAATAAGGAGTACGAGTATTCAGTCGAGTGCCAAGAGGACTCTGCCTGCCCAGC
CGCCGAGGAGAGCCTGCAATCGAGGTGATGGTAGATGCGGTACACAAGCTGAAGTATGAGAACTACACATCCTCCTTCTTCATAA
GAGACATTATCAAGCCTGACCCACCTAAAAATCTGCAACTCAAGCCCTTGAAAAATTCAAGACAGGTGGAGGTGAGCTGGGAGTAC
CCTGATACTTGGAGCACCCCCCATAGCTACTTTTCGCTGACATTCTGCGTCCAGGTGCAGGGCAAGTCAAAGAGAGAGAAGAAGGA
TCGCGTGTTCACTGATAAGACAAGCGCCACAGTGATCTGCAGAAAAAACGCTAGCATTAGCGTCAGAGCACAGGACCGGTATTACT
CCAGCTCCTGGAGCGAATGGGCATCTGTGCCCTGCAGCGGTGGGGGCGGAGGCGGATCTAGAAACCTCCCCGTTGCCACACCTGAT
CCTGGAATGTTCCCCTGTCTGCACCACAGCCAGAACCTGCTGAGAGCAGTGTCTAACATGCTCCAGAAGGCCAGGCAGACCCTGGA
GTTTTACCCCTGCACCAGCGAGGAAATCGATCACGAGGACATCACCAAAGATAAAACCTCCACCGTGGAGGCCTGCCTGCCCCTGG
AACTGACCAAAAACGAGAGCTGCCTGAATAGCAGGGAGACCTCCTTCATCACCAACGGCTCATGCCTTGCCAGCGGAAAACTAGC
TTCATGATGGCCCTGTGCCTGTCTTGATCTATGAGGACCTGAAAATGTACCAGGTCGAATTTAAGACGATGAACGCAAAGCTGCT
GATGGACCCCAAGCGGCAGATCTTTCTGGACCAGAACATGCTGGCAGTCATAGATGAGTTGATGCAGGCATTAAACTTCAACAGCG
AGACCGTGCCTCAGAAGTCCAGCCTCGAGGAGCCAGATTTTTATAAGACCAAGATCAAACATGCATCCTGCTGCATGCTTTCAGG
ATTAGAGCCGTCACCATCGATCGAGTCATGTCTTACCTGAATGCTAGC

TABLE 4A-continued

Sequence optimized Open Reading Frame sequences for human IL12

> hIL12AB_018 (SEQ ID NO: 22)
ATGTGTCACCAACAGTTAGTAATCTCCTGGTTTTCTCTGGTGTTTCTGGCCAGCCCCCTCGTGGCCATCTGGGAGCTTAAAAAGGA
TGTGTACGTGGTGGAGCTGGACTGGTATCCCGATGCACCAGGCGAAATGGTCGTGCTGACCTGCGATACCCCTGAAGAAGATGGCA
TCACCTGGACTCTGGACCAGTCTTCCGAGGTGCTTGGATCTGGCAAGACTCTGACAATACAAGTTAAGGAGTTCGGGGACGCAGGA
CAGTACACCTGCCACAAAGGCGGCGAGGTCCTGAGTCACTCCCTGTTACTGCTCCACAAGAAGAAGGACGGCATTTGGTCCACCGA
CATTCTGAAGGACCAGAAGGAGCCTAAGAATAAAACTTTCCTGAGATGCGAGGCAAAAAACTATAGCGGCCGCTTTACTTGCTGGT
GGCTTACAACAATCTCTACCGATTTAACTTTCTCCGTGAAGTCTAGCAGAGGATCCTCTGACCCGCAAGGAGTGACTTGCGGAGCC
GCCACCTTGAGCGCCGAAAGAGTCCGTGGCGATAACAAAGAATACGAGTACTCCGTGGAGTGCCAGGAAGATTCCGCTGCCCAGC
TGCCGAGGAGTCCCTGCCCATTGAAGTGATGGTGGATGCCGTCCACAAGCTGAAGTACGAAAACTATACCAGCAGCTTCTTCATCC
GGGATATCATTAAGCCCGACCCTCCTAAAAACCTGCAACTTAAGCCCCTAAAGAATAGTCGGCAGGTTGAGGTCAGCTGGGAATAT
CCTGACACATGGAGCACCCCCCACTCTTATTTCTCCCTGACCTTCTGCGTGCAGGTGCAGGGCAAGAGTAAACGGGAGAAAAAGGA
CAGGGTCTTTACCGATAAAACCAGCGCTACGGTTATCTGTCGGAAGAACGCTTCCATCTCCGTCCGCGCTCAGGATCGTTACTACT
CGTCCTCATGGAGCGAGTGGGCCAGCGTGCCCTGCAGCGGCGGCGGTGGAGGCGGATCCAGAAATCTGCCTGTTGCCACACCAGAC
CCTGGCATGTTCCCCTGTCTGCATCATAGCCAGAACCTGCTCAGAGCCGTGAGCAACATGCTCCAGAAGGCCAGGCAGACATTGGA
GTTCTACCCGTGTACATCTGAGGAAATCGATACGAAGATATAACCAAGGACAAAACTCTACAGTAGAGGCTTGTTTGCCCCTGG
AGTTGACCAAAACGAGAGTTGCCTGACAGTCGCGAGACAAGCTTCATTACTAACGGCAGCTGTCTCGCCTCCAGAAAGACATCC
TTCATGATGGCCCTGTGTCTTTCCAGCATATACGAAGACCTGAAAATGTACCAGGTCGAGTTCAAAACAATGAACGCCAAGCTGCT
TATGGACCCCAAGAGACAGATCTTCCTCGACCAAAACATGCTCGCTGTGATCATGATGCTGATGCAGGCTCTCAACTTCAATTCCG
AAACAGTGCCACAGAAGTCCAGTCTGGAAGAAACCCGACTTCTACAAGACCAAGATTAAGCTGTGTATTTTGCTGCATGCGTTTAGA
ATCAGAGCCGTGACCATTGATCGGGTGATGAGCTACCTGAACGCCTCG

> hIL12AB_019 (SEQ ID NO: 23)
ATGTGCCACCAGCAGCTTGTCATCTCCTGGTTTTCTCTTGTCTTCCTGGCCTCGCCGCTGGTGGCCATCTGGGAGCTGAAGAAAGA
TGTCTATGTTGTAGAGCTGGACTGGTACCCAGATGCTCCTGGAGAAATGGTGGTTCTCACCTGTGACACTCCTGAAGAAGATGGCA
TCACCTGGACGCTGGACCAAAGCTCAGAAGTTCTTGGCAGTGGAAAAACGCTGACCATACAAGTAAAAGAATTTGGGGATGCTGGC
CAGTACACGTGCCACAAAGGAGGAAGTTCTCAGCCACAGTTCTTCTTCTTCACAAGAAGAAGATGGCATCTGGTCCACGGA
CATTTTAAAAGACCAGAAGGAGCCCAAGAACAAAACCTTCCTCCGCTGTGAGGCCAAGAACTACAGTGGTCGTTTCACCTGCTGGT
GGCTCACCACCATCTCCACTGACCTCACCTTCTCTGTAAAAAGCAGCCGTGGTTCTTCTGACCCCCAAGGAGTCACCTGTGGGGCT
GCCACGCTCTCGGCAGAAAGAGTTCGAGGGGACAACAAGGAATATGAATATTCTGTGGAATGTCAAGAAGATTCGCCTGCCCGGC
GGCAGAGAAAGTCTTCCCATAGAAGTCATGGTGGATGCCGTCAACAAATTAAAATATGAAAACTACACCAGCAGCTTCTTCATTC
GTGACATCATCAAACCAGACCCGCCCAAGAACCTTCAGTTAAAACCTTTAAAAAACAGCAGACAAGTAGAAGTTTCCTGGGAGTAC
CCGGACACGTGGTCCACGCCGCACTCCTACTTCAGTTTAACCTTCTGTGTACAAGTACAAGGAAAATCAAAAAGAGAAGAAGA
TCGTGTCTTCACTGACAAAACATCTGCCACGGTCATCTGCAGGAAGAATGCCTCCATCTCGGTTCGAGCCCAGGACCGCTACTACA
GCAGCAGCTGGAGTGAGTGGGCATCTGTTCCCTGCAGTGGTGGCGGCGGCGGCAGCCGCAACCTTCCTGTGGCCACGCCGGAC
CCTGGCATGTTCCCGTGCCTTCACCACTCCCAAAATCTTCTTCGTGCTGTTTCTAACATGCTGCAGAAGGCGCGCAAACTTTAGA
ATTCTACCCGTGCACTTCTGAAGAAATAGACCATGAAGACATCACCAAAGATAAAACCAGCACGGTGGAGGCCTGCCTTCCTTTAG
AGCTGACCAAGAATGAATCCTGCCTCAACAGCAGAGAGACCAGCTTCATCACCAATGGCAGCTGCCTGGCCTCGCGCAAGACCAGC
TTCATGATGGCGCTGTGCCTTTCTTCCATCTATGAAGATTTAAAGATGTACCAAGTAGAATTTAAAACCATGAATGCCAAATTATT
AATGGACCCCAAAAGACAAATATTTTTGGATCAAAACATGCTGGCTGTCATTGATGAGCTCATGCAAGCATTAAACTTCAACTCAG
AAACTGTTCCCCAGAAGTCATCTTTAGAAGAGCCGGACTTCTACAAAACAAAAATAAAACTCTGCATTCTTCTTCATGCCTTCCGC
ATCCGTGCTGTCACCATTGACCGTGTCATGTCCTACTTAAATGCTTCT

> hIL12AB_020 (SEQ ID NO: 24)
ATGTGCCACCAGCAGCTGGTGATCAGCTGGTTCAGCCTGGTGTTCCTGGCTAGCCCCTCTGGTGGCCATCTGGGAGCTGAAGAAGGA
CGTGTACGTGGTGGAGTTAGACTGGTACCCCGACGCTCCCGGCGAGATGGTGGTGCTGACCTGCGACACCCCCGAGGAGGACGGA
TCACCTGGACCCTGGATCAGTCAAGCGAGGTGCTGGGAAGCGGCAAGACCCTGACCATCCAGGTGAAGGAGTTCGGCGACGCCGGC
CAATACACTTGCCACAAGGGAGGCGAGGTGCTGTCCCACTCCCTGCTGCTGCACAAAAAGGAAGATGGCATCTGGAGCACCGA
CATCCTGAAAGACCAGAAGGAGCCTAAGAACAAGACATTCCTCAGATGCGAGGCCAAGAATTACTCCGGCAGATTCACCTGTTGGT
GGCTGACCACCATCAGCACAGACCTGACCTTCAGCGTGAAGAGCAGCAGAGGCAGCAGCGACCCCCAGGGCGTGACCTGTGGCGCC
GCCACCCTGAGCGCCGAAAGAGTGCGCGGCGACAACAAGGAGTACGAGTACTCCGTGGAATGCCAGGAGGACAGCGCCTGCCCCGC
CGCCGAGGAGAGCCTGCCCATCGAGGTGATGGTGGACGCCGTCCACAAGCTGAAGTACGAAAACTACACCTCTAGCTTCTTCATCC
GGGACATCATCAAGCCCGATCCCCCCAAGAACCTGCAGCTGAAACCCCTGAAGAACAGCAGACAGGTGGAGGTGAGCTGGGAGTAT
CCCGACACCTGGTCCACCCCCCACAGCTATTTTAGCCTGACCTTCTGCGTGCAAGTGCAGGGCAAGAGCAAGAGAGAAGAAGGA
CCGCGTGTTCACCGACAAAACCAGCGCCACCGTGATCTGCAGAAAGAACGCCAGCATCAGCGTGAGGGCCCAGGATAGATACTACA
GTTCCAGCTGGAGCGAGTGGGCCAGCGTGCCCTGCAGCGGCGGCGGCGGGGAGGCTCTAGAAACCTGCCCGTGGTGCACACCCGAT
CCCGGAATGTTCCCCTGCCTGCACCACAGCCAGAACCTGCTGAGGGCGGTGTCCAACATGCTTCAGAAGGCCCGGCAGACCCTGGA
GTTCTACCCCTGTACCTCTGAGGAGATCGATCATGAGGACATCACAAAGGACAAAACCAGCACCGTGGAGGCCTGCCTGCCCCTGG
AGCTGACCAAGAACGAGAGCTGCCTGAACTCCCGCGAGACCAGCTTCATCACGAACGGCAGCTGCCTGGCCAGCAGGAAGACCTCC
TTCATGATGGCCCTGTGCCTGAGCAGCATCTACGAGGACCTGAAAATGTACCAGGTGGAGTTTAAGACCATGAACGCCAAGCTGCT
GATGGACCCCAAGCGGCAAATCTTCCTGGACCAGAACATGCTGGCAGTGATCGACGAGCTCATGCAGGCCCTGAACTTCAATAGCG
AGACAGTCCCCCAGAAGAGCAGCCTGGAGGAGCCCGACTTTTACAAGACCAAGATCAAGCTGTGCATCCTGCTGCACGCCTTTAGA
ATCCGTGCCGTGACCATTGACAGAGTGATGAGCTACCTGAATGCCAGC

> hIL12AB_021(SEQ ID NO: 25)
ATGTGCCACCAGCAGCTGGTGATCAGCTGGTTCAGCCTGGTGTTCCTGGCCAGCCCTCTGGTTGCCATCTGGGAGCTGAA
GAAAGACGTGTACGTCGTGGAACTGGACTGGTATCCGGACGCCCCGGGCGAGATGGTGGTGCTGACCTGTGACACCCCCGAGGAGG
ACGGCATCACCTGGACGCTGGACCAATCCTCCGAGGTGCTGGGAAGCGGCAAGACCCTGACCATCCAGGTGAAGGAATTCGGGGAC
GCCGGGCAGTACACCTGCCACAAGGGGGGCGAAGTGCTGTCCCACTCGCTGCTGCTGCTGCATAAGAAGGAGGATGGAATCTGGTC
CACCGACATCCTCAAAGATCAGAAGGAGCCCAAGAACAAGACGTTCCTGCGCTGTGAAGCCAAGAATTATTCGGGGCGATTCACGT
GCTGGTGGCTGACAACCATCAGCACCGACCTGACGTTTAGCGTGAAGAGCAGCAGGGGTCCAGCGACCCCCAGGGCGTGACGTGC
GGCGCCGCCACCCTCTCCGCCGAGAGGGTGCGGGGGGACAATAAGGAGTACGAGTACAGCGTGGAATGCCAGGAGGACAGCGCCTG
CCCCGCCGCGGAGGAAAGCCTCCCGATAGAGGTGATGGTGGACGCCGTGCACAAGCTCAAGTACGAAAATTACACCAGCAGCTTTT
TCATCCGGGACATTATCAAGCCCGACCCCCCGAAGAACCTCCAGCTGAAGCCCCTGAAGAACAGCCGGCAGGTGGAAGTCTCCTGG
GAGTATCCCGACACCTGGAGCACCCCGCACAGCTACTTCTCCCTGACCTTCTGTGTGCAGGTGCAGGGCAAGTCCAAGAGGGAAAA
GAAGGACAGGGTTTTCACCGACAAGACCAGCGCGACCGTGATCTGCCGGAAGAACGCCAGCATAAGCGTCCGCGCCCAAGATAGGT
ACTACAGCAGCTCCTGGAGCGAGTGGGCTAGCGTGCCCTGCAGCGGGGGCGGGGGTGGGGCTCCAGGAACCTGCCAGTGGCGACC
CCCGACCCCGGCATGTTCCCCTGCCTCCATCACAGCCAGAACCTGCTGAGGGCCGTCAGCAATATGCTGCAGAAGGCCAGGCAGAC

TABLE 4A-continued

Sequence optimized Open Reading Frame sequences for human IL12

```
CCTGGAATTCTACCCCTGCACGTCGGAGGAGATCGATCACGAGGATATCACAAAAGACAAGACTTCCACCGTGGAGGCCTGCCTGC
CCCTGGAGCTCACCAAGAATGAGTCCTGTCTGAACTCCCGGGAAACCAGCTTCATCACCAACGGGTCCTGCCTGGCCAGCAGGAAG
ACCAGCTTTATGATGGCCCTGTGCCTGTCGAGCATCTACGAGGACCTGAAGATGTACCAGGTCGAGTTCAAGACAATGAACGCCAA
GCTGCTGATGGACCCCAAGAGGCAAATCTTCCTGGACCAGAATATGCTTGCCGTCATCGACGAGCTCATGCAGGCCCTGAACTTCA
ACTCCGAGACCGTGCCCCAGAAGAGCAGCCTGGAGGAGCCCGACTTCTACAAGACCAAGATCAAGCTGTGCATCCTGCTGCACGCG
TTCAGGATCCGGGCAGTCACCATCGACCGTGTGATGTCCTACCTGAACGCCAGC

> hIL12AB_022(SEQ ID NO: 26)
ATGTGCCATCAGCAGCTGGTGATCAGCTGGTTCAGCCTGGTGTTCCTCGCCTCTCCCCTGGTGGCCATCTGGGAGCTCAA
AAAGGACGTGTACGTGGTGGAGCTCGACTGGTACCCAGACGCCCCCGGGGAGATGGTGGTGCTGACCTGCGACACCCCCGAAGAAG
ACGGCATCACGTGGACCCTCGACCAGTCCAGCGAGGTGCTGGGGAGCGGGAAGACTCTGACCATCCAGGTCAAGGAGTTCGGGGAC
GCCGGGCAGTACACGTGCCACAAGGGCGGCGAAGTCTTAAGCACAGCCTGCTCCTGCTGCACAAGAAGGAGGACGGGATCTGGTC
CACAGACATACTGAAGGACCAGAAGGAGCCGAAGAATAAAACCTTTCTGAGGTGCGAGGCCAAGAACTATTCCGGCAGGTTCACGT
GCTGGTGGCTTACAACAATCAGCACAGACCTGACGTTCAGCGTGAAGTCCAGCCGCGGCAGCAGCGACCCCCAGGGGGTGACCTGC
GGCGCCGCCACCCTGAGCGCCGAGCGGGTGCGCGGGGACAACAAGGAGTACGAGTACTCCGTGGAGTGCCAGGAAGACAGCGCCTG
TCCCGCCGCCGAAGAGAGCCTGCCTATCGAGGTCATGGTAGATGCAGTGCATAAGCTGAAGTACGAGAACTATACGAGCAGCTTTT
TCATACGCGACATCATCAAGCCCGACCCCCCCAAGAACCTGCAGCTTAAGCCCCTGAAGAATAGCCGGCAGGTGGAGGTCTCCTGG
GAGTACCCCGACACCTGGTCAACGCCCCACAGCTACTTCTCCCTGACCTTTTGTGTCCAAGTCCAGGGAAAGAGCAAGAGGGAGAA
GAAAGATCGGGTGTTCACCGACAAGACCTCCGCCACGGTGATCTGCAGGAAGAACGCCAGCATCTCCGTGAGGGCGCAAGACAGGT
ACTACTCCAGCAGCTGGTCCGAATGGGCCAGCGTGCCCTGCTCCGGCGGCGGGGCGGCGGCAGCCGAAACCTACCCGTGGCCACG
CCGGATCCCGGCATGTTTCCCTGCCTGCACCACAGCCAGAACCTCCTGAGGGCCGTGTCCAACATGCTGCAGAAGGCCAGGCAGAC
TCTGGAGTTCTACCCCTGCACGAGCGAGGAGATCGATCACGAGGACATCACCAAGGATAAGACCAGCACTGTGGAGGCCTGCCTTC
CCCTGGAGCTGACCAAGAACGAGAGCTGTCTGAACTCCAGGGAAACCTCATTCATCACCAACGGCTCCTGCCTGGCCAGCAGGAAA
ACCAGCTTCATGATGGCCTTGTGTCTCAGCTCCATCTACGAGGACCTGAAGATGTATCAGGTCGAGTTCAAGACAATGAACGCCAA
GCTGCTGATGGACCCCAAAAGGCAGATCTTCCTGGACCAGAACATGCTGGCCGTCATCGACGAGCTGATGCAGGCCCTGAACTTCA
ACAGCGAGACGGTGCCCCAGAAAAGCTCCCTGGAGGAGCCCGACTTCTACAAGACCAAGATCAAGCTGTGCATCCTGCTGCACGCC
TTCAGGATCAGGGCAGTGACCATCGACCGGGTGATGTCATACCTTAACGCCAGC

> hIL12AB_023(SEQ ID NO: 27)
ATGTGCCATCAGCAGCTGGTGATCTCCTGGTTCAGCCTGGTGTTTCTGGCCTCGCCCCTGGTCGCCATCTGGGAGCTGAA
GAAAGACGTGTACGTCGTGGAACTGGACTGGTACCCCGACGCCCCCGGGGAGATGGTGGTGCTGACCTGCGACACGCCGGAGGAGG
ACGGCATCACCTGGACCCTGGATCAAAGCAGCGAGGTGCTGGGCAGCGGCAAGACCCTGACCATCCAAGTGAAGGAATTCGGCGAT
GCCGGCCAGTACACCTGTCACAAAGGGGCGAGGTGCTCAGCCACAGCCTGCTGCTGCACAAGAAGGAGGATGGCATCTGGAG
CACCGATATCCTGAAGGACCAGAAAGAGCCCAAGAACAAGACGTTCCTGAGGTGCGAGGCCAAGAACTACAGCGGTAGGTTCACGT
GTTGGTGGCTGACCACCATCAGCACCGACCTGACGTTCAGCGTGAAGAGCTCCAGGGGCAGCTCCGACCCACAGGGGGTGACGTGC
GGGGCCGCAACCCTCAGCGCCGAAAGGGTGCGGGGGACAACAAGGAGTACGAATACTCCGTGGAAGATTCGGCCTG
CCCCGCCGCGGAGGAGAGCCTCCCCATCGAGGTAATGGTGGACGCCGTGCATAAGCTGAAGTACGAGAACTACACCAGCTCGTTCT
TCATCCGAGACATCATCAAACCCGACCCGCCCAAAAATCTGCAGCTCAAGCCCCTGAAGAACTCCAGGCAGGTGGAGGTGAGCTGG
GAGTACCCCGACACCTGGTCCACCCCGCACAGCTACTTCTCCCTGACATTCTGCGTGCAGGTGCAGGGCAAGAGCAAGCGGGAGAA
GAAGGACAGGGTGTTCACAGACAAGACGAGCGCCACCGTGATCTGCCGAAAGAACGCCATCTCGGTGCGCGCCCAAGGAAGGT
ACTATTCCAGCTCCTGGAGCGAGTGGGCCTCGGTACCCTGCAGCGGCGGCGGGGCGGCGGCAGTAGGAATCTGCCCGTGGCTACC
CCGGACCCGGGCATGTTCCCCTGCCTCCACCACAGCCAGAACCTGCTGAGGGCCGTGAGCAACATGCTGCAGAAGGCCAGACAGAC
GCTGGAGTTCTACCCCTGCACGAGCGAGGAGATCGACCACGAGGACATCACCAAGGATAAATTCCACCGTCGAGGCCTGCCTGC
CCTTGGAGCTGACCAAGAATGAATCTGTCTGAACAGCAGGGAACCTCGTTTATCACCAATGGCAGCTGCCTCGCTCCAGGAAG
ACCAGCTTCATGATGGCCCTCTGTCTGAGCTCCATCTATGAGGACCTGAAGATGTACCAGGTGGAGTTCAAGACCATGAACGCGAA
GCTGCTGATGGACCCCAAGAGGCAGATCTTCGGATCAGAATATGCTGGCGGTGATCGACGAGCTCATGCAGGCCCTCAATTTCA
ATAGCGAGACAGTGCCCCAGAAGTCCTCCCTGGAGGAGCCCGACTTCTACAAGACCAAGATCAAGCTGTGTATCCTGCTGCACGCC
TTCCGGATCCGGGCCGTCACCATCGACCGGGTCATGAGCTACCTCAATGCCAGC

> hIL12AB_024(SEQ ID NO: 28)
ATGTGCCACCAGCAGCTGGTGATCTCCTGGTTCTCCCTGGTGTTCCTGGCCTCGCCCCTGGTGGCCATCTGGGAGCTGAA
GAAGGACGTGTACGTCGTGGAGCTCGACTGGTACCCCGACGCCCGGTGGAGATGGTGGTGCTGACCTGCGACACCCAGAGGAGG
ATGGCATCACCTGGACCCTGGATCAGTCCTCCGAGGTGCTGGGCTCCGGCAAGACGCTGACCATCCAAGTGAAGGAGTTCGGTGAC
GCCGGACAGTATACCTGCCATAAGGGCGGCGAGGTCCTGTCCCACAGCCTCCTCCTCCTGCATAAGAAGGAGGACGGCATCTGGAG
CACCGACATCCTGAAGGACCAGAAGGAGCCCAAGAACAAGACCTTTCTGAGGTGCGAGGCCAAGAACTACAGCGGCCGATTCACCT
GCTGGTGCTCACCACCATATCCACCGACCTGACTTTCTCCGTCAAGTCCTCCCGGGGTCAGCGACCCCCAGGGAGTGACCTGC
GGCGCCGCCACCCTCAGCGCCGAGCGGGTGCGGGGGACAACAAGGAGTACGAATACTCCGTGGAGTGCCAGGAGGACTCCGCCTG
CCCCGGCCGCCGAGGAGAGCCTGCCCATCGAGGTGATGGTCGACGCGGTGCACAAGCTGAAGTACGAGAACTACACCAGCAGTTTCT
TCATCAGGGATATCATCAAGCCAGATCCCCCGAAGAATCTGCAACTGAAGCCGCTGAAAAACTCACGACAGGTGGAGGTGAGCTGG
GAGTACCCCGACACGTGGAGCACCCCACATTCCTACTTCAGCCTGACCTTCTGCGTGCAGGTCCAGGGCAAGAGCAAGCGGGAGAA
GAAGGACAGGGTGTTCACGGATAAGACCAGTGCCACCGTGATCTGCAGGAAGAACGCCTCTATTAGCGTGAGGGCCCAGGATCGGT
ATTACTCCTCGAGCTGGAGCGAATGGGCCTCCGTGCCCTGCAGTGGGGGGTGAGGCGGGAGCAGGAACCTGCCCGTAGCAACC
CCCGACCCCGGGATGTTCCCCTGTCTGCACCACTCGCAGAACCTGCTGCGCGCGGTGAGCAACATGCTCAAAAAGCCCGTCAGAC
CTTAGAGTTCTACCCCTGCACCAGCGAAGAAATCGACCACGAAGACATCACCAAGGACAAAACCAGCACCGTGGAGGCGTGCCTGC
CGCTGGAGCTGACCAAGAACGAGAGTTGCCTCAACTCCAGGGAGACCAGCTTTATCACCAACGGCTCGTGCCTAGCCAGCCGGAAA
ACCAGCTTCATGATGGCCCTGTGCCTGAGCTCCATTTACGAGGACCTGAAGATGTATCAGGTGGAGTTCAAGACCATGAATGCCAA
ACTCCTGATGGACCCCAAGAGGCAGATCTTCCTGGACCAGAACATGCTCGCGGTGATCGATGAGCTGATGCAGGCCCTGAACTTTA
ATAGCGAGACCGTGCCCCAGAAAGCAGCCTGGAGGAGCCGGACTTCTACAAGACCAAAATCAAGCTGTGCATCCTGCTCCACGCC
TTCCGCATCCGGGCCGTGACCATCGACAGGGTGATGAGCTACCTGAACGCCAGC

> hIL12AB_025(SEQ ID NO: 29)
ATGTGCCATCAGCAGCTGGTATTTCCTGGTTCTCCCTGGTGTTCCTGGCCAGCCCCCTCGTGGCGATCTGGGAGCTAAA
AAGGACGTGTACGTGGTGGAGCTGGTACCCGGACGCACCCGGCAGATGGTCGTTCTGACCTGCGATACGCCAGAGGAGG
ACGGCATCACCTGGACCCTCGATCAGAGCAGCGAGGTCCTGGGGAGCGAAAGACCCTGACCATCCAGGTCAAGGAGTTCGGCGAC
GCCGGCCAGTACACCTGCCACAAAGGTGGCGAGGTCCTGAGCCACTCGCTGCTGCTCCTGCATAAGAAGGAGGACGGAATCTGGAG
CACAGACATCCTGAAAGACCAGAAGGAGCCCAAGAACAAGACCTTCCTGAGGTGCGAGGCCAAGAACTACAGCGGGCGCTTCACGT
GCTGGTGGCTGACCACCATCAGCACGGACCTCACCTTCTCCGTGAAGAGCAGCCGGGGATCCAGCGATCCCAAGGCGTCACCTGC
GGCGCGGCCACCCTGAGCGCGGAGAGGGTCAGGGGCGATAATAAGGAGTATGAGTACAGCGTGGAGTGCCAGGAGGACAGCGCCTG
```

TABLE 4A-continued

Sequence optimized Open Reading Frame sequences for human IL12

CCCGGCCGCCGAGGAGTCCCTGCCAATCGAAGTGATGGTCGACGCCGTGCACAAGCTGAAGTACGAGAACTACACCAGCAGCTTCT
TCATCCGGGATATCATCAAGCCCGATCCCCCGAAGAACCTGCAGCTGAAGCCCCTCAAGAACAGCCGGCAGGTGGAGGTGAGTTGG
GAGTACCCCGACACCTGGTCAACGCCCCACAGCTACTTCTCCCTGACCTTCTGTGTGCAGGTGCAGGGAAAGAGCAAGAGGGAGAA
GAAAGACCGGGTCTTCACCGACAAGACCAGCGCCACGGTGATCTGCAGGAAGAACGCAAGCATCTCCGTGAGGGCCCAGGACAGGT
ACTACAGCTCCAGCTGGTCCGAATGGGCCAGCGTGCCCTGTAGCGGCGGCGGGGGCGGTGGCAGCCGCAACCTCCCAGTGGCCACC
CCCGACCCCGGCATGTTCCCCTGCCTGCCACCACAGCCAGAATCTGCTGAGGGCCCTGAGTAACATGCTGCAGAAGGCAAGGCAAAC
CCTCGAATTCTATCCCTGCACCTCCGAGGAGATCGACCACGAGGATATCACCAAGGACAAGACCAGCACCGTCGAGGCCTGTCTCC
CCCTGGAGCTGACCAAGAATGAGAGCTGCCTGAACAGCGGGAGACCAGCTTCATCACCAACGGGAGCTGCCTGGCCTCCAGGAAG
ACCTCGTTCATGATGGCGCTGTGCCTCTCAAGCATATACGAGGATCTGAAGATGTACCAGGTGGAGTTTAAGACGATGAACGCCAA
GCTGCTGATGGACCCGAAGAGGCAGATCTTCCTGGACCAGAACATGCTGGCCGTGATAGACGAGCTCATGCAGGCCCTGAACTTCA
ACTCCGAGACCGTGCCGCAGAAGTCATCCCTCGAGGAGCCCGACTTCTATAAGACCAAGATCAAGCTGTGCATCCTGCTCCACGCC
TTCCGGATAAGGGCCGTGACGATCGACAGGGGTGATGAGCTACCTTAACGCCAGC

> hIL12AB_026(SEQ ID NO: 30)
ATGTGCCACCAGCAGCTCGTGATCAGCTGGTTCTCCCTGGTGTTTCTCGCCAGCCCCCTGGTGGCCATCTGGGAGCTGAA
GAAGGACGTGTACGTGGTGGAGCTGGACTGGTACCCTGACGCCCGGGGGAGATGGTCGTGCTGACCTGCGACACCCCCGAAGAGG
ACGGTATCACCTGGACCCTGGACCAGTCCAGCGAGGTGCTGGGCAGCGGCAAGACCCTGACTATTCAAGTCAAGGAGTTCGGAGAC
GCCGGCCAGTACACCTGCCACAAGGGTGGAGAGGTGTTATCACACAGCCTGCTGCTGCTGCACAAGAAGGAAGACGGGATCTGGAG
CACCGACATCCTGAAGGACCAGAAGGAGCCCAAAAACAAGACCTTCCTGCGGTGCGAGGCCAAGAATATTCGGGCCGCTTTACGT
GCTGGTGGCTGACCACCATCAGCACTGATCTCACCTTCAGCGTGAAGTCCTCCCGGGGGTCGTCCGACCCCCAGGGGGTGACCTGC
GGGGCCGCCACCCTGTCCGCCGAGAGAGTGAGGGGCGATAATAAGGAGTACGAGTACAGCGTTGAGTGCCAGGAAGATAGCGCCTG
TCCCGCCGCCGAGGAGAGCCTGCCCATCGAGGTGATGGTGGACGCCGTCCACAAGCTGAAGTATGAGAACTACACCTCAAGCTTCT
TCATCAGGGACATCATCAAACCCGATCCGCCCAAGAATCCTGCAGCTGAAGCCCCTGAAAAATAGCAGGCAGGTGGAGGTGAGCTGG
GAGTACCCCGACACCTGGTCCACCCCCATAGCTATTTCTCCCTGACGTTCTGCGTGCAGGTGCAAGGGAAGAGCAAGCGGGAGAA
GAAGGACCGGGTGTTCACCGACAAGACCTCCGCCACCGTGATCTGTAGGAAGAACGCGTCGATCTCGGTCAGGGCCCAGGACAGGT
ATTACAGCAGCAGCTGGAGCGAGTGGGCGAGCGTGCCCTGCTCGGGCGGCGGCGGCGGCGGGAGCAGAAATCTGCCCGTGGCCACC
CCAGACCCCGGAATGTTCCCCTGCCTGCACCATTCGCAGAACCTCCTGAGGGCCGTGAGCAACATGCTGCAGAAGGCCCGCCAGAC
GCTGGAGTTCTACCCCTGCACGAGCGAGGAGATCGACCACGAAGACATCACCAAGGACAAAACCAGCACCGTGGAGGCCTGCCTGC
CCCTGGAGCTGACCAAAAACGAATCCTGCCTCAACAGCGGGAGACCAGCTTCATCACCAACGGCAGCTGCCTGGCCAGCCGAAAG
ACCTCCTTCATGATGGCCCTCTGCCTGAGCAGCATCTATGAGGATCTGAAGATGTATCAGGTGGAGTTCAAGACCATGAATGCCAA
GCTGCTGATGGACCCCAAGAGGCAGATATTCCTGGACCAGAATATGCTGGCCGTGATCGACGAGCTGATGCAGGCCCTGAACTTCA
ACAGCGAGACCGTCCCCCAGAAGTCCAGCCTGGAGGAGCCGGACTTTTACAAAACGAAGATCAAGCTGTGCATACTGCTGCACGCC
TTCAGGATCCGGGCCGTGACAATCGACAGGGTGATGTCCTACCTGAACGCCAGC

> hIL12AB_027(SEQ ID NO: 31)
ATGTGTCACCAGCAGCTGGTGATCAGCTGGTTCTCCCTGGTGTTCCTGGCCAGCCCCCTGGTGGCCATCTGGGAGCTCAA
GAAGGACGTCTACGTCGTGGAGCTGGATTGGTACCCCGACGCTCCCGGGGAGATGGTGGTGCTGACCTGCGACACCCCCGAGGAGG
ACGGCATCACCTGGACGCTGGACCAGAGCTCAGAGGTGCTGGGAAGCCAGAAGACACTGACCATCCAGGTGAAGGAGTTCGGGGAT
GCCGGGCAGTATACCTGCCACAAGGGCGGCGAAGTGCTGAGCCATTCCCTGCTGCTGCTGCACAAGAAGGAGGACGGCATATGGTC
CACCGACATCCTGAAGGATCAGAAGGAGCCGAAGAATAAAACCTTCCTGAGGTGCGAGGCCAAGAATTACAGCGGCCGATTCACCT
GCTGGTGGCTGACCACCATCAGCACCGACCTGACCTTCAGTGTGAAGTCCTCACGGGGCAGCTCAGATCCCAGGGCGTGACCTGC
GGGGCCGCGACACTCAGCGCCGAGCGGGTGAGGGGTGATAACAAGGAGTACGAGTATTCTGTGGAGTGCCAGGAAGACTCCGCCTG
TCCCGCCGCCGAGGAGTCCCTGCCCATCGAGGTGATGGTGGACGCCGTCGATAAACTGAAGTACGAGAACTACACCTCCAGCTTCT
TCATCCCGGGATATAATCAAGCCCGACCCTCCGAAAAACCTGCAGCTGAAGCCCCTTAAAAACAGCCGGCAGGTGGAGGTGAGCTGG
GAGTACCCCGACACCTGGAGCACCCCCATAGCTATTTCAGCCTGACCTTCTGCGTGCAGGTGCAGGGAAGTCCAAGCGCGAGAA
AAAGGACCGGGTGTTCACCGACAAGCGAGCGCCACCGTGATCTGCCGGAAGAACGCCAGTATAAGCGTAAGGGCCCAGGATAGGT
ACTACAGCTCCAGCTGGTCGGAGTGGGCCTCCGTGCCCTGTTCCGGCGGCGGGGGGGTGGCAGCAGGAACCTCCCCGTGGCCACG
CCGGACCCCGGCATGTTCCCGTGCCTGCACCACTCCCAAAACCTCCTGCGGGCCGTCAGCAACATGCTGCAAAAGGCGCGCCAGAC
CCTGGAGTTTTACCCCTGTACCTCCGAAGAGATCGACCACGAGGATATCACCAAGGATAAGACCTCCACCGTGGAGGCCTGTCTCC
CCCTGGAGCTGACCAAGAACGAGAGCTGTCTTAACAGCAGAGAGACCTCGTTCATAACGAACGGCTCCTGCCTCGCTTCCAGGAAG
ACGTCGTTCATGATGGCGCTGTGCCTGTCCAGCATCTACGAGGACCTGAAGATGTATCAGGTCGAGTTCAAAACCATGAACGCCAA
GCTGCTGATGGACCCCAAGAGGCAGATCTTCCTGGACCAGAACATGCTGCCGTGATCGACGAGCTGATGCAGGCCCTGAACTTCA
ACAGCGAAACCGTGCCCCAGAAGTCAAGCCTGGAGGAGCCGGACTTCTATAAGACCAAGATCAAGCTGTGTATCCTGCTACACGCT
TTTCGTATCCGGGCCGTGACCATCGACAGGGTTATGTCGTACTTGAACGCCAGC

> hIL12AB_028(SEQ ID NO: 32)
ATGTGCCACCAACAGCTCGTGATCAGCTGGTTCAGCCTGGTGTTCCTGGCCAGCCCGCTGGTGGCCATCTGGGAGCTGAA
GAAGGACGTGTACGTGGTGGAGCTGGACTGGTACCCCGACGCCCCCGGCGAGATGGTGGTCCTGACCTGCGACACGCGGAAGAGG
ACGGCATCACCTGGACCCTGGATCAGTCCAGCGAGGTGCTGGGCTCCGGCAAGACCCTGACCATTCAGGTGAAGGAGTTCGGCGAC
GCCGGTCAGTACACCTGCCACAAGGGCGGCGAGGTGCTGAGCCACAGCCTACTGCTCCTGCACAAAAAGGAGGATGGAATCTGGTC
CACCGACATCCTCAAGGACCAGAAGGAGCCGAAGAACAAGACGTTCCTCCGGTGCGAGGCCAAGAACTACAGCGGCAGGTTTACCT
GCTGGTGGCTGACCACCATCAGCACCGACCTGACATTTTCCGTGAAGAGCAGCCGCGGCAGCAGCGATCCCAGGGCGTGACCTGC
GGGCGGCCACCCTGTCCGCCGAGCGTGTGAGGGGCGACAACAAGGAGTACGAGTACAGCGTGGAATGCCAGGAGGACAGCGCCTG
TCCCGCCGCCGAGGAGAGCCTGCCAATCGAGGTCATGGTGGACGCCGTCCACAAGCTGAAGTACGAGAACTACACCAGCAGCTTCT
TCATCAGGGACATCATCAAACCGGACCCGCCCAAGAACCTGCAGCTGAAACCCTTGAAAAACAGCAGGCAGGTGGAAGTGTCTTGG
GAGTACCCCGACACCTGGTCCACCCCCACAGCTACTTTAGCCTGACCTTCTGTGTGCAGGTCCAGGGCAAGTCCAAGAGGGAGAA
GAAGGACAGGGTGTTCACCGACAAAACCAGCGCCACCGTGATCTGCAGGAAGAACGCCTCCATCAGCGTGCGGGCCAGGACAGGT
ATTACAGCTCGTCGTGGAGCGAGTGGGCCAGCGTGCCCTGCTCCGGGGAGGCGGCGGCGGAAGCCGGAATCTGCCCGTGGCCACC
CCCGATCCCGGCATGTTCCCGTGTCTGCACCACAGCCAGAACTGCTGCGGGCCGTGAGCAACATGCTGCAGAAGGCCCGCCAAAC
CCTGGAGTTCTACCCCTGTACAAGCGAGGAGATCGACCATGAGGACATTACCAAGGACAAGACCAGCACCGTGGAGGCCTGCCTGC
CCCTCGAGCTCACAAAGAACGAATCCTGCCTGAATAGCCGCGAGACCAGCTTTATCACGAACGGGTCCTGCCTCGCCAGCCGGAAG
ACAAGCTTCATGATGGCCCTGTGCCTGAGCAGCATCTACGAGGACCTGAAAATGTACCAAGTGGAGTTCAAAACGATGAACGCCAA
GCTGCTGATGGACCCCAAGCGCAGATCTTCCTGGACCAGAACATGCTGGCCGTCATCGACGAGCTCATGCAGGCCCTGAACTTCA
ACAGCGAGACCGTGCCCCAGAAGAGCAGCCTGGAGGAGCCCGACTTCTACAAGACGAAGATCAAGCTCTGCATCCTGCTGCACGCT
TTCCGCATCCGCGCGGTGACCATCGACCGGGTGATGAGCTACCTCAACGCCAGT

TABLE 4A-continued

Sequence optimized Open Reading Frame sequences for human IL12

> hIL12AB_029(SEQ ID NO: 33)
ATGTGCCACCAACAGCTGGTGATCAGCTGGTTCAGCCTGGTGTTTCTGGCCTCCCCTCTGGTGGCCATCTGGGAGCTGAA
GAAGGACGTGTACGTGGTGGAGCTGGACTGGTACCCTGACGCCCCCGGCGAAATGGTGGTGCTGACGTGCGACACCCCCGAGGAGG
ATGGCATCACCTGGACCCTGGACCAAAGCAGCGAGGTCCTCGGAAGCGGCAAGACCCTCACTATCCAAGTGAAGGAGTTCGGGGAT
GCGGGCCAGTACACCTGCCACAAGGGCGGCGAGGTGCTGTCTCATAGCCTGCTGCTCCTGCATAAGAAGGAAGACGGCATCTGGAG
CACCGACATACTGAAGGATCAGAAGGAGCCCAAGAACAAGACCTTCCTGAGGTGCGAGGCCAAGAACTACTCCGGGCGCTTCACCT
GTTGGTGGCTGACCACCATCTCCACCGACCTGACCTTCAGCGTGAAGAGCAGCAGGGGGAGCAGCGACCCCCAGGGGGTGACCTGC
GGAGCCGCGACCTTGTCGGCCGAGCGGGTGAGGGGCGACAATAAGGAGTACGAGTACTCGGTCGAATGCCAGGAGGACTCCGCCTG
CCCCGCCGCCGAGGAGTCCCTCCCCATCGAAGTGATGGTGGACGCCGTCCACAAGCTGAAGTACGAGAACTACACCAGCAGCTTCT
TCATACGGGATATCATCAAGCCCGACCCCCCGAAGAACCTGCAGCTGAAACCCTTGAAGAACTCCAGGCAGGTGGAGGTGAGCTGG
GAGTACCCCGACACCTGGTCCACCCCGCACTCATACTTCAGCCTGACCTTCTGTGTACAGGTCCAGGGCAAGAGCAAGAGGGAAAA
GAAGGATAGGGTGTTCACCGACAAGACCTCCGCCACGGTGATCTGTCGGAAAAACGCCAGCATCTCCGTGCGGGCCCAGGACAGGT
ACTATTCCAGCAGCTGGAGCGAGTGGGCCTCCGTCCCCTGCTCCGGCGGCGGTGGCGGGGGCAGCAGGAACCTCCCCGTGGCCACC
CCCGATCCCGGGATGTTCCCATGCCTGCACCACAGCCAAAACCTGCTGAGGGCCGTCTCCAATATGCTGCAGAAGGCGAGGCAGAC
CCTGGAGTTCTACCCCTGTACCTCCGAGGAGATCGACCACGAGGATATCACCAAGGACAAGACCTCCACGGTCGAGGCGTGCCTGC
CCCTGGAGCTCACGAAGAACGAGAGCTGCCTTAACTCCAGGGAAACCTCGTTTATCACGAACGGCAGCTGCCTGGCGTCACGGAAG
ACCTCCTTTATGATGGCCCTATGTCTGTCCTCGATCTACGAGGACCTGAAGATGTACCAGGTGGAGTTCAAGACCATGAACGCCAA
GCTGCTGATGGATCCCAAGAGGCAGATTTTCCTGGACCAGAACATGCTGGCCGTGATTGACGAGCTGATGCAGGCGCTGAACTTCA
ACAGCGAGACAGTGCCGCAGAAGAGCTCCCTGGAGGAGCCGGACTTTTACAAGACCAAGATAAAGCTGTGCATCCTGCTCCACGCC
TTCAGAATACGGGCCGTCACCATCGATAGGGTGATGTCTTACCTGAACGCCTCC

> hIL12AB_030(SEQ ID NO: 34)
ATGTGCCACCAGCAGCTGGTGATTAGCTGGTTTAGCCTGGTGTTCCTGGCAAGCCCCCTGGTGGCCATCTGGGAACTGAA
AAAGGACGTGTACGTGGTCGAGCTGGATTGGTACCCCGACGCCCCCGGCGAAATGGTGGTGCTGACGTGTGATACCCCCGAGGAGG
ACGGGATCACCTGGACCCTGGATCAGAGCAGCGAGGTGCTGGGGAGCGGGAAGACCCTGACGATCCAGGTCAAGGAGTTCGGCGAC
GCTGGGCAGTACACCTGTCACAAGGGCGGGGAGGTGCTGTCCCACTCCCTGCTGCTCCTGCATAAGAAGGAGGACGGCATCTGGTC
CACCGACATCCTCAAGGACCAGAAGGAGCCCAAGAACAAGACCTTCCTGCGGTGTGAGGCGAAGAACTACAGCGGCCGTTTCACCT
GCTGGTGGCTGACGACAATCAGCACCGACTTGACGTTCTCCGTGAAGTCCTCCAGAGGCAGCTCCGACCCCCAAGGGGTGACGTGC
GGCGCGGCCACCCTGAGCGCCGAGCGGGTGCGGGGGGACAACAAGGAGTACGAGTACTCCGTGGAGTGCCAGGAGGACAGCGCCTG
TCCCGCAGCCGAGGAGTCCCTGCCCATCGAAGTCATGGTGGACGCCGTCCACAAGCTGAAGTACGAGAACTACACCAGCAGCTTCT
TCATCCGCGATATCATCAAGCCCGATCCCCCCAAAAACCTGCAACTGAAGCCGCTGAAGAATAGCAGGCAGGTGGAGGTGTCCTGG
GAGTACCCGGACACCTGGAGCACGCCCCACAGCTATTTCAGCCTGACCTTTTGCGTGCAGGTCCAGGGGAAGAGCAAGCGGGAGAA
GAAGGACCGCGTGTTTACGGACAAAACCAGCGCCACCGTGATCTGCAGGAAGAACGCCAGCATCAGCGTGAGGGCCCAGGACAGGT
ACTACAGCAGCTCCTGGAGCGAGTGGGCCTCCGTGCCCTGTTCCGGAGGCGGCGGGGGCGGTTCCCGGAACCTCCCCGTGGCCACC
CCCGACCCGGGCATGTTCCCGTGCCTGCACCACTCACAGATTGCTGAGGGCCGTGAGCAATATGCTGCAGAAGGCAGAGCAGAC
CCTGGAGTTTTATCCCTGCACCAGCGAGGAGATCGACCACGAAGACATCACCAAGGACAAGACCAGCACAGTGGAGGCCTGCCTGC
CCCTGGAACTGACCAAGAACGAGTCCTGTCTGAACTCCCGGGAAACCAGCTTCATAACCAACGGCTCCTGTCTCGCCAGCAGGAAG
ACCAGCTTCATGATGGCCCTGTGCCTCAGCTCCATCTACGAGGACCTCAAGATGTACCAGGTTGAGTTCAAGACCATGAACGCCAA
GCTCCTGATGGACCCCAAGAGGCAGATCTTCCTGGACCAGAATATGCTGGCCGTGATCGATGAGTTAATGCAGGCGCTGAACTTCA
ACAGCGAGACGGTGCCCCAAAAGTCCTCGCTGGAGGAGCCCGACTTCTACAAGACCAAGATCAAGCTGTGCATCCTCCTGCACGCC
TTCCGAATCCGGGCCGTAACCATCGACAGGGTGATGAGCTATCTCAACGCCTCC

> hIL12AB_031(SEQ ID NO: 35)
ATGTGCCACCAGCAGCTCGTGATCAGCTGGTTCTCGCTTGTGTTCCTGGCCTCCCCCCTCGTCGCCATCTGGGAGCTGAA
GAAAGACGTGTACGTGGTGGAGCTGGACTGGTATCCCGACGCCCCGGGGAGATGGTGGTGCTGACCTGCGACACCCCGGAAGAGG
ACGGCATCACCTGGACGCTCGACCAGTCGTCCGAAGTGCTGGGGTCGGGCAAGACCCTCACCATCCAGGTGAAGGAGTTCGGAGAC
GCCGGCCAGTACACCTGTCATAAGGGGGGAGAGGTGCTGAGCCACAGCCTCCTGCTGCTGCATAAAAAGGAGGACGGCATCTGGAG
CACCGATATCCTCAAGGACCAGAAGGAGCCCAAGAACAAGACGTTCCTGAGGTGTGAGGCCAAGAACTACAGCGGCCGGTTCACGT
GTTGGTGGCTCACCACCATCTCCACCGACCTCACCTTCTCCGTGAAGTCAAGCAGGGGCAGCTCCGACCCCCAAGGCGTCACCTGC
GGCGCCGCCACCCTGAGCGCCGAGAGGGTCAGGGGGGATAACAAGGAATACGAGTACAGTGTGGAGTGCCAAGAGGATAGCGCCTG
TCCCGCCGCCGAAGAGAGCCTGCCCATCGAAGTGATGGTGGACGCCGTCCACAAGCTGAAGTACGAGAACTACACCCTCCAGCTTCT
TCATCAGGGATATCATCAAGCCCGATCCCCCCAAGAACCTGCAGCTGAAGCCCCTGAAGAACAGCAGGCAGGTGGAGGTGAGCTGG
GAGTATCCCGACACGTGGAGCACCCCGCACAGCTACTTCTCGCTGACCTTCTGCGTGCAGGTGCAAGGGAAGTCAAGAGGGAGAA
GAAGGATAGGGTGTTCACCGACAAAACGAGCGCCACCGTGATCTGCCGGAAGAATGCCAGCATCTCTGTGAGGGCCCAGGACAGGT
ACTATTCCAGCTCCTGGTCGGAGTGGGCCAGCGTGCCCTGTAGCGGCGGGGGCGGCGGCAGGAACCTCCCCGGTTGCCACC
CCCGACCCCGGCATGTTCCCGTGCCTGCACCACTCGCAAAACCTGCTGCGCGCGGTCTCCAACATGCTGCAAAAGCGCGCAGAC
GCTGGAGTTCTACCCCTGCACCAGCGAGGAGATCGATCATGAAGATATCACCAAAGACAAGACCTCGACCGTGGAGGCCTGCCTGC
CCCTGGAGCTCACCAAGAACGAAAGCTGCCTGAACAGCAGGGAGACAAGCTTCATCACCAACGGCAGCTGCCTGGCCTCCCGGAAG
ACCAGCTTCATGATGGCCCTGTGCCTGTCCAGCATCTACGAGGATCTGAAGATGTACCAAGTGGAGTTTAAGACCATGAACGCCAA
GCTGTTAATGGACCCCAAAAGGCAGATCTTCCTGGATCAGAACATGCTGGCCGTCATCGACGAGCTGATGCAAGCCCTGAACTTCA
ACAGCGAGACGTGCCCCAGAAGCAGCCTCGAGGAGCCCGACTTCTATAAGACCAAGATAAAGCTGTGCATTCTGCTGCACGCC
TTCAGAATCAGGGCCGTGACCATCGATAGGGTGATGAGCTACCTGAACGCCAGC

> hIL12AB_032(SEQ ID NO: 36)
ATGTGTCACCAGCAGCTGGTGATTTCCTGGTTCAGTCTGGTGTTTCTTGCCAGCCCCCTGGTGGCCATCTGGGAGCTGAA
GAAAGACGTATACGTCGTGGAGCTGGACTGGTATCCCGACGCTCCCGGCGAGATGGTGGTCCTCACCTGCGACACCCCAGAGGAGG
ACGGCATCACCTGGACCCTGGACCAGAGCTCCGAGGTCCTGGGCAGCGGTAAGACCCTCACCATCCAGGTGAAGGAGTTTGGTGAT
GCCGGGCAGTATACCTGCCACAAGGGCGGCGAGGTGCTGTCCCACAGCCTCTGTTCTGCATAAGAAGGAGGATGGCATCTGGAG
CACCGACATCCTCAAGGACCAGAAAGAGCCCAAGAACAAGACCTTTCTGCGGTGCGAGGCGAAAAATTACTCCGGCCGGTTCACCT
GCTGGTGGCTGACCACCATCAGCACGGACCTGACGTTCTCCGTGAAGTCGAGCAGGGGGAGCTCCGATCCCCAGGGCGTGACCTGC
GGCGCGGCCACCCTGAGCGCCGAGCGCGTCCGCGGGGACAATAAGGAATACGAATATAGCGTGGAGTGCCAGGAGGACAGCGCCTG
CCCGGCCGCCGAGGAGAGCCTCCCGATCGAAGTGATGGTGGATGCCGTCCACAAGCTGAAGTACGAAAACTACACCAGCAGCTTCT
TCATTAGGGACATCATCAAGCCCGACCCCCCCAAAAACCTGCAGCTGAAGCCCCTGAAGAACAGCCGCCAGGTCGAGGTGCATGG
GAGTACCCAGACACCTGGAGCACCCCCCACTCCTACTTCAGCCTGACCTTCTGCGTCCAGGTGCAGGGAAAGTCAAACGGGAGAA
GAAGGATAGGGTCTTTACCGATAAGACGTCGGCCACCGTCATCTGCAGGAAGAACGCCAGCATAAGCGTGCGGGCGCAGGATCGGT
ACTACAGCTCGAGCTGGTCCGAATGGGCCTCCGTGCCCTGTAGCGGAGGGGGTGGCGGGGGCAGCAGGAACCTGCCCGTGGCCACC
CCCGACCCGGGCATGTTCCCTGCCTGCATCACAGTCAGAACCTGCTGAGGGCCGTGAGCAACATGCTCCAGAAGGCCCGCCAGAC

TABLE 4A-continued

Sequence optimized Open Reading Frame sequences for human IL12

CCTGGAGTTTTACCCCTGCACCAGCGAAGAGATCGATCACGAAGACATCACCAAAGACAAGACCTCCACCGTGGAGGCCTGTCTGC
CCCTGGAGCTGACCAAGAACGAGAGCTGTCTGAACAGCAGGGAGACCTCCTTCATCACCAACGGCTCCTGCCTGGCATCCCGGAAG
ACCAGCTTCATGATGGCCCTGTGTCTGAGCTCTATCTACGAGGACCTGAAGATGTACCAGGTCGAGTTCAAGACCATGAACGCCAA
GCTGCTGATGGACCCCAAGCGACAGATATTCTGGACCAGAACATGCTCGCCGTGATCGATGAACTGATGCAAGCCCTGAACTTCA
ATAGCGAGACCGTGCCCCAGAAAAGCAGCCTGGAGGAGCCCGACTTCTACAAGACCAAGATCAAACTGTGCATACTGCTGCACGCG
TTCAGGATCCGGGCCGTCACCATCGACCGGGTGATGTCCTATCTGAATGCCAGC

> hIL12AB_033(SEQ ID NO: 37)
ATGTGCCACCAGCAGCTCGTGATTAGCTGGTTTTCGCTGGTGTTCCTGGCCAGCCCTCTCGTGGCCATCTGGGAGCTGAA
AAAAGACGTGTACGTGGTGGAGCTGGACTGGTACCCGGACGCCCCCGGCGAGATGGTGGTGCTGACGTGCGACACCCCGGAAGAGG
ACGGCATCACCTGGACCCTGGACCAGTCATCCGAGGTCCTGGGCAGCGGCAAGACGCTCACCATCCAGGTGAAGGAGTTCGGCGAC
GCCGGCCAGTACACATGCCATAAGGGCGGGGAGGTGCTGAGCCACAGCCTGCTCCTCCTGCACAAGAAGGAGGATGGCATCTGGTC
TACAGACATCCTGAAGGACCAGAAAGAGCCCAAGAACAAGACCTTCCTCCGGTGCGAGGCCAAGAACTACTCCGGGCGGTTTACTT
GTTGGTGGCTGACCACCATCAGCACCGACCTCACCTTCAGCGTGAAGAGCTCCCGAGGGAGCTCCGACCCCCAGGGGGTCACCTGC
GGCGCCGCCACCCTGAGCGCCGAGCGGGTGAGGGGCGACAACAAGGAGTATGAATACAGCGTGGAATGCCAAGAGGACAGCGCCTG
TCCCGCGGCCGAGGAAAGCCTGCCCATCGAGGTGATGGTGGACGCCGTCCACAAACTCAAGTACGAGAACTACACCAGCAGTTTCT
TCATTCGCGACATCATCAAGCCGGACCCCCCCAAAAACCTGCAGCTCAAACCCCTGAAGAACAGCAGGCAGGTGGAGGTCAGCTGG
GAGTACCCGGACACCTGGAGCACCCCCCATAGCTACTTCAGCCTGACCTTCTGCGTGCAGGTGCAGGGCAAGAGCAAACGCGAGAA
GAAGGACCGGGTGTTTACCGACAAGACCAGCGCCACGGTGATCTGCCGAAAGAATGCAAGCATCTCCGTGAGGGCGCAGGACCGCT
ACTACTCTAGCAGCTGGAGCGAGTGGGCCAGCGTGCCCTGCAGCGGTGGCGGCGGAGGCGGCAGCCGTAACCTCCCCGTGGCCACC
CCCGACCCCGGCATGTTCCCGTGTCTGCACCACTCCCAGAACCTGCTGAGGGCCGTCAGCAATATGCTGCAGAAGGCCCGGCAGAC
GCTGGAGTTCTACCCCTGCACCTCCGAGGAGATCGACCATGAGGACATTACCAAGGACAAGACGAGCACTGTGGAGGCCTGCCTGC
CCCTGGAGCTCACCAAAAACGAGAGCTGCCTGAATAGCAGGGAGACGTCCTTCATCACCAACGGCAGCTGTCTGGCCAGCAGGAAG
ACCAGCTTCATGATGGCCCTGTGCCTCTCCTCCATATATGAGGATCTGAAGATGTACCAGGTGGAGTTCAAGACCATGAACGCCAA
GCTGCTGATGGATCCCAAGAGGCAGATCTTCCTGGACCAGAATATGCTGGCCGTGATTGACGAGCTGATGCAGGCCCTGAACTTTA
ATAGCGAGACCGTCCCCCAGAAGAGCAGCCTGGAGGAGCCCGACTTCTATAAGACCAAGATCAAGCTGTGCATACTGCTGCACGCG
TTTAGGATAAGGGCCGTCACCATCGACAGGGTGATGAGCTACCTGAATGCCAGC

> hIL12AB_034(SEQ ID NO: 38)
ATGTGCCACCAACAGCTGGTGATCTCCTGGTTCAGCCTGGTGTTCCTCGCCAGCCCCCTGGTGGCCATCTGGGAGCTGAA
GAAAGACGTGTACGTGGTGGAGCTGGACTGGTATCCCGACGCCCCCGGCGAGATGGTCGTGCTGACCTGCGACACCCCGGAGGAGG
ACGGCATCACCTGGACCCTGGATCAGTCCTCCGAGGTGCTGGGCAGCGGGAAGACCCTGACCATCCAGGTGAAAGAGTTCGGAGAT
GCCGGCCAGTATACCTGTCACAAGGGGGGTGAGGTGCTGAGCCATAGCCTCTTGCTTCTGCACAAGAAGGAGGACGGCATCTGGTC
CACCGACATCCTCAAGGACCAAAAGGAGCCGAAGAATAAAACGTTCCTGAGGTGCGAAGCCAAGAACTATTCCGGACGGTTCACCT
GCTGGTGGCTGACCACCATCAGCACCGACCTCACCTTCTCCGTAAAGTCAAGCAGGGGCAGCTCCGACCCCCAGGGCGTGACCTGC
GGAGCCGCCACCCTGAGCGCAGAGAGGGTGAGGGGCGACAACAAGGAGTACGAATACTCCGTCGAGTGCCAGGAGGACAGCGCCTG
CCCCGCCGCCGAGGAAAGTCTGCCCATCGAGGTGATGGTGGACGCCGTCCACAAGCTCAAATACGAGAACTACACCAGCAGCTTCT
TCATCCGGGATATCATCAAGCCCGACCCTCCAAAGAATCTGCAGCTGAAACCCCTTAAGAACAGCAGGCAGGTGGAGGTCAGCTGG
GAGTACCCCGACACCTGGAGCACGCCCCACTCCTACTTTAGCCTGACCTTTTGCGTGCAGGTGCAGGGGAAAAGCAAGCGGGAGAA
GAAGGACAGGGTGTTCACCGATAAGACCTCCGCTACCGTGATCTGCAGGAAGAATGCCAGCATCAGCGTGAGGGCCCAGGATCGGT
ACTACTCCAGCTCCTGGAGCGAGTGGGCCAGCGTGCCCTGCTCTGGCGGTGGCGGCGGGGGCAGCCGGAACCTGCCGGTGGCCACT
CCCGACCCGGGCATGTTCCCGTGCCTCCACCATTCCCAGAACCTGCTGCGGGCCGTGTCCAATATGCTCCAGAAGGCAAGGCAGAC
CCTGGAGTTCTACCCCTGCACCAGCGAGGAGATCGATCACGAGGACATCACCAAAGACAAAACCAGCACGGTCGAGGCCTGCCTGC
CCCTGGAACTCACCAAGAACGAAAGCTGTCTCAACAGCCGCGAGACCAGCTTCATAACAAACGGTTCCTGTCTGGCCTCCCGCAAG
ACCAGCTTTATGATGGCCCTCTGTCTGAGCTCCATCTATGAAGACCTGAAAATGTACCAGGTGGAGTTCAAAACCATGAACGCCAA
GCTTCTGATGGACCCCAAGAGGCAGATCTTCCTGGATCAGAACATGCTGGCCGTGATCGACGAGCTGATGCAGGCCCTGAACTTTA
ACTCCGAGACCGTGCCCCAGAAAAGCAGCCTGGAAGAGCCCGATTTCTACAAAACGAAGATCAAGCTGTGCATCCTGCTGCACGCC
TTCCGGATCCGTGCGGTGACCATCGATAGGGTGATGAGCTACCTGAACGCCAGC

> hIL12AB_035(SEQ ID NO: 39)
ATGTGCCACCAACAGCTGGTAATCAGCTGGTTCAGCCTGGTTTTCCTCGCGTCGCCCCTGGTGGCCATCTGGGAGTTAAA
GAAGGACGTGTACGTGGTGGAGCTGGATTGGTACCCCGACGCCCCGGCGAGATGGTCGTCACCTGCGATACCCCGGAGGAG
ACGGGATCACCTGGACCCTGGACCAATCCAGCGAGGTGCTGGGCAGCGGCAAGACCCTGACCATACAGGTGAAGGAATTTGGGGAC
GCCGGGCAGTACACCTGCCACAAGGGCGGGGAAGTGCTGTCCCACTCCCTCCTGCTGCTGCATAAGAAGGAGGACGGCATCTGGAG
CACCGACATCCTGAAGGACCAAAAGGAGCCCAAGAACAAGACCTTCCTGAGGTGCGAGGCCAAAAACTATTCCGGCCGCTTTACCT
GTTGGTGGCTGACCACCATCTCCACCGATCTGACCTTCAGCGTGAAGTCGTCTAGGGGCTCCTCCGACCCCCAGGGCGTAACCTGC
GGCGCCGCCGACCCTGAGCGCCGAGAGGGTGCGGGCGATAACAAAGAGTACGAGTACTCGGTCGAGTGCCAGGAGGACAGCGCCTG
TCCGGCCGCCGAGGAGAGCCTGCCCATCGAGGTGATGGTGGACGCCGTCCACAAGCTGAAGTACGAGAACTACACCAGTTCGTTCT
TCATCAGGGACATCATCAAGCCGGACCCCCCCAAGAACCTCCAGCTGAAGCCCCTGAAGAACAGCAGGCAGGTGGAAGTGTCCTGG
GAGTATCCCGACACCTGGAGCACCCCCCACAGCTACTTCAGCCTGACCTTTTGCGTGCAGGTGCAGGGCAAAAAGCAAGAGGGAAAA
GAAGGACCGGGTGTTCACCGATAAGACGAGCGCCACCGTTATCTGCAGGAAGAACGCCTCCATAAGCGTGAGGGCGCAGGACCGTT
ACTACAGCAGCAGCTGGAGTGAGTGGGCCAAGCGTGCCCTGTAGCGGCGGGGCGGGGCGGGTCCCGCAACCTCCCCGTCGCCACC
CCCGACCCCAGGCATGTTTCCGTGCCTGCACCACAGCCAGAACCTGCTGCGGGCCGTTAGCAACATGCTGCAGAAGGCCAGGCAGAC
CCTCGAGTTCTATCCCTGCACATCTGAGGAGATCGACCACGAAGACATCACTAAGGATAAGACCTCCACCGTGGAGGCCTGTCTGC
CCCTCGAGCTGACCAAGAATGAATCCTGCCTGAACAGCCGAGAGACCAGCTTTATCACCAACGGCAGCTGCCTGGCCAGCAGGAAG
ACCTCCTTCATGATGGCCCTGTGCCTCTCCAGCATCTACGAGGATCTGAAGATGTACCAGGTAGAGTTCAAGACGATGAACGCCAA
GCTCCTGATGGACCCCAAGAGGCAGATATTCTGGACCAGAACATGCTGGCGGTGATCGACGAGCTGATGCAGGCCCTGAATTTCA
ACAGCGAGACGGTGCCACAGAAGTCCAGCCTGGAGGAGCCAGACTTCTACAAGACCAAGATCAAACTGTGCATCCTCCTGCACGCG
TTCAGGATCCGCGCCGTCACCATAGACAGGGTGATGAGTTATCTGAACGCCAGC

> hIL12AB_036(SEQ ID NO: 40)
ATGTGCCATCAGCAGCTGGTAATCAGCTGGTTTAGCCTGGTGTTCCTGGCCAGCCCCACTGGTGGCCATCTGGGAGCTGAA
GAAGGACGTGTACGTGGTGGAACTGGACTGGTACCCCGACGCCCGGCGAGATGGTCGTTGACCTGTGACACCCCGGAGGAAG
ACGGTATCACCTGGACCCTGGATCAGAGCTCCGAGGTGCTGGGCTCCGGCAAGACACTGACCATCCAAGTTAAGGAATTTGGGGAC
GCCGGCCAGTACACCTGCCACAAGGGGGGCGAGGTGCTGTCCCACTCCCTGCTCTTCTGCATAAGAAGGAGGATGGCATCTGGTC
CACCGACATACTGAAGGACCAGAAGGAGCCCAAGAATAAGACCTTCCTGAGATGCGAGGCCAAGAACTACTCGGAAGGTTCACCT
GCTGGTGGCTGACCACCATCAGCACCGACCTGACCTTCTCCGTGAAGAGCTCCGGGGCAGCTCCGACCCCAGGGCGTAACCTGT
GGGGCCGCTACCCTGTCCGCCGAGAGGGTCCGGGGCGACAACAAGGAATACGAGTACAGCGTGGAGTGCCAGGAGGACTCCGCCTG

TABLE 4A-continued

Sequence optimized Open Reading Frame sequences for human IL12

CCCCGCCGCCGAGGAGTCGCTGCCCATAGAGGTGATGGTGGACGCCGTGCACAAGCTCAAGTACGAGAATTACACCAGCAGCTTCT
TTATCAGGGACATAATTAAGCCGGACCCCCCAAAGAATCTGCAGCTGAAGCCCCTGAAGAATAGCCGGCAGGTGGAAGTGTCCTGG
GAGTACCCCGACACCTGGAGCACCCCCCACTCCTATTTCTCACTGACATTCTGCGTGCAGGTGCAAGGGAAAAGCAAGAGGGAGAA
GAAGGATAGGGTGTTCACCGACAAGCAAGCGCCACCGTGATCTGCCGAAAAAATGCCAGCATCAGCGTGAGGGCCCAGGATCGGT
ATTACAGCAGCTCCTGGAGCGAGTGGGCCAGCGTGCCCTGTTCCGGCGGGGAGGGGCGGCTCCCGGAACCTGCCGGTGGCCACC
CCCGACCCTGGCATGTTCCCCTGCCTGCATCACAGCCAGAACCTGCTCCGGGCCGTTCGAACATGCTGCAGAAGGCCCGGCAGAC
CCTCGAGTTTTACCCCTGCACCAGCGAAGAGATCGACCACGAAGACATAACCAAGGACAAGACCAGCACGGTGGAGGCCTGCCTGC
CCCTGGAGCTTACCAAAAACGAGTCCTGCCTGAACAGCCGGGAAACCAGCTTCATAACGAACGGGAGCTGCCTGGCCTCCAGGAAG
ACCAGCTTCATGATGGCGCTGTGTCTGTCCAGCATATACGAGGATCTGAAGATGTATCAGGTGGAATTCAAAACTATGAATGCCAA
GCTCCTGATGGACCCCAAGAGGCAGATCTTCCTGGACCAGAACATGCTAGCCGTGATCGACGAGCTGATGCAGGCCCTCAACTTCA
ACTCGGAGACGGTGCCCCAGAAGTCCAGCCTCGAGGAGCCCGACTTCTACAAGACCAAGATCAAGCTGTGCATACTGCTGCATGCC
TTCAGGATAAGGGCGGTGACTATCGACAGGGTCATGTCCTACCTGAACGCCAGC

> hIL12AB_037(SEQ ID NO: 41)
ATGTGCCACCAACAACTGGTGATCAGCTGGTTCTCCCTGGTGTTCCTGGCCAGCCCCCTGGTGGCCATCTGGGAGCTCAA
AAAAGACGTGTACGTGGTGGAGCTCGATTGGTACCCAGACGCGCCGGGGGAAATGGTGGTGCTGACCTGCGACACCCCAGAGGAGG
ATGGCATCACGTGGACGCTGGATCAGTCCAGCGAGGTGCTGGGGAGCGGCAAGACGCTCACCATCCAGGTGAAGGAATTTGGCGAC
GCGGGCCAGTATACCTGTCACAAGGGCGGCGAGGTGCTGAGCCACTCCCTGCTGCTGCTGCACAAGAAGGAGGATGGGATCTGGTC
AACCGATATCCTGAAAGACCAGAAGGAGCCCAAGAACAAGACCTTCCTGCGCTGCGAGGCCAAGAACTATAGCGGCAGGTTCACCT
GCTGGTGGCTGACCACCATCAGCACCGACCTGACCTTCAGCGTGAAATCCTCCAGGGGCAGCAGCGACCCCCAGGGCGTGACCTGC
GGTGCCGCCACGCTCTCCGCCGAGCGAGTGAGGGGTGACAACAAGGAGTACGAGTACAGCGTGGAATGTCAGGAGGACAGCGCCTG
TCCCGCCGCCGAGGAGTCGCTGCCCATCGAGGTGATGGTCGACGCGGTGCACAAGCTCAAATACGAGAATTACACCAGCAGCTTCT
TCATCAGGGACATCATCAAGCCCGACCCCCCCAAGAACCTGCAGCTGAAGCCCCTTGAAGAACAGCAGGCAGGTGGAGGTGAGCTGG
GAGTACCCCGACACCTGGAGCACCCCCCACTCCTACTTCAGCCTGACGTTCTGTGTGCAGGTGCAGGGGAAGTCCAAGAGGGAGAA
GAAGGACCGGGTGTTCACCGACAAGACCAGCGCCACCGTGATATGCCGCAAGAACGCGTCCATCAGCGTTCGCGCCCAGGACCGCT
ACTACAGCAGCTCCTGGTCCGAATGGGCCAGCGTGCCCTGCAGCGGTGGAGGGGGCGGGGCTCCAGGAATCTGCCGGTGGCCACC
CCCGACCCCGGGATGTTCCCCGTGTCTGCATCACTCCCAGAACCTGCTGCGGGCCGTGAGCAATATGCTGCAGAAGGCCAGGCAGAC
GCTCGAGTTCTACCCCTGCACCTCCGAAGAGATCGACCATGAGGACATCACCAAGGACAAGACCAGCACCGTGGAGGCCTGCCTCC
CCCTGGAGCTGACCAAAAACGAGAGCTGCCTGAACTCCAGGGAGACCAGCTTTATAACCAACGGCAGCTGCCTCGCCTCCAGGAAG
ACCTCGTTTATGATGGCCCTCTGCCTGTCCAGCATCTACGAGGACCTGAAGATGTACCAGGTGGAGTTCAAGACCATGAACGCGAA
GTTGCTCATGGACCCCAAGAGGCAGATCTTCCTGGACCAGAACATGCTCGCGGTGATCGACGAGCTGATGCAAGCCCTGAACTTCA
ACAGCGAGACCGTGCCCCAGAAGAGCAGCCTGGAAGAGCCCGACTTCTACAAGACCAAGATCAAGCTGTGCATCCTGCTGCACGCC
TTCCGGATCCGGGCCGTGACCATCGACAGGGTGATGAGCTACCTCAACGCCTCC

> hIL12AB_038(SEQ ID NO: 42)
ATGTGCCACCAGCAGCTCGTGATCAGCTGGTTCTCCCTCGTCTTCCTGGCCTCCCCGCTGGTGGCCATCTGGGAGCTGAA
GAAGGACGTGTACGTGGTGGAGCTGGACTGGTATCCCGACGCCCCCGGCGAGATGGTGGTGCTGACGTGCGACACCAGAAGAGG
ACGGGATCACATGGACCCTGGATCAGTCGTCCGAGGTGCTGGGGAGCGGCAAGACCCTCAGTCCAAGTGAAGGAGTTCGGGGAC
GCCGGCCAGTACACCTGCCACAAGGGCGGGAGGTGCTCTCCCATAGCCTGCTCCTCCTGCACAAAAAGGAGGATGGCATCTGGAG
CACCGACATCCTGAAGGACCAGAAGGAGCCCAAGAACAAGACATTTCTCAGGTGTGAGGCCAAGAACTATTCGGGCAGGTTTACCT
GTTGGTGGCTCACCACCATCTCTACCGACCTGACGTTCTCCGTCAAGTCAAGCAGGGGGAGCTCGGACCCCCAGGGGGTGACATGT
GGGGCCGCCACCCTGAGCGCGGAGCGTGTCCGCGGCGACAACAAGGAGTACGAGTATTCCGTGGAGTGCCAGGAGGACAGCGCCTG
CCCCGCCGCCGAGGAGTCCCTGCCCATAGAGGTGATGGTGGACGCTGTGCACAAGTTGAAGTACGAGAAATTATACCTCCTCGTTCT
TCATTAGGGACATCATCAAGCCTGACCCCCCGAAGAACCTACAACTCAAGCCCCTCAAGAACTCCCGCCAGGTGGAGGTGTCCTGG
GAGTACCCCGACACCTGGTCCACCCCGCACAGCTACTTCAGCCTGACCTTCTGCGTGCAGGTCCAGGGGAAGAGCAAGCGTGAAAA
GAAAGACAGGGTGTTCACCGACAAGCGAGCGCCACCGTGATCTGCAGGAAAAACGCCTCCATCTCCGTGCGCGCCCAGGACAGGT
ACTACAGTAGCTCCTGGAGCGAATGGGCCAGCGTGCCGTGCAGCGGCGGGGAGGAGGCGGCAGTCGCAACCTGCCCGTGGCCACC
CCCGACCCCGGCATGTTCCCATGCCTGCACCACAGCCAGAACCTGCTGAGGGCAGTCAGCAATATGCTGCAGAAGGCCAGGCAGAC
CCTGGAGTTTTATCCCTGCACCAGCGAGGAGATCGACCACGAGGACATCACCAAGGACAAGACCTCCACCGTCGAGGCCTGCCTGC
CACTGGAGCTGACCAAAAACGAGAGCTGCCTGAACTCCAGGGAGACCTCCTTCATCACCAACGGGAGCTGCCTGGCAGCCGGAAG
ACCAGCTTCATGATGGCGCTGTGCCTCAGCAGCATCTACGAGGATCTCAAGATGTACCAGGTGGAGTTCAAGACCATGAACGCGAA
GCTGCTGATGGACCCCAAGCGGCAGATCTTCCTGGACCAGAACATGCTGGCCGTGATTGACGAGCTCATGCAGGCCCTGAACTTCA
ATAGCGAGACCGTCCCCCAAAAGAGCAGCCTGGAGGAACCCGACTTCTACAAAACGAAGATCAAGCTCTGCATCCTGCTGCACGCC
TTCCGGATCCGGGCCGTGACCATCGATCGTGTGATGAGCTACCTGAACGCCTCG

> hIL12AB_039(SEQ ID NO: 43)
ATGTGCCACCAGCAGCTCGTCATCTCCTGGTTTAGCCTGGTGTTTCTGGCCTCCCCCCTGGTCGCCATCTGGGAGCTGAA
GAAAGACGTGTACGTGGTGGAGCTGGACTGGTACCCGGACGCTCCCGGGGAGATGGTGGTGCTGACCTGCGACACCCCGAGGAGG
ACGGCATCACCTGGACCCTGGACCAGAGCTCCGAGGTGCTCGGGAGCGGCAAGACCCTGACCATTCAGGTGAAAGAGTTCGGCGAC
GCCGGCCAATATACCTGCCACAAGGGGGGGAGGTCCTGTCGCATTCCCTGCTGCTGCTTCACAAAAAGGAGGATGGCATCTGGAG
CACCGACATCCTGAAGGACCAGAAGAACCCAAGAACAAGACGTTCCTGCGCTGCGAGGCCAAGAACTACAGCGGCCGGTTCACCT
GTTGGTGGCTGACCACCATCTCCACCGACCTGACTTTTCTCGGTGAAGAGCAGCCGCGGGAGCAGCGACCCCCAGGGAGTGACCTGC
GGCGCCGCCACCCTGAGCGCCGAAAGGGTGAGGGGCGACAATAAAGAGTACGAGTATTCCGTGGAGTGCCAGGAGGACAGCGCCTG
TCCCGCCGCCGAGGAGTCCCTGCCTATCGAGGTGATGGTCGACGCCGTGCACAAGTCAAGTACGAAAATTACACCAGCAGCTTTT
TCATCAGGGATATCATCAAACCAGACCCCCCCAAGAACCTGCAGCTGAAGCCCCTGAAAACAGCAGGCAGGTGGAAGTGAGCTGG
GAATACCCCGATACCTGGTCCACCCCCACAGCTACTTCAGCCTGACCTTCTGCGTGCAGGTGCAGGGGAAGTCCAAGCGGGAGAA
GAAAGATCGGGTGTTCACGGACAAGACCAGCGCCACCGTGATTTGCAGGAAAAACGCCAGCATCTCCGTGAGGGCTCAGGACAGGT
ACTACAGCTCCAGCTGGAGCGAGTGGGCCTCCGTGCCTTGCAGCGGGGAGGAGGCGGCGGCAGCAGGAATCTGCCCGTCGCAACC
CCCGACCCCGGCATGTTCCCCTGCCTGCACCACAGCCAGAATTCTGCGAGCCGTGAGCAATATGCTCCAGAAGGCCCGGCAGAC
GCTGGAGTTCTACCCCTGCACCTCCGAGGAGATCGACCACGAGGACATCACCAAGGATAAGACGAGCACCGTCGAGGCCTGTCTCC
CCCTGGAGCTCACCAAGAACGAGTCCTGCCTGAATAGCAGGGAGACGTCCTTCATAACCAACGGCAGCTGTCTGGCGTCCAGGAAG
ACCAGCTTCATGATGGCCCTCTGCCTGAGCTCCATCTACGAGGACCTCAAGATGTACCAGGTCGAGTTCAAGACCATGAACGCAAA
ACTGCTCATGGATCCAAAGAGGCAGATCTTTTCTGGACCAGAACATGCTGGCCGTGATCGATGAACTCATGCAGGCCCTGAATTTCA
ATTCCGAGACCGTGCCCCAGAAGAGCTCCTGGAGGAACCCGACTTCTACAAAACAAAGATCAAGCTGTGTATCCTCCTGCACGCC
TTCCGGATCAGGGCCGTCACCATTGACCGGGTGATGTCCTACCTGAACGCCAGC

TABLE 4A-continued

Sequence optimized Open Reading Frame sequences for human IL12

```
> hIL12AB_040(SEQ ID NO: 44)
ATGTGCCATCAGCAGCTGGTGATCAGCTGGTTCAGCCTCGTGTTCCTCGCCAGCCCCCTCGTGGCCATCTGGGAGCTGAA
AAAGGACGTGTACGTGGTGGAGCTGGACTGGTATCCCGACGCCCCGGGCGAGATGGTGGTGCTGACCTGCGACACCCCCGAGGAGG
ACGGCATTACCTGGACACTGGACCAGAGCAGCGAGGTCCTGGGCAGCGGGAAGACCCTGACAATTCAGGTGAAGGAGTTCGGCGAC
GCCGGACAGTACACGTGCCACAAGGGGGGGGAGGTGCTGTCCCACAGCTTCCTCCTGCTGCACAAGAAGGAGGATGGCATCTGGAG
CACCGACATCCTGAAGGATCAGAAGGAGCCCAAGAACAAGACCTTTCTGAGATGCGAGGCCAAGAATTACAGCGGCCGTTTCACCT
GCTGGTGGCTCACCACCATCAGCACCGACCTGACCTTCAGCGTGAAATCCTCCAGGGGCTCCTCCGACCCGCAGGGAGTGACCTGC
GGCGCCGCCACACTGAGCGCCGAGCGGGTCAGAGGGGACAACAAGGAGTACGAGTACAGCGTTGAGTGCCAGGAGGACAGCGCCTG
TCCCGCGGCCGAGGAATCCCTGCCCATCGAGGTGATGGTGGACGCAGTGCACAAGCTGAAGTACGAGAACTATACCTCGAGCTTCT
TCATCCGGGATATCATTAAGCCCGATCCCCCGAAGAACCTGCAGCTCAAACCCCTGAAGAACAGCAGGCAGGTGGAGGTCTCCTGG
GAGTACCCCGACACATGGTCCACCCCCATTCCTATTTCTCCCTGACCTTTTGCGTGCAGGTGCAGGGCAAGAGCAAGAGGGAGAA
AAAGGACAGGGTGTTCACCGACAAGACCTCCGCCACCGTGATCTGCCGTAAGAACGCTAGCATCAGCGTCAGGGCCCAGGACAGGT
ACTATAGCAGCTCCTGGTCCGAGTGGGCCAGCGTCCCGTGCAGCGGCGGGGCGGTGGAGGCTCCCGGAACCTCCCCGTGGCCACC
CCGGACCCCGGGATGTTTCCCTGCCTGCATCACAGCCAGAACCTGCTGAGGGCCGTGTCCAACATGCTGCAGAAGGCCAGGCAGAC
ACTCGAGTTTTACCCCTGCACCAGCGAGGAGATCGACCACGAAGACATCACCAAGGACAAGACCTCCACCGTGGAGGCATGCCTGC
CCCTGGAGCTGACCAAAACGAAAGCTGTCTGAACTCCAGGGAGACCTCCTTTATCACGAACGGCTCATGCCTGGCCTCCAGAAAG
ACCAGCTTCATGATGGCCCTGTGCCTGAGCTCCATCTACGAGGACTTGAAATGTACCAGGTCGAGTTCAAGACCATGAACGCCAA
GCTGCTCATGGACCCCAAAAGGCAGATCTTTCTGGACCAGAATATGCTGGCCGTGATCGACGAGCTCATGCAAGCCCTGAATTTCA
ACAGCGAGACCGTGCCCCAGAAGTCCTCCCTGGAGGAGCCCGACTTCTACAAGACCAAGATCAAGCTGTGCATACTCCTGCACGCG
TTTAGGATCAGGGCGGTGACCATCGATAGGGTGATGAGCTACCTGAATGCCTCC

> hIL12AB_002 (SEQ ID NO: 236)
ATGTGCCACCAGCAGCTGGTGATCAGCTGGTTCAGCCTGGTGTTCCTGGCCAGCCCCCTGGTGGCCATCTGGGAGCTGAAGAAGGA
CGTGTACGTGGTGGAGTTGGATTGGTACCCCGACGCCCCCGGCGAGATGGTGGTGCTGACCTGCGACACCCCCGAGGAGGACGGCA
TCACCTGGACCCTGGACCAGAGCAGCGAGGTGCTGGGCAGCGGCAAGACCCTGACCATCCAGGTGAAGGAGTTCGGCGACGCCGGC
CAGTACACCTGCCACAAGGGCGGCGAGGTGCTGAGCCACAGCTTCCTGCTGCTGCACAAGAAGGAGGACGGCATCTGGAGCACCGA
CATCCTGAAGGACCAGAAGGAGCCCAAGAACAAGACCTTCCTGAGATGCGAGGCCAAGAACTACAGCGGCAGATTCACCTGCTGGT
GGCTGACCACCATCAGCACCGACCTGACCTTCAGCGTGAAGAGCAGCAGAGGCAGCAGCGACCCCCAGGGCGTGACCTGCGGCGCC
GCCACCCTGAGCGCCGAGAGTGAGAGGCGACAACAAGGAGTACGAGTACAGCGTGGAGTGCCAGGAAGATAGCGCCTGCCCCGC
CGCCGAGGAGAGCCTGCCCATCGAGGTGATGGTGGACGCCGTGCACAAGCTGAAGTACGAGAACTACACCAGCAGCTTCTTCATCA
GAGATATCATCAAGCCCGACCCCCCCAAGAACCTGCAGCTGAAGCCCCTGAAGAACAGCAGGCAGGTGGAGGTGAGCTGGGAGTAC
CCCGACACCTGGAGCACCCCCCACAGCTACTTCAGCCTGACCTTCTGCGTGCAGGTGCAGGGCAAGAGCAAGAGAGAGAAGAAGA
TAGAGTGTTCACCGACAAGACCAGCGCCACCGTGATCTGCAGAAAGAACGCCAGCATCAGCGTGAGAGCCCAAGATAGATACTACA
GCAGCAGCTGGAGCGAGTGGGCCAGCGTGCCCTGCAGCGGCGGCGGCGGCGGCAGCAGAAACCTGCCCGTGGCCACCCCCGAC
CCCGGCATGTTCCCCTGCCTGCACCACAGCCAGAACCTGCTGAGAGCCGTGAGCAACATGCTGCAGAAGGCCCGGCAGACCCTGGA
GTTCTACCCCTGCACCAGCGAGGAGATCGACCACGAAGATATCACCAAGGATAAGACCAGCACCGTGGAGGCCTGCCTGCCCCTGG
AGCTGACCAAGAACGAGAGCTGCCTGAACAGCAGAGAGACCAGCTTCATCACCAACGGCAGCTGCCTGGCCAGCAGAAAGACCAGC
TTCATGATGGCCCTGTGCCTGAGCAGCATCTACGAGGACCTGAAGATGTACCAGGTGGAGTTCAAGACCATGAACGCCAAGCTGCT
GATGGACCCCAAGCGGCAGATCTTCCTGGACCAGAACATGCTGGCCGTGATCGACGAGCTGATGCAGGCCCTGAACTTCAACAGCG
AGACCGTGCCCCAGAAGAGCAGCCTGGAGGAGCCCGACTTCTACAAGACCAAGATCAAGCTGTGCATCCTGCTGCACGCCTTCAGA
ATCAGAGCCGTGACCATCGACAGAGTGATGAGCTACCTGAACGCCAGC
```

TABLE 4B

Sequence Optimized Polynucleotides Comprising 5' UTR, ORF, 3' UTR

| | |
|---|---|
| hIL12AB_001 (SEQ ID NO: 55) | TCAAGCTTTTGGACCCTCGTACAGAAGCTAATACGACTCACTATAGGGAAATAAGAGAGAAAAGAAGAGTAAGAAGAAA TATAAGAGCCACCATGTGTCACCAGCAGCTGGTCATTAGCTGGTTTAGCCTTGTGTTCCTGGCCTCCCCCCTTGTCGCT ATTTGGGAGCTCAAGAAGGACGTGTACGTGGTGGAGTTGGATTGGTACCCAGACGCGCCCGGAGAGATGGTAGTTCTGA CCTGTGATACCCCAGAGGAGGACGGCATCACCTGGACGCTGGACCAAAGCAGCGAGGTTTTGGGCTCAGGGAAAACGCT GACCATCCAGGTGAAGGAATTCGGCGACGCCGGGCAGTACACCTGCCATAAGGGAGGAGAGGTGCTGAGCCATTCCCTT CTTCTGCTGCACAAGAAGAGGACGGCATCTGGTCTACCGACATCCTGAAAGACCAGAAGGAGCCCAAGAACAAAACCT TCCTGAGGTGCGAGGCCAAGAACTACTCCGGCAGGTTCACTTGTTGGTGGCTGACCACCATCAGTACAGACCTGACTTT TAGTGTAAAAAGCTCCAGAGGCTCGTCCGATCCCCAAGGGGTGACCTGCGGCAGCCACTCTGAGCGCTGAGCGCGTG CGCGGTGACAATAAAGAGTACGAGTACAGCGTTGAGTGTCAAGAAGATAGCGCTTGCCCTGCCGCCGAGGAGAGCCTGC CTATCGAGGTGATGGTTGACGCAGTGCACAAGCTTAAGTACGAGAATTACACCAGCTCATTCTTCATTAGAGATATAAT CAAGCCTGACCCACCCAAGAACCTGCAGCTGAAGCCACTGAAGAACTCACGGCAGGTCGAAGTGAGCTGGGAGTACCCC GACACCTGGAGCACTCCTCATTCCTATTTCTCTTACATTCTGCGTCCAGGTGCAGGGCAAGAGCAAGCGGGAAAAGA AGGATCGAGTCTTCACCGACAAAAACAAGCGCGACCGTGATTTGCAGGAAGAACGCCAGCATCTCCGTCAGAGCCCAGGA TAGATACTATAGTAGCAGCTGGAGCGAGTGGGCAAGCGTGCCCTGTTCCGGCGGCGGGGGCGGGGGCAGCCGAAACTTG CCTGTCGCTACCCCGGACCCTGGAATGTTTCCGTGTCTGCACCACAGCCAGAACCTGCTGAGAGCTGTGTCGAATATGC TCCAGAAGGCCCGGCAGACCCTTGAGTTCTACCCCTGTACCAGCGAAGAGATCGATCATGAAGATATCACGAAAGATAA AACATCCACCGTCGAGGCTTGTCTCCCGCTGGAGCTGACCAAGAACGAGAGCTGTCTGAATAGCGGGAGACGTCTTTC ATCACGAATGGTAGCTGTCTGGCCAGCAGGAAAACTTCCTTCATGATGGCTCTCTGCCTGAGCTCTATCTATGAAGATC TGAAGATGTATCAGGTGGAGTTTAAAACAATGAACGCCAAGCTCCTGATGGACCCCAAAAAGGCAAATCTTTCTGGACCA GAATATGCTGGCCGTGATAGACGAGCTGATGCAGGCACTGAACTTCAACAGCGAGACAGGTGCCACAGAAATCCAGCCTG GAGGAGCCTGACTTTTACAAAACTAAGATCAAGCTGTGTATCCTGCTGCACGCCTTTAGAATCCGTGCCGTGACTATCG ACAGGGTGATGTCATACCTCAACGCTTCATGATAATAGGCTGGAGCCTCGGTGGCCATGCTTCTTGCCCCTTGGGCCTC CCCCAGCCCCTCCTCCCCTTCCTGCACCCGTACCCCCAAACACCATTGTCACACTCCAGTGGTCTTTGAATAAAGTC TGAGTGGGCGGC |
| hIL12AB_002 (SEQ ID NO: 56) | TCAAGCTTTTGGACCCTCGTACAGAAGCTAATACGACTCACTATAGGGAAATAAGAGAGAAAAGAAGAGTAAGAAGAAA TATAAGAGCCACCATGTGCCACCAGCAGCTGGTGATCAGCTGGTTCAGCCTGGTGTTCCTGGCCAGCCCCCTGGTGGCC ATCTGGGAGCTGAAGAAGGACGTGTACGTGGTGGAGTTGGATTGGTACCCCGACGCCCCCGGCGAGATGGTGGTGCTGA |

TABLE 4B-continued

Sequence Optimized Polynucleotides Comprising 5' UTR, ORF, 3' UTR

| | |
|---|---|
| | CCTGCGACACCCCCGAGGAGGACGGCATCACCTGGACCCTGGACCAGAGCAGCGAGGTGCTGGGCAGCGGCAAGACCCT<br>GACCATCCAGGTGAAGGAGTTCGGCGACGCCGGCCAGTACACCTGCCACAAGGGCGGCGAGGTGCTGAGCCACAGCCTG<br>CTGCTGCTGCACAAGAAGGAGGACGGCATCTGGAGCACCGACATCCTGAAGGACCAGAAGGAGCCCAAGAACAAGACCT<br>TCCTGAGATGCGAGGCCAAGAACTACAGCGGCAGATTCACCTGCTGGTGGCTGACCACCATCAGCACCGACCTGACCTT<br>CAGCGTGAAGAGCAGCAGAGGCAGCAGCGACCCCCAGGGCGTGACCTGCGGCGCCGCCACCCTGAGCGCCGAGAGAGTG<br>AGAGGCGACAACAAGGAGTACGAGTACAGCGTGGAGTGCCAGGAAGATAGCGCCTGCCCCGCCGCCGAGGAGAGCCTGC<br>CCATCGAGGTGATGGTGGACGCCGTGCACAAGCTGAAGTACGAGAACTACACCAGCAGCTTCTTCATCAGAGATATCAT<br>CAAGCCCGACCCCCCAAGAACCTGCAGCTGAAGCCCCTGAAGAACAGCCGGCAGGTGGAGGTGAGCTGGGAGTACCCC<br>GACACCTGGAGCACCCCCACAGCTACTTCAGCCTGACCTTCTGCGTGCAGGTGCAGGGCAAGAGCAAGAGAGAGAAGA<br>AAGATAGAGTGTTCACCGACAAGACCAGCGCCACCGTGATCTGCAGAAAGAACGCCAGCATCAGCGTGAGAGCCCAAGA<br>TAGATACTACAGCAGCAGCTGGAGCGAGTGGGCCAGCGTGCCCTGCAGCGGCGGCGGCGGCAGCAGAAACCTG<br>CCCGTGGCCACCCCCGACCCCGGCATGTTCCCCTGCCTGCACCACAGCCAGAACCTGCTGAGAGCCGTGAGCAACATGC<br>TGCAGAAGGCCCGGCAGACCCTGGAGTTCTACCCCTGCACCAGCGAGGAGATCGACCACGAAGATATCACCAAAGATAA<br>GACCAGCACCGTGGAGGCCTGCCTGCCCCTGGAGCTGACCAAGAACGAGAGCTGCCTGAACAGCAGAGAGACCAGCTTC<br>ATCACCAACGGCAGCTGCCTGGCCAGCAGAAAGACCAGCTTCATGATGGCCCTGTGCCTGAGCAGCATCTACGAGGACC<br>TGAAGATGTACCAGGTGGAGTTCAAGACCATGAACGCCAAGCTGCTGATGGACCCCAAGCGGCAGATCTTCCTGGACCA<br>GAACATGCTGGCCGTGATCGACGAGCTGATGCAGGCCCTGAACTTCAACAGCGAGACCGTGCCCCAGAAGAGCAGCCTG<br>GAGGAGCCCGACTTCTACAAGACCAAGATCAAGCTGTGCATCCTGCTGCACGCCTTCAGAATCAGAGCCGTGACCATCG<br>ACAGAGTGATGAGCTACCTGAACGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_003<br>(SEQ ID<br>NO: 57) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGTCACCAGCAGTTGGTCATCTCTTGGTTTTCCCTGGTTTTTCTGGCATCTCCCCTCGTGGCC<br>ATCTGGGAACTGAAGAAAGACGTTTACGTTGTAGAATTGGATTGGTATCCGGACGCTCCTGGAGAAATGGTGGTCCTCA<br>CCTGTGACACCCCTGAAGAAGACGGAATCACCTGGACCTTGGACCAGAGCAGTGAGGTCTTAGGCTCTGGCAAAACCCT<br>GACCATCCAAGTCAAAGAGTTTGGAGATGCTGGCCAGTACACCTGTCACAAAGGAGGCGAGGTTCTAAGCCATTCGCTC<br>CTGCTGCTTCACAAAAAGGAAGATGGAATTTGGTCCACTGATATTTTAAAGGACCAGAAAGAACCCAAAAATAAGACCT<br>TTCTAAGATGCGAGGCCAAGAATTATTCTGGACGTTTCACCTGCTGGTGGCTGACGACAATCAGTACTGATTTGACATT<br>CAGTGTCAAAAGCAGCAGAGGCTCTTCTGACCCCCAAGGGGTGACGTGCGGAGCTGCTACACTCTCTGCAGAGAGAGTC<br>AGAGGTGACAACAAGGAGTATGAGTACTCAGTGGAGTGCCAGGAAGATAGTGCCTGCCCAGCTGCTGAGGAGAGTCTGC<br>CCATTGAGGTCATGGTGGATGCCGTTCACAAGCTCAAGTATGAAAACTACACCAGCAGCTTCTTCATCAGAGATATCAT<br>CAAACCTGACCCACCCAAGAACTTGCAGCTGAAGCCATTAAAGAATTCTCGGCAGGTGGAGGTCAGCTGGGAGTACCCT<br>GACACCTGGAGTACTCCACATTCCTACTTCTCCCTGACATTCTGCGTTCAGGTCCAGGGCAAGAGCAAGAGAGAAAAGA<br>AAGATAGAGTCTTCACAGATAAGACCTCAGCCACGGTCATCTGCCGCAAAAATGCCAGCATTAGCGTGCGGGCCCAGGA<br>CCGCTACTATAGCTCATCTTGGAGCGAATGGGCATCTGTGCCCTGCAGTGGCGGAGGGGGCGGAGGGAGCAGAAACCTC<br>CCCGTGGCCACTCCAGACCCAGGAATGTTCCCATGCCTTCACCACTCCCAAAACCTGCTGAGGGCCGTCAGCAACATGC<br>TCCAGAAGGCCCGGCAAACTTTAGAATTTTACCCTTGCACTTCTGAAGAGATTGATCATGAAGATATCACAAAAGATAA<br>AACCAGCACAGTGGAGGCCTGTTTACCATTGGAATTAACCAAGAATGAGAGTTGCCTAAATTCCAGAGAGACCTCTTTC<br>ATAACTAATGGAGTTGCCTGGCCTCCAGAAAGACCTCTTTTATGATGGCCCTGTGCCTTAGTAGTATTTATGAAGATT<br>TGAAGATGTACCAGGTGGAGTTCAAGACCATGAATGCAAAGCTTCTGATGGATCCTAAGAGGCAGATCTTTTTAGATCA<br>AAACATGCTGGCAGTTATTGATGAGCTGATGCAGGCCCTGAATTTCAACAGTGAGACGGTGCCACAAAATCCTCCCTT<br>GAAGAACCAGATTTCTACAAGACCAAGATCAAGCTCTGCATACTTCTTCATGCTTTCAGAATTCGGGCAGTGACTATTG<br>ATAGAGTGATGAGCTATCTGAATGCTTCCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_004<br>(SEQ ID<br>NO: 58) | TCAAGCTTTTGGACCCTCGTACAGAAGCTAATACGACTCACTATAGGGAAATAAGAGAGAAAAGAAGAGTAAGAAGAAA<br>TATAAGAGCCACCATGGGCTGCCACCAGCAGCTGGTCATCAGCTGGTTCTCCCTGGTCTTCCTGGCCAGCCCCCTGGTG<br>GCCATCTGGGAGCTGAAGAAAGACGTCTACGTAGTAGAGTTGGATTGGTACCCAGACGCACCTGGAGAAATGGTGGTTC<br>TCACCTGTGACACGCCAGAAGAAGACGGTATCACCTGGACGCTGGACCAGAGCTCAGAAGTTCTTGGCAGTGGAAAAAC<br>GCTGACCATACAAGTAAAAGAATTTGGGGATGCTGGCCAGTACACCTGCCACAAAGGAGGAGAAGTTCTCAGCCACAGC<br>CTGCTGCTGCTGCACAAGAAGGAAGATGGCATCTGGAGCACAGATATTTTAAAAGACCAGAAGGAGCCCAAGAACAAAA<br>CCTTCCTTCGATGTGAGGCCAAGAACTACAGTGGCCGCTTCACCTGCTGGTGGCTCACCACCATCAGCACAGACCTCAC<br>CTTCTCGGTGAAGAGCAGCCGTGGCAGCTCAGACCCCCAAGGAGTCACCTGTGGGGCGGCCACGCTGTCGGCAGAAAGA<br>GTTCGAGGTGACAACAAGGAATATGAATACTCGGTGGAATGTCAAGAAGATTCGGCCTGCCCTGCCCGGCGGCAGAAGAAAGTC<br>TTCCCATAGAAGTCATGGTGGATGCTGTTCACAAATTAAAATATGAAAACTACACCAGCAGCTTCTTCATCAGAGATAT<br>CATCAAGCCAGACCCGCCCAAGAACCTGCAGCTGAAGCCCCTGAAGAACAGCCGGCAGGTGGAAGTTTCCTGGGAGTAC<br>CCAGATACGTGGAGCACGCCGCACAGCTACTTCAGCCTCACCTTCTGTGTACAAGTACAAGGCAAGAGCAAGAGAGAGA<br>AGAAAGATCGTGTCTTCACAGATAAAACCTCGGCGACGGTCATCTGCAGGAAGAATGCCTCCATCTCGGTTCGAGCCCA<br>GGACCGCTACTACAGCAGCAGCTGGAGTGAGTGGGCCTCGGTGCCTGCACCAGCGGTGGCGGCGGCGGCAGCAGAAAC<br>CTTCCTGTGGCCACGCCGGACCCTGGCATGTTCCCGTGCCTGCACCACAGCCAAAATTTACTTCGAGCTGTTTCTAACA<br>TGCTGCAGAAAGCACGGCAAACTTTAGAATTCTACCCCTGCACCTCAGAAGAAATAGACCATGAAGATATCACCAAAGA<br>TAAAACCAGCACTGTAGAGGCCTGCCTGCCCCTGGAGCTCACCAAGAATGAATCCTGCCTCAACAGCAGAGAGACCAGC<br>TTCATCACCAATGGCAGCTGCCTGGCCAGCAGAAAACCAGCTTCATGATGGCGCTCTGCCTGAGCAGCATCTATGAAG<br>ATTTGAAGATGTACCAAGTAGAATTTAAAACCATGAATGCCAAGCTGCTCATGGACCCCAAGCGGCAGATATTTTTGGA<br>TCAAAACATGCTGGCTGTCATTGATGAGCTCATGCAAGCATTAAACTTCAACTCAGAGACGGTGCCCCAGAAGAGCAGC<br>CTGGAGGAGCCAGATTTCTACAAAACCAAGATCAAGCTCTGCATCTTATTACATGCCTTCCGCATCCGGGCGGTCACCA<br>TTGACCGTGTCATGTCCTACTTAAATGCCAGCTGATAATAGGCTGGAGCCTCGGTGGCCATGCTTCTTGCCCCTTGGGC<br>CTCCCCCCAGCCCCTCCTCCCCTTCCTGCACCCGTACCCCCCAAACACCATTGTCACACTCCAGTGGTCTTTGAATAAA<br>GTCTGAGTGGGCGGC |
| hIL12AB_005<br>(SEQ ID<br>NO: 59) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTCATCAGCTGGTTCTCCCTGGTCTTCCTGGCCAGCCCCCTGGTGGCC<br>ATCTGGGAGCTGAAGAAAGACGTCTACGTAGTAGAGTTGGATTGGTACCCAGACGCACCTGGAGAAATGGTGGTTCTCA<br>CCTGTGACACGCCAGAAGAAGACGGTATCACCTGGACGCTGGACCAGAGCTCAGAAGTTCTTGGCAGTGGAAAAACGCT<br>GACCATCAAGTAAAAGAATTTGGGGATGCTGGCCAGTACACCTGCCACAAAGGAGGAGAAGTTCTCAGCCACAGCCTG<br>CTGCTGCTGCACAAGAAGAAGATGGCATCTGGAGCACAGATATTTTAAAAGACCAGAAGGAGCCCAAGAACAAACCT |

TABLE 4B-continued

Sequence Optimized Polynucleotides Comprising 5' UTR, ORF, 3' UTR

| | |
|---|---|
| | TCCTTCGATGTGAGGCCAAGAACTACAGTGGCCGCTTCACCTGCTGGTGGCTCACCACCATCAGCACAGACCTCACCTT<br>CTCGGTGAAGAGCAGCCGTGGCAGCTCAGACCCCAAGGAGTCACCTGTGGGGCGGCCACGCTGTCGGCAGAAAGAGTT<br>CGAGGTGACAACAAGGAATATGAATACTCGGTGGAATGTCAAGAAGATTCGGCCTGCCCGGCGGCAGAAGAAAGTCTTC<br>CCATAGAAGTCATGGTGGATGCTGTTCACAAATTAAAATATGAAAACTACACCAGCAGCTTCTTCATCAGAGATATCAT<br>CAAGCCAGACCCGCCCAAGAACCTGCAGCTGAAGCCCCTGAAGAACAGCCGGCAGGTGGAAGTTTCCTGGGAGTACCCA<br>GATACGTGGAGCACGCCGCACAGCTACTTCAGCCTCACCTTCTGTGTACAAGTACAAGGCAAGAGCAAGAGGAGAAGA<br>AAGATCGTGTCTTCACAGATAAAACCTCGGCGACGGTCATCTGCAGGAAGAATGCCTCCATCTCGGTTCGAGCCCAGGA<br>CCGCTACTACAGCAGCAGCTGGAGTGAGTGGGCCTCGGTGCCCTGCAGTGGTGGCGGCGGCGGCGGCAGCAGAAACCTT<br>CCTGTGGCCACGCCGGACCCTGGCATGTTCCCGTGCCTGCACCACAGCCAAAATTTACTTCGAGCTGTTTCTAACATGC<br>TGCAGAAAGCACGGCAAACTTTAGAATTCTACCCCTGCACCTCAGAAGAAATAGACCATGAAGATATCACCAAAGATAA<br>AACCAGCACTGTAGAGGCCTGCCTGCCCCTGGAGCTCACCAAGAATGAATCCTGCCTCAACAGCAGAGACCAGCTTC<br>ATCACCAATGGCAGCTGCCTGGCCAGCAGGAAAACCAGCTTCATGATGGCGCTCTGCCTGAGCAGCATCTATGAAGATT<br>TGAAGATGTACCAAGTAGAATTTAAAACCATGAATGCCAAGCTGCTCATGGACCCCAAGCGGCAGATATTTTTGGATCA<br>AAACATGCTGGCTGTCATTGATGAGCTCATGCAAGCATTAAACTTCAACTCAGAGACGGTGCCCCAGAAGAGCAGCCTG<br>GAGGAGCCAGATTTCTACAAAACCAAGATCAAGCTCTGCATCTTATTACATGCCTTCCGCATCCGGGCGGTCACCATTG<br>ACCGTGTCATGTCCTACTTAAATGCCAGCTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_006<br>(SEQ ID<br>NO: 60) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTGATCAGCTGGTTCAGCCTGGTGTTCCTGGCCAGCCCCCTGGTGGCC<br>ATCTGGGAGCTGAAGAAGGACGTGTACGTGGTGGAGTTGGATTGGTACCCCGACGCCCCCGGCGAGATGGTGGTGCTGA<br>CCTGTGACACCCCCGAGGAGGACGGCATCACCTGGACCCTGGACCAGAGCAGCGAGGTGCTGGGCAGCGGCAAGACCCT<br>GACCATCCAGGTGAAGGAGTTCGGGGACGCCGGCCAGTACACCTGCCACAAGGGCGGCGAGGTGCTGAGCCACAGCCTG<br>CTGCTGCTGCACAAGAAGGAGGACGGCATCTGGAGCACAGATATCCTGAAGGACCAGAAGGAGCCCAAGAACAAGACCT<br>TCCTGAGATGCGAGGCCAAGAACTACAGCGGCAGATTCACCTGCTGGTGGCTGACCACCATCAGCACAGATTTGACCTT<br>CAGCGTGAAGAGCAGCAGAGGCAGCAGCGACCCCCAGGGCGTGACCTGCGGCGCCGCCACCCTGAGCGCTGAGAGAGTG<br>AGAGGTGACAACAAGGAGTACGAGTACAGCGTGGAGTGCCAGGAAGATAGCGCCTGCCCCGCCGCCGAGGAGAGCCTGC<br>CCATCGAGGTGATGGTGGACGCCGTGCACAAGCTGAAGTACGAGAACTACACCAGCAGCTTCTTCATCAGAGATATCAT<br>CAAGCCCGACCCGCCGAAGAACCTGCAGCTGAAGCCCCTGAAGAACAGCCGGCAGGTGGAGGTGAGCTGGGAGTACCCC<br>GACACCTGGAGCACCCCCCACAGCTACTTCAGCCTGACCTTCTGCGTGCAGGTGCAGGGCAAGAGCAAGAGAGAAGAGA<br>AAGATAGAGTGTTCACAGATAAGACCAGCGCCACCGTGATCTGCAGAAAGAACGCCAGCATCAGCGTGAGAGCCCAAGA<br>TAGATACTACAGCAGCAGCTGGAGCGAGTGGGCCAGCGTGCCCTGCAGCGGCGGCGGCGGCGGCGGCAGCAGAAACCTG<br>CCCGTGGCCACCCCCGACCCCGGCATGTTCCCCTGCCTGCACCACAGCCAGAACCTGCTGAGAGCCGTGAGCAACATGC<br>TGCAGAAGGCCCGGCAGACCCTGGAGTTCTACCCCTGCACCAGCGAGGAGATCGACCACGAAGATATCACCAAAGATAA<br>GACCAGCACCGTGGAGGCCTGCCTGCCCCTGGAGCTGACCAAGAATGAAAGCTGCCTGAACAGCAGAGAGACCAGCTTC<br>ATCACCAACGGCAGCTGCCTGGCAGCAGAAAGACCAGCTTCATGATGGCCCTGTGCCTGAGCAGCATCTACGAGGACC<br>TGAAGATGTACCAGGTGGAGTTCAAGACCATGAACGCCAAGCTGCTGATGGACCCCAAGCGGCAGATCTTCCTGGACCA<br>GAACATGCTGGCCGTGATCGACGAGCTGATGCAGGCCCTGAACTTCAACAGCGAGACCGTGCCCCAGAAGAGCAGCCTG<br>GAGGAGCCCGACTTCTACAAGACCAAGATCAAGCTGTGCATCCTGCTGCACGCCTTCAGAATCAGAGCCGTGACCATCG<br>ACAGAGTGATGAGCTACCTGAACGCCAGCTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_007<br>(SEQ ID<br>NO: 61) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTTGTCATCTCCTGGTTCTCTCTTGTCTTCCTTGCTTCTCCTCTTGTGGCC<br>ATCTGGGAGCTGAAGAAGGACGTTTACGTAGTGGAGTTGGATTGGTACCCTGACGCACCTGGAGAAATGGTGGTTCTCA<br>CCTGTGACACTCCTGAGGAGGACGGTATCACCTGGACGTTGGACCAGAGCTCTGAGGTTCTTGGCAGTGGAAAAACTCT<br>TACTATTCAGGTGAAGGAGTTTGGAGATGCTGGCCAGTACACCTGCCACAAGGGTGGAGAGTTCTCAGCCACAGTTTA<br>CTTCTTCTTCACAAGAAGGAGGATGGCATCTGGTCTACTGACATTTTAAAAGACCAGAAGGAGCCCAAGAACAAACAT<br>TCCTTCGTTGTGAAGCCAAGAACTACAGTGGTCGTTTCACCTGCTGGTGGCTTACTACTATTTCTACTGACCTTACTTT<br>CTCTGTGAAGTCTTCTCGTGGCTCTTCTGACCCTCAGGGTGTCACCTGTGGGGCTGCTACTCTTTCTGCTGAGCGTGTG<br>CGTGGTGACAACAAGGAGTATGAATACTCGGTGGAGTGCCAGGAAGATTCGCCTGCCCTGCTGCTGAGGAGTCTCTTC<br>CTATTGAGGTGATGGTGGATGCTGTGCACAAGTTAAAATATGAAAACTACACTTCTTCTTCTTCATTCGTGACATTAT<br>AAAAACCTGACCCTCCCAAGAACCTTCAGTTAAAACCTTTAAAAAACTCTCGTCAGGTGGAGGTGTCCTGGGAGTACCCT<br>GACACGTGGTCTACTCCTCACTCCTACTTCTCTCTTACTTTCTGTGTCCAGGTGCAGGGCAAGTCCAAGCGTGAGAAGA<br>AGGACCGTGTCTTCACTGACAAAACATCTGCTACTGTCATCTGCAGGAAGAATGCATCCATCTCTGTCGTGCTCAGGA<br>CCGTTACTACAGCTCTTCCTGGTCTGAGTGGCTTCTGTGCCCTGCTCTGGCGGCGGCGGCGGCGGCAGCAGAAATCTT<br>CCTGTGGCTACTCCTGACCCTGGCATGTTCCCCTGCCTTCACCACTCGCAGAACCTTCTTCGTGCTGTGAGCAACATGC<br>TTCAGAAGGCTCGTCAAACTTTAGAATTCTACCCCTGCACTTCTGAGGAGATTGACCATGAAGATATCACCAAAGATAA<br>AACATCTACTGTGGAGGCCTGCCTTCCTTTAGAGCTGACCAAGAATGAATCCTGCTTAAATTCTCGTGAGACGTCTTTC<br>ATCACCAATGGCAGCTGCCTTGCCTCGCGCAAAACATCTTTCATGATGGCTCTTTGCCTTCTTCCATCTATGAAGATT<br>TAAAAATGTACCAGGTGGAGTTCAAGACCATGAATGCAAAGTTCTCATGGACCCCAAGCGTCAGATATTTTTGGACCA<br>GAACATGCTTGCTGTCATTGATGAGCTCATGCAGGCTTTAAACTTCAACTCTGAGACGGTGCCTCAGAAGTCTTCTTTA<br>GAAGAGCCTGACTTCTACAAGACCAAGATAAAACTTTGCATTCTTCTTCATGCTTTTCCGCATCCGTGCTGTGACTATTG<br>ACCGTGTGATGTCCTACTTAAATGCTTCTTGATAATAGGCTGGAGCCTCGGTGGCCAAGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_008<br>(SEQ ID<br>NO: 62) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGTCATCAACAACTCGTGATTAGCTGGTTCAGTCTCGTGTTCCTGGCCTCTCCGCTGGTGGCC<br>ATCTGGGAGCTTAAGAAGGACGTGTACGTGGTGGAGCTCGATTGGTACCCCGACGCACCTGGCGAGATGGTGGTGCTAA<br>CCTGCGATACCCCCGAGGAGGACGGGATCACTTGGACCCTGGACCAGAGTAGCGAAGTCCTGGGCTCTGGCAAACACT<br>CACAATCCAGGTGAAGGAATTCGGAGACGCTGGCAGTACACTTGCCACAAGGGGGTGAAGTGCTGTCTCACAGCCTG<br>CTGTTACTGCACAAGAAGGAGGATGGGATCTGGTCAACCGACATCCTGAAGGATCAGAAGGAGCCTAAGAACAAGACCT<br>TTCTGAGGTGTGAAGCTAAGAACTATTCCGGAAGATTCACTTGCTGGTGGTTGACCACAATCAGCACTGACCTGACCTT<br>TTCCGTGAAGTCCAGCAGAGGAAGCAGCGATCCTCAGGGCGTAACGTGCGGCGCGGCTACCCTGTCAGCTGAGCGGGTT<br>AGAGGCGACAACAAAGAGTATGAGTACTCCGTGGAGTGTCAGGAAGATAGCGCCTGCCCCGCAGCCGAGGAGAGTCTGC |

TABLE 4B-continued

Sequence Optimized Polynucleotides Comprising 5' UTR, ORF, 3' UTR

| | |
|---|---|
| | CCATCGAGGTGATGGTGGACGCTGTCCATAAGTTAAAATACGAAAATTACACAAGTTCCTTTTTCATCCGCGATATTAT<br>CAAACCCGATCCCCCCAAGAACCTGCAGCTGAAGCCCCTGAAGAATAGCCGACAGGTGGAAGTCTCTTGGGAGTATCCT<br>GACACCTGGTCCACGCCTCACAGCTACTTTAGTCTGACTTTCTGTGTCCAGGTCCAGGGCAAGAGCAAGAGAGAGAAA<br>AGGATAGAGTGTTTACTGACAAAACATCTGCTACAGTCATCTGCAGAAAGAACGCCAGTATCTCAGTGAGGGCGCAAGA<br>TAGATACTACAGTAGTAGCTGGAGCGAATGGGCTAGCGTGCCCTGTTCAGGGGCGGCGGAGGGGGCTCCAGGAATCTG<br>CCCGTGGCCACCCCCGACCCTGGGATGTTCCCTTGCCTCCATCACTCAGAAGAGATCGATCACGAAGATATAACAAAGGATAA<br>TCCAAAAGGCCCGCCAGACCCTGGAGTTTTACCCTTGTACTTCAGAAGAGATCGATCACGAAGATATAACAAAGGATAA<br>AACCAGCACCGTGGAGGCCTGTCTGCCTCTGGAACTCACAAAGAATGAAAGCTGTCTGAATTCCAGGGAAACCTCCTTC<br>ATTACTAACGGAAGCTGTCTCGCATCTCGCAAAACATCATTCATGATGGCCCTCTGCCTGTCTTCTATCTATGAAGATC<br>TCAAGATGTATCAGGTGGAGTTCAAAACAATGAACGCCAAGCTGCTGATGGACCCCAAGCGGCAGATCTTCCTGGACCA<br>GAACATGCTGGCAGTGATCGATGAGCTGATGCAAGCCTTGAACTTCAACTCAGAGACGGTGCCGCAAAAGTCCTCGTTG<br>GAGGAACCAGATTTTTACAAAACCAAAATCAAGCTGTGTATCCTTCTTCACGCCTTTCGGATCAGAGCCGTGACTATCG<br>ACCGGGTGATGTCATACCTGAATGCTTCCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_009<br>(SEQ ID<br>NO: 63) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTCATCAGCTGGTTTAGCCTGGTCTTCCTGGCCAGCCCCCTGGTGGCC<br>ATCTGGGAGCTGAAGAAAGACGTCTACGTAGTAGAGTTGGATTGGTACCCAGACGCACCTGGAGAAATGGTGGTTCTCA<br>CCTGCGACACGCCAGAAGAAGACGGTATCACCTGGACGCTGGACCAGAGCAGCGAAGTACTGGGCAGTGGAAAAACGCT<br>GACCATACAAGTAAAAGAATTTGGCGATGCTGGCCAGTACACCTGCCACAAAGGAGGAGAAGTACTGAGCCACAGCCTG<br>CTGCTGCTGCACAAGAAAGAAGATGGCATCTGGAGCACCGACATTTTAAAAGACCAGAAGGAGCCCAAGAACAAAACCT<br>TCCTTCGATGTGAGGCGAAGAACTACAGTGGCCGCTTCACCTGCTGGTGGCTCACCACCATCAGCACCGACCTCACCTT<br>CTCGGTGAAGAGCAGCCGTGGTAGCTCAGACCCCCAAGGAGTCACCTGTGGGGCGGCCACGCTGTCGGCAGAAAGAGTT<br>CGAGGCGACAACAAGGAATATGAATACTCGGTGGAATGTCAAGAAGATTCGGCCTGCCCGGCGGCAGAAGAAAGTCTGC<br>CCATAGAAGTCATGGTGGATGCTGTTCACAAATTAAAAATATGAAAACTACACCAGCAGCTTCTTCATCAGAGATATCAT<br>CAAGCCAGACCCCCCAAGAACCTGCAGCTGAAGCCCCTGAAGAATAGCCGGCAGGTGGAAGTTTCCTGGGAGTACCCA<br>GATACGTGGAGCACGCCGCACAGCTACTTCAGCCTCACCTTCTGTGTACAAGTACAAGGCAAGAGCAAGAGAGAGAAGA<br>AAGATCGTGTCTTCACCGACAAAACCTCGGCGACGGTCATCTGCAGGAAGAATGCAAGCATCTCGGTTCGAGCCCAGGA<br>CCGCTACTACAGCAGCAGCTGGAGTGAGTGGGCCTCGGTGCCCTGCAGTGGTGGCGGCGGCGGCGGCAGCAGAAACCTT<br>CCTGTGGCCACGCCGGACCCTGGCATGTTTCCGTGCCTGCACCACAGCCAAAATTTATTACGAGCTGTTAGCAACATGC<br>TGCAGAAAGCACGGCAAACTTTAGAATTCTACCCCTGCACCTCAGAAGAAATAGACCATGAAGATATCACCAAAGATAA<br>AACCAGCACTGTAGAGGCCTGCCTGCCCCTGGAGCTCACCAAGAACGAGAGCTGCCTCAATAGCAGAGAGACCAGCTTC<br>ATCACCAATGGCAGCTGCCTGGCCAGCAGGAAAACCAGCTTCATGATGGCGCTCTGCCTGAGCAGCATCTATGAAGATC<br>TGAAGATGTACCAAGTAGAATTTAAAACCATGAATGCCAAGCTGCTCATGGACCCCAAGCGGCAGATATTCCTCGACCA<br>AAACATGCTGGCTGTCATTGATGAGCTCATGCAAGCATTAAACTTCAACTCAGAGACGGTTGCCCCAGAAGAGCAGCCTG<br>GAGGAGCCAGATTTCTACAAAACCAAGATCAAGCTCTGCATCTTATTCATGCCTTCCGCATCCGGGCGGTCACCATTG<br>ACCGTGTCATGTCCTACTTAAATGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_010<br>(SEQ ID<br>NO: 64) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTTGTCATCCTGGTTTTTCTCTTGTCTTCCTCGCTTCTCCTCTTGTGGCCC<br>ATCTGGGAGCTGAAGAAAGACGTCTACGTAGTAGAGTTGGATTGGTACCCGGACGCTCCTGGAGAAATGGTGGTTCTCA<br>CCTGCGACACTCCTGAAGAAGACGGTATCACCTGGACGCTGGACCAAAGCAGCGAAGTTTTAGGCTCTGGAAAAACGCT<br>GACCATACAAGTAAAAGAATTTGGCGACGCTGGCCAGTACACGTGCCACAAAGGAGGAGAAGTTTTAAGCCACAGTTTA<br>CTTCTTCTTCACAAGAAAGAAGATGGCATCTGGAGTACAGATATTTTAAAAGACCAGAAGGAGCCTAAGAACAAAACCT<br>TCCTCCGCTGTGAAGCTAAGAACTACAGTGGTCGTTTCACCTGCTGGTGGCTCACCACCATCTCCACTGACCTCACCTT<br>CTCTGTAAAATCAAGCCGTGGTTCTTCTGACCCCCAAGGAGTCACCTGTGGGCTGCCACGCTCAGCGCTGAAAGAGTT<br>CGAGGCGACAACAAGGAATATGAATATTCTGTGGAATGTCAAGAAGATTCTGCCTGCCCGGCGGCAGAAGAAAGTCTTC<br>CCATAGAAGTCATGGTGGACGCTGTTCACAAATTAAAAATATGAAAACTACACCAGCAGCTTCTTCATTCGTGACATCAT<br>CAAACCAGACCTCCTAAGAACCTTCAGTTAAAACGCTGAAGAACGCGGCAGGTGGAAGTTCCTGGGAGTACCCA<br>GATACGTGGAGTACGCCGCACTCCTACTTCAGTTTAACCTTCTGTGTACAAGTACAAGGAAAATCAAAAGAGAGAAGA<br>AAGATCGTGTCTTCACTGACAAAACATCTGCCACGGTCATCTGCCGTAAGAACGCTTCCATCTCGGTTCGAGCCCAGGA<br>CCGCTACTACAGCAGCAGCTGGAGTGAGTGGGCATCTGTTCCCTGCAGTGGTGGCGGCGGCGGCGGCAGCCGCAACCTT<br>CCTGTGGCCACGCCGGACCCTGGCATGTTTCCCGTGCCTTCACCACTCGCAAAATCTTCTTCGTGCTGTTTCTAACATGC<br>TGCAGAAGGCGCGGCAAACTTTAGAATTCTACCCGTGCACTTCTGAAGAAATAGACCATGAAGATATCACCAAAGATAA<br>AACCAGCACGGTGGAGGCCTGCCTTCCTTTAGAACTTACTAAGAACGAAAGTTGCCTTAACAGCCGTGAGACCAGCTTC<br>ATCACCAATGGCAGCTGCCTTGCTAGCAGGAAGACCAGCTTCATGATGGCGCTGTGCCTTTCTTCCATCTATGAAGATC<br>TTAAGATGTACCAAGTAGAATTTAAAACCATGAATGCCAAATTATTAATGGACCCCAAGCGGCAGATATTCCTCGACCA<br>AAACATGCTGGCTGTCATTGATGAGCTCATGCAAGCATTAAACTTCAACTCAGAGACGTGTTCCCCAGAAGTCATCTTTA<br>GAAGAACCAGATTTCTACAAACAAAATAAAACTCTGCATTCTTCTTCATGCCTTCCGCATCCGTGCTGTCACCATTG<br>ACCGTGTCATGTCCTACTTAAATGCTTCTTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_011<br>(SEQ ID<br>NO: 65) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTGATCAGCTGGTTCAGCCTGGTGTTCCTGGCCAGCCCCCTGGTGGCC<br>ATCTGGGAGCTGAAGAAGGACGTGTACGTGGTGGAGTTGGATTGGTACCCGGACGCTCCGGGGGAGATGGTGGTGCTGA<br>CGTGCGACACGCCGGAGGAGGACGGGATCACGTGGACGCTGGACCAGAGCAGCGAGGTGCTGGGGAGCGGGAAGACGCT<br>GACGATCCAGGTGAAGGAGTTCGGGGACGCGGGCCAGTACACGTGCCACAAGGGGGGGAGGTGCTGAGCCACAGCCTG<br>CTGCTGCTGCACAAGAAGGAGGACGGGATCTGGAGCACAGATATCCTGAAGGACCAGAAGGAGCCGAAGAACAAGACGT<br>TCCTGAGGTGCGAGGCGAAGAACTACAGCGGGAGGTTCACGTGCTGGTGGCTGACGACGATCAGCACGGACCTGACGTT<br>CAGCGTGAAGAGCAGCCGCGGGAGCAGCGACCCGCAGGGGGTGACGTGCGGGGCGGCGACGCTGAGCGCGGAGGGGTG<br>AGGGGTGACAACAAGGAGTACGAGTACAGCGTGGAGTGCCAGGAAGATAGCGCGTGCCCGGCGGCGGAGGAGAGCCTGC<br>CGATCGAGGTGATGGTGGACGCGGTGCACAAGCTGAAGTACGAGAACTACACGAGCAGCTTCTTCATCAGAGATATCAT<br>CAAGCCGGACCCGCCGAAGAACCTGCAGCTGAAGCCGCTGAAGAACAGCAGGCAGGTGGAGGTGAGCTGGGAGTACCCA<br>GATACGTGGAGCACGCCGCACAGCTACTTCAGCCTGACGTTCTGCGTGCAGGTGCAGGGGAAGAGCAAGAGGGAGAAGA

TABLE 4B-continued

Sequence Optimized Polynucleotides Comprising 5' UTR, ORF, 3' UTR

|  |  |
|---|---|
|  | AAGATAGGGTGTTCACAGATAAGACGAGCGCGACGGTGATCTGCAGGAAGAACGCGAGCATCAGCGTGAGGGCGAAGA<br>TAGGTACTACAGCAGCAGCAGCTGGAGCGAGTGGGCGAGCGTGCCGTGCAGCGGGGGGGGGGGGGGGAGCAGGAACCTG<br>CCGGTGGCGACGCCGGACCCGGGGATGTTCCCGTGCCTGCACCACAGCCAGAACCTGCTGAGGGCGGTGAGCAACATGC<br>TGCAGAAGGCGAGGCAGACGCTGGAGTTCTACCCGTGCACGAGCGAGGAGATCGACCACGAAGATATCACGAAAGATAA<br>GACGAGCACGGTGGAGGCGTGCCTGCCGCTGGAGCTGACGAAGAACGAGAGCTGCCTGAACAGCAGGGAGACGAGCTTC<br>ATCGACAACGGGACTGCCTGGCGAGCAGGAAGACGAGCTTCATGATGGCGCTGTGCCTGAGCAGCATCTACGAGGACC<br>TGAAGATGTACCAGGTGGAGTTCAAGACGATGAACGCGAAGCTGCTGATGGACCCGAAGAGGCAGATCTTCCTGGACCA<br>GAACATGCTGGCGGTGATCGACGAGCTGATGCAGGCGCTGAACTTCAACAGCGAGACGGTGCCGCAGAAGAGCAGCCTG<br>GAGGAGCCAGATTTCTACAAGACGAAGATCAAGCTGTGCATCCTGCTGCACGCGTTCAGGATCAGGGCGGTGACGATCG<br>ACAGGGTGATGAGCTACCTGAACGCGAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_012<br>(SEQ ID<br>NO: 66) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCATCAGCAGCTGGTGATCAGCTGGTTCAGCCTCGTGTTTCTGGCCAGCCCCCTGGTGGCC<br>ATTTGGGAACTCAAGAAGGACGTGTACGTTGTGGAACTCGACTGGTACCCTGACGCCCCAGGCGAAATGGTGGTCTTAA<br>CCTGCGACACCCCTGAGGAGGACGGAATCACCTGGACCTTGGACCAGAGCTCCGAGGTCCTCGGCAGTGGCAAGACCCT<br>GACCATACAGGTGAAAGAATTTGGAGACGCAGGGCAATACACATGTCACAAGGGCGGGGAGGTTCTTTTCTCACTCCCTT<br>CTGCTTCTACATAAAAAGGAAGACGGAATTTGGTCTACCGACATCCTCAAGGACCAAAAGGAGCCTAAGAATAAAACCT<br>TCTTACGCTGTGAAGCTAAAAACTACAGCGGCAGATTCACTTGCTGGTGGCTCACCACCATTTCTACCGACCTGACCTT<br>CTCGGTGAAGTCTTCAAGGGGCTCTAGTGATCCACAGGGAGTGACATGCGGGGCCGCCACACTGAGCGCTGAACGGGTG<br>AGGGGCGATAACAAGGAGTATGAATACTCTGTCGAGTGTCAGGAGGATTCAGCTTGTCCCGCAGCTGAAGAGTCACTCC<br>CCATAGAGGTTATGGTCGATGCTGTGCATAAACTGAAGTACGAAAACTACACCAGCAGCTTCTTCATTAGAGATATTAT<br>AAAACCTGACCCCCCCAAGAACCTGCAACTTAAACCCCTGAAAAATCTCGGCAGGTCGAAGTTAGCTGGGAGTACCCT<br>GATACTTGGTCCACCCCCACTCGTACTTCTCACTGACTTTCTGTGTGCAGGTGCAGGGCAAGAGCAAGAGAGAGAAA<br>AAGATCGTGTATTCACAGATAAGACCTCTGCCACCGTGATCTGCAGAAAAACGCTTCCATCAGTGTCAGAGCCCAAGA<br>CCGGTACTATAGTAGTAGCTGGAGCGAGTGGGCAAGTGTCCCCTGCTCTGGCGCCGAGGGGGCGGCTCTCGAAACCTC<br>CCCGTCGCTACCCCTGATCCAGGAATGTTCCCTTGCCTGCATCACTCACAGAATCTGCTGAGAGCGGTCAGCAACATGC<br>TGCAGAAAGCTAGGCAAACACTGGAGTTTTATCCTTGTACCTCAGAGGAGATCGACCACGAGGATATTACCAAAGATAA<br>GACCAGCACGGTGGAGGCCTGCTTGCCCCTGGAACTGACAAAGAATGAATCCTGCCTTAATAGCCGTGAGACCTCTTTT<br>ATAACAAACGGATCCTGCCTGGCCAGCAGGAAGACCTCCTTCATGATGGCCCTCTGCCTGTCCTCAATCTACGAAGACC<br>TGAAGATGTACCAGGTGGAATTTAAAACTATGAACGCCAAGCTGTTGATGGACCCCAAGCGGCAGATCTTTCTGGATCA<br>AAATATGCTGGCTGTGATCGACGAACTGATGCAGGCCCTCAACTTTAACAGCGAGACCGTGCCACAAAAGAGCAGTCTT<br>GAGGAGCCCGACTTCTACAAGACCAAGATCAAGCTGTGCATCCTCCTTCATGCCTTCAGGATAAGAGCTGTCACCATCG<br>ACAGAGTCATGAGTTACCTGAATGCATCCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_013<br>(SEQ ID<br>NO: 67) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTTGTGATTTCTTGGTTCTCTCTTGTGTTCCTTGCTTCTCCTCTTGTGGCT<br>ATCTGGGAGCTGAAGAAAGACGTTTACGTAGTAGAGTTGGATTGGTACCCAGACGCACCTGGAGAAATGGTGGTCCTCA<br>CCTGTGACACGCCAGAAGAAGACGGTATCACCTGGACGCTGGACCAGAGCAGTGAAGTTCTTGGAAGTGGAAAAACGCT<br>GACCATACAAGTAAAAGAATTTGGAGATGCTGGCCAGTACACCTGCCACAAAGGAGGAGAAGTTCTCAGCCACAGTTTA<br>TTATTACTTCACAAGAAGAAGATGGCATCTGGTCCACAGATATTTTAAAAGACCAGAAGGAGCCCAAAAATAAAACAT<br>TTCTTCGATGTGAGGCCAAGAACTACAGTGGTCGTTTCACCTGCTGGTGGCTGACCACCATCTCCACAGACCTCACCTT<br>CAGTGTAAAAGCAGCCGTGGTTCTTCTGACCCCCAAGGAGTCACCTGTGGGGCTGCCACGCTCTCTGCAGAAAGAGTT<br>CGAGGTGACAACAAAGAATATGAGTACTCGGTGGAATGTCAAGAAGATTCGGCCTGCCCAGCTGCTGAGGAGAGTCTTC<br>CCATAGAAGTCATGGTGGATGCTGTTCACAAATTAAAATATGAAAACTACACCAGCAGCTTCTTCATCAGAGATATCAT<br>CAAACCTGACCCGCCCAAGAACTTACAGCTGAAGCCGCTGAAAAACAGCCGGCAGGTAGAAGTTTCCTGGGAGTACCCA<br>GATACCTGGTCCACGCCGCACTCCTACTTCTCCCTCACCTTCGTGTACAAGTACAAGGCAAGAGCAAGAGAGAGAAGA<br>AAGATCGTGTCTTCACAGATAAAACATCAGCCACGGTCATCTGCAGGAAAATGCCAGCATCTCGGTGCGGGCCCAGGA<br>CCGCTACTACAGCAGCAGCTGGAGTGAGTGGGCATCTGTGCCCTGCAGTGGTGGGGGTGGTGGCAGCAGAAACCTT<br>CCTGTGGCCACTCCAGACCCTGGCATGTTCCCGTGCCTTCACCACTCCCAAAATTTACTTCGAGCTGTTTCTAACATGC<br>TGCAGAAAGCACGGCAAACTTTAGAATTCTACCCGTGCACTTCTGAAGAAATTGACCATGAAGATATCACAAAGATAA<br>AACCAGCACAGTGGAGGCCTGTCTTCCTTTAGAGCTGACCAAAAATGAATCCTGCCTCAACAGCAGAGAGACCAGCTTC<br>ATCACCAATGGCAGCTGCCTGGCCTCCAGGAAAACCAGCTTCATGATGGCGCTCTGCCTCAGCTCCATCTATGAAGATT<br>TGAAGATGTACCAAGTAGAATTTAAAACCATGAATGCCAAATTATTAATGGACCCCAAGAGGCAGATATTTTTAGATCA<br>AAACATGCTGGCAGTTATTGATGAGCTCATGCAAGCATTAAACTTCAACAGTGAGACGGTACCTCAAAAAAGCAGCTT<br>GAAGAGCCAGATTTCTACAAAACCAAGATCAAACTCTGCATTTTACTTCATGCCTTCCGCATCCGGGCGGTCACCATTG<br>ACCGTGTCATGTCCTACTTAAATGCCTCGTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_014<br>(SEQ ID<br>NO: 68) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTTGTGATTTCTTGGTTCTCTCTTGTGTTCCTTGCTTCTCCTCTTGTGGCT<br>ATTTGGGAGTTAAAAAAGGACGTGTACGTGGTGGAGCTTGACTGGTACCCTGACGCACCTGGCGAGATGGTGGTGCTTA<br>CTTGTGACACTCCTGAGGAGGACGGCATTACTTGGACGCTTGACCAGTCTTCTGAGGTGCTTGGCTCTGGCAAAACACT<br>TACTATTCAGGTGAAGGAGTTCGGGGATGCTGGCCAGTACACTTGCCACAAGGGCGGCGAGGTGCTTTCTCACTCTCTT<br>CTTCTTCTTCACAAGAAGGAGGACGGCATTTGGTCTACTGACATTTTAAAGGACCAGAAGGAGCCCAAGAACAAAACAT<br>TCCTTCGTTGCGAGGCCAAGAACTACTCTGGCCGTTTCACTTGCTGGTGGCTTACTACTATTTCTACTGACCTTACTTT<br>CTCTGTGAAGTCTTCTCGTGGCTCTTCTGACCCTCAGGGCGTGACTTGTGGGGCTGCTACTCTTTCTGCTGAGCGTGTG<br>CGTGGTGACAACAAGGAGTACGAGTACTCTGTGGAGTGCCAGGAAGATTCTGCTTGCCCTGCTGCTGAGGAGTCTCTTC<br>CTATTGAGGTGATGGTGGATGCTGTGCACAAGTTAAAATACGAAAACTACACTTCTTCTTTCTTCATTCGTGACATTAT<br>TAAGCCTGACCCTCCCAAGAACCTTCAGTTAAAACCTTTAAAAAACTCGTCAGGTGGAGGTGTCTTGGGAGTACCCT<br>GACACTTGGTCTACTCCTCACTCTTACTTCTCTCTTACTTTCGCGTGCAGGTGCAGGGCAAGTCTAAGCGTGAGAAGA<br>AGGACCGTGTGTTCACTGACAAAACATCTGCTACTGTGATTTGCAGGAAGAATGCATCTATTTCTGTCGTGCTCAGGA<br>CCGTTACTACTCTTCTTCTTGGTCTGAGTGGGCTTCTGTGCCTTGCTCTGGCGGCGGCGGCGGCTCCAGAAATCTT<br>CCTGTGGCTACTCCTGACCCTGGCATGTTCCCTTGCCTTCACCACTCTCAGAACCTTCTTCGTGCTGTGAGCAACATGC |

TABLE 4B-continued

Sequence Optimized Polynucleotides Comprising 5' UTR, ORF, 3' UTR

| | |
|---|---|
| | TTCAGAAGGCTCGTCAAACTCTTGAGTTCTACCCTTGCACTTCTGAGGAGATTGACCACGAAGATATCACCAAAGATAA<br>AACATCTACTGTGGAGGCTTGCCTTCCTCTTGAGCTTACCAAGAATGAATCTTGCTTAAATTCTCGTGAGACGTCTTTC<br>ATCACCAACGGCTCTTGCCTTGCCTCGCGCAAAACATCTTTCATGATGGCTCTTTGCCTTTCTTCTATTTACGAAGATT<br>TAAAAATGTACCAGGTGGAGTTCAAAACAATGAATGCAAAGCTTCTTATGGACCCCAAGCGTCAGATTTTCCTTGACCA<br>GAACATGCTTGCTGTGATTGACGAGCTTATGCAGGCTTTAAATTTCAACTCTGAGACGGTGCCTCAGAAGTCTTCTCTT<br>GAGGAGCCTGACTTCTACAAGACCAAGATTAAGCTTTGCATTCTTCTTCATGCTTTCCGTATTCGTGCTGTGACTATTG<br>ACCGTGTGATGTCTTACTTAAATGCTTCTTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_015<br>(SEQ ID<br>NO: 69) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGTCACCAGCAGCTGGTGATCAGCTGGTTTAGCCTGGTGTTTCTGGCCAGCCCCCTGGTGGCC<br>ATCTGGGAACTGAAGAAAGACGTGTACGTGGTAGAACTGGATTGGTATCCGGACGCTCCCGGCGAAATGGTGGTGCTGA<br>CCTGTGACACCCCCGAAGAAGACGGAATCACCTGGACCCTGGACCAGAGCAGCGAGGTGCTGGGCAGCGGCAAAACCCT<br>GACCATCCAAGTGAAAGAGTTTGGCGATGCCGGCCAGTACACCTGTCACAAAGGCGGCGAGGTGCTAAGCCATTCGCTG<br>CTGCTGCTGCACAAAAAGGAAGATGGCATCTGGAGCACCGATATCCTGAAGGACCAGAAAGAACCCAAAAATAAGACCT<br>TTCTAAGATGCGAGGCCAAGAATTATAGCGGCCGTTTCACCTGCTGGTGGCTGACGACCATCAGCACCGATCTGACCTT<br>CAGCGTGAAAAGCAGCAGAGGCAGCAGCGACCCCCAAGGCGTGACGTGCGGCGCCGCCACCCTGAGCGCCGAGAGAGTG<br>AGAGGCGACAACAAGGAGTATGAGTACAGCGTGGAGTGCCAGGAAGATAGCGCCTGCCCCGCCGCCGAGGAGAGCCTGC<br>CCATCGAGGTGATGGTGGATGCCGTGCACAAGCTGAAGTATGAAAACTACACCAGCAGCTTCTTCATCAGAGATATCAT<br>CAAACCCGACCCCCCCAAGAACCTGCAGCTGAAGCCCCTGAAGAATAGCCGGCAGGTGGAGGTGAGCTGGGAGTACCCC<br>GACACCTGGAGCACCCCCCATAGCTACTTCAGCCTGACCTTCTGCGTGCAGGTGCAGGGCAAGAGCAAGAGAGAAAAGA<br>AAGATAGAGTGTTCACAGATAAGACCAGCGCCACGGTGATCTGCAGAAAAAATGCCAGCATCAGCGTGAGAGCCCAAGA<br>TAGATACTATAGCAGCAGCTGGAGCGAATGGGCCAGCGTGCCCTGCAGCGGCGGCGGCGGCGGCGGCAGCAGAAACCTG<br>CCCGTGGCCACCCCCGACCCGGCATGTTCCCCTGCCTGCACCACAGCCAAAACCTGCTGAGAGCCGTGAGCAACATGC<br>TGCAGAAGGCCCGGCAGACCCTGGAATTTTACCCCTGCACCAGCGAAGAGATCGATCATGAAGATATCACCAAAGATAA<br>AACCAGCACGTGGAGGCCTGTCTGCCCCTGGAACTGACCAAGAATGAGAGCTGCCTAAATAGCAGAGAGACCAGCTTC<br>ATAACCAATGGCAGCTGCCTGGCCAGCAGAAAGACCAGCTTTATGATGGCCCTGTGCCTGAGCAGCATCTATGAAGACC<br>TGAAGATGTACCAGGTGGAGTTCAAGACCATGAATGCCAAGCTGCTGATGGATCCCAAGCGGCAGATCTTTCTGGATCA<br>AAACATGCTGGCCGTGATCGATGAGCTGATGCAGGCCCTGAATTTCAACAGCGAGACCGTGCCCCAAAAAAGCAGCCTG<br>GAAGAACCGGATTTTTATAAAACCAAAATCAAGCTGTGCATACTGCTGCATGCCTTCAGAATCAGAGCCGTGACCATCG<br>ATAGAGTGATGAGCTATCTGAATGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_016<br>(SEQ ID<br>NO: 70) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTCATCAGCTGGTTCAGCCTGGTCTTCCTGGCCAGCCCCCTGGTGGCC<br>ATCTGGGAGCTGAAGAAGGACGTATACGTAGTGGAGTTGGATTGGTACCCAGACGCTCCTGGGGAGATGGTGGTGCTGA<br>CCTGTGACACCCCAGAAGAGGACGGTATCACCTGGACCCTGGACCAGAGCTCAGAAGTGCTGGGCAGTGGAAAAACCCT<br>GACCATCCAGGTGAAGGAGTTTGGAGATGCTGGCCAGTACACCTGCCACAAGGGTGGTGAAGTGCTGAGCCACAGCCTG<br>CTGCTGCTGCACAAGAAGGAGGATGGCATCTGGAGCACAGATATCCTGAAGGACCAGAAGGACCCAAGAACAAGACCT<br>TCCTTCGCTGTGAAGCCAAGAACTACAGTGGCCGCTTCACCTGCTGGTGGCTGACCACCATCAGCACAGACCTCACCTT<br>CTCGGTGAAGAGCAGCAGAGGCAGCTCAGACCCCCAGGGTGTCACCTGTGGGCGGCCACGCTGTCGGCGGAGAGAGTT<br>CGAGGTGACAACAAGGAGTATGAATACTCGGTGGAGTGCCAGGAAGATTCGGCGTGCCCCGCCGCAGAAGAGAGCCTGC<br>CCATAGAAGTGATGGTGGATGCTGTGCACAAGCTGAAGTATGAAAACTACACCAGCAGCTTCTTCATCAGAGATATCAT<br>CAAGCCAGACCCGCCCAAGAACCTGCAGCTGAAGCCCCTGAAGAACAGCCGGCAGGTGGAGGTTTCCTGGGAGTACCCA<br>GATACGTGGAGCACCCCCCACAGCTACTTCAGCCTGACCTTCTGTGTCCAGGTGCAGGGCAAGAGCAAGAGAGAGAAGA<br>AAGATAGAGTCTTCACAGATAAGACCTCGGCCACGGTCATCTGCAGAAAAAATGCCTCCATCTCGGTTCGAGCCCAAGA<br>TAGATACTACAGCAGCAGCTGGTCAGAATGGGCCTCGGTGCCCTGCAGTGGTGGCGGCGGCGGCGGCAGCAGAAACCTG<br>CCTGTTGCCACCCCAGACCCTGGGATGTTCCCCTGCCTGCACCACAGCCAGAACTTATTACGAGCTGTTTCTAACATGC<br>TGCAGAAGGCCCGGCAGACCCTGGAGTTCTACCCCTGCACCTCAGAAGAGATTGACCATGAAGATATCACCAAAGATAA<br>GACCAGCACTGTAGAGGCCTGCCTGCCCCTGGAGCTGACCAAGAATGAAAGCTGCCTGAACAGCAGAGAGACCAGCTTC<br>ATCACCAATGGAAGCTGCCTGGCCAGCAGAAAGACCAGCTTCATGATGGCCCTGTGCCTGAGCAGCATCTATGAAGACC<br>TGAAGATGTACCAGGTGGAGTTCAAGACCATGAATGCAAAGCTGCTGATGGACCCCAAGCGGCAGATATTTTTGGACCA<br>GAACATGCTGGCTGTCATTGATGAGCTGATGCAGGCCCTGAACTTCAACTCAGAAACTGTACCCCAGAAGAGCAGCCTG<br>GAGGAGCCAGATTTCTACAAGACCAAGATCAAGCTGTGCATCCTGCTTCATGCTTTCAGAATCAGAGCTGTCACCATTG<br>ACCGCGTGATGAGCTACTTAAATGCCTCGTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_017<br>(SEQ ID<br>NO: 71) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTAATCAGCTGGTTTTCCCTCGTCTTTCTGGCATCACCCCTGGTGGCT<br>ATCTGGGAGCTGAAGAAGGACGTGTACGTGGTGGAGCTGGATTGGTACCCTGACGCCCCGGGGGAAATGGTGGTGTTAA<br>CCTGCGACACGCCTGAGGAGGACGGCATCACCTGGACGCTGGACCAGAGCAGCGAGGTGCTTGGGTCTGGTAAAACTCT<br>GACTATTCAGGTGAAAGAGTTCGGGGATGCCGGCCAATATACTTGCCACAAGGGTGGCGAGGTGCTTTTCTCATTCTCTG<br>CTCCTGCTGCACAAGAAGAAGATGGCATTTGGTCTACTGATATTCTGAAAGACCAGAAGGAGCCCAAGAACAAGACCT<br>TTCTGAGATGCGAGGCTAAAAACTACAGCGGAAGATTTACCTGCTGGTGGCTGACCACAATCTCAACCGACCTGACATT<br>TTCAGTGAAGTCCAGCAGAGGGAGCTCCGACCCTCAGGGCGTGACCTGCGGAGCCGCCACTCTGTCCGCAGAAAGAGTG<br>AGAGGTGATAATAAGGAGTACGAGTATTCAGTCGAGTGCCAAGAAGATTCGGCGTGTCCCGCCGCTGAGGAGAGCCTGC<br>CAATCGAGGTGATGGTAGATGCGGTACACAAGCTGAAGTATGAGAACTACACATCCTCCTTCTTCATAAGAGATATTAT<br>CAAGCCTGACCCACCTAAAAATCTGCAACTCAAGCCTTTGAAAAATTCACGGCAGGTGGAGGTGAGCTGGGAGTACCCT<br>GATACTTGGAGCACCCCCATAGCTACTTTTCGCTGACATTCTGCGTCCAGGTGCAGGGCAAGTCAAAGAGAGAGAAGA<br>AGGATCGCGTGTTCACTGATAAAACAAGCGCCACAGTGATCTGCAGAAAAAACGCTAGCATTAGCGTCAGAGCCAAGGA<br>CCGGTATTACTCCAGCTCCTGGAGCGAATGGGCATCTGTGCCCTGCAGCGGTGGGGGCGAGGCGGATCCAGAAACCTC<br>CCCGTTGCCACACCTGATCCTGGAATGTTCCCCTGTCTGCACCACAGCCAGAACCTGCTGAGAGCAGTGTCTAACATGC<br>TCCAGAAGGCCAGGCAGACCCTGGAGTTTTACCCCTGCACCAGCGAGGAAATCGATCACGAAGATATCACCAAAGATAA<br>AACCTCCACCGTGGAGGCCTGCCTGCCCCTGGAACTGACCAAAAACGAGAGCTGCCTGAATAGCAGGGAGACCTCCTTC<br>ATCACCAACGGCTCATGCCTTGCCAGCCGGAAAACTAGCTTCATGATGGCCCTGTGCCTGTCTTCGATCTATGAGGACC |

TABLE 4B-continued

Sequence Optimized Polynucleotides Comprising 5' UTR, ORF, 3' UTR

|||
|---|---|
| | TGAAAATGTACCAGGTCGAATTTAAGACGATGAACGCAAAGCTGCTGATGGACCCCAAGCGGCAGATCTTTCTGGACCA<br>GAACATGCTGGCAGTCATAGATGAGTTGATGCAGGCATTAAACTTCAACAGCGAGACCGTGCCTCAGAAGTCCAGCCTC<br>GAGGAGCCAGATTTTTATAAGACCAAGATCAAACTATGCATCCTGCTGCATGCTTTCAGGATTAGAGCCGTCACCATCG<br>ATCGAGTCATGTCTTACCTGAATGCTAGCTGATAATAGGCTGGAGCCTCGGTGGCCATGCTTCTTGCCCCTTGGGCCTC<br>CCCCCAGCCCTCCTCCCCTTCCTGCACCCGTACCCCCCAAACACCATTGTCACACTCCAGTGGTCTTTGAATAAAGTC<br>TGAGTGGGCGGC |
| hIL12AB_018<br>(SEQ ID<br>NO: 72) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGTCACCAACAGTTAGTAATCTCCTGGTTTTCTCTGGTGTTTCTGGCCAGCCCCTCGTGGCC<br>ATCTGGGAGCTTAAAAAGGACGTTTACGTGGTGGAGTTGGATTGGTATCCCGACGCTCCAGGCGAAATGGTCGTGCTGA<br>CCTGCGATACCCCTGAAGAAGACGGTATCACCTGGACGCTGGACCAGTCTTCCGAGGTGCTTGGATCTGGCAAAACACT<br>GACAATACAAGTTAAGGAGTTCGGGGACGCAGGGCAGTACACCTGCCACAAAGGCGGCGAGGTCCTGAGTCACTCCCTG<br>TTACTGCTCCACAAGAAAGAGGACGGCATTTGGTCCACCGACATTCTGAAGGACCAGAAGGAGCCTAAGAATAAAACTT<br>TCCTGAGATGCGAGGCAAAAAACTATAGCGGCCGCTTTACTTGCTGGTGGCTTACAACAATCTCTACCGATTTAACTTT<br>CTCCGTGAAGTCTAGCAGAGGATCCTCTGACCCGCAAGGAGTGACTTGCGGAGCCGCCACCTTGAGCGCCGAAAGAGTC<br>CGTGGCGATAACAAAGAATACGAGTACTCCGTGGAGTGCCAGGAAGATTCCGCCTGCCCAGCTGCCGAGGAGTCCCTGC<br>CCATTGAAGTGATGGTGGATGCCGTCCACAAGCTGAAGTACGAAAACTATACCAGCAGCTTCTTCATCCGGGATATCAT<br>TAAGCCCGACCCTCCTAAAAACCTGCAACTTAAGCCCCTAAAGAATAGTCGGCAGGTTGAGGTCAGCTGGGAATATCCT<br>GACACATGGAGCACCCCCCACTCTTATTTCTCCCTGACCTTCTGCGTGCAGGTGCAGGGCAAGAGTAACGGGAGAAAA<br>AAGATAGGGTCTTTACCGATAAAACCAGCGCTACGGTTATCTGTCGGAAGAACGCTTCCATCTCCGTCCGCGCTCAGGA<br>TCGTTACTACTCGTCCTCATGGAGCGAGTGGGCCAGCGTGCCTGCAGCGGCGGCGGTGGAGGCGGATCCAGAAATCTG<br>CCTGTTGCCACACCAGACCCTGGCATGTTCCCCTGTCTGCATCATAGCCAGAACCTGCTCAGAGCCGTGAGCAACATGC<br>TCCAGAAGGCCAGGCAAACTTTGGAGTTCTACCCGTGTACATCTGAGGGAAATCGATCACGAAGATATAACCAAAGATAA<br>AACCTCTACAGTAGAGGCTTGTTTGCCCCTGGAGTTGACCAAAAACGAGAGTTGCCTGAACAGTCGCGAGACGAGCTTC<br>ATTACTAACGGCAGCTGTCTCGCCTCCAGAAAAACATCCTTCATGATGGCCCTGTGTCTTTCCAGCATATACGAAGACC<br>TGAAAATGTACCAGGTCGAGTTCAAAACAATGAACGCCAAGCTGCTTATGGACCCCAAGCGGCAGATCTTCCTCGACCA<br>AAACATGCTCGCTGTGATCGATGAGCTGATGCAGGCTCTCAACTTCAATTCCGAACAGTGCCACAGAGTTCCAGTCTG<br>GAAGAACCCGACTTCTACAAGACCAAGATTAAGCTGTGTATTTTGCTGCATGCGTTTAGAATCAGAGCCGTGACCATTG<br>ATCGGGTGATGAGCTACCTGAACGCCTCGTGATAATAGGCTGGAGCCTCGGTGGCCATGCTTCTTGCCCCTTGGGCCTC<br>CCCCCAGCCCTCCTCCCCTTCCTGCACCCGTACCCCCCAAACACCATTGTCACACTCCAGTGGTCTTTGAATAAAGTC<br>TGAGTGGGCGGC |
| hIL12AB_019<br>(SEQ ID<br>NO: 73) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTTGTCATCTCCTGGTTTTCTCTTGTCTTCCTGGCCTCGCCGCTGGTGGCC<br>ATCTGGGAGCTGAAGAAGACGTTTACGTAGTAGAGTTGGATTGGTACCCAGACGCACCTGGAGAAATGGTGGTTCTCA<br>CCTGTGACACTCCTGAAGAAGACGGTATCACCTGGACGCTGGACCAAAGCTCAGAAGTTCTTGGCAGTGGAAAAACGCT<br>GACCATACAAGTAAAAGAATTTGGGGATGCTGGCCAGTACACGTGCCACAAAGGAGGAGAAGTTCTCAGCCACAGTTTA<br>CTTCTTCTTCACAAGAAAGAAGATGGCATCTGGTCCACAGATATTTTAAAAGACCAGAAGGAGCCCAAGAACAAAACCT<br>TCCTCCGCTGTGAGGCCAAGAACTACAGTGGTCGTTTCACCTGCTGGTGGCTCACCACCATCTCCACTGACCTCACCTT<br>CTCTGTAAAAAGCAGCCGTGGTTCTTCTGACCCCCAAGGAGTCACCTGTGGGGCTGCCACGCTCTCGGCAGAAGAGTT<br>CGAGGTGACAACAAGGAATATGAATATTCTGTGGAATGTCAAGGAATTCTGCCTGCCCGGCGGCAGAAGAAAGTCTTC<br>CCATAGAAGTCATGGTGGATGCTGTTCACAAATTAAAATATGAAAACTACACCAGCAGCTTCTTCATTCGTGACATCAT<br>CAAACCAGACCCGCCCAAGAACCTTCAGTTAAAACCTTTAAAAAACAGCCGGCAGGTAGAAGTTTCCTGGGAGTACCCA<br>GATACGTGGTCCACGCCGCACTCCTACTTCAGTTTAACCTTCTGTGTACAAGTACAAGGAAATCAAAAGAGAAGA<br>AAGATCGTGTCTTCACTGACAAAACATCTGCCACGGTCATCTGCAGGAAGAATGCCTCCATCTCGGTTCGAGCCCAGGA<br>CCGCTACTACAGCAGCAGCTGGAGTGAGTGGGCATCTGTTCCCTGCAGTGGTGGCGGCGGCGGCGGCAGCCGCAACCTT<br>CCTGTGGCCACGCCGGACCCTGGCATGTTCCCGTGCCTTCACCACTCCCAAAATCTTCTTCGTGCTGTTTCTAACATGC<br>TGCAGAAGGCGCCAAACTTTAGAATTCTACCCGTGCACTTCTGAGGAAATAGACCATGAAGATATCACCAAAGATAA<br>AACCAGCACGGTGGAGGCCTGCCTTCCTTTAGAGCTGACCAAGAATGAATCCTGCCTCAACAGCAGAGAGACCAGCTTC<br>ATCACCAATGGCAGCTGCCTGGCCTCGCGCAAGACCAGCTTCATGATGGCGCTGTGCCTTTCTTCCATCTATGAAGATT<br>TAAAGATGTACCAAGTAGAATTTAAAACCATGAATGCCAAATTATTAATGGACCCCAAACGGCAGATATTTTGGATCA<br>AAACATGCTGGCTGTCATTGATGAGCTCATGCAAGCATTAAACTTCAACTCAGAAACTGTTCCCCAGAAGTCATCTTTA<br>GAAGAGCCAGATTTCTACAAACAAAATAAAACTCTGCATTCTTCTTCATGCCTTCCGCATCCGTGCTGTCACCATTG<br>ACCGTGTCATGTCCTACTTAAATGCTTCTTGATAATAGGCTGGAGCCTCGGTGGCCATGCTTCTTGCCCCTTGGGCCTC<br>CCCCCAGCCCTCCTCCCCTTCCTGCACCCGTACCCCCCAAACACCATTGTCACACTCCAGTGGTCTTTGAATAAAGTC<br>TGAGTGGGCGGC |
| hIL12AB_020<br>(SEQ ID<br>NO: 74) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTGATCAGCTGGTTCAGCCTGGTGTTCCTGGCTAGCCCTCTGGTGGCC<br>ATCTGGGAGCTGAAGAAGGACGTGTACGTGGTGGAGTTGGATTGGTACCCCGACGCTCCCGGCGAGATGGTGGTGCTGA<br>CCTGCGACACCCCGAGGAGGACGGGATCACCTGGACCCTGGATCAGTCAAGCGAGGTGCTGGGAAGCGGCAAGACCCT<br>GACCATCCAGGTGAAGGAGTTCGGCGACGCCGGCCAATACACTTGCCACAAGGGAGGCGAGGTGCTGTCCCACTCCCTG<br>CTGCTGCTGCACAAAAAGGAAGACGGCATCTGGAGCACCGACATCCTGAAAGACCAGAAGGAGCCTAAGAACAAAACAT<br>TCCTCAGATGCGAGGCCAAGAATTACTCCGGGAGATTCACCTGTTGGTGGCTGACCACCATCAGCACAGACCTGACCTT<br>CAGCGTGAAGAGCAGCAGAGGCAGCTCAGACCCCAGGGCGTGACCTGTGGCGCCGCCACCCTGAGCGCCGAAAGAGTG<br>CGCGGCGACAACAAGGAGTACGAGTACTCCGTGGAATGCCAGGAAGATAGCGCCTGCCCCGCCGCCGAGGAGAGCCTGC<br>CCATCGAGGTGATGGTGGACGCCGTCCACAAGCTGAAGTACGAGAACTACACCTCAGCTTCTTCATCAGAGATATCAT<br>CAAGCCCGATCCCCCCAAGAACCTGCAGCTGAAACCCCTGAAGAACAGCCGGCAGGTGGAGGTGAGCTGGGAGTATCCC<br>GACACCTGGTCCACCCCCCACAGCTATTTTAGCCTGACCTTCTGCGTGCAAGTGCAGGGCAAGAGCAAGAGAGAAGAGAAGA<br>AGGACCGCGTGTTCACCGACAAAACCAGCGCCACCGTGATCTGCAGAAAGAACGCCAGCATCAGCGTGAGGGCCCAGGA<br>TAGATACTACAGTTCCAGCTGGAGCGAGTGGGCCAGCGTGCCCTGCAGCGGCGGCGGCGGGGAGGCTCGAGAACCTG<br>CCCGTGGCTACCCCCGATCCCGGAATGTTCCCCTGCCTGCACCACAGCCAGAACCTGCTGAGGGCGGTGTCCAACATGC<br>TTCAGAAGGCCCGACCCTGGAGTTCTACCCCTGTACCTCTGAGGAGATCGATCATGAAGATATCACCAAAGATAA<br>AACCAGCACCGTGGAGGCCTGCCTGCCCCTGGAGCTGACCAAGAACGAGAGCTGCCTGAACTCCCGCGAGACCAGCTTC<br>ATCACGAACGGCAGCTGCCTGGCCAGCAGGAAGACCTCCTTCATGATGGCCCTGTGCCTGAGCAGCATCTACGAGGACC<br>TGAAAATGTACCAGGTGGAGTTTAAGACCATGAACGCCAAGCTGCTGATGGACCCCAAGCGGCAAATCTTCCTGGACCA<br>GAACATGCTGGCAGTGATCGACGAGCTCATGCAGGCCCTGAACTTCAATAGCGAGACGGTCCCCCAGAAGAGCAGCCTG<br>GAGGAGCCCGACTTTTACAAGACCAAGATCAAGCTGTGCATCCTGCTGCACGCCTTTAGAATCCGTGCCGTGACCATTG |

TABLE 4B-continued

Sequence Optimized Polynucleotides Comprising 5' UTR, ORF, 3' UTR

| | |
|---|---|
| | ACAGAGTGATGAGCTACCTGAATGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_021<br>(SEQ ID<br>NO: 75) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTGATCAGCTGGTTCAGCCTGGTGTTCCTGGCCAGCCCTCTGGTTGCC<br>ATCTGGGAGCTGAAGAAAGACGTGTACGTCGTGGAACTGGACTGGTATCCGGACGCCCCGGGCGAGATGGTGGTGCTGA<br>CCTGTGACACCCCCGAGGAGGACGGCATCACCTGGACGCTGGACCAATCCTCCGAGGTGCTGGGAAGCGGCAAGACCCT<br>GACCATCCAGGTGAAGGAATTCGGGGACGCCGGGCAGTACACCTGCCACAAGGGGGGCGAAGTGCTGTCCCACTCGCTG<br>CTGCTCCTGCATAAGAAGGAGGATGGAATCTGGTCCACCGACATCCTCAAAGATCAGAAGGAGCCCAAGAACAAGACGT<br>TCCTGCGCTGTGAAGCCAAGAATTATTCGGGGCGATTCACGTGCTGGTGGCTGACAACCATCAGCACCGACCTGACGTT<br>TAGCGTGAAGAGCAGCAGGGGGTCCAGCGACCCCCAGGGCGTGACGTGCGGCGCCGCCACCCTCTCCGCCGAGAGGGTG<br>CGGGGGGACAATAAGGAGTACGAGTACAGCGTGGAATGCCAGGAGGACAGCGCCTGCCCCGCCGCGGAGGAAAGCCTCC<br>CGATAGAGGTGATGGTGGACGCCGTGCACAAGCTCAAGTATGAGAATTACACCAGCAGCTTTTTCATCCGGGACATTAT<br>CAAGCCCGACCCCCCGAAGAACCTCCAGCTGAAGCCCCTGAAGAACAGCCGGCAGGTGGAAGTCTCCTGGGAGTATCCC<br>GACACCTGGAGCACCCCGCACAGCTACTTCTCCCTGACCTTCTGTGTGCAGGTGCAGGGCAAGTCCAAGAGGGAAAGA<br>AGGACAGGGTTTTCACCGACAAGACCAGCGCGACCGTGATCTGCCGGAAGAACGCCAGCATAAGCGTCCGCGCCCAAGA<br>TAGGTACTACAGCAGCTCCTGGAGCGAGTGGGCTAGCGTGCCCTGCAGCGGGGCGGGGGTGGGGGCTCCAGGAACCTG<br>CCAGTGGCGACCCCCGACCCCGGCATGTTCCCTGCCTCCATCACAGCCAGAACCTGCTGAGGGCCGTCAGCAATATGC<br>TGCAGAAGGCCAGGCAGACCCTGGAATTCTACCCCTGCACGTCGGAGGAGATCGATCACGAGGATATCACAAAAGACAA<br>GACTTCCACCGTGGAGGCCTGCCTGCCCCTGGAGCTCACCAAGAATGAGTCCTGTCTGAACTCCCGGGAAACCAGCTTC<br>ATCACCAACGGGTCCTGCCTGGCCAGCAGGAAGACCAGCTTTATGATGGCCCTGTGCCTGTCGAGCATCTACGAGGACC<br>TGAAGATGTACCAGGTCGAGTTCAAGACAATGAACGCCAAGCTGCTGATGGACCCCAAGAGGCAAATCTTCCTGGACCA<br>GAATATGCTTGCCGTCATCGACGAGCTCATGCAGGCCCTGAACTTCAACTCCGAGACCGTGCCCCAGAAGAGCAGCCTG<br>GAGGAGCCCGACTTCTACAAGACCAAGATCAAGCTGTGCATCCTGCTGCACGCGTTCAGGATCCGGGCAGTCACCATCG<br>ACCGTGTGATGTCCTACCTGAACGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_022<br>(SEQ ID<br>NO: 76) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCATCAGCAGCTGGTGATCAGCTGGTTCAGCCTGGTGTTCCTCGCCTCTCCCCTGGTGCC<br>ATCTGGGAGCTCAAAAAGGACGTGTACGTGGTGGAGCTCGACTGGTACCCAGACGCCCCCGGGGAGATGGTGGTGCTGA<br>CCTGCGACACCCCCGAAGAAGACGGCATCACGTGGACCCTCGACCAGTCCAGCGAGGTGCTGGGGAGCGGGAAGACTCT<br>GACCATCCAGGTCAAGGAGTTCGGGGACGCCGGGCAGTACACGTGCCACAAGGGCGGCGAAGTCTTAAGCCACAGCCTG<br>CTCCTGCTGCACAAGAAGGAGGACGGGATCTGGTCCACAGACATACTGAAGGACCAGAAGGAGCCGAAGAATAAAACCT<br>TTCTGAGGTGCGAGGCCAAGAACTATTCCGGCAGGTTCACGTGCTGGTGGCTTACAACAATCAGCACAGACCTGACGTT<br>CAGCGTGAAGTCCAGCCGCGGCAGCAGCGACCCCCAGGGGGTGACCTGCGGCGCCGCCACCCTGAGCGCCGAGCGGGTG<br>CGCGGGGACAACAAGGAGTACGAGTACTCCGTGGAGTGCCAGGAAGACAGCGCCTGTCCCGCCGCCGAAGAGAGCCTGC<br>CTATCGAGGTCATGGTAGATGCAGTGCATAAGCTGAAGTACGAGAACTATACGAGCAGCTTTTTCATACGCGACATCAT<br>CAAGCCCGACCCCCCAAGAACCTGCAGCTTAAGCCCCTGAAGAATAGCCGGCAGGTGGAGGTCTCCTGGGAGTACCCC<br>GACACCTGGTCAACGCCCCACAGCTACTTCTCCCTGACCTTTTGTGTCCAAGTCCAGGGAAAGAGCAAGAGGGAGAAGA<br>AAGATCGGGTGTTCACCGACAAGACCTCCGCCACGGTGATCTGCAGGAAGAACGCCAGCATCTCCGTGAGGGCGCAAGA<br>CAGGTACTACTCCAGCAGCTGGTCCGAATGGGCCAGCGTGCCCTGCTCCGGCGGCGGGGGCGGCGGCAGCCGAAACCTA<br>CCCGTGGCCGGATCCCGGCATGTTTCCCTGCCTGCACCACAGCCAGAACCTCCTGAGGGCCGTGTCCAACATGC<br>TGCAGAAGGCCAGGCAGACTCTGGAGTTCTACCCCTGCACGAGCGAGGAGATCGATCACGAGGACATCACCAAGGATAA<br>GACCAGCACTGTGGAGGCCTGCCTTCCCCTGGAGCTGACCAAGAACGAGAGCTGTCTGAACTCCAGGGAGACCTCATTC<br>ATCACCAACGGCTCCTGCCTGGCCAGCAGGAAAACCAGCTTCATGATGGCCTTGTGTCTCAGCTCCATCTACGAGGACC<br>TGAAGATGTATCAGGTCGAGTTCAAGACAATGAACGCCAAGCTGCTGATGGACCCCAAAAGGCAGATCTTCCTGGACCA<br>GAACATGCTGGCCGTCATCGACGAGCTGATGCAGGCCCTGAACTTCAACAGCGAGACGGTGCCCCAGAAAAGCTCCCTG<br>GAGGAGCCCGACTTCTACAAGACCAAGATCAAGCTGTGCATCCTGCTGCACGCCTTCAGGATCAGGGCAGTGACCATCG<br>ACCGGGTGATGTCATACCTTAACGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_023<br>(SEQ ID<br>NO: 77) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCATCAGCAGCTGGTGATCTCCTGGTTCAGCCTGGTGTTTCTGGCCTCGCCCTGTGTCGCC<br>ATCTGGGAGCTGAAGAAAGACGTGTACGTCGTCGAACTGGACTGGTACCCCGACGCCCCCGGGGAGATGGTGGTGCTGA<br>CCTGCGACACGCCGGAGGAGGACGGCATCACCTGGACCCTGGATCAAAGCAGCGAGGTGCTGGGCAGCGGCAAGACCCT<br>GACCATCCAAGTGAAGGAATTCGGCGATGCCGGCCAGTACACCTGTCACAAAGGGGGCGAGGTGCTCAGCCACAGCCTG<br>CTGCTGCTGCACAAGAAGGAGGATGGCATCTGGAGCACCGATATCCTGAAGGACCAGAAAGAGCCCAAGAACAAGACGT<br>TCCTGAGGTGCGAGGCCAAGAACTACAGCGGTAGGTTCACGTGTTGGTGGCTGACCACCATCAGCACCGACCTGACGTT<br>CAGCGTGAAGAGCTCCAGGGGCAGCTCCGACCCACAGGGGGTGACGTGCGGGCCGCAACCCTCAGCGCCGAAAGGGTG<br>CGGGGGGACAACAAGGAGTACGAATACTCCGTGGAGTGCCAGGAAGATTCGGCTGCCCCGCCGCGGAGGAGAGCCTCC<br>CCATCGAGGTAATGGTGGACGCCGTGCATAAGCTGAAGTACGAGAACTACACCAGCTCGTTCTTCATCCGAGACATCAT<br>CAAACCCGACCCGCCAAAATCTGCAGCTCAAGCCCCTCAAGGCAGGTGGAGGTGAGCTGGGAGTACCCC<br>GACACCTGGTCCACCCCGCACAGCTACTTCTCCCTGACATTCTGCGTGCAGGTGCAGGGCAAGAGCAAGCGGGAGAAGA<br>AGGACAGGGTGTTCACCGACAAGACGAGCGCCACCGTGATCTGCCGAAAGAACGCCAGCATCTCGGTGCGCGCCCAGGA<br>TAGGTACTATTCCAGCTCCTGGAGCGAGTGGGCCTCGGTACCCTGCAGCGGCGGCGGGGGCGGCGGCAGTAGGAATCTG<br>CCCGTGGCTACCCCGGACCCCGGGCATGTTCCCCTGCCTCCACCACAGCCAGAACCTGCTGAGGGCCGTGAGCAACATGC<br>TGCAGAAGGCCAGACAGACGCTGGAGTTCTACCCCTGCACGAGCGAGGAGATCGACCACGAGGACATCACCAAGGATAA<br>AACTTCCACCGTCGAGGCCTGCTGCCCTTGGAGCTGACCAAGAATGAATCTGTCTGAACAGCAGGGAGACCTCGTTT<br>ATCACCAATGGCAGCTGCCTCGCCTCCAGGAAGACCAGCTTCATGATGGCCCTCTGTCTGAGCTCCATCTATGAGGACC<br>TGAAGATGTACCAGGTGGAGTTCAAGACCATGAACGCGAAGCTGCTGATGGACCCCAAGAGGCAGATCTTCCTGGATCA<br>GAATATGCTGGCGGTGATCGACGAGCTCATGCAGGCCCTCAATTTCAATAGCGAGACAGTGCCCCAGAAGTCCTCCCTG<br>GAGGAGCCCGACTTCTACAAGACCAAGATCAAGCTGTATCCTGCTGCACGCCTTCCGGATCCGGGCCGTCACCATCG<br>ACCGGGTCATGAGCTACCTCAATGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |

TABLE 4B-continued

Sequence Optimized Polynucleotides Comprising 5' UTR, ORF, 3' UTR hIL12AB_024  TCAAGCTTTTGGACCCTCGTACAGAAGCTAATACGACTCACTATAGGGAAATAAGAGAGAAAAGAAGAGTAAGAAGAAA
(SEQ ID     TATAAGAGCCACCATGTGCCACCAGCAGCTGGTGATCTCCTGGTTCTCCCTGGTGTTCCTGGCCTCGCCCCTGGTGGCC
NO: 78)     ATCTGGGAGCTGAAGAAGGACGTGTACGTCGTGGAGCTCGACTGGTACCCCGACGCCCCTGGCGAGATGGTGGTGCTGA
            CCTGCGACACCCCCAGAGGAGGATGGCATCACCTGGACCCTGGATCAGTCCTCCGAGGTGCTGGGCTCCGGCAAGACGCT
            GACCATCCAAGTGAAGGAGTTCGGTGACGCCGGACTATACCTGCCATAAGGGCGGCGAGGTCCTGTCCCACAGCCTC
            CTCCTCCTGCATAAGAAGGAGGACGGCATCTGGAGCACCGACATCCTGAAGGACCAGAAGGAGCCCAAGAACAAGACCT
            TTCTGAGGTGCGAGGCCAAGAACTACAGCGGCCGATTCACCTGCTGGTGGCTCACCACCATATCCACCGACCTGACTTT
            CTCCGTCAAGTCCTCCCGGGGGTCCAGCGACCCCCAGGGAGTGACCTGCGGCGCCGCCACCCTCAGCGCCGAGCGGGTG
            CGGGGGGACAACAAGGAGTACGAATACTCCGTCGAGTGCCAGGAGGACTCCGCCTGCCCGGCCGCCGAGGAGGAGCCTGC
            CCATCGAGGTGATGGTCGACGCGGTGCACAAGCTGAAGTACGAGAACTACACCAGCAGTTTCTTCATCAGGGATATCAT
            CAAGCCAGATCCCCCGAAGAATCTGCAACTGAAGCCGCTGAAAAACTCACGACAGGTGGAGGTGAGCTGGGAGTACCCC
            GACACGTGGAGCACCCCACATTCCTACTTCAGCCTGACCTTCTGCGTGCAGGTCCAGGGCAAGAGCAAGCGGGAGAAGA
            AGGACAGGGTGTTCACGGATAAGACCAGTGCCACCGTGATCTGCAGGAAGAACGCCTCTATTAGCGTGAGGGCCCAGGA
            TCGGTATTACTCCTCGAGCTGGAGCGAATGGGCCTCCGTGCCTGCCCTGCAGTGGGGGGGGTGGAGGCGGGAGCAGGAACCTG
            CCCGTAGCAACCCCCGACCCCGGGATGTTCCCCTGTCTGCACCACTCGCAGAACCTGCTGCGCGCGGTGAGCAACATGC
            TCCAAAAAGCCCGTCAGACCTTAGAGTTCTACCCCTGCACCAGCGAAGAAATCGACCACGAAGACATCACCAAGGACAA
            AACCAGCACCGTGGAGGCGTGCCTGCCGCTGGAGCTGACCAAGAACGAGAGCTGCCTCAACTCCAGGGAGACCAGCTTT
            ATCACCAACGGCTCGTGCCTAGCCAGCCGGAAAACCAGCTTCATGATGGCCCTGTGCCTGAGCTCCATTTACGAGGACC
            TGAAGATGTATCAGGTGGAGTTCAAGACCATGAATGCCAAACTCCTGATGGACCCCAAGAGGCAGATCTTCCTGGACCA
            GAACATGCTCGCGGTGATCGATGAGCTGATGCAGGCCCTGAACTTTAATAGCGAGACCGTGCCCCAGAAAAGCAGCCTG
            GAGGAGCCGGACTTCTACAAGACCAAAATCAAGCTGTGCATCCTGCTCCACGCCTTCCGCATCCGGGCCGTGACCATCG
            ACAGGGTGATGAGCTACCTGAACGCCAGCTGATAATAGGCTGGAGCCTCGGTGGCCATGCTTCTTGCCCCTTGGGCCTC
            CCCCCAGCCCCTCCTCCCCTTCCTGCACCCGTACCCCCCAAACACCATTGTCACACTCCAGTGGTCTTTGAATAAAGTC
            TGAGTGGGCGGC hIL12AB_025  TCAAGCTTTTGGACCCTCGTACAGAAGCTAATACGACTCACTATAGGGAAATAAGAGAGAAAAGAAGAGTAAGAAGAAA
(SEQ ID     TATAAGAGCCACCATGTGCCATCAGCAGCTGGTGATTTCCTGGTTCTCCCTGGTGTTCCTGGCCAGCCCCCTCGTGGCG
NO: 79)     ATCTGGGAGCTAAAGAAGGACGTGTACGTGGTGGAGCTGGACTGGTACCCGGACGCACCCGGCGAGATGGTCGTTCTGA
            CCTGCGATACGCCAGAGGAGGACGGCATCACCTGGACCCTCGATCAGAGCAGCGAGGTCCTGGGGAGCGGAAAGACCCT
            GACCATCCAGGTCAAGGAGTTCGGCGACGCCGGCCTGTACAAAGGTGGCGAAAGGTCCTGTCCCACTCGCTG
            CTGCTCCTGCATAAGAAGGAGGACGGAATCTGGAGCACAGACATCCTGAAAGACCAGAAGGAGCCCAAGAACAAGACCT
            TCCTGAGGTGCGAGGCCAAGAACTACAGCGGGCGCTTCACGTGCTGGTGGCTGACCACCATCAGCACGGACCTCACCTT
            CTCCGTGAAGAGCAGCCGGGGATCCAGCGATCCCCAAGGCGTCACCTGCGGCGCGGCCACCCTGAGCGCGGAGAGGGTC
            AGGGGCGATAATAAGGAGTATGAGTACAGCGTGGAGTGCCAGGAGGACAGCGCCTGCCCGGCCGCCGAGGAGTCCCTGC
            CAATCGAAGTGATGGTCGACGCCGTGCACAAGCTGAAGTACGAGAACTACACACCAGCAGCTTCTTCATCCGGGATATCAT
            CAAGCCCGATCCCCCGAAGAACCTGCAGCTGAAGCCCCTCAAGAACAGCCGGCAGGTGGAGGTGAGTTGGGAGTACCCC
            GACACCTGGTCAACGCCCACAGCTACTTCTCCCTGACCTTCTGTGTGCAGGTGCAGGGAAAGAGCAAGAGGGAGAAGA
            AGACCCGGGTCTTCACCGACAAGACCAGCGCCACGGTGATCTGCAGGAAGAACGCAAGCATCTCCGTGAGGGCCCAGGA
            CAGGTACTACAGCTCCAGCTGGTCCGAATGGGCCAGCGTGCCCTGTCTAGCGCGCGGGGGGGTGGCAGCCGCAACCTC
            CCAGTGGCCACCCCCGACCCCGGCATGTTCCCCTGCCTGCACCACAGCCAGAATCTGCTGAGGGCCGTGAGTAACATGC
            TGCAGAAGGCAAGGCAAACCCTCGAATTCTATCCCTGCACCTCCGAGGAGATCGACCACGAGGATATCACCAAGGACAA
            GACCAGCACCGTGGAGGCCTGTCTCCCCCTGGAGCTGACCAAGAATGAGAGCTGCCTGAACAGCCGGGAGACCAGCTTC
            ATCACCAACGGCTGCCTGGCCTCCAGGAAGACCTCGTTCATGATGGCGCTGTGCCTCTCAAGCATATACGAGGATC
            TGAAGATGTACCAGGTGGAGTTTAAGACGATGAACGCCAAGCTGCTGATGGACCCGAAGAGGCAGATCTTCCTGGACCA
            GAACATGCTGGCCGTGATAGACGAGCTCATGCAGGCCCTGAACTTCAACTCCGAGACCGTGCCGCAGAAGTCATCCCTC
            GAGGAGCCCGACTTCTATAAGACCAAGATCAAGCTGTGCATCCTGCTCCACGCCTTCCGGATAAGGGCCGTGACGATCG
            ACAGGGTGATGAGCTACCTTAACGCCAGCTGATAATAGGCTGGAGCCTCGGTGGCCATGCTTCTTGCCCCTTGGGCCTC
            CCCCCAGCCCCTCCTCCCCTTCCTGCACCCGTACCCCCCAAACACCATTGTCACACTCCAGTGGTCTTTGAATAAAGTC
            TGAGTGGGCGGC hIL12AB_026  TCAAGCTTTTGGACCCTCGTACAGAAGCTAATACGACTCACTATAGGGAAATAAGAGAGAAAAGAAGAGTAAGAAGAAA
(SEQ ID     TATAAGAGCCACCATGTGCCACCAGCAGCTCGTGATCAGCTGGTTCTCCCTGGTGTTTCTCGCCAGCCCCCTGGTGGCC
NO: 80)     ATCTGGGAGCTGAAGAAGGACGTGTACGTGGTGGAGCTGGACTGGTACCCTGACGCCCCGGGGGAGATGGTCGTGCTGA
            CCTGCGACACCCCCGAAGAGGACGGTATCACCTGGACCCTGGACCAGTCCAGCGAGGTGCTGGGCAGCGGCAAGACCCT
            GACTATTCAAGTCAAGGAGTTCGGAGACGCCGGCCAGTACACCTGCCAAAAGGGTGGAGAGGTGTTATCACACAGCCTG
            CTGCTGCTGCACAAGAAGGAAGACGGGATCTGGAGCACCGACATCCTGAAGGACCAGAAGGAGCCCAAAAACAAGACCT
            TCCTGCGGTGCGAGGCCAAGAACTATTCGGGCCGCTTTACGTGCTGGTGGCTGACCACCATCAGCACTGATCTCACCTT
            CAGCGTGAAGTCCTCCCGGGGGTCGTCCGACCCCCAGGGGGTGACCTGCGGGGCCGCCACCCTGTCCGCCGAGAGAGTG
            AGGGGCGATAATAAGGAGTACGAGTACAGCGTTGAGTGCCAGGAAGATAGCGCCTGTCCCGCCGCCGAGGAGCCTGC
            CCATCGAGGTGATGGTGGACGCCGTCCACAAGCTGAAGTATGAGAACTACACCTCAAGCTTCTTCATCAGGGACATCAT
            CAAACCCGATCCGCCCAAGAATCTGCAGCTGAAGCCCCTGAAAAATAGCAGGCAGGTGGAGGTGAGCTGGGAGTACCCC
            GACACCTGTCCACCCCCATAGCTATTTCTCCCTGACGTTCTGCGTGCAGGTGCAAGGGAAGAGCAAGCGGGAGAAGA
            AGGACCGGGTGTTCACCGACAAGACCTCCGCCACCGTGATCTGTAGGAAGAACGCGTCGATCTCGGTCAGGGCCCAGGA
            CAGGTATTACAGCAGCAGCTGGAGCGAGTGGGCCGCCGCTGCCCTGTGTGGGCGGCGGCGCGCGGCAGCCGCAGAAATCTG
            CCCGTGGCCACCCCAGACCCCGGAATGTTCCCCTGCCTGCACCATTCGCAGAACCTCCTGAGGGCCGTGAGCAACATGC
            TGCAGAAGGCCCGCCAGACGCTGGAGTTCTACCCCTGCACGAGCGAGGAGATCGACCACGAAGACATCACCAAGGACAA
            AACCAGCACCGTGGAGGCCTGCCTGCCCCTGGAGCTGACCAAAAACGAATCCTGCCTCAACAGCCGGGAGACCAGCTTC
            ATCACCAACGGCTGCCTGGCCAGCCGAAAGACCTCCTTCATGATGGCCCTGTGCCTGAGCAGCATCTATGAGGATC
            TGAAGATGTATCAGGTGGAGTTCAAGACCATGAATGCCAAGCTGCTGATGGACCCCAAGAGGCAGATATTCCTGGACCA
            GAATATGCTGGCCGTGATCGACGAGCTGATGCAGGCCCTGAACTTCAACAGCGAGACCGTCCCCCAGAAGTCCAGCCTG
            GAGGAGCCGGACTTTTACAAAACGAAGATCAAGCTGTGCATACTGCTGCACGCCTTCAGGATCCGGGCCGTGACAATCG
            ACAGGGTGATGTCTACCTGAACGCCAGCTGATAATAGGCTGGAGCCTCGGTGGCCATGCTTCTTGCCCCTTGGGCCTC
            CCCCCAGCCCCTCCTCCCCTTCCTGCACCCGTACCCCCCAAACACCATTGTCACACTCCAGTGGTCTTTGAATAAAGTC
            TGAGTGGGCGGC hIL12AB_027  TCAAGCTTTTGGACCCTCGTACAGAAGCTAATACGACTCACTATAGGGAAATAAGAGAGAAAAGAAGAGTAAGAAGAAA
(SEQ ID     TATAAGAGCCACCATGTGTCACCAGCAGCTGGTGATCAGCTGGTTCTCCCTGGTGTTCCTGGCCAGCCCCCTGGTGGCC TABLE 4B-continued Sequence Optimized Polynucleotides Comprising 5' UTR, ORF, 3' UTR

| | |
|---|---|
| NO: 81) | ATCTGGGAGCTCAAGAAGGACGTCTACGTCGTGGAGCTGGATTGGTACCCCGACGCTCCCGGGGAGATGGTGGTGCTGA<br>CCTGCGACACCCCCGAGGAGGACGGCATCACCTGGACGCTGGACCAGAGCTCAGAGGTGCTGGGAAGCGGAAAGACACT<br>GACCATCCAGGTGAAGGAGTTCGGGGATGCCGGGCAGTATACCTGCCACAAGGGCGGCGAAGTGCTGAGCCATTCCCTG<br>CTGCTGCTGCACAAGAAGGAGGACGGCATATGGTCCACCGACATCCTGAAGGATCAGAAGGAGCCGAAGAATAAAACCT<br>TCCTGAGGTGCGAGGCCAAGAATTACAGCGGCCGATTCACCTGCTGGTGGCTGACCACCATCAGCACCGACCTGACCTT<br>CAGTGTGAAGTCCTCACGGGGCAGCTCAGATCCCCAGGGCGTGACCTGCGGGGCCGCGACACTCAGCGCCGAGCGGGTG<br>AGGGGTGATAACAAGGAGTACGAGTATTCTGTGGAGTGCCAGGAAGACTCCGCCTGTCCCGCCGCCGAGGAGTCCCTGC<br>CCATCGAGGTGATGGTGGACGCCGTGCATAAACTGAAGTACGAGAACTACACCTCCAGCTTCTTCATCCGGGATATAAT<br>CAAGCCCGACCCTCCGAAAAACCTGCAGCTGAAGCCCCTTAAAAACAGCCGGCAGGTGGAGGTGAGCTGGGAGTACCCC<br>GACACCTGGAGCACCCCCCATAGCTATTTCAGCCTGACCTTCTGCGTGCAGGTGCAGGGGAAGTCCAAGCGCGAGAAAA<br>AGGACCGGGTGTTCACCGACAAGACGAGCGCCACCGTGATCTGCCGGAAGAACGCCAGTATAAGCGTAAGGGCCCAGGA<br>TAGGTACTACAGCTCCAGCTGGTCGGAGTGGGCCTCCGTGCCCTGTTCCGGCGGCGGGGGGGGTGGCAGCAGGAACCTC<br>CCCCGTGGCCACGCCGGACCCCGGCATGTTCCCGTGCCTGCACCACTCCCAAAACCTCCTGCGGGCCGTCAGCAACATGC<br>TGCAAAAGGCGCGGCAGACCCTGGAGTTTTACCCCTGTACCTCCGAAGAGATCGACCACGAGGATATCACCAAGGATAA<br>GACCTCCACCGTGGAGGCCTGTCTCCCCCTGGAGCTGACCAAGAACGAGAGCTGTCTTAACAGCAGAGAGACCTCGTTC<br>ATAACGAACGGCTCCTGCCTCGCTTCCAGGAAGACGTCGTTCATGATGGCGCTGTGCCTGTCCAGCATCTACGAGGACC<br>TGAAGATGTATCAGGTCGAGTTCAAAACCATGAACGCCAAGCTGCTGATGGACCCCAAGAGGCAGATCTTCCTGGACCA<br>GAACATGCTCGCCGTGATCGACGAGCTGATGCAGGCCCTGAACTTCAACAGCGAAACCGTGCCCCAGAAGTCAAGCCTG<br>GAGGAGCCGGACTTCTATAAGACCAAGATCAAGCTGTGTATCCTGCTACACGCTTTTCGTATCCGGGCCGTGACCATCG<br>ACAGGGTTATGTCGTACTTGAACGCCAGCTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_028<br>(SEQ ID<br>NO: 82) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAACAGCTCGTGATCAGCTGGTTCAGCCTGGTGTTCCTGGCCAGCCCGCTGGTGGCC<br>ATCTGGGAGCTGAAGAAGGACGTGTACGTGGTGGAGCTGGACTGGTACCCCGACGCCCCGGCGAGATGGTGGTCCTGA<br>CCTGCGACACGCCGGAAGAGGACGGCATCACCTGGACCCTGGATCAGTCCAGCGAGGTGCTGGGCTCCGGCAAGACCCT<br>GACCATTCAGGTGAAGGAGTTCGGCGACGCCGGTCAGTACACCTGCCACAAGGGCGGCGAGGTGCTGAGCCACAGCCTA<br>CTGCTCCTGCACAAAAAGGAGGATGGAATCTGGTCCACCGACATCCTCAAGGACCAGAAGGAGCCGAAGAACAAGACGT<br>TCCTCCGGTGCGAGGCCAAGAACTACAGCGGCAGGTTTACCTGCTGGTGGCTGACCACCATCAGCACCGACCTGACATT<br>TTCCGTGAAGAGCAGCCGCGGCAGCAGCGATCCCCAGGGCGTGACCTGCGGGCGACCCACCCTGTTCCGCCGAGCGTGTG<br>AGGGGCGACAACAAGGAGTACGAGTACAGCGTGGAATGCCAGGAGGACAGCGCCTGTCCCGCCGCCGAGGAGAGCCTGC<br>CAATCGAGGTCATGGTGGACGCCGTGCACAAGCTGAAGTACGAGAACTACACGAGCAGCTTCTTCATCAGGGACATCAT<br>CAAACCGGACCCGCCCAAGAACCTGCAGCTGAAACCCTTGAAAAACAGCAGGCAGGTGGAAGTGTCTTGGGAGTACCCC<br>GACACCTGGTCCACCCCCCACAGCTACTTTAGCCTGACCTTCTGTGTGCAGGTCCAGGGCAAGTCCAAGAGGGAGAAGA<br>AGGACAGGGTGTTCACCGACAAAACCAGCGCCACCGTGATCTGCAGGAAGAACGCCTCCATCAGCGTGCGGGCCAGGA<br>CAGGTATTACAGCTCGTCGTGGAGCGAGTGGGCCAGCGTGCCCTGCTCCGGGGGAGGCGGCGGCGGAAGCCGGAATCTG<br>CCCCGTGGCCACCCCCGATCCCGGCATGTTCCCGTGTCTGCACCACAGCCAGAACCTGCTGCGGGCCGTGAGCAACATGC<br>TGCAGAAGGCCCGCCAAACCCTGGAGTTCTACCCCTGTACAAGCGAGGAGATCGACCATGAGGACATTACCAAGGACAA<br>GACCAGCACCGTGGAGGCCTGCCTGCCCCTCGAGCTCACAAAGAACGAATCCTGCCTGAATAGCCGCGAGACCAGCTTT<br>ATCACGAACGGGTCCTGCCTCGCCAGCCGGAAGACAAGCTTCATGATGGCCCTGTGCCTGAGCAGCATCTACGAGGACC<br>TGAAAATGTACAAGTGGAGTTCAAAACGATGAACGCCAAGCTGCTGATGGACCCCAAGCGCAGATCTTCCTGGACCA<br>GAACATGCTGGCCGTCATCGACGAGCTCATGCAGGCCCTGAACTTCAACAGCGAGACCGTGCCCCAGAAGAGCAGCCTG<br>GAGGAGCCCGACTTCTACAAGACGAAGATCAAGCTCTGCATCCTGCTTCCGCATCCGCGCGGTGACCATCG<br>ACCGGGTGATGAGCTACCTCAACGCCAGTTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_029<br>(SEQ ID<br>NO: 83) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAACAGCTGGTGATCAGCTGGTTCAGCCTGGTGTTTCTGGCCTCCCCTCTGGTGGCC<br>ATCTGGGAGCTGAAGAAGGACGTGTACGTGGTGGAGCTGGACTGGTACCCTGACGCCCCGGCGAAATGGTGGTGCTGA<br>CGTGCGACACCCCCGAGGAGGATGGCATCACCTGGACCCTGGACCAAAAGCAGCGAGGTCCTCGGAAGCGGCAAGACCCT<br>CACTATCCAAGTGAAGGAGTTCGGGGATGCGGGCCAGTACACCTGCCACAAGGGCGGCGAGGTGCTGTCTCATAGCCTG<br>CTGCTCCTGCATAAGAAGGAAGACGGCATCTGGAGCACCGACATACTGAAGGATCAGAAGGAGCCCAAGAACAAGACCT<br>TCCTGAGGTGCGAGGCCAAGAACTACTCCGGGCGCTTCACCTGTTGGTGGCTGACCACCATCTCCACCGACCTGACCTT<br>CAGCGTGAAGAGCAGCAGGGGACAGCAGCGACCCCCAGGGGTGACCTGCGGAGCCGCCGACCTTGTCGGCCGAGCGGGTG<br>AGGGGCGACAATAAGGAGTACGAGTACTCGGTCGAATGCCAGGAGGACTCCGCCTGCCCGCCGCCGAGGAGTCCCTCC<br>CCATCGAAGTGATGGTGGACGCCGTCCACAAGCTGAAGTACGAGAACTACACCAGCAGCTTCTTCATACGGGATATCAT<br>CAAGCCCGACCCCCCGAAGAACCTGCAGCTGAAACCCTTGAAGAACTCCAGGCAGGTGGAGGTGAGCTGGGAGTACCCC<br>GACACCTGTCCACCCCGCACTCATACTTCAGCCTGACCTTCTGTGTACAGGTCCAGGGCAAGAGCAAGAGGGAAAAGA<br>AGGATAGGGTGTTCACCGACAAGACCTCCGCCACGGTGATCTGTCGGAAAAACGCCAGCATCTCCGTGCGCGCCAGGA<br>CAGGTACTATTCCAGCAGCTGGAGCGAGTGGGCCTCCGTCCCCTGCTCCGGCGGCGGTGGCGGGGGCAGCAGGAACCTC<br>CCCCGTGGCCACCCCCGATCCCGGGATGTTCCCATGCCTGCACCACAGCCAAAACCTGCTGAGGGCCGTCTCCAATATGC<br>TGCAGAAGGCGAGGCAGACCCTGGAGTTCTACCCCTGTACCTCCGAGGAGATCGACCACGAGGATATCACCAAGGACAA<br>GACCTCCACGGTCGAGGCGTGCCTGCCCCTGGAGCTCACGAAGAACGAGAGCTGCCTTAACTCCAGGGAAACCTCGTTT<br>ATCACGAACGGCAGCTGCCTGGCGTCACGGAAGACCTCCTTTATGATGGCCCTATGTCTGTCCTCGATCTACGAGGACC<br>TGAAGATGTACCAGGTGGAGTTCAAGACCATGAACGCCAAGCTGCTGATGGATCCCAAGAGGCAGATTTTCCTGGACCA<br>GAACATGCTGGCCGTGATTGACGAGCTGATGCAGGCGCTGAACTTCAACAGCGAGACAGTGCCGCAGAAGAGCTCCCTG<br>GAGGAGCCGGACTTTTACAAGACAAAGATAAAGCTGTGCATCCTGCTCCACGCCTTCAGAATACGGGCCGTCACCATCG<br>ATAGGGTGATGTCTTACCTGAACGCCTCCTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_030<br>(SEQ ID<br>NO: 84) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTGGTGATTAGCTGGTTTAGCCTGGTGTTCCTGGCAAGCCCCTGGTGGCC<br>ATCTGGGAACTGAAAAAGGACGTGTACGTGGTCGAGCTGGATTGGTACCCCGACGCCCCGGCGAAATGGTGGTGCTGA<br>CGTGTGATACCCCCGAGGAGGACGGGATCACCTGGACCCTGGATCAGAGCAGCGAGGTGCTGGGGAGCGGAAGACCCT<br>GACGATCCAGGTCAAGGAGTTCGGCGACGCTGGGCAGTACACCTGTCACAAGGGCGGGGAGGTGCTGTCCCACTCCCTG |

TABLE 4B-continued

Sequence Optimized Polynucleotides Comprising 5' UTR, ORF, 3' UTR

|  |  |
|---|---|
|  | CTGCTCCTGCATAAGAAAGAGGACGGCATCTGGTCCACCGACATCCTCAAGGACCAGAAGGAGCCCAAGAACAAGACCT<br>TCCTGCGGTGTGAGGCGAAGAACTACAGCGGCCGTTTCACCTGCTGGTGGCTGACGACAATCAGCACCGACGTTGACGTT<br>CTCCGTGAAGTCCTCCAGAGGCAGCTCCGACCCCCAAGGGGTGACGTGCGGCGCGGCCACCCTGAGCGCCGAGCGGGTG<br>CGGGGGGACAACAAGGAGTACGAGTACTCCGTGGAGTGCCAGGAGGACAGCGCCTGTCCCGCAGCCGAGGAGTCCCTGC<br>CCATCGAAGTCATGGTGGACGCCGTCCACAAGCTGAAGTACGAGAACTACACCAGCAGCTTCTTCATCCGCGATATCAT<br>CAAGCCCGATCCCCCCAAAAACCTGCAACTGAAGCCGCTGAAGAATAGCAGGCAGGTGGAGGTGTCCTGGGAGTACCCG<br>GACACCTGGAGCACGCCCCACAGCTATTTCAGCCTGACCTTTTGCGTGCAGGTCCAGGGGAAGAGCAAGCGGGAGAAGA<br>AGGACCGCGTGTTTACGGACAAAACCAGCGCCACCGTGATCTGCAGGAAGAACGCCAGCATCAGCGTGAGGGCCCAGGA<br>CAGGTACTACAGCAGCTCCTGGAGCGAGTGGGCCTCCGTGCCCTGTTCCGGAGGCGGCGGGGGCGGTTCCCGGAACCTC<br>CCGGTGGCCACCCCCGACCCGGGCATGTTCCCGTGCCTGCACCACTCACAGAATCTGCTGAGGGCCGTGAGCAATATGC<br>TGCAGAAGGCAAGGCAGACCCTGGAGTTTTATCCCTGCACCAGCGAGGAGATCGACCACGAAGACATCACCAAGGACAA<br>GACCAGCACAGTGGAGGCCTGCCTGCCCCTGGAACTGACCAAGAACGAGTCCTGTCTGAACTCCCGGGAAACCAGCTTC<br>ATAACCAACGGCTCCTGTCTCGCCAGCAGGAAGACCAGCTTCATGATGGGCCCTGTGCCTCAGCTCCATCTACGAGGACC<br>TCAAGATGTACCAGGTTGAGTTCAAGACCATGAACGCCAAGCTCCTGATGGACCCAAGAGGCAGATCTTCCTGGACCA<br>GAATATGCTGGCCGTGATCGATGAGTTAATGCAGGCGCTGAACAGCGAGACGGTGCCCCAAAAGTCCTCGCTG<br>GAGGAGCCCGACTTCTACAAGACCAAGATCAAGCTGTGCATCCTCCTGCACGCCTTCCGAATCCGGGCCGTAACCATCG<br>ACAGGGTGATGAGCTATCTCAACGCCTCCTGATAATAGGCTGGAGCCTCGGTGGCCATGCTTCTTGCCCCTTGGGCCTC<br>CCCCCAGCCCCTCCTCCCCTTCCTGCACCCGTACCCCCAAACACCATTGTCACACTCCAGTGGTCTTTGAATAAAGTC<br>TGAGTGGGCGGC |
| hIL12AB_031<br>(SEQ ID<br>NO: 85) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTCGTGATCAGCTGGTTCTCGCTTGTGTTCCTGGCCTCCCCCCTCGTCGCC<br>ATCTGGGAGCTGAAGAAAGACGTGTACGTGGTGGAGCTGGACTGGTATCCCGAGCGCCCCGGGGGAGATGGTGGTGCTGA<br>CCTGCGACACCCCGAAGAGGACGGCATCACCTGGACGCTCGACCAGTCGTCCGAAGTGCTGGGGTCGGGCAAGACCCT<br>CACCATCCAGGTGAAGGAGTTCGGAGACGCCGGCCAGTACACCTGTCATAAGGGGGGGGAGGTGCTGAGCCACAGCCTC<br>CTGCTCCTGCACAAAAAGGAGGACGGCATCTGGAGCACCGATATCCTCAAGGACCAGAAGGAGCCCAAGAACAAGACGT<br>TCCTGAGGTGTGAGGCCAAGAACTACAGCGGGCGGTTCACGTGTTGGTGCTCACCACCATCTCCACCGACCTCACCTT<br>CTCCGTGAAGTCAAGCAGGGGCAGCTCCGACCCCCAAGGCGTCACCTGCGGCGCCGCCACCCTGAGCGCCGAGAGGGTC<br>AGGGGGGATAACAAGGAATACGAGTACAGTGTGGAGTGCCAAGAGGATAGCGCCTGTCCCGCCGCCGAAGAGAGCCTGC<br>CCATCGAAGTGATGGTGGACGCCGTGCACAAGCTGAAGTACGAGAACTACACCTCCAGCTTCTTCATCAGGGATATCAT<br>CAAGCCCGATCCCCCCAAGAACCTGCAGCTGAAGCCCCTGAAGAACAGCAGGCAGGTGGAGGTGAGCTGGGAGTATCCC<br>GACACGTGGAGCACCCCGCACAGCTACTTCTCGCTGACCTTCTGCGTGCAGGTGCAAGGGAAGTCCAAGAGGGAGAAGA<br>AGGATAGGGTGTTCACCGACAAAACGAGCGCCACCGTGATCTGCCGGAAGAATGCCAGCATCTCTGTGAGGGCCCAGGA<br>CAGGTACTATTCCAGCTCCTGGTCGGAGTGGGCCAGCGTGCCCTGTAGCGGCGGGGGCGGGGGCGGCAGCAGGAACCTC<br>CCGGTTGCCACCCCCGACCCCGGCATGTTCCCGTGCCTGCACCACTCGCAAAACCTGCTGCGCGGTCTCCAACATGC<br>TGCAAAAAGCGCGCCAGACGCTGGAGTTCTACCCCTGCACCAGCGAGGAGATCGATCATGAAGATATCACCAAAGACAA<br>GACCTCGACCGTGGAGGCCTGCCTGCCCCTGGAGCTCACCAAGAACGAAAGCTGCCTGAACAGCAGGGAGACAAGCTTC<br>ATCACCAACGGCAGCTGCCTGGCCTCCGGAAGACCAGCTTCATGATGGGCCCTGTGCCTGTCAGCATCTACGAGGATC<br>TGAAGATGTACCAAGTGGAGTTTAAGACCATGAACGCCAAGCTGTTAATGGACCCCAAAAGGCAGATCTTCCTGGATCA<br>GAACATGCTGGCCGTCATCGACGAGCTGATGCAAGCCCTGAACAGCGAGAGCCGTCAACAGCGAGACCAGAGAGAGCCCTC<br>GAGGAGCCCGACTTCTATAAGACCAAGATAAAGCTGTGCATTCTGCTGCACGCCTTCAGAATCAGGGCCGTGACCATCG<br>ATAGGGTGATGAGCTACCTGAACGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCAAACACCATTGTCACACTCCAGTGGTCTTTGAATAAAGTC<br>TGAGTGGGCGGC |
| hIL12AB_032<br>(SEQ ID<br>NO: 86) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGTCACCAGCAGCTGGTGATTTCCTGGTTCAGTCTGGTGTTTCTTGCCAGCCCCCTGGTGGCC<br>ATCTGGGAGCTGAAGAAAGACGTATACGTCGTGGAGCTGGACTGGTATCCCGAGCGCTCCCGGCGAGATGGTGGTCCTCA<br>CCTGCGACACCCCAGAGGAGGACGGCATCACCTGGACCCTGGACCAGAGCTCCGAGGTCCTGGGCAGCGGTAAGACCCT<br>CACCATCCAGGTGAAGGAGTTTGGTGATGCCGGGCAGTATACCTGCCACAAGGGCGGCGAGGTGCTGTCCCACAGCCTC<br>CTGTTACTGCATAAGAAGGAGGATGGCATCTGGAGCACCGACATCCTCAAGGACCAGAAAGAGCCCAAGAACAAGACCT<br>TTCTGCGGTGCGAGGCGAAAAATTACTCCGGCCGGTTCACCTGCTGGTGGCTGACCACCATCAGCACGGACCTGACGTT<br>CTCCGTGAAGTCGAGCAGGGGGAGCTCCGATCCCCAGGGCGTGACCTGCGGCGCGGCCACCCTGAGCGCCGAGCGCGTC<br>CGCGGGGACAATAAGGAATACGAATATAGCGTGGAGTGCCAGGAGGACAGCGCCTGCCCCGCGGCCGAGGAGAGCCTCC<br>CGATCGAGGTGATGGTGGATGCCGTCCACAAGCTCAAATACGAAAACTACACCAGCAGCTTCTTCATTAGGGACATCAT<br>CAAGCCCGACCCCCCAAAAACCTGCAGCTGAAGCCCCTGAAGAACAGCCGCCAGGTCGAGGTGTCATGGGAGTACCCA<br>GACACCTGGAGCACCCCCACTCCTACTTCAGCCTGACCTTCTGCGTCCAGGTGCAGGGAAAGTCCAAACGGGAGAAGA<br>AGGATAGGGTCTTTACCGATAAGACGTCGGCCACCGTCATCTGCAGGAAGAACGCCAGCATAAGCGTGCGGGCGCAGGA<br>TCGGTACTACAGCTCGAGCTGGTCCGAATGGGCCTCCGTGCCCTGTAGCGGAGGGGGTGGCGGGGGCAGCAGGAACCTG<br>CCCGTGGCCACCCCGGACCCGGGCATGTTTCCCTGCCTGCATCACAGTCAGAACCTGCTGAGGGCCGTGAGCAACATGC<br>TCCAGAAGGCCCGCCAGACCCTGGAGTTTTACCCCTGCACCAGCGAAGAGATCGATCACGAAGACATCACCAAAGACAA<br>GACCTCCACCGTGGAGGCCTGTCTGCCCCTGGAGCTGACCAAGAACGAGAGCTGTCTGAACAGCAGGGAGACCTCCTTC<br>ATCACCAACGGCTCCTGCCTGGCATCCCGGAAGACCAGCTTCATGATGGGCCCTGTGTCGAGCTCTATCTACGAGGACC<br>TGAAGATGTACCAGGTCGAGTTCAAGACCATGAACGCCAAGCTGCTGATGGACCCCAAGCGACAGATATTCCTGGACCA<br>GAACATGCTCGCCGTGATCGATGAACTGATGCAAGCCCTGAACTTCATAGCGAGACCGTGCCCCAGAAAGCAGCCTG<br>GAGGAGCCCGACTTCTACAAGACCAAGATCAAACTGTGCATACTGCTGCACGCGTTCAGGATCCGGGCCGTCACCATCG<br>ACCGGGTGATGTCCTATCTGAATGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCAAACACCATTGTCACACTCCAGTGGTCTTTGAATAAAGTC<br>TGAGTGGGCGGC |
| hIL12AB_033<br>(SEQ ID<br>NO: 87) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTCGTGATTAGCTGGTTTTCGCTGGTGTTCCTGGCCAGCCCTCTCGTGGCC<br>ATCTGGGAGCTGAAAAAAGACGTTACGTGGTGGAGCTGGACTGGTACCCGAGCGCCCCGGCAGATGGTGGTGCTGA<br>CGTGCGACACCCCGGAAGAGGACGGCATCACCTGGACCCTGGACCAGTCATCCGAGGTCCTGGGCAGCGGCAAGACGCT<br>CACCATCCAGGTGAAGGAGTTCGGCGACGCCGGCCAGTACACATGCCATAAGGGCGGGAGGTGCTGAGCCACAGCCTG<br>CTCCTCCTGCACAAGAAGGAGGATGGCATCTGGTCCTACAGACATCCTGAAGGACCAGAAAGAGCCCAAGAACAAGACCT<br>TCCTCCGGTGCGAGGCCAAGAACTACTCCGGGCGGTTTACTTGTTGGTGGCTGACCACCATCAGCACCGACCTCACCTT<br>CAGCGTGAAGAGCTCCCGAGGGAGCTCCGACCCCCAGGGGGTCACCTGCGGCGCCGCCACCCTGAGCGCCGAGCGGGTG |

TABLE 4B-continued

Sequence Optimized Polynucleotides Comprising 5' UTR, ORF, 3' UTR

| | |
|---|---|
| | AGGGGCGACAACAAGGAGTATGAATACAGCGTGGAATGCCAAGAGGACAGCGCCTGTCCCGCGGCCGAGGAAAGCCTGC<br>CCATCGAGGTGATGGTGGACGCCGTCCACAAACTCAAGTACGAGAACTACACCAGCAGTTTCTTCATTCGCGACATCAT<br>CAAGCCGGACCCCCCCAAAAACCTGCAGCTCAAACCCCTGAAGAACAGCAGGCAGGTGGAGGTCAGCTGGGAGTACCCG<br>GACACCTGGAGCACCCCCATAGCTACTTCAGCCTGACCTTCTGCGTGCAGGTGCAGGGCAAGAGCAAACGCGAGAAGA<br>AGGACCGGGTGTTTACCGACAAGACCAGCGCCACGGTGATCTGCCGAAAGAATGCAAGCATCTCCGTGAGGGCGCAGGA<br>CCGCTACTACTCTAGCAGCTGGAGCGAGTGGGCCAGCGTGCCCTGCAGCGGTGGCGGCGGAGGCGGCAGCCGTAACCTC<br>CCCGTGGCCACCCCCGACCCCGGCATGTTCCCGTGTCTGCACCACTCCCAGAACCTGCTGAGGGCCGTCAGCAATATGC<br>TGCAGAAGGCCCGGCAGACGCTGGAGTTCTACCCCTGCACCTCCGAGGAGATCGACCATGAGGACATTACCAAGGACAA<br>GACGAGCACTGTGGAGGCCTGCCTGCCCCTGGAGCTCACCAAAAACGAGAGCTGCCTGAATAGCAGGGAGACGTCCTTC<br>ATCACCAACGGCAGCTGTCTGGCCAGCAGGAAGACCAGCTTCATGATGGCCCTGTGCCTCTCCTCCATATATGAGGATC<br>TGAAGATGTACCAGGTGGAGTTCAAGACCATGAACGCCAAGCTGCTGATGGATCCCAAGAGGCAGATCTTCCTGGACCA<br>GAATATGCTGGCCGTGATTGACGAGCTGATGCAGGCCCTGAACTTTAATAGCGAGACCGTCCCCCAGAAGAGCAGCCTG<br>GAGGAGCCCGACTTCTATAAGACCAAGATCAAGCTGTGCATACTGCTGCACGCGTTTAGGATAAGGGCCGTCACCATCG<br>ACAGGGTGATGAGCTACCTGAATGCCAGCTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_034<br>(SEQ ID<br>NO: 88) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAACAGCTGGTGATCTCCTGGTTCAGCCTGGTTTTCCTCGCCAGCCCCCTGGTGGCC<br>ATCTGGGAGCTGAAGAAAGACGTGTACGTGGTGGAGCTGGACTGGTATCCCGACGCCCCCGGCGAGATGGTCGTGCTGA<br>CCTGCGACACCCCGGAGGAGGACGGCATCACCTGGACCCTGGATCAGTCCTCCGAGGTGCTGGGCAGCGGGAAGACCCT<br>GACCATCCAGGTGAAAGAGTTCGGAGATGCCGGCCAGTATACCTGTCACAAGGGGGTGAGGTGCTGAGCCATAGCCTC<br>TTGCTTCTGCACAAGAAGGAGGACGGCATCTGGTCCACCGACATCCTCAAGGACCAAAAGGAGCCGAAGAATAAAACGT<br>TCCTGAGGTGCGAAGCCAAGAACTATTCCGGACGGTTCACCTGCTGGTGGCTGACCACCATCAGCACCGACCTCACCTT<br>CTCCGTAAAGTCAAGCAGGGGCAGCTCCGACCCCCAGGGCGTGACCTGCGGAGCCGCCACCCTGAGCGCAGAGAGGGTG<br>AGGGGCGACAACAAGGAGTACGAATACTCCGTCGAGTGCCAGGAGGACAGCGCCTGCCCCGCCGCCGAGGAAAGTCTGC<br>CCATCGAGGTGATGGTGGACGCCGTGCACAAGCTCAAATACGAGAACTACACCAGCAGTTTCTTCATCCGGGATATCAT<br>CAAGCCCGACCCTCCAAAGAATCTGCAGCTGAAACCCCTTAAGAACAGCAGGCAGGTGGAGGTCAGCTGGGAGTACCCC<br>GACACCTGGAGCACGCCCCACTCCTACTTTAGCCTGACCTTTTGCGTGCAGGTGCAGGGGAAAAGCAAGCGGGAGAAGA<br>AGGACAGGGTGTTCACCGATAAGACCTCCGCTACCGTGATCTGCAGGAAGAACGCCTCAATCAGCGTGAGGGCCCAGGA<br>TCGGTACTACTCCAGCTCCTGGAGCGAGTGGGCCAGCGTGCCCTGCCGGGGTGGCGGCGGGGGAGGCGGCAGCCGGAACCTG<br>CCGGTGGCCACTCCCGACCCGGGCATGTTCCCGTGCCTCCACCATTCCCAGAACCTGCTGCGGGCCGTCTCCAATATGC<br>TCCAGAAGGCAAGGCAGACCCTGGAGTTCTACCCCTGCACCAGCGAGGAGATCGATCACGAGGACATCACCAAAGACAA<br>AACCAGCACGGTCGAGGCCTGCCTGCCCCTGGAACTCACCAAGAACGAAAGCTGTCTCAACAGCCGCGAGACCAGCTTC<br>ATAACCAACGGTTCCTGTCTGGCCTCCCGCAAGACCAGCTTTATGATGGCCCTCTGTCTGAGCTCCATCTATGAAGACC<br>TGAAAATGTACCAGGTGGAGTTCAAAACCATGAACGCCAAGCTTCTGATGGACCCCAAGAGGCAGATCTTCCTGGATCA<br>GAACATGCTGGCCGTGATCGACGAGCTGATGCAGGCCCTGAACTTTAACTCCGAGACCGTGCCCCAGAAAAGCAGCCTG<br>GAAGAGCCCGATTTCTACAAAACGAAGATCAAGCTGTGCATCCTGCTGCACGCCTTCCGGATCCGTGCGGTGACCATCG<br>ATAGGGTGATGAGCTACCTGAACGCCAGCTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_035<br>(SEQ ID<br>NO: 89) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAACAGCTGGTAATCAGCTGGTTTAGCCTGGTGTTCCTTGGCCAGCCCACTGGTGGCC<br>ATCTGGGAGTTAAAGAAGGACGTGTACGTGGTGGAGCTGGATTGGTACCCCGACGCCCCGGGCGAGATGGTCGTGCTCA<br>CCTGCGATACCCCCGAGGAGGACGGGATCACCTGGACCCTGGACCAATCCAGCGAGGTGCTGGGCAGCGGCAAGACCCT<br>GACCATACAGGTGAAGGAATTTGGGGACGCCGGCCAGTACACCTGCCACAAGGGCGGGGAAGTGCTGTCCCACTCCCTC<br>CTGCTGCTGCATAAGAAGGAGGACGGCATCTGGAGCACCGACATCCTGAAGGACCAAAAGGAGCCCAAGAACAAGACCT<br>TCCTGAGGTGCGAGGCCAAAAACTATTCCGGCCGCTTTACCTGTTGGTGGCTGACCACCATCTCCACCGATCTGACCTT<br>CAGCGTGAAGTCGTCTAGGGGCTCCTCCGACCCCCAGGGCGTAACCTGCGGCGCCGCGACCCTGAGCGCCGAGAGGGTG<br>CGGGGCGATAACAAAGAGTACGAGTACTCGGTGGAGTGCCAGGAGGACAGCGCCTGTCCGGCGGCCGAGGAGAGCCTGC<br>CCATCGAGGTGATGGTGGACGCCGTCCACAAGCTGAAGTACGAGAACTACACCAGTTCGTTCTTCATCAGGGACATCAT<br>CAAGCCGGACCCCCCCAAGAACCTCCAGCTGAAGCCCCTGAAGAACAGCAGGCAGGTGGAAGTGTCCTGGGAGTATCCC<br>GACACCTGGAGCACCCCCACAGCTACTTCAGCCTGACCTTTTGCGTGCAGGTGCAGGGCAAAAGCAAGAGGGAAAAGA<br>AGGACCGGGTGTTCACCGATAAGACGAGCGCCACCGTTATCTGCAGGAAGAACGCCTCCATAAGCGTGAGGGCGCAGGA<br>CCGTTACTACAGCAGCAGCTGGAGTGAGTGGGCAAGCGTGCCCTGTAGCGGCGGGGGCGGGGGCGGTCCCGCAACCTC<br>CCCGTCGCCACCCCCGACCCAGGCATGTTCCCGTGCCTGCACCAGCCAGAACCTGCTGCGGGCCGTTAGCAACATGC<br>TGCAGAAGGCCAGGCAGACCCTGGAGTTCTATCCCTGCACATCTGAGGAGATCGACCACGAAGACATCACTAAGGATAA<br>GACCTCCACCGTGGAGGCCTGTCTGCCCCTCGAGCTGACCAAGAATGAATCCTGCCTGAACAGCCGAGAGACCAGCTTT<br>ATCACCAACGGCTCCTGCCTGGCCAGCAGGAAGACCTCCTTCATGATGGCCCTGTGCCTCTCCAGCATCTACGAGGATC<br>TGAAGATGTACCAGGTAGAGTTCAAGACGATGAACGCCAAGCTCCTGATGGACCCCAAGAGGCAGATATTCCTGGACCA<br>GAACATGCTGGCGGTGATCGACGAGCTGATGCAGGCCCTGAATTTCAACAGCGAGACGGTGCCACAGAAGTCCAGCCTG<br>GAGGAGCCAGACTTCTACAAGACCAAGATCAAACTGTGCATCCTCCTGCACGCGTTCAGGATCCGCGCCGTCACCATAG<br>ACAGGGTGATGAGTTATCTGAACGCCAGCTGATAATAGGCTGGAGCCTCGGTGGCCATGCTTCTTGCCCCTTGGGCCTC<br>CCCCCAGCCCTCCTCCCCTTCCTGCACCCGTACCCCCAAACACCATTGTCACACTCCAGTGGTCTTTGAATAAAGTC<br>TGAGTGGGCGGC |
| hIL12AB_036<br>(SEQ ID<br>NO: 90) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCATCAGCAGCTGGTAATCAGCTGGTTTAGCCTGGTGTTCCTGGCCAGCCCACTGGTGGCC<br>ATCTGGGAGCTGAAGAAGGACGTGTACGTGGTGGAACTGGACTGGTACCCCGACGCCCTGGCGAGATGGTGGTACTGA<br>CCTGTGACACCCCGGAGGAAGACGGTATCACCTGGACCCTGGATCAGAGCTCCGAGGTGCTGGGCTCCGGCAAGACACT<br>GACCATCCAAGTTAAGGAATTTGGGGACGCCGGCCAGTACACCTGCCACAAGGGGGGCGAGGTGCTGTCCCACTCCCTG<br>CTGCTTCTGCATAAGAAGGAGGATGGCATCTGGTCCACCGACATCCTGAAGGACCAGAAGGAGCCCAAGAATAAGACCT<br>TCCTGAGGATGCGAGGCCAAGAACTACTCGGGAAGGTTCACCTGCTGGTGGCTGACCACCATCAGCACCGACCTGACCTT<br>CTCCGTGAAGAGCTCCGGGGCAGCTCCGACCCCCAGGGCGTAACCTGTGGGGCCGCTACCCTGTCCGCCGAGAGGGTC<br>CGGGGCGACAACAAGGAATACGAGTACAGCGTGGAGTGCCAGGAGGACTCCGCCTGCCCCGCCGCCGAGGAGTCGCTGC<br>CCATAGAGGTGATGGTGGACGCCGTGCACAAGCTCAAGTACGAGAATTACACCAGCAGCTTCTTTATCAGGGACATAAT<br>TAAGCCGGACCCCCCAAAGAATCTGCAGCTGAAGCCCCTGAAGAATAGCCGGCAGGTGGAAGTGTCCTGGGAGTACCCC |

TABLE 4B-continued

Sequence Optimized Polynucleotides Comprising 5' UTR, ORF, 3' UTR

| | |
|---|---|
| | GACACCTGGAGCACCCCCACTCCTATTTCTCACTGACATTCTGCGTGCAGGTGCAAGGGAAAAGCAAGAGGGAGAAGA<br>AGGATAGGGTGTTCACCGACAAGACAAGCGCCACCGTGATCTGCCGAAAAAATGCCAGCATCAGCGTGAGGGCCCAGGA<br>TCGGTATTACAGCAGCTCCTGGAGCGAGTGGGCCAGCGTGCCCTGTTCCGGCGGGGAGGGGCGGCTCCCGGAACCTG<br>CCGGTGGCCACCCCCGACCCTGGCATGTTCCCCTGCCTGCATCACAGCCAGAACCTGCTCCGGGCCGTGTCGAACATGC<br>TGCAGAAGGCCCGGCAGACCCTCGAGTTTTACCCCTGCACCAGCGAAGAGATCGACCACGAAGACATAACCAAGGACAA<br>GACCAGCACGGTGGAGGCCTGCCTGCCCCTGGAGCTTACCAAAAACGAGTCCTGCCTGAACAGCCGGGAAACCAGCTTC<br>ATAACGAACGGGAGCTGCCTGGCCTCCAGGAAGACCAGCTTCATGATGGCGCTGTGTCTGTCCAGCATATACGAGGATC<br>TGAAGATGTATCAGGTGGAATTCAAAACTATGAATGCCAAGCTCCTGATGGACCCCAAGAGGCAGATCTTCCTGGACCA<br>GAACATGCTAGCCGTGATCGACGAGCTGATGCAGGCCCTCAACTTCAACTCGGAGACGGTGCCCCAGAAGTCCAGCCTC<br>GAGGAGCCCGACTTCTACAAGACCAAGATCAAGCTGTGCATACTGCTGCATGCCTTCAGGATAAGGGCGGTGACTATCG<br>ACAGGGTCATGTCCTACCTGAACGCCAGCTGATAATAGGCTGGAGCCTCGGTGGCCATGCTTCTTGCCCCTTGGGCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_037<br>(SEQ ID<br>NO: 91) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAACAACTGGTGATCAGCTGGTTCTCCCTGGTGTTCCTGGCCAGCCCCCTGGTGGCC<br>ATCTGGGAGCTCAAAAAAGACGTGTACGTGGTGGAGCTCGATTGGTACCCAGACGCGCCGGGGGAAATGGTGGTGCTGA<br>CCTGCGACACCCCAGAGGAGGATGGCATCACGTGGACGCTGGATCAGTCCAGCGAGGTGCTGGGGAGCGGCAAGACGCT<br>CACCATCCAGGTGAAGGAATTTGGCGACGCGGGCCAGTATACCTGTCACAAGGGCGGCGAGGTGCTGAGCCACTCCCTG<br>CTGCTGCTGCACAAGAAGGAGGATGGGATCTGGTCAACCGATATCCTGAAAGACCAGAAGGAGCCCAAGAACAAGACCT<br>TCCTGCGCTGCGAGGCCAAGAACTATAGCGGCAGGTTCACCTGCTGGTGGCTGACCACCATCAGCACCGACCTGACCTT<br>CAGCGTGAAATCCTCCAGGGGCAGCAGCGACCCCCAGGGCGTGACCTGCGGTGCCGCCACGCTCTCCGCCGAGCGAGTG<br>AGGGGTGACAACAAGGAGTACGAGTACAGCGTGGAATGTCAGGAGGACAGCGCCTGTCCCGCCGCCGAGGAGTCGCTGC<br>CCATCGAGGTGATGGTCGACGCGGTGCACAAGCTCAAATACGAGAATTACACCAGCAGCTTCTTCATCAGGGACATCAT<br>CAAGCCCGACCCCCCAAGAACCTGCAGCTGAAGCCCTTGAAGAACAGCAGGCAGGTGGAGGTGAGCTGGGAGTACCCG<br>GACACCTGGAGCACCCCCACTCCTACTTCAGCCTGACGTTCTGTGTGCAGGTGCAGGGGAAGTCCAAGAGGGAGAAGA<br>AGGACCGGGTGTTCACCGACAAGACCAGCGCCACCGTGATCGCCGAAGAACGCGTCCATCAGCGTTCGCGCCCAGGA<br>CCGCTACTACAGCAGCTCCTGGTCCGAATGGGCCAGCGTGCCCTGCAGCGGTGGAGGGGGCGGGGGCTCCAGGAATCTG<br>CCGGTGGCCACCCCCGACCCCGGGATGTTCCCCGTGTCTGCATCACTCCCAGAACCTGCTGCGGGCCGTGAGCAATATGC<br>TGCAGAAGGCCAGGCAGACGCTCGAGTTCTACCCCTGCACCTCCGAAGAGATCGACCATGAGGACATCACCAAGGACAA<br>GACCAGCACCGTGGAGGCCTGCCTCCCCCTGGAGCTGACCAAAAACGAGAGCTGCCTGAACTCCAGGGAGACCAGCTTT<br>ATAACCAACGGCAGCTGCCTCGCCTCCAGGAAGACCTCGTTTATGATGGCCCTCTGCCTGTCCAGCATCTACGAGGACC<br>TGAAGATGTACCAGGTGGAGTTCAAGACCATGAACGCGAAGTTGCTCATGGACCCCAAGAGGCAGATCTTCCTGGACCA<br>GAACATGCTCGCGGTGATCGACGAGCTGATGCAAGCCCTGAACTTCAACAGCGAGACCGTGCCCCAGAAGAGCAGCCTG<br>GAAGAGCCCGACTTCTACAAGACCAAGATCAAGCTGTGCATCCTGCTGCACGCCTTCCGGATCCGGGCCGTGACCATCG<br>ACAGGGTGATGAGCTACCTGAACGCCTCCTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_038<br>(SEQ ID<br>NO: 92) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTCGTGATCAGCTGGTTCTCCCTCGTCTTCCTGGCCTCCCCGCTGGTGGCC<br>ATCTGGGAGCTGAAGAAGACGTGTACGTGGTGGAGCTGGACTGGTATCCCGACGCCCCCGGCGAGATGGTGGTGCTGA<br>CGTGCGACACACCAGAAGAGGACGGGATCACATGGACCCTGGATCAGTCGTCCGAGGTGCTGGGGAGCGGCAAGACCCT<br>CACCATCCAAGTGAAGGAGTTCGGGGACGCGGGCCAGTACACCTGCCACAAGGGCGGGAGGTGCTCTCCCATAGCCTG<br>CTCCTCCTGCACAAAAAGGAGGATGGCATCTGGAGCACCGACATCCTGAAGGACCAGAAGGAGCCCAAGAACAAGACAT<br>TTCTCAGGTGTGAGGCCAAGAACTATTCGGCAGGTTTACCTGTTGGTGGCTCACCACCATCTCTACCGACCTGACGTT<br>CTCCGTCAAGTCAAGCAGGGGGAGCTCGGACCCCCAGGGGGTGACATGTGGGCCGCCACCCTGAGCGCGGAGCGTGTC<br>CGCGGCGACAACAAGGAGTACGAGTATTCCGTGGAGTGCCAGGAGGACAGCGCCTGCCCCGCCGCCGAGGAGTCCCTGC<br>CCATAGAGGTGATGGTGGACGCCGTCCACAAGTTGAAGTACGAAAATTATACCTCCTCGTTCTTCATTAGGGACATCAT<br>CAAGCCTGACCCCCCAAGAACCTACAACTCAAGCCCCTCAAGAACTCCCGCCAGGTGGAGGTGTCCTGGGAGTACCCC<br>GACACCTGGTCCACCCCGCACAGCTACTTCAGCCTGACCTTCTGCGTGCAGGTCCAGGGGAAGAGCAAGCGTGAAAAGA<br>AAGACAGGGTGTTCACCGACAAGACGAGCGCCACCGTGATCTGCGAAGAACGCCTCCATCTCCGTGCGCCCAGGA<br>CAGGTACTACAGTAGCCTCCTGGAGCGAATGGGCCAGCGTGCCGTGCAGCGGCGGGGAGGAGGCGGCAGTCGCAACCTG<br>CCCGTGGCCACCCCCGACCCCGGCATGTTCCCATGCCTGCACCACAGCCAGAACCTGCTGAGGGCAGTCAGCAATATGC<br>TGCAGAAGGCCAGGCAGACCCTGGAGTTTTATCCCTGCACCAGCGAGGAGATCGACCACGAGGACATCACCAAGGACAA<br>GACCTCCACCGTCGAGGCCTGCCTGCCACTGGAGCTGACCAAAAACGAGAGCTGCCTGAACTCCAGGGAGACCTCCTTC<br>ATCACCAACGGGAGCTGCCTGGCCAGCCGGAAGACCAGCTTCATGATGGCGCTGTGCCTCAGCAGCATCTACGAGGATC<br>TCAAGATGTACCAGGTGGAGTTCAAGACCATGAACGCGAAGCTGCTGATGGACCCCAAGCGGCAGATCTTCCTGGACCA<br>GAACATGCTGGCCGTGATTGACGAGCTCATGCAGGCCCTGAACTTCAATAGCGAGACCGTCCCCAAAAGAGCAGCCTG<br>GAGGAACCCGACTTCTACAAAACGAAGATCAAGCTCTGCATCCTGCTGCACGCCTTCCGGATCCGGGCCGTGACCATCG<br>ATCGTGTGATGAGCTACCTGAACGCCTCGTGATAATAGGCTGGAGCCTCGGTGGCCATGCTTCTTGCCCCTTGGGCCTC<br>CCCCCAGCCCCTCCTCCCCTTCCTGCACCCGTACCCCCCAAACACCATTGTCACACTCCAGTGGTCTTTGAATAAAGTC<br>TGAGTGGGCGGC |
| hIL12AB_039<br>(SEQ ID<br>NO: 93) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCACCAGCAGCTCGTCATCCTGGTTTAGCCTGGTGTTTCTGGCCTCCCCCCTGGTCGCC<br>ATCTGGGAGCTGAAGAAAGACGTGTACGTGGTGGAGCTGGACTGGTACCCGGACGCTCCCGGGGAGATGGTGGTGCTGA<br>CCTGCGACACCCCCGAGGAGGACGGCATCACCTGGACCCTGGACCAGAGCTCCGAGGTGCTGGGGAGCGGCAAGACCCT<br>GACCATTCAGGTGAAAGAGTTCGGCGACGCCGGCCAATATACCTGCCACAAGGGGGGAGGTCCTGTCGCATTCCCTG<br>CTGCTGCTTCACAAAAAGGAGGATGGCATCTGGAGCACCGACATCCTGAAGGACCAGAAAGAACCCAAGAACAAGACGT<br>TCCTGCGCTGCGAGGCCAAGAACTACAGCGGCCGGTTCACCTGTTGGTGGCTGACCACCATCTCCACCGACCTGACTTT<br>CTCGGTGAAGAGCAGCCGCGGGAGCAGCGACCCCCAGGGAGTGACCTGCGGCGCCGCCACCCTGAGCGCCGAAGGGTG<br>AGGGGCGACAATAAGGAGTACGAGTATTCCGTGGAGTGCCAGGAGGACAGCGCCTGTCCCGCCGCCGAGGAGTCCCTGC<br>CTATCGAGGTGATGGTCGACGCGGTGCACAAGCTCAAGTACGAAAACTACACCAGCAGCTTTTTCATCAGGGATATCAT<br>CAAACCAGACCCCCCAAGAACCTGCAGCTGAAGCCCTGAAAAACAGCAGGCAGGTGGAAGTGAGCTGGGAATACCCC<br>GATACCTGGTCCACCCCCCACAGCTACTTCAGCCTGACCTTCTGCGTGCAGGTGCAGGGGAAGTCCAAGCGGGAGAAGA<br>AAGATCGGGTGTTCACGGACAAGACCAGCGCCACCGTGATTTGCAGGAAAAACGCCAGCATCTCCGTGAGGGCTCAGGA<br>CAGGTACTACAGCTCCAGCTGGAGCGAGTGGGCCTCCGTGCCTTGCAGCGGGGAGGAGGCGGCGGCAGCAGGAATCTG |

TABLE 4B-continued

Sequence Optimized Polynucleotides Comprising 5' UTR, ORF, 3' UTR

| | |
|---|---|
| | CCCGTCGCAACCCCCGACCCCGGCATGTTCCCCTGCCTGCACCACAGCCAGAATCTGCTGCGAGCCGTGAGCAACATGC<br>TCCAGAAGGCCCGGCAGACGCTGGAGTTCTACCCCTGCACCTCCGAGGAGATCGACCACGAGGACATCACCAAGGATAA<br>GACGAGCACCGTCGAGGCCTGTCTCCCCCTGGAGCTCACCAAGAACGAGTCCTGCCTGAATAGCAGGGAGACGTCCTTC<br>ATAACCAACGGCAGCTGTCTGGCGTCCAGGAAGACCAGCTTCATGATGGCCCTCTGCCTGAGCTCCATCTACGAGGACC<br>TCAAGATGTACCAGGTCGAGTTCAAGACCATGAACGCAAAACTGCTCATGGATCCAAAGAGGCAGATCTTTCTGGACCA<br>GAACATGCTGGCCGTGATCGATGAACTCATGCAGGCCCTGAATTTCAATTCCGAGACCGTGCCCCAGAAGAGCTCCCTG<br>GAGGAACCCGACTTCTACAAAACAAAGATCAAGCTGTGTATCCTCCTGCACGCCTTCCGGATCAGGGCCGTCACCATTG<br>ACCGGGTGATGTCCTACCTGAACGCCAGCTGATAATAGGCTGGAGCCTCGGTGGCCATGCTTCTTGCCCCTTGGGCCTC<br>CCCCCAGCCCCTCCTCCCCTTCCTGCACCCGTACCCCCAAACACCATTGTCACACTCCAGTGGTCTTTGAATAAAGTC<br>TGAGTGGGCGGC |
| hIL12AB_040<br>(SEQ ID<br>NO: 94) | TCAAGCTTTTGGACCCTCGTACAGAAGCTAATACGACTCACTATAGGGAAATAAGAGAGAAAAGAAGAGTAAGAAGAAA<br>TATAAGAGCCACCATGTGCCATCAGCAGCTGGTGATCAGCTGGTTCAGCCTCGTGTTCCTCGCCAGCCCCTCGTGGCC<br>ATCTGGGAGCTGAAAAAGGACGTGTACGTGGTGGAGCTGGACTGGTATCCCGACGCCCCGGGCGAGATGGTGGTGCTGA<br>CCTGCGACACCCCCGAGGAGGACGGCATTACCTGGACACTGGACCAGAGCAGCGAGGTCCTGGGCAGCGGGAAGACCCT<br>GACAATTCAGGTGAAGGAGTTCGGCGACGCCGGACAGTACACGTGCCACAAGGGGGGGGAGGTGCTGTCCCACAGCCTC<br>CTCCTGCTGCACAAGAAGGAGGATGGCATCTGGAGCACCGACATCCTGAAGGATCAGAAGGAGCCCAAGAACAAGACCT<br>TTCTGAGATGCGAGGCCAAGAATTACAGCGGCCGTTTCACCTGCTGGTGGCTCACCACCATCAGCACCGACCTGACCTT<br>CAGCGTGAAATCCTCCAGGGGCTCCTCCGACCCGCAGGGAGTGACCTGCGGCGCCGCCACACTGAGCGCCGAGCGGGTC<br>AGAGGGGACAACAAGGAGTACGAGTACAGCGTTGAGTGCCAGGAGGACAGCGCCTGTCCCGCGGCCGAGGAATCCCTGC<br>CCATCGAGGTGATGGTGGACGCAGTGCACAAGCTGAAGTACGAGAACTATACCTCGAGCTTCTTCATCCGGGATATCAT<br>TAAGCCCGATCCCCCGAAGAACCTGCAGCTCAAACCCCTGAAGAACAGCAGGCAGGTGGAGGTCTCCTGGGAGTACCCC<br>GACACATGGTCCACCCCCCATTCCTATTTCTCCCTGACCTTTTGCGTGCAGGTGCAGGGCAAGAGCAAGAGGGAGAAAA<br>AGGACAGGGTGTTCACCGACAAGACCTCCGCCACCGTGATCTGCCGTAAGAACGCTAGCATCAGCGTCAGGGCCCAGGA<br>CAGGTACTATAGCAGCTCCTGGTCCGAGTGGGCCAGCGTCCCGTGCAGCGGCGGGGGCGGTGGAGGCTCCCGGAACCTC<br>CCCGTGGCCACCCCGGACCCCGGGATGTTTCCCTGCCTGCATCACAGCCAGAACCTGCTGAGGGCCGTGTCCAACATGC<br>TGCAGAAGGCCAGGCAGACACTCGAGTTTTACCCCTGCACCAGCGAGGAGATCGACCACGAAGACATCACCAAGGACAA<br>GACCTCCACCGTGGAGGCATGCCTGCCCCTGGAGCTGACCAAAAACGAAAGCTGTCTGAACTCCAGGGAGACCTCCTTT<br>ATCACGAACGGCTCATGCCTGGCCTCCAGAAAGACCAGCTTCATGATGGCCCTGTGCCTGAGCTCCATCTACGAGGACT<br>TGAAAATGTACCAGGTCGAGTTCAAGACCATGAACGCCAAGCTGCTCATGGACCCCAAAAGGCAGATCTTTCTGGACCA<br>GAATATGCTGGCCGTGATCGACGAGCTCATGCAAGCCCTGAATTTCAACAGCGAGACCGTGCCCCAGAAGTCCTCCCTG<br>GAGGAGCCCGACTTCTACAAGACCAAGATCAAGCTGTGCATACTCCTGCACGCGTTTAGGATCAGGGCGGTGACCATCG<br>ATAGGGTGATGAGCTACCTGAATGCCTCCTGATAATAGGCTGGAGCCTCGGTGGCCATGCTTCTTGCCCCTTGGGCCTC<br>CCCCCAGCCCCTCCTCCCCTTCCTGCACCCGTACCCCCAAACACCATTGTCACACTCCAGTGGTCTTTGAATAAAGTC<br>TGAGTGGGCGGC |

TABLE 4C mRNA Sequences (with T100 tail)

| | |
|---|---|
| hIL12AB_001<br>(SEQ ID<br>NO: 95) | G*GGGAAAUAAGAGAGAAAAGAAGAGUAAGAAGAAAUAUAAGAGCCACCAUGUGUCACCAGCAGCUGGUCAUUAGCUGG<br>UUUAGCCUUGUGUUCCUGGCCUCCCCCCUUGUCGCUAUUUGGGAGCUCAAGAAGGACGUGUACGUGGUGGAGUUGGAUU<br>GGUACCCAGACGCGCCCGGAGAGAUGGUAGUUCUGACCUGUGAUACCCCAGAGGAGGACGGCAUCACCUGGACGCUGGA<br>CCAAAGCAGCGAGGUUUUGGGCUCAGGGAAAACGCUGACCAUCCAGGUGAAGGAAUUCGGCGACGCCGGGCAGUACACC<br>UGCCAUAAGGGAGGAGGAGGUGCUGAGCCAUUCCCUUCUUCUGCUACAAGAAGAAGGAGGACGGCAUCUGGUCUACCGACA<br>UCCUGAAAGACCAGAAGGAGCCCAAGAACAAAACCUUCCUGAGGUGCGAGGCCAAGAACUACCUCCGGCAGGUUCACUUG<br>UUGGUGGCUGACCACCAUCAGUACAGACCUGACUUUUAGUGUAAAAAGCUCCAGAGGCUCGUCCGAUCCCAAGGGGUG<br>ACCUGCGGCGCAGCCACUCUGAGCGCUGAGCGCGUGCGCGGUGACAAUAAAGAGUACGAGUACAGCGUUGAGUGUCAAG<br>AAGAUAGCGCUUGCCCCUGCCGCCGAGGAGAGCCUGCCCAUCGAGGUGAUGGUUGACGCAGUGCACAAGCUUAAGUACGA<br>GAAUUACACCAGCUCAUUCUUCAUUAGAGAUAUAAUCAAGCCUGACCCACCCAAGAACCUGCAGCUGAAGCCCCUGAAA<br>AACUCACGGCAGGUCGAAGUGAGCUGGGAGUACCCCGACACCUGGAGCACUCCUCAUUCCUAUUUCUCUCUUACAUUCU<br>GCGUCCAGGUGCAGGGCAAGAGCAAGCGGGAAAAGAAGGAUCGAGUCUUCACCGACAAAACAAGCGCGACCGUGAUUUG<br>CAGGAAGAACGCCAGCAUCUCCGUCAGAGCCCAGGAUAGAUACUAUAGUAGCAGCUGGAGCGAGUGGGCAAGCGUGCCC<br>UGUUCCGGCGGCGGGGGCGGGGCAGCGAAACUUGCCUGUCGCUACCCCGGACCCUGGAAUGUUUCGUGUCUGCACC<br>ACAGCCAGAACCUGCUGAGAGCCGUGUCGAAUAUGCUCCAGAAGGCCCGGCAGACCCUUGAGUUCUACCCCUGUACCAG<br>CGAAGAGAUCGAUCAUGAAGAUAUCACGAAAGAUAAAACCAUCCACCGUCGAGGCUUGUCUCCCGCUGGAGCUGACCAAG<br>AACGAGAGCUGUCUGAAUAGCCGGGAGACGUCUUUCAUCACGAAUGGUAGCUGUCUGGCCAGCAGGAAAACUUCCUUCA<br>UGAUGGCUCUCUGCCUGAGCUCUAUCUAUGAAGAUCUGAAGAUGUACCAGGUGGAGUUUAAAACAAUGAACGCCAAACU<br>CCUGAUGGACCCCAAAAGGCAAAUCUUUCUGGACCAGAAUAUGCUGGCCGUGAUAGACGAGCUGAUGCAGGCACUGAAC<br>UUCAACAGCGAGACGGUGCCACAGAAAUCCAGCCUGGAGGAGCUGACUUUUACAAAACUAAGAUCAAGCUGUGUAUCC<br>UGCUGCACGCCUUUAGAAUCCGUGCCGUGACUAUCGACAGGGUGAUGCAUACCUCAACGCUUCAUGAUAAUAGGCUGG<br>AGCCUCGGUGGCCAUGCUUCUUGCCCCUUGGGCCUCCCCCCAGCCCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAUCUAG |
| hIL12AB_002<br>(SEQ ID<br>NO: 96) | G*GGGAAAUAAGAGAGAAAAGAAGAGUAAGAAGAAAUAUAAGAGCCACCAUGUGCCACCAGCAGCUGGUGAUCAGCUGG<br>UUCAGCCUGGUGUUCCUGGCCAGCCCCCUGGUGGCCAUCUGGGAGCUGAAGAAGGACGUGUACGUGGUGGAGUUGGAUU<br>GGUACCCCGACGCCCCGGCGAGAUGGUGGUGCUGACCUGGGACACCCCCGAGGAGGACGGCAUCACCUGGACCCUGGA<br>CCAGAGCAGCGAGGUGCUGGGCAGCGGCAAGACCCUGACCAUCCAGGUGAAGGAGUUCGGCGACGCCGGCCAGUACACC<br>UGCCACAAGGGCGGCGAGGUGCUGAGCCACAGCCUGCUGCUGCACAAGAAGGAGGACGGCAUCUGGAGCACCGACA<br>UCCUGAAGGACCAGAAGGAGCCCAAGAACAAGACCUUCCUGAGGUGCGAGGCCAAGAACUACAGCGGCAGAUUCACCUG<br>CUGGUGGCUGACCACCAUCAGCACCGACCUGACCUUCAGCGUGAAGAGCAGCAGAGGCAGCAGCGACCCCCAGGGCGUG<br>ACCUGCGGCGCCGCCACCCUGAGCGCCGAGAGAGUGAGAGGCGACAACAAGGAGUACGAGUACAGCGUGGAGUGCCAGG<br>AAGAUAGCGCCUGCCCCGCCGCCGAGGAGAGCCUGCCCAUCGAGGUGAUGGUGGACGCCGUGCACAAGCUGAAGUACGA<br>GAACUACACCAGCAGCUUCUUCAUCAGAGAUAUCAUCAAGCCCGACCCCCCCAAGAACCUGCAGCUGAAGCCCCUGAAG |

TABLE 4C-continued mRNA Sequences (with T100 tail)

AACAGCCGGCAGGUGGAGGUGAGCUGGGAGUACCCCGACACCUGGAGCACCCCCCACAGCUACUUCAGCCUGACCUUCU
GCGUGCAGGUGCAGGGCAAGAGCAAGAGAGAGGAAGAAAGAUAGAGUGGUCACCGACAAGACCAGCGCCACCGUGAUCUG
CAGAAAGAACGCCAGCAUCAGCGUGAGAGCCCAAGAUAGAUACUACAGCAGCAGCUGGAGCGAGUGGGCCAGCGUGCCC
UGCAGCGGCGGCGGCGGCGGCAGCAGAAACCUGCCCGUGGCCACCCCCGACCCCGGCAUGUUCCCCUGCCUGCACC
ACAGCCAGAACCUGCUGAGAGCCGUGAGCAACAUGCUGCAGAAGGCCCGGCAGACCCUGGAGUUCUACCCCUGCACCAG
CGAGGAGAUCGACCACGAAGAUAUCACCAAAGAUAAGACCAGCACCUGUGGAGGCCUGCCUGCCCCUGGAGCUGACCAG
AACGAGAGCUGCCUGAACAGCAGAGAGACCAGCUUCAUCACCAACGGCAGCUGCCUGGCCUGGCAGAAAGACCAGCUUCA
UGAUGGCCCUGUGCCUGAGCAGCAUCUACGAGGACCUGAAGAUGUACCAGGUGGAGUUCAAGACCAUGAACGCCAAGCU
GCUGAUGGACCCCAAGCGGCAGAUCUUCCUGGACCAGAACAUGCUGGCCGUGAUCGACGAGCUGAUGCAGGCCCUGAAC
UUCAACAGCGAGACCGUGCCCCAGAAGAGCAGCCUGGAGGAGCCCGACUUCUACAAGACCAAGAUCAAGCUGUGCAUCC
UGCUGCACGCCUUCAGAAUCAGAGCCGUGACCAUCGACAGAGUGAUGAGCUACCUGAACGCCAGCUGAUAAUAGGCUGG
AGCCUCGGUGGCCAUGCUUCUUGCCCCUUGGGCCUCCCCCCAGCCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAUCUAG hIL12AB_003 G*GGGAAAUAAGAGAGAAAAGAAGAGUAAGAAGAAAUAUAAGAGCCACCAUGUGUCACCAGCAGUUGGUCAUCUCUUGG
(SEQ ID UUUUCCCUGGUUUUUCUGGCAUCUCCCCUCGUGGCCAUCUGGGAACUGAAGAAAGACGUUUACGUUGUAGAAUUGGAUU
NO: 97) GGUAUCCGGACGCUCCUGGAGAAAUGGUGGUCCUCACCUGUGACACCCCUGAAGAAGACGGAAUCACCUGGACCUUGGA
CCAGAGCAGUGAGGUCUUAGGCUCUGGCAAAACCCUGACCAUCCAAGUCAAAGAGUUUGGAGAUGCUGGCCAGUACACC
UGUCACAAAGGAGGCGAGGUUCUAAGCCAUUCGCUCCUGCUGCUUCAAAAAGGAAGAUGGAAUUUGGUCCACUGAUA
UUUUUAAAGGACCAGAAAGAACCCAAAAAUAAGACCUUUCUAAGAUGCGAGGCAAGAAUUAUUCUGGACGUUUCACCUG
CUGGUGGCUGACGACAAUCAGUACUGAUUUGACAUUCAGUGUCAAAAGCAGCAGAGGCUCUUCUGACCCCCAAGGGGUG
ACGUGCGGAGCUGCUACACUCUGCAGAGAGAGUCCAGGGUGACAACAAGGAGUAGUCAGUGGAGUGCCAGG
AAGAUAGUGCCUGCCCAGCUGCUGAGGAGAGUCUGCCCAUUGAGGUCAUGGUGGAUGCCGUUCACAAGCUCAAGUAUGA
AAACUACACCAGCAGCUUCUUCAUCAGAGAUAUCAUCAAACCUGACCCACCCAAGAACUUGCAGCUGAAGCCAUUAAAG
AAUUCUCGGCAGGUGGAGGUCAGCUGGGAGUACCCUGACACCUGGAGUACUCCACAUUCCUACUUCUCCCUGACAUUCU
GCGUUCAGGUCCAGGGCAAGAGCAAGAGAGAAAAGAAAGAUAGAGUGCUUCACAGAUAAGACCUCAGCCACGGUCAUCUG
CCGCAAAAAAUGCCAGCAUUAGCGUGCGGGCCCAGGACCGCUACUAUAGCUCAUCUUGGAGCGAAUGGGCAUCUGUGCCC
UGCAGUGGCGGAGGGGCCGGAGGGAGCAGAAACCUCCCCGUGGCCACUCCAGACCCAGGAAUGUUCCCAUGCCUUCACC
ACUCCCAAAACCUGCUGAGGGCCGUCAGCAACAUGCUCCAGAAGGCCCGGCAAACUUUAGAAUUUACCCUUGCACUUC
UGAAGACAGUUGAUCAUGAAGGAUAUCACAAAGAUAAAAAUCAUGCGUGGAGGCCUGUUUUACCAUUGGAAUUAACCAAG
AAUGAGAGUUGCCUAAAUUCCAGAGAGACCUCUUUCAUACUAAUGGGAGUUGCCUGGCCUCCAGAAAGACCUCUUUUA
UGAUGGCCCUGUGCCUUAGUAGUAUUUAUGAAGAUUUGAAGAUGUACCAGGUGGAGUUCAAGACCAUGAAUGCAAAGCU
UCUGAUGGAUCCUAAGAGGCAGAUCUUUUUAGAUCAAAACAUGCUGGCAGUUAUUGAUGAGCUGAUGCAGGCCCUGAAU
UUCAACAGUGAGACGGUGCCACAAAAAUCUCCCUUGAAGAACCAGAUUUCUACAAGACCAAGAUCAAGCUGCAUAC
UUCUUCAUGCUUUCAGAAUUCGGGCAGUGACUAUUGACAGAGUGAUAGUCUUCCUGGAAUGCCAGCUGAUAAUAGGCUGG
AGCCUCGGUGGCCAUGCUUCUUGCCCCUUGGGCCUCCCCCCAGCCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAUCUAG hIL12AB_004 G*GGGAAAUAAGAGAGAAAAGAAGAGUAAGAAGAAAUAUAAGAGCCACCAUGGGCUGCCACCAGCAGCUGGUCAUCAGC
(SEQ ID UGGUUCUCCCUGGUCUUCCUGGCCAGCCCCCUGGUGGCCAUCUGGGAGCUGAAGAAAGACGUCUACGUAGUAGAGUUGG
NO: 98) AUUGGUACCCAGACGCACCUGGAGAAAUGGUGGUUCUCACCUGUGACACGCCAGAAGAAGACGGUAUCACCUGGACGCU
GGACCAGAGCUCAGAAGUUCUUGGCAGUGGAAAAACCCUGACCAUCCAAGUCAAAGAGUUUGGAGAUGCUGGCCAGUAC
ACCUGCCACAAAGGAGGAGAAGUUCUCAGCCACAGCCUGCUGCUGCUGCACAAGAAAGAAGAUGGCAUCUGGAGCACAG
AUAUUUUAAAAGACCAGAAGGAGCCCAAGAACAAAACCUUCCUUCGAUGUGAGGCCAAGAACUACAGUGGCCGCUUCAC
CUGCUGGUGGCUCACCACCAUCAGCACAGACCUCACCUUCUCGGUGAAGAGCAGCCGUGGCAGCUCAGACCCCCAAGGA
GUCACCUGUGGGGCGGCUCACGCUGUCGCAGAAUAAUGUUCAAGAUAAUAUCGGUGGAAUGUC
AAGAGAUUCGGCCUGCCCGGCGGCAGAAGAAAGUCUUCCCAUAGAAGUCAUGGUGGAUGCUGUUCACAAAUUAAAAUA
UGAAAACUACACCAGCAGCUUCUUCAUCAGAGAUAUCAUCAAGCCAGACCCGCCCAAGAACCUGCAGCUGAAGCCCCUG
AAGAACAGCCGGCAGGUGGAAGUUUCCUGGGAGUACCCCAGAUACGUGGAGCACGCCGCACAGCUACUUCAGCCUCACCU
UCUGUGUACAAGUACAAGGCAAGAGCAAGAGAGAAGAAAGAUCGUGUCUUCACAGAUAUAAACCUCGGCGACGGUCAU
CUGCAGGAAGAAUGCCUCCAUCUCGGUUCGAGCCCAGGACCGCUACUACAGCAGCAGCUGGAGUGAGUGGGCCUCGGUG
CCCUGCAGUGGUGGCGGCGGCGGCAGCAGAAACCUUCCUGUGGCCACGCCGGACCCUGGCAUGUUCCCGUGCCUGC
ACCACAGCCAAAAUUUACUUCGAGCUGUUUCUAACAUGCUGCAGAAAGCACGGCAAACUUUAGAAUUCUACCCCUGCAC
CUCAGAAGAAAUAUGAAGAUAUCCAAAGAUAAAACCAGCACUGUAGAGGCCUGCCUGCCCCUGGAGCUCACC
AAGAAUGAAUCCUGCCUCAACAGCAGAGACCAGCUUCAUCCAAUGGCAGCUGCCUGGCCUGGCAGGAAAACCAGCU
UCAUGAUGGCGCUCUGCCUGAGCAGCAUCUAUGAAGAUUUGAAGAUGUACAAGUAGAAUUUAAAACCAUGAAUGCCAA
GCUGCUCAUGGACCCCAAGCGGCAGAUAUUUUUGGAUCAAAACAUGCUGGCUGUCAUUGAUGAGCUCAUGCAAGCAUUA
AACUUCAACUCAGAGACGGUCCCCCAGAAGAGCAGCCUGGAGGAGCCAGAUUUCUACAAAACCAAGAUCAAGCUCUGCA
UCUUAUUACAUGCCUUCCGAAUCAGGGCGGUCACCAUUGACCGGGUCAUGAGUUAUUUGAAUGCCAGCUGAUAAUAGGC
UGGAGCCUCGGUGGCCAUGCUUCUUGCCCCUUGGGCCUCCCCCAGCCCCUCCUCCCCUUCCUGCACCCGUACCCCCA
AACACCAUUGUCACACUCCAGUGGUCUUUGAAUAAAGUCUGAGUGGGCGGCAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAAUCUAG hIL12AB_005 G*GGGAAAUAAGAGAGAAAAGAAGAGUAAGAAGAAAUAUAAGAGCCACCAUGUGCCACCAGCAGCUGGUCAUCAGCUGG
(SEQ ID UUCUCCCUGGUCUUCCUGGCCAGCCCCCUGGUGGCCAUCUGGGAGCUGAAGAAAGACGUCUACGUAGUAGAGUUGGAUU
NO: 99) GGUACCCAGACGCACCUGGAGAAAUGGUGGUUCUCACCUGUGACACGCCAGAAGAAGACGGUAUCACCUGGACGCUGGA
CCAGAGCUCAGAAGUUCUUGGCAGUGGAAAAACCGUGACCAUCCAAGUAAAAGAGUUUGGCUGGCCAGUACACC
UGCCACAAAGGAGGAGAAGUUCUCAGCCACAGCCUGCUGCUGCUGCACAAGAAAGAAGAUGGCAUCUGGAGCACAGAUA
UUUUAAAAGACCAGAAGGAGCCCAAGAACAAAACCUUCCUUCGAUGUGAGGCCAAGAACUACAGUGGCCGCUUCACCUG
CUGGUGGCUCACCACCAUCAGCACAGACCUCACCUUCUCGGUGAAGAGCAGCCGUGGCAGCUCAGACCCCCAAGGAGUC
ACCUGUGGGGCCGCCGUGCCACGCUGUCGCAGAAAUGAUUGUCAAGGAACAACAAGGAUAUAACUCGGUGGAAUGUCAAG
AGAUUCGGCCUGCCCGGCGGCAGAAGAAAGUCUUCCCAUAGAAGUCAUGGUGGAUGCUGUUCACAAAUUAAAAUAUGAA
AACUACACCAGCAGCUUCUUCAUCAGAGAUAUCAUCAAGCCAGACCCGCCCAAGAACCUGCAGCUGAAGCCCCUGAAG
AACAGCCGGCAGGUGGAAGUUUCCUGGGAGUACCCCAGAUACGUGGAGCACGCCGCACAGCUACUUCAGCCUCACCUUCU
GUGUACAAGUACAAGGCAAGAGCAAGAGAGAGAAGAAAGAUCGUGUCUUCACAGAUAAAACCUCGGCGACGGUCAUCUG
CAGGAAGAAUGCCUCCAUCUCGGUUCGAGCCCAGGACCGCUACUACAGCAGCAGCUGGAGUGAGUGGGCCUCGGUGCCC

TABLE 4C-continued mRNA Sequences (with T100 tail)

| | |
|---|---|
| | UGCAGUGGUGGCGGCGGCGGCAGCAGAAACCUUCCUGUGGCCACGCCGGACCCUGGCAUGUUCCCGUGCCUGCACC<br>ACAGCCAAAAUUUACUUCGAGCUGUUUCUAACAUGCUGCAGAAAGCACGGCAAACUUUAGAAUUCUACCCCUGGA<br>AGAAGAAAUAGACCAUGAAGAUAUCACCAAAGAUAAAACCAGCACUGUAGAGGCCUGCCUGCCCCUGGAGCUCACCAAG<br>AAUGAAUCCUGCCUCAACAGCAGAGAGACCAGCUUCAUCACCAAUGGCAGCUGCCUGGCCAGCAGGAAAACAGCUUCA<br>UGAUGGCGCUCUGCCUGAGCAGCAUCUAUGAAGAUUUGAAGAUGUACCAAGUAGAAUUUAAAACCAUGAAUGCCAAGCU<br>GCUCAUGGACCCCAAGCGGCAGAUAUUUUUGGAUCAAAACAUGCUGGCUGUCAUUGAUGAGCUCAUGCAAGCAUUAAAC<br>UUCAACUCAGAGACGGUGCCCCAGAAGAGCAGCCUGGAGGAGCCAGAUUUCUACAAAACCAAGAUCAAGCUCUGCAUCU<br>UAUUACAUGCCUUCCGCAUCCGGGCGGUCACCAUUGACCGUGUCAUGUCCUACUUAAAUGCCAGCUGAUAAUAGGCUGG<br>AGCCUCGUGGCCAUGCUUCUUGCCCCUUGGGCCUCCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAUCUAG |
| hIL12AB_006<br>(SEQ ID<br>NO: 100) | G*GGGAAAUAAGAGAGAAAAGAAGAGUAAGAAGAAAUAUAAGAGCCACCAUGUGCCACCAGCAGCUGGUGAUCAGCUGG<br>UUCAGCCUGGUGUUCCUGGCCAGCCCCCUGGUGGCCAUCUGGGAGCUGAAGAAGGACGUGUACGUGGUGGAGUUGGAUU<br>GGUACCCCGACGCCCCGGCGAGAUGGUGGUGCUGACCUGUGACACCCCCGAGGAGGACGGCAUCACCUGGACCCUGGA<br>CCAGAGCAGCGAGGUGCUGGGCAGCGGCAAGACCCUGACCAUCCAGGUGAAGGAGUUCGGGGACGCCCGGCCAGUACACC<br>UGCCACAAGGGCGGCGAGGUGCUGAGCCACAGCCUGCUGCUGCUGCACAAGAAGGAGGACGGCAUCUGGAGCACAGAUA<br>UCCUGAAGGACCAGAAGGAGCCCAAGAACAAGACCUUCCUGAGAUGCGAGGCCAAGAACUACAGCGGCAGAUUCACCUG<br>CUGGUGGCUGACCACCAUCAGCACAGAUUUGACCUUCAGCGUGAAGAGCAGCAGAGGCAGCUGAGCGACCCCCAGGGCGUG<br>ACCUGCGGCGCCGCCACCCUGAGCGCCGAGAGAGUGAGAGGUGACAACAAGGAGUACGAGUACAGCGUGGAGUGCCAGG<br>AAGAUAGCGCCUGCCCCGCCGCCGAGGAGAGCCUGCCAUCGAGGUGAUGGUGGACGCCGUGCACAAGCUGAAGUACGA<br>GAACUACACCAGCAGCUUCUUCAUCAGAGAUAUCAUCAAGCCCGACCCGCCGAAGAACCUGCAGCUGAAGCCCCUGAAG<br>AACAGCCGGCAGGUGGAGGUGAGCUGGGAGUACCCCGACACCUGGAGCACCCCCCACAGCUACUUCAGCCUGACCUUCU<br>GCGUGCAGGUGCAGGGCAAGAGCAAGAGAGAAGAAAUAUAGAGUGUUCACAGAUAAGACCAGCGCCACCGUGAUCUG<br>CAGAAAGAACGCCAGCAUCAGCGUGAGAGCCCAAGAUAGAUCUACAGCAGCAGCUGGAGCGAGUGGGCCAGCGUGCCC<br>UGCAGCGGCGGCGGCGGCGGCGGCAGCAGAAACUGCCCGUGGCCACCCCCGACCCCGGCAUGUUCCCCUGCCUGCACC<br>ACAGCCAGAACCUGCUGAGAGCCGUGAGCAACAUGCUGCAGAAGGCCCGGCAGACCCUGGAGUUCUACCCCUGCACCAG<br>CGAGGAGAUCGACCACGAAGAUAUCACCAAAGAUAAGACCAGCACCGUGGAGGCCUGCCUGCCCCUGGAGCUGACCAAG<br>AAUGAAAGCUGCCUGAACAGCAGAGAGACCAGCUUCAUCACCAACGGCAGCUGCCUGGCCAGCAGAAAGACCAGCUUCA<br>UGAUGGCCCUGUGCCUGAGCAGCAUCUACGAGGACCUGAAGAUGUACCAGGUGGAGUUCAAGACCAUGAACGCCAAGCU<br>GCUGAUGGACCCCAAGCGGCAGAUCUUCCUGGACCAGAACAUGCUGGCCGUGAUCGACGAGCUGAUGCAGGCCCUGAAC<br>UUCAACAGCGAGACCGUGCCCCAGAAGAGCAGCCUGGAGGAGCCCGACUUCUACAAGACCAAGAUCAAGCUGUGCAUCC<br>UGCUGCACGCCUUCAGAAUCAGAGCCGUGACCAUCGACAGAGUGAUGAGCUACCUGAACGCCAGCUGAUAAUAGGCUGG<br>AGCCUCGUGGCCAUGCUUCUUGCCCCUUGGGCCUCCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAUCUAG |
| hIL12AB_007<br>(SEQ ID<br>NO: 101) | G*GGGAAAUAAGAGAGAAAAGAAGAGUAAGAAGAAAUAUAAGAGCCACCAUGUGCCACCAGCAGCUUGUCAUCUCCUGG<br>UUCUCUCUUGUCUUCCUUGCUUCUCCUCUUGUGGCCAUCUGGGAGCUGAAGAAGGACGUUUACGUAGUGGAGUUGGAUU<br>GGUACCCUGACGCACCUGGAGAAAUGGUGGUUCUCACCUGUGACACCCCUGAGGAGGACGGCAUCACCUGGACCUUGGA<br>CCAGUCUUCUGAGGUUCUUGGCAGUGGAAAAACUCUUACUAUUCAGGUGAAGGAGUUUGGAGAUGCUGGCCAGUACACC<br>UGCCACAAGGGUGGUGAAGUUCUCAGCCACAGUUUACUUCUUCUUCACAAGAAGGAGGAUGGCAUCUGGUCUACUGACA<br>UUUUAAAAGACCAGAAGGAGCCCAAGAACAAAACAUUCCUUCGUUGUGAAGCCAAGAACUACAGUGGUCGUUUCACCUG<br>CUGGUGGCUUACUACUGACUCUACUGACCUUACUUUCUUCGUGGCUGUCAUCUUCUGGCUGACCCCCAGGGUGUC<br>ACCUGUGGGGCUGCUACUCUUUCUGCUGAGCGUGUGCGUGGUGACAACAAGGAGUAUGAAUACUCGGUGGAGUGCCAGG<br>AAGAUUCUGCCUGCCCUGCUGCUGAGGAGUCUCUUCCUAUUGAGGUGAUGGUGGAUGCUGUGCACAAGUUAAAUAUGA<br>AAACUACACUUCUUCUUUCUUCAUUCGUGACAUUAUAAAACCUGACCCUCCCAAGAACCUUCAGUUAAAACCUUUAAAA<br>AACUCUCGUCAGGUGGAGGUGUCUGGGAGUAUCCUGACACCUGGAGUACCCCUCACUCUACUUCAGUCUUACUUUCU<br>GUGUCCAGGUGCAGGGCAAGUCCAAGCGUGAGAAGAAGGACCGUGUCUUCACUGACAAAACAUCUGCUACUGUCAUCUG<br>CAGGAAGAAUGCAUCCAUCUCUGUGCGUGCUCAGGACCGUUACUACAGCUCUUCCUGGUCUGAGUGGGCUUCUGUGCCC<br>UGCUCUGGCGGCGGCGGCGGCGGCAGCAGAAAUCUUCCUGUGGCUACUCCUGACCCUGGCAUGUUCCCUGCCUUCACC<br>ACUCGCAGAACCUUCUGCGCUGUGAGCAACAUGCUCCAGAAAGCUCGUCAAACUUUAGAAUUCUACCCCUGCACUUC<br>UGAGGAGAUUGACCAUGAAGAUAUCACCAAAGAUAAAACAUCUACUGUGGAGGCCUGCCUUCCUUUGAGCUGACCAAG<br>AAUGAAUCCUGCUUAAAUUCUGUGAGACGUCUUUCAUCACCAAUGGCAGCUGCCUUGCCUCGCGCAAAACAUCUUUCA<br>UGAUGGCUCUUUGCCUUUCUUCCAUCUAUGAAGAUUUAAAAAUGUACCAGGUGGAGUUCAAGACCAUGAAUGCAAAGCU<br>UCUCAUGGACCCCAAGCGUCAGAUAUUUUUGGACCAGAACAUGCUGGCUGUAUUGAUGAGCUCAUGCAGGCUUUAAAC<br>UUCAACUCUGAGACGGUGCCUCAGAAGUCUUUUUAGAAGAGCCUGACUUCUACAAGACCAAGAUAAAACUUUGCAUUC<br>UUCUUCAUGCUUUCCGCAUCCGUGCUGUGACUAUUGACCGUGUGAUGUCCUACUUAAAUGCUUCUGAUAAUAGGCUGG<br>AGCCUCGUGGCCAAGCUUCUUGCCCCUUGGGCCUCCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAUCUAG |
| hIL12AB_008<br>(SEQ ID<br>NO: 102) | G*GGGAAAUAAGAGAGAAAAGAAGAGUAAGAAGAAAUAUAAGAGCCACCAUGUGUCAUCAACAACUCGUGAUUAGCUGG<br>UUCAGUCUCGUGUUCCUGGCCUCUCCGCUGGUGGCCAUCUGGGAGCUUAAGAAGGACGUGUACGUGGUGGAGCUCGAUU<br>GGUACCCCGACGCCUGGGAGAUGGUGGUGCUGACCUGCGAUACCCCCGAGGAGGACGGCAUCACUUGGACCCUGGA<br>UCAGAGUAGCGAAGUCCUGGGCUCUGGCAAAACACUCACAAUCCAGGUGAAGGAAUUCGGAGAUGCCGGUCAGUACACU<br>UGCCACAAGGGGGGUGAAGUGCUGUCUCACAGCCUGCUGUUACUGCACAAGAAGGAGGAUGGGAUCUGGUCAACCGACA<br>UCCUGAAGGAUCAGAAGGAGCCUAAGAACAAGACCUUUCUGAGGUGUGAAGCUAAGAACUAUUCCGGAAGAUUCACUUG<br>CUGGUGGUUGACCACAAUCAGCACUGACAUCGACUUUUCCGUGAAGAGCAGCCGAGGGAGCGAUCCUCAGGGCGUA<br>ACGUGCGGCGCGGCUACCCUGUCAGCUGAGCGGGUUAGAGGUGACAACAAGAGUAUGAGUACUCCGUGGAGUGUCAGG<br>AAGAUAGCGCCUGCCCCGCAGCCGAGGAGAGUCUGCCAUCGAGGUGAUGGUGGACGCUGUCCAUAAGUUAAAAUACGA<br>AAAUUACACAAGUUCCUUUUUCAUCCGCGAUAUUAUCAAACCCGAUCCCCCAAGAACCUGCAGCUGAAGCCCCUGAAG<br>AAUAGCCGGCAGGUCGAGGUCUCUUGGGAGUAUCCUGACACGCUCUCACUCUACUUCAGUUUGACUUUUGUGUGCAGG<br>GUGUCCAGGUCCAGGGCAAGAGCAAGAGAGAGAAAAGGAUAGAGUGUUUACUGACAAAACAUCUGCUACAGUCAUCUG<br>CAGAAAGAACGCCAGUAUCAGUGUGAGGGCGCAAGAUAGAUCUACAGUAGUAGCUGGAGCGAAUGGGCUAGCGUGCCC<br>UGUUCAGGGGCGGCGGAGGGGGCUCCAGGAAUCUGCCCGUGGCCACCCCCGACCCUGGGAUGUUCCCUUGCCUCCAUC<br>ACUCACAGAACCUGCUCAGAGCAGUGAGCAACAUGCUCAAAAGGCCCGCCAGACCCUGGAGUUUUACCCUUGUACUUC<br>AGAAGAGAUCGAUCACGAAGAUAUAACAAAGGAUAAAACCAGCACCGUGGAGGCCUGUCUGCCUCUGGAACUCACAAAG |

TABLE 4C-continued mRNA Sequences (with T100 tail)

| | |
|---|---|
| | AAUGAAAGCUGUCUGAAUUCCAGGGAAACCUCCUUCAUUACUAACGGAAGCUGUCUCGCAUCUCGCAAAACAUCAUUCA<br>UGAUGGCCCUCUGCCUGUCUUCUAUCUAUGAAGAUCUCAAGAUGAUGUAUCAGGUGGAGUUCAAAACAAUGAACGCCAAGCU<br>GCUGAUGGACCCCAAGCGGCAGAUCUUCCUGGACCAGAACAUGCUGGCAGUGAUCGAUGAGCUGAUGCAAGCCUUGAAC<br>UUCAACUCAGAGACGGUGCCGCAAAAGUCCUCGUUGGAGGAACCAGAUUUUUACAAAACCAAAAUCAAGCUGUGUAUCC<br>UUCUUCACGCCUUUCGGAUCAGAGCCGUGACUAUCGACCGGGUGAUGUCAUACCUGAUGCUUCCUGAUAAUAGGCUGG<br>AGCCUCGGUGGCCAUGCUUCUUGCCCCUUGGGCUCCCCCCAGCCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAUCUAG |
| hIL12AB_009<br>(SEQ ID<br>NO: 103) | G*GGGAAAUAAGAGAGAAAAGAAGAGUAAGAAGAAAUAUAAGAGCCACCAUGUGCCACCAGCAGCUGGUCAUCAGCUGG<br>UUUUAGCCUGGUCUUCCUGGCCAGCCCCCUGGUGGCCAUCUGGGAGCUGAAGAAAGACGUCUACGUAGUAGAGUUGGAUU<br>GGUACCCAGACGCACCUGGAGAAAUGGUGGUUCUCACCUGCGACACGCCAGAAGAAGACGGUAUCACCUGGACGCUGGA<br>CCAGAGCAGCGAAGUACUGGGCAGUGGAAAAACGCUGACCAUACAAGUAAAGAAUUUGGCGAUGCUGGCCAGUACACC<br>UGCCACAAAGGAGGAGAAGUACUGAGCCACAGCCUGCUGCUGCUGCACAAGAAAGAAGAUGGCAUCUGGAGCACCGACA<br>UUUUAAAAGACCAGAAGGAGCCCAAGAACAAAACCUUCCUCCGCUGUGAGGCUGAAGAACUACAGUGGCCGCUUCACCUG<br>CUGGUGGCUCACCACCAUCAGCACCGACCUCACCUUCUCGGUGAAGAGCAGCCGUGGUAGCUCAGACCCCCAAGGAGUC<br>ACCUGUGGGCGGCCACGCUGUCGGCAGAAAGAGUUCGAGGCGACAACAAGGAAUAUGAAUACUCGGUGGAAUGUCAAG<br>AAGAUUCGGCCUGCCCGGCGGCAGAAGAAAGUCUGCCCAUAGAAGUCAUGGUGGAUGCUGUUCACAAAUUAAAAUAUGA<br>AACUACACCAGCGACUUCUUCAUCAGAGAUAUCAUCAAGCCAGCCCCCCCAAGAACCUGCAGCUGAAGCCCCUGAAG<br>AACAGCCGGCAGGUGGAAGUUUCCUGGGAGUACCCAGAUACGUGGAGCACGCCGCACAGCUACUUCAGCCUCACCUUCU<br>GUGUACAAGUACAAGGCAAGAGCAAGGAGAGAAGAAAGAUCGUGUCUUCACCGACAAAACCUCGGCGACGGUCAUCUG<br>CAGGAAGAAUGCAAGCAUCUCGGUUCGAGCCCAGGACCGCUACUACAGCAGCAGCUGGAGUGAGUGGGCCUCGGUGCCC<br>UGCAGUGGUGGCGGCGGCGGCAGCAGAACCUUCCUGUGCCACGCCGGACCCUGGCAUGUUUCCUGUCCUGCACC<br>ACAGCCAAAAUUAUUACGAGCUGUUAGCAACAUGCUGCAGAAAGCACGGCAAAUUUAGAAUUCUACCCCUGCACCUC<br>AGAAGAAAUAGACCAUGAAGAUAUCACCAAAGAUAAAACCAGCACUGUAGAGGCCUGCCUGCCCUGGAGCUCACCAAG<br>AACGAGAGCUGCCUCAAUAGCAGAGAGACCAGCUUCAUCACCAAUGGCAGCUGCCUGGCCAGCAGGAAAACCAGCUUCA<br>UGAUGGCCCUCUGCCUGGACAGCAUCUAUGAAGAUCUGAAGAUGUAUCAGGUGGAGUUUAAAACCAUGAAUGCCAAGCU<br>GCUCAUGGACCCCAAGCGGCAGAUAUUCCUCGACCAAAACAUGCUGGCUGUCAUUGAUGAGCUCAUGCAAGCAUUAAAC<br>UUCAACUCAGAGACGGUGCCCCAGAAGAGCAGCCUGGAGGAGCCAGAUUUCUACAAAACCAAGAUCAAGCUCUGCAUCU<br>UAUUACAUGCCUUCCGCAUCCGGGCGGUCACCAUUGACCGUGUCAUGUCCUACUUAAAUGCCAGCUGAUAAUAGGCUGG<br>AGCCUCGGUGGCCAUGCUUCUUGCCCCUUGGGCUCCCCCCAGCCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAUCUAG |
| hIL12AB_010<br>(SEQ ID<br>NO: 104) | G*GGGAAAUAAGAGAGAAAAGAAGAGUAAGAAGAAAUAUAAGAGCCACCAUGUGCCACCAGCAGCUUGUCAUCUCCUGG<br>UUUUUCUUGUCUUCCUCGCUUCUCCUCUUGUGGCCAUCUGGGAGCUGAAGAAAGACGUCUACGUAGUAGAGUUGGAUU<br>GGUACCCGGACGCUCCUGGAGAAAUGGUGGUUCUCACCUGCGACACUCCUGAAGAAGACGGUAUCACCUGGACGCUGGA<br>CCAAAGCAGCGAAGUUUAGGCUCUGGAAAAACGCUGACCAUACAAGUAAAGAAUUUGGCGACGCUGGCCAGUACACG<br>UGCCACAAAGGAGGAGAAGUUUAGGCCACAGUUUACUUCUUCUUCACAAGAAAGAAGAUGGCAUCUGGAGUACAGAUA<br>UUUUAAAAGACCAGAAGGAGCCCUAAGAACAAAACCUUCCUCCGCUGUGAAAAUCAAGCCGUGGUUCUUCUGACCCCCAAGGAGUC<br>ACCUGUGGGCUGCCACGCUCAGCGCUGAAAGAGUUCGAGGCGACAACAAGGAAUAUGAAUAUUCUGGAAUGUCAAG<br>AAGAUUCUGCCUGCCCGGCGGCAGAAGAAAGUCUUCCCAUAGAAGUCAUGGUGGACGCUGUUCACAAAUUAAAAUAUGA<br>AACUACACCAGCGACUUCUGCAUUCGUGACAUCAUCAAACCUCCUAAGAACCUCUGUAUAAACCGCUGAAG<br>AACAGCCGGCAGGUGGAAGUUUCCUGGGAGUACCCAGAUACGUGGAGUACCGCACUCCUACUUCAGUUUAACCUUCU<br>GUGUACAAGUACAAGGAAAUCAAAAAGAGAGAAGAAAGAUCGUGUCUUCACUGACAAAACAUCUGCCACGGUCAUCUG<br>CCGUAAGAACGCUUCCAUCUCGGUUCGAGCCCAGGACCGCUACUACAGCAGCAGCUGGAGUGAGUGGGCAUCUGUUCCC<br>UGCAGUGGUGGCGGCGGCGGCAGCGCAACCUUCCUGUGCCACGCCGGACCCUGGCAUGUUUCCUGUCCUUCACC<br>ACUCGCAAAAUCUUCUUCGUGCUGUUUCUAACAUGCUGCAGAAGGCCGGCAAAUUUAGAAUUCUACCCCGUGCACUUC<br>UGAAGAAAUAGACCAUGAAGAUAUCACCAAAGAUAAAACCAGCACGGUGGAGGCCUGCCUUCCUUUAGAACUUACUAAG<br>AACGAAAGUUGCCUUAACAGCCGUGAGACCAGCUUCAUCACCAAUGGCAGCUGCCUUGCUAGCAGGAAGACCAGCUUCA<br>UGAUGGCCCUGUGCCUUUCUUCCAUCUAUGAAGAUCUUAAGAUGUAUCAGGUGGAGAUUAAUUUAAAACCAUGAAUGCCAAAUU<br>AUUAAUGGACCCCAAGCGGCAGAUAUUCCUCGACCAAAACAUGCUGGCUGUCAUUGAUGAGCUCAUGCAAGCAUUAAAC<br>UUCAACUCAGAAACUGUUCCCCAGAAGUCAUCUUUAGAAGAACCAGAUUUCUACAAAACAAAAAUAAACUCUGCAUUC<br>UUCUUCAUGCCUUCCGCAUCCGUGCUGUCACCAUUGACCGUGUCAUGUCCUACUUAAAUGCUUCUUGAUAAUAGGCUGG<br>AGCCUCGGUGGCCAUGCUUCUUGCCCCUUGGGCUCCCCCCAGCCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAUCUAG |
| hIL12AB_011<br>(SEQ ID<br>NO: 105) | G*GGGAAAUAAGAGAGAAAAGAAGAGUAAGAAGAAAUAUAAGAGCCACCAUGUGCCACCAGCAGCUGGUGAUCAGCUGG<br>UUCAGCCUGGUGUUCCUGGCCAGCCCCCUGGUGGCCAUCUGGGAGCUGAAGAAGGACGUCUACGUGGUGGAGUUGGAUU<br>GGUACCCGGACGCGCCGGGGGAGAUGGUGGUGCUGACGUGCGACACGCCGGAGGAGGACGGGAUCACGUGGACGCUGGA<br>CCAGAGCAGCGAGGUGCUGGGGAGCGGGAAGACGCUGACGAUCCAGGUGAAGGAGUUCGGGGACGCGGGGCAGUACACG<br>UGCCACAAGGGGGGGAGGUGCUGAGCCACAGCCUGCUGCUGCUGCACAAGGAGGACGGGAUCUGGAGCACAGAUA<br>UCCUGAAGGACCAGAAGGAGCCCGAAGAACAAGACGUUCCUGAGGUGCGAGGCGAAGAACUACAGCGGGCGGUUCACGUG<br>CUGGUGGCUGACGACGAUCAGCACGGACCUGACGUUCAGCGUGAAGAGCAGCAGGGGGAGCAGCGACCCGCAGGGGGUG<br>ACGUGCGGGGCGGCGACGCUGAGCGCGAGAGGGUGAGGGGUGACAACAAGGAGUACGAGUACAGCUGGGAGUGCCAGG<br>AAGAUAGCGCGUGCCCGGCGGCGGAGGAGAGCCUGCCGAUCGAGGUGAUGGUGGACGCGGUGCACAAGCUGAAGUACGA<br>GAACUACACGAGCAGCUUCUUCAUCAGAGAUAUCAUCAAGCCGGACCCGCCGAAGAACCUGCAGCUGAAGCCGCUGAAG<br>AACAGCAGGCAGGUGGAGGUGAGCUGGGAGUACCCAGAUACGUGGAGCACGCCGCACAGCUACUUCAGCCUGACGUUCU<br>GCGUGCAGGUGCAGGGGAAGAGCAAGGGGGAGAAGAAAUAGGGGUGUUCACAGAUAAGACGAGCGCGACGGUGAUCUG<br>CAGGAAGAACGCGAGCAUCAGCGUGAGGGCGCAAGAUAGGUACUACAGCAGCAGCUGGAGCGAGUGGGCGAGCGUGCCG<br>UGCAGUGGUGGCGGCGGCAGCAGGAACCUCCGUGCGACGCCGGACCCUGGCAUGUUCCUGUCCUGCACC<br>ACAGCCAGAACCUGCUGAGGGCGGUGACAACAUGCUGCAGAAGGCGAGGACGCUGGAGUUCUACCCGUGCACGAG<br>CGAGGAGAUCGACCACGAAGAUAUCACGAAAGAUAAGACGAGCACGGUGGAGGCGUGCCUGCCGCUGGAGCUGACGAAG<br>AACGAGAGCUGCCUGAACAGCAGGGAGACGAGCUUCAUCACGAACGGGAGCUGCCUGGCGAGCAGGAAGACGAGCUUCA<br>UGAUGGCGCUGUGCCUGAGCAGCAUCUACGAGGACCUGAAGAUGUACCAGGUGGAGUUCAAGACGAUGAACGCGAAGCU<br>GCUGAUGGACCCCGAAGAGGCAGAUCUUCCUGGACCAGAACAUGCUGGCGGUGAUCGACGAGCUGAUGCAGGCGCUGAAC |

TABLE 4C-continued mRNA Sequences (with T100 tail)

|  |  |
|---|---|
|  | UUCAACAGCGAGACGGUGCCGCAGAAGAGCAGCCUGGAGGAGCCAGAUUUCUACAAGACGAAGAUCAAGCUGUGCAUCC<br>UGCUGCACGCGUUCAGGAUCAGGGCGGUGACGAUCGACAGGGUGAUGAGCUACCUGAACCGCGAGCUGAUAAUAGGCUGG<br>AGCCUCGGUGGCCAUGCUUCUUGCCCCUUGGGCCUCCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAUCUAG |
| hIL12AB_012<br>(SEQ ID<br>NO: 106) | G*GGGAAAUAAGAGAGAAAAGAAGAGUAAGAAGAAAUAUAAGAGCCACCAUGUGCCAUCAGCAGCUGGUGAUCAGCUGG<br>UUCAGCCUCGUGUUUCUGGCCAGCCCCUGGUGGCCAUUUGGGAACUCAAGAAGGACGUGUACGUUGUGGAACUCGACU<br>GGUACCCUGACGCCCCAGGCGAAAUGGUGGUCUUAACCUGCGACACCCCUGAGGAGGACGGAAUCACCUGGACCUUGGA<br>CCAGAGCUCCGAGGUCCUCGGCAGUGGCAAGACCCUGACCAUCAGGGUGAAAGAAUUUGGAGACGCAGGGCAUACACA<br>UGUCACAAGGCGGGGAGGUUCUUUCUCACUCCCUUCUGCUUCUACAUAAAAAGGGAAGACGGAAUUUGGUCUACCGACA<br>UCCUCAAGGACCAAAAGGAGCCUAAGAAUAAAACCUUCUUACGCUGUGAAGCUAAAAACUACAGCGGCAGAUUCACUUG<br>CUGGUGGCUCACCACCAUUUCUACCGACCUGACCUUCUCGGUGAAGUCUUCAAGGGGCUCUAGUGAUCCACAGGGAGUG<br>ACAUGCGGGGCCGCCACACUGAGCGCUGAACGGGUGAGGGGCGAUAACAAGGAGUAUGAAUACUCUGUCGAGUGUCAGG<br>AGGAUUCAGCUUGUCCCGCAGCUGAAGAGUCACUCCCCAUAGAGGUUAUGGUCGAUGCUGUGCAUAAACUGAAGUACGA<br>AAACUACACCAGCAGCUUCUUCAUUAGAGAUAUUAUAAAACCUGACCCCCCAAGAACCUGCAACUUAAACCCCUGAAA<br>AACUCUCGGCAGGUCGAAGUUAGCUGGGAGUACCCUGAUACUUGGUCCACCCCCCACUCGUACUUCUCACUGACUUUCU<br>GUGUGCAGGUGCAGGGCAAGAGCAAGAGAGAGAAAAAAGAUCGUGUAUUCACAGAUAAGACCUCUGCCACCGUGAUCUG<br>CAGAAAAAACGCUUCCAUCAGUGUCAGAGCCCAAGACCGGUACUAUAGUAGUACUGGAGCGAGUGGGCAAGUGUCCCC<br>UGCUCUGGCGGCUGAGGGGGCGGCUCUCGAAACCUCCCCGUCGUACCCCUGAUCCAGGAAUGUUCCCUUGCCUGCAUC<br>ACUCACAGAAUCUGCUGAGAGCGGUCAGCAACAUGCUGCAGAAAGCUAGGCAAACACUGGAGUUUUAUCCUUGUACCUC<br>AGAGGAGAUCGACCACGAGGAUAUUACCAAAGAUAAGACCAGCACGGUGGAGGCCUGCUUGCCCCUGGAACUGACAAAG<br>AAUGAAUCCUGCCUUAAUAGCCGUAGAGACCUCUUUUAUAACAAACGCUGCCUGCCCGGCCAGCAGGAAGACCUCCUUCA<br>UGAUGGCCCUCUGCUGUCCUCAAUCUACGAAGACCUGAAGAUGUACCAGGUGGAAUUUAAAACUAUGAACGCCAAGCU<br>GUUGAUGGACCCCAAGCGGCAGAUCUUUCUGGAUCAAAAUAUGCUGGCUGUGAUCGACGAACUGAUGCAGGCCCUCAAC<br>UUUAACAGCGAGACCGUGCCACAAAAGAGCAGUCUUGAGGAGCCCGACUUCUACAAGACCAAGAUCAAGCUGUGCAUCC<br>UCCUUCAUGCCUUCAGGAUAAGACUGUCACCAUCGACAGAGUGAUGUUACCUGAAUGCAUCCUGAUAAUAGGCUGG<br>AGCCUCGGUGGCCAUGCUUCUUGCCCCUUGGGCCUCCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAUCUAG |
| hIL12AB_013<br>(SEQ ID<br>NO: 107) | G*GGGAAAUAAGAGAGAAAAGAAGAGUAAGAAGAAAUAUAAGAGCCACCAUGUGCCACCAGCAGCUGGUCAUCUCCUGG<br>UUCAGUCUGUCUCUUCCUGGCCUCGCCGCUGGUGGCCAUCUGGGAGCUGAAGAAGACGUUUACGUAGUAGAGUUGGAUU<br>GGUACCCAGACGCACCUGGAGAAAUGGUGGUCCUCACCUGUGACACGCCAGAAGAAGACGGUAUCACCUGGACGCUGGA<br>CCAGAGCAGUGAAGUUCUUGGAAGUGGAAAAACGCUGACCAUCAAGUAAAAGAAUUUGGAGAUGCUGGCCAGUACACC<br>UGCCACAAAGGAGGAGAAGUUCUCAGCCACAGUUUAUUAUUACUUCACAAGAAAGAAGAUGGCACUUCACAGAUA<br>UUUUAAAAGACCAGAAGGAGCCCAAAAAUAAAACAUUUCUUCGAUGUGAGGCCAAGAACUACAGUGGUCGUUUCACCUG<br>CUGGUGGCUGACCACCAUCUCCACAGACCUCACCUUCAGUGUAAAAAGCAGCCGUGGUUCUUCUGACCCCAAGGAGUC<br>ACCCUGUGGGGCUGCCACGCUCUCUGCAGAAAGAGUUCGAGGUGACAACAAAGAAUAUGAGUACUCGGUGGAAUGUCAAG<br>AAGAUUCGGCCUGCCCAGCUGCUGAGGAGAGUCUUCCUAUAGAAGUCAUGGUGGAUGCUGUUCACAAAUUAAAAUAUGA<br>AAACUACACCAGCAGCUUCUUCAUCAGAGAUAUCAUCAAACCUGACCCGCCCAAGAACUUACAGCUGAAGCCGCUGAAA<br>AACAGCCGGCAGGUAGAAGUUCCUGGGAGUACCCAGAUACCUGGUCCACGCCGCACUCCUACUUCUCCCUCACCUUCU<br>GUGUACAAGUACAAGGCAAGAGCAAGAGAGAGAAGAAAGAUCGUGUCUUCACAGAUAAAACAUCAGCCACGGUCAUCUG<br>CAGGAAAAAUGCCAGCACUCCGGUGCGGGCCCAGGACCGCUACUACAGCAGCAGCAGCAGCAGCGGCAUCUGUGCCC<br>UGCAGUGGUGGUGGGGUGGUGGCAGCAGAAACCUUCCUGUGGCCACUCCAGACCCUGGCAUGUUCCGUGCCUUCACC<br>ACUCCCAAAUUUACUUCGAGCUGUUUCUAACAUGCUGCAGAAAGCACGGCAAACUUUAGAAUUCUACCCGUGCACUUC<br>UGAAGAAAUUGACCAUGAAGAUAUCACAAAAGAUAAAACCAGCACAGUGGAGGCCUGCUUCCUUUAGAGCUGACCAAA<br>AAUGAAUCCUGCCUCAACAGCAGAAGACCAGCUUCAACACCAGACUGCUGCCUGGCAGAAACCAGCUUCA<br>UGAUGGCGCUCUGCCUCAGCUCCAUCUAUGAAGAUUUGAAGAUGUACCAAGUAGAAUUUAAAACCAUGAAUGCAAAUU<br>AUUAAUGGACCCCAAGAGGCAGAUAUUUUUAGAUCAAAACAUGCUGGCAGUUAUUGAUGAGCUCAUGCAAGCAUUAAAC<br>UUCAACAGUGAGACGGUACCUCAAAAAAGCAGCCUUGAAGAGCCAGAUUUCUACAAAACCAAGAUCAAACUCUGCAUUU<br>UACUUCAUGCCUUCCGCAUCCGGGCGGUCACCAUUGACCGAGUGAUGAAUCUGAAUGCAUCCUCGUGAUAAUAGGCUGG<br>AGCCUCGGUGGCCAUGCUUCUUGCCCCUUGGGCCUCCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAUCUAG |
| hIL12AB_014<br>(SEQ ID<br>NO: 108) | G*GGGAAAUAAGAGAGAAAAGAAGAGUAAGAAGAAAUAUAAGAGCCACCAUGUGCCACCAGCAGCUUGUGAUUUCUGG<br>UUCUCUCUUGUGUUCCUUGCUUCUCCUCUUGUGGCUAUUUGGGAGUUAAAAAGGACGUGUACGUGGUGGAGCUUGACU<br>GGUACCCUGACGCACCUGGCGAGAUGGUGGUGCUUACUUGUGACACUCCUGAGGAGGACGGCAUUACUUGGACGCUUGA<br>CCAGUCUUCUGAGGUGCUUGGCUGCUGGCAAAACACUUACUAUCCAGGUGAAGGAGUUCGGGGAUGCUGGCCAGUACACU<br>UGCCACAAGGCGGCGAGGUGCUUUCUCACUCUCCUUCACAAGAAGGAGGACGGCAUUUGGUCUACUGACA<br>UUUUAAAAGACCAGAAGGAGCCCAAGAACAAAACAUUCCUUCGUUGCGAGGCCAAGAACUACUCUGGCCGUUUCACUUG<br>CUGGUGGCUUACUACUAUUUCUACCGACCUACUUCUCUGUGAAGUCUUCUCGUGGCUCUUCUGACCCUCAGGGCGUG<br>ACUUGUGGGGCUGCUACUCUUUCUGCUGAGCGUGUGCGUGGUGACAACAAGGAGUACGAGUACUCUGUGGAGUGCCAGG<br>AAGAUUCUGCUUGCCCUGCUGAGGAGUCUCUUCCUAUAGAGGUGAUGGUGGAUGCUGUGCACAAGCUGAAAAUACGA<br>GAACUACACUUCUUCUUCAUUCGUGAUAUUAUUAAGCCUGACCCUCCCAAGAACCUUCAGUUAAAACCUUUAAAA<br>AACUCUCGUCAGGUGGAGGUGCUUGGGAGUACCCUGACACUGGUCUACUCCUCACUCUUACUUCUCUCUUACUUUCU<br>GCGUGCAGGUGCAGGGCAAGUCUAAGCGUGAGAAGAAGGACCGUGUGUUCACUGACAAAACAUCUGCUACUGUGAUUUG<br>CAGGAAGAAUGCCAGCACUCCGGUGCGUCAGGACCGUUACUAUCGUUCAUGAGCAGCUGGAGUGGGCAAGUGCUGUGCCU<br>UGCUCUGGCGGCGGCGGCGGCGGCUCCAGAAAUCUUCCUGUGGCUACUCCUGACCCUGGCAUGUUCCCUUGCCUUCACC<br>ACUCUCAGACCUUCUUCGUGCUGUGAGCAACAUGCUCAGAAGGCUCGCAAACUCUGAGUUCUACCCUUGCACUUC<br>UGAGGAGAUUGACCACGAAGAUAUCACCAAAGAUAAACAUCUACUGUGGAGGCUUGCCUUCCUCUUGAGCUUACCAAG<br>AAUGAAUCCUGCCUUAAUUCUCGUGAGACGUCUUUCUAUCACCAACGCUGCCUGCCCGCGCAAAACUUCA<br>UGAUGGCUCUUUGCCUUUCUUUCUAUUUACGAAGAUUUAAAAAUGUACCAGGUGGAGUCAAAACAUGAAUGCAAAGCU<br>UCUUAUGGACCCCAAGCGUCAGAUUUUCCUUGACCAGAACAUGCUUGCUGUGAUUGACGAGCUUAUGCAGGCUUUAAAU<br>UUCAACUCUGAGACGGUGCCUCAGAAGUCUUUCUUGAGGAGCCUGACUUCUACAAGACCAAGAUUAAGCUUUGCAUUC<br>UCCUUCAUGCUUUCCGUAUUCGUGCUGUGACUAUUGACCGUGUGAUGUGUACCUUAAAUGCUUCUUGAUAAUAGGCUGG<br>AGCCUCGGUGGCCAUGCUUCUUGCCCCUUGGGCCUCCCCCAGCCCCUCCUCCCCUUCCUGCACCCGUACCCCCCAAAC |

TABLE 4C-continued mRNA Sequences (with T100 tail)

ACCAUUGUCACACUCCAGUGGUCUUUGAAUAAAGUCUGAGUGGGCGGCAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAUCUAG hIL12AB_015
(SEQ ID
NO: 109)
G*GGGAAAUAAGAGAGAAAAGAAGAGUAAGAAGAAAUAUAAGAGCCACCAUGUGUCACCAGCAGCUGGUGAUCAGCUGG
UUUAGCCUGGUGUUUCUGGCCAGCCCCUGGUGGCCAUCUGGGAACUGAAGAAAGACGUGUACGUGGUAGAACUGGAUU
GGUAUCCGGACGCUCCCGGCGAAAUGGUGGUGCUGACCUGUGACACCCCCGAAGAAGACGUGAUCACCUGGACCCUGGA
CCAGAGCAGCGAGGUGCUGGGCAGCGGCAAAACCCUGACCAUCCAAGUGAAAGAGUUUGGCGAUGCCGGCCAGUACACC
UGUCACAAAGGCGGCGAGGUGCUAAGCCAUUCGCUGCUGCUGCUGCACAAAAAGGAAGAUGGCAUCUGGAGCACCGAUA
UCCUGAAGGACCAGAAAGAACCCAAAAAUAAGACCUUUCUAAGAUGCGAGGCCAAGAAUUAUAGCGGCCGUUUCACCUG
CUGGUGGCUGACGACCAUCAGCACCACCGAUCUGACCUUCAGCGUGAAAAGCAGCAGAGGCAGCAGCGACCCCCAAGGCGUG
ACGUGCGGCGCCGCCACCCUGAGCGCCGAGAGAGUGAGGCGACAACAAGGAGUAUGGUACAGCGUGGAGUGCCAGG
AAGAUAGCGCCCUGCCCCGCCGCCGAGGAGAGCCUGCCCAUCGAGGUGAUGGUGGAUGCCGUGCACAAGCUGAAGUAUGA
AAACUACACCAGCAGCUUCUUCAUCAGAGAUAUCAUCAAACCCGACCCCCCCAAGAACCUGCAGCUGAAGCCCCUGAAG
AAUAGCCGGCAGGUGGAGGUGAGCUGGGAGUACCCCGACACCUGGAGCACCCCCCAUAGCUACUUCAGCCUGACCUUCU
GCGUGCAGGUGCAGGGCAAGAGCAAGAGAGAAAAGAAAGAUAGAGUGUUCACAGAUAAGACCAGCGCCACGGUGAUCUG
CAGAAAAAAUGCCAGCAUCAGCGUGAGAGCCCAAGAUAGAUACUAUAGCAGCAGCUGGAGCGAAUGGGCCAGCGUGCCC
UGCAGCGGCGGCGGCGGCGGCAGCAGAAACCUGCCCGUGCCACCCCGACCCCGGCAUGUUCCCCUGCCUGCACC
ACAGCCAAAACCUGCUGAGAGCCGUGAGCAACAUGCUGCAGAAGGCCCGGCAGACCCUGGAAUUUUACCCCUGCACCAG
CGAAGAGAUCGAUCAUGAAGAUAUCACCAAAGAUAAAACCAGCACCGUGGAGGCCUGUCUGCCCCUGGAACUGACCAAG
AAUGAGAGCUGCCUAAAAUAGCAGAGAGACCAGCUUCAUAACCAAUGGCAGCUGGCCUGGCCAGCAGAAAGACCAGCUUUA
UGAUGGCCCUGUGCCUGAGCAGCAUCUAUGAAGACCUGAAGAUGUACCAGGUGGAGUUCAAGACCAUGAAUGCCAAGCU
GCUGAUGGAUCCCAAGCGGCAGAUCUUUCUGGAUCAAAACAUGCUGGCCGUGAUCGAUGAGCUGAUGCAGGCCCUGAAU
UUCAACAGCGAGACCGUGCCCCAAAAAGCAGCCUGGAAGAACUCGUGUUUUAUAAAACCAAGAUCAAGCUGUGCAUAC
UGCUGCAUGCCUUCAGAAUCAGAGCCGUGCCAUCGAUAGAGUGAUGAGCUAUCUGAAUGCCAGCUGAUAAUAGGCUGG
AGCCUCGGUGGCAUGCUUCUUGCCCCUUGGGCCUCCCCCAGCCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAUCUAG hIL12AB_016
(SEQ ID
NO: 110)
G*GGGAAAUAAGAGAGAAAAGAAGAGUAAGAAGAAAUAUAAGAGCCACCAUGUGCCACCAGCAGCUGGUCAUCAGCUGG
UUCAGCCUGGUCUUCCUGGCCAGCCCCUGGUGGCCAUCUGGGAGCUGAAGAAGGACGUAUACGUAGUGGAGUUGGAUU
GGUACCCAGACGCUCCUGGGGAGAUGGUGGUGCUGACCUGUGACACCCCAGAAGGAGGACGUGAUCACCUGGACCCUGGA
CCAGAGCUCAGAAGUGCUGGGCAGUGGAAAAACCCUGACCAUCCAGGUGAAGGAGUUUGGAGAUGCUGGCCAGUACACC
UGCCACAAGGGUGGUGAAGUGCUGAGCCACAGCCUGCUGCUGCUGCACAAGAAGGAGGAUGGCAUCUGGAGCACAGAUA
UCCUGAAGGACCAGAAGGAGCCCAAGAACAAGACCUUCCUUCGCUGUGAAGCCAAGAACUACAGUGGCCGCUUCACCUG
CUGGUGGCUGACCACCAUCAGCACAGACUCACCUUCUCGGUGAAGAGCAGCAGAGGCAGCUCAGACCCCCAGGGUGUC
ACCUGUGGGGCGGCCACGCUGUCCGCUGAGAGAGUUCGAGGUGCAACAAGGAGUAUGAAUACUCGGUGGAGUGCCAGG
AAGAUUCGGCGUGCCCGGCGGCAGAAGAGAGCCUGCCCAUAGAAGUGAUGGUGGAUGCUGUGCACAAGCUGAAGUAUGA
AAACUACACCAGCAGCUUCUUCAUCAGAGAUAUCAUCAAGCCAGACCCGCCCAAGAACCUGCAGCUGAAGCCCCUGAAG
AACAGCCGGCAGGUGGAGGUUUCCUGGGAGUACCCAGAUACGUGGAGCACCCCCCACAGCUACUUCAGCCUGACCUUCU
GUGUCCAGGUGCAGGGCAAGAGCAAGAGAGAAAAGAAAGAUCGCGGCUCUUCACAGACAAGACCUCGGCCACCGUGAUCUG
CAGAAAGAAUGCCUCCAUCUCGGUUCGAGCCCAAGAUAGAUACUACAGCAGCAGCUGGUCAGAUGGGCCUCGGUGCCC
UGCAGUGGUGGCGGCGGCGGCGGCAGCAGAAACCUGCUGUUGCCACCCCAGACCCUGGGAUGUUCCCCUGCCUGCACC
ACAGCCAGAACUUAUUACGAGCUGUUUCUAACAUGCUGCAGAAGGCCCGGCAGACCCUGGAGUUCUACCCCUGCACCUC
AGAAGAGAUUGACAUGAAGAUAUCACCAAAGAUAAGACCAGCACCGUGGAGGCCUGUCUGCCCCUGGAACUGACCAAG
AAUGAAAGCUGCCUGAACAGCAGAGAGACCAGCUUCAUCACCAAUGGAAGCUGCCUGGCCAGCAGAAAGACCAGCUUCA
UGAUGGCCCUGUGCCUGAGCAGCAUCUAUGAAGACCUGAAGAUGUACCAGGUGGAGUUCAAGACCAUGAAUGCAAAGCU
GCUGAUGGACCCCAAGCGGCAGAUAUUUUUGGACCAGAACAUGCUGGCUGUCAUUGAUGAGCUGAUGCAGGCCCUGAAC
UUCAACUCAGAACUGUACCCCAGAAGACGCCUGGAGGAACUCGUGUUUUAUCUCAACAAGAUCAAGCUGUGCAUCC
UGCUUCAUGCUUUCAGAAUCAGAGCUGUCACCAUUGACCGCGUGAUGAGCUACUUAAAUGCCUCGUGAUAAUAGGCUGG
AGCCUCGGUGGCAUGCUUCUUGCCCCUUGGGCCUCCCCCAGCCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAUCUAG hIL12AB_017
(SEQ ID
NO: 111)
G*GGGAAAUAAGAGAGAAAAGAAGAGUAAGAAGAAAUAUAAGAGCCACCAUGUGCCACCAGCAGCUGGUAAUCAGCUGG
UUUCCCUCGUCUUUCUGGCAUCACCCCUGGUGGCUAUCUGGGAGCUGAAGAAGGACGUGUACGUGGUGGAGCUGGAUU
GGUACCCUGACGCCCGGGGAAAUGGUGGUGUUAACCUGCGACACCCUGACCUGGACACCGGACGCAUCACCUGGACGCUGGA
CCAGAGCAGCGAGGUGCUUGGGUCUGGUAAAACUCUGACUAUCAGGUGAAAGAGUUCGGGGAUGCCAAUAUACU
UGCCACAAGGGUGGCGAGGUGCUUUCUCAUUCUCUGCUCCUGCUGCACAAGAAGAAGAUGGCAUUUGGUCUACUGAUA
UUCUGAAAGACCAGAAGGAGCCCAAGAACAAGACCUUUCUGAGAUGCGAGGCUAAAAACUACAGCGGAAGAUUUACCUG
CUGGUGGCUGACCACAAUCUCAACCGACCUGACAUUUUCAGUGAAGUCCAGCAGAGGGAGCUCCGACCCUCAGGGCGUG
ACCUGCGGAGCCGCCACUCUGUCCGCAGAAGUGAGAGGUGAUAAUAAGGAGUACAGUCGAAUUGAGUGCGUGCAAG
AAGAUUCUGCCUGCCCAGCCGCCGAGGAGAGCCUGCCAAUCGAGGUGAUGGUGGAUGCGGUACACAAGCUGAAGUAUGA
GAACUACACAUCUCCUUCUUCAUAAGAGAUAUUAUCAAGCCUGACCCACCUAAAAAUCUGCAACUCAAGCCUUUGAAA
AAUUCACGGCAGGUGGAGGUGAGCUGGGAGUACCCUGAUAUUGGAGCACCCCCCAUAGCUAUUUUCGCUGACAUUCU
GCGUCCAGGUGCAGGGCAAGUCAAGAGAGAAGAAGGACCGCGUGUUCACAGAGAAGAAGACCAGCGCAUCUGUGAUCUG
CAGAAAAAACGCUAGCAUUAGCGUCAGAGCACAGGACCGGUAUUACUCCAGCUCCUGGAGCGAAUGGGCAUCUGUGCCC
UGCAGCGUGGGGCGGAGGCGGAUCCAGAAACCUCCCCGUUGCCACACCUGAUCCUGGAAUGUUCCCCUGUCUGCACC
ACAGCCAGAACUGCUGAGAGCAGUGUCUAACAUGCUCCAGAAGGCCAGGCAGACCCUGGAGUUUUACCCCUGCACCAG
CGAGGAAAUCGAUCAUGAAGAUAUCACCAAAGAUAAAACCUCCACCGUGGAGGCCUGUCUGCCCCUGGAACUGACCAAA
AACGAGAGCUGCCUGAAUAGCAGGGAGACCUCCUUCAUCAACCAACGGCUCAUGCCUUGCCAGCCGGAAAACUAGCUUCA
UGAUGGCCCUGUGCCUGUCUUCGAUCUAUGAGGACCUGAAAAUGUACCAGGUCGAAUUUAAGACGAUGAACGCAAAGCU
GCUGAUGGACCCCAAGCGGCAGAUCUUUCUCGGACCAGAACAUGCUGGCAGUCAUAGAUGAGUUGAUGCAGGCAUUAAAC
UUCAACAGCGAGACCGUGCCUCAGAAGUCCCUGGAAGAGCUCGUGUUUUAUCCUGAAUGCUAGCUGAUAAUAGGCUGG
AGCCUCGGUGGCAUGCUUCUUGCCCCUUGGGCCUCCCCCAGCCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAUCUAG

TABLE 4C-continued mRNA Sequences (with T100 tail)

| | |
|---|---|
| hIL12AB_018 (SEQ ID NO: 112) | G*GGGAAAUAAGAGAGAAAAGAAGAGUAAGAAGAAAUAUAAGAGCCACCAUGUGUCACCAACAGUUAGUAAUCUCCUGG UUUUCUCUGGUGUUUCUGGCCAGCCCCCUCGUGGCCAUCUGGGAGCUUAAAAAGGACGUUUACGUGGUGGAGUUGGAUU GGUAUCCCGACGCUCCAGGCGAAAUGGUCGUGCUGACCUGCGAUACCCCUGAAGAAGACGGUAUCACCUGGACGCUGGA CCAGUCUUCCGAGGUGCUUGGAUCUGGCAAAACACUGAACUACAAGUUAAGGAGUUCGGGGACGCAGGGCAGUACACC UGCCACAAAGGCGGCGAGGUCCUGAGUCACUCCCUGUUACUGCUCCACAAGAAAGAGGACGGCAUUUGGUCCACCGACA UUCUGAAGGACCAGAAGGAGCCUAAAGAAUAAAACUUUCCUGGACGAGGCAAAAAACUAUAGCGGCCGCUUUACUUG CUGGUGGCUUACAACAAUCUCUACCGAUUUAACUUUCCGUGAAGUCUAGCAGAGGAUCUCUGACCCGCAAGGAGUG ACUUGCGGAGCCGCCACCUUGAGCGCCGAAAGAGUCCGUGGCGAUAACAAAGAAUACGAGUACUCCGUGGAGUGCCAGG AAGAUUCCGCCUGCCCAGCUGCCGAGGAGUCCCUGCCCAUUGAAGUGAUGGUGGAUGCCGUCCACAAGCUGAAGUACGA AAACUAUACCAGCAGCUUCUUCAUCCGGGAUAUCAUUAAGCCCGACCCUCCUAAAAACCUGCAACUUAAGCCCCUAAAG AAUAGUCGGUUGAGGUCAGCUGGGAAUAUCCUGACACAUGGAGCACCCCCCACUCUUAUUUCUCCCUGACCUUCU GCGUGCAGGUGCAGGGCAAGAGUAAACGGGAGAAAAAGAUAGGGUCUUUACCCGAUAAAACCAGCGCUACGGUUAUCUG UCGGAAGAACGCUUCCAUCUCCGUCCGCGCUCAGGAUCGUUACUACUCGUCCUCAUGGAGCGAGUGGGCCAGCGUGCCC UGCAGCGGCGGCGGUGGAGGCGGAUCCAGAAAUCGCCUGUUGCCACACCAGACCCUGGCAUGUUCCCCUGUCUGCAUC AUAGCCAGAACCUGCUCAGAGCCGUGAGCAACAUGCUCCAGGCAGGCAACUUUGGAGUCUACCCGGUGACAUC UGAGGAAAUCGAUCACGAAGAUAUAACCAAAGAUAAAACCUCUACAGUAGAGGCUUGUUUGCCCCUGGAGUUGACCAAA AACGAGAGUUGCCUGAACAGUCGCGAGACGAGCUUCAUUACUAACGGCAGCUGUCUCGCCUCCAGAAAAACAUCCUUCA UGAUGGCCCUGUGUCUUUCCAGCAUAUACGAAGACCUGAAAAUGUACCAGGUCGAGUUCAAACAAUGAACGCCAAGCU GCUUAUGGACCCCAAGCGGCAGAUCUUCCUCGACCAAAACAUGCUCGCUGUGAUCGAUGAGCUGAUGCAGGCUCUCAAC UUCAAUUCCGAAACAGUGCCACAGAAGUCCAGUCUGGAAGACCCGACUUCUACAAGACCAAGAUUAAGCUGUGUAUUU UGCUGCAUGCGUUUAGAAUCAGAGCCGUGACCAUUGAUCGGGUGAUGAGCUACCUGAACGCCUCGUGAUAAUAGGCUGG AGCCUCGGUGGCCAUGCUUCUUGCCCCUUGGGCCUCCCCCCAGCCCCUCCUCCCCUUCCUGCACCCGUACCCCCCAAAC ACCAUUGUCACACUCCAGUGGUCUUUGAAUAAAGUCUGAGUGGGCGGCAAAAAAAAAAAAAAAAAAAAAAAAAAAA AAAAAAAAAAAAAAAAAAAAAAAAAAAAAAAAAAAAAAAAAAAAAAAAAAAAAAAAAAAAAAAAAAUCUAG |
| hIL12AB_019 (SEQ ID NO: 113) | G*GGGAAAUAAGAGAGAAAAGAAGAGUAAGAAGAAAUAUAAGAGCCACCAUGUGUCACCAGCAGCUUGUCAUCUCCUGG UUUUCUCUUGUCUUCCUGGCCGCGCUGGUGGCCAUCUGGGAGCUGAAGAAAGACGUUUACGUGGUAGAGUUGGAUU GGUACCCAGACGCUCACCUGGAGAAAUGGUGGUUCUCACCUGCGACACUCCUGAAGAAGACGGUAUCACCUGGACGCUGGA CCAAAGCUCAGAAGUUCUUGGCAGUGGAAAAACGCUGAACUACAAGUAAAAGAAUUUGGGGAUGCUGGCCAGUACACG UGCCACAAAGGAGGAGAAGUUCUCAGCCACAGUUUACUUCUUCUUCACAAGAAAGAAGAUGGCAUCUGGUCCACAGAUA UUUUAAAAGACCAGAAGGAGCCCAAGAACAAAACCUUCCUCCGCUGAGGCCAAGAACUACAGUGGCGUUUCACCUG CUGGUGGCUCACCACCAUCUCCACUGACCUCACCUUCCUGUAAAAAGCAGCUGUGGUUCUUCGACCCCAAGGAGUC ACCUGUGGGGCUGCCACGCUCUCGGCAGAAAGAGUUCGAGGUGACAACAAGGAAUAUGAAUAUUCUGUGGAAUGUCAAG AAGAUUCUGCCUGCCCGGCGGCAGAAGAAAGUCUUCCCAUAGAAGUCAUGGUGGAUGCUGUUCACAAAUUAAAAUAUGA AAACUACACCAGCAGCUUCUUCAUUCGUGACAUCAUCAAACCAGACCCGCCCAAGAACCUUCAGUUAAAACCUUUAAAA AACAGCCGGCAGGUGGAAGUUUCUGGGGAUACCCAGAUACGUGGUCCACGCCGCACUCCACUCAGUUUAACCUUCU GUGUACAAGUACAAGGAAAAUCAAAAGAGAGAAGAAAGAUCGUGUCUUCACUGACAAAACAUCUGCCACGGUCAUCUG CAGGAAGAAUGCCUCCAUCUCGGUUCGAGCCCAGGACCGCUACUACAGCAGCAGCUGGAGUGAGUGGGCAUCUGUUCCC UGCAGUGGUGGCGGCGGCGGCGGCAGCCGCAACCUUCCUGUGGCCACGCCGGACCCUGGCAUGUUCCCCGUGCCUUCACC ACUCCCAAAAUCUGCUGUGCUGUUUCUAACAUGCUGCAGGCCUGUCAUUGAUGAGCUGAUGCAGGCAUUAAAC UUCAACUCAGAAACUGUUCCCCAGAAGUCAUCUUUAGAAGAGCCAGAUUUCUACAAAACAAAAAUAAAACUCUGCAUUC UUCUUCAUGCCUUCCGCAUCCGUGCUGUCACCAUUGACGGUGAUGUCCUACUUAAAUGCUUCUUGAUAAUAGGCUGG AGCCUCGGUGGCCAUGCUUCUUGCCCCUUGGGCCUCCCCCCAGCCCCUCCUCCCCUUCCUGCACCCGUACCCCCCAAAC ACCAUUGUCACACUCCAGUGGUCUUUGAAUAAAGUCUGAGUGGGCGGCAAAAAAAAAAAAAAAAAAAAAAAAAAAA AAAAAAAAAAAAAAAAAAAAAAAAAAAAAAAAAAAAAAAAAAAAAAAAAAAAAAAAAAAAAAAAAAAUCUAG |
| hIL12AB_020 (SEQ ID NO: 114) | G*GGGAAAUAAGAGAGAAAAGAAGAGUAAGAAGAAAUAUAAGAGCCACCAUGUGCCACCAGCAGCUGGUGAUCAGCUGG UUCAGCCUGGUGUUCCUGGCUAGCCCUCUGGUGGCCAUCUGGGAGCUGAAGAAGACGUGUACGUGGUGGAGUUGGAUU GGUACCCCGACGCUCCCGGCGAGAUGGUGGUGCUGACCUGCGACACCCCGGAGGAGGACGGGAUCACCUGGACCCUGGA UCAGUCAAGCGAGGUGCUGGGAAGCGGCAAGACCCUGAACUACCAGGUGAAGGAGUUCGGCGACGCCGGCCAAUACACU UGCCACAAGGGAGGCGAGGUGCUGUCCCACUCCCUCCUGCUGCUGCACAAAAAGGAAGACGGCAUCUGGAGCACCGACA UCCUGAAAGACCAGAAGGAGCCCUAAAGAACAAAACAUUCCUCGAUGAGGCAGAAGAUUACAGCGGAGAUUCACCUG UUGGUGGCUGACCACCAUCAGCACAGACCUGACCUUCGUGAAGAACAGCAGAGGCAGCAGCGACCCCCAGGGCGUG ACCUGUGGCGCCGCCACCCUGAGCGCCGAAAGAGUGCGCGGCGACAACAAGGAGUACGAGUACUCCGUGGAAUGCCAGG AAGAUAGCGCCUGCCCCGCCGCCGAGGAGAGCCUGCCCAUCGAGGUGAUGGUGGACGCCGUCCACAAGCUGAAGUACGA GAACUACACCUCUAGCUUCUUCAUCAGAGAUAUCAUCAAGCCUGAUCCCCCCAAGAACCUGCAGCUGAAACCCCUGAAG AACAGCCGGCAGGUGGAGGUGAGCUGGGAGUAUCCGACACCUGGUCCACCCCCAUGCUAUUUUAGCCUGACCUUCU GCGUGCAAGUGCAGGGCAAGAGCAAGAGAGAAGAAGGACCGCGUGUUCACCGACAAAACCAGCGCCACCGUGAUCUG CAGAAAGAACGCCAGCAUCAGCGUGAGGGCCCAGGAUAGAUACUACAGUUCCAGCUGGAGCGAGUGGGCCAGCGUGCCC UGCAGCGGCGGCGGCGGGGGAGGCUCGAGAAACCUGCCCGUGGCUACCCCGAUCCCGGAUGUUCCCCUGCCUGCACC ACAGCCAGAACCUGCUGAGGCCGGUGUCCAACAUGCUUCAGGCAGGCUGUGACCUGAGCGUCGAUGAGCUGAUGCAAACCUCGUGGUCCCUGGAGCUGACCAAG AACGAGAGCUGCCUGAACUCCCGCGAGACCAGCUUCAUCACGAACGGCAGCUGCCUGGCCAGCAGGAAGACCUCUUCA UGAUGGCCCUGUGCCUGAGCAGCAUCUACGAGGACCUGAAAAUGUACCAGGUGGAGUUUAAGACCAUGAACGCCAAGCU GCUGAUGGACCCCAAGCGGCAAAUCUUCCUGGACCAGAACAUGCUGGCCGUGAUCGACGAGCUGAUGCAGGCCCUGAAC UUCAAUAGCGAGACGGUCCCCCAGAAGAGCAGCCUGGAGGAGCCCGACUUUUACAAGACCAAGAUCAAGCUGUGCAUCC UGCUGCACGCCUUUAGAAUCCGUGCCGUGACCAUUGACAGAGUGAUGAGCUACCUGAAUGCCAGCUGAUAAUAGGCUGG AGCCUCGGUGGCCAUGCUUCUUGCCCCUUGGGCCUCCCCCCAGCCCCUCCUCCCCUUCCUGCACCCGUACCCCCCAAAC ACCAUUGUCACACUCCAGUGGUCUUUGAAUAAAGUCUGAGUGGGCGGCAAAAAAAAAAAAAAAAAAAAAAAAAAAA AAAAAAAAAAAAAAAAAAAAAAAAAAAAAAAAAAAAAAAAAAAAAAAAAAAAAAAAAAAAAAAAAAAUCUAG |
| hIL12AB_021 (SEQ ID NO: 115) | G*GGGAAAUAAGAGAGAAAAGAAGAGUAAGAAGAAAUAUAAGAGCCACCAUGUGCCACCAGCAGCUGGUGAUCAGCUGG UUCAGCCUGGUGUUCCUGGCCAGCCCCCUCUGGUUGCCAUCUGGGAGCUGAAGAAAGACGUGUACGUCGUGGAACUGGACU GGUAUCCGGACGCCCCCGGGCGAGAUGGUGGUGCUGACCUGUGACACCCCCGAGGAGGACGGCAUCACCUGGACGCUGGA |

TABLE 4C-continued mRNA Sequences (with T100 tail)

|  |  |
|---|---|
|  | CCAAUCCUCCGAGGUGCUGGGAAGCGGCAAGACCCUGACCAUCCAGGUGAAGGAAUUCGGGGACGCCGGGCAGUACACC<br>UGCCACAAGGGGGCGAAGUGCUGUCCCACUCGCUGCUGCUCCUGAUAAGAAGGAGGAUGGAAUCUGGUCCACCGACA<br>UCCUCAAAGAUCAGAAGGAGCCCAAGAACAAGACGUUCCUGCGCUGUGAAGCCAAGAAUUAUUCGGGGCGAUUCACGUG<br>CUGGUGGCUGACAACCAUCAGCACCGACCUGACGUUUAGCGUGAAGAGCAGCAGGGGGUCCAGCGACCCCCAGGGCGUG<br>ACGUGCGGCGCCGCCACCCUCUCCGCCGAGAGGGUGCGGGGGGACAAUAAGGAGUACGAGUACAGCGUGGAAUGCCAGG<br>AGGACAGCGCCUGCCCCGCCGGAGGAAAGCCUCCCGAUAGAGGUGAUGGUGGACGCCGUGCACAAGCUCAAGUAUGA<br>GAAUUACACCAGCAGCUUUUUCAUCCGGGACAUUAUCAAGCCCGACCCCCCGAAGAACCUCCAGCUGAAGCCCCUGAAG<br>AACAGCCGGCAGGUGGAAGUCUCCUGGGAGUAUCCCGACACCUGGAGCACCCCGCACAGCUACUUCUCCCUGACCUUCU<br>GUGUGCAGGUGCAGGGCAAGUCCAAGAGGGAAAGAAGGACAGGGUUUUCACCGACAAGACCAGCGCGACCGUGAUCUG<br>CCGGAAGAACGCCAGCAUAAGCGUCCGCGCCCAAGAUAGGUACUACAGCAGCUCCUGGAGCGAGUGGGCUAGCGUGCCC<br>UGCAGCGGGGGCGGGGUGGGGGCUCCAGGAACCUGCCAGUGGCGACCCCCGACCCCGGCAUGUUCCCCUGCCUCCAUC<br>ACAGCCAGAAACUGCUGAGGGCGUCAGGCAAUAUGCUGCAGAAGGCCAGGCAGACCCUGGAAUUCUACCCCUGCACGUC<br>GGAGGAGAUCGAUCACGAGGAUAUCACAAAAGACAAGACUUCCACCGUGGAGGCCUGCCUGCCCUGGAGCUCACCAAG<br>AAUGAGUCCUGUCUGAACUCCCGGGAAACCAGCUUCAUCACCAACGGGUCCUGCCUGGCCAGCAGGAAGACCAGCUUUA<br>UGAUGGCCUGUGCCUGUCGAGCAUCUACGAGGACCUGAAGAUGUACCAGGUCGAGUUCAAGACAAUGAACGCCAAGCU<br>GCUGAUGGACCCCAAGAGGCAAAUCUUCCUGGACCAGAAUAUGCUUGCCGUCAUCGACGAGCUCAUGCAGGCCCUGAAC<br>UUCAACUCCGAGACCGUGCCCCAGAAGAGCAGCCUGGAGGAGCCCGACUUCUACAAGACCAAGAUCAAGCUGUGCAUCC<br>UGCUGCACGCGUUCAGGAUCCGGGCAGUCACCAUCGACCGUGUGAUGUCCUACCUGAACGCCAGCUGAUAAUAGGCUGG<br>AGCCUCGGUGGCCAUGCUUCUUGCCCCUUGGGCCUCCCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAAUCUAG |
| hIL12AB_022<br>(SEQ ID<br>NO: 116) | G*GGGAAAUAAGAGAGAAAAGAAGAGUAAGAAGAAAUAUAAGAGCCACCAUGUGCCAUCAGCAGCUGGUGAUCAGCUGG<br>UUCAGCCUGGUGUUCCUCGCCUCUCCCCUGGUGGCCAUCUGGGAGCUCAAAAAGGACGUGUACGUGGUGGAGCUCGACU<br>GGUACCCAGACGCCCCCGGGGAGAUGGUGGUGCUGACCUGCGACACCCCCGAAGAAGACGGCAUCACGUGGACCCUCGA<br>CCAGUCCAGCGAGGUGCUGGGGAGCGGGAAGACUCUGACCAUCCAGGUCAAGGAGUUCGGGGACGCCGGGCAGUACACG<br>UGCCACAAGGGCGGCGAAGUCUUAAGCCACUCGCUGCUGCUGCUCCUGAUAAGAAGGAGGACGGGAUCUGGUCCACAGACA<br>UACUGAAGGACCAGAAGGAGCCGAAGAAUAAAACCUUUCUGAGGUGCGAGGCCAAGAACUAUUCCGGCAGGUUCACGUG<br>CUGGUGGCUUACAACAAUCAGCACAGACCUGACGUUCAGCGUGAAGUCCAGCCGCGGCAGCAGCGACCCCCAGGGGGUG<br>ACCUGCGGCGCCGCCACCCUGAGCGCCGAGCGGGUGCGCGGGGACAACAAGGAGUACGAGUACUCCGUGGAGUGCCAGG<br>AAGACAGCGCCUGCCCCGCCGCCGAAGAGAGCCUGCCUAUCGAGGUCAUGGUGGACGCCGUGCAUAAGCUGAAGUACGA<br>GAACUAUACGAGCAGCUUUUUCAUACGCGACAUCAUCAAGCCCGACCCCCCAAGAACCUGCAGCUUAAGCCCCUGAAG<br>AAUAGCCGGCAGGUGGAGGUCUCCUGGGAGUACCCCGACACCUGGUCAACGCCCCACAGCUACUUCUCCCUGACCUUUU<br>GUGUCCAAGUCCAGGGAAAGAGCAAGAGGGAGAAGAAAGAUCGGGUGUUCACCGACAAGACCUCCGCCACGGUGAUCUG<br>CAGGAAGAACGCCAGCAUCUCCGUGAGGGCGCAAGACAGGUACUACUCCAGCAGCUGGUCCGAAUGGGCCAGCGUGCCC<br>UGCUCCGGCGGCGGGGGCGGCGGCAGCCGAAACCUACCCGGUGCCACGCCGGAUCCCGGCAUGUUUCCCUGCUGCACC<br>ACAGCCAGAACUCCCUGAGGGCCGUGUCCAACAUGCUGCAGAAGGCCAGGCAGACUCGGAGUUCUACCCCUGCACGAG<br>CGAGGAGAUCGAUCACGAGGACAUCACCAAGGAUAAGACCAGCACUGUGGAGGCCUGCCUUCCCCUGGAGCUGACCAAG<br>AACGAGAGCUGUCUGAACUCCAGGGAGACCUCAUUCAUCACCAACGGCUCCUGCCUGGCCAGCAGGAAAACCAGCUUCA<br>UGAUGGCCCUUGUGUCCUCAGCGUCCAUCUACGAGGACCUGAAGAUGUAUCAGGUCGAGUUCAAGACAAUGAACGCCAAGCU<br>GCUGAUGGACCCCAAAAGGCAGAUCUUCCUGGACCAGAACAUGCUGGCCGUCAUCGACGAGCUGAUGCAGGCCCUGAAC<br>UUCAACAGCGAGACGGUGCCCCAGAAAAGCUCCCUGGAGGAGCCCGACUUCUACAAGACCAAGAUCAAGCUGUGCAUCC<br>UGCUGCACGCCUUCAGGAUCAGGGCAGUGACCAUCGACCGGGUGAUGCAUACCUUAACGCCAGCUGAUAAUAGGCUGG<br>AGCCUCGGUGGCCAUGCUUCUUGCCCCUUGGGCCUCUCCCCAGCCCCUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAAUCUAG |
| hIL12AB_023<br>(SEQ ID<br>NO: 117) | G*GGGAAAUAAGAGAGAAAAGAAGAGUAAGAAGAAAUAUAAGAGCCACCAUGUGCCAUCAGCAGCUGGUGAUCUCCUGG<br>UUCAGCCUGGUGUUUCUGGCCUCGCCCCUGGUCGCCAUCUGGGAGCUGAAGAAAGACGUGUACGUCGUCGAACUGGACU<br>GGUACCCCGACGCCCCCGGGGAGAUGGUGGUGCUGACCUGCGACACGCCGGAGGAGGACGGCAUCACCUGGACCCUGGA<br>UCAAAGCAGCGAGGUGCUGGGCAGCGGCAAGACCCUGACCAUCCAAGUGAAGGAAUUCGGCGAUGCCGGCCAGUACACC<br>UGUCACAAGGGGGCUCAGCCAGCCUGCUGCUGCUCAAGAAGGAGGAUGGCAUCUGGAGCACCGAUA<br>UCCUGAAGGACCAGAAAGAGCCCAAGAACAAGACGUUCCUGAGGUGCGAGGCCAAGAACUACAGCGGUAGGUUCACGUG<br>UUGGUGGCUGACCACCAUCAGCACCGACCUGACGUUCAGCGUGAAGAGCUCCAGGGGCAGCUCCGACCCACAGGGGGUG<br>ACGUGCGGGGCCGCAACCCUCAGCGCCGAAAGGGUGCGGGGGGACAACAAGGAGUACGAAUACUCCGUGGAGUGCCAGG<br>AAGAUUCGGCCUGCCCCGCCGGAGGUAAUGGGUGACGCCGUGCAUAAGCUGAAGUACGA<br>GAACUACACCAGCUCGUUCUUCAUCCGAGACAUCAUCAAACCCGACCCGCCCAAAAAUCUGCAGCUCAAGCCCCUGAAG<br>AACUCCAGGCAGGUGGAGGUGAGCUGGGAGUACCCCGACACCUGGUCCACCCCGCACAGCUACUUCUCCCUGACAUUCU<br>GCGUGCAGGUGCAGGGCAAGAGCAAGCGGGAGAAGAAGGACAGGGUGUUCACCGACAAGACGAGCGCCACCGUGAUCUG<br>CCGAAAGAACGCCAGCAUCUCGUGCGCGCCCAGGAUAGGUACUAUUCAGCUCCUGGAGCGAGUGGGCCGUACCC<br>UGCAGCGGCGGCGGGGGCGGCAGUAGGAAUCUGCCGAGGUACCCCGGACGCCCGGGCAUGUUCCCCUGCCUCCACC<br>ACAGCCAGAACUGCUGAGGGCCGUGCAACAUGCUGCAGAAGGCCAGACAGACGCUGGAGUUCUACCCCUGCACGAG<br>CGAGGAGAUCGACCACGAGGACAUCACCAAGGAUAAAUUCCACCGUCGAGGCCUGCCUGCCCUUGGAGCUGACCAAG<br>AAUGAAUCCUGUCUGAACAGCAGGGAGACCUCGUUUAUCACCAAUGGCAGCUGCCUCGCCUCCAGGAAGACCAGCUUCA<br>UGAUGGCCCUCGUCUGCUGAGCUCCAUCUAUGAGGACCUGAAGAUGUACCAGGUUCAAGACCAUGAACGAAGCU<br>GCUGAUGGACCCCAAGAGGCAGAUCUUCCUGGAUCAGAAUAUGCUGGCGGUGAUCGACGAGCUCAUGCAGGCCCUCAAU<br>UUCAAUAGCGAGACAGUGCCCCAGAAGUCCUCCCUGGAGGAGCCCGACUUCUACAAGACCAAGAUCAAGCUGUGUAUCC<br>UGCUGCACGCCUUCCGGAUCCGGGCCGUCACCAUCGACCGGGUGCAUGAGCUACCUCAAUGCCAGCUGAUAAUAGGCUGG<br>AGCCUCGGUGGCCAUGCUUCUUGCCCCUUGGGCCUCCCCCCAGCCCGUCCUCCCCUUCCUGCACCCGUACCCCCCAAAC<br>ACCAUUGUCACACUCCAGUGGUCUUUGAAUAAAGUCUGAGUGGGCGGCAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAAUCUAG |
| hIL12AB_024<br>(SEQ ID<br>NO: 118) | G*GGGAAAUAAGAGAGAAAAGAAGAGUAAGAAGAAAUAUAAGAGCCACCAUGUGCCACCAGCAGCUGGUGAUCUCCUGG<br>UUCUCCCUGGUGUUCCUGGCCUCGCCCCUGGUGGCCAUCUGGGAGCUGAAGAAGGACGUGUACGUCGUGGAGCUCGACU<br>GGUACCCCGACGCCCCUGGCGAGAUGGUGGUGCUGACCUGCGACACCCAGAGGAGGAUGCAUCACCUGGACCCUGGA<br>UCAGUCCUCCGAGGUGCUGGGCUCCGGCAAGACGCUGACCAUCCAAGUGAAGGAGUUCGGUGACGCCGGACAGUAUACC<br>UGCCAUAAGGGCGGCGAGGUCCUGUCCCACAGCCUCCUCCUCCUGCAUAAGAAGGAGGACGGCAUCUGGAGCACCGACA<br>UCCUGAAGGACCAGAAGGAGCCCAAGAACAAGACCUUUCUGAGGUGCGAGGCCAAGAACUACAGCGGCCGAUUCACCUG |

TABLE 4C-continued mRNA Sequences (with T100 tail)

|  |  |
|---|---|
|  | CUGGUGGCUCACCACCAUAUCCACCGACCUGACUUUCUCCGUCAAGUCCUCCCGGGGGUCCAGCGACCCCCAGGGAGUG<br>ACCUGCGGCGCCGCCACCCUCAGCGCCGAGCGGGUGCGGGGGACAACAAGGAGUACGAAUACUCCGUCAGUGUGCCAGG<br>AGGACUCCGCCUGCCCGGCCGCCGAGGAGAGCCUGCCCAUCGAGGUGAUGGUCGACGCGGUGCACAAGCUGAAGUACGA<br>GAACUACACCAGCAGUUUCUUCAUCAGGGAUAUCAUCAAGCCAGAUCCCCGAAGAAUCUGCAACUGAAGCCGCUGAAA<br>AACUCACGACAGGUGGAGGUGAGCUGGGAGUACCCCGACACGUGGAGCACCCCACAUUCCUACUUCAGCCUGACCUUCU<br>GCGUGCAGGUCCAGGGCAAGAGCAAGCGGGAGAAGGAGGACAGGGUUCACGGAUAAGACCAGUGCCACCGUGAUCUG<br>CAGGAAGAACGCCUCUAUUAGCGUGAGGGCCCAGGAUCGGUAUUACUCCUCGAGCUGGAGCGAAUGGGCCUCCGUGCCC<br>UGCAGUGGGGGGGUGGAGGCGGGAGCAGGAACCUGCCCGUAGCAACCCCGACCCCGGGAUGUUCCCCUGUCUGCACC<br>ACUCGCAGAACCUGCUGCGCGCGGUGAGCAACAUGCUCCAAAAAGCCCGUCAGACCUUAGAGUUCUACCCCUGCACCAG<br>CGAAGAAAUCGACCACGAAGACAUCACCAAGGACAAAACCAGCACCGUGGAGGCGUGCCUGCCGCUGGAGCUGACCAAG<br>AACGAGAGCUGCCUCAACUCCAGGGAGACCAGCUUUAUCACCAACGGCUCGUGCUAGCCAGCCGGAAAACCAGCUUCA<br>UGAUGGCCCUGUGCCUGAGCUCCAUUUACGAGGACCUGAAGAUGUAUCAGGUGGAGUUCAAGACCAUGAAUGCCAAACU<br>CCUGAUGGACCCCAAGAGGCAGAUCUUCCUGGACCAGAACAUGCUCGCGGUGAUCGAUGAGCUGAUGCAGGCCCUGAAC<br>UUUAAUAGCGAGACCGUGCCCCAGAAAAGCAGCCUGGAGGAGCCGGACUUCUACAAGACCAAAAUCAAGCUGUGCAUCC<br>UGCUCCACGCCUUCCGCAUCCGGGCCGUGACCAUCGACAGGGUGAUGAGCUACCUGAACGCCAGCUGAUAAUAAGGCUGG<br>AGCCUCGGUGGCCAUGCUUCUUGCCCCUUGGGCCUCCCCCCAGCCCCUCCUCCCCUUCCUGCACCCGUACCCCCCAAAC<br>ACCAUUGUCACACAUCUCCAGUGGUCUUUGAAUAAAGUCUGAGUGGGCGGCAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAUCUAG |
| hIL12AB_025<br>(SEQ ID<br>NO: 119) | G*GGGAAAUAAGAGAGAAAAGAAGAGUAAGAAGAAAUAUAAGAGCCACCAUGUGCCAUCAGCAGCUGGUGAUUUCCUGG<br>UUCUCCCUGGUGUUCCUGGCCAGCCCCUCGUGGCGAUCUGGGAGCUAAAGAAGGACGUGUACGUGGUGGAGCUGGACU<br>GGUACCCGGACGCACCCGGCGAGAUGGUCGUUCUGACCUGCGAUACGCAGAGGAGGACGGCAUCACCUGGACCCUCGA<br>UCAGAGCAGCGAGGUCCUGGGGAGCGGAAAGACCCUGACCAUCCAGGUCAAGGAGUUCGGCGACGCCGGCCAGUACACC<br>UGCCACAAAGGUGGCGAGGUCCUGAGCCACUCGCUGCUGCUCCUGCAUAAGAAGGAGGACGGGAAUCUGGAGCACAGACA<br>UCCUGAAAGACCAGAAGGAGCCCAAGAACAAGACCUUCCUGAGGUGCGAGGCAAGAACUACAGCGGGCGCUUCACGUG<br>CUGGUGGCUGACCACCAUCAGCACGGACCUCACCUUCUCCGUGAAGAGCAGCCGGGGAUCCAGCGAUCCCCAAGGCGUC<br>ACCUGCGGCGGCCCACCCUGAGCGCGAGAGGGUCAGGGCGAUAAUAAGGAGUAUGAGUACAGCGUGAGUGCCAGG<br>AGGACAGCGCCUGCCCGGCCGCCGAGGAGUCCCUGCCAAUCGAAGUGAUGGUCGACGCCGUGCACAAGCUGAAGUACGA<br>GAACUACACCAGCAGCUUCUUCAUCGGGAUAUCAUCAAGCCCGAUCCCCGAAGAACUGCAGCUGAAGCCCCUCAAG<br>AACAGCCGGCAGGUGGAGGUGAGUUGGGAGUACCCCGACACCUGGUCAACGCCCCACAGCUACUUCUCCCCUGACCUUCU<br>GUGUGCAGGUGCAGGGAAAGAGCAAGAGGGGAAGAAGGACCGGGUUUCACCGACAAGACCAGCGCCACGGUGAUCUG<br>CAGGAAGAACGCAAGCAUCUCCGUGAGGGCCCAGGACAGGUACUACAGCUCCAGCUGGUCCGAAUGGGCCAGCGUGCCC<br>UGUAGCGGCGGCGGGGCGGUGGCAGCCGCAACCUCCCAGUGGCCACCCCGACCCCGGCAUGUUCCCCUGCCUGCACC<br>ACAGCCAGAAUCUGCUGAGGGCCGUGAGUAACAUGCUGCAGAAGGCAAGGCAAACCCCUCGAAUUCUAUCCCCUGCACCUC<br>CGAGGAGAUCGACCACGAGGAUCACCAAGGACAAGACCAGCACCGUCGAGGCCUGUCUCCCCCUGGAGCUGACCAAG<br>AAUGAGAGCUGCCUGAACAGCCGGGAGACCAGCUUCAUCACCAACGGGAGCUGCCUGGCCUCCAGGAAGACCUCGUUCA<br>UGAUGGCGCUGUGCCUCUCAAGCAUAUACGAGGAUCUGAAGAUGUACCAGGUGGAGUUUAAGACGAUGAACGCCAAGCU<br>GCUGAUGGACCCGAAGAGGCAGAUCUUCCUGGACCAGAACAUGCUGGCCGUGAUAGACGAGCUCAUGCAGGCCCUGAAC<br>UUCAACUCCGAGACCGUGCCGCAGAAGUCAUCCCCUCGAGGAGCCCGACUUCUAUAAGACCAAGAUCAAGCUGUGCAUCC<br>UGCUCCACGCCUUCCGGAUAAGGGCCGUGACAUCGACAGGGUGAUGAGCUACCUGAACGCCAGCUGAUAAUAAGGCUGG<br>AGCCUCGGUGGCCAUGCUUCUUGCCCCUUGGGCCUCCCCCCAGCCCCUCCUCCCCUUCCUGCACCCGUACCCCCCAAAC<br>ACCAUUGUCACACAUCUCCAGUGGUCUUUGAAUAAAGUCUGAGUGGGCGGCAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAUCUAG |
| hIL12AB_026<br>(SEQ ID<br>NO: 120) | G*GGGAAAUAAGAGAGAAAAGAAGAGUAAGAAGAAAUAUAAGAGCCACCAUGUGCCACCAGCAGCUCGUGAUCAGCUGG<br>UUCUCCCUGGUGUUUCUGCCAGCCCCCUGGUGGCCAUCUGGGAGCUGAAGAAGGACGUGUACGUGGUGGAGCUGGACU<br>GGUACCCUGACGCCCCGGGGGAGAUGGUCGUGCUGACCUGCGACACCCCCGAAGAGGACGGUAUCACCUGGACCCUGGA<br>CCAGUCCAGCGAGGUGCUGGGCAGCGGCAAGACCCUGACAUCAAGUCAAGGAGUUCGGAGACGCCGGCCAGUACACC<br>UGCCACAAGGGUGGAGAGGUGUUAUCACACAGCCUGCUGCUGCUGCAAGAAGGAAGACGGGAUCUGGAGCACCGACA<br>UCCUGAAGGACCAGAAGGAGCCCAAAAACAAGACCUUCCUGCGGUGCGAGGCCAAGAACUAUUCGGGCCGCUUUACGUG<br>CUGGUGGCUGACCACCAUCAGCACUGAUCUCACCUUCAGCGUGAAGUCCUCCCGGGGGUCGUCCGACCCCAGGGGGUG<br>ACCUGCGGGGCCGCCACCCUGUCCGCCGAGAGAGUGAGGGCGAUAAUAAGGAGUAUGAGUAUAGCGUGAGUGUGCCAGG<br>AAGAUAGCGCCUGUCCCGCCGCCGAGGAGAGCCUGCCCAUCGAGGUGAUGGUGGACGCCGUCCACAAGCUGAAGUAUGA<br>GAACUACACCUCAAGCUUCUUCAUCAGGGACAUCAUCAAACCCGAUCCGCCAAGAAUCUGCAGCUGAAGCCCCUGAAA<br>AAUAGCAGGCAGGUGGAGGUGAGCUGGGAGUACCCCGACACCUGGUCCACCCCCAUAGCUAUUUCUCCCUGACGUUCU<br>GCGUGCAGGUGCAAGGGAAGAGCAAGCGGGAGAAGAAGGACCGGGUUUCACCGACAAGACCUCCGCCACCGUGAUCUG<br>UAGGAAGAACGCUCGAUCUCGGUCAGGGCCCAGGACAGGUAUUACAGCAGCAGCUGGAGCGUGGGGGAGCGUGCCC<br>UGCUCGGGCGGCGGCGGCGGGAGCAGAAAUCUGCCCGUGCCACCCCAGACCCCGGAAUGUUCCCCUGCCUGCACC<br>AUUCGCAGAACUCCUGAGGGCCGUGAGCAACAUGCUGCAGAAGGCCCGCCAGACGCUGGAGUUCUACCCCUGCACGAG<br>CGAGGAGAUCGACCACGAGGACAUCACCAAGGACAAAACCAGCACCGUGGAGGCCUGCCUGCCCCUGGAGCUGACCAAA<br>AACGAAUCCUGCCUCAACAGCCGGGAGACCAGCUUCAUCACCAACGGCAGCUGCCUGGCCAGCCGAAAGACCUCCUUCA<br>UGAUGGCCCUCUGCCUGAGCAGCAUCUAUGAGGAUCUGAAGAUGUAUCAGGUGGAGUUCAAGACCAUGAAUGCCAAGCU<br>GCUGAUGGACCCCAAGAGGCAGAUAUUCCUGGACCAGAAUAUGCUGGCCGUGAUCGACGAGCUGAUGCAGGCCCUGAAC<br>UUCAACAGCGAGACCGUCCCCCAGAAGUCCAGCCUGGAGGAGCCGGACUUUUACAAAACGAAGAUCAAGCUGUGCAUAC<br>UGCUGCACGCCUUCAGGAUCCGGGCCGUGACAUCGACAGGGUGAUGAGCUACCUCAACGCCAGCUGAUAAUAAGGCUGG<br>AGCCUCGGUGGCCAUGCUUCUUGCCCCUUGGGCCUCCCCCCAGCCCCUCCUCCCCUUCCUGCACCCGUACCCCCCAAAC<br>ACCAUUGUCACACAUCUCCAGUGGUCUUUGAAUAAAGUCUGAGUGGGCGGCAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAUCUAG |
| hIL12AB_027<br>(SEQ ID<br>NO: 121) | G*GGGAAAUAAGAGAGAAAAGAAGAGUAAGAAGAAAUAUAAGAGCCACCAUGUGUCACCAGCAGCUGGUGAUCAGCUGG<br>UUCUCCCUGGUGUUCCUGGCCAGCCCCCUGGUGGCCAUCUGGGAGCUCAAGAAGGACGUCUACGUCGUGGAGCUGGAUU<br>GGUACCCCGACGCUCCCGGGGAGAUGGUGGUGCUGACCUGCGACACCCCCGAGGAGGACGGCAUCACCUGGACGCUGGA<br>CCAGUCCAGCGAGGUGCUGGGAAGCGGAAAGACCCUCACCAUCCAGGUGAAGGAGUUCGGAGACGCCGGCCAGUAUACC<br>UGCCACAAGGGCGGCGAAGUGCUGAGCCAUUCCCUGCUGCUGCUGCAAGAAGGAGGACGGCAUAUGGUCCACCGACA<br>UCCUGAAGGAUCAGAAGGAGCCCAAGAAUAAACCUUCCUGAGGUGCGAGGCCAAGAAUUACAGCGGCCGAUUCACCUG<br>CUGGUGGCUGACCACCAUCAGCACCGACCUGACCUUCAGUGUGAAGUCCUCACGGGGCAGCUCAGAUCCCCAGGGCGUG<br>ACCUGCGGGGCCGCGACACUCAGCGCCGAGCGGGUGAGGGGUGAUAACAAGGAGUACGAGUAUUCUGUGGAGUGCCAGG<br>AAGACUCCGCCUGUCCCGCCGCCGAGGAGUCCCUGCCCAUCGAGGUGAUGGUGGACGCCGUGCAUAAACUGAAGUACGA |

TABLE 4C-continued mRNA Sequences (with T100 tail)

```
                GAACUACACCUCCAGCUUCUUCAUCCGGGAUAUAAUCAAGCCCGACCCUCCGAAAAACCUGCAGCUGAAGCCCCUUAAA
                AACAGCCGGCAGGUGGAGGUGGAGCUGGGAGUGACCCCGACACCUGGAGCACCCCCCAUAGCUAUUUCAGCCUGACCUUCU
                GCGUGCAGGUGCAGGGGAAGUCCAAGCGCGAGAAAAAGGACCGGGUGUUCACCGACAAGACGAGCGCCACCGUGAUCUG
                CCGGAAGAACGCCAGUAUAAGCGUAAGGGCCCAGGAUAGGUACUACAGCUCCAGCUGGUCGGAGUGGGCCUCCGUGCCC
                UGUUCCGGCGGCGGGGGGGUGGCAGCAGGAACCUCCCCGUGGCCACGCCGGACCCCGGCAUGUUCCCGUGCCUGCACC
                ACUCCCAAAACCUCCUGCGGGCCGUCAGCAACAUGCUGCAAAAGGCCGGCAGACCCUGGAGUGUUUACCCCUGUACCUC
                CGAAGAGAUCGACCACGAGGAUAUCACCAAGGAUAAGACCUCCACCGUGGAGGCCUGUCUCCCCCUGGAGCUGACCAAG
                AACGAGAGCUGUCUUAACAGCAGAGAGACCUCGUUCUAAACGAACGGCUCCUGCCUCGCUUCCAGGAAGACGUCGUUCA
                UGAUGGCGCUGUGCCUGUCCAGCAUCUACGAGGACCUGAAGAUGUAUCAGGUCGAGUUCAAAACCAUGAACGCCAAGCU
                GCUGAUGGACCCCAAGAGGCAGAUCUUCCUGGACCAGAACAUGCUCGCCGUGAUCGACGAGCUGAUGCAGGCCCUGAAC
                UUCAACAGCGAAACCGUGCCCCAGAAGUCAAGCCUGGAGGAGCCGGACUUCUAUAAGACCAAGAUCAAGCUGUGUAUCC
                UGCUACACGCUUUUCGUAUCCGGGCCGUGACCAUCGACAGGGUUAUGUCGUACUUGAACGCCAGCUGAUAAUAGGCUGG
                AGCCUCGUGGCCAUGCUUCUUGCCCCUUGGGCCUCCCCCCAGCCCCUCCUCCCCUUCCUGCACCCGUACCCCCCAAAC
                ACCAUUGUCACACUCCAGUGGUCUUUGAAUAAAGUCUGAGUGGGCGGCAAAAAAAAAAAAAAAAAAAAAAAAAAAAAAA
                AAAAAAAAAAAAAAAAAAAAAAAAAAAAAAAAAAAAAAAAAAAAAAAAAAAAAAAAAAAAAAAAAAAAAAAAAUCUAG hIL12AB_028     G*GGGAAAUAAGAGAGAAAAGAAGAGUAAGAAGAAAUAUAAGAGCCACCAUGUGCCACCAACAGCUCGUGAUCAGCUGG
(SEQ ID         UUCAGCCUGGUGUUCCUGGCCAGCCCGCUGGUGGCCAUCUGGGAGCUGAAGAAGGACGUGUACGUGGUGGAGCUGGACU
NO: 122)        GGUACCCCGACGCCCCCGGCGAGAUGGUGGUCUGACUGCGACACGCCGGAAGAGGACGGCAUCACCUGGACCCUGGA
                UCAGUCCAGCGAGGUGCUGGGCUCCGGCAAGACCCUGACCAUUCAGGUGAAGGAGUUCGGCGACGCCGGUCAGUACACC
                UGCCACAAGGGCGGCGAGGUGCUGAGCCACAGCCUACUGCUCCUGCACAAAAGGAGGAUGGAAUCUGGUCCACCGACA
                UCCUCAAGGACCAGAAGGAGCCGAAGAACAAGACGUUCCUCCGGUGCGAGGCCAAGAACUACAGCGGCAGGUUUACCUG
                CUGGUGGCUGACCACCAUCAGCACCGACCUGACAUUUUCGUGAAGAGCAGCCGCGGCAGCAGCGAUCCCCAGGGCGUG
                ACCUGCGGGGCGGCCACCCUGUCCGCCGAGCGUGUGAGGGGCGACAACAAGGAGUACGAGUACAGCGUGGAAUGCCAGG
                AGGACAGCGCCUGUCCCGCCGCCGAGGAGAGCCUGCCAAUCGAGGUCAUGGUGGACGCCGUGCACAAGCUGAAGUACGA
                GAACUACACGAGCAGCUUCUUCAUCAGGGACAUCAUCAAACGGACCCGCCCAAGAACCUGCAGCUGAAACCCUUGAAA
                AACAGCCGGCAGGUGGAAGUGUCUUGGGAGUACCCCGACACCUGGUCCACCCCCCACAGCUACUACAGCGCCACCGUGACCUUCU
                GUGUGCAGGUCCAGGGCAAGUCCAAGAGGGAGAAGAAGGACAGGGUGUUCACCGACAAAACCAGCGCCACCGUGAUCUG
                CAGGAAGAACGCCUCCAUCAGCGUGCGGGCCCAGGACAGGUAUUACAGCUCGUCGUGGAGCGAGUGGGCCAGCGUGCCC
                UGCUCCGGGGAGGCGGCGGCGGAAGCCGGAAUCUGCCCGUGGCCACCCCCGAUCCCGGCAUGUUCCCGUGCCUGCACC
                ACAGCCAGAACCUGCUGCGGGCCGUGACCAACAUGCUGCAGAAGGCCCGACAAAACCCUGGAGUUCUACCCCUGUACCAAG
                CGAGGAGAUCGACCAUGAGGACAUUACCAAGGACAAGACCAGCACCGUGGAGGCCUGCCUGCCCCUCGAGCUCACAAAG
                AACGAAUCCUGCUGAAUAGCCGCGAGACCAGCUUUAUCACGAACGGGUCCUGCCUCGCCAGCCGGAAGACAAGCUUCA
                UGAUGGCCCUGUGCCUGAGCAGCAUCUACGAGGACCUGAAAAUGUACCAAGUGGAGUUCAAAACGAUGAACGCCAAGCU
                GCUGAUGGACCCCAAGCGCCAGAUCUUCCUGGACCAGAACAUGCUGGCCGUCAUCGACGAGCUCAUGCAGGCCCUGAAC
                UUCAACAGCGAGACCGUGCCCCAGAAGAGCAGCCUGGAGGAGCCCGACUUCUACAAGACGAAGAUCAAGCUCUGCAUCC
                UGCUGCACGCUUUCCGCAUCCGCGCGGUGACCAUCGACCGGGUGAUGAGCUACCUCAACGCCAGUUGAUAAUAGGCUGG
                AGCCUCGUGGCCAUGCUUCUUGCCCCUUGGGCCUCCCCCCAGCCCCUCCUCCCCUUCCUGCACCCGUACCCCCCAAAC
                ACCAUUGUCACACUCCAGUGGUCUUUGAAUAAAGUCUGAGUGGGCGGCAAAAAAAAAAAAAAAAAAAAAAAAAAAAAAA
                AAAAAAAAAAAAAAAAAAAAAAAAAAAAAAAAAAAAAAAAAAAAAAAAAAAAAAAAAAAAAAAAAAAAAAAAAUCUAG hIL12AB_029     G*GGGAAAUAAGAGAGAAAAGAAGAGUAAGAAGAAAUAUAAGAGCCACCAUGUGCCACCAACAGCUGGUGAUCAGCUGG
(SEQ ID         UUCAGCCUGGUGUUUCUGGCCUCCCCCUCUGGUGGCCAUCUGGGAGCUGAAGAAGGACGUGUACGUGGUGGAGCUGGACU
NO: 123)        GGUACCCCUGACGCCCCCGGCGAAAUGGUGGUGCUGACUGCGACACCCCCGAGGAGGAUGGCAUCACCUGGACCCUGGA
                CCAAAGCAGCGAGGUCCUCGGAAGCGGCAAGACCCUCACUAUCCAAGUGAAGGAGUUCGGGGAUGCGGGCCAGUACACC
                UGCCACAAGGGCGGCGAGGUGCUGUCUCAUAGCCUGCUGCUCCUGCAUAAGAAGGAAGACGGCAUCUGGAGCACCGACA
                UACUGAAGGAUCAGAAGGAGCCCAAGAACAAGACCUUCCUGAGGUGCGAGGCCAAGAACUACUCCGGGCGCUUCACCUG
                UUGGUGGCUGACCACCAUCUCCACCGACCUGACCUUCAGCGUGAAGAGCAGCAGGGGCAGCAGCGACCCCCAGGGGGUG
                ACCUGCGGAGCCGCGACCUUGUCGGCCGAGCGGGUGAGGGGCGACAACAAGGAGUACGAGUACUCGGUCGAAUGCCAGG
                AGGACUCCGCCUGCCCCGCCGCCGAGGAGUCCCUCCCCAUCGAAGUGAUGGUGGACGCCGUCCACAAGCUGAAGUACGA
                GAACUACACCAGCAGCUUCUUCAUACGGGAUAUCAUCAAGCCCGACCCCCGAAGAACCUGCAGCUGAAACCCUUGAAG
                AACUCCAGGCAGGUGGAGGUGAGCUGGGAGUACCCCGACACCUGGAGCACCCCCGCACUCAUACUGCAGCCUGACCUUCU
                GUGUACAGGUCCAGGGCAAGAGCAAGAGGGAAAAGAAGGAUAGGGUGUUCACCGACAAGACCUCCGCCACGGUGAUCUG
                UCGGAAAAACGCCAGCAUCUCCGUGCGGGCCCAGGACAGGUACUAUUCCAGCAGCUGGAGCGAGUGGGCCUCCGUCCCC
                UGCUCCGGCGGCGGUGGCGGGGGCAGCAGGAACCUCCCCGUGGCCACCCCCGAUCCCGGGAUGUUCCCAUGCCUGCACC
                ACAGCCAAAACCUGCUGAGGGCCGUCUCCAAUAUGCUGCAGAAGGAGCCCGAUCCUGGAGUUCUACCCCUGUACCUC
                CGAGGAGAUCGACCACGAGGAUAUCACCAAGGACAAGACCUCCACGGUCGAGGCUGCGUGCCCUCCUCGGAGCUCACGAAG
                AACGAGAGCUGCUUUAACUCCAGGGAAACCUCGUUUAUCACGAACGGCAGCUGCCUGGCGUCACGGAAGACCUCCUUUA
                UGAUGGCCCUAUGUCUGUCCUCGAUCUACGAGGACCUGAAGAUGUACCAGGUGGAGUUCAAGACCAUGAACGCCAAGCU
                GCUGAUGGAUCCCAAGAGGCAGAUUUUCCUGGACCAGAACAUGCUGGCCGUCAUUGACGAGCUGAUGCAGGCCCUGAAC
                UUCAACAGCGAGACAGUGCCGCAGAAGAGCUCCCUGGAGGAGCCCGACUUUUACAAGACCAAGAUAAAGCUGUGCAUCC
                UGCUCCACGCCUUCAGAAUACGGGCCGUCACCAUCGAUAGGGUGAUGCUUUACCUGAACGCCUCCUGAUAAUAGGCUGG
                AGCCUCGUGGCCAUGCUUCUUGCCCCUUGGGCCUCCCCCCAGCCCCUCCUCCCCUUCCUGCACCCGUACCCCCCAAAC
                ACCAUUGUCACACUCCAGUGGUCUUUGAAUAAAGUCUGAGUGGGCGGCAAAAAAAAAAAAAAAAAAAAAAAAAAAAAAA
                AAAAAAAAAAAAAAAAAAAAAAAAAAAAAAAAAAAAAAAAAAAAAAAAAAAAAAAAAAAAAAAAAAAAAAAAAUCUAG hIL12AB_030     G*GGGAAAUAAGAGAGAAAAGAAGAGUAAGAAGAAAUAUAAGAGCCACCAUGUGCCACCAGCAGCUGGUGAUUAGCUGG
(SEQ ID         UUUAGCCUGGUGUUCCUGGCAAGCCCCCUGGUGGCCAUCUGGGAACUGAAAAAGGACGUGUACGUGGUCGAGCUGGAUU
NO: 124)        GGUACCCCGACGCCCCCGGCGAAAUGGUGGUGCUGACUGCGACGUGGAUAUCCCCGAGGAGGACGGCAUCACCUGGACCCUGGA
                UCAGACAGCGAGGUCCUGGGGAGCGGGAAGACCCUGACGAUCCAGGUCAAGGAGUUCGGCGACGCUGGGCAGUACACC
                UGUCACAAGGCGCGGGAGGUGCUGUCCCACUCCCUGCUGCUCCUGCAUAAGAAGGAGGACGGCAUCUGGUCCACCGACA
                UCCUCAAGGACCAGAAGGAGCCCAAGAACAAGACCUUCCUGCGGUGUGAGGCGAAGAACUACAGCGGCCGGUUUACCUG
                CUGGUGGCUGACAAUCAGCACCGACCUUACGUUUUCAGUGAAGUCGUCCAGGGGCAGCUCCGACCCCCAGGGGGUG
                ACGUGGCGGCGCGGCCACCCUGAGCGCCGAGCGGGUGCGGGGACAACAAGGAGUACGAGUACUCCGUGGAGUGCCAGG
                AGGACAGCGCCUGUCCCGCAGCCGAGGAGUCCCUGCCCAUCGAGUCAUGGUGGACGCCGUCCACAAGCUGAAGUACGA
                GAACUACACCAGCAGCUUCUUCAUCCGCGAUAUCAUCAAGCCCGAUCCCCCAAAAAACCUGCAACUGAAGCCGCUGAAG
                AAUAGCAGGCAGGUGGAGGUGUCUGGGAGUACCCGGACACCUGGAGCACGCCCCACAGCUAUUUCAGCCUGACCUUUU
                GCGUGCAGGUCCAGGGGAAGAGCAAGCGGGAGAAGAAGGACCGCGUGUUUACGGACAAAACCAGCGCCACCGUGAUCUG
```

TABLE 4C-continued mRNA Sequences (with T100 tail)

CAGGAAGAACGCCAGCAUCAGCGUGAGGGCCCAGGACAGGUACUACAGCAGCUCCUGGAGCGAGUGGGCCUCCGUGCCC
UGUUCCGGAGGCGGCGGGGGCGGUUCCCGGAACCUCCCGGUGGCCACCCCCGACCCGGGCAUGUUCCCGUCCUGCACC
ACUCACAGAAUCUGCUGAGGGCCGUGAGCAAUAUGCUGCAGAAGGCAAGGCAGACCCUGGAGUUUUAUCCCUGCACCAG
CGAGGAGAUCGACCACGAAGACAUCACCAAGGACAAGACCAGCACAGUGGAGGCCUGCCUGCCCUGGAACUGACCAAG
AACGAGUCCUGUCUGAACUCCCGGGAAACCAGCUUCAUAACCAACGGCUCCUGUCUCGCCAGCAGGAAGACCAGCUUCA
UGAUGGCCCUGUGCCUGAGCUCCAUCUACGAGGACCUCAAGAUGUACCAGGUUGAGUUCAAGACCAUGAAUGCCAAGCU
CCUGAUGGACCCCAAGAGGCAGAUCUUCCUGGACCAGAAUAUGCUGGCCGUGAUCGAUGAGUUAAUGCAGGCGCUGAAC
UUCAACAGCGAGACGGUGCCCCAAAAGUCCUCGCUGGAGGAGCCCGACUUCUACAAGACCAAGAUCAAGCUGUGCAUCC
UCCUGCACGCCUUCCGAAUCCGGGCCGUAACCAUCGACAGGGUGAUGAGCUAUCUCAACGCCUCCUGAUAAUAGGCUGG
AGCCUCGGUGGCCAUGCUUCUUGCCCCUUGGGCCUCCCCCCAGCCCCUCCUCCCCUUCCUGCACCCGUACCCCCAAAC
ACCAUUGUCACACUCCAGUGGUCUUUGAAUAAAGUCUGAGUGGGCGGCAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAUCUAG hIL12AB_031
(SEQ ID
NO: 125)
G*GGGAAAUAAGAGAGAAAAGAAGAGUAAGAAGAAAUAUAAGAGCCACCAUGUGCCACCAGCAGCUCGUGAUCAGCUGG
UUCUCGCUUGCUGUUGUUCCUGGCCUCCCCCCUCGUCGCAUCUGGGAGCUGAAGAAAGACGUGUACGUGGUGGAGCUGGACU
GGUAUCCCGACGCCCCGGGGGAGAUGGUGGUGCUGACCUGCGACACCCCGGAAGAGGACGGCAUCACCUGGACGCUCGA
CCAGUCGUCCGAAGUGCUGGGGUCGGGCAAGACCCUCACCAUCCAGGUGAAGGAGUUCGGAGACGCCGGCCAGUACACC
UGUCAUAAGGGGGGGGAGGUGCUGAGCCACAGCCUCCUGCUCCUGCACAAAAAGGAGGACGGCAUCUGGAGCACCGAUA
UCCUCAAGGACCAGAAGGAGCCCAAGAACAAGACGUUCCUGAGGUGUGAGGCCAAGAACUACAGCGGCCGGUUCACGUG
UUGGUGGCUCACCACCAUCUCCACCGACCUCACCUUCUCCGUGAAGCAAGCAGGGGCAGCUCCGACCCCCAAGGCGUC
ACCCUGCGGCGCCGCCACCCUGAGCGCCGAGAGGGUCAGGGGGGAUAACAAGGAAUACGAGUACAGUGUGGAGUGCCAAG
AGGAUAGCGCCUGUCCCGCCGCCGAAGAGAGCCUGCCCAUCGAAGUGAUGGUGGACGCCGUGCACAAGCUGAAGUACGA
GAACUACACCUCCAGCUUCUUCAUCAGGGAUAUCAUCAAGCCCGAUCCCCCCAAGAACCUGCAGCUGAAGCCCCUGAAG
AACAGCAGGCAGGUGGAGGUGAGCUGGGAGUAUCCCGACACGUGGAGCACCCCGCACAGCUACUUCUCGCUGACCUUCU
GCGUGCAGGUGCAAGGGAAGUCCAAGGGGAGAAGAAGGAUAGGGUGUUCACCGACAAAACGAGCGCCACCGUGAUCUG
CCGGAAGAAUGCCAGCAUCUCUGUGAGGGCCCAGGACAGGUACUAUUCCAGCUCCUGGUCGGAGUGGGCCAGCGUGCCC
UGUUAGCGGCCGGGGCGGGGGCGGCAGCAGGAACCUCCCGGUUGCCACCCCCGACCCCGGCAUGUUUCCGUCCUGCACC
ACUCGCAAAACUGCUGCGCGCGGUCUCCAACAUGCUGCAAAAGCGCGCCAGACGCUGGAGUUCUACCCCUGCACCAG
CGAGGAGAUCGAUCAUGAAGAUCACCAAAGACAAGACCUCGACCGUGGAGGCCUGCCUGCCCUGGAGCUCACCAAG
AACGAAAGCUGCCUGAACAGCAGGGAGACAAGCUUCAUCACCAACGGCAGCUGCCUGGCCUCCCGGAAGACCAGCUUCA
UGAUGGCCCUGUGCCUGAGCAGCAUCUACGAGGAUCUAGAACAAGAUGUACCAAGUGGAGUUUUAAGACCAUGAACGCCAAGCU
GUUAAUGGACCCCAAAAGGCAGAUCUUCCUGGAUCAGAACAUGCUGGCCGUCAUCGACGAGCUGAUGCAAGCCCUGAAC
UUCAACAGCGAGACGGUGCCCCAGAAGAGCAGCCUCGAGGAGCCCGACUUCUAUAAGACCAAGAUAAAGCUGUGCAUUC
UGCUGCACGCCUUCAGAAUCAGGGCCGUGACCAUCGAUAGGGUGAUGAGCUACCUGAACGCCAGCUGAUAAUAGGCUGG
AGCCUCGGUGGCCAUGCUUCUUGCCCCUUGGGCCUCCCCCCAGCCCCUCCUCCCCUUCCUGCACCCGUACCCCCAAAC
ACCAUUGUCACACUCCAGUGGUCUUUGAAUAAAGUCUGAGUGGGCGGCAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAUCUAG hIL12AB_032
(SEQ ID
NO: 126)
G*GGGAAAUAAGAGAGAAAAGAAGAGUAAGAAGAAAUAUAAGAGCCACCAUGUGUCACCAGCAGCUGGUGAUUUCCUGG
UUCAGUCUGGUGUUCUUGCCAGCCCCUCGGUGGCCAUCUGGGAGCUGAAGAAAGACGUAUACGUCGUGGAGCUGGACU
GGUAUCCCGACGCUCCCGGCGAGAUGGUGGUCCUCACCUGCGACACCCCAGAGGAGGACGGCAUCACCUGGACCCUGGA
CCAGAGCUCCGAGGUCCUGGGCAGCGGUAAGACCCUCACCAUCCAGGUGAAGGAGUUUGGUGAUGCCGGCCAGUAUACC
UGCCACAAGGGCGGCGAGGUGCUGUCCCACAGCCUCCUGUUACUGCAUAAGAAGGAGGAUGGCAUCUGGAGCACCGACA
UCCUCAAGGACCAGAAGGAGCCCAAGAACAAGACUUUCUGCGGUGCGAGGCGAAAAAUUACUCCGGCCGGUUCACCUG
CUGGUGGCUGACCACCAUCAGCACGGACCUGACGUUCUCCGUGAAGUCGAGCAGGGGGAGCUCCGAUCCCAGGGCGUG
ACCCUGCGGCGCCGCCACCCUGAGCGCCGAGCGCGUCCGCGGGGACAAUAAGGAAUACGAAUAUAGCGUGGAGUGCCAGG
AGGACAGCGCCUGCCCCGCGGCCGAGGAGAGCCUCCCGAUCGAGGUGAUGGUGGAUGCCGUCCACAAGCUCAAAUACGA
AAACUACACCAGCAGCUUCUUCAUUAGGGAACAUCAUCAAGCCCGAUCCCCCCAAAAACCUGCAGCUGAAGCCCCUGAAG
AACAGCCGCCAGGUCGAGGUGCAUGGGAGUACCCAGACACCUGGAGCACCCCCACUCCUACUUCAGCCUGACCUUCU
GCGUCCAGGUGCAGGGAAAGUCCAAACGGGAGAAGAAGGAUAGGGUCUUUACCGAUAAGACGUCGGCCACCGUCAUCUG
CAGGAAGAACGCCAGCAUAAGCGUGCGGGCGCAGGAUCGGUACUACAGCUCGAGCUGGUCCGAAUGGGCCUCCGUGCCC
UGUAGCGGAGGGGGUGGCGGGGGCAGCAGGAACCUGCCGGACACCCCCGGCCCGGGGCAUGUUCCCGUCCUGCAUC
ACAGUCAGAACCUGCUGAGGGCCGUGAGCAACAUGCUCCAGAAGGCCCGCCAGACCCUGGAGUUUUACCCCUGCACCAG
CGAAGAGAUCGAUCACGAAGACAUCACCAAAGACAAGACCUCCACCGUGGAGGCCUGUCUGCCCUGGAGCUGACCAAG
AACGAGAGCUGUCUGAACAGCAGGGAGACCUCCUUCAUCACCAACGGCUCCUGCCUGGCAUCCCGGAAGACCAGCUUCA
UGAUGGCCCUGUGAGCUCUAUCUACGAGGACCUGAAGAUGUACCAGGUCGAGUUCAAGACGAUGAACGCCAAGCU
GCUGAUGGACCCCAAGCGACAGAUAUUCCUGGACCAGAACAUGCUCGCCGUGAUCGAUGAACUGAUGCAAGCCCUGAAC
UUCAAUAGCGAGACCGUGCCCCAGAAAAGCAGCCUGGAGGAGCCCGACUUCUACAAGACCAAGAUCAAACUGUGCAUAC
UGCUGCACGCGUUCAGGAUCCGGGCCGUCACCAUCGACCGGGUGAUGUCCUAUCUGAAUGCCAGCUGAUAAUAGGCUGG
AGCCUCGGUGGCCAUGCUUCUUGCCCCUUGGGCCUCCCCCCAGCCCCUCCUCCCCUUCCUGCACCCGUACCCCCAAAC
ACCAUUGUCACACUCCAGUGGUCUUUGAAUAAAGUCUGAGUGGGCGGCAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAUCUAG hIL12AB_033
(SEQ ID
NO: 127)
G*GGGAAAUAAGAGAGAAAAGAAGAGUAAGAAGAAAUAUAAGAGCCACCAUGUGCCACCAGCAGCUCGUGAUUAGCUGG
UUUUUCGCUGGUGUUCUGGCCCUCUCGUCGGAGCUGAAAAGACGUGUACGUGGUGGAGCUGGACU
GGUAUCCCGGACGCCCCCGGCGAGAUGGUGGUGCUGACGUGCGACACCCGGAAGAGGACGGCAUCACCUGGACCCUGGA
CCAGUCAUCCGAGGUCCUGGGCAGCGGCAAGACGCUCACCAUCCAGGUGAAGGAGUUCGGCGACGCCGGCCAGUACACA
UGCCAUAAGGGCGGGGAGGUGCUGAGCCACAGCCUGCUCCUCCUGCACAAGAAGGAGGAUGGCAUCUGGUCUACAGACA
UCCUGAAGGACCAGAAAGAGCCCAAGAACAAGACUUCCUGCGGUGCGAGGCCAAGAACUACUCCGGCCGGUUUACUUG
UUGGUGGCUGACCACCAUCAGCACCGACCUCACCUUCAGCGUGAAGAGCUCCGAGGAGCUCCGACCCCCAGGGGGUC
ACCCUGCGGCGCCGCCACCCUGAGCGCCGAGCGGGUGAGGGGCGACAACAAGGAGUAUGAUCAGCUGGAAUGCCAAG
AGGACAGCGCCUGUCCCGCGGCCGAGGAAAGCCUGCCCAUCGAGGUGAUGGUGGACGCCGUCCACAAACUCAAGUACGA
GAACUACACCAGCGGUUUCUUCAUUCGCGACAUCAUCAAGCCCGAUCCCCCCAAAACUGCAGCUCAAACCCCUGAAG
AACAGCAGGCAGGUGGAGGUCAGCUGGGAGUACCCGGACACCUGGAGCACCCCCAUACUUCAGCCUGACCUUCU
GCGUGCAGGUGCAGGGCAAGAGCAAACGCGAGAAGAAGGACCGGGUGUUUACCGACAAGACCAGCGCCACCGGUGAUCUG
CCGAAAGAAUGCAAGCAUCUCCGUGAGGGCGCAGGACCGCUACUACUCUAGCAGCUGGAGCGAGUGGGCCAGCGUGCCC
UGCAGCGGUGGCGGCGGAGGCGGCAGCCGUAACCUCCCGUGGCCACCCCGACCCCGGCAUGUUCCGUGUCUGCACC
ACUCCCAGAACCUGCUGAGGGCCGUCAGCAAUAUGCUGCAGAAGGCCCGGCAGACGCUGGAGUUCUACCCCUGCACCUC

TABLE 4C-continued mRNA Sequences (with T100 tail)

|  |  |
|---|---|
|  | CGAGGAGAUCGACCAUGAGGACAUUACCAAGGACAAGACGAGCACUGUGGAGGCCUGCCUGCCCCUGGAGCUCACCAAA<br>AACGAGAGCUGCCUGAAUAGCAGGGAGCGUCCUUCAUCACCAACGGCAGCAGCUGUCUGGCCAGCAGGAAGACCAGCUUCA<br>UGAUGGCCCUGUGCCUCUCCUCCAUAUAUGAGGAUCUGAAGAUGUACCAGGUGGAGUUCAAGACCAUGAACGCCAAGCU<br>GCUGAUGGAUCCCAAGAGGCAGAUCUUCCUGGACCAGAAUAUGCUGGCCGUGAUUGACGAGCUGAUGCAGGCCCUGAAC<br>UUUAAUAGCGAGACCGUCCCCCAGAAGAGCAGCCUGGAGGAGCCCGACUUCUAUAAGACCAAGAUCAAGCUGUGCAUAC<br>UGCUGCACGCGUUUAGGAUAAGGGCCGUCACCAUCGACAGGGUGAUGAGCUACCUGGAUGCCAGCUGAUAAUAGGCUGG<br>AGCCUCGGUGGCCAUGCUUCUUGCCCCUUGGGCCUCCCCCCAGCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAUCUAG |
| hIL12AB_034<br>(SEQ ID<br>NO: 128) | G*GGGAAAUAAGAGAGAAAAGAAGAGUAAGAAGAAAUAUAAGAGCCACCAUGUGCCACCAACAGCUGGUGAUCUCCUGG<br>UUCAGCCUGGUGUUCCUCGCCAGCCCCCUGGUGGCCAUCUGGGAGCUGAAGAAAGACGUGUACGUGGUGGAGCUGGACU<br>GGUAUCCCGACGCCCCCGGCGAGAUGGUCGUGCUGACCUGCGACACCCCGGAGGAGGACGGCAUCACCUGGACCCUGGA<br>UCAGUCCUCCGAGGUGCUGGGCAGCGGGAAGACCCUGACCAUCCAGGUGAAAGAGUUCGGAGAUGCCGGCCAGUAUACC<br>UGUCACAAGGGGGGUGAGGUGCUGAGCCAUAGCCUCUUGCUUCUGCACAAGAAGGAGGACGGCAUCUGGUCCACCGACA<br>UCCUCAAGGACCAAAAGGAGCCGAAGAAUAAAACGUUCCUGAGGUGCGAAGCCAAGAACUAUUCCGGACGGUUCACCUG<br>CUGGUGGCUGACCACCAUCAGCACCGACCUCACCUUCUCCGUAAAGUCAAGCAGGGGCAGCUCCGACCCCCAGGGCGUG<br>ACCUGCGGAGCCGCCACCCUGAGCGCAGAGAGGGUGAGGGGCGACAACAAGGAGUACGAAUACUCCGUCGAGUGCCAGG<br>AGGACAGCGCCUGCCCCGCCGCCGAGGAAAGUCUGCCCAUCGAGGUGAUGGUGGACGCCGUGCACAAGCUCAAAUACGA<br>GAACUACACCAGCAGCUUCUUCAUCCGGGAUAUCAUCAAGCCCGACCCUCCAAAGAAUCUGCAGCUGAAACCCCUUAAG<br>AACAGCAGGCAGGUGGAGGUCAGCUGGGAGUACCCCGACACCUGGAGCACGCCCCACUCCUACUUUAGCCUGACCUUUU<br>GCGUGCAGGUGCAGGGAAAAGCAAGCGGGAGAAGAAGGACAGGGUGUUCACCGAUAAGACCUCCGCUACCGUGAUCUG<br>CAGGAAGAACGCCUCAAUCAGCGUGAGGGCCCAGGAUCGGUACUAUCCAGCUCCUGGAGCGAGUGGGCCAGCGUGCCC<br>UGCUCUGGCGGUGGCGGCGGGGCAGCCGGAACCUGCCGGUGGCCACUCCCGACCCGGGCAUGUUCCGUGCCUCCACC<br>AUUCCCAGAACCUGCUGCGGGCCGUGUCCAAUAUGCUCCAGAAGGCAAGGCAGACCCUGGAGUUCUACCCCUGCACCAG<br>CGAGGAGAUCGAUCACGAGGACAUCACCAAAGACAAAACCAGCACGGUCGAGGCCUGCCUGCCCCUGGAACUCACCAAG<br>AACGAAAGCUGUCUAACAGCCGCGAGACCAGCUUCAUAACGAAUGGUUCUGUCUGGCCUCCCGCAAGACCAGCUUUUA<br>UGAUGGCCCUCGUCUGAGCUCCAUCUAUGAAGACCUGAAAAUGUACCAGGUGGAGUUCAAAACCAUGAACGCCAAGCU<br>UCUGAUGGACCCCAAGAGGCAGAUCUUCCUGGAUCAGAACAUGCUGGCCGUGAUCGACGAGCUGAUGCAGGCCCUGAAC<br>UUUAACUCCGAGACCGUGCCCCAGAAAAGCAGCCUGGAAGAGCCCGAUUUCUACAAAACGAAGAUCAAGCUGUGCAUCC<br>UGCUGCACGCGUUCCGGAUCCGUGCGGUGACCAUCGAUAGGGUGAUGAGCUACCUGGAUGCCAGCUGAUAAUAGGCUGG<br>AGCCUCGGUGGCCAUGCUUCUUGCCCCUUGGGCCUCCCCCAGCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAUCUAG |
| hIL12AB_035<br>(SEQ ID<br>NO: 129) | G*GGGAAAUAAGAGAGAAAAGAAGAGUAAGAAGAAAUAUAAGAGCCACCAUGUGCCACCAACAGCUGGUAAUCAGCUGG<br>UUCAGCCUGGUUUUCCUCGCGUCGCCCCUGGUGGCCAUCUGGGAGUUAAAGAAGGACGUGUACGUGGUGGAGCUGGAUU<br>GGUACCCCGACGCCCCGGGCGAGAUGGUCGUGCUCACCUGCGAUACCCCCGAGGAGGACGGGAUCACCUGGACCCUGGA<br>CCAAUCCAGCGAGGUGCUGGGCAGCGGCAAGACCCUGACCAUCAGGUGAAGGAAUUUGGGGACGCCGGGCAGUACACC<br>UGCCACAAGGGCGAGGUGCUGUCCCACUCCCUGCUGCUGCAUAAGAAGGAGGACGGCAUCUGGUCCACCGACA<br>UCCUGAAGGACCAAAAGGAGCCCAAGAACAAGACCUUCCUGAGGUGCGAGGCCAAAAACUAUUCCGGCCGCUUUACCUG<br>UUGGUGGCUGACCACCAUCUCCACCGAUCUGACCUUCAGCGUGAAGUCGUCUAGGGGCUCCUCCGACCCCCAGGGCGUA<br>ACCUGCGGCGCCGCGACCCUGAGCGCCGAGAGGGUGCGGGCGAUAACAAAGAGUACGAGUACUCGGUGGAGUGCCAGG<br>AGGACAGCGCCUGCCCGGCCGCCGAGGAGAGCCUGCCCAUCGAGGUGAUGGUGGACGCCGUGCCCAAGCUGAAGUACGA<br>GAACUACACCAGUUCGUUCUUCAUCAGGGACAUCAUCAAGCCGGACCCCCCAAGAACCUCCAGCUGAAGCCCCUGAAG<br>AACAGCAGGCAGGUGGAAGUGUCCUGGGAGUAUCCCGACACCUGGAGCACCCCCACAGCUACUUCAGCCUGACCUUUU<br>GCGUGCAGGUGCAGGGCAAAAGCAAGAGGGAAAAGAAGGACCGGGUGUUCACCGAUAAGACGAGCGCCACCGUUAUCUG<br>CAGGAAGAACGCCUCCAUAAGCGUGAGGGCACAGGACGUUACUACACGAGCAGCUGGAGUGAGUGGGCAAGCGUGCCC<br>UGUAGCGGCGGGGGCGGGGGCGGGUCCCGAACCUCCCCGUCGCCACCCCCGACCCAGGCAUGUUCCGUGCCUGCACC<br>ACAGCCAGAACCUGCUGCGGGCCGUUAGCAACAUGCUGCAGAAGGCCAGGCAGACCCUCGAGUUCUAUCCCUGCACAUC<br>UGAGGAGAUCGACCACGAAGACAUCACUAAGGAUAAGACCUCCACCGUGGAGGCCUGUCUGCCCCUCGAGCUGACCAAG<br>AAUGAAUCCUGCCUGAACAGCCGAGAAACCAGCUUUAUCACCAACAGCGCCUGCCUGGCCUCGAGGAAGACCUCCUUCA<br>UGAUGGCCCUGUGCCUCUCCAGCAUCUACGAGGAUCUGAAGAUGUACCAGGUAGAGUUCAAGACGAUGAACGCCAAGCU<br>CCUGAUGGACCCCAAGAGGCAGAUAUUCCUGGACCAGAACAUGCUGGCGGUGAUCGACGAGCUGAUGCAGGCCCUGAAU<br>UUCAACAGCGAGACGGUGCCACAGAAGUCCAGCCUGGAGGAGCCAGACUUCUACAAGACCAAGAUCAAACUGUGCAUCC<br>UCCUGCACGCGUUCCGGAUCCGCGUCACCAUAGACAGGGUGAUGAGUUAUCUGGAAGCGCAGCUGAUAAUAGGCUGG<br>AGCCUCGGUGGCCAUGCUUCUUGCCCCUUGGGCCUCCCCCAGCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAUCUAG |
| hIL12AB_036<br>(SEQ ID<br>NO: 130 | G*GGGAAAUAAGAGAGAAAAGAAGAGUAAGAAGAAAUAUAAGAGCCACCAUGUGCCAUCAGCAGCUGGUAAUCAGCUGG<br>UUUAGCCUGGUGUUCCUGGCCAGCCCACUGGUGGCCAUCUGGGAGCUGAAGAAGGACGUGUACGUGGUGAACUGGACU<br>GGUACCCCGACGCCCCUGGCGAGAUGGUGUACUGACCUGUGACACCCCGGAGGAAGACGGUAUCACCUGGACCCUGGA<br>UCAGAGCUCCGAGGUGCUGGGCUCCGGCAAGACACUGACCAUCCAAGUUAAGGAAUUUGGGGACGCCGGCCAGUACACC<br>UGCCACAAGGGCGAGGUGCUGUCCCACUCCCUGCUGCUGCAUAAGAAGGAGGAUGGCAUCUGGUCCACCGACA<br>UACUGAAGGACCAGAAGGAGCCCAAGAAUAAGACCUUCCUGAGGAUGCGAGGCCAAGAACUAUCGGGAAGUUCACCUG<br>CUGGUGGCUGACCACCAUCAGCACCGACCUGACCUUCUCCGUGAAGAGCUCCGGGGCAGCUCCGACCCCCAGGGCGUA<br>ACCUGUGGGGCCGCUACCCUGUCCGCCGAGAGGGUCCGGGGCGACAACAAGGAAUACGAGUACAGCGUGGAGUGCCAGG<br>AGGACUCCGCCUGCCCCGCCGCCGAGGAAGCGCUGCCCAUAGAGGUGAUGGUGGACGCCGUGCACAAGCUCAAGUACGA<br>GAAUUACACCAGCAGCUUCUUUAUCAGGGACAUAAUUAAGCCGGACCCCCCAAAGAAUCUGCAGCUGAAGCCCCUGAAG<br>AAUAGCCGGCAGGUGGAAGUGUCCUGGGAGUACCCCGACACCUGGAGCACCCCCACUCCUAUUUCUCACUGACAUUCU<br>GCGUGCAGGUGCAAGGGAAAAGCAAGAGGGAGAAGAAGGAUAGGGUGUUCACCGACAAGACAAGCGCCACCGUGAUCUG<br>CCGAAAAAAUGCCAGCAUCAGCGUGAGGGCCCAGGAUCGGUAUUACAGCAGCAGCUGGAGCGAGUGGGGCAAGCGUGCCC<br>UGUUCCGGCGGGGGAGGGGGCGGCUCCCGGAACCUGCCGUGGCCCACCCCGACCCUGGCAUGUUCCCUGCCUGCAUC<br>ACAGCCAGAACCUGCUCCGGGCCGUGUCCAACAUGCUGCAGAAGGCCCGGCAGACCCUCGAGUUUUACCCCUGCACCAG<br>CGAGAGAUCGACCACGAAGACAUAACCAAGGACAAGACCAGCACGGUGGAGGCCUGCCUGCCCCUGGAGCUUACCAAA<br>AACGAGUCCUGCCUGAACAGCCGGGAAACCAGCUUCAUAACGAACGGGAGCUGCCUGGCCUCCAGGAAGACCAGCUUCA<br>UGAUGGCGCUGUGUCUGUCCAGCAUAUACGAGGAUCUGAAGAUGUAUCAGGUGGAAUUCAAAACUAUGAAUGCCAAGCU |

TABLE 4C-continued mRNA Sequences (with T100 tail)

CCUGAUGGACCCCAAGAGGCAGAUCUUCCUGGACCAGAACAUGCUAGCCGUGAUCGACGAGCUGAUGCAGGCCCUCAAC
UUCAACUCGGAGACGGUGCCCCAGAAGUCCAGCCUCGAGGAGCCCGACUUCUACAAGACCAAGAUCAAGCUGUGCAUAC
UGCUGCAUGCCUUCAGGAUAAGGGCGGUGACUAUCGACAGGGUCAUGCCUACCUGAACGCCAGCUGAUAAUAGGCUGG
AGCCUCGUUGGCCAUGCUUCUUGCCCCUUGGGCCUCCCCCCAGCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAUCUAG hIL12AB_037 G*GGGAAAUAAGAGAGAAAAGAAGAGUAAGAAGAAAUAUAAGAGCCACCAUGUGCCACCAACAACUGGUGAUCAGCUGG
(SEQ ID   UUCUCCCUGGUGUUCCUGGCCAGCCCCCUGGUGGCCAUCUGGGAGCUCAAAAAAGACGUGUACGUGGUGGAGCUCGAUU
NO: 131)  GGUACCCAGACGCGCCGGGGGAAAUGGUGGUGCUGACCUGACACCCAGGAGGAGGAUGGCAUCACGUGGACGCUGGA
UCAGUCCAGCGAGGUGCUGGGGAGCGGCAAGACGCUCACCAUCCAGGUGAAGGAAUUUGGCGACGCGGGCCAGUAUACC
UGUCACAAGGGCGGCGAGGUGCUGAGCCACUCCCUGCUGCUGCACAAGAAGGAGGAUGGGAUCUGGUCAACCGAUA
UCCUGAAAGACCAGAAGGAGCCCAAGAACAAGACCUUCCUGCGCUGCGAGGCCAAGAACUAUAGCGGCAGGUUCACCUG
CUGGUGGCUGACCACCAUCAGCACCGACCUGACCUUCAGCGUGAAAUCCUCCAGGGGCAGCAGCGACCCCCAGGGCGUG
ACCUGCGGUGCCGCCACGCUCUCCGCCGAGCGAGUGAGGGGCGACAACAAGGAGUACGAGUACAGCGUGGAAUGUCAGG
AGGACAGCGCCUGUCCCGCCGCCGAGGAGUCGCUGCCCAUCGAGGUGAUGGUCGACGCGGUGCACAAGCUCAAAUACGA
GAAUUACACCAGCAGCUUCUUCAUCAGGGACAUCAUCAAGCCCGACCCCCCCAAGAACCUGCAGCUGAAGCCCUUGAAG
AACAGCAGGCAGGUGGAGGUGAGCUGGGAGUACCCGGACACCUGGAGCACCCCCACUCCUACUUCAGCCUGACGUUCU
GUGUGCAGGUGCAGGGGAAGUCCAAGAGGGAAGAAGGAAGAAGGACCAGCGCCACCGUGAUAUG
CCGCAAGAACGCGUCCAUCAGCGUUCGCGCCCAGGACCGCUACUACAGCAGCUCCUGGUCCGAAUGGGCCAGCGUGCCC
UGCAGCGUUGAGGGGCGGGGCUCCAGGAAUCUGCCGGUGCCACCCCGACCCCGGGAUGUUCCCGUGUCUGCAUC
ACUCCCAGAACCUGCUGCGGGCCGUGAGCAAUAUGCUGCAGAAGGCCAGGCAGACGCUCGAGUUCUACCCCUGCACCUC
CGAAGAGAUCGACCAUGAGGACAUCACCAAGGACAAGACCAGCACCGUGGAGGCCUGCCUGCCCCUGGAGCUGACCAAA
AACGAGAGCUGCCUGAACUCCAGGGAGACCAGCUUUAUAACCAACGGCAGCUGCCUGCCUCCAGGAAGACCUCGUUUA
UGAUGGCCCUCUGCCUGUCCAGCAUCUACGAGGACCUGAAGAUGUACCAGGUGGAGUUCAAGACCAUGAACGCGAAGUU
GCUCAUGGACCCCAAGAGGCAGAUCUUCCUGGACCAGAACAUGCUCGCGGUGAUCGACGAGCUGAUGCAAGCCCUGAAC
UUCAACAGCGAGACCGUGCCCCAGAAGAGCAGCCUGGAGGAGCCCGACUUCUACAAGACCAAGAUCAAGCUGUGCAUCC
UGCUGCACGCCUUCCGGAUCCGGGCCGUGACCAUCGACAGGGUGAUGAGCUACCUCAACGCCUCCUGAUAAUAGGCUGG
AGCCUCGUUGGCCAUGCUUCUUGCCCCUUGGGCCUCCCCCCAGCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAUCUAG hIL12AB_038 G*GGGAAAUAAGAGAGAAAAGAAGAGUAAGAAGAAAUAUAAGAGCCACCAUGUGCCACCAGCAGCUCGUGAUCAGCUGG
(SEQ ID   UUCUCCCUCGUCUUCCUGGCCUCCCCGCUGGUGGCCAUCUGGGAGCUGAAGAAGGACGUGUACGUGGUGGAGCUGGACU
NO: 132)  GGUAUCCCGACGCCCCCGGCGAGAUGGUGGUGCUGACGUGCGACACACCAGAAGAGGACGGGAUCACAUGGACCCUGGA
UCAGUCGUCCGAGGUGCUGGGGAGCGGCAAGACCCUCACCAUCCAAGUGAAGGAGUUCGGGGACGCCGGCCAGUACACC
UGCCACAAGGGCGGGGAGGUGCUCUCCCAUAGCCUGCUCCUCCUGCAAAAAGGAGGAUGGCAUCUGGAGCACCGACA
UCCUGAAGGACCAGAAGGAGCCCAAGAACAAGACAUUCUCAGGUGUGAGGCCAAGAACUAUUCGGGCAGGUUUACCUG
UUGGUGGCUCACCACCAUCUCUACCGACCUGACGUUCUCCGUCAAGUCAAGCAGGGGGAGCUCGGACCCCCAGGGGGUG
ACAUGUGGGCCGCACCCUGACGCGGAGCGUGUCCGGACAACAAGGAGUAGUAUAUCCGUGGAGUGCCAGG
AGGACAGCGCCUGCCCCGCCGCCGAGGAGUCCCUGCCCAUCGAGGUGAUGGUGGACGCCGUCCACAAGUUGAAGUACGA
AAAUUAUACCUCCUCGUUCUUCAUUAGGGACAUCAUCAAGCCUGACCCCCCCAAGAACCUACAACUCAAGCCCCUCAAG
AACUCCCGCCAGGUGGAGGUGUCCUGGGAGUACCCCGACACCUGGUCCACCCCGCACAGCUACUUCAGCCUGACCUUCU
GCGUGCAGGUCCAGGGGAAGAGCAAGCGUGAAAAGAAAGACCGCCCACCGUGAUCUG
CAGGAAAAACGCCUCCAUCUCCGUGCGCGCCCAGGACAGGUACUACAGUAGCUCCUGGAGCGAAUGGGCCAGCGUGCCG
UGCAGCGGCGGGGAGGAGGCGGCAGUCGCAACCUGCCCGUGCCACCCCGACCCCGGCAUGUUCCCAUGCCUGACC
ACAGCCAGAACCUGCUGAGGGCAGUCAGCAAUAUGCUGCAGAAGGCCAGGCAGACCCUGGAGUUUUAUCCCUGCACCAG
CGAGGAGAUCGACCACGAGGACAUCACCAAGGACAAGACCUCCACCGUCGAGGCCUGCCUGCCUCUCACUGGAGCUGACCAAA
AACGAGAGCUGCCUGAACUCCAGGGAGACCUCCUUCAUCCAACGGGAGCUGCCUGGCCAGCCGGAAGACCAGCUUCA
UGAUGGCGCUGUGCCUCAGCAGCAUCUACGAGGAUCUCAAGAUGUACCAGGUGGAGUUCAAGACCAUGAACGCGAAGCU
GCUGAUGGACCCCAAGCGGCAGAUCUUCCUGGACCAGAACAUGCUGGCCGUGAUUGACGAGCUCAUGCAGGCCCUGAAC
UUCAAUAGCGAGACCGUCCCCCAAAAGAGCAGCCUGGAGGAGCCCGACUUCUACAAAGAAGAUCAAGCUCUGCAUCC
UGCUGCACGCCUUCCGGAUCCGGGCCGUGACCAUCGAUCGUGAUGAGCUACCUGAACGCCUCGUGAUAAUAGGCUGG
AGCCUCGUUGGCCAUGCUUCUUGCCCCUUGGGCCUCCCCCCAGCCCUCCUCCCCUUCCUGCACCCGUACCCCCCAAAC
ACCAUUGUCACACUCCAGUGGUCUUUGAAUAAAGUCUGAGUGGGCGGCAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAUCUAG hIL12AB_039 G*GGGAAAUAAGAGAGAAAAGAAGAGUAAGAAGAAAUAUAAGAGCCACCAUGUGCCACCAGCAGCUCGUCAUCUCCUGG
(SEQ ID   UUUAGCCUGGUGUUUCUGGCCUCCCCCCUGGUCGCCAUCUGGGAGCUGAAGAAAGACGUGUACGUGGUGGAGCUGGACU
NO: 133)  GGUACCCGGACGCGCCCGGGGAGAUGGUGGUGCUGACCUGCGACCCCCCGAGGAGGACGGCAUCACCUGGACCCUGGA
CCAGAGCUCCGAGGUGCUGGGAGCGGCAAGACCCUGACCAUUCAGGUGAAAGAGUUCGGCGACGCCGGCCAAUAUACC
UGCCACAAGGGGGGGGAGGUCCUGUCGCAUUCCCUGCUGCUGCUUCACAAAAAGGAGGAUGGCAUCUGGAGCACCGACA
UCCUGAAGGACCAGAAAGAACCCAAGAACAAGACGUUCCUGCGCUGCGAGGCCAAGAACUACAGCGGCCGGUUCACCUG
UUGGUGGCUGACCACCAUCUCCACCGACCUGACUUUCUCGGUGAAGAGCAGCCGCGGGAGCAGCGACCCCCAGGGAGUG
ACCUGCGGCGCCGCCACCCUGACGCGCCGAAAGGUGAGGGGCGACAAUAAGGAGUAUGAGUAUCAGCGUGGAGUGCCAGG
AGGACAGCGCCUGUCCCGCCGCCGAGGAGUCCCUGCCUAUCGAGGUGAUGGUCGACGCGGUGCACAAGCUCAAGUACGA
AAACUACACCAGCAGCUUUUUCAUCAGGGAUAUCAUCAAACCAGACCCCCCCAAGAACCUGCAGCUGAAGCCCCUGAAA
AACAGCAGGCAGGUGGAAGUGAGCUGGGAAUACCCCGAUACCUGGUCCACCCCCACAGCUACUUCAGCCUGACCUUCU
GCGUGCAGGUGCAGGGGAAGUCCAAGCGGGAAAAGAAAGACCGCGUGUUCACCGACAAGACCAGCGCCACCGUGAUUUG
CAGGAAAAACGCCAGCAUCUCCGUGAGGGCUCAGGACAGGUACUACAGCUCCAGCUGGAGCGAGUGGGCCUCCGUGCCU
UGCAGCGGGGAGGAGGCGGCAGCAGGAAUCUGCCCGUCGCAACCCCCGACCCCGGCAUGUUCCCCUGCCUGACC
ACAGCCAGAAUCUGCUGCGAGCCUGAGCAAUAUGCUCCAGAAGGCCCGGCAGACGCUGGAGUUCUACCCCUGCACCUC
CGAGGAGAUCGACCACGAGGAUAUCACCAAGGAUAAGACGAGCACCGUCGAGGCCUGCCUGCCCCUGGAGCUGACCAAA
AACGAGUCCUGCCUGAAUAGCAGGGAGACGUCCUUCAUCAACAACGGCAGCGUCUGGCCGUCCAGGAAGACCAGCUUCA
UGAUGGCCCUCUGCCUGAGCUCCAUCUACGAGGACCUCAAGAUGUACCAGGUCGAGUUCAAGACCAUGAACGCAAAACU
GCUCAUGGAUCCAAAGAGGCAGAUCUUCCUGGACCAGAACAUGCUGGCCGUGAUCGAUGAACUCAUGCAGGCCCUGAAU
UUCAAUUCCGAGACCGUGCCCCAGAAGAGCUCCCUGGAGGAACCCGACUUCUACAAAACAAAGAUCAAGCUGUGUAUCC
UGCUGCACGCCUUCCGGAUCAGGGCCGUCACCAUUGACCGGGUGAUGUCCUACCUGAACGCCAGCUGAUAAUAGGCUGG

TABLE 4C-continued mRNA Sequences (with T100 tail)

|  |  |
|---|---|
|  | AGCCUCGGUGGCCAUGCUUCUUGCCCCUUGGGCCUCCCCCCAGCCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAUCUAG |
| hIL12AB_040<br>(SEQ ID<br>NO: 134) | G*GGGAAAUAAGAGAGAAAAGAAGAGUAAGAAGAAAUAUAAGAGCCACCAUGUGCCAUCAGCAGCUGGUGAUCAGCUGG<br>UUCAGCCUCGUGUUCCUCGCCAGCCCCCUCGUGGCCAUCUGGGAGCUGAAAAAGGACGUGUACGUGGUGGAGCUGGACU<br>GGUAUCCCGACGCCCCGGGCGAGAUGGUGGUGCUGACCUGCGACACCCCCGAGGAGGACGGCAUUACCUGGACACUGGA<br>CCAGAGCAGCGAGGUCCUGGGCAGCGGGAAGACCCUGACAAUUCAGGUGAAGGAGUUCGGCGACGCCGGACAGUACACG<br>UGCCACAAGGGGGGGAGGUGCUGUCCCACAGCCUCCUCCUGCUGCACAAGAAGGAGGAUGGCAUCUGGAGCACCGACA<br>UCCUGAAGGAUCAGAAGGAGCCCAAGAACAAGACCUUUCUGAGAUGCGAGGCCAAGAAUUACAGCGGCCGUUUCACCUG<br>CUGGUGGCUCACCACCAUCAGCACCGACCUGACCUUCAGCGUGAAAUCCUCCAGGGGCUCCUCCGACCCGCAGGGAGUG<br>ACCUGCGGCGCCGCCACACUGAGCGCCGAGCGGGUCGAGGGGACAACAAGGAGUACGAGUACAGCGUUGAGUGCCAGG<br>AGGACAGCGCCUGUCCCGCGGCCGAGGAAUCCUGCCCAUCGAGGUGAUGGUGGACGCAGUGCACAAGCUGAAGUACGA<br>GAACUAUACCUCGAGCUUCUUCAUCCGGGAUAUCAUUAAGCCCGAUCCCCCGAAGAACCUGCAGCUCAAACCCCUGAAG<br>AACAGCAGGCAGGUGGAGGUCUCCUGGGAGUACCCCGACACAUGGUCCACCCCCCAUUCCUAUUUCUCCCUGACCUUUU<br>GCGUGCAGGUGCAGGGCAAGAGCAAGAGGGAGAAAAAGGACAGGGUGUUCACCGACAAGACCUCCGCCACCGUGAUCUG<br>CCGUAAGAACGCUAGCAUCAGCGUCAGGGCCCAGGACAGGUACUAUAGCAGCUCCUGGUCCGAGUGGGCCAGCGUCCCG<br>UGCAGCGGCGGGGGCGGUGGAGGCUCCCGGAACCUCCCCGUGGCCACCCCGGACCCCGGGAUGUUUCCCUGCCUGCAUC<br>ACAGCCAGAACCUGCUGAGGGCCGUGUCCAACAUGCUGCAGAGGCCAGGCAGACACUCGAGUUUUACCCCUGCACCAG<br>CGAGGAGAUCGACCACGAAGACAUCACCAAGGACAAGACCUCCACCGUGGAGGCAUGCCUGCCCCUGGAGCUGACCAAA<br>AACGAAAGCUGUCUGAACUCCAGGGAGACCUCCUUUAUCACGAACGGCUCAUGCCUGGCCUCCAGAAAGACCAGCUUCA<br>UGAUGGCCCUGUGCCUGAGCUCCAUCUACGAGGACUUGAAAAUGUACCAGGUCGAGUUCAAGACCAUGAACGCCAAGCU<br>GCUCAUGGACCCCAAAAGGCAGAUCUUUCUGGACCAGAAUAUGCUGGCCGUGAUCGACGAGCUCAUGCAAGCCCUGAAU<br>UUCAACAGCAGAGCCGUGCCCCAGAAGUCCUCCCUGGAGGAGCCCGACUUCUACAAGACCAAGAUCAAGCUGUGCAUAC<br>UCCUGCACGCGUUUAGGAUCAGGGCGGUGACCAUCGAUAGGGUGAUGAGCUACCUGAAUGCCUCCUGAUAAUAGGCUGG<br>AGCCUCGGUGGCCAUGCUUCUUGCCCCUUGGGCCUCCCCCCAGCCCCUCCUCCCCUUCCUGCACCCGUACCCCCAAAC<br>ACCAUUGUCACACUCCAGUGGUCUUUGAAUAAAGUCUGAGUGGGCGGCAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAAAAAAAAAAAAUCUAG |

TABLE 4D mRNA ORF Sequence

> hIL12AB_002 (SEQ ID NO: 237)
AUGUGCCACCAGCAGCUGGUGAUCAGCUGGUUCAGCCUGGUGUUCCUGGC
CAGCCCCUGGUGGCCAUCUGGGAGCUGAAGAAGGACGUGUACGUGGUGG
AGUUGGAUUGGUACCCCGACGCCCCCGGCGAGAUGGUGGUGCUGACCUGC
GACACCCCCGAGGAGGACGGCAUCACCUGGACCCUGGACCAGAGCAGCGA
GGUGCUGGGCAGCGGCAAGACCCUGACCAUCCAGGUGAAGGAGUUCGGCG
ACGCCGGCCAGUACACCUGCCACAAGGGCGGCGAGGUGCUGAGCCACAGC
CUGCUGCUGCUGCACAAGAAGGAGGACGGCAUCUGGAGCACCGACAUCCU
GAAGGACCAGAAGGAGCCCAAGAACAAGACCUUCCUGAGAUGCGAGGCCA
AGAACUACAGCGGCAGAUUCACCUGCUGGGCUGACCACCAUCAGCACC
GACCUGACCUUCAGCGUGAAGAGCAGCAGAGGCAGCAGCGACCCCCAGGG
CGUGACCUGCGGCGCCGCCACCCUGAGCGCCGAGAGAGUGAGAGGCGACA
ACAAGGAGUACGAGUACAGCGUGGAGUGCCAGGAAGAUAGCGCCUGCCCC
GCCGCCGAGGAGCCUGCCCAUCGAGGUGAUGGUGGACGCCGUGCACAA
GCUGAAGUACGAGAACUACACCAGCAGCUUCUUCAUCAGAGAUAUCAUCA
AGCCCGACCCCCCCAAGAACCUGCAGCUGAAGCCCCUGAAGAACAGCCGG
CAGGUGGAGGUGAGCUGGGAGUACCCCGACACCUGGAGCACCCCCCACAG
CUACUUCAGCCUGACCUUCUGCGUGCAGGUGCAGGGCAAGAGCAAGAGAG
AGAAGAAAGAUAGAGUGUUCACCGACAAGACCAGCGCCACCGUGAUCUGC
AGAAAGAACGCCAGCAUCAGCGUGAGAGCCCAAGAUAGAUACUACAGCAG
CAGCUGGAGCGAGUGGGCCAGCGUGCCCUGCAGCGGCGGCGGCGGCGG
GCAGCAGAAACCUGCCCGUGGCCACCCCCGACCCCGGCAUGUUCCCCUGC
CUGCACCACAGCCAGAACCUGCUGAGAGCCGUGAGCAACAUGCUGCAGAA
GGCCCGGCAGACCCUGGAGUUCUACCCCUGCACCAGCGAGGAGAUCGACC
ACGAAGAUAUCACCAAAGAUAAGACCAGCACCGUGGAGGCCUGCCUGCCC
CUGGAGCUGACCAAGAACGAGAGCUGCCUGAACAGCAGAGAGACCAGCCU
CAUCACCAACGGCAGCUGCCUGGCCAGCAGAAAGACCAGCUUCAUGAUGG
CCCUGUGCCUGAGCAGCAUCUACGAGGACCUGAAGAUGUACCAGGUGGAG
UUCAAGACCAUGAACGCCAAGCUGCUGAUGGACCCCAAGCGGCAGAUCUU
CCUGGACCAGAACAUGCUGGCCGUGAUCGACGAGCUGAUGCAGGCCCUGA
ACUUCAACAGCAGACCGUGCCCCAGAAGAGCAGCCUGGAGGAGCCCGAC
UUCUACAAGACCAAGAUCAAGCUGUGCAUCCUGCUGCACGCCUUCAGAAU
CAGAGCCGUGACCAUCGACAGAGUGAUGAGCUACCUGAACGCCAGC

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding an IL12B and/or IL12A polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the disclosure is greater than the uracil or thymine content in the reference wild-type sequence and still maintain beneficial effects, e.g., increased expression and/or reduced Toll-Like Receptor (TLR) response when compared to the reference wild-type sequence.

In some embodiments, the optimized sequences of the present disclosure contain unique ranges of uracils or thymine (if DNA) in the sequence. The uracil or thymine content of the optimized sequences can be expressed in various ways, e.g., uracil or thymine content of optimized sequences relative to the theoretical minimum (% $U_{TM}$ or % $T_{TM}$), relative to the wild-type (% $U_{WT}$ or % $T_{WT}$), and relative to the total nucleotide content (% $U_{TL}$ or % $T_{TL}$). For DNA it is recognized that thymine is present instead of uracil, and one would substitute T where U appears. Thus, all the disclosures related to, e.g., % $U_{TM}$, % $U_{WT}$, or % $U_{TL}$, with respect to RNA are equally applicable to % $T_{TM}$, % $T_{WT}$, or % $T_{TL}$ with respect to DNA.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$.

In some embodiments, the % $U_{TM}$ of a uracil-modified sequence encoding an IL12B polypeptide of the disclosure is below 196%, below 195%, below 190%, below 185%, below 180%, below 175%, below 170%, below 165%, below 160%, below 155%, below 150%, below 145%, below 140%, below 139%, below 138%, below 137%, below 136%, below 135%, below 134%, below 133%, below 132%, below 131%, below 130%, below 129%, below 128%, below 127%, below 126%, below 125%, below 124%, below 123%, below 122%, below 121%, below 120%, below 119%, below 118%, below 117%, below 116%, or below 115%.

In some embodiments, the % $U_{TM}$ of a uracil-modified sequence encoding an IL12B polypeptide of the disclosure is below 196% and above 100%, above 101%, above 102%, above 103%, above 104%, above 105%, above 106%, above 107%, above 108%, above 109%, above 110%, above 111%, above 112%, above 113%, above 114%, above 115%, above 116%, above 117%, above 118%, above 119%, above 120%, above 121%, above 122%, above 123%, above 124%, above 125%, above 126%, above 127%, above 128%, above 129%, or above 130%, above 135%, above 130%, above 131%, or above 132%.

In some embodiments, the % $U_{TM}$ of a uracil-modified sequence encoding an IL12B polypeptide of the disclosure is between 132% and 150%, between 133% and 150%, between 134% and 150%, between 135% and 150%, between 136% and 150%, between 137% and 150%, between 138% and 150%, between 139% and 150%, between 140% and 150%, between 132% and 151%, between 132% and 152%, between 132% and 153%, between 132% and 154%, between 132% and 155%, between 132% and 156%, between 132% and 157%, between 132% and 158%, between 132% and 159%, between 132% and 160%, between 133% and 151%, between 134% and 152%, between 135% and 153%, between 136% and 154%, between 137% and 155%, between 138% and 156%, between 138% and 157%, between 139% and 158%, between 140% and 159%, or between 141% and 160%.

In some embodiments, the % $U_{TM}$ of a uracil-modified sequence encoding an IL12B polypeptide of the disclosure is between about 133% and about 152%, e.g., between 132.32% and 150.51%.

In some embodiments, the % $U_{TM}$ of a uracil-modified sequence encoding an IL12A polypeptide of the disclosure is below 198%, below 195%, below 190%, below 185%, below 180%, below 175%, below 170%, below 165%, below 160%, below 155%, below 150%, below 145%, below 140%, below 139%, below 138%, below 137%, below 136%, below 135%, below 134%, below 133%, below 132%, below 131%, below 130%, below 129%, below 128%, below 127%, below 126%, below 125%, below 124%, below 123%, below 122%, below 121%, below 120%, below 119%, below 118%, below 117%, below 116%, or below 115%.

In some embodiments, the % $U_{TM}$ of a uracil-modified sequence encoding an IL12A polypeptide of the disclosure is below 198% and above 100%, above 101%, above 102%, above 103%, above 104%, above 105%, above 106%, above 107%, above 108%, above 109%, above 110%, above 111%, above 112%, above 113%, above 114%, above 115%, above 116%, above 117%, above 118%, above 119%, above 120%, above 121%, above 122%, above 123%, above 124%, or above 125%.

In some embodiments, the % $U_{TM}$ of a uracil-modified sequence encoding an IL12A polypeptide of the disclosure is between 125% and 143%, between 126% and 143%, between 127% and 143%, between 128% and 143%, between 129% and 143%, between 130% and 143%, between 131% and 132%, between 133% and 134%, between 135% and 143%, between 125% and 144%, between 125% and 145%, between 125% and 146%, between 125% and 147%, between 125% and 148%, between 125% and 149%, between 125% and 150%, between 125% and 151%, between 125% and 152%, between 125% and 153%, between 125% and 154%, between 125% and 155%, between 126% and 144%, between 127% and 145%, between 128% and 146%, between 129% and 147%, between 130% and 148%, between 131% and 149%, between 132% and 150%, or between 133% and 151%.

In some embodiments, the % $U_{TM}$ of a uracil-modified sequence encoding an IL12A polypeptide of the disclosure is between about 124% and about 145%, e.g., between 125% and 144.42%.

A uracil- or thymine-modified sequence encoding an IL12B polypeptide, IL12A polypeptide, or both IL12B and IL12A polypeptides of the disclosure can also be described according to its uracil or thymine content relative to the uracil or thymine content in the corresponding wild-type nucleic acid sequence (% $U_{WT}$ or % $T_{WT}$).

The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as % $U_{WT}$ or % $T_{WT}$.

In some embodiments, the % $U_{WT}$ or % $T_{WT}$ of a uracil- or thymine-modified sequence encoding an IL12B polypeptide of the disclosure is above 50%, above 55%, above 60%, above 65%, above 70%, above 75%, above 80%, above 85%, above 90%, or above 95%.

In some embodiments, the % $U_{WT}$ or % $T_{WT}$ of a uracil- or thymine modified sequence encoding an IL12B polypeptide of the disclosure is between 55% and 88%, between 56% and 87%, between 57% and 86%, between 58% and 85%, between 59% and 84%, between 60% and 83%, between 61% and 82%, between 62% and 81%, between 63% and 80%, between 64% and 79%, between 65% and 78%, or between 65% and 77%.

In some embodiments, the % $U_{WT}$ or % $T_{WT}$ of a uracil- or thymine-modified sequence encoding an IL12B polypeptide of the disclosure is between 66% and 78%, between 66% and 77%, between 67% and 77%, between 67% and 76%, or between 65% and 77%.

In a particular embodiment, the % $U_{WT}$ or % $T_{WT}$ of a uracil- or thymine-modified sequence encoding an IL12B polypeptide of the disclosure is between about 66% and about 77%, e.g., between 67% and 76%.

In some embodiments, the % $U_{WT}$ or % $T_{WT}$ of a uracil- or thymine-modified sequence encoding an IL12A polypeptide of the disclosure is above 50%, above 55%, above 60%, above 65%, above 70%, above 75%, above 80%, above 85%, above 90%, or above 95%.

In some embodiments, the % $U_{WT}$ or % $T_{WT}$ of a uracil- or thymine modified sequence encoding an IL12A polypeptide of the disclosure is between 50% and 85%, between 51% and 84%, between 52% and 83%, between 53% and 82%, between 54% and 81%, between 55% and 80%, between 56% and 79%, between 57% and 78%, between 58% and 77%, between 59% and 76%, between 60% and 75%, between 61% and 74%, or between 62% and 73%.

In some embodiments, the % $U_{WT}$ or % $T_{WT}$ of a uracil- or thymine-modified sequence encoding an IL12A polypeptide of the disclosure is between 61% and 74%, between 61% and 73%, between 61% and 72%, between 61% and 73%, between 62% and 73%, between 62% and 72%, between 62% and 74%, or between 63% and 72%.

In a particular embodiment, the % $U_{WT}$ or % $T_{WT}$ of a uracil- or thymine-modified sequence encoding an IL12A polypeptide of the disclosure is between about 62% and about 73%, e.g., between 63% and 72%.

The uracil or thymine content of wild-type IL12B relative to the total nucleotide content (%) is about 21%. In some embodiments, the uracil or thymine content of a uracil- or thymine-modified sequence encoding an IL12B polypeptide relative to the total nucleotide content (%) (% $U_{TL}$ or % $T_{TL}$) is less than 21%. In some embodiments, the % $U_{TM}$ or % $T_{TL}$ is less than 20%, less than 19%, less that 18%, less than 17%, less than 16%, less than 15%, less than 14%, less than 13%, less than 12%, less than 11%, or less than 10%. In some embodiments, the % $U_{TL}$ or % $T_{TL}$ is not less than 10%, 9%, 8%, 7%, 6%, 5%, 4%, 3%, 2%, or 1%.

In some embodiments, the uracil or thymine content of a uracil- or thymine-modified sequence encoding an IL12B polypeptide of the disclosure relative to the total nucleotide content (% $U_{TL}$ or % $T_{TL}$) is between 10% and 20%, between 11% and 20%, between 11.5% and 19.5%, between 12% and 19%, between 12% and 18%, between 13% and 18%, between 13% and 17%, between 13% and 16%, between 13% and 16%, between 14% and 16%, between 14% and 17%, or between 13% and 17%.

In a particular embodiment, the uracil or thymine content (% $U_{TL}$ or % $T_{TL}$) of a uracil- or thymine modified sequence encoding an IL12B polypeptide of the disclosure is between about 13% and about 17%, e.g., between 14% and 16%

The uracil or thymine content of wild-type IL12A relative to the total nucleotide content (%) is about 26%. In some embodiments, the uracil or thymine content of a uracil- or thymine-modified sequence encoding an IL12A polypeptide relative to the total nucleotide content (%) (% $U_{TL}$ or % $T_{TL}$) is less than 25%. In some embodiments, the % $U_{TL}$ or % $T_{TL}$ is less than 25%, less than 24%, less than 23%, less than 22%, less than 21%, less than 20%, less than 19%, less that 18%, less than 17%, less than 16%, less than 15%, less than 14%, less than 13%, less than 12%, less than 11%, or less than 10%. In some embodiments, the % $U_{TL}$ or % $T_{TL}$ is not less than 10%, 9%, 8%, 7%, 6%, 5%, 4%, 3%, 2%, or 1%.

In some embodiments, the uracil or thymine content of a uracil- or thymine-modified sequence encoding an IL12A polypeptide of the disclosure relative to the total nucleotide content (% $U_{TL}$ or % $T_{TL}$) is between 10% and 25%, between 11% and 25%, between 12% and 25%, between 13% and 25%, between 14% and 25%, between 15% and 25%, between 16% and 25%, between 10% and 24%, between 10% and 23%, between 11% and 22%, between 11% and 21%, between 11% and 20%, between 11% and 19%, between 11% and 18%, between 12% and 24%, between 12% and 23%, between 13% and 22%, between 14% and 21%, between 13% and 20%, between 15% and 19%, between 15% and 20%, between 16% and 19%, between 16% and 18%, or between 13% and 17%.

In a particular embodiment, the uracil or thymine content (% $U_{TL}$ or % $T_{TL}$) of a uracil- or thymine modified sequence encoding an IL12A polypeptide of the disclosure is between about 15% and about 19%, e.g., between 16% and 18% In some embodiments, a uracil-modified sequence encoding an IL12B polypeptide, an IL12B polypeptide, and/or IL12A and IL12B fusion polypeptides of the disclosure has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster.

Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide.

In some embodiments, a uracil-modified sequence encoding an IL12B and/or IL12A polypeptide of the disclosure has a reduced number of uracil triplets (UUU) with respect to the wild-type nucleic acid sequence. In some embodiments, a uracil-modified sequence encoding an IL12B and/or IL12A polypeptide of the disclosure contains 4, 3, 2, 1 or no uracil triplets (UUU).

In some embodiments, a uracil-modified sequence encoding an IL12B and/or IL12A polypeptide has a reduced number of uracil pairs (UU) with respect to the number of uracil pairs (UU) in the wild-type nucleic acid sequence. In some embodiments, a uracil-modified sequence encoding an IL12B and/or IL12A polypeptide of the disclosure has a number of uracil pairs (UU) corresponding to the minimum possible number of uracil pairs (UU) in the wild-type nucleic acid sequence.

In some embodiments, a uracil-modified sequence encoding an IL12B polypeptide of the disclosure has at least 1, 2, 3, 4, 5, 6, 7, 8, 9, 10, 11, 12, 13, 14, 15, 16, 17, 18, 19, 20, 21, 22, or 23 uracil pairs (UU) less than the number of uracil pairs (UU) in the wild-type nucleic acid sequence. In some embodiments, a uracil-modified sequence encoding an IL12B polypeptide of the disclosure has between 7 and 13, between 8 and 14, between 9 and 15, between 10 and 16, between 11 and 7, between 12 and 18 uracil pairs (UU).

In some embodiments, a uracil-modified sequence encoding an IL12B polypeptide of the disclosure has at least 1, 2, 3, 4, 5, 6, 7, 8, 9, 10, 11, 12, 13, 14, 15, 16, 17, 18, 19, or 20 uracil pairs (UU) less than the number of uracil pairs (UU) in the wild-type nucleic acid sequence. In some embodiments, a uracil-modified sequence encoding an IL12A polypeptide of the disclosure has between 7 and 13, between 8 and 14, between 9 and 15, between 10 and 16, between 11 and 7, between 12 and 18 uracil pairs (UU).

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$.

In some embodiments, a uracil-modified sequence encoding an IL12A or IL12B polypeptide of the disclosure has a % $UU_{wt}$ less than 90%, less than 85%, less than 80%, less than 75%, less than 70%, less than 65%, less than 60%, less than 65%, less than 60%, less than 55%, less than 50%, less than 40%, less than 30%, or less than 20%.

In some embodiments, a uracil-modified sequence encoding an IL12B polypeptide has a % $UU_{wt}$ between 24% and 59%. In a particular embodiment, a uracil-modified sequence encoding an IL12A polypeptide, an IL12B polypeptide, and/or IL12A and IL12B fusion polypeptides of the disclosure has a % $UU_{wt}$ between 29% and 55%.

In some embodiments, a uracil-modified sequence encoding an IL12A polypeptide has a % $UU_{wt}$ between 14% and 57%. In a particular embodiment, a uracil-modified sequence encoding an IL12B polypeptide, an IL12B polypeptide, and/or IL12A and IL12B fusion polypeptides of the disclosure has a % $UU_{wt}$ between 19% and 52%.

In some embodiments, the polynucleotide of the disclosure comprises a uracil-modified sequence encoding an IL12A polypeptide, an IL12B polypeptide, and/or IL12A and IL12B fusion polypeptides disclosed herein. In some embodiments, the uracil-modified sequence encoding an IL12A polypeptide, an IL12B polypeptide, and/or IL12A and IL12B fusion polypeptides comprises at least one chemically modified nucleobase, e.g., 5-methoxyuracil. In some embodiments, at least 95% of a nucleobase (e.g., uracil) in a uracil-modified sequence encoding an IL12A polypeptide, an IL12B polypeptide, and/or IL12A and IL12B fusion polypeptides of the disclosure are modified nucleobases. In some embodiments, at least 95% of uracil in a uracil-modified sequence encoding an IL12A polypeptide, an IL12B polypeptide, and/or IL12A and IL12B fusion polypeptides is 5-methoxyuracil. In some embodiments, the polynucleotide comprising a uracil-modified sequence further comprises a miRNA binding site, e.g., a miRNA binding site that binds to miR-122. In some embodiments, the polynucleotide comprising a uracil-modified sequence is formulated with a delivery agent, e.g., a compound having Formula (I), e.g., any of Compounds 1-147 or any of Compounds 1-232.

In some embodiments, the "guanine content of the sequence optimized ORF encoding IL12B and/or IL12A with respect to the theoretical maximum guanine content of a nucleotide sequence encoding the IL12B and/or IL12A polypeptide," abbreviated as % $G_{TMX}$ is at least 69%, at least 70%, at least 75%, at least about 80%, at least about 85%, at least about 90%, at least about 95%, or about 100%. In some embodiments, the % $G_{TMX}$ is between about 70% and about 80%, between about 71% and about 79%, between about 71% and about 78%, or between about 71% and about 77%.

In some embodiments, the "cytosine content of the ORF relative to the theoretical maximum cytosine content of a nucleotide sequence encoding the IL12B and/or IL12A polypeptide," abbreviated as % $C_{TMX}$, is at least 59%, at least 60%, at least about 65%, at least about 70%, at least about 75%, at least about 80%, at least about 85%, at least about 90%, at least about 95%, or about 100%. In some embodiments, the % $C_{TMX}$ is between about 60% and about 80%, between about 62% and about 80%, between about 63% and about 79%, or between about 68% and about 76%.

In some embodiments, the "guanine and cytosine content (G/C) of the ORF relative to the theoretical maximum G/C content in a nucleotide sequence encoding the IL12B and/or IL12A polypeptide," abbreviated as % $G/C_{TMX}$ is at least about 81%, at least about 85%, at least about 90%, at least about 95%, or about 100%. The % $G/C_{TMX}$ is between about 80% and about 100%, between about 85% and about 99%, between about 90% and about 97%, or between about 91% and about 96%.

In some embodiments, the "G/C content in the ORF relative to the G/C content in the corresponding wild-type ORF," abbreviated as % $G/C_{WT}$ is at least 102%, at least 103%, at least 104%, at least 105%, at least 106%, at least 107%, at least 110%, at least 115%, or at least 120%.

In some embodiments, the average G/C content in the 3rd codon position in the ORF is at least 20%, at least 21%, at least 22%, at least 23%, at least 24%, at least 25%, at least 26%, at least 27%, at least 28%, at least 29%, or at least 30% higher than the average G/C content in the 3rd codon position in the corresponding wild-type ORF.

In some embodiments, the polynucleotide of the disclosure comprises an open reading frame (ORF) encoding an IL12B and/or IL12A polypeptide, wherein the ORF has been sequence optimized, and wherein each of % $U_{TL}$, % $U_{WT}$, % $U_{TM}$, % $G_{TL}$, % $G_{WT}$, % $C_{TMX}$, % $C_{TL}$, % $C_{WT}$, % $C_{TMX}$, % $G/C_{TL}$, % $G/C_{WT}$, or % $G/C_{TMX}$, alone or in a combination thereof is in a range between (i) a maximum corresponding to the parameter's maximum value (MAX) plus about 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV), and (ii) a minimum corresponding to the parameter's minimum value (MIN) less 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV).

9. Methods for Sequence Optimization

In some embodiments, a polynucleotide of the disclosure (e.g., a polynucleotide comprising a nucleotide sequence, e.g., an ORF, encoding an IL12A polypeptide, an IL12B polypeptide, and/or IL12A and IL12B fusion polypeptides (e.g., the wild-type sequence, functional fragment, or variant thereof)) is sequence optimized. A sequence optimized nucleotide sequence (nucleotide sequence is also referred to as "nucleic acid" herein) comprises at least one codon modification with respect to a reference sequence (e.g., a wild-type sequence encoding an IL12A polypeptide, an IL12B polypeptide, and/or IL12A and IL12B fusion polypeptides). Thus, in a sequence optimized nucleic acid, at least one codon is different from a corresponding codon in a reference sequence (e.g., a wild-type sequence).

In general, sequence optimized nucleic acids are generated by at least a step comprising substituting codons in a reference sequence with synonymous codons (i.e., codons that encode the same amino acid). Such substitutions can be effected, for example, by applying a codon substitution map (i.e., a table providing the codons that will encode each amino acid in the codon optimized sequence), or by applying a set of rules (e.g., if glycine is next to neutral amino acid, glycine would be encoded by a certain codon, but if it is next to a polar amino acid, it would be encoded by another codon). In addition to codon substitutions (i.e., "codon optimization") the sequence optimization methods disclosed herein comprise additional optimization steps which are not strictly directed to codon optimization such as the removal of deleterious motifs (destabilizing motif substitution). Compositions and formulations comprising these sequence optimized nucleic acids (e.g., a RNA, e.g., an mRNA) can be administered to a subject in need thereof to facilitate in vivo expression of functionally active IL12.

The recombinant expression of large molecules in cell cultures can be a challenging task with numerous limitations (e.g., poor protein expression levels, stalled translation resulting in truncated expression products, protein misfolding, etc.) These limitations can be reduced or avoided by administering the polynucleotides (e.g., a RNA, e.g., an mRNA), which encode a functionally active IL12 or compositions or formulations comprising the same to a patient suffering from cancer, so the synthesis and delivery of the IL12 polypeptide to treat cancer takes place endogenously.

Changing from an in vitro expression system (e.g., cell culture) to in vivo expression requires the redesign of the nucleic acid sequence encoding the therapeutic agent. Redesigning a naturally occurring gene sequence by choosing different codons without necessarily altering the encoded amino acid sequence can often lead to dramatic increases in protein expression levels (Gustafsson et al., 2004, Journal/ Trends Biotechnol 22, 346-53). Variables such as codon adaptation index (CAI), mRNA secondary structures, cis-regulatory sequences, GC content and many other similar variables have been shown to somewhat correlate with protein expression levels (Villalobos et al., 2006, "Journal/ BMC Bioinformatics 7, 285). However, due to the degeneracy of the genetic code, there are numerous different nucleic acid sequences that can all encode the same therapeutic agent. Each amino acid is encoded by up to six synonymous codons; and the choice between these codons influences gene expression. In addition, codon usage (i.e., the frequency with which different organisms use codons for expressing a polypeptide sequence) differs among organisms (for example, recombinant production of human or humanized therapeutic antibodies frequently takes place in hamster cell cultures).

In some embodiments, a reference nucleic acid sequence can be sequence optimized by applying a codon map. The skilled artisan will appreciate that the T bases in the codon maps disclosed below are present in DNA, whereas the T bases would be replaced by U bases in corresponding RNAs. For example, a sequence optimized nucleic acid disclosed herein in DNA form, e.g., a vector or an in-vitro translation (IVT) template, would have its T bases transcribed as U based in its corresponding transcribed mRNA. In this respect, both sequence optimized DNA sequences (comprising T) and their corresponding RNA sequences (comprising U) are considered sequence optimized nucleic acid of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn may correspond to a 'P'C codon (RNA map in which U has been replaced with pseudouridine).

In one embodiment, a reference sequence encoding IL12A, IL12B, or both IL12A and IL12B can be optimized by replacing all the codons encoding a certain amino acid with only one of the alternative codons provided in a codon map. For example, all the valines in the optimized sequence would be encoded by GTG or GTC or GTT.

Sequence optimized polynucleotides of the disclosure can be generated using one or more codon optimization methods, or a combination thereof. Sequence optimization methods which may be used to sequence optimize nucleic acid sequences are described in detail herein. This list of methods is not comprehensive or limiting.

It will be appreciated that the design principles and rules described for each one of the sequence optimization methods discussed below can be combined in many different ways, for example high G/C content sequence optimization for some regions or uridine content sequence optimization for other regions of the reference nucleic acid sequence, as well as targeted nucleotide mutations to minimize secondary structure throughout the sequence or to eliminate deleterious motifs.

The choice of potential combinations of sequence optimization methods can be, for example, dependent on the specific chemistry used to produce a synthetic polynucleotide. Such a choice can also depend on characteristics of the protein encoded by the sequence optimized nucleic acid, e.g., a full sequence, a functional fragment, or a fusion protein comprising IL12, etc. In some embodiments, such a choice can depend on the specific tissue or cell targeted by the sequence optimized nucleic acid (e.g., a therapeutic synthetic mRNA).

The mechanisms of combining the sequence optimization methods or design rules derived from the application and analysis of the optimization methods can be either simple or complex. For example, the combination can be:

(i) Sequential: Each sequence optimization method or set of design rules applies to a different subsequence of the overall sequence, for example reducing uridine at codon positions 1 to 30 and then selecting high frequency codons for the remainder of the sequence;

(ii) Hierarchical: Several sequence optimization methods or sets of design rules are combined in a hierarchical, deterministic fashion. For example, use the most GC-rich codons, breaking ties (which are common) by choosing the most frequent of those codons.

(iii) Multifactorial/Multiparametric: Machine learning or other modeling techniques are used to design a single sequence that best satisfies multiple overlapping and possibly contradictory requirements. This approach would require the use of a computer applying a number of mathematical techniques, for example, genetic algorithms.

Ultimately, each one of these approaches can result in a specific set of rules which in many cases can be summarized in a single codon table, i.e., a sorted list of codons for each amino acid in the target protein (i.e., an IL12A polypeptide, an IL12B polypeptide, and/or IL12A and IL12B fusion polypeptides), with a specific rule or set of rules indicating how to select a specific codon for each amino acid position.

a. Uridine Content Optimization

The presence of local high concentrations of uridine in a nucleic acid sequence can have detrimental effects on translation, e.g., slow or prematurely terminated translation, especially when modified uridine analogs are used in the production of synthetic mRNAs. Furthermore, high uridine content can also reduce the in vivo half-life of synthetic mRNAs due to TLR activation.

Accordingly, a nucleic acid sequence can be sequence optimized using a method comprising at least one uridine content optimization step. Such a step comprises, e.g., substituting at least one codon in the reference nucleic acid with an alternative codon to generate a uridine-modified sequence, wherein the uridine-modified sequence has at least one of the following properties:

(i) increase or decrease in global uridine content;
(ii) increase or decrease in local uridine content (i.e., changes in uridine content are limited to specific subsequences);
(iii) changes in uridine distribution without altering the global uridine content;
(iv) changes in uridine clustering (e.g., number of clusters, location of clusters, or distance between clusters); or
(v) combinations thereof.

In some embodiments, the sequence optimization process comprises optimizing the global uridine content, i.e., optimizing the percentage of uridine nucleobases in the sequence optimized nucleic acid with respect to the percentage of uridine nucleobases in the reference nucleic acid sequence. For example, 30% of nucleobases may be uridines in the reference sequence and 10% of nucleobases may be uridines in the sequence optimized nucleic acid.

In other embodiments, the sequence optimization process comprises reducing the local uridine content in specific regions of a reference nucleic acid sequence, i.e., reducing the percentage of uridine nucleobases in a subsequence of the sequence optimized nucleic acid with respect to the percentage of uridine nucleobases in the corresponding subsequence of the reference nucleic acid sequence. For example, the reference nucleic acid sequence may have a 5'-end region (e.g., 30 codons) with a local uridine content of 30%, and the uridine content in that same region could be reduced to 10% in the sequence optimized nucleic acid.

In specific embodiments, codons can be replaced in the reference nucleic acid sequence to reduce or modify, for example, the number, size, location, or distribution of uridine clusters that could have deleterious effects on protein translation. Although as a general rule it is desirable to reduce the uridine content of the reference nucleic acid sequence, in certain embodiments the uridine content, and in particular the local uridine content, of some subsequences of the reference nucleic acid sequence can be increased.

The reduction of uridine content to avoid adverse effects on translation can be done in combination with other optimization methods disclosed here to achieve other design goals. For example, uridine content optimization can be combined with ramp design, since using the rarest codons for most amino acids will, with a few exceptions, reduce the U content.

In some embodiments, the uridine-modified sequence is designed to induce a lower Toll-Like Receptor (TLR) response when compared to the reference nucleic acid sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:1529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745.

As used herein, the term "TLR response" is defined as the recognition of single-stranded RNA by a TLR7 receptor, and in some embodiments encompasses the degradation of the RNA and/or physiological responses caused by the recognition of the single-stranded RNA by the receptor. Methods to determine and quantitate the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7.

Suppression of TLR7-mediated response can be accomplished via nucleoside modification. RNA undergoes over hundred different nucleoside modifications in nature (see the RNA Modification Database, available at mods.rna.albany.edu). Human rRNA, for example, has ten times more pseudouridine (Ψ) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uridines in close proximity. See Diebold et al. (2006) Eur. J. Immunol. 36:3256-3267, which is herein incorporated by reference in its entirety. Accordingly, one or more of the optimization methods disclosed herein comprises reducing the uridine content (locally and/or locally) and/or reducing or modifying uridine clustering to reduce or to suppress a TLR7-mediated response.

In some embodiments, the TLR response (e.g., a response mediated by TLR7) caused by the uridine-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the TLR response caused by the reference nucleic acid sequence.

In some embodiments, the TLR response caused by the reference nucleic acid sequence is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uridine-modified sequence.

In some embodiments, the uridine content (average global uridine content) (absolute or relative) of the uridine-modified sequence is higher than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more uridine that the reference nucleic acid sequence.

In other embodiments, the uridine content (average global uridine content) (absolute or relative) of the uridine-modified sequence is lower than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uridine that the reference nucleic acid sequence.

In some embodiments, the uridine content (average global uridine content) (absolute or relative) of the uridine-modified sequence is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the uridine-modified sequence. In some embodiments, the uridine content of the uridine-modified sequence is between about 10% and about 20%. In some particular embodiments, the uridine content of the uridine-modified sequence is between about 12% and about 16%.

In some embodiments, the uridine content of the reference nucleic acid sequence can be measured using a sliding window. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the sliding window is 20 nucleobases in length. Based on the uridine content measured with a sliding window, it is possible to generate a histogram representing the uridine content throughout the length of the reference nucleic acid sequence and sequence optimized nucleic acids.

In some embodiments, a reference nucleic acid sequence can be modified to reduce or eliminate peaks in the histogram that are above or below a certain percentage value. In some embodiments, the reference nucleic acid sequence can be modified to eliminate peaks in the sliding-window representation which are above 65%, 60%, 55%, 50%, 45%, 40%, 35%, or 30% uridine. In another embodiment, the reference nucleic acid sequence can be modified so no peaks are over 30% uridine in the sequence optimized nucleic acid, as measured using a 20 nucleobase sliding window. In some embodiments, the reference nucleic acid sequence can be modified so no more or no less than a predetermined number of peaks in the sequence optimized nucleic sequence, as measured using a 20 nucleobase sliding window, are above or below a certain threshold value. For example, in some embodiments, the reference nucleic acid sequence can be modified so no peaks or no more than 1, 2, 3, 4, 5, 6, 7, 8, 9 or 10 peaks in the sequence optimized nucleic acid are above 10%, 15%, 20%, 25% or 30% uridine. In another embodiment, the sequence optimized nucleic acid contains between 0 peaks and 2 peaks with uridine contents 30% of higher.

In some embodiments, a reference nucleic acid sequence can be sequence optimized to reduce the incidence of consecutive uridines. For example, two consecutive leucines could be encoded by the sequence CUUUUG, which would include a four uridine cluster. Such subsequence could be substituted with CUGCUC, which would effectively remove the uridine cluster. Accordingly, a reference nucleic sequence can be sequence optimized by reducing or eliminating uridine pairs (UU), uridine triplets (UUU) or uridine quadruplets (UUUU). Higher order combinations of U are not considered combinations of lower order combinations. Thus, for example, UUUU is strictly considered a quadruplet, not two consecutive U pairs; or UUUUUU is considered a sextuplet, not three consecutive U pairs, or two consecutive U triplets, etc.

In some embodiments, all uridine pairs (UU) and/or uridine triplets (UUU) and/or uridine quadruplets (UUUU) can be removed from the reference nucleic acid sequence. In other embodiments, uridine pairs (UU) and/or uridine triplets (UUU) and/or uridine quadruplets (UUUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 uridine pairs. In another particular embodiment, the sequence optimized nucleic acid contains no uridine pairs and/or triplets.

Phenylalanine codons, i.e., UUC or UUU, comprise a uridine pair or triples and therefore sequence optimization to reduce uridine content can at most reduce the phenylalanine U triplet to a phenylalanine U pair. In some embodiments, the occurrence of uridine pairs (UU) and/or uridine triplets (UUU) refers only to non-phenylalanine U pairs or triplets. Accordingly, in some embodiments, non-phenylalanine uridine pairs (UU) and/or uridine triplets (UUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 non-phenylalanine uridine pairs and/or triplets. In another particular embodiment, the sequence optimized nucleic acid contains no non-phenylalanine uridine pairs and/or triplets.

In some embodiments, the reduction in uridine combinations (e.g., pairs, triplets, quadruplets) in the sequence optimized nucleic acid can be expressed as a percentage reduction with respect to the uridine combinations present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine triplets present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine quadruplets present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine triplets present in the reference nucleic acid sequence.

In some embodiments, the uridine content in the sequence optimized sequence can be expressed with respect to the theoretical minimum uridine content in the sequence. The term "theoretical minimum uridine content" is defined as the uridine content of a nucleic acid sequence as a percentage of the sequence's length after all the codons in the sequence have been replaced with synonymous codon with the lowest uridine content. In some embodiments, the uridine content of the sequence optimized nucleic acid is identical to the theoretical minimum uridine content of the reference sequence (e.g., a wild type sequence). In some aspects, the uridine content of the sequence optimized nucleic acid is about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195% or about 200% of the theoretical minimum uridine content of the reference sequence (e.g., a wild type sequence).

In some embodiments, the uridine content of the sequence optimized nucleic acid is identical to the theoretical minimum uridine content of the reference sequence (e.g., a wild type sequence).

The reference nucleic acid sequence (e.g., a wild type sequence) can comprise uridine clusters which due to their number, size, location, distribution or combinations thereof have negative effects on translation. As used herein, the term "uridine cluster" refers to a subsequence in a reference nucleic acid sequence or sequence optimized nucleic sequence with contains a uridine content (usually described as a percentage) which is above a certain threshold. Thus, in certain embodiments, if a subsequence comprises more than about 10%, 15%, 20%, 25%, 30%, 35%, 40%, 45%, 50%, 55%, 60% or 65% uridine content, such subsequence would be considered a uridine cluster.

The negative effects of uridine clusters can be, for example, eliciting a TLR7 response. Thus, in some implementations of the nucleic acid sequence optimization methods disclosed herein it is desirable to reduce the number of clusters, size of clusters, location of clusters (e.g., close to the 5' and/or 3' end of a nucleic acid sequence), distance between clusters, or distribution of uridine clusters (e.g., a certain pattern of cluster along a nucleic acid sequence, distribution of clusters with respect to secondary structure elements in the expressed product, or distribution of clusters with respect to the secondary structure of an mRNA).

In some embodiments, the reference nucleic acid sequence comprises at least one uridine cluster, wherein said uridine cluster is a subsequence of the reference nucleic acid sequence wherein the percentage of total uridine nucleobases in said subsequence is above a predetermined threshold. In some embodiments, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some embodiments, the subsequence is longer than 100 nucleobases. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

For example, an amino acid sequence comprising A, D, G, S and R could be encoded by the nucleic acid sequence GCU, GAU, GGU, AGU, CGU. Although such sequence does not contain any uridine pairs, triplets, or quadruplets, one third of the nucleobases would be uridines. Such a uridine cluster could be removed by using alternative codons, for example, by using GCC, GAC, GGC, AGC, and CGC, which would contain no uridines.

In other embodiments, the reference nucleic acid sequence comprises at least one uridine cluster, wherein said uridine cluster is a subsequence of the reference nucleic acid sequence wherein the percentage of uridine nucleobases of said subsequence as measured using a sliding window that is above a predetermined threshold. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

In some embodiments, the reference nucleic acid sequence comprises at least two uridine clusters. In some embodiments, the uridine-modified sequence contains fewer uridine-rich clusters than the reference nucleic acid sequence. In some embodiments, the uridine-modified sequence contains more uridine-rich clusters than the reference nucleic acid sequence. In some embodiments, the uridine-modified sequence contains uridine-rich clusters with are shorter in length than corresponding uridine-rich clusters in the reference nucleic acid sequence. In other embodiments, the uridine-modified sequence contains uridine-rich clusters which are longer in length than the corresponding uridine-rich cluster in the reference nucleic acid sequence.

See, Kariko et al. (2005) Immunity 23:165-175; Kormann et al. (2010) Nature Biotechnology 29:154-157; or Sahin et al. (2014) Nature Reviews Drug Discovery|AOP, published online 19 Sep. 2014m doi:10.1038/nrd4278; all of which are herein incorporated by reference their entireties.

b. Guanine/Cytosine (G/C) Content

A reference nucleic acid sequence can be sequence optimized using methods comprising altering the Guanine/Cytosine (G/C) content (absolute or relative) of the reference nucleic acid sequence. Such optimization can comprise altering (e.g., increasing or decreasing) the global G/C content (absolute or relative) of the reference nucleic acid sequence; introducing local changes in G/C content in the reference nucleic acid sequence (e.g., increase or decrease G/C in selected regions or subsequences in the reference nucleic acid sequence); altering the frequency, size, and distribution of G/C clusters in the reference nucleic acid sequence, or combinations thereof.

In some embodiments, the sequence optimized nucleic acid encoding an IL12A polypeptide, an IL12B polypeptide, and/or IL12A and IL12B fusion polypeptides comprises an overall increase in G/C content (absolute or relative) relative to the G/C content (absolute or relative) of the reference nucleic acid sequence. In some embodiments, the overall increase in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding an IL12A polypeptide, an IL12B polypeptide, and/or IL12A and IL12B fusion polypeptides comprises an overall decrease in G/C content (absolute or relative) relative to the G/C content of the reference nucleic acid sequence. In some embodiments, the overall decrease in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding an IL12A polypeptide, an IL12B polypeptide, and/or IL12A and IL12B fusion polypeptides comprises a local increase in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local increase in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the sequence optimized nucleic acid encoding an IL12A polypeptide, an IL12B polypeptide, and/or IL12A and IL12B fusion polypeptides comprises a local decrease in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local decrease in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the G/C content (absolute or relative) is increased or decreased in a subsequence which is at least about 5, 10, 15, 20, 25, 30, 35, 40, 45, 50, 55, 60, 65, 70, 75, 80, 85, 90, 95, or 100 nucleobases in length.

In some embodiments, the G/C content (absolute or relative) is increased or decreased in a subsequence which is at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleobases in length.

In some embodiments, the G/C content (absolute or relative) is increased or decreased in a subsequence which is at least about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nucleobases in length.

The increases or decreases in G and C content (absolute or relative) described herein can be conducted by replacing synonymous codons with low G/C content with synonymous codons having higher G/C content, or vice versa. For example, L has 6 synonymous codons: two of them have 2 G/C (CUC, CUG), 3 have a single G/C (UUG, CUU, CUA), and one has no G/C (UUA). So if the reference nucleic acid had a CUC codon in a certain position, G/C content at that position could be reduced by replacing CUC with any of the codons having a single G/C or the codon with no G/C.

See, U.S. Publ. Nos. US20140228558, US20050032730 A1; Gustafsson et al. (2012) Protein Expression and Purification 83: 37-46; all of which are incorporated herein by reference in their entireties.

c. Codon Frequency—Codon Usage Bias

Numerous codon optimization methods known in the art are based on the substitution of codons in a reference nucleic acid sequence with codons having higher frequencies. Thus, in some embodiments, a nucleic acid sequence encoding an IL12A polypeptide, an IL12B polypeptide, and/or IL12A and IL12B fusion polypeptides disclosed herein can be sequence optimized using methods comprising the use of modifications in the frequency of use of one or more codons relative to other synonymous codons in the sequence optimized nucleic acid with respect to the frequency of use in the non-codon optimized sequence.

As used herein, the term "codon frequency" refers to codon usage bias, i.e., the differences in the frequency of occurrence of synonymous codons in coding DNA/RNA. It is generally acknowledged that codon preferences reflect a balance between mutational biases and natural selection for translational optimization. Optimal codons help to achieve faster translation rates and high accuracy. As a result of these factors, translational selection is expected to be stronger in highly expressed genes. In the field of bioinformatics and computational biology, many statistical methods have been proposed and used to analyze codon usage bias. See, e.g., Comeron & Aguadé (1998) J. Mol. Evol. 47: 268-74. Methods such as the 'frequency of optimal codons' (Fop) (Ikemura (1981) J. Mol. Biol. 151 (3): 389-409), the Relative Codon Adaptation (RCA) (Fox & Eril (2010) DNA Res. 17 (3): 185-96) or the 'Codon Adaptation Index' (CAI) (Sharp & Li (1987) Nucleic Acids Res. 15 (3): 1281-95) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes (Suzuki et al. (2008) DNA Res. 15 (6): 357-65; Sandhu et al., In Silico Biol. 2008; 8(2):187-92).

The nucleic acid sequence encoding an IL12A polypeptide, an IL12B polypeptide, and/or IL12A and IL12B fusion polypeptides disclosed herein (e.g., a wild type nucleic acid sequence, a mutant nucleic acid sequence, a chimeric nucleic sequence, etc. which can be, for example, an mRNA), can be codon optimized using methods comprising substituting at least one codon in the reference nucleic acid sequence with an alternative codon having a higher or lower codon frequency in the synonymous codon set; wherein the resulting sequence optimized nucleic acid has at least one optimized property with respect to the reference nucleic acid sequence.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the reference nucleic acid sequence encoding an IL12A polypeptide, an IL12B polypeptide, and/or IL12A and IL12B fusion polypeptides are substituted with alternative codons, each alternative codon having a codon frequency higher than the codon frequency of the substituted codon in the synonymous codon set.

In some embodiments, at least one codon in the reference nucleic acid sequence encoding an IL12A polypeptide, an IL12B polypeptide, and/or IL12A and IL12B fusion polypeptides is substituted with an alternative codon having a codon frequency higher than the codon frequency of the substituted codon in the synonymous codon set, and at least one codon in the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding IL12 are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding an IL12A polypeptide, an IL12B polypeptide, and/or IL12A and IL12B fusion polypeptides. In some embodiments, when applied locally, regions of the reference nucleic acid sequence can modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding an IL12A polypeptide, an IL12B polypeptide, and/or IL12A and IL12B fusion polypeptides is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding an IL12A polypeptide, an IL12B polypeptide, and/or IL12A and IL12B fusion polypeptides are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding an IL12A polypeptide, an IL12B polypeptide, and/or IL12A and IL12B fusion polypeptides and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding an IL12A polypeptide, an IL12B polypeptide, and/or IL12A and IL12B fusion polypeptides and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding an IL12A polypeptide, an IL12B polypeptide, and/or IL12A and IL12B fusion polypeptides can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid).

In some embodiments, an sequence optimized nucleic acid encoding an IL12A polypeptide, an IL12B polypeptide, and/or IL12A and IL12B fusion polypeptides can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc.

See, U.S. Pat. Nos. 5,082,767, 8,126,653, 7,561,973, 8,401,798; U.S. Publ. No. US 20080046192, US 20080076161; Int'l. Publ. No. WO2000018778; Welch et al.

(2009) PLoS ONE 4(9): e7002; Gustafsson et al. (2012) Protein Expression and Purification 83: 37-46; Chung et al. (2012) BMC Systems Biology 6:134; all of which are incorporated herein by reference in their entireties.

d. Destabilizing Motif Substitution

There is a variety of motifs that can affect sequence optimization, which fall into various non-exclusive categories, for example:

(i) Primary sequence based motifs: Motifs defined by a simple arrangement of nucleotides.
(ii) Structural motifs: Motifs encoded by an arrangement of nucleotides that tends to form a certain secondary structure.
(iii) Local motifs: Motifs encoded in one contiguous subsequence.
(iv) Distributed motifs: Motifs encoded in two or more disjoint subsequences.
(v) Advantageous motifs: Motifs which improve nucleotide structure or function.
(vi) Disadvantageous motifs: Motifs with detrimental effects on nucleotide structure or function.

There are many motifs that fit into the category of disadvantageous motifs. Some examples include, for example, restriction enzyme motifs, which tend to be relatively short, exact sequences such as the restriction site motifs for XbaI (TCTAGA (SEQ ID NO: 224)), EcoRI (GAATTC (SEQ ID NO: 225)), EcoRII (CCWGG (SEQ ID NO: 226), wherein W means A or T, per the IUPAC ambiguity codes), or HindIII (AAGCTT (SEQ ID NO: 227)); enzyme sites, which tend to be longer and based on consensus not exact sequence, such in the T7 RNA polymerase (GnnnnWnCRnCTCnCnnWnD (SEQ ID NO: 228), wherein n means any nucleotide, R means A or G, W means A or T, D means A or G or T but not C); structural motifs, such as GGGG (SEQ ID NO: 229) repeats (Kim et al. (1991) Nature 351(6324):331-2); or other motifs such as CUG-triplet repeats (Querido et al. (2014) J. Cell Sci. 124:1703-1714).

Accordingly, the nucleic acid sequence encoding an IL12A polypeptide, an IL12B polypeptide, and/or IL12A and IL12B fusion polypeptides disclosed herein can be sequence optimized using methods comprising substituting at least one destabilizing motif in a reference nucleic acid sequence, and removing such disadvantageous motif or replacing it with an advantageous motif.

In some embodiments, the optimization process comprises identifying advantageous and/or disadvantageous motifs in the reference nucleic sequence, wherein such motifs are, e.g., specific subsequences that can cause a loss of stability in the reference nucleic acid sequence prior or during the optimization process. For example, substitution of specific bases during optimization may generate a subsequence (motif) recognized by a restriction enzyme. Accordingly, during the optimization process the appearance of disadvantageous motifs can be monitored by comparing the sequence optimized sequence with a library of motifs known to be disadvantageous. Then, the identification of disadvantageous motifs could be used as a post-hoc filter, i.e., to determine whether a certain modification which potentially could be introduced in the reference nucleic acid sequence should be actually implemented or not.

In some embodiments, the identification of disadvantageous motifs can be used prior to the application of the sequence optimization methods disclosed herein, i.e., the identification of motifs in the reference nucleic acid sequence encoding an IL12A polypeptide, an IL12B polypeptide, and/or IL12A and IL12B fusion polypeptides and their replacement with alternative nucleic acid sequences can be used as a preprocessing step, for example, before uridine reduction.

In other embodiments, the identification of disadvantageous motifs and their removal is used as an additional sequence optimization technique integrated in a multiparametric nucleic acid optimization method comprising two or more of the sequence optimization methods disclosed herein. When used in this fashion, a disadvantageous motif identified during the optimization process would be removed, for example, by substituting the lowest possible number of nucleobases in order to preserve as closely as possible the original design principle(s) (e.g., low U, high frequency, etc.).

See, e.g., U.S. Publ. Nos. US20140228558, US20050032730, or US20140228558, which are herein incorporated by reference in their entireties.

e. Limited Codon Set Optimization

In some particular embodiments, sequence optimization of a reference nucleic acid sequence encoding an L12A polypeptide, an IL12B polypeptide, and/or L12A and IL12B fusion polypeptides can be conducted using a limited codon set, e.g., a codon set wherein less than the native number of codons is used to encode the 20 natural amino acids, a subset of the 20 natural amino acids, or an expanded set of amino acids including, for example, non-natural amino acids.

The genetic code is highly similar among all organisms and can be expressed in a simple table with 64 entries which would encode the 20 standard amino acids involved in protein translation plus start and stop codons. The genetic code is degenerate, i.e., in general, more than one codon specifies each amino acid. For example, the amino acid leucine is specified by the UUA, UUG, CUU, CUC, CUA, or CUG codons, while the amino acid serine is specified by UCA, UCG, UCC, UCU, AGU, or AGC codons (difference in the first, second, or third position). Native genetic codes comprise 62 codons encoding naturally occurring amino acids. Thus, in some embodiments of the methods disclosed herein optimized codon sets (genetic codes) comprising less than 62 codons to encode 20 amino acids can comprise 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 30, 29, 28, 27, 26, 25, 24, 23, 22, 21, or 20 codons.

In some embodiments, the limited codon set comprises less than 20 codons. For example, if a protein contains less than 20 types of amino acids, such protein could be encoded by a codon set with less than 20 codons. Accordingly, in some embodiments, an optimized codon set comprises as many codons as different types of amino acids are present in the protein encoded by the reference nucleic acid sequence. In some embodiments, the optimized codon set comprises 19, 18, 17, 16, 15, 14, 13, 12, 11, 10, 9, 8, 7, 6, 5, 4, 3, 2 or even 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded with less codons than the naturally occurring number of synonymous codons. For example, in some embodiments, Ala can be encoded in the sequence optimized nucleic acid by 3, 2 or 1 codons; Cys can be encoded in the sequence optimized nucleic acid by 1 codon; Asp can be encoded in the sequence optimized nucleic acid by 1 codon; Glu can be encoded in the sequence optimized nucleic acid by 1 codon; Phe can be encoded in the sequence optimized nucleic acid by 1 codon; Gly can be encoded in the sequence optimized nucleic acid by 3 codons, 2 codons or 1 codon; His can be encoded in the sequence optimized nucleic acid by 1 codon; Ile can be encoded in the sequence optimized nucleic acid by 2 codons or 1 codon; Lys can be encoded in the sequence optimized nucleic acid by 1 codon; Leu can be encoded in the sequence optimized nucleic acid by 5 codons, 4 codons, 3 codons, 2 codons or 1 codon; Asn can be encoded in the sequence optimized nucleic acid by 1 codon; Pro can be encoded in the sequence optimized nucleic acid by 3 codons, 2 codons, or 1 codon; Gln can be encoded in the sequence optimized nucleic acid by 1 codon; Arg can be encoded in the sequence optimized nucleic acid by 5 codons, 4 codons, 3 codons, 2 codons, or 1 codon; Ser can be encoded in the sequence optimized nucleic acid by 5 codons, 4 codons, 3 codons, 2 codons, or 1 codon; Thr can be encoded in the sequence optimized nucleic acid by 3 codons, 2 codons, or 1 codon; Val can be encoded in the sequence optimized nucleic acid by 3 codons, 2 codons, or 1 codon; and, Tyr can be encoded in the sequence optimized nucleic acid by 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded by a single codon in the limited codon set.

In some specific embodiments, the sequence optimized nucleic acid is a DNA and the limited codon set consists of 20 codons, wherein each codon encodes one of 20 amino acids. In some embodiments, the sequence optimized nucleic acid is a DNA and the limited codon set comprises at least one codon selected from the group consisting of GCT, GCC, GCA, and GCG; at least a codon selected from the group consisting of CGT, CGC, CGA, CGG, AGA, and AGG; at least a codon selected from AAT or ACC; at least a codon selected from GAT or GAC; at least a codon selected from TGT or TGC; at least a codon selected from CAA or CAG; at least a codon selected from GAA or GAG; at least a codon selected from the group consisting of GGT, GGC, GGA, and GGG; at least a codon selected from CAT or CAC; at least a codon selected from the group consisting of ATT, ATC, and ATA; at least a codon selected from the group consisting of TTA, TTG, CTT, CTC, CTA, and CTG; at least a codon selected from AAA or AAG; an ATG codon; at least a codon selected from TTT or TTC; at least a codon selected from the group consisting of CCT, CCC, CCA, and CCG; at least a codon selected from the group consisting of TCT, TCC, TCA, TCG, AGT, and AGC; at least a codon selected from the group consisting of ACT, ACC, ACA, and ACG; a TGG codon; at least a codon selected from TAT or TAC; and, at least a codon selected from the group consisting of GTT, GTC, GTA, and GTG.

In other embodiments, the sequence optimized nucleic acid is an RNA (e.g., an mRNA) and the limited codon set consists of 20 codons, wherein each codon encodes one of 20 amino acids. In some embodiments, the sequence optimized nucleic acid is an RNA and the limited codon set comprises at least one codon selected from the group consisting of GCU, GCC, GCA, and GCG; at least a codon selected from the group consisting of CGU, CGC, CGA, CGG, AGA, and AGG; at least a codon selected from AAU or ACC; at least a codon selected from GAU or GAC; at least a codon selected from UGU or UGC; at least a codon selected from CAA or CAG; at least a codon selected from GAA or GAG; at least a codon selected from the group consisting of GGU, GGC, GGA, and GGG; at least a codon selected from CAU or CAC; at least a codon selected from the group consisting of AUU, AUC, and AUA; at least a codon selected from the group consisting of UUA, UUG, CUU, CUC, CUA, and CUG; at least a codon selected from AAA or AAG; an AUG codon; at least a codon selected from UUU or UUC; at least a codon selected from the group consisting of CCU, CCC, CCA, and CCG; at least a codon selected from the group consisting of UCU, UCC, UCA, UCG, AGU, and AGC; at least a codon selected from the group consisting of ACU, ACC, ACA, and ACG; a UGG codon; at least a codon selected from UAU or UAC; and, at least a codon selected from the group consisting of GUU, GUC, GUA, and GUG.

In some specific embodiments, the limited codon set has been optimized for in vivo expression of a sequence optimized nucleic acid (e.g., a synthetic mRNA) following administration to a certain tissue or cell.

In some embodiments, the optimized codon set (e.g., a 20 codon set encoding 20 amino acids) complies at least with one of the following properties:
(i) the optimized codon set has a higher average G/C content than the original or native codon set; or,
(ii) the optimized codon set has a lower average U content than the original or native codon set; or,
(iii) the optimized codon set is composed of codons with the highest frequency; or,
(iv) the optimized codon set is composed of codons with the lowest frequency; or,
(v) a combination thereof.

In some specific embodiments, at least one codon in the optimized codon set has the second highest, the third highest, the fourth highest, the fifth highest or the sixth highest frequency in the synonymous codon set. In some specific embodiments, at least one codon in the optimized codon has the second lowest, the third lowest, the fourth lowest, the fifth lowest, or the sixth lowest frequency in the synonymous codon set.

As used herein, the term "native codon set" refers to the codon set used natively by the source organism to encode the reference nucleic acid sequence. As used herein, the term "original codon set" refers to the codon set used to encode the reference nucleic acid sequence before the beginning of sequence optimization, or to a codon set used to encode an optimized variant of the reference nucleic acid sequence at the beginning of a new optimization iteration when sequence optimization is applied iteratively or recursively.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest frequency. In other embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest frequency.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest uridine content. In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest uridine content.

In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average G/C content (absolute or relative) of the original codon set. In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average G/C content (absolute or relative) of the original codon set.

In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average uracil content (absolute or relative) of the original codon set. In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average uracil content (absolute or relative) of the original codon set.

See also U.S. Appl. Publ. No. 2011/0082055, and Int'l. Publ. No. WO2000018778, both of which are incorporated herein by reference in their entireties.

10. Characterization of Sequence Optimized Nucleic Acids

In some embodiments of the disclosure, the polynucleotide (e.g., a RNA, e.g., an mRNA) comprising a sequence optimized nucleic acid (e.g., an ORF) disclosed herein encoding an IL12A polypeptide, an IL12B polypeptide, and/or IL12A and IL12B fusion polypeptides can be can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding an IL12A polypeptide, an IL12B polypeptide, and/or IL12A and IL12B fusion polypeptides after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding an IL12A polypeptide, an IL12B polypeptide, and/or IL12A and IL12B fusion polypeptides disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the disclosure, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the disclosure, the desired property of the polynucleotide is the level of expression of an IL12A polypeptide, an IL12B polypeptide, and/or IL12A and IL12B fusion polypeptides encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the disclosure, the sequence optimization of a nucleic acid sequence disclosed herein, e.g., a nucleic acid sequence encoding an IL12A polypeptide, an IL12B polypeptide, and/or IL12A and IL12B fusion polypeptides, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding an IL12A polypeptide, an IL12B polypeptide, and/or IL12A and IL12B fusion polypeptides or a functional fragment thereof may trigger an immune response, which could be caused by (i) the therapeutic agent (e.g., an mRNA encoding an IL12A polypeptide, an IL12B polypeptide, and/or IL12A and IL12B fusion polypeptides), or (ii) the expression product of such therapeutic agent (e.g., the IL12A polypeptide, IL12B polypeptide, and/or IL12A and IL12B fusion polypeptides encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding an IL12A polypeptide, an IL12B polypeptide, and/or IL12A and IL12B fusion polypeptides or by the expression product of IL12A, IL12B, and/or IL12A and IL12B fusion encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C—X—C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-13 (11-13), interferon α (IFN-α), etc.

11. Modified Nucleotide Sequences Encoding IL12 Polypeptides

In some embodiments, the polynucleotide (e.g., a RNA, e.g., an mRNA) of the disclosure comprises a chemically modified nucleobase, e.g., 5-methoxyuracil. In some embodiments, the mRNA is a uracil-modified sequence comprising an ORF encoding an IL12B polypeptide, IL12A polypeptide, and/IL12B and IL12A fusion polypeptides, wherein the mRNA comprises a chemically modified nucleobase, e.g., 5-methoxyuracil.

In certain aspects of the disclosure, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least about 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that an mRNA provides suitable protein expression levels while inducing little to no immune response. In some embodiments, the uracil content of the ORF (% $U_{TM}$) is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140%. In other embodiments, the uracil content of the ORF is between about 117% and about 134% or between about 118% and 132% of the % $U_{TM}$. In some embodiments, the % $U_{TM}$ is about 115%, about 120%, about 125%, about 130%, about 135%, about 140%, about 145%, or about 150%. In this context, the term "uracil" can refer to 5-methoxyuracil and/or naturally occurring uracil.

In some embodiments, the uracil content in the ORF of the mRNA encoding an IL12A polypeptide, an IL12B polypeptide, and/or IL12A and IL12B fusion polypeptides of the disclosure is less than about 50%, about 40%, about 30%, or about 20% of the total nucleobase content in the ORF. In some embodiments, the uracil content in the ORF is between about 15% and about 25% of the total nucleobase content in the ORF. In other embodiments, the uracil content in the ORF is between about 20% and about 30% of the total nucleobase content in the ORF. In one embodiment, the uracil content in the ORF of the mRNA encoding an IL12A polypeptide, an IL12B polypeptide, and/or IL12A and IL12B fusion polypeptides is less than about 20% of the total nucleobase content in the open reading frame. In this context, the term "uracil" can refer to 5-methoxyuracil and/or naturally occurring uracil.

In further embodiments, the ORF of the mRNA encoding an IL12A polypeptide, an IL12B polypeptide, and/or IL12A and IL12B fusion polypeptides having 5-methoxyuracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the IL12A polypeptide, IL12B polypeptide, and/or IL12A and IL12B fusion polypeptides (% $G_{TMX}$, % $C_{TMX}$, or % $G/C_{TMX}$). In other embodiments, the G, the C, or the G/C content in the ORF is between about 70% and about 80%, between about 71% and about 79%, between about 71% and about 78%, or between about 71% and about 77% of the % $G_{TMX}$, % $C_{TMX}$, or % $G/C_{TMX}$. In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding an IL12A polypeptide, an IL12B polypeptide, and/or IL12A and IL12B fusion polypeptides of the disclosure comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the IL12A polypeptide, IL12B polypeptide, and/or IL12A and IL12B fusion polypeptides. In some embodiments, the ORF of the mRNA encoding an IL12A polypeptide, an IL12B polypeptide, and/or IL12A and IL12B fusion polypeptides of the disclosure contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the IL12A polypeptide, IL12B polypeptide, and/or IL12A and IL12B fusion polypeptides. In a particular embodiment, the ORF of the mRNA encoding the IL12A polypeptide, IL12B polypeptide, and/or IL12A and IL12B fusion polypeptides of the disclosure contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the IL12A polypeptide, IL12B polypeptide, and/or IL12A and IL12B fusion polypeptides contains no non-phenylalanine uracil pairs and/or triplets.

In further embodiments, the ORF of the mRNA encoding an IL12A polypeptide, an IL12B polypeptide, and/or IL12A and IL12B fusion polypeptides of the disclosure comprises 5-methoxyuracil and has an adjusted uracil content containing less uracil-rich clusters than the corresponding wild-type nucleotide sequence encoding the IL12A polypeptide, IL12B polypeptide, and/or IL12A and IL12B fusion polypeptides. In some embodiments, the ORF of the mRNA encoding the IL12A polypeptide, IL12B polypeptide, and/or IL12A and IL12B fusion polypeptides of the disclosure contains uracil-rich clusters that are shorter in length than corresponding uracil-rich clusters in the corresponding wild-type nucleotide sequence encoding the IL12A polypeptide, IL12B polypeptide, and/or IL12A and IL12B fusion polypeptides.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the IL12A polypeptide, IL12B polypeptide, and/or IL12A and IL12B fusion polypeptides-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the IL12A polypeptide, IL12B polypeptide, and/or IL12A and IL12B fusion polypeptides is substituted with an alternative codon having a codon frequency lower than the codon frequency of the substituted codon in the synonymous codon set.

In some embodiments, the adjusted uracil content, IL12A polypeptide, IL12B polypeptide, and/or IL12A and IL12B fusion polypeptides-encoding ORF of the 5-methoxyuracil-comprising mRNA exhibits expression levels of IL12 when administered to a mammalian cell that are higher than expression levels of IL12 from the corresponding wild-type mRNA. In other embodiments, the expression levels of IL12 when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of IL12 when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, IL12 is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the IL12 polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, IL12A polypeptide, IL12B polypeptide, and/or IL12A and IL12B fusion polypeptides-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present disclosure induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for an L12B polypeptide, L12A polypeptide, and/or L12A and IL12B fusion polypeptides but does not comprise 5-methoxyuracil under the same conditions, or relative to the immune response induced by an mRNA that encodes for an IL12A polypeptide, IL12B polypeptide, and/or IL12A and IL12B fusion polypeptides and that comprises 5-methoxyuracil but that does not have adjusted uracil content under the same conditions. The innate immune response can be manifested by increased expression of pro-inflammatory cytokines, activation of intracellular PRRs (RIG-I, MDA5, etc), cell death, and/or termination or reduction in protein translation. In some embodiments, a reduction in the innate immune response can be measured by expression or activity level of Type 1 interferons (e.g., IFN-α, IFN-β, IFN-κ, IFN-6, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the disclosure into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes an IL12A polypeptide, an IL12B polypeptide, and/or IL12A and IL12B fusion polypeptides but does not comprise 5-methoxyuracil, or to an mRNA that encodes an IL12A polypeptide, an IL12B polypeptide, and/or IL12A and IL12B fusion polypeptides and that comprises 5-methoxyuracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for an IL12A polypeptide, an IL12B polypeptide, and/or IL12A and IL12B fusion polypeptides but does not comprise 5-methoxyuracil, or an mRNA that encodes for an IL12A polypeptide, an IL12B polypeptide, and/or IL12A and IL12B fusion polypeptides and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes an IL12A polypeptide, an IL12B polypeptide, and/or IL12A and IL12B fusion polypeptides, wherein uracil in the mRNA is at least about 95% 5-methoxyuracil, wherein the uracil content of the ORF is between about 115% and about 135% of the theoretical minimum uracil content in the corresponding wild-type ORF, and wherein the uracil content in the ORF encoding the IL12A polypeptide, IL12B polypeptide, and/or IL12A and IL12B fusion polypeptides is less than about 30% of the total nucleobase content in the ORF. In some embodiments, the ORF that encodes the IL12A polypeptide, IL12B polypeptide, and/or IL12A and IL12B fusion polypeptides is further modified to increase G/C content of the ORF (absolute or relative) by at least about 40%, as compared to the corresponding wild-type ORF. In yet other embodiments, the ORF encoding the IL12A polypeptide, IL12B polypeptide, and/or IL12A and IL12B fusion polypeptides contains less than 20 non-phenylalanine uracil pairs and/or triplets. In some embodiments, at least one codon in the ORF of the mRNA encoding the IL12A polypeptide, IL12B polypeptide, and/or IL12A and IL12B fusion polypeptides is further substituted with an alternative codon having a codon frequency lower than the codon frequency of the substituted codon in the synonymous codon set. In some embodiments, the expression of the IL12A polypeptide, IL12B polypeptide, and/or IL12A and IL12B fusion polypeptides encoded by an mRNA comprising an ORF wherein uracil in the mRNA is at least about 95% 5-methoxyuracil, and wherein the uracil content of the ORF is between about 115% and about 135% of the theoretical minimum uracil content in the corresponding wild-type ORF, is increased by at least about 10-fold when compared to expression of the IL12A polypeptide, IL12B polypeptide, and/or IL12A and IL12B fusion polypeptides from the corresponding wild-type mRNA. In some embodiments, the mRNA comprises an open ORF wherein uracil in the mRNA is at least about 95% 5-methoxyuracil, and wherein the uracil content of the ORF is between about 115% and about 135% of the theoretical minimum uracil content in the corresponding wild-type ORF, and wherein the mRNA does not substantially induce an innate immune response of a mammalian cell into which the mRNA is introduced.

12. Methods for Modifying Polynucleotides

The disclosure includes modified polynucleotides comprising a polynucleotide described herein (e.g., a polynucleotide comprising a nucleotide sequence encoding an IL12A polypeptide, an IL12B polypeptide, and/or IL12A and IL12B fusion polypeptides). The modified polynucleotides can be chemically modified and/or structurally modified. When the polynucleotides of the present disclosure are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding an IL12A polypeptide, an IL12B polypeptide, and/or IL12A and IL12B fusion polypeptides. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell may exhibit one or more desirable properties, e.g., improved protein expression, reduced immunogenicity, or reduced degradation in the cell, as compared to an unmodified polynucleotide.

a. Structural Modifications

In some embodiments, a polynucleotide of the present disclosure (e.g., a polynucleotide comprising a nucleotide sequence encoding an IL12A polypeptide, an IL12B polypeptide, and/or IL12A and IL12B fusion polypeptides) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG (SEQ ID NO: 230)" can be chemically modified to "AT-5meC-G". The same polynucleotide can be structurally modified from "ATCG (SEQ ID NO: 230)" to "ATCCG (SEQ ID NO: 231)". Here, the dinucleotide "CC" has been inserted, resulting in a structural modification to the polynucleotide.

b. Chemical Modifications

In some embodiments, the polynucleotides of the present disclosure (e.g., a polynucleotide comprising a nucleotide sequence encoding an IL12A polypeptide, an IL12B polypeptide, and/or IL12A and IL12B fusion polypeptides) are chemically modified. As used herein in reference to a polynucleotide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population, including, but not limited to, its nucleobase, sugar, backbone, or any combination thereof. Generally, herein, these terms are not intended to refer to the ribonucleotide modifications in naturally occurring 5'-terminal mRNA cap moieties.

In some embodiments, the polynucleotides of the disclosure (e.g., a polynucleotide comprising a nucleotide sequence encoding an IL12A polypeptide, an IL12B polypeptide, and/or IL12A and IL12B fusion polypeptides) can have a uniform chemical modification of all or any of the same nucleoside type or a population of modifications produced by downward titration of the same starting modification in all or any of the same nucleoside type, or a measured percent of a chemical modification of all any of the same nucleoside type but with random incorporation, such as where all uridines are replaced by a uridine analog, e.g., 5-methoxyuridine. In another embodiment, the polynucleotides can have a uniform chemical modification of two, three, or four of the same nucleoside type throughout the entire polynucleotide (such as all uridines and/or all cytidines, etc. are modified in the same way).

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the composition of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl) cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-

Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-α-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-α-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethyl aminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methylaminomethyl-2-selenouridine; 5-methylaminomethyl-2-thiouridine; 5-methyl aminomethyluridine; 5-Methyldihydrouridine; 5-Oxyacetic acid-Uridine TP; 5-Oxyacetic acid-methyl ester-Uridine TP; N1-methyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylaminocarbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethyl enyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio) pseudouracil; 1 substituted pseudouracil; 1-(aminoalkylaminocarbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio) pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethyl aminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl)

2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio) uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl)pseudouridine TP; (E)-5-(2-Bromo-vinyl)ara-uridine TP; (E)-5-(2-Bromo-vinyl)uridine TP; (Z)-5-(2-Bromo-vinyl)ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl)pseudo-UTP; 1-(2-Amino-2-carboxyethyl)pseudo-UTP; 1-(2-Amino-ethyl)pseudo-UTP; 1-(2-Hydroxyethyl)pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl)pseudo-UTP; 1-(4-Amino-butyl)pseudo-UTP; 1-(4-Aminophenyl)pseudo-UTP; 1-(4-Azidobenzyl)pseudouridine TP; 1-(4-Bromobenzyl)pseudouridine TP; 1-(4-Chlorobenzyl)pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl)pseudouridine TP; 1-(4-Nitro-benzyl)pseudo-UTP; 1(4-Nitro-phenyl)pseudo-UTP; 1-(4-Thiomethoxybenzyl)pseudouridine TP; 1-(4-Trifluoromethoxybenzyl)pseudouridine TP; 1-(4-Trifluoromethylbenzyl)pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl)pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-α-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxypseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluoro-cytidine; 2' methyl, 2'amino, 2'azido, 2'fluoro-adenine; 2'methyl, 2'amino, 2'azido, 2'fluorouridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkylhydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), N1-methylpseudouridine (m1ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyl-adenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, N1-methylpseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases. In one particular embodiment, the at least one chemically modified nucleoside is N1-methylpseudouridine.

(i) Base Modifications

In certain embodiments, the chemical modification is at nucleobases in the polynucleotides (e.g., RNA polynucleotide, such as mRNA polynucleotide).

In some embodiments, a polynucleotide as disclosed herein comprises at least one chemically modified nucleobase.

In some embodiments, the at least one chemically modified nucleobase is selected from the group consisting of pseudouracil (ψ), N1-methylpseudouracil (m1ψ), 2-thiouracil (s2U), 4'-thiouracil, 5-methylcytosine, 2-thio-1-methyl-1-deaza-pseudouracil, 2-thio-1-methyl-pseudouracil, 2-thio-5-aza-uracil, 2-thio-dihydropseudouracil, 2-thio-dihydrouracil, 2-thio-pseudouracil, 4-methoxy-2-thio-pseudouracil, 4-methoxy-pseudouracil, 4-thio-1-methyl-pseudouracil, 4-thio-pseudouracil, 5-aza-uracil, dihydropseudouracil, 5-methyluracil, 5-methoxyuracil, 2'-O-methyl uracil, 1-methyl-pseudouracil (m1ψ), 5-methoxy-uracil (mo5U), 5-methyl-cytosine (m5C), α-thio-guanine, α-thio-adenine, 5-cyano uracil, 4'-thio uracil, 7-deaza-adenine, 1-methyl-adenine (m1A), 2-methyl-adenine (m2A), N6-methyl-adenine (m6A), and 2,6-Di-aminopurine, (I), 1-methyl-inosine (m1I), wyosine (imG), methylwyosine (mimG), 7-deaza-guanine, 7-cyano-7-deaza-guanine (preQ0), 7-aminomethyl-7-deaza-guanine (preQ1), 7-methyl-guanine (m7G), 1-methyl-guanine (m1G), 8-oxo-guanine, 7-methyl-8-oxo-guanine, and two or more combinations thereof.

In some embodiments, the nucleobases in a polynucleotide as disclosed herein are chemically modified by at least about 10%, at least about 20%, at least about 30%, at least about 40%, at least about 50%, at least about 60%, at least about 70%, at least about 80%, at least about 90%, at least 95%, at least 99%, or 100%.

In some embodiments, the chemically modified nucleobases are selected from the group consisting of uracil, adenine, cytosine, guanine, and any combination thereof.

In some embodiments, the uracils in a polynucleotide disclosed herein are chemically modified by at least about 10%, at least about 20%, at least about 30%, at least about 40%, at least about 50%, at least about 60%, at least about 70%, at least about 80%, at least about 90%, at least 95%, at least 99%, or 100%.

In some embodiments, the adenines in a polynucleotide disclosed herein are chemically modified by at least about 10%, at least about 20%, at least about 30%, at least about 40%, at least about 50%, at least about 60%, at least about 70%, at least about 80%, at least about 90%, at least 95%, at least 99%, or 100%.

In some embodiments, the cytosines in a polynucleotide disclosed herein are chemically modified by at least about 10%, at least about 20%, at least about 30%, at least about 40%, at least about 50%, at least about 60%, at least about 70%, at least about 80%, at least about 90%, at least 95%, at least 99%, or 100%.

In some embodiments, the guanines in a polynucleotide disclosed herein are chemically modified by at least about 10%, at least about 20%, at least about 30%, at least about 40%, at least about 50%, at least about 60%, at least about 70%, at least about 80%, at least about 90%, at least 95%, at least 99%, or 100%.

In some embodiments, the polynucleotide (e.g., RNA polynucleotide, such as mRNA polynucleotide) includes a combination of at least two (e.g., 2, 3, 4 or more) of modified nucleobases.

In some embodiments, modified nucleobases in the polynucleotide (e.g., RNA polynucleotide, such as mRNA polynucleotide) are selected from the group consisting of 1-methyl-pseudouridine (m1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, at least 95% of a type of nucleobases (e.g., uracil) in a polynucleotide of the disclosure (e.g., an mRNA polynucleotide encoding an IL12B polypeptide, an IL12A polypeptide, and/or IL12A and IL12B fusion polypeptides) are modified nucleobases. In some embodiments, at least 95% of uracil in a polynucleotide of the present disclosure (e.g., an mRNA polynucleotide encoding an IL12B polypeptide, an IL12A polypeptide, and/or IL12A and IL12B fusion polypeptides) is 5-methoxyuracil.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the nucleobases, sugar, backbone, or any combination thereof in the open reading frame encoding an IL12B polypeptide, an IL12A polypeptide, and/or IL12A and IL12B fusion polypeptides are chemically modified by at least 10%, at least 20%, at least 30%, at least 40%, at least 50%, at least 60%, at least 70%, at least 80%, at least 90%, at least 95%, at least 99%, or 100%.

In some embodiments, the uridine nucleosides in the open reading frame encoding IL12B polypeptide, an IL12A polypeptide, and/or IL12A and IL12B fusion polypeptides are chemically modified by at least 10%, at least 20%, at least 30%, at least 40%, at least 50%, at least 60%, at least 70%, at least 80%, at least 90%, at least 95%, at least 99%, or 100%.

In some embodiments, the adenosine nucleosides in the open reading frame encoding an IL12B polypeptide, an IL12A polypeptide, and/or IL12A and IL12B fusion polypeptides are chemically modified by at least 10%, at least 20%, at least 30%, at least 40%, at least 50%, at least 60%, at least 70%, at least 80%, at least 90%, at least 95%, at least 99%, or 100%.

In some embodiments, the cytidine nucleosides in the open reading frame encoding an IL12B polypeptide, an IL12A polypeptide, and/or IL12A and IL12B fusion polypeptides are chemically modified by at least at least 10%, at least 20%, at least 30%, at least 40%, at least 50%, at least 60%, at least 70%, at least 80%, at least 90%, at least 95%, at least 99%, or 100%.

In some embodiments, the guanosine nucleosides in the open reading frame encoding an IL12B polypeptide, an IL12A polypeptide, and/or IL12A and IL12B fusion polypeptides are chemically modified by at least at least 10%, at least 20%, at least 30%, at least 40%, at least 50%, at least 60%, at least 70%, at least 80%, at least 90%, at least 95%, at least 99%, or 100%.

In some embodiments, the polynucleotides can include any useful linker between the nucleosides, including subunit and heterologous polypeptide linkers as disclosed elsewhere herein. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, $-CH_2-O-N(CH_3)-CH_2-$, $-CH_2-N(CH_3)-N(CH_3)-CH_2-$, $-CH_2-NH-CH_2-$, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, $-N(CH_3)-CH_2-CH_2-$, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

(ii) Sugar Modifications

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $-O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'-2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013052523 and WO2014093924, the contents of each of which are incorporated herein by reference in their entireties.

(iii) Combinations of Modifications

The polynucleotides of the disclosure (e.g., a polynucleotide comprising a nucleotide sequence encoding an IL12A polypeptide, an IL12B polypeptide, and/or IL12A and IL12B fusion polypeptides or a functional fragment or variant thereof) can include a combination of modifications to the sugar, the nucleobase, and/or the internucleoside linkage. These combinations can include any one or more modifications described herein.

Examples of modified nucleotides and modified nucleotide combinations are provided below in Table 5. Combinations of modified nucleotides can be used to form the polynucleotides of the disclosure. Unless otherwise noted, the modified nucleotides can be completely substituted for the natural nucleotides of the polynucleotides of the disclosure. As a non-limiting example, the natural nucleotide uridine can be substituted with a modified nucleoside described herein. In another non-limiting example, the natural nucleotide uridine can be partially substituted or replaced (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein. Any combination of base/sugar or linker can be incorporated into the polynucleotides of the disclosure and such modifications are taught in International Patent Publications WO2013052523 and WO2014093924, and U.S. Publ. Nos. US 20130115272 and US20150307542, the contents of each of which are incorporated herein by reference in its entirety.

TABLE 5

| Combinations | | | |
|---|---|---|---|
| Uracil | Cytosine | Adenine | Guanine |
| 5-Methoxy-UTP | CTP | ATP | GTP |
| 5-Methoxy-UTP | N4Ac-CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4Ac-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4-Ac-CTP | ATP | GTP |
| 5-Methoxy-UTP | 5-Iodo-CTP | ATP | GTP |
| 5-Methoxy-UTP | 5-Bromo-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |

TABLE 5-continued

| Combinations | | | |
|---|---|---|---|
| Uracil | Cytosine | Adenine | Guanine |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | CTP | Alpha-thio-ATP | GTP |
| 5-Methoxy-UTP | 5-Methyl-CTP | Alpha-thio-ATP | GTP |
| 5-Methoxy-UTP | CTP | ATP | Alpha-thio-GTP |
| 5-Methoxy-UTP | 5-Methyl-CTP | ATP | Alpha-thio-GTP |
| 5-Methoxy-UTP | CTP | N6-Me-ATP | GTP |
| 5-Methoxy-UTP | 5-Methyl-CTP | N6-Me-ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | 5-Ethyl-CTP | ATP | GTP |
| 5-Methoxy-UTP | 5-Methoxy-CTP | ATP | GTP |
| 5-Methoxy-UTP | 5-Ethynyl-CTP | ATP | GTP |
| 5-Methoxy-UTP | CTP | ATP | GTP |

TABLE 5-continued

| Combinations | | | |
|---|---|---|---|
| Uracil | Cytosine | Adenine | Guanine |
| 5-Methoxy-UTP | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% 1-Methyl-pseudo-UTP | 5-Methyl-CTP | ATP | GTP |
| 50% 5-Methoxy-UTP + 50% 1-Methyl-pseudo-UTP | 5-Methyl-CTP | ATP | GTP |
| 25% 5-Methoxy-UTP + 75% 1-Methyl-pseudo-UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% 1-Methyl-pseudo-UTP | 75% 5-Methyl-CTP + 25% CTP | ATP | GTP |
| 75% 5-Methoxy-UTP + 25% 1-Methyl-pseudo-UTP | 50% 5-Methyl-CTP + 50% CTP | ATP | GTP |
| 75% 5-Methoxy-UTP + 25% 1-Methyl-pseudo-UTP | 25% 5-Methyl-CTP + 75% CTP | ATP | GTP |
| 50% 5-Methoxy-UTP + 50% 1-Methyl-pseudo-UTP | 75% 5-Methyl-CTP + 25% CTP | ATP | GTP |
| 50% 5-Methoxy-UTP + 50% 1-Methyl-pseudo-UTP | 50% 5-Methyl-CTP + 50% CTP | ATP | GTP |
| 50% 5-Methoxy-UTP + 50% 1-Methyl-pseudo-UTP | 25% 5-Methyl-CTP + 75% CTP | ATP | GTP |
| 25% 5-Methoxy-UTP + 75% 1-Methyl-pseudo-UTP | 75% 5-Methyl-CTP + 25% CTP | ATP | GTP |
| 25% 5-Methoxy-UTP + 75% 1-Methyl-pseudo-UTP | 50% 5-Methyl-CTP + 50% CTP | ATP | GTP |
| 25% 5-Methoxy-UTP + 75% 1-Methyl-pseudo-UTP | 25% 5-Methyl-CTP + 75% CTP | ATP | GTP |
| 75% 5-Methoxy-UTP + 25% 1-Methyl-pseudo-UTP | CTP | ATP | GTP |
| 50% 5-Methoxy-UTP + 50% 1-Methyl-pseudo-UTP | CTP | ATP | GTP |
| 25% 5-Methoxy-UTP + 75% 1-Methyl-pseudo-UTP | CTP | ATP | GTP |
| 5-methoxy-UTP | CTP | ATP | GTP |
| 5-methoxy-UTP | CTP | ATP | GTP |
| 5-methoxy-UTP | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |

TABLE 5-continued

| Uracil | Cytosine | Adenine | Guanine |
|---|---|---|---|
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |

TABLE 5-continued

| Uracil | Cytosine | Adenine | Guanine |
|---|---|---|---|
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | 5-Fluoro-CTP | ATP | GTP |
| 5-Methoxy-UTP | 5-Phenyl-CTP | ATP | GTP |
| 5-Methoxy-UTP | N4-Bz-CTP | ATP | GTP |
| 5-Methoxy-UTP | CTP | N6-Isopentenyl-ATP | GTP |
| 5-Methoxy-UTP | N4-Ac-CTP | ATP | GTP |
| 25% 5-Methoxy-UTP + 75% UTP | 25% N4-Ac-CTP + 75% CTP | ATP | GTP |
| 25% 5-Methoxy-UTP + 75% UTP | 75% N4-Ac-CTP + 25% CTP | ATP | GTP |
| 75% 5-Methoxy-UTP + 25% UTP | 25% N4-Ac-CTP + 75% CTP | ATP | GTP |
| 75% 5-Methoxy-UTP + 25% UTP | 75% N4-Ac-CTP + 25% CTP | ATP | GTP |
| 5-Methoxy-UTP | 5-Hydroxymethyl-CTP | ATP | GTP |
| 25% 5-Methoxy-UTP + 75% UTP | 25% 5-Hydroxymethyl-CTP + 75% CTP | ATP | GTP |
| 25% 5-Methoxy-UTP + 75% UTP | 75% 5-Hydroxymethyl-CTP + 25% CTP | ATP | GTP |
| 75% 5-Methoxy-UTP + 25% UTP | 25% 5-Hydroxymethyl-CTP + 75% CTP | ATP | GTP |
| 75% 5-Methoxy-UTP + 25% UTP | 75% 5-Hydroxymethyl-CTP + 25% CTP | ATP | GTP |
| 5-Methoxy-UTP | N4-Methyl CTP | ATP | GTP |
| 25% 5-Methoxy-UTP + 75% UTP | 25% N4-Methyl CTP + 75% CTP | ATP | GTP |
| 25% 5-Methoxy-UTP + 75% UTP | 75% N4-Methyl CTP + 25% CTP | ATP | GTP |
| 75% 5-Methoxy-UTP + 25% UTP | 25% N4-Methyl CTP + 75% CTP | ATP | GTP |
| 75% 5-Methoxy-UTP + 25% UTP | 75% N4-Methyl CTP + 25% CTP | ATP | GTP |
| 5-Methoxy-UTP | 5-Trifluoromethyl-CTP | ATP | GTP |
| 25% 5-Methoxy-UTP + 75% UTP | 25% 5-Trifluoromethyl-CTP + 75% CTP | ATP | GTP |
| 25% 5-Methoxy-UTP + 75% UTP | 75% 5-Trifluoromethyl-CTP + 25% CTP | ATP | GTP |
| 75% 5-Methoxy-UTP + 25% UTP | 25% 5-Trifluoromethyl-CTP + 75% CTP | ATP | GTP |
| 75% 5-Methoxy-UTP + 25% UTP | 75% 5-Trifluoromethyl-CTP + 25% CTP | ATP | GTP |
| 5-Methoxy-UTP | 5-Bromo-CTP | ATP | GTP |

TABLE 5-continued

| Combinations | | | |
|---|---|---|---|
| Uracil | Cytosine | Adenine | Guanine |
| 25% 5-Methoxy-UTP + 75% UTP | 25% 5-Bromo-CTP + 75% CTP | ATP | GTP |
| 25% 5-Methoxy-UTP + 75% UTP | 75% 5-Bromo-CTP + 25% CTP | ATP | GTP |
| 75% 5-Methoxy-UTP + 25% UTP | 25% 5-Bromo-CTP + 75% CTP | ATP | GTP |
| 75% 5-Methoxy-UTP + 25% UTP | 75% 5-Bromo-CTP + 25% CTP | ATP | GTP |
| 5-Methoxy-UTP | 5-Iodo-CTP | ATP | GTP |
| 25% 5-Methoxy-UTP + 75% UTP | 25% 5-Iodo-CTP + 75% CTP | ATP | GTP |
| 25% 5-Methoxy-UTP + 75% UTP | 75% 5-Iodo-CTP + 25% CTP | ATP | GTP |
| 75% 5-Methoxy-UTP + 25% UTP | 25% 5-Iodo-CTP + 75% CTP | ATP | GTP |
| 75% 5-Methoxy-UTP + 25% UTP | 75% 5-Iodo-CTP + 25% CTP | ATP | GTP |
| 5-Methoxy-UTP | 5-Ethyl-CTP | ATP | GTP |
| 25% 5-Methoxy-UTP + 75% UTP | 25% 5-Ethyl-CTP + 75% CTP | ATP | GTP |
| 25% 5-Methoxy-UTP + 75% UTP | 75% 5-Ethyl-CTP + 25% CTP | ATP | GTP |
| 75% 5-Methoxy-UTP + 25% UTP | 25% 5-Ethyl-CTP + 75% CTP | ATP | GTP |
| 75% 5-Methoxy-UTP + 25% UTP | 75% 5-Ethyl-CTP + 25% CTP | ATP | GTP |
| 5-Methoxy-UTP | 5-Methoxy-CTP | ATP | GTP |
| 25% 5-Methoxy-UTP + 75% UTP | 25% 5-Methoxy-CTP + 75% CTP | ATP | GTP |
| 25% 5-Methoxy-UTP + 75% UTP | 75% 5-Methoxy-CTP + 25% CTP | ATP | GTP |
| 75% 5-Methoxy-UTP + 25% UTP | 25% 5-Methoxy-CTP + 75% CTP | ATP | GTP |
| 75% 5-Methoxy-UTP + 25% UTP | 75% 5-Methoxy-CTP + 25% CTP | ATP | GTP |
| 5-Methoxy-UTP | 5-Ethynyl-CTP | ATP | GTP |
| 25% 5-Methoxy-UTP + 75% UTP | 25% 5-Ethynyl-CTP + 75% CTP | ATP | GTP |
| 25% 5-Methoxy-UTP + 75% UTP | 75% 5-Ethynyl-CTP + 25% CTP | ATP | GTP |
| 75% 5-Methoxy-UTP + 25% UTP | 25% 5-Ethynyl-CTP + 75% CTP | ATP | GTP |
| 75% 5-Methoxy-UTP + 25% UTP | 75% 5-Ethynyl-CTP + 25% CTP | ATP | GTP |
| 5-Methoxy-UTP | 5-Pseudo-iso-CTP | ATP | GTP |
| 25% 5-Methoxy-UTP + 75% UTP | 25% 5-Pseudo-iso-CTP + 75% CTP | ATP | GTP |
| 25% 5-Methoxy-UTP + 75% UTP | 75% 5-Pseudo-iso-CTP + 25% CTP | ATP | GTP |
| 75% 5-Methoxy-UTP + 25% UTP | 25% 5-Pseudo-iso-CTP + 75% CTP | ATP | GTP |
| 75% 5-Methoxy-UTP + 25% UTP | 75% 5-Pseudo-iso-CTP + 25% CTP | ATP | GTP |
| 5-Methoxy-UTP | 5-Formyl-CTP | ATP | GTP |
| 25% 5-Methoxy-UTP + 75% UTP | 25% 5-Formyl-CTP + 75% CTP | ATP | GTP |
| 25% 5-Methoxy-UTP + 75% UTP | 75% 5-Formyl-CTP + 25% CTP | ATP | GTP |
| 75% 5-Methoxy-UTP + 25% UTP | 25% 5-Formyl-CTP + 75% CTP | ATP | GTP |
| 75% 5-Methoxy-UTP + 25% UTP | 75% 5-Formyl-CTP + 25% CTP | ATP | GTP |
| 5-Methoxy-UTP | 5-Aminoallyl-CTP | ATP | GTP |
| 25% 5-Methoxy-UTP + 75% UTP | 25% 5-Aminoallyl-CTP + 75% CTP | ATP | GTP |
| 25% 5-Methoxy-UTP + 75% UTP | 75% 5-Aminoallyl-CTP + 25% CTP | ATP | GTP |
| 75% 5-Methoxy-UTP + 25% UTP | 25% 5-Aminoallyl-CTP + 75% CTP | ATP | GTP |
| 75% 5-Methoxy-UTP + 25% UTP | 75% 5-Aminoallyl-CTP + 25% CTP | ATP | GTP |

13. Untranslated Regions (UTRS)

Untranslated regions (UTRs) are nucleic acid sections of a polynucleotide before a start codon (5'UTR) and after a stop codon (3'UTR) that are not translated. In some embodiments, a polynucleotide (e.g., a ribonucleic acid (RNA), e.g., a messenger RNA (mRNA)) of the disclosure comprising an open reading frame (ORF) encoding an IL12B polypeptide, an IL12A polypeptide, and/or IL12A and IL12B fusion polypeptides further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the IL12 polypeptide. In some embodiments, the UTR is heterologous to the ORF encoding the IL12 polypeptide. In some embodiments, the polynucleotide comprises two or more 5'UTRs or functional fragments thereof, each of which have the same or different nucleotide sequences. In some embodiments, the polynucleotide comprises two or more 3'UTRs or functional fragments thereof, each of which have the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG (SEQ ID NO: 232), where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR. In some embodiments, the 3'UTR can be derived from a different species than the 5'UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present disclosure as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 a polypeptide); an albumin (e.g., human albumin7); a HSD17B4 (hydroxysteroid (17-13) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the 0 subunit of mitochondrial H$^+$-ATP synthase); a growth hormone e (e.g., bovine (bGH) or human (hGH)); an elongation factor (e.g., elongation factor 1 al (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

Other exemplary 5' and 3' UTRs include, but are not limited to, those described in Karikó et al., Mol. Ther. 2008 16(11):1833-1840; Karikó et al., Mol. Ther. 2012 20(5):948-953; Karikó et al., Nucleic Acids Res. 2011 39(21):e142; Strong et al., Gene Therapy 1997 4:624-627; Hansson et al., J. Biol. Chem. 2015 290(9):5661-5672; Yu et al., Vaccine 2007 25(10):1701-1711; Cafri et al., Mol. Ther. 2015 23(8):1391-1400; Andries et al., Mol. Pharm. 2012 9(8):2136-2145; Crowley et al., Gene Ther. 2015 Jun. 30, doi:10.1038/gt.2015.68; Ramunas et al., FASEB J. 2015 29(5):1930-1939; Wang et al., Curr. Gene Ther. 2015 15(4):428-435; Holtkamp et al., Blood 2006 108(13):4009-4017; Kormann et al., Nat. Biotechnol. 2011 29(2):154-157; Poleganov et al., Hum. Gen. Ther. 2015 26(11):751-766; Warren et al., Cell Stem Cell 2010 7(5):618-630; Mandal and Rossi, Nat. Protoc. 2013 8(3):568-582; Holcik and Liebhaber, PNAS 1997 94(6):2410-2414; Ferizi et al., Lab Chip. 2015 15(17):

3561-3571; Thess et al., Mol. Ther. 2015 23(9):1456-1464; Boros et al., PLoS One 2015 10(6):e0131141; Boros et al., J. Photochem. Photobiol. B. 2013 129:93-99; Andries et al., J. Control. Release 2015 217:337-344; Zinckgraf et al., Vaccine 2003 21(15):1640-9; Garneau et al., J. Virol. 2008 82(2):880-892; Holden and Harris, Virology 2004 329(1):119-133; Chiu et al., J. Virol. 2005 79(13):8303-8315; Wang et al., EMBO J. 1997 16(13):4107-4116; Al-Zoghaibi et al., Gene 2007 391(1-2):130-9; Vivinus et al., Eur. J. Biochem. 2001 268(7):1908-1917; Gan and Rhoads, J. Biol. Chem. 1996 271(2):623-626; Boado et al., J. Neurochem. 1996 67(4):1335-1343; Knirsch and Clerch, Biochem. Biophys. Res. Commun. 2000 272(1):164-168; Chung et al., Biochemistry 1998 37(46):16298-16306; Izquierdo and Cuevza, Biochem. J. 2000 346 Pt 3:849-855; Dwyer et al., J. Neurochem. 1996 66(2):449-458; Black et al., Mol. Cell. Biol. 1997 17(5):2756-2763; Izquierdo and Cuevza, Mol. Cell. Biol. 1997 17(9):5255-5268; U.S. Pat. Nos. 8,278,036; 8,748,089; 8,835,108; 9,012,219; US2010/0129877; US2011/0065103; US2011/0086904; US2012/0195936; US2014/020675; US2013/0195967; US2014/029490; US2014/0206753; WO2007/036366; WO2011/015347; WO2012/072096; WO2013/143555; WO2014/071963; WO2013/185067; WO2013/182623; WO2014/089486; WO2013/185069; WO2014/144196; WO2014/152659; 2014/152673; WO2014/152940; WO2014/152774; WO2014/153052; WO2014/152966; WO2014/152513; WO2015/101414; WO2015/101415; WO2015/062738; and WO2015/024667; the contents of each of which are incorporated herein by reference in their entirety.

In some embodiments, the 5'UTR is selected from the group consisting of a 3-globin 5'UTR; a 5'UTR containing a strong Kozak translational initiation signal; a cytochrome b-245 a polypeptide (CYBA) 5'UTR; a hydroxysteroid (17-13) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR; α-globin 3'UTR; a DEN 3'UTR; a PAV barley yellow dwarf virus (BYDV-PAV) 3'UTR; an elongation factor 1 al (EEF1A1) 3'UTR; a manganese superoxide dismutase (MnSOD) 3'UTR; a P subunit of mitochondrial H(+)-ATP synthase (β-mRNA) 3'UTR; a GLUT1 3'UTR; a MEF2A 3'UTR; a β-F1-ATPase 3'UTR; functional fragments thereof and combinations thereof.

Other exemplary UTRs include, but are not limited to, one or more of the UTRs, including any combination of UTRs, disclosed in WO2014/164253, the contents of which are incorporated herein by reference in their entirety. Shown in Table 21 of U.S. Provisional Application No. 61/775,509 and in Table 22 of U.S. Provisional Application No. 61/829,372, the contents of each are incorporated herein by reference in their entirety, is a listing start and stop sites for 5'UTRs and 3'UTRs. In Table 21, each 5'UTR (5'-UTR-005 to 5'-UTR 68511) is identified by its start and stop site relative to its native or wild-type (homologous) transcript (ENST; the identifier used in the ENSEMBL database).

Wild-type UTRs derived from any gene or mRNA can be incorporated into the polynucleotides of the disclosure. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, the contents of which are incorporated herein by reference in their entirety, and sequences available at www.addgene.org/Derrick_Rossi/, last accessed Apr. 16, 2016. UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the disclosure comprise a 5'UTR and/or a 3'UTR selected from any of the UTRs disclosed herein. In some embodiments, the 5'UTR comprises:

```
5'UTR-001 (Upstream UTR)
                                       (SEQ ID NO. 135)
(GGGAAATAAGAGAGAAAAGAAGAGTAAGAAGAAATATAAGAGCCACC);

5'UTR-002 (Upstream UTR)
                                       (SEQ ID NO. 136)
(GGGAGATCAGAGAGAAAAGAAGAGTAAGAAGAAATATAAGAGCCACC);

5'UTR-003 (Upstream UTR)
                                       (SEQ ID NO. 137)
(GGAATAAAAGTCTCAACACAACATATACAAAACAAACGAATCTCAAGCA

ATCAAGCATTCTACTTCTATTGCAGCAATTTAAATCATTTCTTTTAAAGC

AAAAGCAATTTTCTGAAAATTTTCACCATTTACGAACGATAGCAAC);

5'UTR-004 (Upstream UTR)
                                       (SEQ ID NO. 138)
(GGGAGACAAGCUUGGCAUUCCGGUACUGUUGGUAAAGCCACC);

5'UTR-005 (Upstream UTR)
                                       (SEQ ID NO. 139)
(GGGAGATCAGAGAGAAAAGAAGAGTAAGAAGAAATATAAGAGCCACC);

5'UTR-006 (Upstream UTR)
                                       (SEQ ID NO. 140)
(GGAATAAAAGTCTCAACACAACATATACAAAACAAACGAATCTCAAGC

AATCAAGCATTCTACTTCTATTGCAGCAATTTAAATCATTTCTTTTAAA

GCAAAAGCAATTTTCTGAAAATTTTCACCATTTACGAACGATAGCAAC);

5'UTR-007 (Upstream UTR)
                                       (SEQ ID NO. 141)
(GGGAGACAAGCUUGGCAUUCCGGUACUGUUGGUAAAGCCACC);

5'UTR-008 (Upstream UTR)
                                       (SEQ ID NO. 142)
(GGGAATTAACAGAGAAAAGAAGAGTAAGAAGAAATATAAGAGCCACC);
```

5'UTR-009 (Upstream UTR)
(SEQ ID NO. 143)
(GGGAAATTAGACAGAAAAGAAGAGTAAGAAGAAATATAAGAGCCACC);

5'UTR-010, Upstream
(SEQ ID NO. 144)
(GGGAAATAAGAGAGTAAAGAACAGTAAGAAGAAATATAAGAGCCACC);

5'UTR-011 (Upstream UTR)
(SEQ ID NO. 145)
(GGGAAAAAAGAGAGAAAAGAAGACTAAGAAGAAATATAAGAGCCACC);

5'UTR-012 (Upstream UTR)
(SEQ ID NO. 146)
(GGGAAATAAGAGAGAAAAGAAGAGTAAGAAGATATATAAGAGCCACC);

5'UTR-013 (Upstream UTR)
(SEQ ID NO. 147)
(GGGAAATAAGAGACAAAACAAGAGTAAGAAGAAATATAAGAGCCACC);

5'UTR-014 (Upstream UTR)
(SEQ ID NO. 148)
(GGGAAATTAGAGAGTAAAGAACAGTAAGTAGAATTAAAAGAGCCACC);

5'UTR-15 (Upstream UTR)
(SEQ ID NO. 149)
(GGGAAATAAGAGAGAATAGAAGAGTAAGAAGAAATATAAGAGCCACC);

5'UTR-016 (Upstream UTR)
(SEQ ID NO. 150)
(GGGAAATAAGAGAGAAAAGAAGAGTAAGAAGAAAATTAAGAGCCACC);

5'UTR-017 (Upstream UTR)
(SEQ ID NO. 151)
(GGGAAATAAGAGAGAAAAGAAGAGTAAGAAGAAATTTAAGAGCCACC);

5'UTR-018 (Upstream UTR)
(SEQ ID NO. 152)
(TCAAGCTTTTGGACCCTCGTACAGAAGCTAATACGACTCACTATAGGGA
AATAAGAGAGAAAAGAAGAGTAAGAAGAAATATAAGAGCCACC);

142-3p 5'UTR-001 (Upstream UTR including
miR142-3p)
(SEQ ID NO. 153)
(TGATAATAGTCCATAAAGTAGGAAACACTACAGCTGGAGCCTCGGTGGC
CATGCTTCTTGCCCCTTGGGCCTCCCCCCAGCCCCTCCTCCCCTTCCTGC
ACCCGTACCCCCGTGGTCTTTGAATAAAGTCTGAGTGGGCGGC);

142-3p 5'UTR-002 (Upstream UTR including
miR142-3p)
(SEQ ID NO. 154)
(TGATAATAGGCTGGAGCCTCGGTGGCTCCATAAAGTAGGAAACACTACA
CATGCTTCTTGCCCCTTGGGCCTCCCCCCAGCCCCTCCTCCCCTTCCTGC
ACCCGTACCCCCGTGGTCTTTGAATAAAGTCTGAGTGGGCGGC);

142-3p 5'UTR-003 (Upstream UTR including
miR142-3p)
(SEQ ID NO. 155)
(TGATAATAGGCTGGAGCCTCGGTGGCCATGCTTCTTGCCCCTTCCATAA
AGTAGGAAACACTACATGGGCCTCCCCCCAGCCCCTCCTCCCCTTCCTGC
ACCCGTACCCCCGTGGTCTTTGAATAAAGTCTGAGTGGGCGGC);

142-3p 5'UTR-004 (Upstream UTR including
miR142-3p)
(SEQ ID NO. 156)
(TGATAATAGGCTGGAGCCTCGGTGGCCATGCTTCTTGCCCCTTGGGCCT
CCCCCCAGTCCATAAAGTAGGAAACACTACACCCCTCCTCCCCTTCCTGC
ACCCGTACCCCCGTGGTCTTTGAATAAAGTCTGAGTGGGCGGC);

142-3p 5'UTR-005 (Upstream UTR including
miR142-3p)
(SEQ ID NO. 157)
(TGATAATAGGCTGGAGCCTCGGTGGCCATGCTTCTTGCCCCTTGGGCCT
CCCCCCAGCCCCTCCTCCCCTTCTCCATAAAGTAGGAAACACTACACTGC
ACCCGTACCCCCGTGGTCTTTGAATAAAGTCTGAGTGGGCGGC);

142-3p 5'UTR-006 (Upstream UTR including
miR142-3p)
(SEQ ID NO. 158)
(TGATAATAGGCTGGAGCCTCGGTGGCCATGCTTCTTGCCCCTTGGGCCT
CCCCCCAGCCCCTCCTCCCCTTCCTGCACCCGTACCCCCTCCATAAAGTA
GGAAACACTACAGTGGTCTTTGAATAAAGTCTGAGTGGGCGGC);
or 142-3p 5'UTR-007 (Upstream UTR including
miR142-3p)
(SEQ ID NO. 159)
(TGATAATAGGCTGGAGCCTCGGTGGCCATGCTTCTTGCCCCTTGGGCCT
CCCCCCAGCCCCTCCTCCCCTTCCTGCACCCGTACCCCCGTGGTCTTTGA
ATAAAGTTCCATAAAGTAGGAAACACTACACTGAGTGGGCGGC).

In some embodiments, the 3'UTR comprises:

3'UTR-001 (Creatine Kinase UTR)
(SEQ ID NO. 160)
(GCGCCTGCCCACCTGCCACCGACTGCTGGAACCCAGCCAGTGGGAGGGC
CTGGCCCACCAGAGTCCTGCTCCCTCACTCCTCGCCCCGCCCCTGTCCC
AGAGTCCCACCTGGGGGCTCTCTCCACCCTTCTCAGAGTTCCAGTTTCAA
CCAGAGTTCCAACCAATGGGCTCCATCCTCTGGATTCTGGCCAATGAAAT
ATCTCCCTGGCAGGGTCCTCTTCTTTTTCCCAGAGCTCCACCCCAACCAGG
AGCTCTAGTTAATGGAGAGCTCCCAGCACACTCGGAGCTTGTGCTTTGTC
TCCACGCAAAGCGATAAATAAAAGCATTGGTGGCCTTTGGTCTTTGAATA
AAGCCTGAGTAGGAAGTCTAGA);

3'UTR-002 (Myoglobin UTR)
(SEQ ID NO. 161)
(GCCCCTGCCGCTCCCACCCCCACCCATCTGGGCCCCGGGTTCAAGAGAG
AGCGGGGTCTGATCTCGTGTAGCCATATAGAGTTTGCTTCTGAGTGTCTG
CTTTGTTTAGTAGAGGTGGGCAGGAGGAGCTGAGGGGCTGGGCTGGGGT
GTTGAAGTTGGCTTTGCATGCCCAGCGATGCGCCTCCCTGTGGGATGTCA
TCACCCTGGGAACCGGGAGTGGCCCTTGGCTCACTGTGTTCTGCATGGTT
TGGATCTGAATTAATTGTCCTTTCTTCTAAATCCCAACCGAACTTCTTCC
AACCTCCAAACTGGCTGTAACCCCAAATCCAAGCCATTAACTACACCTGA
CAGTAGCAATTGTCTGATTAATCACTGGCCCCTTGAAGACAGCAGAATGT
CCCTTTGCAATGAGGAGGAGATCTGGGCTGGGCGGGCCAGCTGGGGAAGC
ATTTGACTATCTGGAACTTGTGTGTGCCTCCTCAGGTATGGCAGTGACTC
ACCTGGTTTTAATAAAACAACCTGCAACATCTCATGGTCTTTGAATAAAG
CCTGAGTAGGAAGTCTAGA);

3'UTR-003 (α-actin UTR)
(SEQ ID NO. 162)
(ACACACTCCACCTCCAGCACGCGACTTCTCAGGACGACGAATCTTCTCA
ATGGGGGGGCGGCTGAGCTCCAGCCACCCCGCAGTCACTTTCTTTGTAAC
AACTTCCGTTGCTGCCATCGTAAACTGACACAGTGTTTATAACGTGTACA
TACATTAACTTATTACCTCATTTTGTTATTTTTCGAAACAAAGCCCTGTG
GAAGAAAATGGAAAACTTGAAGAAGCATTAAAGTCATTCTGTTAAGCTGC
GTAAATGGTCTTTGAATAAAGCCTGAGTAGGAAGTCTAGA);

3'UTR-004 (Albumin UTR)
(SEQ ID NO. 163)
(CATCACATTTAAAAGCATCTCAGCCTACCATGAGAATAAGAGAAAGAAA
ATGAAGATCAAAAGCTTATTCATCTGTTTTTCTTTTTCGTTGGTGTAAAG
CCAACACCCTGTCTAAAAAACATAAATTTCTTTAATCATTTTGCCTCTTT
TCTCTGTGCTTCAATTAATAAAAAATGGAAAGAATCTAATAGAGTGGTAC
AGCACTGTTATTTTTCAAAGATGTGTTGCTATCCTGAAAATTCTGTAGGT
TCTGTGGAAGTTCCAGTGTTCTCTCTTATTCCACTTCGGTAGAGGATTTC
TAGTTTCTTGTGGGCTAATTAAATAAATCATTAATACTCTTCTAATGGTC
TTTGAATAAAGCCTGAGTAGGAAGTCTAGA);

3'UTR-005 (α-globin UTR)
(SEQ ID NO. 164)
(GCTGCCTTCTGCGGGGCTTGCCTTCTGGCCATGCCCTTCTTCTCTCCCT
TGCACCTGTACCTCTTGGTCTTTGAATAAAGCCTGAGTAGGAAGGCGGCC
GCTCGAGCATGCATCTAGA);

3'UTR-006 (G-CSF UTR)
(SEQ ID NO. 165)
(GCCAAGCCCTCCCCATCCCATGTATTTATCTCTATTTAATATTTATGTC
TATTTAAGCCTCATATTTAAAGACAGGGAAGAGCAGAACGGAGCCCCAGG
CCTCTGTGTCCTTCCCTGCATTTCTGAGTTTCATTCTCCTGCCTGTAGCA
GTGAGAAAAAGCTCCTGTCCTCCCATCCCCTGGACTGGGAGGTAGATAGG
TAAATACCAAGTATTTATTACTATGACTGCTCCCCAGCCCTGGCTCTGCA
ATGGGCACTGGGATGAGCCGCTGTGAGCCCCTGGTCCTGAGGGTCCCCAC
CTGGGACCCTTGAGAGTATCAGGTCTCCCACGTGGGAGACAAGAAATCCC
TGTTTAATATTTAAACAGCAGTGTTCCCCATCTGGGTCCTTGCACCCCTC
ACTCTGGCCTCAGCCGACTGCACAGCGGCCCCTGCATCCCCTTGGCTGTG
AGGCCCCTGGACAAGCAGAGGTGGCCAGAGCTGGGAGGCATGGCCCTGGG
GTCCCACGAATTTGCTGGGGAATCTCGTTTTTCTTCTTAAGACTTTTGGG
ACATGGTTTGACTCCCGAACATCACCGACGCGTCTCCTGTTTTTCTGGGT
GGCCTCGGGACACCTGCCCTGCCCCCACGAGGGTCAGGACTGTGACTCTT
TTTAGGGCCAGGCAGGTGCCTGGACATTTGCCTTGCTGGACGGGGACTGG
GGATGTGGAGGGAGCAGACAGGAGGAATCATGTCAGGCCTGTGTGTGAA
AGGAAGCTCCACTGTCACCCTCCACCTCTTCACCCCCCACTCACCAGTGT
CCCCTCCACTGTCACATTGTAACTGAACTTCAGGATAATAAAGTGTTTGC
CTCCATGGTCTTTGAATAAAGCCTGAGTAGGAAGGCGGCCGCTCGAGCAT
GCATCTAGA);

3'UTR-007 (Col1a2; collagen, type I, alpha 2 UTR)
(SEQ ID NO. 166)
(ACTCAATCTAAATTAAAAAGAAAGAAATTTGAAAAAACTTTCTCTTTG
CCATTTCTTCTTCTTCTTTTTTAACTGAAAGCTGAATCCTTCCATTTCTT
CTGCACATCTACTTGCTTAAATTGTGGGCAAAAGAGAAAAAGAAGGATTG
ATCAGAGCATTGTGCAATACAGTTTCATTAACTCCTTCCCCCGCTCCCCC
AAAAATTTGAATTTTTTTTTCAACACTCTTACACCTGTTATGGAAAATGT
CAACCTTTGTAAGAAAACCAAAATAAAAATTGAAAAATAAAACCATAAA
CATTTGCACCACTTGTGGCTTTTGAATATCTTCCACAGAGGGAAGTTTAA
AACCCAAACTTCCAAAGGTTTAAACTACCTCAAAACACTTTCCCATGAGT
GTGATCCACATTGTTAGGTGCTGACCTAGACAGAGATGAACTGAGGTCCT
TGTTTTGTTTTGTTCATAATACAAAGGTGCTAATTAATAGTATTTCAGAT
ACTTGAAGAATGTTGATGGTGCTAGAAGAATTTGAGAAGAAATACTCCTG
TATTGAGTTGTATCGTGTGGTGTATTTTTTAAAAAATTTGATTTAGCATT
CATATTTTCCATCTTATTCCCAATTAAAAGTATGCAGATTATTTGCCCAA
ATCTTCTTCAGATTCAGCATTTGTTCTTTGCCAGTCTCATTTTCATCTTC
TTCCATGGTTCCACAGAAGCTTTGTTTCTTGGGCAAGCAGAAAAATTAAA
TTGTACCTATTTTGTATATGTGAGATGTTTAAATAAATTGTGAAAAAAAT
GAAATAAAGCATGTTTGGTTTTCCAAAAGAACATAT);

3'UTR-008 (Col6a2; collagen, type VI, alpha 2 UTR)
(SEQ ID NO. 167)
(CGCCGCCGCCCGGGCCCCGCAGTCGAGGGTCGTGAGCCCACCCCGTCCA
TGGTGCTAAGCGGGCCCGGGTCCCACACGGCCAGCACCGCTGCTCACTCG
GACGACGCCCTGGGCCTGCACCTCTCCAGCTCCTCCCACGGGGTCCCCGT
AGCCCCGGCCCCCGCCCAGCCCCAGGTCTCCCCAGGCCCTCCGCAGGCTG
CCCGGCCTCCCTCCCCCTGCAGCCATCCCAAGGCTCCTGACCTACCTGGC
CCCTGAGCTCTGGAGCAAGCCCTGACCCAATAAAGGCTTTGAACCCAT);

3'UTR-009 (RPN1; ribophorin I UTR)
(SEQ ID NO. 168)
(GGGGCTAGAGCCCTCTCCGCACAGCGTGGAGACGGGGCAAGGAGGGGGG
TTATTAGGATTGGTGGTTTTGTTTTGCTTTGTTTAAAGCCGTGGGAAAAT
GGCACAACTTTACCTCTGTGGGAGATGCAACACTGAGAGCCAAGGGGTGG
GAGTTGGGATAATTTTTATATAAAAGAAGTTTTTCCACTTTGAATTGCTA
AAAGTGGCATTTTTCCTATGTGCAGTCACTCCTCTCATTTCTAAAATAGG
GACGTGGCCAGGCACGGTGGCTCATGCCTGTAATCCCAGCACTTTGGGAG
GCCGAGGCAGGCGGCTCACGAGGTCAGGAGATCGAGACTATCCTGGCTAA
CACGGTAAAACCCTGTCTCTACTAAAAGTACAAAAAATTAGCTGGGCGTG
GTGGTGGGCACCTGTAGTCCCAGCTACTCGGGAGGCTGAGGCAGGAGAAA
GGCATGAATCCAAGAGGCAGAGCTTGCAGTGAGCTGAGATCACGCCATTG
CACTCCAGCCTGGGCAACAGTGTTAAGACTCTGTCTCAAATATAAATAAA
TAAATAAATAAATAAATAAATAAAAATAAAGCGAGATGTTGCCCTC
AAA);

3'UTR-010 (LRP1; low density lipoprotein
receptor-related protein 1 UTR)
(SEQ ID NO. 169)
(GGCCCTGCCCCGTCGGACTGCCCCCAGAAAGCCTCCTGCCCCCTGCCAG

TGAAGTCCTTCAGTGAGCCCCTCCCCAGCCAGCCCTTCCCTGGCCCCGCC

GGATGTATAAATGTAAAAATGAAGGAATTACATTTTATATGTGAGCGAGC

AAGCCGGCAAGCGAGCACAGTATTATTTCTCCATCCCCTCCCTGCCTGCT

CCTTGGCACCCCATGCTGCCTTCAGGGAGACAGGCAGGGAGGGCTTGGG

GCTGCACCTCCTACCCTCCCACCAGAACGCACCCCACTGGGAGAGCTGGT

GGTGCAGCCTTCCCCTCCCTGTATAAGACACTTTGCCAAGGCTCTCCCCT

CTCGCCCCATCCCTGCTTGCCCGCTCCCACAGCTTCCTGAGGGCTAATTC

TGGGAAGGGAGAGTTCTTTGCTGCCCCTGTCTGGAAGACGTGGCTCTGGG

TGAGGTAGGCGGGAAAGGATGGAGTGTTTTAGTTCTTGGGGGAGGCCACC

CCAAACCCCAGCCCCAACTCCAGGGGCACCTATGAGATGGCCATGCTCAA

CCCCCCTCCCAGACAGGCCCTCCCTGTCTCCAGGGCCCCCACCGAGGTTC

CCAGGGCTGGAGACTTCCTCTGGTAAACATTCCTCCAGCCTCCCCTCCCC

TGGGGACGCCAAGGAGGTGGGCCACACCCAGGAAGGGAAAGCGGGCAGCC

CCGTTTTGGGGACGTGAACGTTTTAATAATTTTTGCTGAATTCCTTTACA

ACTAAATAACACAGATATTGTTATAAATAAAATTGT);

3'UTR-011 (Nnt1; cardiotrophin-like cytokine
factor 1 UTR)
(SEQ ID NO. 170)
(ATATTAAGGATCAAGCTGTTAGCTAATAATGCCACCTCTGCAGTTTTGG

GAACAGGCAAATAAAGTATCAGTATACATGGTGATGTACATCTGTAGCAA

AGCTCTTGGAGAAAATGAAGACTGAAGAAAGCAAAGCAAAAACTGTATAG

AGAGATTTTTCAAAAGCAGTAATCCCTCAATTTTAAAAAAGGATTGAAAA

TTCTAAATGTCTTTCTGTGCATATTTTTTGTGTTAGGAATCAAAAGTATT

TTATAAAAGGAGAAAGAACAGCCTCATTTTAGATGTAGTCCTGTTGGATT

TTTTTATGCCTCCTCAGTAACCAGAAATGTTTTAAAAAACTAAGTGTTTAG

GATTTCAAGACAACATTATACATGGCTCTGAAATATCTGACACAATGTAA

ACATTGCAGGCACCTGCATTTTATGTTTTTTTTTCAACAAATGTGACTA

ATTTGAAACTTTTATGAACTTCTGAGCTGTCCCCTTGCAATTCAACCGCA

GTTTGAATTAATCATATCAAATCAGTTTTAATTTTTTAAATTGTACTTCA

GAGTCTATATTTCAAGGGCACATTTTCTCACTACTATTTTAATACATTAA

AGGACTAAATAATCTTTCAGAGATGCTGGAAACAAATCATTTGCTTTATA

TGTTTCATTAGAATACCAATGAAACATACAACTTGAAAATTAGTAATAGT

ATTTTTGAAGATCCCATTTCTAATTGGAGATCTCTTTAATTTCGATCAAC

TTATAATGTGTAGTACTATATTAAGTGCACTTGAGTGGAATTCAACATTT

GACTAATAAAATGAGTTCATCATGTTGGCAAGTGATGTGGCAATTATCTC

TGGTGACAAAAGAGTAAAATCAAATATTTCTGCCTGTTACAAATATCAAG

GAAGACCTGCTACTATGAAATAGATGACATTAATCTGTCTTCACTGTTTA

TAATACGGATGGATTTTTTTCAAATCAGTGTGTGTTTTGAGGTCTTATG

TAATTGATGACATTTGAGAGAAATGGTGGCTTTTTTTAGCTACCTCTTTG

TTCATTTAAGCACCAGTAAAGATCATGTCTTTTTATAGAAGTGTAGATTT

TCTTTGTGACTTTGCTATCGTGCCTAAAGCTCTAAATATAGGTGAATGTG

TGATGAATACTCAGATTATTTGTCTCTCTATATAATTAGTTTGGTACTAA

GTTTCTCAAAAAATTATTAACACATGAAAGACAATCTCTAAACCAGAAAA

AGAAGTAGTACAAATTTTGTTACTGTAATGCTCGCGTTTAGTGAGTTTAA

AACACACAGTATCTTTTGGTTTTATAATCAGTTTCTATTTTGCTGTGCCT

GAGATTAAGATCTGTGTATGTGTGTGTGTGTGTGCGTTTGTGTGTT

AAAGCAGAAAAGACTTTTTTAAAAGTTTTAAGTGATAAATGCAATTTGTT

AATTGATCTTAGATCACTAGTAAACTCAGGGCTGAATTATACCATGTATA

TTCTATTAGAAGAAAGTAAACACCATCTTTATTCCTGCCCTTTTTCTTCT

CTCAAAGTAGTTGTAGTTATATCTAGAAAGAAGCAATTTTGATTTCTTGA

AAAGGTAGTTCCTGCACTCAGTTTAAACTAAAAATAATCATACTTGGATT

TTATTTATTTTTGTCATAGTAAAAATTTTAATTTATATATATTTTTATTT

AGTATTATCTTATTCTTTGCTATTTGCCAATCCTTTGTCATCAATTGTGT

TAAATGAATTGAAAATTCATGCCCTGTTCATTTTATTTTACTTTATTGGT

TAGGATATTTAAAGGATTTTTGTATATATAATTTCTTAAATTAATATTCC

AAAAGGTTAGTGGACTTAGATTATAAATTATGGCAAAAATCTAAAAACAA

CAAAAATGATTTTTATACATTCTATTTCATTATTCCTCTTTTTCCAATAA

GTCATACAATTGGTAGATATGACTTATTTTATTTTTGTATTATTCACTAT

ATCTTTATGATATTTAAGTATAAATAATTAAAAAAATTTATTGTACCTTA

TAGTCTGTCACCAAAAAAAAAAAATTATCTGTAGGTAGTGAAATGCTAAT

GTTGATTTGTCTTTAAGGGCTTGTTAACTATCCTTTATTTTCTCATTTGT

CTTAAATTAGGAGTTTGTGTTTAAATTACTCATCTAAGCAAAAAATGTAT

ATAAATCCCATTACTGGGTATATACCCAAAGGATTATAAATCATGCTGCT

ATAAAGACACATGCACACGTATGTTTATTGCAGCACTATTCACAATAGCA

AAGACTTGGAACCAACCCAAATGTCCATCAATGATAGACTTGATTAAGAA

AATGTGCACATATACACCATGGAATACTATGCAGCCATAAAAAAGGATGA

GTTCATGTCCTTTGTAGGGACATGGATAAAGCTGGAAACCATCATTCTGA

GCAAACTATTGCAAGGACAGAAAACCAAACACTGCATGTTCTCACTCATA

GGTGGGAATTGAACAATGAGAACACTTGGACACAAGGTGGGGAACACCAC

ACACCAGGGCCTGTCATGGGGTGGGGGGAGTGGGGAGGGATAGCATTAGG

AGATATACCTAATGTAAATGATGAGTTAATGGGTGCAGCACACCAACATG

GCACATGTATACATATGTAGCAAACCTGCACGTTGTGCACATGTACCCTA

GAACTTAAAGTATAATTAAAAAAAAAAAGAAAACAGAAGCTATTTATAAA

GAAGTTATTTGCTGAAATAAATGTGATCTTTCCCATTAAAAAAATAAAGA

AATTTTGGGGTAAAAAACACAATATATTGTATTCTTGAAAAATTCTAAG

AGAGTGGATGTGAAGTGTTCTCACCACAAAAGTGATAACTAATTGAGGTA

ATGCACATATTAATTAGAAAGATTTTGTCATTCCACAATGTATATATACT

TAAAAATATGTTATACACAATAAATACATACATTAAAAAAATAAGTAAATG

TA);

3'UTR-012 (Col6a1; collagen, type VI, alpha 1 UTR)
(SEQ ID NO. 171)
(CCCACCCTGCACGCCGGCACCAAACCCTGTCCTCCCACCCCTCCCCACT
CATCACTAAACAGAGTAAAATGTGATGCGAATTTTCCCGACCAACCTGAT
TCGCTAGATTTTTTTTAAGGAAAAGCTTGGAAAGCCAGGACACAACGCTG
CTGCCTGCTTTGTGCAGGGTCCTCCGGGGCTCAGCCCTGAGTTGGCATCA
CCTGCGCAGGGCCCTCTGGGGCTCAGCCCTGAGCTAGTGTCACCTGCACA
GGGCCCTCTGAGGCTCAGCCCTGAGCTGGCGTCACCTGTGCAGGGCCCTC
TGGGGCTCAGCCCTGAGCTGGCCTCACCTGGGTTCCCCACCCCGGGCTCT
CCTGCCCTGCCCTCCTGCCCGCCCTCCCTCCTGCCTGCGCAGCTCCTTCC
CTAGGCACCTCTGTGCTGCATCCCACCAGCCTGAGCAAGACGCCCTCTCG
GGGCCTGTGCCGCACTAGCCTCCCTCTCCTCTGTCCCCATAGCTGGTTTT
TCCCACCCAATCCTCACCTAACAGTTACTTTACAATTAAACTCAAAGCAAG
CTCTTCTCCTCAGCTTGGGGCAGCCATTGGCCTCTGTCTCGTTTTGGGAA
ACCAAGGTCAGGAGGCCGTTGCAGACATAAATCTCGGCGACTCGGCCCCG
TCTCCTGAGGGTCCTGCTGGTGACCGGCCTGGACCTTGGCCCTACAGCCC
TGGAGGCCGCTGCTGACCAGCACTGACCCCGACCTCAGAGAGTACTCGCA
GGGGCGCTGGCTGCACTCAAGACCCTCGAGATTAACGGTGCTAACCCCGT
CTGCTCCTCCCTCCCGCAGAGACTGGGGCCTGGACTGGACATGAGAGCCC
CTTGGTGCCACAGAGGGCTGTGTCTTACTAGAAACAACGCAAACCTCTCC
TTCCTCAGAATAGTGATGTGTTCGACGTTTTATCAAAGGCCCCCTTTCTA
TGTTCATGTTAGTTTTGCTCCTTCTGTGTTTTTTCTGAACCATATCCAT
GTTGCTGACTTTTCCAAATAAAGGTTTTCACTCCTCTC);

3'UTR-013 (Calr; calreticulin UTR)
(SEQ ID NO. 172)
(AGAGGCCTGCCTCCAGGGCTGGACTGAGGCCTGAGCGCTCCTGCCGCAG
AGCTGGCCGCGCCAAATAATGTCTCTGTGAGACTCGAGAACTTTCATTTT
TTTCCAGGCTGGTTCGGATTTGGGGTGGATTTTGGTTTTGTTCCCCTCCT
CCACTCTCCCCCACCCCCTCCCCGCCCTTTTTTTTTTTTTTTTTAAACT
GGTATTTTATCTTTGATTCTCCTTCAGCCCTCACCCCTGGTTCTCATCTT
TCTTGATCAACATCTTTTCTTGCCTCTGTCCCCTTCTCTCATCTCTTAGC
TCCCCTCCAACCTGGGGGGCAGTGGTGTGGAGAAGCCACAGGCCTGAGAT
TCATCTGCTCTCCTTCCTGGAGCCCAGAGGAGGGCAGCAGAAGGGGGTG
GTGTCTCCAACCCCCCAGCACTGAGGAAGAACGGGGCTCTTCTCATTTCA
CCCCTCCCTTTCTCCCCTGCCCCAGGACTGGGCCACTTCTGGGTGGGGC
AGTGGGTCCCAGATTGGCTCACACTGAGAATGTAAGAACTACAAACAAAA
TTTCTATTAAATTAAATTTTGTGTCTCC);

3'UTR-014 (Col1a1; collagen, type I, alpha 1 UTR)
(SEQ ID NO. 173)
(CTCCCTCCATCCCAACCTGGCTCCCTCCCACCCAACCAACTTTCCCCCC
AACCCGGAAACAGACAAGCAACCCAAACTGAACCCCCTCAAAAGCCAAA
AATGGGAGACAATTTCACATGGACTTTGGAAAATATTTTTTCCTTTGCA
TTCATCTCTCAAACTTAGTTTTTATCTTTGACCAACCGAACATGACCAAA
AACCAAAAGTGCATTCAACCTTACCAAAAAAAAAAAAAAAAAAGAATAA
ATAAATAACTTTTTAAAAAAGGAAGCTTGGTCCACTTGCTTGAAGACCCA
TGCGGGGGTAAGTCCCTTTCTGCCCGTTGGGCTTATGAAACCCCAATGCT
GCCCTTTCTGCTCCTTTCTCCACACCCCCCTTGGGGCCTCCCCTCCACTC
CTTCCCAAATCTGTCTCCCCAGAAGACACAGGAAACAATGTATTGTCTGC
CCAGCAATCAAAGGCAATGCTCAAACACCCAAGTGGCCCCCACCCTCAGC
CCGCTCCTGCCCGCCCAGCACCCCCAGGCCCTGGGGACCTGGGGTTCTC
AGACTGCCAAAGAAGCCTTGCCATCTGGCGCTCCCATGGCTCTTGCAACA
TCTCCCCTTCGTTTTTGAGGGGGTCATGCCGGGGGAGCCACCAGCCCCTC
ACTGGGTTCGGAGGAGAGTCAGGAAGGGCCACGACAAAGCAGAAACATCG
GATTTGGGGAACGCGTGTCAATCCCTTGTGCCGCAGGGCTGGGCGGGAGA
GACTGTTCTGTTCCTTGTGTAACTGTGTTGCTGAAAGACTACCTCGTTCT
TGTCTTGATGTGTCACCGGGGCAACTGCCTGGGGGCGGGGATGGGGGCAG
GGTGGAAGCGGCTCCCCATTTTATACCAAAGGTGCTACATCTATGTGATG
GGTGGGGTGGGAGGGAATCACTGGTGCTATAGAAATTGAGATGCCCCCC
CAGGCCAGCAAATGTTCCTTTTTGTTCAAAGTCTATTTTTATTCCTTGAT
ATTTTTCTTTTTTTTTTTTTTTTTGTGGATGGGGACTTGTGAATTTTTT
CTAAAGGTGCTATTTAACATGGGAGGAGAGCGTGTGCGGCTCCAGCCCAG
CCCGCTGCTCACTTTCCACCCTCTCTCCACCTGCCTCTGGCTTCTCAGGC
CTCTGCTCTCCGACCTCTCTCCTCTGAAACCCTCCTCCACAGCTGCAGCC
CATCCTCCCGGCTCCCTCCTAGTCTGTCCTGCGTCCTCTGTCCCCGGGTT
TCAGAGACAACTTCCCAAAGCACAAAGCAGTTTTTCCCCCTAGGGGTGGG
AGGAAGCAAAAGACTCTGTACCTATTTTGTATGTGTATAATAATTTGAGA
TGTTTTTAATTATTTTGATTGCTGGAATAAAGCATGTGGAAATGACCCAA
ACATAATCCGCAGTGGCCTCCTAATTTCCTTCTTTGGAGTTGGGGGAGGG
GTAGACATGGGAAGGGGCTTTGGGGTGATGGGCTTGCCTTCCATTCCTG
CCCTTTCCCTCCCCACTATTCTCTTCTAGATCCCTCCATAACCCCACTCC
CCTTTCTCTCACCCTTCTTATACCGCAAACCTTTCTACTTCCTCTTTCAT
TTTCTATTCTTGCAATTTCCTTGCACCTTTTCCAAATCCTCTTCTCCCCT
GCAATACCATACAGGCAATCCACGTGCACAACACACACACACTCTTCA
CATCTGGGTTGTCCAAACCTCATACCCACTCCCCTTCAAGCCCATCCAC
TCTCCACCCCCTGGATGCCCTGCACTTGGTGGCGGTGGGATGCTCATGGA
TACTGGGAGGGTGAGGGGAGTGGAACCCGTGAGGAGGACCTGGGGGCCTC
TCCTTGAACTGACATGAAGGGTCATCTGGCCTCTGCTCCCTTCTCACCCA
CGCTGACCTCCTGCCGAAGGAGCAACGCAACAGGAGAGGGGTCTGCTGAG
CCTGGCGAGGGTCTGGGAGGGACCAGGAGGAAGGCGTGCTCCCTGCTCGC
TGTCCTGGCCCTGGGGAGTGAGGGAGACAGACACCTGGGAGAGCTGTGG
GGAAGGCACTCGCACCGTGCTCTTGGGAAGGAAGGAGACCTGGCCCTGCT
CACCACGGACTGGGTGCCTCGACCTCCTGAATCCCAGAACACAACCCCC
CTGGGCTGGGGTGGTCTGGGGAACCATCGTGCCCCCGCCTCCCGCCTACT
CCTTTTTAAGCTT);

3'UTR-015 (Plod1; procollagen-lysine, 2-oxoglutarate 5-dioxygenase 1 UTR)

(SEQ ID NO. 174)
(TTGGCCAGGCCTGACCCTCTTGGACCTTTCTTCTTTGCCGACAACCACT

GCCCAGCAGCCTCTGGGACCTCGGGGTCCCAGGGAACCCAGTCCAGCCTC

CTGGCTGTTGACTTCCCATTGCTCTTGGAGCCACCAATCAAAGAGATTCA

AAGAGATTCCTGCAGGCCAGAGGCGGAACACACCTTTATGGCTGGGGCTC

TCCGTGGTGTTCTGGACCCAGCCCCTGGAGACACCATTCACTTTTACTGC

TTTGTAGTGACTCGTGCTCTCCAACCTGTCTTCCTGAAAAACCAAGGCCC

CCTTCCCCCACCTCTTCCATGGGGTGAGACTTGAGCAGAACAGGGGCTTC

CCCAAGTTGCCCAGAAAGACTGTCTGGGTGAGAAGCCATGGCCAGAGCTT

CTCCCAGGCACAGGTGTTGCACCAGGGACTTCTGCTTCAAGTTTTGGGGT

AAAGACACCTGGATCAGACTCCAAGGGCTGCCCTGAGTCTGGGACTTCTG

CCTCCATGGCTGGTCATGAGAGCAAACCGTAGTCCCCTGGAGACAGCGAC

TCCAGAGAACCTCTTGGGAGACAGAAGAGGCATCTGTGCACAGCTCGATC

TTCTACTTGCCTGTGGGGAGGGGAGTGACAGGTCCACACACCACACTGGG

TCACCCTGTCCTGGATGCCTCTGAAGAGAGGGACAGACCGTCAGAAACTG

GAGAGTTTCTATTAAAGGTCATTTAAACCA);

3'UTR-016 (Nucb1; nucleobindin 1 UTR)

(SEQ ID NO. 175)
(TCCTCCGGGACCCCAGCCCTCAGGATTCCTGATGCTCCAAGGCGACTGA

TGGGCGCTGGATGAAGTGGCACAGTCAGCTTCCCTGGGGGCTGGTGTCAT

GTTGGGCTCCTGGGGCGGGGCACGGCCTGGCATTTCACGCATTGCTGCC

ACCCCAGGTCCACCTGTCTCCACTTTCACAGCCTCCAAGTCTGTGGCTCT

TCCCTTCTGTCCTCCGAGGGGCTTGCCTTCTCTCGTGTCCAGTGAGGTGC

TCAGTGATCGGCTTAACTTAGAGAAGCCCGCCCCCTCCCCTTCTCCGTCT

GTCCCAAGAGGGTCTGCTCTGAGCCTGCGTTCCTAGGTGGCTCGGCCTCA

GCTGCCTGGGTTGTGGCCGCCCTAGCATCCTGTATGCCCACAGCTACTGG

AATCCCCGCTGCTGCTCCGGGCCAAGCTTCTGGTTGATTAATGAGGGCAT

GGGGTGGTCCCTCAAGACCTTCCCCTACCTTTTGTGGAACCAGTGATGCC

TCAAAGACAGTGTCCCCTCCACAGCTGGGTGCCAGGGGCAGGGATCCTC

AGTATAGCCGGTGAACCCTGATACCAGGAGCCTGGGCCTCCCTGAACCCC

TGGCTTCCAGCCATCTCATCGCCAGCCTCCTCCTGGACCTCTTGGCCCCC

AGCCCCTTCCCCACACAGCCCCAGAAGGGTCCCAGAGCTGACCCCACTCC

AGGACCTAGGCCCAGCCCCTCAGCCTCATCTGGAGCCCCTGAAGACCAGT

CCCACCCACCTTTCTGGCCTCATCTGACACTGCTCCGCATCCTGCTGTGT

GTCCTGTTCCATGTTCCGGTTCCATCCAAATACACTTTCTGGAACAAA);

3'UTR-017 (α-globin)

(SEQ ID NO. 176)
(GCTGGAGCCTCGGTGGCCATGCTTCTTGCCCCTTGGGCCTCCCCCCAGC

CCCTCCTCCCCTTCCTGCACCCGTACCCCCGTGGTCTTTGAATAAAGTCT

GAGTGGGCGGC);
or

3'UTR-018

(SEQ ID NO. 177)
(TGATAATAGGCTGGAGCCTCGGTGGCCATGCTTCTTGCCCCTTGGGCCT

CCCCCCAGCCCCTCCTCCCCTTCCTGCACCCGTACCCCCGTGGTCTTTGA

ATAAAGTCTGAGTGGGCGGC).

In certain embodiments, the 5'UTR and/or 3'UTR sequence of the disclosure comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of the 5'UTR sequences disclosed herein and/or 3'UTR sequences comprises any of the 3'UTR sequences disclosed herein, and any combination thereof.

In certain embodiments, the 3' UTR sequence comprises one or more miRNA binding sites, e.g., miR-122 binding sites, or any other heterologous nucleotide sequences therein, without disrupting the function of the 3' UTR. Some examples of 3' UTR sequences comprising a miRNA binding site are listed in TABLE 6. In some embodiments, the 3' UTR sequence comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of SEQ ID NOs: 238-240. In certain embodiments, the 3' UTR sequence comprises a nucleotide sequence at least about 60%, at least about 70%, at least about 80%, at least about 90%, at least about 95%, at least about 96%, at least about 97%, at least about 98%, at least about 99%, or about 100% identical to SEQ ID NO: 238. In certain embodiments, the 3' UTR sequence comprises a nucleotide sequence at least about 60%, at least about 70%, at least about 80%, at least about 90%, at least about 95%, at least about 96%, at least about 97%, at least about 98%, at least about 99%, or about 100% identical to SEQ ID NO: 239. In certain embodiments, the 3' UTR sequence comprises a nucleotide sequence at least about 60%, at least about 70%, at least about 80%, at least about 90%, at least about 95%, at least about 96%, at least about 97%, at least about 98%, at least about 99%, or about 100% identical to SEQ ID NO: 240.

TABLE 6

Exemplary 3' UTR with miRNA Binding Sites

| 3' UTR Identifier/ miRNA BS | Name/ Description | Sequence | SEQ ID NO. |
|---|---|---|---|
| 3UTR-018 + miR-122-5p binding site | Downstream URT | UAAUAGGCUGGAGCCUCGGUGGCCAUGCUUCUUGCC CCUUGGGCCUCCCCCCAGCCCCUCCUCCCCUUCCUG CACCCGUACCCCCCAAACACCAUUGUCACACUCCAG UGGUCUUUGAAUAAAGUCUGAGUGGGCGGC | SEQ ID NO: 238 |
| 3UTR-018 + miR-122-3p binding site | Downstream URT | UAAUAGGCUGGAGCCUCGGUGGCCAUGCUUCUUGCC CCUUGGGCCUCCCCCCAGCCCCUCCUCCCCUUCCUG CACCCGUACCCCCUAUUUAGUGUGAUAAUGGCGUUG UGGUCUUUGAAUAAAGUCUGAGUGGGCGGC | SEQ ID NO: 239 |
| 3UTR-019 + miR-122 binding site | Downstream URT | UGAUAAUAGGCUGGAGCCUCGGUGGCCAUGCUUCUU GCCCCUUGGGCCUCCCCCCAGCCCCUCCUCCCCUUC CUGCACCCGUACCCCC<u>AAACACCAUUGUCACACUC</u> <u>C</u>AGUGGUCUUUGAAUAAAGUCUGAGUGGGCGGC | SEQ ID NO: 240 |

*miRNA binding site is boxed or underlined.

The polynucleotides of the disclosure can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

It is also within the scope of the present disclosure to have patterned UTRs. As used herein "patterned UTRs" include a repeating or alternating pattern, such as ABABAB or AABBAABBAABB or ABCABCABC or variants thereof repeated once, twice, or more than 3 times. In these patterns, each letter, A, B, or C represent a different UTR nucleic acid sequence.

Other non-UTR sequences can be used as regions or subregions within the polynucleotides of the disclosure. For example, introns or portions of intron sequences can be incorporated into the polynucleotides of the disclosure. Incorporation of intronic sequences can increase protein production as well as polynucleotide expression levels. In some embodiments, the polynucleotide of the disclosure comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide of the disclosure comprises 5' and/or 3' sequence associated with the 5' and/or 3' ends of rubella virus (RV) genomic RNA, respectively, or deletion derivatives thereof, including the 5' proximal open reading frame of RV RNA encoding non-structural proteins (e.g., see Pogue et al., J. Virol. 67(12): 7106-7117, the contents of which are incorporated herein by reference in their entirety). Viral capsid sequences can also be used as a translational enhancer, e.g., the 5' portion of a capsid sequence, (e.g., semliki forest virus and sindbis virus capsid RNAs as described in Sjöberg et al., Biotechnology (NY) 1994 12(11):1127-1131, and Frolov and Schlesinger J. Virol. 1996 70(2): 1182-1190, the contents of each of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation. The conservation of these sequences has been shown across 14 species including humans. See, e.g., Panek et al., "An evolutionary conserved pattern of 18S rRNA sequence complementarity to mRNA 5'UTRs and its implications for eukaryotic gene translation regulation," Nucleic Acids Research 2013, doi: 10.1093/nar/gkt548, incorporated herein by reference in its entirety.

In one non-limiting example, the TEE comprises the TEE sequence in the 5'-leader of the Gtx homeodomain protein. See Chappell et al., PNAS 2004 101:9590-9594, incorporated herein by reference in its entirety.

In another non-limiting example, the TEE comprises a TEE having one or more of the sequences of SEQ ID NOs: 1-35 in US2009/0226470, US2013/0177581, and WO2009/075886; SEQ ID NOs: 1-5 and 7-645 in WO2012/009644; and SEQ ID NO: 1 WO1999/024595, U.S. Pat. Nos. 6,310,197, and 6,849,405; the contents of each of which are incorporated herein by reference in their entirety.

In some embodiments, the TEE is an internal ribosome entry site (IRES), HCV-IRES, or an IRES element such as, but not limited to, those described in: U.S. Pat. No. 7,468,275, US2007/0048776, US2011/0124100, WO2007/025008, and WO2001/055369; the contents of each of which re incorporated herein by reference in their entirety. The IRES elements can include, but are not limited to, the Gtx sequences (e.g., Gtx9-nt, Gtx8-nt, Gtx7-nt) as described by Chappell et al., PNAS 2004 101:9590-9594, Zhou et al., PNAS 2005 102:6273-6278, US2007/0048776, US2011/

0124100, and WO2007/025008; the contents of each of which are incorporated herein by reference in their entirety.

"Translational enhancer polynucleotide" or "translation enhancer polynucleotide sequence" refer to a polynucleotide that includes one or more of the TEE provided herein and/or known in the art (see. e.g., U.S. Pat. Nos. 6,310,197, 6,849,405, 7,456,273, 7,183,395, US2009/0226470, US2007/0048776, US2011/0124100, US2009/0093049, US2013/0177581, WO2009/075886, WO2007/025008, WO2012/009644, WO2001/055371, WO1999/024595, EP2610341A1, and EP2610340A1; the contents of each of which are incorporated herein by reference in their entirety), or their variants, homologs, or functional derivatives. In some embodiments, the polynucleotide of the disclosure comprises one or multiple copies of a TEE. The TEE in a translational enhancer polynucleotide can be organized in one or more sequence segments. A sequence segment can harbor one or more of the TEEs provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the disclosure comprises a translational enhancer polynucleotide sequence.

In some embodiments, a 5'UTR and/or 3'UTR of a polynucleotide of the disclosure comprises at least one TEE or portion thereof that is disclosed in: WO1999/024595, WO2012/009644, WO2009/075886, WO2007/025008, WO1999/024595, WO2001/055371, EP2610341A1, EP2610340A1, U.S. Pat. Nos. 6,310,197, 6,849,405, 7,456,273, 7,183,395, US2009/0226470, US2011/0124100, US2007/0048776, US2009/0093049, or US2013/0177581, the contents of each are incorporated herein by reference in their entirety.

In some embodiments, a 5'UTR and/or 3'UTR of a polynucleotide of the disclosure comprises a TEE that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to a TEE disclosed in: US2009/0226470, US2007/0048776, US2013/0177581, US2011/0124100, WO1999/024595, WO2012/009644, WO2009/075886, WO2007/025008, EP2610341A1, EP2610340A1, U.S. Pat. Nos. 6,310,197, 6,849,405, 7,456,273, 7,183,395, Chappell et al., PNAS 2004 101:9590-9594, Zhou et al., PNAS 2005 102:6273-6278, and Supplemental Table 1 and in Supplemental Table 2 of Wellensiek et al., "Genome-wide profiling of human cap-independent translation-enhancing elements," Nature Methods 2013, DOI:10.1038/NMETH.2522; the contents of each of which are incorporated herein by reference in their entirety.

In some embodiments, a 5'UTR and/or 3'UTR of a polynucleotide of the disclosure comprises a TEE which is selected from a 5-30 nucleotide fragment, a 5-25 nucleotide fragment, a 5-20 nucleotide fragment, a 5-15 nucleotide fragment, or a 5-10 nucleotide fragment (including a fragment of 5, 6, 7, 8, 9, 10, 11, 12, 13, 14, 15, 16, 17, 18, 19, 20, 21, 22, 23, 24, 25, 26, 27, 28, 29, or 30 nucleotides) of a TEE sequence disclosed in: US2009/0226470, US2007/0048776, US2013/0177581, US2011/0124100, WO1999/024595, WO2012/009644, WO2009/075886, WO2007/025008, EP2610341A1, EP2610340A1, U.S. Pat. Nos. 6,310,197, 6,849,405, 7,456,273, 7,183,395, Chappell et al., PNAS 2004 101:9590-9594, Zhou et al., PNAS 2005 102:6273-6278, and Supplemental Table 1 and in Supplemental Table 2 of Wellensiek et al., "Genome-wide profiling of human cap-independent translation-enhancing elements," Nature Methods 2013, DOI: 10.103 8/NMETH.2522.

In some embodiments, a 5'UTR and/or 3'UTR of a polynucleotide of the disclosure comprises a TEE which is a transcription regulatory element described in any of U.S. Pat. Nos. 7,456,273, 7,183,395, US2009/0093049, and WO2001/055371, the contents of each of which are incorporated herein by reference in their entirety. The transcription regulatory elements can be identified by methods known in the art, such as, but not limited to, the methods described in U.S. Pat. Nos. 7,456,273, 7,183,395, US2009/0093049, and WO2001/055371.

In some embodiments, a 5'UTR and/or 3'UTR comprising at least one TEE described herein can be incorporated in a monocistronic sequence such as, but not limited to, a vector system or a nucleic acid vector. As non-limiting examples, the vector systems and nucleic acid vectors can include those described in U.S. Pat. Nos. 7,456,273, 7,183,395, US2007/0048776, US2009/0093049, US2011/0124100, WO2007/025008, and WO2001/055371.

In some embodiments, a 5'UTR and/or 3'UTR of a polynucleotide of the disclosure comprises a TEE or portion thereof described herein. In some embodiments, the TEEs in the 3'UTR can be the same and/or different from the TEE located in the 5'UTR.

In some embodiments, a 5'UTR and/or 3'UTR of a polynucleotide of the disclosure can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In one embodiment, the 5'UTR of a polynucleotide of the disclosure can include 1-60, 1-55, 1-50, 1-45, 1-40, 1-35, 1-30, 1-25, 1-20, 1-15, 1-10, 9, 8, 7, 6, 5, 4, 3, 2, or 1 TEE sequences. The TEE sequences in the 5'UTR of the polynucleotide of the disclosure can be the same or different TEE sequences. A combination of different TEE sequences in the 5'UTR of the polynucleotide of the disclosure can include combinations in which more than one copy of any of the different TEE sequences are incorporated. The TEE sequences can be in a pattern such as ABABAB or AABBAABBAABB or ABCABCABC or variants thereof repeated one, two, three, or more than three times. In these patterns, each letter, A, B, or C represent a different TEE nucleotide sequence.

In some embodiments, the TEE can be identified by the methods described in US2007/0048776, US2011/0124100, WO2007/025008, WO2012/009644, the contents of each of which are incorporated herein by reference in their entirety.

In some embodiments, the 5'UTR and/or 3'UTR comprises a spacer to separate two TEE sequences. As a non-limiting example, the spacer can be a 15 nucleotide spacer and/or other spacers known in the art. As another non-limiting example, the 5'UTR and/or 3'UTR comprises a TEE sequence-spacer module repeated at least once, at least twice, at least 3 times, at least 4 times, at least 5 times, at least 6 times, at least 7 times, at least 8 times, at least 9 times, at least 10 times, or more than 10 times in the 5'UTR and/or 3'UTR, respectively. In some embodiments, the 5'UTR and/or 3'UTR comprises a TEE sequence-spacer module repeated 1, 2, 3, 4, 5, 6, 7, 8, 9, or 10 times.

In some embodiments, the spacer separating two TEE sequences can include other sequences known in the art that can regulate the translation of the polynucleotide of the disclosure, e.g., miR sequences described herein (e.g., miR binding sites and miR seeds). As a non-limiting example, each spacer used to separate two TEE sequences can include a different miR sequence or component of a miR sequence (e.g., miR seed sequence).

In some embodiments, a polynucleotide of the disclosure comprises a miR and/or TEE sequence. In some embodiments, the incorporation of a miR sequence and/or a TEE sequence into a polynucleotide of the disclosure can change the shape of the stem loop region, which can increase and/or decrease translation. See e.g., Kedde et al., Nature Cell Biology 2010 12(10):1014-20, herein incorporated by reference in its entirety).

14. Microrna (miRNA) Binding Sites

Sensor sequences include, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the disclosure comprising an open reading frame (ORF) encoding an IL12B polypeptide, an IL12A polypeptide, and/or IL12B and IL12A fusion polypeptides further comprises a sensor sequence. In some embodiments, the sensor sequence is a miRNA binding site.

A miRNA is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the disclosure comprises one or more microRNA target sequences, microRNA sequences, or microRNA seeds. Such sequences can correspond to any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the disclosure comprising an ORF encoding an IL12B polypeptide, an IL12A polypeptide, and/or IL12B and IL12A fusion polypeptides further comprises a miRNA binding site. In exemplary embodiments, a 5'UTR and/or 3'UTR of the polynucleotide (e.g., a ribonucleic acid (RNA), e.g., a messenger RNA (mRNA)) comprises a miRNA binding site.

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the disclosure, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds to the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the disclosure, the polynucleotide can be targeted for degradation or reduced translation, provided the miRNA in question is available. This can reduce off-target effects upon delivery of the polynucleotide. For example, if a polynucleotide of the disclosure is not intended to be delivered to a tissue or cell but ends up there, then a miRNA abundant in the tissue or cell can inhibit the expression of the gene of interest if one or multiple binding sites of the miRNA are engineered into the 5'UTR and/or 3'UTR of the polynucleotide.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

In one embodiment, a polynucleotide of the disclosure can include at least one miRNA-binding site in the 5'UTR and/or 3'UTR in order to direct cytotoxic or cytoprotective mRNA therapeutics to specific cells such as, but not limited to, normal and/or cancerous cells. In another embodiment, a polynucleotide of the disclosure can include two, three, four, five, six, seven, eight, nine, ten, or more miRNA-binding sites in the 5'-UTR and/or 3'-UTR in order to direct cytotoxic or cytoprotective mRNA therapeutics to specific cells such as, but not limited to, normal and/or cancerous cells.

Regulation of expression in multiple tissues can be accomplished through introduction or removal of one or more miRNA binding sites. The decision whether to remove or insert a miRNA binding site can be made based on miRNA expression patterns and/or their profilings in diseases. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Some microRNAs, e.g., miR-122, are abundant in normal tissue but are present in much lower levels in cancer or tumor tissue. Thus, engineering microRNA target sequences (i.e., microRNA binding site) into the polynucleotides encoding an IL12B polypeptide, an IL12A polypeptide, and/or IL12B and IL12A fusion polypeptides (e.g., in a 3'UTR like region or other region) can effectively target the molecule for degradation or reduced translation in normal tissue (where the microRNA is abundant) while providing high levels of translation in the cancer or tumor tissue (where the microRNA is present in much lower levels). This provides a tumor-targeting approach for the methods and compositions of the disclosure.

Further examples of the miRNA binding sites that can be useful for the present disclosure include immune cell specific miRNAs including, but not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

MiRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the disclosure to regulate expression of the polynucleotide in the liver. Liver specific miRNA binding sites can be engineered alone or further in combination with immune cell (e.g., APC) miRNA binding sites in a polynucleotide of the disclosure.

MiRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. MiRNA binding sites from any lung specific miRNA can be introduced to or removed from a polynucleotide of the disclosure to regulate expression of the polynucleotide in the lung. Lung specific miRNA binding sites can be engineered alone or further in combination with immune cell (e.g., APC) miRNA binding sites in a polynucleotide of the disclosure.

MiRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. MiRNA binding sites from any heart specific microRNA can be introduced to or removed from a polynucleotide of the disclosure to regulate expression of the polynucleotide in the heart. Heart specific miRNA binding sites can be engineered alone or further in combination with immune cell (e.g., APC) miRNA binding sites in a polynucleotide of the disclosure.

MiRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. MiRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. MiRNA binding sites from any CNS specific miRNA can be introduced to or removed from a polynucleotide of the disclosure to regulate expression of the polynucleotide in the nervous system. Nervous system specific miRNA binding sites can be engineered alone or further in combination with immune cell (e.g., APC) miRNA binding sites in a polynucleotide of the disclosure.

MiRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the disclosure to regulate expression of the polynucleotide in the pancreas. Pancreas specific miRNA binding sites can be engineered alone or further in combination with immune cell (e.g. APC) miRNA binding sites in a polynucleotide of the disclosure.

MiRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. MiRNA binding sites from any kidney specific miRNA can be introduced to or removed from a polynucleotide of the disclosure to regulate expression of the polynucleotide in the kidney. Kidney specific miRNA binding sites can be engineered alone or further in combination with immune cell (e.g., APC) miRNA binding sites in a polynucleotide of the disclosure.

MiRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the disclosure to regulate expression of the polynucleotide in the muscle. Muscle specific miRNA binding sites can be engineered alone or further in combination with immune cell (e.g., APC) miRNA binding sites in a polynucleotide of the disclosure.

MiRNAs are also differentially expressed in different types of cells, such as, but not limited to, endothelial cells, epithelial cells, and adipocytes.

MiRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). MiRNA binding sites from any endothelial cell specific miRNA can be introduced to or removed from a polynucleotide of the disclosure to regulate expression of the polynucleotide in the endothelial cells.

MiRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR- 34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. MiRNA binding sites from any epithelial cell specific miRNA can be introduced to or removed from a polynucleotide of the disclosure to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In one embodiment, the binding sites of embryonic stem cell specific miRNAs can be included in or removed from the 3'UTR of a polynucleotide of the disclosure to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

Many miRNA expression studies are conducted to profile the differential expression of miRNAs in various cancer cells/tissues and other diseases. Some miRNAs are abnormally over-expressed in certain cancer cells and others are under-expressed. For example, miRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in its entirety.)

As a non-limiting example, miRNA binding sites for miRNAs that are over-expressed in certain cancer and/or tumor cells can be removed from the 3'UTR of a polynucleotide of the disclosure, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

MiRNA can also regulate complex biological processes such as angiogenesis (e.g., miR-132) (Anand and Cheresh Curr Opin Hematol 2011 18:171-176). In the polynucleotides of the disclosure, miRNA binding sites that are involved in such processes can be removed or introduced, in order to tailor the expression of the polynucleotides to biologically relevant cell types or relevant biological processes. In this context, the polynucleotides of the disclosure are defined as auxotrophic polynucleotides.

In some embodiments, the microRNA binding site (e.g., miR-122 binding site) is fully complementary to miRNA (e.g., miR-122), thereby degrading the mRNA fused to the miRNA binding site. In other embodiments, the miRNA binding site is not fully complementary to the corresponding miRNA. In certain embodiments, the miRNA binding site (e.g., miR-122 binding site) is the same length as the corresponding miRNA (e.g., miR-122). In other embodiments, the microRNA binding site (e.g., miR-122 binding site) is one nucleotide shorter than the corresponding microRNA (e.g., miR-122, which has 22 nts) at the 5' terminus, the 3' terminus, or both. In still other embodiments, the microRNA binding site (e.g., miR-122 binding site) is two nucleotides shorter than the corresponding microRNA (e.g., miR-122) at the 5' terminus, the 3' terminus, or both. In yet other embodiments, the microRNA binding site (e.g., miR-122 binding site) is three nucleotides shorter than the corresponding microRNA (e.g., miR-122) at the 5' terminus, the 3' terminus, or both. In some embodiments, the microRNA binding site (e.g., miR-122 binding site) is four nucleotides shorter than the corresponding microRNA (e.g., miR-122) at the 5' terminus, the 3' terminus, or both. In other embodiments, the microRNA binding site (e.g., miR-122 binding site) is five nucleotides shorter than the corresponding microRNA (e.g., miR-122) at the 5' terminus, the 3' terminus, or both. In some embodiments, the microRNA binding site (e.g., miR-122 binding site) is six nucleotides shorter than the corresponding microRNA (e.g., miR-122) at the 5' terminus, the 3' terminus, or both. In other embodiments, the microRNA binding site (e.g., miR-122 binding site) is seven nucleotides shorter than the corresponding microRNA (e.g., miR-122) at the 5' terminus or the 3' terminus. In other embodiments, the microRNA binding site (e.g., miR-122 binding site) is eight nucleotides shorter than the corresponding microRNA (e.g., miR-122) at the 5' terminus or the 3' terminus. In other embodiments, the microRNA binding site (e.g., miR-122 binding site) is nine nucleotides shorter than the corresponding microRNA (e.g., miR-122) at the 5' terminus or the 3' terminus. In other embodiments, the microRNA binding site (e.g., miR-122 binding site) is ten nucleotides shorter than the corresponding microRNA (e.g., miR-122) at the 5' terminus or the 3' terminus. In other embodiments, the microRNA binding site (e.g., miR-122 binding site) is eleven nucleotides shorter than the corresponding microRNA (e.g., miR-122) at the 5' terminus or the 3' terminus. In other embodiments, the microRNA binding site (e.g., miR-122 binding site) is twelve nucleotides shorter than the corresponding microRNA (e.g., miR-122) at the 5' terminus or the 3' terminus. The miRNA binding sites that are shorter than the corresponding miRNAs are still capable of degrading the mRNA incorporating one or more of the miRNA binding sites or preventing the mRNA from translation.

In some embodiments, the microRNA binding site (e.g., miR-122 binding site) has sufficient complementarity to miRNA (e.g., miR-122) so that a RISC complex comprising the miRNA (e.g., miR-122) cleaves the polynucleotide comprising the microRNA binding site. In other embodiments, the microRNA binding site (e.g., miR-122 binding site) has imperfect complementarity so that a RISC complex comprising the miRNA (e.g., miR-122) induces instability in the polynucleotide comprising the microRNA binding site. In another embodiment, the microRNA binding site (e.g., miR-122 binding site) has imperfect complementarity so that a RISC complex comprising the miRNA (e.g., miR-122) represses transcription of the polynucleotide comprising the microRNA binding site. In one embodiment, the miRNA binding site (e.g., miR-122 binding site) has one mismatch from the corresponding miRNA (e.g., miR-122). In another embodiment, the miRNA binding site has two mismatches from the corresponding miRNA. In other embodiments, the miRNA binding site has three mismatches from the corresponding miRNA. In other embodiments, the miRNA binding site has four mismatches from the corresponding miRNA. In some embodiments, the miRNA binding site has five mismatches from the corresponding miRNA. In other embodiments, the miRNA binding site has six mismatches from the corresponding miRNA. In certain embodiments, the miRNA binding site has seven mismatches from the corresponding miRNA. In other embodiments, the miRNA binding site has eight mismatches from the corresponding miRNA. In other embodiments, the miRNA binding site has nine mismatches from the corresponding miRNA. In other embodiments, the miRNA binding site has ten mismatches from the corresponding miRNA. In other embodiments, the miRNA binding site has eleven mismatches from the corresponding miRNA. In other embodiments, the miRNA binding site has twelve mismatches from the corresponding miRNA.

In certain embodiments, the miRNA binding site (e.g., miR-122 binding site) has at least about ten contiguous nucleotides complementary to at least about ten contiguous nucleotides of the corresponding miRNA (e.g., miR-122), at least about eleven contiguous nucleotides complementary to at least about eleven contiguous nucleotides of the corresponding miRNA, at least about twelve contiguous nucleotides complementary to at least about twelve contiguous nucleotides of the corresponding miRNA, at least about thirteen contiguous nucleotides complementary to at least about thirteen contiguous nucleotides of the corresponding miRNA, or at least about fourteen contiguous nucleotides complementary to at least about fourteen contiguous nucleotides of the corresponding miRNA. In some embodiments, the miRNA binding sites have at least about fifteen contiguous nucleotides complementary to at least about fifteen contiguous nucleotides of the corresponding miRNA, at least about sixteen contiguous nucleotides complementary to at least about sixteen contiguous nucleotides of the corresponding miRNA, at least about seventeen contiguous nucleotides complementary to at least about seventeen contiguous nucleotides of the corresponding miRNA, at least about eighteen contiguous nucleotides complementary to at least about eighteen contiguous nucleotides of the corresponding miRNA, at least about nineteen contiguous nucleotides complementary to at least about nineteen contiguous nucleotides of the corresponding miRNA, at least about twenty contiguous nucleotides complementary to at least about twenty contiguous nucleotides of the corresponding miRNA, or at least about twenty one contiguous nucleotides complementary to at least about twenty one contiguous nucleotides of the corresponding miRNA.

In some embodiments, the polynucleotides comprise an mRNA encoding an IL12B polypeptide, an IL12A polypeptide, and/or IL12B and IL12A fusion polypeptides and at least one miR-122 binding site, at least two miR-122 binding sites, at least three miR-122 binding sites, at least four miR-122 binding sites, or at least five miR-122 binding sites. In one aspect, the miRNA binding site binds miR-122 or is complementary to miR-122. In another aspect, the miRNA binding site binds to miR-122-3p or miR-122-5p. In a particular aspect, the miRNA binding site comprises a nucleotide sequence at least 80%, at least 85%, at least 90%, at least 95%, or 100% identical to SEQ ID NO: 52 or 54, wherein the miRNA binding site binds to miR-122. In another particular aspect, the miRNA binding site comprises a nucleotide sequence at least 80%, at least 85%, at least 90%, at least 95%, or 100% identical to SEQ ID NO: 54, wherein the miRNA binding site binds to miR-122. These sequences are shown below in Table 7.

TABLE 7

| miR-122 and miR-122 binding sites | | |
|---|---|---|
| SEQ ID NO. | Description | Sequence |
| SEQ ID NO: 50 | miR-122 | CCUUAGCAGAGCUGUGGAGUGUGA CAAUGGUGUUUGUGUCUAAACUAU CAAACGCCAUUAUCACACUAAAUA GCUACUGCUAGGC |
| SEQ ID NO: 51 | miR-122-3p | AACGCCAUUAUCACACUAAAUA |
| SEQ ID NO: 52 | miR-122-3p binding site | UAUUUAGUGUGAUAAUGGCGUU |
| SEQ ID NO: 53 | miR-122-5p | UGGAGUGUGACAAUGGUGUUUG |
| SEQ ID NO: 54 | miR-122-5p binding site | CAAACACCAUUGUCACACUCCA |

In some embodiments, a miRNA binding site (e.g., miR-122 binding site) is inserted in the polynucleotide of the disclosure in any position of the polynucleotide (e.g., 3' UTR); the insertion site in the polynucleotide can be anywhere in the polynucleotide as long as the insertion of the miRNA binding site in the polynucleotide does not interfere with the translation of the functional IL12B polypeptide, IL12A polypeptide, and/or IL12B and IL12A fusion polypeptides in the absence of the corresponding miRNA (e.g., miR-122); and in the presence of the miRNA (e.g., miR-122), the insertion of the miRNA binding site in the polynucleotide and the binding of the miRNA binding site to the corresponding miRNA are capable of degrading the polynucleotide or preventing the translation of the polynucleotide. In one embodiment, a miRNA binding site is inserted in a 3'UTR of the polynucleotide.

In certain embodiments, a miRNA binding site is inserted in at least about 30 nucleotides downstream from the stop codon of the an IL12B polypeptide, an IL12A polypeptide, and/or IL12B and IL12A fusion polypeptides-encoding mRNA. In other embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of the polynucleotide, e.g., the IL12B polypeptide, IL12A polypeptide, and/or IL12B and IL12A fusion polypeptides encoding mRNA. In other embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of the polynucleotide, e.g., the IL12B polypeptide, IL12A polypeptide, and/or IL12B and IL12A fusion polypeptides-encoding mRNA. In some embodiments, the miRNA binding site is inserted downstream of the stop codon in the nucleic acid sequence encoding an IL12 polypeptide as disclosed herein. In some embodiments, the miRNA binding site is inserted downstream of the stop codon in the nucleic acid sequence encoding membrane domain as disclosed herein. In some embodiments, the miRNA binding site is inserted downstream of the stop codon in the nucleic acid sequence encoding heterologous polypeptide as disclosed herein.

In some embodiments, a miRNA binding site is inserted in the polynucleotide of the disclosure in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the disclosure comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the disclosure. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the disclosure.

MiRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the disclosure can further include this structured 5'UTR in order to enhance microRNA mediated gene regulation.

At least one miRNA binding site can be engineered into the 3'UTR of a polynucleotide of the disclosure. In this context, at least two, at least three, at least four, at least five, at least six, at least seven, at least eight, at least nine, at least ten, or more miRNA binding sites can be engineered into a 3'UTR of a polynucleotide of the disclosure. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the disclosure. In one embodiment, miRNA binding sites incorporated into a polynucleotide of the disclosure can be the same or can be different miRNA sites. A combination of different miRNA binding sites incorporated into a polynucleotide of the disclosure can include combinations in which more than one copy of any of the different miRNA sites are incorporated. In another embodiment, miRNA binding sites incorporated into a polynucleotide of the disclosure can target the same or different tissues in the body. As a non-limiting example, through the introduction of tissue-, cell-type-, or disease-specific miRNA binding sites in the 3'-UTR of a polynucleotide of the disclosure, the degree of expression in specific cell types (e.g., hepatocytes, myeloid cells, endothelial cells, cancer cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the disclosure. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In one embodiment, a polynucleotide of the disclosure can be engineered to include more than one miRNA site expressed in different tissues or different cell types of a subject. As a non-limiting example, a polynucleotide of the disclosure can be engineered to include miR-192 and miR-122 to regulate expression of the polynucleotide in the liver and kidneys of a subject. In another embodiment, a polynucleotide of the disclosure can be engineered to include more than one miRNA site for the same tissue.

In some embodiments, the therapeutic window and or differential expression associated with the polypeptide encoded by a polynucleotide of the disclosure can be altered with a miRNA binding site. For example, a polynucleotide encoding a polypeptide that provides a death signal can be designed to be more highly expressed in cancer cells by virtue of the miRNA signature of those cells. Where a cancer cell expresses a lower level of a particular miRNA, the polynucleotide encoding the binding site for that miRNA (or miRNAs) would be more highly expressed. Hence, the polypeptide that provides a death signal triggers or induces cell death in the cancer cell. Neighboring noncancer cells, harboring a higher expression of the same miRNA would be less affected by the encoded death signal as the polynucleotide would be expressed at a lower level due to the effects of the miRNA binding to the binding site or "sensor" encoded in the 3'UTR. Conversely, cell survival or cytoprotective signals can be delivered to tissues containing cancer and non-cancerous cells where a miRNA has a higher expression in the cancer cells—the result being a lower survival signal to the cancer cell and a larger survival signal to the normal cell. Multiple polynucleotides can be designed and administered having different signals based on the use of miRNA binding sites as described herein.

In some embodiments, the expression of a polynucleotide of the disclosure can be controlled by incorporating at least one sensor sequence in the polynucleotide and formulating the polynucleotide for administration. As a non-limiting example, a polynucleotide of the disclosure can be targeted to a tissue or cell by incorporating a miRNA binding site and formulating the polynucleotide in a lipid nanoparticle comprising a cationic lipid, including any of the lipids described herein.

A polynucleotide of the disclosure can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the disclosure can be designed for optimal protein expression in a tissue or cell, or in the context of a biological condition.

In some embodiments, a polynucleotide of the disclosure can be designed to incorporate miRNA binding sites that either have 100% identity to known miRNA seed sequences or have less than 100% identity to miRNA seed sequences. In some embodiments, a polynucleotide of the disclosure can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g., Kedde et al., "A Pumilio-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the disclosure can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the disclosure described herein.

In another embodiment, a miRNA sequence in the 5'UTR of a polynucleotide of the disclosure can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the disclosure can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site. As another non-limiting example, the site of translation initiation may be located within a miR-122 sequence such as the seed sequence or the mir-122 binding site.

In some embodiments, a polynucleotide of the disclosure can include at least one miRNA in order to dampen expression of the encoded polypeptide in a tissue or cell of interest.

As a non-limiting example, a polynucleotide of the disclosure can include at least one miR-122 binding site in order to dampen expression of an encoded polypeptide of interest in the liver. As another non-limiting example a polynucleotide of the disclosure can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the disclosure can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the disclosure more unstable in antigen presenting cells. Non-limiting examples of these miRNAs include mir-122-5p or mir-122-3p.

In one embodiment, a polynucleotide of the disclosure comprises at least one miRNA sequence in a region of the polynucleotide that can interact with a RNA binding protein.

In some embodiments, the polynucleotide of the disclosure (e.g., a RNA, e.g., an mRNA) comprising (i) a sequence-optimized nucleotide sequence (e.g., an ORF) encoding an IL12B polypeptide, an IL12A polypeptide, and/or IL12B and IL12A fusion polypeptides (e.g., the wild-type sequence, functional fragment, or variant thereof) and (ii) a miRNA binding site (e.g., a miRNA binding site that binds to miR-122).

In some embodiments, the polynucleotide of the disclosure comprises a uracil-modified sequence encoding an IL12B polypeptide, an IL12A polypeptide, and/or IL12B and IL12A fusion polypeptides disclosed herein and a miRNA binding site disclosed herein, e.g., a miRNA binding site that binds to miR-122. In some embodiments, the uracil-modified sequence encoding an IL12B polypeptide, an IL12A polypeptide, and/or IL12B and IL12A fusion polypeptides comprises at least one chemically modified nucleobase, e.g., 5-methoxyuracil. In some embodiments, at least 95% of a type of nucleobase (e.g., uracil) in a uracil-modified sequence encoding an IL12B polypeptide, an IL12A polypeptide, and/or IL12B and IL12A fusion polypeptides of the disclosure are modified nucleobases. In some embodiments, at least 95% of uracil in a uracil-modified sequence encoding an IL12B polypeptide, an IL12A polypeptide, and/or IL12B and IL12A fusion polypeptides is 5-methoxyuridine. In some embodiments, the polynucleotide comprising a nucleotide sequence encoding an IL12B polypeptide, an IL12A polypeptide, and/or IL12B and IL12A fusion polypeptides disclosed herein and a miRNA binding site is formulated with a delivery agent, e.g., a compound having the Formula (I), e.g., any of Compounds 1-147 or any of Compounds 1-232.

15. 3' UTR and the AU Rich Elements

In certain embodiments, a polynucleotide of the present disclosure (e.g., a polynucleotide comprising a nucleotide sequence (e.g., an ORF) encoding an IL12B polypeptide, an IL12A polypeptide, and/or IL12B and IL12A fusion polypeptides of the disclosure) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the disclosure comprises a binding site for regulatory proteins or microRNAs. In some embodiments, the 3'-UTR has a silencer region, which binds to repressor proteins and inhibits the expression of the mRNA. In other embodiments, the 3'-UTR comprises an AU-rich element. Proteins bind AREs to affect the stability or decay rate of transcripts in a localized manner or affect translation initiation. In other embodiments, the 3'-UTR comprises the sequence AAUAAA that directs addition of several hundred adenine residues called the poly(A) tail to the end of the mRNA transcript.

Natural or wild type 3' UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA (U/A)(U/A) nonamers. Molecules containing this type of AREs include GM-CSF and TNF-α. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides of the disclosure. When engineering specific polynucleotides, one or more copies of an ARE can be introduced to make polynucleotides of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using polynucleotides of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

In certain embodiments, the 3' UTR useful for the polynucleotides of the disclosure comprises a 3'UTR selected from those shown in this application.

In certain embodiments, the 3' UTR sequence useful for the disclosure comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3'UTR sequences listed herein and any combination thereof.

16. Regions Having a 5' Cap

The disclosure also includes a polynucleotide that comprises both a 5' Cap and a polynucleotide of the present disclosure (e.g., a polynucleotide comprising a nucleotide sequence encoding an IL12B polypeptide, an IL12A polypeptide, and/or IL12B and IL12A fusion polypeptides).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present disclosure (e.g., a polynucleotide comprising a nucleotide sequence encoding an IL12B polypeptide, an IL12A polypeptide, and/or IL12B and IL12A fusion polypeptides) incorporate a cap moiety.

In some embodiments, polynucleotides of the present disclosure (e.g., a polynucleotide comprising a nucleotide sequence encoding an IL12B polypeptide, an IL12A polypeptide, and/or IL12B and IL12A fusion polypeptides) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, Mass.) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and selenophosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the disclosure.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which may equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In some embodiments, the cap is a dinucleotide cap analog. As a non-limiting example, the dinucleotide cap analog can be modified at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m$^{3'-O}$G(5')ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present disclosure is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the disclosure (e.g., a polynucleotide comprising a nucleotide sequence encoding an IL12B polypeptide, an IL12A polypeptide, and/or IL12B and IL12A fusion polypeptides) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present disclosure are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')N1mpNp (cap 1), and 7mG(5')-ppp(5')N1mpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present disclosure, 5' terminal caps can include endogenous caps or cap analogs. According to the present disclosure, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

In certain embodiments, the 5' terminal cap structure is a Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

17. Poly-A Tails

In some embodiments, the polynucleotides of the present disclosure (e.g., a polynucleotide comprising a nucleotide sequence encoding an IL12B polypeptide, an IL12A polypeptide, and/or IL12B and IL12A fusion polypeptides) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present disclosure, terminal groups on the poly A tail can be incorporated for stabilization. Polynucleotides of the present disclosure can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present disclosure can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present disclosure. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present disclosure are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

18. Start Codon Region

The disclosure also includes a polynucleotide that comprises both a start codon region and the polynucleotide described herein (e.g., a polynucleotide comprising a nucleotide sequence encoding an IL12B polypeptide, an IL12A polypeptide, and/or IL12B and IL12A fusion polypeptides). In some embodiments, the polynucleotides of the present disclosure can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/ UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miR binding site. The perfect complement of a miR binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

19. Stop Codon Region

The disclosure also includes a polynucleotide that comprises both a stop codon region and the polynucleotide described herein (e.g., a polynucleotide comprising a nucleotide sequence encoding an IL12B polypeptide, an IL12A polypeptide, and/or IL12B and IL12A fusion polypeptides). In some embodiments, the polynucleotides of the present disclosure can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present disclosure include the stop codon TGA in the case or DNA, or the stop codon UGA in the case of RNA, and one additional stop codon. In a further embodiment the addition stop codon can be TAA or UAA. In another embodiment, the polynucleotides of the present disclosure include three consecutive stop codons, four stop codons, or more.

20. Insertions and Substitutions

The disclosure also includes a polynucleotide of the present disclosure that further comprises insertions and/or substitutions.

In some embodiments, the 5'UTR of the polynucleotide can be replaced by the insertion of at least one region and/or string of nucleosides of the same base. The region and/or string of nucleotides can include, but is not limited to, at least 3, at least 4, at least 5, at least 6, at least 7 or at least 8 nucleotides and the nucleotides can be natural and/or unnatural. As a non-limiting example, the group of nucleotides can include 5-8 adenine, cytosine, thymine, a string of any of the other nucleotides disclosed herein and/or combinations thereof.

In some embodiments, the 5'UTR of the polynucleotide can be replaced by the insertion of at least two regions and/or strings of nucleotides of two different bases such as, but not limited to, adenine, cytosine, thymine, any of the other nucleotides disclosed herein and/or combinations thereof. For example, the 5'UTR can be replaced by inserting 5-8 adenine bases followed by the insertion of 5-8 cytosine bases. In another example, the 5'UTR can be replaced by inserting 5-8 cytosine bases followed by the insertion of 5-8 adenine bases.

In some embodiments, the polynucleotide can include at least one substitution and/or insertion downstream of the transcription start site that can be recognized by an RNA polymerase. As a non-limiting example, at least one substitution and/or insertion can occur downstream of the transcription start site by substituting at least one nucleic acid in the region just downstream of the transcription start site (such as, but not limited to, +1 to +6). Changes to region of nucleotides just downstream of the transcription start site can affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleoside can cause a silent mutation of the sequence or can cause a mutation in the amino acid sequence.

In some embodiments, the polynucleotide can include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In some embodiments, the polynucleotide can include the substitution of at least 1, at least 2, at least 3, at least 4, at least 5 or at least 6 guanine bases in the region just downstream of the transcription start site. As a non-limiting example, if the nucleotides in the region are GGGAGA, the guanine bases can be substituted by at least 1, at least 2, at least 3 or at least 4 adenine nucleotides (SEQ ID NO: 233). In another non-limiting example, if the nucleotides in the region are GGGAGA the guanine bases can be substituted by at least 1, at least 2, at least 3 or at least 4 cytosine bases (SEQ ID NO: 234). In another non-limiting example, if the nucleotides in the region are GGGAGA the guanine bases can be substituted by at least 1, at least 2, at least 3 or at least 4 thymine, and/or any of the nucleotides described herein (SEQ ID NO: 235).

In some embodiments, the polynucleotide can include at least one substitution and/or insertion upstream of the start codon. For the purpose of clarity, one of skill in the art would appreciate that the start codon is the first codon of the protein coding region whereas the transcription start site is the site where transcription begins. The polynucleotide can include, but is not limited to, at least 1, at least 2, at least 3, at least 4, at least 5, at least 6, at least 7 or at least 8 substitutions and/or insertions of nucleotide bases. The nucleotide bases can be inserted or substituted at 1, at least 1, at least 2, at least 3, at least 4 or at least 5 locations upstream of the start codon. The nucleotides inserted and/or substituted can be the same base (e.g., all A or all C or all T or all G), two different bases (e.g., A and C, A and T, or C and T), three different bases (e.g., A, C and T or A, C and T) or at least four different bases.

As a non-limiting example, the guanine base upstream of the coding region in the polynucleotide can be substituted with adenine, cytosine, thymine, or any of the nucleotides described herein. In another non-limiting example the substitution of guanine bases in the polynucleotide can be designed so as to leave one guanine base in the region downstream of the transcription start site and before the start codon (see Esvelt et al. Nature (2011) 472(7344):499-503; the contents of which is herein incorporated by reference in its entirety). As a non-limiting example, at least 5 nucleotides can be inserted at 1 location downstream of the transcription start site but upstream of the start codon and the at least 5 nucleotides can be the same base type.

21. Polynucleotide Comprising an mRNA Encoding an IL12 Polypeptide

In certain embodiments, a polynucleotide of the present disclosure, for example a polynucleotide comprising an mRNA nucleotide sequence encoding an IL12B polypeptide, an IL12A polypeptide, and/or IL12B and IL12A fusion polypeptides, comprises from 5' to 3' end:
(i) a 5' cap provided above;
(ii) a 5' UTR, such as the sequences provided above;
(iii) an open reading frame encoding an IL12B polypeptide, an IL12A polypeptide, and/or IL12B and IL12A fusion polypeptides, e.g., a sequence optimized nucleic acid sequence encoding IL12 disclosed herein;
(iv) at least one stop codon;
(v) a 3' UTR, such as the sequences provided above; and
(vi) a poly-A tail provided above.

In some embodiments, the polynucleotide further comprises a miRNA binding site, e.g., a miRNA binding site that binds to miRNA-142. In some embodiments, the 5'UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type IL12 (e.g., isoform 1, 2, 3, or 4).

22. Methods of Making Polynucleotides

The present disclosure also provides methods for making a polynucleotide of the disclosure (e.g., a polynucleotide comprising a nucleotide sequence encoding an IL12B polypeptide, an IL12A polypeptide, and/or IL12B and IL12A fusion polypeptides) or a complement thereof.

In some aspects, a polynucleotide (e.g., a RNA, e.g., an mRNA) disclosed herein, and encoding an IL12B polypeptide, an IL12A polypeptide, and/or IL12B and IL12A fusion polypeptides, can be constructed using in vitro transcription. In other aspects, a polynucleotide (e.g., a RNA, e.g., an mRNA) disclosed herein, and encoding an IL12B polypeptide, an IL12A polypeptide, and/or IL12B and IL12A fusion polypeptides, can be constructed by chemical synthesis using an oligonucleotide synthesizer.

In other aspects, a polynucleotide (e.g., a RNA, e.g., an mRNA) disclosed herein, and encoding an IL12B polypeptide, an IL12A polypeptide, and/or IL12B and IL12A fusion polypeptides is made by using a host cell. In certain aspects, a polynucleotide (e.g., a RNA, e.g., an mRNA) disclosed herein, and encoding an IL12B polypeptide, an IL12A polypeptide, and/or IL12B and IL12A fusion polypeptides is made by one or more combination of the IVT, chemical synthesis, host cell expression, or any other methods known in the art. In other embodiments, a host cell is a eukaryotic cell, e.g., in vitro mammalian cells.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding an IL12B polypeptide, an IL12A polypeptide, and/or IL12B and IL12A fusion polypeptides. The resultant polynucleotides, e.g., mRNAs, can then be examined for their ability to produce protein and/or produce a therapeutic outcome.

a. In Vitro Transcription/Enzymatic Synthesis

The polynucleotides of the present disclosure disclosed herein (e.g., a polynucleotide comprising a nucleotide sequence encoding an IL12B polypeptide, an IL12A polypeptide, and/or IL12B and IL12A fusion polypeptides) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present disclosure. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, deletional variants and/or covalent derivatives.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli*, *Bacillus* DNA polymerase I, *Thermus aquaticus* (Taq) DNA polymerases, and the T7 RNA and DNA polymerases, is among the best studied of these families. Another large family is DNA polymerase α (pol α) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present disclosure is a SynS RNA polymerase. (see Zhu et al. Nucleic Acids Research 2013, doi: 10.1093/nar/gkt1193, which is herein incorporated by reference in its entirety). The SynS RNA polymerase was recently characterized from marine cyanophage SynS by Zhu et al. where they also identified the promoter sequence (see Zhu et al. Nucleic Acids Research 2013, the contents of which is herein incorporated by reference in its entirety). Zhu et al. found that SynS RNA polymerase catalyzed RNA synthesis over a wider range of temperatures and salinity as compared to T7 RNA polymerase. Additionally, the requirement for the initiating nucleotide at the promoter was found to be less stringent for SynS RNA polymerase as compared to the T7 RNA polymerase making SynS RNA polymerase promising for RNA synthesis.

In one aspect, a SynS RNA polymerase can be used in the synthesis of the polynucleotides described herein. As a non-limiting example, a SynS RNA polymerase can be used in the synthesis of the polynucleotide requiring a precise 3'-terminus.

In one aspect, a SynS promoter can be used in the synthesis of the polynucleotides. As a non-limiting example, the SynS promoter can be 5'-ATTGGGCACCCGTAAGGG-3' (SEQ ID NO: 47) as described by Zhu et al. (Nucleic Acids Research 2013).

In one aspect, a SynS RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a SynS RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the disclosure.

Polymerase chain reaction (PCR) has wide applications in rapid amplification of a target gene, as well as genome mapping and sequencing. The key components for synthesizing DNA molecules comprise target DNA molecules as a template, primers complementary to the ends of target DNA strands, deoxynucleoside triphosphates (dNTPs) as building blocks, and a DNA polymerase. As PCR progresses through denaturation, annealing and extension steps, the newly produced DNA molecules can act as a template for the next circle of replication, achieving exponentially amplification of the target DNA. PCR requires a cycle of heating and cooling for denaturation and annealing. Variations of the basic PCR include asymmetric PCR (Innis et al., PNAS 85: 9436-9440 (1988)), inverse PCR (Ochman et al., Genetics 120(3): 621-623, (1988)), reverse transcription PCR (RT-PCR) (Freeman et al., BioTechniques 26(1): 112-22, 124-5 (1999), the contents of which are incorporated herein by reference in their entirety and so on). In RT-PCR, a single stranded RNA is the desired target and is converted to a double stranded DNA first by reverse transcriptase.

A variety of isothermal in vitro nucleic acid amplification techniques have been developed as alternatives or complements of PCR. For example, strand displacement amplification (SDA) is based on the ability of a restriction enzyme to form a nick (Walker et al., PNAS 89: 392-396 (1992), which is incorporated herein by reference in its entirety)). A restriction enzyme recognition sequence is inserted into an annealed primer sequence. Primers are extended by a DNA polymerase and dNTPs to form a duplex. Only one strand of the duplex is cleaved by the restriction enzyme. Each single strand chain is then available as a template for subsequent synthesis. SDA does not require the complicated temperature control cycle of PCR.

Nucleic acid sequence-based amplification (NASBA), also called transcription mediated amplification (TMA), is also an isothermal amplification method that utilizes a combination of DNA polymerase, reverse transcriptase, RNAse H, and T7 RNA polymerase. (Compton, Nature 350:91-92 (1991)) the contents of which are incorporated herein by reference in their entirety. A target RNA is used as a template and a reverse transcriptase synthesizes its complementary DNA strand. RNAse H hydrolyzes the RNA template, making space for a DNA polymerase to synthesize a DNA strand complementary to the first DNA strand which is complementary to the RNA target, forming a DNA duplex. T7 RNA polymerase continuously generates complementary RNA strands of this DNA duplex. These RNA strands act as templates for new cycles of DNA synthesis, resulting in amplification of the target gene.

Rolling-circle amplification (RCA) amplifies a single stranded circular polynucleotide and involves numerous rounds of isothermal enzymatic synthesis where Φ29 DNA polymerase extends a primer by continuously progressing around the polynucleotide circle to replicate its sequence over and over again. Therefore, a linear copy of the circular template is achieved. A primer can then be annealed to this linear copy and its complementary chain can be synthesized. See Lizardi et al., Nature Genetics 19:225-232 (1998), the contents of which are incorporated herein by reference in their entirety. A single stranded circular DNA can also serve as a template for RNA synthesis in the presence of an RNA polymerase. (Daubendiek et al., JACS 117:7818-7819 (1995), the contents of which are incorporated herein by reference in their entirety). An inverse rapid amplification of cDNA ends (RACE) RCA is described by Polidoros et al. A messenger RNA (mRNA) is reverse transcribed into cDNA, followed by RNAse H treatment to separate the cDNA. The cDNA is then circularized by CircLigase into a circular DNA. The amplification of the resulting circular DNA is achieved with RCA. (Polidoros et al., BioTechniques 41:35-42 (2006), the contents of which are incorporated herein by reference in their entirety).

Any of the foregoing methods can be utilized in the manufacture of one or more regions of the polynucleotides of the present disclosure.

Assembling polynucleotides or nucleic acids by a ligase is also widely used. DNA or RNA ligases promote intermolecular ligation of the 5' and 3' ends of polynucleotide chains through the formation of a phosphodiester bond. Ligase chain reaction (LCR) is a promising diagnosing technique based on the principle that two adjacent polynucleotide probes hybridize to one strand of a target gene and couple to each other by a ligase. If a target gene is not present, or if there is a mismatch at the target gene, such as a single-nucleotide polymorphism (SNP), the probes cannot ligase. (Wiedmann et al., PCR Methods and Application, vol. 3 (4), s51-s64 (1994), the contents of which are incorporated herein by reference in their entirety). LCR can be combined with various amplification techniques to increase sensitivity of detection or to increase the amount of products if it is used in synthesizing polynucleotides and nucleic acids.

Several library preparation kits for nucleic acids are now commercially available. They include enzymes and buffers to convert a small amount of nucleic acid samples into an indexed library for downstream applications. For example, DNA fragments can be placed in a NEBNEXT® ULTRA™ DNA Library Prep Kit by NEWENGLAND BIOLABS® for end preparation, ligation, size selection, clean-up, PCR amplification and final clean-up.

Continued development is going on to improvement the amplification techniques. For example, U.S. Pat. No. 8,367,328 to Asada et al. the contents of which are incorporated herein by reference in their entirety, teaches utilizing a reaction enhancer to increase the efficiency of DNA synthesis reactions by DNA polymerases. The reaction enhancer comprises an acidic substance or cationic complexes of an acidic substance. U.S. Pat. No. 7,384,739 to Kitabayashi et al. the contents of which are incorporated herein by reference in their entirety, teaches a carboxylate ion-supplying substance that promotes enzymatic DNA synthesis, wherein the carboxylate ion-supplying substance is selected from oxalic acid, malonic acid, esters of oxalic acid, esters of malonic acid, salts of malonic acid, and esters of maleic acid. U.S. Pat. No. 7,378,262 to Sobek et al. the contents of which are incorporated herein by reference in their entirety, discloses an enzyme composition to increase fidelity of DNA amplifications. The composition comprises one enzyme with 3' exonuclease activity but no polymerase activity and another enzyme that is a polymerase. Both of the enzymes are thermostable and are reversibly modified to be inactive at lower temperatures.

U.S. Pat. No. 7,550,264 to Getts et al. teaches multiple round of synthesis of sense RNA molecules are performed by attaching oligodeoxynucleotides tails onto the 3' end of cDNA molecules and initiating RNA transcription using RNA polymerase, the contents of which are incorporated herein by reference in their entirety. U.S. Pat. Pub. No. 2013/0183718 to Rohayem teaches RNA synthesis by RNA-dependent RNA polymerases (RdRp) displaying an RNA polymerase activity on single-stranded DNA templates, the contents of which are incorporated herein by reference in their entirety. Oligonucleotides with non-standard nucleotides can be synthesized with enzymatic polymerization by contacting a template comprising non-standard nucleotides with a mixture of nucleotides that are complementary to the nucleotides of the template as disclosed in U.S. Pat. No. 6,617,106 to Benner, the contents of which are incorporated herein by reference in their entirety.

b. Chemical Synthesis

Standard methods can be applied to synthesize an isolated polynucleotide sequence encoding an isolated polypeptide of interest, such as a polynucleotide of the disclosure (e.g., a polynucleotide comprising a nucleotide sequence encoding an IL12B polypeptide, an IL12A polypeptide, and/or IL12B and IL12A fusion polypeptides). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. No. 8,999,380 or 8,710,200, all of which are herein incorporated by reference in their entireties.

c. Purification of Polynucleotides Encoding IL12

Purification of the polynucleotides described herein (e.g., a polynucleotide comprising a nucleotide sequence encoding an IL12B polypeptide, an IL12A polypeptide, and/or IL12B and IL12A fusion polypeptides) can include, but is not limited to, polynucleotide clean-up, quality assurance and quality control. Clean-up can be performed by methods known in the arts such as, but not limited to, AGENCOURT® beads (Beckman Coulter Genomics, Danvers, Mass.), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the disclosure (e.g., a polynucleotide comprising a nucleotide sequence encoding an IL12B polypeptide, an IL12A polypeptide, and/or IL12B and IL12A fusion polypeptides) removes impurities that can reduce or remove an unwanted immune response, e.g., reducing cytokine activity.

In some embodiments, the polynucleotide of the disclosure (e.g., a polynucleotide comprising a nucleotide sequence encoding an IL12B polypeptide, an IL12A polypeptide, and/or IL12B and IL12A fusion polypeptides) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the disclosure (e.g., a polynucleotide comprising a nucleotide sequence an IL12B polypeptide, an IL12A polypeptide, and/or IL12B and IL12A fusion polypeptides) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded IL12 protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding an IL12B polypeptide, an IL12A polypeptide, and/or IL12B and IL12A fusion polypeptides comprising one or more of the point mutations known in the art.

In some embodiments, the use of RP-HPLC purified polynucleotide increases IL12 protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of IL12 protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional IL12 protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of IL12 protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable IL12 activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional IL12 in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding IL12

In some embodiments, the polynucleotides of the present disclosure (e.g., a polynucleotide comprising a nucleotide sequence encoding an IL12B polypeptide, an IL12A polypeptide, and/or IL12B and IL12A fusion polypeptides), their expression products, as well as degradation products and metabolites can be quantified according to methods known in the art.

In some embodiments, the polynucleotides of the present disclosure can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present disclosure differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

23. Pharmaceutical Compositions and Formulations

The present disclosure provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes an IL12B polypeptide, an IL12A polypeptide, and/or IL12B and IL12A fusion polypeptides. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes an IL12B polypeptide, an IL12A polypeptide, and/or IL12B and IL12A fusion polypeptides. In some embodiments, the polynucleotide further comprises a miRNA binding site, e.g., a miRNA binding site that binds miR-122.

Pharmaceutical compositions or formulation can optionally comprise one or more additional active substances, e.g., therapeutically and/or prophylactically active substances. Pharmaceutical compositions or formulation of the present disclosure can be sterile and/or pyrogen-free. General considerations in the formulation and/or manufacture of pharmaceutical agents can be found, for example, in *Remington: The Science and Practice of Pharmacy* 21$^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition can comprise between 0.1% and 99% (w/w) of the active ingredient. By way of example, the composition can comprise between 0.1% and 100%, e.g., between 0.5 and 50%, between 1 and 30%, between 5 and 80%, or at least 80% (w/w) active ingredient.

In some embodiments, the compositions and formulations described herein can contain at least one polynucleotide of the disclosure. As a non-limiting example, the composition or formulation can contain 1, 2, 3, 4 or 5 polynucleotides of the disclosure. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an IVT polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals. Modification of pharmaceutical compositions or formulations suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions or formulation is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

The present disclosure provides pharmaceutical formulations that comprise a polynucleotide described herein (e.g., a polynucleotide comprising a nucleotide sequence encoding an IL12B polypeptide, an IL12A polypeptide, and/or IL12B and IL12A fusion polypeptides). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent, (e.g., a compound having the Formula (I), e.g., any of Compounds 1-147 or any of Compounds 1-232).

A pharmaceutically acceptable excipient, as used herein, includes, but is not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, Md., 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, acorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here may contain a cyroprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here may contain a bulking agent in lyophilized polynucleotide formulations to yield a "pharmaceutically elegant" cake, stabilize the lyophilized polynucleotides during long term (e.g., 36 month) storage. Exemplary bulking agents of the present disclosure can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

24. Delivery Agents a. Lipid Compound

The present disclosure provides pharmaceutical compositions with advantageous properties. In particular, the present application provides pharmaceutical compositions comprising:

(a) a polynucleotide comprising a nucleotide sequence encoding an IL12B polypeptide, an IL12A polypeptide, and/or IL12B and IL12A fusion polypeptides; and
(b) a delivery agent.

In some embodiments, the delivery agent for the present disclosure comprises any one or more compounds disclosed in International Application No. PCT/US2016/052352, filed on Sep. 16, 2016, and published as WO 2017/049245, which is incorporated herein by reference in its entirety.

In some embodiments, the delivery agent comprises a compound having the formula (I)

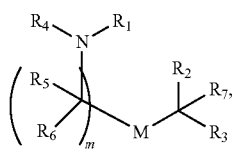

(I)

wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O) OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of C-18 alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In some embodiments, a subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O) OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C($=NR_9$)$N(R)_2$, —N(R)C($=CHR_9$)$N(R)_2$, —$OC(O)N(R)_2$, —N(R)C(O)OR, —N(OR)C(O)R, —$N(OR)S(O)_2R$, —N(OR)C(O)OR, —N(OR)C(O)$N(R)_2$, —N(OR)C(S)N($R)_2$, —N(OR)C($=NR_9$)$N(R)_2$, —N(OR)C($=CHR_9$)$N(R)_2$, —C($=NR_9$)$N(R)_2$, —C($=NR_9$)R, —C(O)N(R)OR, and a 5- to 14-membered heterocycloalkyl having one or more heteroatoms selected from N, O, and S which is substituted with one or more substituents selected from oxo ($=$O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle; each R is independently selected from the group consisting of $C_{1-3}$ alkyl, $C_{2-3}$ alkenyl, and H; each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, and a 5- to 14-membered heterocycloalkyl having one or more heteroatoms selected from N, O, and S which is substituted with one or more substituents selected from oxo ($=$O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CH R$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which R$_1$ is selected from the group consisting of C$_{5-20}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In still another embodiments, another subset of compounds of Formula (I) includes those in which
$R_1$ is selected from the group consisting of $C_{5-20}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2$H, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-8}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In yet another embodiments, another subset of compounds of Formula (I) includes those in which
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is —$(CH_2)_nQ$ or —$(CH_2)_n$CHQR, where Q is —$N(R)_2$, and n is selected from 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-8}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In yet another embodiments, another subset of compounds of Formula (I) includes those in which
$R_1$ is selected from the group consisting of $C_{5-20}$ alkyl, $C_{5-20}$ alkenyl, —R*YR", —YR", and —R"M'R';
$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is —$(CH_2)_nQ$ or —$(CH_2)_n$CHQR, where Q is —$N(R)_2$, and n is selected from 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of C-8 alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In still other embodiments, another subset of compounds of Formula (I) includes those in which
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of —$(CH_2)_nQ$, —$(CH_2)_n$CHQR, —CHQR, and —$CQ(R)_2$, where Q is —$N(R)_2$, and n is selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which R$_1$ is selected from the group consisting of C$_{5-20}$ alkyl, C$_{5-20}$ alkenyl, —R*YR", —YR", and —R"M'R';

R$_2$ and R$_3$ are independently selected from the group consisting of C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In certain embodiments, a subset of compounds of Formula (I) includes those of Formula (IA):

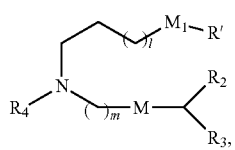

(IA)

or a salt or stereoisomer thereof, wherein 1 is selected from 1, 2, 3, 4, and 5; m is selected from 5, 6, 7, 8, and 9; M$_1$ is a bond or M'; R$_4$ is unsubstituted C$_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, a subset of compounds of Formula (I) includes those of Formula (IA), or a salt or stereoisomer thereof, wherein 1 is selected from 1, 2, 3, 4, and 5; m is selected from 5, 6, 7, 8, and 9;

M$_1$ is a bond or M';

R$_4$ is unsubstituted C$_{1-3}$ alkyl, or —(CH$_2$)$_n$Q, in which Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and R$_2$ and R$_3$ are independently selected from the group consisting of H, C$_{1-14}$ alkyl, and C$_{2-14}$ alkenyl.

In certain embodiments, a subset of compounds of Formula (I) includes those of Formula (II):

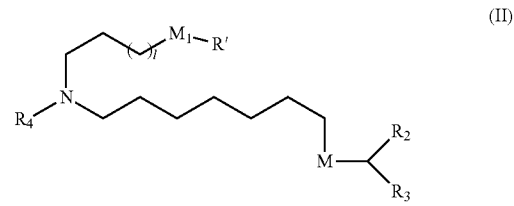

(II)

or a salt or stereoisomer thereof, wherein 1 is selected from 1, 2, 3, 4, and 5; M$_1$ is a bond or M'; R$_4$ is unsubstituted C$_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC (=CHR$_9$)N(R)$_2$, —OC(O)N(R)$_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, a subset of compounds of Formula (I) includes those of Formula (II), or a salt or stereoisomer thereof, wherein 1 is selected from 1, 2, 3, 4, and 5;

M$_1$ is a bond or M';

R$_4$ is unsubstituted C$_{1-3}$ alkyl, or —(CH$_2$)$_n$Q, in which n is 2, 3, or 4, and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and R$_2$ and R$_3$ are independently selected from the group consisting of H, C$_{1-14}$ alkyl, and C$_{2-14}$ alkenyl.

In some embodiments, the compound of formula (I) is of the formula (IIa),

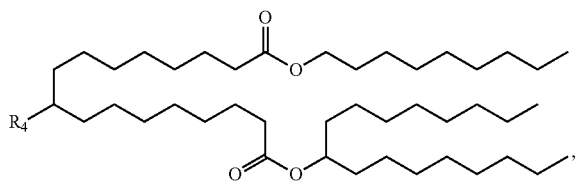

(IIa)

or a salt thereof, wherein $R_4$ is as described above.

In some embodiments, the compound of formula (I) is of the formula (IIb),

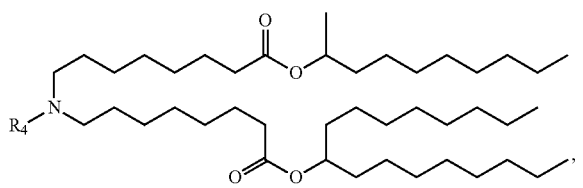

(IIb)

or a salt thereof, wherein $R_4$ is as described above.

In some embodiments, the compound of formula (I) is of the formula (IIc),

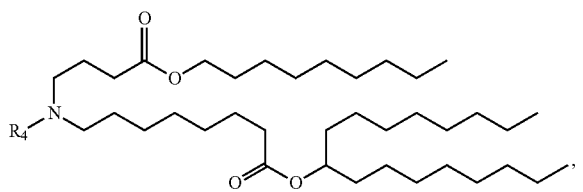

(IIc)

or a salt thereof, wherein $R_4$ is as described above.

In some embodiments, the compound of formula (I) is of the formula (IIe):

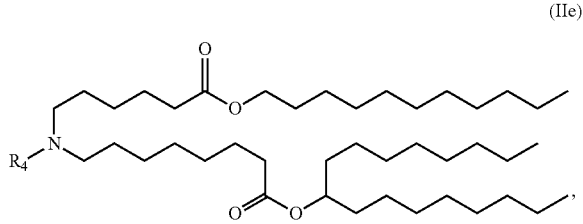

(IIe)

or a salt thereof, wherein $R_4$ is as described above.

In some embodiments, the compound of formula (IIa), (IIb), (IIc), or (IIe) comprises an $R_4$ which is selected from —$(CH_2)_nQ$ and —$(CH_2)_nCHQR$, wherein Q, R and n are as defined above.

In some embodiments, Q is selected from the group consisting of —OR, —OH, —O$(CH_2)_n$N(R)$_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle, wherein R is as defined above. In some aspects, n is 1 or 2. In some embodiments, Q is OH, —NHC(S)N(R)$_2$, or —NHC(O)N(R)$_2$.

In some embodiments, the compound of formula (I) is of the formula (IId),

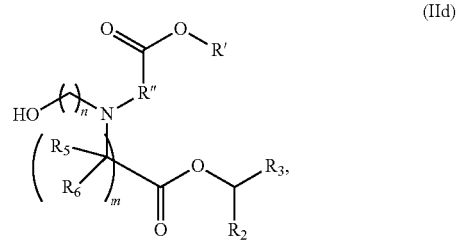

(IId)

or a salt thereof, wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined above.

In some aspects of the compound of formula (IId), $R_2$ is $C_8$ alkyl. In some aspects of the compound of formula (IId), $R_3$ is $C_5$-$C_9$ alkyl. In some aspects of the compound of formula (IId), m is 5, 7, or 9. In some aspects of the compound of formula (IId), each $R_5$ is H. In some aspects of the compound of formula (IId), each $R_6$ is H.

In another aspect, the present application provides a lipid composition (e.g., a lipid nanoparticle (LNP)) comprising: (1) a compound having the formula (I); (2) optionally a helper lipid (e.g. a phospholipid); (3) optionally a structural lipid (e.g. a sterol); (4) optionally a lipid conjugate (e.g. a PEG-lipid); and (5) optionally a quaternary amine compound. In exemplary embodiments, the lipid composition (e.g., LNP) further comprises a polynucleotide encoding an IL12B polypeptide, IL12A polypeptide, or both IL12B and IL12A polypeptides, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "$C_{1-14}$ alkyl" means a linear or branched, saturated hydrocarbon including 1-14 carbon atoms. An alkyl group may be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "$C_{2-14}$ alkenyl" means a linear or branched hydrocarbon including 2-14 carbon atoms and at least one double bond. An alkenyl group may include one, two, three, four, or more double bonds. For example, $C_{18}$ alkenyl may include one or more double bonds. A $C_{18}$ alkenyl group including two double bonds may be a linoleyl group. An alkenyl group may be optionally substituted.

As used herein, the term "carbocycle" or "carbocyclic group" means a mono- or multi-cyclic system including one or more rings of carbon atoms. Rings may be three, four, five, six, seven, eight, nine, ten, eleven, twelve, thirteen, fourteen, or fifteen membered rings.

The notation "$C_{3-6}$ carbocycle" means a carbocycle including a single ring having 3-6 carbon atoms. Carbocycles may include one or more double bonds and may be aromatic (e.g., aryl groups). Examples of carbocycles include cyclopropyl, cyclopentyl, cyclohexyl, phenyl, naphthyl, and 1,2-dihydronaphthyl groups. Carbocycles may be optionally substituted.

As used herein, the term "heterocycle" or "heterocyclic group" means a mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, or twelve membered rings. Heterocycles may include one or more double bonds and may be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles may be optionally substituted.

As used herein, a "biodegradable group" is a group that may facilitate faster metabolism of a lipid in a subject. A biodegradable group may be, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R'''', in which each OR are alkoxy groups that can be the same or different and R'''' is an alkyl or alkenyl group), a phosphate (e.g., P(O)$_4^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., S(O)$_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

The compounds of any one of formulae (I), (IA), (II), (IIa), (IIb), (IIc), (IId), and (IIe) include one or more of the following features when applicable.

In some embodiments, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, 5- to 14-membered aromatic or non-aromatic heterocycle having one or more heteroatoms selected from N, O, S, and P, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5.

In another embodiment, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and a 5- to 14-membered heterocycloalkyl having one or more heteroatoms selected from N, O, and S which is substituted with one or more substituents selected from oxo (═O), OH, amino, and $C_{1-3}$ alkyl, and each n is independently selected from 1, 2, 3, 4, and 5.

In another embodiment, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl.

In another embodiment, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5.

In another embodiment, $R_4$ is unsubstituted $C_{14}$ alkyl, e.g., unsubstituted methyl.

In certain embodiments, the disclosure provides a compound having the Formula (I), wherein $R_4$ is —(CH$_2$)$_n$Q or —(CH$_2$)$_n$CHQR, where Q is —N(R)$_2$, and n is selected from 3, 4, and 5.

In certain embodiments, the disclosure provides a compound having the Formula (I), wherein $R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5.

In certain embodiments, the disclosure provides a compound having the Formula (I), wherein $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle, and $R_4$ is —$(CH_2)_nQ$ or —$(CH_2)_nCHQR$, where Q is —$N(R)_2$, and n is selected from 3, 4, and 5.

In certain embodiments, $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle.

In some embodiments, $R_1$ is selected from the group consisting of $C_{5-20}$ alkyl and $C_{5-20}$ alkenyl.

In other embodiments, $R_1$ is selected from the group consisting of —R*YR", —YR", and —R"M'R'.

In certain embodiments, $R_1$ is selected from —R*YR" and —YR". In some embodiments, Y is a cyclopropyl group. In some embodiments, R* is $C_8$ alkyl or $C_8$ alkenyl. In certain embodiments, R" is $C_{3-12}$ alkyl. For example, R" may be $C_3$ alkyl. For example, R" may be $C_{4-8}$ alkyl (e.g., $C_4$, $C_5$, $C_6$, $C_7$, or $C_8$ alkyl).

In some embodiments, $R_1$ is $C_{5-20}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{5-20}$ alkenyl. In certain embodiments, $R_1$ is $C_{18}$ alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

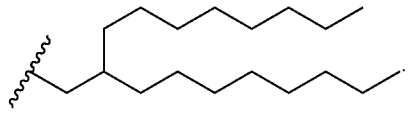 [SMILES: *CC(CCCCCCCC)CCCCCCCC]

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_{4-9}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

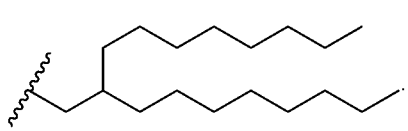 [SMILES: *CC(CCCCCCCC)CCCCCCCC]

In certain embodiments, R' is unsubstituted $C_{1-18}$ alkyl. In certain embodiments, R' is substituted $C_{1-18}$ alkyl (e.g., CI-15 alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' may be selected from the group consisting of phenyl, oxazole, and thiazole.

In some embodiments, M is —C(O)O— In some embodiments, M is —OC(O)—. In some embodiments, M is —C(O)N(R')—. In some embodiments, M is —P(O)(OR')O—.

In other embodiments, M is an aryl group or heteroaryl group. For example, M may be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from —$(CH_2)_nQ$ and —$(CH_2)_nCHQR$.

In some embodiments, Q is selected from the group consisting of —OR, —OH, —$O(CH_2)_nN(R)_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), —C(R)N(R)$_2$C(O)OR, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (=O), OH, amino, and C$_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted C$_{6-10}$ aryl (such as phenyl) or C$_{3-6}$ cycloalkyl.

In some embodiments, n is 1. In other embodiments, n is 2. In further embodiments, n is 3. In certain other embodiments, n is 4. For example, R$_4$ may be —(CH$_2$)$_2$OH. For example, R$_4$ may be —(CH$_2$)$_3$OH. For example, R$_4$ may be —(CH$_2$)$_4$OH. For example, R$_4$ may be benzyl. For example, R$_4$ may be 4-methoxybenzyl.

In some embodiments, R$_4$ is a C$_{3-6}$ carbocycle. In some embodiments, R$_4$ is a C$_{3-6}$ cycloalkyl. For example, R$_4$ may be cyclohexyl optionally substituted with e.g., OH, halo, C$_{1-6}$ alkyl, etc. For example, R$_4$ may be 2-hydroxycyclohexyl.

In some embodiments, R is H.

In some embodiments, R is unsubstituted C$_{1-3}$ alkyl or unsubstituted C$_{2-3}$ alkenyl. For example, R$_4$ may be —CH$_2$CH(OH)CH$_3$ or —CH$_2$CH(OH)CH$_2$CH$_3$.

In some embodiments, R is substituted C$_{1-3}$ alkyl, e.g., CH$_2$OH. For example, R$_4$ may be —CH$_2$CH(OH)CH$_2$OH.

In some embodiments, R$_2$ and R$_3$, together with the atom to which they are attached, form a heterocycle or carbocycle. In some embodiments, R$_2$ and R$_3$, together with the atom to which they are attached, form a 5- to 14-membered aromatic or non-aromatic heterocycle having one or more heteroatoms selected from N, O, S, and P. In some embodiments, R$_2$ and R$_3$, together with the atom to which they are attached, form an optionally substituted C$_{3-20}$ carbocycle (e.g., C$_{3-18}$ carbocycle, C$_{3-15}$ carbocycle, C$_{3-12}$ carbocycle, or C$_{3-10}$ carbocycle), either aromatic or non-aromatic. In some embodiments, R$_2$ and R$_3$, together with the atom to which they are attached, form a C$_{3-6}$ carbocycle. In other embodiments, R$_2$ and R$_3$, together with the atom to which they are attached, form a C$_6$ carbocycle, such as a cyclohexyl or phenyl group. In certain embodiments, the heterocycle or C$_{3-6}$ carbocycle is substituted with one or more alkyl groups (e.g., at the same ring atom or at adjacent or non-adjacent ring atoms). For example, R$_2$ and R$_3$, together with the atom to which they are attached, may form a cyclohexyl or phenyl group bearing one or more C$_5$ alkyl substitutions. In certain embodiments, the heterocycle or C$_{3-6}$ carbocycle formed by R$_2$ and R$_3$, is substituted with a carbocycle groups. For example, R$_2$ and R$_3$, together with the atom to which they are attached, may form a cyclohexyl or phenyl group that is substituted with cyclohexyl. In some embodiments, R$_2$ and R$_3$, together with the atom to which they are attached, form a C$_{7-15}$ carbocycle, such as a cycloheptyl, cyclopentadecanyl, or naphthyl group.

In some embodiments, R$_4$ is selected from —(CH$_2$)$_n$Q and —(CH$_2$)$_n$CHQR. In some embodiments, Q is selected from the group consisting of —OR, —OH, —O(CH$_2$)$_n$N(R)$_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle. In other embodiments, Q is selected from the group consisting of an imidazole, a pyrimidine, and a purine.

In some embodiments, R$_2$ and R$_3$, together with the atom to which they are attached, form a heterocycle or carbocycle. In some embodiments, R$_2$ and R$_3$, together with the atom to which they are attached, form a C$_{3-6}$ carbocycle, such as a phenyl group. In certain embodiments, the heterocycle or C$_{3-6}$ carbocycle is substituted with one or more alkyl groups (e.g., at the same ring atom or at adjacent or non-adjacent ring atoms). For example, R$_2$ and R$_3$, together with the atom to which they are attached, may form a phenyl group bearing one or more C$_5$ alkyl substitutions.

In some embodiments, the pharmaceutical compositions of the present disclosure, the compound of formula (I) is selected from the group consisting of:

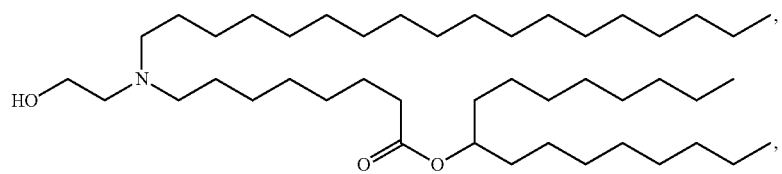

(Compound 1)

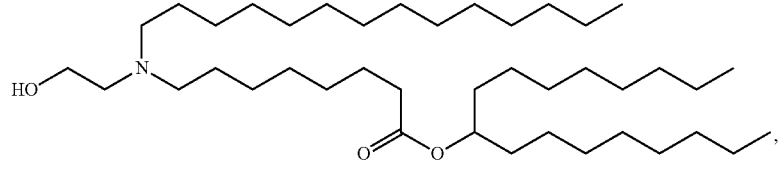

(Compound 2)

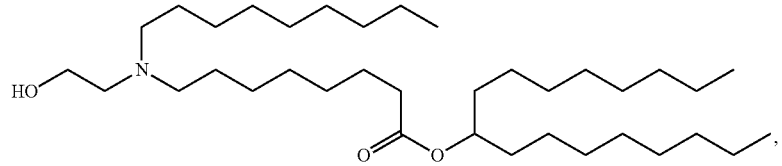

(Compound 3)

-continued
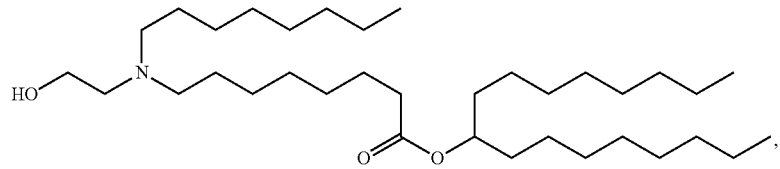
(Compound 4)
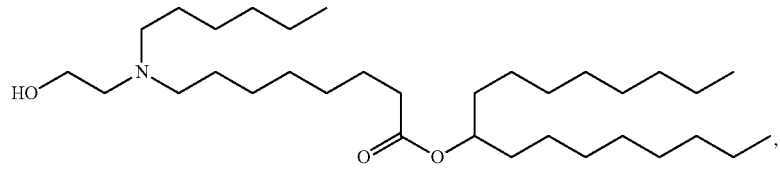
(Compound 5)
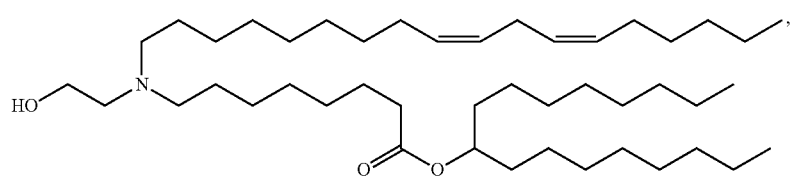
(Compound 6)
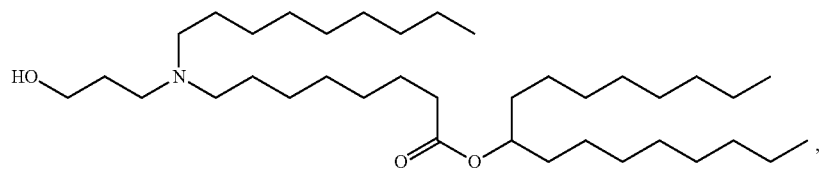
(Compound 7)
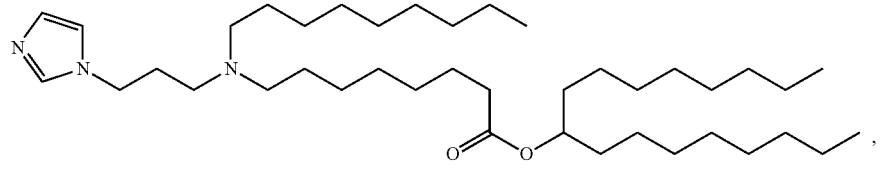
(Compound 8)
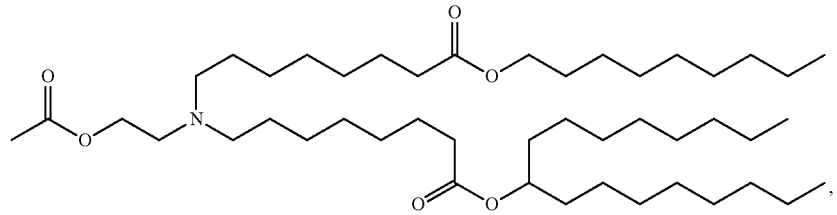
(Compound 9)
(Compound 10)
(Compound 11)
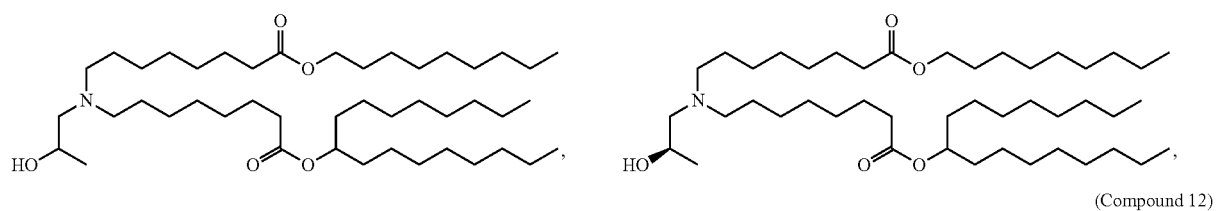
(Compound 12)
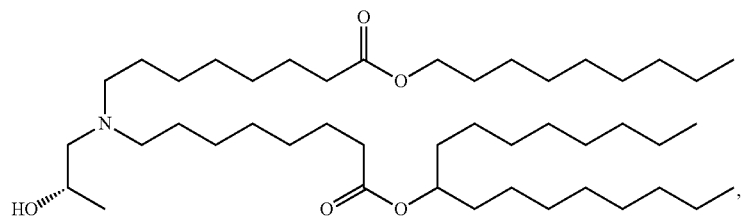

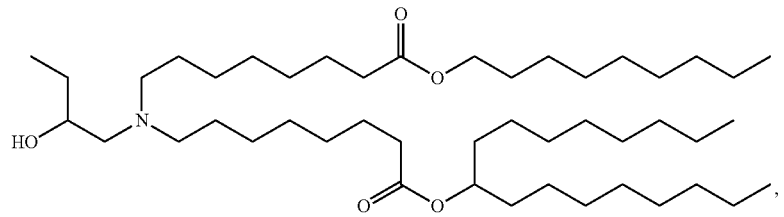
(Compound 13)
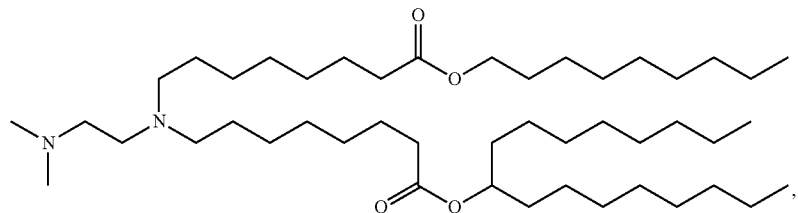
(Compound 14)
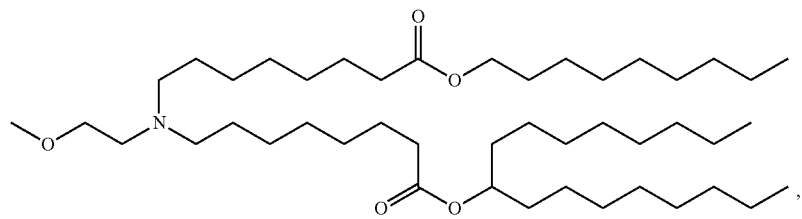
(Compound 15)
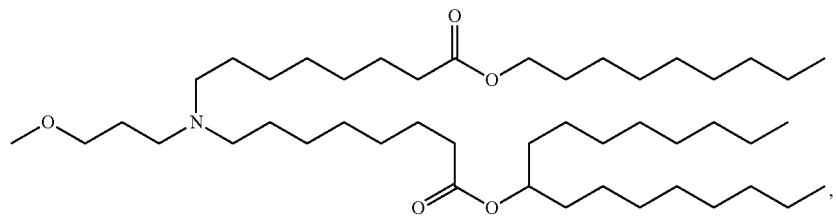
(Compound 16)
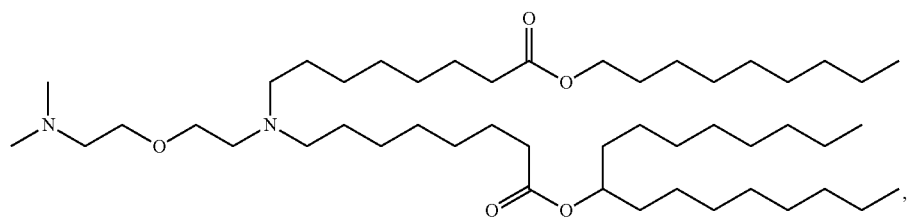
(Compound 17)
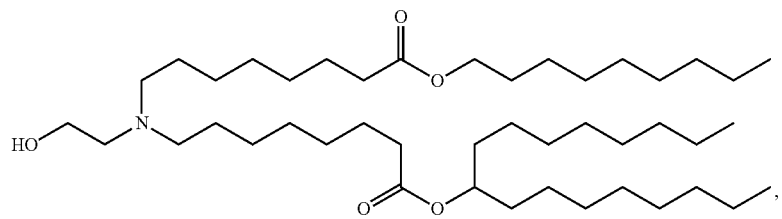
(Compound 18)
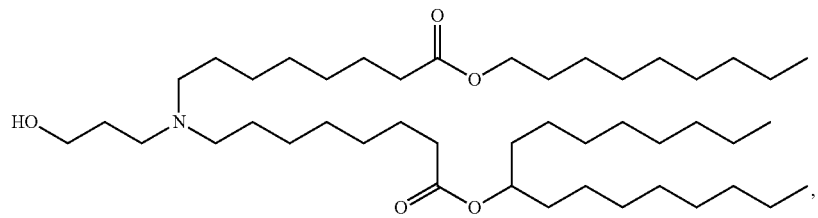
(Compound 19)

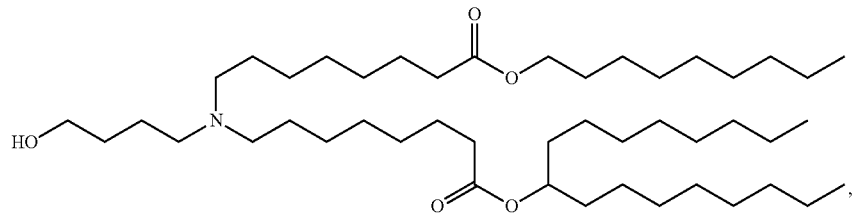
(Compound 20)
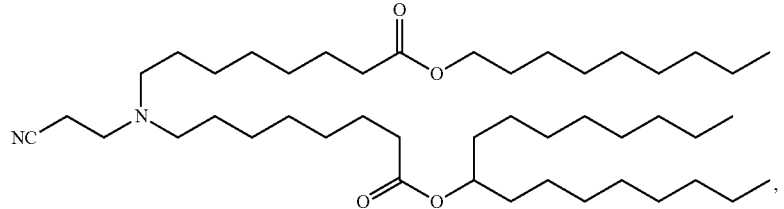
(Compound 21)
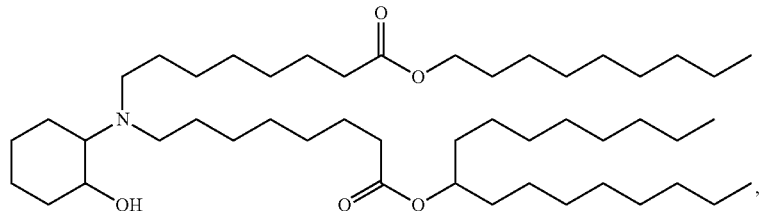
(Compound 22)
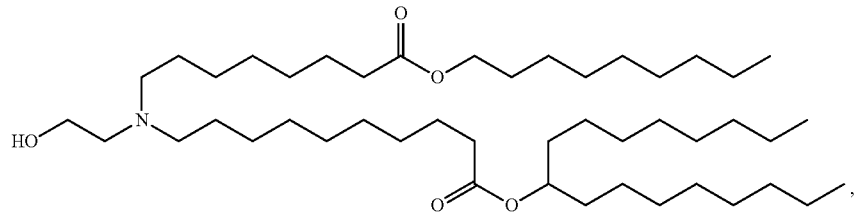
(Compound 23)
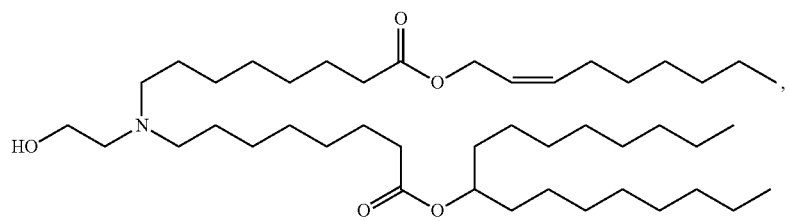
(Compound 24)
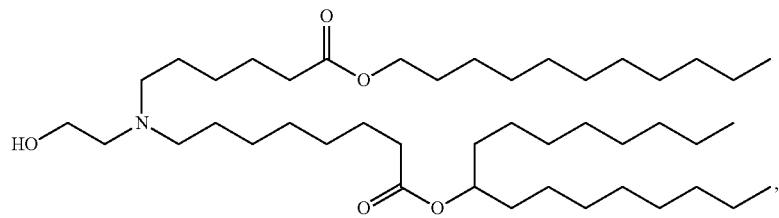
(Compound 25)
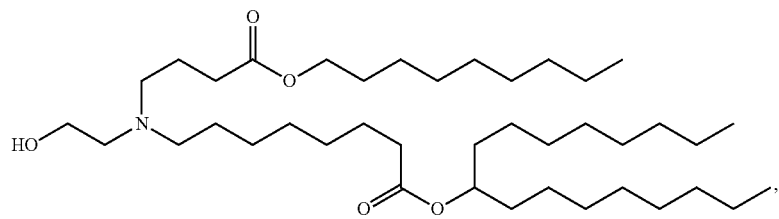
(Compound 26)

-continued
(Compound 27)
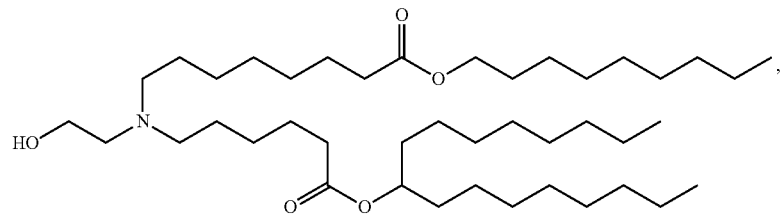
(Compound 28)
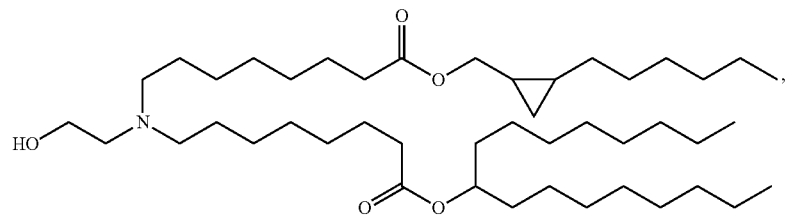
(Compound 29)
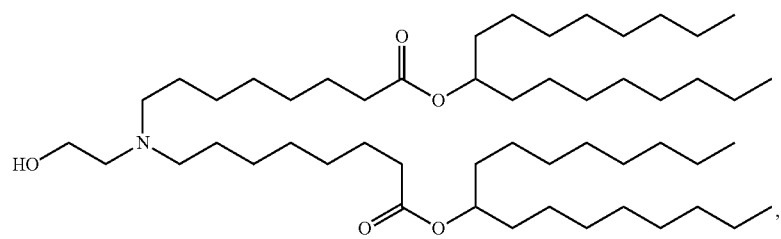
(Compound 30)
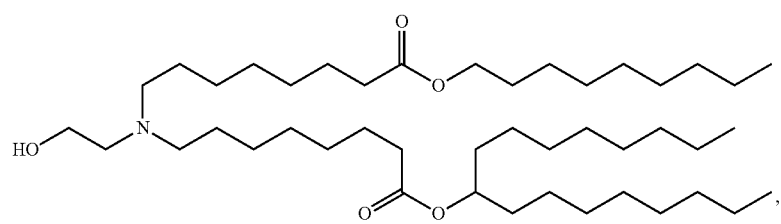
(Compound 31)
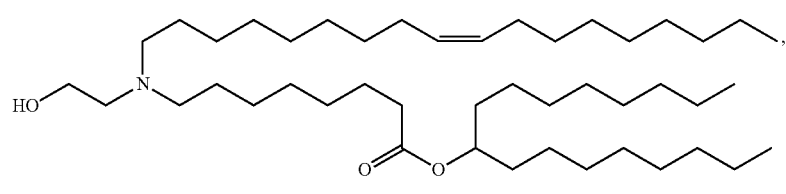
(Compound 32)
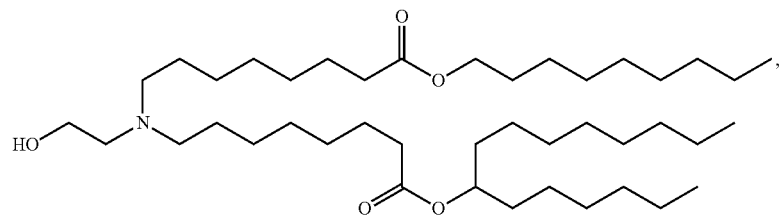
(Compound 33)
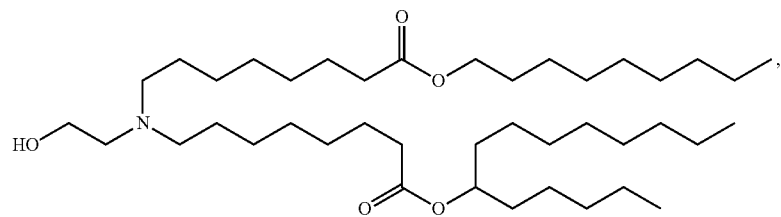

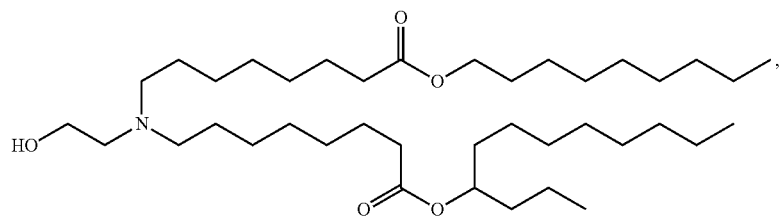
(Compound 34)
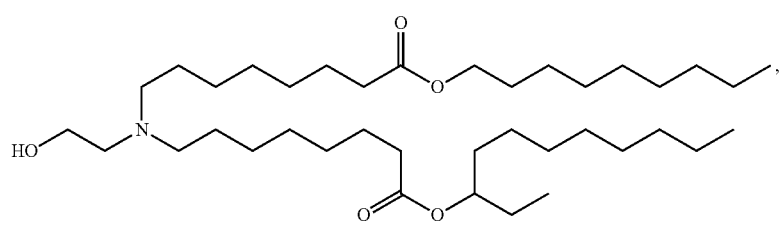
(Compound 35)
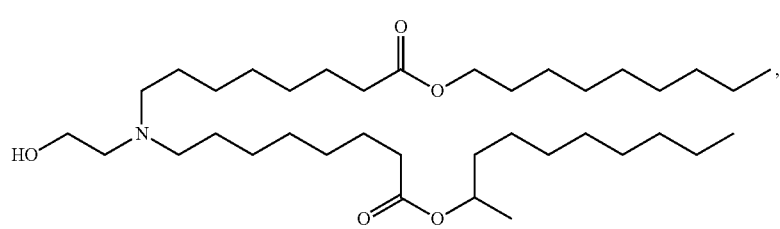
(Compound 36)
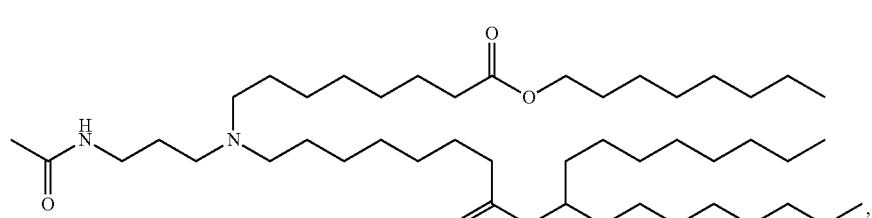
(Compound 37)
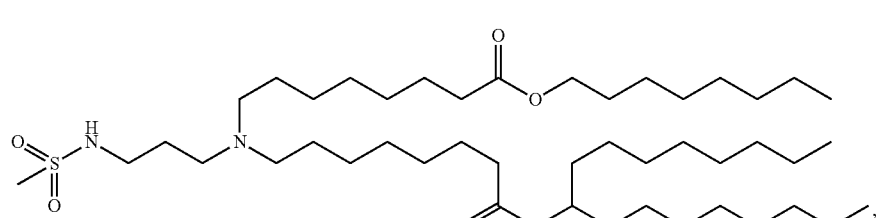
(Compound 38)
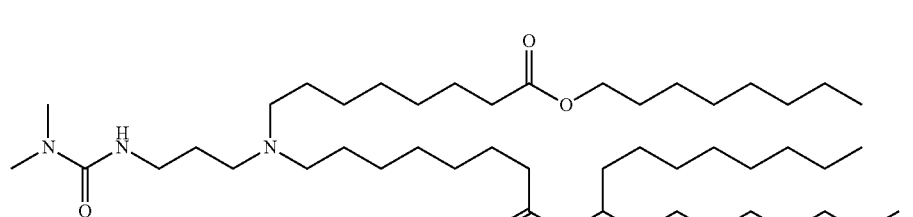
(Compound 39)
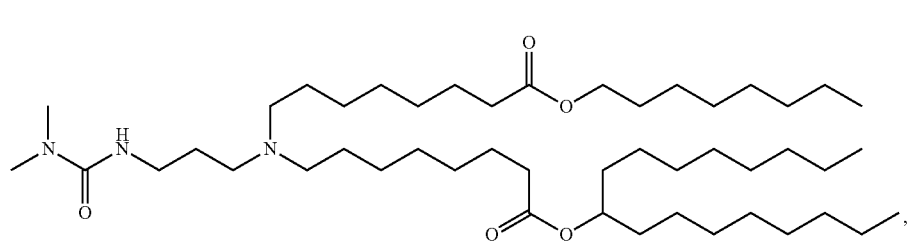
(Compound 40)

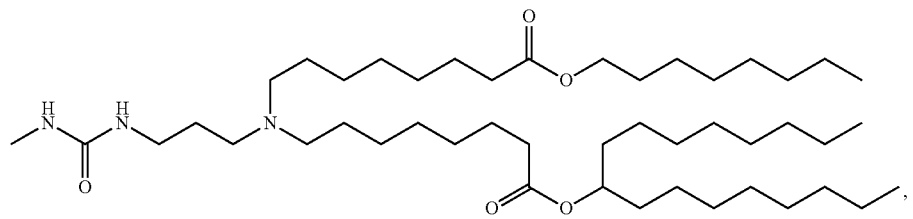
(Compound 41)
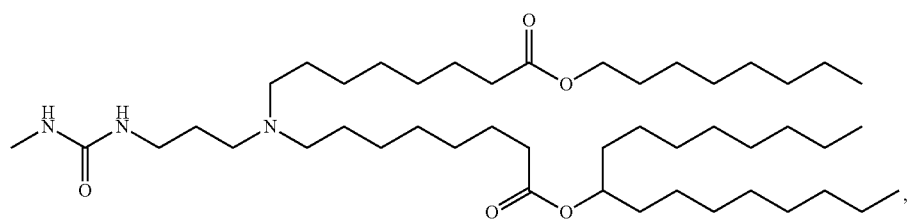
(Compound 42)
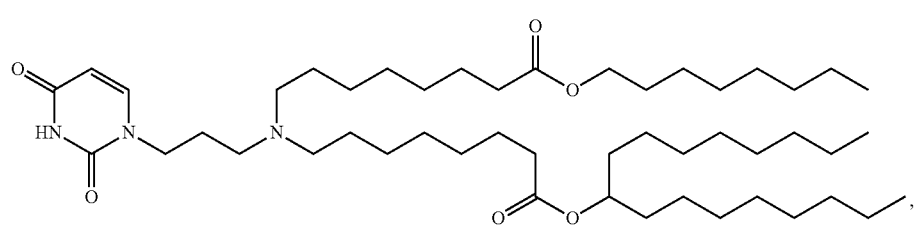
(Compound 43)
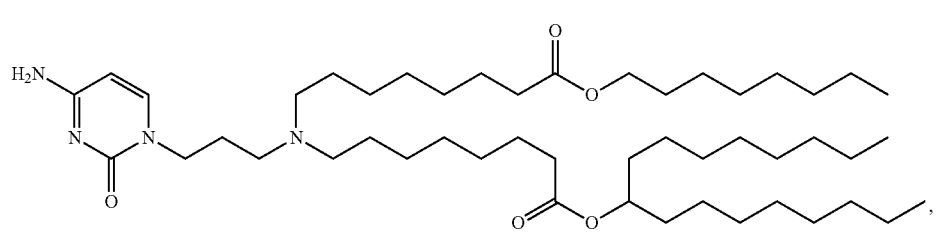
(Compound 44)
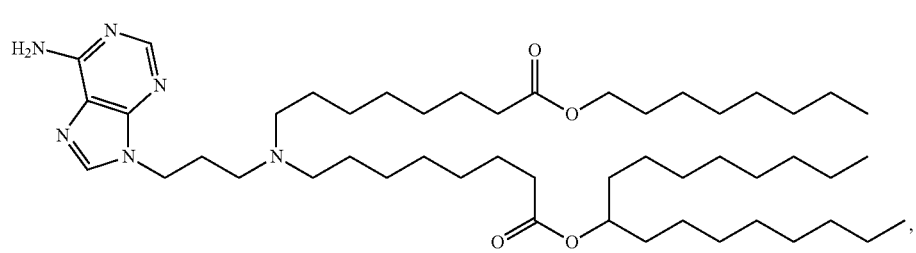
(Compound 45)
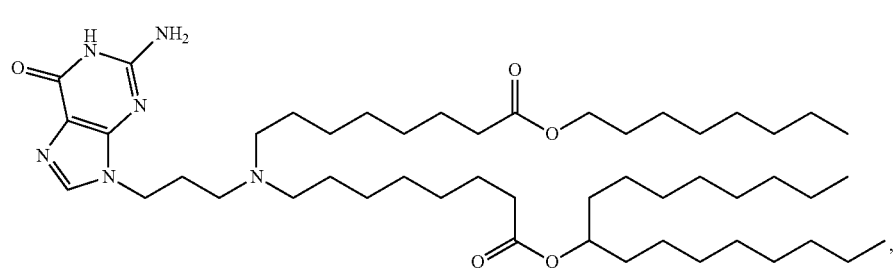
(Compound 46)
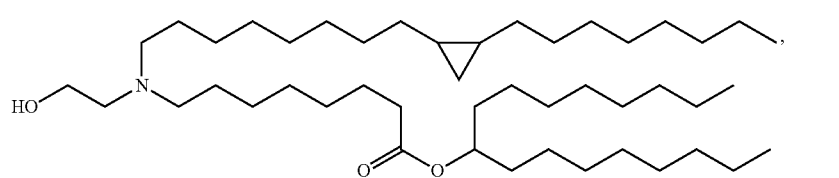
(Compound 47)

-continued
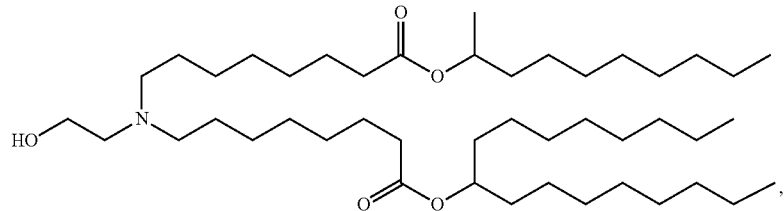
(Compound 48)
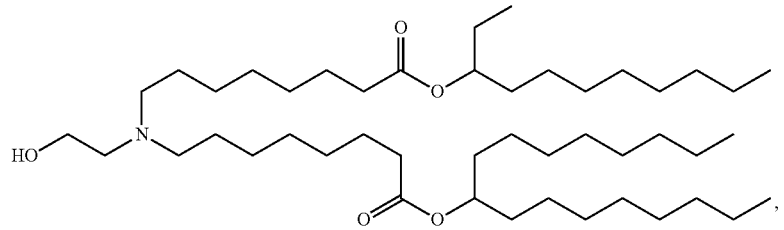
(Compound 49)
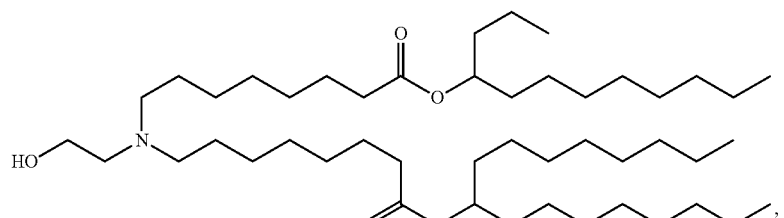
(Compound 50)
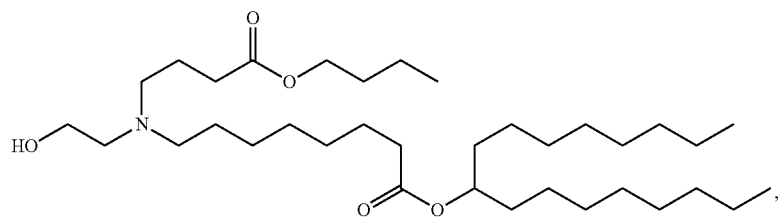
(Compound 51)
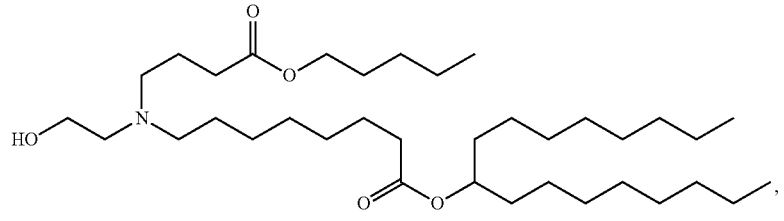
(Compound 52)
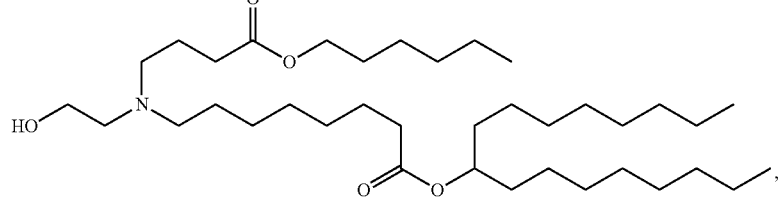
(Compound 53)
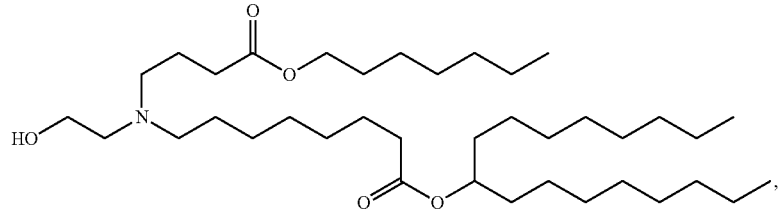
(Compound 54)

-continued
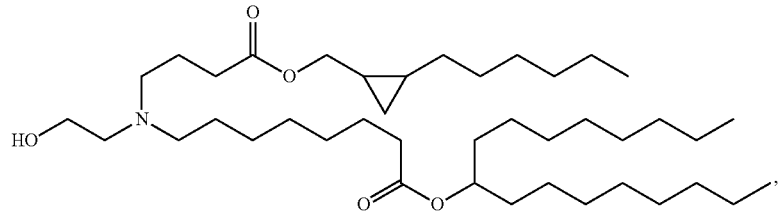
(Compound 55)
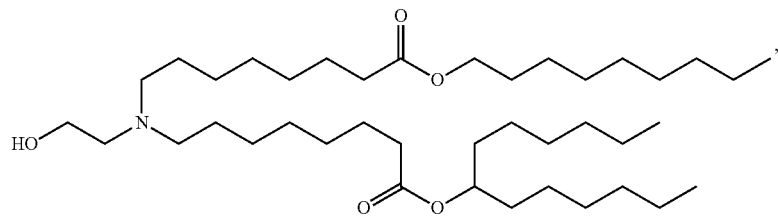
(Compound 56)
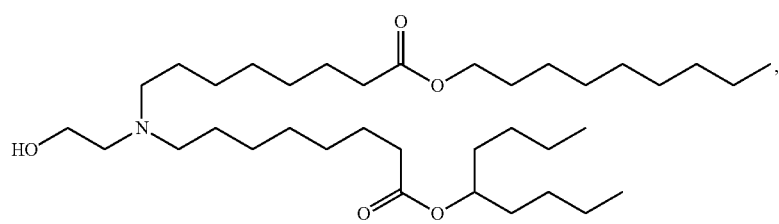
(Compound 57)
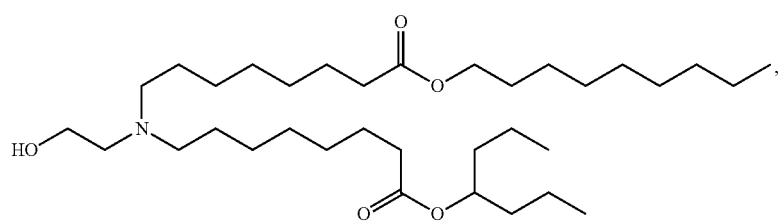
(Compound 58)
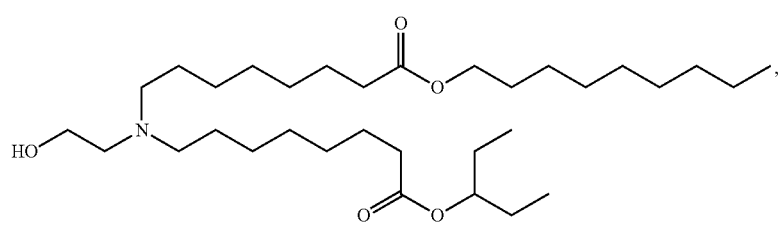
(Compound 59)
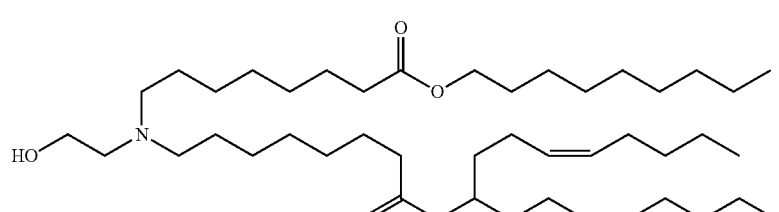
(Compound 60)
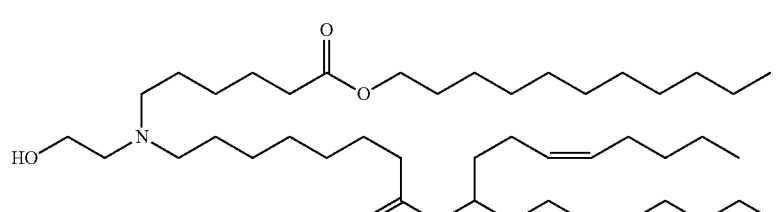
(Compound 61)

(Compound 62)
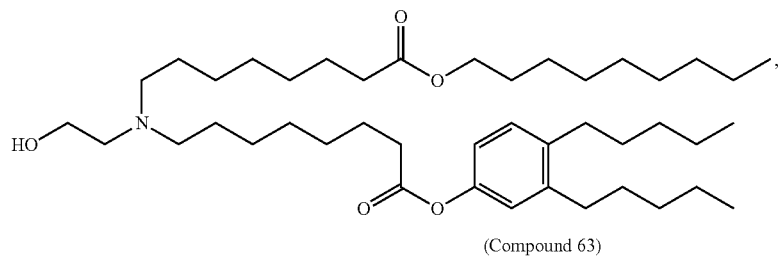
(Compound 63)
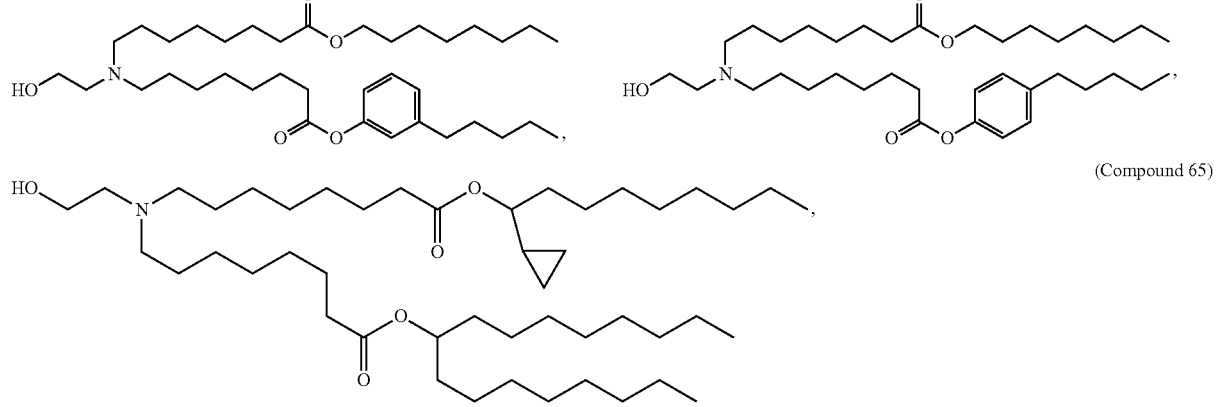
(Compound 64)
(Compound 65)
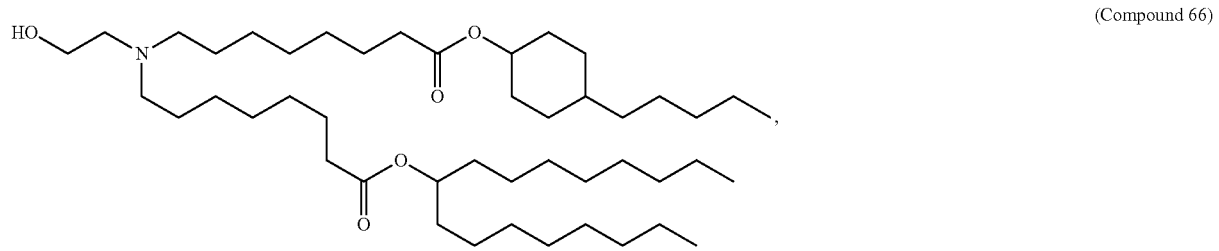
(Compound 66)
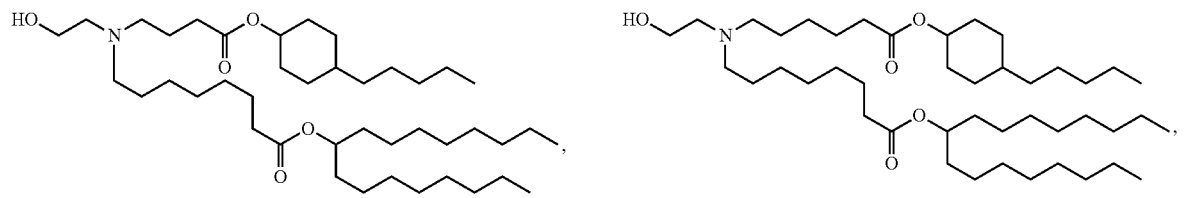
(Compound 67)
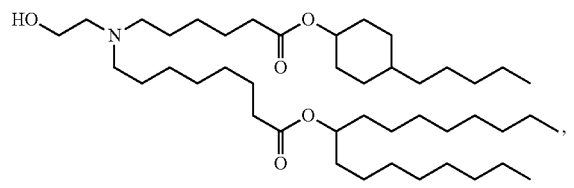
(Compound 68)
(Compound 69)
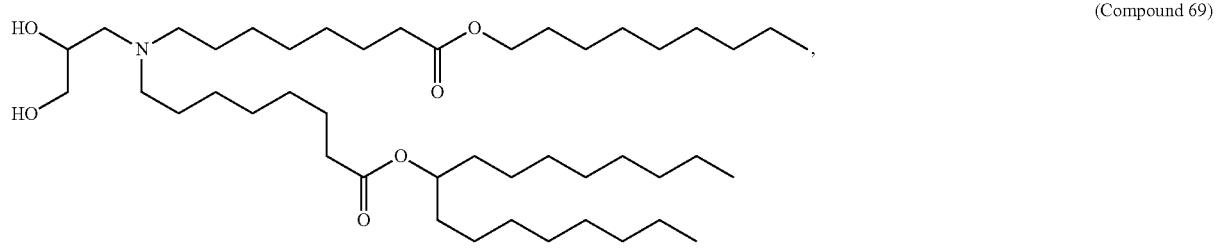
(Compound 70)
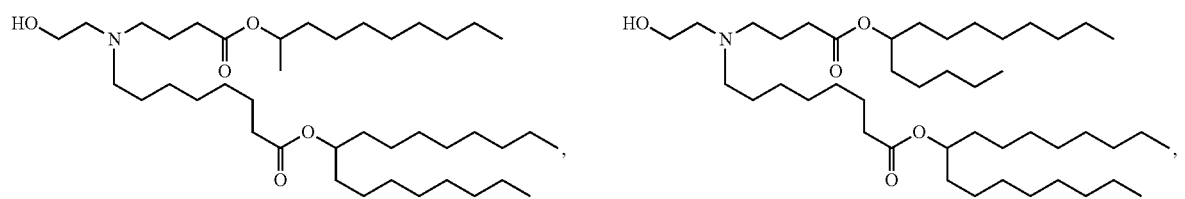
(Compound 71)
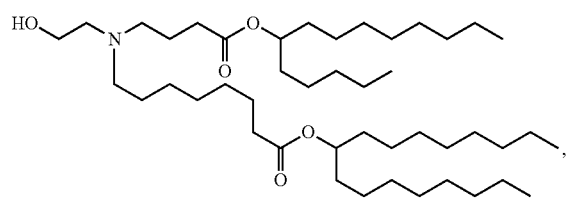

(Compound 72)
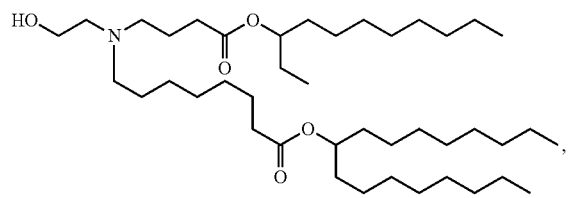
(Compound 73)
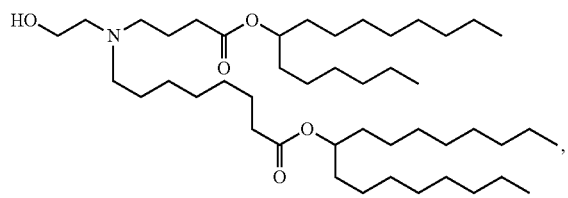
(Compound 74)
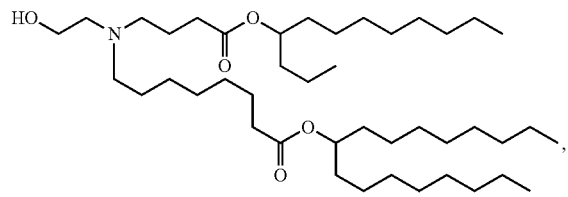
(Compound 75)
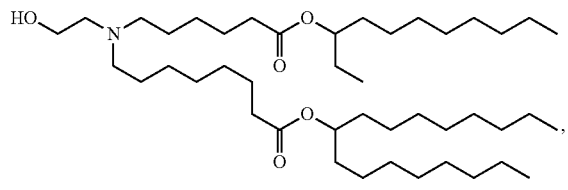
(Compound 76)
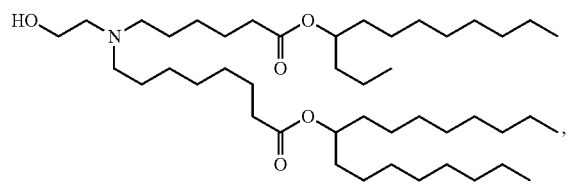
(Compound 77)
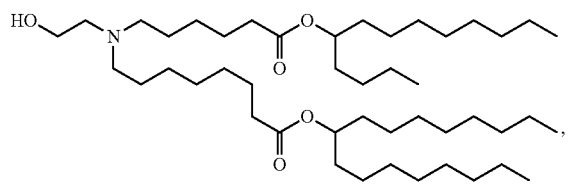
(Compound 78)
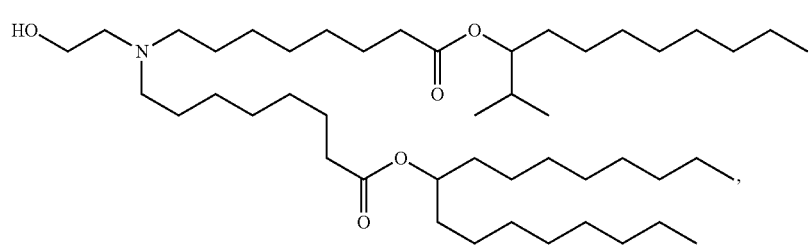
(Compound 79)
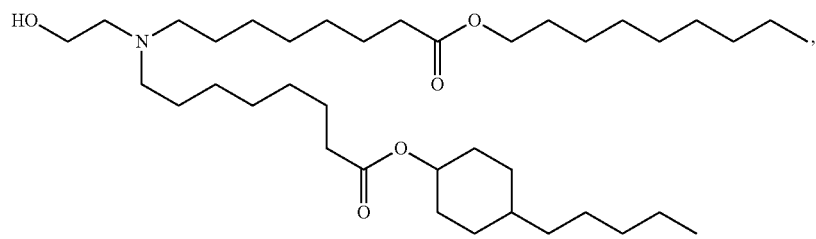
(Compound 80)
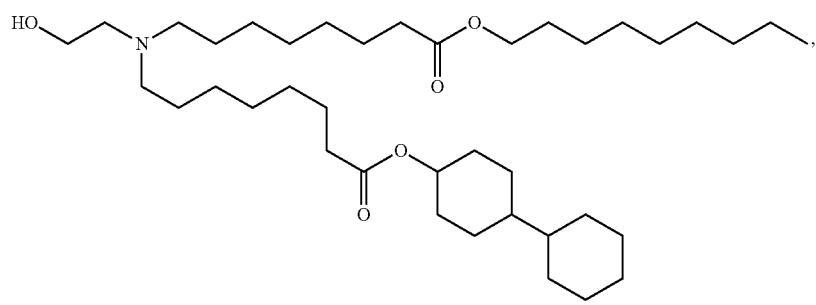

-continued
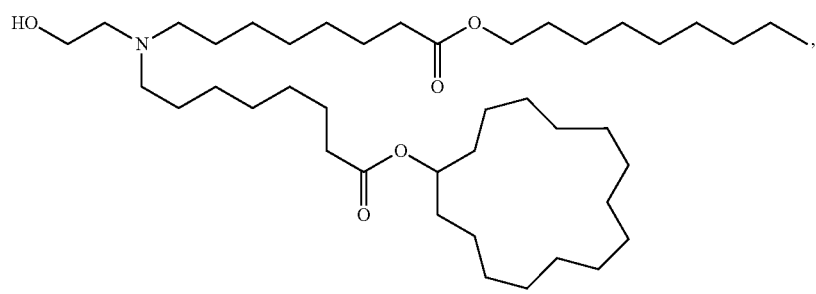
(Compound 81)
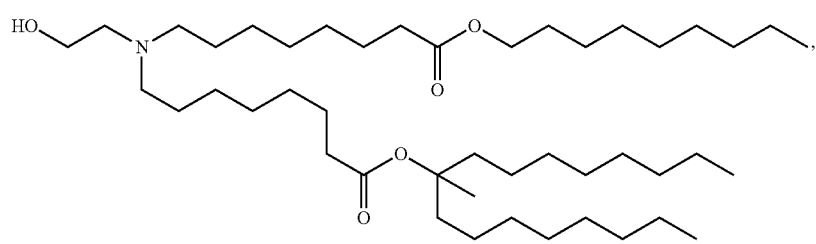
(Compound 82)
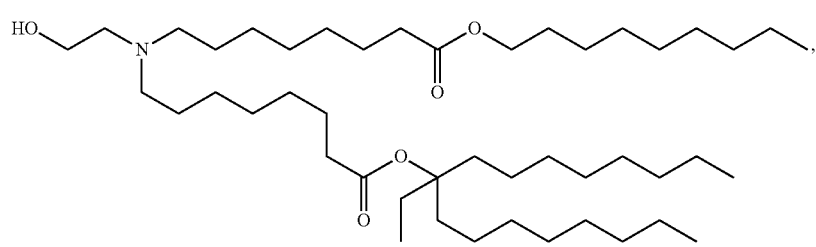
(Compound 83)
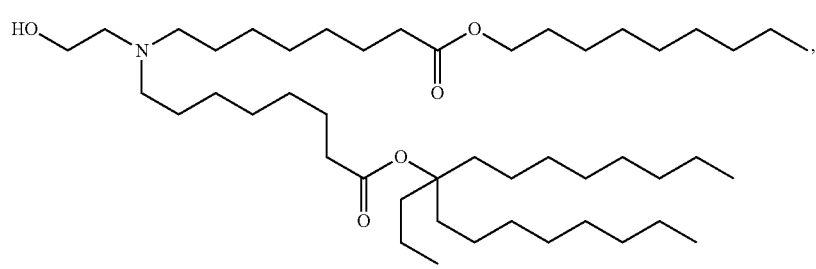
(Compound 84)
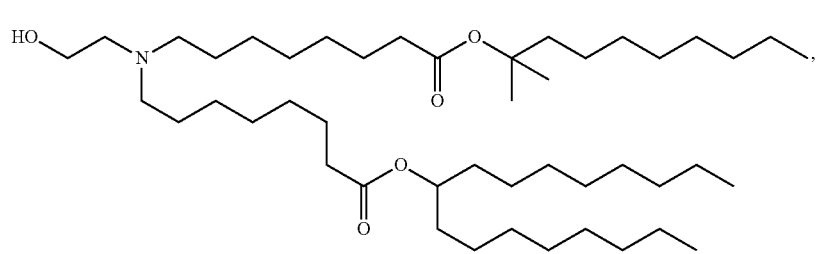
(Compound 85)
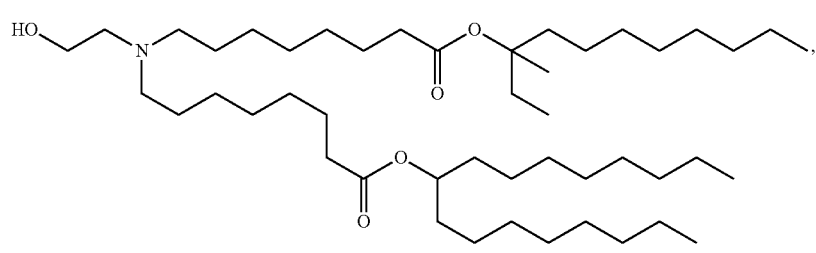
(Compound 86)

-continued
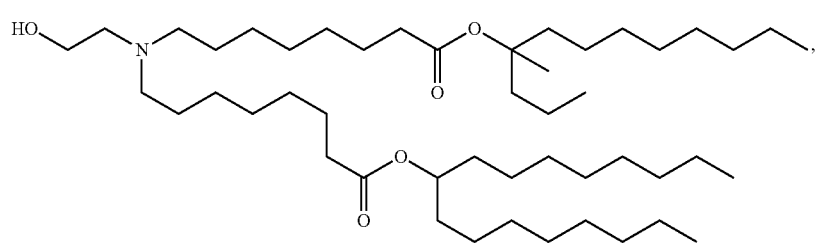
(Compound 87)
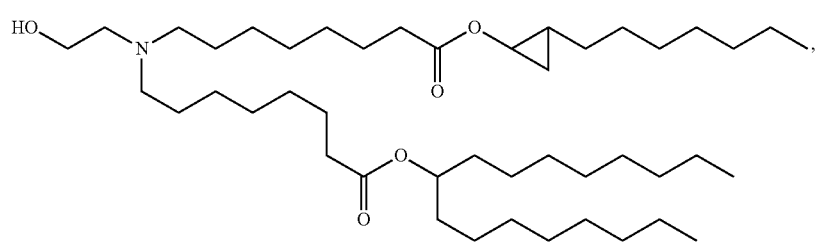
(Compound 88)
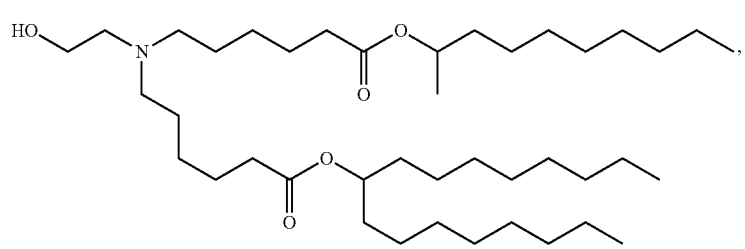
(Compound 89)
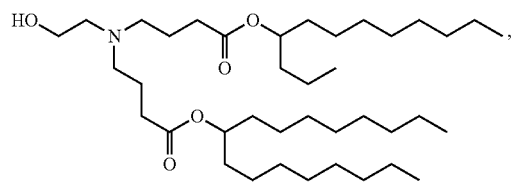
(Compound 90)
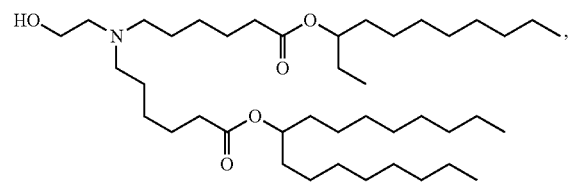
(Compound 91)
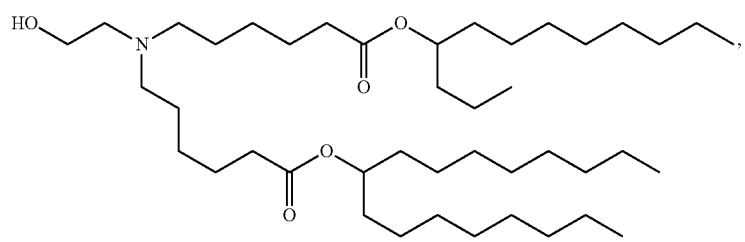
(Compound 92)
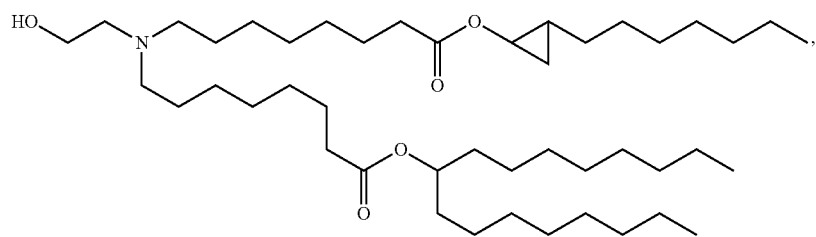
(Compound 93)
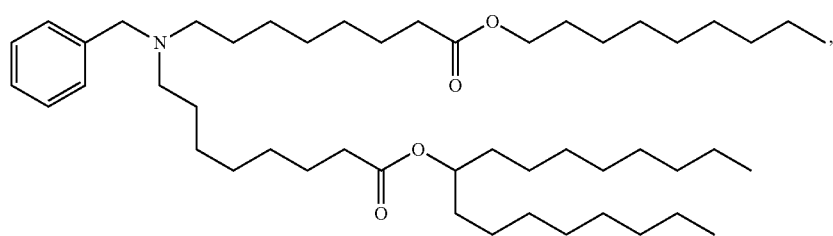
(Compound 94)

-continued
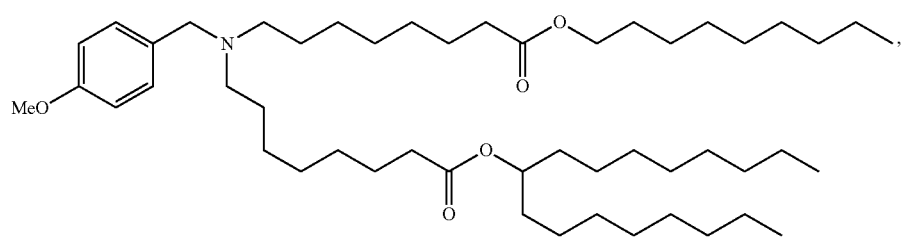
(Compound 95)
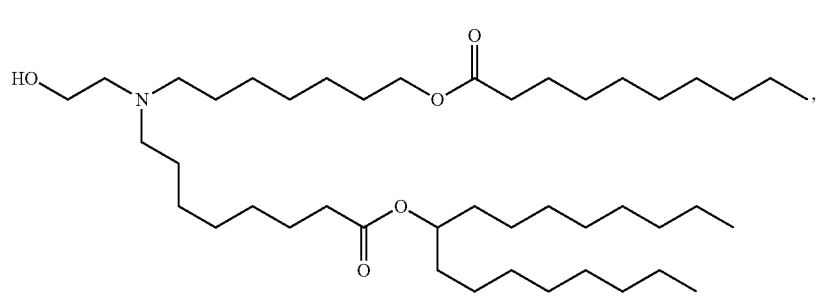
(Compound 96)
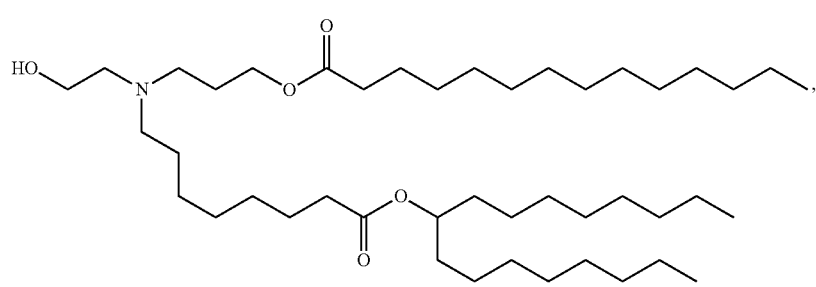
(Compound 97)
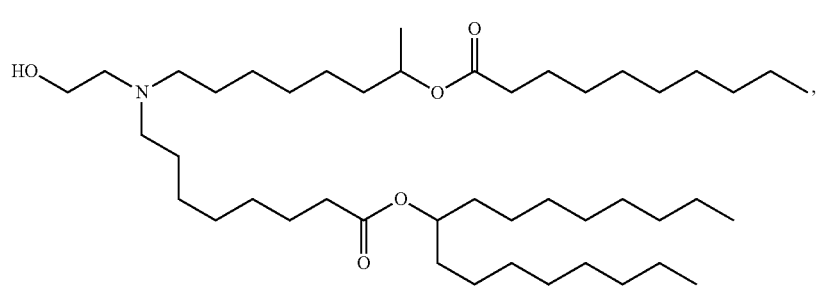
(Compound 98)
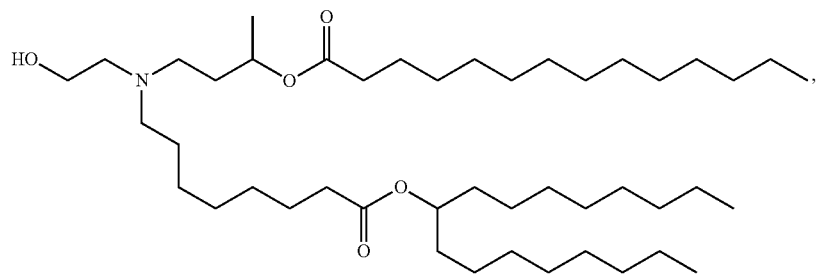
(Compound 99)

-continued
(Compound 100)
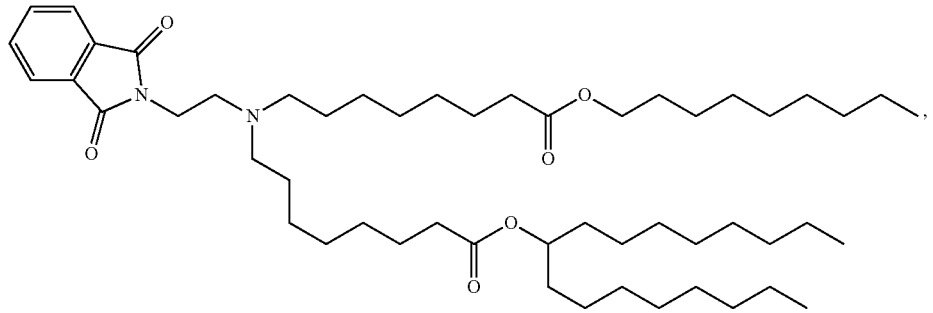
(Compound 101)
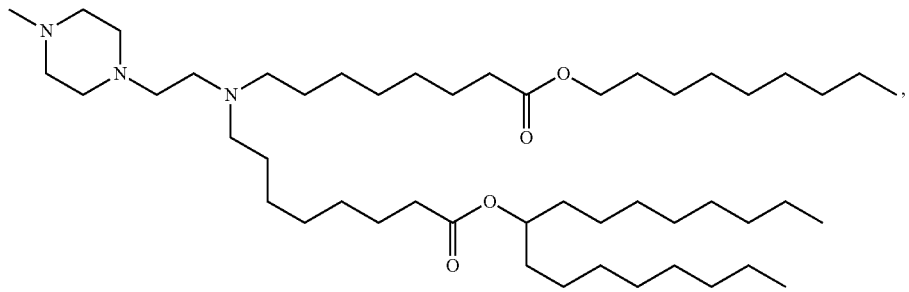
(Compound 102)
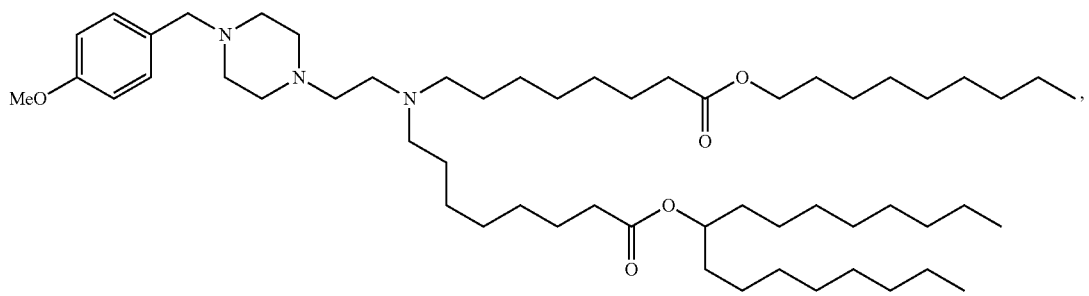
(Compound 103)
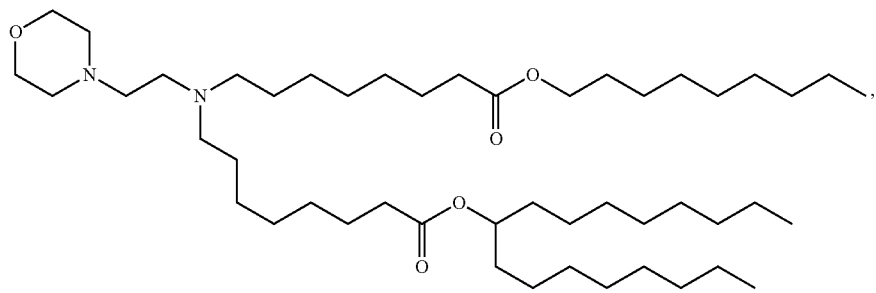
(Compound 104)
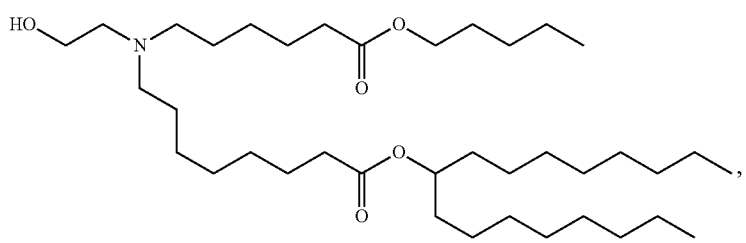

-continued
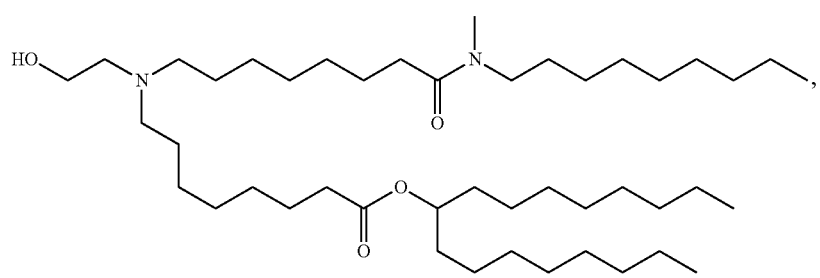
(Compound 105)
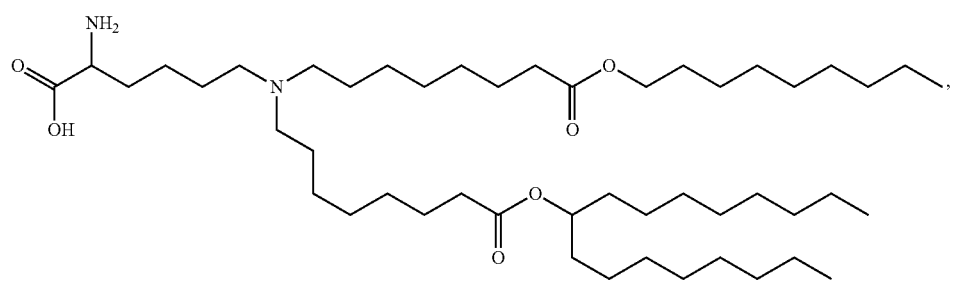
(Compound 106)
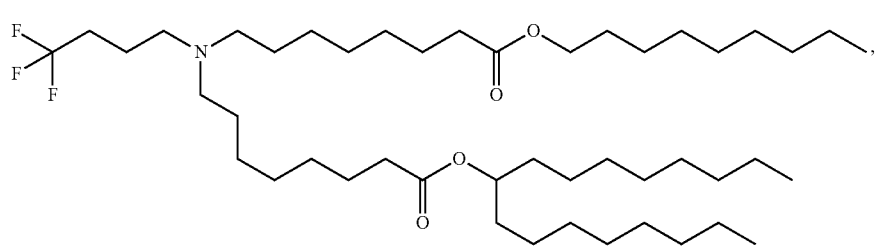
(Compound 107)
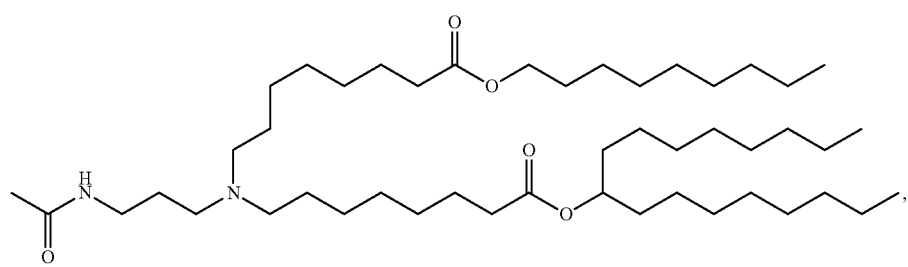
(Compound 108)
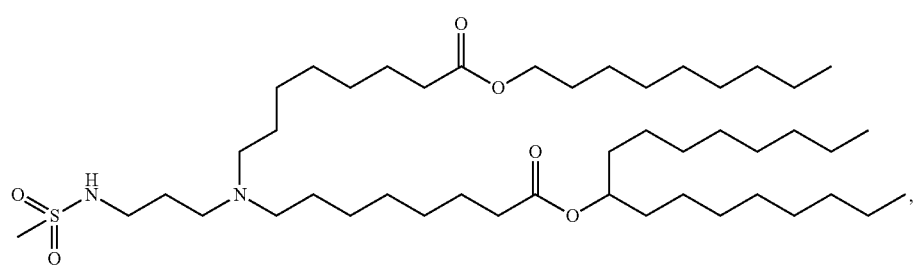
(Compound 109)
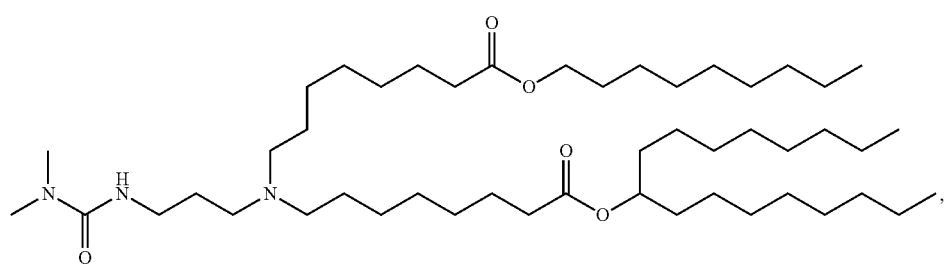
(Compound 110)

(Compound 111)
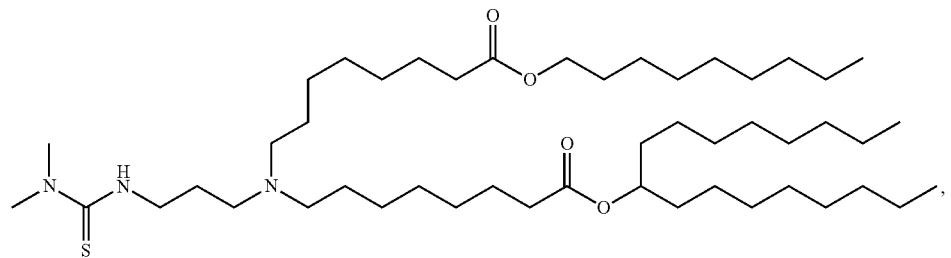
(Compound 112)
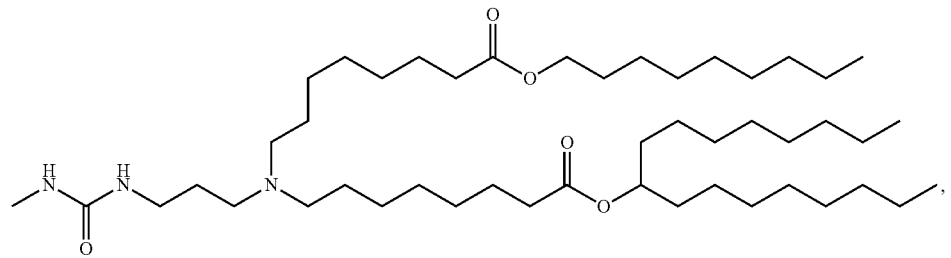
(Compound 113)
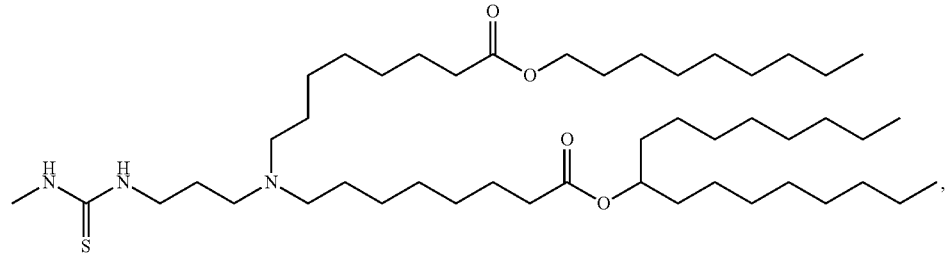
(Compound 114)
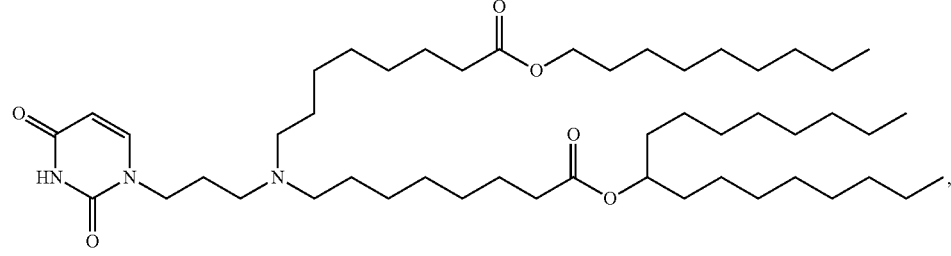
(Compound 115)
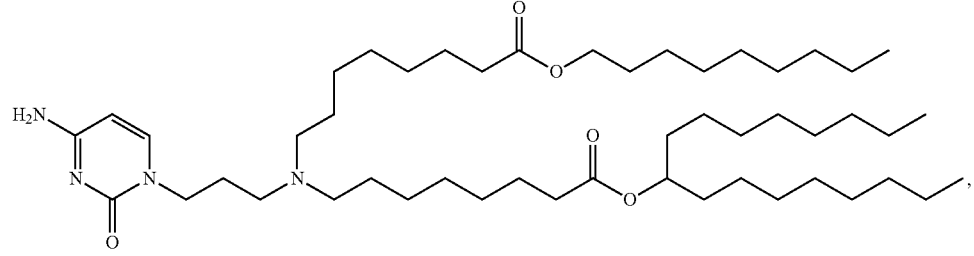
(Compound 116)
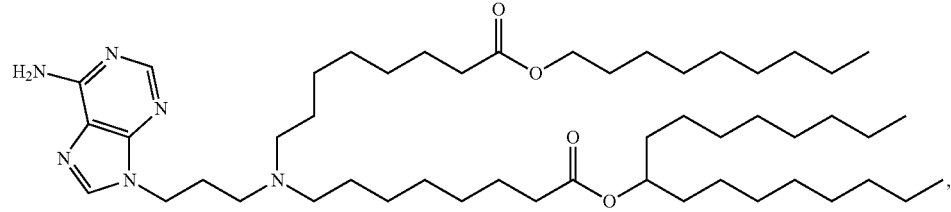

(Compound 117)
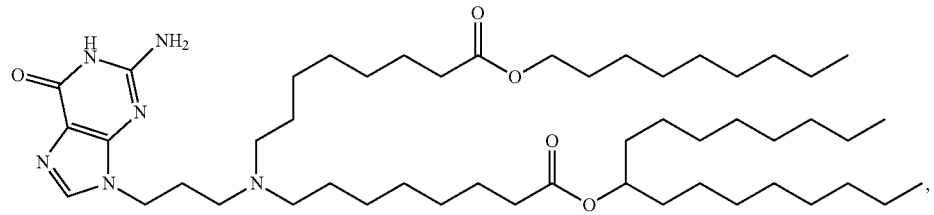
(Compound 118)
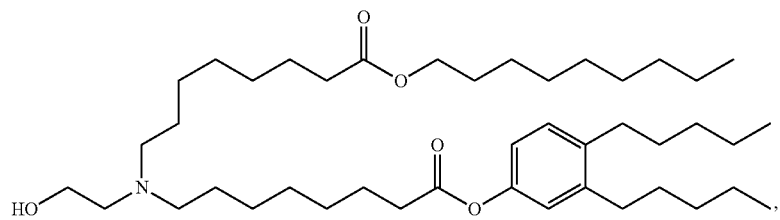
(Compound 119)
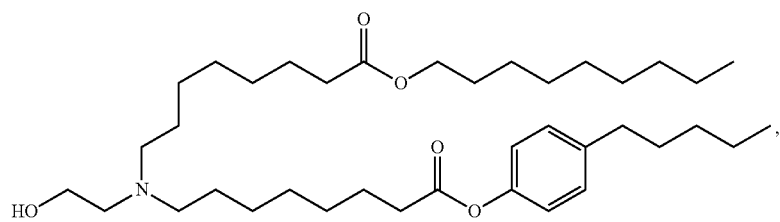
(Compound 120)
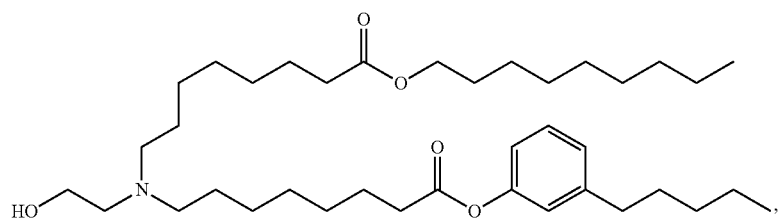
(Compound 121)
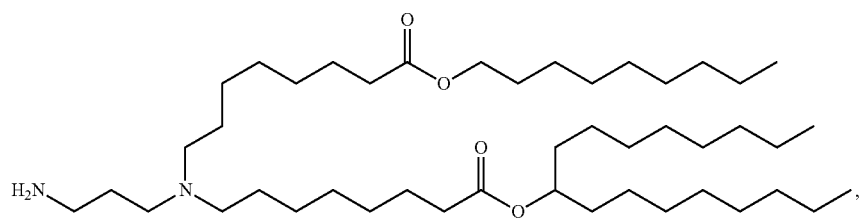
(Compound 122)
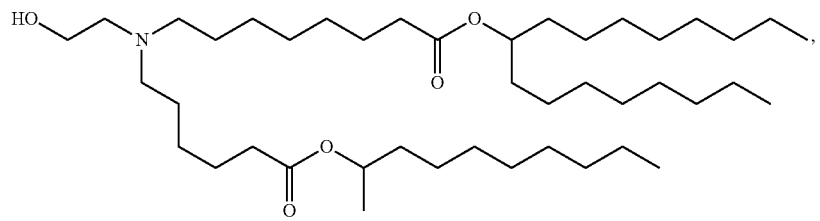
(Compound 123)
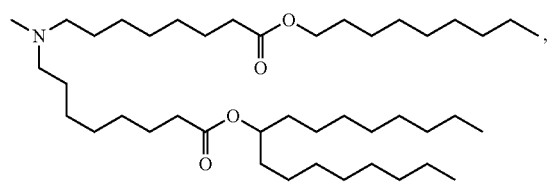
(Compound 124)
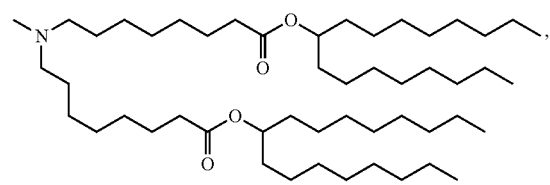

-continued
(Compound 125)
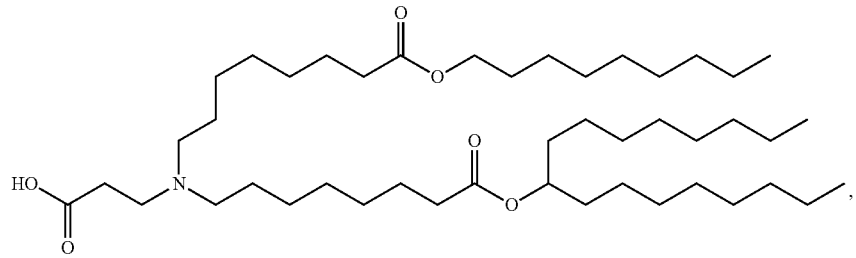
(Compound 126)
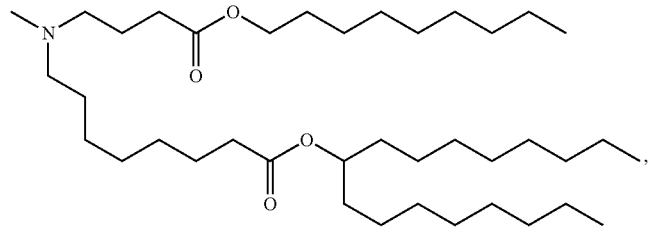
(Compound 127)
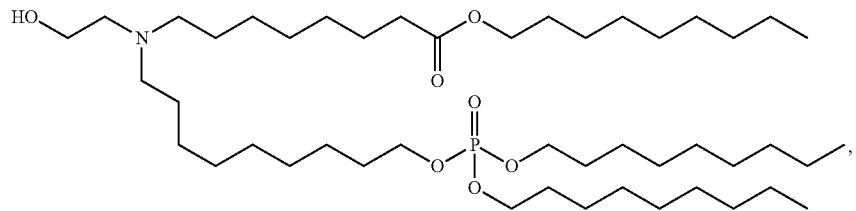
(Compound 128)
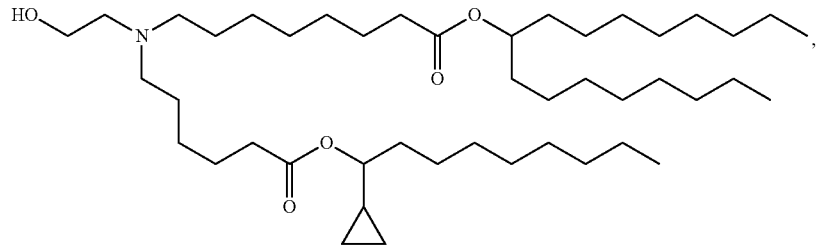
(Compound 129)
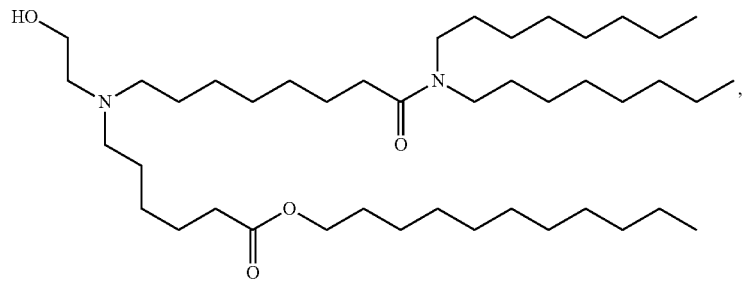
(Compound 130)
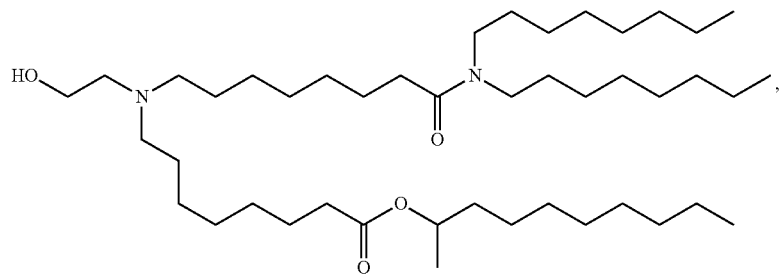

-continued
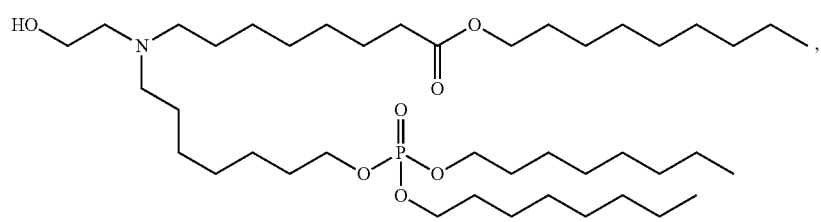
(Compound 131)
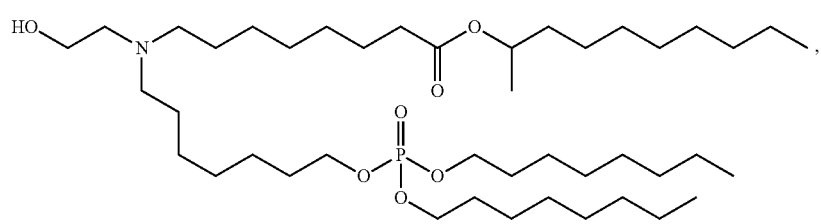
(Compound 132)
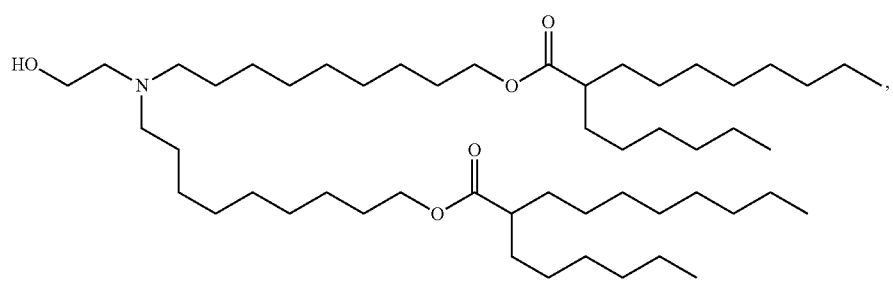
(Compound 133)
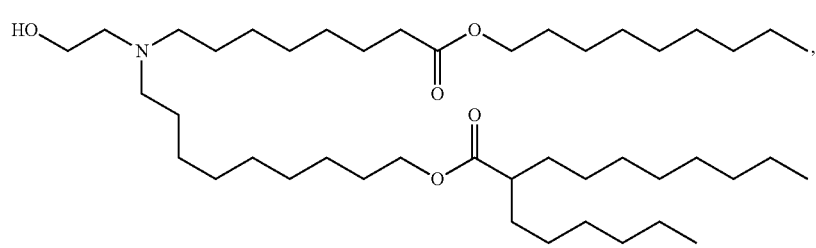
(Compound 134)
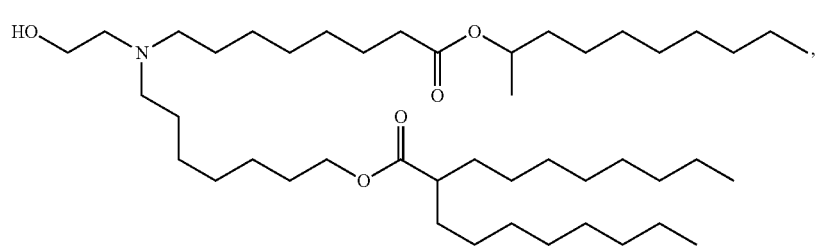
(Compound 135)
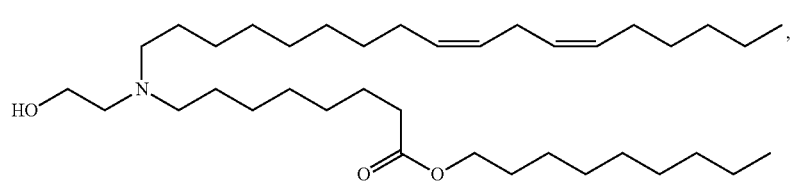
(Compound 136)
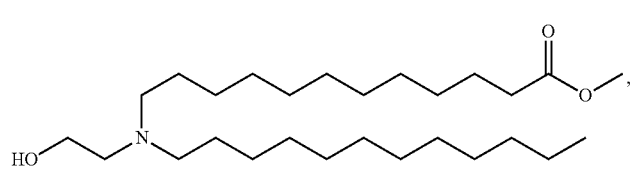
(Compound 137)

-continued
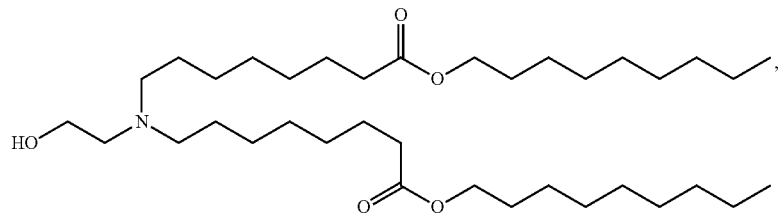
(Compound 138)
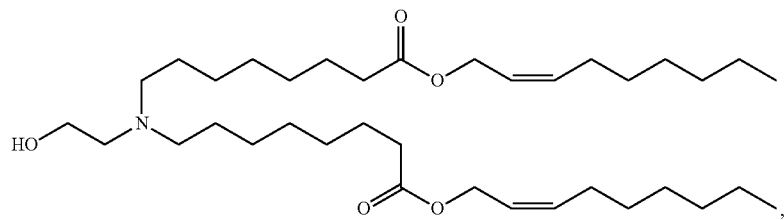
(Compound 139)
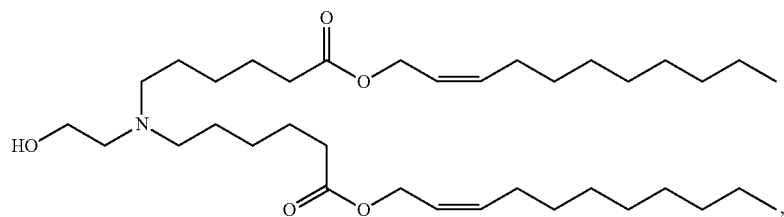
(Compound 140)
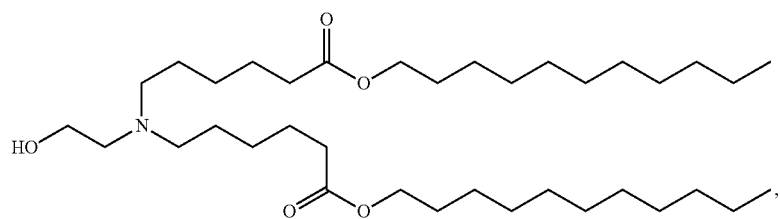
(Compound 141)
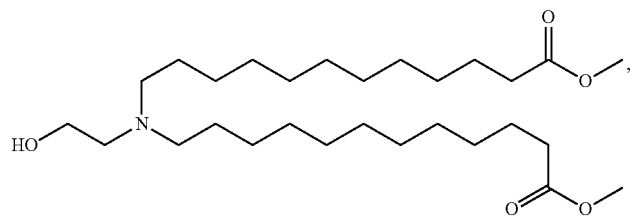
(Compound 142)
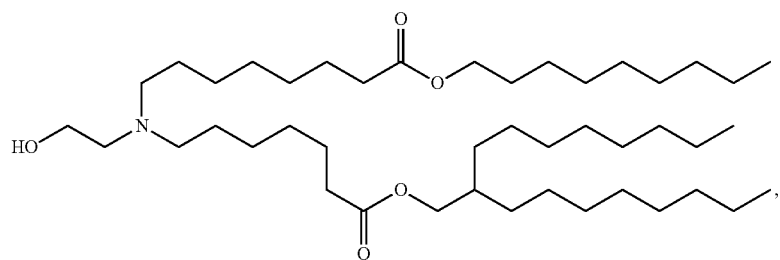
(Compound 143)

(Compound 144)
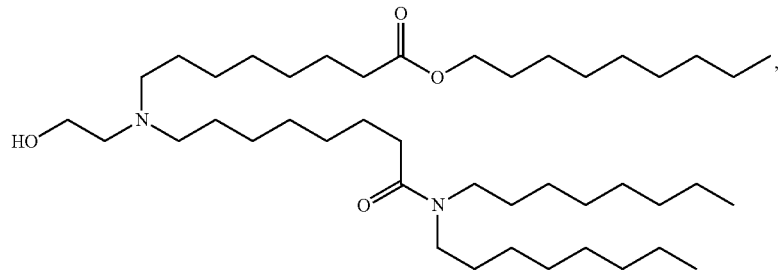
(Compound 145)
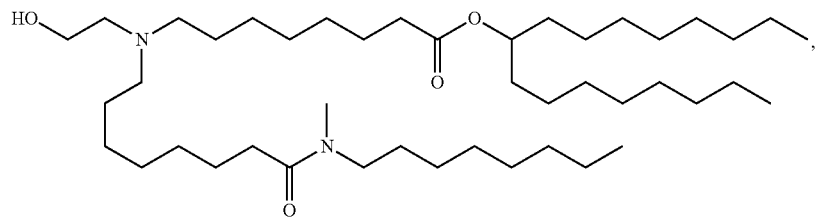
(Compound 146)
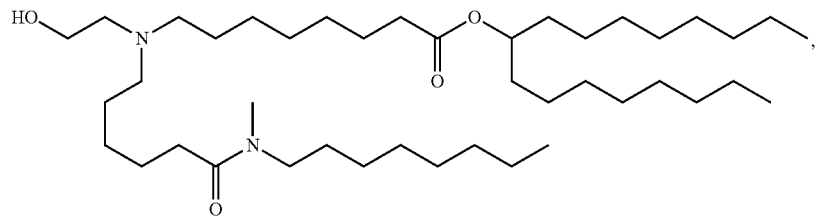
(Compound 147)
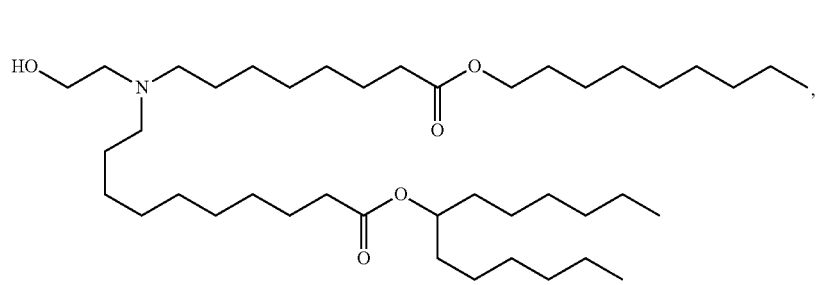
(Compound 148)
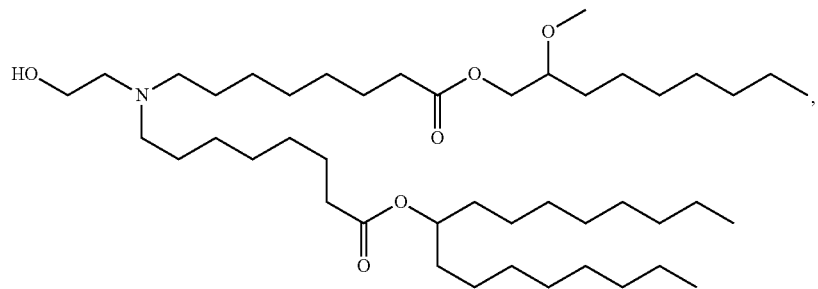
(Compound 149) (Compound 150)
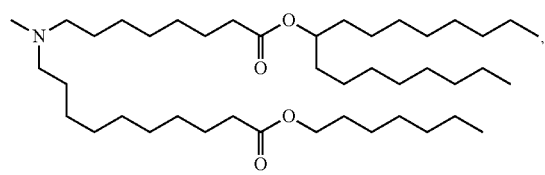

(Compound 151)
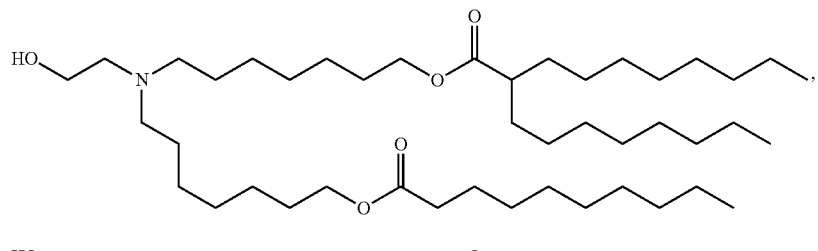
(Compound 152)
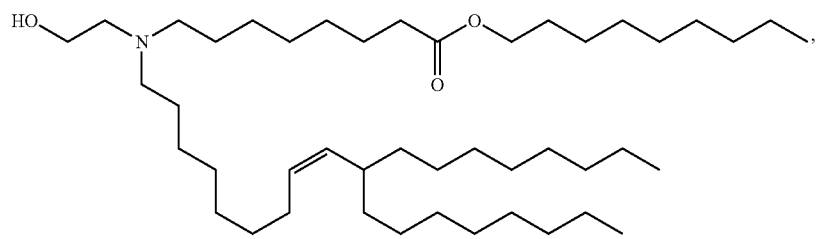
(Compound 153)
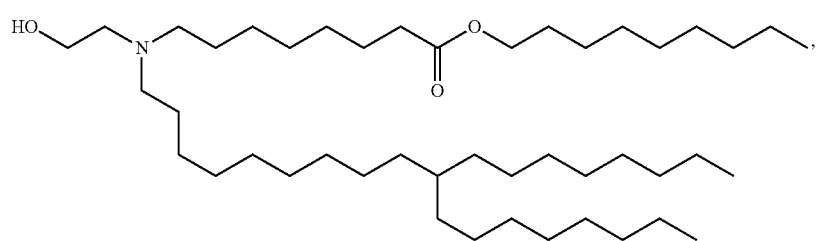
(Compound 154)
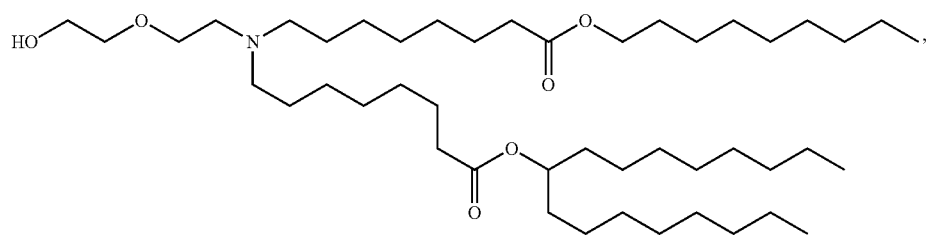
(Compound 155)
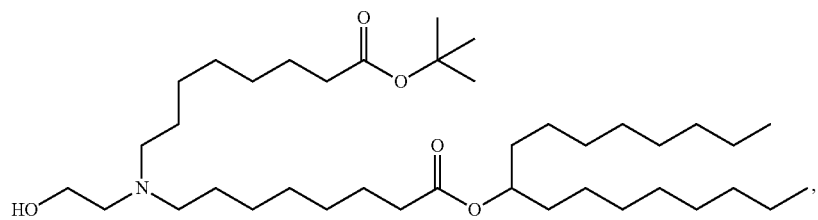
(Compound 156)
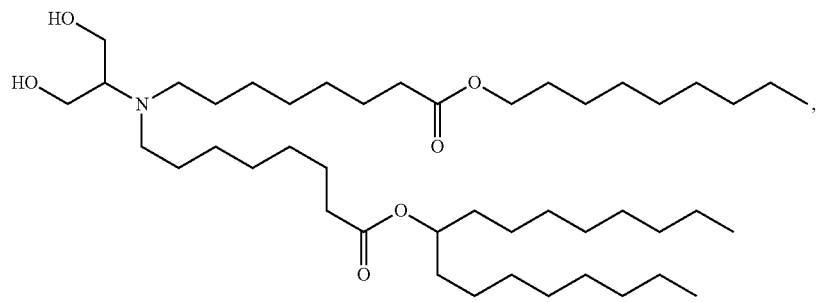

-continued
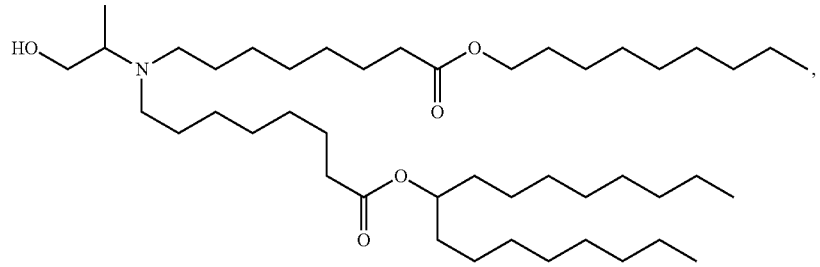
(Compound 157)
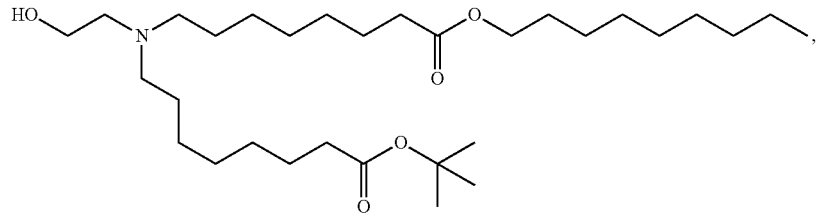
(Compound 158)
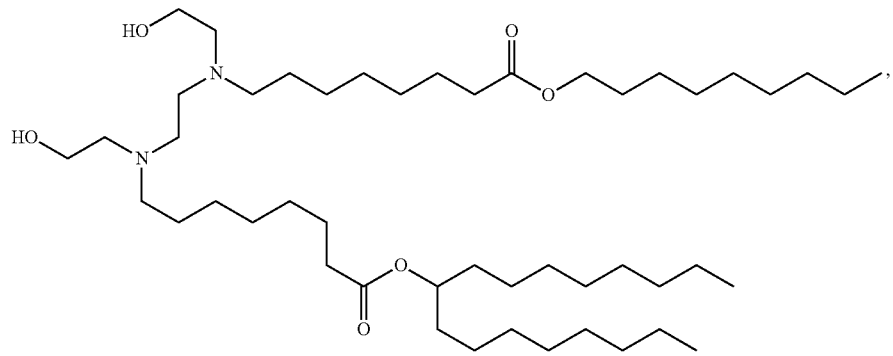
(Compound 159)
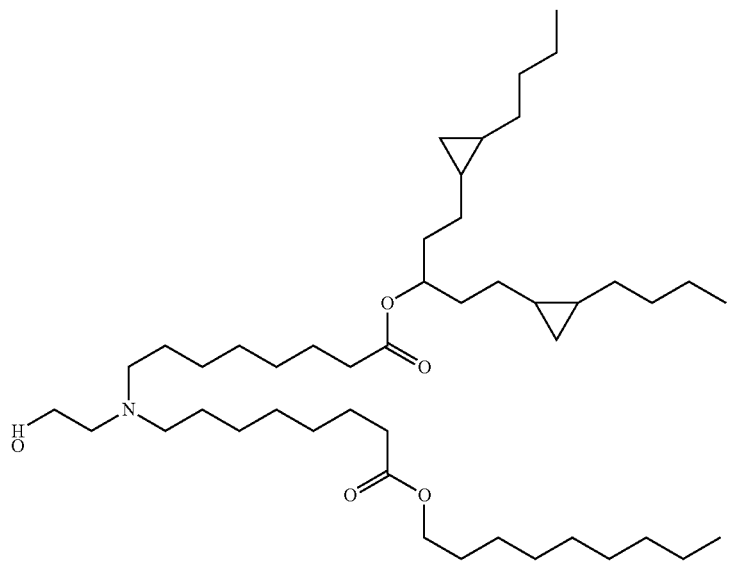
(Compound 160)
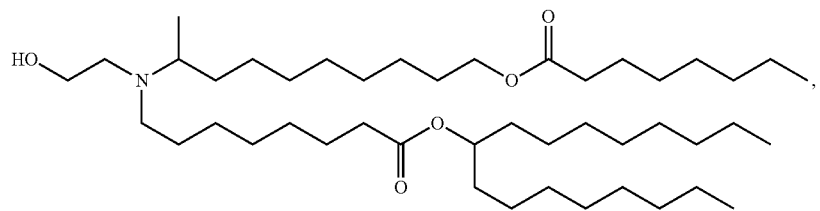
(Compound 161)

-continued
(Compound 162)
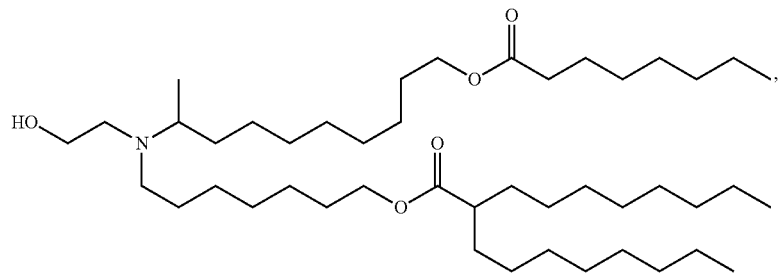
(Compound 163)
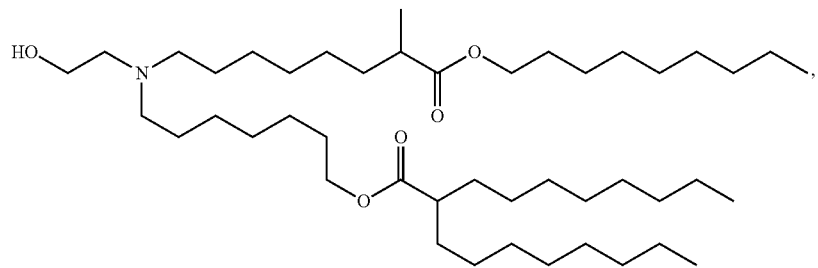
(Compound 164)
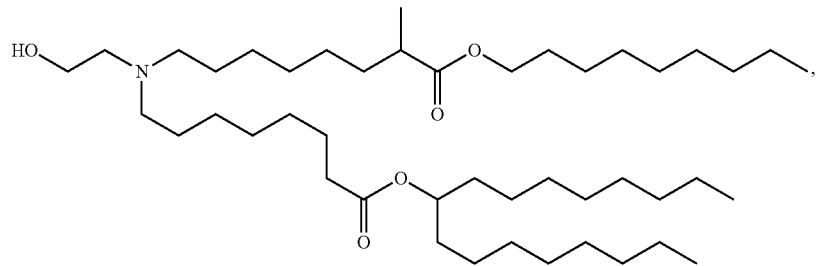
(Compound 165)
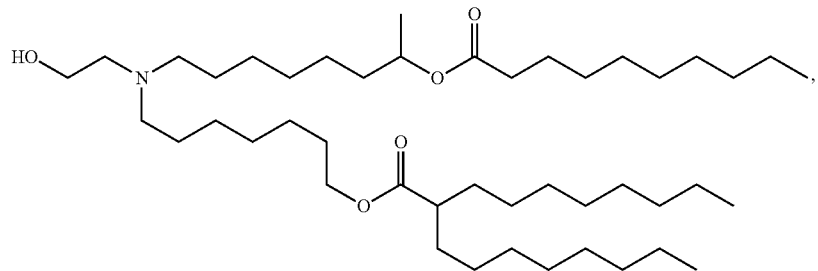
(Compound 166)
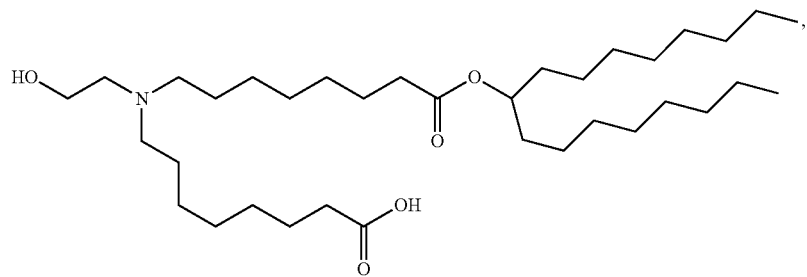

-continued
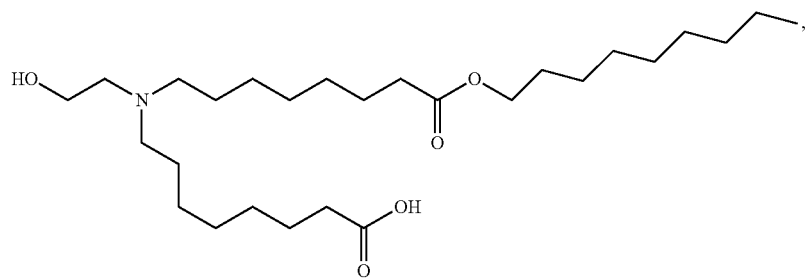
(Compound 167)
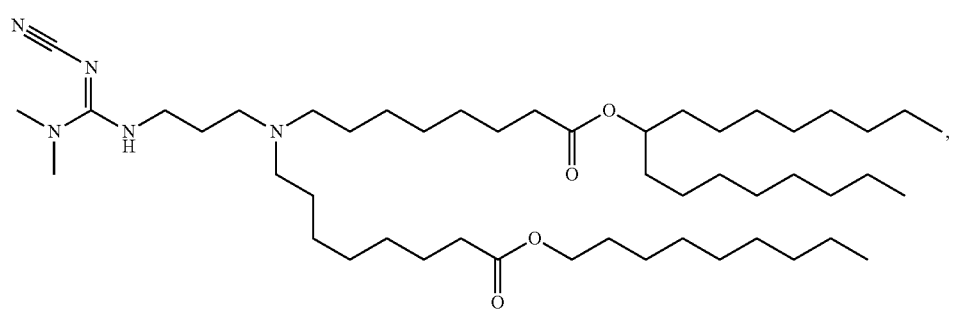
(Compound 168)
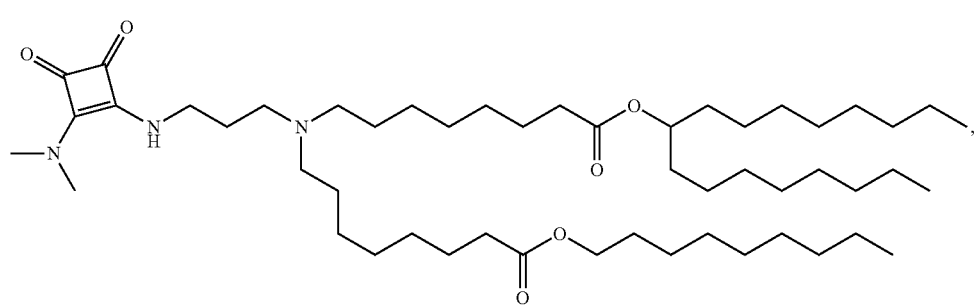
(Compound 169)
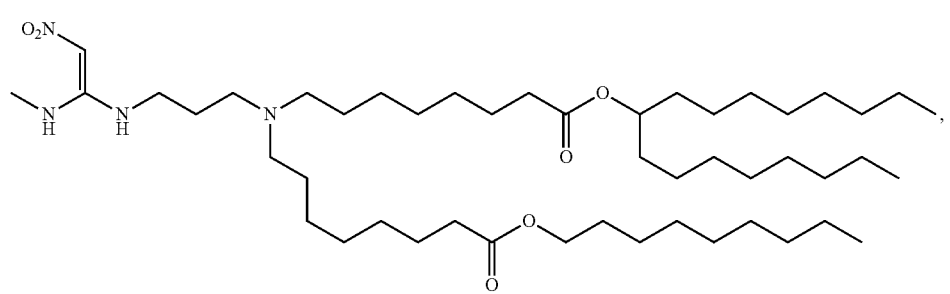
(Compound 170)
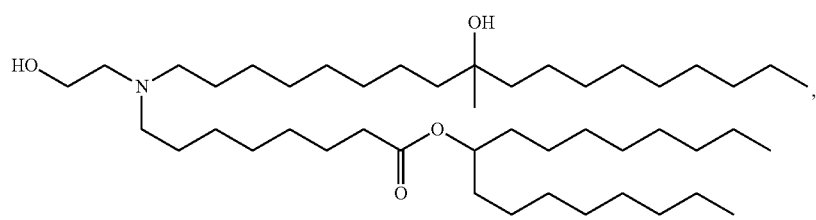
(Compound 171)
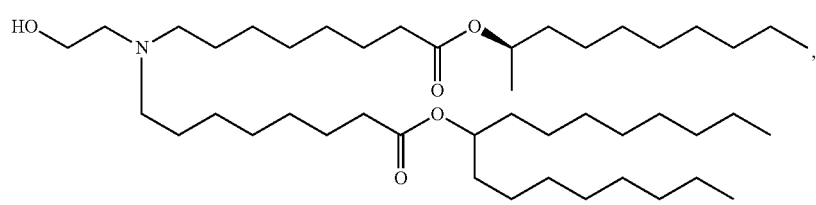
(Compound 172)

(Compound 173)
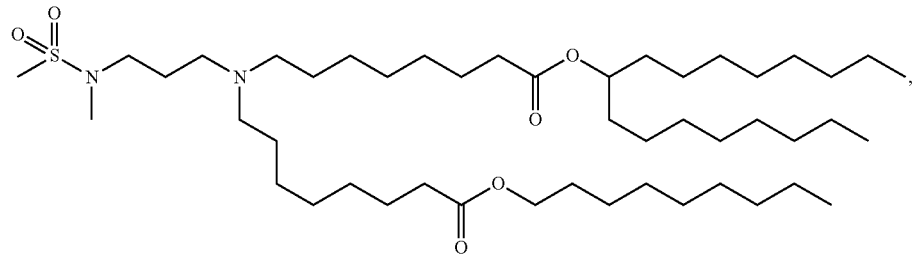
(Compound 174)
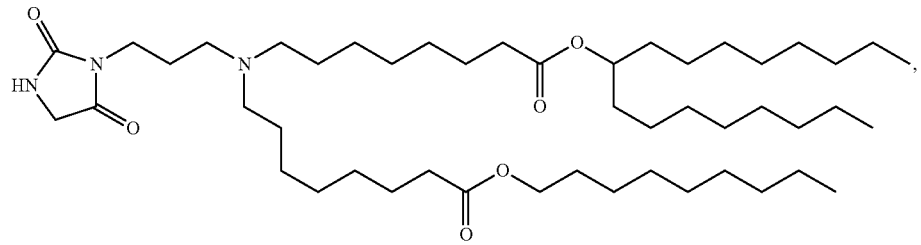
(Compound 175)
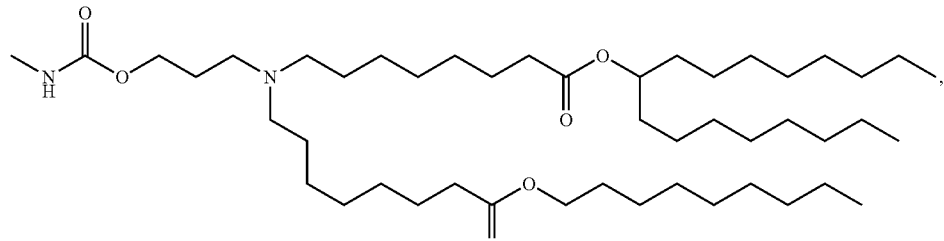
(Compound 176)
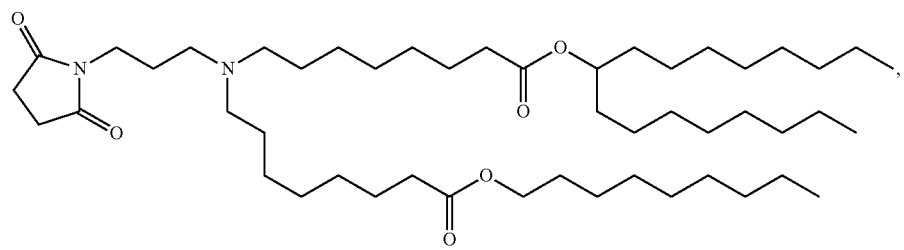
(Compound 177)
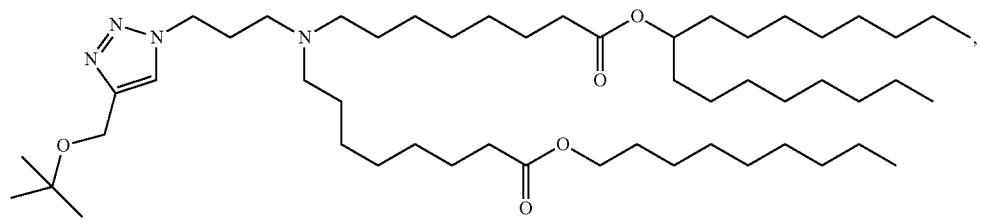
(Compound 178)
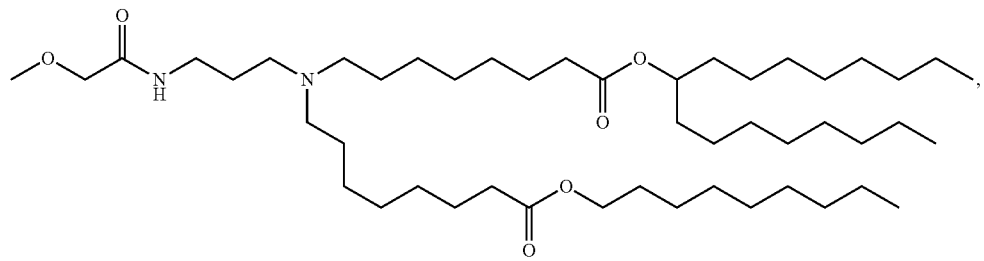

-continued
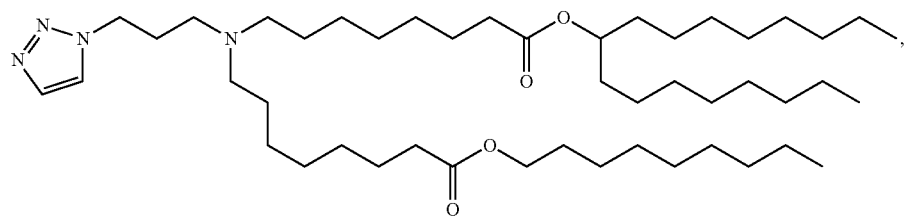
(Compound 179)
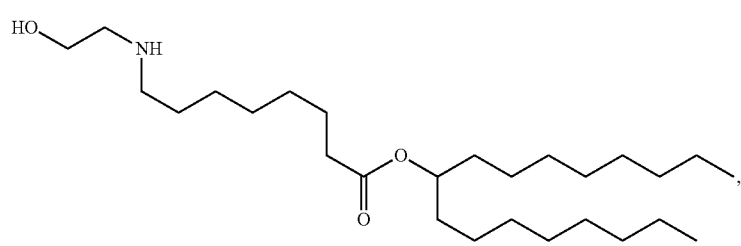
(Compound 180)
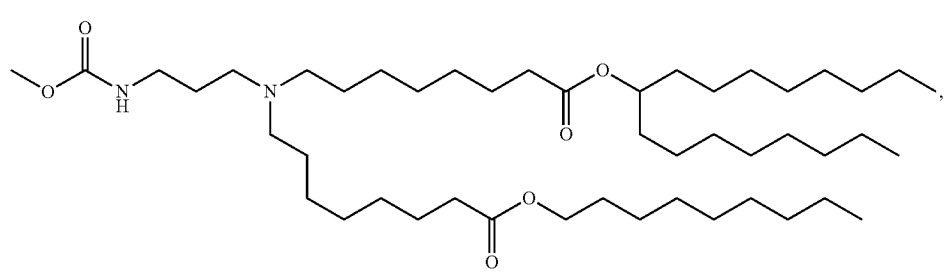
(Compound 181)
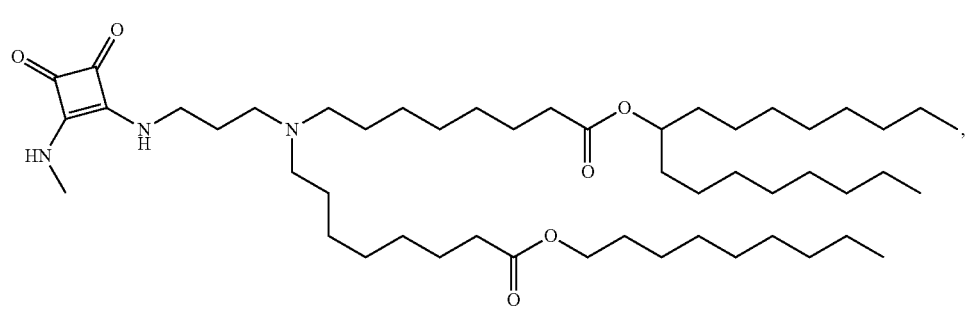
(Compound 182)
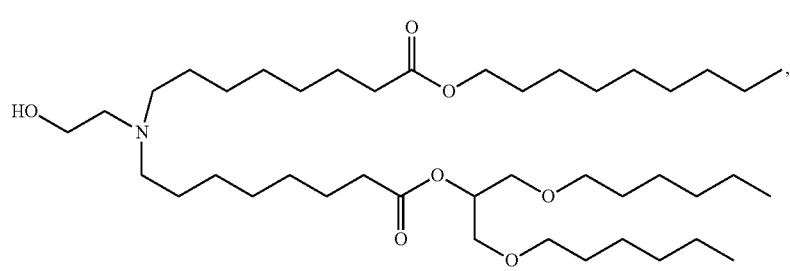
(Compound 183)
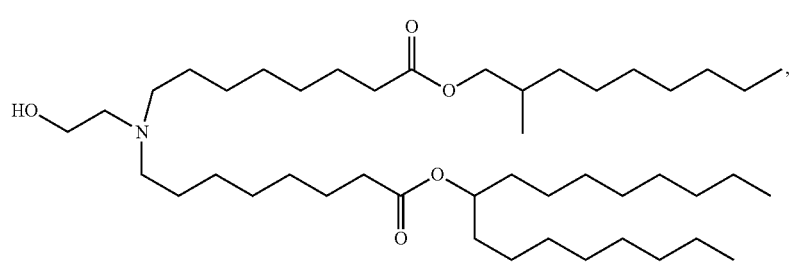
(Compound 184)

-continued
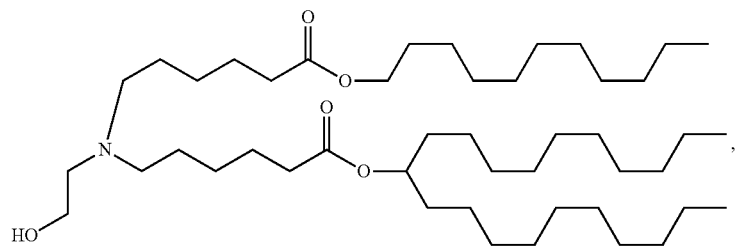
(Compound 185)
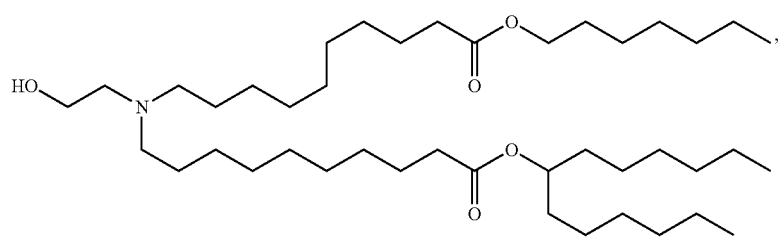
(Compound 186)
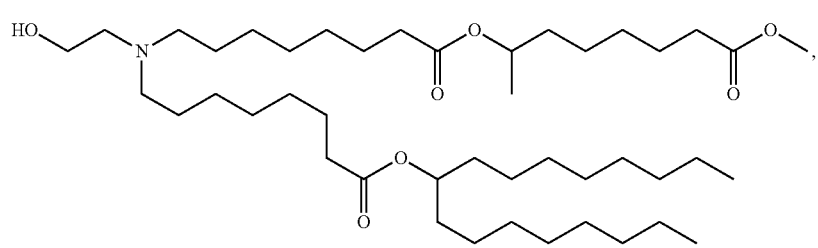
(Compound 187)
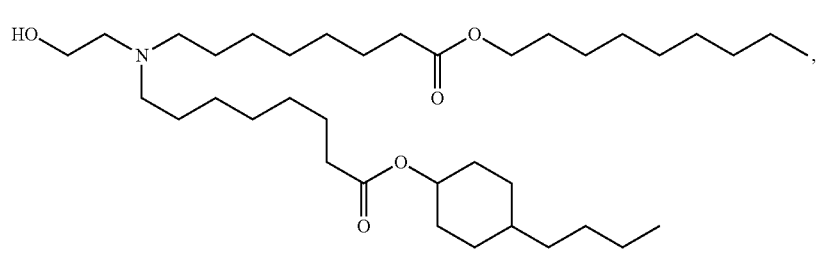
(Compound 188)
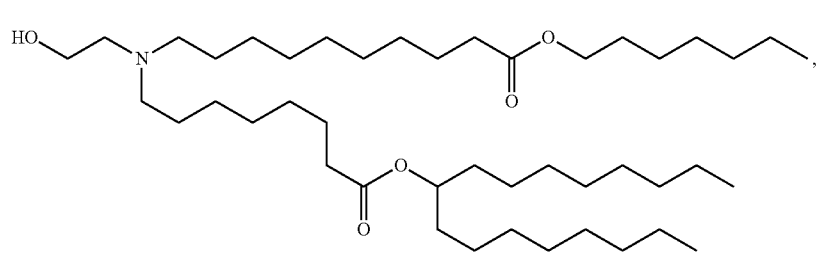
(Compound 189)
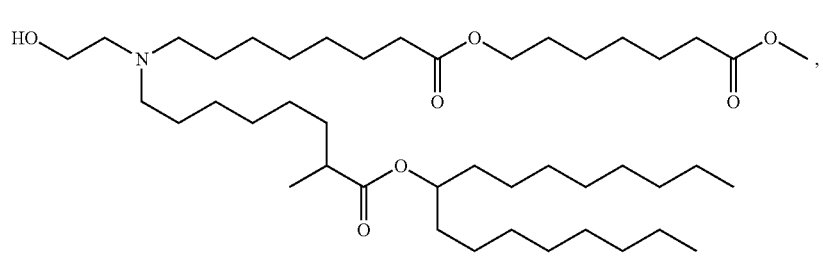
(Compound 190)

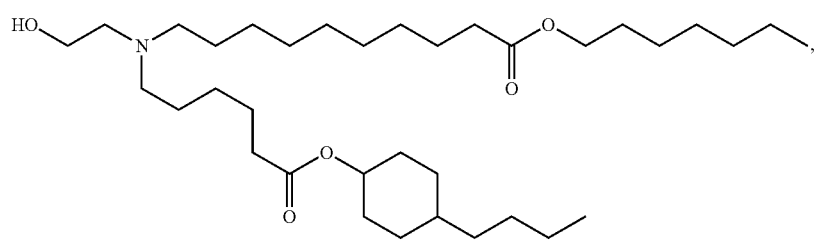
(Compound 191)
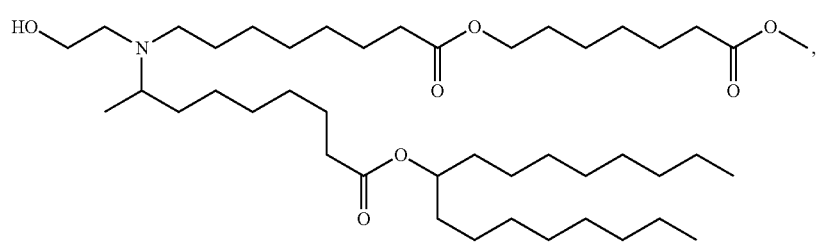
(Compound 192)
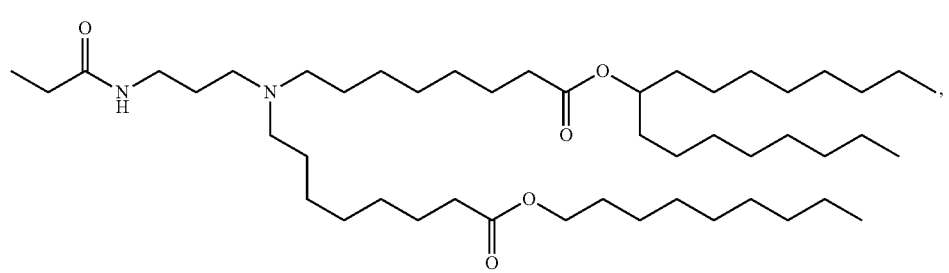
(Compound 193)
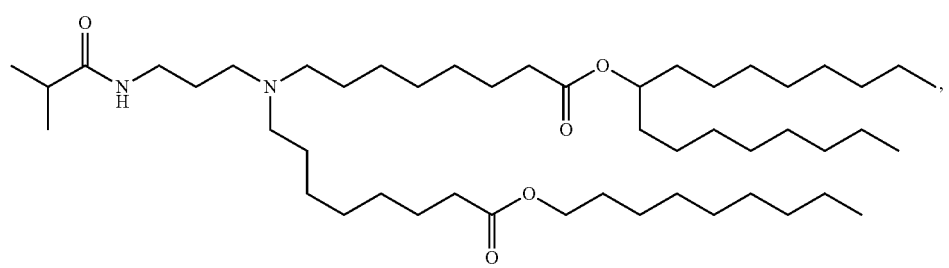
(Compound 194)
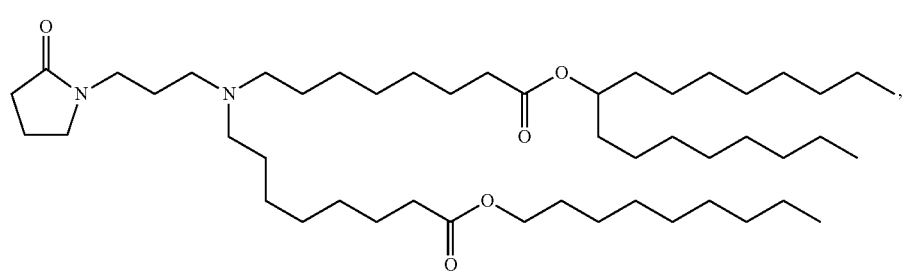
(Compound 195)
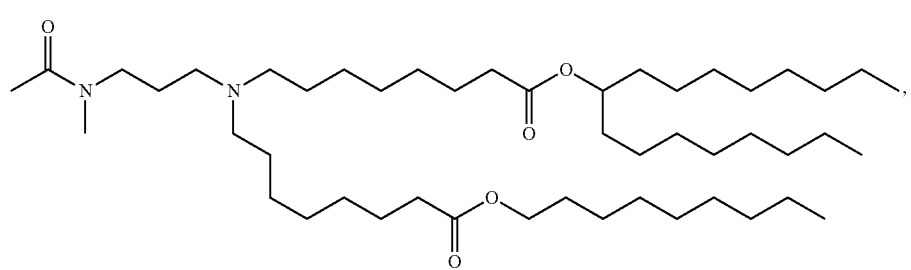
(Compound 196)

(Compound 197)
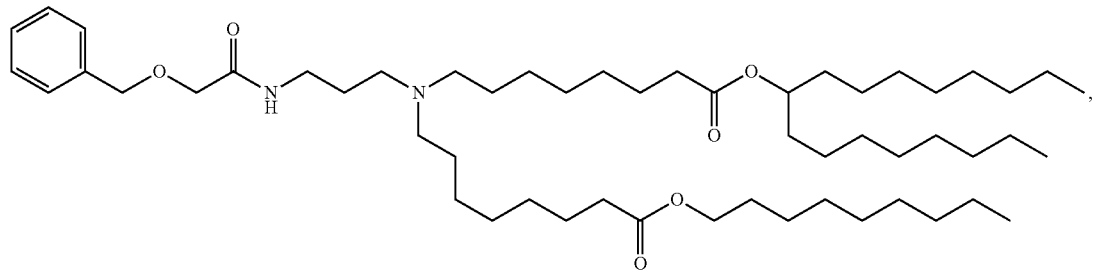
(Compound 198)
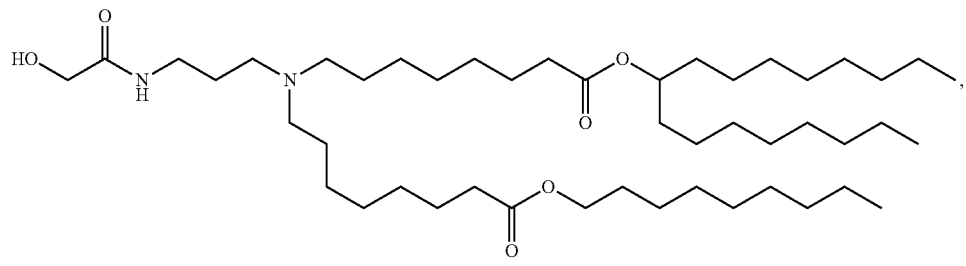
(Compound 199)
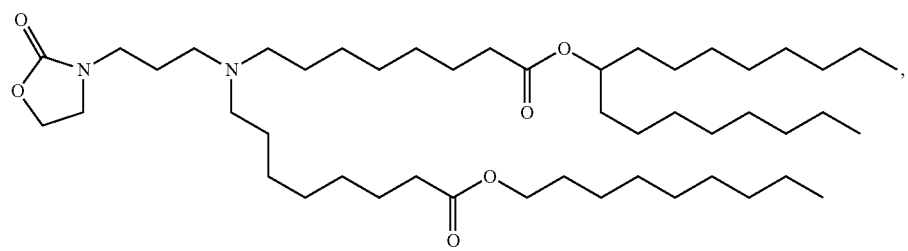
(Compound 200)
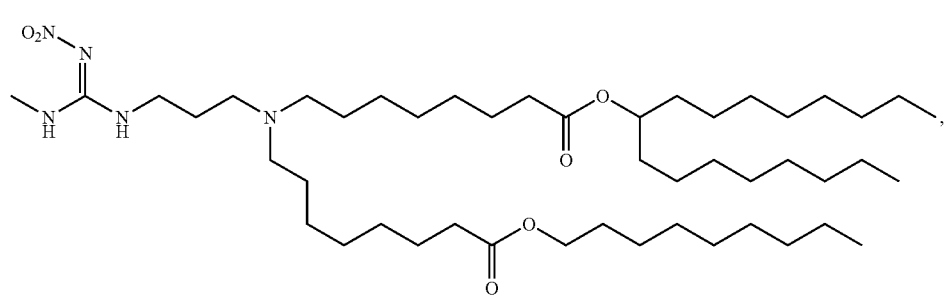
(Compound 201)
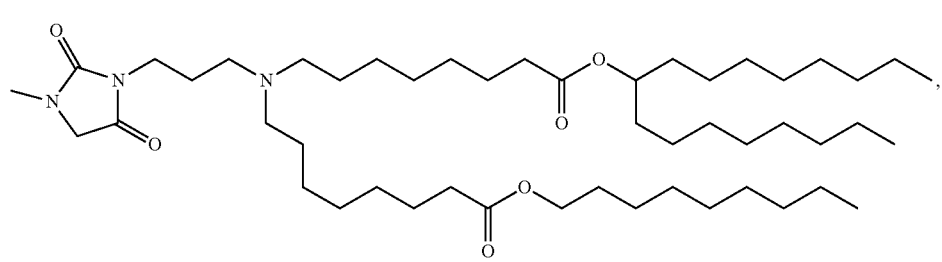
(Compound 202)
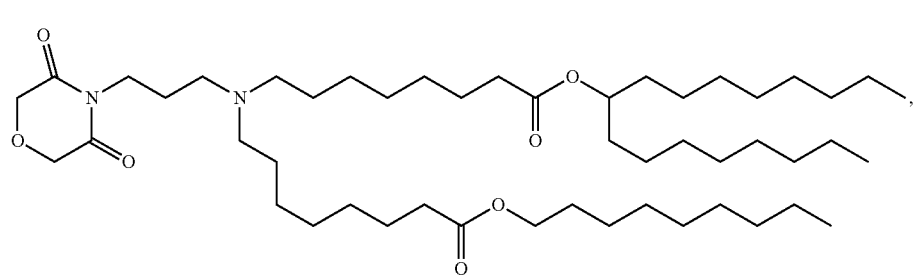

(Compound 203)
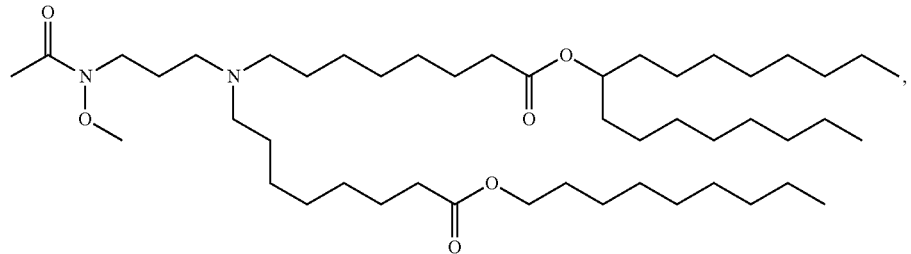
(Compound 204)
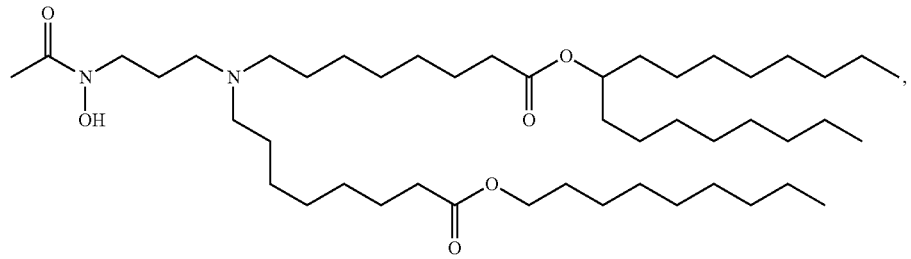
(Compound 205)
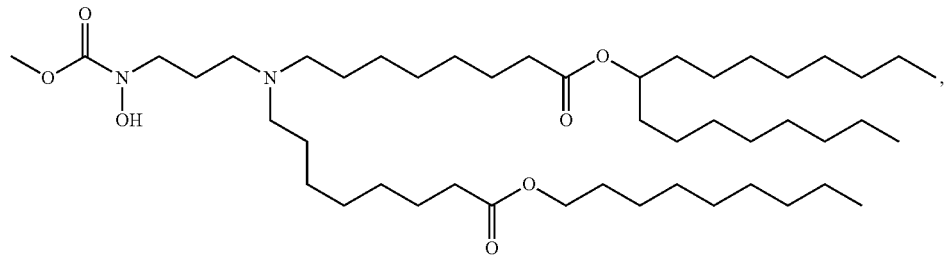
(Compound 206)
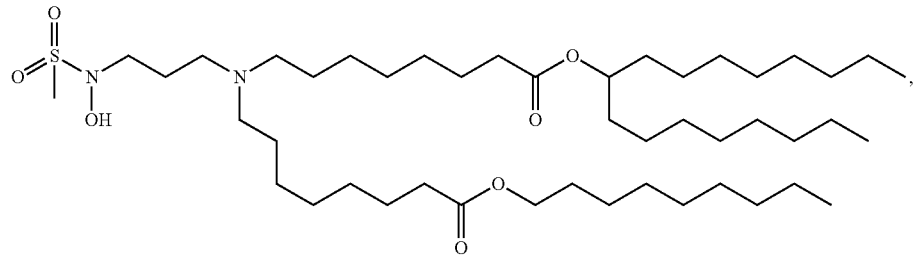
(Compound 207)
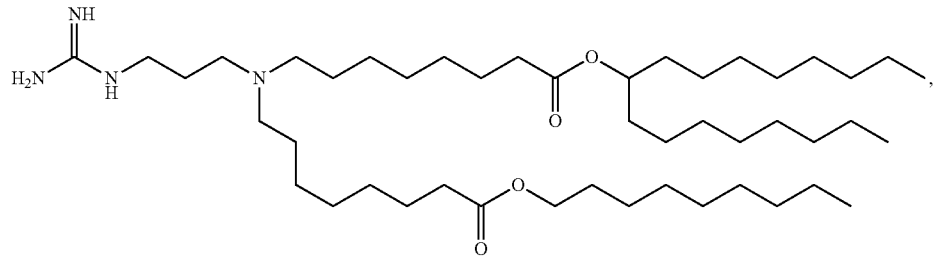
(Compound 208)
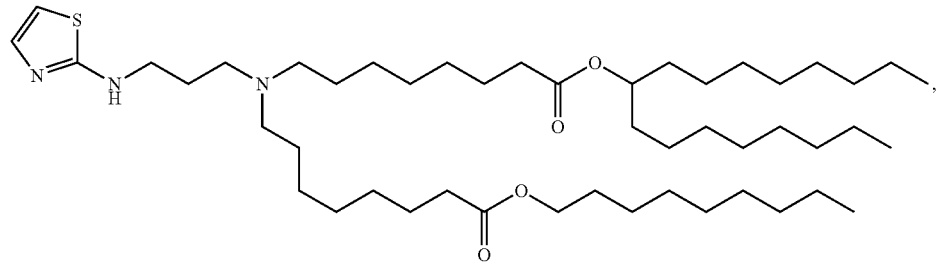

(Compound 209)
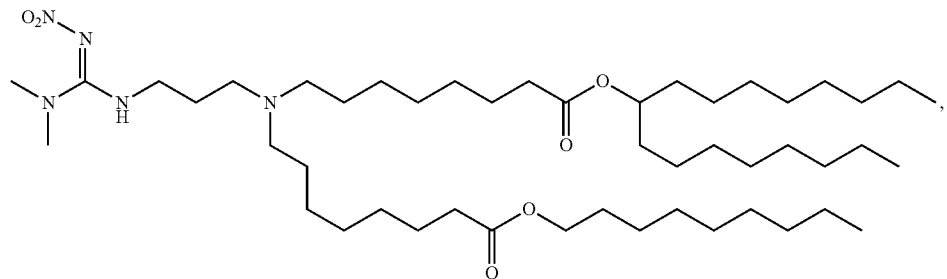
(Compound 210)
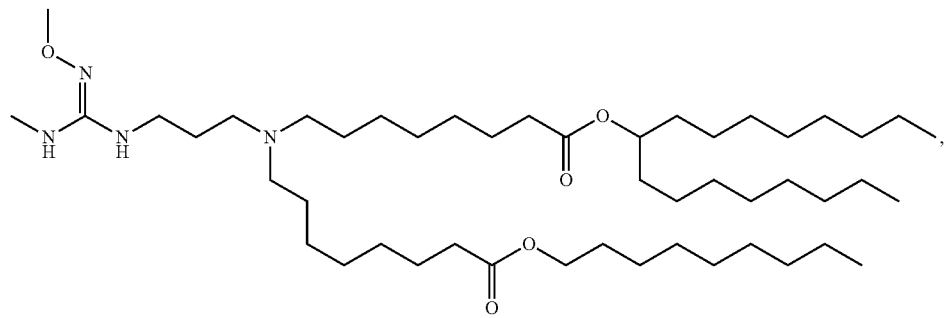
(Compound 211)
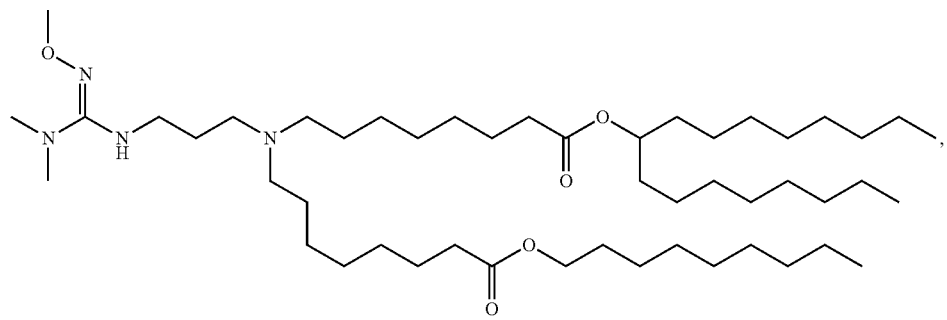
(Compound 212)
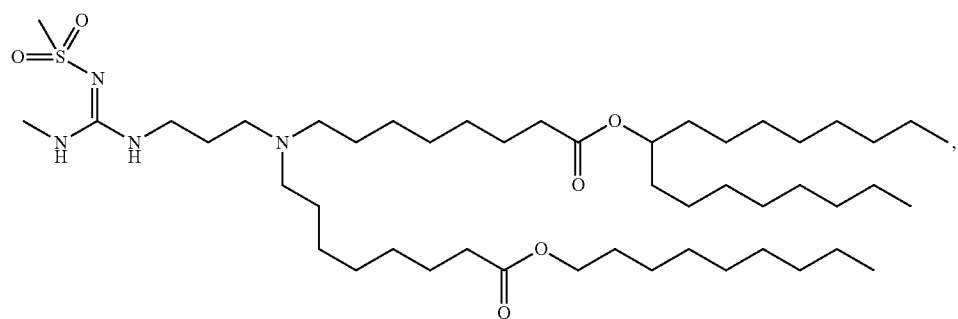
(Compound 213)
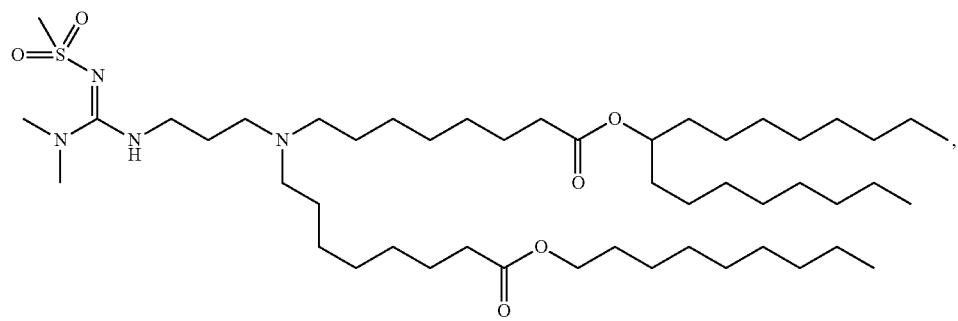

(Compound 214)
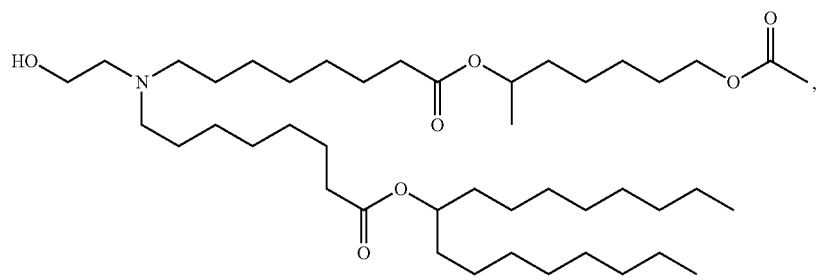
(Compound 215)
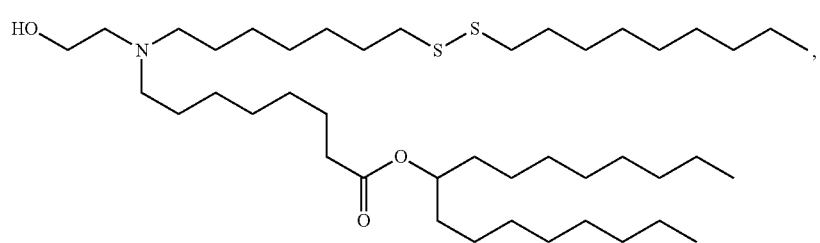
(Compound 216)
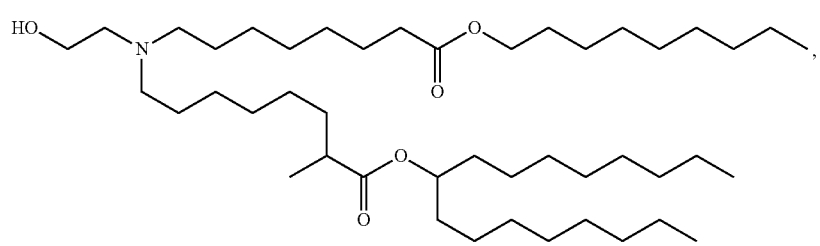
(Compound 217)
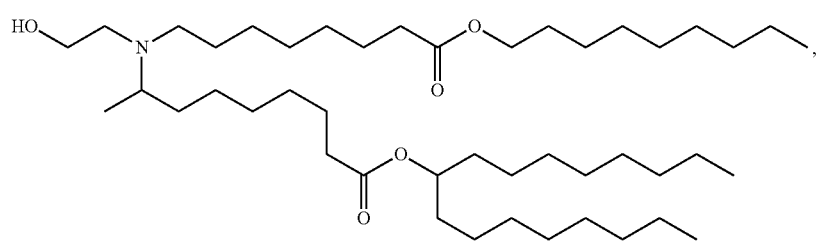
(Compound 218)
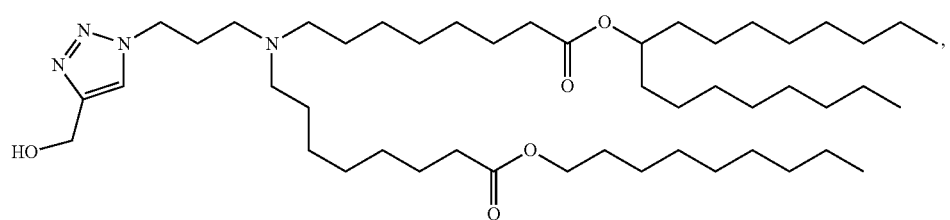
(Compound 219)
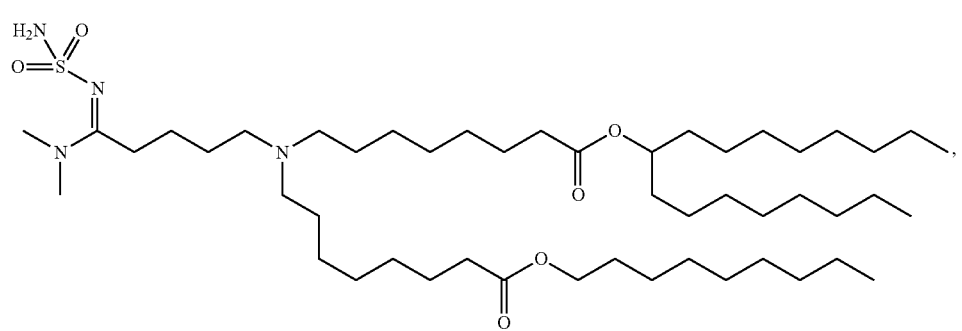

(Compound 220)
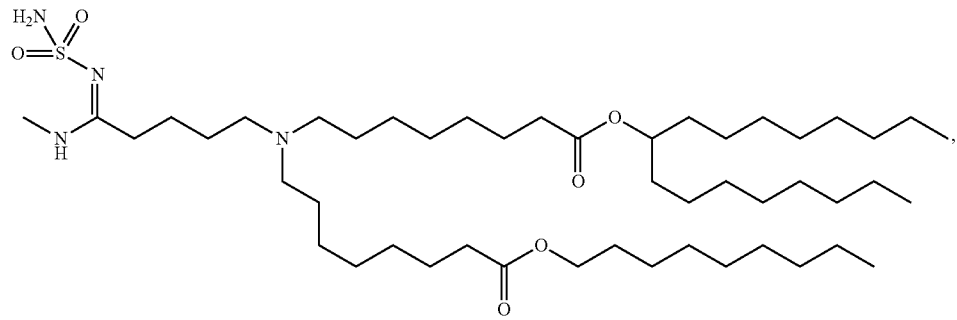
(Compound 221)
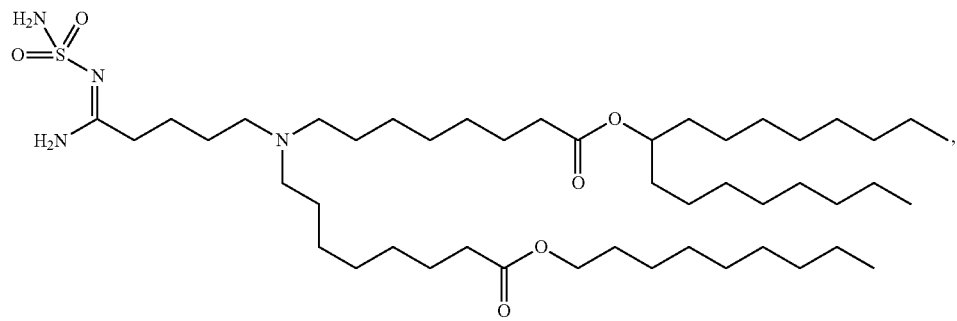
(Compound 222)
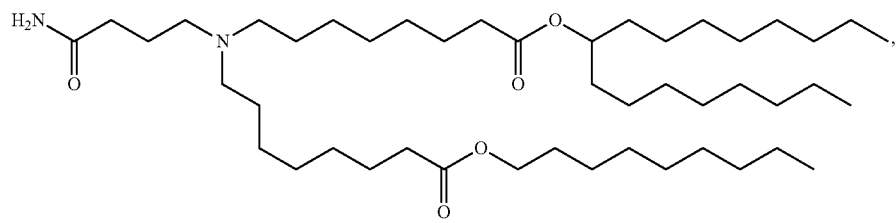
(Compound 223)
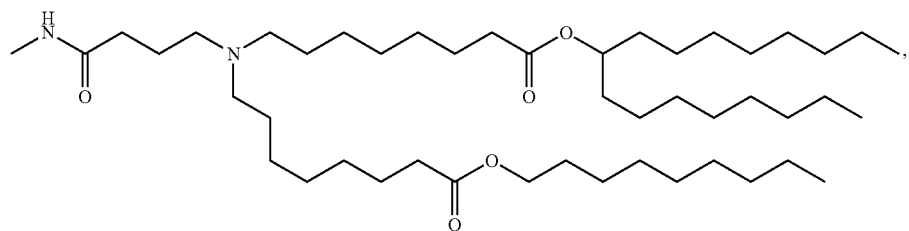
(Compound 224)
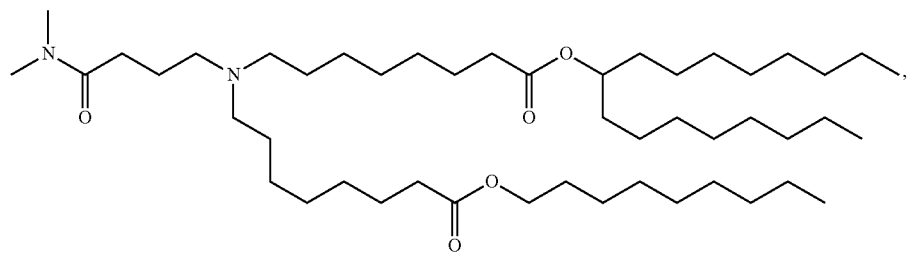
(Compound 225)
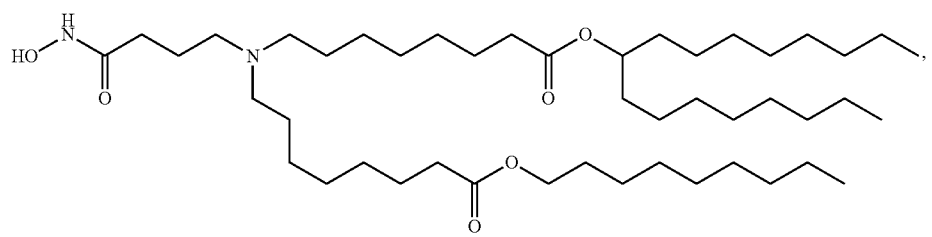

(Compound 226)
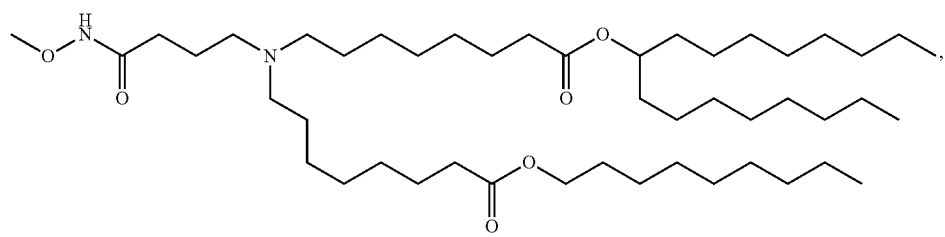
(Compound 227)
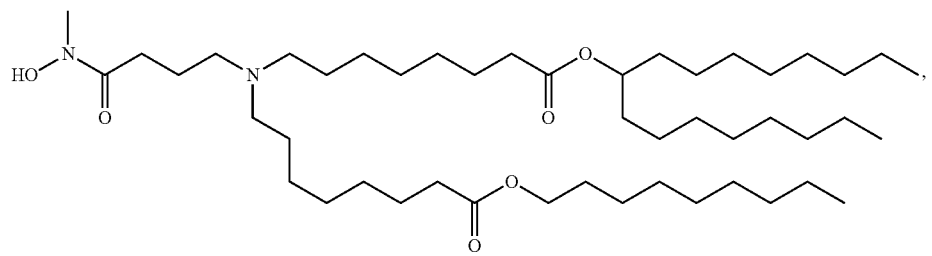
(Compound 228)
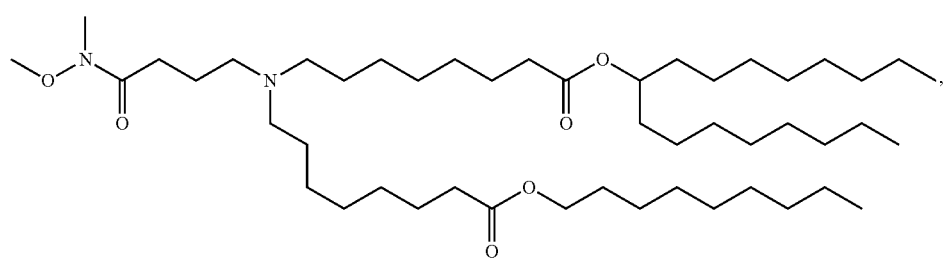
(Compound 229)
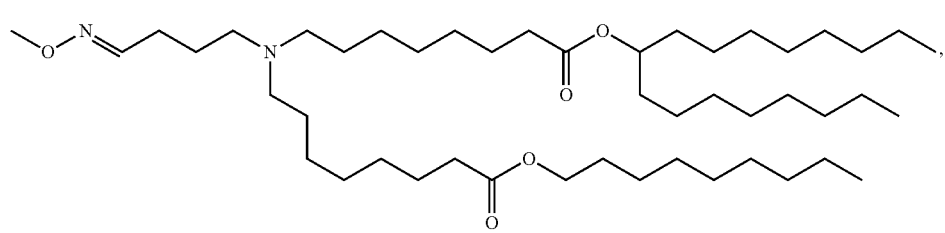
(Compound 230)
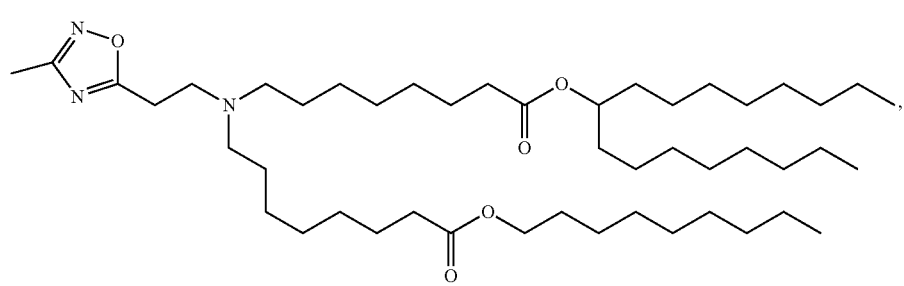
(Compound 231)
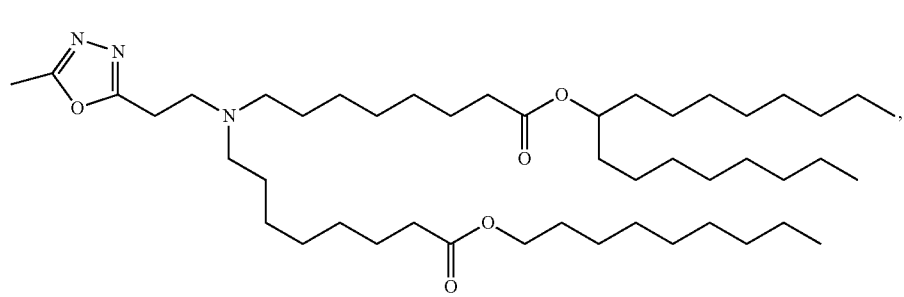

-continued

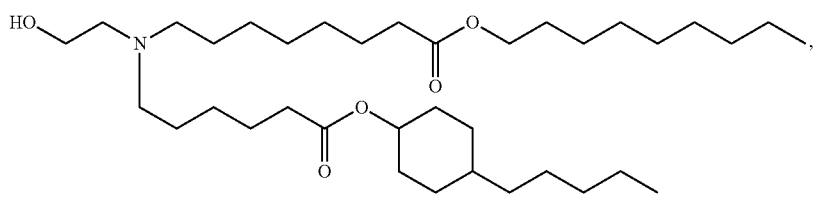
(Compound 232)

and salts or stereoisomers thereof.

In other embodiments, the compound of Formula (I) is selected from the group consisting of Compound 1-Compound 147, or salt or stereoisomers thereof.

Amine moieties of the lipid compounds disclosed herein can be protonated under certain conditions. For example, the central amine moiety of a lipid according to formula (I) is typically protonated (i.e., positively charged) at a pH below the pKa of the amino moiety and is substantially not charged at a pH above the pKa. Such lipids may be referred to ionizable amino lipids.

In one specific embodiment, the ionizable amino lipid is Compound 18.

In some embodiments, the amount the ionizable amino lipid, e.g., compound of formula (I), ranges from about 1 mol % to 99 mol % in the lipid composition.

In one embodiment, the amount of the ionizable amino lipid, e.g., compound of formula (I), is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of formula (I), ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., compound of formula (I), is about 50 mol % in the lipid composition.

In addition to the ionizable amino lipid disclosed herein, e.g., compound of formula (I), the lipid composition of the pharmaceutical compositions disclosed herein can comprise additional components such as phospholipids, structural lipids, quaternary amine compounds, PEG-lipids, and any combination thereof.

In other aspects, the lipid nanoparticle comprises a molar ratio of about 20-60% ionizable amino lipid:5-25% phospholipid lipid:25-55% sterol; and 0.5-15% PEG-modified lipid. In other aspects, the lipid nanoparticle carrier comprises a molar ratio of about 20-60% Compound 18: 5-25% phospholipid:25-55% cholesterol; and 0.5-15% PEG-modified lipid. In other aspects, the lipid nanoparticle carrier comprises a molar ratio of about 50% ionizable amino lipid:about 10% phospholipid:about 38.5% cholesterol; and about 1.5% PEG-modified lipid. In other aspects, the lipid nanoparticle carrier comprises a molar ratio of about 50% Compound 18:about 10% phospholipid:about 38.5% cholesterol; and about 1.5% PEG-modified lipid. In other aspects, the lipid nanoparticle carrier comprises a molar ratio of about 49.83% ionizable amino lipid:about 9.83% phospholipid:about 30.33% cholesterol; and about 2.0% PEG-modified lipid. In other aspects, the lipid nanoparticle carrier comprises a molar ratio of about 49.83% Compound 18:about 9.83% phospholipid:about 30.33% cholesterol; and about 2.0% PEG-modified lipid.

b. Additional Components in the Lipid Composition
   (i) Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties. For example, a phospholipid can be a lipid according to formula (VII):

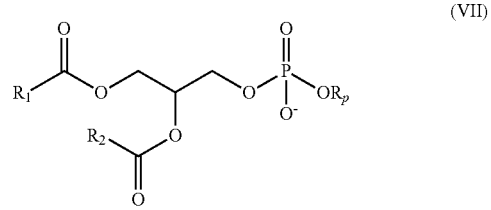
(VII)

in which $R_p$ represents a phospholipid moiety and $R_1$ and $R_2$ represent fatty acid moieties with or without unsaturation that may be the same or different.

A phospholipid moiety may be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety may be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements (e.g., a therapeutic agent) of a lipid-containing composition (e.g., LNPs) to pass through the membrane permitting, e.g., delivery of the one or more elements to a target tissue (e.g., tumoral tissue).

Non-natural phospholipid species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, a pharmaceutical composition for intratumoral delivery disclosed herein can comprise more than one phospholipid. When more than one phospholipid is used, such phospholipids can belong to the same phospholipid class (e.g., MSPC and DSPC) or different classes (e.g., MSPC and MSPE).

Phospholipids may be of a symmetric or an asymmetric type. As used herein, the term "symmetric phospholipid" includes glycerophospholipids having matching fatty acid moieties and sphingolipids in which the variable fatty acid moiety and the hydrocarbon chain of the sphingosine backbone include a comparable number of carbon atoms. As used herein, the term "asymmetric phospholipid" includes lysolipids, glycerophospholipids having different fatty acid moieties (e.g., fatty acid moieties with different numbers of carbon atoms and/or unsaturations (e.g., double bonds)), and sphingolipids in which the variable fatty acid moiety and the hydrocarbon chain of the sphingosine backbone include a dissimilar number of carbon atoms (e.g., the variable fatty acid moiety include at least two more carbon atoms than the hydrocarbon chain or at least two fewer carbon atoms than the hydrocarbon chain).

In some embodiments, the lipid composition of a pharmaceutical composition disclosed herein comprises at least one symmetric phospholipid. Symmetric phospholipids may be selected from the non-limiting group consisting of
1,2-dipropionyl-sn-glycero-3-phosphocholine (03:0 PC),
1,2-dibutyryl-sn-glycero-3-phosphocholine (04:0 PC),
1,2-dipentanoyl-sn-glycero-3-phosphocholine (05:0 PC),
1,2-dihexanoyl-sn-glycero-3-phosphocholine (06:0 PC),
1,2-diheptanoyl-sn-glycero-3-phosphocholine (07:0 PC),
1,2-dioctanoyl-sn-glycero-3-phosphocholine (08:0 PC),
1,2-dinonanoyl-sn-glycero-3-phosphocholine (09:0 PC),
1,2-didecanoyl-sn-glycero-3-phosphocholine (10:0 PC),
1,2-diundecanoyl-sn-glycero-3-phosphocholine (11:0 PC, DUPC),
1,2-dilauroyl-sn-glycero-3-phosphocholine (12:0 PC),
1,2-ditridecanoyl-sn-glycero-3-phosphocholine (13:0 PC),
1,2-dimyristoyl-sn-glycero-3-phosphocholine (14:0 PC, DMPC),
1,2-dipentadecanoyl-sn-glycero-3-phosphocholine (15:0 PC),
1,2-dipalmitoyl-sn-glycero-3-phosphocholine (16:0 PC, DPPC),
1,2-diphytanoyl-sn-glycero-3-phosphocholine (4ME 16:0 PC),
1,2-diheptadecanoyl-sn-glycero-3-phosphocholine (17:0 PC),
1,2-distearoyl-sn-glycero-3-phosphocholine (18:0 PC, DSPC),
1,2-dinonadecanoyl-sn-glycero-3-phosphocholine (19:0 PC),
1,2-diarachidoyl-sn-glycero-3-phosphocholine (20:0 PC),
1,2-dihenarachidoyl-sn-glycero-3-phosphocholine (21:0 PC),
1,2-dibehenoyl-sn-glycero-3-phosphocholine (22:0 PC),
1,2-ditricosanoyl-sn-glycero-3-phosphocholine (23:0 PC),
1,2-dilignoceroyl-sn-glycero-3-phosphocholine (24:0 PC),
1,2-dimyristoleoyl-sn-glycero-3-phosphocholine (14:1 (Δ9-Cis) PC),
1,2-dimyristelaidoyl-sn-glycero-3-phosphocholine (14:1 (Δ9-Trans) PC),
1,2-dipalmitoleoyl-sn-glycero-3-phosphocholine (16:1 (Δ9-Cis) PC),
1,2-dipalmitelaidoyl-sn-glycero-3-phosphocholine (16:1 (Δ9-Trans) PC),
1,2-dipetroselenoyl-sn-glycero-3-phosphocholine (18:1 (Δ6-Cis) PC),
1,2-dioleoyl-sn-glycero-3-phosphocholine (18:1 (Δ9-Cis) PC, DOPC),
1,2-dielaidoyl-sn-glycero-3-phosphocholine (18:1 (Δ9-Trans) PC),
1,2-dilinoleoyl-sn-glycero-3-phosphocholine (18:2 (Cis) PC, DLPC),
1,2-dilinolenoyl-sn-glycero-3-phosphocholine (18:3 (Cis) PC, DLnPC),
1,2-dieicosenoyl-sn-glycero-3-phosphocholine (20:1 (Cis) PC),
1,2-diarachidonoyl-sn-glycero-3-phosphocholine (20:4 (Cis) PC, DAPC),
1,2-dierucoyl-sn-glycero-3-phosphocholine (22:1 (Cis) PC),
1,2-didocosahexaenoyl-sn-glycero-3-phosphocholine (22:6 (Cis) PC, DHAPC),
1,2-dinervonoyl-sn-glycero-3-phosphocholine (24:1 (Cis) PC),
1,2-dihexanoyl-sn-glycero-3-phosphoethanolamine (06:0 PE),
1,2-dioctanoyl-sn-glycero-3-phosphoethanolamine (08:0 PE),
1,2-didecanoyl-sn-glycero-3-phosphoethanolamine (10:0 PE),
1,2-dilauroyl-sn-glycero-3-phosphoethanolamine (12:0 PE),
1,2-dimyristoyl-sn-glycero-3-phosphoethanolamine (14:0 PE),
1,2-dipentadecanoyl-sn-glycero-3-phosphoethanolamine (15:0 PE),
1,2-dipalmitoyl-sn-glycero-3-phosphoethanolamine (16:0 PE),
1,2-diphytanoyl-sn-glycero-3-phosphoethanol amine (4ME 16:0 PE),
1,2-diheptadecanoyl-sn-glycero-3-phosphoethanolamine (17:0 PE),
1,2-distearoyl-sn-glycero-3-phosphoethanolamine (18:0 PE, DSPE),
1,2-dipalmitoleoyl-sn-glycero-3-phosphoethanolamine (16:1 PE),
1,2-dioleoyl-sn-glycero-3-phosphoethanolamine (18:1 (Δ9-Cis) PE, DOPE),
1,2-dielaidoyl-sn-glycero-3-phosphoethanolamine (18:1 (Δ9-Trans) PE),
1,2-dilinoleoyl-sn-glycero-3-phosphoethanolamine (18:2 PE, DLPE),
1,2-dilinolenoyl-sn-glycero-3-phosphoethanolamine (18:3 PE, DLnPE),
1,2-diarachidonoyl-sn-glycero-3-phosphoethanolamine (20:4 PE, DAPE),
1,2-didocosahexaenoyl-sn-glycero-3-phosphoethanolamine (22:6 PE, DHAPE),
1,2-di-O-octadecenyl-sn-glycero-3-phosphocholine (18:0 Diether PC),
1,2-dioleoyl-sn-glycero-3-phospho-rac-(1-glycerol) sodium salt (DOPG), and
any combination thereof.

In some embodiments, the lipid composition of a pharmaceutical composition disclosed herein comprises at least one symmetric phospholipid selected from the non-limiting group consisting of DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof.

In some embodiments, the lipid composition of a pharmaceutical composition disclosed herein comprises at least one asymmetric phospholipid. Asymmetric phospholipids may be selected from the non-limiting group consisting of
1-myristoyl-2-palmitoyl-sn-glycero-3-phosphocholine (14:0-16:0 PC, MPPC),
1-myristoyl-2-stearoyl-sn-glycero-3-phosphocholine (14:0-18:0 PC, MSPC),
1-palmitoyl-2-acetyl-sn-glycero-3-phosphocholine (16:0-02:0 PC),
1-palmitoyl-2-myristoyl-sn-glycero-3-phosphocholine (16:0-14:0 PC, PMPC),
1-palmitoyl-2-stearoyl-sn-glycero-3-phosphocholine (16:0-18:0 PC, PSPC),
1-palmitoyl-2-oleoyl-sn-glycero-3-phosphocholine (16:0-18:1 PC, POPC),
1-palmitoyl-2-linoleoyl-sn-glycero-3-phosphocholine (16:0-18:2 PC, PLPC),
1-palmitoyl-2-arachidonoyl-sn-glycero-3-phosphocholine (16:0-20:4 PC),
1-palmitoyl-2-docosahexaenoyl-sn-glycero-3-phosphocholine (14:0-22:6 PC),
1-stearoyl-2-myristoyl-sn-glycero-3-phosphocholine (18:0-14:0 PC, SMPC),
1-stearoyl-2-palmitoyl-sn-glycero-3-phosphocholine (18:0-16:0 PC, SPPC),
1-stearoyl-2-oleoyl-sn-glycero-3-phosphocholine (18:0-18:1 PC, SOPC),
1-stearoyl-2-linoleoyl-sn-glycero-3-phosphocholine (18:0-18:2 PC),
1-stearoyl-2-arachidonoyl-sn-glycero-3-phosphocholine (18:0-20:4 PC),
1-stearoyl-2-docosahexaenoyl-sn-glycero-3-phosphocholine (18:0-22:6 PC),
1-oleoyl-2-myristoyl-sn-glycero-3-phosphocholine (18:1-14:0 PC, OMPC),
1-oleoyl-2-palmitoyl-sn-glycero-3-phosphocholine (18:1-16:0 PC, OPPC),
1-oleoyl-2-stearoyl-sn-glycero-3-phosphocholine (18:1-18:0 PC, OSPC),
1-palmitoyl-2-oleoyl-sn-glycero-3-phosphoethanolamine (16:0-18:1 PE, POPE),
1-palmitoyl-2-linoleoyl-sn-glycero-3-phosphoethanolamine (16:0-18:2 PE),
1-palmitoyl-2-arachidonoyl-sn-glycero-3-phosphoethanolamine (16:0-20:4 PE),
1-palmitoyl-2-docosahexaenoyl-sn-glycero-3-phosphoethanolamine (16:0-22:6 PE),
1-stearoyl-2-oleoyl-sn-glycero-3-phosphoethanolamine (18:0-18:1 PE),
1-stearoyl-2-linoleoyl-sn-glycero-3-phosphoethanolamine (18:0-18:2 PE),
1-stearoyl-2-arachidonoyl-sn-glycero-3-phosphoethanolamine (18:0-20:4 PE),
1-stearoyl-2-docosahexaenoyl-sn-glycero-3-phosphoethanolamine (18:0-22:6 PE),
1-oleoyl-2-cholesterylhemisuccinoyl-sn-glycero-3-phosphocholine (OChemsPC), and
any combination thereof.

Asymmetric lipids useful in the lipid composition may also be lysolipids. Lysolipids may be selected from the non-limiting group consisting of
1-hexanoyl-2-hydroxy-sn-glycero-3-phosphocholine (06:0 Lyso PC),
1-heptanoyl-2-hydroxy-sn-glycero-3-phosphocholine (07:0 Lyso PC),
1-octanoyl-2-hydroxy-sn-glycero-3-phosphocholine (08:0 Lyso PC),
1-nonanoyl-2-hydroxy-sn-glycero-3-phosphocholine (09:0 Lyso PC),
1-decanoyl-2-hydroxy-sn-glycero-3-phosphocholine (10:0 Lyso PC),
1-undecanoyl-2-hydroxy-sn-glycero-3-phosphocholine (11:0 Lyso PC),
1-lauroyl-2-hydroxy-sn-glycero-3-phosphocholine (12:0 Lyso PC),
1-tridecanoyl-2-hydroxy-sn-glycero-3-phosphocholine (13:0 Lyso PC),
1-myristoyl-2-hydroxy-sn-glycero-3-phosphocholine (14:0 Lyso PC),
1-pentadecanoyl-2-hydroxy-sn-glycero-3-phosphocholine (15:0 Lyso PC),
1-palmitoyl-2-hydroxy-sn-glycero-3-phosphocholine (16:0 Lyso PC),
1-heptadecanoyl-2-hydroxy-sn-glycero-3-phosphocholine (17:0 Lyso PC),
1-stearoyl-2-hydroxy-sn-glycero-3-phosphocholine (18:0 Lyso PC),
1-oleoyl-2-hydroxy-sn-glycero-3-phosphocholine (18:1 Lyso PC),
1-nonadecanoyl-2-hydroxy-sn-glycero-3-phosphocholine (19:0 Lyso PC),
1-arachidoyl-2-hydroxy-sn-glycero-3-phosphocholine (20:0 Lyso PC),
1-behenoyl-2-hydroxy-sn-glycero-3-phosphocholine (22:0 Lyso PC),
1-lignoceroyl-2-hydroxy-sn-glycero-3-phosphocholine (24:0 Lyso PC),
1-hexacosanoyl-2-hydroxy-sn-glycero-3-phosphocholine (26:0 Lyso PC),
1-myristoyl-2-hydroxy-sn-glycero-3-phosphoethanolamine (14:0 Lyso PE),
1-palmitoyl-2-hydroxy-sn-glycero-3-phosphoethanolamine (16:0 Lyso PE),
1-stearoyl-2-hydroxy-sn-glycero-3-phosphoethanolamine (18:0 Lyso PE),
1-oleoyl-2-hydroxy-sn-glycero-3-phosphoethanolamine (18:1 Lyso PE),
1-hexadecyl-sn-glycero-3-phosphocholine (C16 Lyso PC), and
any combination thereof.

In some embodiment, the lipid composition of a pharmaceutical composition disclosed herein comprises at least one asymmetric phospholipid selected from the group consisting of MPPC, MSPC, PMPC, PSPC, SMPC, SPPC, and any combination thereof. In some embodiments, the asymmetric phospholipid is 1-myristoyl-2-stearoyl-sn-glycero-3-phosphocholine (MSPC). In a particular embodiment, the asymmetric phospholipid is one or more phospholipid disclosed in International Application No. PCT/US 17/27492, filed on Apr. 13, 2017, which is incorporated herein by reference in its entireties.

In some embodiments, the lipid compositions disclosed herein may contain one or more symmetric phospholipids, one or more asymmetric phospholipids, or a combination thereof. When multiple phospholipids are present, they can be present in equimolar ratios, or non-equimolar ratios.

In one embodiment, the lipid composition of a pharmaceutical composition disclosed herein comprises a total amount of phospholipid (e.g., MSPC) which ranges from about 1 mol % to about 20 mol %, from about 5 mol % to about 20 mol %, from about 10 mol % to about 20 mol %, from about 15 mol % to about 20 mol %, from about 1 mol % to about 15 mol %, from about 5 mol % to about 15 mol %, from about 10 mol % to about 15 mol %, from about 5 mol % to about 10 mol % in the lipid composition. In one embodiment, the amount of the phospholipid is from about 8 mol % to about 15 mol % in the lipid composition. In one embodiment, the amount of the phospholipid (e.g., MSPC) is about 10 mol % in the lipid composition.

In some aspects, the amount of a specific phospholipid (e.g., MSPC) is at least about 1, 2, 3, 4, 5, 6, 7, 8, 9, 10, 11, 12, 13, 14, 15, 16, 17, 18, 19 or 20 mol % in the lipid composition.

(ii) Quaternary Amine Compounds

The lipid composition of a pharmaceutical composition disclosed herein can comprise one or more quaternary amine compounds (e.g., DOTAP). The term "quaternary amine compound" is used to include those compounds having one or more quaternary amine groups (e.g., trialkylamino groups) and permanently carrying a positive charge and existing in a form of a salt. For example, the one or more quaternary amine groups can be present in a lipid or a polymer (e.g., PEG). In some embodiments, the quaternary amine compound comprises (1) a quaternary amine group and (2) at least one hydrophobic tail group comprising (i) a hydrocarbon chain, linear or branched, and saturated or unsaturated, and (ii) optionally an ether, ester, carbonyl, or ketal linkage between the quaternary amine group and the hydrocarbon chain. In some embodiments, the quaternary amine group can be a trimethylammonium group. In some embodiments, the quaternary amine compound comprises two identical hydrocarbon chains. In some embodiments, the quaternary amine compound comprises two different hydrocarbon chains.

In some embodiments, the lipid composition of a pharmaceutical composition disclosed herein comprises at least one quaternary amine compound. Quaternary amine compound may be selected from the non-limiting group consisting of 1,2-dioleoyl-3-trimethylammonium-propane (DOTAP),
N-[1-(2,3-dioleoyloxy)propyl]-N,N,N-trimethylammonium chloride (DOTMA),
1-[2-(oleoyloxy)ethyl]-2-oleyl-3-(2-hydroxyethyl)imidazolinium chloride (DOTIM),
2,3-dioleyloxy-N-[2(sperminecarboxamido)ethyl]-N,N-dimethyl-1-propanaminium trifluoroacetate (DOSPA),
N,N-distearyl-N,N-dimethylammonium bromide (DDAB),
N-(1,2-dimyristyloxyprop-3-yl)-N,N-dimethyl-N-hydroxyethyl ammonium bromide (DMRIE),
N-(1,2-dioleoyloxyprop-3-yl)-N,N-dimethyl-N-hydroxyethyl ammonium bromide (DORIE),
N,N-dioleyl-N,N-dimethyl ammonium chloride (DODAC),
1,2-dilauroyl-sn-glycero-3-ethylphosphocholine (DLePC),
1,2-distearoyl-3-trimethylammonium-propane (DSTAP),
1,2-dipalmitoyl-3-trimethylammonium-propane (DPTAP),
1,2-dilinoleoyl-3-trimethylammonium-propane (DLTAP),
1,2-dimyristoyl-3-trimethylammonium-propane (DMTAP)
1,2-distearoyl-sn-glycero-3-ethylphosphocholine (DSePC)
1,2-dipalmitoyl-sn-glycero-3-ethylphosphocholine (DPePC),
1,2-dimyristoyl-sn-glycero-3-ethylphosphocholine (DMePC),
1,2-dioleoyl-sn-glycero-3-ethylphosphocholine (DOePC),
1,2-di-(9Z-tetradecenoyl)-sn-glycero-3-ethylphosphocholine (14:1 EPC),
1-palmitoyl-2-oleoyl-sn-glycero-3-ethylphosphocholine (16:0-18:1 EPC),
and any combination thereof.

In one embodiment, the quaternary amine compound is 1,2-dioleoyl-3-trimethylammonium-propane (DOTAP).

Quaternary amine compounds are known in the art, such as those described in US 2013/0245107 A1, US 2014/0363493 A1, U.S. Pat. No. 8,158,601, WO 2015/123264 A1, and WO 2015/148247 A1, which are incorporated herein by reference in their entirety.

In one embodiment, the amount of the quaternary amine compound (e.g., DOTAP) in the lipid composition disclosed herein ranges from about 0.01 mol % to about 20 mol %.

In one embodiment, the amount of the quaternary amine compound (e.g., DOTAP) in the lipid composition disclosed herein ranges from about 0.5 mol % to about 20 mol %, from about 0.5 mol % to about 15 mol %, from about 0.5 mol % to about 10 mol %, from about 1 mol % to about 20 mol %, from about 1 mol % to about 15 mol %, from about 1 mol % to about 10 mol %, from about 2 mol % to about 20 mol %, from about 2 mol % to about 15 mol %, from about 2 mol % to about 10 mol %, from about 3 mol % to about 20 mol %, from about 3 mol % to about 15 mol %, from about 3 mol % to about 10 mol %, from about 4 mol % to about 20 mol %, from about 4 mol % to about 15 mol %, from about 4 mol % to about 10 mol %, from about 5 mol % to about 20 mol %, from about 5 mol % to about 15 mol %, from about 5 mol % to about 10 mol %, from about 6 mol % to about 20 mol %, from about 6 mol % to about 15 mol %, from about 6 mol % to about 10 mol %, from about 7 mol % to about 20 mol %, from about 7 mol % to about 15 mol %, from about 7 mol % to about 10 mol %, from about 8 mol % to about 20 mol %, from about 8 mol % to about 15 mol %, from about 8 mol % to about 10 mol %, from about 9 mol % to about 20 mol %, from about 9 mol % to about 15 mol %, from about 9 mol % to about 10 mol %.

In one embodiment, the amount of the quaternary amine compound (e.g., DOTAP) in the lipid composition disclosed herein ranges from about 5 mol % to about 10 mol %.

In one embodiment, the amount of the quaternary amine compound (e.g., DOTAP) in the lipid composition disclosed herein is about 5 mol %. In one embodiment, the amount of the quaternary amine compound (e.g., DOTAP) in the lipid composition disclosed herein is about 10 mol %.

In some embodiments, the amount of the quaternary amine compound (e.g., DOTAP) is at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 mol % in the lipid composition disclosed herein.

In some embodiments, the lipid composition of the pharmaceutical compositions disclosed herein comprises a compound of formula (I). In one embodiment, the mole ratio of the compound of formula (I) (e.g., Compounds 18, 25, 26 or 48) to the quaternary amine compound (e.g., DOTA) is about 100:1 to about 2.5:1. In one embodiment, the mole ratio of the compound of formula (I) (e.g., Compounds 18, 25, 26 or 48) to the quaternary amine compound (e.g., DOTAP) is about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, or about 2.5:1. In one embodiment, the mole ratio of the compound of formula (I) (e.g., Compounds 18, 25, 26 or 48) to the quaternary amine compound (e.g., DOTAP) in the lipid composition disclosed herein is about 10:1.

In some embodiments, the lipid composition of the pharmaceutical compositions disclosed herein comprises the lipid composition disclosed in International Application No. PCT/US2017/027492, filed Apr. 13, 2017, which is incorporated herein by reference in its entirety.

In some aspects, the lipid composition of the pharmaceutical compositions disclosed herein does not comprise a quaternary amine compound. In some aspects, the lipid composition of the pharmaceutical compositions disclosed herein does not comprise DOTAP.

(iii) Structural Lipids

The lipid composition of a pharmaceutical composition disclosed herein can comprise one or more structural lipids. As used herein, the term "structural lipid" refers to sterols and also to lipids containing sterol moieties. In some embodiments, the structural lipid is selected from the group consisting of cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol.

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 23.5 mol %, about 28.5 mol %, about 33.5 mol %, or about 38.5 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

In some aspects, the lipid composition component of the pharmaceutical compositions for intratumoral delivery disclosed does not comprise cholesterol.

(iv) Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid may be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons. In one embodiment, the PEG-lipid is PEG2k-DMG.

In one embodiment, the lipid nanoparticles described herein may comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

In some embodiments, the lipid composition disclosed herein comprises an ionizable amino lipid, e.g., a compound of formula (I), and an asymmetric phospholipid. In some embodiments, the lipid composition comprises compound 18 and MSPC.

In some embodiments, the lipid composition disclosed herein comprises an ionizable amino lipid, e.g., a compound of formula (I), and a quaternary amine compound. In some embodiments, the lipid composition comprises compound 18 and DOTAP.

In some embodiments, the lipid composition disclosed herein comprises an ionizable amino lipid, e.g., a compound of formula (I), an asymmetric phospholipid, and a quaternary amine compound. In some embodiments, the lipid composition comprises compound 18, MSPC and DOTAP.

In one embodiment, the lipid composition comprises about 50 mol % of a compound of formula (I) (e.g. Compounds 18, 25, 26 or 48), about 10 mol % of DSPC or MSPC, about 33.5 mol % of cholesterol, about 1.5 mol % of PEG-DMG, and about 5 mol % of DOTAP. In one embodiment, the lipid composition comprises about 50 mol % of a compound of formula (I) (e.g. Compounds 18, 25, 26 or 48), about 10 mol % of DSPC or MSPC, about 28.5 mol % of cholesterol, about 1.5 mol % of PEG-DMG, and about 10 mol % of DOTAP.

In some embodiments, the lipid nanoparticle comprises a molar ratio of about 20-60% ionizable amino lipid:5-25% phospholipid:25-55% sterol; and 0.5-15% PEG-modified lipid. In other aspects, the lipid nanoparticle carrier comprises a molar ratio of about 20-60% Compound 18: 5-25% phospholipid:25-55% cholesterol; and 0.5-15% PEG-modified lipid. In other aspects, the lipid nanoparticle carrier comprises a molar ratio of about 50% ionizable amino lipid:about 10% phospholipid:about 38.5% cholesterol; and about 1.5% PEG-modified lipid. In other aspects, the lipid nanoparticle carrier comprises a molar ratio of about 50% Compound 18: about 10% phospholipid:about 38.5% cholesterol; and about 1.5% PEG-modified lipid. In other aspects, the lipid nanoparticle carrier comprises a molar ratio of about 49.83% ionizable amino lipid:about 9.83% phospholipid:about 30.33% cholesterol; and about 2.0% PEG-modified lipid. In other aspects, the lipid nanoparticle carrier comprises a molar ratio of about 49.83% Compound 18: about 9.83% phospholipid:about 30.33% cholesterol; and about 2.0% PEG-modified lipid.

The components of the lipid nanoparticle may be tailored for optimal delivery of the polynucleotides based on the desired outcome. As a non-limiting example, the lipid nanoparticle may comprise 40-60 mol % an ionizable amino lipid (e.g., a compound of formula (I)), 8-16 mol % phospholipid, 30-45 mol % cholesterol, 1-5 mol % PEG lipid, and optionally 1-15 mol % quaternary amine compound.

In some embodiments, the lipid nanoparticle may comprise 45-65 mol % of an ionizable amino lipid (e.g., a compound of formula (I)), 5-10 mol % phospholipid, 25-40 mol % cholesterol, 0.5-5 mol % PEG lipid, and optionally 1-15 mol % quaternary amine compound.

Non-limiting examples of nucleic acid lipid particles are disclosed in U.S. Patent Publication No. 20140121263, herein incorporated by reference in its entirety.

(v) Other Ionizable Amino Lipids

The lipid composition of the pharmaceutical composition disclosed herein can comprise one or more ionizable lipids in addition to a lipid according to formula (I). As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as 'cationic lipid." For example, an ionizable molecule may comprise an amine group, referred to as ionizable amino lipids.

Ionizable lipids may be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraazaoctatriacontane (KL25), 1,2-dilinoleyloxy-N,N-dimethylaminopropane (DLin-DMA), 2,2-dilinoleyl-4-dimethyl aminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z, 16Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9, 12-di en-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)). In addition to these, an ionizable amino lipid may also be a lipid including a cyclic amine group.

Ionizable lipids can also be the compounds disclosed in International Publication No. WO 2015/199952 A1, hereby incorporated by reference in its entirety. For example, the ionizable amino lipids include, but not limited to:

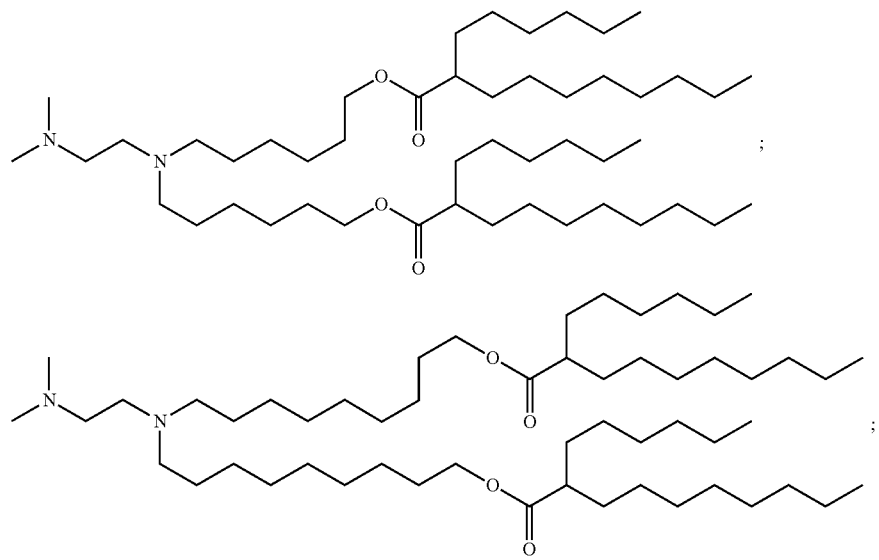

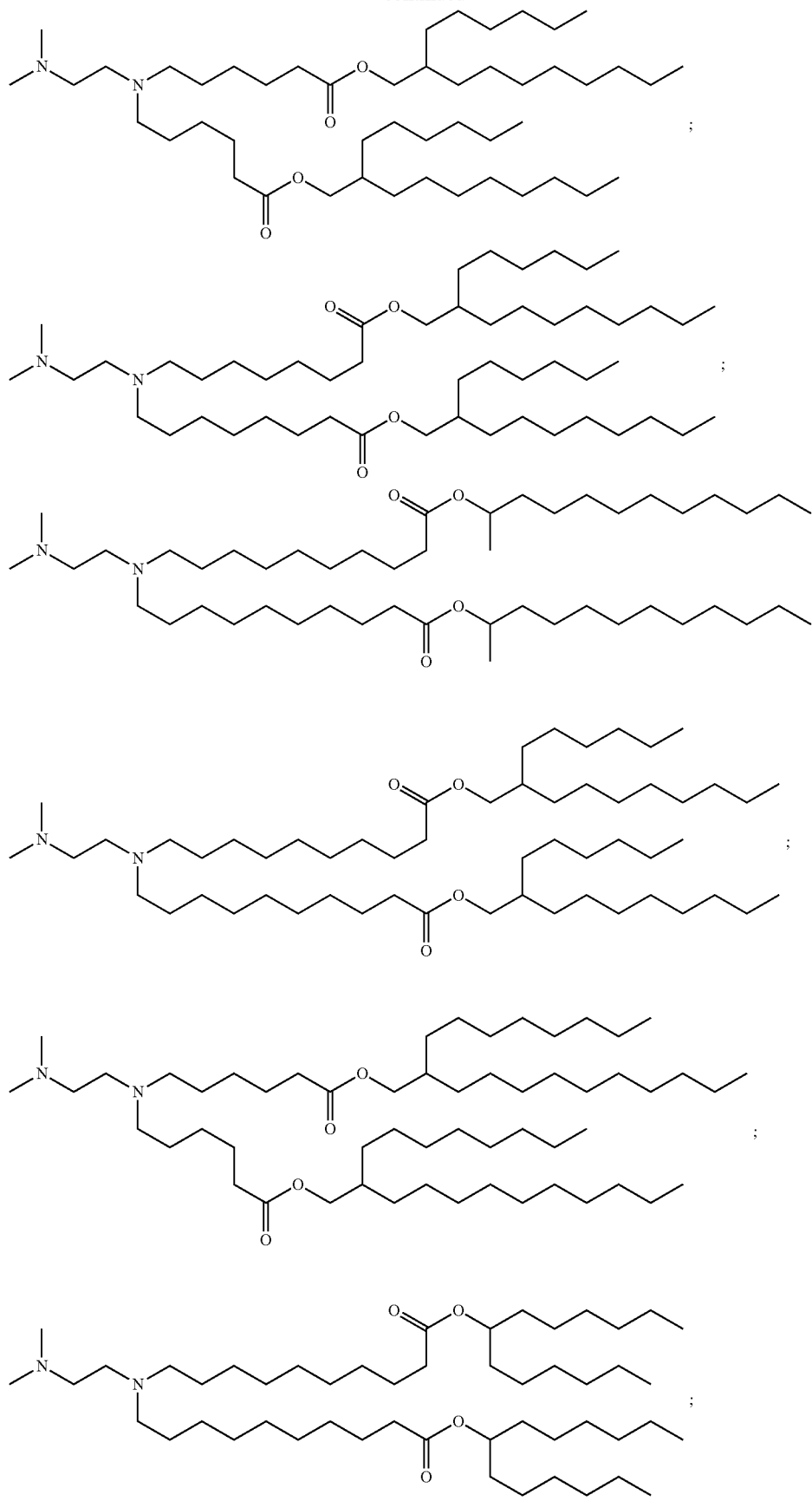

-continued

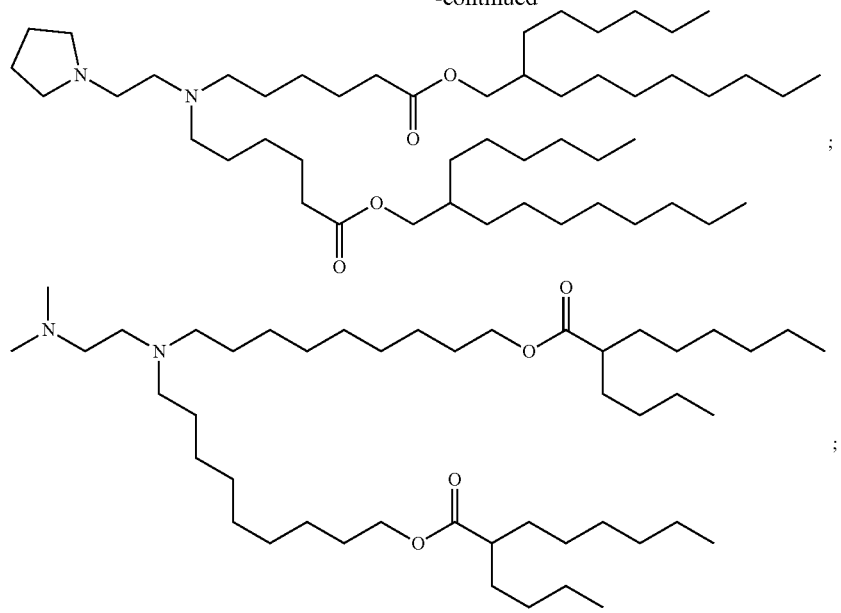

and any combination thereof.

(vi) Other Lipid Composition Components

The lipid composition of a pharmaceutical composition disclosed herein may include one or more components in addition to those described above. For example, the lipid composition may include one or more permeability enhancer molecules, carbohydrates, polymers, surface altering agents (e.g., surfactants), or other components. For example, a permeability enhancer molecule may be a molecule described by U.S. Patent Application Publication No. 2005/0222064. Carbohydrates may include simple sugars (e.g., glucose) and polysaccharides (e.g., glycogen and derivatives and analogs thereof). The lipid composition may include a buffer such as, but not limited to, citrate or phosphate at a pH of 7, salt and/or sugar. Salt and/or sugar may be included in the formulations described herein for isotonicity.

A polymer may be included in and/or used to encapsulate or partially encapsulate a pharmaceutical composition disclosed herein (e.g., a pharmaceutical composition in lipid nanoparticle form). A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein may comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein may comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

In one embodiment, formulations comprising the polynucleotides and lipid nanoparticles described herein may comprise 0.15 mg/ml to 2 mg/ml of the polynucleotide described herein (e.g., mRNA). In some embodiments, the formulation may further comprise 10 mM of citrate buffer and the formulation may additionally comprise up to 10% w/w of sucrose (e.g., at least 1% w/w, at least 2% w/w, at least 3% w/w, at least 4% w/w, at least 5% w/w, at least 6% w/w, at least 7% w/w, at least 8% w/w, at least 9% w/w or 10% w/w).

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as a compound of formula (I) as described herein, and (ii) a polynucleotide encoding an IL12B polypeptide, an IL12A polypeptide, and/or IL12B and IL12A fusion polypeptides. In such nanoparticle composition, the lipid composition disclosed herein can encapsulate the polynucleotide encoding an IL12B polypeptide, an IL12A polypeptide, and/or IL12B and IL12A fusion polypeptides.

Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or crosslinked to one another. Lipid bilayers may include one or more ligands, proteins, or channels.

Nanoparticle compositions of the present disclosure comprise at least one compound according to formula (I). For example, the nanoparticle composition can include one or more of Compounds 1-147, or one or more of Compounds 1-342. Nanoparticle compositions can also include a variety of other components. For example, the nanoparticle composition may include one or more other lipids in addition to a lipid according to formula (I), such as (i) at least one phospholipid, (ii) at least one quaternary amine compound, (iii) at least one structural lipid, (iv) at least one PEG-lipid, or (v) any combination thereof.

In some embodiments, the nanoparticle composition comprises a compound of formula (I), (e.g., Compounds 18, 25, 26 or 48). In some embodiments, the nanoparticle composition comprises a compound of formula (I) (e.g., Compounds 18, 25, 26 or 48) and a phospholipid (e.g., DSPC or MSPC). In some embodiments, the nanoparticle composition comprises a compound of formula (I) (e.g., Compounds 18, 25, 26 or 48), a phospholipid (e.g., DSPC or MSPC), and a quaternary amine compound (e.g., DOTAP). In some embodiments, the nanoparticle composition comprises a compound of formula (I) (e.g., Compounds 18, 25, 26 or 48), and a quaternary amine compound (e.g., DOTAP).

In some embodiments, the nanoparticle composition comprises a lipid composition consisting or consisting essentially of compound of formula (I) (e.g., Compounds 18, 25, 26 or 48). In some embodiments, the nanoparticle composition comprises a lipid composition consisting or consisting essentially of a compound of formula (I) (e.g., Compounds 18, 25, 26 or 48) and a phospholipid (e.g., DSPC or MSPC). In some embodiments, the nanoparticle composition comprises a lipid composition consisting or consisting essentially of a compound of formula (I) (e.g., Compounds 18, 25, 26 or 48), a phospholipid (e.g., DSPC or MSPC), and a quaternary amine compound (e.g., DOTAP). In some embodiments, the nanoparticle composition comprises a lipid composition consisting or consisting essentially of a compound of formula (I) (e.g., Compounds 18, 25, 26 or 48), and a quaternary amine compound (e.g., DOTAP).

In one embodiment, the nanoparticle composition comprises (1) a lipid composition comprising about 50 mole % of a compound of formula (I) (e.g., Compounds 18, 25, 26 or 48); about 10 mole % of DSPC or MSPC; about 33.5 mole % of cholesterol; about 1.5 mole % of PEG-DMG (e.g., $PEG_{2k}$-DMG); about 5 mole % of DOTAP; and (2) a polynucleotide.

In one embodiment, the nanoparticle composition comprises (1) a lipid composition comprising about 50 mole % of a compound of formula (I) (e.g., Compounds 18, 25, 26 or 48); about 10 mole % of DSPC or MSPC; about 28.5 mole % of cholesterol; about 1.5 mole % of PEG-DMG (e.g., $PEG_{2k}$-DMG); about 10 mole % of DOTAP; and (2) a polynucleotide.

In one embodiment, the nanoparticle composition comprises (1) a lipid composition comprising about 50 mole % of a compound of formula (I) (e.g., Compounds 18, 25, 26 or 48); about 10 mole % of DSPC or MSPC; about 23.5 mole % of cholesterol; about 1.5 mole % of PEG-DMG (e.g., $PEG_{2k}$-DMG); about 15 mole % of DOTAP; and (2) a polynucleotide.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a nanoparticle composition, such as particle size, polydispersity index, and zeta potential.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". For example, an ionizable molecule may comprise an amine group, referred to as ionizable amino lipids. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding an IL12B polypeptide, an IL12A polypeptide, and/or IL12B and IL12A fusion polypeptides are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 m or shorter (e.g., 1 µm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition may be relatively homogenous. A polydispersity index may be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein may be from about 0.10 to about 0.20.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition disclosed herein may be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles may be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles may be from about 10 mV to about 50 mV, from about 15 mV to about 45 mV, from about 20 mV to about 40 mV, and from about 25 mV to about 35 mV. In some embodiments, the zeta potential of the lipid nanoparticles may be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" may refer to complete, substantial, or partial enclosure, confinement, surrounding, or encasement.

Encapsulation efficiency is desirably high (e.g., close to 100%). The encapsulation efficiency may be measured, for example, by comparing the amount of the polynucleotide in a solution containing the nanoparticle composition before and after breaking up the nanoparticle composition with one or more organic solvents or detergents.

Fluorescence may be used to measure the amount of free polynucleotide in a solution. For the nanoparticle compositions described herein, the encapsulation efficiency of a polynucleotide may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition may depend on the size (expressed as length, or molecular mass), sequence, and other characteristics of the mRNA. The relative amounts of a polynucleotide in a nanoparticle composition may also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

25. Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding an IL12B polypeptide, an IL12A polypeptide, and/or IL12B and IL12A fusion polypeptides) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that may primarily be composed of a lipid bilayer and may be used as a delivery vehicle for the administration of pharmaceutical formulations. Liposomes can be of different sizes. A multilamellar vesicle (MLV) may be hundreds of nanometers in diameter, and may contain a series of concentric bilayers separated by narrow aqueous compartments. A small unicellular vesicle (SUV) may be smaller than 50 nm in diameter, and a large unilamellar vesicle (LUV) may be between 50 and 500 nm in diameter. Liposome design may include, but is not limited to, opsonins or ligands to improve the attachment of liposomes to unhealthy tissue or to activate events such as, but not limited to, endocytosis. Liposomes may contain a low or a high pH value in order to improve the delivery of the pharmaceutical formulations.

The formation of liposomes may depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles may be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein may be encapsulated by the liposome and/or it may be contained in an aqueous core that may then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid). In some embodiments, the lipid is a cationic lipid. In some embodiments, lipid nanoparticle formulations further comprise other components, including a phospholipid, a structural lipid, a quaternary amine compound, and a molecule capable of reducing particle aggregation, for example a PEG or PEG-modified lipid.

Cationic and ionizable lipids may include those as described in, e.g., Intl. Pub. Nos. WO2015199952, WO 2015130584, WO 2015011633, and WO2012040184 WO2013126803, WO2011153120, WO2011149733, WO2011090965, WO2011043913, WO2011022460, WO2012061259, WO2012054365, WO2012044638, WO2010080724, WO2010021865, WO2008103276, and WO2013086373; U.S. Pat. Nos. 7,893,302, 7,404,969, 8,283,333, and 8,466,122; and U.S. Pub. Nos. US20110224447, US20120295832, US20150315112, US20100036115, US20120202871, US20130064894, US20130129785, US20130150625, US20130178541, US20130123338 and US20130225836, each of which is herein incorporated by reference in its entirety. In some embodiments, the amount of the cationic and ionizable lipids in the lipid composition ranges from about 0.01 mol % to about 99 mol %.

Exemplary ionizable lipids include, but not limited to, any one of Compounds 1-147 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-2000, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1 S,2R)-2-octylcyclopropyl] nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl] methyl}cyclopropyl]nonadecan-10-amine, N,N-dimethyl-1-[(1 S,2R)-2-octylcyclopropyl]hexadecan-8-amine, N,N-dimethyl-[(1R,2 S)-2-undecylcyclopropyl]tetradecan-5-amine, N,N-dimethyl-3-{7-[(1S,2R)-2-octylcyclopropyl] heptyl}dodecan-1-amine, 1-[(1R,2S)-2-heptylcyclopropyl]-N,N-dimethyloctadecan-9-amine, 1-[(1 S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azetidine, (2 S)-1-(hexyloxy)-N,N-dimethyl-3-[(9Z, 12Z)-octadeca-9, 12-dien-1-yloxy]propan-2-amine, (2S)-1-(heptyloxy)-N,N-dimethyl-3-[(9Z,12Z)-octadeca-9, 12-dien-1-yloxy]propan-2-amine, N,N-dimethyl-1-(nonyloxy)-3-[(9Z,12Z)-octadeca-9,12-dien-1-yl oxy]propan-2-amine, N,N-dimethyl-1-[(9Z)-octadec-9-en-1-yloxy]-3-(octyloxy)propan-2-amine; (2S)—N,N-dimethyl-1-[(6Z,9Z, 12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11, 14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13, 16-dien-1-yloxy]-3-(hexyloxy)-N,N-dimethylpropan-2-amine, (2S)-1-[(13Z)-docos-13-en-1-yloxy]-3-(hexyloxy)-

N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9, 12-dien-1-yloxy]propan-2-amine, (2R)-1-[(3,7-dimethyloctyl)oxy]-N,N-dimethyl-3-[(9Z, 12Z)-octadeca-9,12-dien-1-yloxy]propan-2-amine, N,N-dimethyl-1-(octyloxy)-3-({8-[(1 S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC and/or MSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The quaternary amine compound as described herein include 1,2-dioleoyl-3-trimethylammonium-propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), N,N-distearyl-N,N-dimethylammonium bromide (DDAB), N-(1, 2-dimyristyloxyprop-3-yl)-N,N-dimethyl-N-hydroxyethyl ammonium bromide (DMRIE), N-(1,2-dioleoyloxyprop-3-yl)-N,N-dimethyl-N-hydroxyethyl ammonium bromide (DORIE), N,N-dioleyl-N,N-dimethylammonium chloride (DODAC), 1,2-dilauroyl-sn-glycero-3-ethylphosphocholine (DLePC), 1,2-distearoyl-3-trimethyl ammonium-propane (DSTAP), 1,2-dipalmitoyl-3-trimethylammonium-propane (DPTAP), 1,2-dilinoleoyl-3-trimethylammonium-propane (DLTAP), 1,2-dimyristoyl-3-trimethylammonium-propane (DMTAP), 1,2-distearoyl-sn-glycero-3-ethylphosphocholine (DSePC), 1,2-dipalmitoyl-sn-glycero-3-ethylphosphocholine (DPePC), 1,2-dimyristoyl-sn-glycero-3-ethylphosphocholine (DMePC), 1,2-dioleoyl-sn-glycero-3-ethylphosphocholine (DOePC), 1,2-di-(9Z-tetradecenoyl)-sn-glycero-3-ethylphosphocholine (14:1 EPC), 1-palmitoyl-2-oleoyl-sn-glycero-3-ethylosphocholine (16:0-18:1 EPC), and any combination thereof. In some embodiments, the amount of the quaternary amine compounds (e.g., DOTAP) in the lipid composition ranges from about 0.01 mol % to about 20 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid may be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0.1 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation may also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present disclosure in a subject. Further, the conjugate can inhibit phagocytic clearance of the nanoparticles in a subject. In some embodiments, the conjugate may be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP may be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles may penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin 34 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations may be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which may be spherical with an average diameter between 10 to 1000 nm. SLN possess a solid lipid core matrix that can solubilize lipophilic molecules and may be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the disclosure, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the disclosure may be enclosed, surrounded or encased within the delivery agent. "Partially encapsulation" means that less than 10, 10, 20, 30, 40 50 or less of the pharmaceutical composition or compound of the disclosure may be enclosed, surrounded or encased within the delivery agent.

Advantageously, encapsulation can be determined by measuring the escape or the activity of the pharmaceutical composition or compound of the disclosure using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the disclosure are encapsulated in the delivery agent.

In some embodiments, the polynucleotide controlled release formulation can include at least one controlled release coating (e.g., OPADRY®, EUDRAGIT RL®, EUDRAGIT RS® and cellulose derivatives such as ethylcellulose aqueous dispersions (AQUACOAT® and SURELEASE®)). In some embodiments, the polynucleotide controlled release formulation can comprise a polymer system as described in U.S. Pub. No. US20130130348, or a PEG and/or PEG related polymer derivative as described in U.S. Pat. No. 8,404,222, each of which is incorporated by reference in its entirety.

In some embodiments, the polynucleotides described herein can be encapsulated in a therapeutic nanoparticle, referred to herein as "therapeutic nanoparticle polynucleotides." Therapeutic nanoparticles may be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to about 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles may comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding an IL12B polypeptide, an IL12A polypeptide, and/or IL12B and IL12A fusion polypeptides) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethyl-enetetramine hydrochloride (TETA-5LAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids may be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding an IL12B polypeptide, an IL12A polypeptide, and/or IL12B and IL12A fusion polypeptides) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, intratumorally, or subcutaneously.

d. Nanoparticle Mimics

In some embodiments, the polynucleotides described herein (e.g., a polynucleotide comprising a nucleotide sequence encoding an IL12B polypeptide, an IL12A polypeptide, and/or IL12B and IL12A fusion polypeptides) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Nanotubes

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) attached or otherwise bound to (e.g., through steric, ionic, covalent and/or other forces) at least one nanotube, such as, but not limited to, rosette nanotubes, rosette nanotubes having twin bases with a linker, carbon nanotubes and/or single-walled carbon nanotubes. Nanotubes and nanotube formulations comprising a polynucleotide are described in, e.g., Intl. Pub. No. WO2014152211, herein incorporated by reference in its entirety.

f. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

g. Inorganic Nanoparticles, Semi-Conductive and Metallic Nanoparticles

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in inorganic nanoparticles, or water-dispersible nanoparticles comprising a semiconductive or metallic material. The inorganic nanoparticles can include, but are not limited to, clay substances that are water swellable. The water-dispersible nanoparticles can be hydrophobic or hydrophilic nanoparticles. As a non-limiting example, the inorganic, semi-conductive and metallic nanoparticles are described in, e.g., U.S. Pat. Nos. 5,585,108 and 8,257,745; and U.S. Pub. Nos. US20120228565, US 20120265001 and US 20120283503, each of which is herein incorporated by reference in their entirety.

h. Surgical Sealants: Gels and Hydrogels

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in a surgical sealant. Surgical sealants such as gels and hydrogels are described in Intl. Appl. No. PCT/US2014/027077, herein incorporated by reference in its entirety.

i. Suspension Formulations

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in suspensions. In some embodiments, suspensions comprise a polynucleotide, water immiscible oil depots, surfactants and/or co-surfactants and/or co-solvents. Suspensions can be formed by first preparing an aqueous solution of a polynucleotide and an oil-based phase comprising one or more surfactants, and then mixing the two phases (aqueous and oil-based).

Exemplary oils for suspension formulations can include, but are not limited to, sesame oil and Miglyol (comprising esters of saturated coconut and palmkernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, Capmul®, labrasol, isopropyl myristate, and/or Span 80. In some embodiments, suspensions can comprise co-solvents including, but not limited to ethanol, glycerol and/or propylene glycol.

In some embodiments, suspensions can provide modulation of the release of the polynucleotides into the surrounding environment by diffusion from a water immiscible depot followed by resolubilization into a surrounding environment (e.g., an aqueous environment).

In some embodiments, the polynucleotides can be formulated such that upon injection, an emulsion forms spontaneously (e.g., when delivered to an aqueous phase), which may provide a high surface area to volume ratio for release of polynucleotides from an oil phase to an aqueous phase. In some embodiments, the polynucleotide is formulated in a nanoemulsion, which can comprise a liquid hydrophobic core surrounded by or coated with a lipid or surfactant layer. Exemplary nanoemulsions and their preparations are described in, e.g., U.S. Pat. No. 8,496,945, herein incorporated by reference in its entirety.

j. Cations and Anions

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) and a cation or anion, such as $Zn^{2+}$, $Ca^{2+}$, $Cu^{2+}$, $Mg^{2+}$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles may improve polynucleotide bioavailability by acting as a long-acting depot and/or reducing the rate of degradation by nucleases.

k. Molded Nanoparticles and Microparticles

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in molded nanoparticles in various sizes, shapes and chemistry. For example, the nanoparticles and/or microparticles can be made using the PRINT® technology by LIQUIDA TECHNOLOGIES® (Morrisville, N.C.) (e.g., International Pub. No. WO2007024323, herein incorporated by reference in its entirety).

In some embodiments, the polynucleotides described herein (e.g., a polynucleotide comprising a nucleotide sequence encoding an IL12B polypeptide, an IL12A polypeptide, and/or IL12B and IL12A fusion polypeptides) is formulated in microparticles. The microparticles may contain a core of the polynucleotide and a cortex of a biocompatible and/or biodegradable polymer, including but not limited to, poly(α-hydroxy acid), a polyhydroxy butyric acid, a polycaprolactone, a polyorthoester and a polyanhydride. The microparticle may have adsorbent surfaces to adsorb polynucleotides. The microparticles may have a diameter of from at least 1 micron to at least 100 microns (e.g., at least 1 micron, at least 10 micron, at least 20 micron, at least 30 micron, at least 50 micron, at least 75 micron, at least 95 micron, and at least 100 micron). In some embodiment, the compositions or formulations of the present disclosure are microemulsions comprising microparticles and polynucleotides. Exemplary microparticles, microemulsions and their preparations are described in, e.g., U.S. Pat. Nos. 8,460,709, 8,309,139 and 8,206,749; U.S. Pub. Nos. US20130129830, US2013195923 and US20130195898; and Intl. Pub. No. WO2013075068, each of which is herein incorporated by reference in its entirety.

l. NanoJackets and NanoLiposomes

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in NanoJackets and NanoLiposomes by Keystone Nano (State College, Pa.). NanoJackets are made of materials that are naturally found in the body including calcium, phosphate and may also include a small amount of silicates. Nanojackets may have a size ranging from 5 to 50 nm.

NanoLiposomes are made of lipids such as, but not limited to, lipids that naturally occur in the body. NanoLiposomes may have a size ranging from 60-80 nm. In some embodiments, the polynucleotides disclosed herein are formulated in a NanoLiposome such as, but not limited to, Ceramide NanoLiposomes.

m. Cells or Minicells

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) that is transfected ex vivo into cells, which are subsequently transplanted into a subject. Cell-based formulations of the polynucleotide disclosed herein can be used to ensure cell transfection (e.g., in the cellular carrier), alter the biodistribution of the polynucleotide (e.g., by targeting the cell carrier to specific tissues or cell types), and/or increase the translation of encoded protein.

Exemplary cells include, but are not limited to, red blood cells, virosomes, and electroporated cells (see e.g., Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety).

A variety of methods are known in the art and are suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In some embodiments, the polynucleotides described herein can be delivered in synthetic virus-like particles (VLPs) synthesized by the methods as described in Intl. Pub Nos. WO2011085231 and WO2013116656; and U.S. Pub. No. 20110171248, each of which is herein incorporated by reference in its entirety.

The technique of sonoporation, or cellular sonication, is the use of sound (e.g., ultrasonic frequencies) for modifying the permeability of the cell plasma membrane. Sonoporation methods are known to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; U.S. Pub. Nos. US20100196983 and US20100009424; all herein incorporated by reference in their entirety).

In some embodiments, the polynucleotides described herein can be delivered by electroporation. Electroporation techniques are known to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). Electroporation devices are sold by many companies worldwide including, but not limited to BTX® Instruments (Holliston, Mass.) (e.g., the AgilePulse In vivo System) and Inovio (Blue Bell, Pa.) (e.g., Inovio SP-5P intramuscular delivery device or the CELLECTRA® 3000 intradermal delivery device).

In some embodiments, the cells are selected from the group consisting of mammalian cells, bacterial cells, plant, microbial, algal and fungal cells. In some embodiments, the cells are mammalian cells, such as, but not limited to, human, mouse, rat, goat, horse, rabbit, hamster or cow cells. In a further embodiment, the cells can be from an established cell line, including, but not limited to, HeLa, NSO, SP2/0, KEK 293T, Vero, Caco, Caco-2, MDCK, COS-1, COS-7, K562, Jurkat, CHO-K1, DG44, CHOK1SV, CHO—S, Huvec, CV-1, Huh-7, NIH3T3, HEK293, 293, A549, HepG2, IMR-90, MCF-7, U-20S, Per.C6, SF9, SF21 or Chinese Hamster Ovary (CHO) cells.

In certain embodiments, the cells are fungal cells, such as, but not limited to, *Chrysosporium* cells, *Aspergillus* cells, *Trichoderma* cells, *Dictyostelium* cells, *Candida* cells, *Saccharomyces* cells, *Schizosaccharomyces* cells, and *Penicillium* cells.

In certain embodiments, the cells are bacterial cells such as, but not limited to, *E. coli, B. subtilis*, or BL21 cells. Primary and secondary cells to be transfected by the methods of the disclosure can be obtained from a variety of tissues and include, but are not limited to, all cell types that can be maintained in culture. The primary and secondary cells include, but are not limited to, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells may also be obtained from a donor of the same species or from another species (e.g., mouse, rat, rabbit, cat, dog, pig, cow, bird, sheep, goat, horse).

In some embodiments, the compositions or formulations of the present disclosure comprise the polynucleotides described herein in bacterial minicells. As a non-limiting example, bacterial minicells can be those described in Intl. Pub. No. WO2013088250 or U.S. Pub. No. US20130177499, each of which is herein incorporated by reference in its entirety.

n. Semi-Solid Compositions

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in a hydrophobic matrix to form a semi-solid or paste-like composition. As a non-limiting example, the semi-solid or paste-like composition can be made by the methods described in Intl. Pub. No. WO201307604, herein incorporated by reference in its entirety.

o. Exosomes

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in exosomes, which can be loaded with at least one polynucleotide and delivered to cells, tissues and/or organisms. As a non-limiting example, the polynucleotides can be loaded in the exosomes as described in Intl. Pub. No. WO2013084000, herein incorporated by reference in its entirety.

p. Silk-Based Delivery

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) that is formulated for silk-based delivery. The silk-based delivery system can be formed by contacting a silk fibroin solution with a polynucleotide described herein. As a non-limiting example, a sustained release silk-based delivery system and methods of making such system are described in U.S. Pub. No. US20130177611, herein incorporated by reference in its entirety.

q. Amino Acid Lipids

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations may deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

r. Microvesicles

In some embodiments, the compositions or formulations of the present disclosure comprise the polynucleotides described herein (e.g., a polynucleotide comprising a nucleotide sequence encoding an IL12B polypeptide, an L12A polypeptide, and/or IL12B and IL12A fusion polypeptides) in a microvesicle formulation. Exemplary microvesicles include those described in U.S. Pub. No. US20130209544 (herein incorporated by reference in its entirety). In some embodiments, the microvesicle is an ARRDC1-mediated microvesicles (ARMMs) as described in Intl. Pub. No. WO2013119602 (herein incorporated by reference in its entirety).

s. Interpolyelectrolyte Complexes

In some embodiments, the compositions or formulations of the present disclosure comprise the polynucleotides described herein (e.g., a polynucleotide comprising a nucleotide sequence encoding an IL12B polypeptide, an L12A polypeptide, and/or IL12B and IL12A fusion polypeptides) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

t. Crystalline Polymeric Systems

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

u. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, Calif.) formulations from MIRUS® Bio (Madison, Wis.) and Roche Madison (Madison, Wis.), PHASERX™ polymer formulations such as, without limitation, SMARTT POLYMER TECHNOLOGY™ (PHASERX®, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly (lactic-co-glycolic acid) (PLGA) polymers. RONDEL™ (RNAi/Oligonucleotide Nanoparticle Delivery) polymers (Arrowhead Research Corporation, Pasadena, Calif.) and pH responsive co-block polymers such as PHASERX® (Seattle, Wash.).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc. Deerfield, Ill.), PEG-based sealants, and COSEAL® (Baxter International, Inc. Deerfield, Ill.).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles may efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art, the polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

v. Peptides and Proteins

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

w. Conjugates

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fructose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, Wash.).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835,393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

x. Micro-Organs

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in a micro-organ that can then express an encoded polypeptide of interest in a long-lasting therapeutic formulation. Exemplary micro-organs and formulations are described in Intl. Pub. No. WO2014152211 (herein incorporated by reference in its entirety).

y. Pseudovirions

In some embodiments, the compositions or formulations of the present disclosure comprise the polynucleotides described herein (e.g., a polynucleotide comprising a nucleotide sequence encoding an IL12B polypeptide, an IL12A polypeptide, and/or IL12B and IL12A fusion polypeptides) in pseudovirions (e.g., pseudovirions developed by Aura Biosciences, Cambridge, Mass.).

In some embodiments, the pseudovirion used for delivering the polynucleotides can be derived from viruses such as, but not limited to, herpes and papillomaviruses as described in, e.g., U.S. Pub. Nos. US20130012450, US20130012566, US21030012426 and US20120207840; and Intl. Pub. No. WO2013009717, each of which is herein incorporated by reference in its entirety.

The pseudovirion can be a virus-like particle (VLP) prepared by the methods described in U.S. Pub. Nos. US20120015899 and US20130177587, and Intl. Pub. Nos. WO2010047839, WO2013116656, WO2013106525 and WO2013122262. In one aspect, the VLP can be bacteriophages MS, Qβ, R17, fr, GA, Sp, MI, I, MXI, NL95, AP205, f2, PP7, and the plant viruses Turnip crinkle virus (TCV), Tomato bushy stunt virus (TBSV), Southern bean mosaic virus (SBMV) and members of the genus Bromovirus including Broad bean mottle virus, Brome mosaic virus, Cassia yellow blotch virus, Cowpea chlorotic mottle virus (CCMV), Melandrium yellow fleck virus, and Spring beauty latent virus. In another aspect, the VLP can be derived from the influenza virus as described in U.S. Pub. No. US20130177587 and U.S. Pat. No. 8,506,967. In one aspect, the VLP can comprise a B7-1 and/or B7-2 molecule anchored to a lipid membrane or the exterior of the particle such as described in Intl. Pub. No. WO2013116656. In one aspect, the VLP can be derived from norovirus, rotavirus recombinant VP6 protein or double layered VP2/VP6 such as the VLP as described in Intl. Pub. No. WO2012049366. Each of the references is herein incorporated by reference in its entirety.

In some embodiments, the pseudovirion can be a human papilloma virus-like particle as described in Intl. Pub. No. WO2010120266 and U.S. Pub. No. US20120171290. In some embodiments, the virus-like particle (VLP) can be a self-assembled particle. In one aspect, the pseudovirions can be virion derived nanoparticles as described in U.S. Pub. Nos. US20130116408 and US20130115247; and Intl. Pub. No. WO2013119877. Each of the references is herein incorporated by reference in their entirety.

Non-limiting examples of formulations and methods for formulating the polynucleotides described herein are also provided in Intl. Pub. No WO2013090648 (incorporated herein by reference in their entirety).

26. Compositions and Formulations for Use

Certain aspects of the disclosure are directed to compositions or formulations comprising any of the polynucleotides disclosed above.

In some embodiments, the composition or formulation comprises:

(i) a polynucleotide (e.g., a RNA, e.g., an mRNA) comprising a sequence-optimized nucleotide sequence (e.g., an ORF) encoding an IL12B polypeptide, an IL12A polypeptide, and/or IL12B and IL12A fusion polypeptides (e.g., the wild-type sequence, functional fragment, or variant thereof), wherein the polynucleotide comprises at least one chemically modified nucleobase, e.g., 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils), and wherein the polynucleotide further comprises a miRNA binding site, e.g., a miRNA binding site that binds to miR-122 (e.g., a miR-122-3p or miR-122-5p binding site); and (ii) a delivery agent comprising a compound having Formula (I), e.g., any of Compounds 1-147 (e.g., Compound 18, 25, 26 or 48) or any of Compounds 1-232.

In some embodiments, the uracil or thymine content of the ORF relative to the theoretical minimum uracil or thymine content of a nucleotide sequence encoding the IL12B polypeptide, the IL12A polypeptide, and/or IL12B and IL12A fusion polypeptides (% $U_{TM}$ or % $T_{TM}$), is between about 100% and about 150%.

In some embodiments, the polynucleotides, compositions or formulations above are used to treat and/or prevent an IL12-related diseases, disorders or conditions, e.g., cancer.

27. Forms of Administration

The polynucleotides, pharmaceutical compositions and formulations of the disclosure described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedullaris), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present disclosure (e.g., a polynucleotide comprising a nucleotide sequence encoding an IL12B polypeptide, an IL12A polypeptide, and/or IL12B and IL12A fusion polypeptides or a functional fragment or variant thereof) can be delivered to a cell naked. As used herein in, "naked" refers to delivering polynucleotides free from agents that promote transfection. For example, the polynucleotides delivered to the cell may contain no modifications. The naked polynucleotides can be delivered to the cell using routes of administration known in the art and described herein.

The polynucleotides of the present disclosure (e.g., a polynucleotide comprising a nucleotide sequence encoding an IL12B polypeptide, I an IL12A polypeptide, and/or IL12B and IL12A fusion polypeptides or a functional fragment or variant thereof) can be formulated, using the methods described herein. The formulations can contain polynucleotides that can be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

The compositions can also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like.

The present disclosure encompasses the delivery of polynucleotides of the disclosure (e.g., a polynucleotide comprising a nucleotide sequence encoding an IL12B polypeptide, an IL12A polypeptide, and/or IL12B and IL12A fusion polypeptides or a functional fragment or variant thereof) in forms suitable for parenteral and injectable administration. Liquid dosage forms for parenteral administration include, but are not limited to, pharmaceutically acceptable emulsions, microemulsions, solutions, suspensions, syrups, and/or elixirs. In addition to active ingredients, liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

A pharmaceutical composition for parenteral administration can comprise at least one inactive ingredient. Any or none of the inactive ingredients used may have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation may also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

28. Kits and Devices a. Kits

The disclosure provides a variety of kits for conveniently and/or effectively using the claimed nucleotides of the present disclosure. Typically kits will comprise sufficient amounts and/or numbers of components to allow a user to perform multiple treatments of a subject(s) and/or to perform multiple experiments.

In one aspect, the present disclosure provides kits comprising the molecules (polynucleotides) of the disclosure.

Said kits can be for protein production, comprising a first polynucleotides comprising a translatable region. The kit may further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components may also be varied in order to increase the stability of modified RNA in the buffer solution over a period of time and/or under a variety of conditions. In one aspect, the present disclosure provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present disclosure provides kits for protein production, comprising a polynucleotide comprising a translatable region, wherein the polynucleotide exhibits reduced degradation by a cellular nuclease, and packaging and instructions.

In one aspect, the present disclosure provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present disclosure provides for devices that may incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present disclosure according to single, multi- or split-dosing regimens taught herein. Such devices are taught in, for example, International Application Publ. No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present disclosure. These include, for example, those methods and devices having multiple needles, hybrid devices employing for example lumens or catheters as well as devices utilizing heat, electric current or radiation driven mechanisms.

According to the present disclosure, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present disclosure on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present disclosure according to the single, multi- or split dosing regimens taught herein. Such methods and devices are described in International Application Publication No. WO2013151666, the contents of which are incorporated herein by reference in their entirety.

29. Definitions

In order that the present disclosure can be more readily understood, certain terms are first defined. As used in this application, except as otherwise expressly provided herein, each of the following terms shall have the meaning set forth below. Additional definitions are set forth throughout the application.

The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of an disclosure is disclosed as having a plurality of alternatives, examples of that disclosure in which each alternative is excluded singly or in any combination with the other alternatives are also hereby disclosed; more than one element of an disclosure can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art. In general, such interval of accuracy is +10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type IL12 sequence) with another amino acid residue. An amino acid can be substituted in a parent or reference sequence (e.g., a wild type IL12 polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue, i.e., In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association may, but need not, be causatively linked to the disease. For example, symptoms, sequelae, or any effects causing a decrease in the quality of life of a patient of cancer are considered associated with cancer and in some embodiments of the present disclosure can be treated, ameliorated, or prevented by administering the polynucleotides of the present disclosure to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions may affect the same outcome or a different outcome. The structure that produces the function can be the same or different. For example, bifunctional modified RNAs of the present disclosure may encode an IL12 peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that may ameliorate or treat a disease or conditions, but would also maintain a population modified RNA present in the subject for a prolonged period of time. In other aspects, a bifunctionally modified mRNA can be a chimeric molecule comprising, for example, an RNA encoding an IL12 peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present disclosure can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising an IL12B polypeptide, IL12A polypeptide, or both IL12B and IL12A polypeptides, and a second part (e.g., genetically fused to the first part) comprising a second therapeutic protein (e.g., a protein with a distinct enzymatic activity, an antigen binding moiety, or a moiety capable of extending the plasma half-life of IL12, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an polynucleotide or polypeptide or may apply to a portion, region or feature thereof.

Controlled Release: As used herein, the term "controlled release" refers to a pharmaceutical composition or compound release profile that conforms to a particular pattern of release to effect a therapeutic outcome.

Covalent Derivative: The term "covalent derivative" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present disclosure can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject may involve administering a nanoparticle composition including the polynucleotide to the subject (e.g., by an intravenous, intramuscular, intradermal, or subcutaneous route). Administration of a nanoparticle composition to a mammal or mammalian cell may involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties that are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels can be located at any position in the peptides or proteins disclosed herein. They can be within the amino acids, the peptides, or proteins, or located at the N- or C-termini.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., an IL12 deficiency), an effective amount of an agent is, for example, an amount of mRNA expressing sufficient PBGF to ameliorate, reduce, eliminate, or prevent the symptoms associated with the IL12 deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the disclosure, having an optical purity or enantiomeric excess (as determined by methods standard in the art) of at least 80% (i.e., at least 90% of one enantiomer and at most 10% of the other enantiomer), at least 90%, or at least 98%.

Encapsulate. As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency may be given as 97%. As used herein, "encapsulation" may refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the disclosure are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it may be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present disclosure include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., IL12) wherein N-terminal, and/or C-terminal, and/or internal subsequences have been deleted. In some preferred aspects of the present disclosure, the fragments of a protein of the present disclosure are functional fragments.

Functional: As used herein, a "functional" biological molecule is a biological molecule in a form in which it exhibits a property and/or activity by which it is characterized. Thus, a functional fragment of a polynucleotide of the present disclosure is a polynucleotide capable of expressing a functional IL12 fragment. As used herein, a functional fragment of IL12 refers to a fragment of wild type IL12 (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present disclosure, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C—X—C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL12), interleukin-13 (11-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,16SZ)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the disclosure. It is recognized that the compounds of the disclosure can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the disclosure, the chemical structures depicted herein, and therefore the compounds of the disclosure, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the disclosure can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" (including a subunit linker and a heterologous polypeptide linker as referred to herein) refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

Modified: As used herein "modified" refers to a changed state or structure of a molecule of the disclosure. Molecules can be modified in many ways including chemically, structurally, and functionally. In some embodiments, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who may seek or be in need of treatment, requires treatment, is receiving treatment, will receive treatment, or a subject who is under care by a trained professional for a particular disease or condition.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in Remington's Pharmaceutical Sciences, 17$^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

Pharmaceutically acceptable solvate: The term "pharmaceutically acceptable solvate," as used herein, means a compound of the disclosure wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ' 'C codon (RNA map in which U has been replaced with pseudouridine).

Standard A-T and G-C base pairs form under conditions which allow the formation of hydrogen bonds between the N3-H and C4-oxy of thymidine and the Ni and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-3-D-ribofuranosyl-2-oxy-4-amino-pyrimidine) to form isocytosine (1-β3-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity that is in a form predicate for that substance, molecule or entity to act as a therapeutic upon chemical or physical alteration. Prodrugs may by covalently bonded or sequestered in some way and that release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine (v) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3$ $\psi$), and 2'-O-methyl-pseudouridine ($\psi$m).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Repeated transfection: As used herein, the term "repeated transfection" refers to transfection of the same cell culture with a polynucleotide a plurality of times. The cell culture can be transfected at least twice, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times at least 18 times, at least 19 times, at least 20 times, at least 25 times, at least 30 times, at least 35 times, at least 40 times, at least 45 times, at least 50 times or more.

Salts: In some aspects, the pharmaceutical composition for intratumoral delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample. As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it may be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound may possess (e.g., a compound of any formula described herein), in particular all possible stereochemically and conformationally isomeric forms, all diastereomers, enantiomers and/or conformers of the basic molecular structure. Some compounds of the present disclosure may exist in different tautomeric forms, all of the latter being included within the scope of the present disclosure.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present disclosure can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

The presence of a therapeutic agent in an off-target issue can be the result of: (i) leakage of a polynucleotide from the administration site to peripheral tissue or distant off-target tissue (e.g., liver) via diffusion or through the bloodstream (e.g., a polynucleotide intended to express a polypeptide in a certain tissue would reach the liver and the polypeptide would be expressed in the liver); or (ii) leakage of an polypeptide after administration of a polynucleotide encoding such polypeptide to peripheral tissue or distant off-target tissue (e.g., liver) via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the disclosure can be characterized as having both an N-terminus (terminated by an amino acid with a free amino group ($NH_2$)) and a C-terminus (terminated by an amino acid with a free carboxyl group (COOH)). Proteins of the disclosure are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding an IL12B polypeptide, IL12A polypeptide, or both IL12B and IL12A polypeptides can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Transcription: As used herein, the term "transcription" refers to methods to introduce exogenous nucleic acids into a cell. Methods of transfection include, but are not limited to, chemical methods, physical treatments and cationic lipids or mixtures.

Transfection: As used herein, "transfection" refers to the introduction of a polynucleotide into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a disease, e.g., acute intermittent porphyria. For example, "treating" acute intermittent porphyria can refer to diminishing symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a 3-Ni-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g., polymorphisms, isoforms, etc) and artificial variants in which at least one amino acid residue in a native or starting sequence (e.g., a wild type sequence) has been removed and a different amino acid inserted in its place at the same position. These variants can be described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

The terms "invention" and "disclosure" can be used interchangeably when describing or used, for example, in the phrases "the present invention" or "the present disclosure."

30. Equivalents and Scope

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting. The present disclosure is further described in the following examples, which do not limit the scope of the disclosure described in the claims.

EXAMPLES

Example 1: In Vivo Anti-Tumor Efficacy of IL12 Modified mRNA in a Colon Adenocarcinoma (MC38) Syngeneic Model (Intravenous Administration)

The in vivo anti-tumor efficacy of IL12 mRNA, administered as a single intravenous (IV) dose in mice bearing M38 adenocarcinoma tumors, was assessed.
A. Preparation of IL12 Modified mRNA and Control
A polynucleotide (mRNA) comprising a codon-optimized nucleotide sequence encoding a wild-type murine IL12 polypeptide (murine IL12) and a miRNA binding site (miR-122) in its 3' UTR were prepared (mIL12_miR122) (sequence set forth below).

(SEQ ID NO: 241)
GGGAAAUAAGAGAGAAAAGAAGAGUAAGAAGAAAUAUAAGAGCCACCAUG

UGUCCUCAGAAGCUAACCAUCUCCUGGUUUGCCAUCGUUUUGCUGGUGUC

UCCACUCAUGGCCAUGUGGGAGCUGGAGAAAGACGUUUAUGUUGUAGAGG

UGGACUGGACUCCCGAUGCCCCUGGAGAAACAGUGAACCUCACCUGUGAC

ACGCCUGAAGAAGAUGACAUCACCUGGACCUCAGACCAGAGACAUGGAGU

CAUAGGCUCUGGAAAGACCCUGACCAUCACUGUCAAAGAGUUCCUAGAUG

CUGGCCAGUACACCUGCCACAAAGGAGGCGAGACUCUGAGCCACUCACAU

CUGCUGCUCCACAAGAAGGAAAAUGGAAUUUGGUCCACUGAAAUUUUAAA

AAAUUUCAAAAACAAGACUUUCCUGAAGUGUGAAGCACCAAAUUACUCCG

GACGGUUCACGUGCUCAUGGCUGGUGCAAAGAAACAUGGACUUGAAGUUC

AACAUCAAGAGCAGUAGCAGUUCCCUGACUCUCGGGCAGUGACAUGUGG

AAUGGCGUCUCUGUCUGCAGAGAAGGUCACACUGGACCAAAGGGACUAUG

AGAAGUAUUCAGUGUCCUGCCAGGAGGAUGUCACCUGCCCAACUGCCGAG

GAGACCCUGCCCAUUGAACUGGCGUUGGAAGCACGGCAGCAGAAUAAAUA

UGAGAACUACAGCACCAGCUUCUUCAUCAGGGACAUCAUCAAACCAGACC

CGCCCAAGAACUUGCAGAUGAAGCCUUUGAAGAACUCACAGGUGGAGGUC

AGCUGGGAGUACCCUGACUCCUGGAGCACUCCCCAUUCCUACUUCUCCCU

CAAGUUCUUUGUUCGAAUCCAGCGCAAGAAAGAAAAGAUGAAGGAGACAG

AGGAGGGGUGUAACCAGAAAGGUGCGUUCCUCGUAGAGAAGACAUCUACC

GAAGUCCAAUGCAAAGGCGGGAAUGUCUGCGUGCAAGCUCAGGAUCGCUA

UUACAAUUCCUCAUGCAGCAAGUGGGCAUGUGUUCCCUGCAGGGUCCGAU

CCGGAGGCGGAGGGAGCGGAGGCGGAGGGAGCGGAGGCGGAGGGAGCAGG

GUCAUUCCAGUCUCUGGACCUGCCAGGUGUCUUAGCCAGUCCCGAAACCU

GCUGAAGACCACAGAUGACAUGGUGAAGACGGCCAGAGAAAAACUGAAAC

AUUAUUCCUGCACUGCUGAAGACAUCGAUCAUGAAGACAUCACACGGGAC

CAAACCAGCACAUUGAAGACCUGUUUACCACUGGAACUACACAAGAACGA

GAGUUGCCUGGCUACUAGAGAGACUUCUUCCACAACAAGAGGGAGCUGCC

UGCCCCCACAGAAGACGUCUUUGAUGAUGACCCUGUGCCUUGGUAGCAUC

UAUGAGGACUUGAAGAUGUACCAGACAGAGUUCCAGGCCAUCAACGCAGC

ACUUCAGAAUCACAACCAUCAGCAGAUCAUUUUAGACAAGGGCAUGCUGG

UGGCCAUCGAUGAGCUGAUGCAGUCUCUGAAUCAUAAUGGCGAGACUCUG

CGCCAGAAACCUCCUGUGGGAGAAGCAGACCCUUACAGAGUGAAAAUGAA

GCUCUGCAUCCUGCUUCACGCCUUCAGCACCCGCGUCGUGACCAUCAACA

GGGUGAUGGGCUAUCUGAGCUCCGCCUGAUAAUAGGCUGGAGCCUCGGUG

GCCAUGCUUCUUGCCCCUUGGGCCUCCCCCCAGCCCCUCCUCCCUUCCU

GCACCCGUACCCCCCAAACACCAUUGUCACACUCCAGUGGUCUUUGAAUA

AAGUCUGAGUGGGCGGC

The miR-122 binding element was incorporated to decrease protein production from the liver. A negative control mRNA was also prepared (non-translatable version of mRNAs), e.g., NST-FIX. The mRNAs were fully modified with N1-methylpseudouridine. Both modified mRNAs were formulated in MC3 lipid nanoparticles (LNP).

B. MC-38 Colon Adenocarcinoma Mouse Model

MC-38 colon adenocarcinoma tumors were implanted subcutaneously in mice as described in Rosenberg et al., Science 233:1318-1321 (1986)).

Eleven days after tumor implantation, two groups of animals were administered a single intravenous dose of LNP-formulated IL12 modified mRNA (at a dose of either 0.1 mg/kg (Group 4) or 0.05 mg/kg (Group 5). Two groups of control animals were treated with equivalent doses of negative control mRNA (NST-FIX LNP) (Group 7 and Group 8), PBS (Group 1), or recombinant murine IL12 protein, 1 μg (Group 2).

Tumor volume was measured using manual calipers. Mean tumor volume to day 24 (FIG. 5) was recorded in cubic millimeters ($mm^3$).

C. Results

Intravenous administration of murine IL12 mRNA resulted in dose dependent plasma IL12 (FIG. 2A) and IFNγ (FIG. 2B) levels and increased IL12 and IFNγ AUC (Table 8), each of which were higher than those levels following administration of a comparable amount of recombinant IL12 protein by intraperitoneal injection (FIGS. 2A-2B).

TABLE 8

AUC levels for IL12 and IFNγ plasma levels.

| Treatment | IL12 AUC (ng/mL) * $hr_{0.5-196}$ | IFNγ AUC (ng/mL) * $hr_{0.5-196}$ |
| --- | --- | --- |
| 0.1 mpk IL12 mRNA | 18805 (↑10.4x) | 5290 (↑21.3x) |
| 0.05 mpk IL12 mRNA | 7500 (↑4.1x) | 1856 (↑7.5x) |
| ~0.05 mpk IL12 protein | 1801 | 248 |

The numbers in parentheses indicate the x-fold increase for mRNA over protein.

FIG. 3 depicts the robust efficacy of a single intravenous (IV) dose of murine IL12 mRNA in lipid nanoparticle (LNP), at doses of 0.1 mg/kg (Group 4) and 0.05 mg/kg (Group 5) (as indicated by lines with the inverted triangles), compared to Groups 1 (PBS), 2 (IL12 protein), 7 and 8 (controls NST-FIX, 0.1 mg/kg and 0.05 mg/kg, respectively).

Figure 4B:
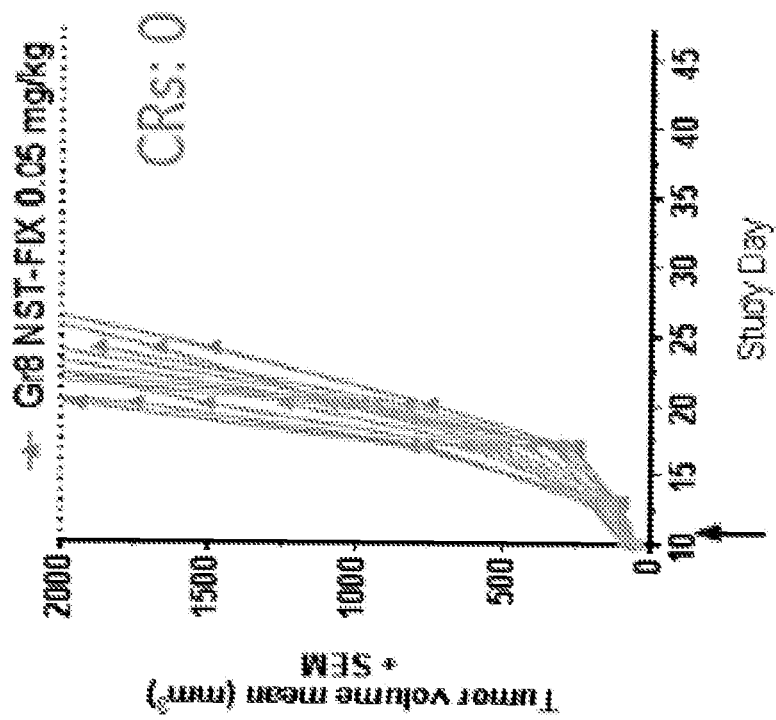
Figure 4A:
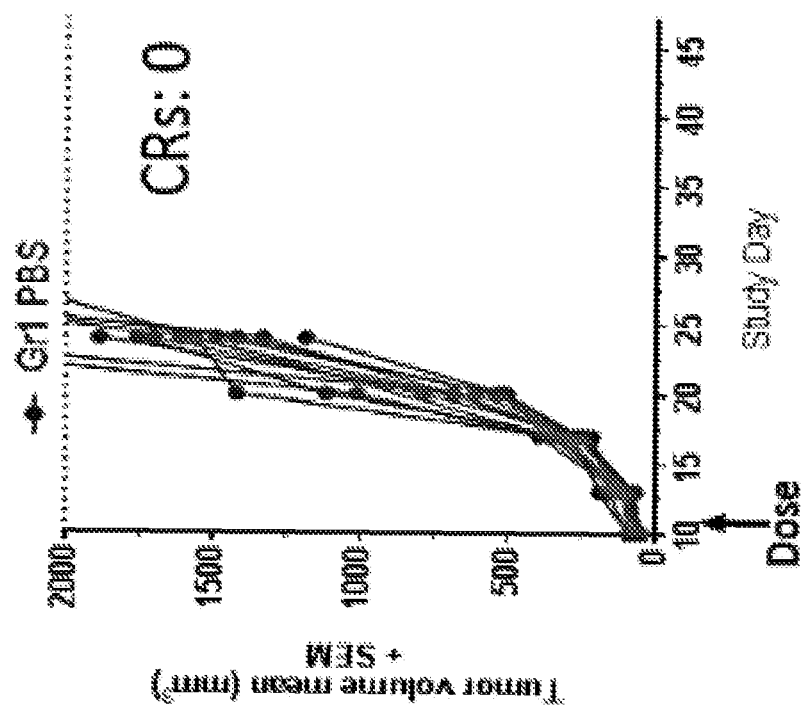
Figures 4C, 4D:
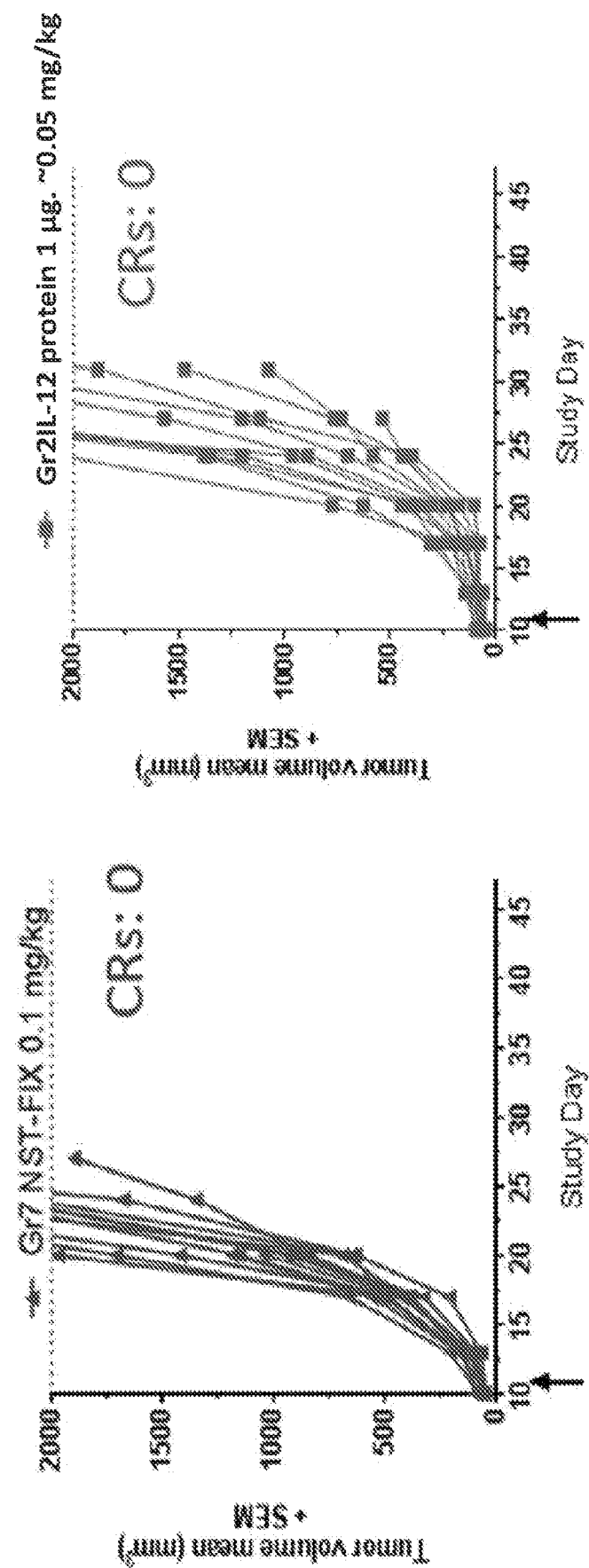
Figure 4F:
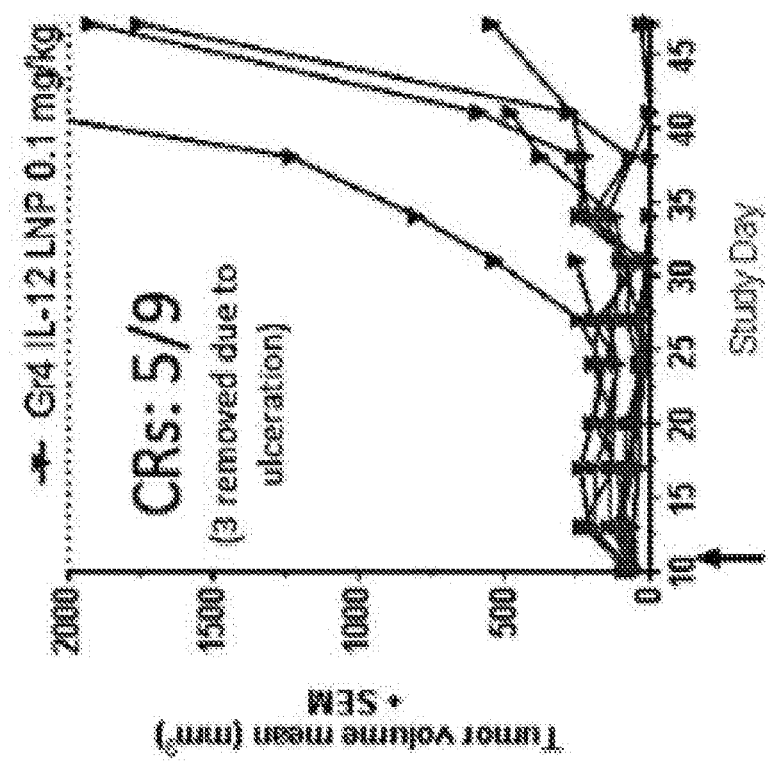
Figure 4E:
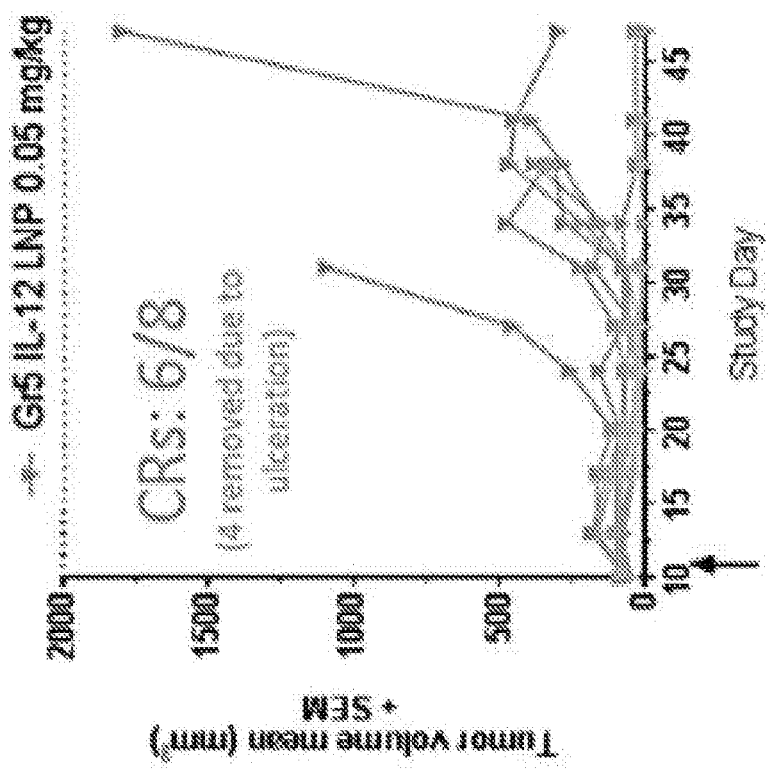

FIGS. 4A-4F depict the mean tumor volume and the number of complete responses (CR) seen following administration of a single intravenous (IV) dose of: murine IL12 mRNA in lipid nanoparticle (LNP), at doses of 0.1 mg/kg (Group 4)(FIG. 4F) and 0.05 mg/kg (Group 5)(FIG. 4E), PBS (Group 1)(FIG. 4A), IL12 protein (Group 2)(FIG. 4D), controls NST-FIX, 0.1 mg/kg and 0.05 mg/kg (Groups 7 and 8, respectively) (FIGS. 4C and 4B, respectively). Complete responses (CRs) are shown in FIGS. 4E and 4F only. FIG. 4E shows that 6 of 8 CRs (i.e., 75% CR) were seen in Group 5 (IL12 mRNA in lipid nanoparticle (LNP), at a dose of 0.05 mg/kg). FIG. 4F shows that 5 of 9 CRs (i.e., 56% CR) were seen in Group 4 (IL12 mRNA in lipid nanoparticle (LNP), at a dose of 0.1 mg/kg). Aside from the IL12 mRNA groups, no other group observed any CRs.

FIG. 5 depicts the survival benefit at day 47 post tumor-implantation from a single intravenous (IV) dose of murine IL12 mRNA in lipid nanoparticle (LNP) at a dose of 0.05 mg/kg (Group 5) and at a dose of 0.1 mg/kg (Group 4).

Notably, FIGS. 3-5 demonstrate the advantage of administering intravenous murine IL12 mRNA over protein in terms of improved pharmacokinetics (PK), pharmacodynamics (PD), and therapeutic efficacy, with a single IV dose.

Table 9 depicts the tolerability advantage of local (intratumoral) administration of IL12 mRNA over systemic (intravenous) administration. Nine (9) of 10 mice intratumorally administered IL12 mRNA were viable at day 20 compared to 3 of 12 mice intravenously administered IL12 mRNA.

TABLE 9

Intravenous and intratumoral tolerability of murine IL12 administration.

| Route | IL12 mRNA in LNP (mg/kg) | Treatment tolerability outcome (to Day 20) | Plasma levels of IL12 24 hr post dose (ng/ml) |
| --- | --- | --- | --- |
| Intravenous | 0.2 | 3/12 viable | 1592 |
| Intratumoral | ~0.2 (4 μg fixed) | 9/10 viable | 89 |

Example 2: In Vivo Anti-Tumor Efficacy of Murine IL12 Modified mRNA in a Colon Adenocarcinoma (MC38) Model (Intratumoral Administration)

The in vivo anti-tumor efficacy of murine IL12 mRNA, administered intratumorally in mice bearing M38 adenocarcinoma tumors, was assessed.

A. Preparation of IL12 Modified mRNA and Control

The mIL12_miR122 polynucleotide as described in Example 1 was prepared. A negative control mRNA, NST-FIX mRNA, was also prepared. Both modified mRNAs were formulated in MC3 lipid nanoparticles (LNP) as described in Example 1.

B. MC-38 Colon Adenocarcinoma Mouse Model

MC-38 colon adenocarcinoma tumors were implanted subcutaneously in mice as described in Rosenberg et al., Science 233:1318-1321 (1986)).

Eleven days after tumor implantation, animals were administered a single intratumoral dose of MC3 LNP-formulated murine IL12 modified mRNA (4 μg mRNA per dose). Two groups of control animals were treated with an equivalent dose and regimen of negative control mRNA (NST-FIX LNP) or PBS.

Figure 6A:
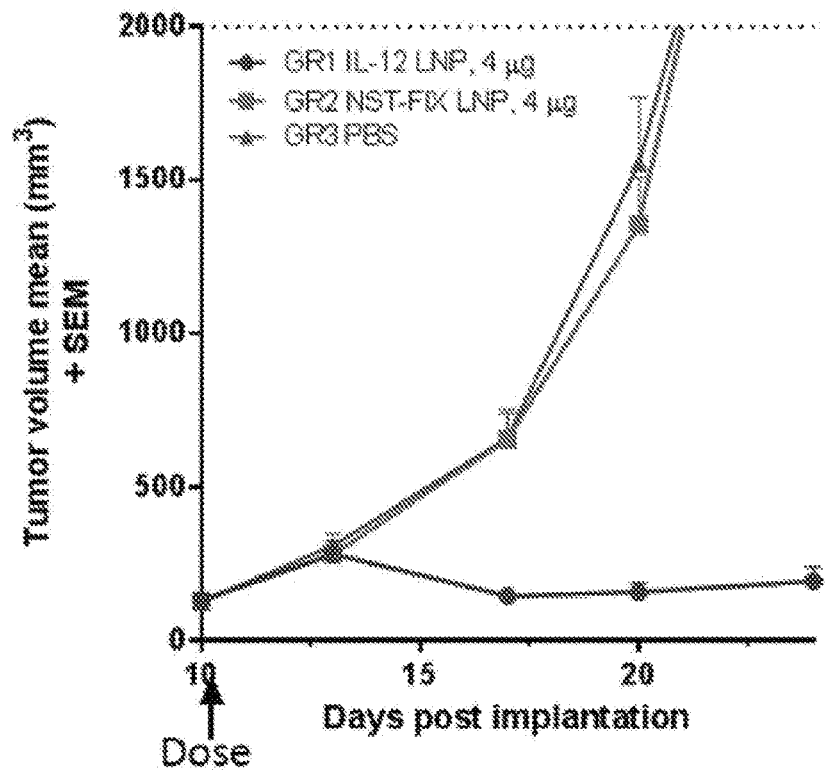
Figure 6B:
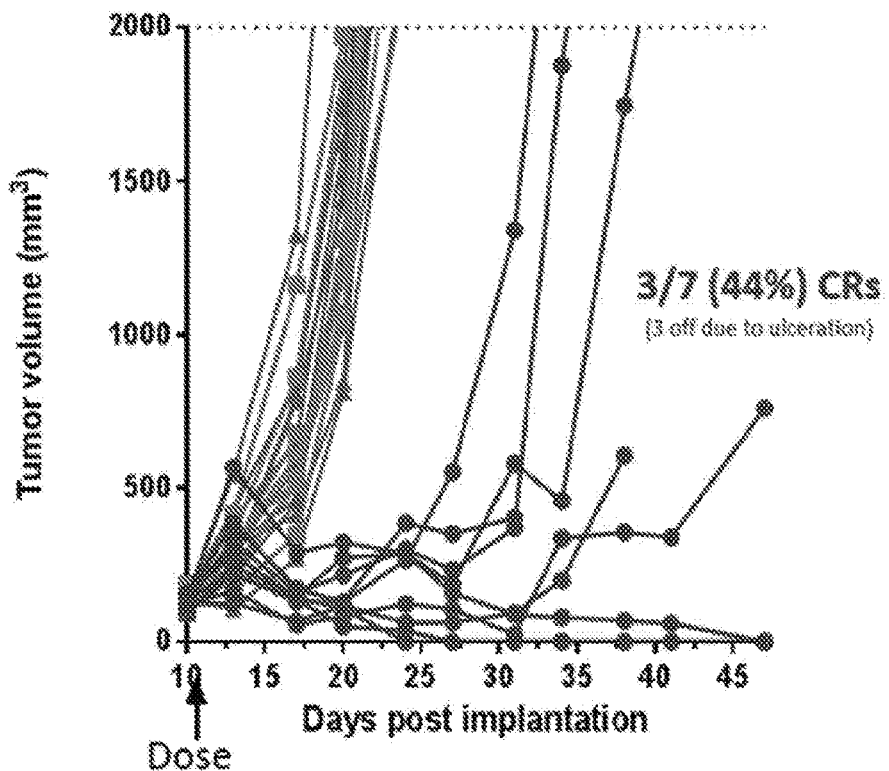

Tumor volume was measured at the indicated time points in FIG. 6B using manual calipers. Tumor volume mean to day 24 (FIG. 6A) and individual tumor volume to day 47 (FIG. 6B) were recorded in cubic millimeters ($mm^3$). Endpoints in the study were either death of the animal or a tumor volume reaching 1500 $mm^3$.

C. Results

FIG. 6A shows that mean tumor volume was reduced when MC3 LNP-formulated murine IL12 modified mRNA was administered. In contrast, administering a control modified mRNA (NST-FIX) or PBS to the mice had little effect on reducing the tumor volume mean when assessed up to day 24.

FIG. 6B shows that administering about 4 μg MC3 LNP-formulated murine IL12 modified mRNA per animal to the mice decreased individual tumor volumes in some animals compared to animals administered control modified mRNA (NST-FIX) or PBS. Complete responses (CRs) were seen in 3 of 7 animals (44%), with 3 animals removed due to ulceration. These data show that mIL12_miR122 polynucleotides have anti-tumor efficacy when administered intratumorally in vivo.

Example 3: In Vivo Anti-Tumor Efficacy of IL12 Modified mRNA in a B-Cell Lymphoma (A20) Syngeneic Model The in vivo anti-tumor efficacy of murine IL12 mRNA, administered intratumorally in mice bearing A20 B-cell lymphoma tumors, was assessed.

A. Preparation of IL12 modified mRNAs and controls

A polynucleotide comprising a codon-optimized nucleotide sequence encoding an IL12 polypeptide (murine IL12) without a miRNA binding site (miRless) was prepared (IL12 miRless) (sequence set forth below).

(SEQ ID NO: 242)
GGGAAAUAAGAGAGAAAAGAAGAGUAAGAAGAAAUAUAAGAGCCACCAUG

UGUCCUCAGAAGCUAACCAUCUCCUGGUUUGCCAUCGUUUUGCUGGUGUC

UCCACUCAUGGCCAUGUGGGAGCUGGAGAAAGACGUUUAUGUUGUAGAGG

UGGACUGGACUCCCGAUGCCCCUGGAGAAACAGUGAACCUCACCUGUGAC

ACGCCUGAAGAAGAUGACAUCACCUGGACCUCAGACCAGAGACAUGGAGU

CAUAGGCUCUGGAAAGACCCUGACCAUCACUGUCAAAGAGUUCCUAGAUG

CUGGCCAGUACACCUGCCACAAAGGAGGCGAGACUCUGAGCCACUCACAU

CUGCUGCUCCAAGAAGGAAAAUGGAAUUUGGUCCACUGAAAUUUUAAA

AAAUUUCAAAAACAAGACUUUCCUGAAGUGUGAAGCACCAAAUUACUCCG

GACGUUCACGUGCUCAUGGCUGGUGCAAAGAAACAUGGACUUGAAGUUC

AACAUCAAGAGCAGUAGCAGUUCCCUGACUCUCGGGCAGUGACAUGUGG

AAUGGCGUCUCUGUCUGCAGAGAAGGUCACACUGGACCAAAGGGACUAUG

AGAAGUAUUCAGUGUCCUGCCAGGAGGAUGUCACCUGCCCAACUGCCGAG

GAGACCCUGCCCAUUGAACUGGCGUUGGAAGCACGGCAGCAGAAUAAAUA

UGAGAACUACAGCACCAGCUUCUUCAUCAGGGACAUCAUCAAACCAGACC

CGCCCAAGAACUUGCAGAUGAAGCCUUUGAAGAACUCACAGGUGGAGGUC

AGCUGGGAGUACCCUGACUCCUGGAGCACUCCCCAUUCCUACUUCUCCCU

CAAGUUCUUUGUUCGAAUCCAGCGCAAGAAAGAAAAGAUGAAGGAGACAG

AGGAGGGUGUAACCAGAAAGGUGCGUUCCUCGUAGAGAAGACAUCUACC

GAAGUCCAAUGCAAAGGCGGGAAUGUCUGCGUGCAAGCUCAGGAUCGCUA

UUACAAUUCCUCAUGCAGCAAGUGGGCAUGUGUUCCUGCAGGGUCCGAU

CCGGAGGCGGAGGGAGCGGAGGCGGAGGGAGCGGAGGCGGAGGGAGCAGG

GUCAUUCCAGUCUCUGGACCUGCCAGGUGUCUUAGCCAGUCCCGAAACCU

GCUGAAGACCACAGAUGACAUGGUGAAGACGGCCAGAGAAAACUGAAAC

AUUAUUCCUGCACUGCUGAAGACAUCGAUCAUGAAGCAUCACACGGGAC

CAAACCAGCACAUUGAAGACCUGUUUACCACUGGAACUACACAAGAACGA

GAGUUGCCUGGCUACUAGAGAGACUUCUUCCACAACAAGAGGGAGCUGCC

UGCCCCCACAGAAGACGUCUUUGAUGAUGACCCUGUGCCUUGGUAGCAUC

UAUGAGGACUUGAAGAUGUACCAGACAGAGUUCCAGGCCAUCAACGCAGC

ACUUCAGAAUCACAACCAUCAGCAGAUCAUUUUAGACAAGGGCAUGCUGG

UGGCCAUCGAUGAGCUGAUGCAGUCUCUGAAUCAUAAUGGCGAGACUCUG

CGCCAGAAACCUCCUGUGGGAGAAGCAGACCCUUACAGAGUGAAAAUGAA

-continued
GCUCUGCAUCCUGCUUCACGCCUUCAGCACCCGCGUCGUGACCAUCAACA

GGGUGAUGGGCUAUCUGAGCUCCGCCUGAUAAUAGGCUGGAGCCUCGGUG

GCCAUGCUUCUUGCCCCUUGGGCCUCCCCCCAGCCCCUCCUCCCCUUCCU

GCACCCGUACCCCCGUGGUCUUUGAAUAAAGUCUGAGUGGGCGGC

The mIL12_miR122 polynucleotide as described in Example 1 was prepared. A negative control mRNA (NST) was also prepared (non-translatable version of the same mRNA) (NST IL12_miRless). All modified mRNAs were formulated in MC3 lipid nanoparticles (LNP) as described in Example 1.

B. A20 B-Cell Lymphoma Tumor Model

Mouse models of B-cell lymphoma using the A20 cell line are useful for analyzing tumors. (Kim et al., *Journal of Immunology* 122:549-554 (1979); Donnou et al., *Advances in Hematology* 2012:701704 (2012), incorporated herein by reference in their entirety). A20 cells are derived from a B cell lymphoma from a BALB/c mouse and are typically grown in syngeneic mice as a subcutaneous implant. 500,000 A20 cells were implanted subcutaneously in BALB/c mice to generate subcutaneous tumors. Tumors were monitored for size and palpability.

Once the tumors reached an average size of 100 mm$^3$, the mice were cohorted into three groups. One test group was administered intratumorally mIL12_miRless in MC3-based lipid nanoparticles (LNP) at a dose of 5 μg mRNA per animal. The second test group was administered intratumorally mIL12_miR122 in MC3-based lipid nanoparticles (LNP) at a dose of 5 μg mRNA per animal. The control group was administered an equivalent dose of non-translated control mRNA (NST). Animals were dosed on day 10 post implantation. Results are shown in FIGS. 7A-7C.

The study was carried out through day 50 post implantation. Endpoints in the study were either death of the animal or a pre-determined endpoint of 2000 mm$^3$ tumor volume.

C. Results

Figure 7A:
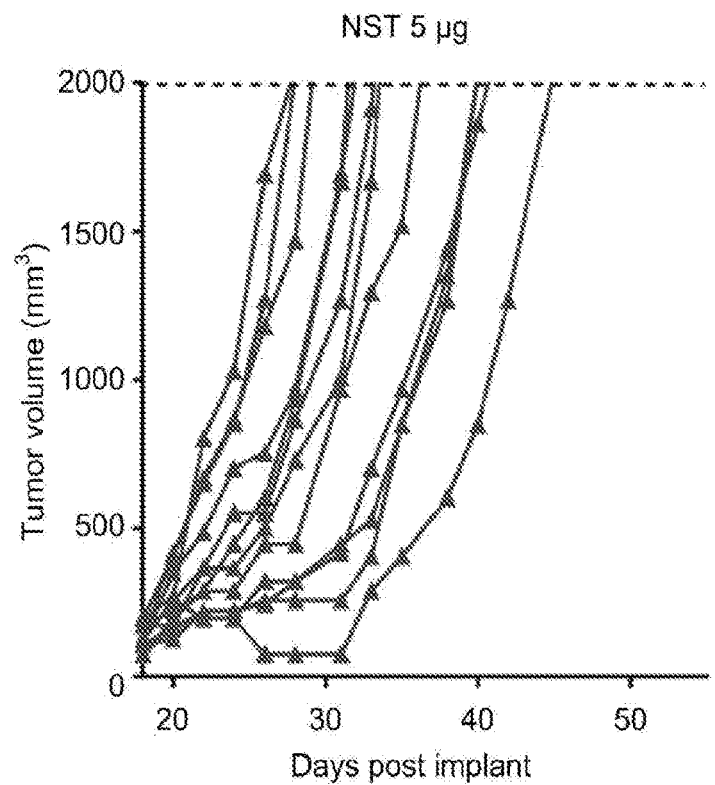
Figure 7B:
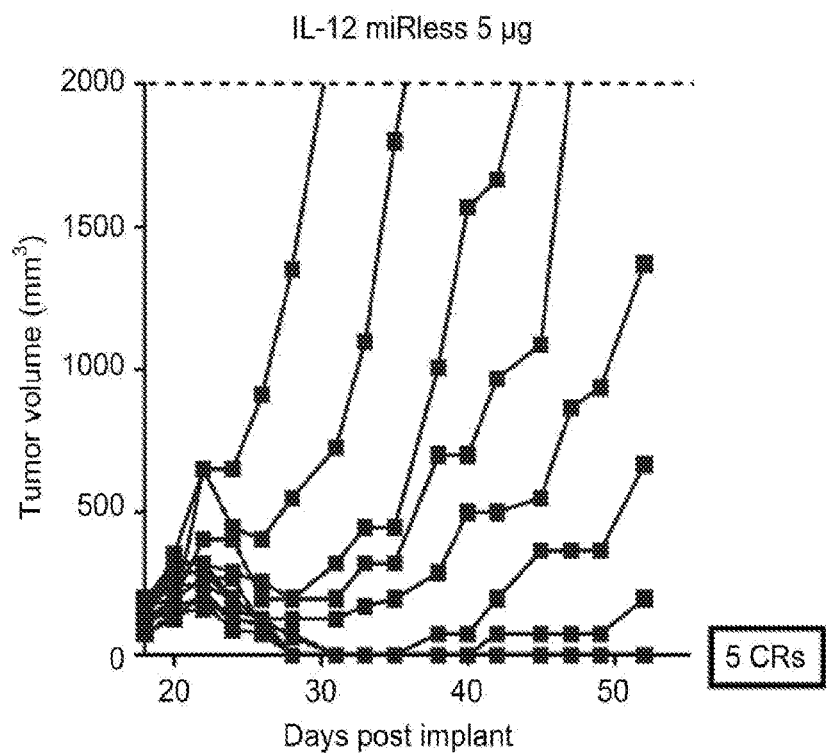

FIG. 7A shows that tumor volume (measured in mm$^3$) increased over time in all 12 animals treated with 5 μg control NST mRNA. FIG. 7B shows that tumor volume decreased over time in some animals treated with mIL12_miRless compared to animals administered control mRNA (NST). Complete responses (CRs) were seen in 5 of 12 animals (42%). Therefore, the intratumoral administration of murine IL12 mRNAs is efficacious in the A20 tumor model.

FIG. 7C shows changes in tumor volume in animals treated with 5 μg mIL12-miR122 (FIG. 7C). Complete responses (CR) were achieved in 6 out of 12 mice in the IL12-miR122 group (FIG. 7C).

The data in FIGS. 7A-7C show that mIL12_miRless and mIL12-miR122 polynucleotides have comparable anti-tumor efficacy when administered intratumorally in vivo.

Example 4: Single and Multidose In Vivo Anti-Tumor Efficacy of a Modified IL12 mRNA The in vivo anti-tumor efficacy of a modified murine IL12 mRNA, administered as a single 0.5 μg dose and a multidose (0.5 μg for 7 days×6), was studied in BALB/C mice bearing A20 B-cell lymphoma tumors.

A. Modified IL12 mRNA

The mIL12_miR122 polynucleotide and mIL12_miRless polynucleotide as described in Examples 1 and 3, respectively, were prepared. One group of mIL12_miR122 mRNA was formulated in MC3-based lipid nanoparticles (LNP) as described in Example 1. Another group of mIL12_miR122 mRNA was formulated in Compound 18-based lipid nanoparticles (LNP).

B. Dosing

On day 10 post implantation, two groups of mice bearing A20 tumors (n=12 in each group) were administered a single 0.5 μg dose of murine IL12 mRNA in the form of IL12 miRless- or IL12 miR122-mRNA in MC3-based LNP.

Also on day 10 post implantation, another group of mice bearing A20 tumors was intratumorally administered weekly dosing of 0.5 μg of IL12 miR122 mRNA in MC3-based LNP for 7 days×6.

Also on day 10 post implantation, another group of mice bearing A20 tumors was intratumorally administered weekly dosing of 0.5 μg of IL12 miR122 mRNA in Compound 18-based LNP for 7 days×6.

Finally, 10 days post implantation, another group of mice bearing A20 tumors (n=12 per group) was administered weekly dosing of 0.5 μg non-translated negative control mRNA (NST) in either MC3-based LNP or Compound 18-based LNP for 7 days×6.

C. Results

As shown in FIGS. 8A-8B, in vivo anti-tumor efficacy in a B-cell lymphoma tumor model (A20) was achieved after mice bearing A20 tumors were administered a single dose of 0.5 μg murine IL12 mRNA in MC3-based lipid nanoparticle (LNP). FIG. 8A depicts decreased tumor volume in some mice administered IL12 miRless (0.5 g), and that four (4) complete responses (CR) were achieved. FIG. 8B depicts decreased tumor volume in some mice administered IL12 miR122 (0.5 μg), and that three (3) complete responses (CR) were achieved.

As shown in FIG. 8C, in vivo anti-tumor efficacy was enhanced with a weekly dosing regimen of IL12 miR122 mRNA in MC3-based LNP (0.5 μg mRNA for 7 days×6), compared to single dosing (see FIG. 8B). FIG. 8C shows that five (5) CRs were achieved in the 12 A20-bearing mice administered weekly dosing of 0.5 μg IL12 miR122 mRNA for seven (7) days×6.

In vivo anti-tumor efficacy of IL12 mRNA in Compound-18 LNPs was enhanced as compared to the in vivo tumor efficacy of IL12 mRNA in MC3 LNPs, as can be seen by delay in tumor growth (FIG. 8D). FIG. 8D shows the individual tumor volumes for 12 mice administered 0.5 μg of murine IL12 mRNA in compound 18-based LNP for 7 days×6. Complete responses (CR) were also achieved in 5 out of 12 animals.

As shown in FIGS. 8E-8F, tumor growth was observed in mice bearing A20 tumors administered weekly dosing (7 days×6) of 0.5 μg non-translated negative control mRNA (NST) in MC3-based lipid nanoparticle (LNP) (FIG. 8E) and 0.5 μg NST in Compound 18-based LNP (FIG. 8F).

This data shows that polynucleotides comprising modified murine IL12 mRNA (both miR122 and miRless) show anti-tumor efficacy at low doses (0.5 μg). It also shows that in vivo anti-tumor efficacy can potentially be enhanced with a multiple dosing regimen. Finally, the data shows in vivo anti-tumor efficacy when 0.5 μg IL12 miR122 mRNA in MC3-based and Compound 18-based LNP is administered intratumorally weekly (for 7 days×6). In contrast, tumor growth was observed in mice bearing A20 tumors administered weekly dosing (7 days×6) of 0.5 μg non-translated negative control mRNA (NST) in MC3-based lipid nanoparticle (LNP) and in Compound 18-based LNP.

Example 5: Analysis of Levels of IL12 p70, IFNγ, IP10, IL6, GCSF, and GROα in Plasma and Tumors of A20-Bearing Mice Following Administration of Murine IL12 mRNA On day 10 post implantation, groups of mice bearing A20 tumors (n=12 in each group) were administered a dose of miR122 IL12 mRNA (at 5 μg, 2.5 μg, or 0.5 μg) in MC3-based LNP or Compound 18-based LNP, NST or IL12 protein at the same dosages, or PBS.

The levels of tumor and plasma IL12 p70, as well as the level of other cytokines, were determined at 6 and 24 hours after administration of the dosages. The levels of IL12 (p70) were determined using a sandwich ELISA commercial kit (R&D Systems, Minneapolis, Minn., USA). The levels of IFNγ, IP10, IL6, G-CSF, and GROα were also determined.

Results:

FIGS. 9A-9B show dose-dependent levels of IL12 in plasma (FIG. 9A) and tumor (FIG. 9B) at 6 hours and 24 hours following administration of the indicated doses of murine IL12 mRNA in an MC3-based LNP to mice bearing A20 tumors.

FIGS. 9C-9D show elevated levels of IL12 in plasma and tumor following administration of the indicated doses of murine IL12 mRNA in Compound 18-based LNPs compared to murine IL12 mRNA in MC3-based LNPs. FIG. 9C shows plasma IL12 levels at 6 hours and 24 hours; FIG. 9D shows tumor IL12 levels at 6 hours and 24 hours. Table 10 shows the fold increase of IL12 in plasma and tumor after the murine IL12 mRNA administration (6 hrs and 24 hrs).

TABLE 10

Fold increase of IL12 from Compound 18 compared to MC3.

|  | mRNA dose | 6 hr | 24 hr |
| --- | --- | --- | --- |
| Plasma | 0.5 μg | 9.3 | 2.8 |
|  | 2.5 μg | 2.7 | 7.2 |
| Tumor | 0.5 μg | 1.8 | 2.9 |
|  | 2.5 μg | 2.3 | 2.1 |

FIGS. 9E-9F show increased levels of IFNγ at 6 hours and 24 hours in plasma (FIG. 9E) and in tumor (FIG. 9F) following administration of murine IL12 mRNA to mice bearing A20 tumors.

FIGS. 9G-9H show increased levels of IP10 at 6 hours and 24 hours in plasma (FIG. 9G) and in tumor (FIG. 911) following administration of murine IL12 mRNA to mice bearing A20 tumors.

FIGS. 9I-9J show decreased levels of IL6 at 6 hours and 24 hours in plasma (FIG. 9I) and in tumor (FIG. 9J) following administration of murine IL12 mRNA in Compound 18-based LNP compared to murine IL12 mRNA in MC3-based LNP.

FIGS. 9K-9L show decreased levels of G-CSF at 6 hours and 24 hours in plasma (FIG. 9K) and in tumor (FIG. 9L) following administration of murine IL12 mRNA in Compound 18-based LNP compared to murine IL12 mRNA in MC3-based LNP.

FIGS. 9M-9N show decreased levels of GROα at 6 hours and at 24 hours in plasma (FIG. 9M) and tumor (FIG. 9N) following administration of murine IL12 mRNA in Compound 18-based LNP compared to murine IL12 mRNA in MC3-based LNP.

The data in this example show dose dependent levels of IL12 in plasma and tumor with intratumoral administration of murine IL12 mRNA (FIGS. 9A and 9B). The data also show increased IL12 levels in plasma and tumor from Compound 18-based LNPs compared to MC3-based LNP (FIGS. 9C and 9D), as well as increased IFNγ and IP10 levels, attributable to administration of murine IL12 mRNA (FIGS. 9E-9H). Finally, this example shows decreased levels of IL6, G-CSF, and GROα in plasma and tumor with Compound 18-formulated murine IL12 mRNA compared to MC3-formulated murine IL12 mRNA (FIGS. 9I-9N).

Example 6: In Vivo Anti-Tumor Efficacy of Intravenous (IV) Administration of IL12 miR122 mRNA in a Subcutaneous A20 Model A. Study Design 500,000 A20 cells were implanted subcutaneously in BALB/c mice. A20 tumor-bearing mice were cohorted into 2 treatment groups (N=10) when tumor averages reached approximately ~100 mm$^3$. Mice were IV dosed with 0.5 mg/kg murine mRNA in a Compound 18 PEG containing LNP every 7 days (Q7D).

The control group were treated with negative control mRNA formulated in LNP, whereas the treatment group were dosed with LNPs containing murine IL12 mRNA with a miR122 binding element with in the 3' UTR. Use of the Compound 18-containing LNP and incorporation of the miR122 binding element were meant to mitigate potential protein production from the liver.

Tumor volumes and body weights were measured twice a week, and general clinical observations made in accordance with an accepted IACUC protocol until a pre-determined endpoint of 2000 mm$^3$ tumor volume was reached.

B. Efficacy Data

The individual tumor volumes from mice treated with weekly dosing of murine IL12 mRNA plus a miR122 binding element formulated in a Compound 18 PEG-containing LNP are shown in FIG. 10B compared to appropriate negative controls in FIG. 10A. Dosing days are indicated by vertical red hashed lines, and the pre-determined endpoint of 2000 mm$^3$ tumor volume indicated by horizontal black hashed line.

C. Assessment of Side Effects/Toxicity

The individual body weights from mice treated with weekly dosing of murine IL12 mRNA plus a miR122 binding element formulated in a Compound 18 PEG-containing LNP are shown in FIG. 10D compared to appropriate negative controls in FIG. 10C.

D. Conclusion

The intravenous administration of murine IL12 mRNA delayed the growth of A20 tumors as compared to an appropriate negative control (i.e., IV treatment of identically formulated mRNA with a miR122 binding element that had no start "NST" codons). The efficacious dosing of 0.5 mg/kg Q7D was well-tolerated as determined by general clinical observations and more quantitatively by body weight measurements.

Example 7: In Vivo Anti-Tumor Efficacy of Intraperitoneal (IP) Administration of Murine IL12 Modified mRNA in an IP MC38 Model A. Study Design The luciferase reporter gene was integrated within the MC-38 colon cell line to enable measurement of bioluminescence from these cells if grown in a context that tumor burden could not be assessed by caliper in live animals. The light output from these cells has been correlated with tumor burden.

500,000 MC-38 luciferase-enabled (MC38-luc) cells were inoculated in the peritoneal cavity as a model of colon cancer metastasis to this space. Mice were assigned to various treatment groups based on bioluminescent signal, and treatment started 7 days post disease induction.

Mice were treated with a single intraperitoneal (IP) dose of murine mRNA formulated in a LNP (MC3:cholesterol:DSPC:PEG-DMGat mol % s of 50:38.5:10:1.5) and compared to a single IP dose of 1 μg recombinant mouse IL12 protein. A single dose of 2 fixed dose levels of mRNA (2 μg and 4 μg) were administered at day 7 post disease induction, and murine IL12 mRNAs with and without a miR122 binding element were assessed in different treatment groups compared to appropriate negative controls (non-start NST mRNA with a miR122 binding element encapsulated in an identically formulated LNP).

Tumor volumes and body weights were frequently measured, and general clinical observations made in accordance with appropriate IACUC protocols.

B. Efficacy Data

Bioluminescence (BL) was used as a surrogate for tumor burden and measured on several days including day 22 post disease induction as depicted in FIG. 11A. Treatment groups and dose levels are indicated in FIG. 11B. Mice were administered no treatment, 2 μg mIL12_miRless, 2 μg mIL12_miR122, 2 μg NST_OX40L_122, 4 μg mIL12_miRless, 4 μg mIL12_miR122, 4 g NST_OX40L_122, and 1 μg rm IL12. Mice treated with murine IL12 mRNA in all arms exhibited lower BL signal than negative controls.

C. Assessment of Side Effects/Toxicity:

The treatments were generally well tolerated, and no treatment groups exhibited a body weight loss average of over 10% (FIG. 11B).

D. Conclusion

As shown in FIGS. 11A and 11B, mice treated out to 150 days post implantation with both fixed doses of murine IL12 mRNA exhibited lower levels of BL signal as a measure of tumor burden compared to negative controls, and this inhibited BL level was associated with an apparent survival benefit of intraperitoneally-dosed murine IL12 mRNA. Murine IL12 mRNA that contained a miR122 binding domain within the 3' UTR exhibited similar efficacy to mRNA without this regulatory element (miR-less). The effective doses employed were considered generally well-tolerated.

Mice treated with fixed doses of murine IL12 mRNA exhibited lower levels of BL signal as a measure of tumor burden compared to negative controls, and this inhibited BL level was associated with an apparent survival benefit of intraperitoneally-dosed murine IL12 mRNA.

Example 8: Analysis of Levels of IL12 and IFNγ in Mice Following Administration of Murine IL12 mRNA Mice bearing MC38 tumors were administered one or more doses of murine miR122 IL12 mRNA in standard Compound 18-based LNP intratumorally (iTu). In particular, mice were given a single intratumoral (iTu) dose of murine miR122 L12 mRNA (at 0.05 μg, 0.5 μg, or 5.0 μg) in LNP, multiple iTu doses (4×) of murine miR122 IL12 mRNA at the same levels, or 5.0 μg NST as a control.

The levels of plasma IL12 and IFNγ were determined at 24 hours after administration of the dosages. The levels of IL12 and IFNγ were determined using a Luminex-based multiplex panel (ProcartaPlex Mouse Cytokine & Chemokine Panel 1A 36 plex, Affymetrix eBioscience).

FIG. 17A shows dose-dependent levels of IL12 in plasma at 24 hours following administration of the indicated doses of murine IL12 mRNA to mice bearing tumors. The plasma concentration of IL12 (ng/ml) is shown below in Table 11.

TABLE 11

IL12 protein levels in plasma (ng/ml).

| Dose | $1^{st}$ | $2^{nd}$ | $3^{rd}$ | $4^{th}$ |
|---|---|---|---|---|
| 5 ug NST | 0.007 ± 0.0008 | 0.001 ± 0.0012 | 0.006 ± n/a | — |
| 0.05 ug IL12_122 | 0.320 ± 0.117 | 0.165 ± 0.095 | 0.559 ± 0.725 | 0.143 ± 0.054 |
| 0.5 ug IL12_122 | 1.59 ± 1.65 | 2.02 ± 1.49 | 5.30 ± 9.57 | 1.21 ± 1.21 |
| 5 ug IL12_122 | 195.8 ± 123.3 | 176.8 ± 221.4 | 86.61 ± 40.53 | 69.87 ± 62.50 |

FIG. 17B shows increased levels of IFNγ at 24 hours in plasma following administration of murine IL12 mRNA to mice bearing tumors. This figure therefore shows that administration of murine IL12 mRNA induces IFNγ expression over multiple doses.

Alternatively, mice bearing MC38 colon adenocarcinoma cells within the peritoneal cavity as a model of carcinomatosis were given a single fixed intraperitoneal (IP) dose of murine miR122 IL12 mRNA (at 2 µg or 4 µg), murine miRless IL12 mRNA (at 2 µg or 4 µg), or recombinant IL12 protein (rmIL12) (at 1 µg), on day 7 after MC38 cells were seeded. The levels of plasma IL12 and IFNγ were determined after administration of the dosage using standard techniques.

FIGS. 18A-18B show increased levels of IL12 in plasma (FIG. 18A) and IFNγ in plasma (FIG. 18B) following intraperitoneal (IP) administration of murine IL12 mRNA to mice bearing MC38 tumors.

These data show that both intratumoral and intraperitoneal administration of IL-12 induces increased plasma levels of IFNγ. Additionally, multiple dosing of IL-12 in an MC38 tumor model induces repeated levels of both plasma IL-12 and IFNγ.

Example 9: In Vivo Anti-Tumor Efficacy of Intratumoral (iTu) Administration of IL12 miR122 mRNA in an A20 Model A20 tumor cells were implanted subcutaneously in mice. A20 tumor-bearing mice were cohorted into 2 treatment groups (N=12). Mice were iTu dosed with 0.5 µg mRNA in Compound 18-LNP, every 7 days (Q7D).

The control group was treated with negative control mRNA formulated in the same LNP, whereas the treatment group was dosed with LNPs containing murine IL12 mRNA with a miR122 binding site in the 3' UTR (mIL12-miR122).

Tumor volumes were measured over the course of 90 days after implantation with A20 cells, and general clinical observations made in accordance with an accepted IACUC protocol until a pre-determined endpoint of 2000 mm³ tumor volume was reached.

The individual tumor volumes from mice treated with iTu dosing of mL12-miR122 formulated in Compound 18-LNP are shown in FIG. 19B compared to the negative control in FIG. 19A. FIG. 19B shows that four mice achieved complete response by Day 90.

Apparent complete responders (4/12) from FIG. 19B were re-challenged with A20 tumor cells. Individual tumor volumes from re-challenged mice are shown in FIG. 19D compared to tumor growth in naïve mice challenged with A20 in FIG. 19C. FIG. 19C shows that 9 out of 10 control mice bearing newly implanted tumors reached its end point (2000 mm³ tumor volume) by Day 45. However, FIG. 19D shows that all four complete responders from FIG. 19B rechalleged with A20 tumor did not show any tumor growth through Day 60. This indicates that the mIL12-miR122 mRNA administration provided the mice an immune memory response that is sufficient to prevent tumor growth upon rechallenge.

Example 10: In Vivo Anti-Tumor Efficacy of Intratumoral (iTu) Administration of IL12 miR122 mRNA in an MC38-S Model MC38-S cells were implanted into mice. Generally, MC38-S, also described as MC38-2, is a more sensitive cell line to therapy. Without being bound by theory, one explanation for this observation is the increased levels of CD45+ T cells, CD8+ Treg cells, Tumor associated macrophages (TAMs), and DCs observed as well as observations that MC38-S tumors are slower growing and more sensitive to tested IMTs. All of these characteristics of MC38-S tumors are by comparison to MC38-R tumors (also described as MC38-1 or MC38-M) and both are useful models.

MC38-S tumor-bearing mice were cohorted into 4 treatment groups (N=15). Mice were iTu dosed with 0.05 µg, 0.5 µg, or 5 µg murine IL12 mRNA in Compound-18 LNP. As a negative control, mice were iTu dosed with NST-FIX mRNA or untreated. In single and multiple dose studies, mice in the experimental and control groups received the same dosing regimen.

Tumor volumes and survival were measured in each group over the course of 80 days after implantation with MC38-S cells and general clinical observations made in accordance with an accepted protocol until a pre-determined endpoint of 1500 mm³ tumor volume was reached.

The individual tumor volumes from mice treated with a single iTu dose of 0.05 µg murine IL12 mRNA are shown in FIG. 20A and FIG. 21A, mice treated with a single iTu dose of 0.5 µg murine IL12 mRNA are shown in FIG. 20B and FIG. 21B, mice treated with a single iTu dose of 5 µg murine IL12 mRNA formulated are shown in FIG. 20C and FIG. 21C, compared to appropriate negative controls in FIG. 20D. The pre-determined endpoint of 1500 mm³ tumor volume indicated by horizontal black hashed line. FIGS. 20A and 21A show that six out of 15 mice achieved complete response. FIGS. 20B, 21B, 20C, and 21C show that 13 out of 15 mice achieved complete response, indicating that a low dose of 0.5 µg may be sufficient to exert a maximally effective response given the similar response seen with 5 µg.

The individual tumor volumes from mice treated with two iTu doses of 0.05 µg murine IL12 mRNA are shown in FIG. 21D, mice treated with two iTu doses of 0.5 µg murine IL12 mRNA are shown in FIG. 21E, and mice treated with two iTu doses of 5 µg murine IL12 mRNA are shown in FIG.

21F. The pre-determined endpoint of 1500 mm$^3$ tumor volume indicated by horizontal black hashed line. FIG. 21D shows that 9 out of 15 mice achieved complete response. FIGS. 21E and 21F show that 14 out of 15 mice achieved a complete response. This data shows that in some tumor types, a single administration of murine IL12 mRNA can achieve an anti-tumor effect that is sufficient to reduce or eliminate the tumor.

A dose response trend was clear between 0.05 and 0.5 µg dose levels. A threshold appeared to be achieved ≤0.5 µg murine IL12 mRNA. Two doses of IL12 mRNA were also beneficial above a single dose. All mice administered any dose of murine IL12 mRNA displayed a survival benefit (FIG. 22). Therefore, the intratumoral administration of murine IL12 mRNA delayed or reduced the growth or size of MC38-S tumors as compared to an appropriate negative control and provided a survival benefit.

Example 11: In Vivo Anti-Tumor Efficacy of Intratumoral (iTu) Administration of IL12 miR122 mRNA in an MC38-R Model MC38-R cells were implanted into mice. Generally, MC38-R, also referred to herein as MC38-1 or MC38-M, is a more resistant cell line to therapy. Without being bound by theory, one explanation for this observation is the reduced levels of CD45+ T cells, CD8+ Treg cells, and DCs, and more cells that bear markers of "myeloid derived suppressor cells" were observed, as well as observations that MC38-R tumors are faster growing and generally less sensitive to tested immune-mediated therapies. All of these characteristics of MC38-R tumors are by comparison to MC38-S tumors and both are useful models.

MC38-R tumor-bearing mice were cohorted into 4 treatment groups (N=13). Mice were iTu dosed with 0.05 µg, 0.5 µg, or 5 µg murine IL12 mRNA in Compound-18 LNP. As a negative control, mice were iTu dosed with NST-FIX mRNA or untreated. In single and multiple dose studies, mice in the experimental and control groups received the same dosing regimen.

Tumor volumes and survival were measured in each group over the course of 75 days after implantation with MC38-R cells.

The individual tumor volumes from mice treated with a single iTu dose of 0.05 µg murine IL12 mRNA are shown in FIG. 23A and FIG. 23E, mice treated with a single iTu dose of 0.5 µg murine IL12 mRNA formulated in an LNP are shown in FIG. 23B and FIG. 23F, mice treated with a single iTu dose of 5 µg murine IL12 mRNA formulated in an LNP are shown in FIG. 23C and FIG. 23G, compared to appropriate negative controls in FIG. 23D. The pre-determined endpoint of 2000 mm$^3$ tumor volume indicated by horizontal black hashed line. FIGS. 23A and 23E show that no mice bearing MC38-R tumor after administration of 0.05 µg of murine IL12 mRNA achieved complete response. FIGS. 23B and 23F show that two mice bearing MC38-R tumor after administration of 0.5 µg of murine IL12 mRNA achieved complete response. FIGS. 23C and 23G show that four mice bearing MC38-R tumor after administration of 5 µg of murine IL12 mRNA achieved complete response.

The individual tumor volumes from mice treated with multiple iTu doses of 0.05 g murine IL12 mRNA are shown in FIG. 23H, mice treated with two iTu doses of 0.5 g murine IL12 mRNA formulated in an LNP are shown in FIG. 23I, and mice treated with two iTu doses of 5 µg murine IL12 mRNA formulated in an LNP are shown in FIG. 23J. The pre-determined endpoint of 2000 mm$^3$ tumor volume indicated by horizontal black hashed line. FIGS. 23H-23J show that multiple administrations have similar efficacy as single administration.

These results indicate that despite the demonstrated resistance of MC38-R tumors to other immune mediated therapies, such as anti-PD1 and anti-PD-L1 antagonist antibodies, mice administered murine IL12 mRNA displayed a survival benefit (FIG. 24). Survival events included tumor burden endpoints and animals off study due to ulceration/eschar which occurred in treated and non-treated mice. The intratumoral administration of murine IL12 mRNA delayed the growth of MC38-R tumors as compared to an appropriate negative control and provided a survival benefit and was generally well tolerated.

The levels of tumor and plasma IL12 p70, as well as the level of other cytokines, were determined at 24 hours after administration of the dosages. The results show dose dependent levels of IL12 in plasma with intratumoral administration of murine IL12 mRNA as shown previously. The results also show sustained dose-dependent expression of TNFα, IL-10, IL-13, IL-15/15R, IL-27, MIP-113, MIP-1α, MCP-1, MCP-3, M-CSF, IL-4, and IL-5 after multiple murine IL12 dosing (data not shown). GM-CSF, IL-18, IL-3, RANTES and IL-6 had elevated expression levels only following 5 µg murine IL12 dosing (data not shown).

Example 12: CD8+ T Cells Involved in IL12 mRNA Efficacy

To evaluate the role of CD8+ T cells in mediating IL12 mRNA induced efficacy, MC38-R cells were implanted into mice, the CD8+ T cell-depleting clone 24.3 was used to deplete CD8+ T cells and CD8+ T cell levels were monitored in blood to confirm depletion over the course of the efficacy study. The 24.3 clone or a control antibody was given to mice 2 days prior to administration of murine IL12 mRNA. The depleting or control antibody was given at 0.5 mg daily for 3 consecutive days, 3 days off, then another five antibody doses at 0.2 mg given every 4 days. Flow cytometry was performed throughout the experiment to confirm CD8+ T cell depletion.

Using the 24.3 clone, CD8+ T cells were depleted over the course of 28 days, whereas an antibody control did not deplete CD8+ T cells (FIG. 25). CD8+ T cell numbers in blood were significantly decreased at all time points examined by flow cytometry, thus confirming effective depletion.

Mice given 0.5 µg murine IL12 mRNA after CD8+ T cell depletion via clone 24.3 displayed increased tumor volume (FIG. 26D) compared to mice given 0.5 µg murine IL12 mRNA after mock CD8+ T cell depletion (FIG. 26B). Likewise, mice given 0.5 µg murine IL12 mRNA after CD8+ T cell depletion displayed poor survival compared to mice given 0.5 µg murine IL12 mRNA after mock CD8+ T cell depletion (FIG. 26E). FIG. 26A shows tumor volume in mice treated with negative control mRNA after mock CD8+ T cell depletion, and FIG. 26C shows tumor volume in mice treated with negative control mRNA after CD8+ T cell depletion. Although murine IL12 mRNA treatment appeared to result in some delay in tumor growth even with CD8+ T cell depletion, there were no complete responders in the absence of cytotoxic T cells in contrast to the clear survival benefit observed with murine IL12 mRNA treatment and mock depletion. The results indicate that CD8+ T cells play an essential role in IL12 mRNA mediated efficacy.

Example 13: Significant Changes in the Immune Infiltrate in MC38-R and B16F10-AP3 Tumors Following Intratumoral Administration of IL12 mRNA Significant changes occurred in the immune cell infiltrate in both MC38-R and B16F10-AP3 tumors following treatment with IL12 mRNA. MC38-R tumors were treated intratumorally with 0.05 µg or 0.5 µg murine IL12 mRNA and B16F10-AP3 tumors were treated intratumorally with 0.1 µg or 0.5 µg murine IL12 mRNA.

In both the MC38-R and B16F10-AP3 models the percentage of CD11b+ myeloid cells within the tumor staining positive for PDL1 expression increased significantly at most time points, following IL12 mRNA treatment (FIG. 27A and FIG. 27B).

IL12 mRNA treatment further correlated with an increase in CD8+ T cell within tumors in both MC38-R and B16F10-AP3 mouse models at late time points. In particular, the percent of T cells, as evidenced by the proportion of CD8+ T cells out of the immune infiltrate (CD45+ cells) and the number of CD8+ positive cells per mg of tumor tissue, was statistically higher 7 days after administration of 0.5 µg murine IL12 mRNA in both mouse models (FIGS. 28A and 28B). Furthermore, a significantly higher number of T cells were observed in tumors in B16F10-AP3 mice treated with 0.1 µg murine IL12 mRNA, as evidenced by the proportion of CD8+ T cells out of the immune infiltrate (CD45+ cells) (FIG. 28B). Both the percent of CD45 positive cells and the cells per mg are informative. At day 7, tumors in treatment groups are smaller than controls, particularly for the 0.1 µg and 0.5 µg groups.

An increased ratio of CD8+ cells to T regulatory (Treg) cells (CD8:Treg) was seen in both MC38-R (FIG. 29A) and B16F10-AP3 (FIG. 29B) mouse models, demonstrating an improved effector to suppressor ratio. In particular, MC38-R mice treated with 0.05 µg or 0.5 µg murine IL12 mRNA exhibited statistically significant higher ratios of CD8+ T cells to Treg cells as compared to negative controls, resulting from both an increase in CD8+ cells and a decrease in Treg cells in tumor tissue at day 7 (FIG. 29A). Similarly, B16F10-AP3 mice treated with 0.1 µg or 0.5 µg murine IL12 mRNA exhibited statistically higher ratios of CD8+ T cells to Treg cells as compared to negative controls, resulting from an increase in CD8+ cells (FIG. 29B).

Expression of CD69, which is indicative of activation of T lymphocytes and NK cells, was increased on CD8+ T cells in both MC38-R and B16F10-AP3 tumors (FIGS. 30A-30B).

Activation of natural killer (NK) cells was also seen in both MC38-R and B16F10-AP3 tumors treated with IL-12 mRNA (FIGS. 31A and 31B).

An increase in cross-presenting dendritic cells was observed in both MC38-R and B16F10-AP3 tumor models. CD103+ cDC increases were observed in both MC38-R (FIG. 32A) and B16F10-AP3 tumors (FIG. 32B) at day 7. In addition, a greater percent of activated CD8+ cDCs were found in the draining lymph node following treatment with murine IL12 mRNA at each of 24 hrs, 72 hrs, and day 7 as compared to controls in B16F10-AP3 tumors (FIG. 32C).

Example 14: In Vivo Anti-Tumor Efficacy of IL12 Modified mRNA in Combination with Anti-PD-L1 Antibody in an MC38-R Model Given the increased expression of PD-L1 (see Example 11 above) after administration of murine IL12 mRNA, the efficacy of a combination therapy of murine IL12 mRNA and an anti-PD-L1 antibody was studied. To evaluate the efficacy of anti-PD-L1 antibody monotherapy, mice bearing MC38-R tumor were administered a murine anti-PD-L1 antibody obtained from clone 80. FIG. 33A shows tumor volume changes in mice after administration of an antibody control. FIG. 33B shows tumor volume changes after administration of the anti-PD-L1 antibody. All mice reached the end point (i.e., 2000 mm$^3$ tumor) demonstrating insensitivity of this model to anti-PD-L1 treatment.

Mice bearing MC38-R tumor were administered iTu either (i) murine IL12 mRNA alone, or (ii) murine IL12 mRNA and a murine anti-PD-L1 antibody in combination. Three dosages of mRNA were tested, i.e., 0.05 µg (data not shown), 0.5 µg, and 5 µg. Tumor volumes and survival were measured in each group (n=15) over the course of 90 days after implantation with MC38-R cells and general clinical observations made in accordance with an accepted protocol until a pre-determined endpoint of 2000 mm$^3$ tumor volume was reached.

Figures 33E, 33F:
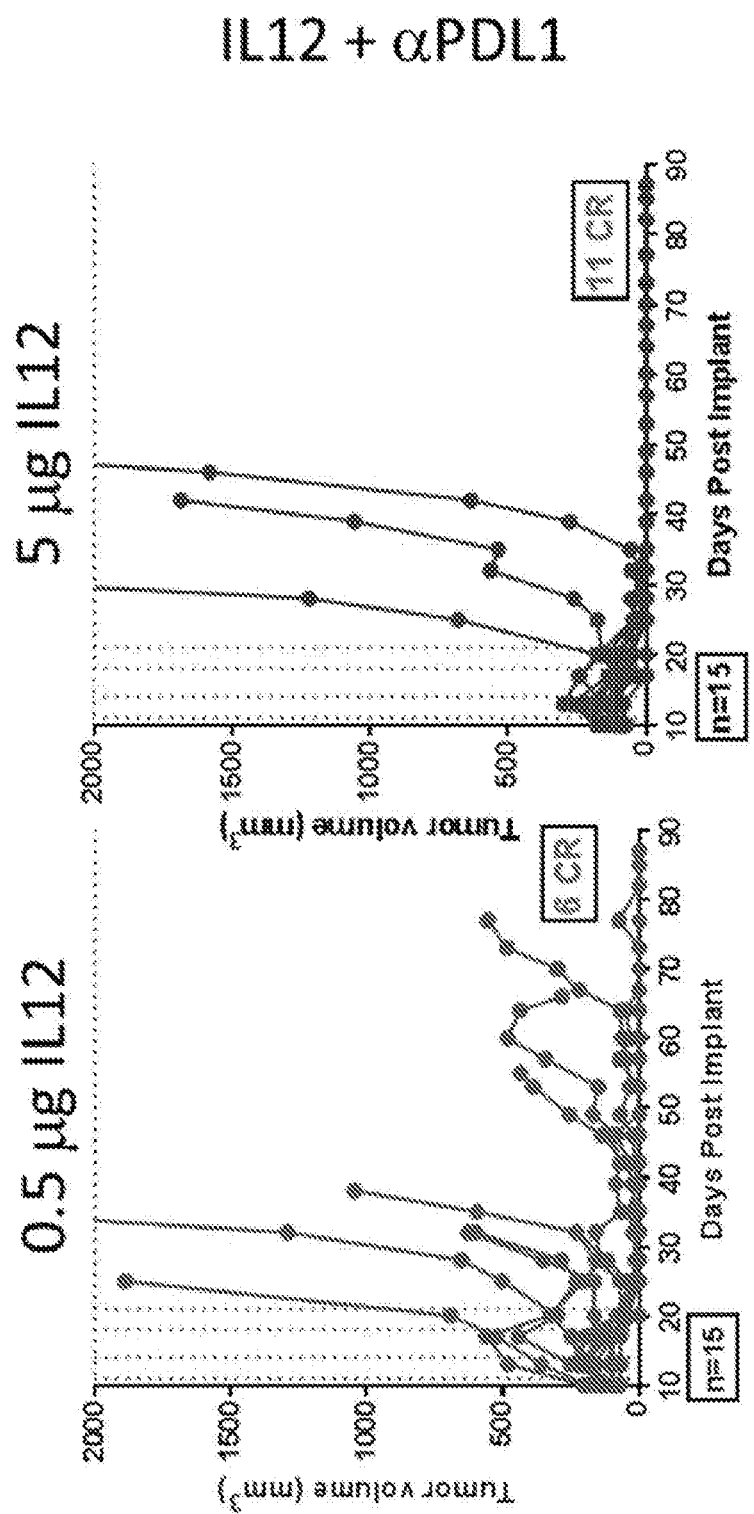
Figure 33G:
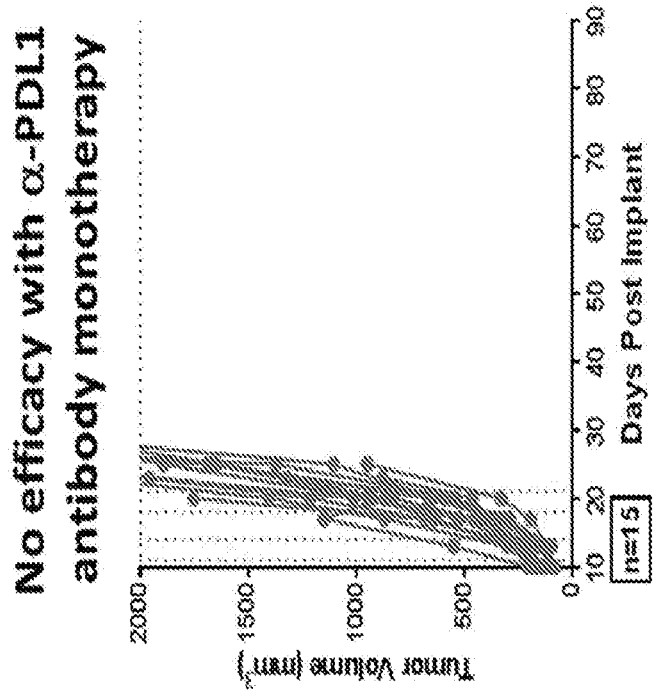

FIGS. 33C and 33E show that the combination therapy with 0.5 µg murine IL12 mRNA resulted in complete response in 6 out of 15 mice while only 1 out of 15 mice achieved complete response after administration of murine IL12 mRNA alone. FIGS. 33D and 33F show that 11 out of 15 mice achieved complete response in the combination therapy with 5 µg murine IL12 mRNA while only 5 out of 15 mice achieved complete response after administration of murine IL12 mRNA alone. FIG. 33G shows data that confirm a murine anti-PD-L1 antibody alone did not have any anti-tumor efficacy in mice bearing MC38-R in this study. The results show that the combination therapy of murine IL12 mRNA and a checkpoint inhibitor, e.g., an anti-PD-L1 antibody, can display synergistic efficacy in tumors otherwise resistant to checkpoint inhibitor therapy, e.g., MC38-R.

Example 15: In Vivo Anti-Tumor Efficacy of Intratumoral Administration of IL12 Modified mRNA in Combination with an Anti-PD-L1 Antibody MC-38 colon adenocarcinoma tumors were implanted subcutaneously in mice as described in Rosenberg et al., Science 233:1318-1321 (1986)).

MC38-R or B16F10-AP3 mice tumor bearing-mice were administered a single intratumoral dose of LNP-formulated murine IL12 modified mRNA (IL12 mRNA with miR122 formulated with Compound 18-based LNP) at a dose of either 0.05 µg, 0.5 µg, or 5 µg, alone or in combination with an intraperitoneal dose of anti-PD-L1 antibody (clone 80). Additional doses were administered as indicated below.

A. Results

To test the effect of combined treatment with a murine IL12 mRNA and an anti-PD-L1 antibody (αPD-L1), MC38-R mice were treated eleven days post implant with a murine anti-PD-L1 antibody alone (FIG. 34A), 0.5 µg murine IL12 mRNA alone (FIG. 34B), or both a murine anti-PD-L1 antibody and 0.5 µg murine IL12 mRNA (FIG. 34C). Treatment using an anti-PD-L1 antibody alone had little effect on tumor growth (FIG. 34A), and treatment with a single dose of 0.5 µg murine IL12 mRNA resulted in one CR (FIG. 34B). When murine IL12 mRNA intratumoral treatment was combined with anti-PD-L1 administration (administered in six doses), there was a large increase in the number of CRs observed. Eight out of fifteen mice (53%)

exhibited a complete response following a single dose of 0.5 µg murine IL12 mRNA in combination with an anti-PD-L1 antibody (FIG. 34C), The synergistic effect of combination treatment using murine IL12 mRNA and an anti-PD-L1 antibody was further observed in B16F10-AP3 mice, which are thought to be immunologically barren and are also resistant to checkpoint blockade therapies such as anti-PDL1. While untreated B16F10-AP3 mice (FIG. 35A) and B16F10-AP3 treated with an anti-PD-L1 antibody alone (FIG. 35B) or a single dose of 0.5 µg murine IL12 mRNA alone (FIG. 35C) yielded no CRs, mice treated with a single dose of 0.5 µg murine IL12 mRNA in combination with an anti-PD-L1 antibody (administered in six doses on days 11, 14, 18, 21, 25, and 28) resulted in two CRs out of fifteen mice (FIG. 35D).

Example 16: Abscopal Effect Following Murine IL12 mRNA Administration within a Distal Tumor To investigate potential abscopal effects of murine IL12 mRNA intratumoral administration, MC38 colon adenocarcinoma tumors were implanted bilaterally in mice (MC38-S; FIG. 36A). In an ongoing study, 17/20 MC38-S tumors treated with 0.5 µg murine IL12 mRNA (FIG. 36D) and 19/20 MC38-S tumors treated with 5 µg murine IL12 mRNA (FIG. 36F) have thus far exhibited a complete response after about 50 months. In addition, 3/20 distal tumors in the 0.5 µg murine IL12 mRNA-treated mice (FIG. 36E) and 16/20 distal tumors in the 5 µg murine IL12 mRNA-treated mice have thus far exhibited a complete response after about 50 months (FIG. 36G). The results with negative control are shown in FIGS. 36B and 36C.

These abscopal effects are amplified when murine IL12 mRNA treatment is combined with anti-PD-L1 treatment, in an ongoing study. Mice implanted with bilateral MC38 tumors were administered intratumorally into one tumor either 0.5 µg murine L12 mRNA (FIG. 37C-37D) or 5 µg murine IL12 mRNA (FIG. 37E-37F) either as a monotherapy (FIGS. 37C and 37E) or combined with an anti-PD-L1 antibody (administered by IP injection of 20 mg/kg twice per week for two weeks; FIGS. 37D and 37F). Thus far, 3/20 CRs and 16/20 CRs were observed bilaterally in the 0.5 µg (FIG. 37C) and 5 µg (FIG. 37E) murine IL12 mRNA-treated mice, and 8/20 CRs and 20/20 CRs were observed bilaterally in the mice treated with a combination of anti-PD-L1 and 0.5 µg (FIG. 37D) or 5 µg (FIG. 37F) murine IL12 mRNA. The results with negative control are shown in FIGS. 37A and 37B.

Example 17: Evaluation of Codon-Optimized mRNAs Encoding Human IL12

In addition to the mIL12_miR122 construct generated in Example 1, 20 codon-optimized mRNAs encoding human IL12 polypeptide (hIL12AB_001-020) were prepared. These mRNAs also had a miR-122 binding site in the 3'UTR.

The mRNAs were fully modified with N1-methylpseudouridine. The modified mRNAs were formulated in MC3 lipid nanoparticles (LNP) for screening. HeLa cells were transfected using a standard transfection protocol and expression was determined ~22 hours post-transfection. Expression was normalized to that from the wild-type muIL12 construct. Most constructs tested had expression equal to or up to ~2-fold over the miL12 miR122 construct.

Constructs having high expression in HeLa cells were also tested for expression in MC38 cells, Heb3B cells and A20 cells to confirm expression in various tumor cell lines.

Variants hIL12AB_002, hIL12AB_006 and hIL12AB_021 were further selected for testing in vivo. C57B16 mice were implanted subcutaneously with A20 cells (A20 tumor model). Tumors were allowed to grow and tumors subsequently injected intratumorally with LNP-encapsulated mRNAs. Plasma, tumor, liver and spleen were collected 6 and 24 hours post-administration of a single intratumoral dose of mRNA. (n=6 per group.) Variants hIL12AB_002 and hIL12AB_006, in particular, showed good expression as compared to mIL12_miR122 mRNA, e.g., in plasma and tumor.

Based on the collective screening in vitro and in vivo, hIL12AB_002 was selected as a preferred mRNA encoding hIL12AB (FIG. 38).

Other Embodiments

It is to be understood that the words which have been used are words of description rather than limitation, and that changes can be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A method for treating cancer in a subject by inducing an anti-tumor immune response, comprising administering intratumorally to the subject a lipid nanoparticle (LNP) encapsulated messenger RNA (mRNA) comprising an open reading frame (ORF) encoding a human IL-12 polypeptide, wherein the LNP comprises a molar ratio of about 20-60% ionizable amino lipid; 5-25% phospholipid; 25-55% sterol; and 0.5-15% PEG-modified lipid.

2. The method of claim 1, wherein the ORF encodes a human IL-12B polypeptide operably linked to a human IL-12A polypeptide.

3. The method of claim 2, wherein the IL-12B polypeptide is operably linked to the IL-12A polypeptide by a peptide linker, and wherein the peptide linker comprises a Gly/Ser linker.

4. The method of claim 1, wherein the human IL12 polypeptide comprises an amino acid sequence set forth in SEQ ID NO: 48.

5. The method of claim 1, wherein the anti-tumor response comprises a T-cell response, IFNγ production, or both a T-cell response and IFNγ production.

6. A method for treating cancer in a subject by inducing an anti-tumor immune response, comprising administering intratumorally to the subject a LNP encapsulated mRNA comprising an ORF encoding a human IL-12 polypeptide, wherein the LNP comprises an ionizable amino lipid; a phospholipid; a sterol; and a PEG-modified lipid, and wherein the mRNA comprises an ORF comprising a nucleotide sequence at least 90% identical to SEQ ID NO: 237.

7. The method of claim 6, wherein the mRNA comprises the nucleotide sequence as set forth in SEQ ID NO: 237.

8. The method of claim 7, wherein the mRNA comprises a 3' UTR comprising a microRNA binding site, wherein the microRNA binding site is a miR-122-3p or a miR-122-5p binding site.

9. The method of claim 8, wherein the miR-122-5p binding site comprises the sequence set forth in SEQ ID NO: 54.

10. The method of claim 7, wherein the mRNA comprises a 3' UTR comprising the sequence set forth in SEQ ID NO: 240.

11. The method of claim 10, wherein the mRNA comprises a 5' UTR comprising the sequence set forth in SEQ ID NO: 135.

12. The method of claim 7, wherein the mRNA is fully modified with chemically-modified uridines.

13. The method of claim 12, wherein the chemically-modified uridines are N1-methylpseudouridines (m1ψ).

14. The method of claim 6, wherein the anti-tumor response comprises a T-cell response, IFNγ production, or both a T-cell response and IFNγ production.

15. The method of claim 1, wherein the mRNA comprises a nucleotide sequence at least 90% to SEQ ID NO: 96.

16. The method of claim 15, wherein the mRNA comprises the nucleotide sequence as set forth in SEQ ID NO: 96.

17. The method of claim 16, wherein the mRNA is fully modified with N1-methylpseudouridines (m1ψ).

18. The method of claim 1, wherein the ionizable amino lipid comprises a compound having the formula

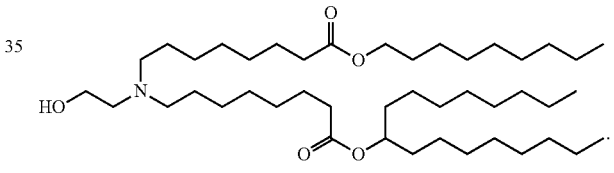

(Compound 18)

19. The method of claim 1, wherein the LNP comprises a molar ratio of about 50% ionizable amino lipid; 10% phospholipid; 38.5% cholesterol; and 1.5% PEG-modified lipid.

20. The method of claim 19, wherein the ionizable amino lipid comprises a compound having the formula

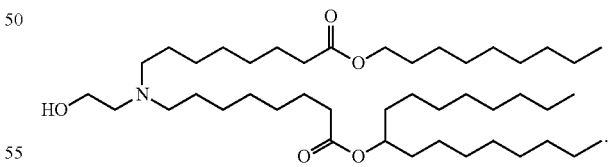

(Compound 18)

* * * * *

UNITED STATES PATENT AND TRADEMARK OFFICE
CERTIFICATE OF CORRECTION

PATENT NO. : 10,646,549 B2
APPLICATION NO. : 16/192274
DATED : May 12, 2020
INVENTOR(S) : Joshua P. Frederick et al.

It is certified that error appears in the above-identified patent and that said Letters Patent is hereby corrected as shown below:

On the Title Page

At Column 1, in item (72), Line 6 of the "Inventors" section, delete "Iain Mcfadyen" and insert -- Iain McFadyen --.

Signed and Sealed this
Sixteenth Day of June, 2020

Andrei Iancu
*Director of the United States Patent and Trademark Office*

SEQUENCE LISTING

<160> NUMBER OF SEQ ID NOS: 242

<210> SEQ ID NO 1
<211> LENGTH: 306
<212> TYPE: PRT
<213> ORGANISM: Artificial Sequence
<220> FEATURE:
<223> OTHER INFORMATION: Wild Type IL12B without signal (IL12B) Amino Acids

<400> SEQUENCE: 1

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 2
<211> LENGTH: 918
<212> TYPE: DNA
<213> ORGANISM: Artificial Sequence
<220> FEATURE:
<223> OTHER INFORMATION: Wild Type IL12B without signal (IL12B) Nucleic Acids

<400> SEQUENCE: 2

```
atatgggaac tgaagaaaga tgtttatgtc gtagaattgg attggtatcc ggatgcccct      60
ggagaaatgg tggtcctcac ctgtgacacc cctgaagaag atggtatcac ctggaccttg     120
gaccagagca gtgaggtctt aggctctggc aaaaccctga ccatccaagt caaagagttt     180
ggagatgctg ccagtacac ctgtcacaaa ggaggcgagg ttctaagcca ttcgctcctg      240
ctgcttcaca aaaggaaga tggaatttgg tccactgata ttttaaagga ccagaaagaa     300
cccaaaaata gaccttct aagatgcgag gccaagaatt attctggacg tttcacctgc       360
tggtggctga cgacaatcag tactgatttg acattcagtg tcaaaagcag cagaggctct     420
tctgacccc aagggggtgac gtgcggagct gctacactct ctgcagagag agtcagaggg     480
gacaacaagg agtatgagta ctcagtggag tgccaggagg acagtgcctg cccagctgct     540
gaggagagtc tgcccattga ggtcatggtg gatgccgttc acaagctcaa gtatgaaaac     600
tacaccagca gcttcttcat cagggacatc atcaaacctg acccacccaa gaacttgcag     660
ctgaagccat taagaattc tcggcaggtg gaggtcagct gggagtaccc tgacacctgg     720
agtactccac attcctactt ctccctgaca ttctgcgttc aggtccaggg caagagcaag     780
agagaaaaga agatagagt cttcacggac aagacctcag ccacggtcat ctgccgcaaa     840
aatgccagca ttagcgtgcg ggcccaggac cgctactata gctcatcttg agcgaatgg      900
gcatctgtgc cctgcagt                                                    918
```

<210> SEQ ID NO 3
<211> LENGTH: 197
<212> TYPE: PRT
<213> ORGANISM: Artificial Sequence
<220> FEATURE:
<223> OTHER INFORMATION: Wild Type IL12A without signal peptide Amino acids

<400> SEQUENCE: 3

```
Arg Asn Leu Pro Val Ala Thr Pro Asp Pro Gly Met Phe Pro Cys Leu
  1               5                  10                  15

His His Ser Gln Asn Leu Leu Arg Ala Val Ser Asn Met Leu Gln Lys
             20                  25                  30

Ala Arg Gln Thr Leu Glu Phe Tyr Pro Cys Thr Ser Glu Glu Ile Asp
         35                  40                  45

His Glu Asp Ile Thr Lys Asp Lys Thr Ser Thr Val Glu Ala Cys Leu
     50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
```

```
                 130                135                140
Met Gln Ala Leu Asn Phe Asn Ser Glu Thr Val Pro Gln Lys Ser Ser
145                 150                155                160

Leu Glu Glu Pro Asp Phe Tyr Lys Thr Lys Ile Lys Leu Cys Ile Leu
                165                170                175

Leu His Ala Phe Arg Ile Arg Ala Val Thr Ile Asp Arg Val Met Ser
            180                185                190

Tyr Leu Asn Ala Ser
        195
```

<210> SEQ ID NO 4
<211> LENGTH: 591
<212> TYPE: DNA
<213> ORGANISM: Artificial Sequence
<220> FEATURE:
<223> OTHER INFORMATION: Wild Type IL12A without signal peptide Nucleic
      acids

<400> SEQUENCE: 4

```
agaaacctcc ccgtggccac tccagaccca ggaatgttcc catgccttca ccactcccaa      60
aacctgctga gggccgtcag caacatgctc cagaaggcca gacaaactct agaattttac     120
ccttgcactt ctgaagagat tgatcatgaa gatatcacaa agataaaaac cagcacagtg     180
gaggcctgtt taccattgga attaaccaag aatgagagtt gcctaaattc cagagagacc     240
tctttcataa ctaatgggag ttgcctggcc tccagaaaga cctcttttat gatggcctg      300 tgccttagta gtatttatga agacttgaag atgtaccagg tggagttcaa gaccatgaat     360
gcaaagcttc tgatggatcc taagaggcag atctttctag atcaaaacat gctggcagtt     420
attgatgagc tgatgcaggc cctgaatttc aacagtgaga ctgtgccaca aaaatcctcc     480
cttgaagaac cggattttta taaaactaaa atcaagctct gcatacttct tcatgctttc     540
agaattcggg cagtgactat tgatagagtg atgagctatc tgaatgcttc c             591
```

<210> SEQ ID NO 5
<211> LENGTH: 1596
<212> TYPE: DNA
<213> ORGANISM: Artificial Sequence
<220> FEATURE:
<223> OTHER INFORMATION: hIL12AB_001

<400> SEQUENCE: 5

```
atgtgtcacc agcagctggt cattagctgg tttagccttg tgttcctggc ctccccccttt      60 gtcgctattt gggagctcaa gaaggacgtg tacgtggtgg agctggactg gtacccagac     120
gcgcccggag agatggtagt tctgacctgt gatacccccag aggaggacgg catcacctgg     180
actctggaca aaagcagcga ggttttgggc tcagggaaaa cgctgaccat ccaggtgaag     240
gaattcggcg acgccggaca gtacacctgc cataagggag agaggtgct gagccattcc     300 cttcttctgc tgcacaagaa agaggacggc atctggtcta ccgacatcct gaaagaccag     360
aaggagccca gaacaaaac cttcctgagg tgcgaggcca gaactactc cggcaggttc     420 acttgttggt ggctgaccac catcagtaca gacctgactt ttagtgtaaa aagctccaga     480
ggctcgtccg atccccaagg ggtgacctgc ggcgcagcca ctctgagcgc tgagcgcgtg     540
cgcggtgaca ataagagta cgagtacagc gttgagtgtc aagaagacag cgcttgccct     600
gccgccgagg agagcctgcc tatcgagtg atggttgacg cagtgcacaa gcttaagtac     660
gagaattaca ccagctcatt cttcattaga gatataatca agcctgaccc acccaagaac     720
```

```
ctgcagctga agccactgaa aaactcacgg caggtcgaag tgagctggga gtaccccgac    780
acctggagca ctcctcattc ctatttctct cttacattct gcgtccaggt gcagggcaag    840
agcaagcggg aaaagaagga tcgagtcttc accgacaaaa caagcgcgac cgtgatttgc    900
aggaagaacg ccagcatctc cgtcagagcc aggatagat  actatagtag cagctggagc    960
gagtgggcaa gcgtgccctg ttccggcggc gggggcgggg gcagccgaaa cttgcctgtc   1020
gctaccccgg accctggaat gtttccgtgt ctgcaccaca gccagaacct gctgagagcc   1080
gtgtcgaata tgctccagaa ggcccggcag acccttgagt tctacccctg taccagcgaa   1140
gagatcgatc atgaggacat cacgaaagac aagacttcca ccgtcgaggc ttgtctcccg   1200
ctggagctga ccaagaacga gagctgtctg aatagccggg agacatcttt catcacgaat   1260
ggtagctgtc tggccagcag gaaaacttcc ttcatgatgg ctctctgcct gagctctatc   1320
tatgaagatc tgaagatgta tcaggtggag tttaagacta tgaacgccaa actcctgatg   1380
gacccaaaaa ggcaaatctt tctggaccag aatatgctgg ccgtgataga cgagctgatg   1440
caggcactga acttcaacag cgagacagtg ccacagaaat ccagcctgga ggagcctgac   1500
ttttacaaaa ctaagatcaa gctgtgtatc ctgctgcacg cctttagaat ccgtgccgtg   1560
actatcgaca gggtgatgtc atacctcaac gcttca                             1596

<210> SEQ ID NO 6
<211> LENGTH: 1596
<212> TYPE: DNA
<213> ORGANISM: Artificial Sequence
<220> FEATURE:
<223> OTHER INFORMATION: hIL12AB_002

<400> SEQUENCE: 6
atgtgccacc agcagctggt gatcagctgg ttcagcctgg tgttcctggc cagcccctg     60
gtggccatct gggagctgaa gaaggacgtg tacgtggtgg agctggactg gtaccccgac   120
gccccggcg agatggtggt gctgacctgc gacacccccg aggaggacgg catcacctgg   180
accctggacc agagcagcga ggtgctgggc agcggcaaga ccctgaccat ccaggtgaag   240
gagttcggcg acgccggcca gtacacctgc cacaagggcg cgaggtgct  gagccacagc   300
ctgctgctgc tgcacaagaa ggaggacggc atctggagca ccgacatcct gaaggaccag   360
aaggagccca gaacaagac cttcctgaga tgcgaggcca gaactacag cggcagattc   420
acctgctggt ggctgaccac catcagcacc gacctgacct tcagcgtgaa gagcagcaga   480
ggcagcagcg accccagggc gtgacctgc ggcgccgcca ccctgagcgc cgagagagtg   540
agaggcgaca acaaggagta cgagtacagc gtggagtgcc aggaggacag cgcctgcccc   600
gccgccgagg agagcctgcc catcgaggtg atggtggacg ccgtgcacaa gctgaagtac   660
gagaactaca ccagcagctt cttcatcaga gacatcatca gcccgaccc ccccaagaac    720
ctgcagctga agcccctgaa gaacagcaga caggtggagg tgagctggga gtaccccgac   780
acctggagca ccccccacag ctacttcagc ctgaccttct gcgtgcaggt gcagggcaag   840
agcaagagag agaagaagga cagagtgttc accgacaaga ccagcgccac cgtgatctgc   900
agaaagaacg ccagcatcag cgtgagagcc aggacagat  actacagcag cagctggagc   960
gagtgggcca gcgtgccctg cagcggcggc ggcggcggcg gcagcagaaa cctgccgtg   1020
gccaccccg accccggcat gttccctgc ctgcaccaca gccagaacct gctgagagcc   1080
gtgagcaaca tgctgcagaa ggccagacag accctgagt tctacccctg caccagcgag   1140
gagatcgacc acgaggacat caccaaggac aagaccagca ccgtggaggc ctgcctgccc   1200
```

| ctggagctga | ccaagaacga | gagctgcctg | aacagcagag | agaccagctt | catcaccaac | 1260 |
| gcagctgcc | tggccagcag | aaagaccagc | ttcatgatgg | ccctgtgcct | gagcagcatc | 1320 |
| tacgaggacc | tgaagatgta | ccaggtggag | ttcaagacca | tgaacgccaa | gctgctgatg | 1380 |
| gaccccaaga | gacagatctt | cctggaccag | aacatgctgg | ccgtgatcga | cgagctgatg | 1440 |
| caggccctga | acttcaacag | cgagaccgtg | ccccagaaga | gcagcctgga | ggagcccgac | 1500 |
| ttctacaaga | ccaagatcaa | gctgtgcatc | ctgctgcacg | ccttcagaat | cagagccgtg | 1560 |
| accatcgaca | gagtgatgag | ctacctgaac | gccagc | | | 1596 |

```
<210> SEQ ID NO 7
<211> LENGTH: 1596
<212> TYPE: DNA
<213> ORGANISM: Artificial Sequence
<220> FEATURE:
<223> OTHER INFORMATION: hIL12AB_003

<400> SEQUENCE: 7
```

| atgtgtcacc | agcagttggt | catctcttgg | ttttccctgg | ttttctggc | atctcccctc | 60 |
| gtggccatat | gggaactgaa | gaaagatgtt | tatgtcgtag | aattggattg | gtatccggat | 120 |
| gcccctggag | aaatggtggt | cctcacctgt | gacacccctg | aagaagatgg | tatcacctgg | 180 |
| accttggacc | agagcagtga | ggtcttaggc | tctggcaaaa | ccctgaccat | ccaagtcaaa | 240 |
| gagtttggag | atgctggcca | gtacacctgt | cacaaaggag | gcgaggttct | aagccattcg | 300 |
| ctcctgctgc | ttcacaaaaa | ggaagatgga | atttggtcca | ctgatatttt | aaaggaccag | 360 |
| aaagaaccca | aaaataagac | ctttctaaga | tgcgaggcca | agaattattc | tggacgtttc | 420 |
| acctgctggt | ggctgacgac | aatcagtact | gatttgacat | tcagtgtcaa | agcagcaga | 480 |
| gctcttctg | acccccaagg | ggtgacgtgc | ggagctgcta | cactctctgc | agagagagtc | 540 |
| agaggggaca | caaggagta | tgagtactca | gtggagtgcc | aggaggacag | tgcctgccca | 600 |
| gctgctgagg | agagtctgcc | cattgaggtc | atggtggatg | ccgttcacaa | gctcaagtat | 660 |
| gaaaactaca | ccagcagctt | cttcatcagg | gacatcatca | acctgaccc | acccaagaac | 720 |
| ttgcagctga | agccattaaa | gaattctcgg | caggtggagg | tcagctggga | gtaccctgac | 780 |
| acctggagta | ctccacattc | ctacttctcc | ctgacattct | gcgttcaggt | ccagggcaag | 840 |
| agcaagagag | aaaagaaaga | tagagtcttc | acggacaaga | cctcagccac | ggtcatctgc | 900 |
| cgcaaaaatg | ccagcattag | cgtgcgggcc | caggaccgct | actatagctc | atcttggagc | 960 |
| gaatgggcat | ctgtgccctg | cagtggcgga | ggggcggag | ggagcagaaa | cctccccgtg | 1020 |
| gccactccag | acccaggaat | gttcccatgc | cttcaccact | cccaaaacct | gctgagggcc | 1080 |
| gtcagcaaca | tgctccagaa | ggccagacaa | actttagaat | ttacccttg | cacttctgaa | 1140 |
| gagattgatc | atgaagatat | cacaaaagat | aaaaccagca | cagtggaggc | ctgtttacca | 1200 |
| ttggaattaa | ccaagaatga | gagttgccta | aattccagag | agacctcttt | cataactaat | 1260 |
| gggagttgcc | tggcctccag | aaagacctct | tttatgatgg | ccctgtgcct | tagtagtatt | 1320 |
| tatgaagact | tgaagatgta | ccaggtggag | ttcaagacca | tgaatgcaaa | gcttctgatg | 1380 |
| gatcctaaga | ggcagatctt | tttagatcaa | aacatgctgg | cagttattga | tgagctgatg | 1440 |
| caggccctga | atttcaacag | tgagactgtg | ccacaaaaat | cctcccttga | agaaccggac | 1500 |
| ttctacaaga | ccaagatcaa | gctctgcata | cttcttcatg | ctttcagaat | tcgggcagtg | 1560 |
| actattgata | gagtgatgag | ctatctgaat | gcttcc | | | 1596 |

<210> SEQ ID NO 8
<211> LENGTH: 1599
<212> TYPE: DNA
<213> ORGANISM: Artificial Sequence
<220> FEATURE:
<223> OTHER INFORMATION: hIL12AB_004

<400> SEQUENCE: 8

```
atgggctgcc accagcagct ggtcatcagc tggttctccc tggtcttcct ggccagcccc     60
ctggtggcca tctgggagct gaagaaagat gtctatgttg tagagctgga ctggtaccca    120
gatgctcctg gagaaatggt ggttctcacc tgtgacacgc agaagaaga tggcatcacc     180
tggacgctgg accagagctc agaagttctt ggcagtggaa aaacgctgac catacaagta    240
aaagaatttg gggatgctgg ccagtacacc tgccacaaag gagagaagt ctctcagcca c    300
agcctgctgc tgctgcacaa gaaagaagat ggcatctgga gcacagacat tttaaaagac    360
cagaaggagc ccaagaacaa aaccttcctt cgatgtgagg ccaagaacta cagtggccgc    420
ttcacctgct ggtggctcac caccatcagc acagacctca ccttctcggt gaagagcagc    480
cgtggcagct cagaccccca aggagtcacc tgtggggcgg ccacgctgtc ggcagaaaga    540
gttcgagggg acaacaagga atatgaatac tcggtggaat gtcaagaaga ctcggcctgc    600
ccggcggcag aagaaagtct tcccatagaa gtcatggtgg atgctgttca caaattaaaa    660
tatgaaaact acaccagcag cttcttcatc agagacatca tcaagccaga cccgcccaag    720
aacctgcagc tgaagcccct gaagaacagc agacaagtgg aagtttcctg ggagtaccca    780
gacacgtgga gcacgccgca cagctacttc agcctcacct tctgtgtaca agtacaaggc    840
aagagcaaga gagagaagaa agatcgtgtc ttcacagaca aaacctcggc gacggtcatc    900
tgcaggaaga atgcctccat ctcggttcga gcccaggacc gctactacag cagcagctgg    960
agtgagtggg cctcggtgcc ctgcagtggt ggcggcggcg gcggcagcag aaaccttcct   1020
gtggccacgc cggaccctgg catgttcccg tgcctgcacc acagccaaaa tttacttcga   1080
gctgtttcta acatgctgca gaaagcaaga caaactttag aattctaccc ctgcacctca   1140
gaagaaatag accatgaaga catcaccaaa gataaaacca gcactgtaga ggcctgcctg   1200
cccctggagc tcaccaagaa tgaatcctgc ctcaacagca gagagaccag cttcatcacc   1260
aatggcagct gcctggccag caggaaaacc agcttcatga tggcgctctg cctgagcagc   1320
atctatgaag atttgaagat gtaccaagta gaatttaaaa ccatgaatgc aagctgctc    1380
atggaccccca agagacaaat attttttgat caaaacatgc tggctgtcat tgatgagctc   1440
atgcaagcat taacttcaa ctcagagacg gtgcccagag agcagcct ggaggagcca      1500
gacttctaca aaaccaagat caagctctgc atcttattac atgccttccg catccgggcg   1560
gtcaccattg accgtgtcat gtcctactta aatgccagc                          1599
```

<210> SEQ ID NO 9
<211> LENGTH: 1596
<212> TYPE: DNA
<213> ORGANISM: Artificial Sequence
<220> FEATURE:
<223> OTHER INFORMATION: hIL12AB_005

<400> SEQUENCE: 9

```
atgtgccacc agcagctggt catcagctgg ttctccctgg tcttcctggc cagccccctg     60
gtggccatct gggagctgaa gaaagatgtc tatgttgtag agctggactg gtacccagat    120
gctcctggag aaatggtggt tctcacctgt gacacgccag aagaagatgg catcacctgg    180
```

```
acgctggacc agagctcaga agttcttggc agtggaaaaa cgctgaccat acaagtaaaa     240
gaatttgggg atgctggcca gtacacctgc cacaaaggag gagaagttct cagccacagc    300
ctgctgctgc tgcacaagaa agaagatggc atctggagca cagacatttt aaaagaccag    360
aaggagccca gaacaaaac cttccttcga tgtgaggcca agaactacag tggccgcttc    420
acctgctggt ggctcaccac catcagcaca gacctcacct tctcggtgaa gagcagccgt    480
ggcagctcag accccaagg agtcacctgt ggggcggcca cgctgtcggc agaaagagtt    540
cgagggaca caaggaata tgaatactcg gtggaatgtc aagaagactc ggcctgcccg    600
gcggcagaag aaagtcttcc catagaagtc atggtggatg ctgttcacaa attaaaatat    660
gaaaactaca ccagcagctt cttcatcaga gacatcatca gccagacccc gcccaagaac    720
ctgcagctga agcccctgaa gaacagcaga caagtggaag tttcctggga gtacccagac    780
acgtggagca cgccgcacag ctacttcagc ctcaccttct gtgtacaagt acaaggcaag    840
agcaagagag agaagaaaga tcgtgtcttc acagacaaaa cctcggcgac ggtcatctgc    900
aggaagaatg cctccatctc ggttcgagcc caggaccgct actacagcag cagctggagt    960
gagtgggcct cggtgccctg cagtggtggc ggcggcggcg gcagcagaaa ccttcctgtg   1020
gccacgccgg accctggcat gttcccgtgc ctgcaccaca gccaaaattt acttcgagct   1080
gtttctaaca tgctgcagaa agcaagacaa acttagaat tctaccctg cacctcagaa   1140
gaaatagacc atgaagacat caccaaagat aaaaccagca ctgtagaggc ctgcctgccc   1200
ctggagctca ccaagaatga atcctgcctc aacagcagag agaccagctt catcaccaat   1260
ggcagctgcc tggccagcag gaaaaccagc ttcatgatgg cgctctgcct gagcagcatc   1320
tatgaagatt tgaagatgta ccaagtagaa tttaaaacca tgaatgccaa gctgctcatg   1380
gaccccaaga gacaaatatt tttggatcaa aacatgctgg ctgtcattga tgagctcatg   1440
caagcattaa acttcaactc agagacggtg ccccagaaga gcagcctgga ggagccagac   1500
ttctacaaaa ccaagatcaa gctctgcatc ttattacatg ccttccgcat ccgggcggtc   1560
accattgacc gtgtcatgtc ctacttaaat gccagc                             1596
```

<210> SEQ ID NO 10
<211> LENGTH: 1596
<212> TYPE: DNA
<213> ORGANISM: Artificial Sequence
<220> FEATURE:
<223> OTHER INFORMATION: hIL12AB_006

<400> SEQUENCE: 10

```
atgtgccacc agcagctggt gatcagctgg ttcagcctgg tgttcctggc agcccccctg      60
gtggccatct gggagctgaa gaaggacgtg tacgtggtgg agctggactg gtaccccgac    120
gcccccggcg agatggtggt gctgacctgt gacacccccg aggaggacgg catcacctgg    180
accctggacc agagcagcga ggtgctgggc agcggcaaga ccctgaccat ccaggtgaag    240
gagttcgggg acgccggcca gtacacctgc cacaagggcg gcgaggtgct gagccacagc    300
ctgctgctgc tgcacaagaa ggaggacggc atctggagca cagatatcct gaaggaccag    360
aaggagccca gaacaagac cttcctgaga tgcgaggcca agaactacag cggcagattc    420
acctgctggt ggctgaccac catcagcaca gacttgacct tcagcgtgaa gagcagcaga    480
ggcagcagcg accccaggg cgtgacctgc ggcgccgcca cctgagcgc cgagagagtg    540
agaggggaca caaggagta cgagtacagc gtggagtgcc aggaggacag cgcctgcccc    600
```

```
gccgccgagg agagcctgcc catcgaggtg atggtggacg ccgtgcacaa gctgaagtac      660
gagaactaca ccagcagctt cttcatcaga gacatcatca gcccgaccc gccgaagaac       720 ctgcagctga agcccctgaa gaacagcaga caggtggagg tgagctggga gtaccccgac      780
acctggagca cccccacag ctacttcagc ctgaccttct gcgtgcaggt gcagggcaag       840
agcaagagag agaagaagga cagagtgttc acagataaga ccagcgccac cgtgatctgc      900
agaaagaacg ccagcatcag cgtgagagcc caggacagat actacagcag cagctggagc      960
gagtgggcca gcgtgccctg cagcggcggc ggcggcggcg gcagcagaaa cctgccgtg      1020 gccacccccg accccggcat gttccccctgc ctgcaccaca gccagaaccct gctgagagcc    1080 gtgagcaaca tgctgcagaa ggccagacag accctggagt tctaccccctg caccagcgag    1140 gagatcgacc acgaggacat caccaaggac aagaccagca cgtggaggc ctgcctgccc      1200 ctggagctga ccaagaatga agctgcctg aacagcagag agaccagctt catcaccaac      1260
ggcagctgcc tggccagcag aaagaccagc ttcatgatgg ccctgtgcct gagcagcatc     1320
tacgaggacc tgaagatgta ccaggtggag ttcaagacca tgaacgccaa gctgctgatg     1380
gaccccaaga cagatcttt cctggaccag aacatgctgg ccgtgatcga cgagctgatg     1440
caggccctga acttcaacag cgagaccgtg ccccagaaga gcagcctgga ggagcccgac     1500
ttctacaaga ccaagatcaa gctgtgcatc ctgctgcacg ccttcagaat cagagccgtg     1560
accatcgaca gagtgatgag ctacctgaac gccagc                               1596
```

<210> SEQ ID NO 11
<211> LENGTH: 1596
<212> TYPE: DNA
<213> ORGANISM: Artificial Sequence
<220> FEATURE:
<223> OTHER INFORMATION: hIL12AB_007

<400> SEQUENCE: 11

```
atgtgccacc agcagcttgt catctcctgg ttctctcttg tcttccttgc ttctcctctt       60
gtggccatct gggagctgaa gaaggatgtt tatgttgtgg agttggactg gtaccctgat     120
gctcctggag aaatggtggt tctcacctgt gacactcctg aggaggatgg catcacctgg     180
actttggacc agtcttctga ggttcttggc agtggaaaaa ctcttactat tcaggtgaag     240
gagtttggag atgctggcca gtacacctgc cacaagggtg gtgaagttct cagccacagt     300
ttacttcttc ttcacaagaa ggaggatggc atctggtcta ctgacatttt aaaagaccag     360
aaggagccca gaacaagac tttccttcgt tgtgaagcca gaactacag tggtcgtttc       420 acctgctggt ggcttactac tatttctact gaccttactt tctctgtgaa gtcttctcgt     480
ggctcttctg accctcaggg tgtcacctgt ggggctgcta ctctttctgc tgagcgtgtg     540
cgtggggaca caaggagta tgaatactcg gtggagtgcc aggaggactc tgcctgccct     600 gctgctgagag agtctcttcc tattgaggtg atggtggatg ctgtgcacaa gttaaaatat   660
gaaaactaca cttcttcttt cttcattcgt gacattataa acctgacccc tccaagaac    720 cttcagttaa aacctttaaa aaactctcgt caggtggagg tgtcctggga gtaccctgac    780
acgtggtcta ctcctcactc ctacttctct cttactttct gtgtccaggt gcagggcaag    840
tccaagcgtg agaagaagga ccgtgtcttc actgacaaga cttctgctac tgtcatctgc   900
aggaagaatg catccatctc tgtgcgtgct caggaccgtt actacagctc ttcctggtct   960
gagtgggctt ctgtgccctg ctctggcggc ggcggcggcg gcagcagaaa tcttcctgtg  1020
gctactcctg accctggcat gttccccctgc cttcaccact cgcagaacct tcttcgtgct  1080
```

```
gtgagcaaca tgcttcagaa ggctcgtcag actttagaat tctacccctg cacttctgag    1140
gagattgacc atgaagacat caccaaggac aagacttcta ctgtggaggc ctgccttcct    1200
ttagagctga ccaagaatga atcctgctta aattctcgtg agacttcttt catcaccaat    1260
ggcagctgcc ttgcctcgcg caagacttct ttcatgatgg ctctttgcct ttcttccatc    1320
tatgaagact aaaaatgta ccaggtggag ttcaagacca tgaatgcaaa gcttctcatg    1380
gaccccaagc gtcagatatt tttggaccag aacatgcttg ctgtcattga tgagctcatg    1440
caggctttaa acttcaactc tgagactgtg cctcagaagt cttctttaga agagcctgac    1500
ttctacaaga ccaagataaa actttgcatt cttcttcatg ctttccgcat ccgtgctgtg    1560
actattgacc gtgtgatgtc ctacttaaat gcttct                              1596
```

<210> SEQ ID NO 12
<211> LENGTH: 1596
<212> TYPE: DNA
<213> ORGANISM: Artificial Sequence
<220> FEATURE:
<223> OTHER INFORMATION: hIL12AB_008

<400> SEQUENCE: 12

```
atgtgtcatc aacaactcgt gattagctgg ttcagtctcg tgttcctggc ctctccgctg     60
gtggccatct gggagcttaa gaaggacgtg tacgtggtgg agctcgattg taccccgat    120 gctcctggcg agatggtggt gctaacctgc gataccccg aggaggacgg gatcacttgg    180
accctggatc agagtagcga agtcctgggc tctggcaaga cactcacaat ccaggtgaag    240
gaattcggag acgctggtca gtacacttgc cacaagggg gtgaagtgct gtctcacagc    300
ctgctgttac tgcacaagaa ggaggatggg atctggtcaa ccgacatcct gaaggatcag    360
aaggagccta gaacaagac ctttctgagg tgtgaagcta agaactattc cggaagattc    420
acttgctggt ggttgaccac aatcagcact gacctgacct tttccgtgaa gtccagcaga    480
ggaagcagcg atcctcaggg cgtaacgtgc ggcgcggcta cctgtcagc tgagcgggtt    540 agaggcgaca caaagagta tgagtactcc gtggagtgtc aggaggacag cgcctgcccc    600
gcagccgagg agagtctgcc catcgagtg atggtggacg ctgtccataa gttaaaatac    660
gaaaattaca aagttccttt tttcatccgc gatattatca aacccgatcc ccccaagaac    720
ctgcagctga agcccctgaa gaatagccga caggtggaag tctcttggga gtatcctgac    780
acctggtcca cgcctcacag ctactttagt ctgacttt ct gtgtccaggt ccagggcaag    840
agcaagagag agaaaaagga tagagtgttt actgacaaga catctgctac agtcatctgc    900
agaaagaacg ccagtatctc agtgagggcg caggacagat actacagtag tagctggagc    960
gaatgggcta gcgtgccctg ttcaggggc ggcggagggg ctccaggaa tctgcccgtg   1020 gccaccccg acctgggat gttcccttgc ctccatcact cacagaacct gctcagagca   1080
gtgagcaaca tgctccaaaa ggcccgccag accctggagt ttaccccttg tacttcagaa   1140
gagatcgatc acgaagacat aacaaaggat aaaaccagca ccgtggaggc ctgtctgcct   1200
ctagaactca caaagaatga aagctgtctg aattccaggg aaacctcctt cattactaac   1260
ggaagctgtc tcgcatctcg caaaacatca ttcatgatgg ccctctgcct gtcttctatc   1320
tatgaagatc tcaagatgta tcaggtggag ttcaaaacaa tgaacgccaa gctgctgatg   1380
gaccccaaga cacagatctt cctggaccag aacatgctgg cagtgatcga tgagctgatg   1440
caagccttga acttcaactc agagacagtg ccgcaaaagt cctcgttgga ggaaccagat   1500
```

```
ttttacaaaa ccaaaatcaa gctgtgtatc cttcttcacg cctttcggat cagagccgtg    1560
actatcgacc gggtgatgtc atacctgaat gcttcc                              1596

<210> SEQ ID NO 13
<211> LENGTH: 1596
<212> TYPE: DNA
<213> ORGANISM: Artificial Sequence
<220> FEATURE:
<223> OTHER INFORMATION: hIL12AB_009

<400> SEQUENCE: 13
atgtgccacc agcagctggt catcagctgg tttagcctgg tcttcctggc cagcccctg     60 gtggccatct gggagctgaa gaaagatgtc tatgttgtag agctggactg gtacccagat   120
gctcctggag aaatggtggt tctcacctgc gacacgccag aagaagatgg catcacctgg   180
acgctggacc agagcagcga agtactgggc agtggaaaaa cgctgaccat acaagtaaaa   240
gaatttggcg atgctggcca gtacacctgc cacaaaggag agaagtact gagccacagc    300 ctgctgctgc tgcacaagaa agaagatggc atctggagca ccgacatttt aaaagaccag   360
aaggagccca gaacaaaac cttccttcga tgtgaggcga agaactacag tggccgcttc   420
acctgctggt ggctcaccac catcagcacc gacctcacct tctcggtgaa gagcagccgt   480
ggtagctcag accccaagg agtcacctgt ggggcggcca cgctgtcggc agaaagagtt   540
cgaggcgaca caaggaata tgaatactcg gtggaatgtc aagaagactc ggcctgcccg   600
gcggcagaag aaagtctgcc catagaagtc atggtggatg ctgttcacaa attaaaatat   660
gaaaactaca ccagcagctt cttcatcaga gacatcatca gccagaccc cccaagaac    720 ctgcagctga gcccctgaa gaacagcaga caagtggaag tttcctggga gtacccagac   780
acgtggagca cgccgcacag ctacttcagc ctcaccttct gtgtacaagt acaaggcaag   840
agcaagagag agaagaaaga tcgtgtcttc accgacaaaa cctcggcgac ggtcatctgc   900
aggaagaatg caagcatctc ggttcgagcc caggaccgct actacagcag cagctggagt   960
gagtgggcct cggtgccctg cagtggtggc ggcggcggcg gcagcagaaa ccttcctgtg  1020
gccacgccgg accctggcat gtttccgtgc ctgcaccaca ccaaaatttt attacgagct  1080
gttagcaaca tgctgcagaa agcaagacaa actttagaat ctacccctg cacctcagaa  1140 gaaatagacc atgaagacat caccaaagat aaaaccagca ctgtagaggc ctgcctgccc  1200
ctggagctca ccaagaacga gagctgcctc aatagcagag agaccagctt catcaccaat  1260
ggcagctgcc tggccagcag gaaaaccagc ttcatgatgg cgctctgcct gagcagcatc  1320
tatgaagatc tgaagatgta ccaagtagaa tttaaaacca tgaatgccaa gctgctcatg  1380
gaccccaaga caaaatatt cctcgaccaa aacatgctgg ctgtcattga tgagctcatg  1440
caagcattaa acttcaactc agagacggtg ccccagaaga gcagcctgga ggagccagac  1500
ttctacaaaa ccaagatcaa gctctgcatc ttattacatg ccttccgcat ccgggcggtc  1560
accattgacc gtgtcatgtc ctacttaaat gccagc                            1596

<210> SEQ ID NO 14
<211> LENGTH: 1596
<212> TYPE: DNA
<213> ORGANISM: Artificial Sequence
<220> FEATURE:
<223> OTHER INFORMATION: hIL12AB_010

<400> SEQUENCE: 14
atgtgccacc agcagcttgt catctcctgg ttttctcttg tcttcctcgc ttctcctctt    60
```

```
gtggccatct gggagctgaa gaaagatgtc tatgttgtag agctggactg gtacccggac      120
gctcctggag aaatggtggt tctcacctgc gacactcctg aagaagatgg catcacctgg      180
acgctggacc aaagcagcga agttttaggc tctggaaaaa cgctgaccat acaagtaaaa      240
gaatttggcg acgctggcca gtacacgtgc cacaaaggag agaagtttt aagccacagt      300 ttacttcttc ttcacaagaa agaagatggc atctggagta cggacatttt aaaagaccag      360
aaggagccta gaacaaaac cttcctccgc tgtgaagcta agaactacag tggtcgtttc      420
acctgctggt ggctcaccac catctccact gacctcacct tctctgtaaa atcaagccgt      480
ggttcttctg accccaagg agtcacctgt ggggctgcca cgctcagcgc tgaaagagtt      540
cgaggcgaca caaggaata tgaatattct gtggaatgtc aagaagattc tgcctgcccg      600
gcggcagaag aaagtcttcc catagaagtc atggtggacg ctgttcacaa attaaaatat      660
gaaaactaca ccagcagctt cttcattcgt gacatcatca accagaccc tcctaagaac      720 cttcagttaa accgctgaa gaacagcaga caagtgaag tttcctggga gtacccggac      780
acgtggagta cgccgcactc ctacttcagt ttaaccttct gtgtacaagt acaaggaaaa      840
tcaaaaagag agaagaaaga tcgtgtcttc actgacaaaa catctgccac ggtcatctgc      900
cgtaagaacg cttccatctc ggttcgagcc caggaccgct actacagcag cagctggagt      960
gagtgggcat ctgttccctg cagtggtggc ggcggcggcg cagccgcaa ccttcctgtg      1020 gccacgccgg accctggcat gttcccgtgc cttcaccact cgcaaaatct tcttcgtgct      1080
gtttctaaca tgctgcagaa ggcgagacaa actttagaat ctacccgtg cacttctgaa      1140 gaaatagacc atgaagacat caccaaggac aaaaccagca cggtggaggc ctgccttcct      1200
ttagaactta ctaagaacga agttgccctt aacagccgtg agaccagctt catcaccaat      1260
ggcagctgcc ttgctagcag gaagaccagc ttcatgatgg cgctgtgcct tcttccatc      1320 tatgaagatc ttaagatgta ccaagtagaa tttaaaacca tgaatgccaa attattaatg      1380
gaccccaaga gacaaatatt cctcgaccaa acatgctgg ctgtcattga tgagctcatg      1440
caagcattaa acttcaactc agaaactgtt ccccagaagt catctttaga agaaccggac      1500
ttctacaaaa caaaaataaa actctgcatt cttcttcatg ccttccgcat ccgtgctgtc      1560
accattgacc gtgtcatgtc ctacttaaat gcttct                               1596
```

<210> SEQ ID NO 15
<211> LENGTH: 1596
<212> TYPE: DNA
<213> ORGANISM: Artificial Sequence
<220> FEATURE:
<223> OTHER INFORMATION: hIL12AB_011

<400> SEQUENCE: 15

```
atgtgccacc agcagctggt gatcagctgg ttcagcctgg tgttcctggc agcccctg       60 gtggccatct gggagctgaa gaaggacgtg tacgtggtgg agctggactg gtacccggac      120
gcgccggggg agatggtggt gctgacgtgc gacacgccgg aggaggacgg gatcacgtgg      180
acgctggacc agagcagcga ggtgctgggg agcgggaaga cgctgacgat ccaggtgaag      240
gagttcgggg acgcggggca gtacacgtgc cacaaggggg ggaggtgct gagccacagc      300 ctgctgctgc tgcacaagaa ggaggacggg atctggagca cggacatcct gaaggaccag      360
aaggagccga gaacaagac gttcctgagg tgcgaggcga gaactacag cgggaggttc      420 acgtgctggt ggctgacgac gatcagcacg gacctgacgt tcagcgtgaa gagcagcagg      480
```

```
gggagcagcg acccgcaggg ggtgacgtgc ggggcggcga cgctgagcgc ggagagggtg    540 agggggaca acaaggagta cgagtacagc gtggagtgcc aggaggacag cgcgtgcccg    600
gcggcggagg agagcctgcc gatcgaggtg atggtggacg cggtgcacaa gctgaagtac    660
gagaactaca cgagcagctt cttcatcagg gacatcatca gcccggaccc gccgaagaac    720
ctgcagctga agccgctgaa gaacagcagg caggtggagg tgagctggga gtacccggac    780
acgtggagca cgccgcacag ctacttcagc ctgacgttct gcgtgcaggt gcaggggaag    840
agcaagaggg agaagaagga cagggtgttc acggacaaga cgagcgcgac ggtgatctgc    900
aggaagaacg cgagcatcag cgtgagggcg caggacaggt actacagcag cagctggagc    960
gagtgggcga gcgtgccgtg cagcgggggg ggggggggg ggagcaggaa cctgccggtg   1020
gcgacgccgg acccggggat gttcccgtgc ctgcaccaca gccagaacct gctgagggcg   1080
gtgagcaaca tgctgcagaa ggcgaggcag acgctggagt tctacccgtg cacgagcgag   1140
gagatcgacc acgaggacat cacgaaggac aagacgagca cggtggaggc gtgcctgccg   1200
ctggagctga cgaagaacga gagctgcctg aacagcaggg agacgagctt catcacgaac   1260
gggagctgcc tggcgagcag gaagacgagc ttcatgatgg cgctgtgcct gagcagcatc   1320
tacgaggacc tgaagatgta ccaggtggag ttcaagacga tgaacgcgaa gctgctgatg   1380
gacccgaaga ggcagatctt cctggaccag aacatgctgg cggtgatcga cgagctgatg   1440
caggcgctga acttcaacag cgagacggtg ccgcagaaga cagcctgga ggagccggac   1500 ttctacaaga cgaagatcaa gctgtgcatc ctgctgcacg cgttcaggat cagggcggtg   1560
acgatcgaca gggtgatgag ctacctgaac gcgagc                             1596

<210> SEQ ID NO 16
<211> LENGTH: 1596
<212> TYPE: DNA
<213> ORGANISM: Artificial Sequence
<220> FEATURE:
<223> OTHER INFORMATION: hIL12AB_012

<400> SEQUENCE: 16
atgtgccatc agcagctggt gatcagctgg ttcagcctcg tgtttctggc cagccccctg     60
gtggccattt gggaactcaa gaaggacgtg tatgtagtgg aactcgactg gtaccctgac    120
gccccaggcg aaatggtggt cttaacctgc gacacccctg aggaggacgg aatcacctgg    180
accttggacc agagctccga ggtcctcggc agtggcaaga ccctgaccat acaggtgaaa    240
gaatttggag acgcagggca atacacatgt cacaagggcg gggaggttct ttctcactcc    300
cttctgcttc tacataaaaa ggaagacgga atttggtcta ccgacatcct caaggaccaa    360
aaggagccta gaataaaaac cttcttacgc tgtgaagcta aaaactacag cggcagattc    420
acttgctggt ggctcaccac catttctacc gacctgacct tctcggtgaa gtcttcaagg    480
ggctctagtg atccacaggg agtgacatgc ggggccgcca cactgagcgc tgaacgggtg    540
aggggcgata caaggagta tgaatactct gtcgagtgtc aggaggattc agcttgtccc    600
gcagctgaag agtcactccc catagaggtt atggtcgatg ctgtgcataa actgaagtac    660
gaaaactaca ccagcagctt cttcattcgg gacattataa aacctgaccc ccccaagaac    720
ctgcaactta aaccctgaa aaactctcgg caggtcgaag ttagctggga gtaccctgat    780
acttggtcca ccccccactc gtacttctca ctgactttct gtgtgcaggt cagggcaag    840 agcaagagag agaaaaaaga tcgtgtattc acagacaaga cctctgccac cgtgatctgc    900
agaaaaaacg cttccatcag tgtcagagcc caagaccggt actatagtag tagctggagc    960
```

```
gagtgggcaa gtgtcccctg ctctggcggc ggaggggggcg gctctcgaaa cctccccgtc    1020
gctacccctg atccaggaat gttcccttgc ctgcatcact cacagaatct gctgagagcg    1080
gtcagcaaca tgctgcagaa agctaggcaa acactggagt tttatccttg tacctcagag    1140
gagatcgacc acgaggatat taccaaggac aagaccagca cggtggaggc ctgcttgccc    1200
ctggaactga caaagaatga atcctgcctt aatagccgtg agacctcttt tataacaaac    1260
ggatcctgcc tggccagcag gaagacctcc ttcatgatgg ccctctgcct gtcctcaatc    1320
tacgaagacc tgaagatgta ccaggtggaa tttaaaacta tgaacgccaa gctgttgatg    1380
gaccccaagc ggcagatctt tctggatcaa aatatgctgg ctgtgatcga cgaactgatg    1440
caggccctca actttaacag cgagaccgtg ccacaaaaga gcagtcttga ggagcccgac    1500
ttctacaaga ccaagatcaa gctgtgcatc ctccttcatg ccttcaggat aagagctgtc    1560
accatcgaca gagtcatgag ttacctgaat gcatcc                              1596
```

<210> SEQ ID NO 17
<211> LENGTH: 1596
<212> TYPE: DNA
<213> ORGANISM: Artificial Sequence
<220> FEATURE:
<223> OTHER INFORMATION: hIL12AB_013

<400> SEQUENCE: 17

```
atgtgccacc agcagctggt catctcctgg ttcagtcttg tcttcctggc ctcgccgctg     60
gtggccatct gggagctgaa gaaagatgtt tatgttgtag agctggactg gtacccagat    120
gctcctggag aaatggtggt cctcacctgt gacacgccag aagaagatgg catcacctgg    180
acgctggacc agagcagtga agttcttgga agtggaaaaa cgctgaccat acaagtaaaa    240
gaatttggag atgctggcca gtacacctgc cacaaaggag agaagttcct cagccacagt    300
ttattattac ttcacaagaa agaagatggc atctggtcca cggacatttt aaaagaccag    360
aaggagccca aaaataaaac atttcttcga tgtgaggcca agaactacag tggtcgtttc    420
acctgctggt ggctgaccac catctccaca gacctcacct tcagtgtaaa agcagccgt    480 ggttcttctg accccaaggg agtcacctgt ggggctgcca cgctctctgc agaaagagtt    540 cgagggaca caaagaata tgagtactcg gtggaatgtc aagaagactc ggcctgccca    600
gctgctgagg agagtcttcc catagaagtc atggtggatg ctgttcacaa attaaaatat    660
gaaaactaca ccagcagctt cttcatcaga gacatcatca aacctgaccc gcccaagaac    720
ttacagctga agccgctgaa aaacagcaga caagtagaag tttcctggga gtacccggac    780
acctggtcca cgccgcactc ctacttctcc ctcaccttct gtgtacaagt acaaggcaag    840
agcaagagag agaagaaaga tcgtgtcttc acggacaaaa catcagccac ggtcatctgc    900
aggaaaaatg ccagcatctc ggtgcgggcc caggaccgct actacagcag cagctggagt    960
gagtgggcat ctgtgccctg cagtggtggt ggggtggtg gcagcagaaa ccttcctgtg   1020
gccactccag accctggcat gttcccgtgc cttcaccact cccaaaattt acttcgagct   1080
gtttctaaca tgctgcagaa agcaagacaa acttagaat tctacccgtg cacttctgaa   1140
gaaattgacc atgaagacat cacaaaagat aaaaccagca cagtggaggc ctgtcttcct   1200
ttagagctga ccaaaaatga atcctgcctc aacagcagag accagcttt catcaccaat   1260 ggcagctgcc tggcctccag gaaaaccagc ttcatgatgg cgctctgcct cagctccatc   1320
tatgaagatt tgaagatgta ccaagtagaa tttaaaacca tgaatgccaa attattaatg   1380
```

```
gaccccaaga ggcagatatt tttagatcaa acatgctgg cagttattga tgagctcatg    1440
caagcattaa acttcaacag tgagactgta cctcaaaaaa gcagccttga agagccggac   1500
ttctacaaaa ccaagatcaa actctgcatt ttacttcatg ccttccgcat ccgggcggtc   1560
accattgacc gtgtcatgtc ctacttaaat gcctcg                            1596
```

<210> SEQ ID NO 18
<211> LENGTH: 1596
<212> TYPE: DNA
<213> ORGANISM: Artificial Sequence
<220> FEATURE:
<223> OTHER INFORMATION: hIL12AB_014

<400> SEQUENCE: 18

```
atgtgccacc agcagcttgt gatttcttgg ttctctcttg tgttccttgc ttctcctctt   60
gtggctattt gggagttaaa aaaggacgtg tacgtggtgg agcttgactg gtaccctgat   120
gctcctggcg agatggtggt gcttactgt gacactcctg aggaggacgg cattacttgg   180
actcttgacc agtcttctga ggtgcttggc tctggcaaga ctcttactat tcaggtgaag   240
gagttcgggg atgctggcca gtacacttgc cacaagggcg cgaggtgct ttctcactct   300 cttcttcttc ttcacaagaa ggaggacggc atttggtcta ctgacatttt aaaagaccag   360
aaggagccca gaacaagac tttccttcgt tgcgaggcca agaactactc tggccgtttc   420
acttgctggt ggcttactac tatttctact gaccttactt tctctgtgaa gtcttctcgt   480
ggctcttctg accctcaggg cgtgacttgt ggggctgcta ctctttctgc tgagcgtgtg   540
cgtggggaca caaggagta cgagtactct gtggagtgcc aggaggactc tgcttgccct   600
gctgctgagg agtctcttcc tattgaggtg atggtggatg ctgtgcacaa gttaaaatac   660
gagaactaca cttcttcttt cttcattcgt gacattatta gcctgacccc tcccaagaac   720
cttcagttaa aacctttaaa aaactctcgt caggtggagg tgtcttggga gtaccctgac   780
acttggtcta ctcctcactc ttacttctct cttactttct gcgtgcaggt gcagggcaag   840
tctaagcgtg agaagaagga ccgtgtgttc actgacaaga cttctgctac tgtgatttgc   900
aggaagaatg catctatttc tgtgcgtgct caggaccgtt actactcttc ttcttggtct   960
gagtgggctt ctgtgccttg ctctggcggc ggcggcggcg gctctagaaa tcttcctgtg   1020
gctactcctg accctggcat gttcccttgc cttcaccact ctcagaacct tcttcgtgct   1080
gtgagcaaca tgcttcagaa ggctcgtcag actcttgagt tctaccctg cacttctgag   1140 gagattgacc acgaggacat caccaaggac aagacttcta ctgtggaggc ttgccttcct   1200
cttgagctta ccaagaatga atcttgctta aattctcgtg agacttcttt catcaccaac   1260
ggctcttgcc ttgcctcgcg caagacttct ttcatgatgg ctcttgcct ttcttctatt   1320 tacgaggact aaaaatgta ccaggtggag ttcaagacta tgaatgcaaa gcttcttatg   1380
gaccccaagc gtcagatttt ccttgaccag aacatgcttg ctgtgattga cgagcttatg   1440
caggctttaa atttcaactc tgagactgtg cctcagaagt cttctcttga ggagcctgac   1500
ttctacaaga ccaagattaa gctttgcatt cttcttcatg ctttccgtat cgtgctgtg   1560 actattgacc gtgtgatgtc ttacttaaat gcttct                            1596
```

<210> SEQ ID NO 19
<211> LENGTH: 1596
<212> TYPE: DNA
<213> ORGANISM: Artificial Sequence
<220> FEATURE:
<223> OTHER INFORMATION: hIL12AB_015

<400> SEQUENCE: 19

```
atgtgtcacc agcagctggt gatcagctgg tttagcctgg tgtttctggc cagcccctg      60
gtggccatat gggaactgaa gaaagatgtg tatgtggtag aactggattg gtatccggat    120
gcccccggcg aaatggtggt gctgacctgt gacaccccg aagaagatgg tatcacctgg     180
accctggacc agagcagcga ggtgctgggc agcggcaaaa ccctgaccat ccaagtgaaa    240
gagtttggcg atgccggcca gtacacctgt cacaaaggcg cgaggtgct aagccattcg     300
ctgctgctgc tgcacaaaaa ggaagatggc atctggagca ccgatatcct gaaggaccag    360
aaagaaccca aaataagac ctttctaaga tgcgaggcca gaattatag cggccgtttc      420
acctgctggt ggctgacgac catcagcacc gatctgacct cagcgtgaa aagcagcaga    480
ggcagcagcg acccccaagg cgtgacgtgc ggcgccgcca ccctgagcgc cgagagagtg    540
agaggcgaca acaaggagta tgagtacagc gtggagtgcc aggaggacag cgcctgcccc   600
gccgccgagg agagcctgcc catcgaggtg atggtggatg ccgtgcacaa gctgaagtat   660
gaaaactaca ccagcagctt cttcatcaga gacatcatca aacccgaccc ccccaagaac   720
ctgcagctga gcccctgaa gaatagcaga caggtggagg tgagctggga gtaccccgac   780
acctggagca ccccccatag ctacttcagc ctgacctct gcgtgcaggt gcagggcaag    840
agcaagagag aaaagaaaga tagagtgttc acggacaaga ccagcgccac ggtgatctgc   900
agaaaaatg ccagcatcag cgtgagagcc caggacagat actatagcag cagctggagc   960
gaatgggcca gcgtgccctg cagcggcggc ggcggcggcg gcagcagaaa cctgcccgtg  1020
gccacccccg acccggcat gttcccctgc ctgcaccaca gccaaaacct gctgagagcc  1080
gtgagcaaca tgctgcagaa ggccagacaa accctggaat tttacccctg caccagcgaa  1140
gagatcgatc atgaagatat caccaaagat aaaccagca ccgtggaggc ctgtctgccc   1200
ctggaactga ccaagaatga gagctgccta aatagcagag agaccagctt cataaccaat  1260
ggcagctgcc tggccagcag aaagaccagc tttatgatgg ccctgtgcct gagcagcatc  1320
tatgaagacc tgaagatgta ccaggtggag ttcaagacca tgaatgccaa gctgctgatg  1380
gatcccaaga gacagatctt tctggatcaa aacatgctgg ccgtgatcga tgagctgatg  1440
caggccctga atttcaacag cgagaccgtg ccccaaaaaa gcagcctgga agaaccggat  1500
ttttataaaa ccaaaatcaa gctgtgcata ctgctgcatg ccttcagaat cagagccgtg  1560
accatcgata gagtgatgag ctatctgaat gccagc                            1596
```

<210> SEQ ID NO 20
<211> LENGTH: 1596
<212> TYPE: DNA
<213> ORGANISM: Artificial Sequence
<220> FEATURE:
<223> OTHER INFORMATION: hIL12AB_016

<400> SEQUENCE: 20

```
atgtgccacc agcagctggt catcagctgg ttcagcctgg tcttcctggc cagcccctg      60
gtggccatct gggagctgaa gaaggatgtt tatgttgtgg agctggactg gtacccagat    120
gcccctgggg agatggtggt gctgacctgt gacaccccag aagaggatgg catcacctgg    180
accctggacc agagctcaga agtgctgggc agtggaaaaa ccctgaccat ccaggtgaag    240
gagtttggag atgctggcca gtacacctgc cacaagggtg tgaagtgct gagccacagc     300
ctgctgctgc tgcacaagaa ggaggatggc atctggagca cagacatcct gaaggaccag    360
```

```
aaggagccca agaacaagac cttccttcgc tgtgaagcca agaactacag tggccgcttc      420
acctgctggt ggctgaccac catcagcaca gacctcacct tctcggtgaa gagcagcaga      480
ggcagctcag accccccaggg tgtcacctgt ggggcggcca cgctgtcggc ggagagagtt     540
cgaggggaca caaggagta tgaatactcg gtggagtgcc aggaggactc ggcgtgcccg       600
gcggcagaag agagcctgcc catagaagtg atggtggatg ctgtgcacaa gctgaagtat      660
gaaaactaca ccagcagctt cttcatcaga gacatcatca gccagaccc gcccaagaac       720 ctgcagctga agcccctgaa aacagcaga caagtggagg tttcctggga gtacccagac       780
acgtggagca cccccacag ctacttcagc ctgaccttct gtgtccaggt gcagggcaag       840
agcaagagag agaagaagga cagagtcttc acagacaaga cctcggccac ggtcatctgc      900
agaaagaatg cctccatctc ggttcgagcc caggacagat actacagcag cagctggtca     960
gaatgggcct cggtgccctg cagtggtggc ggcggcggcg gcagcagaaa cctgcctgtt     1020
gccaccccag accctgggat gttccccctgc ctgcaccaca gccagaactt attacgagct   1080
gtttctaaca tgctgcagaa ggccagacaa accctggagt tctaccctg cacctcagaa     1140 gagattgacc atgaagacat caccaaggac aagaccagca ctgtagaggc ctgcctgccc    1200
ctggagctga ccaagaatga aagctgcctg aacagcgag agaccagctt catcaccaat     1260
ggaagctgcc tggccagcag aaagaccagc ttcatgatgg ccctgtgcct gagcagcatc   1320
tatgaagacc tgaagatgta ccaggtggag ttcaagacca tgaatgcaaa gctgctgatg    1380 gacccccaaga gacaaatatt tttggaccag aacatgctgg ctgtcattga tgagctgatg   1440
caggccctga acttcaactc agaaactgta ccccagaaga gcagcctgga ggagccagac   1500
ttctacaaga ccaagatcaa gctgtgcatc ctgcttcatg ctttcagaat cagagctgtc   1560
accattgacc gcgtgatgag ctacttaaat gcctcg                              1596
```

<210> SEQ ID NO 21
<211> LENGTH: 1596
<212> TYPE: DNA
<213> ORGANISM: Artificial Sequence
<220> FEATURE:
<223> OTHER INFORMATION: hIL12AB_017

<400> SEQUENCE: 21

```
atgtgccacc agcagctggt aatcagctgg ttttccctcg tctttctggc atcacccctg       60
gtggctatct gggagctgaa gaaggacgtg tacgtggtgg agctggattg gtaccctgac      120
gccccggggg aaatggtggt gttaacatgc gacacgcctg aggaggacgg catcacctgg      180
acactggacc agagcagcga ggtgcttggg tctggtaaaa ctctgactat tcaggtgaaa       240
gagttcgggg atgccggcca atatacttgc cacaagggtg gcgaggtgct ttctcattct      300
ctgctcctgc tgcacaagaa agaagatggc atttggtcta ctgatattct gaaagaccag      360
aaggagccca gaacaagac ctttctgaga tgcgaggcta aaaactacag cggaagattt       420
acctgctggt ggctgaccac aatctcaacc gacctgacat tttcagtgaa gtccagcaga      480
gggagctccg accctcaggg cgtgacctgc ggagccgcca ctctgtccgc agaaagagtg      540
agaggtgata taaggagta cgagtattca gtcgagtgcc aagaggactc tgcctgccca       600
gccgccgagg agagcctgcc aatcgaggtg atggtagatg cggtacacaa gctgaagtat      660
gagaactaca catcctcctt cttcataaga gacattatca gcctgaccc acctaaaaat      720 ctgcaactca gcctttgaa aaattcaaga caggtggagg tgagctggga gtaccctgat     780
acttggagca ccccccatag ctacttttcg ctgacattct gcgtccaggt gcagggcaag    840
```

```
tcaaagagag agaagaagga tcgcgtgttc actgataaga caagcgccac agtgatctgc    900
agaaaaaacg ctagcattag cgtcagagca caggaccggt attactccag ctcctggagc    960
gaatgggcat ctgtgccctg cagcggtggg ggcggaggcg gatctagaaa cctccccgtt   1020
gccacacctg atcctggaat gttccccgt ctgcaccaca gccagaacct gctgagagca   1080
gtgtctaaca tgctccagaa ggccaggcag accctggagt tttacccctg caccagcgag   1140
gaaatcgatc acgaggacat caccaaagat aaaacctcca ccgtggaggc ctgcctgccc   1200
ctggaactga ccaaaaacga gagctgcctg aatagcaggg agacctcctt catcaccaac   1260
ggctcatgcc ttgccagccg gaaaactagc ttcatgatgg ccctgtgcct gtcttcgatc   1320
tatgaggacc tgaaaatgta ccaggtcgaa tttaagacga tgaacgcaaa gctgctgatg   1380
gaccccaagc ggcagatctt tctggaccag aacatgctgg cagtcataga tgagttgatg   1440
caggcattaa acttcaacag cgagaccgtg cctcagaagt ccagcctcga ggagccagat   1500
ttttataaga ccaagatcaa actatgcatc ctgctgcatg ctttcaggat tagagccgtc   1560
accatcgatc gagtcatgtc ttacctgaat gctagc                             1596
```

<210> SEQ ID NO 22
<211> LENGTH: 1596
<212> TYPE: DNA
<213> ORGANISM: Artificial Sequence
<220> FEATURE:
<223> OTHER INFORMATION: hIL12AB_018

<400> SEQUENCE: 22

```
atgtgtcacc aacagttagt aatctcctgg ttttctctgg tgtttctggc cagccccctc     60
gtggccatct gggagcttaa aaaggatgtg tacgtggtgg agctggactg gtatcccgat    120
gcaccaggcg aaatggtcgt gctgacctgc gataccctg aagaagatgg catcacctgg    180
actctggacc agtcttccga ggtgcttgga tctggcaaga ctctgacaat acaagttaag    240
gagttcgggg acgcaggaca gtacacctgc cacaaaggcg gcgaggtcct gagtcactcc    300
ctgttactgc tccacaagaa agaggacggc atttggtcca ccgacattct gaaggaccag    360
aaggagccta agaataaaac tttcctgaga tgcgaggcaa aaaactatag cggccgcttt    420
acttgctggt ggcttacaac aatctctacc gatttaactt ctccgtgaa gtctagcaga    480 ggatcctctg acccgcaagg agtgacttgc ggagccgcca ccttgagcgc cgaaagagtc    540
cgtggcgata caaagaata cgagtactcc gtggagtgcc aggaagattc cgcctgccca    600
gctgccgagg agtccctgcc cattgaagtg atggtggatg ccgtcacaa gctgaagtac    660 gaaaactata ccagcagctt cttcatccgg gatatcatta gcccgaccc tcctaaaaac    720 ctgcaactta gcccctaaa gaatagtcgg caggttgagg tcagctggga atatcctgac    780
acatggagca cccccactc ttatttctcc ctgaccttct gcgtgcaggt gcagggcaag    840
agtaaacggg agaaaaagga cagggtctttt accgataaaa ccagcgctac ggttatctgt    900
cggaagaacg cttccatctc cgtccgcgct caggatcgtt actactcgtc ctcatggagc    960
gagtgggcca gcgtgccctg cagcggcggc ggtggaggcg gatccagaaa tctgcctgtt   1020
gccacaccag accctggcat gttccctgt ctgcatcata gccagaacct gctcagagcc   1080
gtgagcaaca tgctccagaa ggccaggcag acattggagt tctacccgtg tacatctgag   1140
gaaatcgatc acgaagatat aaccaaggac aaaacctcta cagtagaggc ttgtttgccc   1200
ctggagttga ccaaaaacga gagttgcctg aacagtcgcg agacaagctt cattactaac   1260
```

| | |
|---|---|
| ggcagctgtc tcgcctccag aaagacatcc ttcatgatgg ccctgtgtct ttccagcata | 1320 |
| tacgaagacc tgaaaatgta ccaggtcgag ttcaaaacaa tgaacgccaa gctgcttatg | 1380 |
| gaccccaaga gacagatctt cctcgaccaa acatgctcg ctgtgatcga tgagctgatg | 1440 |
| caggctctca acttcaattc cgaaacagtg ccacagaagt ccagtctgga agaacccgac | 1500 |
| ttctacaaga ccaagattaa gctgtgtatt tgctgcatg cgtttagaat cagagccgtg | 1560 |
| accattgatc gggtgatgag ctacctgaac gcctcg | 1596 |

<210> SEQ ID NO 23
<211> LENGTH: 1596
<212> TYPE: DNA
<213> ORGANISM: Artificial Sequence
<220> FEATURE:
<223> OTHER INFORMATION: hIL12AB_019

<400> SEQUENCE: 23

| | |
|---|---|
| atgtgccacc agcagcttgt catctcctgg ttttctcttg tcttcctggc ctcgccgctg | 60 |
| gtggccatct gggagctgaa gaaagatgtc tatgttgtag agctggactg gtacccagat | 120 |
| gctcctggag aaatggtggt tctcacctgt gacactcctg aagaagatgg catcacctgg | 180 |
| acgctggacc aaagctcaga agttcttggc agtggaaaaa cgctgaccat acaagtaaaa | 240 |
| gaatttgggg atgctggcca gtacacgtgc cacaaaggag agaagttct cagccacagt | 300 |
| ttacttcttc ttcacaagaa agaagatggc atctggtcca cggacatttt aaaagaccag | 360 |
| aaggagccca gaacaaaac cttcctccgc tgtgaggcca gaactacag tggtcgtttc | 420 |
| acctgctggt ggctcaccac catctccact gacctcacct tctctgtaaa aagcagccgt | 480 |
| ggttcttctg accccaagg agtcacctgt ggggctgcca cgctctcggc agaaagagtt | 540 |
| cgaggggaca caaggaata tgaatattct gtggaatgtc aagaagattc tgcctgcccg | 600 |
| gcggcagaag aaagtcttcc catagaagtc atggtggatg ctgttcacaa attaaaatat | 660 |
| gaaaactaca ccagcagctt cttcattcgt gacatcatca accagaccc gcccaagaac | 720 |
| cttcagttaa accttttaaa aaacagcaga caagtagaag tttcctggga gtacccggac | 780 |
| acgtggtcca cgccgcactc ctacttcagt ttaaccttct gtgtacaagt acaaggaaaa | 840 |
| tcaaaaagag agaagaaaga tcgtgtcttc actgacaaaa catctgccac ggtcatctgc | 900 |
| aggaagaatg cctccatctc ggttcgagcc caggaccgct actacagcag cagctggagt | 960 |
| gagtgggcat ctgttccctg cagtggtggc ggcggcggcg gcagccgcaa ccttcctgtg | 1020 |
| gccacgccgg accctggcat gttcccgtgc cttcaccact cccaaaatct tcttcgtgct | 1080 |
| gtttctaaca tgctgcagaa ggcgcgccaa actttagaat ctaccgtg cacttctgaa | 1140 |
| gaaatagacc atgaagacat caccaaagat aaaaccagca cggtggaggc ctgccttcct | 1200 |
| ttagagctga ccaagaatga atcctgcctc aacagcagag agaccagctt catcaccaat | 1260 |
| ggcagctgcc tggcctcgcg caagaccagc ttcatgatgg cgctgtgcct tcttccatc | 1320 |
| tatgaagatt taaagatgta ccaagtagaa tttaaaacca tgaatgccaa attattaatg | 1380 |
| gaccccaaaa gacaaatatt tttggatcaa acatgctgg ctgtcattga tgagctcatg | 1440 |
| caagcattaa acttcaactc agaaactgtt cccagaagt catctttaga agagccggac | 1500 |
| ttctacaaaa caaaaataaa actctgcatt cttcttcatg ccttccgcat ccgtgctgtc | 1560 |
| accattgacc gtgtcatgtc ctacttaaat gcttct | 1596 |

<210> SEQ ID NO 24
<211> LENGTH: 1596

<212> TYPE: DNA
<213> ORGANISM: Artificial Sequence
<220> FEATURE:
<223> OTHER INFORMATION: hIL12AB_020

<400> SEQUENCE: 24

```
atgtgccacc agcagctggt gatcagctgg ttcagcctgg tgttcctggc tagccctctg      60
gtggccatct gggagctgaa aaggacgtg tacgtggtgg agttagactg gtaccccgac     120
gctcccggcg agatggtggt gctgacctgc gacacccccg aggaggacgg gatcacctgg     180
acctggatc agtcaagcga ggtgctggga agcggcaaga ccctgaccat ccaggtgaag     240
gagttcggcg acgccggcca atacacttgc acaaggggag gcgaggtgct gtcccactcc     300
ctcctgctgc tgcacaaaaa ggaagacggc atctggagca ccgacatcct gaaagaccag     360
aaggagccta gaacaagac attcctcaga tgcgaggcca gaattactc cgggagattc     420
acctgttggt ggctgaccac catcagcaca gacctgacct tcagcgtgaa gagcagcaga     480
ggcagcagcg accccagg cgtgacctgt ggcgccgcca cctgagcgc cgaaagagtg     540
cgcggcgaca caaggagta cgagtactcc gtggaatgcc aggaggacag cgcctgcccc     600
gccgccgagg agagcctgcc catcgaggtg atggtggacg ccgtccacaa gctgaagtac     660
gagaactaca cctctagctt cttcatccgg gacatcatca gcccgatcc ccccaagaac     720
ctgcagctga aacccctgaa gaacagcaga caggtggagg tgagctggga gtatccgac     780
acctggtcca ccccccacag ctattttagc ctgaccttct gcgtgcaagt gcagggcaag     840
agcaagagag agaagaagga ccgcgtgttc accgacaaaa ccagcgccac cgtgatctgc     900
agaaagaacg ccagcatcag cgtgagggcc caggatagat actacagttc cagctggagc     960
gagtgggcca gcgtgccctg cagcggcggc ggcgggggag gctctagaaa cctgcccgtg    1020
gctaccccg atcccggaat gttcccctgc ctgcaccaca gccagaacct gctgagggcg    1080
gtgtccaaca tgcttcagaa ggcccggcag accctggagt ctacccctg tacctctgag    1140
gagatcgatc atgaggacat cacaaaggac aaaaccagca ccgtggaggc ctgcctgccc    1200
ctggagctga ccaagaacga gagctgcctg aactcccgcg agaccagctt catcacgaac    1260
ggcagctgcc tggccagcag gaagacctcc ttcatgatgg ccctgtgcct gagcagcatc    1320
tacgaggacc tgaaaatgta ccaggtggag tttaagacca tgaacgccaa gctgctgatg    1380
gaccccaagc ggcaaatctt cctggaccag aacatgctgg cagtgatcga cgagctcatg    1440
caggccctga acttcaatag cgagacagtc ccccagaaga gcagcctgga ggagcccgac    1500
ttttacaaga ccaagatcaa gctgtgcatc ctgctgcacg cctttagaat ccgtgccgtg    1560
accattgaca gagtgatgag ctacctgaat gccagc                              1596
```

<210> SEQ ID NO 25
<211> LENGTH: 1596
<212> TYPE: DNA
<213> ORGANISM: Artificial Sequence
<220> FEATURE:
<223> OTHER INFORMATION: hIL12AB_021

<400> SEQUENCE: 25

```
atgtgccacc agcagctggt gatcagctgg ttcagcctgg tgttcctggc cagccctctg      60
gttgccatct gggagctgaa gaaagacgtg tacgtcgtgg aactggactg gtatccggac     120
gccccgggcg agatggtggt gctgacctgt gacacccccg aggaggacgg catcacctgg     180
acgctggacc aatcctccga ggtgctggga agcggcaaga ccctgaccat ccaggtgaag     240
```

```
gaattcgggg acgccgggca gtacacctgc cacaaggggg gcgaagtgct gtcccactcg      300
ctgctgctcc tgcataagaa ggaggatgga atctggtcca ccgacatcct caaagatcag      360
aaggagccca gaacaagac gttcctgcgc tgtgaagcca gaattattc ggggcgattc        420
acgtgctggt ggctgacaac catcagcacc gacctgacgt ttagcgtgaa gagcagcagg      480
gggtccagcg accccaggg cgtgacgtgc ggcgccgcca ccctctccgc cgagagggtg       540
cggggggaca taaggagta cgagtacagc gtggaatgcc aggaggacag cgcctgcccc       600
gccgcggagg aaagcctccc gatagaggtg atggtggacg ccgtgcacaa gctcaagtat      660
gagaattaca ccagcagctt tttcatccgg gacattatca gcccgaccc cccgaagaac       720
ctccagctga gcccctgaa gaacagccgg caggtggaag tctcctggga gtatcccgac       780
acctggagca ccccgcacag ctacttctcc ctgaccttct gtgtgcaggt gcagggcaag      840
tccaagaggg aaaagaagga cagggttttc accgacaaga ccagcgcgac cgtgatctgc      900
cggaagaacg ccagcataag cgtccgcgcc caagataggt actacagcag ctcctggagc      960
gagtgggcta gcgtgccctg cagcggggc ggggtggg gctccaggaa cctgccagtg        1020
gcgaccccg accccggcat gttccctgc ctccatcaca gccagaacct gctgagggcc       1080
gtcagcaata tgctgcagaa ggccaggcag accctggaat ctaccccctg cacgtcggag     1140
gagatcgatc acgaggatat cacaaaaagac aagacttcca ccgtggaggc ctgcctgccc    1200
ctggagctca ccaagaatga gtcctgtctg aactcccggg aaaccagctt catcaccaac     1260
gggtcctgcc tggccagcag gaagaccagc tttatgatgg ccctgtgcct gtcgagcatc     1320
tacgaggacc tgaagatgta ccaggtcgag ttcaagacaa tgaacgccaa gctgctgatg    1380
gaccccaaga ggcaaatctt cctggaccag aatatgcttg ccgtcatcga cgagctcatg   1440
cagggcctga acttcaactc cgagaccgtg ccccagaaga gcagcctgga ggagcccgac    1500
ttctacaaga ccaagatcaa gctgtgcatc ctgctgcacg cgttcaggat ccgggcagtc    1560
accatcgacc gtgtgatgtc ctacctgaac gccagc                             1596
```

<210> SEQ ID NO 26
<211> LENGTH: 1596
<212> TYPE: DNA
<213> ORGANISM: Artificial Sequence
<220> FEATURE:
<223> OTHER INFORMATION: hIL12AB_022

<400> SEQUENCE: 26

```
atgtgccatc agcagctggt gatcagctgg ttcagcctgg tgttcctcgc ctctcccctg       60
gtggccatct gggagctcaa aaaggacgtg tacgtggtgg agctcgactg gtacccagac      120
gcccccgggg agatggtggt gctgacctgc gacacccccg aagaagacgg catcacgtgg      180
accctcgacc agtccagcga ggtgctgggg agcgggaaga ctctgaccat ccaggtcaag      240
gagttcgggg acgccgggca gtacacgtgc cacaagggcg gcgaagtctt aagccacagc     300
ctgctcctgc tgcacaagaa ggaggacggg atctggtcca cagacatact gaaggaccag     360
aaggagccga gaataaaac ctttctgagg tgcgaggcca gaactattc ggcaggttc        420
acgtgctggt ggcttacaac aatcagcaca gacctgacgt tcagcgtgaa gtccagccgc    480
ggcagcagcg accccaggg ggtgacctgc ggcgccgcca cctgagcgc cgagcgggtg      540
cgcggggaca caaggagta cgagtactcc gtggagtgcc aggaagacag cgcctgtccc    600
gccgccgaag agagcctgcc tatcgaggtc atggtagatg cagtgcataa gctgaagtac   660
gagaactata cgagcagctt tttcatacgc gacatcatca gcccgaccc cccaagaac    720
```

```
ctgcagctta agcccctgaa gaatagccgg caggtggagg tctcctggga gtaccccgac      780
acctggtcaa cgccccacag ctacttctcc ctgacctttt gtgtccaagt ccagggaaag      840
agcaagaggg agaagaaaga tcgggtgttc accgacaaga cctccgccac ggtgatctgc      900
aggaagaacg ccagcatctc cgtgagggcg caagacaggg actactccag cagctggtcc      960
gaatgggcca gcgtgcccty ctccggcggc ggggcggcg gcagccgaaa cctacccgtg     1020
gccacgccgg atcccggcat gtttccctgc ctgcaccaca gccagaacct cctgagggcc     1080
gtgtccaaca tgctgcagaa ggccaggcag actctggagt tctaccccty cacgagcgag     1140
gagatcgatc acgaggacat caccaaggat aagaccagca ctgtggaggc ctgccttccc     1200
ctggagctga ccaagaacga gctgtctg aactccaggg agacctcatt catcaccaac     1260
ggctcctgcc tggccagcag gaaaaccagc ttcatgatgg ccttgtgtct cagctccatc     1320
tacgaggacc tgaagatgta tcaggtcgag ttcaagacaa tgaacgccaa gctgctgatg     1380
gaccccaaaa ggcagatctt cctggaccag aacatgctgg ccgtcatcga cgagctgatg     1440
caggccctga acttcaacag cgagacggtg ccccagaaaa gctccctgga ggagcccgac     1500
ttctacaaga ccaagatcaa gctgtgcatc ctgctgcacg ccttcaggat cagggcagtg     1560
accatcgacc gggtgatgtc ataccttaac gccagc                               1596
```

<210> SEQ ID NO 27
<211> LENGTH: 1596
<212> TYPE: DNA
<213> ORGANISM: Artificial Sequence
<220> FEATURE:
<223> OTHER INFORMATION: hIL12AB_023

<400> SEQUENCE: 27

```
atgtgccatc agcagctggt gatctcctgg ttcagcctgg tgtttctggc ctcgcccctg       60
gtcgccatct gggagctgaa gaaagacgtg tacgtcgtcg aactggactg gtaccccgac      120
gccccggggg agatggtggt gctgacctgc gacacgccgg aggaggacgg catcacctgg      180
accctggatc aaagcagcga ggtgctgggc agcggcaaga ccctgaccat ccaagtgaag      240
gaattcggcg atgccggcca gtacacctgt cacaaagggg gcgaggtgct cagccacagc      300
ctgctgctgc tgcacaagaa ggaggatggc atctggagca ccgatatcct gaaggaccag      360
aaagagccca gaacaagac gttcctgagg tgcgaggcca gaactacag cggtaggttc      420
acgtgttggt ggctgaccac catcagcacc gacctgacgt tcagcgtgaa gagctccagg      480
ggcagctccg acccacaggg ggtgacgtgc ggggccgcaa ccctcagcgc cgaaagggtg      540
cgggggggaca caaggagta cgaatactcc gtggagtgcc aggaagattc ggcctgcccc      600
gccgcggagg agagcctccc catcgaggta atggtgacg ccgtgcataa gctgaagtac      660
gagaactaca ccagctcgtt cttcatccga gacatcatca acccgaccc gcccaaaaat      720
ctgcagctca gcccctgaa gaactccagg caggtggagt gagctggga gtaccccgac      780
acctggtcca ccccgcacag ctacttctcc ctgacattct gcgtgcaggt gcagggcaag      840
agcaagcggg agaagaagga cagggtgttc accgacaaga cgagcgccac cgtgatctgc      900
cgaaagaacg ccagcatctc ggtgcgcgcc caggataggg actattccag ctcctggagc      960
gagtgggcct cggtaccctg cagcggcggc ggggcggcg gcagtaggaa tctgccccgtg     1020
gctacccgg accgggcat gttccccctgc ctccaccaca gccagaacct gctgagggcc     1080
gtgagcaaca tgctgcagaa ggccagacag acgctggagt tctaccccctg cacgagcgag     1140
```

```
gagatcgacc acgaggacat caccaaggat aaaacttcca ccgtcgaggc ctgcctgccc   1200
ttggagctga ccaagaatga atcctgtctg aacagcaggg agacctcgtt tatcaccaat   1260
ggcagctgcc tcgcctccag gaagaccagc ttcatgatgg ccctctgtct gagctccatc   1320
tatgaggacc tgaagatgta ccaggtggag ttcaagacca tgaacgcgaa gctgctgatg   1380
gaccccaaga ggcagatctt cctggatcag aatatgctgg cggtgatcga cgagctcatg   1440
caggccctca atttcaatag cgagacagtg ccccagaagt cctccctgga ggagcccgac   1500
ttctacaaga ccaagatcaa gctgtgtatc ctgctgcacg ccttccggat ccgggccgtc   1560
accatcgacc gggtcatgag ctacctcaat gccagc                             1596
```

<210> SEQ ID NO 28
<211> LENGTH: 1596
<212> TYPE: DNA
<213> ORGANISM: Artificial Sequence
<220> FEATURE:
<223> OTHER INFORMATION: hIL12AB_024

<400> SEQUENCE: 28

```
atgtgccacc agcagctggt gatctcctgg ttctccctgg tgttcctggc ctcgcccctg     60
gtggccatct gggagctgaa gaaggacgtg tacgtcgtgg agctcgactg gtaccccgac    120
gcccctggcg agatggtggt gctgacctgc gacacccag aggaggatgg catcacctgg    180
accctggatc agtcctccga ggtgctgggc tccggcaaga cgctgaccat ccaagtgaag    240
gagttcggtg acgccggaca gtataccctgc cataagggcg gcgaggtcct gtcccacagc    300
ctcctcctcc tgcataagaa ggaggacggc atctggagca ccgacatcct gaaggaccag    360
aaggagccca gaacaagac ctttctgagg tgcgaggcca gaactacag cggccgattc     420 acctgctggt ggctcaccac catatccacc gacctgactt tctccgtcaa gtcctcccgg    480
gggtccagcg accccagggg agtgacctgc ggcgccgcca ccctcagcgc cgagcgggtg    540 cgggggggaca caaggagta cgaatactcc gtcgagtgcc aggaggactc cgcctgcccg    600
gccgccgagg agagcctgcc catcgaggtg atggtcgacg cggtgcacaa gctgaagtac    660
gagaactaca ccagcagttt cttcatcagg gatatcatca gccagatcc cccgaagaat    720 ctgcaactga gccgctgaa aaactcacga caggtggagg tgagctggga gtaccccgac    780
acgtggagca ccccacattc ctacttcagc ctgaccttct gcgtgcaggt ccagggcaag    840
agcaagcggg agaagaagga cagggtgttc acggataaga ccagtgccac cgtgatctgc    900
aggaagaacg cctctattag cgtgagggcc caggatcggt attactcctc gagctggagc    960
gaatgggcct ccgtgccctg cagtgggggg ggtggaggcg ggagcaggaa cctgccgta   1020 gcaacccccg accccgggat gttccctgt ctgcaccact gcagaaacct gctgcgcgcg   1080
gtgagcaaca tgctccaaaa agcccgtcag acctagagt tctacccctg caccagcgaa   1140
gaaatcgacc acgaagacat caccaaggac aaaaccagca ccgtggaggc gtgcctgccg   1200
ctggagctga ccaagaacga gagctgcctc aactccaggg agaccagctt tatcaccaac   1260
ggctcgtgcc tagccagccg gaaaaccagc ttcatgatgg ccctgtgcct gagctccatt   1320
tacgaggacc tgaagatgta tcaggtggag ttcaagacca tgaatgccaa actcctgatg   1380
gaccccaaga ggcagatctt cctggaccag aacatgctcg cggtgatcga tgagctgatg   1440
caggccctga ctttaatag cgagaccgtg ccccagaaaa gcagcctgga ggagccggac   1500
ttctacaaga ccaaaatcaa gctgtgcatc ctgctccacg ccttccgcat ccgggccgtc   1560
accatcgaca gggtgatgag ctacctgaac gccagc                             1596
```

<210> SEQ ID NO 29
<211> LENGTH: 1596
<212> TYPE: DNA
<213> ORGANISM: Artificial Sequence
<220> FEATURE:
<223> OTHER INFORMATION: hIL12AB_025

<400> SEQUENCE: 29

| | |
|---|---:|
| atgtgccatc agcagctggt gatttcctgg ttctccctgg tgttcctggc cagcccctc | 60 |
| gtggcgatct gggagctaaa gaaggacgtg tacgtggtgg agctggactg tacccggac | 120 |
| gcacccggcg agatggtcgt tctgacctgc gatacgccag aggaggacgg catcacctgg | 180 |
| accctcgatc agagcagcga ggtcctgggg agcggaaaga ccctgaccat ccaggtcaag | 240 |
| gagttcggcg acgccggcca gtacacctgc cacaaaggtg gcgaggtcct gagccactcg | 300 |
| ctgctgctcc tgcataagaa ggaggacgga atctggagca cagacatcct gaaagaccag | 360 |
| aaggagccca gaacaagac cttcctgagg tgcgaggcca gaactacag cgggcgcttc | 420 |
| acgtgctggt ggctgaccac catcagcacg gacctcacct tctccgtgaa gagcagccgg | 480 |
| ggatccagcg atccccaagg cgtcacctgc ggcgcgccca cctgagcgc ggagagggtc | 540 |
| aggggcgata taaggagta tgagtacagc gtggagtgcc aggaggacag cgcctgcccg | 600 |
| gccgccgagg agtccctgcc aatcgaagtg atggtcgacg ccgtgcacaa gctgaagtac | 660 |
| gagaactaca ccagcagctt cttcatccgg gatatcatca gcccgatcc cccgaagaac | 720 |
| ctgcagctga gcccctcaa gaacagccgg caggtgagg tgagttggga gtaccccgac | 780 |
| acctggtcaa cgccccacag ctacttctcc ctgacctct gtgtgcaggt gcagggaaag | 840 |
| agcaagaggg agaagaaaga ccgggtcttc accgacaaga ccagcgccac ggtgatctgc | 900 |
| aggaagaacg caagcatctc cgtgagggcc caggacaggt actacagctc cagctggtcc | 960 |
| gaatgggcca gcgtgccctg tagcggcggc ggggcggtg cagccgcaa cctcccagtg | 1020 |
| gccaccccg accccggcat gttcccctgc ctgcaccaca ccagaatct gctgagggcc | 1080 |
| gtgagtaaca tgctgcagaa ggcaaggcaa accctcgaat ctatccctg cacctccgag | 1140 |
| gagatcgacc acgaggatat caccaaggac aagaccagca ccgtcgaggc ctgtctcccc | 1200 |
| ctggagctga ccaagaatga gagctgcctg aacagccggg agaccagctt catcaccaac | 1260 |
| gggagctgcc tggcctccag gaagacctcg ttcatgatgg cgctgtgcct ctcaagcata | 1320 |
| tacgaggatc tgaagatgta ccaggtggag tttaagacga tgaacgccaa gctgctgatg | 1380 |
| gacccgaaga ggcagatctt cctggaccag aacatgctgg ccgtgataga cgagctcatg | 1440 |
| caggccctga acttcaactc cgagaccgtg ccgcagaagt catccctcga ggagcccgac | 1500 |
| ttctataaga ccaagatcaa gctgtgcatc ctgctccacg ccttccggat aagggccgtg | 1560 |
| acgatcgaca gggtgatgag ctaccttaac gccagc | 1596 |

<210> SEQ ID NO 30
<211> LENGTH: 1596
<212> TYPE: DNA
<213> ORGANISM: Artificial Sequence
<220> FEATURE:
<223> OTHER INFORMATION: hIL12AB_026

<400> SEQUENCE: 30

| | |
|---|---:|
| atgtgccacc agcagctcgt gatcagctgg ttctccctgg tgtttctcgc cagcccctg | 60 |
| gtggccatct gggagctgaa gaaggacgtg tacgtggtgg agctggactg taccctgac | 120 |

```
gccccgggggg agatggtcgt gctgacctgc gacacccccg aagaggacgg tatcacctgg    180
accctggacc agtccagcga ggtgctgggc agcggcaaga ccctgactat tcaagtcaag    240
gagttcggag acgccggcca gtacacctgc cacaagggtg agaggtgtt atcacacagc     300 ctgctgctgc tgcacaagaa ggaagacggg atctggagca ccgacatcct gaaggaccag    360
aaggagccca aaacaagac cttcctgcgg tgcgaggcca gaactattc gggccgcttt      420 acgtgctggt ggctgaccac catcagcact gatctcacct tcagcgtgaa gtcctcccgg    480
gggtcgtccg accccagg ggtgacctgc ggggccgcca ccctgtccgc cgagagagtg      540
aggggcgata taaggagta cgagtacagc gttgagtgcc aggaagatag cgcctgtccc    600
gccgccgagg agagcctgcc catcgaggtg atggtggacg ccgtccacaa gctgaagtat   660
gagaactaca cctcaagctt cttcatcagg gacatcatca aacccgatcc gcccaagaat   720
ctgcagctga agcccctgaa aaatagcagg caggtggagg tgagctggga gtaccccgac   780
acctggtcca ccccccatag ctatttctcc ctgacgttct gcgtgcaggt gcaagggaag    840
agcaagcggg agaagaagga ccgggtgttc accgacaaga cctccgccac cgtgatctgt    900
aggaagaacg cgtcgatctc ggtcagggcc caggacaggt attacagcag cagctggagc   960
gagtgggcga gcgtgccctg ctcggccggc ggcggcggcg ggagcagaaa tctgcccgtg   1020
gccaccccag accccggaat gttccctgc ctgcaccatt cgcagaacct cctgagggcc    1080
gtgagcaaca tgctgcagaa ggcccgccag acgctgagt tctaccccctg cacgagcgag   1140 gagatcgacc acgaagacat caccaaggac aaaaccagca ccgtggaggc ctgcctgccc   1200
ctggagctga ccaaaaacga atcctgcctc aacagccggg agaccagctt catcaccaac   1260
ggcagctgcc tggccagccg aaagacctcc ttcatgatgg ccctctgcct gagcagcatc   1320
tatgaggatc tgaagatgta tcaggtggag ttcaagacca tgaatgccaa gctgctgatg   1380
gaccccaaga ggcagatatt cctggaccag aatatgctgg ccgtgatcga cgagctgatg   1440
caggccctga acttcaacag cgagaccgtc ccccagaagt ccagcctgga ggagccggac   1500
ttttacaaaa cgaagatcaa gctgtgcata ctgctgcacg ccttcaggat ccgggccgtg   1560
acaatcgaca gggtgatgtc ctacctgaac gccagc                              1596
```

<210> SEQ ID NO 31
<211> LENGTH: 1596
<212> TYPE: DNA
<213> ORGANISM: Artificial Sequence
<220> FEATURE:
<223> OTHER INFORMATION: hIL12AB_027

<400> SEQUENCE: 31

```
atgtgtcacc agcagctggt gatcagctgg ttctccctgg tgttcctggc cagcccctg     60 gtggccatct gggagctcaa gaaggacgtc tacgtcgtgg agctggattg gtaccccgac   120
gctcccgggg agatggtggt gctgacctgc gacacccccg aagaggacgg catcacctgg   180
acgctggacc agagctcaga ggtgctggga agcggaaaga cactgaccat ccaggtgaag   240
gagttcgggg atgccgggca gtatacctgc cacaagggcg gcgaagtgct gagccattcc   300
ctgctgctgc tgcacaagaa ggaggacggc atatggtcca ccgacatcct gaaggatcag   360
aaggagccga gaataaaac cttcctgagg tgcgaggcca gaattacag cggccgattc     420 acctgctggt ggctgaccac catcagcacc gacctgacct tcagtgtgaa gtcctcacgg   480
ggcagctcag atccccaggg cgtgacctgc ggggccgcga cactcagcgc cgagcgggtg   540
aggggtgata caaggagta cgagtattct gtggagtgcc aggaagactc cgcctgtccc   600
```

```
gccgccgagg agtccctgcc catcgaggtg atggtggacg ccgtgcataa actgaagtac    660
gagaactaca cctccagctt cttcatccgg gatataatca agcccgaccc tccgaaaaac    720
ctgcagctga agccccttaa aaacagccgg caggtggagg tgagctggga gtaccccgac    780
acctggagca ccccccatag ctatttcagc ctgaccttct gcgtgcaggt gcaggggaag    840
tccaagcgcg agaaaaagga ccgggtgttc accgacaaga cgagcgccac cgtgatctgc    900
cggaagaacg ccagtataag cgtaagggcc caggataggt actacagctc cagctggtcg    960
gagtgggcct ccgtgccctg ttccggcggc ggggggggtg gcagcaggaa cctccccgtg   1020
gccacgccgg accccggcat gttcccgtgc ctgcaccact cccaaaacct cctgcgggcc   1080
gtcagcaaca tgctgcaaaa ggcgcggcag accctggagt tttaccccctg tacctccgaa   1140 gagatcgacc acgaggatat caccaaggat aagacctcca ccgtggaggc ctgtctcccc   1200
ctggagctga ccaagaacga gagctgtctt aacagcagag agacctcgtt cataacgaac   1260
ggctcctgcc tcgcttccag gaagacgtcg ttcatgatgg cgctgtgcct gtccagcatc   1320
tacgaggacc tgaagatgta tcaggtcgag ttcaaaacca tgaacgccaa gctgctgatg   1380
gaccccaaga ggcagatctt cctggaccag aacatgctcg ccgtgatcga cgagctgatg   1440
caggccctga acttcaacag cgaaaccgtg ccccagaagt caagcctgga ggagccggac   1500
ttctataaga ccaagatcaa gctgtgtatc ctgctcacgc ttttcgtat ccgggccgtg   1560 accatcgaca gggttatgtc gtacttgaac gccagc                             1596
```

<210> SEQ ID NO 32
<211> LENGTH: 1596
<212> TYPE: DNA
<213> ORGANISM: Artificial Sequence
<220> FEATURE:
<223> OTHER INFORMATION: hIL12AB_028

<400> SEQUENCE: 32

```
atgtgccacc aacagctcgt gatcagctgg ttcagcctgg tgttcctggc cagcccgctg     60
gtggccatct gggagctgaa gaaggacgtg tacgtggtgg agctggactg gtaccccgac    120 gccccggcg agatggtggt cctgacctgc gacacgccgg aagaggacgg catcacctgg    180
accctggatc agtccagcga ggtgctgggc tccggcaaga ccctgaccat tcaggtgaag    240
gagttcggcg acgccggtca gtacacctgc cacaagggcg cgaggtgct gagccacagc    300 ctactgctcc tgcacaaaaa ggaggatgga atctggtcca ccgacatcct caaggaccag    360
aaggagccga gaacaagac gttcctccgg tgcgaggcca gaactacag cggcaggttt    420 acctgctggt ggctgaccac catcagcacc gacctgacat tttccgtgaa gagcagccgc    480
ggcagcagcg atccccaggg cgtgacctgc ggggcggcca cctgtccgc cgagcgtgtg    540 aggggcgaca acaaggagta cgagtacagc gtggaatgcc aggaggacag cgcctgtccc    600
gccgccgagg agagcctgcc aatcgaggtc atggtgacg ccgtgcacaa gctgaagtac    660
gagaactaca cgagcagctt cttcatcagg gacatcatca aaccggaccc gcccaagaac    720
ctgcagctga aacccttgaa aaacagcagg caggtggaag tgtcttggga gtaccccgac    780
acctggtcca ccccccacag ctactttagc ctgaccttct gtgtgcaggt ccagggcaag    840
tccaagaggg agaagaagga cagggtgttc accgacaaaa ccagcgccac cgtgatctgc    900
aggaagaacg cctccatcag cgtgcgggcc caggacaggt attacagctc gtcgtggagc    960
gagtgggcca gcgtgccctg ctccggggga ggcggcggcg gaagccggaa tctgcccgtg   1020
```

| | |
|---|---|
| gccacccccg atcccggcat gttcccgtgt ctgcaccaca gccagaacct gctgcgggcc | 1080 |
| gtgagcaaca tgctgcagaa ggcccgccaa accctggagt tctaccctg tacaagcgag | 1140 |
| gagatcgacc atgaggacat taccaaggac aagaccagcc cgtggaggc ctgcctgccc | 1200 |
| ctcgagctca caaagaacga atcctgcctg aatagccgcg agaccagctt tatcacgaac | 1260 |
| gggtcctgcc tcgccagccg gaagacaagc ttcatgatgg ccctgtgcct gagcagcatc | 1320 |
| tacgaggacc tgaaaatgta ccaagtggag ttcaaaacga tgaacgccaa gctgctgatg | 1380 |
| gaccccaagc gccagatctt cctggaccag aacatgctgg ccgtcatcga cgagctcatg | 1440 |
| caggccctga acttcaacag cgagaccgtg ccccagaaga gcagcctgga ggagcccgac | 1500 |
| ttctacaaga cgaagatcaa gctctgcatc ctgctgcacg cttttccgca tccgcgcggtg | 1560 |
| accatcgacc gggtgatgag ctacctcaac gccagt | 1596 |

<210> SEQ ID NO 33
<211> LENGTH: 1596
<212> TYPE: DNA
<213> ORGANISM: Artificial Sequence
<220> FEATURE:
<223> OTHER INFORMATION: hIL12AB_029

<400> SEQUENCE: 33

| | |
|---|---|
| atgtgccacc aacagctggt gatcagctgg ttcagcctgg tgtttctggc ctcccctctg | 60 |
| gtggccatct gggagctgaa gaaggacgtg tacgtggtgg agctggactg gtaccctgac | 120 |
| gcccccggcg aaatggtggt gctgacgtgc gacacccccg aggaggatgg catcacctgg | 180 |
| accctggacc aaagcagcga ggtcctcgga agcggcaaga ccctcactat ccaagtgaag | 240 |
| gagttcgggg atgcgggcca gtacacctgc cacaagggcg gcgaggtgct gtctcatagc | 300 |
| ctgctgctcc tgcataagaa ggaagacggc atctggagca ccgacatact gaaggatcag | 360 |
| aaggagccca gaacaagac cttcctgagg tgcgaggcca gaactactc cgggcgcttc | 420 |
| acctgttggt ggctgaccac catctccacc gacctgacct tcagcgtgaa gagcagcagg | 480 |
| gggagcagcg accccagg ggtgacctgc ggagccgcga ccttgtcggc cgagcgggtg | 540 |
| aggggcgaca taaggagta cgagtactcg gtcgaatgcc aggaggactc cgcctgcccc | 600 |
| gccgccgagg agtccctccc catcgaagtg atggtggacg ccgtccacaa gctgaagtac | 660 |
| gagaactaca ccagcagctt cttcatacgg gatatcatca gccccgaccc ccgaagaac | 720 |
| ctgcagctga accccttgaa gaactccagg caggtggagg tgagctggga gtaccccgac | 780 |
| acctggtcca ccccgcactc atacttcagc ctgaccttct gtgtacaggt ccagggcaag | 840 |
| agcaagaggg aaaagaagga tagggtgttc accgacaaga cctccgccac ggtgatctgt | 900 |
| cggaaaaacg ccagcatctc cgtgcgggcc caggacaggt actattccag cagctggagc | 960 |
| gagtgggcct ccgtcccctg ctccggcggc ggtggcgggg gcagcaggaa cctcccgtg | 1020 |
| gccacccccg atcccgggat gttcccatgc ctgcaccaca gccaaaacct gctgagggcc | 1080 |
| gtctccaata tgctgcagaa ggcgaggcag accctggagt tctaccctg tacctccgag | 1140 |
| gagatcgacc acgaggatat caccaaggac aagacctcca cggtcgaggc gtgcctgccc | 1200 |
| ctggagctca cgaagaacga gagctgcctt aactccaggg aaacctcgtt tatcacgaac | 1260 |
| ggcagctgcc tggcgtcacg gaagacctcc tttatgatgg ccctatgtct gtcctcgatc | 1320 |
| tacgaggacc tgaagatgta ccaggtggag ttcaagacca tgaacgccaa gctgctgatg | 1380 |
| gatcccaaga ggcagatttt cctggaccag aacatgctgg ccgtgattga cgagctgatg | 1440 |
| caggcgctga acttcaacag cgagacagtg ccgcagaaga gctccctgga ggagccggac | 1500 |

-continued

```
ttttacaaga ccaagataaa gctgtgcatc ctgctccacg ccttcagaat acgggccgtc    1560
accatcgata gggtgatgtc ttacctgaac gcctcc                              1596
```

<210> SEQ ID NO 34
<211> LENGTH: 1596
<212> TYPE: DNA
<213> ORGANISM: Artificial Sequence
<220> FEATURE:
<223> OTHER INFORMATION: hIL12AB_030

<400> SEQUENCE: 34

```
atgtgccacc agcagctggt gattagctgg tttagcctgg tgttcctggc aagcccctg     60 gtggccatct gggaactgaa aaaggacgtg tacgtggtcg agctggattg taccccgac    120 gcccccggcg aaatggtggt gctgacgtgt gataccccg aggaggacgg gatcacctgg    180
accctggatc agagcagcga ggtgctgggg agcgggaaga ccctgacgat ccaggtcaag    240
gagttcggcg acgctgggca gtacacctgt cacaagggcg gggaggtgct gtcccactcc    300
ctgctgctcc tgcataagaa agaggacggc atctggtcca ccgacatcct caaggaccag    360
aaggagccca gaacaagac cttcctgcgg tgtgaggcga agaactacag cggccgtttc    420
acctgctggt ggctgacgac aatcagcacc gacttgacgt tctccgtgaa gtcctccaga    480
ggcagctccg accccaagg ggtgacgtgc ggcgcggcca ccctgagcgc cgagcgggtg    540
cggggggaca acaaggagta cgagtactcc gtggagtgcc aggaggacag cgcctgtccc    600
gcagccgagg agtccctgcc catcgaagtc atggtggacg ccgtccacaa gctgaagtac    660
gagaactaca ccagcagctt cttcatccgc gatatcatca gcccgatccc cccaaaaaac    720
ctgcaactga gccgctgaa gaatagcagg caggtggagg tgtcctggga gtacccggac    780
acctggagca cgccccacag ctatttcagc ctgacctttt gcgtgcaggt ccaggggaag    840
agcaagcggg agaagaagga ccgcgtgttt acggacaaaa ccagcgccac cgtgatctgc    900
aggaagaacg ccagcatcag cgtgagggcc aggacaggt actacagcag ctcctggagc    960
gagtgggcct ccgtgccctg ttccggaggc ggcggggggcg gttccccgaa cctcccggtg   1020
gccacccccg acccggcat gttccccgtgc ctgcaccact cacagaatct gctgagggcc   1080
gtgagcaata tgctgcagaa ggcaaggcag accctggagt tttatccctg caccagcgag   1140
gagatcgacc acgaagacat caccaaggac aagaccagca cagtggaggc ctgcctgccc   1200
ctggaactga ccaagaacga gtcctgtctg aactcccggg aaaccagctt cataaccaac   1260
ggctcctgtc tcgccagcag gaagaccagc ttcatgatgg ccctgtgcct cagctccatc   1320
tacgaggacc tcaagatgta ccaggttgag ttcaagacca tgaacgccaa gctcctgatg   1380
gaccccaaga ggcagatctt cctggaccag aatatgctgg ccgtgatcga tgagttaatg   1440
caggcgctga acttcaacag cgagacggtg ccccaaaagt cctcgctgga ggagcccgac   1500
ttctacaaga ccaagatcaa gctgtgcatc ctcctgcacg ccttccgaat ccgggccgta   1560
accatcgaca gggtgatgag ctatctcaac gcctcc                             1596
```

<210> SEQ ID NO 35
<211> LENGTH: 1596
<212> TYPE: DNA
<213> ORGANISM: Artificial Sequence
<220> FEATURE:
<223> OTHER INFORMATION: hIL12AB_031

<400> SEQUENCE: 35

| | |
|---|---:|
| atgtgccacc agcagctcgt gatcagctgg ttctcgcttg tgttcctggc ctcccccctc | 60 |
| gtcgccatct gggagctgaa gaaagacgtg tacgtggtgg agctggactg gtatcccgac | 120 |
| gccccggggg agatggtggt gctgacctgc gacacccccgg aagaggacgg catcacctgg | 180 |
| acgctcgacc agtcgtccga agtgctgggg tcgggcaaga ccctcaccat ccaggtgaag | 240 |
| gagttcggag acgccggcca gtacacctgt cataagggggg gggaggtgct gagccacagc | 300 |
| ctcctgctcc tgcacaaaaa ggaggacggc atctggagca ccgatatcct caaggaccag | 360 |
| aaggagccca gaacaagac gttcctgagg tgtgaggcca gaactacag cgggcggttc | 420 |
| acgtgttggt ggctcaccac catctccacc gacctcacct tctccgtgaa gtcaagcagg | 480 |
| ggcagctccg acccccaagg cgtcacctgc ggcgccgcca cctgagcgc cgagagggtc | 540 |
| aggggggata caaggaata cgagtacagt gtggagtgcc aagaggatag cgcctgtccc | 600 |
| gccgccaag agagcctgcc catcgaagtg atggtggacg ccgtgcacaa gctgaagtac | 660 |
| gagaactaca cctccagctt cttcatcagg atatcatca agcccgatcc ccccaagaac | 720 |
| ctgcagctga agcccctgaa gaacagcagg caggtggagg tgagctggga gtatcccgac | 780 |
| acgtggagca ccccgcacag ctacttctcg ctgaccttct gcgtgcaggt gcaagggaag | 840 |
| tccaagaggg agaagaagga tagggtgttc accgacaaaa cgagcgccac cgtgatctgc | 900 |
| cggaagaatg ccagcatctc tgtgagggcc caggacaggt actattccag ctcctggtcg | 960 |
| gagtgggcca gcgtgccctg tagcggcggg ggcgggggcg gcagcaggaa cctcccggtt | 1020 |
| gccacccccg acccccggcat gttttccgtgc ctgcaccact cgcaaaacct gctgcgcgcg | 1080 |
| gtctccaaca tgctgcaaaa agcgcgccag acgctggagt ctaccccctg caccagcgag | 1140 |
| gagatcgatc atgaagatat caccaaagac aagacctcga ccgtggaggc ctgcctgccc | 1200 |
| ctggagctca ccaagaacga aagctgcctg aacagcaggg agacaagctt catcaccaac | 1260 |
| ggcagctgcc tggcctcccg gaagaccagc ttcatgatgg ccctgtgcct gtccagcatc | 1320 |
| tacgaggatc tgaagatgta ccaagtggag tttaagacca tgaacgccaa gctgttaatg | 1380 |
| gaccccaaaa ggcagatctt cctggatcag aacatgctgg ccgtcatcga cgagctgatg | 1440 |
| caagccctga acttcaacag cgagacggtg ccccagaaga gcagcctcga ggagcccgac | 1500 |
| ttctataaga ccaagataaa gctgtgcatt ctgctgcacg ccttcagaat cagggccgtg | 1560 |
| accatcgata gggtgatgag ctacctgaac gccagc | 1596 |

<210> SEQ ID NO 36
<211> LENGTH: 1596
<212> TYPE: DNA
<213> ORGANISM: Artificial Sequence
<220> FEATURE:
<223> OTHER INFORMATION: hIL12AB_032

<400> SEQUENCE: 36

| | |
|---|---:|
| atgtgtcacc agcagctggt gatttcctgg ttcagtctgg tgtttcttgc cagccccctg | 60 |
| gtggccatct gggagctgaa gaaagacgta tacgtcgtgg agctggactg gtatcccgac | 120 |
| gctcccggcg agatggtggt cctcacctgc gacacccccag aggaggacgg catcacctgg | 180 |
| accctggacc agagctccga ggtcctgggc agcggtaaga ccctcaccat ccaggtgaag | 240 |
| gagtttggtg atgccgggca gtatacctgc cacaagggcg gcgaggtgct gtcccacagc | 300 |
| ctcctgttac tgcataagaa ggaggatggc atctggagca ccgacatcct caaggaccag | 360 |
| aaagagccca gaacaagac ctttctgcgg tgcgaggcga aaaattactc cggccggttc | 420 |
| acctgctggt ggctgaccac catcagcacg gacctgacgt tctccgtgaa gtcgagcagg | 480 |

```
gggagctccg atccccaggg cgtgacctgc ggcgcggcca ccctgagcgc cgagcgcgtc      540
cgcggggaca ataaggaata cgaatatagc gtggagtgcc aggaggacag cgcctgcccc      600
gcggccgagg agagcctccc gatcgaggtg atggtggatg ccgtccacaa gctcaaatac      660
gaaaactaca ccagcagctt cttcattagg gacatcatca agcccgaccc ccccaaaaac      720
ctgcagctga gcccctgaa gaacagccgc caggtcgagg tgtcatggga gtacccagac       780
acctggagca ccccccactc ctacttcagc ctgaccttct gcgtccaggt gcagggaaag      840
tccaaacggg agaagaagga tagggtcttt accgataaga cgtcggccac cgtcatctgc      900
aggaagaacg ccagcataag cgtgcgggcg caggatcggt actacagctc gagctggtcc      960
gaatgggcct ccgtgccctg tagcggaggg ggtggcgggg gcagcaggaa cctgcccgtg     1020
gccaccccgg acccgggcat gtttccctgc ctgcatcaca gtcagaacct gctgagggcc     1080
gtgagcaaca tgctccagaa ggcccgccag accctggagt tttacccctg caccagcgaa     1140
gagatcgatc acgaagacat caccaaagac aagacctcca ccgtggaggc ctgtctgccc     1200
ctggagctga ccaagaacga gagctgtctg aacagcaggg agacctcctt catcaccaac     1260
ggctcctgcc tggcatcccg gaagaccagc ttcatgatgg ccctgtgtct gagctctatc     1320
tacgaggacc tgaagatgta ccaggtcgag ttcaagacca tgaacgccaa gctgctgatg     1380
gaccccaagc gacagatatt cctggaccag aacatgctcg ccgtgatcga tgaactgatg     1440
caagccctga acttcaatag cgagaccgtg ccccagaaaa gcagcctgga ggagcccgac     1500
ttctacaaga ccaagatcaa actgtgcata ctgctgcacg cgttcaggat ccgggccgtc     1560
accatcgacc gggtgatgtc ctatctgaat gccagc                              1596

<210> SEQ ID NO 37
<211> LENGTH: 1596
<212> TYPE: DNA
<213> ORGANISM: Artificial Sequence
<220> FEATURE:
<223> OTHER INFORMATION: hIL12AB_033

<400> SEQUENCE: 37
atgtgccacc agcagctcgt gattagctgg ttttcgctgg tgttcctggc cagccctctc       60
gtggccatct gggagctgaa aaaagacgtg tacgtggtgg agctggactg gtacccggac      120
gcccccggcg agatggtggt gctgacgtgc gacacccccg aagaggacgg catcacctgg      180
accctggacc agtcatccga ggtcctgggc agcggcaaga cgctcaccat ccaggtgaag      240
gagttcggcg acgccggcca gtacacatgc cataagggcg ggaggtgct gagccacagc     300 ctgctcctcc tgcacaagaa ggaggatggc atctggtcta cagacatcct gaaggaccag      360
aaagagccca gaacaagac cttcctccgg tgcgaggcca gaactactc cgggcggttt       420 acttgttggt ggctgaccac catcagcacc gacctcacct tcagcgtgaa gagctcccga      480
gggagctccg accccagg ggtcacctgc ggcgccgcca ccctgagcgc cgagcgggtg       540
aggggcgaca caaggagta tgaatacagc gtggaatgcc aagaggacag cgcctgtccc       600
gcggccgagg aaagcctgcc catcgaggtg atggtggacg ccgtccacaa actcaagtac      660
gagaactaca ccagcagttt cttcattcgc gacatcatca gccggaccc ccccaaaaac      720 ctgcagctca aaccctgaa gaacagcagg caggtggagg tcagctggga gtacccggac      780
acctggagca ccccccatag ctacttcagc ctgaccttct gcgtgcaggt gcagggcaag      840
agcaaacgcg agaagaagga ccgggtgttt accgacaaga ccagcgccac ggtgatctgc      900
```

```
cgaaagaatg caagcatctc cgtgagggcg caggaccgct actactctag cagctggagc    960
gagtgggcca gcgtgccctg cagcggtggc ggcggaggcg gcagccgtaa cctccccgtg   1020
gccaccccg  accccggcat gttcccgtgt ctgcaccact cccagaacct gctgagggcc   1080
gtcagcaata tgctgcagaa ggcccggcag acgctggagt tctacccctg cacctccgag   1140
gagatcgacc atgaggacat taccaaggac aagacgagca ctgtggaggc ctgcctgccc   1200
ctggagctca ccaaaaacga gagctgcctg aatagcaggg agacgtcctt catcaccaac   1260
ggcagctgtc tggccagcag gaagaccagc ttcatgatgg ccctgtgcct ctcctccata   1320
tatgaggatc tgaagatgta ccaggtggag ttcaagacca tgaacgccaa gctgctgatg   1380
gatcccaaga ggcagatctt cctggaccag aatatgctgg ccgtgattga cgagctgatg   1440
caggccctga actttaatag cgagaccgtc ccccagaaga gcagcctgga ggagcccgac   1500
ttctataaga ccaagatcaa gctgtgcata ctgctgcacg cgtttaggat aagggccgtc   1560
accatcgaca gggtgatgag ctacctgaat gccagc                            1596
```

<210> SEQ ID NO 38
<211> LENGTH: 1596
<212> TYPE: DNA
<213> ORGANISM: Artificial Sequence
<220> FEATURE:
<223> OTHER INFORMATION: hIL12AB_034

<400> SEQUENCE: 38

```
atgtgccacc aacagctggt gatctcctgg ttcagcctgg tgttcctcgc cagcccctg     60
gtggccatct gggagctgaa gaaagacgtg tacgtggtgg agctggactg gtatcccgac   120
gcccccggcg agatggtcgt gctgacctgc gacacccccg aggaggacgg catcacctgg   180
accctggatc agtcctccga ggtgctgggc agcgggaaga ccctgaccat ccaggtgaaa   240
gagttcggag atgccggcca gtatacctgt cacaaggggg gtgaggtgct gagccatagc   300
ctcttgcttc tgcacaagaa ggaggacggc atctggtcca ccgacatcct caaggaccaa   360
aaggagccga gaataaaac gttcctgagg tgcgaagcca agaactattc cggacggttc   420
acctgctggt ggctgaccac catcagcacc gacctcacct tctccgtaaa gtcaagcagg   480
ggcagctccg accccagggg cgtgacctgc ggagccgcca cctgagcgc agagagggtg   540
aggggcgaca caaggagta cgaatactcc gtcgagtgcc aggaggacag cgcctgcccc   600
gccgccgagg aaagtctgcc catcgaggtg atggtggacg ccgtgcacaa gctcaaatac   660
gagaactaca ccagcagctt cttcatccgg gatatcatca gcccgaccc tccaaagaat   720
ctgcagctga aacccttaa gaacagcagg caggtggagg tcagctggga gtaccccgac   780
acctggagca cgccccactc ctactttagc ctgaccttt gcgtgcaggt caggggaaa   840
agcaagcggg agaagaagga cagggtgttc accgataaga cctccgctac cgtgatctgc   900
aggaagaacg cctcaatcag cgtgagggcc caggatcggt actactccag ctcctggagc   960
gagtgggcca gcgtgccctg ctctggcggt ggcggcgggg gcagccggaa cctgccggtg   1020
gccactcccg acccgggcat gttcccgtgc ctccaccatt cccagaacct gctgcgggcc   1080
gtgtccaata tgctccagaa ggcaaggcag accctggagt tctaccctg caccagcgag   1140
gagatcgatc acgaggacat caccaaagac aaaaccagca cggtcgaggc ctgcctgccc   1200
ctggaactca ccaagaacga aagctgtctc aacagccgcg agaccagctt cataaccaac   1260
ggttcctgtc tggcctcccg caagaccagc tttatgatgg ccctctgtct gagctccatc   1320
tatgaagacc tgaaaatgta ccaggtggag ttcaaaacca tgaacgccaa gcttctgatg   1380
```

```
gaccccaaga ggcagatctt cctggatcag aacatgctgg ccgtgatcga cgagctgatg    1440
caggccctga actttaactc cgagaccgtg ccccagaaaa gcagcctgga agagcccgat    1500
ttctacaaaa cgaagatcaa gctgtgcatc ctgctgcacg ccttccggat ccgtgcggtg    1560
accatcgata gggtgatgag ctacctgaac gccagc                              1596
```

<210> SEQ ID NO 39
<211> LENGTH: 1596
<212> TYPE: DNA
<213> ORGANISM: Artificial Sequence
<220> FEATURE:
<223> OTHER INFORMATION: hIL12AB_035

<400> SEQUENCE: 39

```
atgtgccacc aacagctggt aatcagctgg ttcagcctgg ttttcctcgc gtcgcccctg      60
gtggccatct gggagttaaa gaaggacgtg tacgtggtgg agctggattg taccccgac     120 gccccgggcg agatggtcgt gctcacctgc gataccccg aggaggacgg gatcacctgg     180
accctggacc aatccagcga ggtgctgggc agcggcaaga ccctgaccat acaggtgaag    240
gaatttgggg acgccgggca gtacacctgc cacaagggcg gggaagtgct gtcccactcc    300
ctcctgctgc tgcataagaa ggaggacggc atctggagca ccgacatcct gaaggaccaa    360
aaggagccca gaacaagac cttcctgagg tgcgaggcca aaaactattc cggccgcttt    420
acctgttggt ggctgaccac catctccacc gatctgacct tcagcgtgaa gtcgtctagg    480
ggctcctccg accccagggg cgtaacctgc ggcgccgcga ccctgagcgc cgagagggtg    540
cggggcgata caaagagta cgagtactcg gtggagtgcc aggaggacag cgcctgtccg    600
gcggccgagg agagcctgcc catcgaggtg atggtggacg ccgtccacaa gctgaagtac    660
gagaactaca ccagttcgtt cttcatcagg gacatcatca gccggacccc cccaagaac    720 ctccagctga agcccctgaa gaacagcagg caggtggaag tgtcctggga gtatcccgac    780
acctggagca ccccccacag ctacttcagc ctgacctttt gcgtgcaggt gcagggcaaa    840
agcaagaggg aaaagaagga ccgggtgttc accgataaga cgagcgccac cgttatctgc    900
aggaagaacg cctccataag cgtgagggcg caggaccgtt actacagcag cagctggagt    960
gagtgggcaa gcgtgccctg tagcggcggg gcgggggcg gtcccgcaa cctccccgtc    1020 gccaccccg acccaggcat gtttccgtgc ctgcaccaca gcagaaacct gctgcgggcc    1080
gttagcaaca tgctgcagaa ggccaggcag accctcgagt tctatccctg cacatctgag    1140
gagatcgacc acgaagacat cactaaggat aagacctcca ccgtggaggc ctgtctgccc    1200
ctcgagctga ccaagaatga atcctgcctg aacagccgag agaccagctt tatcaccaac    1260
ggctcctgcc tggccagcag gaagacctcc ttcatgatgg ccctgtgcct ctccagcatc    1320
tacgaggatc tgaagatgta ccaggtagag ttcaagacga tgaacgccaa gctcctgatg    1380
gaccccaaga ggcagatatt cctggaccag aacatgctgg cggtgatcga cgagctgatg    1440
caggccctga atttcaacag cgagacggtg ccacagaagt ccagcctgga ggagccagac    1500
ttctacaaga ccaagatcaa actgtgcatc ctcctgcacg cgttcaggat ccgcgccgtc    1560
accatagaca gggtgatgag ttatctgaac gccagc                              1596
```

<210> SEQ ID NO 40
<211> LENGTH: 1596
<212> TYPE: DNA
<213> ORGANISM: Artificial Sequence
<220> FEATURE:

<223> OTHER INFORMATION: hIL12AB_036

<400> SEQUENCE: 40

```
atgtgccatc agcagctggt aatcagctgg tttagcctgg tgttcctggc cagcccactg        60
gtggccatct gggagctgaa gaaggacgtg tacgtggtgg aactggactg gtaccccgac       120
gcccctggcg agatggtggt actgacctgt gacaccccgg aggaagacgg tatcacctgg       180
accctggatc agagctccga ggtgctgggc tccggcaaga cactgaccat ccaagttaag       240
gaatttgggg acgccggcca gtacacctgc cacaagggg gcgaggtgct gtcccactcc       300
ctgctgcttc tgcataagaa ggaggatggc atctggtcca ccgacatact gaaggaccag       360
aaggagccca gaataagac cttcctgaga tgcgaggcca gaactactc gggaaggttc        420
acctgctggt ggctgaccac catcagcacc gacctgacct ctccgtgaa gagctcccgg        480
ggcagctccg accccaggg cgtaacctgt ggggccgcta ccctgtccgc cgagagggtc        540
cggggcgaca caaggaata cgagtacagc gtggagtgcc aggaggactc cgcctgcccc        600
gccgccgagg agtcgctgcc catagaggtg atggtggacg ccgtgcacaa gctcaagtac       660
gagaattaca ccagcagctt ctttatcagg acataatta gccggaccc cccaaagaat        720
ctgcagctga agccctgaa gatagccgg caggtggaag tgtcctggga gtaccccgac         780
acctggagca ccccccactc ctatttctca ctgacattct gcgtgcaggt gcaagggaaa       840
agcaagaggg agaagaagga tgggtgttc accgacaaga caagcgccac cgtgatctgc        900
cgaaaaaatg ccagcatcag cgtgagggcc caggatcggt attacagcag ctcctggagc       960
gagtgggcca gcgtgccctg ttccggcggg gagggggcg ctcccggaa cctgccggtg        1020
gccaccccg acctggcat gttcccctgc ctgcatcaca ccagaacct gctccgggcc        1080
gtgtcgaaca tgctgcagaa ggcccggcag accctcgagt tttaccctg caccagcgaa       1140
gagatcgacc acgaagacat aaccaaggac aagaccagca cggtggaggc ctgcctgccc       1200
ctggagctta ccaaaaacga gtcctgcctg aacagccggg aaaccagctt cataacgaac       1260
gggagctgcc tggcctccag gaagaccagc ttcatgatgg cgctgtgtct gtccagcata       1320
tacgaggatc tgaagatgta tcaggtggaa ttcaaaacta tgaatgccaa gctcctgatg       1380
gaccccaaga ggcagatctt cctggaccag aacatgctag ccgtgatcga cgagctgatg       1440
caggccctca acttcaactc ggagacggtg ccccagaagt ccagcctcga ggagcccgac       1500
ttctacaaga ccaagatcaa gctgtgcata ctgctgcatg ccttcaggat aagggcggtg       1560
actatcgaca gggtcatgtc ctacctgaac gccagc                                1596
```

<210> SEQ ID NO 41
<211> LENGTH: 1596
<212> TYPE: DNA
<213> ORGANISM: Artificial Sequence
<220> FEATURE:
<223> OTHER INFORMATION: hIL12AB_037

<400> SEQUENCE: 41

```
atgtgccacc aacaactggt gatcagctgg ttctcccctgg tgttcctggc cagcccctg        60
gtggccatct gggagctcaa aaagacgtg tacgtggtgg agctcgattg gtacccagac        120
gcgccggggg aaatggtggt gctgacctgc gacacccag aggaggatgg catcacgtgg        180
acgctggatc agtccagcga ggtgctgggg agcggcaaga cgctcaccat ccaggtgaag       240
gaatttggcg acgcgggcca gtatacctgt cacaagggcg cgaggtgct gagccactcc        300
ctgctgctgc tgcacaagaa ggaggatggg atctggtcaa ccgatatcct gaaagaccag       360
```

```
aaggagccca agaacaagac cttcctgcgc tgcgaggcca agaactatag cggcaggttc    420
acctgctggt ggctgaccac catcagcacc gacctgacct tcagcgtgaa atcctccagg    480
ggcagcagcg accccaggg cgtgacctgc ggtgccgcca cgctctccgc cgagcgagtg     540
aggggtgaca caaggagta cgagtacagc gtggaatgtc aggaggacag cgcctgtccc     600
gccgccgagg agtcgctgcc catcgaggtg atggtcgacg cggtgcacaa gctcaaatac    660
gagaattaca ccagcagctt cttcatcagg gacatcatca agcccgaccc ccccaagaac    720
ctgcagctga agcccttgaa gaacagcagg caggtggagg tgagctggga gtacccggac    780
acctggagca cccccactc ctacttcagc ctgacgttct gtgtgcaggt gcaggggaag     840
tccaagaggg agaagaagga ccgggtgttc accgacaaga ccagcgccac cgtgatatgc    900
cgcaagaacg cgtccatcag cgttcgcgcc caggaccgct actacagcag ctcctggtcc    960
gaatgggcca gcgtgccctg cagcggtgga ggggcgggg gctccaggaa tctgccggtg    1020 gccaccccg accccgggat gttcccgtgt ctgcatcact cccagaacct gctgcgggcc   1080
gtgagcaata tgctgcagaa ggccaggcag acgctcgagt tctacccctg cacctccgaa   1140
gagatcgacc atgaggacat caccaaggac aagaccagca ccgtggaggc ctgcctcccc   1200
ctggagctga ccaaaaacga gagctgcctg aactccaggg agaccagctt tataaccaac   1260
ggcagctgcc tcgcctccag gaagacctcg tttatgatgg ccctctgcct gtccagcatc   1320
tacgaggacc tgaagatgta ccaggtggag ttcaagacca tgaacgcgaa gttgctcatg   1380
gaccccaaga gcagatctt cctggaccag aacatgctcg cggtgatcga cgagctgatg   1440
caagccctga acttcaacag cgagaccgtg ccccagaaga gcagcctgga agagcccgac   1500
ttctacaaga ccaagatcaa gctgtgcatc ctgctgcacg ccttccggat ccgggccgtg   1560
accatcgaca gggtgatgag ctacctcaac gcctcc                            1596
```

<210> SEQ ID NO 42
<211> LENGTH: 1596
<212> TYPE: DNA
<213> ORGANISM: Artificial Sequence
<220> FEATURE:
<223> OTHER INFORMATION: hIL12AB_038

<400> SEQUENCE: 42

```
atgtgccacc agcagctcgt gatcagctgg ttctccctcg tcttcctggc ctccccgctg     60
gtggccatct gggagctgaa gaaggacgtg tacgtggtgg agctggactg gtatcccgac    120
gcccccggcg agatggtggt gctgacgtgc gacacaccag aagaggacgg gatcacatgg    180
accctggatc agtcgtccga ggtgctgggg agcggcaaga ccctcaccat ccaagtgaag    240
gagttcgggg acgccggcca gtacacctgc cacaagggcg ggaggtgct ctcccatagc     300 ctgctcctcc tgcacaaaaa ggaggatggc atctggagca ccgacatcct gaaggaccag    360
aaggagccca gaacaagac atttctcagg tgtgaggcca agaactattc gggcaggttt     420
acctgttggt ggctcaccac catctctacc gacctgacgt tctccgtcaa gtcaagcagg   480
gggagctcgg accccagggg ggtgacatgt gggccgcca ccctgagcgc ggagcgtgtc    540
cgcggcgaca caaggagta cgagtattcc gtggagtgcc aggaggacag cgcctgcccc    600
gccgccgagg agtccctgcc catagaggtg atggtggacg ccgtccacaa gttgaagtac    660
gaaaattata cctcctcgtt cttcattagg gacatcatca gcctgaccc cccgaagaac    720 ctacaactca agcccctcaa gaactcccgc caggtggagg tgtcctggga gtaccccgac    780
```

| | |
|---|---|
| acctggtcca ccccgcacag ctacttcagc ctgaccttct gcgtgcaggt ccaggggaag | 840 |
| agcaagcgtg aaaagaaaga cagggtgttc accgacaaga cgagcgccac cgtgatctgc | 900 |
| aggaaaaacg cctccatctc cgtgcgcgcc caggacaggt actacagtag ctcctggagc | 960 |
| gaatgggcca gcgtgccgtg cagcggcggg ggaggaggcg gcagtcgcaa cctgcccgtg | 1020 |
| gccaccccg accccggcat gttcccatgc ctgcaccaca gccagaacct gctgagggca | 1080 |
| gtcagcaata tgctgcagaa ggccaggcag accctggagt tttatccctg caccagcgag | 1140 |
| gagatcgacc acgaggacat caccaaggac aagacctcca ccgtcgaggc ctgcctgcca | 1200 |
| ctggagctga ccaaaaacga gagctgcctg aactccaggg agacctcctt catcaccaac | 1260 |
| gggagctgcc tggccagccg gaagaccagc ttcatgatgg cgctgtgcct cagcagcatc | 1320 |
| tacgaggatc tcaagatgta ccaggtggag ttcaagacca tgaacgcgaa gctgctgatg | 1380 |
| gaccccaagc ggcagatctt cctggaccag aacatgctgg ccgtgattga cgagctcatg | 1440 |
| caggccctga acttcaatag cgagaccgtc cccaaaaga gcagcctgga ggaacccgac | 1500 |
| ttctacaaaa cgaagatcaa gctctgcatc ctgctgcacg ccttccggat ccgggccgtg | 1560 |
| accatcgatc gtgtgatgag ctacctgaac gcctcg | 1596 |

<210> SEQ ID NO 43
<211> LENGTH: 1596
<212> TYPE: DNA
<213> ORGANISM: Artificial Sequence
<220> FEATURE:
<223> OTHER INFORMATION: hIL12AB_039

<400> SEQUENCE: 43

| | |
|---|---|
| atgtgccacc agcagctcgt catctcctgg tttagcctgg tgtttctggc ctcccccctg | 60 |
| gtcgccatct gggagctgaa gaaagacgtg tacgtggtgg agctggactg gtacccggac | 120 |
| gctcccgggg agatggtggt gctgacctgc gacacccccg aggaggacgg catcacctgg | 180 |
| accctggacc agagctccga ggtgctgggg agcggcaaga ccctgaccat tcaggtgaaa | 240 |
| gagttcggcg acgccggcca atatacctgc cacaaggggg gggaggtcct gtcgcattcc | 300 |
| ctgctgctgc ttcacaaaaa ggaggatggc atctggagca ccgacatcct gaaggaccag | 360 |
| aaagaaccca gaacaagac gttcctgcgc tgcgaggcca agaactacag cggccggttc | 420 |
| acctgttggt ggctgaccac catctccacc gacctgactt tctcggtgaa gagcagccgc | 480 |
| gggagcagcg acccccaggg agtgacctgc ggcgccgcca cctgagcgc cgaaagggtg | 540 |
| aggggcgaca taaagagta cgagtattcc gtggagtgcc aggaggacag cgcctgtccc | 600 |
| gccgccgagg agtccctgcc tatcgaggtg atggtcgacg cggtgcacaa gctcaagtac | 660 |
| gaaaactaca ccagcagctt tttcatcagg gatatcatca accagaccc ccaagaac | 720 |
| ctgcagctga agcccctgaa aaacagcagg caggtggaag tgagctggga taccccgat | 780 |
| acctggtcca cccccacag ctacttcagc ctgaccttct gcgtgcaggt cagggggaag | 840 |
| tccaagcggg agaagaaaga tcgggtgttc acggacaaga ccagcgccac cgtgatttgc | 900 |
| aggaaaaacg ccagcatctc cgtgagggct caggacaggt actacagctc cagctggagc | 960 |
| gagtgggcct ccgtgccttg cagcggggga ggagcggcg cagcaggaa tctgcccgtc | 1020 |
| gcaaccccg accccggcat gttccctgc ctgcaccaca gccagaatct gctgcagcc | 1080 |
| gtgagcaaca tgctgcagaa ggccggcag acgctggagt tctaccctg cacctccgag | 1140 |
| gagatcgacc acgaggacat caccaaggat aagacgagca ccgtcgaggc ctgtctcccc | 1200 |
| ctggagctca ccaagaacga gtcctgcctg aatagcaggg agacgtcctt cataaccaac | 1260 |

```
ggcagctgtc tggcgtccag gaagaccagc ttcatgatgg ccctctgcct gagctccatc    1320
tacgaggacc tcaagatgta ccaggtcgag ttcaagacca tgaacgcaaa actgctcatg    1380
gatccaaaga ggcagatctt tctggaccag aacatgctgg ccgtgatcga tgaactcatg    1440
caggccctga atttcaattc cgagaccgtg ccccagaaga gctccctgga ggaacccgac    1500
ttctacaaaa caaagatcaa gctgtgtatc ctcctgcacg ccttccggat cagggccgtc    1560
accattgacc gggtgatgtc ctacctgaac gccagc                              1596
```

<210> SEQ ID NO 44
<211> LENGTH: 1596
<212> TYPE: DNA
<213> ORGANISM: Artificial Sequence
<220> FEATURE:
<223> OTHER INFORMATION: hIL12AB_040

<400> SEQUENCE: 44

```
atgtgccatc agcagctggt gatcagctgg ttcagcctcg tgttcctcgc cagcccctc     60 gtggccatct gggagctgaa aaaggacgtg tacgtggtgg agctggactg gtatcccgac    120
gccccgggcg agatggtggt gctgacctgc gacacccccg aggaggacgg cattacctgg    180
acactggacc agagcagcga ggtcctgggc agcgggaaga ccctgacaat tcaggtgaag    240
gagttcggcg acgccggaca gtacacgtgc cacaaggggg gggaggtgct gtcccacagc    300
ctcctcctgc tgcacaagaa ggaggatggc atctggagca ccgacatcct gaaggatcag    360
aaggagccca gaacaagac ctttctgaga tgcgaggcca gaattacag cggccgtttc    420 acctgctggt ggctcaccac catcagcacc gacctgacct tcagcgtgaa atcctccagg    480
ggctcctccg acccgcaggg agtgacctgc ggcgccgcca cactgagcgc cgagcgggtc    540 agagggaca caaggagta cgagtacagc gttgagtgcc aggaggacag cgcctgtccc    600
gcggccgaga atccctgcc catcgaggtg atggtggacg cagtgcacaa gctgaagtac    660
gagaactata cctcgagctt cttcatccgg gatatcatta agcccgatcc cccgaagaac    720
ctgcagctca accccctgaa gaacagcagg caggtggagg tctcctggga gtaccccgac    780
acatggtcca ccccccattc ctatttctcc ctgaccttt gcgtgcaggt gcagggcaag    840
agcaagaggg agaaaaagga cagggtgttc accgacaaga cctccgccac cgtgatctgc    900
cgtaagaacg ctagcatcag cgtcagggcc caggacaggt actatagcag ctcctggtcc    960
gagtgggcca gcgtcccgtg cagcggcggg ggcggtggag gctcccggaa cctccccgtg    1020
gccaccccgg accccgggat gtttcctgc ctgcatcaca gccagaacct gctgagggcc    1080
gtgtccaaca tgctgcagaa ggccaggcag acactcgagt tttacccctg caccagcgag    1140
gagatcgacc acgaagacat caccaaggac aagacctcca ccgtggaggc atgcctgccc    1200
ctggagctga ccaaaaacga aagctgtctg aactccaggg agacctcctt tatcacgaac    1260
ggctcatgcc tggcctccag aaagaccagc ttcatgatgg ccctgtgcct gagctccatc    1320
tacgaggact tgaaaatgta ccaggtcgag ttcaagacca tgaacgccaa gctgctcatg    1380
gaccccaaaa ggcagatctt tctggaccag aatatgctgg ccgtgatcga cgagctcatg    1440
caagccctga atttcaacag cgagaccgtg ccccagaagt cctccctgga ggagcccgac    1500
ttctacaaga ccaagatcaa gctgtgcata ctcctgcacg cgtttaggat cagggcggtg    1560
accatcgata gggtgatgag ctacctgaat gcctcc                              1596
```

<210> SEQ ID NO 45

```
<211> LENGTH: 22
<212> TYPE: PRT
<213> ORGANISM: Artificial Sequence
<220> FEATURE:
<223> OTHER INFORMATION: Wild Type IL12B signal peptide Amino acids

<400> SEQUENCE: 45

Met Cys His Gln Gln Leu Val Ile Ser Trp Phe Ser Leu Val Phe Leu
1               5                   10                  15

Ala Ser Pro Leu Val Ala
            20

<210> SEQ ID NO 46
<211> LENGTH: 66
<212> TYPE: DNA
<213> ORGANISM: Artificial Sequence
<220> FEATURE:
<223> OTHER INFORMATION: Wild Type IL12B signal peptide Nucleic acids

<400> SEQUENCE: 46
atgtgtcacc agcagttggt catctcttgg ttttccctgg ttttctggc atctcccctc        60 gtggcc                                                                  66

<210> SEQ ID NO 47
<211> LENGTH: 18
<212> TYPE: DNA
<213> ORGANISM: Artificial Sequence
<220> FEATURE:
<223> OTHER INFORMATION: Syn5 promoter

<400> SEQUENCE: 47
attgggcacc cgtaaggg                                                     18

<210> SEQ ID NO 48
<211> LENGTH: 532
<212> TYPE: PRT
<213> ORGANISM: Artificial Sequence
<220> FEATURE:
<223> OTHER INFORMATION: hIL12AB_001

<400> SEQUENCE: 48

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160
```

Gly Ser Ser Asp Pro Gln Val Thr Cys Gly Ala Ala Thr Leu Ser
                165                 170                 175

Ala Glu Arg Val Arg Gly Asp Asn Lys Glu Tyr Glu Tyr Ser Val Glu
180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Ser Arg
                325                 330                 335

Asn Leu Pro Val Ala Thr Pro Asp Pro Gly Met Phe Pro Cys Leu His
            340                 345                 350

His Ser Gln Asn Leu Leu Arg Ala Val Ser Asn Met Leu Gln Lys Ala
        355                 360                 365

Arg Gln Thr Leu Glu Phe Tyr Pro Cys Thr Ser Glu Glu Ile Asp His
    370                 375                 380

Glu Asp Ile Thr Lys Asp Lys Thr Ser Thr Val Glu Ala Cys Leu Pro
385                 390                 395                 400

Leu Glu Leu Thr Lys Asn Glu Ser Cys Leu Asn Ser Arg Glu Thr Ser
                405                 410                 415

Phe Ile Thr Asn Gly Ser Cys Leu Ala Ser Arg Lys Thr Ser Phe Met
            420                 425                 430

Met Ala Leu Cys Leu Ser Ser Ile Tyr Glu Asp Leu Lys Met Tyr Gln
        435                 440                 445

Val Glu Phe Lys Thr Met Asn Ala Lys Leu Leu Met Asp Pro Lys Arg
    450                 455                 460

Gln Ile Phe Leu Asp Gln Asn Met Leu Ala Val Ile Asp Glu Leu Met
465                 470                 475                 480

Gln Ala Leu Asn Phe Asn Ser Glu Thr Val Pro Gln Lys Ser Ser Leu
                485                 490                 495

Glu Glu Pro Asp Phe Tyr Lys Thr Lys Ile Lys Leu Cys Ile Leu Leu
            500                 505                 510

His Ala Phe Arg Ile Arg Ala Val Thr Ile Asp Arg Val Met Ser Tyr
        515                 520                 525

Leu Asn Ala Ser
    530

<210> SEQ ID NO 49
<211> LENGTH: 533
<212> TYPE: PRT
<213> ORGANISM: Artificial Sequence
<220> FEATURE:

<223> OTHER INFORMATION: hIL12AB_004

<400> SEQUENCE: 49

```
Met Gly Cys His Gln Gln Leu Val Ile Ser Trp Phe Ser Leu Val Phe
1               5                   10                  15

Leu Ala Ser Pro Leu Val Ala Ile Trp Glu Leu Lys Lys Asp Val Tyr
                20                  25                  30

Val Val Glu Leu Asp Trp Tyr Pro Asp Ala Pro Gly Glu Met Val Val
            35                  40                  45

Leu Thr Cys Asp Thr Pro Glu Glu Asp Gly Ile Thr Trp Thr Leu Asp
50                  55                  60

Gln Ser Ser Glu Val Leu Gly Ser Gly Lys Thr Leu Thr Ile Gln Val
65                  70                  75                  80

Lys Glu Phe Gly Asp Ala Gly Gln Tyr Thr Cys His Lys Gly Gly Glu
                85                  90                  95

Val Leu Ser His Ser Leu Leu Leu Leu His Lys Lys Glu Asp Gly Ile
            100                 105                 110

Trp Ser Thr Asp Ile Leu Lys Asp Gln Lys Glu Pro Lys Asn Lys Thr
        115                 120                 125

Phe Leu Arg Cys Glu Ala Lys Asn Tyr Ser Gly Arg Phe Thr Cys Trp
130                 135                 140

Trp Leu Thr Thr Ile Ser Thr Asp Leu Thr Phe Ser Val Lys Ser Ser
145                 150                 155                 160

Arg Gly Ser Ser Asp Pro Gln Gly Val Thr Cys Gly Ala Ala Thr Leu
                165                 170                 175

Ser Ala Glu Arg Val Arg Gly Asp Asn Lys Glu Tyr Glu Tyr Ser Val
            180                 185                 190

Glu Cys Gln Glu Asp Ser Ala Cys Pro Ala Ala Glu Glu Ser Leu Pro
        195                 200                 205

Ile Glu Val Met Val Asp Ala Val His Lys Leu Lys Tyr Glu Asn Tyr
210                 215                 220

Thr Ser Ser Phe Phe Ile Arg Asp Ile Ile Lys Pro Asp Pro Pro Lys
225                 230                 235                 240

Asn Leu Gln Leu Lys Pro Leu Lys Asn Ser Arg Gln Val Glu Val Ser
                245                 250                 255

Trp Glu Tyr Pro Asp Thr Trp Ser Thr Pro His Ser Tyr Phe Ser Leu
            260                 265                 270

Thr Phe Cys Val Gln Val Gln Gly Lys Ser Lys Arg Glu Lys Lys Asp
        275                 280                 285

Arg Val Phe Thr Asp Lys Thr Ser Ala Thr Val Ile Cys Arg Lys Asn
290                 295                 300

Ala Ser Ile Ser Val Arg Ala Gln Asp Arg Tyr Tyr Ser Ser Ser Trp
305                 310                 315                 320

Ser Glu Trp Ala Ser Val Pro Cys Ser Gly Gly Gly Gly Ser
                325                 330                 335

Arg Asn Leu Pro Val Ala Thr Pro Asp Pro Gly Met Phe Pro Cys Leu
            340                 345                 350

His His Ser Gln Asn Leu Leu Arg Ala Val Ser Asn Met Leu Gln Lys
        355                 360                 365

Ala Arg Gln Thr Leu Glu Phe Tyr Pro Cys Thr Ser Glu Glu Ile Asp
370                 375                 380

His Glu Asp Ile Thr Lys Asp Lys Thr Ser Thr Val Glu Ala Cys Leu
385                 390                 395                 400
```

-continued

```
Pro Leu Glu Leu Thr Lys Asn Glu Ser Cys Leu Asn Ser Arg Glu Thr
                405                 410                 415
Ser Phe Ile Thr Asn Gly Ser Cys Leu Ala Ser Arg Lys Thr Ser Phe
            420                 425                 430
Met Met Ala Leu Cys Leu Ser Ser Ile Tyr Glu Asp Leu Lys Met Tyr
        435                 440                 445
Gln Val Glu Phe Lys Thr Met Asn Ala Lys Leu Leu Met Asp Pro Lys
    450                 455                 460
Arg Gln Ile Phe Leu Asp Gln Asn Met Leu Ala Val Ile Asp Glu Leu
465                 470                 475                 480
Met Gln Ala Leu Asn Phe Asn Ser Glu Thr Val Pro Gln Lys Ser Ser
                485                 490                 495
Leu Glu Glu Pro Asp Phe Tyr Lys Thr Lys Ile Lys Leu Cys Ile Leu
            500                 505                 510
Leu His Ala Phe Arg Ile Arg Ala Val Thr Ile Asp Arg Val Met Ser
        515                 520                 525
Tyr Leu Asn Ala Ser
    530
```

```
<210> SEQ ID NO 50
<211> LENGTH: 85
<212> TYPE: RNA
<213> ORGANISM: Artificial Sequence
<220> FEATURE:
<223> OTHER INFORMATION: miR-122

<400> SEQUENCE: 50
ccuuagcaga gcuguggagu gugacaaugg uguuuguguc uaaacuauca aacgccauua    60
ucacacuaaa uagcuacugc uaggc                                         85

<210> SEQ ID NO 51
<211> LENGTH: 22
<212> TYPE: RNA
<213> ORGANISM: Artificial Sequence
<220> FEATURE:
<223> OTHER INFORMATION: miR-122-3p

<400> SEQUENCE: 51
aacgccauua ucacacuaaa ua                                            22

<210> SEQ ID NO 52
<211> LENGTH: 22
<212> TYPE: RNA
<213> ORGANISM: Artificial Sequence
<220> FEATURE:
<223> OTHER INFORMATION: miR-122-3p binding site

<400> SEQUENCE: 52
uauuuagugu gauaauggcg uu                                            22

<210> SEQ ID NO 53
<211> LENGTH: 22
<212> TYPE: RNA
<213> ORGANISM: Artificial Sequence
<220> FEATURE:
<223> OTHER INFORMATION: miR-122-5p

<400> SEQUENCE: 53
uggaguguga caaugguguu ug                                            22

<210> SEQ ID NO 54
```

```
<211> LENGTH: 22
<212> TYPE: RNA
<213> ORGANISM: Artificial Sequence
<220> FEATURE:
<223> OTHER INFORMATION: miR-122-5p binding site

<400> SEQUENCE: 54
caaacaccau ugucacacuc ca                                             22

<210> SEQ ID NO 55
<211> LENGTH: 1829
<212> TYPE: DNA
<213> ORGANISM: Artificial Sequence
<220> FEATURE:
<223> OTHER INFORMATION: hIL12AB_001

<400> SEQUENCE: 55
tcaagctttt ggaccctcgt acagaagcta atacgactca ctatagggaa ataagagaga     60
aaagaagagt aagaagaaat ataagagcca ccatgtgtca ccagcagctg gtcattagct    120
ggtttagcct tgtgttcctg gcctccccc ttgtcgctat ttgggagctc aagaaggacg     180
tgtacgtggt ggagttggat tggtacccag acgcgcccgg agagatggta gttctgacct    240 gtgataccc agaggaggac ggcatcacct ggacgctgga ccaaagcagc gaggttttgg     300
gctcagggaa aacgctgacc atccaggtga aggaattcgg cgacgccggg cagtacacct    360
gccataaggg aggagaggtg ctgagccatt cccttcttct gctgcacaag aaagaggacg    420
gcatctggtc taccgacatc ctgaaagacc agaaggagcc caagaacaaa accttcctga    480
ggtgcgaggc caagaactac tccggcaggt tcacttgttg gtggctgacc accatcagta    540
cagacctgac ttttagtgta aaaagctcca gaggctcgtc cgatccccaa ggggtgacct    600
gcggcgcagc cactctgagc gctgagcgcg tgcgcggtga caataaagag tacgagtaca    660
gcgttgagtg tcaagaagat agcgcttgcc ctgccgccga ggagagcctg cctatcgagg    720
tgatggttga cgcagtgcac aagcttaagt acgagaatta caccagctca ttcttcatta    780
gagatataat caagcctgac ccacccaaga acctgcagct gaagccactg aaaaactcac    840
ggcaggtcga agtgagctgg gagtaccccg acacctggag cactcctcat tcctatttct    900
ctcttacatt ctgcgtccag gtgcagggca agagcaagcg ggaaaagaag gatcgagtct    960
tcaccgacaa aacaagcgcg accgtgattt gcaggaagaa cgccagcatc tccgtcagag   1020
cccaggatag atactatagt agcagctgga gcgagtgggc aagcgtgccc tgttccggcg   1080 gcggggcgg gggcagccga aacttgcctg tcgctacccc ggaccctgga atgtttccgt    1140
gtctgcacca cagccagaac ctgctgagag ccgtgtcgaa tatgctccag aaggcccggc   1200
agacccttga gttctacccc tgtaccagcg aagagatcga tcatgaagat atcacgaaag   1260
ataaaacatc caccgtcgag gcttgtctcc cgctggagct gaccaagaac gagagctgtc   1320
tgaatagccg ggagacgtct ttcatcacga atggtagctg tctggccagc aggaaaactt   1380
ccttcatgat ggctctctgc ctgagctcta tctatgaaga tctgaagatg tatcaggtgg   1440
agtttaaaac aatgaacgcc aaactcctga tggacccaaa aaggcaaatc tttctggacc   1500
agaatatgct ggccgtgata gacgagctga tgcaggcact gaacttcaac agcgagacgg   1560
tgccacagaa atccagcctg gaggagcctg acttttacaa aactaagatc aagctgtgta   1620
tcctgctgca cgcctttaga atccgtgccg tgactatcga cagggtgatg tcatacctca   1680
acgcttcatg ataataggct ggagcctcgg tggccatgct tcttgcccct tgggcctccc   1740
cccagcccct cctcccttc ctgcacccgt accccccaaa caccattgtc acactccagt    1800
```

```
ggtctttgaa taaagtctga gtgggcggc                                     1829
```

<210> SEQ ID NO 56
<211> LENGTH: 1829
<212> TYPE: DNA
<213> ORGANISM: Artificial Sequence
<220> FEATURE:
<223> OTHER INFORMATION: hIL12AB_002

<400> SEQUENCE: 56

```
tcaagctttt ggaccctcgt acagaagcta atacgactca ctatagggaa ataagagaga     60
aagaagagt aagaagaaat ataagagcca ccatgtgcca ccagcagctg gtgatcagct    120
ggttcagcct ggtgttcctg gccagccccc tggtggccat ctgggagctg aagaaggacg    180
tgtacgtggt ggagttggat tggtaccccg acgcccccgg cgagatggtg gtgctgacct    240
gcgacacccc cgaggaggac ggcatcacct ggaccctgga ccagagcagc gaggtgctgg    300
gcagcggcaa gaccctgacc atccaggtga aggagttcgg cgacgccggc cagtacacct    360
gccacaaggg cggcgaggtg ctgagccaca gcctgctgct gctgcacaag aaggaggacg    420
gcatctggag caccgacatc ctgaaggacc agaaggagcc caagaacaag accttcctga    480
gatgcgaggc caagaactac agcggcagat tcacctgctg gtggctgacc accatcagca    540
ccgacctgac cttcagcgtg aagagcagca gaggcagcag cgaccccag ggcgtgacct    600
gcggcgccgc caccctgagc gccgagagag tgagaggcga caacaaggag tacgagtaca    660
gcgtggagtg ccaggaagat agcgcctgcc ccgccgccga ggagagcctg cccatcgagg    720
tgatggtgga cgccgtgcac aagctgaagt acgagaacta caccagcagc ttcttcatca    780
gagatatcat caagcccgac ccccccaaga acctgcagct gaagcccctg aagaacagcc    840
ggcaggtgga ggtgagctgg gagtaccccg acacctggag caccccccac agctacttca    900
gcctgacctt ctgcgtgcag gtgcagggca gagcaagag agagaagaaa gatagagtgt    960
tcaccgacaa gaccagcgcc accgtgatct gcagaaagaa cgccagcatc agcgtgagag   1020
cccaagatag atactacagc agcagctgga gcgagtgggc cagcgtgccc tgcagcggcg   1080
gcggcggcgg cggcagcaga aacctgcccg tggccacccc cgaccccggc atgttcccct   1140
gcctgcacca cagccagaac ctgctgagag ccgtgagcaa catgctgcag aaggcccggc   1200
agaccctgga gttctacccc tgcaccagcg aggagatcga ccacgaagat atcaccaaag   1260
ataagaccag caccgtggag gcctgcctgc cctggagct gaccaagaac gagagctgcc   1320
tgaacagcag agagaccagc ttcatcacca acggcagctg cctggccagc agaaagacca   1380
gcttcatgat ggccctgtgc ctgagcagca tctacgagga cctgaagatg taccaggtgg   1440
agttcaagac catgaacgcc aagctgctga tggaccccaa gcggcagatc ttcctggacc   1500
agaacatgct ggccgtgatc gacgagctga tgcaggccct gaacttcaac agcgagaccg   1560
tgccccagaa gagcagcctg gaggagcccg acttctacaa gaccaagatc aagctgtgca   1620
tcctgctgca cgccttcaga atcagagccg tgaccatcga cagagtgatg agctacctga   1680
acgccagctg ataataggct ggagcctcgg tggccatgct tcttgcccct tgggcctccc   1740
cccagccct cctcccttc ctgcacccgt accccaaa caccattgtc acactccagt   1800
ggtctttgaa taaagtctga gtgggcggc                                     1829
```

<210> SEQ ID NO 57
<211> LENGTH: 1829
<212> TYPE: DNA

<213> ORGANISM: Artificial Sequence
<220> FEATURE:
<223> OTHER INFORMATION: hIL12AB_003

<400> SEQUENCE: 57

```
tcaagctttt ggaccctcgt acagaagcta atacgactca ctatagggaa ataagagaga      60
aaagaagagt aagaagaaat ataagagcca ccatgtgtca ccagcagttg gtcatctctt     120
ggttttccct ggttttttctg gcatctcccc tcgtggccat ctgggaactg aagaaagacg    180
tttacgttgt agaattggat tggtatccgg acgctcctgg agaaatggtg gtcctcacct    240
gtgacacccc tgaagaagac ggaatcacct ggaccttgga ccagagcagt gaggtcttag    300
gctctggcaa aaccctgacc atccaagtca aagagtttgg agatgctggc cagtacacct    360
gtcacaaagg aggcgaggtt ctaagccatt cgctcctgct gcttcacaaa aggaagatg     420
gaatttggtc cactgatatt ttaaaggacc agaaagaacc caaaaataag accttctaa    480
gatgcgaggc caagaattat tctggacgtt tcacctgctg gtggctgacg acaatcagta    540
ctgatttgac attcagtgtc aaaagcagca gggctcttc tgaccccaa ggggtgacgt     600
gcggagctgc tacactctct gcagagagag tcagaggtga caacaaggag tatgagtact    660
cagtggagtg ccaggaagat agtgcctgcc cagctgctga ggagagtctg cccattgagg    720
tcatggtgga tgccgttcac aagctcaagt atgaaaacta caccagcagc ttcttcatca    780
gagatatcat caaacctgac ccacccaaga acttgcagct gaagccatta aagaattctc    840
ggcaggtgga ggtcagctgg gagtaccctg acacctggag tactccacat tcctacttct    900
ccctgacatt ctgcgttcag gtccagggca agagcaagag agaaaagaaa gatagagtct    960
tcacagataa gacctcagcc acggtcatct gccgcaaaaa tgccagcatt agcgtgcggg   1020
cccaggaccg ctactatagc tcatcttgga gcgaatgggc atctgtgccc tgcagtggcg   1080
gaggggggcgg agggagcaga aacctcccccg tggccactcc agacccagga atgttcccat   1140
gccttcacca ctcccaaaac ctgctgaggg ccgtcagcaa catgctccag aaggcccggc   1200
aaactttaga attttaccct tgcacttctg aagagattga tcatgaagat atcacaaaag   1260
ataaaaccag cacagtggag gcctgtttac cattggaatt aaccaagaat gagagttgcc   1320
taaattccag agagacctct ttcataacta atgggagttg cctggcctcc agaaagacct   1380
ctttatgat ggcctgtgc cttagtagta tttatgaaga tttgaagatg taccaggtgg    1440
agttcaagac catgaatgca aagcttctga tggatcctaa gaggcagatc tttttagatc   1500
aaaacatgct ggcagttatt gatgagctga tgcaggccct gaatttcaac agtgagacgg   1560
tgccacaaaa atcctccctt gaagaaccag atttctacaa gaccaagatc aagctctgca   1620
tacttcttca tgctttcaga attcgggcag tgactattga tagagtgatg agctatctga    1680
atgcttcctg ataataggct ggagcctcgg tggccatgct tcttgcccct tgggcctccc    1740
cccagcccct cctcccttc ctgcacccgt accccccaaa caccattgtc acactccagt    1800
ggtctttgaa taaagtctga gtgggcggc                                      1829
```

<210> SEQ ID NO 58
<211> LENGTH: 1832
<212> TYPE: DNA
<213> ORGANISM: Artificial Sequence
<220> FEATURE:
<223> OTHER INFORMATION: hIL12AB_004

<400> SEQUENCE: 58

```
tcaagctttt ggaccctcgt acagaagcta atacgactca ctatagggaa ataagagaga      60
```

| | |
|---|---|
| aaagaagagt aagaagaaat ataagagcca ccatgggctg ccaccagcag ctggtcatca | 120 |
| gctggttctc cctggtcttc ctggccagcc cctggtggc catctgggag ctgaagaaag | 180 |
| acgtctacgt agtagagttg gattggtacc cagacgcacc tggagaaatg gtggttctca | 240 |
| cctgtgacac gccagaagaa gacggtatca cctggacgct ggaccagagc tcagaagttc | 300 |
| ttggcagtgg aaaaacgctg accatacaag taaaagaatt tggggatgct ggccagtaca | 360 |
| cctgccacaa aggaggagaa gttctcagcc acagcctgct gctgctgcac aagaaagaag | 420 |
| atggcatctg gagcacagat attttaaaag accagaagga gcccaagaac aaaaccttcc | 480 |
| ttcgatgtga ggccaagaac tacagtggcc gcttcacctg ctggtggctc accaccatca | 540 |
| gcacagacct caccttctcg gtgaagagca gccgtggcag ctcagacccc caaggagtca | 600 |
| cctgtggggc ggccacgctg tcggcagaaa gagttcgagg tgacaacaag gaatatgaat | 660 |
| actcggtgga atgtcaagaa gattcggcct gcccggcggc agaagaaagt cttcccatag | 720 |
| aagtcatggt ggatgctgtt cacaaattaa aatatgaaaa ctacaccagc agcttcttca | 780 |
| tcagagatat catcaagcca gacccgccca gaacctgca gctgaagccc tgaagaaca | 840 |
| gccggcaggt ggaagtttcc tgggagtacc cagatacgtg gagcacgccg cacagctact | 900 |
| tcagcctcac cttctgtgta caagtacaag gcaagagcaa gagagagaag aaagatcgtg | 960 |
| tcttcacaga taaaacctcg gcgacggtca tctgcaggaa gaatgcctcc atctcggttc | 1020 |
| gagcccagga ccgctactac agcagcagct ggagtgagtg ggcctcggtg ccctgcagtg | 1080 |
| gtggcggcgg cggcggcagc agaaaccttc ctgtggccac gccggaccct ggcatgttcc | 1140 |
| cgtgcctgca ccacagccaa aatttacttc gagctgtttc taacatgctg cagaaagcac | 1200 |
| ggcaaacttt agaattctac ccctgcacct cagaagaaat agaccatgaa gatatcacca | 1260 |
| aagataaaac cagcactgta gaggcctgcc tgccctgga gctcaccaag aatgaatcct | 1320 |
| gcctcaacag cagagagacc agcttcatca ccaatggcag ctgcctggcc agcaggaaaa | 1380 |
| ccagcttcat gatggcgctc tgcctgagca gcatctatga agatttgaag atgtaccaag | 1440 |
| tagaatttaa aaccatgaat gccaagctgc tcatggaccc caagcggcag atattttggg | 1500 |
| atcaaaacat gctggctgtc attgatgagc tcatgcaagc attaaacttc aactcagaga | 1560 |
| cggtgcccca aaagagcagc ctggaggagc cagatttcta caaaaccaag atcaagctct | 1620 |
| gcatcttatt acatgccttc cgcatccggg cggtcaccat tgaccgtgtc atgtcctact | 1680 |
| taaatgccag ctgataatag gctggagcct cggtggccat gcttcttgcc ccttgggcct | 1740 |
| ccccccagcc cctcctcccc ttcctgcacc cgtaccccc aaacaccatt gtcacactcc | 1800 |
| agtggtcttt gaataaagtc tgagtgggcg gc | 1832 |

<210> SEQ ID NO 59
<211> LENGTH: 1829
<212> TYPE: DNA
<213> ORGANISM: Artificial Sequence
<220> FEATURE:
<223> OTHER INFORMATION: hIL12AB_005

<400> SEQUENCE: 59

| | |
|---|---|
| tcaagctttt ggaccctcgt acagaagcta atacgactca ctatagggaa ataagagaga | 60 |
| aagaagagt aagaagaaat ataagagcca ccatgtgcca ccagcagctg gtcatcagct | 120 |
| ggttctccct ggtcttcctg gccagccccc tggtggccat ctgggagctg aagaagacg | 180 |
| tctacgtagt agagttggat tggtacccag acgcacctgg agaaatggtg gttctcacct | 240 |

```
gtgacacgcc agaagaagac ggtatcacct ggacgctgga ccagagctca gaagttcttg    300
gcagtggaaa acgctgacc atacaagtaa aagaatttgg ggatgctggc cagtacacct      360
gccacaaagg aggagaagtt ctcagccaca gcctgctgct gctgcacaag aaagaagatg    420
gcatctggag cacagatatt ttaaaagacc agaaggagcc caagaacaaa accttccttc    480
gatgtgaggc caagaactac agtggccgct tcacctgctg gtggctcacc accatcagca    540
cagacctcac cttctcggtg aagagcagcc gtggcagctc agaccccaa ggagtcacct      600 gtggggcgga cacgctgtcg gcagaaagag ttcgaggtga caacaaggaa tatgaatact    660
cggtggaatg tcaagaagat tcggcctgcc cggcggcaga agaaagtctt cccatagaag    720
tcatggtgga tgctgttcac aaattaaaat atgaaaacta caccagcagc ttcttcatca    780
gagatatcat caagccagac cgcccaaga acctgcagct gaagcccctg aagaacagcc      840
ggcaggtgga agtttcctgg gagtacccag atacgtggag cacgccgcac agctacttca    900
gcctcacctt ctgtgtacaa gtacaaggca agagcaagag agagaagaaa gatcgtgtct    960
tcacagataa aacctcggcg acggtcatct gcaggaagaa tgcctccatc tcggttcgag    1020
cccaggaccg ctactacagc agcagctgga gtgagtgggc ctcggtgccc tgcagtggtg    1080
gcggcggcgg cggcagcaga aaccttcctg tggccacgcc ggaccctggc atgttccgt    1140 gcctgcacca cagccaaaat ttacttcgag ctgtttctaa catgctgcag aaagcacggc    1200
aaactttaga attctacccc tgcacctcag aagaaataga ccatgaagat atcaccaaag    1260
ataaaaccag cactgtagag gcctgcctgc ccctggagct caccaagaat gaatcctgcc    1320
tcaacagcag agagaccagc ttcatcacca tggcagctg cctggccagc aggaaaacca    1380
gcttcatgat ggcgctctgc ctgagcagca tctatgaaga tttgaagatg taccaagtag    1440
aatttaaaac catgaatgcc aagctgctca tggacccca gcggcagata ttttgggatc      1500
aaaacatgct ggctgtcatt gatgagctca tgcaagcatt aaacttcaac tcagagacgg    1560
tgccccagaa gagcagcctg gaggagccag atttctacaa aaccaagatc aagctctgca    1620
tcttattaca tgccttccgc atccgggcgg tcaccattga ccgtgtcatg tcctacttaa    1680
atgccagctg ataataggct ggagcctcgg tggccatgct tcttgcccct tgggcctccc    1740
cccagcccct cctcccttc ctgcacccgt acccccaaa caccattgtc acactccagt      1800
ggtctttgaa taaagtctga gtgggcggc                                      1829
```

<210> SEQ ID NO 60
<211> LENGTH: 1829
<212> TYPE: DNA
<213> ORGANISM: Artificial Sequence
<220> FEATURE:
<223> OTHER INFORMATION: hIL12AB_006

<400> SEQUENCE: 60

```
tcaagctttt ggaccctcgt acagaagcta atacgactca ctatagggaa ataagagaga     60
aaagaagagt aagaagaaat ataagagcca ccatgtgcca ccagcagctg gtgatcagct    120
ggttcagcct ggtgttcctg gccagccccc tggtggccat ctgggagctg aagaaggacg    180
tgtacgtggt ggagttggat tggtaccccg acgcccccgg cgagatggtg gtgctgacct    240
gtgacacccc cgaggaggac ggcatcacct ggaccctgga ccagagcagc gaggtgctgg    300
gcagcggcaa gaccctgacc atccaggtga aggagttcgg ggacgccggc cagtacacct    360
gccacaaggg cggcgaggtg ctgagccaca gcctgctgct gctgcacaag aaggaggacg    420
gcatctggag cacagatatc ctgaaggacc agaaggagcc caagaacaag accttcctga    480
```

```
gatgcgaggc caagaactac agcggcagat tcacctgctg gtggctgacc accatcagca    540
cagatttgac cttcagcgtg aagagcagca gaggcagcag cgaccccag ggcgtgacct      600 gcggcgccgc caccctgagc gccgagagag tgagaggtga caacaaggag tacgagtaca    660
gcgtggagtg ccaggaagat agcgcctgcc ccgccgccga ggagagcctg cccatcgagg    720
tgatggtgga cgccgtgcac aagctgaagt acgagaacta caccagcagc ttcttcatca    780
gagatatcat caagcccgac ccgccgaaga acctgcagct gaagcccctg aagaacagcc    840
ggcaggtgga ggtgagctgg gagtaccccg acacctggag caccccccac agctacttca    900
gcctgacctt ctgcgtgcag gtgcagggca gagcaagag agagaagaaa gatagagtgt    960
tcacagataa gaccagcgcc accgtgatct gcagaaagaa cgccagcatc agcgtgagag   1020
cccaagatag atactacagc agcagctgga gcgagtgggc cagcgtgccc tgcagcggcg   1080
gcggcggcgg cggcagcaga aacctgcccg tggccacccc cgaccccggc atgttcccct   1140
gcctgcacca cagccagaac ctgctgagag ccgtgagcaa catgctgcag aaggcccggc   1200 agacccctgga gttctacccc tgcaccagcg aggagatcga ccacgaagat atcaccaaag   1260
ataagaccag caccgtggag gcctgcctgc ccctggagct gaccaagaat gaaagctgcc   1320
tgaacagcag agagaccagc ttcatcacca cggcagctg cctggccagc agaaagacca   1380
gcttcatgat ggccctgtgc ctgagcagca tctacgagga cctgaagatg taccaggtgg   1440
agttcaagac catgaacgcc aagctgctga tggaccccaa gcggcagatc ttcctggacc   1500
agaacatgct ggccgtgatc gacgagctga tgcaggccct gaacttcaac agcgagaccg   1560
tgccccagaa gagcagcctg gaggagcccg acttctacaa gaccaagatc aagctgtgca   1620
tcctgctgca cgccttcaga atcagagccg tgaccatcga cagagtgatg agctacctga   1680
acgccagctg ataataggct ggagcctcgg tggccatgct tcttgcccct tgggcctccc   1740
cccagcccct cctcccctc ctgcacccgt accccccaaa caccattgtc acactccagt   1800
ggtctttgaa taaagtctga gtgggcggc                                        1829
```

<210> SEQ ID NO 61
<211> LENGTH: 1829
<212> TYPE: DNA
<213> ORGANISM: Artificial Sequence
<220> FEATURE:
<223> OTHER INFORMATION: hIL12AB_007

<400> SEQUENCE: 61

```
tcaagctttt ggaccctcgt acagaagcta atacgactca ctataggaa ataagagaga       60 aaagaagagt aagaagaaat ataagagcca ccatgtgcca ccagcagctt gtcatctcct     120
ggttctctct tgtcttcctt gcttctcctc ttgtggccat ctgggagctg aagaaggacg    180
tttacgtagt ggagttggat tggtaccctg acgcacctgg agaaatggtg gttctcacct   240
gtgacactcc tgaggaggac ggtatcacct ggacgttgga ccagtcttct gaggttcttg   300
gcagtggaaa aactcttact attcaggtga aggagtttgg agatgctggc agtacacct    360 gccacaaggg tggtgaagtt ctcagccaca gtttacttct tcttcacaag aaggaggatg    420
gcatctggtc tactgcactt ttaaaagacc agaaggagcc caagaacaaa acattccttc    480
gttgtgaagc caagaactac agtggtcgtt tcacctgctg gtggcttact actatttcta   540
ctgaccttac tttctctgtg aagtcttctc gtggctcttc tgaccctcag ggtgtcacct   600 gtgggctgc tactctttct gctgagcgtg tgcgtggtga caacaaggag tatgaatact    660
```

```
cggtggagtg ccaggaagat tctgcctgcc ctgctgctga ggagtctctt cctattgagg    720
tgatggtgga tgctgtgcac aagttaaaat atgaaaacta cacttcttct ttcttcattc    780
gtgacattat aaaacctgac cctcccaaga accttcagtt aaaaccttta aaaaactctc    840
gtcaggtgga ggtgtcctgg gagtaccctg acacgtggtc tactcctcac tcctacttct    900
ctcttacttt ctgtgtccag gtgcagggca agtccaagcg tgagaagaag gaccgtgtct    960
tcactgacaa acatctgct actgtcatct gcaggaagaa tgcatccatc tctgtgcgtg    1020
ctcaggaccg ttactacagc tcttcctggt ctgagtgggc ttctgtgccc tgctctggcg    1080
gcggcggcgg cggcagcaga aatcttcctg tggctactcc tgaccctggc atgttcccct    1140
gccttcacca ctcgcagaac cttcttcgtg ctgtgagcaa catgcttcag aaggctcgtc    1200
aaactttaga attctacccc tgcacttctg aggagattga ccatgaagat atcaccaaag    1260
ataaaacatc tactgtggag gcctgccttc ctttagagct gaccaagaat gaatcctgct    1320
taaattctcg tgagacgtct ttcatcacca atggcagctg ccttgcctcg cgcaaaacat    1380 cttttcatgat ggctctttgc ctttcttcca tctatgaaga tttaaaaatg taccaggtgg    1440
agttcaagac catgaatgca aagcttctca tggaccccaa gcgtcagata tttttggacc    1500
agaacatgct tgctgtcatt gatgagctca tgcaggcttt aaacttcaac tctgagacgg    1560
tgcctcagaa gtcttcttta gaagagcctg acttctacaa gaccaagata aaactttgca    1620
ttcttcttca tgctttccgc atccgtgctg tgactattga ccgtgtgatg tcctacttaa    1680
atgcttcttg ataataggct ggagcctcgg tggccaagct tcttgcccct tgggcctccc    1740
cccagcccct cctcccttc ctgcacccgt accccccaaa caccattgtc acactccagt    1800
ggtctttgaa taaagtctga gtgggcggc                                      1829
```

<210> SEQ ID NO 62  
<211> LENGTH: 1829  
<212> TYPE: DNA  
<213> ORGANISM: Artificial Sequence  
<220> FEATURE:  
<223> OTHER INFORMATION: hIL12AB_008

<400> SEQUENCE: 62

```
tcaagctttt ggaccctcgt acagaagcta atacgactca ctatagggaa ataagagaga     60
aaagaagagt aagaagaaat ataagagcca ccatgtgtca tcaacaactc gtgattagct    120
ggttcagtct cgtgttcctg gcctctccgc tggtggccat ctgggagctt aagaaggacg    180
tgtacgtggt ggagctcgat tggtaccccg acgcacctgg cgagatggtg gtgctaacct    240 gcgataccc cgaggaggac gggatcactt ggaccctgga tcagagtagc gaagtcctgg    300
gctctggcaa acactcaca atccaggtga aggaattcgg agacgctggt cagtacactt    360
gccacaaggg gggtgaagtg ctgtctcaca gcctgctgtt actgcacaag aaggaggatg    420
ggatctggtc aaccgacatc ctgaaggatc agaaggagcc taagaacaag acctttctga    480
ggtgtgaagc taagaactat tccggaagat tcacttgctg gtggttgacc acaatcagca    540
ctgacctgac cttttccgtg aagtccagca gaggaagcag cgatcctcag ggcgtaacgt    600 gcggcgcgg taccctgtca gctgagcggg ttagaggcga caacaaagag tatgagtact    660
ccgtggagtg tcaggaagat agcgcctgcc ccgcagccga ggagagtctg cccatcgagg    720
tgatggtgga cgctgtccat aagttaaaat acgaaaatta cacaagttcc ttttcatcc    780 gcgatattat caaacccgat ccccccaaga acctgcagct gaagcccctg aagaatagcc    840
gacaggtgga agtctcttgg gagtatcctg acacctggtc cacgcctcac agctacttta    900
```

-continued

```
gtctgacttt ctgtgtccag gtccagggca agagcaagag agagaaaaag gatagagtgt     960
ttactgacaa aacatctgct acagtcatct gcagaaagaa cgccagtatc tcagtgaggg    1020
cgcaagatag atactacagt agtagctgga gcgaatgggc tagcgtgccc tgttcagggg    1080
gcggcggagg gggctccagg aatctgcccg tggccacccc cgaccctggg atgttccctt    1140
gcctccatca ctcacagaac ctgctcagag cagtgagcaa catgctccaa aaggcccgcc    1200
agaccctgga gttttaccct tgtacttcag aagagatcga tcacgaagat ataacaaagg    1260
ataaaaccag caccgtggag gcctgtctgc ctctggaact cacaaagaat gaaagctgtc    1320
tgaattccag ggaaacctcc ttcattacta acggaagctg tctcgcatct cgcaaaacat    1380
cattcatgat ggccctctgc ctgtcttcta tctatgaaga tctcaagatg tatcaggtgg    1440
agttcaaaac aatgaacgcc aagctgctga tggaccccaa gcggcagatc ttcctggacc    1500
agaacatgct ggcagtgatc gatgagctga tgcaagcctt gaacttcaac tcagagacgg    1560
tgccgcaaaa gtcctcgttg gaggaaccag attttttacaa aaccaaaatc aagctgtgta    1620
tccttcttca cgcctttcgg atcagagccg tgactatcga ccgggtgatg tcatacctga    1680
atgcttcctg ataataggct ggagcctcgg tggccatgct tcttgcccct tgggcctccc    1740
cccagcccct cctccccttc ctgcacccgt accccccaaa caccattgtc acactccagt    1800
ggtctttgaa taaagtctga gtgggcggc                                      1829
```

<210> SEQ ID NO 63
<211> LENGTH: 1829
<212> TYPE: DNA
<213> ORGANISM: Artificial Sequence
<220> FEATURE:
<223> OTHER INFORMATION: hIL12AB_009

<400> SEQUENCE: 63

```
tcaagctttt ggaccctcgt acagaagcta atacgactca ctatagggaa ataagagaga      60
aaagaagagt aagaagaaat ataagagcca ccatgtgcca ccagcagctg gtcatcagct     120
ggtttagcct ggtcttcctg gccagccccc tggtggccat ctgggagctg aagaaagacg     180
tctacgtagt agagttggat tggtacccag acgcacctgg agaaatggtg gttctcacct     240
gcgacacgcc agaagaagac ggtatcacct ggacgctgga ccagagcagc gaagtactgg     300
gcagtggaaa aacgctgacc atacaagtaa agaatttgg cgatgctggc cagtacacct     360
gccacaaagg aggagaagta ctgagccaca gcctgctgct gctgcacaag aaagaagatg     420
gcatctggag caccgacatt ttaaaagacc agaaggagcc caagaacaaa accttccttc     480
gatgtgaggc gaagaactac agtggccgct tcacctgctg gtggctcacc accatcagca     540
ccgacctcac cttctcggtg aagagcagcc gtggtagctc agacccccaa ggagtcacct     600
gtggggcggc cacgctgtcg gcagaaagag ttcgaggcga caacaaggaa tatgaatact     660
cggtggaatg tcaagaagat tcggcctgcc ggcggcagaa agaaagtctg cccatagaag     720
tcatggtgga tgctgttcac aaattaaaat atgaaaacta caccagcagc ttcttcatca     780
gagatatcat caagccagac ccccccaaga acctgcagct gaagcccctg aagaacagcc     840
ggcaggtgga agtttcctgg gagtacccag atacgtggag cacgccgcac agctacttca     900
gcctcacctt ctgtgtacaa gtacaaggca agagcaagag agagaagaaa gatcgtgtct     960
tcaccgacaa aacctcggcg acggtcatct gcaggaagaa tgcaagcatc tcggttcgag    1020
cccaggaccg ctactacagc agcagctgga gtgagtgggc ctcggtgccc tgcagtggtg    1080
```

| | |
|---|---|
| gcggcggcgg cggcagcaga aaccttcctg tggccacgcc ggaccctggc atgtttccgt | 1140 |
| gcctgcacca cagccaaaat ttattacgag ctgttagcaa catgctgcag aaagcacggc | 1200 |
| aaactttaga attctacccc tgcacctcag aagaaataga ccatgaagat atcaccaaag | 1260 |
| ataaaaccag cactgtagag gcctgcctgc ccctggagct caccaagaac gagagctgcc | 1320 |
| tcaatagcag agagaccagc ttcatcacca atggcagctg cctggccagc aggaaaacca | 1380 |
| gcttcatgat ggcgctctgc ctgagcagca tctatgaaga tctgaagatg taccaagtag | 1440 |
| aatttaaaac catgaatgcc aagctgctca tggaccccaa gcggcagata ttcctcgacc | 1500 |
| aaaacatgct ggctgtcatt gatgagctca tgcaagcatt aaacttcaac tcagagacgg | 1560 |
| tgccccagaa gagcagcctg gaggagccag atttctacaa aaccaagatc aagctctgca | 1620 |
| tcttattaca tgccttccgc atccggcggg tcaccattga ccgtgtcatg tcctacttaa | 1680 |
| atgccagctg ataataggct ggagcctcgg tggccatgct tcttgcccct gggcctcccc | 1740 |
| cccagcccct cctccccttc ctgcacccgt accccccaaa caccattgtc acactccagt | 1800 |
| ggtctttgaa taaagtctga gtgggcggc | 1829 |

<210> SEQ ID NO 64
<211> LENGTH: 1829
<212> TYPE: DNA
<213> ORGANISM: Artificial Sequence
<220> FEATURE:
<223> OTHER INFORMATION: hIL12AB_010

<400> SEQUENCE: 64

| | |
|---|---|
| tcaagctttt ggaccctcgt acagaagcta atacgactca ctatagggaa ataagagaga | 60 |
| aaagaagagt aagaagaaat ataagagcca ccatgtgcca ccagcagctt gtcatctcct | 120 |
| ggttttctct tgtcttcctc gcttctcctc ttgtggccat ctgggagctg aagaaagacg | 180 |
| tctacgtagt agagttggat tggtacccgg acgctcctgg agaaatggtg gttctcacct | 240 |
| gcgacactcc tgaagaagac ggtatcacct ggacgctgga ccaaagcagc gaagttttag | 300 |
| gctctggaaa aacgctgacc atacaagtaa agaatttgg cgacgctggc cagtacacgt | 360 |
| gccacaaagg aggagaagtt ttaagccaca gtttacttct tcttcacaag aaagaagatg | 420 |
| gcatctggag tacagatatt ttaaaagacc agaaggagcc taagaacaaa accttcctcc | 480 |
| gctgtgaagc taagaactac agtggtcgtt tcacctgctg gtggctcacc accatctcca | 540 |
| ctgacctcac cttctctgta aaatcaagcc gtggttcttc tgacccccaa ggagtcacct | 600 |
| gtggggctgc cacgctcagc gctgaaagag ttcgaggcga caacaaggaa tatgaatatt | 660 |
| ctgtggaatg tcaagaagat tctgcctgcc cggcggcaga agaaagtctt cccatagaag | 720 |
| tcatggtgga cgctgttcac aaattaaaat atgaaaacta caccagcagc ttcttcattc | 780 |
| gtgacatcat caaaccagac cctcctaaga accttcagtt aaaaccgctg aagaacagcc | 840 |
| ggcaggtgga agtttcctgg gagtaccag atacgtggag tacgccgcac tcctacttca | 900 |
| gtttaacctt ctgtgtacaa gtacaaggaa atcaaaaag agaagaaaa gatcgtgtct | 960 |
| tcactgacaa acatctgcc acggtcatct gccgtaagaa cgcttccatc tcggttcgag | 1020 |
| cccaggaccg ctactacagc agcagctgga gtgagtgggc atctgttccc tgcagtggtg | 1080 |
| gcggcggcgg cggcagccgc aaccttcctg tggccacgcc ggaccctggc atgtttccgt | 1140 |
| gccttcacca ctcgcaaaat cttcttcgtg ctgtttctaa catgctgcag aaggcgcggc | 1200 |
| aaactttaga attctacccg tgcacttctg aagaaataga ccatgaagat atcaccaaag | 1260 |
| ataaaaccag cacggtggag gcctgccttc ctttagaact tactaagaac gaaagttgcc | 1320 |

```
ttaacagccg tgagaccagc ttcatcacca atggcagctg ccttgctagc aggaagacca    1380
gcttcatgat ggcgctgtgc ctttcttcca tctatgaaga tcttaagatg taccaagtag    1440
aatttaaaac catgaatgcc aaattattaa tggaccccaa gcggcagata ttcctcgacc    1500
aaaacatgct ggctgtcatt gatgagctca tgcaagcatt aaacttcaac tcagaaactg    1560
ttccccagaa gtcatcttta gaagaaccag atttctacaa aacaaaaata aaactctgca    1620
ttcttcttca tgccttccgc atccgtgctg tcaccattga ccgtgtcatg tcctacttaa    1680
atgcttcttg ataataggct ggagcctcgg tggccatgct tcttgcccct tgggcctccc    1740
cccagcccct cctcccccttc ctgcacccgt acccccaaa caccattgtc acactccagt    1800
ggtctttgaa taaagtctga gtgggcggc                                      1829
```

<210> SEQ ID NO 65
<211> LENGTH: 1829
<212> TYPE: DNA
<213> ORGANISM: Artificial Sequence
<220> FEATURE:
<223> OTHER INFORMATION: hIL12AB_011

<400> SEQUENCE: 65

```
tcaagctttt ggaccctcgt acagaagcta atacgactca ctatagggaa ataagagaga      60
aaagaagagt aagaagaaat ataagagcca ccatgtgcca ccagcagctg gtgatcagct     120
ggttcagcct ggtgttcctg ccagcccccc tggtggccat ctgggagctg aagaaggacg     180
tgtacgtggt ggagttggat tggtacccgg acgcgccggg ggagatggtg gtgctgacgt     240
gcgacacgcc ggaggaggac gggatcacgt ggacgctgga ccagagcagc gaggtgctgg     300
ggagcgggaa gacgctgacg atccaggtga aggagttcgg ggacgcgggg cagtacacgt     360
gccacaaggg gggggaggtg ctgagccaca gcctgctgct gctgcacaag aaggaggacg     420
ggatctggag cacagatatc ctgaaggacc agaaggagcc gaagaacaag acgttcctga     480
ggtgcgaggc gaagaactac agcggaggt tcacgtgctg gtggctgacg acgatcagca     540
cggacctgac gttcagcgtg aagagcagca ggggagcag cgacccgcag ggggtgacgt     600
gcggggcggc gacgctgagc gcggagaggg tgaggggtga caacaaggag tacgagtaca     660
gcgtggagtg ccaggaagat agcgcgtgcc cggcggcgga ggagagcctg ccgatcgagg     720
tgatggtgga cgcggtgcac aagctgaagt acgagaacta cacgagcagc ttcttcatca     780
gagatatcat caagccggac ccgccgaaga acctgcagct gaagccgctg aagaacagca     840
ggcaggtgga ggtgagctgg gagtacccag atacgtggag cacgccgcac agctacttca     900
gcctgacgtt ctgcgtgcag gtgcagggga gagcaagag ggagaagaaa gatagggtgt     960
tcacagataa cgagcgcg acggtgatct gcaggaagaa cgcgagcatc agcgtgaggg    1020
cgcaagatag gtactacagc agcagctgga gcgagtgggc gagcgtgccg tgcagcgggg    1080
gggggggggg gggagcagg aacctgccgg tggcgacgcc ggaccccgggg atgttcccgt    1140 gcctgcacca cagccagaac ctgctgaggg cggtgagcaa catgctgcag aaggcgaggc    1200
agacgctgga gttctacccg tgcacgagcg aggagatcga ccacgaagat atcacgaaag    1260
ataagacgag cacggtggag gcgtgcctgc cgctggagct gacgaagaac gagagctgcc    1320
tgaacagcag ggagacgagc ttcatcacga cgggagctg cctggcgagc aggaagacga    1380
gcttcatgat ggcgctgtgc ctgagcagca tctacgagga cctgaagatg taccaggtgg    1440
agttcaagac gatgaacgcg aagctgctga tggacccgaa gaggcagatc ttcctggacc    1500
```

| | | | | |
|---|---|---|---|---|
| agaacatgct | ggcggtgatc | gacgagctga | tgcaggcgct | gaacttcaac agcgagacgg | 1560 |
| tgccgcagaa | gagcagcctg | gaggagccag | atttctacaa | gacgaagatc aagctgtgca | 1620 |
| tcctgctgca | cgcgttcagg | atcagggcgg | tgacgatcga | cagggtgatg agctacctga | 1680 |
| acgcgagctg | ataataggct | ggagcctcgg | tggccatgct | tcttgcccct tgggcctccc | 1740 |
| cccagcccct | cctccccttc | ctgcacccgt | acccccaaa | caccattgtc acactccagt | 1800 |
| ggtctttgaa | taaagtctga | gtgggcggc | | | 1829 |

<210> SEQ ID NO 66
<211> LENGTH: 1829
<212> TYPE: DNA
<213> ORGANISM: Artificial Sequence
<220> FEATURE:
<223> OTHER INFORMATION: hIL12AB_012

<400> SEQUENCE: 66

| | | | | |
|---|---|---|---|---|
| tcaagctttt | ggaccctcgt | acagaagcta | atacgactca | ctatagggaa ataagagaga | 60 |
| aagaagagt | aagaagaaat | ataagagcca | ccatgtgcca | tcagcagctg gtgatcagct | 120 |
| ggttcagcct | cgtgtttctg | gccagccccc | tggtggccat | ttgggaactc aagaaggacg | 180 |
| tgtacgttgt | ggaactcgac | tggtaccctg | acgcccagg | cgaaatggtg gtcttaacct | 240 |
| gcgacacccc | tgaggaggac | ggaatcacct | ggaccttgga | ccagagctcc gaggtcctcg | 300 |
| gcagtggcaa | gaccctgacc | atacaggtga | agaatttgg | agacgcaggg caatacacat | 360 |
| gtcacaaggg | cggggaggtt | ctttctcact | cccttctgct | tctacataaa aggaagacg | 420 |
| gaatttggtc | taccgacatc | ctcaaggacc | aaaaggagcc | taagaataaa accttcttac | 480 |
| gctgtgaagc | taaaaactac | agcggcagat | tcacttgctg | gtggctcacc accatttcta | 540 |
| ccgacctgac | cttctcggtg | aagtcttcaa | ggggctctag | tgatccacag ggagtggacat | 600 |
| gcggggccgc | cacactgagc | gctgaacggg | tgaggggcga | taacaaggag tatgaatact | 660 |
| ctgtcgagtg | tcaggaggat | tcagcttgtc | ccgcagctga | agagtcactc cccatagagg | 720 |
| ttatggtcga | tgctgtgcat | aaactgaagt | acgaaaacta | caccagcagc ttcttcatta | 780 |
| gagatattat | aaaacctgac | cccccaaga | acctgcaact | taaaccctg aaaaactctc | 840 |
| ggcaggtcga | agttagctgg | gagtaccctg | atacttggtc | caccccccac tcgtacttct | 900 |
| cactgacttt | ctgtgtgcag | gtgcagggca | agagcaagag | agagaaaaaa gatcgtgtat | 960 |
| tcacagataa | gacctctgcc | accgtgatct | gcagaaaaaa | cgcttccatc agtgtcagag | 1020 |
| cccaagaccg | gtactatagt | agtagctgga | gcgagtgggc | aagtgtcccc tgctctggcg | 1080 |
| gcggagggg | cggctctcga | aacctccccg | tcgctacccc | tgatccagga atgttccctt | 1140 |
| gcctgcatca | ctcacagaat | ctgctgagag | cggtcagcaa | catgctgcag aaagctaggc | 1200 |
| aaacactgga | gttttatcct | tgtacctcag | aggagatcga | ccacgaggat attaccaaag | 1260 |
| ataagaccag | cacggtggag | gcctgcttgc | cctggaact | gacaaagaat gaatcctgcc | 1320 |
| ttaatagccg | tgagacctct | tttataacaa | acgatcctg | cctggccagc aggaagacct | 1380 |
| ccttcatgat | ggccctctgc | ctgtcctcaa | tctacgaaga | cctgaagatg taccaggtgg | 1440 |
| aatttaaaac | tatgaacgcc | aagctgttga | tggaccccaa | cgcgcagatc tttctggatc | 1500 |
| aaaatatgct | ggctgtgatc | gacgaactga | tgcaggccct | caactttaac agcgagaccg | 1560 |
| tgccacaaaa | gagcagtctt | gaggagcccg | acttctacaa | gaccaagatc aagctgtgca | 1620 |
| tcctccttca | tgccttcagg | ataagagctg | tcaccatcga | cagagtcatg agttacctga | 1680 |
| atgcatcctg | ataataggct | ggagcctcgg | tggccatgct | tcttgcccct tgggcctccc | 1740 |

```
cccagccct cctccccttc ctgcacccgt accccccaaa caccattgtc acactccagt      1800
ggtctttgaa taaagtctga gtgggcggc                                       1829

<210> SEQ ID NO 67
<211> LENGTH: 1829
<212> TYPE: DNA
<213> ORGANISM: Artificial Sequence
<220> FEATURE:
<223> OTHER INFORMATION: hIL12AB_013

<400> SEQUENCE: 67
tcaagctttt ggaccctcgt acagaagcta atacgactca ctatagggaa ataagagaga       60
aaagaagagt aagaagaaat ataagagcca ccatgtgcca ccagcagctg gtcatctcct      120
ggttcagtct tgtcttcctg gcctcgccgc tggtggccat ctgggagctg aagaagacg       180 tttacgtagt agagttggat tggtacccag acgcacctgg agaaatggtg gtcctcacct      240
gtgacacgcc agaagaagac ggtatcacct ggacgctgga ccagagcagt gaagttcttg      300
gaagtggaaa acgctgacc atacaagtaa agaatttgg agatgctggc cagtacacct       360
gccacaaagg aggagaagtt ctcagccaca gtttattatt acttcacaag aaagaagatg      420
gcatctggtc cacagatatt ttaaaagacc agaaggagcc caaaaataaa acatttcttc      480
gatgtgaggc caagaactac agtggtcgtt tcacctgctg gtggctgacc accatctcca      540
cagacctcac cttcagtgta aaaagcagcc gtggttcttc gaccccaa ggagtcacct       600 gtggggctgc cacgctctct gcagaaagag ttcgaggtga acaaaagaa tatgagtact       660 cggtggaatg tcaagaagat tcggcctgcc cagctgctga ggagagtctt cccatagaag      720
tcatggtgga tgctgttcac aaattaaaat atgaaaacta caccagcagc ttcttcatca      780
gagatatcat caaacctgac ccgcccaaga acttacagct gaagccgctg aaaaacagcc      840
ggcaggtaga agtttcctgg gagtaccag ataccggtc cacgccgcac tcctacttct       900
ccctcacctt ctgtgtacaa gtacaaggca agagcaagag agagaagaaa gatcgtgtct      960
tcacagataa acatcagcc acggtcatct gcaggaaaaa tgccagcatc tcggtgcggg     1020
cccaggaccg ctactacagc agcagctgga gtgagtgggc atctgtgccc tgcagtggtg     1080 gtggggtgg tggcagcaga aaccttcctg tggccactcc agaccctggc atgttcccgt     1140
gccttcacca ctcccaaaat ttacttcgag ctgtttctaa catgctgcag aaagcacggc     1200
aaactttaga attctacccg tgcacttctg aagaaattga ccatgaagat atcacaaaag     1260
ataaaaccag cacagtggag gcctgtcttc ctttagagct gaccaaaaat gaatcctgcc     1320
tcaacagcag agagaccagc ttcatcacca atggcagctg cctggcctcc aggaaaacca     1380
gcttcatgat ggcgctctgc ctcagctcca tctatgaaga tttgaagatg taccaagtag     1440
aatttaaaac catgaatgcc aaattattaa tggaccccaa gaggcagata ttttagatc      1500 aaacatgct ggcagttatt gatgagctca tgcaagcatt aaacttcaac agtgagacgg     1560
tacctcaaaa aagcagcctt gaagagccag atttctacaa aaccaagatc aaactctgca     1620
ttttacttca tgccttccgc atccgggcgg tcaccattga ccgtgtcatg tcctacttaa     1680
atgcctcgtg ataataggct ggagcctcgg tggccatgct tcttgcccct tgggcctccc     1740 cccagccct cctccccttc ctgcacccgt accccccaaa caccattgtc acactccagt      1800
ggtctttgaa taaagtctga gtgggcggc                                      1829

<210> SEQ ID NO 68
```

<211> LENGTH: 1829
<212> TYPE: DNA
<213> ORGANISM: Artificial Sequence
<220> FEATURE:
<223> OTHER INFORMATION: hIL12AB_014

<400> SEQUENCE: 68

```
tcaagctttt ggaccctcgt acagaagcta atacgactca ctataggaa ataagagaga      60
aaagaagagt aagaagaaat ataagagcca ccatgtgcca ccagcagctt gtgatttctt    120
ggttctctct tgtgttcctt gcttctcctc ttgtggctat ttgggagtta aaaaaggacg    180
tgtacgtggt ggagcttgac tggtaccctg acgcacctgg cgagatggtg gtgcttactt    240
gtgacactcc tgaggaggac ggcattactt ggacgcttga ccagtcttct gaggtgcttg    300
gctctggcaa aacacttact attcaggtga aggagttcgg ggatgctggc cagtacactt    360
gccacaaggg cggcgaggtg ctttctcact ctcttcttct tcttcacaag aaggaggacg    420
gcatttggtc tactgacatt ttaaaagacc agaaggagcc caagaacaaa acattccttc    480
gttgcgaggc caagaactac tctggccgtt tcacttgctg gtggcttact actatttcta    540
ctgaccttac tttctctgtg aagtcttctc gtggctcttc tgaccctcag ggcgtgactt    600
gtggggctgc tactctttct gctgagcgtg tgcgtggtga caacaaggag tacgagtact    660
ctgtggagtg ccaggaagat tctgcttgcc ctgctgctga ggagtctctt cctattgagg    720
tgatggtgga tgctgtgcac aagttaaaat acgagaacta cacttcttct ttcttcattc    780
gtgacattat taagcctgac cctcccaaga accttcagtt aaaacccttta aaaaactctc    840
gtcaggtgga ggtgtcttgg gagtaccctg acacttggtc tactcctcac tcttacttct    900
ctcttacttt ctgcgtgcag gtgcagggca gtctaagcg tgagaagaag accgtgtgt    960
tcactgacaa aacatctgct actgtgattt gcaggaagaa tgcatctatt tctgtgcgtg   1020
ctcaggaccg ttactactct tcttcttggt ctgagtgggc ttctgtgcct tgctctggcg   1080
gcggcggcgg cggctccaga aatcttcctg tggctactcc tgaccctggc atgttccctt   1140
gccttcacca ctctcagaac cttcttcgtg ctgtgagcaa catgcttcag aaggctcgtc   1200
aaactcttga gttctaccct tgcacttctg aggagattga ccacgaagat atcaccaaag   1260
ataaaacatc tactgtggag gcttgccttc ctcttgagct taccaagaat gaatcttgct   1320
taaattctcg tgagacgtct ttcatcacca acggctcttg ccttgcctcg cgcaaaacat   1380
ctttcatgat ggctctttgc ctttcttcta tttacgaaga tttaaaaatg taccaggtgg   1440
agttcaaaac aatgaatgca aagcttctta tggaccccaa cgtcagatt ttccttgacc   1500
agaacatgct tgctgtgatt gacgagctta tgcaggcttt aaatttcaac tctgagacgg   1560
tgcctcagaa gtcttctctt gaggagcctg acttctacaa gaccaagatt aagctttgca   1620
ttcttcttca tgctttccgt attcgtgctg tgactattga ccgtgtgatg tcttacttaa   1680
atgcttcttg ataataggct ggagcctcgg tggccatgct tcttgcccct tgggcctccc   1740
cccagccct cctccccttc ctgcacccgt acccccaaa caccattgtc acactccagt   1800
ggtctttgaa taaagtctga gtgggcggc                                    1829
```

<210> SEQ ID NO 69
<211> LENGTH: 1829
<212> TYPE: DNA
<213> ORGANISM: Artificial Sequence
<220> FEATURE:
<223> OTHER INFORMATION: hIL12AB_015

<400> SEQUENCE: 69

```
tcaagcttttt ggaccctcgt acagaagcta atacgactca ctatagggaa ataagagaga      60
aaagaagagt aagaagaaat ataagagcca ccatgtgtca ccagcagctg gtgatcagct     120
ggtttagcct ggtgtttctg ccagcccccc tggtggccat ctgggaactg aagaaagacg     180
tgtacgtggt agaactggat tggtatccgg acgctcccgg cgaaatggtg gtgctgacct     240
gtgacacccc cgaagaagac ggaatcacct ggaccctgga ccagagcagc gaggtgctgg     300
gcagcggcaa aaccctgacc atccaagtga aagagtttgg cgatgccggc agtacacctt     360
gtcacaaagg cggcgaggtg ctaagccatt cgctgctgct gctgcacaaa aaggaagatg     420
gcatctggag caccgatatc ctgaaggacc agaaagaacc caaaaataag accttttctaa    480 gatgcgaggc caagaattat agcggccgtt tcacctgctg gtggctgacg accatcagca    540
ccgatctgac cttcagcgtg aaaagcagca gaggcagcag cgaccccaa ggcgtgacgt     600 gcggcgccgc caccctgagc gccgagagag tgagaggcga caacaaggag tatgagtaca    660
gcgtggagtg ccaggaagat agcgcctgcc ccgccgccga ggagagcctg cccatcgagg    720
tgatggtgga tgccgtgcac aagctgaagt atgaaaacta caccagcagc ttcttcatca    780
gagatatcat caaacccgac cccccccaaga acctgcagct gaagcccctg aagaatagcc    840
ggcaggtgga ggtgagctgg gagtaccccg acacctggag caccccccat agctacttca    900
gcctgacctt ctgcgtgcag gtgcagggca gagcaagag agaaaagaaa gatagagtgt    960
tcacagataa gaccagcgcc acggtgatct gcagaaaaaa tgccagcatc agcgtgagag   1020
cccaagatag atactatagc agcagctgga gcgaatgggc cagcgtgccc tgcagcggcg   1080
gcggcggcgg cggcagcaga aacctgcccg tggccacccc cgaccccggc atgttcccct   1140
gcctgcacca cagccaaaac ctgctgagag ccgtgagcaa catgctgcag aaggcccggc   1200
agaccctgga atttttaccc ctgcaccagc gaagagatcga tcatgaagat atcaccaaag   1260
ataaaaccag caccgtggag gcctgtctgc ccctggaact gaccaagaat gagagctgcc   1320
taaatagcag agagaccagc ttcataacca atggcagctg cctggccagc agaaagacca   1380
gctttatgat ggccctgtgc ctgagcagca tctatgaaga cctgaagatg taccaggtgg   1440
agttcaagac catgaatgcc aagctgctga tggatcccaa gcggcagatc tttctggatc   1500
aaaacatgct ggccgtgatc gatgagctga tgcaggccct gaatttcaac agcgagaccg   1560
tgccccaaaa aagcagcctg gaagaaccgg attttttataa aaccaaaatc aagctgtgca   1620
tactgctgca tgccttcaga atcagagccg tgaccatcga tagagtgatg agctatctga   1680
atgccagctg ataataggct ggagcctcgg tggccatgct tcttgcccct ggggcctccc   1740
cccagcccct cctcccttc ctgcacccgt accccccaaa caccattgtc acactccagt   1800
ggtctttgaa taaagtctga gtgggcggc                                     1829
```

<210> SEQ ID NO 70
<211> LENGTH: 1829
<212> TYPE: DNA
<213> ORGANISM: Artificial Sequence
<220> FEATURE:
<223> OTHER INFORMATION: hIL12AB_016

<400> SEQUENCE: 70

```
tcaagcttttt ggaccctcgt acagaagcta atacgactca ctatagggaa ataagagaga      60
aaagaagagt aagaagaaat ataagagcca ccatgtgcca ccagcagctg gtcatcagct     120
ggttcagcct ggtcttcctg ccagcccccc tggtggccat ctgggagctg aagaaggacg     180
```

| | |
|---|---|
| tatacgtagt ggagttggat tggtacccag acgctcctgg ggagatggtg gtgctgacct | 240 |
| gtgacacccc agaagaggac ggtatcacct ggaccctgga ccagagctca gaagtgctgg | 300 |
| gcagtggaaa accctgacc atccaggtga aggagtttgg agatgctggc cagtacacct | 360 |
| gccacaaggg tggtgaagtg ctgagccaca gcctgctgct gctgcacaag aaggaggatg | 420 |
| gcatctggag cacagatatc ctgaaggacc agaaggagcc caagaacaag accttccttc | 480 |
| gctgtgaagc caagaactac agtggccgct tcacctgctg gtggctgacc accatcagca | 540 |
| cagacctcac cttctcggtg aagagcagca gaggcagctc agacccccag ggtgtcacct | 600 |
| gtggggcggc cacgctgtcg gcggagagag ttcgaggtga caacaaggag tatgaatact | 660 |
| cggtggagtg ccaggaagat cggcgtgcc cggcggcaga agagagcctg cccatagaag | 720 |
| tgatggtgga tgctgtgcac aagctgaagt atgaaaacta caccagcagc ttcttcatca | 780 |
| gagatatcat caagccagac cgcccaaga acctgcagct gaagcccctg aagaacagcc | 840 |
| ggcaggtgga ggtttcctgg gagtaccag atacgtggag caccccccac agctacttca | 900 |
| gcctgacctt ctgtgtccag gtgcagggca gagcaagag agagaagaaa gatagagtct | 960 |
| tcacagataa gacctcggcc acggtcatct gcagaaagaa tgcctccatc tcggttcgag | 1020 |
| cccaagatag atactacagc agcagctggt cagaatgggc ctcggtgccc tgcagtggtg | 1080 |
| gcggcggcgg cggcagcaga aacctgcctg ttgccacccc agaccctggg atgttcccct | 1140 |
| gcctgcacca cagccagaac ttattacgag ctgtttctaa catgctgcag aaggcccggc | 1200 |
| agacccctgga gttctacccc tgcacctcag aagagattga ccatgaagat atcaccaaag | 1260 |
| ataagaccag cactgtagag gcctgcctgc cctggagct gaccaagaat gaaagctgcc | 1320 |
| tgaacagcag agagaccagc ttcatcacca tggaagctg cctggccagc agaaagacca | 1380 |
| gcttcatgat ggcccctgtgc ctgagcagca tctatgaaga cctgaagatg taccaggtgg | 1440 |
| agttcaagac catgaatgca aagctgctga tggaccccaa gcggcagata ttttttggacc | 1500 |
| agaacatgct ggctgtcatt gatgagctga tgcaggccct gaacttcaac tcagaaactg | 1560 |
| taccccagaa gagcagcctg gaggagccag atttctacaa gaccaagatc aagctgtgca | 1620 |
| tcctgcttca tgctttcaga atcagagctg tcaccattga ccgcgtgatg agctacttaa | 1680 |
| atgcctcgtg ataataggct ggagcctcgg tggccatgct tcttgcccct tgggcctccc | 1740 |
| cccagcccct cctcccttc ctgcacccgt acccccaaa caccattgtc acactccagt | 1800 |
| ggtctttgaa taaagtctga gtgggcggc | 1829 |

<210> SEQ ID NO 71
<211> LENGTH: 1829
<212> TYPE: DNA
<213> ORGANISM: Artificial Sequence
<220> FEATURE:
<223> OTHER INFORMATION: hIL12AB_017

<400> SEQUENCE: 71

| | |
|---|---|
| tcaagctttt ggaccctcgt acagaagcta atacgactca ctatagggaa ataagagaga | 60 |
| aaagaagagt aagaagaaat ataagagcca ccatgtgcca ccagcagctg gtaatcagct | 120 |
| ggttttccct cgtctttctg gcatcacccc tggtggctat ctgggagctg aagaaggacg | 180 |
| tgtacgtggt ggagctggat tggtaccctg acgccccggg ggaaatggtg gtgttaacct | 240 |
| gcgacacgcc tgaggaggac ggcatcacct ggacgctgga ccagagcagc gaggtgcttg | 300 |
| ggtctggtaa aactctgact attcaggtga agagttcgg ggatgccggc caatatactt | 360 |
| gccacaaggg tggcgaggtg ctttctcatt ctctgctcct gctgcacaag aaagaagatg | 420 |

```
gcatttggtc tactgatatt ctgaaagacc agaaggagcc caagaacaag acctttctga      480
gatgcgaggc taaaaactac agcggaagat ttacctgctg gtggctgacc acaatctcaa      540
ccgacctgac attttcagtg aagtccagca gagggagctc cgaccctcag ggcgtgacct      600
gcggagccgc cactctgtcc gcagaaagag tgagaggtga taataaggag tacgagtatt      660
cagtcgagtg ccaagaagat tctgcctgcc cagccgccga ggagagcctg ccaatcgagg      720
tgatggtaga tgcggtacac aagctgaagt atgagaacta cacatcctcc ttcttcataa      780
gagatattat caagcctgac ccacctaaaa atctgcaact caagcctttg aaaaattcac      840
ggcaggtgga ggtgagctgg gagtaccctg atacttggag cacccccat agctactttt      900 cgctgacatt ctgcgtccag gtgcagggca agtcaaagag agagaagaag gatcgcgtgt      960
tcactgataa aacaagcgcc acagtgatct gcagaaaaaa cgctagcatt agcgtcagag     1020
cacaggaccg gtattactcc agctcctgga gcgaatgggc atctgtgccc tgcagcggtg     1080
ggggcggagg cggatccaga aacctccccg ttgccacacc tgatcctgga atgttcccct     1140
gtctgcacca cagccagaac ctgctgagag cagtgtctaa catgctccag aaggccaggc     1200
agaccctgga gttttacccc tgcaccagca ggaaatcga tcacgaagat atcaccaaag     1260
ataaaacctc caccgtggag gcctgcctgc ccctggaact gaccaaaaac gagagctgcc     1320
tgaatagcag ggagacctcc ttcatcacca acggctcatg ccttgccagc cggaaaacta     1380
gcttcatgat ggccctgtgc ctgtcttcga tctatgagga cctgaaaatg taccaggtcg     1440
aatttaagac gatgaacgca aagctgctga tggaccccaa gcggcagatc tttctggacc     1500
agaacatgct ggcagtcata gatgagttga tgcaggcatt aaacttcaac agcgagaccg     1560
tgcctcagaa gtccagcctc gaggagccag atttttataa gaccaagatc aaactatgca     1620
tcctgctgca tgctttcagg attagagccg tcaccatcga tcgagtcatg tcttacctga     1680
atgctagctg ataataggct ggagcctcgg tggccatgct tcttgcccct tgggcctccc     1740
cccagcccct cctccccttc ctgcacccgt accccccaaa caccattgtc acactccagt     1800
ggtctttgaa taaagtctga gtgggcggc                                       1829
```

<210> SEQ ID NO 72
<211> LENGTH: 1829
<212> TYPE: DNA
<213> ORGANISM: Artificial Sequence
<220> FEATURE:
<223> OTHER INFORMATION: hIL12AB_018

<400> SEQUENCE: 72

```
tcaagctttt ggaccctcgt acagaagcta atacgactca ctatagggaa ataagagaga       60
aaagaagagt aagaagaaat ataagagcca ccatgtgtca ccaacagtta gtaatctcct      120
ggttttctct ggtgtttctg ccagccccc tcgtggccat ctgggagctt aaaaaggacg      180
tttacgtggt ggagttggat tggtatcccg acgctccagg cgaaatggtc gtgctgacct      240
gcgatacccc tgaagaagac ggtatcacct ggacgctgga ccagtcttcc gaggtgcttg      300
gatctggcaa aacactgaca atacaagtta aggagttcgg ggacgcaggg cagtacacct      360
gccacaaagg cggcgaggtc ctgagtcact cctgttact gctccacaag aaagaggacg      420
gcatttggtc caccgacatt ctgaaggacc agaaggagcc taagaataaa actttcctga      480
gatgcgaggc aaaaaactat agcggccgct ttacttgctg gtggcttaca acaatctcta      540
ccgatttaac tttctccgtg aagtctagca gaggatcctc tgacccgcaa ggagtgactt      600
```

```
gcggagccgc caccttgagc gccgaaagag tccgtggcga taacaaagaa tacgagtact    660
ccgtggagtg ccaggaagat tccgcctgcc cagctgccga ggagtccctg cccattgaag    720
tgatggtgga tgccgtccac aagctgaagt acgaaaacta taccagcagc ttcttcatcc    780
gggatatcat taagcccgac cctcctaaaa acctgcaact taagccccta agaatagtc     840 ggcaggttga ggtcagctgg gaatatcctg acacatggag cacccccac tcttatttct     900 ccctgacctt ctgcgtgcag gtgcagggca agagtaaacg ggagaaaaaa gatagggtct    960
ttaccgataa aaccagcgct acggttatct gtcggaagaa cgcttccatc tccgtccgcg   1020
ctcaggatcg ttactactcg tcctcatgga gcgagtgggc cagcgtgccc tgcagcggcg   1080
gcggtggagg cggatccaga aatctgcctg ttgccacacc agaccctggc atgttcccct   1140
gtctgcatca tagccagaac ctgctcagag ccgtgagcaa catgctccag aaggccaggc   1200
aaactttgga gttctacccg tgtacatctg aggaaatcga tcacgaagat ataaccaaag   1260
ataaaacctc tacagtagag gcttgtttgc ccctggagtt gaccaaaaac gagagttgcc   1320
tgaacagtcg cgagacgagc ttcattacta acggcagctg tctcgcctcc agaaaaacat   1380
ccttcatgat ggccctgtgt ctttccagca tatacgaaga cctgaaaatg taccaggtcg   1440
agttcaaaac aatgaacgcc aagctgctta tggaccccaa cgcgcagatc ttcctcgacc   1500
aaaacatgct cgctgtgatc gatgagctga tgcaggctct caacttcaat tccgaaacag   1560
tgccacagaa gtccagtctg gaagaacccg acttctacaa gaccaagatt aagctgtgta   1620
ttttgctgca tgcgtttaga atcagagccg tgaccattga tcgggtgatg agctacctga   1680
acgcctcgtg ataataggct ggagcctcgg tggccatgct tcttgccct tgggcctccc    1740 cccagcccct cctcccccttc ctgcacccgt acccccccaaa caccattgtc acactccagt   1800
ggtctttgaa taaagtctga gtgggcggc                                     1829

<210> SEQ ID NO 73
<211> LENGTH: 1829
<212> TYPE: DNA
<213> ORGANISM: Artificial Sequence
<220> FEATURE:
<223> OTHER INFORMATION: hIL12AB_019

<400> SEQUENCE: 73
tcaagctttt ggaccctcgt acagaagcta atacgactca ctatagggaa ataagagaga     60 aagaagagt aagaagaaat ataagagcca ccatgtgcca ccagcagctt gtcatctcct    120
ggttttctct tgtcttcctg gcctcgccgc tggtggccat ctgggagctg aagaaagacg    180
tttacgtagt agagttggat tggtacccag acgcacctgg agaaatggtg ttctcaccct    240
gtgacactcc tgaagaagac ggtatcacct ggacgctgga ccaaagctca gaagttcttg    300
gcagtggaaa aacgctgacc atacaagtaa aagaatttgg ggatgctggc cagtacacgt    360
gccacaaagg aggagaagtt tcagccacag tttacttct tcttcacaag aaagaagatg    420
gcatctggtc cacagatatt ttaaaagacc agaaggagcc caagaacaaa accttcctcc    480
gctgtgaggc caagaactac agtggtcgtt tcacctgctg gtggctcacc accatctcca    540
ctgacctcac cttctctgta aaagcagcc gtggttcttc tgacccccaa ggagtcacct    600
gtggggctgc cacgctctcg gcagaaagag ttcgaggtga acaaggaa tatgaatatt     660 ctgtggaatg tcaagaagat tctgcctgcc cggcggcaga agaaagtctt cccatagaag    720
tcatggtgga tgctgttcac aaattaaat atgaaaacta caccagcagc ttcttcattc    780
gtgacatcat caaaccagac ccgcccaaga accttcagtt aaaacccta aaaaacagcc    840
```

```
ggcaggtaga agtttcctgg gagtacccag atacgtggtc cacgccgcac tcctacttca     900
gtttaacctt ctgtgtacaa gtacaaggaa atcaaaaag agagaagaaa gatcgtgtct      960
tcactgacaa aacatctgcc acggtcatct gcaggaagaa tgcctccatc tcggttcgag    1020
cccaggaccg ctactacagc agcagctgga gtgagtgggc atctgttccc tgcagtggtg    1080
gcggcggcgg cggcagccgc aaccttcctg tggccacgcc ggaccctggc atgttcccgt    1140
gccttcacca ctcccaaaat cttcttcgtg ctgtttctaa catgctgcag aaggcgcgcc    1200
aaactttaga attctacccg tgcacttctg aagaaataga ccatgaagat atcaccaaag    1260
ataaaaccag cacggtggag gcctgccttc ctttagagct gaccaagaat gaatcctgcc    1320
tcaacagcag agagaccagc ttcatcacca atggcagctg cctggcctcg cgcaagacca    1380
gcttcatgat ggcgctgtgc ctttcttcca tctatgaaga tttaaagatg taccaagtag    1440
aatttaaaac catgaatgcc aaattattaa tggaccccaa acggcagata ttttttggatc    1500
aaaacatgct ggctgtcatt gatgagctca tgcaagcatt aaacttcaac tcagaaactg    1560
ttccccagaa gtcatcttta aagagccag atttctacaa aacaaaaata aaactctgca    1620
ttcttcttca tgccttccgc atccgtgctg tcaccattga ccgtgtcatg tcctacttaa    1680
atgcttcttg ataataggct ggagcctcgg tggccatgct tcttgcccct tgggcctccc    1740
cccagcccct cctcccttc ctgcacccgt accccccaaa caccattgtc acactccagt    1800
ggtctttgaa taaagtctga gtgggcggc                                      1829

<210> SEQ ID NO 74
<211> LENGTH: 1829
<212> TYPE: DNA
<213> ORGANISM: Artificial Sequence
<220> FEATURE:
<223> OTHER INFORMATION: hIL12AB_020

<400> SEQUENCE: 74
tcaagctttt ggaccctcgt acagaagcta atacgactca ctatagggaa ataagagaga      60
aagaagagt aagaagaaat ataagagcca ccatgtgcca ccagcagctg gtgatcagct      120
ggttcagcct ggtgttcctg ctagccctc tggtggccat ctgggagctg aagaaggacg      180
tgtacgtggt ggagttggat tggtaccccg acgctcccgg cgagatggtg gtgctgacct      240
gcgacacccc cgaggaggac gggatcacct ggaccctgga tcagtcaagc gaggtgctgg      300
aagcggcaa gaccctgacc atccaggtga aggagttcgg cgacgccggc caatacactt      360
gccacaaggg aggcgaggtg ctgtcccact ccctcctgct gctgcacaaa aaggaagacg      420
gcatctggag caccgacatc ctgaaagacc agaaggagcc taagaacaaa acattcctca      480
gatgcgaggc caagaattac tccgggagat tcacctgttg gtggctgacc accatcagca      540
cagacctgac cttcagcgtg aagagcagca gaggcagcag cgaccccag ggcgtgacct      600
gtggcgccgc cacctgagc gccgaaagag tgcgcggcga caacaaggag tacgagtact      660
ccgtggaatg ccaggaagat agcgcctgcc ccgccgccga ggagagcctg cccatcgagg      720
tgatggtgga cgccgtccac aagctgaagt acgagaacta cacctctagc ttcttcatca      780
gagatatcat caagcccgat ccccccaaga acctgcagct gaaaccctg aagaacagcc      840
ggcaggtgga ggtgagctgg gagtatcccg acacctggtc caccccccac agctattta      900
gcctgacctt ctgcgtgcaa gtgcagggca gagcaagag agagaagaag gaccgcgtgt      960
tcaccgacaa aaccagcgcc accgtgatct gcagaaagaa cgccagcatc agcgtgaggg     1020
```

| | |
|---|---|
| cccaggatag atactacagt tccagctgga gcgagtgggc cagcgtgccc tgcagcggcg | 1080 |
| gcggcggggg aggctcgaga aacctgcccg tggctacccc cgatcccgga atgttcccct | 1140 |
| gcctgcacca cagccagaac ctgctgaggg cggtgtccaa catgcttcag aaggcccggc | 1200 |
| agaccctgga gttctacccc tgtacctctg aggagatcga tcatgaagat atcacaaaag | 1260 |
| ataaaaccag caccgtggag gcctgcctgc ccctggagct gaccaagaac gagagctgcc | 1320 |
| tgaactcccg cgagaccagc ttcatcacga acggcagctg cctggccagc aggaagacct | 1380 |
| ccttcatgat ggccctgtgc ctgagcagca tctacgagga cctgaaaatg taccaggtgg | 1440 |
| agtttaagac catgaacgcc aagctgctga tggaccccaa gcggcaaatc ttcctggacc | 1500 |
| agaacatgct ggcagtgatc gacgagctca tgcaggccct gaacttcaat agcgagacgg | 1560 |
| tcccccagaa gagcagcctg gaggagcccg acttttacaa gaccaagatc aagctgtgca | 1620 |
| tcctgctgca cgcctttaga atccgtgccg tgaccattga cagagtgatg agctacctga | 1680 |
| atgccagctg ataataggct ggagcctcgg tggccatgct tcttgcccct tgggcctccc | 1740 |
| cccagcccct cctcccttc ctgcacccgt accccccaaa caccattgtc acactccagt | 1800 |
| ggtctttgaa taaagtctga gtgggcggc | 1829 |

<210> SEQ ID NO 75
<211> LENGTH: 1829
<212> TYPE: DNA
<213> ORGANISM: Artificial Sequence
<220> FEATURE:
<223> OTHER INFORMATION: hIL12AB_021

<400> SEQUENCE: 75

| | |
|---|---|
| tcaagctttt ggaccctcgt acagaagcta atacgactca ctatagggaa ataagagaga | 60 |
| aaagaagagt aagaagaaat ataagagcca ccatgtgcca ccagcagctg gtgatcagct | 120 |
| ggttcagcct ggtgttcctg gccagccctc tggttgccat ctgggagctg aagaaagacg | 180 |
| tgtacgtcgt ggaactggac tggtatccgg acgccccggg cgagatggtg gtgctgacct | 240 |
| gtgacacccc cgaggaggac ggcatcacct ggacgctgga ccaatcctcc gaggtgctgg | 300 |
| gaagcggcaa gaccctgacc atccaggtga aggaattcgg ggacgccggg cagtacacct | 360 |
| gccacaaggg gggcgaagtg ctgtcccact cgctgctgct cctgcataag aaggaggatg | 420 |
| gaatctggtc caccgacatc ctcaaagatc agaaggagcc caagaacaag cgttcctgc | 480 |
| gctgtgaagc caagaattat tcggggcgat tcacgtgctg gtggctgaca accatcagca | 540 |
| ccgacctgac gtttagcgtg aagagcagca ggggtccag cgaccccag ggcgtgacgt | 600 |
| gcggcgccgc cacctctctcc gccgagaggg tgcgggggga caataaggag tacgagtaca | 660 |
| gcgtggaatg ccaggaggac agcgcctgcc ccgccgcgga ggaaagcctc ccgatagagg | 720 |
| tgatggtgga cgccgtgcac aagctcaagt atgagaatta caccagcagc tttttcatcc | 780 |
| gggacattat caagcccgac ccccgaaga acctccagct gaagcccctg aagaacagcc | 840 |
| ggcaggtgga agtctcctgg gagtatcccg acacctggag caccccgcac agctacttct | 900 |
| ccctgacctt ctgtgtgcag gtgcagggca gtccaagag ggaaaagaag gacagggttt | 960 |
| tcaccgacaa gaccagcgcg accgtgatct gccggaagaa cgccagcata agcgtccgcg | 1020 |
| cccaagatag gtactacagc agctcctgga gcgagtgggc tagcgtgccc tgcagcgggg | 1080 |
| gcggggggtgg gggctccagg aacctgccag tggcgacccc cgaccccggc atgttccct | 1140 |
| gcctccatca cagccagaac ctgctgaggg ccgtcagcaa tatgctgcag aaggccaggc | 1200 |
| agaccctgga attctacccc tgcacgtcgg aggagatcga tcacgaggat atcacaaaag | 1260 |

-continued

| | |
|---|---|
| acaagacttc caccgtggag gcctgcctgc ccctggagct caccaagaat gagtcctgtc | 1320 |
| tgaactcccg ggaaaccagc ttcatcacca acgggtcctg cctggccagc aggaagacca | 1380 |
| gctttatgat ggccctgtgc ctgtcgagca tctacgagga cctgaagatg taccaggtcg | 1440 |
| agttcaagac aatgaacgcc aagctgctga tggaccccaa gaggcaaatc ttcctggacc | 1500 |
| agaatatgct tgccgtcatc gacgagctca tgcaggccct gaacttcaac tccgagaccg | 1560 |
| tgccccagaa gagcagcctg gaggagcccg acttctacaa gaccaagatc aagctgtgca | 1620 |
| tcctgctgca cgcgttcagg atccgggcag tcaccatcga ccgtgtgatg tcctacctga | 1680 |
| acgccagctg ataataggct ggagcctcgg tggccatgct tcttgcccct tgggcctccc | 1740 |
| cccagcccct cctcccttc ctgcacccgt accccccaaa caccattgtc acactccagt | 1800 |
| ggtctttgaa taaagtctga gtgggcggc | 1829 |

<210> SEQ ID NO 76
<211> LENGTH: 1829
<212> TYPE: DNA
<213> ORGANISM: Artificial Sequence
<220> FEATURE:
<223> OTHER INFORMATION: hIL12AB_022

<400> SEQUENCE: 76

| | |
|---|---|
| tcaagctttt ggaccctcgt acagaagcta atacgactca ctatagggaa ataagagaga | 60 |
| aaagaagagt aagaagaaat ataagagcca ccatgtgcca tcagcagctg gtgatcagct | 120 |
| ggttcagcct ggtgttcctc gcctctcccc tggtggccat ctgggagctc aaaaaggacg | 180 |
| tgtacgtggt ggagctcgac tggtacccag acgcccccgg ggagatggtg gtgctgacct | 240 |
| gcgacacccc cgaagaagac ggcatcacgt ggacccctcga ccagtccagc gaggtgctgg | 300 |
| ggagcgggaa gactctgacc atccaggtca aggagttcgg gacgccgggg cagtacacgt | 360 |
| gcccacaagg gcggcgaagtc ttaagccaca gcctgctcct gctgcacaag aaggaggacg | 420 |
| ggatctggtc cacagacata ctgaaggacc agaaggagcc gaagaataaa acctttctga | 480 |
| ggtgcgaggc caagaactat tccggcaggt tcacgtgctg gtggcttaca acaatcagca | 540 |
| cagacctgac gttcagcgtg aagtccagcc gcggcagcag cgaccccag ggggtgacct | 600 |
| gcggcgccgc cacctgagc gccgagcggg tgcgcgggga caacaaggag tacgagtact | 660 |
| ccgtggagtg ccaggaagac agcgcctgtc cgccgccga agagagcctg cctatcgagg | 720 |
| tcatggtaga tgcagtgcat aagctgaagt acgagaacta tacgagcagc ttttcatac | 780 |
| gcgacatcat caagccccgac ccccccaaga acctgcagct taagcccctg aagaatagcc | 840 |
| ggcaggtgga ggtctcctgg gagtaccccg acacctggtc aacgccccac agctacttct | 900 |
| ccctgacctt ttgtgtccaa gtccagggaa agagcaagag ggaagagaaa gatcgggtgt | 960 |
| tcaccgacaa gacctccgcc acggtgatct gcaggaagaa cgccagcatc tccgtgaggg | 1020 |
| cgcaagacag gtactactcc agcagctggt ccgaatgggc cagcgtgccc tgctccggcg | 1080 |
| gcggggggcgg cggcagccga aacctacccg tggccacgcc ggatcccggc atgtttccct | 1140 |
| gcctgcacca cagccagaac ctcctgaggg ccgtgtccaa catgctgcag aaggccaggc | 1200 |
| agactctgga gttctacccc tgcacagcg aggagatcga tcacgaggac atcaccaagg | 1260 |
| ataagaccag cactgtggag gcctgccttc ccctggagct gaccaagaac gagagctgtc | 1320 |
| tgaactccag ggagacctca ttcatcacca acggctcctg cctggccagc aggaaaacca | 1380 |
| gcttcatgat ggccttgtgt ctcagctcca tctacgagga cctgaagatg tatcaggtcg | 1440 |

| | |
|---|---|
| agttcaagac aatgaacgcc aagctgctga tggaccccaa aaggcagatc ttcctggacc | 1500 |
| agaaacatgct ggccgtcatc gacgagctga tgcaggccct gaacttcaac agcgagacgg | 1560 |
| tgccccagaa aagctccctg gaggagcccg acttctacaa gaccaagatc aagctgtgca | 1620 |
| tcctgctgca cgccttcagg atcagggcag tgaccatcga ccgggtgatg tcatacctta | 1680 |
| acgccagctg ataataggct ggagcctcgg tggccatgct tcttgcccct tgggcctccc | 1740 |
| cccagcccct cctcccctct ctgcacccgt accccccaaa caccattgtc acactccagt | 1800 |
| ggtctttgaa taaagtctga gtgggcggc | 1829 |

<210> SEQ ID NO 77
<211> LENGTH: 1829
<212> TYPE: DNA
<213> ORGANISM: Artificial Sequence
<220> FEATURE:
<223> OTHER INFORMATION: hIL12AB_023

<400> SEQUENCE: 77

| | |
|---|---|
| tcaagctttt ggaccctcgt acagaagcta atacgactca ctataggaa ataagagaga | 60 |
| aaagaagagt aagaagaaat aagagccca ccatgtgcca tcagcagctg gtgatctcct | 120 |
| ggttcagcct ggtgtttctg gcctcgcccc tggtcgccat ctgggagctg aagaaagacg | 180 |
| tgtacgtcgt cgaactggac tggtaccccg acgcccccgg ggagatggtg gtgctgacct | 240 |
| gcgacacgcc ggaggaggac ggcatcacct ggaccctgga tcaaagcagc gaggtgctgg | 300 |
| gcagcggcaa gaccctgacc atccaagtga aggaattcgg cgatgccggc cagtacacct | 360 |
| gtcacaaagg gggcgaggtg ctcagccaca gcctgctgct gctgcacaag aaggaggatg | 420 |
| gcatctggag caccgatatc ctgaaggacc agaaagagcc caagaacaag acgttcctga | 480 |
| ggtgcgaggc caagaactac agcggtaggt tcacgtgttg gtggctgacc accatcagca | 540 |
| ccgacctgac gttcagcgtg aagagctcca ggggcagctc cgacccacag ggggtgacgt | 600 |
| gcggggccgc aaccctcagc gccgaaaggg tgcgggggga caacaaggag tacgaatact | 660 |
| ccgtggagtg ccaggaagat tcggcctgcc ccgccgcgga ggagagcctc cccatcgagg | 720 |
| taatggtgga cgccgtgcat aagctgaagt acgagaacta caccagctcg ttcttcatcc | 780 |
| gagacatcat caaacccgac ccgcccaaaa atctgcagct caagcccctg aagaactcca | 840 |
| ggcaggtgga ggtgagctgg gagtaccccg acacctggtc caccccgcac agctacttct | 900 |
| ccctgacatt ctgcgtgcag gtgcagggca agagcaagcg ggagaagaag acagggtgt | 960 |
| tcaccgacaa gacgagcgcc accgtgatct gccgaaagaa cgccagcatc tcggtgcgcg | 1020 |
| cccaggatag gtactattcc agctcctgga gcgagtgggc ctcggtaccc tgcagcggcg | 1080 |
| gcggggcgg cggcagtagg aatctgcccg tggctacccc ggacccgggc atgttcccct | 1140 |
| gcctccacca cagccagaac ctgctgaggg ccgtgagcaa catgctgcag aaggccagac | 1200 |
| agacgctgga gttctacccc tgcacgagcg aggagatcga ccacgaggac atcaccaagg | 1260 |
| ataaaacttc caccgtcgag gcctgcctgc ccttggagct gaccaagaat gaatcctgtc | 1320 |
| tgaacagcag ggagacctcg tttatcacca atggcagctg cctcgcctcc aggaagacca | 1380 |
| gcttcatgat ggccctctgt ctgagctcca tctatgagga cctgaagatg taccaggtgg | 1440 |
| agttcaagac catgaacgcg aagctgctga tggaccccaa gaggcagatc ttcctggatc | 1500 |
| agaaatatgct ggcggtgatc gacgagctca tgcaggccct caatttcaat agcgagacag | 1560 |
| tgccccagaa gtcctccctg gaggagcccg acttctacaa gaccaagatc aagctgtgta | 1620 |
| tcctgctgca cgccttccgg atccgggccg tcaccatcga ccgggtcatg agctacctca | 1680 |

```
atgccagctg ataataggct ggagcctcgg tggccatgct tcttgcccct tgggcctccc    1740
cccagcccct cctcccctte ctgcacccgt accccccaaa caccattgtc acactccagt    1800
ggtctttgaa taaagtctga gtgggcggc                                      1829
```

<210> SEQ ID NO 78
<211> LENGTH: 1829
<212> TYPE: DNA
<213> ORGANISM: Artificial Sequence
<220> FEATURE:
<223> OTHER INFORMATION: hIL12AB_024

<400> SEQUENCE: 78

```
tcaagctttt ggaccctcgt acagaagcta atacgactca ctatagggaa ataagagaga      60
aaagaagagt aagaagaaat ataagagcca ccatgtgcca ccagcagctg gtgatctcct     120
ggttctccct ggtgttcctg gcctcgcccc tggtggccat ctgggagctg aagaaggacg     180
tgtacgtcgt ggagctcgac tggtaccccg acgcccctgg cgagatggtg gtgctgacct     240
gcgacacccc agaggaggat ggcatcacct ggaccctgga tcagtcctcc gaggtgctgg     300
gctccggcaa gacgctgacc atccaagtga aggagttcgg tgacgccgga cagtatacct     360
gccataaggg cggcgaggtc ctgtcccaca gcctcctcct cctgcataag aaggaggacg     420
gcatctggag caccgacatc ctgaaggacc agaaggagcc caagaacaag acctttctga     480
ggtgcgaggc caagaactac agcggccgat tcacctgctg gtggctcacc accatatcca     540
ccgacctgac tttctccgtc aagtcctccc ggggtccag cgaccccag ggagtgacct     600 gcggcgccgc caccctcagc gccgagcggg tgcgggggga caacaaggag tacgaatact     660
ccgtcgagtg ccaggaggac tccgcctgcc cggccgccga ggagagcctg cccatcgagg     720
tgatggtcga cgcggtgcac aagctgaagt acgagaacta caccagcagt ttcttcatca     780
gggatatcat caagccagat cccccgaaga atctgcaact gaagccgctg aaaaactcac     840
gacaggtgga ggtgagctgg gagtaccccg acacgtggag caccccacat tcctacttca     900
gcctgacctt ctgcgtgcag gtccagggca gagcaagcg ggagaagaag gacagggtgt     960
tcacggataa gaccagtgcc accgtgatct gcaggaagaa cgcctctatt agcgtgagg     1020 cccaggatcg gtattactcc tcgagctgga gcgaatgggc ctccgtgccc tgcagtgggg     1080
ggggtggagg cggagcagg aacctgcccg tagcaacccc cgaccccggg atgttccccc     1140
gtctgcacca ctcgcagaac ctgctgcgcg cggtgagcaa catgctccaa aaagcccgtc     1200
agaccttaga gttctacccc tgcaccagcg aagaaatcga ccacgaagac atcaccaagg     1260
acaaaaccag caccgtggag gcgtgcctgc cgctggagct gaccaagaac gagagctgcc     1320
tcaactccag ggagaccagc tttatcacca acggctcgtg cctagccagc cggaaaacca     1380
gcttcatgat ggccctgtgc ctgagctcca tttacgagga cctgaagatg tatcaggtgg     1440
agttcaagac catgaatgcc aaactcctga tggaccccaa gaggcagatc ttcctggacc     1500
agaacatgct cgcggtgatc gatgagctga tgcaggccct gaactttaat agcgagaccg     1560
tgccccagaa aagcagcctg gaggagccgg acttctacaa gaccaaaatc aagctgtgca     1620
tcctgctcca cgccttccgc atccgggccg tgaccatcga cagggtgatg agctacctga     1680
acgccagctg ataataggct ggagcctcgg tggccatgct tcttgcccct tgggcctccc    1740
cccagcccct cctcccctte ctgcacccgt accccccaaa caccattgtc acactccagt    1800
ggtctttgaa taaagtctga gtgggcggc                                      1829
```

-continued

<210> SEQ ID NO 79
<211> LENGTH: 1829
<212> TYPE: DNA
<213> ORGANISM: Artificial Sequence
<220> FEATURE:
<223> OTHER INFORMATION: hIL12AB_025

<400> SEQUENCE: 79

| | | | | | |
|---|---|---|---|---|---|
| tcaagctttt | ggaccctcgt | acagaagcta | atacgactca | ctatagggaa | ataagagaga | 60 |
| aaagaagagt | aagaagaaat | ataagagcca | ccatgtgcca | tcagcagctg | gtgatttcct | 120 |
| ggttctccct | ggtgttcctg | gccagccccc | tcgtggcgat | ctgggagcta | agaaggacg | 180 |
| tgtacgtggt | ggagctggac | tggtacccgg | acgcacccgg | cgagatggtc | gttctgacct | 240 |
| gcgatacgcc | agaggaggac | ggcatcacct | ggaccctcga | tcagagcagc | gaggtcctgg | 300 |
| ggagcggaaa | gaccctgacc | atccaggtca | aggagttcgg | cgacgccggc | cagtacacct | 360 |
| gccacaaagg | tggcgaggtc | ctgagccact | cgctgctgct | cctgcataag | aaggaggacg | 420 |
| gaatctggag | cacagacatc | ctgaaagacc | agaaggagcc | caagaacaag | accttcctga | 480 |
| ggtgcgaggc | caagaactac | agcgggcgct | tcacgtgctg | gtggctgacc | accatcagca | 540 |
| cggacctcac | cttctccgtg | aagagcagcc | ggggatccag | cgatcccaa | ggcgtcacct | 600 |
| gcggcgcggc | caccctgagc | gcggagaggg | tcaggggcga | taataaggag | tatgagtaca | 660 |
| gcgtggagtg | ccaggaggac | agcgcctgcc | cggccgccga | ggagtccctg | ccaatcgaag | 720 |
| tgatggtcga | cgccgtgcac | aagctgaagt | acgagaacta | caccagcagc | ttcttcatcc | 780 |
| gggatatcat | caagcccgat | cccccgaaga | acctgcagct | gaagcccctc | aagaacagcc | 840 |
| ggcaggtgga | ggtgagttgg | gagtaccccg | acacctggtc | aacgccccac | agctacttct | 900 |
| ccctgacctt | ctgtgtgcag | gtgcaggaa | agagcaagag | ggagaagaaa | gaccgggtct | 960 |
| tcaccgacaa | gaccagcgcc | acggtgatct | gcaggaagaa | cgcaagcatc | tccgtgaggg | 1020 |
| cccaggacag | gtactacagc | tccagctggt | ccgaatgggc | cagcgtgccc | tgtagcggcg | 1080 |
| gcggggggcgg | tggcagccgc | aacctcccag | tggccacccc | cgaccccggc | atgttcccct | 1140 |
| gcctgcacca | cagccagaat | ctgctgaggg | ccgtgagtaa | catgctgcag | aaggcaaggc | 1200 |
| aaacctcga | attctatccc | tgcacctccg | aggagatcga | ccacgaggat | atcaccaagg | 1260 |
| acaagaccag | caccgtcgag | gcctgtctcc | ccctggagct | gaccaagaat | gagagctgcc | 1320 |
| tgaacagccg | ggagaccagc | ttcatcacca | acgggagctg | cctggcctcc | aggaagacct | 1380 |
| cgttcatgat | ggcgctgtgc | ctctcaagca | tatacgagga | tctgaagatg | taccaggtgg | 1440 |
| agtttaagac | gatgaacgcc | aagctgctga | tggacccgaa | gaggcagatc | ttcctggacc | 1500 |
| agaacatgct | ggccgtgata | gacgagctca | tgcaggccct | gaacttcaac | tccgagaccg | 1560 |
| tgccgcagaa | gtcatccctc | gaggagcccg | acttctataa | gaccaagatc | aagctgtgca | 1620 |
| tcctgctcca | cgccttccgg | ataagggcc | tgacgatcga | cagggtgatg | agctaccta | 1680 |
| acgccagctg | ataataggct | ggagcctcgg | tggccatgct | tcttgcccct | tgggcctccc | 1740 |
| cccagcccct | cctcccctc | ctgcacccgt | acccccaaa | caccattgtc | acactccagt | 1800 |
| ggtctttgaa | taaagtctga | gtgggcggc | | | | 1829 |

<210> SEQ ID NO 80
<211> LENGTH: 1829
<212> TYPE: DNA
<213> ORGANISM: Artificial Sequence
<220> FEATURE:
<223> OTHER INFORMATION: hIL12AB_026

<400> SEQUENCE: 80

```
tcaagctttt ggaccctcgt acagaagcta atacgactca ctatagggaa ataagagaga      60
aagaagagt aagaagaaat ataagagcca ccatgtgcca ccagcagctc gtgatcagct     120
ggttctccct ggtgtttctc gccagccccc tggtggccat ctgggagctg aagaaggacg     180
tgtacgtggt ggagctggac tggtaccctg acgccccggg ggagatggtc gtgctgacct     240
gcgacacccc cgaagaggac ggtatcacct ggacctgga ccagtccagc gaggtgctgg      300
gcagcggcaa gaccctgact attcaagtca aggagttcgg agacgccggc cagtacacct     360
gccacaaggg tggagaggtg ttatcacaca gcctgctgct gctgcacaag aaggaagacg     420
ggatctggag caccgacatc ctgaaggacc agaaggagcc caaaaacaag accttcctgc     480
ggtgcgaggc caagaactat cgggccgct ttacgtgctg gtggctgacc accatcagca      540
ctgatctcac cttcagcgtg aagtcctccc ggggtcgtc cgaccccag ggggtgacct       600
gcggggccgc caccctgtcc gccgagagag tgagggcga taataaggag tacgagtaca      660
gcgttgagtg ccaggaagat agcgcctgtc cgccgccga ggagagcctg cccatcgagg      720
tgatggtgga cgccgtccac aagctgaagt atgagaacta cacctcaagc ttcttcatca     780
gggacatcat caaacccgat ccgcccaaga atctgcagct gaagcccctg aaaaatagca     840
ggcaggtgga ggtgagctgg gagtaccccg acacctggtc caccccccat agctatttct     900
ccctgacgtt ctgcgtgcag gtcaagggaa gagcaagcg ggagaagaag accgggtgt      960
tcaccgacaa gacctccgcc accgtgatct gtaggaagaa cgcgtcgatc tcggtcaggg    1020
cccaggacag gtattacagc agcagctgga gcgagtgggc gagcgtgccc tgctcgggcg    1080
gcggcggcgg cggagcagaa aatctgcccg tggccacccc agaccccgga atgttcccct    1140
gcctgcacca ttcgcagaac ctcctgaggg ccgtgagcaa catgctgcag aaggcccgcc    1200
agacgctgga gttctacccc tgcacgagcg aggagatcga ccacgaagac atcaccaagg    1260
acaaaaccag caccgtggag gcctgcctgc cctggagct gaccaaaaac gaatcctgcc     1320
tcaacgcccg ggagaccagc ttcatcacca acggcagctg cctggccagc cgaaagacct    1380
ccttcatgat ggccctctgc ctgagcagca tctatgagga tctgaagatg tatcaggtgg    1440
agttcaagac catgaatgcc aagctgctga tggaccccaa gaggcagata ttcctggacc    1500
agaatatgct ggccgtgatc gacgagctga tgcaggccct gaacttcaac agcgagaccg    1560
tcccccagaa gtccagcctg gaggagccgg acttttacaa aacgaagatc aagctgtgca    1620
tactgctgca cgccttcagg atccgggccg tgacaatcga cagggtgatg tcctacctga    1680
acgccagctg ataataggct ggagcctcgg tggccatgct tcttgcccct tgggcctccc    1740
cccagccct cctccccttc ctgcacccgt accccccaaa caccattgtc acactccagt     1800
ggtctttgaa taaagtctga gtgggcggc                                      1829
```

<210> SEQ ID NO 81
<211> LENGTH: 1829
<212> TYPE: DNA
<213> ORGANISM: Artificial Sequence
<220> FEATURE:
<223> OTHER INFORMATION: hIL12AB_027

<400> SEQUENCE: 81

```
tcaagctttt ggaccctcgt acagaagcta atacgactca ctatagggaa ataagagaga      60
aagaagagt aagaagaaat ataagagcca ccatgtgtca ccagcagctg gtgatcagct     120
```

| | |
|---|---|
| ggttctccct ggtgttcctg ccagccccc tggtggccat ctgggagctc aagaaggacg | 180 |
| tctacgtcgt ggagctggat tggtacccg acgctcccgg ggagatggtg gtgctgacct | 240 |
| gcgacacccc cgaggaggac ggcatcacct ggacgctgga ccagagctca gaggtgctgg | 300 |
| gaagcggaaa gacactgacc atccaggtga aggagttcgg ggatgccggg cagtatacct | 360 |
| gccacaaggg cggcgaagtg ctgagccatt ccctgctgct gctgcacaag aaggaggacg | 420 |
| gcatatggtc caccgacatc ctgaaggatc agaaggagcc gaagaataaa accttcctga | 480 |
| ggtgcgaggc caagaattac agcggccgat tcacctgctg gtggctgacc accatcagca | 540 |
| ccgacctgac cttcagtgtg aagtcctcac ggggcagctc agatccccag ggcgtgacct | 600 |
| gcggggccgc gacactcagc gccgagcggg tgaggggtga taacaaggag tacgagtatt | 660 |
| ctgtggagtg ccaggaagac tccgcctgtc ccgccgccga ggagtccctg cccatcgagg | 720 |
| tgatggtgga cgccgtgcat aaactgaagt acgagaacta cacctccagc ttcttcatcc | 780 |
| gggatataat caagcccgac cctccgaaaa acctgcagct gaagcccctt aaaaacagcc | 840 |
| ggcaggtgga ggtgagctgg gagtaccccg acacctggag cacccccat agctatttca | 900 |
| gcctgacctt ctgcgtgcag gtgcagggga agtccaagcg cgagaaaaag gaccgggtgt | 960 |
| tcaccgacaa gacgagcgcc accgtgatct gccggaagaa cgccagtata agcgtaaggg | 1020 |
| cccaggatag gtactacagc tccagctggt cggagtgggc ctccgtgccc tgttccggcg | 1080 |
| gcgggggggg tggcagcagg aacctccccg tggccacgcc ggaccccggc atgttcccgt | 1140 |
| gcctgcacca ctcccaaaac ctcctgcggg ccgtcagcaa catgctgcaa aaggcgcggc | 1200 |
| agaccctgga gttttacccc gtacctccg aagagatcga ccacgaggat atcaccaagg | 1260 |
| ataagacctc caccgtggag gcctgtctcc cctggagct gaccaagaac gagagctgtc | 1320 |
| ttaacagcag agagacctcg ttcataacga acggctcctg cctcgcttcc aggaagacgt | 1380 |
| cgttcatgat ggcgctgtgc ctgtccagca tctacgagga cctgaagatg tatcaggtcg | 1440 |
| agttcaaaac catgaacgcc aagctgctga tggaccccaa gaggcagatc ttcctggacc | 1500 |
| agaacatgct cgccgtgatc gacgagctga tgcaggccct gaacttcaac agcgaaaccg | 1560 |
| tgccccagaa gtcaagcctg gaggagcgga acttctataa gaccaagatc aagctgtgta | 1620 |
| tcctgctaca cgcttttcgt atccgggccg tgaccatcga cagggttatg tcgtacttga | 1680 |
| acgccagctg ataataggct ggagcctcgg tggccatgct tcttgcccct tgggcctccc | 1740 |
| cccagcccct cctcccttc ctgcacccgt acccccaaa caccattgtc acactccagt | 1800 |
| ggtctttgaa taaagtctga gtgggcggc | 1829 |

<210> SEQ ID NO 82
<211> LENGTH: 1829
<212> TYPE: DNA
<213> ORGANISM: Artificial Sequence
<220> FEATURE:
<223> OTHER INFORMATION: hIL12AB_028

<400> SEQUENCE: 82

| | |
|---|---|
| tcaagctttt ggaccctcgt acagaagcta atacgactca ctatagggaa ataagagaga | 60 |
| aaagaagagt aagaagaaat ataagagcca ccatgtgcca ccaacagctc gtgatcagct | 120 |
| ggttcagcct ggtgttcctg ccagcccgc tggtggccat ctgggagctg aagaaggacg | 180 |
| tgtacgtggt ggagctggac tggtacccg acgcccccgg cgagatggtg gtcctgacct | 240 |
| gcgacacgcc ggaagaggac ggcatcacct ggaccctgga tcagtccagc gaggtgctgg | 300 |
| gctccggcaa gaccctgacc attcaggtga aggagttcgg cgacgccggt cagtacacct | 360 |

```
gccacaaggg cggcgaggtg ctgagccaca gcctactgct cctgcacaaa aaggaggatg    420
gaatctggtc caccgacatc ctcaaggacc agaaggagcc gaagaacaag acgttcctcc    480
ggtgcgaggc caagaactac agcggcaggt ttacctgctg gtggctgacc accatcagca    540
ccgacctgac attttccgtg aagagcagcc gcggcagcag cgatcccag  ggcgtgacct    600 gcggggcggc caccctgtcc gccgagcgtg tgagggcga  caacaaggag tacgagtaca    660
gcgtggaatg ccaggaggac agcgcctgtc ccgccgccga ggagagcctg ccaatcgagg    720
tcatggtgga cgccgtgcac aagctgaagt acgagaacta cacgagcagc ttcttcatca    780
gggacatcat caaaccggac cgcccaaga  acctgcagct gaaacccttg aaaaacagca    840
ggcaggtgga agtgtcttgg gagtaccccg acacctggtc cacccccac  agctacttta    900 gcctgacctt ctgtgtgcag gtccagggca agtccaagag ggagaagaag acagggtgt    960 tcaccgacaa aaccagcgcc accgtgatct gcaggaagaa cgcctccatc agcgtgcggg   1020
cccaggacag gtattacagc tcgtcgtgga gcgagtgggc cagcgtgccc tgctccgggg   1080
gaggcggcgg cggaagccgg aatctgcccg tggccacccc cgatcccggc atgttcccgt   1140
gtctgcacca cagccagaac ctgctgcggg ccgtgagcaa catgctgcag aaggcccgcc   1200
aaaccctgga gttctacccc tgtacaagcg aggagatcga ccatgaggac attaccaagg   1260
acaagaccag caccgtggag gcctgcctgc ccctcgagct cacaaagaac gaatcctgcc   1320
tgaatagccg cgagaccagc tttatcacga acgggtcctg cctcgccagc cggaagacaa   1380
gcttcatgat ggccctgtgc ctgagcagca tctacgagga cctgaaaatg taccaagtgg   1440
agttcaaaac gatgaacgcc aagctgctga tggacccaa  cgccagatc  ttcctggacc   1500 agaacatgct ggccgtcatc gacgagctca tgcaggccct gaacttcaac agcgagaccg   1560
tgccccagaa gagcagcctg gaggagcccg acttctacaa gacgaagatc aagctctgca   1620
tcctgctgca cgctttccgc atccgcgcgg tgaccatcga ccgggtgatg agctacctca   1680
acgccagttg ataataggct ggagcctcgg tggccatgct tcttgcccct tgggcctccc   1740
cccagcccct cctcccccttc ctgcacccgt accccccaaa caccattgtc acactccagt   1800
ggtctttgaa taaagtctga gtgggcggc                                     1829
```

<210> SEQ ID NO 83
<211> LENGTH: 1829
<212> TYPE: DNA
<213> ORGANISM: Artificial Sequence
<220> FEATURE:
<223> OTHER INFORMATION: hIL12AB_029

<400> SEQUENCE: 83

```
tcaagctttt ggaccctcgt acagaagcta atacgactca ctatagggaa ataagagaga     60
aaagaagagt aagaagaaat ataagagcca ccatgtgcca ccaacagctg gtgatcagct    120
ggttcagcct ggtgtttctg gcctcccctc tggtggccat ctgggagctg aagaaggacg    180
tgtacgtggt ggagctggac tggtaccctg acgcccccgg cgaaatggtg gtgctgacgt    240
gcgacacccc cgaggaggat ggcatcacct ggacccTGGA ccaaagcagc gaggtcctcg    300
gaagcggcaa gaccctcact atccaagtga aggagttcgg ggatgcgggc cagtacacct    360
gccacaaggg cggcgaggtg ctgtctcata gcctgctgct cctgcataag aaggaagacg    420
gcatctggag caccgacata ctgaaggatc agaaggagcc caagaacaag accttcctga    480
ggtgcgaggc caagaactac tccgggcgct tcacctgttg gtggctgacc accatctcca    540
```

```
ccgacctgac cttcagcgtg aagagcagca gggggagcag cgaccccag ggggtgacct    600
gcggagccgc gaccttgtcg gccgagcggg tgagggcga caataaggag tacgagtact    660
cggtcgaatg ccaggaggac tccgcctgcc ccgccgccga ggagtccctc cccatcgaag    720
tgatggtgga cgccgtccac aagctgaagt acgagaacta caccagcagc ttcttcatac    780
gggatatcat caagcccgac cccccgaaga acctgcagct gaaacccttg aagaactcca    840
ggcaggtgga ggtgagctgg gagtaccccg acacctggtc caccccgcac tcatacttca    900
gcctgacctt ctgtgtacag gtccagggca agagcaagag ggaaaagaag gatagggtgt    960
tcaccgacaa gacctccgcc acggtgatct gtcggaaaaa cgccagcatc tccgtgcggg   1020
cccaggacag gtactattcc agcagctgga gcgagtgggc ctccgtcccc tgctccggcg   1080
gcggtggcgg gggcagcagg aacctccccg tggccacccc cgatcccggg atgttcccat   1140
gcctgcacca cagccaaaac ctgctgaggg ccgtctccaa tatgctgcag aaggcgaggc   1200
agaccctgga gttctacccc tgtacctccg aggagatcga ccacgaggat atcaccaagg   1260
acaagacctc cacggtcgag gcgtgcctgc ccctggagct cacgaagaac gagagctgcc   1320
ttaactccag ggaaacctcg tttatcacga acggcagctg cctggcgtca cggaagacct   1380
cctttatgat ggccctatgt ctgtcctcga tctacgagga cctgaagatg taccaggtgg   1440
agttcaagac catgaacgcc aagctgctga tggatcccaa gaggcagatt ttcctggacc   1500
agaacatgct ggccgtgatt gacgagctga tgcaggcgct gaacttcaac agcgagacag   1560
tgccgcagaa gagctccctg gaggagccgg acttttacaa gaccaagata aagctgtgca   1620
tcctgctcca cgccttcaga atacgggccg tcaccatcga tagggtgatg tcttacctga   1680
acgcctcctg ataataggct ggagcctcgg tggccatgct tcttgcccct tgggcctccc   1740
cccagcccct cctccccttc ctgcacccgt accccccaaa caccattgtc acactccagt   1800
ggtctttgaa taaagtctga gtgggcggc                                    1829
```

<210> SEQ ID NO 84
<211> LENGTH: 1829
<212> TYPE: DNA
<213> ORGANISM: Artificial Sequence
<220> FEATURE:
<223> OTHER INFORMATION: hIL12AB_030

<400> SEQUENCE: 84

```
tcaagctttt ggaccctcgt acagaagcta atacgactca ctatagggaa ataagagaga    60
aaagaagagt aagaagaaat ataagagcca ccatgtgcca ccagcagctg gtgattagct   120
ggtttagcct ggtgttcctg gcaagccccc tggtggccat ctgggaactg aaaaaggacg   180
tgtacgtggt cgagctggat tggtacccg acgcccccgg cgaaatggtg gtgctgacgt   240
gtgataccc cgaggaggac gggatcacct ggaccctgga tcagagcagc gaggtgctgg   300
ggagcgggaa gacgctgacg atccaggtca aggagttcgg cgacgctggg cagtacacct   360
gtcacaaggg cggggaggtg ctgtcccact ccctgctgct cctgcataag aaagaggacg   420
gcatctggtc caccgacatc ctcaaggacc agaaggagcc caagaacaag accttcctgc   480
ggtgtgaggc gaagaactac agcggccgtt caccctgctg gtggctgacg acaatcagca   540
ccgacttgac gttctccgtg aagtcctcca gaggcagctc cgaccccaa gggtgacgt   600
gcggcgcggc cacctgagc gccgagcggg tgcgggggga caacaaggag tacgagtact   660
ccgtggagtg ccaggaggac agcgcctgtc ccgcagccga ggagtccctg cccatcgaag   720
tcatggtgga cgccgtccac aagctgaagt acgagaacta caccagcagc ttcttcatcc   780
```

```
gcgatatcat caagcccgat ccccccaaaa acctgcaact gaagccgctg aagaatagca      840
ggcaggtgga ggtgtcctgg gagtacccgg acacctggag cacgccccac agctatttca      900
gcctgacctt ttgcgtgcag gtccagggga agagcaagcg ggagaagaag accgcgtgt      960 ttacggacaa aaccagcgcc accgtgatct gcaggaagaa cgccagcatc agcgtgaggg      1020
cccaggacag gtactacagc agctcctgga gcgagtgggc ctccgtgccc tgttccggag      1080
gcggcggggg cggttcccgg aacctcccgg tggccacccc cgacccgggc atgttcccgt      1140
gcctgcacca ctcacagaat ctgctgaggg ccgtgagcaa tatgctgcag aaggcaaggc      1200
agaccctgga gttttatccc tgcaccagcg aggagatcga ccacgaagac atcaccaagg      1260
acaagaccag cacagtggag gcctgcctgc ccctggaact gaccaagaac gagtcctgtc      1320
tgaactcccg ggaaaccagc ttcataacca acggctcctg tctcgccagc aggaagacca      1380
gcttcatgat ggccctgtgc ctcagctcca tctacgagga cctcaagatg taccaggttg      1440
agttcaagac catgaacgcc aagctcctga tggaccccaa gaggcagatc ttcctggacc      1500
agaatatgct ggccgtgatc gatgagttaa tgcaggcgct gaacttcaac agcgagacgg      1560
tgccccaaaa gtcctcgctg gaggagcccg acttctacaa gaccaagatc aagctgtgca      1620
tcctcctgca cgccttccga atccgggccg taaccatcga cagggtgatg agctatctca      1680
acgcctcctg ataataggct ggagcctcgg tggccatgct cttgcccct tgggcctccc      1740 cccagcccct cctcccttc ctgcacccgt accccccaaa caccattgtc acactccagt      1800
ggtctttgaa taaagtctga gtgggcggc                                       1829

<210> SEQ ID NO 85
<211> LENGTH: 1829
<212> TYPE: DNA
<213> ORGANISM: Artificial Sequence
<220> FEATURE:
<223> OTHER INFORMATION: hIL12AB_031

<400> SEQUENCE: 85
tcaagctttt ggaccctcgt acagaagcta atacgactca ctatagggaa ataagagaga      60
aaagaagagt aagaagaaat ataagagcca ccatgtgcca ccagcagctc gtgatcagct      120
ggttctcgct tgtgttcctg gcctcccccc tcgtcgccat ctgggagctg aagaaagacg      180
tgtacgtggt ggagctggac tggtatcccg acgccccggg ggagatggtg gtgctgacct      240
gcgacacccc ggaagaggac ggcatcacct ggacgctcga ccagtcgtcc gaagtgctgg      300
ggtcgggcaa gaccctcacc atccaggtga aggagttcgg agacgccggc cagtacacct      360
gtcataaggg ggggaggtg ctgagccaca gcctcctgct cctgcacaaa aaggaggacg      420
gcatctggag caccgatatc ctcaaggacc agaaggagcc caagaacaag acgttcctga      480
ggtgtgaggc caagaactac agcggcggt tcacgtgttg gtggctcacc accatctcca      540
ccgacctcac cttctccgtg aagtcaagca ggggcagctc cgaccccaa ggcgtcacct      600 gcggcgccgc caccctgagc gccgagaggg tcagggggga taacaaggaa tacgagtaca      660
gtgtggagtg ccaagaggat agcgcctgtc ccgccgccga agagagcctg cccatcgaag      720
tgatggtgga cgccgtgcac aagctgaagt acgagaacta cacctccagc ttcttcatca      780
gggatatcat caagcccgat ccccccaaga acctgcagct gaagcccctg aagaacagca      840
ggcaggtgga ggtgagctgg gagtatcccg acacgtggag cacccgcac agctacttct      900 cgctgacctt ctgcgtgcag gtgcaaggga agtccaagag ggagaagaag gataggggtgt      960
```

```
tcaccgacaa acgagcgcc accgtgatct gccggaagaa tgccagcatc tctgtgaggg    1020
cccaggacag gtactattcc agctcctggt cggagtgggc cagcgtgccc tgtagcggcg    1080 ggggcgggg cggcagcagg aacctcccgg ttgccacccc cgaccccggc atgtttccgt    1140
gcctgcacca ctcgcaaaac ctgctgcgcg cggtctccaa catgctgcaa aaagcgcgcc    1200
agacgctgga gttctacccc tgcaccagcg aggagatcga tcatgaagat atcaccaaag    1260
acaagacctc gaccgtggag gcctgcctgc ccctggagct caccaagaac gaaagctgcc    1320
tgaacagcag ggagacaagc ttcatcacca acggcagctg cctggcctcc cggaagacca    1380
gcttcatgat ggccctgtgc ctgtccagca tctacgagga tctgaagatg taccaagtgg    1440
agtttaagac catgaacgcc aagctgttaa tggaccccaa aaggcagatc ttcctggatc    1500
agaacatgct ggccgtcatc gacgagctga tgcaagccct gaacttcaac agcgagacgg    1560
tgccccagaa gagcagcctc gaggagcccg acttctataa gaccaagata aagctgtgca    1620
ttctgctgca cgccttcaga atcagggccg tgaccatcga tagggtgatg agctacctga    1680
acgccagctg ataataggct ggagcctcgg tggccatgct tcttgcccct tgggcctccc    1740
cccagcccct cctcccttc ctgcacccgt accccccaaa caccattgtc acactccagt    1800
ggtctttgaa taaagtctga gtgggcggc                                      1829

<210> SEQ ID NO 86
<211> LENGTH: 1829
<212> TYPE: DNA
<213> ORGANISM: Artificial Sequence
<220> FEATURE:
<223> OTHER INFORMATION: hIL12AB_032

<400> SEQUENCE: 86
tcaagctttt ggaccctcgt acagaagcta atacgactca ctatagggaa ataagagaga    60
aaagaagagt aagaagaaat ataagagcca ccatgtgtca ccagcagctg gtgatttcct    120
ggttcagtct ggtgtttctt gccagccccc tggtggccat ctgggagctg aagaaagacg    180
tatacgtcgt ggagctggac tggtatcccg acgctcccgg cgagatggtg gtcctcacct    240
gcgacacccc agaggaggac ggcatcacct ggaccctgga ccagagctcc gaggtcctgg    300
gcagcggtaa gaccctcacc atccaggtga aggagtttgg tgatgccggg cagtatacct    360
gccacaaggg cggcgaggtg ctgtcccaca gcctcctgtt actgcataag aaggaggatg    420
gcatctggag caccgacatc ctcaaggacc agaaagagcc caagaacaag acctttctgc    480
ggtgcgaggc gaaaaattac tccggccggt tcacctgctg gtggctgacc accatcagca    540
cggacctgac gttctccgtg aagtcgagca ggggagctc cgatcccag ggcgtgacct    600 gcggcgcggc cacctgagc gccgagcgcg tccgcgggga caataaggaa tacgaatata    660
gcgtggagtg ccaggaggac agcgcctgcc ccgcggccga ggagagcctc ccgatcgagg    720
tgatggtgga tgccgtccac aagctcaaat acgaaaacta caccagcagc ttcttcatta    780
gggacatcat caagcccgac ccccccaaaa acctgcagct gaagcccctg aagaacagcc    840
gccaggtcga ggtgtcatgg gagtacccag acacctggag caccccccac tcctacttca    900
gcctgacctt ctgcgtccag gtgcaggaa agtccaaacg ggagaagaag gatagggtct    960
ttaccgataa gacgtcggcc accgtcatct gcaggaagaa cgccagcata agcgtgcggg    1020
cgcaggatcg gtactacagc tcgagctggt ccgaatgggc ctccgtgccc tgtagcggag    1080
ggggtggcgg gggcagcagg aacctgcccg tggccacccc ggaccgggc atgtttcct    1140 gcctgcatca cagtcagaac ctgctgaggg ccgtgagcaa catgctccag aaggcccgcc    1200
```

| agaccctgga | gttttacccc | tgcaccagcg | aagagatcga | tcacgaagac | atcaccaaag | 1260 |
| acaagacctc | caccgtggag | gcctgtctgc | ccctggagct | gaccaagaac | gagagctgtc | 1320 |
| tgaacagcag | ggagacctcc | ttcatcacca | acggctcctg | cctggcatcc | cggaagacca | 1380 |
| gcttcatgat | ggccctgtgt | ctgagctcta | tctacgagga | cctgaagatg | taccaggtcg | 1440 |
| agttcaagac | catgaacgcc | aagctgctga | tggaccccaa | gcgacagata | ttcctggacc | 1500 |
| agaacatgct | cgccgtgatc | gatgaactga | tgcaagccct | gaacttcaat | agcgagaccg | 1560 |
| tgccccagaa | aagcagcctg | gaggagcccg | acttctacaa | gaccaagatc | aaactgtgca | 1620 |
| tactgctgca | cgccttcagg | atccgggccg | tcaccatcga | ccgggtgatg | tcctatctga | 1680 |
| atgccagctg | ataataggct | ggagcctcgg | tggccatgct | tcttgcccct | gggcctccc | 1740 |
| cccagcccct | cctccccttc | ctgcacccgt | acccccaaa | caccattgtc | acactccagt | 1800 |
| ggtctttgaa | taaagtctga | gtgggcggc | | | | 1829 |

<210> SEQ ID NO 87
<211> LENGTH: 1829
<212> TYPE: DNA
<213> ORGANISM: Artificial Sequence
<220> FEATURE:
<223> OTHER INFORMATION: hIL12AB_033

<400> SEQUENCE: 87

| tcaagctttt | ggaccctcgt | acagaagcta | atacgactca | ctatagggaa | ataagagaga | 60 |
| aaagaagagt | aagaagaaat | ataagagcca | ccatgtgcca | ccagcagctc | gtgattagct | 120 |
| ggttttcgct | ggtgttcctg | gccagccctc | tcgtggccat | ctgggagctg | aaaaaagacg | 180 |
| tgtacgtggt | ggagctggac | tggtaccccg | acgcccccgg | cgagatggtg | gtgctgacgt | 240 |
| gcgacacccc | ggaagaggac | ggcatcacct | ggaccctgga | ccagtcatcc | gaggtcctgg | 300 |
| gcagcggcaa | gacgctcacc | atccaggtga | aggagttcgg | cgacgccggc | cagtacacat | 360 |
| gccataaggg | cgggaggtg | ctgagccaca | gcctgctcct | cctgcacaag | aaggaggatg | 420 |
| gcatctggtc | tacagacatc | ctgaaggacc | agaaagagcc | caagaacaag | accttcctcc | 480 |
| ggtgcgaggc | caagaactac | tccgggcggt | ttacttgttg | gtggctgacc | accatcagca | 540 |
| ccgacctcac | cttcagcgtg | aagagctccc | gagggagctc | cgaccccag | ggggtcacct | 600 |
| gcggcgccgc | caccctgagc | gccgagcggg | tgaggggcga | caacaaggag | tatgaataca | 660 |
| gcgtggaatg | ccaagaggac | agcgcctgtc | ccgcggccga | ggaaagcctg | cccatcgagg | 720 |
| tgatggtgga | cgccgtccac | aaactcaagt | acgagaacta | caccagcagt | ttcttcattc | 780 |
| gcgacatcat | caagccggac | cccccaaaa | acctgcagct | caaacccctg | aagaacagca | 840 |
| ggcaggtgga | ggtcagctgg | gagtaccggg | acacctggag | cacccccat | agctacttca | 900 |
| gcctgacctt | ctgcgtgcag | gtgcagggca | agagcaaacg | cgagaagaag | gaccgggtgt | 960 |
| ttaccgacaa | gaccagcgcc | acggtgatct | gccgaaagaa | tgcaagcatc | tccgtgaggg | 1020 |
| cgcaggaccg | ctactactct | agcagctgga | gcgagtgggc | cagcgtgccc | tgcagcggtg | 1080 |
| gcggcggagg | cggcagccgt | aacctccccg | tggccacccc | cgaccccggc | atgttcccgt | 1140 |
| gtctgcacca | ctcccagaac | ctgctgaggg | ccgtcagcaa | tatgctgcag | aaggcccggc | 1200 |
| agacgctgga | gttctacccc | tgcacctccg | aggagatcga | ccatgaggac | attaccaagg | 1260 |
| acaagacgag | cactgtggag | gcctgcctgc | ccctggagct | caccaaaaac | gagagctgcc | 1320 |
| tgaatagcag | ggagacgtcc | ttcatcacca | acggcagctg | tctggccagc | aggaagacca | 1380 |

```
gcttcatgat ggccctgtgc ctctcctcca tatatgagga tctgaagatg taccaggtgg    1440
agttcaagac catgaacgcc aagctgctga tggatcccaa gaggcagatc ttcctggacc    1500
agaatatgct ggccgtgatt gacgagctga tgcaggccct gaactttaat agcgagaccg    1560
tcccccagaa gagcagcctg gaggagcccg acttctataa gaccaagatc aagctgtgca    1620
tactgctgca cgcgtttagg ataagggccg tcaccatcga cagggtgatg agctacctga    1680
atgccagctg ataataggct ggagcctcgg tggccatgct tcttgcccct tgggcctccc    1740
cccagcccct cctcccttc ctgcacccgt acccccaaa caccattgtc acactccagt     1800
ggtctttgaa taaagtctga gtgggcggc                                     1829
```

<210> SEQ ID NO 88
<211> LENGTH: 1829
<212> TYPE: DNA
<213> ORGANISM: Artificial Sequence
<220> FEATURE:
<223> OTHER INFORMATION: hIL12AB_034

<400> SEQUENCE: 88

```
tcaagctttt ggaccctcgt acagaagcta atacgactca ctatagggaa ataagagaga     60 aagaagagt aagaagaaat ataagagcca ccatgtgcca ccaacagctg gtgatctcct     120
ggttcagcct ggtgttcctc gccagccccc tggtggccat ctgggagctg aagaaagacg    180
tgtacgtggt ggagctggac tggtatcccg acgcccccgg cgagatggtc gtgctgacct    240
gcgacacccc ggaggaggac ggcatcacct ggaccctgga tcagtcctcc gaggtgctgg    300
gcagcgggaa gaccctgacc atccaggtga aagagttcgg agatgccggc cagtataccT    360
gtcacaaggg gggtgaggtg ctgagccata gcctcttgct tctgcacaag aaggaggacg    420
gcatctggtc caccgacatc ctcaaggacc aaaaggagcc gaagaataaa cgttcctga    480 ggtgcgaagc caagaactat tccggacggt tcacctgctg gtggctgacc accatcagca    540
ccgacctcac cttctccgta aagtcaagca ggggcagctc cgaccccag ggcgtgacct     600 gcggagccgc caccctgagc gcagagaggg tgaggggcga caacaaggag tacgaatact    660
ccgtcgagtg ccaggaggac agcgcctgcc ccgccgccga ggaaagtctg cccatcgagg    720
tgatggtgga cgccgtgcac aagctcaaat acgagaacta caccagcagc ttcttcatcc    780
gggatatcat caagcccgac cctccaaaga atctgcagct gaaacccctt aagaacagca    840
ggcaggtgga ggtcagctgg gagtaccccg acacctggag cacgcccac tcctactta     900 gcctgacctt ttgcgtgcag gtgcagggga aagcaagcg ggagaagaag acagggtgt    960 tcaccgataa gacctccgct accgtgatct gcaggaagaa cgcctcaatc agcgtgaggg    1020
cccaggatcg gtactactcc agctcctgga gcgagtgggc cagcgtgccc tgctctggcg    1080
gtggcggcgg gggcagccgg aacctgccgg tggccactcc cgacccgggc atgttcccgt    1140
gcctccacca ttcccagaac ctgctgcggg ccgtgtccaa tatgctccag aaggcaaggc    1200
agaccctgga gttctacccc tgcaccagcg aggagatcga tcacgaggac atcaccaaag    1260
acaaaaccag cacggtcgag gcctgcctgc ccctggaact caccaagaac gaaagctgtc    1320
tcaacagccg cgagaccagc ttcataacca acggttcctg tctggcctcc cgcaagacca    1380
gctttatgat ggccctctgt ctgagctcca tctatgaaga cctgaaaatg taccaggtgg    1440
agttcaaaac catgaacgcc aagcttctga tggaccccaa gaggcagatc ttcctggatc    1500
agaacatgct ggccgtgatc gacgagctga tgcaggccct gaactttaac tccgagaccg    1560
tgccccagaa aagcagcctg gaagagcccg atttctacaa aacgaagatc aagctgtgca    1620
```

```
tcctgctgca cgccttccgg atccgtgcgg tgaccatcga tagggtgatg agctacctga    1680
acgccagctg ataataggct ggagcctcgg tggccatgct tcttgcccct tgggcctccc    1740
cccagcccct cctccccttc ctgcacccgt acccccaaa caccattgtc acactccagt    1800
ggtctttgaa taaagtctga gtgggcggc                                      1829
```

<210> SEQ ID NO 89
<211> LENGTH: 1829
<212> TYPE: DNA
<213> ORGANISM: Artificial Sequence
<220> FEATURE:
<223> OTHER INFORMATION: hIL12AB_035

<400> SEQUENCE: 89

```
tcaagctttt ggaccctcgt acagaagcta atacgactca ctatagggaa ataagagaga      60
aaagaagagt aagaagaaat ataagagcca ccatgtgcca ccaacagctg gtaatcagct     120
ggttcagcct ggttttcctc gcgtcgcccc tggtggccat ctgggagtta agaaggacg      180 tgtacgtggt ggagctggat tggtaccccg acgccccggg cgagatggtc gtgctcacct     240
gcgatacccc cgaggaggac gggatcacct ggacccggga ccaatccagc gaggtgctgg     300
gcagcggcaa gaccctgacc atacaggtga aggaatttgg ggacgccggg cagtacacct     360
gccacaaggg cggggaagtg ctgtcccact ccctcctgct gctgcataag aaggaggacg     420
gcatctggag caccgacatc ctgaaggacc aaaaggagcc caagaacaag accttcctga     480
ggtgcgaggc caaaaactat tccggccgct ttacctgttg gtggctgacc accatctcca     540
ccgatctgac cttcagcgtg aagtcgtcta ggggctcctc cgaccccag ggcgtaacct     600 gcggcgccgc gaccctgagc gccgagaggg tgcggggcga taacaaagag tacgagtact     660
cggtggagtg ccaggaggac agcgcctgtc cggcggccga ggagagcctg cccatcgagg     720
tgatggtgga cgccgtccac aagctgaagt acgagaacta caccagttcg ttcttcatca     780
gggacatcat caagccggac cccccaaga acctccagct gaagcccctg aagaacagca     840
ggcaggtgga agtgtcctgg gagtatcccg acacctggag caccccccac agctacttca     900
gcctgacctt ttgcgtgcag gtgcagggca aaagcaagag ggaaaagaag gaccgggtgt     960
tcaccgataa gacgacgcc accgttatct gcaggaagaa cgcctccata agcgtgaggg    1020
cgcaggaccg ttactacagc agcagctgga gtgagtgggc aagcgtgccc tgtagcggcg    1080
ggggcggggg cgggtcccgc aacctccccg tcgccacccc cgacccaggc atgttccgt     1140 gcctgcacca cagccagaac ctgctgcggg ccgttagcaa catgctgcag aaggccaggc    1200
agaccctcga gttctatccc tgcacatctg aggagatcga ccacgaagac atcactaagg    1260
ataagacctc caccgtggag gcctgtctgc ccctcgagct gaccaagaat gaatcctgcc    1320
tgaacagccg agagaccagc tttatcacca acggctcctg cctggccagc aggaagacct    1380
ccttcatgat ggccctgtgc ctctccagca tctacgagga tctgaagatg taccaggtag    1440
agttcaagac gatgaacgcc aagctcctga tggaccccaa gaggcagata ttcctggacc    1500
agaacatgct ggcggtgatc gacgagctga tgcaggccct gaatttcaac agcgagacgg    1560
tgccacagaa gtccagcctg gaggagccag acttctacaa gaccaagatc aaactgtgca    1620
tcctcctgca cgcgttcagg atccgcgccg tcaccataga cagggtgatg agttatctga    1680
acgccagctg ataataggct ggagcctcgg tggccatgct tcttgcccct tgggcctccc    1740
cccagcccct cctccccttc ctgcacccgt acccccaaa caccattgtc acactccagt     1800
```

```
ggtctttgaa taaagtctga gtgggcggc                                   1829
```

<210> SEQ ID NO 90
<211> LENGTH: 1829
<212> TYPE: DNA
<213> ORGANISM: Artificial Sequence
<220> FEATURE:
<223> OTHER INFORMATION: hIL12AB_036

<400> SEQUENCE: 90

```
tcaagctttt ggaccctcgt acagaagcta atacgactca ctatagggaa ataagagaga   60
aaagaagagt aagaagaaat ataagagcca ccatgtgcca tcagcagctg gtaatcagct  120
ggtttagcct ggtgttcctg gccagcccac tggtggccat ctgggagctg aagaaggacg  180
tgtacgtggt ggaactggac tggtaccccg acgcccctgg cgagatggtg gtactgacct  240
gtgacacccc ggaggaagac ggtatcacct ggaccctgga tcagagctcc gaggtgctgg  300
gctccggcaa gacactgacc atccaagtta aggaatttgg ggacgccggc cagtacacct  360
gccacaaggg gggcgaggtg ctgtcccact ccctgctgct tctgcataag aaggaggatg  420
gcatctggtc caccgacata ctgaaggacc agaaggagcc caagaataag accttcctga  480
gatgcgaggc caagaactac tcgggaaggt tcacctgctg gtggctgacc accatcagca  540
ccgacctgac cttctccgtg aagagctccc ggggcagctc cgaccccag ggcgtaacct  600
gtggggccgc taccctgtcc gccgagaggg tccgggggcga caacaaggaa tacgagtaca  660
gcgtggagtg ccaggaggac tccgcctgcc ccgccgccga ggagtcgctg cccatagagg  720
tgatggtgga cgccgtgcac aagctcaagt acgagaatta caccagcagc ttctttatca  780
gggacataat taagccggac ccccaaaga atctgcagct gaagcccctg aagaatagcc  840
ggcaggtgga agtgtcctgg gagtaccccg acacctggag caccccccac tcctatttct  900
cactgacatt ctgcgtgcag gtgcaaggga aaagcaagag ggagaagaag atagggtgt  960
tcaccgacaa gacaagcgcc accgtgatct gccgaaaaaa tgccagcatc agcgtgaggg 1020
cccaggatcg gtattacagc agctcctgga gcgagtgggc cagcgtgccc tgttccggcg 1080
ggggagggggg cggctcccgg aacctgccgg tggccacccc cgaccctggc atgttccccct 1140
gcctgcatca cagccagaac ctgctccggg ccgtgtcgaa catgctgcag aaggcccggc 1200
agaccctcga gttttacccc tgcaccagca aagagatcga ccacgaagac ataaccaagg 1260
acaagaccag cacggtggag gcctgcctgc cctggagct taccaaaaac gagtcctgcc 1320
tgaacagccg ggaaaccagc ttcataacga acgggagctg cctggcctcc aggaagacca 1380
gcttcatgat ggcgctgtgt ctgtccagca tatacgagga tctgaagatg tatcaggtgg 1440
aattcaaaac tatgaatgcc aagctcctga tggaccccaa gaggcagatc ttcctggacc 1500
agaacatgct agccgtgatc gacgagctga tgcaggccct caacttcaac tcggagacgg 1560
tgccccagaa gtccagcctc gaggagccccc acttctacaa gaccaagatc aagctgtgca 1620
tactgctgca tgccttcagg ataagggcgg tgactatcga cagggtcatg tcctacctga 1680
acgccagctg ataataggct ggagcctcgg tggccatgct tcttgcccct tgggcctccc 1740
cccagcccct cctcccccttc ctgcacccgt acccccaaa caccattgtc acactccagt 1800
ggtctttgaa taaagtctga gtgggcggc                                  1829
```

<210> SEQ ID NO 91
<211> LENGTH: 1829
<212> TYPE: DNA
<213> ORGANISM: Artificial Sequence
<220> FEATURE:
<223> OTHER INFORMATION: hIL12AB_037

<400> SEQUENCE: 91

```
tcaagctttt ggaccctcgt acagaagcta atacgactca ctatagggaa ataagagaga      60
aaagaagagt aagaagaaat ataagagcca ccatgtgcca ccaacaactg gtgatcagct     120
ggttctccct ggtgttcctg gccagccccc tggtggccat ctgggagctc aaaaaagacg     180
tgtacgtggt ggagctcgat tggtacccag acgcgccggg ggaaatggtg gtgctgacct     240
gcgacacccc agaggaggat ggcatcacgt ggacgctgga tcagtccagc gaggtgctgg     300
ggagcggcaa gacgctcacc atccaggtga aggaatttgg cgacgcgggc cagtatacct     360
gtcacaaggg cggcgaggtg ctgagccact ccctgctgct gctgcacaag aaggaggatg     420
ggatctggtc aaccgatatc ctgaaagacc agaaggagcc caagaacaag accttcctgc     480
gctgcgaggc caagaactat agcggcaggt tcacctgctg gtggctgacc accatcagca     540
ccgacctgac cttcagcgtg aaatcctcca ggggcagcag cgaccccag ggcgtgacct     600
gcggtgccgc cacgctctcc gccgagcgag tgaggggtga caacaaggag tacgagtaca     660
gcgtggaatg tcaggaggac agcgcctgtc ccgccgccga ggagtcgctg cccatcgagg     720
tgatggtcga cgcggtgcac aagctcaaat acgagaatta caccagcagc ttcttcatca     780
gggacatcat caagcccgac ccccccaaga acctgcagct gaagcccttg aagaacagca     840
ggcaggtgga ggtgagctgg gagtacccgg acacctggag cacccccac tcctacttca     900
gcctgacgtt ctgtgtgcag gtgcagggga agtccaagag ggagaagaag accgggtgt     960
tcaccgacaa gaccagcgcc accgtgatat gccgcaagaa cgcgtccatc agcgttcgcg    1020
cccaggaccg ctactacagc agctcctggt ccgaatgggc cagcgtgccc tgcagcggtg    1080
gagggggcgg gggctccagg aatctgccgg tggccacccc cgaccccggg atgttcccgt    1140
gtctgcatca ctcccagaac ctgctgcggg ccgtgagcaa tatgctgcag aaggccaggc    1200
agacgctcga gttctacccc tgcacctccg aagagatcga ccatgaggac atcaccaagg    1260
acaagaccag caccgtggag gcctgcctcc ccctggagct gaccaaaaac gagagctgcc    1320
tgaactccag ggagaccagc tttataacca acggcagctg cctcgcctcc aggaagacct    1380
cgtttatgat ggccctctgc ctgtccagca tctacgagga cctgaagatg taccaggtgg    1440
agttcaagac catgaacgcg aagttgctca tggacccca gaggcagatc ttcctggacc    1500
agaacatgct cgcggtgatc gacgagctga tgcaagccct gaacttcaac agcgagaccg    1560
tgccccagaa gagcagcctg gaagagcccg acttctacaa gaccaagatc aagctgtgca    1620
tcctgctgca cgccttccgg atccgggccg tgaccatcga cagggtgatg agctacctca    1680
acgcctcctg ataataggct ggagcctcgg tggccatgct tcttgccct tgggcctccc    1740
cccagcccct cctccccttc ctgcacccgt accccccaaa caccattgtc acactccagt    1800
ggtctttgaa taaagtctga gtgggcggc                                      1829
```

<210> SEQ ID NO 92
<211> LENGTH: 1829
<212> TYPE: DNA
<213> ORGANISM: Artificial Sequence
<220> FEATURE:
<223> OTHER INFORMATION: hIL12AB_038

<400> SEQUENCE: 92

```
tcaagctttt ggaccctcgt acagaagcta atacgactca ctatagggaa ataagagaga      60
```

| | |
|---|---|
| aaagaagagt aagaagaaat ataagagcca ccatgtgcca ccagcagctc gtgatcagct | 120 |
| ggttctccct cgtcttcctg gcctccccgc tggtggccat ctgggagctg aagaaggacg | 180 |
| tgtacgtggt ggagctggac tggtatcccg acgccccgg cgagatggtg gtgctgacgt | 240 |
| gcgacacacc agaagaggac gggatcacat ggacccctgga tcagtcgtcc gaggtgctgg | 300 |
| ggagcggcaa gaccctcacc atccaagtga aggagttcgg ggacgccggc cagtacacct | 360 |
| gccacaaggg cggggaggtg ctctcccata gcctgctcct cctgcacaaa aaggaggatg | 420 |
| gcatctggag caccgacatc ctgaaggacc agaaggagcc caagaacaag acatttctca | 480 |
| ggtgtgaggc caagaactat cgggcaggt ttacctgttg gtggctcacc accatctcta | 540 |
| ccgacctgac gttctccgtc aagtcaagca gggggagctc ggaccccag ggggtgacat | 600 |
| gtggggccgc caccctgagc gcggagcgtg tccgcggcga caacaaggag tacgagtatt | 660 |
| ccgtggagtg ccaggaggac agcgcctgcc ccgccgccga ggagtccctg cccatagagg | 720 |
| tgatggtgga cgccgtccac aagttgaagt acgaaaatta tacctcctcg ttcttcatta | 780 |
| gggacatcat caagcctgac cccccgaaga acctacaact caagcccctc aagaactccc | 840 |
| gccaggtgga ggtgtcctgg gagtaccccg acacctggtc caccccgcac agctacttca | 900 |
| gcctgacctt ctgcgtgcag gtccagggga gagcaagcg tgaaaagaaa gacagggtgt | 960 |
| tcaccgacaa gacgagcgcc accgtgatct gcaggaaaaa cgcctccatc tccgtgcgcg | 1020 |
| cccaggacag gtactacagt agctcctgga gcgaatgggc cagcgtgccg tgcagcggcg | 1080 |
| ggggaggagg cggcagtcgc aacctgcccg tggccacccc cgaccccggc atgttcccat | 1140 |
| gcctgcacca cagccagaac ctgctgaggg cagtcagcaa tatgctgcag aaggccaggc | 1200 |
| agaccctgga gttttatccc tgcaccagcg aggagatcga ccacgaggac atcaccaagg | 1260 |
| acaagacctc caccgtcgag gcctgcctgc cactggagct gaccaaaaac gagagctgcc | 1320 |
| tgaactccag ggagacctcc ttcatcacca acgggagctg cctggccagc cggaagacca | 1380 |
| gcttcatgat ggcgctgtgc ctcagcagca tctacgagga tctcaagatg taccaggtgg | 1440 |
| agttcaagac catgaacgcg aagctgctga tggaccccaa gcggcagatc ttcctggacc | 1500 |
| agaacatgct ggccgtgatt gacgagctca tgcaggccct gaacttcaat agcgagaccg | 1560 |
| tccccaaaa gagcagcctg gaggaacccg acttctacaa aacgaagatc aagctctgca | 1620 |
| tcctgctgca cgccttccgg atccgggccg tgaccatcga tcgtgtgatg agctacctga | 1680 |
| acgcctcgtg ataataggct ggagcctcgg tggccatgct tcttgcccct tgggcctccc | 1740 |
| cccagccccct cctcccctc ctgcacccgt accccccaaa caccattgtc acactccagt | 1800 |
| ggtctttgaa taaagtctga gtgggcggc | 1829 |

<210> SEQ ID NO 93
<211> LENGTH: 1829
<212> TYPE: DNA
<213> ORGANISM: Artificial Sequence
<220> FEATURE:
<223> OTHER INFORMATION: hIL12AB_039

<400> SEQUENCE: 93

| | |
|---|---|
| tcaagctttt ggaccctcgt acagaagcta atacgactca ctatagggaa ataagagaga | 60 |
| aaagaagagt aagaagaaat ataagagcca ccatgtgcca ccagcagctc gtcatctcct | 120 |
| ggtttagcct ggtgtttctg gcctcccccc tggtcgccat ctgggagctg aagaaagacg | 180 |
| tgtacgtggt ggagctggac tggtacccgg acgctcccgg ggagatggtg gtgctgacct | 240 |
| gcgacacccc cgaggaggac ggcatcacct ggaccctgga ccagagctcc gaggtgctgg | 300 |

```
ggagcggcaa gaccctgacc attcaggtga aagagttcgg cgacgccggc caatatacct      360
gccacaaggg gggggaggtc ctgtcgcatt ccctgctgct gcttcacaaa aaggaggatg      420
gcatctggag caccgacatc ctgaaggacc agaaagaacc caagaacaag acgttcctgc      480
gctgcgaggc caagaactac agcggccggt tcacctgttg gtggctgacc accatctcca      540
ccgacctgac tttctcggtg aagagcagcc gcgggagcag cgaccccag ggagtgacct       600
gcggcgccgc caccctgagc gccgaaaggg tgaggggcga caataaagag tacgagtatt      660
ccgtggagtg ccaggaggac agcgcctgtc ccgccgccga ggagtccctg cctatcgagg      720
tgatggtcga cgcggtgcac aagctcaagt acgaaaacta caccagcagc ttttttcatca     780
gggatatcat caaaccagac ccccccaaga acctgcagct gaagcccctg aaaaacagca      840
ggcaggtgga agtgagctgg gaataccccg atacctggtc cacccccac agctacttca       900
gcctgacctt ctgcgtgcag gtgcagggga agtccaagcg ggagaagaaa gatcgggtgt      960
tcacggacaa gaccagcgcc accgtgattt gcaggaaaaa cgccagcatc tccgtgaggg      1020
ctcaggacag gtactacagc tccagctgga gcgagtgggc ctccgtgcct gcagcgggg      1080
gaggaggcgg cggcagcagg aatctgcccg tcgcaacccc cgaccccggc atgttcccct      1140
gcctgcacca cagccagaat ctgctgcgag ccgtgagcaa catgctccag aaggcccggc      1200
agacgctgga gttctacccc tgcacctccg aggagatcga ccacgaggac atcaccaagg      1260
ataagacgag caccgtcgag gcctgtctcc ccctggagct caccaagaac gagtcctgcc      1320
tgaatagcag ggagacgtcc ttcataacca acggcagctg tctggcgtcc aggaagacca      1380
gcttcatgat ggccctctgc ctgagctcca tctacgagga cctcaagatg taccaggtcg      1440
agttcaagac catgaacgca aaactgctca tggatccaaa gaggcagatc tttctggacc      1500
agaacatgct ggccgtgatc gatgaactca tgcaggccct gaatttcaat tccgagaccg      1560
tgccccagaa gagctccctg gaggaacccg acttctacaa aacaaagatc aagctgtgta      1620
tcctcctgca cgccttccgg atcagggccg tcaccattga ccgggtgatg tcctacctga      1680
acgccagctg ataataggct ggagcctcgg tggccatgct tcttgcccct tgggcctccc      1740
cccagcccct cctcccttc ctgcacccgt acccccaaa caccattgtc acactccagt        1800
ggtctttgaa taaagtctga gtgggcggc                                        1829
```

<210> SEQ ID NO 94
<211> LENGTH: 1829
<212> TYPE: DNA
<213> ORGANISM: Artificial Sequence
<220> FEATURE:
<223> OTHER INFORMATION: hIL12AB_040

<400> SEQUENCE: 94

```
tcaagctttt ggaccctcgt acagaagcta atacgactca ctatagggaa ataagagaga      60
aaagaagagt aagaagaaat ataagagcca ccatgtgcca tcagcagctg gtgatcagct      120
ggttcagcct cgtgttcctc gccagccccc tcgtggccat ctgggagctg aaaaaggacg      180
tgtacgtggt ggagctggac tggtatcccg acgcccgggg cgagatggtg gtgctgacct      240
gcgacacccc cgaggaggac ggcattacct ggacactgga ccagagcagc gaggtcctgg      300
gcagcgggaa gaccctgaca attcaggtga aggagttcgg cgacgccgga cagtacacgt      360
gccacaaggg gggggaggtg ctgtcccaca gcctcctcct gctgcacaag aaggaggatg      420
gcatctggag caccgacatc ctgaaggatc agaaggagcc caagaacaag acctttctga      480
```

| | |
|---|---|
| gatgcgaggc caagaattac agcggccgtt tcacctgctg gtggctcacc accatcagca | 540 |
| ccgacctgac cttcagcgtg aaatcctcca ggggctcctc cgacccgcag ggagtgacct | 600 |
| gcggcgccgc cacactgagc gccgagcggg tcagagggga caacaaggag tacgagtaca | 660 |
| gcgttgagtg ccaggaggac agcgcctgtc ccgcggccga ggaatccctg ccatcgagg | 720 |
| tgatggtgga cgcagtgcac aagctgaagt acgagaacta tacctcgagc ttcttcatcc | 780 |
| gggatatcat taagcccgat cccccgaaga acctgcagct caaaccctg aagaacagca | 840 |
| ggcaggtgga ggtctcctgg gagtaccccg acacatggtc cacccccat tcctatttct | 900 |
| ccctgacctt ttgcgtgcag gtgcagggca agagcaagag ggagaaaaag gacagggtgt | 960 |
| tcaccgacaa gacctccgcc accgtgatct gccgtaagaa cgctagcatc agcgtcaggg | 1020 |
| cccaggacag gtactatagc agctcctggt ccgagtgggc cagcgtcccg tgcagcggcg | 1080 |
| ggggcggtgg aggctcccgg aacctccccg tggccacccc ggaccccggg atgtttccct | 1140 |
| gcctgcatca cagccagaac ctgctgaggg ccgtgtccaa catgctgcag aaggccaggc | 1200 |
| agacactcga gttttacccc tgcaccagcg aggagatcga ccacgaagac atcaccaagg | 1260 |
| acaagacctc caccgtggag gcatgcctgc cctggagct gaccaaaaac gaaagctgtc | 1320 |
| tgaactccag ggagacctcc tttatcacga acggctcatg cctggcctcc agaaagacca | 1380 |
| gcttcatgat ggccctgtgc ctgagctcca tctacgagga cttgaaaatg taccaggtcg | 1440 |
| agttcaagac catgaacgcc aagctgctca tggaccccaa aaggcagatc tttctggacc | 1500 |
| agaatatgct ggccgtgatc gacgagctca tgcaagccct gaatttcaac agcgagaccg | 1560 |
| tgccccagaa gtcctccctg gaggagcccg acttctacaa gaccaagatc aagctgtgca | 1620 |
| tactcctgca cgcgtttagg atcagggcgg tgaccatcga taggtgatg agctacctga | 1680 |
| atgcctcctg ataataggct ggagcctcgg tggccatgct tcttgcccct tgggcctccc | 1740 |
| cccagcccct cctcccttc ctgcacccgt accccccaaa caccattgtc acactccagt | 1800 |
| ggtctttgaa taaagtctga gtgggcggc | 1829 |

<210> SEQ ID NO 95
<211> LENGTH: 1890
<212> TYPE: DNA
<213> ORGANISM: Artificial Sequence
<220> FEATURE:
<223> OTHER INFORMATION: hIL12AB_001
<220> FEATURE:
<221> NAME/KEY: misc_feature
<222> LOCATION: (1)..(1)
<223> OTHER INFORMATION: 5' terminal guanosine cap

<400> SEQUENCE: 95

| | |
|---|---|
| ggggaaataa gagagaaaag aagagtaaga agaaatataa gagccaccat gtgtcaccag | 60 |
| cagctggtca ttagctggtt tagccttgtg ttcctggcct cccccttgt cgctatttgg | 120 |
| gagctcaaga aggacgtgta cgtggtggag ttggattggt acccagacgc gcccggagag | 180 |
| atggtagttc tgacctgtga taccccagag gaggacggca tcacctggac gctgaccaa | 240 |
| agcagcgagg ttttgggctc agggaaaacg ctgaccatcc aggtgaagga attcggcgac | 300 |
| gccgggcagt acacctgcca taagggagga gaggtgctga gcattccct tcttctgctg | 360 |
| cacaagaaag aggacggcat ctggtctacc gacatcctga agaccagaa ggagcccaag | 420 |
| aacaaaacct tcctgaggtg cgaggccaag aactactccg gcaggttcac ttgttggtgg | 480 |
| ctgaccacca tcagtacaga cctgactttt agtgtaaaaa gctccagagg ctcgtccgat | 540 |
| ccccaagggg tgacctgcgg cgcagccact ctgagcgctg agcgcgtgcg cggtgacaat | 600 |

```
aaagagtacg agtacagcgt tgagtgtcaa aagatagcg cttgccctgc cgccgaggag      660
agcctgccta tcgaggtgat ggttgacgca gtgcacaagc ttaagtacga gaattacacc      720
agctcattct tcattagaga tataatcaag cctgacccac ccaagaacct gcagctgaag      780
ccactgaaaa actcacggca ggtcgaagtg agctgggagt accccgacac ctggagcact      840
cctcattcct atttctctct tacattctgc gtccaggtgc agggcaagag caagcgggaa      900
aagaaggatc gagtcttcac cgacaaaaca agcgcgaccg tgatttgcag gaagaacgcc      960
agcatctccg tcagagccca ggatagatac tatagtagca gctggagcga gtgggcaagc     1020
gtgccctgtt ccggcggcgg gggcgggggc agccgaaact tgcctgtcgc taccccggac     1080
cctggaatgt ttccgtgtct gcaccacagc cagaacctgc tgagagccgt gtcgaatatg     1140
ctccagaagg cccggcagac ccttgagttc taccccctgta ccagcgaaga gatcgatcat     1200
gaagatatca cgaaagataa aacatccacc gtcgaggctt gtctcccgct ggagctgacc     1260
aagaacgaga gctgtctgaa tagccgggag acgtctttca tcacgaatgg tagctgtctg     1320
gccagcagga aaacttcctt catgatggct ctctgcctga gctctatcta tgaagatctg     1380
aagatgtatc aggtggagtt taaaacaatg aacgccaaac tcctgatgga cccaaaaagg     1440
caaatctttc tggaccagaa tatgctggcc gtgatagacg agctgatgca ggcactgaac     1500
ttcaacagcg agacggtgcc acagaaatcc agcctggagg agcctgactt ttacaaaact     1560
aagatcaagc tgtgtatcct gctgcacgcc tttagaatcc gtgccgtgac tatcgacagg     1620
gtgatgtcat acctcaacgc ttcatgataa taggctggag cctcggtggc catgcttctt     1680
gccccttggg cctccccca gcccctcctc cccttcctgc acccgtaccc cccaaacacc     1740
attgtcacac tccagtggtc tttgaataaa gtctgagtgg gcggcaaaaa aaaaaaaaaa     1800
aaaaaaaaaa aaaaaaaaaa aaaaaaaaaa aaaaaaaaaa aaaaaaaaaa aaaaaaaaaa     1860
aaaaaaaaaa aaaaaaaaaa aaaaatctag                                      1890
```

<210> SEQ ID NO 96
<211> LENGTH: 1890
<212> TYPE: DNA
<213> ORGANISM: Artificial Sequence
<220> FEATURE:
<223> OTHER INFORMATION: hIL12AB_002
<220> FEATURE:
<221> NAME/KEY: misc_feature
<222> LOCATION: (1)..(1)
<223> OTHER INFORMATION: 5' terminal guanosine cap

<400> SEQUENCE: 96

```
ggggaaataa gagagaaaag aagagtaaga agaaatataa gagccaccat gtgccaccag       60
cagctggtga tcagctggtt cagcctggtg ttcctggcca gccccctggt ggccatctgg      120
gagctgaaga aggacgtgta cgtggtggag ttggattggt accccgacgc ccccggcgag      180
atggtggtgc tgacctgcga cacccccgag gaggacggca tcacctggac cctgaccag      240 agcagcgagg tgctgggcag cggcaagacc ctgaccatcc aggtgaagga gttcggcgac      300
gccggccagt acacctgcca caagggcggc gaggtgctga gccacagcct gctgctgctg      360
cacaagaagg aggacggcat ctggagcacc gacatcctga aggaccagaa ggagcccaag      420
aacaagacct tcctgagatg cgaggccaag aactacagcg gcagattcac ctgctggtgg      480
ctgaccacca tcagcaccga cctgaccttc agcgtgaaga gcagcagagg cagcagcgac      540
ccccagggcg tgacctgcgg cgccgccacc ctgagcgccg agagagtgag aggcgacaac      600
```

```
aaggagtacg agtacagcgt ggagtgccag gaagatagcg cctgccccgc cgccgaggag    660
agcctgccca tcgaggtgat ggtggacgcc gtgcacaagc tgaagtacga gaactacacc    720
agcagcttct tcatcagaga tatcatcaag cccgaccccc ccaagaacct gcagctgaag    780
cccctgaaga cagccggca ggtggaggtg agctgggagt accccgacac ctggagcacc     840
ccccacagct acttcagcct gaccttctgc gtgcaggtgc agggcaagag caagagagag    900
aagaaagata gagtgttcac cgacaagacc agcgccaccg tgatctgcag aaagaacgcc    960
agcatcagcg tgagagccca agatagatac tacagcagca gctggagcga gtgggccagc   1020
gtgccctgca cgcggcggcg cggcggcggc agcagaaacc tgcccgtggc caccccccgac  1080
cccggcatgt tccctgcct gcaccacagc cagaacctgc tgagagccgt gagcaacatg    1140
ctgcagaagg cccggcagac cctggagttc taccccctgca ccagcgagga gatcgaccac   1200
gaagatatca ccaaagataa gaccagcacc gtggaggcct gcctgccct ggagctgacc    1260
aagaacgaga gctgcctgaa cagcagagag accagcttca tcaccaacgg cagctgcctg   1320
gccagcagaa agaccagctt catgatggcc ctgtgcctga gcagcatcta cgaggacctg   1380
aagatgtacc aggtggagtt caagaccatg aacgccaagc tgctgatgga ccccaagcgg   1440
cagatcttcc tggaccagaa catgctggcc gtgatcgacg agctgatgca ggccctgaac   1500
ttcaacagcg agaccgtgcc ccagaagagc agcctggagg agcccgactt ctacaagacc   1560
aagatcaagc tgtgcatcct gctgcacgcc ttcagaatca gagccgtgac catcgacaga   1620
gtgatgagct acctgaacgc cagctgataa taggctggag cctcggtggc catgcttctt   1680
gccccttggg cctccccca gcccctcctc cccttcctgc acccgtaccc cccaaacacc    1740
attgtcacac tccagtggtc tttgaataaa gtctgagtgg cggcaaaaa aaaaaaaaa    1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaatctag                                   1890

<210> SEQ ID NO 97
<211> LENGTH: 1890
<212> TYPE: DNA
<213> ORGANISM: Artificial Sequence
<220> FEATURE:
<223> OTHER INFORMATION: hIL12AB_003
<220> FEATURE:
<221> NAME/KEY: misc_feature
<222> LOCATION: (1)..(1)
<223> OTHER INFORMATION: 5' terminal guanosine cap

<400> SEQUENCE: 97
ggggaaataa gagagaaaag aagagtaaga agaaatataa gagccaccat gtgtcaccag     60
cagttggtca tctcttggtt ttccctggtt tttctggcat ctcccctcgt ggccatctgg    120
gaactgaaga aagacgttta cgttgtagaa ttggattggt atccggacgc tcctggagaa    180
atggtggtcc tcacctgtga cacccctgaa gaagacggaa tcacctggac cttggaccag    240
agcagtgagg tcttaggctc tggcaaaacc ctgaccatcc aagtcaaaga gtttggagat    300
gctggccagt acacctgtca caaggaggc gaggttctaa gccattcgct cctgctgctt   360
cacaaaaagg aagatggaat tggtccact gatatttaa aggaccagaa agaacccaaa     420
aataagacct ttctaagatg cgaggccaag aattattctg acgtttcac ctgctggtgg    480
ctgacgacaa tcagtactga tttgacattc agtgtcaaaa gcagcagagg ctcttctgac   540
ccccaagggg tgacgtgcgg agctgctaca ctctctgcag agagagtcag aggtgacaac   600
aaggagtatg agtactcagt ggagtgccag gaagatagtg cctgcccagc tgctgaggag   660
```

```
agtctgccca ttgaggtcat ggtggatgcc gttcacaagc tcaagtatga aaactacacc      720
agcagcttct tcatcagaga tatcatcaaa cctgacccac ccaagaactt gcagctgaag      780
ccattaaaga attctcggca ggtggaggtc agctgggagt accctgacac ctggagtact      840
ccacattcct acttctccct gacattctgc gttcaggtcc agggcaagag caagagagaa      900
aagaaagata gagtcttcac agataagacc tcagccacgg tcatctgccg caaaaatgcc      960
agcattagcg tgcgggccca ggaccgctac tatagctcat cttggagcga atgggcatct     1020
gtgccctgca gtggcggagg gggcggaggg agcagaaacc tccccgtggc cactccagac     1080
ccaggaatgt tcccatgcct tcaccactcc caaaacctgc tgagggccgt cagcaacatg     1140
ctccagaagg cccggcaaac tttagaattt taccctgca cttctgaaga gattgatcat     1200
gaagatatca caaagataa aaccagcaca gtggaggcct gtttaccatt ggaattaacc     1260
aagaatgaga gttgcctaaa ttccagagag acctctttca taactaatgg agttgcctg     1320 gcctccagaa agacctcttt tatgatggcc ctgtgcctta gtagtattta tgaagatttg     1380
aagatgtacc aggtggagtt caagaccatg aatgcaaagc ttctgatgga tcctaagagg     1440
cagatctttt tagatcaaaa catgctggca gttattgatg agctgatgca ggccctgaat     1500
ttcaacagtg agacggtgcc acaaaaatcc tcccttgaag aaccagattt ctacaagacc     1560
aagatcaagc tctgcatact tcttcatgct ttcagaattc gggcagtgac tattgataga     1620
gtgatgagct atctgaatgc ttcctgataa taggctggag cctcggtggc catgcttctt     1680
gccccttggg cctcccccca gcccctcctc cccttcctgc acccgtaccc cccaaacacc     1740
attgtcacac tccagtggtc tttgaataaa gtctgagtgg gcggcaaaaa aaaaaaaaa      1800 aaaaaaaaaa aaaaaaaaaa aaaaaaaaaa aaaaaaaaaa aaaaaaaaaa aaaaaaaaaa     1860
aaaaaaaaaa aaaaaaaaa aaaatctag                                        1890

<210> SEQ ID NO 98
<211> LENGTH: 1893
<212> TYPE: DNA
<213> ORGANISM: Artificial Sequence
<220> FEATURE:
<223> OTHER INFORMATION: hIL12AB_004
<220> FEATURE:
<221> NAME/KEY: misc_feature
<222> LOCATION: (1)..(1)
<223> OTHER INFORMATION: 5' terminal guanosine cap

<400> SEQUENCE: 98
ggggaaataa gagagaaaag aagagtaaga agaaatataa gagccaccat gggctgccac       60
cagcagctgg tcatcagctg gttctccctg gtcttcctgg ccagcccct ggtggccatc      120 tgggagctga gaaagacgt ctacgtagta gagttggatt ggtacccaga cgcacctgga      180
gaaatggtgg ttctcaccctg tgacacgcca aagaagacg tatcacctg gacgctggac      240 cagagctcag aagttcttgg cagtggaaaa acgctgacca tacaagtaaa gaatttggg     300 gatgctggcc agtacacctg ccacaaagga ggagaagttc tcagccacag cctgctgctg     360
ctgcacaaga aagaagatgg catctggagc acagatattt taaaagacca gaaggagccc    420
aagaacaaaa ccttccttcg atgtgaggcc aagaactaca gtggccgctt cacctgctgg    480
tggctcacca ccatcagcac agacctcacc ttctcggtga agagcagccg tggcagctca    540 gaccccaag gagtcacctg tggggcggcc acgctgtcgg cagaaagagt tcgaggtgac    600
aacaaggaat atgaatactc ggtggaatgt caagaagatt cggcctgccc ggcggcagaa    660
```

-continued

```
gaaagtcttc ccatagaagt catggtggat gctgttcaca aattaaaata tgaaaactac    720
accagcagct tcttcatcag agatatcatc aagccagacc cgcccaagaa cctgcagctg    780
aagcccctga gaacagccg gcaggtggaa gtttcctggg agtacccaga tacgtggagc    840
acgccgcaca gctacttcag cctcaccttc tgtgtacaag tacaaggcaa gagcaagaga    900
gagaagaaag atcgtgtctt cacagataaa acctcggcga cggtcatctg caggaagaat    960
gcctccatct cggttcgagc ccaggaccgc tactacagca gcagctggag tgagtgggcc   1020
tcggtgccct gcagtggtgg cggcggcggc ggcagcagaa accttcctgt ggccacgccg   1080
gaccctggca tgttcccgtg cctgcaccac agccaaaatt tacttcgagc tgtttctaac   1140
atgctgcaga aagcacggca aactttagaa ttctacccct gcacctcaga agaaatagac   1200
catgaagata tcaccaaaga taaaaccagc actgtagagg cctgcctgcc cctggagctc   1260
accaagaatg aatcctgcct caacagcaga gagaccagct catcaccaa tggcagctgc   1320 ctggccagca ggaaaaccag cttcatgatg gcgctctgcc tgagcagcat ctatgaagat   1380
ttgaagatgt accaagtaga atttaaaacc atgaatgcca agctgctcat ggaccccaag   1440
cggcagatat ttttggatca aaacatgctg ctgtcattg atgagctcat gcaagcatta   1500
aacttcaact cagagacggt gccccagaag agcagcctgg aggagccaga tttctacaaa   1560
accaagatca agctctgcat cttattacat gccttccgca tccgggcggt caccattgac   1620
cgtgtcatgt cctacttaaa tgccagctga taataggctg gagcctcggt ggccatgctt   1680 cttgccctt gggcctcccc ccagcccctc ctccccttcc tgcacccgta cccccccaaac   1740 accattgtca cactccagtg gtctttgaat aaagtctgag tgggcggcaa aaaaaaaaa   1800 aaaaaaaaaa aaaaaaaaaa aaaaaaaaaa aaaaaaaaa aaaaaaaaa aaaaaaaaaa   1860 aaaaaaaaaa aaaaaaaaaa aaaaaaaatc tag                                1893
```

<210> SEQ ID NO 99
<211> LENGTH: 1890
<212> TYPE: DNA
<213> ORGANISM: Artificial Sequence
<220> FEATURE:
<223> OTHER INFORMATION: hIL12AB_005
<220> FEATURE:
<221> NAME/KEY: misc_feature
<222> LOCATION: (1)..(1)
<223> OTHER INFORMATION: 5' terminal guanosine cap

<400> SEQUENCE: 99

```
ggggaaataa gagagaaaag aagagtaaga agaaatataa gagccaccat gtgccaccag     60
cagctggtca tcagctggtt ctccctggtc ttcctggcca gcccctggt ggccatctgg    120 gagctgaaga aagacgtcta cgtagtagag ttggattggt acccagacgc acctggagaa    180
atggtggttc tcacctgtga cacgccagaa gaagacggta tcacctggac gctggaccag    240
agctcagaag ttcttggcag tggaaaaacg ctgaccatac aagtaaaaga atttgggat    300 gctggccagt acacctgcca caaggagga gaagttctca gccacagcct gctgctgctg    360
cacaagaaag aagatggcat ctggagcaca gatattttaa aagaccagaa ggagcccaag    420
aacaaaacct tccttcgatg tgaggccaag aactacagtg gccgcttcac ctgctggtgg    480
ctcaccacca tcagcacaga cctcaccttc tcggtgaaga cagccgtgg cagctcagac    540 ccccaaggag tcacctgtgg ggcggccacg ctgtcggcag aaagagttcg aggtgacaac    600
aaggaatatg aatactcggt ggaatgtcaa gaagattcgg cctgccccgc ggcagaagaa    660
agtcttccca tagaagtcat ggtggatgct gttcacaaat aaaatatga aaactacacc    720
```

```
agcagcttct tcatcagaga tatcatcaag ccagacccgc ccaagaacct gcagctgaag      780
cccctgaaga acagccggca ggtggaagtt tcctgggagt acccagatac gtggagcacg      840
ccgcacagct acttcagcct caccttctgt gtacaagtac aaggcaagag caagagagag      900
aagaaagatc gtgtcttcac agataaaacc tcggcgacgg tcatctgcag gaagaatgcc      960
tccatctcgg ttcgagccca ggaccgctac acagcagca gctggagtga gtgggcctcg     1020
gtgccctgca gtggtggcgg cggcggcggc agcagaaacc ttcctgtggc cacgccggac     1080
cctggcatgt tcccgtgcct gcaccacagc caaaatttac ttcgagctgt ttctaacatg     1140
ctgcagaaag cacggcaaac tttagaattc taccccctgca cctcagaaga aatagaccat     1200
gaagatatca ccaaagataa accagcact gtagaggcct gcctgcccct ggagctcacc     1260
aagaatgaat cctgcctcaa cagcagagag accagcttca tcaccaatgg cagctgcctg     1320
gccagcagga aaccagcttt catgatggcg ctctgcctga gcagcatcta tgaagatttg     1380
aagatgtacc aagtagaatt taaaaccatg aatgccaagc tgctcatgga ccccaagcgg     1440
cagatatttt tggatcaaaa catgctggct gtcattgatg agctcatgca agcattaaac     1500
ttcaactcag agacggtgcc ccagaagagc agcctggagg agccagattt ctacaaaacc     1560
aagatcaagc tctgcatctt attacatgcc ttccgcatcc gggcggtcac cattgaccgt     1620
gtcatgtcct acttaaatgc cagctgataa taggctggag cctcggtggc catgcttctt     1680
gccccttggg cctcccccca gcccctcctc cccttcctgc acccgtaccc cccaaacacc     1740
attgtcacac tccagtggtc tttgaataaa gtctgagtgg gcggcaaaaa aaaaaaaaaa     1800
aaaaaaaaaa aaaaaaaaaa aaaaaaaaaa aaaaaaaaaa aaaaaaaaaa aaaaaaaaaa     1860
aaaaaaaaaa aaaaaaaaaa aaaaatctag                                      1890

<210> SEQ ID NO 100
<211> LENGTH: 1890
<212> TYPE: DNA
<213> ORGANISM: Artificial Sequence
<220> FEATURE:
<223> OTHER INFORMATION: hIL12AB_006
<220> FEATURE:
<221> NAME/KEY: misc_feature
<222> LOCATION: (1)..(1)
<223> OTHER INFORMATION: 5' terminal guanosine cap

<400> SEQUENCE: 100
ggggaaataa gagagaaaag aagagtaaga agaaatataa gagccaccat gtgccaccag       60
cagctggtga tcagctggtt cagcctggtg ttcctggcca gcccccctggt ggccatctgg      120 gagctgaaga aggacgtgta cgtggtggag ttggattggt accccgacgc ccccggcgag      180
atggtggtgc tgacctgtga caccccccgag gaggacggca tcacctggac cctgaccagg     240
agcagcgagg tgctgggcag cggcaagacc ctgaccatcc aggtgaagga gttcggggac     300
gccggccagt acacctgcca caagggcggc gaggtgctga gccacagcct gctgctgctg     360
cacaagaagg aggacggcat ctggagcaca gatatcctga aggaccagaa ggagcccaag     420
aacaagacct tcctgagatg cgaggccaag aactacagcg gcagattcac ctgctggtgg     480
ctgaccacca tcagcacaga tttgaccttc agcgtgaaga gcagcagagg cagcagcgac     540
ccccagggcg tgacctgcgg cgccgccacc ctgagcgccg agagagtgag aggtgacaac     600
aaggagtacg agtacagcgt ggagtgccag gaagatagcg cctgccccgc cgccgaggag     660
agcctgccca tcgaggtgat ggtggacgcc gtgcacaagc tgaagtacga gaactacacc      720
```

```
agcagcttct tcatcagaga tatcatcaag cccgacccgc cgaagaacct gcagctgaag      780
cccctgaaga acagccggca ggtggaggtg agctgggagt accccgacac ctggagcacc      840
ccccacagct acttcagcct gaccttctgc gtgcaggtgc agggcaagag caagagagag      900
aagaaagata gagtgttcac agataagacc agcgccaccg tgatctgcag aaagaacgcc      960
agcatcagcg tgagagccca agatagatac tacagcagca gctggagcga gtgggccagc     1020
gtgccctgca gcggcggcgg cggcggcggc agcagaaacc tgcccgtggc cacccccgac     1080
cccggcatgt tcccctgcct gcaccacagc cagaacctgc tgagagccgt gagcaacatg     1140
ctgcagaagg cccggcagac cctggagttc taccccctgca ccagcgagga gatcgaccac     1200
gaagatatca ccaaagataa gaccagcacc gtggaggcct gcctgccccct ggagctgacc    1260 aagaatgaaa gctgcctgaa cagcagagag accagcttca tcaccaacgg cagctgcctg     1320
gccagcagaa agaccagctt catgatggcc ctgtgcctga gcagcatcta cgaggacctg     1380
aagatgtacc aggtggagtt caagaccatg aacgccaagc tgctgatgga ccccaagcgg     1440
cagatcttcc tggaccagaa catgctggcc gtgatcgacg agctgatgca ggccctgaac     1500
ttcaacagcg agaccgtgcc ccagaagagc agcctggagg agcccgactt ctacaagacc     1560
aagatcaagc tgtgcatcct gctgcacgcc ttcagaatca gagccgtgac catcgacaga     1620
gtgatgagct acctgaacgc cagctgataa taggctggag cctcggtggc catgcttctt     1680
gccccttggg cctcccccca gcccctcctc cccttcctgc acccgtaccc cccaaacacc     1740
attgtcacac tccagtggtc tttgaataaa gtctgagtgg cggcaaaaa aaaaaaaaa      1800 aaaaaaaaaa aaaaaaaaaa aaaaaaaaaa aaaaaaaaaa aaaaaaaaaa aaaaaaaaaa     1860
aaaaaaaaaa aaaaaaaaaa aaaaatctag                                      1890

<210> SEQ ID NO 101
<211> LENGTH: 1890
<212> TYPE: DNA
<213> ORGANISM: Artificial Sequence
<220> FEATURE:
<223> OTHER INFORMATION: hIL12AB_007
<220> FEATURE:
<221> NAME/KEY: misc_feature
<222> LOCATION: (1)..(1)
<223> OTHER INFORMATION: 5' terminal guanosine cap

<400> SEQUENCE: 101
ggggaaataa gagagaaaag aagagtaaga agaaatataa gagccaccat gtgccaccag       60
cagcttgtca tctcctggtt ctctcttgtc ttccttgctt ctcctcttgt ggccatctgg      120
gagctgaaga aggacgttta cgtagtggag ttggattggt accctgacgc acctggagaa      180
atggtggttc tcacctgtga cactcctgag gaggacggta tcacctggac gttgaccag       240 tcttctgagg ttcttggcag tggaaaaact cttactattc aggtgaagga gtttggagat      300
gctggccagt acacctgcca caagggtggt gaagttctca gccacagttt acttcttctt     360
cacaagaagg aggatggcat ctggtctact gacatttaa aagaccagaa ggagcccaag      420
aacaaaacat tccttcgttt tgaagccaag aactacagtg gtcgtttcac ctgctggtgg     480
cttactacta tttctactga ccttactttc tctgtgaagt cttctcgtgg ctcttctgac      540
cctcagggtg tcacctgtgg ggctgctact cttctgctg agcgtgtgcg tggtgacaac     600
aaggagtatg aatactcggt gggagtgcca gaagattctg cctgccctgc tgctgaggag     660
tctcttccta ttgaggtgat ggtggatgct gtgcacaagt taaatatga aaactacact      720 tcttcttttct tcattcgtga cattataaaa cctgacccctc ccaagaacct tcagttaaaa    780
```

```
cctttaaaaa actctcgtca ggtggaggtg tcctgggagt accctgacac gtggtctact      840
cctcactcct acttctctct tactttctgt gtccaggtgc agggcaagtc caagcgtgag      900
aagaaggacc gtgtcttcac tgacaaaaca tctgctactg tcatctgcag gaagaatgca      960
tccatctctg tgcgtgctca ggaccgttac tacagctctt cctggtctga gtgggcttct     1020
gtgccctgct ctggcggcgg cggcggcggc agcagaaatc ttcctgtggc tactcctgac     1080
cctggcatgt tccctgcct tcaccactcg cagaaccttc ttcgtgctgt gagcaacatg      1140
cttcagaagg ctcgtcaaac tttagaattc taccctgca cttctgagga gattgaccat      1200
gaagatatca ccaaagataa aacatctact gtggaggcct gccttccttt agagctgacc     1260
aagaatgaat cctgcttaaa ttctcgtgag acgtctttca tcaccaatgg cagctgcctt     1320
gcctcgcgca aaacatcttt catgatggct ctttgccttt cttccatcta tgaagattta     1380
aaaatgtacc aggtggagtt caagaccatg aatgcaaagc ttctcatgga ccccaagcgt     1440
cagatatttt tggaccagaa catgcttgct gtcattgatg agctcatgca ggctttaaac     1500
ttcaactctg agacggtgcc tcagaagtct tctttagaag agcctgactt ctacaagacc     1560
aagataaaac tttgcattct tcttcatgct ttccgcatcc gtgctgtgac tattgaccgt     1620
gtgatgtcct acttaaatgc ttcttgataa taggctggag cctcggtggc caagcttctt     1680
gccccttggg cctcccccca gccctcctc ccttcctgc acccgtaccc cccaaacacc       1740
attgtcacac tccagtggtc tttgaataaa gtctgagtgg gcggcaaaaa aaaaaaaaaa     1800
aaaaaaaaaa aaaaaaaaaa aaaaaaaaaa aaaaaaaaaa aaaaaaaaaa aaaaaaaaaa     1860
aaaaaaaaaa aaaaaaaaaa aaaaatctag                                       1890
```

<210> SEQ ID NO 102
<211> LENGTH: 1890
<212> TYPE: DNA
<213> ORGANISM: Artificial Sequence
<220> FEATURE:
<223> OTHER INFORMATION: hIL12AB_008
<220> FEATURE:
<221> NAME/KEY: misc_feature
<222> LOCATION: (1)..(1)
<223> OTHER INFORMATION: 5' terminal guanosine cap

<400> SEQUENCE: 102

```
ggggaaataa gagagaaaag aagagtaaga agaaatataa gagccaccat gtgtcatcaa       60
caactcgtga ttagctggtt cagtctcgtg ttcctggcct ctccgctggt ggccatctgg      120
gagcttaaga aggacgtgta cgtggtggag ctcgattggt accccgacgc acctggcgag      180
atggtggtgc taacctgcga tacccccgag gaggacggga tcacttggac cctggatcag      240
agtagcgaag tcctgggctc tggcaaaaca ctcacaatcc aggtgaagga attcggagac      300
gctggtcagt acacttgcca caagggggt gaagtgctgt ctcacagcct gctgttactg      360
cacaagaagg aggatgggat ctggtcaacc gacatcctga aggatcagaa ggagcctaag      420
aacaagacct ttctgaggtg tgaagctaag aactattccg gaagattcac ttgctggtgg      480
ttgaccacaa tcagcactga cctgaccttt ccgtgaagt ccagcagagg aagcagcgat       540
cctcagggcg taacgtgcgg cgcggctacc ctgtcagctg agcgggttag aggcgacaac      600
aaagagtatg agtactccgt ggagtgtcag gaagatagcg cctgccccgc agccgaggag      660
agtctgccca tcgaggtgat ggtggacgct gtccataagt aaaatacga aaattacaca      720 agttcctttt tcatccgcga tattatcaaa cccgatcccc caagaacct gcagctgaag      780
```

| | |
|---|---|
| cccctgaaga atagccgaca ggtggaagtc tcttgggagt atcctgacac ctggtccacg | 840 |
| cctcacagct actttagtct gactttctgt gtccaggtcc agggcaagag caagagagag | 900 |
| aaaaaggata gagtgtttac tgacaaaaca tctgctacag tcatctgcag aaagaacgcc | 960 |
| agtatctcag tgagggcgca agatagatac tacagtagta gctggagcga atgggctagc | 1020 |
| gtgccctgtt caggggcgg cggagggggc tccaggaatc tgcccgtggc caccccgac | 1080 |
| cctgggatgt tcccttgcct ccatcactca cagaacctgc tcagagcagt gagcaacatg | 1140 |
| ctccaaaagg cccgccagac cctggagttt taccccttgta cttcagaaga gatcgatcac | 1200 |
| gaagatataa caaggataa aaccagcacc gtggaggcct gtctgcctct ggaactcaca | 1260 |
| aagaatgaaa gctgtctgaa ttccagggaa acctccttca ttactaacgg aagctgtctc | 1320 |
| gcatctcgca aaacatcatt catgatggcc ctctgcctgt cttctatcta tgaagatctc | 1380 |
| aagatgtatc aggtggagtt caaaacaatg aacgccaagc tgctgatgga ccccaagcgg | 1440 |
| cagatcttcc tggaccagaa catgctggca gtgatcgatg agctgatgca agccttgaac | 1500 |
| ttcaactcag agacggtgcc gcaaaagtcc tcgttggagg aaccagattt ttacaaaacc | 1560 |
| aaaatcaagc tgtgtatcct tcttcacgcc tttcggatca gagccgtgac tatcgaccgg | 1620 |
| gtgatgtcat acctgaatgc ttcctgataa taggctggag cctcggtggc catgcttctt | 1680 |
| gcccccttggg cctcccccca gcccctcctc cccttcctgc acccgtaccc cccaaacacc | 1740 |
| attgtcacac tccagtggtc tttgaataaa gtctgagtgg gcggcaaaaa aaaaaaaaa | 1800 |
| aaaaaaaaaa aaaaaaaaaa aaaaaaaaaa aaaaaaaaa aaaaaaaaa aaaaaaaaa | 1860 |
| aaaaaaaaaa aaaaaaaaaa aaaatctag | 1890 |

<210> SEQ ID NO 103
<211> LENGTH: 1890
<212> TYPE: DNA
<213> ORGANISM: Artificial Sequence
<220> FEATURE:
<223> OTHER INFORMATION: hIL12AB_009
<220> FEATURE:
<221> NAME/KEY: misc_feature
<222> LOCATION: (1)..(1)
<223> OTHER INFORMATION: 5' terminal guanosine cap

<400> SEQUENCE: 103

| | |
|---|---|
| ggggaaataa gagagaaaag aagagtaaga agaaatataa gagccaccat gtgccaccag | 60 |
| cagctggtca tcagctggtt tagcctggtc ttcctggcca gccccctggt ggccatctgg | 120 |
| gagctgaaga aagacgtcta cgtagtagag ttggattggt acccagacgc acctggagaa | 180 |
| atggtggttc tcacctgcga cacgccagaa gaagacggta tcacctggac gctggaccag | 240 |
| agcagcgaag tactgggcag tggaaaaacg ctgaccatac aagtaaaaga atttggcgat | 300 |
| gctggccagt acacctgcca caaggagga gaagtactga gccacagcct gctgctgctg | 360 |
| cacaagaaag aagatggcat ctggagcacc gacattttaa agaccagaa ggagcccaag | 420 |
| aacaaaacct tccttcgatg tgaggcgaag aactacagtg gccgcttcac ctgctggtgg | 480 |
| ctcaccacca tcagcaccga cctcaccttc tcggtgaaga gcagccgtgg tagctcagac | 540 |
| ccccaaggag tcacctgtgg ggcggccacg ctgtcggcag aaagagttcg aggcgacaac | 600 |
| aaggaatatg aatactcggt ggaatgtcaa gaagattcgg cctgcccggc ggcagaagaa | 660 |
| agtctgccca tagaagtcat ggtggatgct gttcacaaat taaatatga aaactacacc | 720 |
| agcagcttct tcatcagaga tatcatcaag ccagaccccc caagaacct gcagctgaag | 780 |
| cccctgaaga acagccggca ggtggaagtt tcctgggagt acccagatac gtggagcacg | 840 |

```
ccgcacagct acttcagcct caccttctgt gtacaagtac aaggcaagag caagagagag      900
aagaaagatc gtgtcttcac cgacaaaacc tcggcgacgg tcatctgcag gaagaatgca      960
agcatctcgg ttcgagccca ggaccgctac tacagcagca gctggagtga gtgggcctcg     1020
gtgccctgca gtggtggcgg cggcggcggc agcagaaacc ttcctgtggc cacgccggac     1080
cctggcatgt ttccgtgcct gcaccacagc caaaatttat tacgagctgt tagcaacatg     1140
ctgcagaaag cacggcaaac tttagaattc taccccctgca cctcagaaga aatagaccat     1200
gaagatatca ccaaagataa aaccagcact gtagaggcct gcctgcccct ggagctcacc     1260
aagaacgaga gctgcctcaa tagcagagag accagcttca tcaccaatgg cagctgcctg     1320
gccagcagga aaaccagctt catgatggcg ctctgcctga gcagcatcta tgaagatctg     1380
aagatgtacc aagtagaatt taaaaccatg aatgccaagc tgctcatgga ccccaagcgg     1440
cagatattcc tcgaccaaaa catgctggct gtcattgatg agctcatgca agcattaaac     1500
ttcaactcag agacggtgcc ccagaagagc agcctggagg agccagattt ctacaaaacc     1560
aagatcaagc tctgcatctt attacatgcc ttccgcatcc gggcggtcac cattgaccgt     1620
gtcatgtcct acttaaatgc cagctgataa taggctggag cctcggtggc catgcttctt     1680
gccccttggg cctcccccca gcccctcctc cccttcctgc acccgtaccc cccaaacacc     1740
attgtcacac tccagtggtc tttgaataaa gtctgagtgg gcggcaaaaa aaaaaaaaa      1800
aaaaaaaaaa aaaaaaaaaa aaaaaaaaaa aaaaaaaaa aaaaaaaaaa aaaaaaaaaa     1860
aaaaaaaaaa aaaaaaaaaa aaaaatctag                                    1890

<210> SEQ ID NO 104
<211> LENGTH: 1890
<212> TYPE: DNA
<213> ORGANISM: Artificial Sequence
<220> FEATURE:
<223> OTHER INFORMATION: hIL12AB_010
<220> FEATURE:
<221> NAME/KEY: misc_feature
<222> LOCATION: (1)..(1)
<223> OTHER INFORMATION: 5' terminal guanosine cap

<400> SEQUENCE: 104
ggggaaataa gagagaaaag aagagtaaga agaaatataa gagccaccat gtgccaccag       60
cagcttgtca tctcctggtt ttctcttgtc ttcctcgctt ctcctcttgt ggccatctgg      120
gagctgaaga agacgtctca cgtagtagag ttggattggt acccggacgc tcctggagaa      180
atggtggttc tcacctgcga cactcctgaa gaagacggta tcacctggac gctggaccaa      240
agcagcgaag ttttaggctc tggaaaaacg ctgaccatac aagtaaaaga atttggcgac      300
gctggccagt acacgtgcca caaggaggga gaagttttaa gccacagttt acttcttctt      360
cacaagaaag aagatggcat ctggagtaca gatattttaa aagaccagaa ggagcctaag      420
aacaaaacct tcctccgctg tgaagctaag aactacagtg tcgtttcac ctgctggtgg      480
ctcaccacca tctccactga cctcaccttc tctgtaaaat caagccgtgg ttcttctgac      540
cccaaggag tcacctgtgg ggctgccacg ctcagcgctg aaagagttcg aggcgacaac      600
aaggaatatg aatattctgt ggaatgtcaa gaagattctg cctgccccgc ggcagaagaa      660
agtcttccca tagaagtcat ggtggacgct gttcacaaat taaatatga aaactacacc      720
agcagcttct tcattcgtga catcatcaaa ccagaccctc ctaagaacct tcagttaaaa      780
ccgctgaaga acagccggca ggtggaagtt tcctgggagt acccagatac gtggagtacg      840
```

```
ccgcactcct acttcagttt aaccttctgt gtacaagtac aaggaaaatc aaaaagagag    900
aagaaagatc gtgtcttcac tgacaaaaca tctgccacgg tcatctgccg taagaacgct    960
tccatctcgg ttcgagccca ggaccgctac tacagcagca gctggagtga gtgggcatct   1020
gttccctgca gtggtggcgg cggcggcggc agccgcaacc ttcctgtggc cacgccggac   1080
cctggcatgt tcccgtgcct tcaccactcg caaaatcttc ttcgtgctgt ttctaacatg   1140
ctgcagaagg cgcggcaaac tttagaattc tacccgtgca cttctgaaga aatagaccat   1200
gaagatatca ccaaagataa aaccagcacg gtggaggcct gccttccttt agaacttact   1260
aagaacgaaa gttgccttaa cagccgtgag accagcttca tcaccaatgg cagctgcctt   1320
gctagcagga agaccagctt catgatggcg ctgtgccttt cttccatcta tgaagatctt   1380
aagatgtacc aagtagaatt taaaaccatg aatgccaaat tattaatgga ccccaagcgg   1440
cagatattcc tcgaccaaaa catgctggct gtcattgatg agctcatgca agcattaaac   1500
ttcaactcag aaactgttcc ccagaagtca tctttagaag aaccagattt ctacaaaaca   1560
aaaataaaac tctgcattct tcttcatgcc ttccgcatcc gtgctgtcac cattgaccgt   1620
gtcatgtcct acttaaatgc ttcttgataa taggctggag cctcggtggc catgcttctt   1680
gccccttggg cctcccccca gcccctcctc cccttcctgc acccgtaccc cccaaacacc   1740
attgtcacac tccagtggtc tttgaataaa gtctgagtgg cggcaaaaa aaaaaaaaa    1800 aaaaaaaaaa aaaaaaaaaa aaaaaaaaa aaaaaaaaaa aaaaaaaaaa aaaaaaaaa    1860 aaaaaaaaaa aaaaaaaaaa aaaatctag                                    1890
```

<210> SEQ ID NO 105
<211> LENGTH: 1890
<212> TYPE: DNA
<213> ORGANISM: Artificial Sequence
<220> FEATURE:
<223> OTHER INFORMATION: hIL12AB_011
<220> FEATURE:
<221> NAME/KEY: misc_feature
<222> LOCATION: (1)..(1)
<223> OTHER INFORMATION: 5' terminal guanosine cap

<400> SEQUENCE: 105

```
ggggaaataa gagagaaaag aagagtaaga agaaatataa gagccaccat gtgccaccag     60
cagctggtga tcagctggtt cagcctggtg ttcctggcca gccccctggt ggccatctgg    120
gagctgaaga aggacgtgta cgtggtggag ttggattggt acccggacgc gccggggag    180 atggtggtgc tgacgtgcga cacgccggag gaggacggga tcacgtggac gctgaccag    240 agcagcgagg tgctggggag cgggaagacg ctgacgatcc aggtgaagga gttcggggac    300
gcggggcagt acacgtgcca caagggggg gaggtgctga gccacagcct gctgctgctg    360
cacaagaagg aggacgggat ctggagcaca gatatcctga aggaccagaa ggagccgaag    420
aacaagacgt tcctgaggtg cgaggcgaag aactacagcg gaggttcac gtgctggtgg    480 ctgacgacga tcagcacgga cctgacgttc agcgtgaaga gcagcagggg gagcagcgac    540
ccgcaggggg tgacgtgcgg ggcggcgacg ctgagcgcgg agagggtgag gggtgacaac    600
aaggagtacg agtacagcgt ggagtgccag gaagatagcg cgtgcccggc ggcggaggag    660
agcctgccga tcgaggtgat ggtggacgcg gtgcacaagc tgaagtacga gaactacacg    720
agcagcttct tcatcagaga tatcatcaag ccgaccccgc cgaagaacct gcagctgaag    780
ccgctgaaga acagcaggca ggtggaggtg agctgggagt acccagatac gtggagcacg    840
ccgcacagct acttcagcct gacgttctgc gtgcaggtgc aggggaagag caagaggagg    900
```

```
aagaaagata gggtgttcac agataagacg agcgcgacgg tgatctgcag gaagaacgcg      960
agcatcagcg tgagggcgca agataggtac tacagcagca gctggagcga gtgggcgagc     1020
gtgccgtgca gcggggggg gggggggggg agcaggaacc tgccggtggc gacgccggac      1080
ccggggatgt tcccgtgcct gcaccacagc cagaacctgc tgagggcggt gagcaacatg     1140
ctgcagaagg cgaggcagac gctggagttc tacccgtgca cgagcgagga gatcgaccac     1200
gaagatatca cgaaagataa gacgagcacg gtggaggcgt gcctgccgct ggagctgacg     1260
aagaacgaga gctgcctgaa cagcagggag acgagcttca tcacgaacgg gagctgcctg     1320
gcgagcagga agacgagctt catgatggcg ctgtgcctga gcagcatcta cgaggacctg     1380
aagatgtacc aggtggagtt caagacgatg aacgcgaagc tgctgatgga cccgaagagg     1440
cagatcttcc tggaccagaa catgctggcg gtgatcgacg agctgatgca ggcgctgaac     1500
ttcaacagcg agacggtgcc gcagaagagc agcctggagg agccagattt ctacaagacg     1560
aagatcaagc tgtgcatcct gctgcacgcg ttcaggatca gggcggtgac gatcgacagg     1620
gtgatgagct acctgaacgc gagctgataa taggctggag cctcggtggc catgcttctt     1680
gccccttggg cctcccccca gcccctcctc cccttcctgc acccgtaccc cccaaacacc     1740
attgtcacac tccagtggtc tttgaataaa gtctgagtgg cggcaaaaa aaaaaaaaaa     1800
aaaaaaaaaa aaaaaaaaaa aaaaaaaaaa aaaaaaaaaa aaaaaaaaaa aaaaaaaaaa     1860
aaaaaaaaaa aaaaaaaaaa aaaaatctag                                     1890

<210> SEQ ID NO 106
<211> LENGTH: 1890
<212> TYPE: DNA
<213> ORGANISM: Artificial Sequence
<220> FEATURE:
<223> OTHER INFORMATION: hIL12AB_012
<220> FEATURE:
<221> NAME/KEY: misc_feature
<222> LOCATION: (1)..(1)
<223> OTHER INFORMATION: 5' terminal guanosine cap

<400> SEQUENCE: 106
ggggaaataa gagagaaaag aagagtaaga agaaatataa gagccaccat gtgccatcag       60
cagctggtga tcagctggtt cagcctcgtg tttctggcca gccccctggt ggccatttgg      120
gaactcaaga aggacgtgta cgttgtggaa ctcgactggt accctgacgc cccaggcgaa      180
atggtggtct aacctgcga caccctgag gaggacggaa tcacctggac cttggaccag       240
agctccgagg tcctcggcag tggcaagacc ctgaccatac aggtgaaaga atttggagac      300
gcagggcaat acacatgtca aagggcggg gaggttcttt ctcactccct tctgcttcta      360
cataaaaagg aagacggaat ttggtctacc gacatcctca aggaccaaaa ggagcctaag      420
aataaaacct tcttacgctg tgaagctaaa aactacagcg gcagattcac ttgctggtgg      480
ctcaccacca tttctaccga cctgaccttc tcggtgaagt cttcaagggg ctctagtgat      540
ccacagggag tgacatgcgg ggccgccaca ctgagcgctg aacgggtgag gggcgataac      600
aaggagtatg aatactctgt cgagtgtcag gaggattcag cttgtcccgc agctgaagag      660
tcactcccca tagaggttat ggtcgatgct gtgcataaac tgaagtacga aaactacacc      720
agcagcttct tcattagaga tattataaaa cctgaccccc ccaagaacct gcaacttaaa      780
cccctgaaaa actctcggca ggtcgaagtt agctgggagt accctgatac ttggtccacc      840
ccccactcgt acttctcact gactttctgt gtgcaggtgc agggcaagag caagagagag      900
```

```
aaaaaagatc gtgtattcac agataagacc tctgccaccg tgatctgcag aaaaaacgct      960
tccatcagtg tcagagccca agaccggtac tatagtagta gctggagcga gtgggcaagt     1020
gtcccctgct ctggcggcgg agggggcggc tctcgaaacc tccccgtcgc taccoctgat     1080 ccaggaatgt tcccttgcct gcatcactca cagaatctgc tgagagcggt cagcaacatg     1140
ctgcagaaag ctaggcaaac actggagttt tatccttgta cctcagagga gatcgaccac     1200
gaggatatta ccaaagataa gaccagcacg gtggaggcct gcttgccoct ggaactgaca     1260 aagaatgaat cctgccttaa tagccgtgag acctctttta taacaaacgg atcctgcctg     1320
gccagcagga agacctccett catgatggcc ctctgcctgt cctcaatcta cgaagacctg     1380
aagatgtacc aggtggaatt taaaactatg aacgccaagc tgttgatgga ccccaagcgg     1440
cagatctttc tggatcaaaa tatgctggct gtgatcgacg aactgatgca ggccctcaac     1500
tttaacagcg agaccgtgcc acaaaagagc agtcttgagg agcccgactt ctacaagacc     1560
aagatcaagc tgtgcatcct ccttcatgcc ttcaggataa gagctgtcac catcgacaga     1620
gtcatgagtt acctgaatgc atcctgataa taggctggag cctcggtggc catgcttctt     1680
gccccttggg cctcccccca gccctcctc cccttcctgc accgtaccc cccaaacacc       1740 attgtcacac tccagtggtc tttgaataaa gtctgagtgg gcggcaaaaa aaaaaaaaa      1800 aaaaaaaaaa aaaaaaaaaa aaaaaaaaaa aaaaaaaaa aaaaaaaaaa aaaaaaaaaa      1860
aaaaaaaaaa aaaaaaaaaa aaaaatctag                                     1890

<210> SEQ ID NO 107
<211> LENGTH: 1890
<212> TYPE: DNA
<213> ORGANISM: Artificial Sequence
<220> FEATURE:
<223> OTHER INFORMATION: hIL12AB_013
<220> FEATURE:
<221> NAME/KEY: misc_feature
<222> LOCATION: (1)..(1)
<223> OTHER INFORMATION: 5' terminal guanosine cap

<400> SEQUENCE: 107
ggggaaataa gagagaaaag aagagtaaga agaaatataa gagccaccat gtgccaccag       60
cagctggtca tctcctggtt cagtcttgtc ttcctggcct cgccgctggt ggccatctgg      120
gagctgaaga aagacgttta cgtagtagag ttggattggt acccagacgc acctggagaa      180
atggtggtcc tcacctgtga cacgccagaa gaagacggta tcacctggac gctggaccag      240
agcagtgaag ttcttggaag tggaaaaacg ctgaccatac aagtaaaaga atttggagat      300
gctggccagt acacctgcca caaggagga gaagttctca gccacagttt attattactt       360
cacaagaaag aagatggcat ctggtccaca gatattttaa agaccagaa ggagcccaaa       420 aataaaacat tcttcgatg tgaggccaag aactacagtg tcgtttcac ctgctggtgg        480 ctgaccacca tctccacaga cctcaccttc agtgtaaaaa gcagccgtgg ttcttctgac      540
ccccaaggag tcacctgtgg ggctgccacg ctctctgcag aaagagttcg aggtgacaac      600
aaagaatatg agtactcggt ggaatgtcaa gaagattcgg cctgcccagc tgctgaggag      660
agtcttccca tagaagtcat ggtggatgct gttcacaaat taaatatga aaactacacc       720 agcagcttct tcatcagaga tatcatcaaa cctgacccgc caagaactt acagctgaag       780 ccgctgaaaa acagccggca ggtagaagtt tcctgggagt acccagatac ctggtccacg     840
ccgcactcct acttctccct caccttctgt gtacaagtac aaggcaagag caagagagag     900
aagaaagatc gtgtcttcac agataaaaca tcagccacgg tcatctgcag gaaaaatgcc     960
```

```
agcatctcgg tgcgggccca ggaccgctac tacagcagca gctggagtga gtgggcatct    1020
gtgccctgca gtggtggtgg gggtggtggc agcagaaacc ttcctgtggc cactccagac    1080
cctggcatgt tcccgtgcct tcaccactcc caaaatttac ttcgagctgt ttctaacatg    1140
ctgcagaaag cacggcaaac tttagaattc tacccgtgca cttctgaaga aattgaccat    1200
gaagatatca caaagataa aaccagcaca gtggaggcct gtcttccttt agagctgacc    1260
aaaaatgaat cctgcctcaa cagcagagag accagcttca tcaccaatgg cagctgcctg    1320
gcctccagga aaccagcctt catgatggcg ctctgcctca gctccatcta tgaagatttg    1380
aagatgtacc aagtagaatt taaaaccatg aatgccaaat tattaatgga ccccaagagg    1440
cagatatttt tagatcaaaa catgctggca gttattgatg agctcatgca agcattaaac    1500
ttcaacagtg agacggtacc tcaaaaaagc agccttgaag agccagattt ctacaaaacc    1560
aagatcaaac tctgcatttt acttcatgcc ttccgcatcc gggcggtcac cattgaccgt    1620
gtcatgtcct acttaaatgc ctcgtgataa taggctggag cctcggtggc catgcttctt    1680
gccccttggg cctcccccca gcccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890

<210> SEQ ID NO 108
<211> LENGTH: 1890
<212> TYPE: DNA
<213> ORGANISM: Artificial Sequence
<220> FEATURE:
<223> OTHER INFORMATION: hIL12AB_014
<220> FEATURE:
<221> NAME/KEY: misc_feature
<222> LOCATION: (1)..(1)
<223> OTHER INFORMATION: 5' terminal guanosine cap

<400> SEQUENCE: 108
ggggaaataa gagagaaaag aagagtaaga agaaatataa gagccaccat gtgccaccag      60
cagcttgtga tttcttggtt ctctcttgtg ttccttgctt ctcctcttgt ggctatttgg     120
gagttaaaaa aggacgtgta cgtggtggag cttgactggt accctgacgc acctggcgag     180
atggtggtgc ttacttgtga cactcctgag gaggacggca ttacttggac gcttgaccag     240
tcttctgagg tgcttggctc tggcaaaaca cttactattc aggtgaagga gttcggggat     300
gctggccagt acacttgcca caagggcggc gaggtgcttt ctcactctct tcttcttctt     360
cacaagaagg aggacggcat ttggtctact gacattttaa aagaccagaa ggagcccaag     420
aacaaaacat tccttcgttg cgaggccaag aactactctg ccgtttcac ttgctggtgg     480 cttactacta tttctactga ccttactttc tctgtgaagt cttctcgtgg ctcttctgac     540
cctcagggcg tgacttgtgg ggctgctact cttctctgctg agcgtgtgcg tggtgacaac     600
aaggagtacg agtactctgt ggagtgccag gaagattctg cttgccctgc tgctgaggag     660
tctcttccta ttgaggtgat ggtggatgct gtgcacaagt aaaatacga gaactacact     720 tcttctttct tcattcgtga cattattaag cctgaccctc ccaagaacct tcagttaaaa     780
cctttaaaaa actctcgtca ggtggaggtg tcttgggagt accctgacac ttggtctact     840
cctcactctt acttctctct tactttctgc gtgcaggtgc agggcaagtc taagcgtgag     900
aagaaggacc gtgtgttcac tgacaaaaca tctgctactg tgatttgcag gaagaatgca     960
```

```
tctatttctg tgcgtgctca ggaccgttac tactcttctt cttggtctga gtgggcttct    1020
gtgccttgct ctggcggcgg cggcggcggc tccagaaatc ttcctgtggc tactcctgac    1080
cctggcatgt tcccttgcct tcaccactct cagaaccttc ttcgtgctgt gagcaacatg    1140
cttcagaagg ctcgtcaaac tcttgagttc taccccttgca cttctgagga gattgaccac    1200
gaagatatca ccaaagataa acatctact gtggaggctt gccttcctct tgagcttacc    1260
aagaatgaat cttgcttaaa ttctcgtgag acgtctttca tcaccaacgg ctcttgcctt    1320
gcctcgcgca aaacatcttt catgatggct ctttgccttt cttctattta cgaagattta    1380
aaaatgtacc aggtggagtt caaaacaatg aatgcaaagc ttcttatgga ccccaagcgt    1440
cagattttcc ttgaccagaa catgcttgct gtgattgacg agcttatgca ggctttaaat    1500
ttcaactctg agacggtgcc tcagaagtct tctcttgagg agcctgactt ctacaagacc    1560
aagattaagc tttgcattct tcttcatgct ttccgtattc gtgctgtgac tattgaccgt    1620
gtgatgtctt acttaaatgc ttcttgataa taggctggag cctcggtggc catgcttctt    1680 gcccccttggg cctcccccca gcccctcctc cccttcctgc acccgtaccc cccaaacacc    1740
attgtcacac tccagtggtc tttgaataaa gtctgagtgg gcggcaaaaa aaaaaaaaa    1800 aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890
```

<210> SEQ ID NO 109
<211> LENGTH: 1890
<212> TYPE: DNA
<213> ORGANISM: Artificial Sequence
<220> FEATURE:
<223> OTHER INFORMATION: hIL12AB_015
<220> FEATURE:
<221> NAME/KEY: misc_feature
<222> LOCATION: (1)..(1)
<223> OTHER INFORMATION: 5' terminal guanosine cap

<400> SEQUENCE: 109

```
ggggaaataa gagagaaaag aagagtaaga agaaatataa gagccaccat gtgtcaccag      60
cagctggtga tcagctggtt tagcctggtg tttctggcca gccccctggt ggccatctgg     120
gaactgaaga aagacgtgta cgtggtagaa ctggattggt atccggacgc tcccggcgaa     180
atggtggtgc tgacctgtga caccccgaa gaagacggaa tcacctggac cctggaccag     240
agcagcgagg tgctgggcag cggcaaaacc ctgaccatcc aagtgaaaga gtttggcgat     300
gccggccagt acacctgtca caaggcggc gaggtgctaa gccattcgct gctgctgctg     360
cacaaaaagg aagatggcat ctggagcacc gatatcctga aggaccagaa agaacccaaa     420
aataagacct ttctaagatg cgaggccaag aattatagcg gccgtttcac ctgctggtgg     480
ctgacgacca tcagcaccga tctgaccttc agcgtgaaaa gcagcagagg cagcagcgac     540
ccccaaggcg tgacgtgcgg cgccgccacc ctgagcgccg agagtgag aggcgacaac     600 aaggagtatg agtacagcgt ggagtgccag gaagatagcc cctgccccgc cgccgaggag     660
agcctgccca tcgaggtgat ggtggatgcc gtgcacaagc tgaagtatga aaactacacc     720
agcagcttct tcatcagaga tatcatcaaa cccgaccccc ccaagaacct gcagctgaag     780 ccccctgaaga atagccggca ggtggaggtg agctgggagt accccgacac ctggagcacc     840
ccccatagct acttcagcct gaccttctgc gtgcaggtgc agggcaagag caagagagaa     900
aagaaagata gagtgttcac agataagacc agcgccacgg tgatctgcag aaaaaatgcc     960
agcatcagcg tgagagccca agatagatac tatagcagca gctggagcga atgggccagc    1020
```

```
gtgccctgca gcggcggcgg cggcggcggc agcagaaacc tgcccgtggc cacccccgac    1080
cccggcatgt tcccctgcct gcaccacagc caaaacctgc tgagagccgt gagcaacatg    1140
ctgcagaagg cccggcagac cctggaattt taccccctgca ccagcgaaga gatcgatcat    1200
```
```
ctgcagaagg cccggcagac cctggaattt taccccctgca ccagcgaaga gatcgatcat    1200
gaagatatca ccaaagataa aaccagcacc gtggaggcct gtctgcccct ggaactgacc    1260
aagaatgaga gctgcctaaa tagcagagag accagcttca taccaatgg cagctgcctg     1320 gccagcagaa agaccagctt tatgatggcc ctgtgcctga gcagcatcta tgaagacctg    1380
aagatgtacc aggtggagtt caagaccatg aatgccaagc tgctgatgga tcccaagcgg    1440
cagatctttc tggatcaaaa catgctggcc gtgatcgatg agctgatgca ggccctgaat    1500
ttcaacagcg agaccgtgcc ccaaaaaagc agcctggaag aaccggattt ttataaaacc    1560
aaaatcaagc tgtgcatact gctgcatgcc ttcagaatca gagccgtgac catcgataga    1620
gtgatgagct atctgaatgc cagctgataa taggctggag cctcggtggc catgcttctt    1680
gccccttggg cctcccccca gcccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890
```

<210> SEQ ID NO 110
<211> LENGTH: 1890
<212> TYPE: DNA
<213> ORGANISM: Artificial Sequence
<220> FEATURE:
<223> OTHER INFORMATION: hIL12AB_016
<220> FEATURE:
<221> NAME/KEY: misc_feature
<222> LOCATION: (1)..(1)
<223> OTHER INFORMATION: 5' terminal guanosine cap

<400> SEQUENCE: 110

```
ggggaaataa gagagaaaag aagagtaaga agaaatataa gagccaccat gtgccaccag     60
cagctggtca tcagctggtt cagcctggtc ttcctggcca gccccctggt ggccatctgg    120
gagctgaaga aggacgtata cgtagtgga gttggattgg tacccagacgc tcctggggag    180 atggtggtgc tgacctgtga caccccagaa gaggacggta tcacctggac cctggaccag    240
agctcagaag tgctgggcag tggaaaaacc ctgaccatcc aggtgaagga gtttggagat    300
gctggccagt acacctgcca caagggtggt gaagtgctga gccacagcct gctgctgctg    360
cacaagaagg aggatggcat ctggagcaca gatatcctga aggaccagaa ggagcccaag    420
aacaagacct tccttcgctg tgaagccaag aactacagtg ccgcttcac ctgctggtgg    480 ctgaccacca tcagcacaga cctcaccttc tcggtgaaga gcagcagagg cagctcagac    540
ccccagggtg tcacctgtgg ggcggccacg ctgtcggcgg agagagttcg aggtgacaac    600
aaggagtatg aatactcggt ggagtgccag gaagattcgg cgtgccccgc ggcagaagag    660
agcctgccca tagaagtgat ggtggatgct gtgcacaagc tgaagtatga aaactacacc    720
agcagcttct tcatcagaga tatcatcaag ccagaccgc ccaagaacct gcagctgaag    780 ccctgaaga acagccggca ggtggaggtt cctgggagt acccagatac gtggagcacc    840
ccccacagct acttcagcct gaccttctgt gtccaggtgc agggcaagag caagagagag    900
aagaaagata gagtcttcac agataagacc tcggccacgg tcatctgcag aaagaatgcc    960
tccatctcgg ttcgagccca agatagatac tacagcagca gctggtcaga atgggcctcg    1020
```

-continued

| | |
|---|---|
| gtgccctgca gtggtggcgg cggcggcggc agcagaaacc tgcctgttgc caccccagac | 1080 |
| cctgggatgt tccctgcct gcaccacagc cagaacttat tacgagctgt ttctaacatg | 1140 |
| ctgcagaagg cccggcagac cctggagttc taccctgca cctcagaaga gattgaccat | 1200 |
| gaagatatca ccaaagataa gaccagcact gtagaggcct gcctgcccct ggagctgacc | 1260 |
| aagaatgaaa gctgcctgaa cagcagagag accagcttca tcaccaatgg aagctgcctg | 1320 |
| gccagcagaa agaccagctt catgatggcc ctgtgcctga gcagcatcta tgaagacctg | 1380 |
| aagatgtacc aggtggagtt caagaccatg aatgcaaagc tgctgatgga ccccaagcgg | 1440 |
| cagatatttt tggaccagaa catgctggct gtcattgatg agctgatgca ggccctgaac | 1500 |
| ttcaactcag aaactgtacc ccagaagagc agcctggagg agccagattt ctacaagacc | 1560 |
| aagatcaagc tgtgcatcct gcttcatgct ttcagaatca gagctgtcac cattgaccgc | 1620 |
| gtgatgagct acttaaatgc ctcgtgataa taggctggag cctcggtggc catgcttctt | 1680 |
| gcccctggg cctccccca gccctcctc cccttcctgc accgtaccc cccaaacacc | 1740 |
| attgtcacac tccagtggtc tttgaataaa gtctgagtgg gcggcaaaaa aaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 111
<211> LENGTH: 1890
<212> TYPE: DNA
<213> ORGANISM: Artificial Sequence
<220> FEATURE:
<223> OTHER INFORMATION: hIL12AB_017
<220> FEATURE:
<221> NAME/KEY: misc_feature
<222> LOCATION: (1)..(1)
<223> OTHER INFORMATION: 5' terminal guanosine cap

<400> SEQUENCE: 111

| | |
|---|---|
| ggggaaataa gagagaaaag aagagtaaga agaaatataa gagccaccat gtgccaccag | 60 |
| cagctggtaa tcagctggtt ttccctcgtc tttctggcat caccctggt ggctatctgg | 120 |
| gagctgaaga aggacgtgta cgtggtggag ctggattggt accctgacgc cccgggggaa | 180 |
| atggtggtgt taacctgcga cacgcctgag gaggacggca tcacctggac gctggaccag | 240 |
| agcagcgagt gcttgggtc tggtaaaact ctgactattc aggtgaaaga gttcggggat | 300 |
| gccggccaat atacttgcca caagggtggc gaggtgcttt ctcattctct gctcctgctg | 360 |
| cacaagaaag aagatggcat ttggtctact gatattctga agaccagaa ggagcccaag | 420 |
| aacaagacct ttctgagatg cgaggctaaa aactacagcg gaagatttac ctgctggtgg | 480 |
| ctgaccacaa tctcaaccga cctgacattt tcagtgaagt ccagcagagg gagctccgac | 540 |
| cctcagggcg tgacctgcgg agccgccact ctgtccgcag aaagagtgag aggtgataat | 600 |
| aaggagtacg agtattcagt cgagtgccaa gaagattctg cctgcccagc cgccgaggag | 660 |
| agcctgccaa tcgaggtgat ggtagatgcg gtacacaagc tgaagtatga aactacaca | 720 |
| tcctccttct tcataagaga tattatcaag cctgacccac ctaaaaatct gcaactcaag | 780 |
| cctttgaaaa attcacggca ggtggaggtg agctgggagt accctgatac ttggagcacc | 840 |
| ccccatagct actttccgct gacattctgc gtccaggtgc agggcaagtc aaagagagag | 900 |
| aagaaggatc gcgtgttcac tgataaaaca agcgccacag tgatctgcag aaaaaacgct | 960 |
| agcattagcg tcagagcaca ggaccggtat tactccagct cctggagcga atgggcatct | 1020 |
| gtgccctgca gcggtggggg cggaggcgga tccagaaacc tccccgttgc cacacctgat | 1080 |

```
cctggaatgt tcccctgtct gcaccacagc cagaacctgc tgagagcagt gtctaacatg    1140
ctccagaagg ccaggcagac cctggagttt taccccctgca ccagcgagga aatcgatcac    1200
gaagatatca ccaaagataa aacctccacc gtggaggcct gcctgcccct ggaactgacc    1260
aaaaacgaga gctgcctgaa tagcagggag acctccttca tcaccaacgg ctcatgcctt    1320
gccagccgga aaactagctt catgatggcc ctgtgcctgt cttcgatcta tgaggacctg    1380
aaaatgtacc aggtcgaatt taagacgatg aacgcaaagc tgctgatgga ccccaagcgg    1440
cagatctttc tggaccagaa catgctggca gtcatagatg agttgatgca ggcattaaac    1500
ttcaacagcg agaccgtgcc tcagaagtcc agcctcgagg agccagattt ttataagacc    1560
aagatcaaac tatgcatcct gctgcatgct ttcaggatta gagccgtcac catcgatcga    1620
gtcatgtctt acctgaatgc tagctgataa taggctggag cctcggtggc catgcttctt    1680
gccccttggg cctcccccca gcccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890

<210> SEQ ID NO 112
<211> LENGTH: 1890
<212> TYPE: DNA
<213> ORGANISM: Artificial Sequence
<220> FEATURE:
<223> OTHER INFORMATION: hIL12AB_018
<220> FEATURE:
<221> NAME/KEY: misc_feature
<222> LOCATION: (1)..(1)
<223> OTHER INFORMATION: 5' terminal guanosine cap

<400> SEQUENCE: 112
ggggaaataa gagagaaaag aagagtaaga agaaatataa gagccaccat gtgtcaccaa    60
cagttagtaa tctcctggtt ttctctggtg tttctggcca gccccctcgt ggccatctgg    120
gagcttaaaa aggacgttta cgtggtggag ttggattggt atcccgacgc tccaggcgaa    180
atggtcgtgc tgacctgcga taccccctgaa gaagacggta tcacctggac gctggaccag    240
tcttccgagg tgcttggatc tggcaaaaca ctgacaatac aagttaagga gttcggggac    300
gcagggcagt acacctgcca caaggcggc gaggtcctga gtcactccct gttactgctc    360
cacaagaaag aggacggcat ttggtccacc gacattctga aggaccagaa ggagcctaag    420
aataaaactt tcctgagatg cgaggcaaaa aactatagcg gccgctttac ttgctggtgg    480
cttacaacaa tctctaccga tttaactttc tccgtgaagt ctagcagagg atcctctgac    540
ccgcaaggag tgacttgcgg agccgccacc ttgagcgccg aaaagagtcc tggcgataac    600
aaagaatacg agtactccgt ggagtgccag gaagattccg cctgcccagc tgccgaggag    660
tccctgccca ttgaagtgat ggtggatgcc gtccacaagc tgaagtacga aaactatacc    720
agcagcttct tcatccggga tatcattaag cccgaccctc ctaaaaacct gcaacttaag    780
cccctaaaga atagtcggca ggttgaggtc agctgggaat atcctgacac atggagcacc    840
ccccactctt atttctccct gaccttctgc gtgcaggtgc agggcaagag taaacgggag    900
aaaaaagata gggtctttac cgataaaacc agcgctacgg ttatctgtcg gaagaacgct    960
tccatctccg tccgcgctca ggatcgttac tactcgtcct catggagcga gtgggccagc    1020
gtgccctgca gcggcggcgg tggaggcgga tccagaaatc tgcctgttgc cacaccagac    1080
```

| | |
|---|---|
| cctggcatgt tcccctgtct gcatcatagc cagaacctgc tcagagccgt gagcaacatg | 1140 |
| ctccagaagg ccaggcaaac tttggagttc tacccgtgta catctgagga aatcgatcac | 1200 |
| gaagatataa ccaaagataa aacctctaca gtagaggctt gtttgcccct ggagttgacc | 1260 |
| aaaaacgaga gttgcctgaa cagtcgcgag acgagcttca ttactaacgg cagctgtctc | 1320 |
| gcctccagaa aaacatcctt catgatggcc ctgtgtcttt ccagcatata cgaagacctg | 1380 |
| aaaatgtacc aggtcgagtt caaaacaatg aacgccaagc tgcttatgga ccccaagcgg | 1440 |
| cagatcttcc tcgaccaaaa catgctcgct gtgatcgatg agctgatgca ggctctcaac | 1500 |
| ttcaattccg aaacagtgcc acagaagtcc agtctggaag aacccgactt ctacaagacc | 1560 |
| aagattaagc tgtgtatttt gctgcatgcg tttagaatca gagccgtgac cattgatcgg | 1620 |
| gtgatgagct acctgaacgc ctcgtgataa taggctggag cctcggtggc catgcttctt | 1680 |
| gccccttggg cctcccccca gcccctcctc cccttcctgc acccgtaccc cccaaacacc | 1740 |
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 113
<211> LENGTH: 1890
<212> TYPE: DNA
<213> ORGANISM: Artificial Sequence
<220> FEATURE:
<223> OTHER INFORMATION: hIL12AB_019
<220> FEATURE:
<221> NAME/KEY: misc_feature
<222> LOCATION: (1)..(1)
<223> OTHER INFORMATION: 5' terminal guanosine cap

<400> SEQUENCE: 113

| | |
|---|---|
| ggggaaataa gagagaaaag aagagtaaga agaaatataa gagccaccat gtgccaccag | 60 |
| cagcttgtca tctcctggtt ttctcttgtc ttcctggcct cgccgctggt ggccatctgg | 120 |
| gagctgaaga agacgtttta cgtagtagag ttggattggt acccagacgc acctggagaa | 180 |
| atggtggttc tcacctgtga cactcctgaa gaagacggta tcacctggac gctggaccaa | 240 |
| agctcagaag ttcttggcag tggaaaaacg ctgaccatac aagtaaaaga atttggggat | 300 |
| gctggccagt acacgtgcca caaggaggag aagttctcag ccacagtttt acttcttctt | 360 |
| cacaagaaag aagatggcat ctggtccaca gatattttaa agaccagaag ggagcccaag | 420 |
| aacaaaacct tctccgctg tgaggccaag aactacagtg tcgtttcac ctgctggtgg | 480 |
| ctcaccacca tctccactga cctcaccttc tctgtaaaaa gcagccgtgg ttcttctgac | 540 |
| ccccaaggag tcacctgtgg ggctgccacg ctctcggcag aaagagttcg aggtgacaac | 600 |
| aaggaatatg aatattctgt ggaatgtcaa gaagattctg cctgcccggc ggcagaagaa | 660 |
| agtcttccca tagaagtcat ggtggatgct gttcacaaat taaatatga aaactacacc | 720 |
| agcagcttct tcattcgtga catcatcaaa ccagaccccgc ccaagaacct tcagttaaaa | 780 |
| cctttaaaaa acagccggca ggtagaagtt tcctgggagt acccagatac gtggtccacg | 840 |
| ccgcactcct acttcagttt aaccttctgt gtacaagtac aaggaaaatc aaaagagag | 900 |
| aagaaagatc gtgtcttcac tgacaaaaca tctgccacgg tcatctgcag gaagaatgcc | 960 |
| tccatctcgg ttcagcccca ggaccgctac tacagcagca gctggagtga gtgggcatct | 1020 |
| gttccctgca gtggtggcgg cggcggcggc agccgcaacc ttcctgtggc cacgccggac | 1080 |
| cctggcatgt tcccgtgcct tcaccactcc caaaatcttc ttcgtgctgt ttctaacatg | 1140 |

-continued

```
ctgcagaagg cgcgccaaac tttagaattc tacccgtgca cttctgaaga aatagaccat    1200
gaagatatca ccaaagataa aaccagcacg gtggaggcct gccttccttt agagctgacc    1260
aagaatgaat cctgcctcaa cagcagagag accagcttca tcaccaatgg cagctgcctg    1320
gcctcgcgca agaccagctt catgatgcg ctgtgccttt cttccatcta tgaagattta    1380
aagatgtacc aagtagaatt taaaaccatg aatgccaaat tattaatgga ccccaaacgg    1440
cagatatttt tggatcaaaa catgctggct gtcattgatg agctcatgca agcattaaac    1500
ttcaactcag aaactgttcc ccagaagtca tctttagaag accagattt ctacaaaaca    1560 aaaataaaac tctgcattct tcttcatgcc ttccgcatcc gtgctgtcac cattgaccgt    1620
gtcatgtcct acttaaatgc ttcttgataa taggctggag cctcggtggc catgcttctt    1680
gccccttggg cctccccca gccctcctc ccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaatctag                                      1890
```

```
<210> SEQ ID NO 114
<211> LENGTH: 1890
<212> TYPE: DNA
<213> ORGANISM: Artificial Sequence
<220> FEATURE:
<223> OTHER INFORMATION: hIL12AB_020
<220> FEATURE:
<221> NAME/KEY: misc_feature
<222> LOCATION: (1)..(1)
<223> OTHER INFORMATION: 5' terminal guanosine cap

<400> SEQUENCE: 114
```

```
ggggaaataa gagagaaaag aagagtaaga agaaatataa gagccaccat gtgccaccag      60
cagctggtga tcagctggtt cagcctggtt ttcctggcta gccctctggt ggccatctgg     120
gagctgaaga aggacgtgta cgtggtggag ttggattggt accccgacgc tcccggcgag     180
atggtggtgc tgacctgcga caccccccgag gaggacggga tcacctggac cctggatcag     240
tcaagcgagg tgctgggaag cggcaagacc ctgaccatcc aggtgaagga gttcggcgac     300
gccggccaat acacttgcca caagggaggc gaggtgctgt cccactccct cctgctgctg     360
cacaaaaagg aagacggcat ctggagcacc gacatcctga agaccagaa ggagcctaag     420 aacaaaacat tcctcagatg cgaggccaag aattactccg ggagattcac ctgttggtgg     480
ctgaccacca tcagcacaga cctgaccttc agcgtgaaga gcagcagagg cagcagcgac     540
ccccagggcg tgacctgtgg cgccgccacc ctgagcgccg aaagagtgcg cggcgacaac     600
aaggagtacg agtactccgt ggaatgccag gaagatagcg cctgccccgc cgccgaggag     660
agcctgccca tcgaggtgat ggtggacgcc gtccacaagc tgaagtacga aactacacc     720 tctagcttct tcatcagaga tatcatcaag cccgatcccc caagaacct gcagctgaaa     780 cccctgaaga acagccggca ggtggaggtg agctgggagt atcccgacac ctggtccacc     840
ccccacagct atttagcct gaccttctgc gtgcaagtgc agggcaagag caagagagag     900
aagaaggacc gcgtgttcac cgacaaaacc agcgccaccg tgatctgcag aaagaacgcc     960
agcatcagcg tgagggccca ggatagata tacagttcca gctggagcga gtgggccagc    1020
gtgccctgca gcgcggcggc cggggaggc tcgagaaacc tgcccgtggc tacccccgat    1080
cccggaatgt tcccctgcct gcaccacagc cagaacctgc tgagggcggt gtccaacatg    1140
```

| | | | |
|---|---|---|---|
| cttcagaagg | cccggcagac | cctggagttc | taccc ctgta cctctgagga gatcgatcat | 1200 |
| gaagatatca | caaaagataa | aaccagcacc | gtggaggcct gcctgcccct ggagctgacc | 1260 |
| aagaacgaga | gctgcctgaa | ctcccgcgag | accagcttca tcacgaacgg cagctgcctg | 1320 |
| gccagcagga | agacctcctt | catgatggcc | ctgtgcctga gcagcatcta cgaggacctg | 1380 |
| aaaatgtacc | aggtggagtt | taagaccatg | aacgccaagc tgctgatgga ccccaagcgg | 1440 |
| caaatcttcc | tggaccagaa | catgctggca | gtgatcgacg agctcatgca ggccctgaac | 1500 |
| ttcaatagcg | agacggtccc | ccagaagagc | agcctggagg agcccgactt ttacaagacc | 1560 |
| aagatcaagc | tgtgcatcct | gctgcacgcc | tttagaatcc gtgccgtgac cattgacaga | 1620 |
| gtgatgagct | acctgaatgc | cagctgataa | taggctggag cctcggtggc catgcttctt | 1680 |
| gccccttggg | cctcccccca | gcccctcctc | ccttcctgc acccgtaccc cccaaacacc | 1740 |
| attgtcacac | tccagtggtc | tttgaataaa | gtctgagtgg gcggcaaaaa aaaaaaaaa | 1800 |
| aaaaaaaaaa | aaaaaaaaaa | aaaaaaaaaa | aaaaaaaaaa aaaaaaaaaa aaaaaaaaaa | 1860 |
| aaaaaaaaaa | aaaaaaaaaa | aaaatctag | | 1890 |

<210> SEQ ID NO 115
<211> LENGTH: 1890
<212> TYPE: DNA
<213> ORGANISM: Artificial Sequence
<220> FEATURE:
<223> OTHER INFORMATION: hIL12AB_021
<220> FEATURE:
<221> NAME/KEY: misc_feature
<222> LOCATION: (1)..(1)
<223> OTHER INFORMATION: 5' terminal guanosine cap

<400> SEQUENCE: 115

| | | | |
|---|---|---|---|
| ggggaaataa | gagagaaaag | aagagtaaga | agaaatataa gagccaccat gtgccaccag | 60 |
| cagctggtga | tcagctggtt | cagcctggtg | ttcctggcca gccctctggt tgccatctgg | 120 |
| gagctgaaga | aagacgtgta | cgtcgtggaa | ctggactggt atccggacgc cccgggcgag | 180 |
| atggtggtgc | tgacctgtga | caccccccgag | gaggacggca tcacctggac gctggaccaa | 240 |
| tcctccgagg | tgctgggaag | cggcaagacc | ctgaccatcc aggtgaagga attcggggac | 300 |
| gccgggcagt | acacctgcca | caaggggggc | gaagtgctgt cccactcgct gctgctcctg | 360 |
| cataagaagg | aggatggaat | ctggtccacc | gacatcctca agatcagaa ggagcccaag | 420 |
| aacaagacgt | tcctgcgctg | tgaagccaag | aattattcgg ggcgattcac gtgctggtgg | 480 |
| ctgacaacca | tcagcaccga | cctgacgttt | agcgtgaaga gcagcagggg gtccagcgac | 540 |
| ccccagggcg | tgacgtgcgg | cgccgccacc | ctctccgccg agagggtgcg ggggggacaat | 600 |
| aaggagtacg | agtacagcgt | ggaatgccag | gaggacagcg cctgccccgc cgcggaggaa | 660 |
| agcctcccga | tagaggtgat | ggtggacgcc | gtgcacaagc tcaagtatga gaattacacc | 720 |
| agcagctttt | tcatccggga | cattatcaag | cccgaccccc cgaagaacct ccagctgaag | 780 |
| cccctgaaga | acagccggca | ggtggaagtc | tcctgggagt atcccgacac ctggagcacc | 840 |
| ccgcacagct | acttctccct | gaccttctgt | gtgcaggtgc agggcaagtc caagagggaa | 900 |
| aagaaggaca | gggtttttca | cgacaagacc | agcgcgaccg tgatctgccg gaagaacgcc | 960 |
| agcataagcg | tccgcgccca | agataggtac | tacagcagct cctggagcga gtgggctagc | 1020 |
| gtgccctgca | gcggggggcgg | gggtggggc | tccaggaacc tgccagtggc gaccccgac | 1080 |
| cccggcatgt | tccctgcct | ccatcacagc | cagaacctgc tgagggccgt cagcaatatg | 1140 |
| ctgcagaagg | ccaggcagac | cctggaattc | taccccctgca cgtcggagga gatcgatcac | 1200 |

```
gaggatatca caaaagacaa gacttccacc gtggaggcct gcctgcccct ggagctcacc    1260
aagaatgagt cctgtctgaa ctcccgggaa accagcttca tcaccaacgg gtcctgcctg    1320
gccagcagga agaccagctt tatgatggcc ctgtgcctgt cgagcatcta cgaggacctg    1380
aagatgtacc aggtcgagtt caagacaatg aacgccaagc tgctgatgga ccccaagagg    1440
caaatcttcc tggaccagaa tatgcttgcc gtcatcgacg agctcatgca ggccctgaac    1500
ttcaactccg agaccgtgcc ccagaagagc agcctggagg agcccgactt ctacaagacc    1560
aagatcaagc tgtgcatcct gctgcacgcg ttcaggatcc gggcagtcac catcgaccgt    1620
gtgatgtcct acctgaacgc cagctgataa taggctggag cctcggtggc catgcttctt    1680
gccccttggg cctccccca gccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                    1890

<210> SEQ ID NO 116
<211> LENGTH: 1890
<212> TYPE: DNA
<213> ORGANISM: Artificial Sequence
<220> FEATURE:
<223> OTHER INFORMATION: hIL12AB_022
<220> FEATURE:
<221> NAME/KEY: misc_feature
<222> LOCATION: (1)..(1)
<223> OTHER INFORMATION: 5' terminal guanosine cap

<400> SEQUENCE: 116
ggggaaataa gagagaaaag aagagtaaga agaaatataa gagccaccat gtgccatcag      60
cagctggtga tcagctggtt cagcctggtg ttcctcgcct ctcccctggt ggccatctgg     120
gagctcaaaa aggacgtgta cgtggtggag ctcgactggt acccagacgc cccgggggag     180
atggtggtgc tgacctgcga caccccgaa gaagacggca tcacgtggac cctcgaccag     240
tccagcgagg tgctggggag cgggaagact ctgaccatcc aggtcaagga gttcggggac     300
gccgggcagt acacgtgcca aagggcggc gaagtcttaa gccacagcct gctcctgctg     360
cacaagaagg aggacgggat ctggtccaca gacatactga aggaccagaa ggagccgaag     420
aataaaacct ttctgaggtg cgaggccaag aactattccg gcaggttcac gtgctggtgg     480
cttacaacaa tcagcacaga cctgacgttc agcgtgaagt ccagccgcgg cagcagcgac     540 ccccagggg tgacctgcgg cgccgccacc ctgagcgccg agcgggtgcg cggggacaac     600
aaggagtacg agtactccgt ggagtgccag gaagacagcg cctgtccgcc gccgaagag     660 agcctgccta tcgaggtcat ggtagatgca gtgcataagc tgaagtacga gaactatacg     720
agcagctttt tcatacgcga catcatcaag cccgaccccc caagaacct gcagcttaag     780 cccctgaaga atagccggca ggtggaggtc tcctgggagt accccgacac ctggtcaacg     840
ccccacagct acttctccct gaccttttgt gtccaagtcc agggaaagag caagagggag     900
aagaaagatc gggtgttcac cgacaagacc tccgccacgg tgatctgcag gaagaacgcc     960
agcatctccg tgagggcgca agacaggtac tactccagca gctggtccga atgggccagc    1020 gtgcctgct ccggcggcgg gggcggcggc agccgaaacc tacccgtggc cacgccggat    1080 cccgcatgt ttcctgcct gcaccacagc cagaacctcc tgggcgct gtccaacatg    1140 ctgcagaagg ccaggcagac tctggagttc tacccctgca cgagcgagga gatcgatcac    1200
```

-continued

| | |
|---|---|
| gaggacatca ccaaggataa gaccagcact gtggaggcct gccttcccct ggagctgacc | 1260 |
| aagaacgaga gctgtctgaa ctccagggag acctcattca tcaccaacgg ctcctgcctg | 1320 |
| gccagcagga aaaccagctt catgatggcc ttgtgtctca gctccatcta cgaggacctg | 1380 |
| aagatgtatc aggtcgagtt caagacaatg aacgccaagc tgctgatgga ccccaaaagg | 1440 |
| cagatcttcc tggaccagaa catgctggcc gtcatcgacg agctgatgca ggccctgaac | 1500 |
| ttcaacagcg agacggtgcc ccagaaaagc tccctggagg agcccgactt ctacaagacc | 1560 |
| aagatcaagc tgtgcatcct gctgcacgcc ttcaggatca gggcagtgac catcgaccgg | 1620 |
| gtgatgtcat accttaacgc cagctgataa taggctggag cctcggtggc catgcttctt | 1680 |
| gccccttggg cctcccccca gcccctcctc cccttcctgc acccgtaccc cccaaacacc | 1740 |
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 117
<211> LENGTH: 1890
<212> TYPE: DNA
<213> ORGANISM: Artificial Sequence
<220> FEATURE:
<223> OTHER INFORMATION: hIL12AB_023
<220> FEATURE:
<221> NAME/KEY: misc_feature
<222> LOCATION: (1)..(1)
<223> OTHER INFORMATION: 5' terminal guanosine cap

<400> SEQUENCE: 117

| | |
|---|---|
| ggggaaataa gagagaaaag aagagtaaga agaaatataa gagccaccat gtgccatcag | 60 |
| cagctggtga tctcctggtt cagcctggtg tttctggcct cgcccctggt cgccatctgg | 120 |
| gagctgaaga agacgtgta cgtcgtcgaa ctggactggt accccgacgc ccccggggag | 180 |
| atggtggtgc tgacctgcga cacgccggag gaggacggca tcacctggac cctggatcaa | 240 |
| agcagcgagg tgctgggcag cggcaagacc ctgaccatcc aagtgaagga attcggcgat | 300 |
| gccggccagt acacctgtca aaagggggc gaggtgctca gccacagcct gctgctgctg | 360 |
| cacaagaagg aggatggcat ctggagcacc gatatcctga aggaccagaa agagcccaag | 420 |
| aacaagacgt tcctgaggtg cgaggccaag aactacagcg gtaggttcac gtgttggtgg | 480 |
| ctgaccacca tcagcaccga cctgacgttc agcgtgaaga gctccagggg cagctccgac | 540 |
| ccacaggggg tgacgtgcgg ggccgcaacc ctcagcgccg aaagggtgcg ggggacaac | 600 |
| aaggagtacg aatactccgt ggagtgccag gaagattcgg cctgccccgc cgcggaggag | 660 |
| agcctcccca tcgaggtaat ggtggacgcc gtgcataagc tgaagtacga gaactacacc | 720 |
| agctcgttct tcatccgaga catcatcaaa cccgacccgc ccaaaaatct gcagctcaag | 780 |
| cccctgaaga actccaggca ggtggaggtg agctgggagt accccgacac ctggtccacc | 840 |
| ccgcacagct acttctccct gacattctgc gtgcaggtgc agggcaagag caagcgggag | 900 |
| aagaaggaca gggtgttcac cgacaagacg agcgccaccg tgatctgccg aaagaacgcc | 960 |
| agcatctcgg tgcgcgccca ggataggtac tattccagct cctggagcga gtgggcctcg | 1020 |
| gtaccctgca gcggcggcgg gggcggcggc agtaggaatc tgcccgtggc taccccggac | 1080 |
| ccgggcatgt tccctgcct ccaccacagc cagaacctgc tgagggccgt gagcaacatg | 1140 |
| ctgcagaagg ccagacagac gctggagttc taccctgca cgagcgagga gatcgaccac | 1200 |
| gaggacatca ccaaggataa aacttccacc gtcgaggcct gcctgccctt ggagctgacc | 1260 |

```
aagaatgaat cctgtctgaa cagcagggag acctcgttta tcaccaatgg cagctgcctc      1320
gcctccagga agaccagctt catgatggcc ctctgtctga gctccatcta tgaggacctg      1380
aagatgtacc aggtggagtt caagaccatg aacgcgaagc tgctgatgga ccccaagagg      1440
cagatcttcc tggatcagaa tatgctggcg gtgatcgacg agctcatgca ggccctcaat      1500
ttcaatagcg agacagtgcc ccagaagtcc tccctggagg agcccgactt ctacaagacc      1560
aagatcaagc tgtgtatcct gctgcacgcc ttccggatcc gggccgtcac catcgaccgg      1620
gtcatgagct acctcaatgc cagctgataa taggctggag cctcggtggc catgcttctt      1680
gccccttggg cctcccccca gccctcctc cccttcctgc acccgtaccc cccaaacacc      1740
attgtcacac tccagtggtc tttgaataaa gtctgagtgg gcggcaaaaa aaaaaaaaaa      1800
aaaaaaaaaa aaaaaaaaaa aaaaaaaaaa aaaaaaaaaa aaaaaaaaaa aaaaaaaaaa      1860
aaaaaaaaaa aaaaaaaaaa aaaaatctag                                       1890
```

<210> SEQ ID NO 118
<211> LENGTH: 1890
<212> TYPE: DNA
<213> ORGANISM: Artificial Sequence
<220> FEATURE:
<223> OTHER INFORMATION: hIL12AB_024
<220> FEATURE:
<221> NAME/KEY: misc_feature
<222> LOCATION: (1)..(1)
<223> OTHER INFORMATION: 5' terminal guanosine cap

<400> SEQUENCE: 118

```
ggggaaataa gagagaaaag aagagtaaga agaaatataa gagccaccat gtgccaccag        60
cagctggtga tctcctggtt ctccctggtg ttcctggcct cgcccctggt ggccatctgg       120
gagctgaaga aggacgtgta cgtcgtggag ctcgactgga cccccgacgc ccctggcgag       180
atggtggtgc tgacctgcga caccccagag gaggatggca tcacctggac cctggatcag       240
tcctccgagg tgctgggctc cggcaagacg ctgaccatcc aagtgaagga gttcggtgac       300
gccggacagt atacctgcca taagggcggc gaggtcctgt cccacagcct cctcctcctg       360
cataagaagg aggacggcat ctggagcacc gacatcctga aggaccagaa ggagcccaag       420
aacaagacct ttctgaggtg cgaggccaag aactacagcg gccgattcac ctgctggtgg       480
ctcaccacca tatccaccga cctgactttc tccgtcaagt cctcccgggg gtccagcgac       540
ccccagggag tgacctgcgg cgccgccacc ctcagcgccg agcgggtgcg ggggacaac       600 aaggagtacg aatactccgt cgagtgccag gaggactccg cctgcccggc cgccgaggag       660
agcctgccca tcgaggtgat ggtcgacgcg gtgcacaagc tgaagtacga aactacacc       720 agcagtttct tcatcaggga tatcatcaag ccagatcccc gaagaatct gcaactgaag       780 ccgctgaaaa actcacgaca ggtggaggtg agctgggagt accccgacac gtggagcacc       840
ccacattcct acttcagcct gaccttctgc gtgcaggtcc agggcaagag caagcgggag       900
aagaaggaca gggtgttcac ggataagacc agtgccaccg tgatctgcag gaagaacgcc       960
tctattagcg tgagggccca ggatcggtat actcctcga gctggagcga atgggcctcc      1020
gtgccctgca gtggggggg tggaggcggg agcaggaacc tgcccgtagc aaccccgac       1080 cccgggatgt tccctgtct gcaccactcg cagaacctgc tgcgcgcggt gagcaacatg      1140
ctccaaaaag cccgtcagac cttagagttc taccccctgca ccagcgaaga aatcgaccac      1200
gaagacatca ccaaggacaa aaccagcacc gtggaggcgt gcctgccgct ggagctgacc      1260
```

| | |
|---|---|
| aagaacgaga gctgcctcaa ctccagggag accagcttta tcaccaacgg ctcgtgccta | 1320 |
| gccagccgga aaaccagctt catgatggcc ctgtgcctga gctccattta cgaggacctg | 1380 |
| aagatgtatc aggtggagtt caagaccatg aatgccaaac tcctgatgga ccccaagagg | 1440 |
| cagatcttcc tggaccagaa catgctcgcg gtgatcgatg agctgatgca ggccctgaac | 1500 |
| tttaatagcg agaccgtgcc ccagaaaagc agcctggagg agccggactt ctacaagacc | 1560 |
| aaaatcaagc tgtgcatcct gctccacgcc ttccgcatcc gggccgtgac catcgacagg | 1620 |
| gtgatgagct acctgaacgc cagctgataa taggctggag cctcggtggc catgcttctt | 1680 |
| gccccttggg cctcccccca gccctcctc cccttcctgc acccgtaccc cccaaacacc | 1740 |
| attgtcacac tccagtggtc tttgaataaa gtctgagtgg gcggcaaaaa aaaaaaaaa | 1800 |
| aaaaaaaaaa aaaaaaaaa aaaaaaaaa aaaaaaaaa aaaaaaaaa aaaaaaaaa | 1860 |
| aaaaaaaaaa aaaaaaaaa aaaatctag | 1890 |

<210> SEQ ID NO 119
<211> LENGTH: 1890
<212> TYPE: DNA
<213> ORGANISM: Artificial Sequence
<220> FEATURE:
<223> OTHER INFORMATION: hIL12AB_025
<220> FEATURE:
<221> NAME/KEY: misc_feature
<222> LOCATION: (1)..(1)
<223> OTHER INFORMATION: 5' terminal guanosine cap

<400> SEQUENCE: 119

| | |
|---|---|
| ggggaaataa gagagaaaag aagagtaaga agaaatataa gagccaccat gtgccatcag | 60 |
| cagctggtga tttcctggtt ctccctggtg ttcctggcca ccccctcgt ggcgatctgg | 120 |
| gagctaaaga aggacgtgta cgtggtggag ctggactggt acccggacgc acccggcgag | 180 |
| atggtcgttc tgacctgcga tacgccagag gaggacggca tcacctggac cctcgatcag | 240 |
| agcagcgagg tcctggggag cggaaagacc ctgaccatcc aggtcaagga gttcggcgac | 300 |
| gccggccagt acacctgcca caaggtggc gaggtcctga ccactcgct gctgctcctg | 360 |
| cataagaagg aggacggaat ctggagcaca gacatcctga agaccagaa ggagcccaag | 420 |
| aacaagacct tcctgaggtg cgaggccaag aactacagcg gcgcttcac gtgctggtgg | 480 |
| ctgaccacca tcagcacgga cctcaccttc tccgtgaaga gcagccgggg atccagcgat | 540 |
| ccccaaggcg tcacctgcgg cgcggccacc ctgagcgcgg agagggtcag gggcgataat | 600 |
| aaggagtatg agtacagcgt ggagtgccag gaggacagcg cctgcccggc cgccgaggag | 660 |
| tccctgccaa tcgaagtgat ggtcgacgcc gtgcacaagc tgaagtacga gaactacacc | 720 |
| agcagcttct tcatccggga tatcatcaag cccgatcccc cgaagaacct gcagctgaag | 780 |
| ccctcaaga acagccggca ggtggaggtg agttgggagt accccgacac ctggtcaacg | 840 |
| ccccacagct acttctccct gaccttctgt gtgcaggtgc agggaaagag caagagggag | 900 |
| aagaaagacc gggtcttcac cgacaagacc agcgccacgg tgatctgcag gaagaacgca | 960 |
| agcatctccg tgagggccca ggacaggtac tacagctcca gctggtccga atgggccagc | 1020 |
| gtgccctgta gcgcggcgg gggcggtggc agccgcaacc tccagtggc cacccccgac | 1080 |
| cccggcatgt tcccctgcct gcaccacagc cagaatctgc tgagggccgt gagtaacatg | 1140 |
| ctgcagaagg caaggcaaac cctcgaattc tatccctgca cctccgagga gatcgaccac | 1200 |
| gaggatatca ccaaggacaa gaccagcacc gtcgaggcct gtctcccct ggagctgacc | 1260 |
| aagaatgaga gctgcctgaa cagccgggag accagcttca tcaccaacgg gagctgcctg | 1320 |

```
gcctccagga agacctcgtt catgatggcg ctgtgcctct caagcatata cgaggatctg    1380
aagatgtacc aggtggagtt taagacgatg aacgccaagc tgctgatgga cccgaagagg    1440
cagatcttcc tggaccagaa catgctggcc gtgatagacg agctcatgca ggccctgaac    1500
ttcaactccg agaccgtgcc gcagaagtca tccctcgagg agcccgactt ctataagacc    1560
aagatcaagc tgtgcatcct gctccacgcc ttccggataa gggccgtgac gatcgacagg    1620
gtgatgagct accttaacgc cagctgataa taggctggag cctcggtggc catgcttctt    1680
gccccttggg cctcccccca gcccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890

<210> SEQ ID NO 120
<211> LENGTH: 1890
<212> TYPE: DNA
<213> ORGANISM: Artificial Sequence
<220> FEATURE:
<223> OTHER INFORMATION: hIL12AB_026
<220> FEATURE:
<221> NAME/KEY: misc_feature
<222> LOCATION: (1)..(1)
<223> OTHER INFORMATION: 5' terminal guanosine cap

<400> SEQUENCE: 120
ggggaaataa gagagaaaag aagagtaaga agaaatataa gagccaccat gtgccaccag      60
cagctcgtga tcagctggtt ctccctggtg tttctcgcca gcccctggt ggccatctgg      120 gagctgaaga aggacgtgta cgtggtggag ctggactggt accctgacgc cccgggggag     180
atggtcgtgc tgacctgcga caccccgaa gaggacggta tcacctggac cctgaccag     240 tccagcgagg tgctgggcag cggcaagacc ctgactattc aagtcaagga gttcggagac    300
gccggccagt acacctgcca caagggtgga gaggtgttat cacacagcct gctgctgctg    360
cacaagaagg aagacgggat ctggagcacc gacatcctga aggaccagaa ggagcccaaa    420
aacaagacct tcctgcggtg cgaggccaag aactattcgg ccgctttac gtgctggtgg    480 ctgaccacca tcagcactga tctcaccttc agcgtgaagt cctcccgggg gtcgtccgac    540 ccccagggggg tgacctgcgg ggccgccacc ctgtccgccg agagagtgag gggcgataat    600
aaggagtacg agtacagcgt tgagtgccag gaagatagcg cctgtcccgc cgccgaggag    660
agcctgccca tcgaggtgat ggtggacgcc gtccacaagc tgaagtatga gaactacacc    720
tcaagcttct tcatcaggga catcatcaaa cccgatccgc caagaatctg cagctgaag    780 ccctgaaaa atagcaggca ggtggaggtg agctgggagt ccccgacac ctggtccacc     840 ccccatagct atttctccct gacgttctgc gtgcaggtgc aagggaagag caagcgggag    900
aagaaggacc gggtgttcac cgacaagacc tccgccaccg tgatctgtag gaagaacgcg    960
tcgatctcgg tcagggccca ggacaggtat tacagcagca gctggagcga gtgggcgagc   1020
gtgccctgct cggcggcgg cggcggcggg agcagaaatc tgcccgtggc caccccagac   1080
cccggaatgt tccctgcct gcaccattcg cagaacctcc tgagggccgt gagcaacatg    1140
ctgcagaagg cccgccagac gctggagttc taccctgca cgagcgagga gatcgaccac    1200
gaagacatca ccaaggacaa aaccagcacc gtggaggcct gctgcccct ggagctgacc    1260 aaaaacgaat cctgcctcaa cagccgggag accagcttca tcaccaacgg cagctgcctg    1320
```

```
gccagccgaa agacctcctt catgatggcc ctctgcctga gcagcatcta tgaggatctg    1380
aagatgtatc aggtggagtt caagaccatg aatgccaagc tgctgatgga ccccaagagg    1440
cagatattcc tggaccagaa tatgctggcc gtgatcgacg agctgatgca ggccctgaac    1500
ttcaacagcg agaccgtccc ccagaagtcc agcctggagg agccggactt ttacaaaacg    1560
aagatcaagc tgtgcatact gctgcacgcc ttcaggatcc gggccgtgac aatcgacagg    1620
gtgatgtcct acctgaacgc cagctgataa taggctggag cctcggtggc catgcttctt    1680
gccccttggg cctcccccca gccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890
```

<210> SEQ ID NO 121
<211> LENGTH: 1890
<212> TYPE: DNA
<213> ORGANISM: Artificial Sequence
<220> FEATURE:
<223> OTHER INFORMATION: hIL12AB_027
<220> FEATURE:
<221> NAME/KEY: misc_feature
<222> LOCATION: (1)..(1)
<223> OTHER INFORMATION: 5' terminal guanosine cap

<400> SEQUENCE: 121

```
ggggaaataa gagagaaaag aagagtaaga agaaatataa gagccaccat gtgtcaccag      60
cagctggtga tcagctggtt ctccctggtg ttcctggcca gccccctggt ggccatctgg     120
gagctcaaga aggacgtcta cgtcgtggag ctggattggt accccgacgc tcccggggag     180
atggtggtgc tgacctgcga cacccccgag gaggacggca tcacctggac gctggaccag     240
agctcagagg tgctgggaag cggaaagaca ctgaccatcc aggtgaagga gttcggggat     300
gccgggcagt atacctgcca caagggcggc gaagtgctga ccattccct gctgctgctg     360 cacaagaagg aggacggcat atggtccacc gacatcctga aggatcagaa ggagccgaag     420
aataaaacct tcctgaggtg cgaggccaag aattacagcg gccgattcac ctgctggtgg     480
ctgaccacca tcagcaccga cctgaccttc agtgtgaagt cctcacgggg cagctcagat     540
ccccagggcg tgacctgcgg ggccgcgaca ctcagcgccg agcgggtgag gggtgataac     600
aaggagtacg agtattctgt ggagtgccag gaagactccg cctgtccgc cgccgaggag     660 tccctgccca tcgaggtgat ggtggacgcc gtgcataaac tgaagtacga gaactacacc     720
tccagcttct tcatccggga tataatcaag cccgaccctc gaaaaacct gcagctgaag     780 ccccttaaaa acagccggca ggtggaggtg agctgggagt accccgacac ctggagcacc     840
ccccatagct atttcagcct gaccttctgc gtgcaggtgc aggggaagtc caagcgcgag     900
aaaaaggacc gggtgttcac cgacaagacg agcgccaccg tgatctgccg gaagaacgcc     960
agtataagcg taagggccca ggataggtac tacagctcca gctggtcgga gtgggcctcc    1020
gtgccctgtt ccggcggcgg ggggggtggc agcaggaacc tccccgtggc cacgccggac    1080
cccggcatgt tccgtgcct gcaccactcc caaaacctcc tgcgggccgt cagcaacatg    1140
ctgcaaaagg cgcggcagac cctggagttt taccctgta cctccgaaga gatcgaccac    1200
gaggatatca ccaaggataa gacctccacc gtggaggcct gtctccccct ggagctgacc    1260
aagaacgaga gctgtcttaa cagcagagag acctcgttca taacgaacgg ctcctgcctc    1320
gcttccagga agacgtcgtt catgatggcg ctgtgcctgt ccagcatcta cgaggacctg    1380
```

```
aagatgtatc aggtcgagtt caaaaccatg aacgccaagc tgctgatgga cccc aagagg    1440 cagatcttcc tggaccagaa catgctcgcc gtgatcgacg agctgatgca ggccctgaac    1500
ttcaacagcg aaaccgtgcc ccagaagtca agcctggagg agccggactt ctataagacc    1560
aagatcaagc tgtgtatcct gctacacgct tttcgtatcc gggccgtgac catcgacagg    1620
gttatgtcgt acttgaacgc cagctgataa taggctggag cctcggtggc catgcttctt    1680
gccccttggg cctcccccca gcccctcctc cccttcctgc acccgtaccc cccaaacacc    1740
attgtcacac tccagtggtc tttgaataaa gtctgagtgg gcggcaaaaa aaaaaaaaa    1800 aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                    1890
```

<210> SEQ ID NO 122
<211> LENGTH: 1890
<212> TYPE: DNA
<213> ORGANISM: Artificial Sequence
<220> FEATURE:
<223> OTHER INFORMATION: hIL12AB_028
<220> FEATURE:
<221> NAME/KEY: misc_feature
<222> LOCATION: (1)..(1)
<223> OTHER INFORMATION: 5' terminal guanosine cap

<400> SEQUENCE: 122

```
ggggaaataa gagagaaaag aagagtaaga agaaatataa gagccaccat gtgccaccaa      60
cagctcgtga tcagctggtt cagcctggtg ttcctggcca gcccgctggt ggccatctgg     120
gagctgaaga aggacgtgta cgtggtggag ctggactggt accccgacgc ccccggcgag     180
atggtggtcc tgacctgcga cacgccggaa gaggacggca tcacctggac cctggatcag     240
tccagcgagg tgctgggctc cggcaagacc ctgaccattc aggtgaagga gttcggcgac     300
gccggtcagt acacctgcca caagggcggc gaggtgctga gccacagcct actgctcctg     360
cacaaaaagg aggatggaat ctggtccacc gacatcctca aggaccagaa ggagccgaag     420
aacaagacgt tcctccggtg cgaggccaag aactacagcg gcaggtttac ctgctggtgg     480
ctgaccacca tcagcaccga cctgacattt ccgtgaaga gcagccgcgg cagcagcgat     540
ccccagggcg tgacctgcgg ggcggccacc ctgtccgccg agcgtgtgag gggcgacaac     600
aaggagtacg agtacagcgt ggaatgccag gaggacagcg cctgtcccgc cgccgaggag     660
agcctgccaa tcgaggtcat ggtggacgcc gtgcacaagc tgaagtacga aactacacg     720 agcagcttct tcatcaggga catcatcaaa ccggaccccgc caagaaccct gcagctgaaa     780 ccccttgaaaa acagcaggca ggtggaagtg tcttgggagt accccgacac ctggtccacc     840
ccccacagct acttttagcct gaccttctgt gtgcaggtcc agggcaagtc caagagggag     900
aagaaggaca gggtgttcac cgacaaaacc agcgccaccg tgatctgcag aagaacgcc     960 tccatcagcg tgcgggccca ggacaggtat acagctcgt cgtggagcga gtgggccagc     1020
gtgccctgct ccggggagg cggcggcgga agccggaatc tgcccgtggc cacccccgat     1080
cccggcatgt tccccgtgtct gcaccacagc cagaacctgc tgcgggccgt gagcaacatg     1140
ctgcagaagg cccgccaaac cctggagttc taccccctgta caagcgagga gatcgaccat     1200
gaggacatta ccaaggacaa gaccagcacc gtggaggcct gcctgccccct cgagctcaca     1260 aagaacgaat cctgcctgaa tagccgcgag accagcttta tcacgaacgg gtcctgcctc     1320
gccagccgga agacaagctt catgatggcc ctgtgcctga gcagcatcta cgaggacctg     1380
```

-continued

| | |
|---|---|
| aaaatgtacc aagtggagtt caaaacgatg aacgccaagc tgctgatgga ccccaagcgc | 1440 |
| cagatcttcc tggaccagaa catgctggcc gtcatcgacg agctcatgca ggccctgaac | 1500 |
| ttcaacagcg agaccgtgcc ccagaagagc agcctggagg agcccgactt ctacaagacg | 1560 |
| aagatcaagc tctgcatcct gctgcacgct ttccgcatcc gcgcggtgac catcgaccgg | 1620 |
| gtgatgagct acctcaacgc cagttgataa taggctggag cctcggtggc catgcttctt | 1680 |
| gccccttggg cctcccccca gccctcctc cccttcctgc acccgtaccc cccaaacacc | 1740 |
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 123
<211> LENGTH: 1890
<212> TYPE: DNA
<213> ORGANISM: Artificial Sequence
<220> FEATURE:
<223> OTHER INFORMATION: hIL12AB_029
<220> FEATURE:
<221> NAME/KEY: misc_feature
<222> LOCATION: (1)..(1)
<223> OTHER INFORMATION: 5' terminal guanosine cap

<400> SEQUENCE: 123

| | |
|---|---|
| ggggaaataa gagagaaaag aagagtaaga agaaatataa gagccaccat gtgccaccaa | 60 |
| cagctggtga tcagctggtt cagcctggtg tttctggcct cccctctggt ggccatctgg | 120 |
| gagctgaaga aggacgtgta cgtggtggag ctggactggt accctgacgc ccccggcgaa | 180 |
| atggtggtgc tgacgtgcga caccccggag gaggatggca tcacctggac cctggaccaa | 240 |
| agcagcgagg tcctcggaag cggcaagacc ctcactatcc aagtgaagga gttcggggat | 300 |
| gcgggccagt acacctgcca caagggcggc gaggtgctgt ctcatagcct gctgctcctg | 360 |
| cataagaagg aagacggcat ctggagcacc gacatactga aggatcagaa ggagcccaag | 420 |
| aacaagacct tcctgaggtg cgaggccaag aactactccg ggcgcttcac ctgttggtgg | 480 |
| ctgaccacca tctccaccga cctgaccttc agcgtgaaga gcagcagggg gagcagcgac | 540 |
| ccccaggggg tgacctgcgg agccgcgacc ttgtcggccg agcgggtgag gggcgacaat | 600 |
| aaggagtacg agtactcggt cgaatgccag gaggactccg cctgccccgc cgccgaggag | 660 |
| tccctcccca tcgaagtgat ggtggacgcc gtccacaagc tgaagtacga aactacacc | 720 |
| agcagcttct tcatacggga tatcatcaag cccgaccccc gaagaacct gcagctgaaa | 780 |
| cccttgaaga actccaggca ggtggaggtg agctgggagt accccgacac ctggtccacc | 840 |
| ccgcactcat acttcagcct gaccttctgt gtacaggtcc agggcaagag caagagggaa | 900 |
| aagaaggata gggtgttcac cgacaagacc tccgccacgg tgatctgtcg gaaaaacgcc | 960 |
| agcatctccg tgcgggccca ggacaggtac tattccagca gctggagcga gtgggcctcc | 1020 |
| gtcccctgct ccggcggcgg tggcgggggc agcaggaacc tccccgtggc caccccgat | 1080 |
| cccgggatgt tccatgcct gcaccacagc caaaacctgc tgagggccgt ctccaatatg | 1140 |
| ctgcagaagg cgaggcagac cctggagttc tacccctgta cctccgagga gatcgaccac | 1200 |
| gaggatatca ccaaggacaa gacctccacg gtcgaggcgt gcctgccct ggagctcacg | 1260 |
| aagaacgaga gctgccttaa ctccagggaa acctcgttta tcacgaacgg cagctgcctg | 1320 |
| gcgtcacgga agacctcctt tatgatggcc ctatgtctgt cctcgatcta cgaggacctg | 1380 |
| aagatgtacc aggtggagtt caagaccatg aacgccaagc tgctgatgga tcccaagagg | 1440 |

```
cagattttcc tggaccagaa catgctggcc gtgattgacg agctgatgca ggcgctgaac   1500
ttcaacagcg agacagtgcc gcagaagagc tccctggagg agccggactt ttacaagacc   1560
aagataaagc tgtgcatcct gctccacgcc ttcagaatac gggccgtcac catcgatagg   1620
gtgatgtctt acctgaacgc ctcctgataa taggctggag cctcgtggcc catgcttctt   1680
gccccttggg cctccccca gccctcctc cccttcctgc accgtaccc cccaaacacc   1740 attgtcacac tccagtggtc tttgaataaa gtctgagtgg gcggcaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaatctag                                    1890
```

<210> SEQ ID NO 124
<211> LENGTH: 1890
<212> TYPE: DNA
<213> ORGANISM: Artificial Sequence
<220> FEATURE:
<223> OTHER INFORMATION: hIL12AB_030
<220> FEATURE:
<221> NAME/KEY: misc_feature
<222> LOCATION: (1)..(1)
<223> OTHER INFORMATION: 5' terminal guanosine cap

<400> SEQUENCE: 124

```
gggaaataa gagagaaaag aagagtaaga agaaatataa gagccaccat gtgccaccag     60
cagctggtga ttagctggtt tagcctggtg ttcctggcaa gcccctggt ggccatctgg    120 gaactgaaaa aggacgtgta cgtggtcgag ctgattggt accccgacgc ccccggcgaa    180
atggtggtgc tgacgtgtga taccccgag gaggacggga tcacctggac cctggatcag    240
agcagcgagg tgctggggag cgggaagacc ctgacgatcc aggtcaagga gttcggcgac    300
gctgggcagt acacctgtca aagggcggg gaggtgctgt cccactccct gctgctcctg    360
cataagaaag aggacggcat ctggtccacc gacatcctca aggaccagaa ggagcccaag    420
aacaagacct tcctgcggtg tgaggcgaag aactacagcg gccgtttcac ctgctggtgg    480
ctgacgacaa tcagcaccga cttgacgttc tccgtgaagt cctccagagg cagctccgac    540
ccccaagggg tgacgtgcgg cgcggccacc ctgagcgccg agcgggtgcg ggggacaac    600 aaggagtacg agtactccgt ggagtgccag gaggacagcg cctgtcccgc agccgaggag    660
tccctgccca tcgaagtcat ggtggacgcc gtccacaagc tgaagtacga gaactacacc    720
agcagcttct tcatccgcga tatcatcaag cccgatcccc ccaaaaacct gcaactgaag    780
ccgctgaaga atagcaggca ggtggaggtg tcctgggagt acccggacac ctggagcacg    840
ccccacagct atttcagcct gaccttttgc gtgcaggtcc aggggaagag caagcgggag    900
aagaaggacc gcgtgtttac ggacaaaacc agcgccaccg tgatctgcag gaagaacgcc    960
agcatcagcg tgagggccca ggacaggtac tacagcagct cctggagcga gtgggcctcc   1020 gtgcccgtt ccggaggcgg cggggcggt tccggaacc tccggtggc acccccgac       1080 ccgggcatgt tcccgtgcct gcaccactca cagaatctgc tgagggccgt gagcaatatg   1140
ctgcagaagg caaggcagac cctggagttt tatccctgca ccagcgagga gatcgaccac   1200
gaagacatca ccaaggacaa gaccagcaca gtggaggcct gctgcccct ggaactgacc   1260 aagaacgagt cctgtctgaa ctcccgggaa accagcttca taaccaacgg ctcctgtctc   1320
gccagcagga agaccagctt catgatggcc ctgtgcctca gctccatcta cgaggacctc   1380
aagatgtacc aggttgagtt caagaccatg aacgccaagc tcctgatgga ccccaagagg   1440
```

-continued

```
cagatcttcc tggaccagaa tatgctggcc gtgatcgatg agttaatgca ggcgctgaac   1500
ttcaacagcg agacggtgcc ccaaaagtcc tcgctggagg agcccgactt ctacaagacc   1560
aagatcaagc tgtgcatcct cctgcacgcc ttccgaatcc gggccgtaac catcgacagg   1620
gtgatgagct atctcaacgc ctcctgataa taggctggag cctcggtggc catgcttctt   1680
gccccttggg cctcccccca gcccctcctc cccttcctgc acccgtaccc cccaaacacc   1740
attgtcacac tccagtggtc tttgaataaa gtctgagtgg gcggcaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaatctag                                   1890
```

<210> SEQ ID NO 125
<211> LENGTH: 1890
<212> TYPE: DNA
<213> ORGANISM: Artificial Sequence
<220> FEATURE:
<223> OTHER INFORMATION: hIL12AB_031
<220> FEATURE:
<221> NAME/KEY: misc_feature
<222> LOCATION: (1)..(1)
<223> OTHER INFORMATION: 5' terminal guanosine cap

<400> SEQUENCE: 125

```
ggggaaataa gagagaaaag aagagtaaga agaaatataa gagccaccat gtgccaccag     60
cagctcgtga tcagctggtt ctcgcttgtg ttcctggcct ccccctcgt cgccatctgg    120 gagctgaaga agacgtgta cgtggtggag ctggactggt atcccgacgc cccggggag    180 atggtggtgc tgacctgcga caccccggaa gaggacggca tcacctggac gctcgaccag    240
tcgtccgaag tgctggggtc gggcaagacc ctcaccatcc aggtgaagga gttcggagac    300
gccggccagt acacctgtca taaggggggg gaggtgctga gccacagcct cctgctcctg    360
cacaaaaagg aggacggcat ctggagcacc gatatcctca aggaccagaa ggagcccaag    420
aacaagacgt tcctgaggtg tgaggccaag aactacagcg gcggttcac gtgttggtgg    480 ctcaccacca tctccaccga cctcaccttc tccgtgaagt caagcagggg cagctccgac    540
ccccaaggcg tcacctgcgg cgccgccacc ctgagcgccg agagggtcag gggggataac    600
aaggaatacg agtacagtgt ggagtgccaa gaggatagcg cctgtcccgc cgccgaagag    660
agcctgccca tcgaagtgat ggtggacgcc gtgcacaagc tgaagtacga aaactacacc    720
tccagcttct tcatcaggga tatcatcaag cccgatcccc caagaacct gcagctgaag    780 cccctgaaga acagcaggca ggtggaggtg agctgggagt atcccgacac gtggagcacc    840
ccgcacagct acttctcgct gaccttctgc gtgcaggtgc aagggaagtc caagagggag    900
aagaaggata gggtgttcac cgacaaaacg agcgccaccg tgatctgccg gaagaatgcc    960
agcatctctg tgagggccca ggacaggtac tattccagct cctggtcgga gtgggccagc   1020
gtgccctgta gcgcgggggg cggggcggc agcaggaacc tccggttgc acccccgac    1080 cccggcatgt ttccgtgcct gcaccactcg caaaacctgc tgcgcgcggt ctccaacatg   1140
ctgcaaaaag cgcgccagac gctggagttc taccccctgca ccagcgagga gatcgatcat   1200
gaagatatca ccaaagacaa gacctcgacc gtggaggcct gcctgccct ggagctcacc   1260 aagaacgaaa gctgcctgaa cagcagggag acaagcttca tcaccaacgg cagctgcctg   1320
gcctcccgga gaccagcttt catgatggcc ctgtgcctgt ccagcatcta cgaggatctg   1380
aagatgtacc aagtggagtt taagaccatg aacgccaagc tgttaatgga ccccaaaagg   1440
cagatcttcc tggatcagaa catgctggcc gtcatcgacg agctgatgca agccctgaac   1500
```

```
ttcaacagcg agacggtgcc ccagaagagc agcctcgagg agcccgactt ctataagacc   1560
aagataaagc tgtgcattct gctgcacgcc ttcagaatca gggccgtgac catcgatagg   1620
gtgatgagct acctgaacgc cagctgataa taggctggag cctcggtggc catgcttctt   1680
gccccttggg cctcccccca gcccctcctc cccttcctgc acccgtaccc cccaaacacc   1740
attgtcacac tccagtggtc tttgaataaa gtctgagtgg gcggcaaaaa aaaaaaaaa   1800 aaaaaaaaaa aaaaaaaaaa aaaaaaaaaa aaaaaaaaaa aaaaaaaaaa aaaaaaaaaa   1860
aaaaaaaaaa aaaaaaaaaa aaaaatctag                                     1890
```

<210> SEQ ID NO 126
<211> LENGTH: 1890
<212> TYPE: DNA
<213> ORGANISM: Artificial Sequence
<220> FEATURE:
<223> OTHER INFORMATION: hIL12AB_032
<220> FEATURE:
<221> NAME/KEY: misc_feature
<222> LOCATION: (1)..(1)
<223> OTHER INFORMATION: 5' terminal guanosine cap

<400> SEQUENCE: 126

```
ggggaaataa gagagaaaag aagagtaaga agaaatataa gagccaccat gtgtcaccag     60
cagctggtga tttcctggtt cagtctggtg tttcttgcca gccccctggt ggccatctgg   120
gagctgaaga aagacgtata cgtcgtggag ctggactggt atcccgacgc tcccggcgag   180
atggtggtcc tcacctgcga caccccagag gaggacggca tcacctggac cctggaccag   240
agctccgagg tcctgggcag cggtaagacc ctcaccatcc aggtgaagga gtttggtgat   300
gccgggcagt atacctgcca caagggcggc gaggtgctgt cccacagcct cctgttactg   360
cataagaagg aggatggcat ctggagcacc gacatcctca aggaccagaa agagcccaag   420
aacaagacct ttctgcggtg cgaggcgaaa aattactccg gccggttcac ctgctggtgg   480
ctgaccacca tcagcacgga cctgacgttc tccgtgaagt cgagcagggg gagctccgat   540
ccccagggcg tgacctgcgg cgcggccacc ctgagcgccg agcgcgtccg cggggacaat   600
aaggaatacg aatatagcgt ggagtgccag gaggacagcc cctgccccgc ggccgaggag   660
agcctcccga tcgaggtgat ggtggatgcc gtccacaagc tcaaatacga aaactacacc   720
agcagcttct tcattaggga catcatcaag cccgaccccc ccaaaaacct gcagctgaag   780
cccctgaaga acagccgcca ggtcgaggtg tcatgggagt acccagacac ctggagcacc   840
ccccactcct acttcagcct gaccttctgc gtccaggtgc agggaaagtc caacgggag   900 aagaaggata gggtctttac cgataagacg tcggccaccg tcatctgcag gaagaacgcc   960
agcataagcg tgcgggcgca ggatcggtac tacagctcga gctggtccga atgggcctcc  1020
gtgccctgta gcggaggggg tggcggggc agcaggaacc tgcccgtggc caccccggac  1080
ccgggcatgt tccctgcct gcatcacagt cagaacctgc tgagggccgt gagcaacatg  1140
ctccagaagg cccgccagac cctggagttt taccccctgca ccagcgaaga gatcgatcac  1200
gaagacatca ccaaagacaa gacctccacc gtggaggcct gtctgccct ggagctgacc  1260 aagaacgaga gctgtctgaa cagcagggag acctccttca tcaccaacgg ctcctgcctg  1320
gcatcccgga gaccagctt catgatggcc ctgtgtctga gctctatcta cgaggacctg  1380
aagatgtacc aggtcgagtt caagaccatg aacgccaagc tgctgatgga ccccaagcga  1440
cagatattcc tggaccagaa catgctcgcc gtgatcgatg aactgatgca agccctgaac  1500
```

| | |
|---|---:|
| ttcaatagcg agaccgtgcc ccagaaaagc agcctggagg agcccgactt ctacaagacc | 1560 |
| aagatcaaac tgtgcatact gctgcacgcg ttcaggatcc gggccgtcac catcgaccgg | 1620 |
| gtgatgtcct atctgaatgc cagctgataa taggctggag cctcggtggc catgcttctt | 1680 |
| gccccttggg cctcccccca gccctcctc cccttcctgc acccgtaccc cccaaacacc | 1740 |
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 127
<211> LENGTH: 1890
<212> TYPE: DNA
<213> ORGANISM: Artificial Sequence
<220> FEATURE:
<223> OTHER INFORMATION: hIL12AB_033
<220> FEATURE:
<221> NAME/KEY: misc_feature
<222> LOCATION: (1)..(1)
<223> OTHER INFORMATION: 5' terminal guanosine cap

<400> SEQUENCE: 127

| | |
|---|---:|
| ggggaaataa gagagaaaag aagagtaaga agaaatataa gagccaccat gtgccaccag | 60 |
| cagctcgtga ttagctggtt ttcgctggtg ttcctggcca gccctctcgt ggccatctgg | 120 |
| gagctgaaaa aagacgtgta cgtggtggag ctggactggt acccggacgc ccccggcgag | 180 |
| atggtggtgc tgacgtgcga cacccccgaa gaggacggca tcacctggac cctggaccag | 240 |
| tcatccgagg tcctgggcag cggcaagacg ctcaccatcc aggtgaagga gttcggcgac | 300 |
| gccggccagt acacatgcca taagggcggg gaggtgctga gccacagcct gctcctcctg | 360 |
| cacaagaagg aggatggcat ctggtctaca gacatcctga aggaccagaa agagcccaag | 420 |
| aacaagacct tcctccggtg cgaggccaag aactactccg ggcggtttac ttgttggtgg | 480 |
| ctgaccacca tcagcaccga cctcaccttc agcgtgaaga gctcccgagg gagctccgac | 540 |
| ccccaggggg tcacctgcgg cgccgccacc ctgagcgccg agcgggtgag ggcgacaac | 600 |
| aaggagtatg aatacagcgt ggaatgccaa gaggacagcg cctgtcccgc ggccgaggaa | 660 |
| agcctgccca tcgaggtgat ggtggacgcc gtccacaaac tcaagtacga aactacacc | 720 |
| agcagtttct tcattcgcga catcatcaag ccggaccccc ccaaaaacct gcagctcaaa | 780 |
| cccctgaaga acagcaggca ggtggaggtc agctgggagt acccggacac ctggagcacc | 840 |
| ccccatagct acttcagcct gaccttctgc gtgcaggtgc agggcaagag caaacgcgag | 900 |
| aagaaggacc gggtgtttac cgacaagacc agcgccacgg tgatctgccg aaagaatgca | 960 |
| agcatctccg tgagggcgca ggaccgctac tactctagca gctggagcga gtgggccagc | 1020 |
| gtgccctgca gcggtggcgg cggaggcggc agccgtaacc tccccgtggc caccccgac | 1080 |
| cccggcatgt tccgtgtct gcaccactcc cagaacctgc tgagggccgt cagcaatatg | 1140 |
| ctgcagaagg cccggcagac gctggagttc taccctgca cctccgagga gatcgaccat | 1200 |
| gaggacatta ccaaggacaa gacgagcact gtggaggcct gcctgccct ggagctcacc | 1260 |
| aaaaacgaga gctgcctgaa tagcagggag acgtccttca tcaccaacgg cagctgtctg | 1320 |
| gccagcagga agaccagctt catgatggcc ctgtgcctct cctccatata tgaggatctg | 1380 |
| aagatgtacc aggtggagtt caagaccatg aacgccaagc tgctgatgga tcccaagagg | 1440 |
| cagatcttcc tggaccagaa tatgctggcc gtgattgacg agctgatgca ggccctgaac | 1500 |
| tttaatagcg agaccgtccc ccagaagagc agcctggagg agcccgactt ctataagacc | 1560 |

| aagatcaagc tgtgcatact gctgcacgcg tttaggataa gggccgtcac catcgacagg | 1620 |
| gtgatgagct acctgaatgc cagctgataa taggctggag cctcggtggc catgcttctt | 1680 |
| gccccttggg cctcccccca gcccctcctc cccttcctgc accgtacccc cccaaacacc | 1740 |
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 128
<211> LENGTH: 1890
<212> TYPE: DNA
<213> ORGANISM: Artificial Sequence
<220> FEATURE:
<223> OTHER INFORMATION: hIL12AB_034
<220> FEATURE:
<221> NAME/KEY: misc_feature
<222> LOCATION: (1)..(1)
<223> OTHER INFORMATION: 5' terminal guanosine cap

<400> SEQUENCE: 128

| ggggaaataa gagagaaaag aagagtaaga agaaatataa gagccaccat gtgccaccaa | 60 |
| cagctggtga tctcctggtt cagcctggtg ttcctcgcca gccccctggt ggccatctgg | 120 |
| gagctgaaga agacgtgta cgtggtggag ctggactggt atcccgacgc ccccggcgag | 180 |
| atggtcgtgc tgacctgcga caccccggag gaggacggca tcacctggac cctggatcag | 240 |
| tcctccgagg tgctgggcag cgggaagacc ctgaccatcc aggtgaaaga gttcggagat | 300 |
| gccggccagt atacctgtca caaggggggt gaggtgctga gccatagcct cttgcttctg | 360 |
| cacaagaagg aggacggcat ctggtccacc gacatcctca aggaccaaaa ggagccgaag | 420 |
| aataaaacgt tcctgaggtg cgaagccaag aactattccg gacggttcac ctgctggtgg | 480 |
| ctgaccacca tcagcaccga cctcaccttc tccgtaaagt caagcagggg cagctccgac | 540 |
| ccccagggcg tgacctgcgg agccgccacc ctgagcgcag agagggtgag gggcgacaac | 600 |
| aaggagtacg aatactccgt cgagtgccag gaggacagcg cctgccccgc cgccgaggaa | 660 |
| agtctgccca tcgaggtgat ggtggacgcc gtgcacaagc tcaaatacga gaactacacc | 720 |
| agcagcttct tcatccggga tatcatcaag cccgacccct caaagaatct gcagctgaaa | 780 |
| ccccttaaga cagcaggca ggtggaggtc agctgggagt accccgacac ctggagcacg | 840 |
| ccccactcct actttagcct gaccttttgc gtgcaggtgc aggggaaaag caagcgggag | 900 |
| aagaaggaca gggtgttcac cgataagacc tccgctaccg tgatctgcag gaagaacgcc | 960 |
| tcaatcagcg tgagggccca ggatcggtac tactccagct cctggagcga gtgggccagc | 1020 |
| gtgccctgct ctggcggtgg cggcggggc agccggaacc tgccggtggc cactcccgac | 1080 |
| ccgggcatgt tcccgtgcct ccaccattcc agaacctgc tgcgggccgt gtccaatatg | 1140 |
| ctccagaagg caaggcagac cctggagttc taccccctgca ccagcgagga gatcgatcac | 1200 |
| gaggacatca ccaaagacaa aaccagcacg gtcgaggcct gcctgccct ggaactcacc | 1260 |
| aagaacgaaa gctgtctcaa cagccgcgag accagcttca taaccaacgg ttcctgtctg | 1320 |
| gcctcccgca agaccagctt tatgatggcc ctctgtctga ctccatcta tgaagacctg | 1380 |
| aaaatgtacc aggtggagtt caaaaccatg aacgccaagc ttctgatgga ccccaagagg | 1440 |
| cagatcttcc tggatcagaa catgctggcc gtgatcgacg agctgatgca ggccctgaac | 1500 |
| tttaactccg agaccgtgcc ccagaaaagc agcctggaag agcccgattt ctacaaaacg | 1560 |

```
aagatcaagc tgtgcatcct gctgcacgcc ttccggatcc gtgcggtgac catcgatagg    1620
gtgatgagct acctgaacgc cagctgataa taggctggag cctcggtggc catgcttctt    1680
gccccttggg cctcccccca gcccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890
```

<210> SEQ ID NO 129
<211> LENGTH: 1890
<212> TYPE: DNA
<213> ORGANISM: Artificial Sequence
<220> FEATURE:
<223> OTHER INFORMATION: hIL12AB_035
<220> FEATURE:
<221> NAME/KEY: misc_feature
<222> LOCATION: (1)..(1)
<223> OTHER INFORMATION: 5' terminal guanosine cap

<400> SEQUENCE: 129

```
ggggaaataa gagagaaaag aagagtaaga agaaatataa gagccaccat gtgccaccaa      60
cagctggtaa tcagctggtt cagcctggtt ttcctcgcgt cgcccctggt ggccatctgg     120
gagttaaaga aggacgtgta cgtggtggag ctggattggt accccgacgc cccgggcgag     180
atggtcgtgc tcacctgcga taccccgag gaggacggga tcacctggac cctgaccaa      240 tccagcgagg tgctgggcag cggcaagacc ctgaccatac aggtgaagga atttggggac     300
gccgggcagt acacctgcca caagggcggg gaagtgctgt cccactccct cctgctgctg     360
cataagaagg aggacggcat ctggagcacc gacatcctga aggaccaaaa ggagcccaag     420
aacaagacct tcctgaggtg cgaggccaaa aactattccg ccgctttac ctgttggtgg      480 ctgaccacca tctccaccga tctgaccttc agcgtgaagt cgtctagggg ctcctccgac     540
ccccagggcg taacctgcgg cgccgcgacc ctgagcgccg agagggtgcg gggcgataac     600
aaagagtacg agtactcggt ggagtgccag gaggacagcg cctgtccggc ggccgaggag     660
agcctgccca tcgaggtgat ggtggacgcc gtccacaagc tgaagtacga gaactacacc     720
agttcgttct tcatcaggga catcatcaag ccggacccc caagaacct ccagctgaag       780 cccctgaaga acagcaggca ggtggaagtg tcctgggagt atcccgacac ctggagcacc     840
ccccacagct acttcagcct gacctttgc gtgcaggtgc agggcaaaag caagagggaa       900
aagaaggacc gggtgttcac cgataagacg agcgccaccg ttatctgcag gaagaacgcc     960
tccataagcg tgagggcgca ggaccgttac tacagcagca gctggagtga gtgggcaagc    1020
gtgccctgta gcggcggggg cggggcgggg tcccgcaacc tccccgtcgc cacccccgac    1080
ccaggcatgt ttccgtgcct gcaccacagc cagaacctgc tgcgggccgt tagcaacatg    1140
ctgcagaagg ccaggcagac cctcgagttc tatccctgca catctgagga gatcgaccac    1200
gaagacatca ctaaggataa gaccccacc gtggaggcct gtctgccct cgagctgacc      1260 aagaatgaat cctgcctgaa cagccgagag accagcttta tcaccaacgg ctcctgcctg    1320
gccagcagga gaccctcctt catgatggcc ctgtgcctct ccagcatcta cgaggatctg    1380
aagatgtacc aggtagagtt caagacgatg aacgccaagc tcctgatgga ccccaagagg    1440
cagatattcc tggaccagaa catgctggcc gtgatcgacg agctgatgca ggccctgaat    1500
ttcaacagcg agacggtgcc acagaagtcc agcctggagg agccagactt ctacaagacc    1560
aagatcaaac tgtgcatcct cctgcacgcg ttcaggatcc gcgccgtcac catagacagg    1620
```

-continued

```
gtgatgagtt atctgaacgc cagctgataa taggctggag cctcggtggc catgcttctt    1680
gccccttggg cctcccccca gcccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890
```

<210> SEQ ID NO 130
<211> LENGTH: 1890
<212> TYPE: DNA
<213> ORGANISM: Artificial Sequence
<220> FEATURE:
<223> OTHER INFORMATION: hIL12AB_036
<220> FEATURE:
<221> NAME/KEY: misc_feature
<222> LOCATION: (1)..(1)
<223> OTHER INFORMATION: 5' terminal guanosine cap

<400> SEQUENCE: 130

```
ggggaaataa gagagaaaag aagagtaaga agaaatataa gagccaccat gtgccatcag      60
cagctggtaa tcagctggtt tagcctggtg ttcctggcca gcccactggt ggccatctgg     120
gagctgaaga aggacgtgta cgtggtggaa ctggactggt accccgacgc ccctggcgag     180
atggtggtac tgacctgtga cacccccgag gaagacggta tcacctggac cctggatcag     240
agctccgagg tgctgggctc cggcaagaca ctgaccatcc aagttaagga atttggggac     300
gccggccagt acacctgcca caggggggc gaggtgctgt cccactccct gctgcttctg     360
cataagaagg aggatggcat ctggtccacc gacatactga aggaccagaa ggagcccaag     420
aataagacct tcctgagatg cgaggccaag aactactcgg gaaggttcac ctgctggtgg     480
ctgaccacca tcagcaccga cctgaccttc tccgtgaaga gctcccgggg cagctccgac     540
ccccagggcg taacctgtgg ggccgctacc ctgtccgccg agagggtccg gggcgacaac     600
aaggaatacg agtacagcgt ggagtgccag gaggactccg cctgccccgc cgccgaggag     660
tcgctgccca tagaggtgat ggtggacgcc gtgcacaagc tcaagtacga gaattacacc     720
agcagcttct ttatcaggga cataattaag ccggaccccc caaagaatct gcagctgaag     780
cccctgaaga atagccggca ggtggaagtg tcctgggagt accccgacac ctggagcacc     840
ccccactcct atttctcact gacattctgc gtgcaggtgc aagggaaaag caagagggag     900
aagaaggata gggtgttcac cgacaagaca agcgccaccg tgatctgccg aaaaaatgcc     960
agcatcagcg tgagggccca ggatcggtat acagcagct cctggagcga gtgggccagc    1020
gtgccctgtt ccggcgggg aggggcggc tcccggaacc tgccggtggc caccccgac     1080 cctggcatgt tccctgcct gcatcacagc cagaacctgc tccgggccgt gtcgaacatg    1140
ctgcagaagg cccggcagac cctcgagttt taccccctgc cagcgaagg atcgaccac     1200 gaagacataa ccaaggacaa gaccagcacg gtggaggcct gctgcccct ggagcttacc    1260 aaaaacgagt cctgcctgaa cagccgggaa accagcttca taacgaacgg gagctgcctg    1320
gcctccagga agaccagctt catgatggcg ctgtgtctgt ccagcatata cgaggatctg    1380
aagatgtatc aggtggaatt caaaactatg aatgccaagc tcctgatgga ccccaagagg    1440
cagatcttcc tggaccagaa catgctagcc gtgatcgacg agctgatgca ggccctcaac    1500
ttcaactcgg agacggtgcc ccagaagtcc agcctcgagg agccccgactt ctacaagacc    1560 aagatcaagc tgtgcatact gctgcatgcc ttcaggataa gggcggtgac tatcgacagg    1620
```

| gtcatgtcct acctgaacgc cagctgataa taggctggag cctcggtggc catgcttctt | 1680 |
| gccccttggg cctcccccca gcccctcctc cccttcctgc acccgtaccc cccaaacacc | 1740 |
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

```
<210> SEQ ID NO 131
<211> LENGTH: 1890
<212> TYPE: DNA
<213> ORGANISM: Artificial Sequence
<220> FEATURE:
<223> OTHER INFORMATION: hIL12AB_037
<220> FEATURE:
<221> NAME/KEY: misc_feature
<222> LOCATION: (1)..(1)
<223> OTHER INFORMATION: 5' terminal guanosine cap

<400> SEQUENCE: 131
```

| ggggaaataa gagagaaaag aagagtaaga agaaatataa gagccaccat gtgccaccaa | 60 |
| caactggtga tcagctggtt ctccctggtg ttcctggcca gccccctggt ggccatctgg | 120 |
| gagctcaaaa aagacgtgta cgtggtggag ctcgattggt acccagacgc gccggggaa | 180 |
| atggtggtgc tgacctgcga cacccccagag gaggatggca tcacgtggac gctggatcag | 240 |
| tccagcgagg tgctggggag cggcaagacg ctcaccatcc aggtgaagga atttggcgac | 300 |
| gcgggccagt atacctgtca caagggcggc gaggtgctga gccactccct gctgctgctg | 360 |
| cacaagaagg aggatgggat ctggtcaacc gatatcctga agaccagaa ggagcccaag | 420 |
| aacaagacct tcctgcgctg cgaggccaag aactatagcg gcaggttcac ctgctggtgg | 480 |
| ctgaccacca tcagcaccga cctgaccttc agcgtgaaat cctccagggg cagcagcgac | 540 |
| ccccagggcg tgacctgcgg tgccgccacg ctctccgccg agcgagtgag gggtgacaac | 600 |
| aaggagtacg agtacagcgt ggaatgtcag gaggacagcg cctgtcccgc cgccgaggag | 660 |
| tcgctgccca tcgaggtgat ggtcgacgcg gtgcacaagc tcaaatacga gaattacacc | 720 |
| agcagcttct tcatcaggga catcatcaag cccgaccccc ccaagaacct gcagctgaag | 780 |
| cccttgaaga acagcaggca ggtggaggtg agctgggagt acccggacac ctggagcacc | 840 |
| ccccactcct acttcagcct gacgttctgt gtgcaggtgc aggggaagtc caagagggag | 900 |
| aagaaggacc gggtgttcac cgacaagacc agcgccaccg tgatatgccg caagaacgcg | 960 |
| tccatcagcg ttcgcgccca ggaccgctac tacagcagct cctggtccga atgggccagc | 1020 |
| gtgccctgca gcggtggagg gggcgggggc tccaggaatc tgccggtggc caccccgac | 1080 |
| cccgggatgt tcccgtgtct gcatcactcc agaacctgc tgcgggccgt gagcaatatg | 1140 |
| ctgcagaagg ccaggcagac gctcgagttc taccccctgca cctccgaaga gatcgaccat | 1200 |
| gaggacatca ccaaggacaa gaccagcacc gtggaggcct gcctcccct ggagctgacc | 1260 |
| aaaaacgaga gctgcctgaa ctccagggag accagcttta taaccaacgg cagctgcctc | 1320 |
| gcctccagga agacctcgtt tatgatggcc ctctgcctgt ccagcatcta cgaggacctg | 1380 |
| aagatgtacc aggtggagtt caagaccatg aacgcgaagt tgctcatgga ccccaagagg | 1440 |
| cagatcttcc tggaccagaa catgctcgcg gtgatcgacg agctgatgca agccctgaac | 1500 |
| ttcaacagcg agaccgtgcc ccagaagagc agcctggaag agcccgactt ctacaagacc | 1560 |
| aagatcaagc tgtgcatcct gctgcacgcc ttccggatcc gggccgtgac catcgacagg | 1620 |
| gtgatgagct acctcaacgc ctcctgataa taggctggag cctcggtggc catgcttctt | 1680 |

-continued

| | |
|---|---|
| gccccttggg cctcccccca gcccctcctc cccttcctgc acccgtaccc cccaaacacc | 1740 |
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 132
<211> LENGTH: 1890
<212> TYPE: DNA
<213> ORGANISM: Artificial Sequence
<220> FEATURE:
<223> OTHER INFORMATION: hIL12AB_038
<220> FEATURE:
<221> NAME/KEY: misc_feature
<222> LOCATION: (1)..(1)
<223> OTHER INFORMATION: 5' terminal guanosine cap

<400> SEQUENCE: 132

| | |
|---|---|
| ggggaaataa gagagaaaag aagagtaaga agaaatataa gagccaccat gtgccaccag | 60 |
| cagctcgtga tcagctggtt ctccctcgtc ttcctggcct cccgctggt ggccatctgg | 120 |
| gagctgaaga aggacgtgta cgtggtggag ctggactggt atcccgacgc ccccggcgag | 180 |
| atggtggtgc tgacgtgcga cacaccagaa gaggacggga tcacatggac cctggatcag | 240 |
| tcgtccgagg tgctggggag cggcaagacc ctcaccatcc aagtgaagga gttcggggac | 300 |
| gccggccagt acacctgcca caagggcggg gaggtgctct cccatagcct gctcctcctg | 360 |
| cacaaaaagg aggatggcat ctggagcacc gacatcctga aggaccagaa ggagcccaag | 420 |
| aacaagacat ttctcaggtg tgaggccaag aactattcgg gcaggtttac ctgttggtgg | 480 |
| ctcaccacca tctctaccga cctgacgttc tccgtcaagt caagcagggg gagctcggac | 540 |
| ccccagggg tgacatgtgg ggccgccacc ctgagcgcgg agcgtgtccg cggcgacaac | 600 |
| aaggagtacg agtattccgt ggagtgccag gaggacagcg cctgccccgc cgccgaggag | 660 |
| tccctgccca tagaggtgat ggtggacgcc gtccacaagt tgaagtacga aaattatacc | 720 |
| tcctcgttct tcattaggga catcatcaag cctgaccccc cgaagaacct acaactcaag | 780 |
| cccctcaaga actcccgcca ggtggaggtg tcctgggagt accccgacac ctggtccacc | 840 |
| ccgcacagct acttcagcct gaccttctgc gtgcaggtcc aggggaagag caagcgtgaa | 900 |
| aagaaagaca gggtgttcac cgacaagacg agcgccaccg tgatctgcag gaaaacgcc | 960 |
| tccatctccg tgcgcgccca ggacaggtac tacagtagct cctggagcga atgggccagc | 1020 |
| gtgccgtgca gcggcggggg aggaggcggc agtcgcaacc tgcccgtggc cacccccgac | 1080 |
| cccggcatgt tcccatgcct gcaccacagc cagaacctgc tgagggcagt cagcaatatg | 1140 |
| ctgcagaagg ccaggcagac cctggagttt tatccctgca ccagcgagga gatcgaccac | 1200 |
| gaggacatca ccaaggacaa gaccccacc gtcgaggcct gcctgccact ggagctgacc | 1260 |
| aaaaacgaga gctgcctgaa ctccagggag acctccttca tcaccaacgg gagctgcctg | 1320 |
| gccagccgga agaccagctt catgatggcg ctgtgcctca gcagcatcta cgaggatctc | 1380 |
| aagatgtacc aggtggagtt caagaccatg aacgcgaagc tgctgatgga ccccaagcgg | 1440 |
| cagatcttcc tggaccagaa catgctggcc gtgattgacg agctcatgca ggccctgaac | 1500 |
| ttcaatagcg agaccgtccc ccaaaagagc agcctggagg aacccgactt ctacaaaacg | 1560 |
| aagatcaagc tctgcatcct gctgcacgcc ttccggatcc gggccgtgac catcgatcgt | 1620 |
| gtgatgagct acctgaacgc ctcgtgataa taggctggag cctcggtggc catgcttctt | 1680 |

```
gccccttggg cctcccccca gccccctcctc cccttcctgc acccgtaccc cccaaacacc    1740
attgtcacac tccagtggtc tttgaataaa gtctgagtgg gcggcaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaatctag                                     1890

<210> SEQ ID NO 133
<211> LENGTH: 1890
<212> TYPE: DNA
<213> ORGANISM: Artificial Sequence
<220> FEATURE:
<223> OTHER INFORMATION: hIL12AB_039
<220> FEATURE:
<221> NAME/KEY: misc_feature
<222> LOCATION: (1)..(1)
<223> OTHER INFORMATION: 5' terminal guanosine cap

<400> SEQUENCE: 133
ggggaaataa gagagaaaag aagagtaaga agaaatataa gagccaccat gtgccaccag      60
cagctcgtca tctcctggtt tagcctggtg tttctggcct cccccctggt cgccatctgg     120
gagctgaaga agacgtgta cgtggtggag ctggactggt acccggacgc tcccggggag     180
atggtggtgc tgacctgcga caccccccgag gaggacggca tcacctggac cctgaccag     240 agctccgagg tgctggggag cggcaagacc ctgaccattc aggtgaaaga gttcggcgac     300
gccggccaat atacctgcca caggggggg gaggtcctgt cgcattccct gctgctgctt     360
cacaaaaagg aggatggcat ctggagcacc gacatcctga aggaccagaa agaacccaag     420
aacaagacgt tcctgcgctg cgaggccaag aactacagcg gccggttcac ctgttggtgg     480
ctgaccacca tctccaccga cctgactttc tcggtgaaga gcagccgcgg gagcagcgac     540
ccccagggag tgacctgcgg cgccgccacc ctgagcgccg aaagggtgag gggcgacaat     600
aaagagtacg agtattccgt ggagtgccag gaggacagcg cctgtcccgc cgccgaggag     660
tccctgccta tcgaggtgat ggtcgacgcg gtgcacaagc tcaagtacga aaactacacc     720
agcagctttt tcatcaggga tatcatcaaa ccagaccccc ccaagaacct gcagctgaag     780
cccctgaaaa acagcaggca ggtggaagtg agctgggaat accccgatac ctggtccacc     840
ccccacagct acttcagcct gaccttctgc gtgcaggtgc aggggaagtc caagcgggag     900
aagaaagatc gggtgttcac ggacaagacc agcgccaccg tgatttgcag gaaaaacgcc     960
agcatctccg tgagggctca ggacaggtac tacagctcca gctggagcga gtgggcctcc    1020 gtgcccttgca gcggggagg aggcggcggc agcaggaatc tgcccgtcgc aaccccgac    1080 cccggcatgt tccctgcct gcaccacagc cagaatctgc tgcgagccgt gagcaacatg    1140
ctccagaagg cccggcagac gctggagttc taccccctgca cctccgagga gatcgaccac    1200
gaggacatca ccaaggataa gacgagcacc gtcgaggcct gtctcccct ggagctcacc    1260 aagaacgagt cctgcctgaa tagcagggag acgtccttca taaccaacgg cagctgtctg    1320
gcgtccagga gaccagcttc catgatggcc ctctgcctga gctccatcta cgaggacctc    1380
aagatgtacc aggtcgagtt caagaccatg aacgcaaaac tgctcatgga tccaaagagg    1440
cagatctttc tggaccagaa catgctggcc gtgatcgatg aactcatgca ggccctgaat    1500
ttcaattccg agaccgtgcc ccagaagagc tccctggagg aacccgactt ctacaaaaca    1560
aagatcaagc tgtgtatcct cctgcacgcc ttcggatca gggccgtcac cattgaccgg    1620
gtgatgtcct acctgaacgc cagctgataa taggctggag cctcggtggc catgcttctt    1680
gccccttggg cctcccccca gccccctcctc cccttcctgc acccgtaccc cccaaacacc    1740
```

-continued

| | |
|---|---|
| attgtcacac tccagtggtc tttgaataaa gtctgagtgg gcggcaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaatctag | 1890 |

<210> SEQ ID NO 134
<211> LENGTH: 1890
<212> TYPE: DNA
<213> ORGANISM: Artificial Sequence
<220> FEATURE:
<223> OTHER INFORMATION: hIL12AB_040
<220> FEATURE:
<221> NAME/KEY: misc_feature
<222> LOCATION: (1)..(1)
<223> OTHER INFORMATION: 5' terminal guanosine cap

<400> SEQUENCE: 134

| | |
|---|---|
| ggggaaataa gagagaaaag aagagtaaga agaaatataa gagccaccat gtgccatcag | 60 |
| cagctggtga tcagctggtt cagcctcgtg ttcctcgcca gccccctcgt ggccatctgg | 120 |
| gagctgaaaa aggacgtgta cgtggtggag ctggactggt atcccgacgc cccgggcgag | 180 |
| atggtggtgc tgacctgcga cacccccgag gaggacggca ttacctggac actggaccag | 240 |
| agcagcgagg tcctgggcag cgggaagacc ctgacaattc aggtgaagga gttcggcgac | 300 |
| gccggacagt acacgtgcca aggggggga ggtgctgtg cccacagcct cctcctgctg | 360 |
| cacaagaagg aggatggcat ctggagcacc gacatcctga aggatcagaa ggagcccaag | 420 |
| aacaagacct ttctgagatg cgaggccaag aattacagcg ccgtttcac ctgctggtgg | 480 |
| ctcaccacca tcagcaccga cctgaccttc agcgtgaaat cctccagggg ctcctccgac | 540 |
| ccgcagggag tgacctgcgg cgccgccaca ctgagcgccg agcgggtcag aggggacaac | 600 |
| aaggagtacg agtacagcgt tgagtgccag gaggacagcg cctgtcccgc ggccgaggaa | 660 |
| tccctgccca tcgaggtgat ggtggacgca gtgcacaagc tgaagtacga gaactatacc | 720 |
| tcgagcttct tcatccggga tatcattaag cccgatcccc cgaagaacct gcagctcaaa | 780 |
| cccctgaaga acagcaggca ggtggaggtc tcctgggagt accccgacac atggtccacc | 840 |
| ccccattcct atttctccct gacctttgc gtgcaggtgc agggcaagag caagagggag | 900 |
| aaaaaggaca gggtgttcac cgacaagacc tccgccaccg tgatctgccg taagaacgct | 960 |
| agcatcagcg tcagggccca ggacaggtac tatagcagct cctggtccga gtgggccagc | 1020 |
| gtcccgtgca gcggcggggg cggtggaggc tccggaacc tccccgtggc accccggac | 1080 |
| cccgggatgt ttccctgcct gcatcacagc cagaacctgc tgagggccgt gtccaacatg | 1140 |
| ctgcagaagg ccaggcagac actcgagttt taccccctgca ccagcgagga atcgaccac | 1200 |
| gaagacatca ccaaggacaa gacctccacc gtggaggcat gctgcccct ggagctgacc | 1260 |
| aaaaacgaaa gctgtctgaa ctccagggag acctccttta tcacgaacgg ctcatgcctg | 1320 |
| gcctccagaa agaccagctt catgatggcc ctgtgcctga gctccatcta cgaggacttg | 1380 |
| aaaatgtacc aggtcgagtt caagaccatg aacgccaagc tgctcatgga ccccaaaagg | 1440 |
| cagatctttc tggaccagaa tatgctggcc gtgatcgacg agctcatgca agccctgaat | 1500 |
| ttcaacagcg agaccgtgcc ccagaagtcc tccctggagg agcccgactt ctacaagacc | 1560 |
| aagatcaagc tgtgcatact cctgcacgcg tttaggatca gggcggtgac catcgatagg | 1620 |
| gtgatgagct acctgaatgc ctcctgtaa taggctggag cctcggtggc catgcttctt | 1680 |
| gccccttggg cctcccccca gccctcctc cccttcctgc accgtaccc cccaaacacc | 1740 |

```
attgtcacac tccagtggtc tttgaataaa gtctgagtgg gcggcaaaaa aaaaaaaaaa      1800
aaaaaaaaaa aaaaaaaaaa aaaaaaaaaa aaaaaaaaaa aaaaaaaaaa aaaaaaaaaa      1860
aaaaaaaaaa aaaaaaaaaa aaaaatctag                                       1890

<210> SEQ ID NO 135
<211> LENGTH: 47
<212> TYPE: DNA
<213> ORGANISM: Artificial Sequence
<220> FEATURE:
<223> OTHER INFORMATION: 5'UTR-001 (Upstream UTR)

<400> SEQUENCE: 135
gggaaataag agagaaaaga agagtaagaa gaaatataag agccacc                    47

<210> SEQ ID NO 136
<211> LENGTH: 47
<212> TYPE: DNA
<213> ORGANISM: Artificial Sequence
<220> FEATURE:
<223> OTHER INFORMATION: 5'UTR-002 (Upstream UTR)

<400> SEQUENCE: 136
gggagatcag agagaaaaga agagtaagaa gaaatataag agccacc                    47

<210> SEQ ID NO 137
<211> LENGTH: 145
<212> TYPE: DNA
<213> ORGANISM: Artificial Sequence
<220> FEATURE:
<223> OTHER INFORMATION: 5'UTR-003 (Upstream UTR)

<400> SEQUENCE: 137
ggaataaaag tctcaacaca acatatacaa aacaaacgaa tctcaagcaa tcaagcattc      60
tacttctatt gcagcaattt aaatcatttc ttttaaagca aaagcaatttt tctgaaaatt    120 ttcaccattt acgaacgata gcaac                                            145

<210> SEQ ID NO 138
<211> LENGTH: 42
<212> TYPE: RNA
<213> ORGANISM: Artificial Sequence
<220> FEATURE:
<223> OTHER INFORMATION: 5'UTR-004 (Upstream UTR)

<400> SEQUENCE: 138
gggagacaag cuuggcauuc cgguacuguu gguaaagcca cc                         42

<210> SEQ ID NO 139
<211> LENGTH: 47
<212> TYPE: DNA
<213> ORGANISM: Artificial Sequence
<220> FEATURE:
<223> OTHER INFORMATION: 5'UTR-005 (Upstream UTR)

<400> SEQUENCE: 139
gggagatcag agagaaaaga agagtaagaa gaaatataag agccacc                    47

<210> SEQ ID NO 140
<211> LENGTH: 145
<212> TYPE: DNA
<213> ORGANISM: Artificial Sequence
<220> FEATURE:
<223> OTHER INFORMATION: 5'UTR-006 (Upstream UTR)

<400> SEQUENCE: 140
```

```
ggaataaaag tctcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gcaac                                        145
```

<210> SEQ ID NO 141
<211> LENGTH: 42
<212> TYPE: RNA
<213> ORGANISM: Artificial Sequence
<220> FEATURE:
<223> OTHER INFORMATION: 5'UTR-007 (Upstream UTR)

<400> SEQUENCE: 141

```
gggagacaag cuuggcauuc cgguacuguu gguaaagcca cc                       42
```

<210> SEQ ID NO 142
<211> LENGTH: 47
<212> TYPE: DNA
<213> ORGANISM: Artificial Sequence
<220> FEATURE:
<223> OTHER INFORMATION: 5'UTR-008 (Upstream UTR)

<400> SEQUENCE: 142

```
gggaattaac agagaaaaga agagtaagaa gaaatataag agccacc                  47
```

<210> SEQ ID NO 143
<211> LENGTH: 47
<212> TYPE: DNA
<213> ORGANISM: Artificial Sequence
<220> FEATURE:
<223> OTHER INFORMATION: 5'UTR-009 (Upstream UTR)

<400> SEQUENCE: 143

```
gggaaattag acagaaaaga agagtaagaa gaaatataag agccacc                  47
```

<210> SEQ ID NO 144
<211> LENGTH: 47
<212> TYPE: DNA
<213> ORGANISM: Artificial Sequence
<220> FEATURE:
<223> OTHER INFORMATION: 5'UTR-010 (Upstream UTR)

<400> SEQUENCE: 144

```
gggaaataag agagtaaaga acagtaagaa gaaatataag agccacc                  47
```

<210> SEQ ID NO 145
<211> LENGTH: 47
<212> TYPE: DNA
<213> ORGANISM: Artificial Sequence
<220> FEATURE:
<223> OTHER INFORMATION: 5'UTR-011 (Upstream UTR)

<400> SEQUENCE: 145

```
gggaaaaaag agagaaaaga agactaagaa gaaatataag agccacc                  47
```

<210> SEQ ID NO 146
<211> LENGTH: 47
<212> TYPE: DNA
<213> ORGANISM: Artificial Sequence
<220> FEATURE:
<223> OTHER INFORMATION: 5'UTR-012 (Upstream UTR)

<400> SEQUENCE: 146

```
gggaaataag agagaaaaga agagtaagaa gatatataag agccacc                  47
```

```
<210> SEQ ID NO 147
<211> LENGTH: 47
<212> TYPE: DNA
<213> ORGANISM: Artificial Sequence
<220> FEATURE:
<223> OTHER INFORMATION: 5'UTR-013 (Upstream UTR)

<400> SEQUENCE: 147
gggaaataag agacaaaaca agagtaagaa gaaatataag agccacc        47

<210> SEQ ID NO 148
<211> LENGTH: 47
<212> TYPE: DNA
<213> ORGANISM: Artificial Sequence
<220> FEATURE:
<223> OTHER INFORMATION: 5'UTR-014 (Upstream UTR)

<400> SEQUENCE: 148
gggaaattag agagtaaaga acagtaagta gaattaaaag agccacc        47

<210> SEQ ID NO 149
<211> LENGTH: 47
<212> TYPE: DNA
<213> ORGANISM: Artificial Sequence
<220> FEATURE:
<223> OTHER INFORMATION: 5'UTR-015 (Upstream UTR)

<400> SEQUENCE: 149
gggaaataag agagaataga agagtaagaa gaaatataag agccacc        47

<210> SEQ ID NO 150
<211> LENGTH: 47
<212> TYPE: DNA
<213> ORGANISM: Artificial Sequence
<220> FEATURE:
<223> OTHER INFORMATION: 5'UTR-016 (Upstream UTR)

<400> SEQUENCE: 150
gggaaataag agagaaaaga agagtaagaa gaaaattaag agccacc        47

<210> SEQ ID NO 151
<211> LENGTH: 47
<212> TYPE: DNA
<213> ORGANISM: Artificial Sequence
<220> FEATURE:
<223> OTHER INFORMATION: 5'UTR-017 (Upstream UTR)

<400> SEQUENCE: 151
gggaaataag agagaaaaga agagtaagaa gaaatttaag agccacc        47

<210> SEQ ID NO 152
<211> LENGTH: 92
<212> TYPE: DNA
<213> ORGANISM: Artificial Sequence
<220> FEATURE:
<223> OTHER INFORMATION: 5'UTR-018 (Upstream UTR)

<400> SEQUENCE: 152
tcaagctttt ggaccctcgt acagaagcta atacgactca ctatagggaa ataagagaga   60
aaagaagagt aagaagaaat ataagagcca cc                                 92

<210> SEQ ID NO 153
<211> LENGTH: 142
<212> TYPE: DNA
<213> ORGANISM: Artificial Sequence
```

```
<220> FEATURE:
<223> OTHER INFORMATION: 142-3p 5'UTR-001 (Upstream UTR including
      miR142-3p)

<400> SEQUENCE: 153
tgataatagt ccataaagta ggaaacacta cagctggagc ctcggtggcc atgcttcttg      60 cccccttgggc ctcccccccag ccctcctcc ccttcctgca cccgtacccc cgtggtcttt    120
gaataaagtc tgagtgggcg gc                                              142

<210> SEQ ID NO 154
<211> LENGTH: 142
<212> TYPE: DNA
<213> ORGANISM: Artificial Sequence
<220> FEATURE:
<223> OTHER INFORMATION: 142-3p 5'UTR-002 (Upstream UTR including
      miR142-3p)

<400> SEQUENCE: 154
tgataatagg ctggagcctc ggtggctcca taaagtagga aacactacac atgcttcttg      60 cccccttgggc ctcccccccag ccctcctcc ccttcctgca cccgtacccc cgtggtcttt    120
gaataaagtc tgagtgggcg gc                                              142

<210> SEQ ID NO 155
<211> LENGTH: 142
<212> TYPE: DNA
<213> ORGANISM: Artificial Sequence
<220> FEATURE:
<223> OTHER INFORMATION: 142-3p 5'UTR-003 (Upstream UTR including
      miR142-3p)

<400> SEQUENCE: 155
tgataatagg ctggagcctc ggtggccatg cttcttgccc cttccataaa gtaggaaaca      60
ctacatgggc ctcccccccag ccctcctcc ccttcctgca cccgtacccc cgtggtcttt    120
gaataaagtc tgagtgggcg gc                                              142

<210> SEQ ID NO 156
<211> LENGTH: 142
<212> TYPE: DNA
<213> ORGANISM: Artificial Sequence
<220> FEATURE:
<223> OTHER INFORMATION: 142-3p 5'UTR-004 (Upstream UTR including
      miR142-3p)

<400> SEQUENCE: 156
tgataatagg ctggagcctc ggtggccatg cttcttgccc cttgggcctc ccccagtcc       60 ataaagtagg aaacactaca cccctcctcc ccttcctgca cccgtacccc cgtggtcttt    120
gaataaagtc tgagtgggcg gc                                              142

<210> SEQ ID NO 157
<211> LENGTH: 142
<212> TYPE: DNA
<213> ORGANISM: Artificial Sequence
<220> FEATURE:
<223> OTHER INFORMATION: 142-3p 5'UTR-005 (Upstream UTR including
      miR142-3p)

<400> SEQUENCE: 157
tgataatagg ctggagcctc ggtggccatg cttcttgccc cttgggcctc ccccagccc       60 ctcctcccct tctccataaa gtaggaaaca ctacactgca cccgtacccc cgtggtcttt    120
gaataaagtc tgagtgggcg gc                                              142
```

```
<210> SEQ ID NO 158
<211> LENGTH: 142
<212> TYPE: DNA
<213> ORGANISM: Artificial Sequence
<220> FEATURE:
<223> OTHER INFORMATION: 142-3p 5'UTR-006 (Upstream UTR including
      miR142-3p)

<400> SEQUENCE: 158
tgataatagg ctggagcctc ggtggccatg cttcttgccc cttgggcctc ccccagccc      60 ctcctcccct tcctgcaccc gtaccccctc cataaagtag gaaacactac agtggtcttt    120
gaataaagtc tgagtgggcg gc                                             142

<210> SEQ ID NO 159
<211> LENGTH: 142
<212> TYPE: DNA
<213> ORGANISM: Artificial Sequence
<220> FEATURE:
<223> OTHER INFORMATION: 142-3p 5'UTR-007 (Upstream UTR including
      miR142-3p)

<400> SEQUENCE: 159
tgataatagg ctggagcctc ggtggccatg cttcttgccc cttgggcctc ccccagccc      60 ctcctcccct tcctgcaccc gtaccccccgt ggtctttgaa taaagttcca taaagtagga  120
aacactacac tgagtgggcg gc                                             142

<210> SEQ ID NO 160
<211> LENGTH: 371
<212> TYPE: DNA
<213> ORGANISM: Artificial Sequence
<220> FEATURE:
<223> OTHER INFORMATION: 3'UTR-001 (Creatine Kinase UTR)

<400> SEQUENCE: 160
gcgcctgccc acctgccacc gactgctgga acccagccag tgggagggcc tggcccacca     60
gagtcctgct ccctcactcc tcgccccgcc ccctgtccca gagtcccacc tgggggctct   120
ctccacccct ctcagagttc cagtttcaac cagagttcca accaatgggc tccatcctct   180
ggattctggc caatgaaata tctccctggc agggtcctct tcttttccca gagctccacc   240
ccaaccagga gctctagtta atggagagct cccagcacac tcggagcttg tgctttgtct   300
ccacgcaaag cgataaataa aagcattggt ggcctttggt ctttgaataa agcctgagta   360
ggaagtctag a                                                         371

<210> SEQ ID NO 161
<211> LENGTH: 568
<212> TYPE: DNA
<213> ORGANISM: Artificial Sequence
<220> FEATURE:
<223> OTHER INFORMATION: 3'UTR-002 (Myoglobin UTR)

<400> SEQUENCE: 161 gccccctgccg ctcccacccc cacccatctg ggccccgggt tcaagagaga gcggggtctg   60
atctcgtgta gccatataga gtttgcttct gagtgtctgc tttgtttagt agaggtgggc   120
aggaggagct gaggggctgg ggctggggtg ttgaagttgg ctttgcatgc ccagcgatgc   180
gcctccctgt gggatgtcat caccctggga accgggagtg gcccttggct cactgtgttc   240
tgcatggttt ggatctgaat taattgtcct ttcttctaaa tcccaaccga acttcttcca   300
```

```
acctccaaac tggctgtaac cccaaatcca agccattaac tacacctgac agtagcaatt     360
gtctgattaa tcactggccc cttgaagaca gcagaatgtc cctttgcaat gaggaggaga     420
tctgggctgg gcgggccagc tggggaagca tttgactatc tggaacttgt gtgtgcctcc     480
tcaggtatgg cagtgactca cctggtttta ataaaacaac ctgcaacatc tcatggtctt     540
tgaataaagc ctgagtagga agtctaga                                        568
```

<210> SEQ ID NO 162
<211> LENGTH: 289
<212> TYPE: DNA
<213> ORGANISM: Artificial Sequence
<220> FEATURE:
<223> OTHER INFORMATION: 3'UTR-003 (alpha-actin UTR)

<400> SEQUENCE: 162

```
acacactcca cctccagcac gcgacttctc aggacgacga atcttctcaa tggggggggcg     60 gctgagctcc agccaccccg cagtcacttt ctttgtaaca acttccgttg ctgccatcgt    120
aaactgacac agtgtttata acgtgtacat acattaactt attacctcat tttgttattt    180
ttcgaaacaa agccctgtgg aagaaaatgg aaaacttgaa gaagcattaa agtcattctg    240
ttaagctgcg taaatggtct ttgaataaag cctgagtagg aagtctaga               289
```

<210> SEQ ID NO 163
<211> LENGTH: 379
<212> TYPE: DNA
<213> ORGANISM: Artificial Sequence
<220> FEATURE:
<223> OTHER INFORMATION: 3'UTR-004 (Albumin UTR)

<400> SEQUENCE: 163

```
catcacattt aaaagcatct cagcctacca tgagaataag agaaagaaaa tgaagatcaa     60
aagcttattc atctgttttt cttttttcgtt ggtgtaaagc caacaccctg tctaaaaaac   120
ataaatttct ttaatcattt tgcctctttt ctctgtgctt caattaataa aaatgaaa     180 gaatctaata gagtggtaca gcactgttat ttttcaaaga tgtgttgcta tcctgaaaat    240
tctgtaggtt ctgtggaagt tccagtgttc tctcttattc cacttcggta gaggatttct    300
agtttcttgt gggctaatta ataaatcat taatactctt ctaatggtct ttgaataaag    360
cctgagtagg aagtctaga                                                 379
```

<210> SEQ ID NO 164
<211> LENGTH: 118
<212> TYPE: DNA
<213> ORGANISM: Artificial Sequence
<220> FEATURE:
<223> OTHER INFORMATION: 3'UTR-005 (alpha-globin UTR)

<400> SEQUENCE: 164

```
gctgccttct gcggggcttg ccttctggcc atgcccttct tctctccctt gcacctgtac     60
ctcttggtct ttgaataaag cctgagtagg aaggcggccg ctcgagcatg catctaga    118
```

<210> SEQ ID NO 165
<211> LENGTH: 908
<212> TYPE: DNA
<213> ORGANISM: Artificial Sequence
<220> FEATURE:
<223> OTHER INFORMATION: 3'UTR-006 (G-CSF UTR)

<400> SEQUENCE: 165

```
gccaagccct cccccatccca tgtatttatc tctatttaat atttatgtct atttaagcct     60
```

```
catatttaaa gacagggaag agcagaacgg agccccaggc ctctgtgtcc ttccctgcat      120
ttctgagttt cattctcctg cctgtagcag tgagaaaaag ctcctgtcct cccatccct       180 ggactgggag gtagataggt aaataccaag tatttattac tatgactgct ccccagccct      240
ggctctgcaa tgggcactgg gatgagccgc tgtgagcccc tggtcctgag ggtccccacc      300 tgggacctt gagagtatca ggtctcccac gtgggagaca agaaatccct gtttaatatt       360
taaacagcag tgttccccat ctgggtcctt gcacccctca ctctggcctc agccgactgc      420
acagcggccc ctgcatcccc ttggctgtga ggcccctgga caagcagagg tggccagagc      480
tgggaggcat ggccctgggg tcccacgaat tgctgggga atctcgtttt tcttcttaag       540
acttttggga catggtttga ctcccgaaca tcaccgacgc gtctcctgtt tttctgggtg      600
gcctcgggac acctgccctg cccccacgag ggtcaggact gtgactcttt ttagggccag      660
gcaggtgcct ggacatttgc cttgctggac ggggactggg gatgtgggag ggagcagaca      720
ggaggaatca tgtcaggcct gtgtgtgaaa ggaagctcca ctgtcaccct ccacctcttc      780 acccccact caccagtgtc ccctccactg tcacattgta actgaacttc aggataataa      840
agtgtttgcc tccatggtct ttgaataaag cctgagtagg aaggcggccg ctcgagcatg      900
catctaga                                                              908
```

<210> SEQ ID NO 166
<211> LENGTH: 835
<212> TYPE: DNA
<213> ORGANISM: Artificial Sequence
<220> FEATURE:
<223> OTHER INFORMATION: 3'UTR-007 (Col1a2; collagen, type I, alpha 2
      UTR)

<400> SEQUENCE: 166

```
actcaatcta aattaaaaaa gaaagaaatt tgaaaaaact ttctctttgc catttcttct       60 tcttctttt taactgaaag ctgaatcctt ccatttcttc tgcacatcta cttgcttaaa      120
ttgtgggcaa aagagaaaaa gaaggattga tcagagcatt gtgcaataca gtttcattaa      180
ctccttcccc cgctccccca aaatttgaa ttttttttc aacactctta cacctgttat       240
ggaaaatgtc aacctttgta agaaaaccaa ataaaaatt gaaaaataaa aaccataaac      300
atttgcacca cttgtggctt ttgaatatct tccacagagg gaagtttaaa acccaaactt      360
ccaaaggttt aaactacctc aaaacacttt cccatgagtg tgatccacat tgttaggtgc      420
tgacctagac agagatgaac tgaggtcctt gttttgtttt gttcataata caaaggtgct      480
aattaatagt atttcagata cttgaagaat gttgatggtg ctagaagaat ttgagaagaa      540
atactcctgt attgagttgt atcgtgtggt gtattttta aaaatttga tttagcattc       600 atattttcca tcttattccc aattaaaagt atgcagatta tttgcccaaa tcttcttcag      660
attcagcatt tgttctttgc cagtctcatt ttcatcttct tccatggttc cacagaagct      720
ttgtttcttg ggcaagcaga aaaattaaat tgtacctatt ttgtatatgt gagatgttta      780
aataaattgt gaaaaaatg aaataaagca tgtttggttt tccaaaagaa catat          835
```

<210> SEQ ID NO 167
<211> LENGTH: 297
<212> TYPE: DNA
<213> ORGANISM: Artificial Sequence
<220> FEATURE:
<223> OTHER INFORMATION: 3'UTR-008 (Col6a2; collagen, type VI, alpha 2
      UTR)

<400> SEQUENCE: 167

```
cgccgccgcc cgggccccgc agtcgagggt cgtgagccca ccccgtccat ggtgctaagc    60
gggcccgggt cccacacggc cagcaccgct gctcactcgg acgacgccct gggcctgcac   120
ctctccagct cctcccacgg ggtccccgta gccccggccc ccgcccagcc ccaggtctcc   180
ccaggccctc cgcaggctgc ccggcctccc tcccctgca gccatcccaa ggctcctgac    240
ctacctggcc cctgagctct ggagcaagcc ctgacccaat aaaggctttg aacccat       297
```

<210> SEQ ID NO 168
<211> LENGTH: 602
<212> TYPE: DNA
<213> ORGANISM: Artificial Sequence
<220> FEATURE:
<223> OTHER INFORMATION: 3'UTR-009 (RPN1; ribophorin I UTR)

<400> SEQUENCE: 168

```
ggggctagag ccctctccgc acagcgtgga gacggggcaa ggaggggggt tattaggatt    60
ggtggttttg ttttgctttg tttaaagccg tgggaaaatg gcacaacttt acctctgtgg   120
gagatgcaac actgagagcc aaggggtggg agttgggata attttatat aaaagaagtt    180
tttccacttt gaattgctaa aagtggcatt tttcctatgt gcagtcactc ctctcatttc   240
taaaataggg acgtggccag gcacggtggc tcatgcctgt aatcccagca ctttgggagg   300
ccgaggcagg cggctcacga ggtcaggaga tcgagactat cctggctaac acggtaaaac   360
cctgtctcta ctaaaagtac aaaaaattag ctgggcgtgg tggtgggcac ctgtagtccc   420
agctactcgg gaggctgagg caggagaaag gcatgaatcc aagaggcaga gcttgcagtg   480
agctgagatc acgccattgc actccagcct gggcaacagt gttaagactc tgtctcaaat   540
ataaataaat aaataaataa ataaataaat aaataaaaat aaagcgagat gttgccctca   600
aa                                                                  602
```

<210> SEQ ID NO 169
<211> LENGTH: 785
<212> TYPE: DNA
<213> ORGANISM: Artificial Sequence
<220> FEATURE:
<223> OTHER INFORMATION: 3'UTR-010 (LRP1; low density lipoprotein
      receptor-related protein 1 UTR)

<400> SEQUENCE: 169

```
ggccctgccc cgtcggactg cccccagaaa gcctcctgcc ccctgccagt gaagtccttc    60
agtgagcccc tccccagcca gcccttccct ggccccgccg gatgtataaa tgtaaaaatg   120
aaggaattac attttatatg tgagcgagca agccggcaag cgagcacagt attatttctc   180
catcccctcc ctgcctgctc cttggcaccc ccatgctgcc ttcagggaga caggcaggga   240
gggcttgggg ctgcacctcc taccctccca ccagaacgca ccccactggg agagctggtg   300
gtgcagcctt cccctccctg tataagacac tttgccaagg ctctcccctc tcgccccatc   360
cctgcttgcc cgctcccaca gcttcctgag ggctaattct gggaagggag agttctttgc   420
tgccctgtc tggaagacgt ggctctgggt gaggtaggcg ggaaaggatg gagtgtttta   480
gttcttgggg gaggccaccc caaacccag ccccaactcc aggggcacct atgagatggc   540
catgctcaac cccctccca gacaggccct cctgtctcc agggcccca ccgaggttcc   600
cagggctgga gacttcctct ggtaaacatt cctccagcct cccctcccct gggacgcca    660
aggaggtggg ccacacccag gaagggaaag cgggcagccc cgttttgggg acgtgaacgt   720
```

```
tttaataatt tttgctgaat tcctttacaa ctaaataaca cagatattgt tataaataaa    780
attgt                                                                785

<210> SEQ ID NO 170
<211> LENGTH: 3001
<212> TYPE: DNA
<213> ORGANISM: Artificial Sequence
<220> FEATURE:
<223> OTHER INFORMATION: 3'UTR-011 (Nnt1; cardiotrophin-like cytokine
      factor 1 UTR)

<400> SEQUENCE: 170
atattaagga tcaagctgtt agctaataat gccacctctg cagttttggg aacaggcaaa     60
taaagtatca gtatacatgg tgatgtacat ctgtagcaaa gctcttggag aaaatgaaga   120
ctgaagaaag caaagcaaaa actgtataga gagattttcc aaaagcagta atccctcaat   180
tttaaaaaag gattgaaaat tctaaatgtc tttctgtgca tattttttgt gttaggaatc   240
aaaagtattt tataaaagga gaaagaacag cctcattttta gatgtagtcc tgttggattt   300
tttatgcctc ctcagtaacc agaaatgttt taaaaaacta agtgtttagg atttcaagac   360
aacattatac atggctctga atatctgac acaatgtaaa cattgcaggc acctgcattt    420
tatgtttttt ttttcaacaa atgtgactaa tttgaaactt ttatgaactt ctgagctgtc   480
cccttgcaat tcaaccgcag tttgaattaa tcatatcaaa tcagttttaa ttttttaaat   540
tgtacttcag agtctatatt tcaagggcac attttctcac tactatttta atacattaaa   600
ggactaaata atcttttcaga gatgctggaa acaaatcatt tgctttatat gtttcattag   660
aataccaatg aaacatacaa cttgaaaatt agtaatagta ttttttgaaga tcccatttct   720 aattggagat ctctttaatt tcgatcaact tataatgtgt agtactatat taagtgcact   780
tgagtggaat tcaacatttg actaataaaa tgagttcatc atgttggcaa gtgatgtggc   840
aattatctct ggtgacaaaa gagtaaaatc aaatatttct gcctgttaca aatatcaagg   900
aagacctgct actatgaaat agatgacatt aatctgtctt cactgtttat aatacggatg   960 gattttttt caaatcagtg tgtgttttga ggtcttatgt aattgatgac atttgagaga   1020
aatggtggct ttttttagct acctctttgt tcatttaagc accagtaaag atcatgtctt   1080
tttatagaag tgtagatttt ctttgtgact ttgctatcgt gcctaaagct ctaaatatag   1140
gtgaatgtgt gatgaatact cagattattt gtctctctat ataattagtt tggtactaag   1200
tttctcaaaa aattattaac acatgaaaga caatctctaa accagaaaaa gaagtagtac   1260
aaattttgtt actgtaatgc tcgcgtttag tgagtttaaa acacacagta tcttttggtt   1320
ttataatcag tttctatttt gctgtgcctg agattaagat ctgtgtatgt gtgtgtgtgt   1380
gtgtgtgcgt ttgtgtgtta aagcagaaaa gactttttta aaagttttaa gtgataaatg   1440
caatttgtta attgatctta gatcactagt aaactcaggg ctgaattata ccatgtatat   1500
tctattagaa gaaagtaaac accatcttta ttcctgccct tttcttctc tcaaagtagt    1560 tgtagttata tctagaaaga agcaattttg atttcttgaa aaggtagttc ctgcactcag   1620
tttaaactaa aaataatcat acttggattt tatttatttt tgtcatagta aaaattttaa   1680
tttatatata ttttttattta gtattatctt attctttgct atttgccaat cctttgtcat   1740
caattgtgtt aaatgaattg aaaattcatg ccctgttcat tttatttttac tttattggtt   1800 aggatatttta aaggattttt gtatatataa tttcttaaat taatattcca aaaggttagt   1860
ggacttagat tataaattat ggcaaaaatc taaaaacaac aaaaatgatt tttatacatt   1920
```

-continued

```
ctatttcatt attcctcttt ttccaataag tcatacaatt ggtagatatg acttattta      1980
tttttgtatt attcactata tctttatgat atttaagtat aaataattaa aaaaattat      2040
tgtaccttat agtctgtcac caaaaaaaaa aaattatctg taggtagtga aatgctaatg      2100
ttgatttgtc tttaagggct tgttaactat cctttatttt ctcatttgtc ttaaattagg      2160
agtttgtgtt taaattactc atctaagcaa aaaatgtata taaatcccat tactgggtat      2220
atacccaaag gattataaat catgctgcta taaagacaca tgcacacgta tgtttattgc      2280
agcactattc acaatagcaa agacttggaa ccaacccaaa tgtccatcaa tgatagactt      2340
gattaagaaa atgtgcacat atacaccatg gaatactatg cagccataaa aaaggatgag      2400
ttcatgtcct ttgtagggac atggataaag ctggaaacca tcattctgag caaactattg      2460
caaggacaga aaaccaaaca ctgcatgttc tcactcatag gtgggaattg aacaatgaga      2520
acacttggac acaaggtggg gaacaccaca caccagggcc tgtcatgggg tgggggagt       2580
ggggagggat agcattagga gatataccta atgtaaatga tgagttaatg ggtgcagcac      2640
accaacatgg cacatgtata catatgtagc aaacctgcac gttgtgcaca tgtaccctag      2700
aacttaaagt ataattaaaa aaaaaagaa aacagaagct atttataaag aagttatttg       2760
ctgaaataaa tgtgatcttt cccattaaaa aaataaagaa attttggggt aaaaaaacac      2820
aatatattgt attcttgaaa aattctaaga gagtggatgt gaagtgttct caccacaaaa      2880
gtgataacta attgaggtaa tgcacatatt aattagaaag attttgtcat tccacaatgt      2940
atatatactt aaaaatatgt tatacacaat aaatacatac attaaaaaat aagtaaatgt      3000
a                                                                     3001
```

<210> SEQ ID NO 171
<211> LENGTH: 1037
<212> TYPE: DNA
<213> ORGANISM: Artificial Sequence
<220> FEATURE:
<223> OTHER INFORMATION: 3'UTR-012 (Col6a1; collagen, type VI, alpha 1
      UTR)

<400> SEQUENCE: 171

```
cccaccctgc acgccggcac caaaccctgt cctcccaccc ctccccactc atcactaaac        60
agagtaaaat gtgatgcgaa ttttcccgac caacctgatt cgctagattt ttttttaagga     120
aaaagcttgga aagccaggac acaacgctgc tgcctgcttt gtgcagggtc ctccggggct      180
cagccctgag ttggcatcac ctgcgcaggg ccctctgggg ctcagccctg agctagtgtc      240
acctgcacag ggccctctga ggctcagccc tgagctggcg tcacctgtgc agggccctct      300
ggggctcagc cctgagctgg cctcacctgg gttccccacc ccgggctctc ctgccctgcc      360
ctcctgcccg ccctccctcc tgcctgcgca gctccttccc taggcacctc tgtgctgcat      420
cccaccagcc tgagcaagac gccctctcgg ggcctgtgcc gcactagcct ccctctcctc      480
tgtccccata gctggttttt cccaccaatc ctcacctaac agttactta caattaaact       540
caaagcaagc tcttctcctc agcttggggc agccattggc ctctgtctcg ttttgggaaa      600
ccaaggtcag gaggccgttg cagacataaa tctcggcgac tcggcccgt ctcctgaggg       660
tcctgctggt gaccggcctg gaccttggcc ctacagccct ggaggccgct gctgaccagc      720
actgaccccg acctcagaga gtactcgcag gggcgctggc tgcactcaag ccctcgaga      780
ttaacggtgc taacccgtc tgctcctccc tcccgcagag actggggcct ggactggaca      840
tgagagcccc ttggtgccac agagggctgt gtcttactag aaacaacgca aacctctcct      900
```

```
tcctcagaat agtgatgtgt tcgacgtttt atcaaaggcc ccctttctat gttcatgtta      960
gttttgctcc ttctgtgttt ttttctgaac catatccatg ttgctgactt ttccaaataa     1020
aggttttcac tcctctc                                                    1037

<210> SEQ ID NO 172
<211> LENGTH: 577
<212> TYPE: DNA
<213> ORGANISM: Artificial Sequence
<220> FEATURE:
<223> OTHER INFORMATION: 3'UTR-013 (Calr; calreticulin UTR)

<400> SEQUENCE: 172
agaggcctgc ctccagggct ggactgaggc ctgagcgctc ctgccgcaga gctggccgcg       60
ccaaataatg tctctgtgag actcgagaac tttcattttt ttccaggctg gttcggattt      120
ggggtggatt ttggttttgt tccctcctc cactctcccc cacccctcc ccgccctttt       180 tttttttttt ttttaaactg gtattttatc tttgattctc cttcagccct cacccctggt      240
tctcatcttt cttgatcaac atcttttctt gcctctgtcc ccttctctca tctcttagct      300
cccctccaac ctgggggca gtggtgtgga aagccacag gcctgagatt tcatctgctc       360
tccttcctgg agcccagagg agggcagcag aaggggggtgg tgtctccaac cccccagcac     420
tgaggaagaa cggggctctt ctcatttcac ccctcccttt ctcccctgcc cccaggactg      480
ggccacttct gggtggggca gtgggtccca gattggctca cactgagaat gtaagaacta      540
caaacaaaat ttctattaaa ttaaattttg tgtctcc                               577

<210> SEQ ID NO 173
<211> LENGTH: 2212
<212> TYPE: DNA
<213> ORGANISM: Artificial Sequence
<220> FEATURE:
<223> OTHER INFORMATION: 3'UTR-014 (Col1a1; collagen, type I, alpha 1
     UTR)

<400> SEQUENCE: 173
ctccctccat cccaacctgg ctccctccca cccaaccaac tttccccca acccggaaac       60 agacaagcaa cccaaactga accccctcaa aagccaaaaa atgggagaca atttcacatg      120
gactttggaa aatattttt tccttgcat tcatctctca aacttagttt ttatctttga       180
ccaaccgaac atgaccaaaa accaaaagtg cattcaacct taccaaaaaa aaaaaaaaaa      240
aaagaataaa taataactt tttaaaaaag gaagcttggt ccacttgctt gaagacccat      300 gcggggtaa gtcccttct gccgttggg cttatgaaac cccaatgctg ccctttctgc       360
tcctttctcc acaccccct tggggcctcc cctccactcc ttcccaaatc tgtctcccca     420
gaagacacag gaaacaatgt attgtctgcc cagcaatcaa aggcaatgct caaacaccca      480
agtggccccc accctcagcc cgctcctgcc cgcccagcac cccaggcccc tggggaccct     540 gggggttctca gactgccaaa gaagccttgc catctggcgc tcccatggct cttgcaacat    600 ctcccctttcg tttttgaggg ggtcatgccg ggggagccac cagcccctca ctgggttcgg    660
aggagagtca ggaagggcca cgacaaagca gaaacatcgg atttggggaa cgcgtgtcaa     720
tcccttgtgc cgcagggctg ggcgggagag actgttctgt tccttgtgta actgtgttgc    780
tgaaagacta cctcgttctt gtcttgatgt gtcaccgggg caactgcctg gggcggggga    840
tgggggcagg gtgaagcgg ctccccattt tataccaaag gtgctacatc tatgtgatgg    900
gtggggtggg gagggaatca ctggtgctat agaaattgag atgcccccc aggccagcaa    960
```

-continued

| | |
|---|---|
| atgttccttt tgttcaaag tctatttta ttccttgata ttttctttt ttttttttt | 1020 |
| ttttgtgga tggggacttg tgaatttttc taaaggtgct atttaacatg ggaggagagc | 1080 |
| gtgtgcggct ccagcccagc ccgctgctca ctttccaccc tctctccacc tgcctctggc | 1140 |
| ttctcaggcc tctgctctcc gacctctctc tctgaaacc ctcctccaca gctgcagccc | 1200 |
| atcctcccgg ctccctccta gtctgtcctg cgtcctctgt ccccgggttt cagagacaac | 1260 |
| ttcccaaagc acaaagcagt ttttccccct aggggtggga ggaagcaaaa gactctgtac | 1320 |
| ctattttgta tgtgtataat aatttgagat gttttaatt attttgattg ctggaataaa | 1380 |
| gcatgtggaa atgacccaaa cataatccgc agtggcctcc taatttcctt ctttggagtt | 1440 |
| ggggagggg tagacatggg gaaggggctt tggggtgatg ggcttgcctt ccattcctgc | 1500 |
| cctttccctc cccactattc tcttctagat ccctccataa ccccactccc ctttctctca | 1560 |
| cccttcttat accgcaaacc tttctacttc ctctttcatt ttctattctt gcaatttcct | 1620 |
| tgcaccttt ccaaatcctc ttctcccctg caataccata caggcaatcc acgtgcacaa | 1680 |
| cacacacaca cactcttcac atctggggtt gtccaaacct catacccact ccccttcaag | 1740 |
| cccatccact ctccaccccc tggatgccct gcacttggtg gcggtgggat gctcatggat | 1800 |
| actgggaggg tgaggggagt ggaacccgtg aggaggacct gggggcctct ccttgaactg | 1860 |
| acatgaaggg tcatctggcc tctgctccct tctcacccac gctgacctcc tgccgaagga | 1920 |
| gcaacgcaac aggagagggg tctgctgagc ctggcgaggg tctgggaggg accaggagga | 1980 |
| aggcgtgctc cctgctcgct gtcctggccc tgggggagtg agggagacag acacctggga | 2040 |
| gagctgtggg gaaggcactc gcaccgtgct cttgggaagg aaggagacct ggccctgctc | 2100 |
| accacggact gggtgcctcg acctcctgaa tccccagaac acaaccccc tgggctgggg | 2160 |
| tggtctgggg aaccatcgtg ccccgcctc ccgcctactc ctttttaagc tt | 2212 |

<210> SEQ ID NO 174
<211> LENGTH: 729
<212> TYPE: DNA
<213> ORGANISM: Artificial Sequence
<220> FEATURE:
<223> OTHER INFORMATION: 3'UTR-015 (Plod1; procollagen-lysine,
2-oxoglutarate 5-dioxygenase 1 UTR)

<400> SEQUENCE: 174

| | |
|---|---|
| ttggccaggc ctgaccctct tggacctttc ttctttgccg acaaccactg cccagcagcc | 60 |
| tctgggacct cggggtccca gggaacccag tccagcctcc tggctgttga cttcccattg | 120 |
| ctcttggagc caccaatcaa agagattcaa agagattcct gcaggccaga ggcggaacac | 180 |
| acctttatgg ctggggctct ccgtggtgtt ctggacccag cccctggaga caccattcac | 240 |
| ttttactgct ttgtagtgac tcgtgctctc caacctgtct tcctgaaaaa ccaaggcccc | 300 |
| cttccccac ctcttccatg gggtgagact tgagcagaac aggggcttcc ccaagttgcc | 360 |
| cagaaagact gtctgggtga aagccatgg ccagagcttc tcccaggcac aggtgttgca | 420 |
| ccagggactt ctgcttcaag ttttggggta aagacacctg gatcagactc caagggctgc | 480 |
| cctgagtctg ggacttctgc ctccatggct ggtcatgaga gcaaaccgta gtcccctgga | 540 |
| gacagcgact ccagagaacc tcttgggaga cagaagaggc atctgtgcac agctcgatct | 600 |
| tctacttgcc tgtggggagg ggagtgacag gtccacacac cacactgggt caccctgtcc | 660 |
| tggatgcctc tgaagagagg gacagaccgt cagaaactgg agagtttcta ttaaaggtca | 720 |
| tttaaacca | 729 |

<210> SEQ ID NO 175
<211> LENGTH: 847
<212> TYPE: DNA
<213> ORGANISM: Artificial Sequence
<220> FEATURE:
<223> OTHER INFORMATION: 3'UTR-016 (Nucb1; nucleobindin 1 UTR)

<400> SEQUENCE: 175

| | | |
|---|---|---|
| tcctccggga ccccagccct caggattcct gatgctccaa ggcgactgat gggcgctgga | 60 |
| tgaagtggca cagtcagctt ccctgggggc tggtgtcatg ttgggctcct ggggcggggg | 120 |
| cacggcctgg catttcacgc attgctgcca ccccaggtcc acctgtctcc actttcacag | 180 |
| cctccaagtc tgtggctctt cccttctgtc ctccgagggg cttgccttct ctcgtgtcca | 240 |
| gtgaggtgct cagtgatcgg cttaacttag agaagcccgc cccctcccct tctccgtctg | 300 |
| tcccaagagg gtctgctctg agcctgcgtt cctaggtggc tcggcctcag ctgcctgggt | 360 |
| tgtggccgcc ctagcatcct gtatgcccac agctactgga atccccgctg ctgctccggg | 420 |
| ccaagcttct ggttgattaa tgagggcatg gggtggtccc tcaagacctt cccctacctt | 480 |
| ttgtggaacc agtgatgcct caaagacagt gtcccctcca cagctgggtg ccaggggcag | 540 |
| gggatcctca gtatagccgg tgaaccctga taccaggagc ctgggcctcc ctgaacccct | 600 |
| ggcttccagc catctcatcg ccagcctcct cctggacctc ttggccccca gccccttccc | 660 |
| cacacagccc cagaagggtc ccagagctga ccccactcca ggacctaggc ccagcccctc | 720 |
| agcctcatct ggagcccctg aagaccagtc ccacccacct ttctggcctc atctgacact | 780 |
| gctccgcatc ctgctgtgtg tcctgttcca tgttccggtt ccatccaaat acactttctg | 840 |
| gaacaaa | 847 |

<210> SEQ ID NO 176
<211> LENGTH: 110
<212> TYPE: DNA
<213> ORGANISM: Artificial Sequence
<220> FEATURE:
<223> OTHER INFORMATION: 3'UTR-017 (alpha-globin)

<400> SEQUENCE: 176

| | | |
|---|---|---|
| gctggagcct cggtggccat gcttcttgcc ccttgggcct ccccccagcc cctcctcccc | 60 |
| ttcctgcacc cgtaccccccg tggtctttga ataaagtctg agtgggcggc | 110 |

<210> SEQ ID NO 177
<211> LENGTH: 119
<212> TYPE: DNA
<213> ORGANISM: Artificial Sequence
<220> FEATURE:
<223> OTHER INFORMATION: 3'UTR-018

<400> SEQUENCE: 177

| | | |
|---|---|---|
| tgataatagg ctggagcctc ggtggccatg cttcttgccc cttgggcctc ccccagccc | 60 |
| ctcctcccct tcctgcaccc gtaccccccgt ggtctttgaa taaagtctga gtgggcggc | 119 |

<210> SEQ ID NO 178
<211> LENGTH: 183
<212> TYPE: PRT
<213> ORGANISM: Artificial Sequence
<220> FEATURE:
<223> OTHER INFORMATION: Tumor necrosis factor ligand superfamily member 4 isoform 1 [Homo sapiens]

<400> SEQUENCE: 178

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
                35                  40                  45

Ala Leu Gln Val Ser His Arg Tyr Pro Arg Ile Gln Ser Ile Lys Val
50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 179
<211> LENGTH: 133
<212> TYPE: PRT
<213> ORGANISM: Artificial Sequence
<220> FEATURE:
<223> OTHER INFORMATION: TNFSF4 isoform 2 [Homo sapiens]

<400> SEQUENCE: 179

Met Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
                35                  40                  45

Gly Phe Tyr Leu Ile Ser Leu Lys Gly Tyr Phe Ser Gln Glu Val Asn
50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
            115                 120                 125

Glu Phe Cys Val Leu
        130

<210> SEQ ID NO 180
<211> LENGTH: 198
<212> TYPE: PRT
<213> ORGANISM: Artificial Sequence
<220> FEATURE:
```

<223> OTHER INFORMATION: TNFSF4 [Mus musculus]

<400> SEQUENCE: 180

```
Met Glu Gly Glu Val Gln Pro Leu Asp Glu Asn Leu Glu Asn Gly
1               5                   10                  15
Ser Arg Pro Arg Phe Lys Trp Lys Lys Thr Leu Arg Leu Val Val Ser
            20                  25                  30
Gly Ile Lys Gly Ala Gly Met Leu Leu Cys Phe Ile Tyr Val Cys Leu
        35                  40                  45
Gln Leu Ser Ser Ser Pro Ala Lys Asp Pro Pro Ile Gln Arg Leu Arg
    50                  55                  60
Gly Ala Val Thr Arg Cys Glu Asp Gly Gln Leu Phe Ile Ser Ser Tyr
65                  70                  75                  80
Lys Asn Glu Tyr Gln Thr Met Glu Val Gln Asn Asn Ser Val Val Ile
                85                  90                  95
Lys Cys Asp Gly Leu Tyr Ile Ile Tyr Leu Lys Gly Ser Phe Phe Gln
            100                 105                 110
Glu Val Lys Ile Asp Leu His Phe Arg Glu Asp His Asn Pro Ile Ser
        115                 120                 125
Ile Pro Met Leu Asn Asp Gly Arg Arg Ile Val Phe Thr Val Val Ala
    130                 135                 140
Ser Leu Ala Phe Lys Asp Lys Val Tyr Leu Thr Val Asn Ala Pro Asp
145                 150                 155                 160
Thr Leu Cys Glu His Leu Gln Ile Asn Asp Gly Glu Leu Ile Val Val
                165                 170                 175
Gln Leu Thr Pro Gly Tyr Cys Ala Pro Glu Gly Ser Tyr His Ser Thr
            180                 185                 190
Val Asn Gln Val Pro Leu
        195
```

<210> SEQ ID NO 181
<211> LENGTH: 549
<212> TYPE: RNA
<213> ORGANISM: Artificial Sequence
<220> FEATURE:
<223> OTHER INFORMATION: TNFSF4, ORF [Homo sapiens]

<400> SEQUENCE: 181

```
auggaaggg uccaaccccu ggaagagaau gugggaaaug cagccaggcc aagauucgag     60
aggaacaagc uauugcuggu ggccucugua auucaggggac uggggcugcu ccugugcuuc   120
accuacaucu gccugcacuu cucugcucuu cagguaucac aucgguaucc ucgaauucaa   180
aguaucaaag uacaauuuac cgaauauaag aaggagaaag guuucauccu cacuucccaa   240
aaggaggaug aaaucaugaa ggugcagaac aacucaguca ucaucaacug ugauggguuu   300
uaucucaucu cccugaaggg cuacuucucc caggaaguca acauuagccu ucauuaccag   360
aaggaugagg agcccccucuu ccaacugaag aaggucaggu cugucaacuc cuugauggug   420
gccucucuga cuuacaaaga caaagucuac uugaauguga ccacugacaa uaccucccug   480
gaugacuucc augugaaugg cggagaacug auucuuaucc aucaaaaucc uggugaauuc   540
ugugucuuu                                                           549
```

<210> SEQ ID NO 182
<211> LENGTH: 3484
<212> TYPE: RNA
<213> ORGANISM: Artificial Sequence
<220> FEATURE:

<223> OTHER INFORMATION: TNFSF4, transcript variant 1, mRNA, NM_003326

<400> SEQUENCE: 182

| | | | | | |
|---|---|---|---|---|---:|
| ggcccuggga | ccuuugccua | uuuucugauu | gauaggcuuu | guuugucuu | uaccuccuuc | 60 |
| uuucugggga | aaacuucagu | uuuaucgcac | guucccuuu | uccauaucuu | caucuucccu | 120 |
| cuacccagau | ugugaagaug | gaaagggucc | aaccccugga | agagaaugug | ggaaaugcag | 180 |
| ccaggccaag | auucgagagg | aacaagcuau | ugcugguggc | cucuguaauu | cagggacugg | 240 |
| ggcugcuccu | gugcuucacc | uacaucugcc | ugcacuucuc | ugcucuucag | guaucacauc | 300 |
| gguaccuucg | aauucaaagu | aucaaagua c| aauuuaccga | auauaagaag | gagaaagguu | 360 |
| ucauccucac | uucccaaaag | gaggaugaaa | ucaugaaggu | gcagaacaac | ucagucauca | 420 |
| ucaacuguga | ugggutuuuau | cucaucuccc | ugaaggcua | cuucccccag | gaagucaaca | 480 |
| uuagccuuca | uuaccagaag | gaugaggagc | cccucuucca | acugaagaag | gucaggucug | 540 |
| ucaacuccuu | gaugguggcc | ucucugacuu | acaaagacaa | agucuacuug | aaugugacca | 600 |
| cugacaauac | cucccuggau | gacuuccaug | ugaauggcgg | agaacugauu | cuuauccauc | 660 |
| aaaauccugg | ugaauucugu | guccuuuag g| gggcugaugg | caauaucuaa | aaccaggcac | 720 |
| cagcaugaac | accaagcugg | ggguggacag | ggcauggauu | cuucauugca | agugaaggag | 780 |
| ccucccagcu | cagccacgug | ggaugugaca | agaagcagau | ccuggcccuc | ccgcccccac | 840 |
| cccucaggga | uauuuaaaac | uuauuuuaua | uaccaguuaa | ucuuauuuau | ccuuauauuu | 900 |
| ucuaaauugc | cuagccguca | caccccaaga | uugccuugag | ccuacuaggc | accuuuguga | 960 |
| gaaagaaaaa | auagaugccu | cuucuucaag | augcauuguu | ucuauggu c| aggcaauugu | 1020 |
| cauaauaaac | uuaugucauu | gaaaacggua | ccugacuacc | auuugcugga | aauuugacau | 1080 |
| gugugugca | uuaucaaaau | gaagaggagc | aaggagugaa | ggagugggu | uaugaaucug | 1140 |
| ccaaaggugg | uaugaaccaa | ccccuggaag | ccaaagcggc | cucuccaagg | uuaaauugau | 1200 |
| ugcaguuugc | uauugccua | aauuuaaacu | ucucauuug | gugggguuc | aaaagaagaa | 1260 |
| ucagcuugug | aaaaaucagg | acuugaagag | agccgucuaa | gaaauaccac | gugcuuuuuu | 1320 |
| ucuuuaccau | uuugcuuucc | cagccuccaa | acauaguuaa | uagaaauuuc | ccuucaagaa | 1380 |
| acugucuggg | gaugugaugc | uuugaaaaau | cuaaucagug | acuuaagaga | gauuuucuug | 1440 |
| uauacaggga | gagugagaua | acuuauugug | aagguuagc | uuuacuguac | aggauagcag | 1500 |
| ggaacuggac | aucucagggu | aaaagucagu | acggauuuua | auagccuggg | gaggaaaaca | 1560 |
| cauucuuugc | cacagacagg | caaagcaaca | caugcucauc | cuccugccua | ugcugagaua | 1620 |
| cgcacucagc | uccaugucuu | guacacacag | aaacauugcu | gguucaaga | aaugagguga | 1680 |
| uccuauuauc | aaauucaauc | ugaugucaaa | uagcacuaag | aaguuauugu | gccuuaugaa | 1740 |
| aaauaaugau | cucugucuag | aaauaccaua | gaccauauau | agucucacau | ugauaauuga | 1800 |
| aacuagaagg | gucauaaauc | agccuaugcc | agggcuucaa | uggaauagua | ucccccuuaug | 1860 |
| uuuaguugaa | augucccccuu | aacuugauau | aaugucuuau | gcuauggcg | cuguggacaa | 1920 |
| ucugauuuuu | caugucaacu | uccagauga | uuuguaacuu | cucugugcca | aaccuuuuau | 1980 |
| aaacauaaau | uuuugagaua | uguauuuuaa | aauugcagca | caugcuuccc | ugacauuuuc | 2040 |
| aauagaggau | acaacaucac | agaaucuuuc | uggaugauuc | uguguuauca | aggaauugua | 2100 |
| cugugcuaca | uuaucucua | gaaucuccag | aaaggugggag | ggcuguucgc | ccuuacacua | 2160 |
| aauggucuca | guuggauuuu | uuuuuccugu | uuucuauuuc | cucuuaagua | caccuucaac | 2220 |
| uauauuccca | ucccucuauu | uuaaucuguu | augaaggaag | guaaauaaaa | augcuaaaua | 2280 |

| | |
|---|---|
| gaagaaauug uagguaaggu aagaggaauc aaguucugag uggcugccaa ggcacucaca | 2340 |
| gaaucauaau cauggcuaaa uauuuaugga gggccuacug uggaccaggc acugggcuaa | 2400 |
| auacuuacau uuacaagaau cauucugaga cagauauuca augauaucug gcuucacuac | 2460 |
| ucagaagauu gugugugugu uugugugugu gugugugugu gauuucacu uuuguuauu | 2520 |
| gaccauguuc ugcaaaauug caguuacuca gugagugaua uccgaaaaag uaaacguuua | 2580 |
| ugacuauagg uaauauuuaa gaaaaugcau gguucauuuu uaaguuugga auuuuuaucu | 2640 |
| auauuucuca cagaugugca gugcacaugc aggccuaagu auauguugug uguguuguuu | 2700 |
| gucuuugaug ucauggucc cucucuuagg ugcucacucg cuuugggugc accuggccug | 2760 |
| cucuucccau guuggccucu gcaaccacac agggauauuu cugcuaugca ccagccucac | 2820 |
| uccaccuucc uuccaucaaa aauaugugug ugugucucag ucccuguaag ucaugucuu | 2880 |
| cacagggaga auuaacccuu cgauauacau ggcagaguuu gugggaaaaa gaauugaaug | 2940 |
| aaaagucagg agaucagaau uuuaaauuug acuuagccac uaacuagcca guaaccuug | 3000 |
| ggaaagucau uccccauuuc uggqucuugc uuuucuuucu guuaaaugag aggaauguua | 3060 |
| aauaucuaac aguuuagaau cuuaugcuua caguguuauc ugaaugca cauauuaaau | 3120 |
| gucuauguuc uuguugcuau gagucaagga guguaaccuu cuccuuuacu auguugaaug | 3180 |
| uauuuuuuc uggacaagcu uacaucuucc ucagccaucu uugugagucc uucaagagca | 3240 |
| guuaucaauu guuaguuaga uauuuucuau uuagagaaug cuuaagggau ccaaucccg | 3300 |
| auccaaauca uaauuuguuc uuaaguauac ugggcagguc cccuauuuua agucauaauu | 3360 |
| uuguauuuag ugcuuuccug gcucucagag aguauuaaua uugauauuaa uaauauaguu | 3420 |
| aauaguaaua uugcuauuua cauggaaaca aauaaaagau cucagaauuc acuaaaaaaa | 3480 |
| aaaa | 3484 |

<210> SEQ ID NO 183
<211> LENGTH: 1609
<212> TYPE: RNA
<213> ORGANISM: Artificial Sequence
<220> FEATURE:
<223> OTHER INFORMATION: Mus musculus Tnfsf4, mRNA, NM_009452

<400> SEQUENCE: 183

| | |
|---|---|
| auugcuuuuu gucuccuguu cuggaccuuu uaucuucuga cccgcaggcu ugacuuugcc | 60 |
| cuuauuggcu ccuuuguggu gaagagcagu cuuccccag guuccccgcc acagcuguau | 120 |
| cucccucugca ccccgacugc agaugaugaa ggggaagggg uucaaccccu ggaugagaau | 180 |
| cuggaaaacg gaucaaggcc aagauucaag uggaagaaga cgcuaaggcu gguggucucu | 240 |
| gggaucaagg gagcagggau gcuucugugc uucaucuaug ucugccugca acucucuucc | 300 |
| ucuccggcaa aggacccucc aauccaaaga cucagaggag caguuaccag augugaggau | 360 |
| gggcaacuau ucaucagcuc auacaagaau gaguacaaa cuggaggu gcagaacaau | 420 |
| ucgguuguca ucaagugcga ugggcuuuau aucaucuacc ugaagggcuc cuuuuccag | 480 |
| gaggucaaga uugaccuuca uuccggggag gaucauaauc ccaucucuau uccaaugcug | 540 |
| aacgaugguc gaaggauugu cuucacugug guggccucu uggcuuucaa agauaaaguu | 600 |
| uaccugacug uaaaugcucc ugauacucuc ugcgaacacc uccagauaaa ugaugggggag | 660 |
| cugauuguug uccagcuaac gccuggauac ugugcuccug aaggaucuua ccacagcacu | 720 |
| gugaaccaag uaccacugug aauuccacuc ugagggugga cgggacacag guucuuucuc | 780 |

```
gagagagaug agugcauccu gcucaugaga ugugacugaa ugcagagccu acccuacuuc    840
cucacucagg gauauuuaaa ucaugucuua cauaacaguu gaccucucau ucccaggauu    900
gccuugagcc ugcuaagagc uguucuggga augaaaaaaa aaauaaaugu cucuucaaga    960
cacauugcuu cugucggnca gaagcucauc guaauaaaca ucugccacug aaaauggcgc   1020
uugauugcua ucuucuagaa uuuugauguu gucaaaagaa agcaaaacau ggaaagggug   1080
guguccaccg gccaguagga gcuggagugc ucucuucaag guuaaggnga uagaaguuua   1140
caugnugccu aaaacugucu cucaucucau gggggcuug gaaagaagau uaccccgugg    1200
aaagcaggac uugaagauga cuguuuaagc aacaaggugc acucuuuucc uggcccccuga  1260 auacacauaa aagacaacuu ccuucaaaga acuaccuagg gacuaugaua cccaccaaag   1320
aaccacguca gcgaugcaaa gaaaaccagg agagcuuugu uuauuuugca gaguauacga   1380
gagauuuuac ccugaggccu auuuuauua uacaggauga gagugaacug gaugucucag    1440
gauaaaggcc aagaaggauu uuucacaguc ugacaagac uguuuuugua gguucucucu    1500
ccaaaacuuu uagguaaauu uuugauaauu uuaaaauuuu uaguuauauu uuggaccau    1560 uuucaauaga agauugaaac auuuccagau gguuucauau ccccacaag               1609
```

<210> SEQ ID NO 184
<211> LENGTH: 737
<212> TYPE: RNA
<213> ORGANISM: Artificial Sequence
<220> FEATURE:
<223> OTHER INFORMATION: mRNA sequence: Human OX40L with 5'-UTR, 3'-UTR, and miR-122 binding site

<400> SEQUENCE: 184

```
gggaaauaag agagaaaaga agaguaagaa gaaauauaag agccaccaug gaaagggucc      60
aaccccugga agagaaugug ggaaaugcag ccaggccaag auucgagagg aacaagcuau    120
ugcugguggc cucuguaauu cagggacugg ggcugcuccu gugcuucacc uacaucugcc    180
ugcacuucuc ugcucuucag guaucacauc gguauccucg aauucaaagu aucaaaguac    240
aauuuaccga uauaagaag gagaaagguu ucaccucuac uucccaaaag gaggaugaaa    300
ucaugaaggu gcagaacaac ucagucauca ucaacuguga ugggguuuau cucaucuccc    360
ugaagggcua cuucucccag gaagucaaca uuagccuuca uuaccagaag gaugaggagc    420
cccucuucca acugaagaag gucaggucug ucaacuccuu gauggnggcc ucucugacuu    480
acaaagacaa agucuacuug aaugugacca cugacaauac cucccuggau gacuuccaug    540
ugaauggcgg agaacugauu cuuauccauc aaaauccugg ugaauucugu guccuuugau    600
aauaggcugg agccucgggg gccaugcuuc uugccccuug ggccuccccc cagccccucc    660
uccccuuccu gcaccgguac cccccaaaca ccauugucac acuccagugg ucuuugaaua    720
aagucugagu gggcggc                                                  737
```

<210> SEQ ID NO 185
<211> LENGTH: 782
<212> TYPE: RNA
<213> ORGANISM: Artificial Sequence
<220> FEATURE:
<223> OTHER INFORMATION: mRNA sequence: murine OX40L with 5'-UTR, 3'-UTR, and miR-122 binding site

<400> SEQUENCE: 185

```
gggaaauaag agagaaaaga agaguaagaa gaaauauaag agccaccaug gaaggggaag     60
ggguucaacc ccuggaugag aaucuggaaa acggaucaag gccaagauuc aaguggaaga   120
```

```
agacgcuaag gcuggugguc ucugggauca agggagcagg gaugcuucug ugcuucaucu    180
augucugccu gcaacucucu uccucuccgg caaaggaccc uccaauccaa agacucagag    240
gagcaguuac cagaugugag gaugggcaac uauucaucag cucauacaag aaugaguauc    300
aaacuaugga ggugcagaac aauucgguug ucaucaagug cgaugggcuu uauaucaucu    360
accugaaggg cuccuuuuuc caggagguca agauugaccu ucauuccgg gaggaucaua     420 aucccaucuc uauccaaug cugaacgaug gucgaaggau ugucuucacu guggugccu      480 cuuuggcuuu caaagauaaa guuuaccuga cuguaaaugc uccugauacu cucugcgaac    540
accuccagau aaaugauggg gagcugauug uuguccagcu aacgccugga uacgugcuc     600 cugaaggauc uuaccacagc acugugaacc aaguaccacu gugauaauag gcuggagccu    660
cgguggccau gcuucuugcc ccuugggccu cccccagcc ccuccucccc uuccugcacc     720
cguacccccc aaacaccauu gucacacucc aguggucuuu gaauaaaguc ugaguggcg     780 gc                                                                   782

<210> SEQ ID NO 186
<211> LENGTH: 549
<212> TYPE: DNA
<213> ORGANISM: Artificial Sequence
<220> FEATURE:
<223> OTHER INFORMATION: Codon optimized human OX40L sequences

<400> SEQUENCE: 186
atggaaaggg tccaacccct ggaagagaat gtgggaaatg cagccaggcc aagattcgag     60
aggaacaagc tattgctggt ggcctctgta attcagggac tggggctgct cctgtgcttc    120
acctacatct gcctgcactt ctctgctctt caggtatcac atcggtatcc tcgaattcaa    180
agtatcaaag tacaatttac cgaatataag aaggagaaag gtttcatcct cacttcccaa    240
aaggaggatg aaatcatgaa ggtgcagaac aactcagtca tcatcaactg tgatgggttt    300
tatctcatct ccctgaaggg ctacttctcc caggaagtca acattagcct tcattaccag    360
aaggatgagg agcccctctt ccaactgaag aaggtcaggt ctgtcaactc cttgatggtg    420
gcctctctga cttacaaaga caaagtctac ttgaatgtga ccactgacaa tacctccctg    480
gatgacttcc atgtgaatgg cggagaactg attcttatcc atcaaaatcc tggtgaattc    540
tgtgtccctt                                                           549

<210> SEQ ID NO 187
<211> LENGTH: 594
<212> TYPE: DNA
<213> ORGANISM: Artificial Sequence
<220> FEATURE:
<223> OTHER INFORMATION: Codon optimized mouse OX40L sequences

<400> SEQUENCE: 187
atggaagggg aagggttca acccctggat gagaatctgg aaaacggatc aaggccaaga     60
ttcaagtgga gaagacgct aaggctggtg gtctctggga tcaagggagc agggatgctt    120
ctgtgcttca tctatgtctg cctgcaactc tcttcctctc cggcaaagga ccctccaatc    180
caaagactca gaggagcagt taccagatgt gaggatgggg aactattcat cagctcatac    240
aagaatgagt atcaaactat ggaggtgcag aacaattcgg ttgtcatcaa gtgcgatggg    300
ctttatatca tctacctgaa gggctccttt tccaggagg tcaagattga ccttcatttc    360
cgggaggatc ataatcccat ctctattcca atgctgaacg atggtcgaag gattgtcttc    420
```

```
actgtggtgg cctctttggc tttcaaagat aaagtttacc tgactgtaaa tgctcctgat    480
actctctgcg aacacctcca gataaatgat ggggagctga ttgttgtcca gctaacgcct    540
ggatactgtg ctcctgaagg atcttaccac agcactgtga accaagtacc actg          594
```

```
<210> SEQ ID NO 188
<211> LENGTH: 549
<212> TYPE: RNA
<213> ORGANISM: Artificial Sequence
<220> FEATURE:
<223> OTHER INFORMATION: Codon-optimized sequence 1 for ENSP 281834

<400> SEQUENCE: 188
auggagagag ugcagcccu ggaggagaac gugggcaacg ccgccagacc cagauucgag      60
agaaacaagc ugcugcuggu ggccagcgug auccagggcc ugggccugcu gcugugcuuc    120
accuacaucu gccugcacuu cagcgcccug caggugagcc acagauaccc cagaauccag    180
agcaucaagg ugcaguucac cgaguacaag aaggagaagg cuucauccu gaccagccag      240 aaggaggacg agaucaugaa ggugcagaac aacagcguga ucaucaacug cgacggcuuc    300
uaccugauca gccugaaggg cuacuucagc caggagguga acaucagccu gcacuaccag    360
aaggacgagg agcccuguu ccagcugaag aaggugagaa gcgugaacag ccugauggu      420 gccagccuga ccuacaagga caagguguac cugaacguga ccaccgacaa caccagccug    480
gacgacuucc acgugaacgg cggcgagcug auccugaucc accagaaccc cggcgaguuc    540
ugcgugcug                                                             549
```

```
<210> SEQ ID NO 189
<211> LENGTH: 549
<212> TYPE: RNA
<213> ORGANISM: Artificial Sequence
<220> FEATURE:
<223> OTHER INFORMATION: Codon-optimized sequence 2 for ENSP 281834

<400> SEQUENCE: 189
auggagcgug ugcagccucu ugaggagaau gugggaaaug cagcccggcc ucgauucgaa      60
cguaauaaac uccugcucgu ggccuccgug auccagggu ucgguuuauu gcuguguuuu      120
accuauauau gcuuacacuu uagugcauua caggucucac accgguaccc ucgcauucag    180
ucuauaaaag ugcaguuuac cgaguauaag aaggagaaag guuuauacu gacuucucag      240 aaagaggacg agaucaugaa ggugcagaau aauagcguca uuaucaacug cgauggauuc    300
uaucuaauuu cccuaaaggg guacuucagc caggagguca auauucacu gcacuaucaa      360 aaggacgagg agcccuguu ucaacugaag aaagugcgau caguuaacuc ucugauggu      420 ucugauggu gccucucuga ccuauaagga caaagucuac uugaacguga caacgacaa caccucacug    480 gaugacuuuc augugaaugg gggggaacug auucuuaucc aucagaaucc aggagaauuc    540
ugugugcuc                                                             549
```

```
<210> SEQ ID NO 190
<211> LENGTH: 549
<212> TYPE: RNA
<213> ORGANISM: Artificial Sequence
<220> FEATURE:
<223> OTHER INFORMATION: Codon-optimized sequence 3 for ENSP 281834

<400> SEQUENCE: 190
auggagcggg ugcagccccu ggaggagaau gugggcaaug cugcccggcc cagguuugaa      60
agaaacaagc ugcugcuggu ggccagcguc auccagggcc ugggccugcu gcugugcuuc    120
```

```
accuacaucu gccugcacuu cagcgcccug caggugagcc accgcuaccc ccgcauccag    180
agcaucaagg ugcaguucac agaguacaag aaggagaagg cuucauccu gaccagccag     240 aaggaggaug agaucaugaa ggugcagaac aacagcguca ucaucaacug ugauggcuuc    300
uaccugauca gccugaaggg cuacuucagc caggagguga acaucagccu gcacuaccag    360
aaggaugagg agccccucuu ccagcugaag aaggugcgcu cugugaacag ccugaugguug   420 gccagccuga ccuacaagga caagguguac cugaauguga ccacagacaa caccagccug    480
gaugacuucc acgugaaugg aggagagcug auccugaucc accagaaccc uggagaguuc    540
ugugugcug                                                           549

<210> SEQ ID NO 191
<211> LENGTH: 549
<212> TYPE: RNA
<213> ORGANISM: Artificial Sequence
<220> FEATURE:
<223> OTHER INFORMATION: Codon-optimized sequence 4 for ENSP 281834

<400> SEQUENCE: 191
auggagcggg ugcagcccu ggaggagaac gugggcaacg ccgcccgccc gcguuuugag    60
cgaaauaagu uacugcuugu ugcaucugug auacaggggu uggguuuacu ucuuugcuuu   120
acauauauuu gucuccacuu uaguagcgcuu caggaucccc aucguaccc gcgcauccag    180 ucaaucaagg uccaguucac ugaauauaaa aaggagaaag gauucauucu gacuucacaa    240
aaagaggacg aaaucaugaa agucagaaac aacucuguaa uuauaaacug cgauggguuc    300
uaucugauca gucugaaggg auauuuuagc caggaaguaa auauucacu acauuaucag    360 aaggacgaag aacccacuuuu ucaacugaag aaaguccggu ccgugaacuc ccugaugguu    420
gcuagccuua ccuacaagga uaaagucuau uuaaacguca aacagauaa cacuagccuc    480 gacgauuucc augugaacgg aggugaacug auauugaucc aucaaaaccc cggcgaguuc    540
ugcguuuua                                                           549

<210> SEQ ID NO 192
<211> LENGTH: 549
<212> TYPE: RNA
<213> ORGANISM: Artificial Sequence
<220> FEATURE:
<223> OTHER INFORMATION: Codon-optimized sequence 5 for ENSP 281834

<400> SEQUENCE: 192
auggagcggg uccagcccu cgaggagaac guuggugaug ccgcacgucc cagguuugaa    60
cgcaacaagc ugcuguuggu ggccagcguc auucagggc ugggguuuguu gcugugcuuc    120 acuuacaucu gucugcauuu uaguugcacu caggugccc accgcuaccc ccguauccaa    180
uccauuaaag uccaauuuac cgaauacaaa aaagagaagg guuucauucu uaccucccag    240
aaggaggaug aaauuaugaa ggugcagaac aauucuguua ucaucaacug ugacggauuc    300
uaucugauuu cacugaaggg auacuuuccc caggagguga caucaagucu gcauuaucag   360
aaggacgaag aaccgcuuuu ucaacugaag aagguuagga gugugaacuc cuuaaugguua    420 gccagccuga cauauaagga caagguauau cugaacguca ccacugauaa caccucuuua    480 gacgauuuc augugaaugg gggagaauug auacucauuc accagaaucc gggugaguuu    540
uguguucug                                                          549

<210> SEQ ID NO 193
```

```
<211> LENGTH: 399
<212> TYPE: RNA
<213> ORGANISM: Artificial Sequence
<220> FEATURE:
<223> OTHER INFORMATION: Codon-optimized sequence 1 for ENSP 356691

<400> SEQUENCE: 193
auggugagcc acagauaccc cagaauccag agcaucaagg ugcaguucac cgaguacaag       60
aaggagaagg gcuucauccu gaccagccag aaggaggacg agaucaugaa ggugcagaac     120
aacagcguga ucaucaacug cgacggcuuc uaccugauca gccugaaggg cuacuucagc     180
caggagguga acaucagccu gcacuaccag aaggacgagg agccccuguu ccagcugaag     240
aaggugagaa gcgugaacag ccugauggug gccagccuga ccuacaagga caagguguac     300
cugaacguga ccaccgacaa caccagccug gacgacuucc acgugaacgg cggcgagcug     360
auccugaucc accagaaccc cggcgaguuc ugcgugcug                            399

<210> SEQ ID NO 194
<211> LENGTH: 399
<212> TYPE: RNA
<213> ORGANISM: Artificial Sequence
<220> FEATURE:
<223> OTHER INFORMATION: Codon-optimized sequence 2 for ENSP 356691

<400> SEQUENCE: 194
augguuucuc accguuaccc acggauccag ucuaucaagg uucaguuuac cgaguacaaa       60
aaggaaaaag guucauccu caccucucag aaagaggacg aaaucaugaa ggugcagaau      120
aacucuguaa ucauuaauug cgacgguuuu uaucugauuu cacugaaggg cuacuuuagu     180
caggaaguua auauuaguuu gcacuaccaa aaggacgagg agccucucuu ccaacuaaaa     240
aagguaagau ccguuaauuc ccuuaugg ug gccuccuuaa cuuauaagga cAagguguau     300
cugaauguga ccacagauaa cacaucccug gacgacuuuc auguaaaugg cggcgaguua     360
auucugauac accagaaccc uggcgaguuc ugcgugcug                            399

<210> SEQ ID NO 195
<211> LENGTH: 399
<212> TYPE: RNA
<213> ORGANISM: Artificial Sequence
<220> FEATURE:
<223> OTHER INFORMATION: Codon-optimized sequence 3 for ENSP 356691

<400> SEQUENCE: 195
auggugagcc accgcuaccc ccgcauccag agcaucaagg ugcaguucac agaguacaag       60
aaggagaagg gcuucauccu gaccagccag aaggaggaug agaucaugaa ggugcagaac     120
aacagcguca ucaucaacug ugauggcuuc uaccugauca gccugaaggg cuacuucagc     180
caggagguga acaucagccu gcacuaccag aaggaugagg agccccucuu ccagcugaag     240
aaggugcgcu cugugaacag ccugauggug gccagccuga ccuacaagga caagguguac     300
cugaauguga ccacagacaa caccagccug gaugacuucc acgugaauggagagagcug      360 auccugaucc accagaaccc uggagaguuc ugugugcug                            399

<210> SEQ ID NO 196
<211> LENGTH: 399
<212> TYPE: RNA
<213> ORGANISM: Artificial Sequence
<220> FEATURE:
<223> OTHER INFORMATION: Codon-optimized sequence 4 for ENSP 356691

<400> SEQUENCE: 196
```

```
auggugagcc accgguaccc ccggauccag agcaucaagg ugcaguucac cgaauacaag      60
aaggagaagg guuuuauccu gacgagccag aaggaagacg agauuaugaa ggccaaaac     120 aacucaguca ucauaaacug cgauggauuu uaccugaucu cucugaaagg guacuucucc    180
caggaaguga auauuagcuu gcacuaucaa aaagaugagc agcccucuauu ccagcucaag   240 aaggucagaa gcgucaauag ucugaugguc gcaucauuaa ccauaaaga caaaguauau    300 cuaaauguga cgacagacaa uacaucccuc gaugauuuc acgucaacgg aggcgaacuc    360
auucugaucc accagaaucc aggggaauuu ugcgugcug                          399

<210> SEQ ID NO 197
<211> LENGTH: 399
<212> TYPE: RNA
<213> ORGANISM: Artificial Sequence
<220> FEATURE:
<223> OTHER INFORMATION: Codon-optimized sequence 5 for ENSP 356691

<400> SEQUENCE: 197
auggucucac accgguaccc ccguauccag aguauuaagg ugcaauucac ggaguauaaa     60
aaagaaaagg gauucauucu gacgucucag aaggaagaug agaucaugaa gguccagaac    120
aauucuguga ucauuaauug cgauggauuu uaucugauuu cacuuaaagg auauuuuucc    180
caggagguua auaucaguuu gcacuaucag aaagacgagg agccauuauu ccagcugaag    240
aaggugagau cagugaauag ccugaugguu gcgucacuga cguauaaaga caaaguuuau    300
cuaaacguua ccacugauaa uacaucccuu gaugauuuuc augugaacgg gggugaacug    360
auccuuauac accagaaccc cggagaguuc uguguguug                          399

<210> SEQ ID NO 198
<211> LENGTH: 399
<212> TYPE: RNA
<213> ORGANISM: Artificial Sequence
<220> FEATURE:
<223> OTHER INFORMATION: Codon-optimized sequence 1 for ENSP 439704

<400> SEQUENCE: 198
auggugagcc acagauaccc cagaauccag agcaucaagg ugcaguucac cgaguacaag     60
aaggagaagg gcuucauccu gaccagccag aaggaggacg agaucaugaa ggugcagaac    120
aacagcguga ucaucaacug cgacggcuuc uaccugauca gccugaaggg cuacuucagc    180
caggagguga acaucagccu gcacuaccag aaggacgagg agccccuguu ccagcugaag    240
aaggugagaa gcgugaacag ccugaugggug gccagccuga ccuacaagga caagguguac    300
cugaacguga ccaccgacaa caccagcccug gacgacuucc acgugaacgg cggcgagcug    360
auccugaucc accagaaccc cggcgaguuc ugcgugcug                           399

<210> SEQ ID NO 199
<211> LENGTH: 399
<212> TYPE: RNA
<213> ORGANISM: Artificial Sequence
<220> FEATURE:
<223> OTHER INFORMATION: Codon-optimized sequence 2 for ENSP 439704

<400> SEQUENCE: 199
auggugucac accgguaccc ucggauccag ucuauuaaag uucaauuuac ggaguacaag     60
aaagaaaaag gcuuuauccu uacaagccaa aaggaagacg agaucaugaa agugcaaaac    120
aacaguguga uuauaaauug ugauggcuuc uaccuuauua gucugaaggg cuacuuuagu    180
```

```
caggaaguca auauuagccu acacuaccag aaagacgagg agccccucuu ucaacugaaa        240
aaggugcgcu ccgugaauuc guugaugguc gccucucuga ccuacaaaga uaagguguau        300
cuuaacguua cuaccgacaa uacuagucug gacgacuuuc acgucaacgg aggcgaacuu        360
auucugaucc accagaaccc cggcgaauuc ugcgugcug                              399

<210> SEQ ID NO 200
<211> LENGTH: 399
<212> TYPE: RNA
<213> ORGANISM: Artificial Sequence
<220> FEATURE:
<223> OTHER INFORMATION: Codon-optimized sequence 3 for ENSP 439704

<400> SEQUENCE: 200
auggugagcc accgcuaccc ccgcauccag agcaucaagg ugcaguucac agaguacaag         60
aaggagaagg gcuucauccu gaccagccag aaggaggaug agaucaugaa ggugcagaac        120
aacagcguca ucaucaacug gauggcuuc uaccugauca gccugaaggg cuacuucagc         180
caggagguga acaucagccu gcacuaccag aaggaugagc agccccucuu ccagcugaag        240
aaggugcgcu cugugaacag cugcugaugg ugccagccuga ccuacaagga caagguguac       300
cugaauguga ccacagacaa caccagccug gaugacuucc acgugaaugg aggagagcug       360
auccugaucc accagaaccc uggagaguuc uguguggcug                              399

<210> SEQ ID NO 201
<211> LENGTH: 399
<212> TYPE: RNA
<213> ORGANISM: Artificial Sequence
<220> FEATURE:
<223> OTHER INFORMATION: Codon-optimized sequence 4 for ENSP 439704

<400> SEQUENCE: 201
auggugagcc accgguaccc ccggauccag agcaucaagg ugcaguucac agaguacaag         60
aaggagaagg gauuuauucu cacaagucag aaagaagaug agaucaugaa gguucagaac        120
aacucaguca uuauuaauug cgacggauuc uaucucauua gccucaaagg cuauuucagc        180
caggagguca auaucagccu gcacuaccag aaggaugagc aaccucucuu ucagcugaaa        240
aaaguccgcu cugugaauuc ccucaugguc gcuucccuga ccuacaagga uaaaguuuau       300
uugaacguua caacagauaa uacaucgcug gacgacuucc augugaaugg uggcgaacua       360
auucuaauac accaaaauuc aggcgaauuu uguguccuu                              399

<210> SEQ ID NO 202
<211> LENGTH: 399
<212> TYPE: RNA
<213> ORGANISM: Artificial Sequence
<220> FEATURE:
<223> OTHER INFORMATION: Codon-optimized sequence 5 for ENSP 439704

<400> SEQUENCE: 202
augguauccc auagauaccc acguauucaa agcauuaagg ugcaguucac agaguacaaa         60
aaggagaagg guuucauacu gacgucacag aaggaggacg agauaaugaa ggugcagaau        120
aauaguguga ucaucaauug ugauggauuc uauuugauca gcucaaagg uuauuucuca        180 caggaaguca acauucccu gcacuaccag aaggacgaag agccuuuguu ucagcugaag        240
aaggugcgcu cagugaacag uuugaugguua gccucccuaa cuauaaaga uaaaguuuau       300 cugaacguga caaccgauaa cacacccuug gacgacuuc acgucaaugg aggugaguua        360
auccugaucc aucagaaucc cggagaauuc ugcguucuu                              399
```

```
<210> SEQ ID NO 203
<211> LENGTH: 2
<212> TYPE: PRT
<213> ORGANISM: Artificial Sequence
<220> FEATURE:
<223> OTHER INFORMATION: GS linker
<220> FEATURE:
<221> NAME/KEY: repeat_unit
<222> LOCATION: (1)..(1)
<223> OTHER INFORMATION: G can be repeated n times, wherein n is 1 to
      100
<220> FEATURE:
<221> NAME/KEY: misc_feature
<222> LOCATION: (1)..(2)
<223> OTHER INFORMATION: sequence can be repeated n times, wherein n is
      1 to 100

<400> SEQUENCE: 203

Gly Ser
1

<210> SEQ ID NO 204
<211> LENGTH: 5
<212> TYPE: PRT
<213> ORGANISM: Artificial Sequence
<220> FEATURE:
<223> OTHER INFORMATION: GS linker
<220> FEATURE:
<221> NAME/KEY: misc_feature
<222> LOCATION: (1)..(5)
<223> OTHER INFORMATION: sequence can be repeated n times, wherein n is
      1 to 5

<400> SEQUENCE: 204

Gly Gly Gly Gly Ser
1               5

<210> SEQ ID NO 205
<211> LENGTH: 10
<212> TYPE: PRT
<213> ORGANISM: Artificial Sequence
<220> FEATURE:
<223> OTHER INFORMATION: GS linker

<400> SEQUENCE: 205

Gly Gly Ser Gly Gly Gly Gly Ser Gly Gly
1               5                   10

<210> SEQ ID NO 206
<211> LENGTH: 8
<212> TYPE: PRT
<213> ORGANISM: Artificial Sequence
<220> FEATURE:
<223> OTHER INFORMATION: GS linker

<400> SEQUENCE: 206

Gly Gly Ser Gly Gly Gly Gly Gly
1               5

<210> SEQ ID NO 207
<211> LENGTH: 8
<212> TYPE: PRT
<213> ORGANISM: Artificial Sequence
<220> FEATURE:
<223> OTHER INFORMATION: GS linker

<400> SEQUENCE: 207

Gly Ser Gly Ser Gly Ser Gly Ser
```

```
1               5

<210> SEQ ID NO 208
<211> LENGTH: 1
<212> TYPE: PRT
<213> ORGANISM: Artificial Sequence
<220> FEATURE:
<223> OTHER INFORMATION: Gly-rich linker
<220> FEATURE:
<221> NAME/KEY: misc_feature
<222> LOCATION: (1)..(1)
<223> OTHER INFORMATION: sequence can be repeated n times, wherein n is
      1 to 100

<400> SEQUENCE: 208

Gly
1

<210> SEQ ID NO 209
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (1)..(5)
<223> OTHER INFORMATION: sequence can be repeated n times, wherein n is
      1 to 100

<400> SEQUENCE: 209

Glu Ala Ala Ala Lys
1               5

<210> SEQ ID NO 210
<211> LENGTH: 16
<212> TYPE: PRT
<213> ORGANISM: Artificial Sequence
<220> FEATURE:
<223> OTHER INFORMATION: linker

<400> SEQUENCE: 210

Gly Gly Gly Gly Ser Leu Val Pro Arg Gly Ser Gly Gly Gly Gly Ser
1               5                   10                  15

<210> SEQ ID NO 211
<211> LENGTH: 6
<212> TYPE: PRT
<213> ORGANISM: Artificial Sequence
<220> FEATURE:
<223> OTHER INFORMATION: linker

<400> SEQUENCE: 211

Gly Ser Gly Ser Gly Ser
1               5

<210> SEQ ID NO 212
<211> LENGTH: 15
<212> TYPE: PRT
<213> ORGANISM: Artificial Sequence
<220> FEATURE:
<223> OTHER INFORMATION: linker

<400> SEQUENCE: 212

Gly Gly Gly Gly Ser Leu Val Pro Arg Gly Ser Gly Gly Gly Gly
1               5                   10                  15

<210> SEQ ID NO 213
```

```
<211> LENGTH: 11
<212> TYPE: PRT
<213> ORGANISM: Artificial Sequence
<220> FEATURE:
<223> OTHER INFORMATION: linker

<400> SEQUENCE: 213

Gly Gly Ser Gly Gly His Met Gly Ser Gly Gly
1               5                   10

<210> SEQ ID NO 214
<211> LENGTH: 11
<212> TYPE: PRT
<213> ORGANISM: Artificial Sequence
<220> FEATURE:
<223> OTHER INFORMATION: linker

<400> SEQUENCE: 214

Gly Gly Ser Gly Gly Ser Gly Gly Ser Gly Gly
1               5                   10

<210> SEQ ID NO 215
<211> LENGTH: 5
<212> TYPE: PRT
<213> ORGANISM: Artificial Sequence
<220> FEATURE:
<223> OTHER INFORMATION: linker

<400> SEQUENCE: 215

Gly Gly Ser Gly Gly
1               5

<210> SEQ ID NO 216
<211> LENGTH: 8
<212> TYPE: PRT
<213> ORGANISM: Artificial Sequence
<220> FEATURE:
<223> OTHER INFORMATION: linker

<400> SEQUENCE: 216

Gly Ser Gly Ser Gly Ser Gly Ser
1               5

<210> SEQ ID NO 217
<211> LENGTH: 18
<212> TYPE: PRT
<213> ORGANISM: Artificial Sequence
<220> FEATURE:
<223> OTHER INFORMATION: linker

<400> SEQUENCE: 217

Gly Gly Gly Ser Glu Gly Gly Ser Glu Gly Gly Ser Glu Gly
1               5                   10                  15

Gly Gly

<210> SEQ ID NO 218
<211> LENGTH: 8
<212> TYPE: PRT
<213> ORGANISM: Artificial Sequence
<220> FEATURE:
<223> OTHER INFORMATION: linker

<400> SEQUENCE: 218

Ala Ala Gly Ala Ala Thr Ala Ala
1               5
```

```
<210> SEQ ID NO 219
<211> LENGTH: 5
<212> TYPE: PRT
<213> ORGANISM: Artificial Sequence
<220> FEATURE:
<223> OTHER INFORMATION: linker

<400> SEQUENCE: 219

Gly Gly Ser Ser Gly
1               5

<210> SEQ ID NO 220
<211> LENGTH: 11
<212> TYPE: PRT
<213> ORGANISM: Artificial Sequence
<220> FEATURE:
<223> OTHER INFORMATION: linker

<400> SEQUENCE: 220

Gly Ser Gly Gly Gly Thr Gly Gly Gly Ser Gly
1               5                   10

<210> SEQ ID NO 221
<211> LENGTH: 12
<212> TYPE: PRT
<213> ORGANISM: Artificial Sequence
<220> FEATURE:
<223> OTHER INFORMATION: linker

<400> SEQUENCE: 221

Gly Ser Gly Ser Gly Ser Gly Ser Gly Gly Ser Gly
1               5                   10

<210> SEQ ID NO 222
<211> LENGTH: 14
<212> TYPE: PRT
<213> ORGANISM: Artificial Sequence
<220> FEATURE:
<223> OTHER INFORMATION: linker

<400> SEQUENCE: 222

Gly Ser Gly Gly Ser Gly Ser Gly Gly Ser Gly Gly Ser Gly
1               5                   10

<210> SEQ ID NO 223
<211> LENGTH: 14
<212> TYPE: PRT
<213> ORGANISM: Artificial Sequence
<220> FEATURE:
<223> OTHER INFORMATION: linker

<400> SEQUENCE: 223

Gly Ser Gly Gly Ser Gly Gly Ser Gly Gly Ser Gly Gly Ser
1               5                   10

<210> SEQ ID NO 224
<211> LENGTH: 6
<212> TYPE: DNA
<213> ORGANISM: Artificial Sequence
<220> FEATURE:
<223> OTHER INFORMATION: restriction site motif for Xba1

<400> SEQUENCE: 224 tctaga                                                                    6

<210> SEQ ID NO 225
<211> LENGTH: 6
```

```
<212> TYPE: DNA
<213> ORGANISM: Artificial Sequence
<220> FEATURE:
<223> OTHER INFORMATION: restriction site motif for EcoRI

<400> SEQUENCE: 225 gaattc                                                                    6

<210> SEQ ID NO 226
<211> LENGTH: 5
<212> TYPE: DNA
<213> ORGANISM: Artificial Sequence
<220> FEATURE:
<223> OTHER INFORMATION: restriction site motif for EcoRII

<400> SEQUENCE: 226 ccwgg                                                                     5

<210> SEQ ID NO 227
<211> LENGTH: 6
<212> TYPE: DNA
<213> ORGANISM: Artificial Sequence
<220> FEATURE:
<223> OTHER INFORMATION: restriction site motif for HindIII

<400> SEQUENCE: 227 aagctt                                                                    6

<210> SEQ ID NO 228
<211> LENGTH: 20
<212> TYPE: DNA
<213> ORGANISM: Artificial Sequence
<220> FEATURE:
<223> OTHER INFORMATION: enzyme site in the T7 RNA polymerase
<220> FEATURE:
<221> NAME/KEY: misc_feature
<222> LOCATION: (2)..(5)
<223> OTHER INFORMATION: n may be any nucleotide
<220> FEATURE:
<221> NAME/KEY: misc_feature
<222> LOCATION: (7)..(7)
<223> OTHER INFORMATION: n may be any nucleotide
<220> FEATURE:
<221> NAME/KEY: misc_feature
<222> LOCATION: (10)..(10)
<223> OTHER INFORMATION: n may be any nucleotide
<220> FEATURE:
<221> NAME/KEY: misc_feature
<222> LOCATION: (14)..(14)
<223> OTHER INFORMATION: n may be any nucleotide
<220> FEATURE:
<221> NAME/KEY: misc_feature
<222> LOCATION: (16)..(17)
<223> OTHER INFORMATION: n may be any nucleotide
<220> FEATURE:
<221> NAME/KEY: misc_feature
<222> LOCATION: (19)..(19)
<223> OTHER INFORMATION: n may be any nucleotide

<400> SEQUENCE: 228
gnnnnwncrn ctcncnnwnd                                                    20

<210> SEQ ID NO 229
<211> LENGTH: 4
<212> TYPE: DNA
<213> ORGANISM: Artificial Sequence
<220> FEATURE:
<223> OTHER INFORMATION: structural motif

<400> SEQUENCE: 229
```

```
gggg                                                              4

<210> SEQ ID NO 230
<211> LENGTH: 4
<212> TYPE: DNA
<213> ORGANISM: Artificial Sequence
<220> FEATURE:
<223> OTHER INFORMATION: synthetic polynucleotide

<400> SEQUENCE: 230 atcg                                                              4

<210> SEQ ID NO 231
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 231 atcccg                                                            6

<210> SEQ ID NO 232
<211> LENGTH: 9
<212> TYPE: RNA
<213> ORGANISM: Artificial Sequence
<220> FEATURE:
<223> OTHER INFORMATION: Kozak sequence

<400> SEQUENCE: 232 ccrccaugg                                                         9

<210> SEQ ID NO 233
<211> LENGTH: 6
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(6)
<223> OTHER INFORMATION: guanine bases can be substituted by at least 1,
      at least 2, at least 3 or at least 4 adenine nucleotides

<400> SEQUENCE: 233 gggaga                                                            6

<210> SEQ ID NO 234
<211> LENGTH: 6
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(6)
<223> OTHER INFORMATION: guanine bases can be substituted by at least 1,
      at least 2, at least 3 or at least 4 cytosine bases

<400> SEQUENCE: 234 gggaga                                                            6

<210> SEQ ID NO 235
<211> LENGTH: 6
<212> TYPE: DNA
<213> ORGANISM: Artificial Sequence
<220> FEATURE:
<223> OTHER INFORMATION: synthetic polynucleotide
```

<220> FEATURE:
<221> NAME/KEY: misc_feature
<222> LOCATION: (1)..(6)
<223> OTHER INFORMATION: guanine bases can be substituted by at least 1,
at least 2, at least 3 or at least 4 thymine

<400> SEQUENCE: 235 gggaga                                                                    6

<210> SEQ ID NO 236
<211> LENGTH: 1596
<212> TYPE: DNA
<213> ORGANISM: Artificial Sequence
<220> FEATURE:
<223> OTHER INFORMATION: hIL12AB_002

<400> SEQUENCE: 236

```
atgtgccacc agcagctggt gatcagctgg ttcagcctgg tgttcctggc cagcccctg     60
gtggccatct gggagctgaa gaaggacgtg tacgtggtgg agttggattg taccccgac    120
gcccccggcg agatggtggt gctgacctgc gacaccccg aggaggacgg catcacctgg    180
accctggacc agagcagcga ggtgctgggc agcggcaaga ccctgaccat ccaggtgaag    240
gagttcggcg acgccggcca gtacacctgc cacaagggcg cgaggtgct gagccacagc    300
ctgctgctgc tgcacaagaa ggaggacggc atctggagca ccgacatcct gaaggaccag    360
aaggagccca gaacaagac cttcctgaga tgcgaggcca gaactacag cggcagattc    420
acctgctggt ggctgaccac catcagcacc gacctgacct tcagcgtgaa gagcagcaga    480
ggcagcagcg accccagggg cgtgacctgc ggcgccgcca ccctgagcgc cgagagagtg    540
agaggcgaca caaggagta cgagtacagc gtggagtgcc aggaagatag cgcctgcccc    600
gccgccgagg agagcctgcc catcgaggtg atggtggacg ccgtgcacaa gctgaagtac    660
gagaactaca ccagcagctt cttcatcaga gatatcatca gcccgacccc cccaagaac    720
ctgcagctga gcccctgaa gaacagccgg caggtggagg tgagctggga gtaccccgac    780
acctggagca cccccacag ctacttcagc ctgaccttct gcgtgcaggt gcagggcaag    840
agcaagagag agaagaaaga tagagtgttc accgacaaga ccagcgccac cgtgatctgc    900
agaaagaacg ccagcatcag cgtgagagcc caagatagat actacagcag cagctggagc    960
gagtgggcca gcgtgccctg cagcggcggc ggcggcggcg gcagcagaaa cctgcccgtg   1020
gccacccccg accccggcat gttccctgc ctgcaccaca gccagaacct gctgagagcc   1080
gtgagcaaca tgctgcagaa ggccggcag accctggagt ctacccctg caccagcgag   1140
gagatcgacc acgaagatat caccaaagat aagaccagca ccgtggaggc ctgcctgccc   1200
ctggagctga ccaagaacga gagctgcctg aacagcagag agaccagctt catcaccaac   1260
ggcagctgcc tggccagcag aaagaccagc ttcatgatgg ccctgtgcct gagcagcatc   1320
tacgaggacc tgaagatgta ccaggtggag ttcaagacca tgaacgccaa gctgctgatg   1380
gaccccaagc ggcagatctt cctggaccag aacatgctgg ccgtgatcga cgagctgatg   1440
caggccctga acttcaacag cgagaccgtg ccccagaaga gcagcctgga ggagcccgac   1500
ttctacaaga ccaagatcaa gctgtgcatc ctgctgcacg ccttcagaat cagagccgtg   1560
accatcgaca gagtgatgag ctacctgaac gccagc                             1596
```

<210> SEQ ID NO 237
<211> LENGTH: 1596
<212> TYPE: RNA
<213> ORGANISM: Artificial Sequence

```
<220> FEATURE:
<223> OTHER INFORMATION: hIL12AB_002

<400> SEQUENCE: 237
augugccacc agcagcuggu gaucagcugg uucagccugg uguuccuggc cagcccccug      60
guggccaucu gggagcugaa gaaggacgug uacguggugg aguuggauug guaccccgac     120
gcccccggcg agauguggu gcugaccugc gacaccccg aggaggacgg caucaccugg       180
acccuggacc agagcagcga ggugcugggc agcggcaaga cccugaccau ccaggugaag     240
gaguucggcg acgccggcca guacaccugc acaagggcg gcgaggugcu gagccacagc     300
cugcugcugc ugcacaagaa ggaggacggc aucuggagca ccgacauccu gaaggaccag    360
aaggagccca gaacaagac cuuccugaga ugcgaggcca gaacuacag cggcagauuc      420 accugcuggu ggcugaccac caucagcacc gaccugaccu ucagcgugaa gagcagcaga    480
ggcagcagcg acccccaggg cgugaccugc ggcgccgcca cccugagcgc cgagagagug   540
agaggcgaca caaggagua cgaguacagc guggagugcc aggaagauag cgccugcccc    600
gccgccgagg agagccugcc caucgaggug augguggacg ccgugcacaa gcugaaguac   660
gagaacuaca ccagcagcuu cuucaucaga gauaucauca gcccgaccc ccccaagaac    720 cugcagcuga gcccccugaa gaacagccgg caggugggag ugagcuggga guaccccgac   780
accuggagca ccccccacag cuacuucagc cugaccuucu gcgugcaggu cagggcaag    840 agcaagagag agaagaaaga uagagguuc accgacaaga ccagcgccac cgugaucugc   900
agaaagaacg ccagcaucag cgugagagcc caagauagau acuacagcag cagcuggagc  960
gaguggccca gcgugcccug cagcggcggc ggcggcggcg gcagcagaaa ccugcccgug  1020 gccaccccg accccggcau guucccccgc cugcaccaca gccagaaccu gcugagagcc  1080
gugagcaaca ugcugcagaa ggcccggcag acccuggagu cuacccccug caccagcgag  1140
gagaucgacc acgaagauau caccaaagau aagaccagca ccguggaggc cugccugccc  1200
cuggagcuga ccaagaacga gagcugccug aacagcagag agaccagcuu caucaccaac  1260
ggcagcugcc uggccagcag aaagaccagc uucaugaugg cccugugccu gagcagcauc  1320
uacgaggacc ugaagaugua ccagguggag uucaagacca ugaacgccaa gcugcugaug  1380
gaccccaagc ggcagaucuu ccuggaccag aacaugcugg ccgugaucga cgagcugaug  1440
caggcccuga acuucaacag cgagaccgug ccccagaaga gcagccugga ggagcccgac  1500
uucuacaaga ccaagaucaa gcugugcauc cugcugcacg ccuucagaau cagagccgug  1560
accaucgaca gagugaugag cuaccugaac gccagc                             1596

<210> SEQ ID NO 238
<211> LENGTH: 138
<212> TYPE: RNA
<213> ORGANISM: Artificial Sequence
<220> FEATURE:
<223> OTHER INFORMATION: 3UTR-018 + miR-122-5p binding site

<400> SEQUENCE: 238
uaauaggcug gagccucggu ggccaugcuu cuugccccuu gggccucccc ccagccccuc     60 cucccccuucc ugcacccgua ccccccaaac accauuguca cacuccagug gucuuugaau   120
aaagucugag ugggcggc                                                  138

<210> SEQ ID NO 239
<211> LENGTH: 138
<212> TYPE: RNA
```

<213> ORGANISM: Artificial Sequence
<220> FEATURE:
<223> OTHER INFORMATION: 3UTR-018 + miR-122-3p binding site

<400> SEQUENCE: 239

```
uaauaggcug gagccucggu ggccaugcuu cuugccccuu ggccuccccc ccagcccuc      60
cuccccuucc ugcacccgua cccccuauuu agugugauaa uggcguugug gucuuugaau    120
aaagucugag ugggcggc                                                  138
```

<210> SEQ ID NO 240
<211> LENGTH: 141
<212> TYPE: RNA
<213> ORGANISM: Artificial Sequence
<220> FEATURE:
<223> OTHER INFORMATION: 3UTR-019 + miR-122 binding site

<400> SEQUENCE: 240

```
ugauaauagg cuggagccuc gguggccaug cuucuugccc cuuggccuc ccccagccc       60
cuccucccu uccugcaccc guaccccca aacaccauug ucacaucca guggucuuug      120
aauaaagucu gaguggggcgg c                                            141
```

<210> SEQ ID NO 241
<211> LENGTH: 1817
<212> TYPE: RNA
<213> ORGANISM: Artificial Sequence
<220> FEATURE:
<223> OTHER INFORMATION: mIL12_miR122

<400> SEQUENCE: 241

```
gggaaauaag agagaaaaga agaguaagaa gaaauauaag agccaccaug uguccucaga     60
agcuaaccau ucccuggumu gccaucguuu gcuggugguc uccacucaug gccauguggg    120
agcuggagaa agacguuuau guuguagagg uggacuggac ucccgaugcc ccuggagaaa    180
cagugaaccu caccugugac acgcugaag aagaugacau caccggacc ucagaccaga     240
gacauggagu cauaggcucu ggaaagaccc ugaccaucac ugucaaagag uuccuagaug    300
cuggccagua caccgccac aaaggaggcg agacucugag ccacucacau cugcugcucc    360
acaagaagga aaauggaauu uggucacug aaauuuuaaa aaauucaaa aacaagacuu      420
uccugaagug ugaagcacca aauuacuccg gacgguucac gugcucaugg cuggugcaaa    480
gaaacaugga cuugaaguc aacaucaaga gcaguagcag uucccugac ucucgggcag      540
ugacaugugg aauggcgucu cugucugcag agaaggucac acuggaccaa agggacuaug    600
agaaguauuc agugccugc caggaggau ucaccugcc aacugccgag gagacccugc       660
ccauugaacu ggcguggaa gcacggcagc agaauaaaua ugagaacuac agcaccagcu     720
ucuucaucag ggacauaau aaaaccagacc cgcccaagaa cuugcagaug aagcccuuga    780
agaacucaca gguggagguc agcugggagu acccugaccu cggagcacuc ccccaucccu    840
acuucucccu caaguucuuu guucgaauc agcgcaagaa agaaaagaug aaggagacag    900
aggagggug uaaccagaaa ggugcguucc ucguagagaa gacaucuacc gaaguccaau     960
gcaaaggcgg gaaugucugc gugcaagcuc aggaucgcua uuacaauucc ucaugcagca   1020
aguggcaug uguccccugc agggccggau ccggaggcgg agggagcgga ggcggagaga    1080
gcggaggcgg agggagcagg gucauuccag ucucuggacc ugccagugu cuuagccagu    1140
ccccgaaaccu gcgaagacc acagaugaca ugguggaagc ggccagagaa aaacugaaac   1200
auuuuccug cacugcugaa gacaucgauc augaagacau cacacgggac caaaccagca    1260
```

```
cauugaagac cuguuuacca cuggaacuac acaagaacga gaguugccug gcuacuagag   1320
agacuucuuc cacaacaaga gggagcugcc ugcccccaca gaagacgucu uugaugauga   1380
cccugugccu ugguagcauc uaugaggacu ugaagaugua ccagacagag uuccaggcca   1440
ucaacgcagc acuucagaau cacaaccauc agcagaucau uuuagacaag ggcaugcugg   1500
uggccaucga ugagcugaug cagucucuga aucauaaugg cgagacucug cgccagaaac   1560
cuccuguggg agaagcagac ccuuacagag ugaaaaugaa gcucugcauc cugcuucacg   1620
ccuucagcac ccgcgucgug accaucaaca gggugauggg cuaucugagc uccgccugau   1680
aauaggcugg agccucggug gccaugcuuc uugccccuug ggccuccccc agccccucc    1740 uccccuuccu gcacccguac cccccaaaca ccauugucac acuccagugg ucuuugaaua   1800
aagucugagu gggcggc                                                  1817

<210> SEQ ID NO 242
<211> LENGTH: 1795
<212> TYPE: RNA
<213> ORGANISM: Artificial Sequence
<220> FEATURE:
<223> OTHER INFORMATION: IL12 miRless (murine)

<400> SEQUENCE: 242
gggaaauaag agagaaaaga agaguaagaa gaaauauaag agccaccaug uguccucaga     60
agcuaaccau cuccugguuu gccaucguuu ugcuggguguc uccacucaug gccauguggg   120
agcuggagaa agacguuuau guugguagagg uggacuggac ucccgaugcc ccuggagaaa   180
cagugaaccu caccugugac acgccugaag aagaugacau caccuggacc ucagaccaga   240
gacauggagu cauaggcucu ggaaagaccc ugaccaucac ugucaaagag uuccuagaug   300
cuggccagua caccugccac aaaggaggcg agacucuag ccacucacau cugcugcucc     360
acaagaagga aaauggaauu uggucccacug aaauuuuaaa aaauuucaaa aacaagacuu   420
uccugaagug ugaagcacca aauuacuccg gacgguucac gugcucaugg cugguugcaaa   480 gaaacaugga cuugaaguuc aacaucaaga gcaguagcag uucccccugac ucucgggcag   540 ugacaugugg aauggcgucu cugucugcag agaaggucac acuggaccaa agggacuaug   600
agaaguauuc agugcccugc caggaggaug ucaccugccc aacugccgag agacccugc    660 ccauugaacu ggcguuggaa gcacggcagc agaauaaaua ugagaacuac agcaccagcu   720
ucuucaucag ggacaucauc aaaccagacc cgcccaagaa cuugcagaug aagccuuuga   780
agaacucaca gguggagguc agcugggagu acccugacuc cuggagcacu ccccauuccu   840
acuucucccu caaguucuuu guucgaaucc agcgcaagaa agaaaagaug aaggagacag   900
aggaggggug uaaccagaaa ggugcguucc ucguagagaa gacaucuacc gaagcccaau   960
gcaaaggcgg gaaugucugc gugcaagcuc aggaucgcua uuacaauucc ucaugcagca  1020 aguggggcaug uguucccugc aggguccgau ccggaggcgg agggagcgga ggcggaggga  1080
gcggaggcgg agggagcagg gucauuccag ucucuggacc ugccaggugu cuuagccagu  1140
cccgaaaccu gcugaagacc acagaugaca uggugaagac ggccagagaa aaacugaaac  1200
auuauuccug cacugcugaa gacaucgauc augaagacau cacgggac caaaccagca   1260 cauugaagac cuguuuacca cuggaacuac acaagaacga gaguugccug gcuacuagag   1320
agacuucuuc cacaacaaga gggagcugcc ugcccccaca gaagacgucu uugaugauga   1380
cccugugccu ugguagcauc uaugaggacu ugaagaugua ccagacagag uuccaggcca   1440
```

```
ucaacgcagc acuucagaau cacaaccauc agcagaucau uuuagacaag ggcaugcugg    1500
uggccaucga ugagcugaug cagucucuga aucauaaugg cgagacucug cgccagaaac    1560
cuccuguggg agaagcagac ccuuacagag ugaaaaugaa gcucugcauc cugcuucacg    1620
ccuucagcac ccgcgucgug accaucaaca gggugauggg cuaucugagc uccgccugau    1680
aauaggcugg agccucggug gccaugcuuc uugccccuug ggccucccc  cagccccucc    1740 uccccuuccu gcacccguac ccccgugguc uuugaauaaa gucugagugg gcggc         1795
```